(12) United States Patent
Härter et al.

(10) Patent No.: US 10,428,083 B2
(45) Date of Patent: Oct. 1, 2019

(54) HETEROCYCLYLMETHYL-THIENOURACILE AS ANTAGONISTS OF THE ADENOSINE-A2B-RECEPTOR

(71) Applicant: BAYER PHARMA AKTIENGESELLSCHAFT, Berlin (DE)

(72) Inventors: Michael Härter, Leverkusen (DE); Dirk Kosemund, Berlin (DE); Martina Delbeck, Heiligenhaus (DE); Bernd Kalthof, Wuppertal (DE); Pierre Wasnaire, Düsseldorf (DE); Frank Süßmeier, Munich (DE); Klemens Lustig, Wuppertal (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/560,265

(22) PCT Filed: Mar. 21, 2016

(86) PCT No.: PCT/EP2016/056106
§ 371 (c)(1),
(2) Date: Sep. 21, 2017

(87) PCT Pub. No.: WO2016/150901
PCT Pub. Date: Sep. 29, 2016

(65) Prior Publication Data
US 2018/0065981 A1 Mar. 8, 2018

(30) Foreign Application Priority Data

Mar. 26, 2015 (EP) .................... 15161165
Jun. 30, 2015 (EP) .................... 15174566
Sep. 10, 2015 (EP) .................... 15184732

(51) Int. Cl.
| A61K 31/519 | (2006.01) |
| C07D 495/04 | (2006.01) |
| A61K 45/06 | (2006.01) |

(52) U.S. Cl.
CPC .......... *C07D 495/04* (2013.01); *A61K 31/519* (2013.01); *A61K 45/06* (2013.01)

(58) Field of Classification Search
None
See application file for complete search history.

(56) References Cited

U.S. PATENT DOCUMENTS

| 6,077,814 A | 6/2000 | Morita et al. |
| 6,140,325 A | 10/2000 | Furuya et al. |
| 2004/0122028 A1 | 6/2004 | Ingall et al. |

FOREIGN PATENT DOCUMENTS

| DE | 1900755 | 8/1970 |
| DE | 2036171 | 1/1972 |
| GB | 2363377 A | 12/2001 |
| WO | WO 98/54190 A1 | 12/1998 |
| WO | WO 00/06568 | 2/2000 |
| WO | WO 00/06569 | 2/2000 |
| WO | WO 00/12514 A1 | 3/2000 |
| WO | WO 00/61583 A1 | 10/2000 |
| WO | WO 01/19355 | 3/2001 |
| WO | WO 01/19776 | 3/2001 |
| WO | WO 01/19778 | 3/2001 |
| WO | WO 01/19780 | 3/2001 |
| WO | WO 02/42301 | 5/2002 |
| WO | WO 02/064598 A1 | 8/2002 |
| WO | WO 02/070462 | 9/2002 |
| WO | WO 02/070510 | 9/2002 |
| WO | WO 03/095451 | 11/2003 |
| WO | WO 2004/014916 A1 | 2/2004 |
| WO | WO 2006/029115 A2 | 3/2006 |
| WO | WO 2007/103776 A2 | 9/2007 |
| WO | WO 2008/070529 A2 | 6/2008 |
| WO | WO 2009/037468 A1 | 3/2009 |
| WO | WO 2011/147809 | 12/2011 |
| WO | WO 2012/004258 | 1/2012 |
| WO | WO 2012/028647 | 3/2012 |
| WO | WO 2012/037393 A1 | 3/2012 |
| WO | WO 2012/059549 | 5/2012 |
| WO | WO 2013/071169 A1 | 5/2013 |
| WO | WO 2014/182943 A1 | 11/2014 |
| WO | WO 2014/182950 A1 | 11/2014 |
| WO | WO 2015/052065 A1 | 4/2015 |

OTHER PUBLICATIONS

Aldrich P.E. , W.A. Sheppard, J. Org. Chem. 1964, 29 (1), 11-15.
Amatruda T. T. , D. A. Steele, V. Z. Slepak, M. I. Simon, Proc. Natl. Acad. Sci. USA 88, 5587-5591 (1991).
Barnes P. J. , N. Engl. J. Med. 343, 269-280 (2000).
Beck et al., Pneumologe 10, 105-111 (2013).
Behr et al., Eur. Respir. J. 31, 1357-1367 (2008).
Blanco I. et al., Am. J. Respir. Crit. Care Med. 2010, 181, 270-278.
Blay J. et al.,Cancer Res. 57 (13), 2602-2605 (1997).
Bovolenta S., M. Foti, S. Lohmer, S. Corazza, J Biomol. Screen. 12, 694-704 (2007).
Cavarra et al., Am. J. Physiol. Lung Cell. Mol. Physiol. 287, L1186-L1192 (2004).
Cekic C. et al., J. Immunol. 188 (1), 198-205 (2012).
Cowan et al., Nature Med. 6, 698-702 (2000).
Csoka B. et al., FASEB J. 26 (1), 376-386 (2012).

(Continued)

*Primary Examiner* — Samantha L Shterengarts
(74) *Attorney, Agent, or Firm* — McBee Moore Woodward & Vanik IP, LLC

(57) ABSTRACT

The present application relates to novel thieno[2,3-d]pyrimidine-2,4-dione ("thienouracil") derivatives bearing a particular type of (azaheterocyclyl)methyl substituent, to processes for the preparation thereof, to the use thereof alone or in combinations for treatment and/or prevention of diseases and to the use thereof for production of medicaments for treatment and/or prevention of diseases, especially for treatment and/or prevention of pulmonary and cardiovascular disorders and of cancer.

17 Claims, No Drawings

(56) References Cited

OTHER PUBLICATIONS

De Luca L., A. Porcheddu, G. Giacomelli, I. Murgia, Synlett 2010 (16), 2439-2442.
Desmet C. J. et al., Proc. Natl. Acad. Sci. USA 110 (13), 5139-5144 (2013).
Estenne et al., Am. J. Respir. Crit. Care Med. 166, 440-444 (2002).
Findeisen K. et al., Synthesis 1972, 599-605.
Gessi S. et al., Biochim. Biophys. Acta Biomembranes 1808 (5), 1400-1412 (2011).
Ghofrani et al., Herz 2005, 30, 296-302.
Giaid et al., N. Engl. J. Med. 329, 1967-1968 (1993).
Greene T.W. and P.G.M. Wuts, Protective Groups in Organic Synthesis, Wiley, New York, 1999.
Häusler S. F. M. et al., Cancer Immunol. Immunother. 60 (10), 1405-1418 (2011).
Hay et al., Arch. 65, 81-94 (1991).
Hill S. J., J. G. Baker, S. Rhees, Curr. Opin. Pharmacol. 1, 526-532 (2001).
Hirota K. et al., J. Heterocycl. Chem. 27 (3), 717-721 (1990).
Hoeper et al., J. Am. Coll. Cardiol., 2009, 54 (1), Suppl. S, p. 85-p. 96.
Hughes D. L., Org. Prep. Proced. Int. 28 (2), 127 (1996).
Hughes D. L., Org. Reactions 42, 335 (1992).
Humbert M. et al., J. Am. Coll. Cardiol. 2004, 43, 13S-24S.
Ito T. et al., Curr. Med. Chem. 2007, 14, 719-733.
Jacobson, K. A. et al., Neuropharmacology 36: 1157-1165 (1997).
Jin D. et al., Cancer Res. 70 (6), 2245-2255 (2010).
Kaji W. et al., J. Toxicol. Sci. 39 (2), 191-198 (2014).
Karmouty-Quintana et al., Am. J. Respir. Cell. Mol. Biol., publ. online, Jul. 15, 2013.
Karmouty-Quintana et al., Faseb J. 26, 2546-2557 (2012).
Kim S. J. et al., Eur. J. Med. Chem. 2007, 42 (9), 1176-1183.
Lazo et al., Cancer Chemother. 15, 44-50 (1994).
Lettieri et al., Chest 129, 746-752 (2006).
Levine et al., Jrnl. Am. Chem. Soc., 2014, 136, 7132-7139.
Ley et al., Am. J. Respir. Crit. Care Med. 183, 431-440-2011.
Linden et al., Mol. Pharmacol. 56: 705-713 (1999).
Luthin, D. R. et al., Mol. Pharmacol. 47: 5 307-313 (1995).
Ma D.-F. et al., Hum. Pathol. 41 (11), 1550-1557 (2010).
McKibben B. P. et al., Tetrahedron Lett. 40, 5471-5474 (1999).
Merighi S. et al., Mol. Pharmacol. 72 (2), 395-406 (2007).
Merighi S. et al., Neoplasia 11 (10), 1064-1073 (2009).
Montani D. and G. Simonneau, in: A. J. Peacock et al. (Eds.), Pulmonary Circulation. Diseases and their treatment, 3rd edition, Hodder Arnold Publ., 2011, p. 197-206.
Naeije, in: A. J. Peacock et al. (Eds.), Pulmonary Circulation. Diseases and their treatment, 3rd edition, Hodder Arnold Publ., 2011, S. 3.
Novitskiy S. V. et al., Blood 112 (5), 1822-1831 (2008).
Ntantie E. et al., Sci. Signal. 6 (277), ra39 (2013).
Oka et al., Circ. Res. 100, 923-929 (2007).
Rosenzweig E. B., Expert Opin. Emerging Drugs 2006, 11, 609-619.
Rückert et al., J. Immunol. 174, 5507-5515 (2005).
Ryzhov S. et al., J. Immunol. 187 (11), 6120-6129 (2011).
Ryzhov S. et al., Neoplasia 10 (9), 987-995 (2008).
Salvatore, C. A. et al., Proc. Natl. Acad. Sci. U.S.A.90: 10365-10369 (1993).
Sawada et al., Exp. Lung Res. 33, 277-288 (2007).
Schulte G., B. B. Fredholm, Cell Signal. 15 (9), 813-827 -2003.
Selmann et al., PLoS One 2, e482 (2007).
Shimbori et al., Exp. Lung Res. 36, 292-301 (2010).
Spychala J., Pharmacol. Ther. 87 (2-3), 161-173 (2000).
Stagg J. et al., Proc. Natl. Acad. Sci. USA 107 (4), 1547-1552 (2010).
Stehle, J. H. et al., Mol. Endocrinol. 6: 384-393 (1992).
Steiner et al., Circ. Res. 104, 236-244 (2009).
Stolz D. et al., Eur. Respir. J. 2008, 32, 619-628.
Stricter et al., Chest 136, 1364-1370 (2009).
Sun et al., J. Clin. Invest. 116, 2173-2182 (2006).
Tanaka K et al., Chem. Pharm. Bull. 35 (4), 1397-1404 (1987).
Toldo et al., J. Pharmacol. Exp. Ther. 343, 587-595 (2012).
Townsend-Nicholson, A. and Schofield, P. R., J. Biol. Chem. 269: 2373-2376 (1994).
Wie Q. et al., Purinergic Signal. 9 (2), 271-280 (2013).
Yang M. et al., Immunol. Cell Biol. 88 (2), 165-171 (2010).
Yokoe I. et al., Chem. Pharm. Bull. 42 (8), 1697-1699 (1994).
Zhong et al., Am. J. Respir. Cell. Mol. Biol. 32, 2-8 (2005).
Zhou et al., PLoS One 5, e9224 (2010).
Zmitek J. et al., Org. Prep. Proc. Int. 23 (6), 721-728 (1991).
International Search Report dated Mar. 21, 2016 in a corresponding International Application No. PCT/EP2016/056106 (12 pages).

HETEROCYCLYLMETHYL-THIENOURACILE AS ANTAGONISTS OF THE ADENOSINE-A2B-RECEPTOR

This application is the U.S. national phase of International Application No. PCT/EP2016/056106 filed Mar. 21, 2016 which designated the U.S. and claims priority to EP Patent Application No. 15161165.4 filed Mar. 26, 2015, EP Patent Application No. 15174566.8 filed Jun. 30, 2015 and EP Patent Application No. 15184732.4 filed Sep. 10, 2015, the entire contents of each of which are hereby incorporated by reference.

The present application relates to novel thieno[2,3-d]pyrimidine-2,4-dione ("thienouracil") derivatives bearing a particular type of (azaheterocyclyl)methyl substituent, to processes for the preparation thereof, to the use thereof alone or in combinations for treatment and/or prevention of diseases and to the use thereof for production of medicaments for treatment and/or prevention of diseases, especially for treatment and/or prevention of pulmonary and cardiovascular disorders and of cancer.

The endogenous purine nucleoside adenosine is formed ubiquitously and modulates, as important signal molecule, a large number of physiological and pathophysiological processes. Most of it is formed during the intra- and extracellular degradation of adenine nucleotides, and a smaller amount is formed during the intracellular hydrolysis of S-adenosyl homocysteine. Under physiological conditions, extracellular adenosine can be re-phosphorylated by adenosine kinase to adenosine monophosphate (AMP) or rearranged by adenosine deaminase to inosine. The extracellular concentration is between 30 and 300 nM. As a result of tissue damage caused, for example, by hypoxia, in inflammation reaction and during oxidative stress, there is an increased formation and accumulation of adenosine, such that the extracellular concentration may increase to up to 15 µM.

The biological actions of adenosine are mediated via G-protein-coupled receptors located at the plasma membrane. Currently, four adenosine receptor subtypes have been demonstrated: A1 adenosine receptor (A1R), A2a adenosine receptor (A2aR), A2b adenosine receptor (A2bR) and A3 adenosine receptor (A3R). From among the adenosine receptors mentioned above, the A2b receptor has the weakest affinity for adenosine. For this reason, in contrast to the other adenosine receptors, it is not activated under normal physiological conditions. A1 and A3 receptors are coupled to Gi proteins which inhibit adenylate cyclase, whereas A2a and A2b receptors, via Gs proteins, stimulate adenylate cyclase, thus causing an intracellular increase of cAMP. Via Gq proteins, both the A1, the A3 and the A2b receptor activate phospholipase C which cleaves membrane-bound phosphatidylinositol-4,5-bisphosphate into inositol-1,4,5-triphosphate and diacylglycerol. This in turn leads to an increase of the intracellular calcium concentration and activation of further target proteins such as protein kinase C and the MAP kinases.

A2b receptors are expressed on pulmonary epithelial and smooth muscle cells, vascular endothelial and smooth muscle cells, fibroblasts and also inflammatory cells. Expression of the A2b receptor at the cell surface is a dynamic process and is greatly enhanced, for example, by hypoxia, inflammatory factors and free radicals. The adenosine-activated A2b receptors lead to formation and release of pro-inflammatory and pro-fibrotic cytokines such as, for example, IL-6, IL-4 and IL-8. Studies have shown that the A2b receptor plays an important role at the chronic stage of pulmonary disorders during tissue remodelling and promotes inter alia differentiation of fibroblasts in myofibroblasts, resulting in enhanced synthesis and deposition of collagen.

In pulmonary tissue samples of patients suffering from idiopathic pulmonary fibrosis, COPD and pulmonary hypertension associated with COPD [Zhou et al., *PLoS One* 5, e9224 (2010); Selmann et al., *PLoS One* 2, e482 (2007)] and various animal models of fibro-proliferative pulmonary disorders [Karmouty-Quintana et al., *Am. J. Respir. Cell. Mol. Biol.*, publ. online, 15. July 2013; Karmouty-Quintana et al., *Faseb J.* 26, 2546-2557 (2012); Sun et al., *J. Clin. Invest.* 116, 2173-2182 (2006)], it was possible to detect an increased expression of the A2b receptor. In the animal model of bleomycin-induced pulmonary fibrosis and pulmonary hypertension in the mouse, a genetic knock-out of the A2b receptor resulted both in inhibition of the progression of pulmonary fibrosis and pulmonary vascular remodeling and the resulting pulmonary hypertension [Karmouty-Quintana et al., *Faseb J.* 26, 2546-2557 (2012)]. It is assumed that the release of inter alia endothelin-1 (ET-1) and interleukin-6 (IL-6) from vascular cells, which is modulated by the A2b receptor, plays a role during the development of pulmonary hypertension associated with pulmonary fibrosis. Stimulation of human pulmonary arterial endothelial and smooth muscle cells with 5'-(N-ethylcarboxamido)adenosine (NECA), an adenosine analogue, results in the release of ET-1 and IL-6, which can be prevented by A2b receptor inhibition [Karmouty-Quintana et al., *Faseb J.* 26, 2546-2557 (2012)]. Elevated endothelin-1- and IL-6 concentrations were found in lung tissue and serum of patients suffering from pulmonary hypertension [Giaid et al., *N. Engl. J. Med.* 329, 1967-1968 (1993); Steiner et al., *Circ. Res.* 104, 236-244 (2009)]. Furthermore, it is assumed that the A2b receptor-mediated release of inter alia IL-6 and other profibrotic mediators and stimulation of the differentiation of fibroblasts in myofibroblasts in the lung leads to induction of fibrosis. Stimulation of human fibroblasts with NECA leads to the release of IL-6 which is increased by hypoxia and can be prevented by inhibiting the A2b receptor. It was possible to demonstrate an increased IL-6 expression in patients suffering from idiopathic pulmonary fibrosis and in animal models of pulmonary fibrosis [Zhong et al., *Am. J. Respir. Cell. Mol. Biol.* 32, 2-8 (2005); Cavarra et al., *Am. J. Physiol. Lung Cell. Mol. Physiol.* 287, L1186-L1192 (2004)].

The A2b receptor also plays an important role in tissue remodelling after myocardial infarction. In the animal model of the permanent ligature of the coronary artery in the mouse, inhibition of the A2b receptor resulted in a reduction of caspase-1 activity and the invasion of inflammatory cells in heart tissue and the cytokines and adhesion molecules in plasma and in an improvement of systolic and diastolic heart function [Toldo et al., *J. Pharmacol. Exp. Ther.* 343, 587-595 (2012)].

In tumours and surrounding tissue, the local adenosine concentration is frequently greatly elevated as a result of the occurrence of hypoxia, as a result of necrotic processes or else because of genetic and epigenetic changes in tumour cells which lead to elevated extracellular production of adenosine with simultaneously reduced degradation and reduced cellular uptake of adenosine [J. Blay et al., *Cancer Res.* 57 (13), 2602-2605 (1997); G. Schulte, B. B. Fredholm, *Cell Signal.* 15 (9), 813-827 (2003)]. This leads to activation of the above-described adenosine receptors in tumour cells, tumour-associated cells and cells in the tissue surrounding the tumour. The signalling chains initiated as a result trigger various kinds of processes, the majority of which promote tumour growth and the spread thereof to other sites in the organism. For that reason, the inhibition of the adenosine signalling pathways constitutes a valuable strategy for treatment of cancer. For example, the inhibition of the A2b receptor-mediated adenosine signalling pathway with the A2b receptor antagonist MRS1754 leads to reduced growth of colon cancer cell lines [D.-F. Ma et al., *Hum. Pathol.* 41 (11), 1550-1557 (2010)]. The A2b receptor antagonist PSB603 reduces the growth of several prostate cancer cell lines [Q. Wei et al., *Purinergic Signal.* 9 (2), 271-280 (2013)].

The influence of adenosine on tumour metastases appears to be greater than the direct influence on the proliferation of tumour cells. This involves A2b receptor-mediated adenosine signalling chains in particular, and the blockage of the A2b receptor—both genetically and pharmacologically with A2b receptor antagonists—leads to reduced migration of tumour cells in vitro and reduced formation of metastases in animal models [J. Stagg et al., *Proc. Natl. Acad. Sci. USA* 107 (4), 1547-1552 (2010); C. J. Desmet et al., *Proc. Natl. Acad. Sci. USA* 110 (13), 5139-5144 (2013); E. Ntantie et al., *Sci. Signal.* 6 (277), ra39 (2013)].

Adenosine also affects the tumour-associated vascular endothelium: A2b receptor-mediated adenosine signalling chains lead to release of pro-angiogenic factors from various human tumour cell lines, but also from tumour-associated immune cells, and thus stimulate neovascularization, which promotes tumour growth [S. Ryzhov et al., *Neoplasia* 10 (9), 987-995 (2008); S. Merighi et al., *Mol. Pharmacol.* 72 (2), 395-406 (2007); S. Merighi et al., *Neoplasia* 11 (10), 1064-1073 (2009)].

There is increasingly better understanding of the importance of the immune system in suppression of tumour development, tumour growth and metastasis. It is found in this context that adenosine is capable of reducing the immune reaction [S. Gessi et al., *Biochim. Biophys. Acta Biomembranes* 1808 (5), 1400-1412 (2011); J. Stagg et al., *Proc. Natl. Acad. Sci. USA* 107 (4), 1547-1552 (2010); D. Jin et al., *Cancer Res.* 70 (6), 2245-2255 (2010); S. F. M. Häiusler et al., *Cancer Immunol. Immunother.* 60 (10), 1405-1418 (2011); J. Spychala, *Pharmacol. Ther.* 87 (2-3), 161-173 (2000)]. The inhibition of the A2b receptor-mediated adenosine signalling pathway with the A2b receptor antagonist PSB603, in contrast, leads to a reduction in tumour growth and metastasis in melanoma animal models, which is attributed to inhibition of tumour-induced suppression of the immune system [W. Kaji et al., *J. Toxicol. Sci.* 39 (2), 191-198 (2014)]. This improvement is caused by a reduction in the proportion of regulatory T cells, which reduce the immune response, in the overall immune cell infiltrate in the presence of the A2b receptor antagonist. At the same time, the populations of cytotoxic CD8+ T cells and CD4+ T helper cells are increased. Furthermore, immunosuppressant effects of adenosine on further cells in the immune system have been described (M1 and M2 macrophages, dendritic cells, myeloid suppressor cells), some of which are mediated by the A2b receptor [B. Csoka et al., *FASEB J.* 26 (1), 376-386 (2012); S. V. Novitskiy et al., *Blood* 112 (5), 1822-1831 (2008); M. Yang et al., *Immunol. Cell Biol.* 88 (2), 165-171 (2010); S. Ryzhov et al., *J. Immunol.* 187 (11), 6120-6129 (2011)]. In animal models of bladder tumours and breast tumours, the A2b receptor antagonist ATL801 brings about slowing of tumour growth and a distinct reduction in metastasis [C. Cekic et al., *J. Immunol.* 188 (1), 198-205 (2012)]. These effects are accompanied by an ATL801-induced increase in the number of tumour antigen-presenting dendritic cells and a significant increase in the interferon γ level and, as a result, elevated concentrations of chemokine CXCL10, which in turn leads to activation of CXCR3+ T cells and ultimately to improved immune defence against tumour growth and metastasis.

It is therefore assumed that the A2b receptor plays an important role in many disorders, injuries and pathological changes whose aetiology and/or progression is associated with inflammatory events and/or proliferative and fibroproliferative tissue and vessel remodelling. These can be in particular disorders of and/or damage to the lung, the cardiovascular system or the kidney, or it can be a blood disorder, a neoplastic disease or other inflammatory disorders.

Disorders of and damage to the lung which may be mentioned in this context are in particular idiopathic pulmonary fibrosis, pulmonary hypertension, bronchiolitis obliterans syndrome (BOS), chronic-obstructive pulmonary disease (COPD), asthma and cystic fibrosis. Disorders of and damage to the cardiovascular system in which the A2b receptor is involved are, for example, tissue changes following myocardial infarction and associated with heart failure. Renal disorders are, for example, renal insufficiency and kidney failure. A blood disorder is, for example, sickle cell anaemia. Examples of tissue degradation and remodelling during neoplastic processes are the invasion of cancer cells into healthy tissue (formation of metastases) and neovascularization (neoangiogenesis). Another inflammatory disease where the A2b receptor is involved is, for example, multiple sclerosis.

Idiopathic fibrosis of the lung or idiopathic pulmonary fibrosis (IPF) is a progressive lung disease which, left untreated, results in death on average within 2.5 to 3.5 years after diagnosis. At the time of diagnosis, the patients are in most cases more than 60 years old, men being slightly more frequently affected than women. Onset of IPF is insidious and characterized by increasing shortness of breath and dry tickly cough. IPF belongs to the group of idiopathic interstitial pneumonias (IIP), a heterogeneous group of pulmonary disorders characterized by fibrosis and inflammation of varying severity which can be distinguished using clinical, imaging and fine tissue criteria. Within this group, idiopathic pulmonary fibrosis is of particular significance owing to its frequency and aggressive progression [Ley et al., *Am. J. Respir. Crit. Care Med.* 183, 431-440 (2011)]. IPF may either occur sporadically or be hereditary. As yet, the causes are unknown. However, in recent years there have been numerous indications that chronic damage of the alveolar epithelium leads to the release of profibrotic cytokines/ mediators followed by increased fibroblast proliferation and increased collagen fibre formation, resulting in a patchy fibrosis and the typical honeycomb structure of the lung [Strieter et al., *Chest* 136, 1364-1370 (2009)]. The clinical sequelae of fibrotization are a decrease in the elasticity of the pulmonary tissue, a reduced diffusing capacity and the development of severe hypoxia. With regard to lung function, a corresponding worsening of the forced vital capacity (FVC) and the diffusing capacity (DLCO) can be detected. Essential and prognostically important comorbidities of IPF are acute exacerbation and pulmonal hypertension [Beck et al., *Pneumologe* 10, 105-111 (2013)]. The prevalence of pulmonary hypertension in interstitial pulmonary disorders is 10-40% [Lettieri et al., *Chest* 129, 746-752 (2006); Behr et al., *Eur. Respir. J.* 31, 1357-1367 (2008)]. Currently, there is no curative treatment for IPF—except for lung transplantation.

Pulmonary hypertension (PH) is a progressive lung disease which, left untreated, results in death on average within 2.8 years after diagnosis. By definition, the mean pulmonary aterial pressure (mPAP) in case of chronic pulmonary hypertension is >25 mmHg at rest or >30 mmHg during exertion (normal value <20 mmHg). The pathophysiology of pulmonary hypertension is characterized by vasoconstriction and remodelling of the pulmonary vessels. In chronic PH, there is a neomuscularization of primarily unmuscularized lung vessels, and the circumference of the vascular musculature of the vessels already muscularized increases. This increasing obliteration of the pulmonary circulation results in progressive stress on the right heart, which leads to a reduced output from the right heart and eventually ends in right heart failure [M. Humbert et al., *J. Am. Coll. Cardiol.* 2004, 43, 13S-24S]. Idiopathic (or primary) pulmonary arterial hypertension (IPAH) is a very rare disorder, whereas secondary pulmonary hypertension (non-PAH PH, NPAHPH) is very common, and it is thought that the latter is currently the third most common group of cardiovascular disorders after coronary heart disease and systemic hypertension [Naeije, in: A. J. Peacock et al. (Eds.), *Pulmonary Circulation. Diseases and their treatment,* 3$^{rd}$ edition, Hodder Arnold Publ., 2011, S. 3]. Since 2008, pulmonary hypertension is classified in accordance with the Dana Point classification into various sub-groups according to the respective aetiology [D. Montana and G. Simonneau, in: A. J. Peacock et al. (Eds.), *Pulmonary Circulation. Diseases and their treatment,* 3$^{rd}$ edition, Hodder Arnold Publ., 2011, p. 197-206].

Despite all the advances in the therapy of PH there is as yet no prospect of cure of this serious disorder. Standard therapies available on the market (for example prostacyclin analogues, endothelin receptor antagonists, phosphodiesterase inhibitors) are able to improve the quality of life, the exercise tolerance and the prognosis of the patients. These are therapeutic principles which are administered systemically and act primarily haemodynamically by modulating vessel tone. The applicability of these medicaments is limited owing to side effects, some of which are serious, and/or complicated administration forms. The period over which the clinical situation of the patients can be improved or stabilized by specific monotherapy is limited (for example owing to the development of tolerance). Eventually the therapy escalates and thus a combination therapy is applied, where a plurality of medicaments must be given concurrently. Currently, these standard therapeutics are approved only for the treatment of pulmonary arterial hypertension (PAH). In the case of secondary forms of PH such as PH-COPD, these therapeutic principles (for example sildenafil, bosentan) fail in clinical studies since, as a result of non-selective vasodilatation, they lead to a reduction (de-saturation) of the arterial oxygen content in the patients. The probable reason for this is an unfavourable effect on the ventilation-perfusion adaptation in the lung in heterogeneous lung disorders owing to the systemic administration of non-selective vasodilatators [I. Blanco et al., *Am. J. Respir. Crit. Care Med.* 2010, 181, 270-278; D. Stolz et al., *Eur. Respir. J.* 2008, 32, 619-628].

Novel combination therapies are one of the most promising future therapeutic options for the treatment of pulmonary hypertension. In this connection, the finding of novel pharmacological mechanisms for the treatment of PH is of particular interest [Ghofrani et al., *Herz* 2005, 30, 296-302; E. B. Rosenzweig, *Expert Opin. Emerging Drugs* 2006, 11, 609-619; T. Ito et al., *Curr. Med. Chem.* 2007, 14, 719-733]. In particular novel therapeutic approaches which can be combined with the therapy concepts already on the market may form the basis of a more efficient treatment and thus be of great advantage for the patients.

In the context of the present invention, the term "pulmonary hypertension" includes both primary and secondary sub-forms (NPAHPH) as defined according to the Dana Point classification in accordance with their respective aetiology [D. Montana and G. Simonneau, in: A. J. Peacock et al. (Eds.), *Pulmonary Circulation. Diseases and their treatment,* 3' edition, Hodder Arnold Publ., 2011, pp. 197-206; Hoeper et al., *J. Am. Coll. Cardiol.,* 2009, 54 (1), Suppl. S, p 85-p 96]. These include in particular in group 1 pulmonary arterial hypertension (PAH), which, among others, embraces the idiopathic and the familial forms (IPAH and FPAH, respectively). Furthermore, PAH also embraces persistent pulmonary hypertension of the newborn and the associated pulmonary arterial hypertension (APAH) associated with collagenoses, congenital systemic pulmonary shunt lesions, portal hypertension, HIV infections, the intake of certain drugs and medicaments (for example of appetite suppressants), with disorders having a significant venous/capillary component such as pulmonary venoocclusive disorder and pulmonary capillary haemangiomatosis, or with other disorders such as disorders of the thyroid, glycogen storage diseases, Gaucher disease, hereditary teleangiectasia, haemoglobinopathies, myeloproliferative disorders and splenectomy. Group 2 of the Dana Point classification comprises PH patients having a causative left heart disorder, such as ventricular, atrial or valvular disorders. Group 3 comprises forms of pulmonary hypertension associated with a lung disorder, for example with chronic obstructive lung disease (COPD), interstitial lung disease (ILD), pulmonary fibrosis (IPF), and/or hypoxaemia (e.g. sleep apnoe syndrome, alveolar hypoventilation, chronic high-altitude sickness, hereditary deformities). Group 4 includes PH patients having chronic thrombotic and/or embolic disorders, for example in the case of thromboembolic obstruction of proximal and distal pulmonary arteries (CTEPH) or non-thrombotic embolisms (e.g. as a result of tumour disorders, parasites, foreign bodies). Less common forms of pulmonary hypertension, such as in patients suffering from sarcoidosis, histiocytosis X or lymphangiomatosis, are summarized in group 5.

Bronchiolitis obliterans syndrome (BOS) is a chronic rejection reaction after a lung transplant. Within the first five years after a lung transplant about 50-60% of all patients are affected, and within the first nine years more than 90% of patients [Estenne et al., *Am. J. Respir. Crit. Care Med.* 166, 440-444 (2003)]. The cause of the disease has not been elucidated. In spite of numerous improvements in the treatment of transplantation patients, the number of BOS cases has hardly changed over the last years. BOS is the most important long-term complication in lung transplantations and is considered to be the main reason for the fact that survival rates are still markedly below those for other organ transplantations. BOS is an inflammatory event which is associated with changes in the lung tissue affecting primarily the small respiratory passages. Damage and inflammatory changes of the epithelial cells and the subepithelial structures of the smaller respiratory passages lead, owing to ineffective regeneration of the epithelium and aberrant tissue repair, to excessive fibroproliferation. There is scarring and finally destruction of the bronchi and also clots of granulation tissue in the small respiratory passages and alveolae, occasionally with vascular involvement. The diagnosis is based on the lung function. In BOS, there is a worsening of the FEV1 compared to the average of the two best values measured postoperatively. Currently, there is no curative treatment of BOS. Some of the patients show improvements under intensified immunosuppression; patients not showing any response experience persistent deterioration, such that retransplantation is indicated.

Chronic obstructive pulmonary disease (COPD) is a slowly progressing pulmonary disease characterized by an obstruction of respiratory flow which is caused by pulmonary emphysema and/or chronic bronchitis. The first symptoms of the disease generally manifest themselves during the fourth or fifth decade of life. In the subsequent years of life, shortness of breath frequently becomes worse, and there are instances of coughing combined with copious and purulent sputum, and stenotic respiration extending as far as breathlessness (dyspnoea). COPD is primarily a smokers' disease: smoking is the cause of 90% of all cases of COPD and of 80-90% of all COPD-related deaths. COPD is a big medical problem and constitutes the sixth most frequent cause of death worldwide. Of people over the age of 45, about 4-6% are affected. Although the obstruction of the respiratory flow may only be partial and temporal, COPD cannot be cured. Accordingly, the aim of the treatment is to improve the quality of life, to alleviate the symptoms, to prevent acute worsening and to slow the progressive impairment of lung function. Existing pharmacotherapies, which have hardly changed over the last two or three decades, are the use of bronchodilators to open blocked respiratory passages, and in certain situations corticosteroids to control the inflammation of the lung [P. J. Barnes, *N. Engl. J. Med.* 343, 269-280 (2000)]. The chronic inflammation of the lung, caused by cigarette smoke or other irritants, is the driving force of the development of the disease. The basic mechanism comprises immune cells which, during the inflammatory reaction of the lung, release proteases and various cytokines which cause pulmonary emphysema and remodelling of the bronchi.

It is therefore an object of the present invention to provide novel substances which act as potent and selective antagonists of the adenosine A2b receptor and are suitable as such for treatment and/or prevention in particular of pulmonary and cardiovascular disorders and of cancer.

WO 2009/037468-A1 discloses 2-aminothieno[3,2-d]pyrimidine-4-carboxamides as adenosine A2b antagonists for treatment of asthma, COPD, diabetes and cancer. Antagonists of the adenosine A2a receptor that are especially suitable for treatment of CNS and addiction disorders are 6-heteroaryl-substituted thieno[2,3-d]pyrimidine-2,4-diones described in WO 2007/103776-A2, and 6-styryl-substituted thieno[2,3-d]pyrimidine-2,4-diones described in WO 2008/070529-A2. WO 98/54190-A1, WO 00/12514-A1, GB 2 363 377-A and US 2004/0122028-A1 disclose various thieno[2,3-d]pyrimidine-2,4-diones which can be used, inter alia, for treatment of inflammatory and proliferative disorders. U.S. Pat. No. 6,140,325 discloses carboxylate-substituted thieno[2,3-d]pyrimidine-2,4-diones as endothelin receptor antagonists. WO 00/61583-A1 claims xanthine analogues suitable for treatment of inflammatory, neurodegenerative and autoimmune disorders. WO 02/064598-A1 and WO 2004/014916-A1 describe bicyclic pyrimidinediones as inhibitors of matrix metalloproteinases (MMPs), especially of MMP-13. WO 2013/071169-A1, WO 2014/182943-A1 and WO 2014/182950-A1 recently disclosed thieno[2,3-d]pyrimidine-2,4-diones as ACC inhibitors for treatment of infections and metabolic disorders.

The present invention provides compounds of the general formula (I)

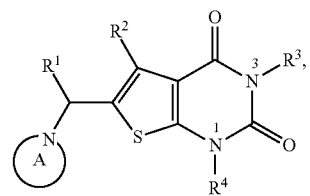

in which
the ring A is an azaheterocycle of the formula

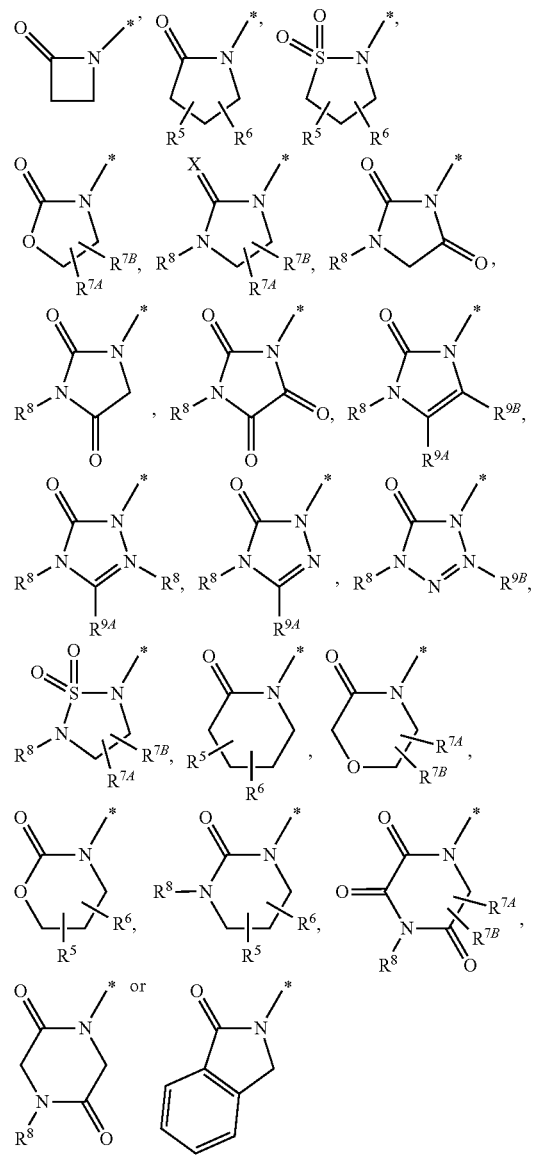

in which * marks the bond to the adjoining $CH(R^1)$ group,
$R^5$ is hydrogen, $(C_1\text{-}C_4)$-alkyl, hydroxyl, $(C_1\text{-}C_4)$-alkoxy, amino, $(C_1\text{-}C_5)$-alkanoylamino or $(C_1\text{-}C_4)$-alkoxycarbonylamino,
$R^6$ is hydrogen, methyl or ethyl,
$R^{7A}$ and $R^{7B}$ are the same or different and are independently hydrogen or $(C_1\text{-}C_4)$-alkyl, $R^8$ is hydrogen, $(C_1-C_4)$-alkyl, $(C_2-C_4)$-alkenyl, $(C_1-C_5)$-alkanoyl or $(C_1-C_4)$-alkoxycarbonyl,
  where $(C_1-C_4)$-alkyl may be up to disubstituted by hydroxyl,
$R^{9A}$ and $R^{9B}$ are the same or different and are independently hydrogen or $(C_1-C_4)$-alkyl
and
X is O, $N(R^{10})$ or S, in which
  $R^{10}$ is hydrogen, cyano or $(C_1-C_4)$-alkoxycarbonyl,
$R^1$ is hydrogen or methyl,
$R^2$ is hydrogen, methyl or ethyl, where methyl and ethyl may be up to trisubstituted by fluorine,
$R^3$ is $(C_2-C_6)$-alkyl, $(C_2-C_6)$-alkenyl or $(C_2-C_6)$-alkynyl,
  where $(C_2-C_6)$-alkyl may be substituted by a radical selected from the group of hydroxyl, methoxy, ethoxy, trifluoromethoxy, cyclopropyl, cyclobutyl, oxetanyl and phenyl, and up to trisubstituted by fluorine,
  and
  $(C_2-C_6)$-alkenyl may be up to trisubstituted by fluorine,
    where the cyclopropyl and cyclobutyl groups mentioned may in turn be up to disubstituted, identically or differently, by a radical selected from fluorine and methyl,
or
$R^3$ is a group of the formula —$CH_2$—$R^{14}$ in which
  $R^{14}$ is cyclopropyl, cyclobutyl, oxetanyl or tetrahydrofuranyl,
    where cyclopropyl, cyclobutyl and oxetanyl may be up to disubstituted, identically or differently, by a radical selected from fluorine and methyl,
and
$R^4$ is $(C_1-C_6)$-alkyl or $(C_2-C_6)$-alkenyl,
  where $(C_1-C_6)$-alkyl may be up to pentasubstituted and $(C_2-C_6)$-alkenyl up to trisubstituted by fluorine
  and
  where one $CH_2$ group in $(C_1-C_6)$-alkyl may exchanged for —O—, —S— or —$S(O)_2$—, with the proviso that there are at least two carbon atoms between such a heteroatom and the uracil $N^1$ atom,
or
$R^4$ is a group of the formula —$(CH_2)_m$—CN, —$(CH_2)_n$—$R^{11}$ or —$(CH_2)_p$—$R^{12}$, in which
  m is the number 1, 2, 3 or 4,
  n is the number 2 or 3,
  p is the number 1 or 2,
  $R^{11}$ is dimethylamino, diethylamino or azetidino
  and
  $R^{12}$ is $(C_3-C_6)$-cycloalkyl, oxetanyl, tetrahydrofuranyl, tetrahydropyranyl or 5-membered azaheteroaryl,
    where $(C_3-C_6)$-cycloalkyl may be up to disubstituted, identically or differently, by a radical selected from fluorine and methyl
    and
    azaheteroaryl may be up to disubstituted, identically or differently, by a radical selected from methyl and trifluoromethyl,
or
$R^4$ is a group of the formula —$(CH_2)_2$—O—$R^{13}$ in which
  $R^{13}$ is $(C_3-C_6)$-cycloalkyl,
and the salts, solvates and solvates of the salts thereof.

Compounds of the invention are the compounds of the formula (I) and the salts, solvates and solvates of the salts thereof, the compounds of the formulae (I-1), (I-2), (I-3), (I-4), (I-4a), (I-5), (I-6), (I-7), (I-8), (I-9), (I-10), (I-11) and (I-12) below that are encompassed by formula (I) and the salts, solvates and solvates of the salts thereof, the compounds of the formula (I-A) below and the salts, solvates and solvates of the salts thereof, and the compounds cited hereinafter as working examples that are encompassed by the formulae (I) and (I-A) and the salts, solvates and solvates of the salts thereof, if the compounds cited hereinafter are not already salts, solvates and solvates of the salts.

Preferred salts in the context of the present invention are physiologically acceptable salts of the compounds of the invention. Also encompassed are salts which are not themselves suitable for pharmaceutical applications but can be used, for example, for the isolation, purification or storage of the compounds of the invention.

Physiologically acceptable salts of the compounds of the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, formic acid, acetic acid, trifluoroacetic acid, propionic acid, succinic acid, fumaric acid, maleic acid, lactic acid, tartaric acid, malic acid, citric acid, gluconic acid, benzoic acid and embonic acid.

Solvates in the context of the invention are described as those forms of the compounds of the invention which form a complex in the solid or liquid state by coordination with solvent molecules. Hydrates are a specific form of the solvates in which the coordination is with water. Solvates preferred in the context of the present invention are hydrates.

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatography processes are preferably used for this purpose, especially HPLC chromatography on an achiral or chiral phase.

If the compounds of the invention can occur in tautomeric forms, the present invention encompasses all the tautomeric forms.

In the context of the present invention, unless specified otherwise, the substituents and radicals are defined as follows:

$(C_1-C_6)$-Alkyl and $(C_1-C_4)$-alkyl in the context of the invention are a straight-chain or branched alkyl radical having, respectively, 1 to 6 and 1 to 4 carbon atoms. Preferred examples include: methyl, ethyl, n-propyl, isopropyl, n-butyl, isobutyl, sec-butyl, tert-butyl, n-pentyl, 2-pentyl, 3-pentyl, neopentyl, n-hexyl, 2-hexyl and 3-hexyl.

$(C_2-C_6)$-Alkyl, $(C_2-C_5)$-alkyl and $(C_2-C_4)$-alkyl in the context of the invention are a straight-chain or branched alkyl radical having, respectively, 2 to 6, 2 to 5 and 2 to 4 carbon atoms. Preferred examples include: ethyl, n-propyl, isopropyl, n-butyl, isobutyl, sec-butyl, tert-butyl, n-pentyl, 2-pentyl, 3-pentyl, neopentyl, n-hexyl, 2-hexyl and 3-hexyl.

$(C_2-C_6)$-Alkenyl and $(C_2-C_4)$-alkenyl in the context of the invention are a straight-chain or branched alkenyl radical having one double bond and, respectively, 2 to 6 and 2 to 4 carbon atoms. Preference is given to a straight-chain or branched alkenyl radical having 2 to 4 carbon atoms. Preferred examples include: vinyl, prop-1-en-1-yl, prop-2-en-1-yl (allyl), prop-1-en-2-yl (isopropenyl), 2-methylprop-2-en-1-yl, but-1-en-1-yl, but-1-en-2-yl, but-2-en-1-yl, but-2- en-2-yl, but-3-en-1-yl, pent-2-en-1-yl, pent-3-en-1-yl, pent-4-en-1-yl, 3-methylbut-2-en-1-yl and 4-methylpent-3-en-1-yl.

In the context of the invention, $(C_2-C_6)$-alkynyl is a straight-chain or branched alkynyl radical having one triple bond and 2 to 6 carbon atoms. Preference is given to a straight-chain or branched alkynyl radical having 2 to 4 carbon atoms [$(C_2-C_4)$-alkynyl]. Preferred examples include: ethinyl, prop-1-yn-1-yl, prop-2-yn-1-yl (propargyl), but-1-yn-1-yl, but-2-yn-1-yl, but-3-yn-1-yl and but-3-yn-2-yl.

$(C_3-C_6)$-Cycloalkyl in the context of the invention is a monocyclic saturated cycloalkyl group having 3 to 6 ring carbon atoms. Preferred examples include: cyclopropyl, cyclobutyl, cyclopentyl and cyclohexyl.

$(C_1-C_5)$-Alkanoyl in the context of the invention is a straight-chain or branched alkyl radical which has 1 to 5 carbon atoms and bears an oxo group in the 1 position and is joined via the 1 position. Preferred examples include: formyl, acetyl, propionyl (propanoyl), n-butyryl (n-butanoyl), isobutyryl (iso-butanoyl), valeryl (n-pentanoyl), isovaleryl (iso-pentanoyl) and pivaloyl (neo-pentanoyl).

$(C_1-C_5)$-Alkanoylamino in the context of the invention is an amino group having a straight-chain or branched alkanoyl substituent which has 1 to 5 carbon atoms and is bonded to the nitrogen atom via the carbonyl group. Preferred examples include: formylamino, acetylamino, propionylamino, n-butyrylamino, isobutyrylamino, valerylamino, isovalerylamino and pivaloylamino.

$(C_1-C_4)$-Alkoxy in the context of the invention is a straight-chain or branched alkoxy radical having 1 to 4 carbon atoms. Preferred examples include: methoxy, ethoxy, n-propoxy, isopropoxy, n-butoxy, isobutoxy, sec-butoxy and tert-butoxy.

$(C_1-C_4)$-Alkoxycarbonyl in the context of the invention is a straight-chain or branched alkoxy radical which has 1 to 4 carbon atoms and is joined via a carbonyl group [—C(=O)—] bonded to the oxygen atom. Preferred examples include: methoxycarbonyl, ethoxycarbonyl, n-propoxycarbonyl, isopropoxycarbonyl, n-butoxycarbonyl and tert-butoxycarbonyl.

$(C_1-C_4)$-Alkoxycarbonylamino in the context of the invention is an amino group having a straight-chain or branched alkoxycarbonyl substituent which has 1 to 4 carbon atoms in the alkoxy radical and is bonded to the nitrogen atom via the carbonyl group. Preferred examples include: methoxycarbonylamino, ethoxycarbonylamino, n-propoxycarbonylamino, isopropoxycarbonylamino, n-butoxycarbonylamino and tert-butoxycarbonylamino.

5-Membered azaheteroaryl in the definition of the $R^{12}$ radical is an aromatic heterocycle (heteroaromatic) which has a total of 5 ring atoms and contains one ring nitrogen atom and, in addition, may contain one or two further ring heteroatoms from the group of N, O and/or S and which is joined via a ring carbon atom or alternatively, if allowed by the valency, via a ring nitrogen atom. Examples include: pyrrolyl, pyrazolyl, imidazolyl, 1,2-oxazolyl, 1,3-oxazolyl, 1,2-thiazolyl, 1,3-thiazolyl, 1,2,3-triazolyl, 1,2,4-triazolyl, 1,2,4-oxadiazolyl, 1,2,5-oxadiazolyl, 1,3,4-oxadiazolyl and 1,3,4-thiadiazolyl. Preference is given to 1,2-oxazolyl, 1,3-oxazolyl, 1,2,4-oxadiazolyl, 1,2,5-oxadiazolyl and 1,3,4-oxadiazolyl.

An oxo group in the context of the invention is an oxygen atom attached to a carbon atom via a double bond.

In the context of the present invention, all radicals which occur more than once are defined independently of one another. When radicals in the compounds of the invention are substituted, the radicals may be mono- or polysubstituted, unless specified otherwise. Substitution by one substituent or by two identical or different substituents is preferred. Particular preference is given to substitution by one substituent.

Preference is given in the context of the present invention to compounds of the formula (I) in which
the ring A is an azaheterocycle of the formula

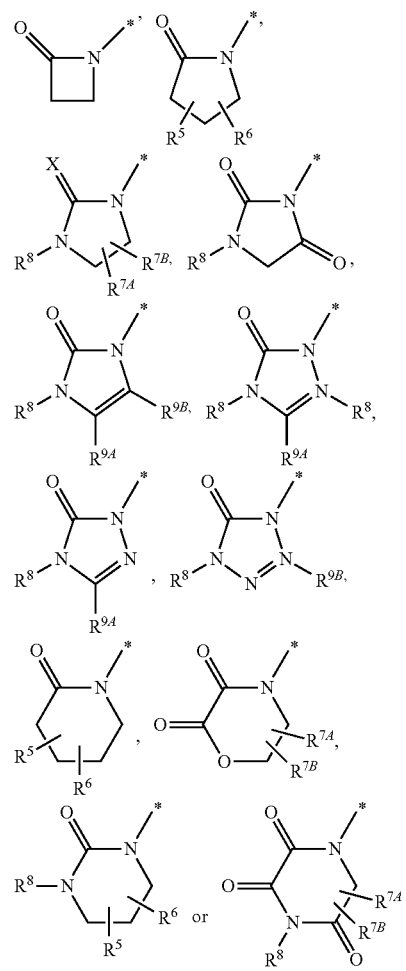

in which * marks the bond to the adjoining $CH(R^1)$ group,
$R^5$ is hydrogen, $(C_1-C_4)$-alkyl, hydroxyl, $(C_1-C_4)$-alkoxy, amino, $(C_1-C_5)$-alkanoylamino or $(C_1-C_4)$-alkoxycarbonylamino,
$R^6$ is hydrogen, methyl or ethyl,
$R^{7A}$ and $R^{7B}$ are the same or different and are independently hydrogen or $(C_1-C_4)$-alkyl,
$R^8$ is hydrogen, $(C_1-C_4)$-alkyl, $(C_2-C_4)$-alkenyl, $(C_1-C_5)$-alkanoyl or $(C_1-C_4)$-alkoxycarbonyl,
where $(C_1-C_4)$-alkyl may be up to disubstituted by hydroxyl,
$R^{9A}$ and $R^{9B}$ are the same or different and are independently hydrogen or $(C_1-C_4)$-alkyl
and
X is O, $N(R^{10})$ or S, in which
$R^{10}$ is hydrogen, cyano or $(C_1-C_4)$-alkoxycarbonyl,
$R^1$ is hydrogen,
$R^2$ is methyl or ethyl which may be up to trisubstituted by fluorine, $R^3$ is $(C_2-C_6)$-alkyl, $(C_2-C_6)$-alkenyl or $(C_2-C_6)$-alkynyl,
  where $(C_2-C_6)$-alkyl may be substituted by a radical selected from the group of hydroxyl, methoxy, ethoxy, trifluoromethoxy, cyclopropyl, cyclobutyl, oxetanyl and phenyl, and up to trisubstituted by fluorine,
  and
  $(C_2-C_6)$-alkenyl may be up to trisubstituted by fluorine,
    where the cyclopropyl and cyclobutyl groups mentioned may in turn be up to disubstituted, identically or differently, by a radical selected from fluorine and methyl,
or
$R^3$ is a group of the formula $—CH_2—R^{14}$ in which
  $R^{14}$ is cyclopropyl, cyclobutyl, oxetanyl or tetrahydrofuranyl,
    where cyclopropyl and cyclobutyl may be up to disubstituted, identically or differently, by a radical selected from fluorine and methyl,
and
$R^4$ is $(C_1-C_6)$-alkyl or $(C_2-C_6)$-alkenyl,
  where $(C_1-C_6)$-alkyl and $(C_2-C_6)$-alkenyl may be up to trisubstituted by fluorine
  and
  where one $CH_2$ group in $(C_1-C_6)$-alkyl may exchanged for $—O—$, $—S—$ or $—S(O)_2—$, with the proviso that there are at least two carbon atoms between such a heteroatom and the uracil $N^1$ atom,
or
$R^4$ is a group of the formula $—(CH_2)_m—CN$, $—(CH_2)_n—R^{11}$ or $—(CH_2)_p—R^{12}$, in which
  m is the number 1, 2, 3 or 4,
  n is the number 2 or 3,
  p is the number 1 or 2,
  $R^{11}$ is dimethylamino, diethylamino or azetidino
  and
  $R^{12}$ is $(C_3-C_6)$-cycloalkyl, oxetanyl, tetrahydrofuranyl, tetrahydropyranyl or 5-membered azaheteroaryl,
    where $(C_3-C_6)$-cycloalkyl may be up to disubstituted, identically or differently, by a radical selected from fluorine and methyl
    and
    azaheteroaryl may be up to disubstituted, identically or differently, by a radical selected from methyl and trifluoromethyl,
or
$R^4$ is a group of the formula $—(CH_2)_2—O—R^{13}$ in which
  $R^{13}$ is cyclopropyl or cyclobutyl,
and the salts, solvates and solvates of the salts thereof.

In the context of the present invention, particular preference is given to compounds of the formula (I) in which the ring A is an azaheterocycle of the formula

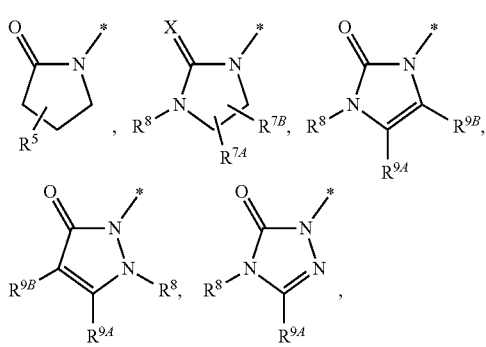

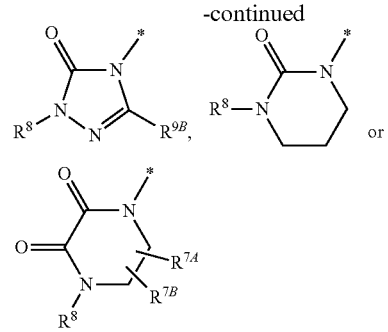

in which * marks the bond to the adjoining $CH(R^1)$ group,
$R^5$ is hydroxy, methoxy or ethoxy,
$R^{7A}$ and $R^{7B}$ are each independently hydrogen or methyl,
$R^8$ is hydrogen, methyl, ethyl, n-propyl, 2-hydroxyethyl, 3-hydroxypropyl, 2,3-dihydroxypropyl, allyl, formyl or acetyl,
$R^{9A}$ and $R^{9B}$ are each independently hydrogen or methyl
and
X is O, $N(R^{10})$ or S, in which
  $R^{10}$ is cyano or $(C_1-C_4)$-alkoxycarbonyl,
$R^1$ is hydrogen,
$R^2$ is methyl or ethyl which may be up to trisubstituted by fluorine,
$R^3$ is $(C_2-C_5)$-alkyl or $(C_2-C_4)$-alkenyl,
  where $(C_2-C_5)$-alkyl may be substituted by a radical selected from the group of hydroxyl, methoxy, cyclopropyl, cyclobutyl, oxetanyl and phenyl, and up to trisubstituted by fluorine,
  and
  $(C_2-C_4)$-alkenyl may be up to trisubstituted by fluorine,
    where the cyclopropyl and cyclobutyl groups mentioned may in turn be up to disubstituted by fluorine,
or
$R^3$ is a group of the formula $—CH_2—R^{14}$ in which
  $R^{14}$ is cyclopropyl, cyclobutyl or oxetanyl,
    where cyclopropyl and cyclobutyl may be up to disubstituted, identically or differently, by a radical selected from fluorine and methyl,
and
$R^4$ is $(C_1-C_6)$-alkyl or $(C_2-C_6)$-alkenyl,
  where $(C_1-C_6)$-alkyl and $(C_2-C_6)$-alkenyl may be up to trisubstituted by fluorine
  and
  where one $CH_2$ group in $(C_1-C_6)$-alkyl may be exchanged for $—O—$ or $—S—$, with the proviso that there are at least two carbon atoms between such a heteroatom and the uracil $N^1$ atom,
or
$R^4$ is the $—CH_2—R^{12}$ group in which
  $R^{12}$ is $(C_3-C_6)$-cycloalkyl, oxetanyl, tetrahydrofuranyl or tetrahydropyranyl,
    where $(C_3-C_6)$-cycloalkyl may be up to disubstituted, identically or differently, by a radical selected from fluorine and methyl,
and the salts, solvates and solvates of the salts thereof.

A particular embodiment of the present invention relates to compounds of the formula (I) in which the ring A is an azaheterocycle of the formula

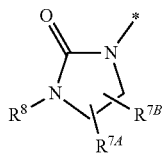

in which * marks the bond to the adjoining CH(R$^1$) group and
R$^{7A}$, R$^{7B}$ and R$^8$ are each independently hydrogen or methyl,
and the salts, solvates and solvates of the salts thereof.

A further particular embodiment of the present invention relates to compounds of the formula (I) in which
the ring A is an azaheterocycle of the formula

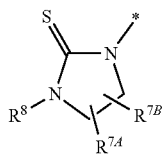

in which * marks the bond to the adjoining CH(R$^1$) group and
R$^{7A}$, R$^{7B}$ and R$^8$ are each independently hydrogen or methyl,
and the salts, solvates and solvates of the salts thereof.

A further particular embodiment of the present invention relates to compounds of the formula (I) in which
the ring A is an azaheterocycle of the formula

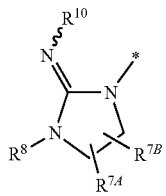

in which * marks the bond to the adjoining CH(R$^1$) group,
R$^{7A}$, R$^{7B}$ and R$^8$ are each independently hydrogen or methyl
and
R$^{10}$ is cyano, methoxycarbonyl, ethoxycarbonyl or tert-butoxycarbonyl,
and the salts, solvates and solvates of the salts thereof.

A further particular embodiment of the present invention relates to compounds of the formula (I) in which
the ring A is an azaheterocycle of the formula

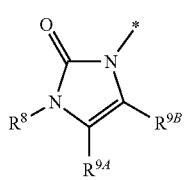

in which * marks the bond to the adjoining CH(R$^1$) group and
R$^8$, R$^{9A}$ and R$^{9B}$ are each independently hydrogen or methyl,
and the salts, solvates and solvates of the salts thereof.

A further particular embodiment of the present invention relates to compounds of the formula (I) in which
the ring A is an azaheterocycle of the formula

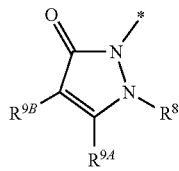

in which * marks the bond to the adjoining CH(R$^1$) group and
R$^8$, R$^{9A}$ and R$^{9B}$ are each independently hydrogen or methyl,
and the salts, solvates and solvates of the salts thereof.

A further particular embodiment of the present invention relates to compounds of the formula (I) in which
the ring A is an azaheterocycle of the formula

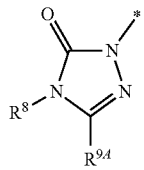

in which * marks the bond to the adjoining CH(R$^1$) group and
R$^8$ and R$^{9A}$ are each independently hydrogen or methyl,
and the salts, solvates and solvates of the salts thereof.

A further particular embodiment of the present invention relates to compounds of the formula (I) in which
the ring A is an azaheterocycle of the formula

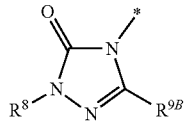

in which * marks the bond to the adjoining CH(R$^1$) group and
R$^8$ and R$^{9B}$ are each independently hydrogen or methyl,
and the salts, solvates and solvates of the salts thereof.

A further particular embodiment of the present invention relates to compounds of the formula (I) in which
the ring A is an azaheterocycle of the formula

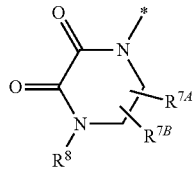

in which * marks the bond to the adjoining $CH(R^1)$ group
and
$R^{7A}$, $R^{7B}$ and $R^8$ are each independently hydrogen or methyl,
and the salts, solvates and solvates of the salts thereof.

A further particular embodiment of the present invention relates to compounds of the formula (I) in which
$R^1$ is hydrogen,
and the salts, solvates and solvates of the salts thereof.

A further particular embodiment of the present invention relates to compounds of the formula (I) in which
$R^2$ is methyl, difluoromethyl or trifluoromethyl,
and the salts, solvates and solvates of the salts thereof.

A further particular embodiment of the present invention relates to compounds of the formula (I) in which
$R^3$ is $(C_2\text{-}C_4)$-alkyl which may be substituted by hydroxyl, methoxy, cyclopropyl or oxetanyl or up to trisubstituted by fluorine,
and the salts, solvates and solvates of the salts thereof.

A further particular embodiment of the present invention relates to compounds of the formula (I) in which
$R^3$ is $(C_2\text{-}C_5)$-alkyl which may be substituted by hydroxyl, methoxy, cyclopropyl or oxetanyl or up to trisubstituted by fluorine,
where cyclopropyl may itself be up to disubstituted, identically or differently, by a radical selected from fluorine and methyl,
and the salts, solvates and solvates of the salts thereof.

A further particular embodiment of the present invention relates to compounds of the formula (I) in which
$R^3$ is a group of the formula $-CH_2-R^{14}$ in which
$R^{14}$ is cyclopropyl, cyclobutyl or oxetanyl,
where cyclopropyl and cyclobutyl may be up to disubstituted, identically or differently, by a radical selected from fluorine and methyl,
and the salts, solvates and solvates of the salts thereof.

A further particular embodiment of the present invention relates to compounds of the formula (I) in which
$R^4$ is $(C_1\text{-}C_4)$-alkyl which may be up to trisubstituted by fluorine, is 2-methoxyethyl or 2-ethoxyethyl or is the $-CH_2-R^{12}$ group in which
$R^{12}$ is cyclopropyl, cyclobutyl, oxetanyl, tetrahydrofuranyl or tetrahydropyranyl,
where cyclopropyl and cyclobutyl may be up to disubstituted by fluorine,
and the salts, solvates and solvates of the salts thereof.

Compounds of the formula (I) which are especially preferred in the context of the present invention are those in which
the ring A is an azaheterocycle of the formula

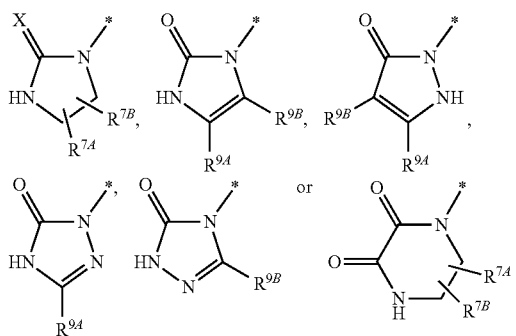

in which * marks the bond to the adjoining $CH(R^1)$ group,
$R^{7A}$ and $R^{7B}$ are each independently hydrogen or methyl,
$R^{9A}$ and $R^{9B}$ are each independently hydrogen or methyl
and
X is O, $N(R^{10})$ or S, in which
$R^{10}$ is cyano, methoxycarbonyl, ethoxycarbonyl or tert-butoxycarbonyl,
$R^1$ is hydrogen,
$R^2$ is methyl, difluoromethyl or trifluoromethyl,
$R^3$ is $(C_2\text{-}C_5)$-alkyl which may be substituted by hydroxyl, methoxy or cyclopropyl or up to trisubstituted by fluorine,
where cyclopropyl may in turn be up to disubstituted by fluorine,
and
$R^4$ is $(C_1\text{-}C_4)$-alkyl which may be up to trisubstituted by fluorine, is 2-methoxyethyl or 2-ethoxyethyl or is the $-CH_2-R^{12}$ group in which
$R^{12}$ is cyclopropyl, cyclobutyl, oxetanyl, tetrahydrofuranyl or tetrahydropyranyl,
where cyclopropyl and cyclobutyl may be up to disubstituted by fluorine,
and the salts, solvates and solvates of the salts thereof.

Irrespective of the particular combinations of the radicals specified, the individual radical definitions specified in the particular combinations or preferred combinations of radicals are also replaced as desired by radical definitions from other combinations.

Very particular preference is given to combinations of two or more of the abovementioned preferred ranges.

The present invention also encompasses all suitable isotopic variants of the compounds of the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulphur, fluorine, chlorine, bromine and iodine, such as $^2H$ (deuterium), $^3H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound of the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^3H$ or $^{14}C$ isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds of the invention may therefore possibly also constitute a preferred embodiment of the present invention. Isotopic variants of the compounds of the invention can be prepared by commonly used processes known to those skilled in the art, for example by the methods described further down and the procedures described in the working examples, by using corresponding isotopic modifications of the respective reagents and/or starting compounds.

A particular embodiment of such isotopic variants of the compounds of the invention is that of compounds of the formula (I-A)

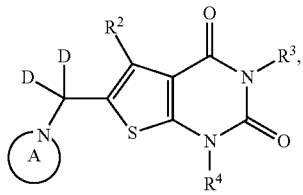

(I-A)

in which the ring A and the $R^2$, $R^3$ and $R^4$ radicals are as defined above,
and the salts, solvates and solvates of the salts thereof. The compounds of the formula (I-A) and the use of these compounds for the purposes mentioned in the rest of the description therefore likewise form part of the subject-matter of the present invention.

Furthermore, the present invention also encompasses prodrugs of the compounds of the invention.

The term "prodrugs" refers here to compounds which may themselves be biologically active or inactive, but are converted while present in the body, for example by a metabolic or hydrolytic route, to compounds of the invention.

The inventive compounds of the formula (I) may, depending on the respective nature of the azaheterocycle A, be prepared by different routes, some of which are also alternative routes.

For instance, inventive compounds of the formula (I-1)

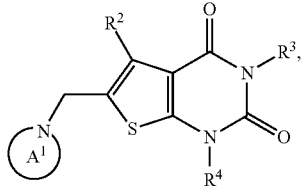

(I-1)

in which
the ring $A^1$ is an azaheterocycle of the formula

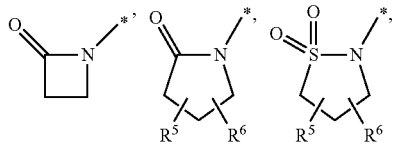

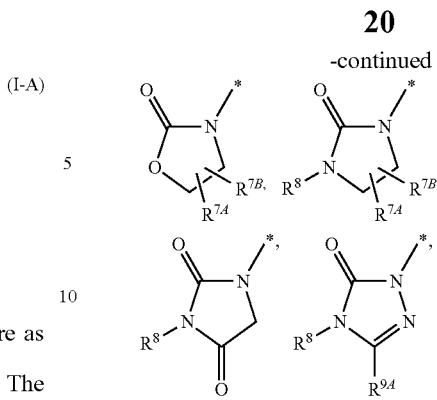

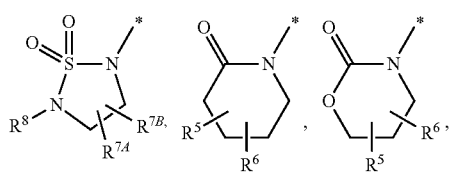

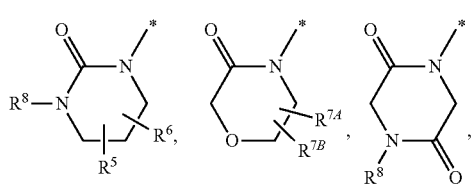

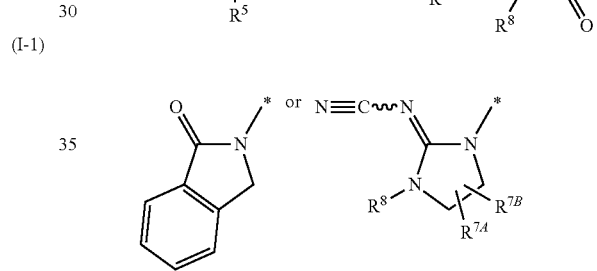

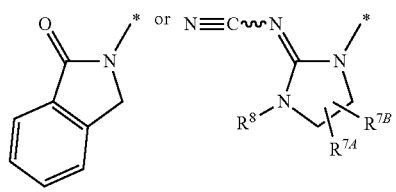

in which * marks the bond to the adjoining $CH_2$ group
and
$R^5$, $R^6$, $R^{7A}$, $R^{7B}$, $R^8$ and $R^{9A}$ are as defined above,
and
$R^2$, $R^3$ and $R^4$ are as defined above,
can be prepared by a general method according to the following Reaction Scheme 1:

Scheme 1

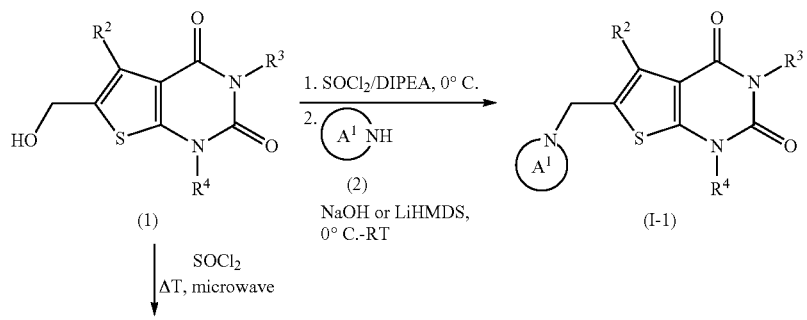

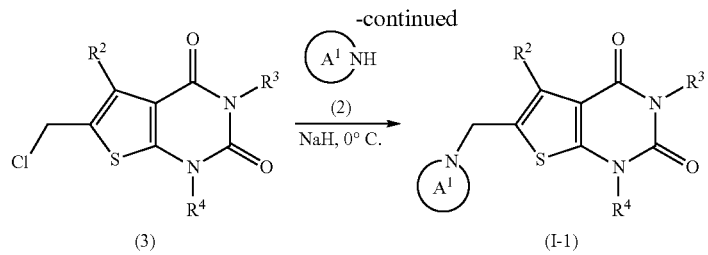

In the "one-pot" variant of this process, an alcohol of the formula (1) is converted first with a chlorinating agent, such as preferably thionyl chloride, in the presence of a tertiary amine base, for example N,N-diisopropylethylamine or triethylamine, to the corresponding chloro compound [corresponding to formula (3)]. This chloro compound is not isolated but admixed in the same reaction vessel with a solution of the deprotonated azaheterocycle of the formula (2), in order thus to obtain the target compound of the formula (I-1) in one step. Suitable bases for the deprotonation of the heterocycle (2) are strong bases, for example alkali metal hydrides or alkali metal amides; preference is given to using sodium hydride or lithium hexamethyldisilazide. The chlorination step is typically effected in a halogenated hydrocarbon as inert solvent—preference being given here to dichloromethane—in the temperature range around 0° C. The solution of the deprotonated heterocycle (2) is added at the same temperature. The substitution reaction to give (I-1) is then preferably effected at RT. Suitable solvents for preparation of the deprotonated heterocycle (2) are especially N,N-dimethylformamide (DMF), tetrahydrofuran (THF) or mixtures thereof. The deprotonation itself is preferably effected within a temperature range between 0° C. and +60° C.

Less hydrolysis-sensitive chloro compounds of the formula (3) can be prepared and also isolated by—similarly to the manner above—reacting alcohols of the formula (1) with a chlorinating agent, such as preferably thionyl chloride, in an inert solvent, for example chloroform or dichloromethane. The reaction is effected here preferably within a temperature range between RT and +80° C., and it has been found to be particularly advantageous for the heating above the boiling point of the particular solvent to use a microwave oven with employment of closed reaction vessels. In a subsequent, separate reaction step, the isolated chloro compounds of the formula (3) are then reacted under similar conditions, as elucidated above, with a solution of the deprotonated heterocycle (2).

In place of the $R^8$ radical in the azaheterocycle of the formula (2) in question, in the process described above, it is first also possible to use a suitable amide protecting group if appropriate or necessary for avoidance of side reactions. Detachment of such a protecting group at the end of the above reaction sequence may be followed by a further derivatization within the scope of definition of $R^8$ via appropriate alkylation or acylation reactions, as familiar to those skilled in the art [with regard to the suitability, introduction and removal of amide protecting groups see, for example, T. W. Greene and P. G. M. Wuts, *Protective Groups in Organic Synthesis*, Wiley, New York, 1999].

Inventive compounds of the formula (I-2)

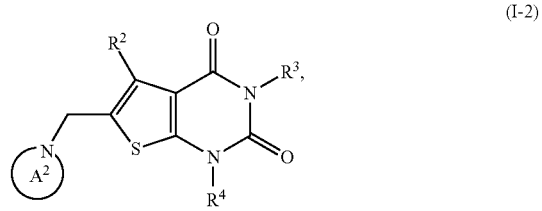

in which
the ring $A^2$ is an α-hydroxylactam of the formula

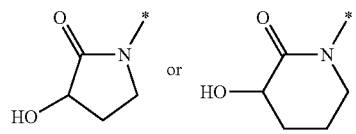 [SMILES: *N1CCC(O)C1=O ; *N1CCCC(O)C1=O]

in which * marks the bond to the adjoining $CH_2$ group
and
$R^2$, $R^3$ and $R^4$ are as defined above,
may alternatively also be prepared by a specific process according to the following Reaction Scheme 2:

Scheme 2

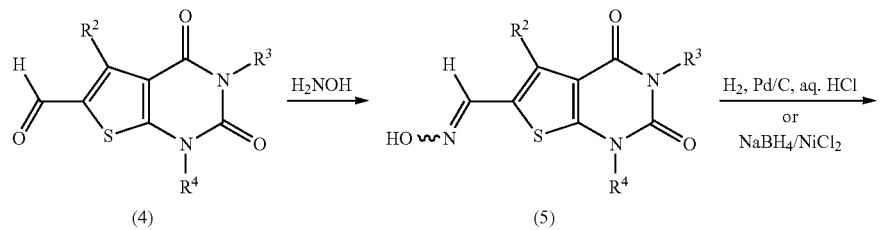

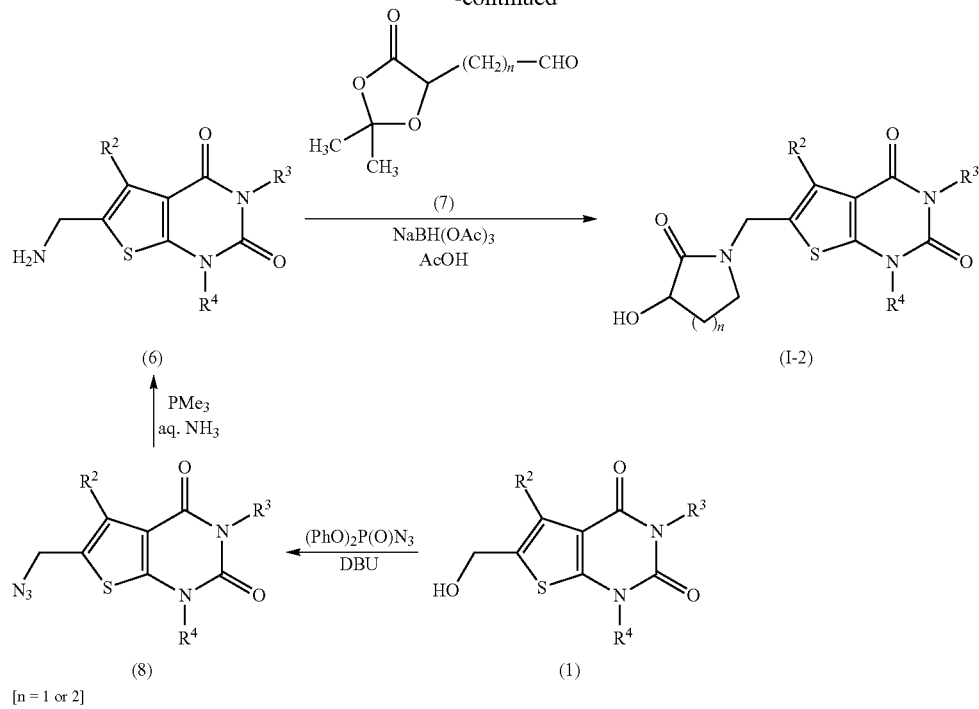

Here, aldehydes of the formula (4) are first converted with hydroxylamine to the corresponding oximes of the formula (5). The reaction is preferably effected at RT using an aqueous hydroxylamine solution in a water-miscible ether such as tetrahydrofuran (THF) as solvent. The subsequent reduction to give the aminomethyl compounds (6) can be effected by hydrogenation in the presence of a noble metal catalyst. Preferred reaction conditions are hydrogen pressure 1 bar at RT in the presence of a catalytic amount of palladium (10% on charcoal) in methanol or ethanol as solvent. Preferably, the hydrogenation is effected in the presence of aqueous mineral acid, for example concentrated hydrochloric acid. Alternatively, the reduction to the aminomethyl compounds (6) can also be effected with sodium borohydride in the presence of suitable metal salts, for example nickel chloride or cobalt chloride. Preferred reaction conditions here include the use of sodium borohydride in combination with nickel(II) chloride hexahydrate in methanol as solvent at RT. Another route to the aminomethyl compounds of the formula (6) proceeds from the alcohols of the formula (1). These are first converted to the corresponding azides of the formula (8) by reacting them with diphenylphosphoryl azide in the presence of an amine base, for example DBU, at 0° C. to RT in tetrahydrofuran (THF). The reduction of azides (8) to the aminomethyl compounds (6) can then be effected, for example, by reacting with trimethylphosphine in tetrahydrofuran (THF) and concentrated aqueous ammonia at RT.

The aminomethyl compounds of the formula (6) obtained by one of the routes mentioned are then reacted in the last reaction step with aldehydes of the formula (7) in the manner of a reductive amination. A suitable reducing agent here is especially sodium triacetoxyborohydride in the presence of acetic acid. A suitable solvent is 1,2-dichloroethane, and the reaction is preferably effected at RT. The initial step of reductive amination is followed by a spontaneous cyclization reaction which gives the hydroxylactams of the formula (I-2) with release of acetone.

Inventive compounds of the formula (I-3)

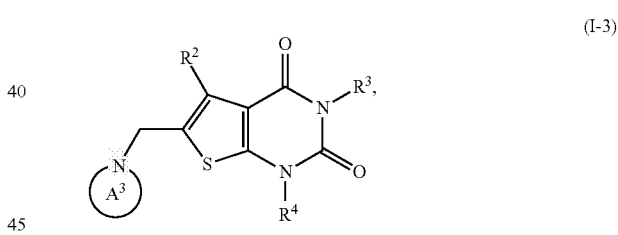

in which
the ring $A^3$ is an azaheterocycle of the formula

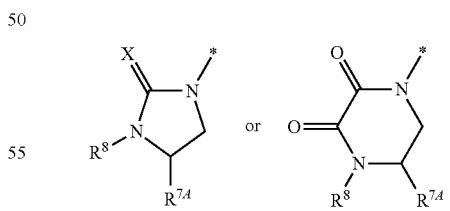

in which * marks the bond to the adjoining $CH_2$ group and $R^{7A}$, $R^8$ and X are as defined above, and $R^2$, $R^3$ and $R^4$ are as defined above, can be obtained according to the following Reaction Scheme 3:

Scheme 3

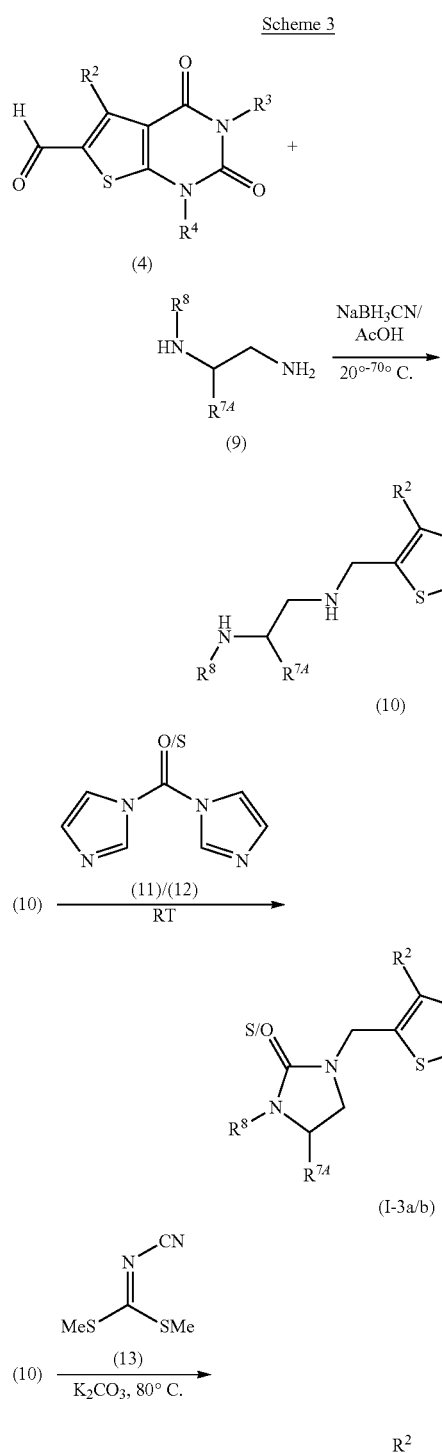

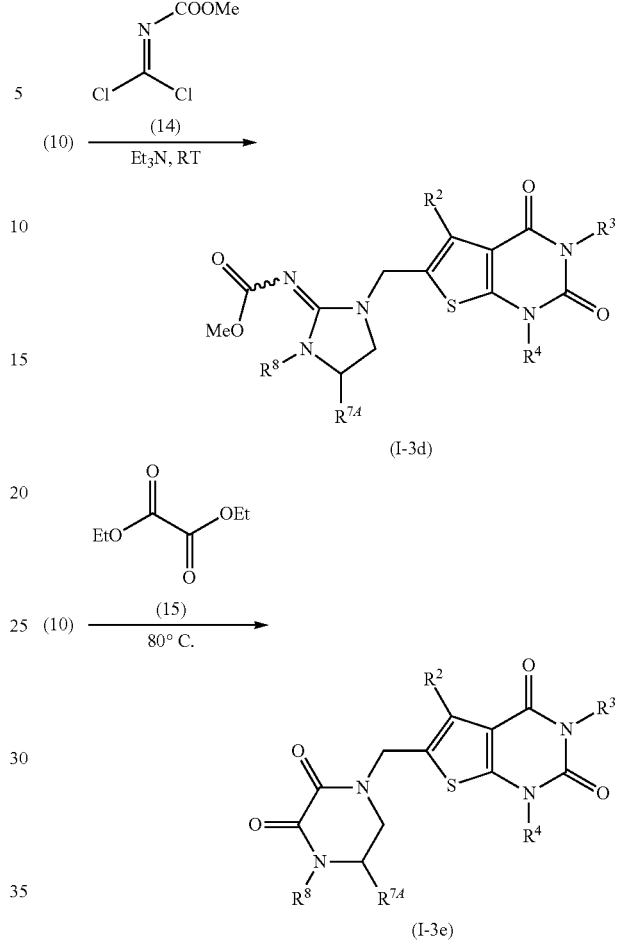

Aldehydes of the formula (4) are first reacted here with 1,2-diaminoethane derivatives of the formula (9) in a reductive amination to give the diamino compounds of the formula (10). A suitable reducing agent is especially sodium cyanoborohydride in the presence of acetic acid. A suitable solvent is methanol, optionally in a mixture with dichloromethane, and the reaction is preferably effected within a temperature range between RT and +70° C.

The target compounds of the formulae (I-3a) and (I-3b) are obtained by subsequent reaction of the diamino compounds (10) with N,N'-carbonyldiimidazole (11) [for (I-3a)] or N,N'-thiocarbonyldiimidazole (12) [for (I-3b)]. The reactions are preferably effected at RT and in solvents such as tetrahydrofuran (THF), 1,4-dioxane or dimethyl sulphoxide (DMSO), optionally in the presence of a tertiary amine base, for example triethylamine. The products of the formula (I-3c) are obtained by reaction of the diamino compounds (10) with dimethyl N-cyanodithioiminocarbonate (13). The reaction is preferably effected in N,N-dimethylformamide (DMF) as solvent in the presence of alkali metal carbonates, for example potassium carbonate, as base at elevated temperatures around +80° C. The products of the formula (I-3d) are obtained by reaction of the diamino compounds (10) with methyl (dichloromethylene)carbonate (14). The reaction is preferably effected in dichloromethane as solvent in the presence of a tertiary amine base, for example triethylamine, at RT. Finally, the products of the formula (I-3e) are obtained by reaction of the diamino compounds (10) with diethyl oxalate (15). The reaction is preferably effected in ethanol as solvent at elevated temperatures around +80° C.

Inventive compounds of the formula (I-4)

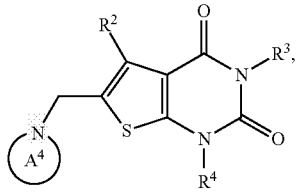
(I-4)

in which
the ring $A^4$ is a cyclic urea derivative of the formula

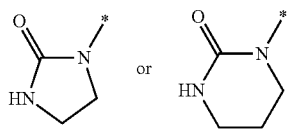 [SMILES: *N1CCNC1=O ; *N1CCCNC1=O]

in which * marks the bond to the adjoining $CH_2$ group and
$R^2$, $R^3$ and $R^4$ are as defined above,
are also obtainable by an alternative route according to the following Reaction Scheme 4:

Scheme 4

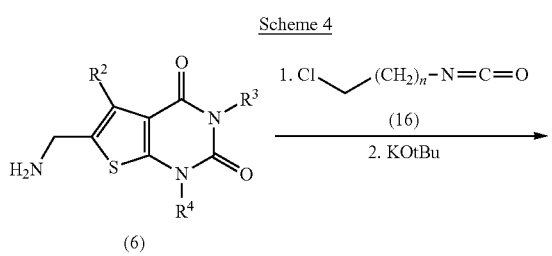
(I-4)

[n = 1 or 2].

The aminomethyl compounds of the formula (6) described in Scheme 2 above are reacted here in a one-pot process first with chloroalkyl isocyanates of the formula (16), at first forming an open-chain urea derivative. The reaction is preferably effected at RT in a solvent mixture of N,N-dimethylformamide (DMF) and tetrahydrofuran (THF). The subsequent addition of a strong base, for example potassium tert-butoxide, to the reaction mixture at RT then results in the ring closure to give the target compounds of the formula (I-4).

Inventive compounds of the formula (I-4a)

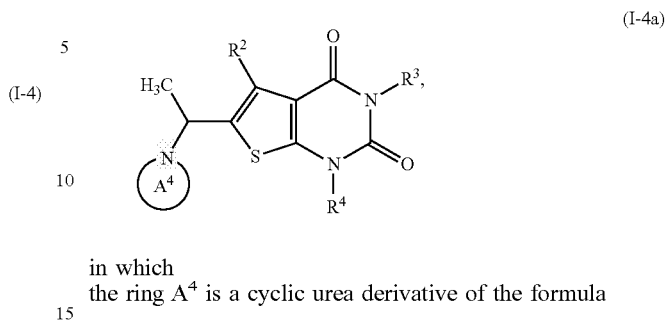
(I-4a)

in which
the ring $A^4$ is a cyclic urea derivative of the formula

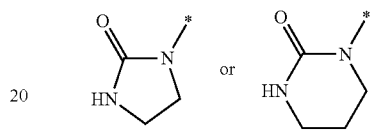

in which * marks the bond to the adjoining $CH_2$ group and
$R^2$, $R^3$ and $R^4$ are as defined above,
can be obtained in an analogous manner according to Reaction Scheme 4a:

Scheme 4a

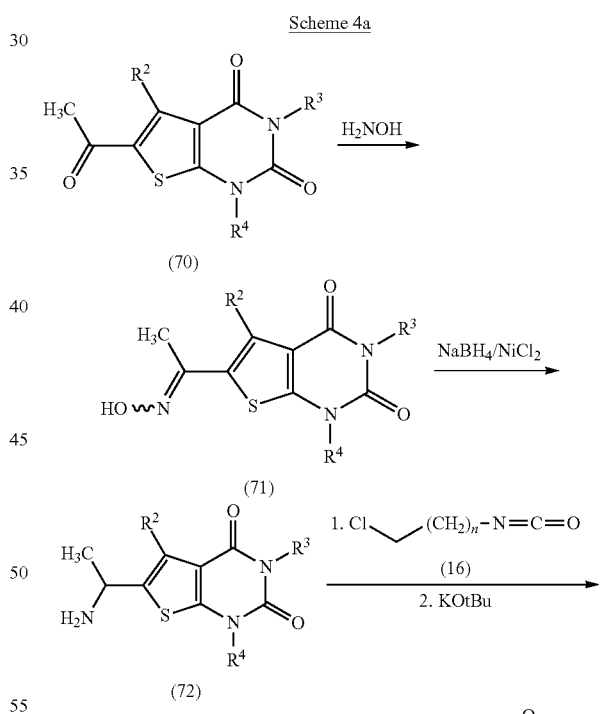

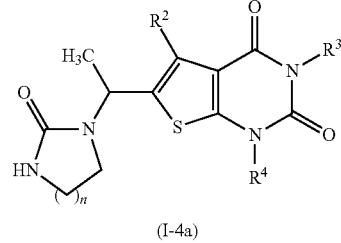
(I-4a)

[n = 1 or 2].

Here, methyl ketones of the formula (70) are first converted with hydroxylamine to the corresponding oximes of the formula (71). The reaction is effected using an aqueous hydroxylamine solution, preferably at elevated temperature, in an alcoholic solvent such as ethanol. The subsequent reduction to give the 1-aminoethyl compounds of the formula (72) is conducted with the aid of sodium borohydride in the presence of a suitable metal salt, for example nickel chloride or cobalt chloride. Preferred reaction conditions include the use of sodium borohydride in combination with nickel(II) chloride hexahydrate in methanol as solvent at RT [cf. also synthesis sequence (4)→(5)→(6) in Scheme 2]. Finally, the 1-aminoethyl compounds of the formula (72) are reacted in a one-pot process first with chloroalkyl isocyanates of the formula (16), at first forming an open-chain urea derivative. The reaction is preferably effected at RT in a solvent mixture of N,N-dimethylformamide (DMF) and tetrahydrofuran (THF). The subsequent addition of a strong base, for example potassium tert-butoxide, to the reaction mixture at RT then results in the ring closure to give the target compounds of the formula (I-4a) [cf. Scheme 4].

Inventive compounds of the formula (I-5)

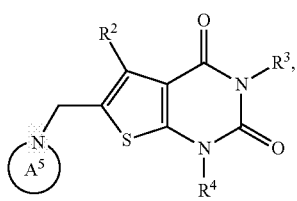

(I-5)

in which
the ring $A^5$ is an azaheterocycle of the formula

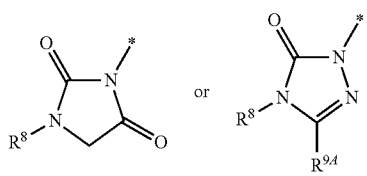

in which * marks the bond to the adjoining $CH_2$ group
and
$R^8$ and $R^{9A}$ are as defined above,
and
$R^2$, $R^3$ and $R^4$ are as defined above,
can be prepared according to the following Reaction Scheme 5:

Scheme 5

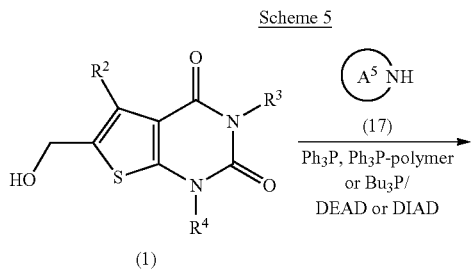

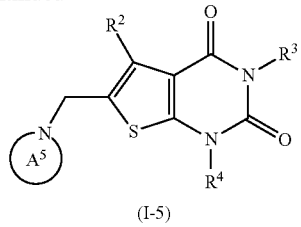

(I-5)

Alcohols of the formula (1) are reacted here with azaheterocycles of the formula (17) in the manner of a Mitsunobu reaction to give the products of the formula (I-5). Suitable reagents for this transformation are, for example, triphenylphosphine, polymer-bound triphenylphosphine, tributylphosphine or trimethylphosphine, each in combination with diethyl azodicarboxylate (DEAD), diisopropyl diazodicarboxylate (DIAD) or azodicarboxylic acid dipiperidide (ADDP) [cf., for example, D. L. Hughes, *Org. Reactions* 42, 335 (1992); D. L. Hughes, *Org. Prep. Proced. Int.* 28 (2), 127 (1996)]. The reaction is preferably conducted in tetrahydrofuran (THF) or dichloromethane as solvent within a temperature range between 0° C. and RT.

In place of the $R^8$ radical in the azaheterocycle of the formula (17), in the process described above, it is first also possible to use a suitable amide protecting group if appropriate or necessary for avoidance of side reactions. Detachment of such a protecting group at the end of the above reaction sequence may be followed by a further derivatization within the scope of definition of $R^8$ via appropriate alkylation or acylation reactions, as familiar to those skilled in the art [with regard to the suitability, introduction and removal of amide protecting groups see, for example, T. W. Greene and P. G. M. Wuts, *Protective Groups in Organic Synthesis*, Wiley, New York, 1999].

Inventive compounds of the formula (I-6)

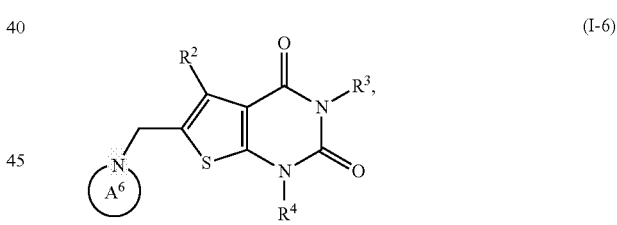

(I-6)

in which
the ring $A^6$ is an imidazol-2-one derivative of the formula

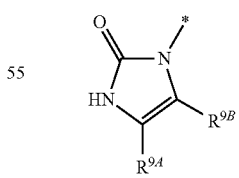

in which * marks the bond to the adjoining $CH_2$ group
and
$R^{9A}$ and $R^{9B}$ are as defined above,
and
$R^2$, $R^3$ and $R^4$ are as defined above,
can be obtained according to the following Reaction Scheme 6:

Scheme 6

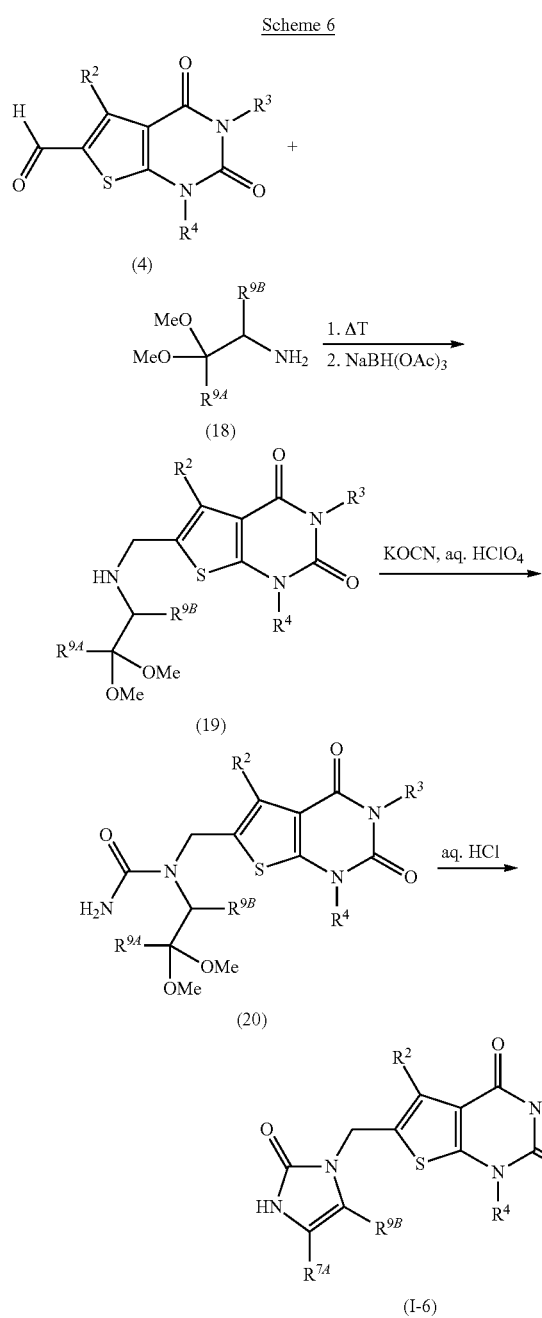

possible to use other standard acetals and ketals in this process, especially cyclic examples such as 1,3-dioxolane or 1,3-dioxane derivatives.

Inventive compounds of the formula (I-7)

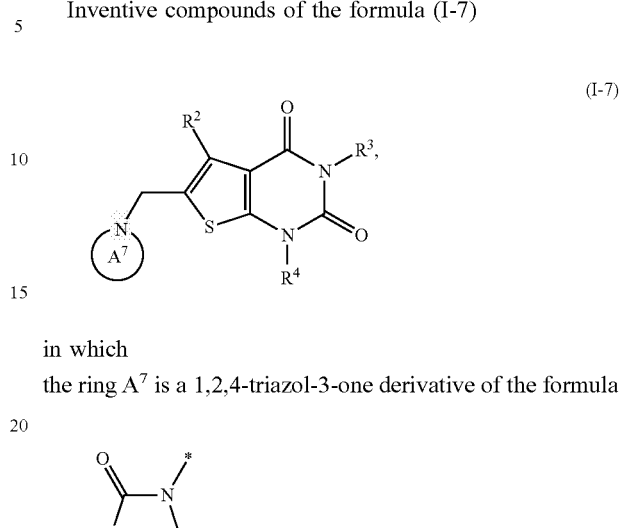

in which the ring $A^7$ is a 1,2,4-triazol-3-one derivative of the formula in which * marks the bond to the adjoining $CH_2$ group and $R^{9B}$ is as defined above, and $R^2$, $R^3$ and $R^4$ are as defined above, are prepared according to the following Reaction Scheme 7:

Scheme 7

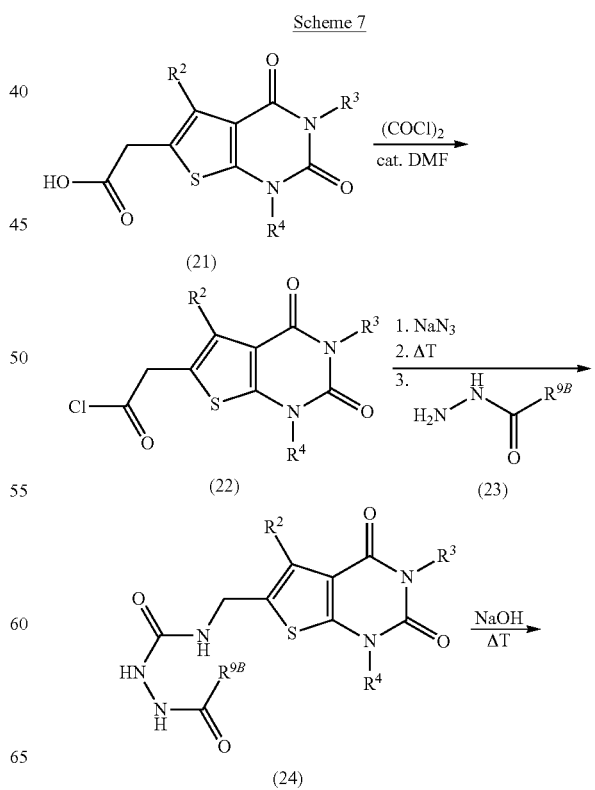

Aldehydes of the formula (4) are first heated to reflux here with amino acetals or amino ketals of the formula (18) in a suitable solvent, such as methanol or dichloromethane, in the manner of a reductive amination and then reduced at RT with sodium triacetoxyborohydride to the compounds of the formula (19). These are subsequently converted with potassium cyanate and aqueous perchloric acid in methanol at RT to the urea derivatives of the formula (20). In the last reaction step, the simultaneous acid-catalysed acetal or ketal cleavage and ring closure to give the target compounds of the formula (I-6) are effected. The reaction is effected in methanol at RT with hydrochloric acid of different concentration (from 0.5 mol/l up to concentrated hydrochloric acid).

In the formulae (18), (19) and (20), the dimethyl acetals or dimethyl ketals are shown in each case; however, it is also

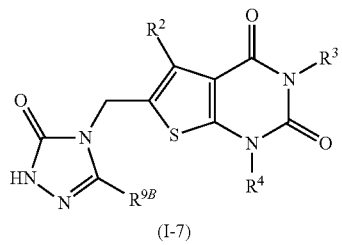

(I-7)

Carboxylic acids of the formula (21) are first converted here in a customary manner, for example by reaction with oxalyl chloride in dichloromethane at RT, in the presence of a catalytic amount of N,N-dimethylformamide (DMF), to the corresponding acid chlorides (22). Subsequently, in a multistage one-pot method, the open-chain intermediates of the formula (24) are prepared by first converting the acyl chlorides of the formula (22), dissolved in toluene and at RT, with sodium azide to the corresponding carbonyl azides. After filtration to remove inorganic salts, the solutions thus obtained are heated to reflux in toluene, which gives the corresponding isocyanates in the manner of a Curtius rearrangement. The latter are admixed in the last step of the reaction at RT with a solution of an acyl hydrazine of the formula (23) in tetrahydrofuran (THF) and thus give the open-chain intermediates of the formula (24). Heating of these intermediates with inorganic bases, for example sodium hydroxide, in an alcoholic solvent such as methanol leads ultimately, through cyclization, to the target compounds of the formula (I-7).

Inventive compounds of the formula (I-8)

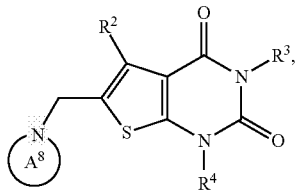

(I-8)

in which
the ring $A^8$ is a pyrazol-3-one derivative of the formula

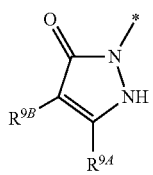

in which * marks the bond to the adjoining $CH_2$ group and
$R^{9A}$ and $R^{9B}$ are as defined above,
and
$R^2$, $R^3$ and $R^4$ are as defined above, are obtainable according to Reaction Scheme 8:

Scheme 8

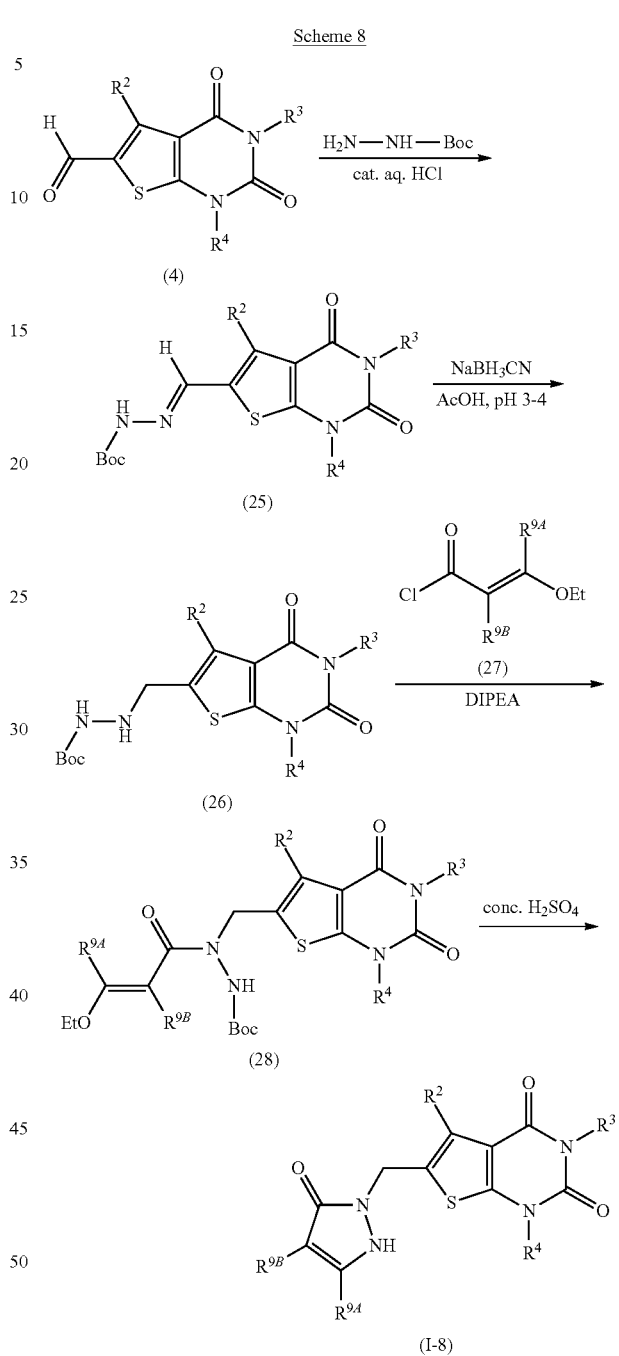

Aldehydes of the formula (4) are converted here by reaction with Boc-protected hydrazine in ethanol and in the presence of a catalytic amount of concentrated hydrochloric acid at RT to the hydrazones of the formula (25), which are then converted with sodium cyanoborohydride in methanol at +65° C. to the hydrazine derivatives of the formula (26). The exact control of the pH plays a major role in the latter reaction: in the presence of Bromocresol Green as indicator, addition of acetic acid in portions maintains a pH of about 3-4 over the entire reaction time. The subsequent reaction with the acryloyl chlorides of the formula (27) is conducted under standard conditions, for example in dichloromethane as solvent within a temperature range between 0° C. and RT and in the presence of a tertiary amine base, for example N,N-diisopropylethylamine. The final acid-catalysed removal of the Boc protecting group and the subsequent ring closure to give the target compounds of the formula (I-8) are effected at RT either in pure concentrated sulphuric acid or in dichloromethane with an added catalytic amount of concentrated sulphuric acid.

Inventive compounds of the formula (I-9)

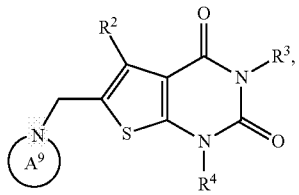
(I-9)

in which
the ring $A^9$ is an azaheterocycle of the formula

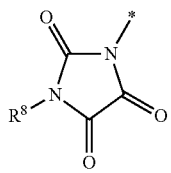

in which * marks the bond to the adjoining CH$_2$ group and
$R^8$ is as defined above,
and
$R^2$, $R^3$ and $R^4$ are as defined above,
can be obtained according to the following Reaction Scheme 9:

Scheme 9

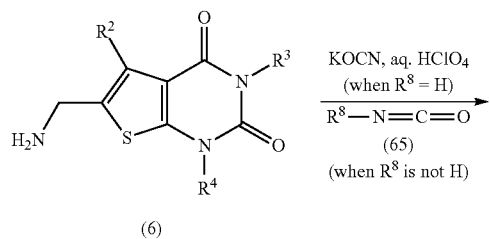

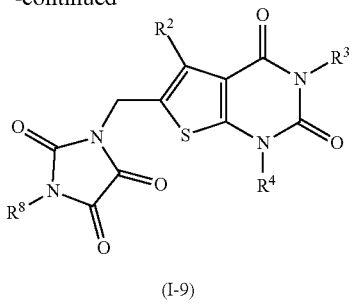
(I-9)

The aminomethyl compound of the formula (6) described above in Scheme 2 is converted here, in the case that $R^8$ in the target product (I-9) is hydrogen, with a mixture of potassium cyanate and aqueous perchloric acid in methanol at RT or, when $R^8$ is different from hydrogen, with an isocyanate of the formula (65) to the corresponding urea derivative of the formula (66). The isocyanate reaction can be effected in an ethereal solvent, for example tetrahydrofuran (THF) or 1,4-dioxane, optionally with addition of a tertiary amine base, for example triethylamine; alternatively, the reaction can, for example, also be conducted in pyridine as solvent and as base. The reaction with the isocyanate (65) is generally effected within a temperature range between 0° C. and about +50° C., preferably at RT. Subsequent ring formation to give the target compound (I-9) is achieved by reaction of (66) with an oxalic acid derivative, for example oxalyl chloride or diethyl oxalate. The reaction with oxalyl chloride is preferably conducted in an ethereal solvent, for example tetrahydrofuran (THF) or 1,4-dioxane, or in a halogenated hydrocarbon, for example dichloromethane or 1,2-dichloroethane, or in acetonitrile. The reaction can be effected in the presence of a standard amine base, for example triethylamine, N,N-diisopropylethylamine or pyridine, and is generally conducted within a temperature range between 0° C. and about +60° C., preferably at 0° C. to RT. The reaction with diethyl oxalate is preferably effected in an alcoholic solvent such as methanol or ethanol, in the presence of sodium methoxide or sodium ethoxide as base. The reaction temperature here is in the range between RT and the boiling point of the alcohol in question.

In place of the $R^8$ radical in the isocyanate of the formula (65), in the process described above, it is also possible to use a temporary amide protecting group if appropriate or necessary for avoidance of side reactions. Detachment of such a protecting group at the end of the above reaction sequence may be followed by a further derivatization within the scope of definition of $R^8$ via appropriate alkylation or acylation reactions, as familiar to those skilled in the art [with regard to the suitability, introduction and removal of amide protecting groups see, for example, T. W. Greene and P. G. M. Wuts, *Protective Groups in Organic Synthesis*, Wiley, New York, 1999].

Inventive compounds of the formula (I-10)

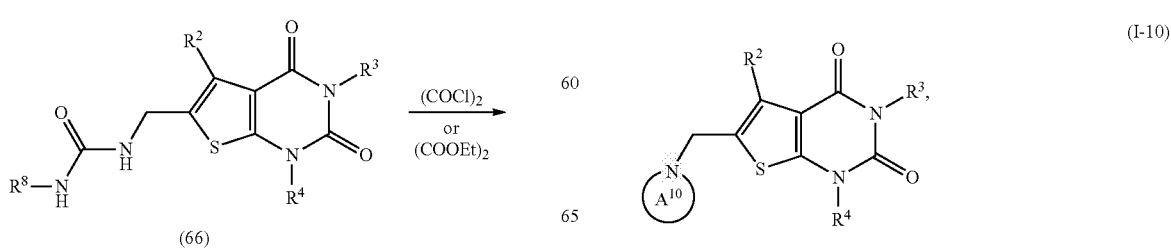

in which
the ring $A^{10}$ is a 1,2,4-triazol-3-one derivative of the formula

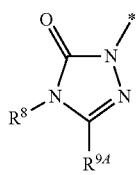

in which * marks the bond to the adjoining CH$_2$ group
and
$R^8$ and $R^{9A}$ are as defined above,
and
$R^2$, $R^3$ and $R^4$ are as defined above,
can be prepared according to the following Reaction Scheme 10:

acid within a temperature range between 0° C. and RT, preferably at +10° C. to +20° C. Subsequently, the hydrazonocarboxylic acid (69) is converted with diphenylphosphoryl azide (DPPA) to the corresponding carbonyl azide which then gives the corresponding isocyanate in situ in the manner of a Curtius rearrangement, and then the latter cyclizes spontaneously to give the triazolone derivative of the formula (I-10a). The reaction is effected in an inert solvent, for example toluene, and in the presence of a tertiary amine base, for example triethylamine. The reaction is conducted initially within a temperature range between about +40° C. and +80° C.; later on, the reaction temperature is then increased to +100° C. to +110° C.

By using appropriate 2-oxocarboxylic acids (68), it is also possible in principle by this process to obtain those inventive compounds of the formula (I-10a) in which $R^{9A}$ is (C$_1$-C$_4$)-alkyl. In addition, it is possible by downstream reactions in the form of alkylation and acylation reactions as commonly

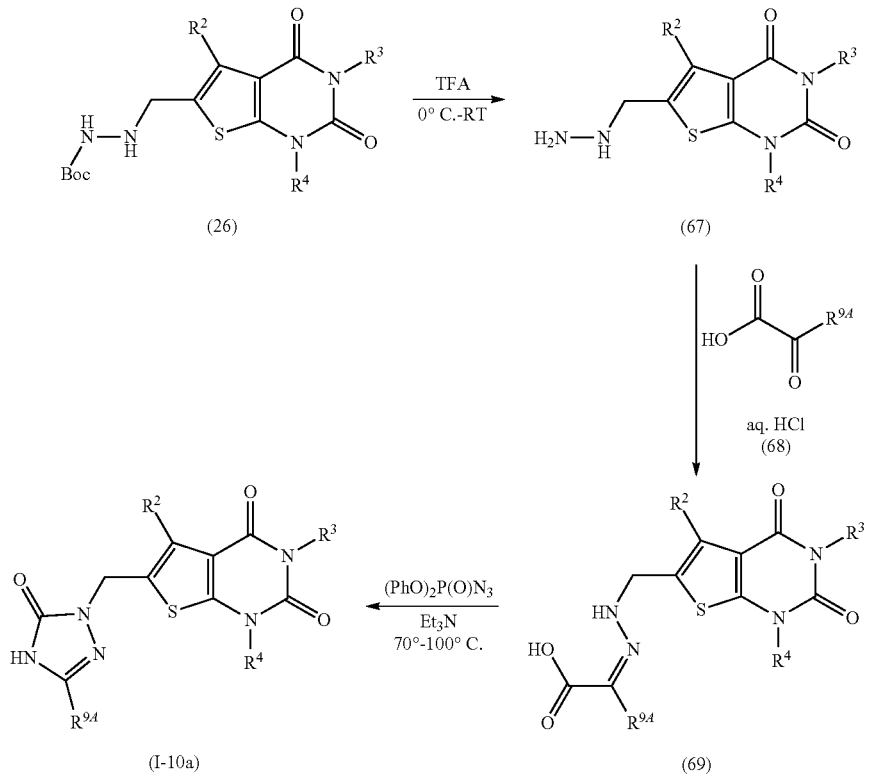

Scheme 10

In this process, the protected hydrazine derivative of the formula (26) (see Scheme 8) is converted first with trifluoroacetic acid in dichloromethane to the free hydrazine of the formula (67). The Boc detachment is effected within a temperature range between 0° C. and RT, preferably at 0° C. In order to avoid breakdown of the product, the reaction time chosen should be no longer than required; in addition, subsequent workup and purifying operations should be conducted at RT. In analogy to a previously described two-stage process [see U.S. Pat. No. 6,077,814, Referential Production Examples 1-4], the hydrazine of the formula (67) is first condensed with glyoxylic acid (68) [$R^{9A}$=H] under acid catalysis to give the hydrazone of the formula (69). The reaction is effected in water in the presence of hydrochloric known to those skilled in the art to obtain those inventive compounds of the formula (I-10) in which $R^8$ within the above-specified scope of definition is different from hydrogen.

Inventive compounds of the formula (I-11)

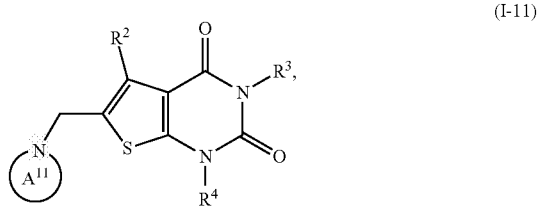

(I-11)

in which the ring $A^{11}$ is a dihydro-1,2,4-triazol-3-one of the formula

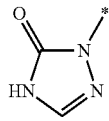

in which * marks the bond to the adjoining CH$_2$ group
and
R$^2$, R$^3$ and R$^4$ are as defined above,
can also be prepared by an alternative route according to Reaction Scheme 11:

Scheme 11

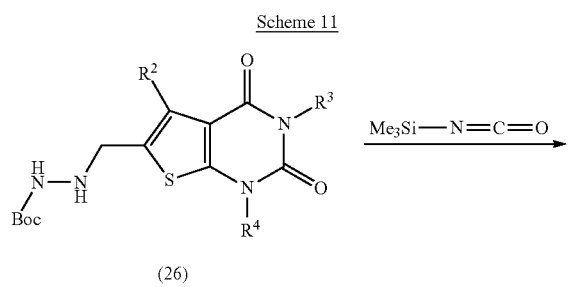

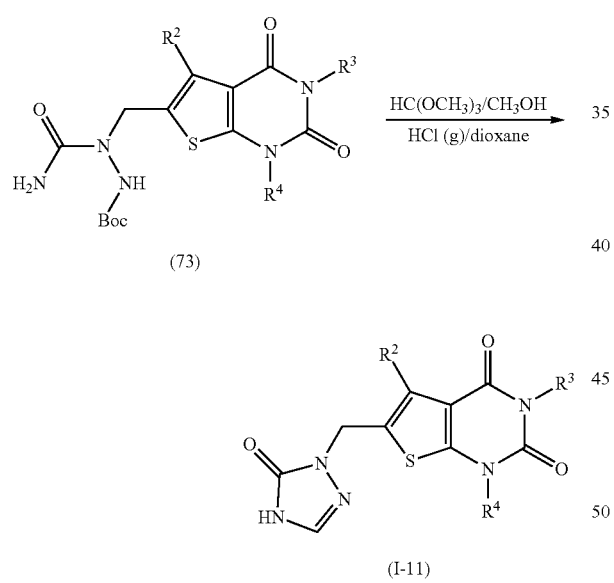

Compounds of the formula (26) (see Scheme 8) are first reacted here with trimethylsilyl isocyanate to give urea derivatives of the formula (73). The reaction is conducted in an alcohol as solvent, preferably in isopropanol, at elevated temperature, preferably at about 50° C. Under these conditions, there is also simultaneous detachment of the trimethylsilyl group. The ring closure to give the target compounds of the formula (I-11) is achieved by acid-mediated reaction with trimethyl orthoformate. For this purpose, the compounds of the formula (73) are treated in the presence of hydrogen chloride with an excess of trimethyl orthoformate in methanol. The reaction is preferably conducted at room temperature.

Inventive compounds of the formula (I-12)

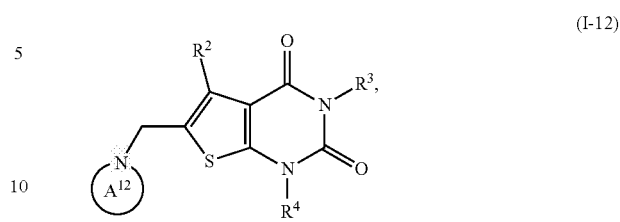

in which
the ring $A^{12}$ is a piperazine-2,5-dione derivative of the formula

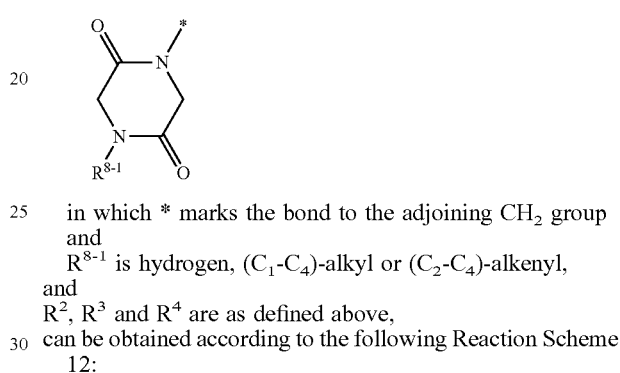

in which * marks the bond to the adjoining CH$_2$ group
and
R$^{8-1}$ is hydrogen, (C$_1$-C$_4$)-alkyl or (C$_2$-C$_4$)-alkenyl,
and
R$^2$, R$^3$ and R$^4$ are as defined above,
can be obtained according to the following Reaction Scheme 12:

Scheme 12

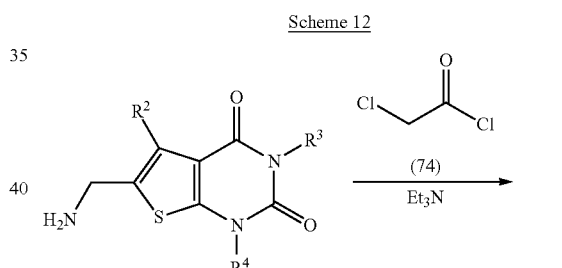

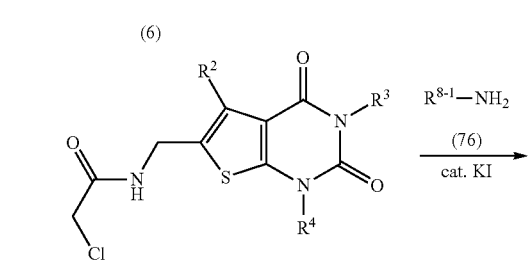

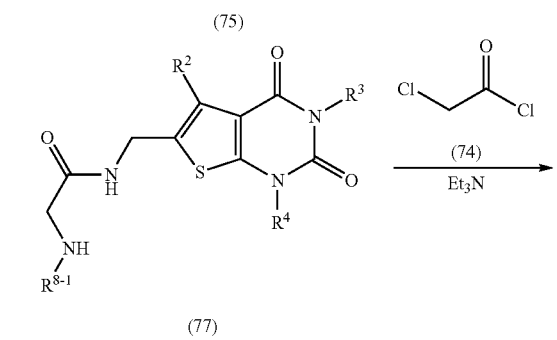

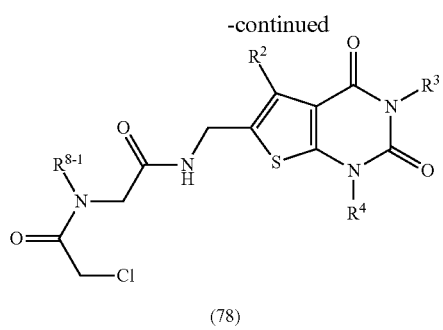

(78)

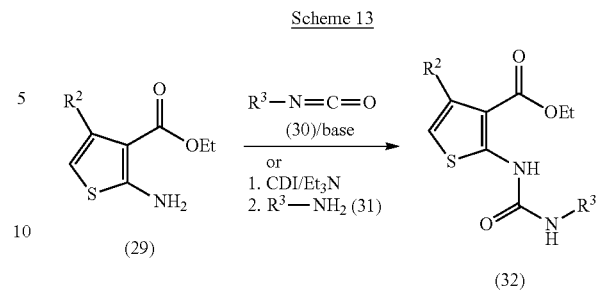

Scheme 13

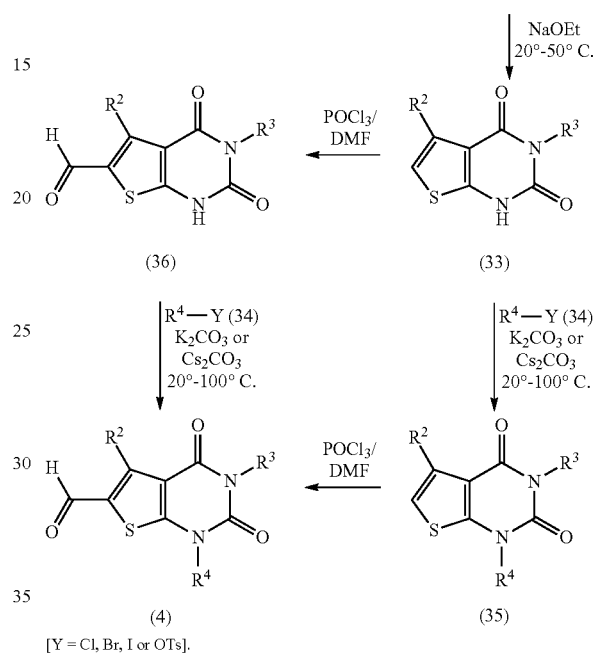

[Y = Cl, Br, I or OTs].

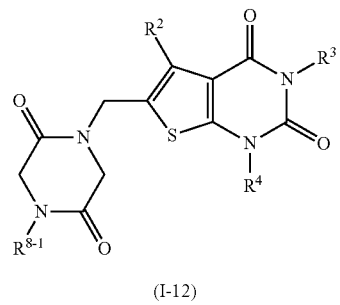

(I-12)

The aminomethyl compounds of the formula (6) (see Scheme 2) are first reacted here with chloroacetyl chloride (74) to give α-chloro amides of the formula (75). The reaction is effected in an inert solvent, for example and with preference dichloromethane, in the presence of a customary tertiary amine base, for example triethylamine or N,N-diisopropylethylamine, within a temperature range between 0° C. and RT. The compounds of the formula (75) are then reacted with ammonia or a primary amine of the formula (76) to give α-amino amides of the formula (77). This reaction is effected either with concentrated aqueous ammonia or the corresponding primary amine (76) in N,N-dimethylformamide (DMF) as solvent in the presence of a catalytic amount of potassium iodide at a temperature of about +50° C. The α-amino amides (77) are then reacted again with chloroacetyl chloride (74) under the same conditions as described above to give α-chloro amides of the formula (78). The subsequent ring closure to give the target compounds of the formula (I-12) is achieved with the aid of a strong base, for example potassium tert-butoxide, in the presence of a catalytic amount of potassium iodide. The reaction is conducted in an ethereal solvent, for example and with preference tetrahydrofuran (THF), at RT.

Further examples of the inventive compounds of formula (I) having substitution on the azaheterocycle A can be obtained in an analogous manner by using correspondingly substituted starting compounds in the above-described processes of Schemes 1-12. Any hydroxyl, amino and/or amido groups present in such starting compounds can, if appropriate or necessary, also be used in temporarily protected form and then released again at the end of the particular reaction sequence [with regard to the suitability, introduction and removal of such protecting groups see, for example, T. W. Greene and P. G. M. Wuts, Protective Groups in Organic Synthesis, Wiley, New York, 1999].

The synthesis of the thienouracil intermediates of the formulae (1), (4), (21) and (70) used for the preparation of the compounds of the invention [see Schemes 1-12] is shown in the following Reaction Schemes 13-21:

2-Aminothiophene-3-carboxylic esters of the formula (29) are converted here to the ureas of the formula (32) either with isocyanates of the formula (30) or, after activation with N,N'-carbonyldiimidazole (CDI), by reaction with amines of the formula (31). The reaction with the isocyanates (30) is preferably effected in an ethereal solvent, for example in tetrahydrofuran (THF), and in the presence of a tertiary amine base, for example triethylamine, under reflux conditions, or in pure pyridine as solvent and base at a temperature of about +50° C. The activation of the 2-aminothiophene-3-carboxylic ester (29) with CDI is likewise conducted in the presence of a tertiary amine base, for example triethylamine, in an inert solvent, preferably in tetrahydrofuran (THF) or dichloromethane, at RT and sometimes takes prolonged reaction times of several days. After addition of the amine component (31) to the CDI-activated 2-aminothiophene-3-carboxylic ester, there is generally rapid further reaction at RT to give the ureas of the formula (32). Subsequent treatment with alkali metal alkoxides in the corresponding alcohol as solvent (for example and with preference sodium ethoxide in ethanol) achieves ring closure to give the thienouracils of the formula (33) in a clean reaction. Depending on the substituent $R^3$, the reaction already proceeds at RT, or it requires a somewhat elevated temperature around +50° C.

The subsequent alkylation with the compounds of the formula (34) is conducted in the presence of an inorganic base, for example potassium carbonate or caesium carbonate, in an inert solvent, for example and with preference N,N-dimethylformamide (DMF), tetrahydrofuran (THF), acetonitrile or mixtures thereof. The reaction temperature is typically between RT and about +100° C. In the case of volatile alkylating agents (34), it is found to be helpful to use closed reaction vessels and heating by means of a microwave oven. Depending on the nature of the leaving group Y, it may be advantageous to conduct the alkylation in the presence of a catalytic amount of potassium iodide. The compounds of the formula (35) thus obtained are then converted in a Vilsmeier-Haack reaction with a mixture of phosphorus oxychloride and N,N-dimethylformamide (DMF) in an exothermic reaction to the aldehydes of the formula (4). Typically, the heat released during the reaction is sufficient to achieve full conversion. Sometimes, however, it may also be necessary to heat the mixture to about +90° C. for a while after the heat of reaction has abated.

The above reaction sequence of alkylation and formylation can also be conducted in the reverse sequence, by first converting the thienouracils of the formula (33) under the conditions of the Vilsmeier-Haack reaction already described to the formyl derivatives of the formula (36) and then alkylating the latter under the conditions likewise already described with the compounds of the formula (34) to give the target aldehydes of the formula (4).

Scheme 14

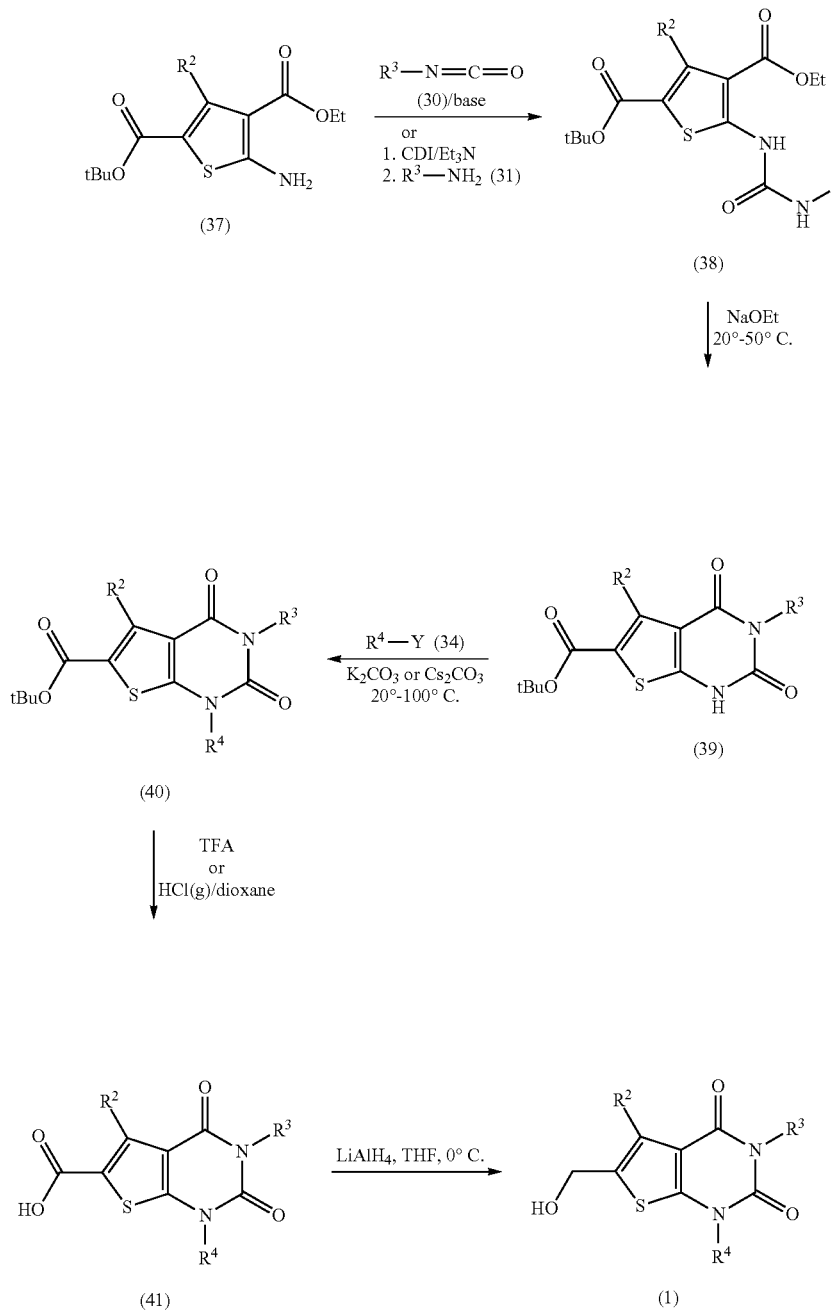

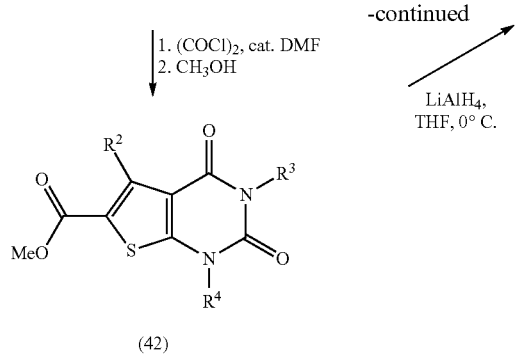

(42)

[Y = Cl, Br, I or OTs].

It is possible to obtain the thienouracil tert-butyl esters of the formula (40) from 5-aminothiophene-2,4-dicarboxylic esters of the formula (37) in an entirely analogous manner to the reactions described in Scheme 13 for the preparation of the intermediates (32), (33) and (35). Subsequent treatment of the tert-butyl esters (40) at RT with either trifluoroacetic acid in dichloromethane or a solution of hydrogen chloride in 1,4-dioxane gives the carboxylic acids of the formula (41). These can either be converted to the alcohols of the formula (1) directly by reduction with lithium aluminium hydride at about 0° C. in an inert solvent, for example and with preference tetrahydrofuran (THF), or after prior conversion to the corresponding methyl esters of the formula (42). The latter can be obtained in a one-pot process by first converting the carboxylic acids of the formula (41) with oxalyl chloride in dichloromethane at RT and in the presence of a catalytic amount of N,N-dimethylformamide (DMF) to the corresponding acid chlorides, which then, methyl esters of the formula (42) by quenching with methanol.

Scheme 15

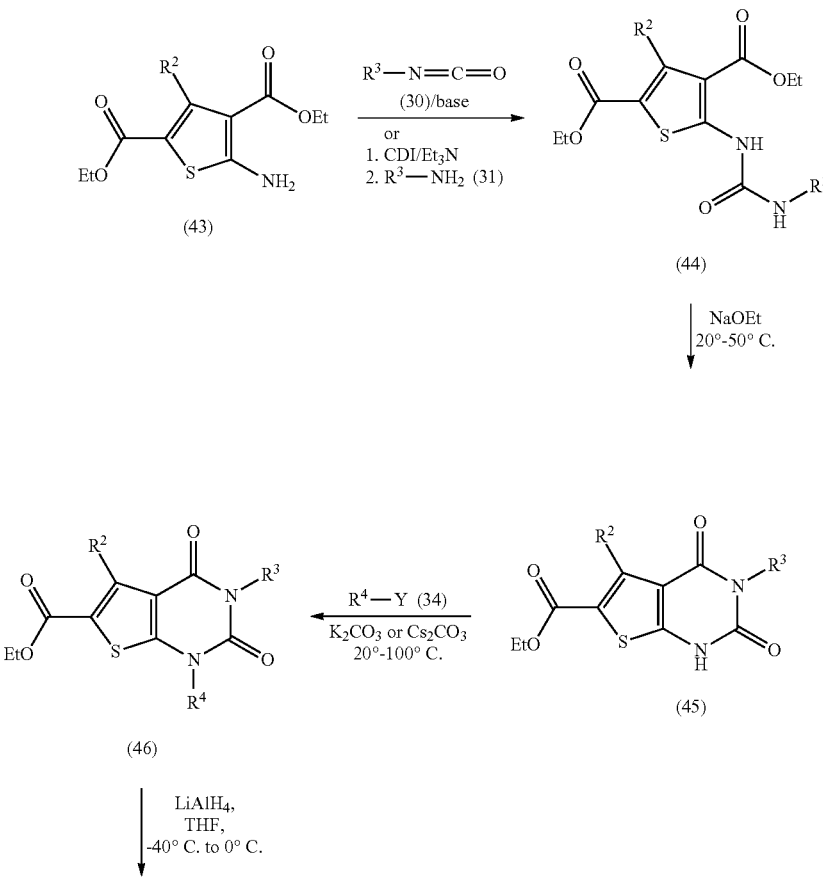

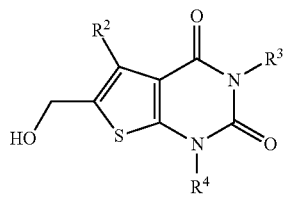

(1)

[Y = Cl, Br, I or OTs].

It is possible to obtain the thienouracil ethyl esters of the formula (46) from diethyl 5-aminothiophene-2,4-dicarboxylates of the formula (43), likewise in an entirely analogous manner to the reactions described in Scheme 13 for the preparation of the intermediates (32), (33) and (35). The subsequent reduction with a complex metal hydride, for example and with preference lithium aluminium hydride, then gives the alcohols of the formula (1) in a similar manner to that described above in Scheme 14. The reaction is effected typically in a temperature range between −40° C. and 0° C. in an inert solvent, for example and with preference tetrahydrofuran (THF).

Scheme 16

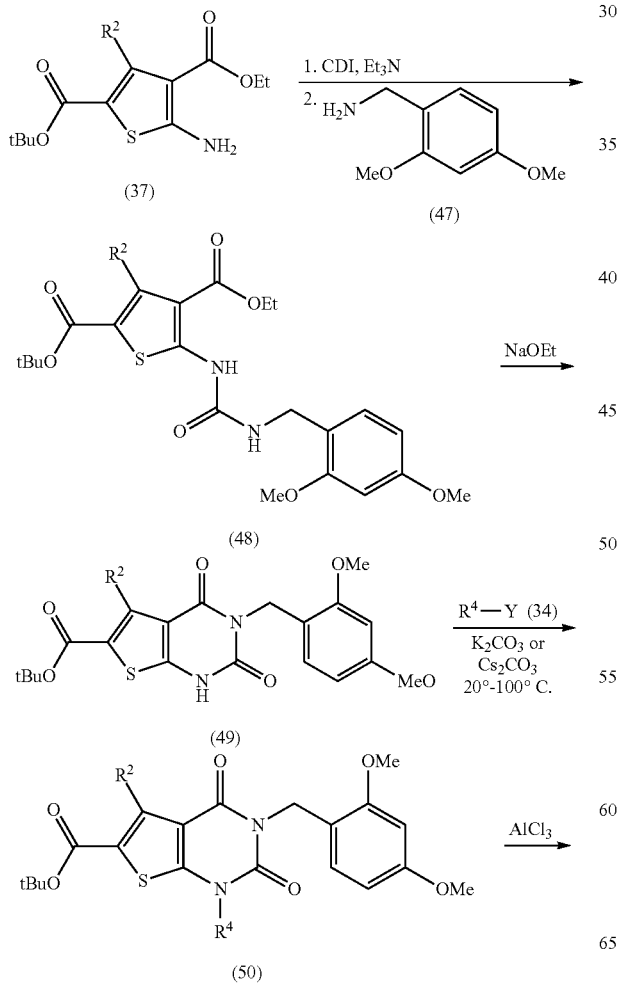

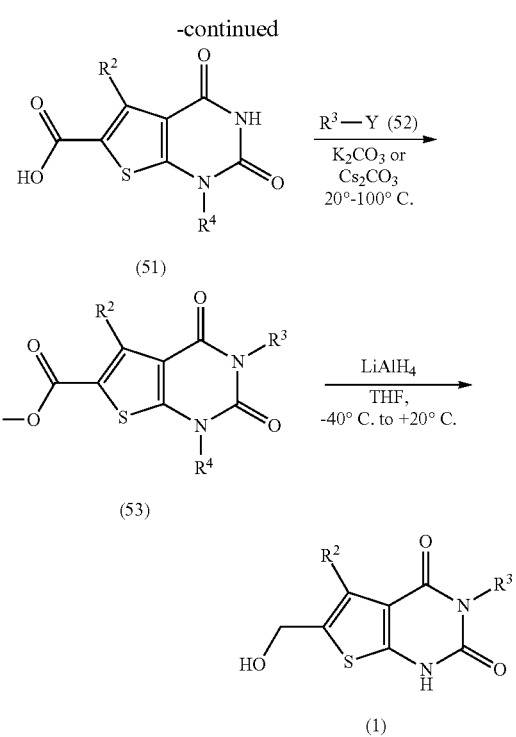

[Y = Cl, Br, I or OTs].

Analogously to the process described in Scheme 14 [compound (37) to compound (40)], it is possible to prepare the $N^3$-protected thienouracil tert-butyl esters of the formula (50) from 5-aminothiophene-2,4-dicarboxylic esters of the formula (37) and 2,4-dimethoxybenzylamine (47). In the subsequent treatment with aluminium trichloride, which is effected in toluene at about +65° C., simultaneous detachment of the 2,4-dimethoxybenzyl protecting group and the tert-butyl ester affords the carboxylic acids of the formula (51). These are subsequently converted in a double N,O alkylation with the compounds of the formula (52) to give the compounds of the formula (53). This alkylation is conducted under the same conditions as already described for the alkylation steps in the preceding synthesis schemes (see, for example, Scheme 13). The final reduction with a complex metal hydride, for example and with preference lithium aluminium hydride, then gives the target alcohols of the formula (1). The reaction is effected typically within a temperature range between −40° C. and RT in an inert solvent, for example and with preference tetrahydrofuran (THF).

Scheme 17

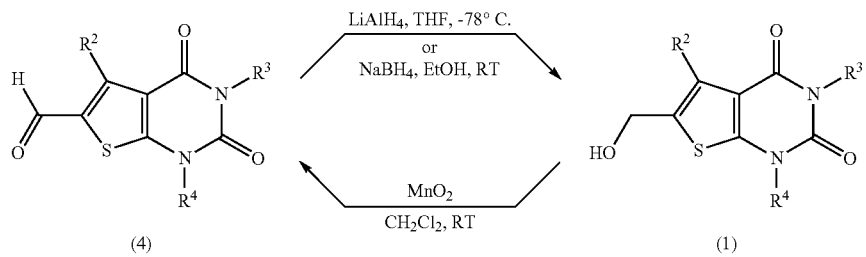

(4) → (1)

The aldehydes of the formula (4) and alcohols of the formula (1) obtained by one of the above-described processes can, if it seems desirable for synthesis purposes, be interconverted by several methods that are familiar to those skilled in the art. For example, the alcohols of the formula (1) can be oxidized with manganese dioxide in dichloromethane at RT to the aldehydes of the formula (4). Conversely, the aldehydes of the formula (4) can be reduced with complex hydrides, for example lithium aluminium hydride or sodium borohydride, to the alcohols of the formula (1). The reduction with lithium aluminium hydride is preferably effected in tetrahydrofuran (THF) at −78° C., whereas the reduction with sodium borohydride can be effected, for example, in ethanol at RT.

Scheme 18

(35) → (54) → (56)

-continued

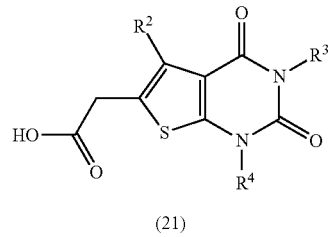

(21)

The thienouracil intermediates of the formula (21) can be obtained from the thienouracils of the formula (35), the preparation of which is described in Scheme 13, by first converting the compounds of the formula (35) with N-bromosuccinimide (NBS), N-iodosuccinimide (NIS) or N-chlorosuccinimide (NCS) to the corresponding halides of the formula (54) (here: halogen=bromine). The reaction is preferably effected in chloroform within a temperature range between 0° C. and RT. Subsequent Negishi coupling with the zinc organyl (55) affords the tert-butyl ester derivatives of the formula (56). The coupling reaction is preferably conducted in an ethereal solvent, for example tetrahydrofuran (THF), at a temperature of about +60° C. A multitude of homogeneous palladium(0) catalysts in combination with various phosphine ligands are suitable for this reaction; preference is given to using tris(dibenzylideneacetone)dipalladium(0) in conjunction with 1,2,3,4,5-pentaphenyl-1′-(di-tert-butylphosphino)ferrocene (Q-Phos). The subsequent cleavage of the tert-butyl ester moiety, for example with trifluoroacetic acid in dichloromethane at RT, gives the target carboxylic acids of the formula (21) in a clean reaction.

6-Acetylthienouracils of the formula (70) (see Scheme 4a) can be obtained in a simple manner by the method shown in Scheme 19:

Scheme 19

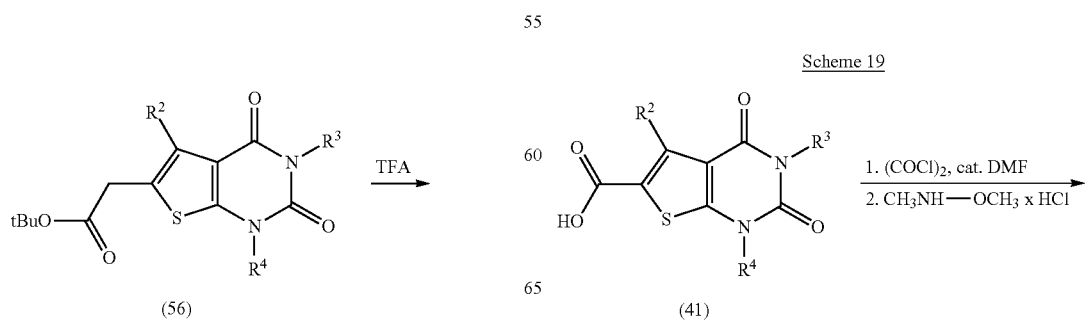

(56) → (41)

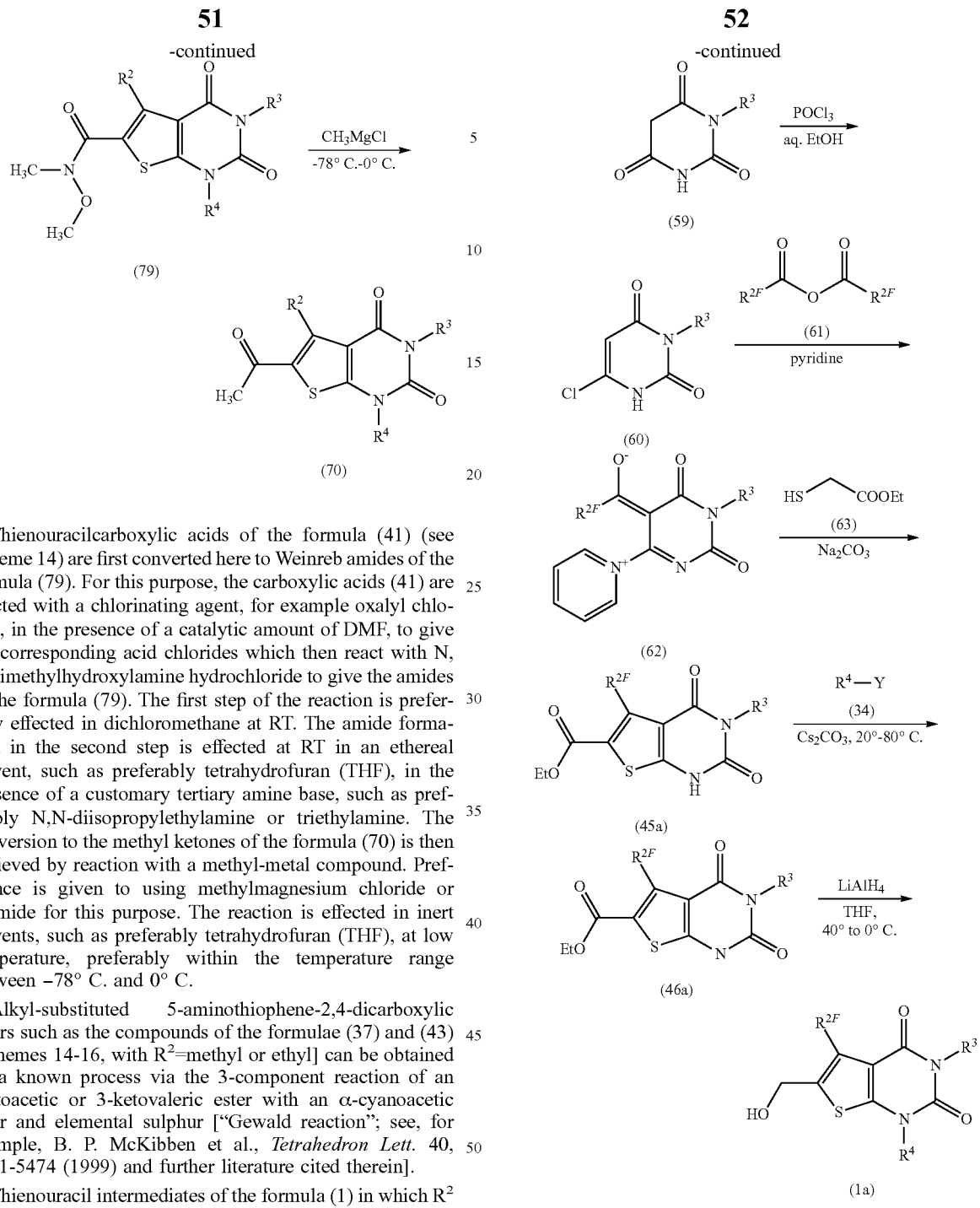

Thienouracilcarboxylic acids of the formula (41) (see Scheme 14) are first converted here to Weinreb amides of the formula (79). For this purpose, the carboxylic acids (41) are reacted with a chlorinating agent, for example oxalyl chloride, in the presence of a catalytic amount of DMF, to give the corresponding acid chlorides which then react with N,O-dimethylhydroxylamine hydrochloride to give the amides of the formula (79). The first step of the reaction is preferably effected in dichloromethane at RT. The amide formation in the second step is effected at RT in an ethereal solvent, such as preferably tetrahydrofuran (THF), in the presence of a customary tertiary amine base, such as preferably N,N-diisopropylethylamine or triethylamine. The conversion to the methyl ketones of the formula (70) is then achieved by reaction with a methyl-metal compound. Preference is given to using methylmagnesium chloride or bromide for this purpose. The reaction is effected in inert solvents, such as preferably tetrahydrofuran (THF), at low temperature, preferably within the temperature range between −78° C. and 0° C.

Alkyl-substituted 5-aminothiophene-2,4-dicarboxylic esters such as the compounds of the formulae (37) and (43) [Schemes 14-16, with $R^2$=methyl or ethyl] can be obtained by a known process via the 3-component reaction of an acetoacetic or 3-ketovaleric ester with an α-cyanoacetic ester and elemental sulphur ["Gewald reaction"; see, for example, B. P. McKibben et al., *Tetrahedron Lett.* 40, 5471-5474 (1999) and further literature cited therein].

Thienouracil intermediates of the formula (1) in which $R^2$ is difluoromethyl or trifluoromethyl are also obtainable in an advantageous manner by the process shown in Scheme 20 via the betaine compound (62):

Scheme 20

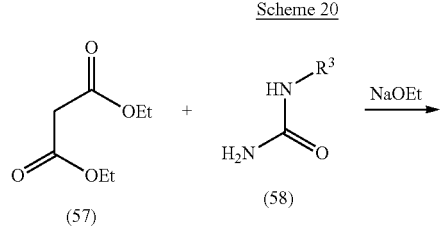

[$R^{2F}$ = CHF$_2$ or CF$_3$; Y = Cl, Br, I or OTs].

The process begins with a base-induced condensation of the malonic ester (57) with the urea derivative (58) to give the barbituric acid derivative of the formula (59). The condensation is typically effected with the aid of an alkali metal alkoxide such as sodium methoxide or potassium methoxide, sodium ethoxide or potassium ethoxide or sodium tert-butoxide or potassium tert-butoxide in the alcohol in question as solvent or with the aid of an alkali metal hydride such as sodium hydride or potassium hydride, in tetrahydrofuran or N,N-dimethylformamide as inert solvent; preference is given to using sodium ethoxide in ethanol. The reaction is generally conducted within a temperature range of +20° C. to +100° C. The conversion of the compound (59) to the 6-chloropyrimidinedione (60) is effected by treatment with excess phosphorus oxychloride in an aqueous alcohol such as methanol or ethanol as solvent within a temperature range of 0° C. to +100° C. The subsequent conversion to the pyridinium enolate betaine (62) is conducted analogously to a method described in the literature for synthesis of 3-substituted chromone derivatives [I. Yokoe et al., *Chem. Pharm. Bull.* 42 (8), 1697-1699 (1994)] by reacting the 6-chloropyrimidinedione (60) with the anhydride (61) in the presence of a relatively large excess of pyridine (about ten-fold). The reaction is generally effected within a temperature range of 0° C. to +40° C., and the inert solvent used is preferably acetonitrile. Bases suitable for the subsequent condensation of the betaine (62) with the mercaptoacetic ester (63) to give the thienouracils of the formula (45a) are especially alkali metal carbonates such as lithium carbonate, sodium carbonate, potassium carbonate or caesium carbonate, alkali metal alkoxides such as sodium methoxide or potassium methoxide, sodium ethoxide or potassium ethoxide or sodium tert-butoxide or potassium tert-butoxide, or alkali metal hydrides such as sodium hydride or potassium hydride; preference is given to using sodium carbonate or potassium carbonate [cf. also K. Hirota et al., *J. Heterocycl. Chem.* 27 (3), 717-721 (1990)]. The reaction is preferably conducted in an alcoholic solvent such as methanol, ethanol, isopropanol or tert-butanol, or in an inert polar-aprotic solvent such as N,N-dimethylformamide (DMF), N-methylpyrrolidinone (NMP) or N,N'-dimethylpropyleneurea (DMPU), within a temperature range of +20° C. to +150° C., and it has been found to be advantageous to run the reaction under microwave irradiation. The solvent used is preferably ethanol.

The alkylation of the compounds of the formula (45a) with the compounds of the formula (34) is effected analogously to the alkylation reactions already described in Scheme 13 and affords the ethyl esters of the formula (46a) which are converted in a final reduction with a complex metal hydride, for example lithium aluminium hydride, to the alcohols of the formula (1a). The reduction is typically conducted in an ethereal solvent, for example tetrahydrofuran (THF), and is generally effected within a temperature range of −40° C. to 0° C.

Thienouracil intermediates of the formula (1) in which $R^2$ is hydrogen can also be obtained by the process shown in Scheme 21:

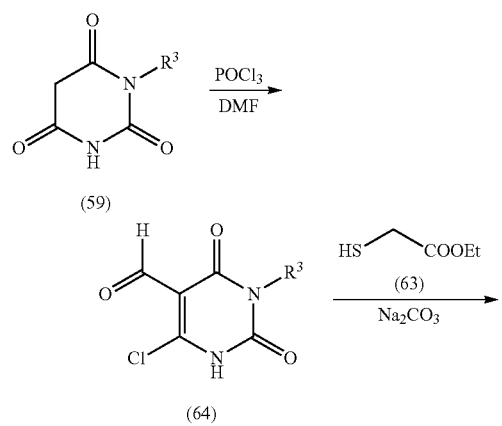

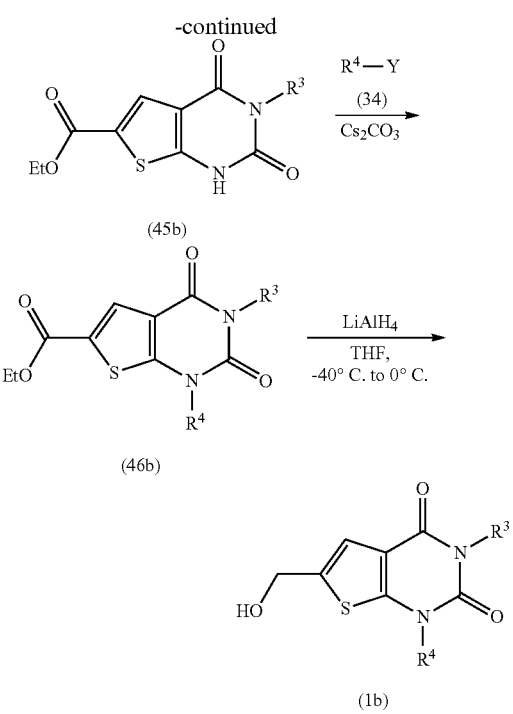

[Y = Cl, Br, I or OTs].

In this process, the barbituric acid derivative of the formula (59) (see Scheme 20) is first converted with a mixture of phosphorus oxychloride and N,N-dimethylformamide to a compound of the formula (64) and the latter is then condensed in the presence of a base with the mercaptoacetic ester (63) to give the thienouracil of the formula (45b). The conversion of the compound (59) to the 6-chloro-5-formylpyrimidinedione (64) is effected via a regioselective Vilsmeier-Haack reaction by treatment with a preformed mixture of phosphorus oxychloride and N,N-dimethylformamide which is used in a large excess and simultaneously also serves as solvent [cf., for example, K. Tanaka et al., *Chem. Pharm. Bull.* 35 (4), 1397-1404 (1987)]. The reaction is generally effected within a temperature range of +20° C. to +120° C. The subsequent reactions—the condensation to give the thienouracils of the formula (45b), the alkylation to give the compounds of the formula (46b) and the reduction to give the alcohols of the formula (1b)—are conducted analogously to the conditions as already described in Scheme 20.

The compounds of the formulae (2), (7), (9), (11), (12), (13), (14), (15), (16), (17), (18), (23), (27), (29), (30), (31), (34), (47), (52), (55), (57), (58), (61), (63), (65), (68), (74) and (76) detailed above are either commercially available or described as such in the literature, or they can be prepared from other commercially available compounds by literature methods familiar to those skilled in the art. Numerous detailed procedures and further literature references can also be found in the Experimental, in the section on the preparation of the starting compounds and intermediates.

The compounds of the invention have valuable pharmacological properties and can be used for prevention and treatment of diseases in humans and animals.

The compounds of the invention are potent and selective antagonists of the adenosine A2b receptor and are therefore suitable in particular for the treatment and/or prevention of disorders and pathological processes, especially those where the A2b receptor is involved in the course of an inflammatory event and/or tissue or vessel reconstruction.

In the context of the present invention, these include in particular disorders such as the group of the interstitial idiopathic pneumonias which includes idiopathic pulmonary fibrosis (IPF), acute interstitial pneumonia, non-specific interstitial pneumonias, lymphoid interstitial pneumonias, respiratory bronchiolitis with interstitial lung disease, cryptogenic organizing pneumonias, desquamative interstitial pneumonias and non-classifiable idiopathic interstitial pneumonias, furthermore granulomatous interstitial lung diseases, interstitial lung diseases of known aetiology and other interstitial lung diseases of unknown aetiology, pulmonary arterial hypertension (PAH) and other forms of pulmonary hypertension (PH), bronchiolitis obliterans syndrome (BOS), chronic-obstructive pulmonary disease (COPD), acute respiratory distress syndrome (ARDS), acute lung injury (ALI), alpha-1-antitrypsin deficiency (AATD), pulmonary emphysema (for example pulmonary emphysema induced by cigarette smoke), cystic fibrosis (CF), inflammatory and fibrotic disorders of the kidney, chronic intestinal inflammations (IBD, Crohn's disease, ulcerative colitis), peritonitis, peritoneal fibrosis, rheumatoid disorders, multiple sclerosis, inflammatory and fibrotic skin disorders, sickle cell anaemia and inflammatory and fibrotic eye disorders.

The compounds of the invention can additionally be used for treatment and/or prevention of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of bronchiectasis, pneumonia, farmer's lung and related disorders, coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

In addition, the compounds of the invention can be used for the treatment and/or prevention of cardiovascular disorders such as, for example, high blood pressure (hypertension), heart failure, coronary heart disease, stable and unstable angina pectoris, renal hypertension, peripheral and cardiac vascular disorders, arrhythmias, atrial and ventricular arrhythmias and impaired conduction such as, for example, atrioventricular blocks degrees I-III, supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, furthermore for the treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, micro- and macrovascular damage (vasculitis), and also to prevent restenoses, for example after thrombolysis therapies, percutaneous transluminal angioplasties (PTA), percutaneous transluminal coronary angioplasties (PTCA), heart transplants and bypass operations.

In the context of the present invention, the term "heart failure" encompasses both acute and chronic forms of heart failure, and also specific or related disease types thereof, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders and diastolic and systolic heart failure.

The compounds of the invention are also suitable for the treatment and/or prevention of renal disorders, in particular renal insufficiency and kidney failure. In the context of the present invention, the terms "renal insufficiency" and "kidney failure" encompass both acute and chronic manifestations thereof and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immuno-complex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or need for dialysis. The present invention also encompasses the use of the compounds of the invention for the treatment and/or prevention of sequelae of renal insufficiency, for example hypertension, pulmonary oedema, heart failure, uraemia, anaemia, electrolyte disturbances (for example hyperkalaemia, hyponatraemia) and disturbances in bone and carbohydrate metabolism.

In addition, the compounds of the invention are suitable for the treatment and/or prevention of disorders of the urogenital system such as, for example, benign prostate syndrome (BPS), benign prostate hyperplasia (BPH), benign prostate enlargement (BPE), bladder outlet obstruction (BOO), lower urinary tract syndromes (LUTS), neurogenic overactive bladder (OAB), incontinence such as, for example, mixed urinary incontinence, urge urinary incontinence, stress urinary incontinence or overflow urinary incontinence (MUI, UUI, SUI, OUI), pelvic pain, and also erectile dysfunction and female sexual dysfunction.

In addition, the compounds of the invention have antiinflammatory action and can therefore be used as antiinflammatory agents for treatment and/or prevention of sepsis (SIRS), multiple organ failure (MODS, MOF), inflammatory disorders of the kidney, chronic intestinal inflammations (IBD, Crohn's disease, ulcerative colitis), pancreatitis, peritonitis, cystitis, urethritis, prostatitis, epidimytitis, oophoritis, salpingitis, vulvovaginitis, rheumatoid disorders, inflammatory disorders of the central nervous system, multiple sclerosis, infammatory skin disorders and inflammatory eye disorders.

Furthermore, the compounds of the invention are suitable for treatment and/or prevention of fibrotic disorders of the internal organs, for example the lung, the heart, the kidney, the bone marrow and in particular the liver, and also dermatological fibroses and fibrotic eye disorders. In the context of the present invention, the term "fibrotic disorders" includes in particular disorders such as hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis, peritoneal fibrosis and similar fibrotic disorders, scleroderma, morphoea, keloids, hypertrophic scarring, naevi, diabetic retinopathy, proliferative vitroretinopathy and disorders of the connective tissue (for example sarcoidosis). The compounds of the invention can likewise be used for promoting wound healing, for controlling postoperative scarring, for example as a result of glaucoma operations and cosmetically for ageing or keratinized skin.

The compounds of the invention can also be employed for the treatment and/or prevention of anaemias such as haemolytic anaemias, in particular haemoglobinopathies such as sickle cell anaemia and thalassaemias, megaloblastic anaemias, iron deficiency anaemias, anaemias owing to acute blood loss, displacement anaemias and aplastic anaemias.

Moreover, the compounds according to the invention are suitable for the treatment of cancers such as, for example, skin cancer, brain tumours, head and neck tumours, oesophageal cancer, breast cancer, bone marrow tumours, leukaemias, liposarcomas, carcinomas of the gastrointestinal tract, of the liver, the pancreas, the lung, the kidney, the ureter, the prostate and the genital tract, bladder cancer and also of malignant tumours of the lymphoproliferative system, for example Hodgkin and Non-Hodgkin lymphoma.

In addition, the compounds of the invention can be used for treatment and/or prevention of arteriosclerosis, impaired lipid metabolism and dyslipidaemias (hypolipoproteinaemia, hypertriglyceridaemias, hyperlipidaemia, combined hyperlipidaemias, hypercholesterolaemia, abetalipoproteinaemia, sitosterolaemia), xanthomatosis, Tangier disease, adiposity, obesity, metabolic disorders (metabolic syndrome, hyperglycaemia, insulin-dependent diabetes, non-insulin-dependent diabetes, gestational diabetes, hyperinsulinaemia, insulin resistance, glucose intolerance and diabetic sequelae, such as retinopathy, nephropathy and neuropathy), of disorders of the gastrointestinal tract and the abdomen (glossitis, gingivitis, periodontitis, oesophagitis, eosinophilic gastroenteritis, mastocytosis, Crohn's disease, colitis, proctitis, anus pruritis, diarrhoea, coeliac disease, hepatitis, hepatic fibrosis, cirrhosis of the liver, pancreatitis and cholecystitis), of disorders of the central nervous system and neurodegenerative disorders (stroke, Alzheimer's disease, Parkinson's disease, dementia, epilepsy, depressions, multiple sclerosis), immune disorders, thyroid disorders (hyperthyreosis), skin disorders (psoriasis, acne, eczema, neurodermitis, various forms of dermatitis, for example dermatitis abacribus, actinic dermatitis, allergic dermatitis, ammonia dermatitis, facticial dermatitis, autogenic dermatitis, atopic dermatitis, dermatitis calorica, dermatitis combustionis, dermatitis congelationis, dermatitis cosmetica, dermatitis escharotica, exfoliative dermatitis, dermatitis gangraenose, stasis dermatitis, dermatitis herpetiformis, lichenoid dermatitis, dermatitis linearis, dermatitis maligna, medicinal eruption dermatitis, dermatitis palmaris and plantaris, parasitic dermatitis, photoallergic contact dermatitis, phototoxic dermatitis, dermatitis pustularis, seborrhoeic dermatitis, sunburn, toxic dermatitis, Meleney's ulcer, dermatitis veneata, infectious dermatitis, pyogenic dermatitis and rosacea-like dermatitis, and also keratitis, bullosis, vasculitis, cellulitis, panniculitis, lupus erythematosus, erythema, lymphomas, skin cancer, Sweet syndrome, Weber-Christian syndrome, scar formation, wart formation, chilblains), of inflammatory eye diseases (saccoidosis, blepharitis, conjunctivitis, iritis, uveitis, chorioiditis, ophthalmitis), viral diseases (caused by influenza, adeno- and coronaviruses, for example HPV, HCMV, HIV, SARS), of disorders of the skeletal bone and the joints and also the skeletal muscle (various forms of arthritis, for example arthritis alcaptonurica, arthritis ankylosans, arthritis dysenterica, arthritis exsudativa, arthritis fungosa, arthritis gonorrhoica, arthritis mutilans, arthritis psoriatica, arthritis purulenta, arthritis rheumatica, arthritis serosa, arthritis syphilitica, arthritis tuberculosa, arthritis urica, arthritis villonodularis pigmentosa, atypical arthritis, haemophilic arthritis, juvenile chronic arthritis, rheumatoid arthritis and metastatic arthritis, and additionally Still syndrome, Felty syndrome, Sjörgen syndrome, Clutton syndrome, Poncet syndrome, Pott syndrome and Reiter syndrome, various forms of arthropathy, for example arthropathie deformans, arthropathie neuropathica, arthropathie ovaripriva, arthropathie psoriatica and arthropathie tabica, systemic scleroses, various forms of inflammatory myopathy, for example myopathie epidemica, myopathie fibrosa, myopathie myoglobinurica, myopathie ossificans, myopathie ossificans neurotica, myopathie ossificans progressiva multiplex, myopathie purulenta, myopathie rheumatica, myopathie trichinosa, myopathie tropica and myopathie typhosa, and also Giinther syndrome and Miinchmeyer syndrome), of inflammatory changes of the arteries (various forms of arteritis, for example endarteritis, mesarteritis, periarteritis, panarteritis, arteritis rheumatica, arteritis deformans, arteritis temporalis, arteritis cranialis, arteritis gigantocellularis and arteritis granulomatosa, and also Horton syndrome, Churg-Strauss syndrome and Takayasu arteritis), of Muckle-Well syndrome, of Kikuchi disease, of polychondritis, dermatosclerosis and also other disorders having an inflammatory or immunological component, for example cataract, cachexia, osteoporosis, gout, incontinence, leprosy, Sezary syndrome and paraneoplastic syndrome, for rejection reactions after organ transplants and for wound healing and angiogenesis, especially in the case of chronic wounds.

Because of their profile of properties, the compounds of the invention are particularly suitable for the treatment and/or prevention of interstitial lung diseases, especially idiopathic pulmonary fibrosis (IPF), and also of pulmonary hypertension (PH), bronchiolitis obliterans syndrome (BOS), chronic obstructive pulmonary disease (COPD), asthma, cystic fibrosis (CF), myocardial infarction, heart failure and haemoglobinopathies, in particular sickle cell anaemia.

The aforementioned well-characterized diseases in humans can also occur with comparable aetiology in other mammals and can likewise be treated therein with the compounds of the present invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is used here synonymously with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention thus further provides for the use of the compounds of the invention for treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides a medicament comprising at least one of the compounds of the invention for treatment and/or prevention of disorders, especially of the aforementioned disorders.

The present invention further provides for the use of the compounds of the invention in a method for treatment and/or prevention of disorders, especially of the aforementioned disorders.

The present invention further provides a method for treatment and/or prevention of disorders, especially of the aforementioned disorders, using an effective amount of at least one of the compounds of the invention.

The compounds of the invention can be used alone or, if required, in combination with one or more other pharmacologically active substances, provided that this combination does not lead to undesirable and unacceptable side effects. Accordingly, the present invention further provides medicaments comprising at least one of the compounds of the invention and one or more further active ingredients, especially for treatment and/or prevention of the aforementioned disorders. Preferred examples of combination active ingredients suitable for the purpose include:

organic nitrates and NO donors, for example sodium nitroprusside, nitroglycerin, isosorbide mononitrate, isosorbide dinitrate, molsidomine or SIN-1, and inhaled NO;

compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil, tadalafil, udenafil, dasantafil, avanafil, mirodenafil or lodenafil;

NO- and haem-independent activators of soluble guanylate cyclase (sGC), such as in particular the compounds described in WO 01/19355, WO 01/19776, WO 01/19778, WO 01/19780, WO 02/070462 and WO 02/070510;

NO-independent but haem-dependent stimulators of soluble guanylate cyclase (sGC), such as in particular riociguat, nelociguat and vericiguat, and the compounds described in WO 00/06568, WO 00/06569, WO 02/42301, WO 03/095451, WO 2011/147809, WO 2012/004258, WO 2012/028647 and WO 2012/059549;

prostacyclin analogues and IP receptor agonists, by way of example and with preference iloprost, beraprost, treprostinil, epoprostenol or selexipag;

endothelin receptor antagonists, by way of example and with preference bosentan, darusentan, ambrisentan or sitaxsentan;

compounds which inhibit human neutrophile elastase (HNE), by way of example and with preference sivelestat or DX-890 (reltran);

compounds which inhibit the signal transduction cascade, by way of example and with preference from the group of the kinase inhibitors, in particular from the group of the tyrosine kinase and/or serine/threonine kinase inhibitors, by way of example and with preference nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;

compounds which inhibit the degradation and alteration of the extracellular matrix, by way of example and with preference inhibitors of the matrix metalloproteases (MMPs), especially inhibitors of stromelysin, collagenases, gelatinases and aggrecanases (in this context particularly of MMP-1, MMP-3, MMP-8, MMP-9, MMP-10, MMP-11 and MMP-13) and of metalloelastase (MMP-12);

compounds which block the binding of serotonin to its receptors, by way of example and with preference antagonists of the 5-$HT_{2B}$ receptor such as PRX-08066;

antagonists of growth factors, cytokines and chemokines, by way of example and with preference antagonists of TGF-β, CTGF, IL-1, IL-4, IL-5, IL-6, IL-8, IL-13 and integrins;

Rho kinase-inhibiting compounds, by way of example and with preference fasudil, Y-27632, SLx-2119, BF-66851, BF-66852, BF-66853, KI-23095 or BA-1049;

compounds which inhibit soluble epoxide hydrolase (sEH), for example N,N'-dicyclohexylurea, 12-(3-adamantan-1-ylureido)dodecanoic acid or 1-adamantan-1-yl-3-{5-[2-(2-ethoxyethoxy)ethoxy]pentyl}urea;

compounds which influence the energy metabolism of the heart, by way of example and with preference etomoxir, dichloroacetate, ranolazine or trimetazidine;

anti-obstructive agents as used, for example, for treatment of chronic obstructive pulmonary disease (COPD) or bronchial asthma, by way of example and with preference from the group of the inhalatively or systemically administered agonists of the beta-adrenergic receptor (beta-mimetics) and the inhalatively administered antimuscarinergic substances;

antiinflammatory, immunomodulating, immunosuppressive and/or cytotoxic agents, by way of example and with preference from the group of the systemically or inhalatively administered corticosteroids and also acetylcysteine, montelukast, tipelukast, azathioprine, cyclophosphamide, hydroxycarbamide, azithromycin, IFN-γ, pirfenidone or etanercept;

antifibrotic agents, by way of example and with preference pirfenidone, lysophosphatidic acid receptor 1 (LPA-1) antagonists, sphingosine-1-phosphate receptor 3 (S1P3) antagonists, autotaxin inhibitors, FP receptor antagonists, lysyl oxidase (LOX) inhibitors, lysyl oxidase-like-2 inhibitors, vasoactive intestinal peptidw (VIP), VIP analogues, $α_vβ_6$-integrin antagonists, interferons, KCa3.1 blockers, CTGF inhibitors, IL-4 antagonists, IL-13 antagonists, TGF-β antagonists, inhibitors of the WNT signalling pathway or CCR2 antagonists;

therapeutic antibodies and antibody-active ingredient conjugates, by way of example and with preference bevacizumab, cetuximab, trastuzumab, trastuzumab emtansin, brentuximab vedotin or anetumab ravtansin;

immunotherapeutic antibodies, by way of example and with preference ipilimumab, nivolumab, pembrolizumab, pidilizumab, BMS-935559, MPDL3280A, MEDI4736, MSB0010718C or AMP-224;

antithrombotic agents, by way of example and with preference from the group of platelet aggregation inhibitors, the anticoagulants and the profibrinolytic substances;

hypotensive active ingredients, by way of example and with preference from the group of the calcium antagonists, angiotensin AII antagonists, ACE inhibitors, vasopeptidase inhibitors, endothelin antagonists, renin inhibitors, alpha receptor blockers, beta receptor blockers, mineralocorticoid receptor antagonists and also the diuretics;

lipid metabolism modifiers, by way of example and with preference from the group of the thyroid receptor agonists, cholesterol synthesis inhibitors, by way of example and with preference HMG-CoA reductase or squalene synthesis inhibitors, of the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists; and/or chemotherapeutics as used, for example, for treatment of neoplasms in the lung or other organs.

In a preferred embodiment of the invention, the compounds of the invention are administered in combination with a beta-adrenergic receptor agonist, by way of example and with preference albuterol, isoproterenol, metaproterenol, terbutalin, fenoterol, formoterol, reproterol, salbutamol or salmeterol.

In a preferred embodiment of the invention, the compounds of the invention are administered in combination with an antimuscarinergic substance, by way of example and with preference ipratropium bromide, tiotropium bromide or oxitropium bromide.

In a preferred embodiment of the invention, the compounds of the invention are administered in combination with a corticosteroid, by way of example and with preference prednisone, prednisolone, methylprednisolone, triamcinolone, dexamethasone, beclomethasone, betamethasone, flunisolide, budesonide or fluticasone.

Antithrombotic agents are preferably understood to mean compounds from the group of the platelet aggregation inhibitors, the anticoagulants and the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, melagatran, dabigatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds of the invention are administered in combination with a factor Xa inhibitor, by way of example and with preference rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an alpha-1-receptor blocker, by way of example and with preference prazosin.

In a preferred embodiment of the invention, the compounds of the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with an angiotensin AII antagonist, by way of example and with preference losartan, candesartan, valsartan, telmisartan, irbesartan, olmesartan, eprosartan or azilsartan.

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone, eplerenone or finerenone.

In a preferred embodiment of the invention, the compounds of the invention are administered in combination with a diuretic, by way of example and with preference furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein(a) antagonists.

In a preferred embodiment of the invention, the compounds of the invention are administered in combination with a CETP inhibitor, by way of example and with preference torcetrapib (CP-529 414), JJT-705 or CETP vaccine (Avant).

In a preferred embodiment of the invention, the compounds of the invention are administered in combination with a thyroid receptor agonist such as, for example and preferably, D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds of the invention are administered in combination with a PPAR-gamma agonist, by way of example and with preference pioglitazone or rosiglitazone.

In a preferred embodiment of the invention, the compounds of the invention are administered in combination with a PPAR-delta agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorbent, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

Particular preference is given to combinations of the compounds of the invention with one or more further active ingredients selected from the group consisting of PDE 5 inhibitors, sGC activators, sGC stimulators, prostacyclin analogues, IP receptor agonists, endothelin antagonists, antifibrotic agents, antiinflammatory, immunomodulating, immunosuppressant and/or cytotoxic agents and/or compounds that inhibit the signal transduction cascade.

The present invention further provides medicaments which comprise at least one compound of the invention, typically together with one or more inert, nontoxic, pharmaceutically suitable excipients, and for the use thereof for the aforementioned purposes.

The compounds of the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds of the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. inhalatively, intramuscularly, subcutaneously, intracutaneously, percutaneously or intraperitoneally). Administration forms suitable for parenteral administration include preparations for injection and infusion in the form of solutions, suspensions, emulsions, lyophilisates or sterile powders.

For the other administration routes, suitable examples are inhalable medicament forms (including powder inhalers, nebulizers, metered aerosols), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral and parenteral administration are preferred, especially oral, intravenous and intrapulmonary (inhalative) administration.

The compounds of the invention can be converted to the administration forms mentioned. This can be accomplished in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight. In the case of intrapulmonary administration, the amount is generally about 0.1 to 50 mg per inhalation.

It may nevertheless be necessary in some cases to deviate from the stated amounts, specifically as a function of the body weight, route of administration, individual response to the active ingredient, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not restricted to the examples.

A. Examples
Abbreviations and Acronyms:
abs. absolute
Ac acetyl
aq. aqueous, aqueous solution
Boc tert-butoxycarbonyl
br. broad (in NMR signal)
Ex. Example
Bu butyl
c concentration
ca. circa, about
cat. catalytic
CDI N,N'-carbonyldiimidazole
CI chemical ionization (in MS)
conc. concentrated, concentrated solution
d doublet (in NMR)
d day(s)
DAD diode array detector (in HPLC)
dba dibenzylideneacetone
DBU diazabicyclo[5.4.0]undec-7-ene
TLC thin-layer chromatography
DCI direct chemical ionization (in MS)
dd doublet of doublets (in NMR)
DEAD diethyl azodicarboxylate
DIAD diisopropyl azodicarboxylate
DIPEA N,N-diisopropylethylamine
DME 1,2-dimethoxyethane
DMF N,N-dimethylformamide
DMSO dimethyl sulphoxide
dq doublet of quartets (in NMR)
dt doublet of triplets (in NMR)
ΔT temperature increase, heating (of a reaction mixture)
of th. of theory (in chemical yield)
ee enantiomeric excess
EI electron impact ionization (in MS)
eq. equivalent(s)
ESI electrospray ionization (in MS)
Et ethyl
GC gas chromatography
GC/MS gas chromatography-coupled mass spectrometry
h hour(s)
HPLC high-pressure, high-performance liquid chromatography
iPr isopropyl
conc. concentrated (in the case of a solution)
LC liquid chromatography
LC/MS liquid chromatography-coupled mass spectrometry
LiHMDS lithium hexamethyldisilazide
Lit. literature (reference)
m multiplet (in NMR)
Me methyl
min minute(s)
MPLC medium-pressure liquid chromatography (on silica gel; also referred to as flash chromatography)
MS mass spectrometry
NBS N-bromosuccinimide
NMM N-methylmorpholine
NMO N-methylmorpholine N-oxide
NMP N-methyl-2-pyrrolidinone
NMR nuclear magnetic resonance spectrometry
Pd/C palladium on activated carbon
PEG polyethylene glycol
Ph phenyl
Pr propyl
q quartet (in NMR)
Q-Phos 1,2,3,4,5-pentaphenyl-1'-(di-tert-butylphosphino)ferrocene
quant. quantitative (in chemical yield)
quin quintet (in NMR)
$R_f$ retention index (in TLC)
RP reverse phase (in HPLC)
RT room temperature
$R_t$ retention time (in HPLC, LC/MS)
s singlet (in NMR)
sept septet (in NMR)
sext sextet (in NMR)
SFC supercritical liquid chromatography
t triplet (in NMR)
TBME tert-butyl methyl ether
tBu tert-butyl
TFA trifluoroacetic acid
THF tetrahydrofuran
TMS tetramethylsilane
Ts para-toluenesulphonyl
UV ultraviolet spectrometry
v/v volume to volume ratio (of a solution)
tog. together
HPLC, LC/MS and GC/MS Methods:
Method 1 (LC/MS):
Instrument: Waters Acquity SQD UPLC System; column: Waters Acquity UPLC HSS T3 1.8 μm 50 mm×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; temperature: 50° C.; flow rate: 0.40 ml/min; UV detection: 210-400 nm.
Method 2 (LC/MS):
Instrument: Waters Acquity SQD UPLC System; column: Waters Acquity UPLC HSS T3 1.8 μm 50 mm×1 mm; eluent A: 1 l water+0.25 ml 99% formic acid, eluent B: 1 l acetonitrile+0.25 ml 99% formic acid; gradient: 0.0 min 95% A→6.0 min 5% A→7.5 min 5% A; temperature: 50° C.; flow rate: 0.35 ml/min; UV detection: 210-400 nm.

Method 3 (LC/MS):

Instrument: Waters Acquity UPLC-MS SingleQuad; column: Waters Acquity UPLC BEH C18 1.7 µm 50 mm×2.1 mm; eluent A: water+0.1% by vol. of formic acid (99%), eluent B: acetonitrile; gradient: 0.0-1.6 min 1-99% B, 1.6-2.0 min 99% B; flow rate: 0.8 ml/min; temperature: 60° C.; DAD scan: 210-400 nm.

Method 4 (LC/MS):

Instrument: Micromass Quattro Premier with Waters UPLC Acquity; column: Thermo Hypersil GOLD 1.9 µ50×1 mm; eluent A: 1 l water+0.5 ml 50% formic acid, eluent B: 1 l acetonitrile+0.5 ml 50% formic acid; gradient: 0.0 min 97% A→0.5 min 97% A→3.2 min 5% A→4.0 min 5% A; temperature: 50° C.; flow rate: 0.30 ml/min; UV detection: 210 nm.

Method 5 (LC/MS):

Instrument: Agilent MS Quad 6150 with HPLC Agilent 1290; column: Waters Acquity UPLC HSS T3 1.8 µm 50 mm×2.1 mm; eluent A: 1 l water+0.25 ml 99% formic acid, eluent B: 1 l acetonitrile+0.25 ml 99% formic acid; gradient: 0.0 min 90% A→0.3 min 90% A→1.7 min 5% A→3.0 min 5% A; flow rate: 1.20 ml/min; temperature: 50° C.; UV detection: 205-305 nm.

Method 6 (LC/MS):

Instrument: Waters Micromass Quattro Micro with HPLC Waters UPLC Acquity; column: Waters BEH C18 1.7 µm, 50 mm×2.1 mm; eluent A: 1 l water+0.01 mol ammonium formate, eluent B: 1 l acetonitrile; gradient: 0.0 min 95% A→0.1 min 95% A→2.0 min 15% A→2.5 min 15% A→2.51 min 10% A→3.0 min 10% A; flow rate: 0.5 ml/min; temperature: 40° C.; UV detection: 210 nm.

Method 7 (GC-MS):

Instrument: Thermo DFS, Trace GC Ultra; column: Restek RTX-35, 15 m×200 µm×0.33 µm; constant flow rate of helium: 1.20 ml/min; oven: 60° C.; inlet: 220° C.; gradient: 60° C., 30° C./min→300° C. (hold for 3.33 min).

Method 8 (Preparative HPLC):

Column: Chromatorex C18, 10 µm, 125 mm×30 mm; eluent: acetonitrile/water with 0.1% formic acid; gradient: 20:80→95:5 within 20 min.

Method 9 (Preparative HPLC):

Column: Chromatorex C18, 10 µm, 125 mm×30 mm; eluent: acetonitrile/water with 0.1% formic acid; gradient: 30:70→95:5 within 20 min.

Method 10 (Preparative HPLC):

Column: Chromatorex C18, 10 µm, 125 mm×30 mm; eluent A: water+0.05% trifluoroacetic acid, eluent B: acetonitrile+0.05% trifluoroacetic acid; gradient: 0.0 min 75% A→5.0 min 75% A→7.0 min 60% A→16 min 45% A→18 min 45% A.

Method 11 (Preparative HPLC):

Column: Chromatorex C18, 10 µm, 125 mm×30 mm; eluent: acetonitrile/water with 0.1% formic acid; gradient: 15:85→95:5 within 20 min.

Method 12 (Preparative HPLC):

Column: Reprosil-Pur C18, 10 µm, 125 mm×30 mm; eluent: acetonitrile/water with 0.05% trifluoroacetic acid; gradient: 10:90→100:0 within 12 min.

Method 13 (Preparative HPLC):

Column: Reprosil-Pur C18, 10 µm, 125 mm×30 mm; eluent: acetonitrile/water with 0.05% trifluoroacetic acid; gradient: 30:70→100:0 within 18 min.

Method 14 (Preparative HPLC):

Column: Chromatorex C18, 10 µm, 125 mm×30 mm; eluent: acetonitrile/water with 0.1% formic acid; gradient: 10:90→100:0 within 10 min.

Method 15 (Preparative HPLC):

Column: Chromatorex C18, 10 µm, 290 mm×100 mm; eluent A: acetonitrile, eluent B: water; gradient: 0-5 min 10% A, 5-30 min 10%→55% A, 30-32 min 55% A, 32-35.4 min 90% A.

Method 16 (Preparative HPLC):

Instrument: Agilent 1260; column: Phenomenex Luna 5 µm C18, 100 mm×21.2 mm; eluent A: water+0.1% formic acid, eluent B: acetonitrile; gradient: 0.0 min 20% B→1 min 20% B→10 min 80% B→12 min 95% B→18 min 95% B→18.1 min 20% B→20 min 20% B; flow rate: 25 ml/min; UV detection: 210 nm.

Method 17 (LC/MS):

Instrument MS: Thermo Scientific FT-MS; UHPLC instrument: Thermo Scientific UltiMate 3000; column: Waters HSST3 C18 1.8 µm, 75 mm×2.1 mm; eluent A: 1 l water+0.01% formic acid, eluent B: 1 l acetonitrile+0.01% formic acid; gradient: 0.0 min 10% B→2.5 min 95% B→3.5 min 95% B; temperature: 50° C.; flow rate: 0.90 ml/min; UV detection: 210-300 nm.

Method 18 (Preparative HPLC):

Column: Chromatorex C18, 10 µm, 250 mm×30 mm; eluent: acetonitrile/water with 0.1% trifluoroacetic acid; gradient: 10:90→95:5 within 30 min.

Further Details:

The descriptions of the coupling patterns of $^1$H NMR signals which follow are guided by the visual appearance of the signals in question and do not necessarily correspond to a strict, physically correct interpretation. In general, the stated chemical shift refers to the centre of the signal in question; in the case of broad multiplets, an interval is generally given.

Melting points and melting-point ranges, if stated, are uncorrected.

In cases where the reaction products were obtained by trituration, stirring or recrystallization, it was frequently possible to isolate further amounts of product from the respective mother liquor by chromatography. However, a description of this chromatography is dispensed with hereinbelow unless a large part of the total yield could only be isolated in this step.

All reactants or reagents whose preparation is not described explicitly hereinafter were purchased commercially from generally accessible sources. For all other reactants or reagents whose preparation is likewise not described hereinafter and which were not commercially obtainable or were obtained from sources which are not generally accessible, a reference is given to the published literature in which their preparation is described.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, for example "hydrochloride", "formate", "acetate", "trifluoroacetate", "sodium salt" or "x HCl", "x HCOOH", "x $CH_3COOH$", "x $CF_3COOH$", "x Na" should therefore not be understood in a stoichiometric sense in the case of such salts, but are merely of descriptive character with regard to the salt-forming components present.

STARTING COMPOUNDS AND INTERMEDIATES

Example 1A 2-tert-Butyl 4-ethyl 5-amino-3-methylthiophene-2,4-dicarboxylate

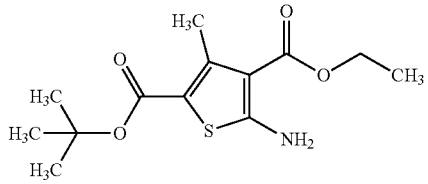 [SMILES: CCOC(=O)c1c(N)sc(C(=O)OC(C)(C)C)c1C]

10.0 g (63.2 mmol) of tert-butyl acetoacetate, 7.15 g (63.2 mmol) of ethyl cyanoacetate and 2.23 g (69.5 mmol) of sulphur were initially charged in 15 ml of ethanol and warmed to 45° C. 7.5 ml (72.7 mmol) of diethylamine were added dropwise to this mixture. The reaction mixture was then stirred at 65° C. for 8 h. All the volatile constituents were then removed on a rotary evaporator. About 500 ml of water were added to the remaining residue, and the mixture was extracted three times with in each case about 200 ml of ethyl acetate. The combined organic extracts were washed with about 200 ml of saturated sodium chloride solution and dried over anhydrous magnesium sulphate. After filtration, the mixture was evaporated to dryness. The crude product obtained was purified by MPLC (about 300 g of silica gel, cyclohexane/ethyl acetate 10:1). After combination of the product fractions, evaporation and drying of the residue under high vacuum, 9.72 g (52% of theory) of the title compound were obtained.

$^1$H-NMR (400 MHz, CDCl$_3$, δ/ppm): 6.44 (br. s, 2H), 4.31 (q, 2H), 2.66 (s, 3H), 1.54 (s, 9H), 1.37 (t, 3H).

LC/MS (Method 1, ESIpos): R$_t$=1.20 min, m/z=286 [M+H]$^+$.

Example 2A 2-tert-Butyl 4-ethyl 3-methyl-5-{[(2-phenylethyl)carbamoyl]amino}thiophene-2,4-dicarboxylate

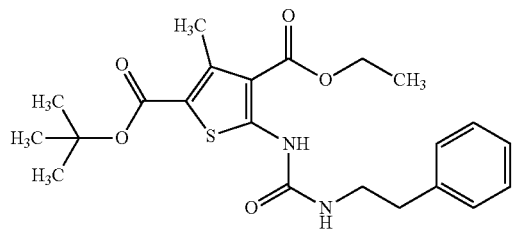 [SMILES: CCOC(=O)c1c(NC(=O)NCCc2ccccc2)sc(C(=O)OC(C)(C)C)c1C]

10.0 g (35.0 mmol) of 2-tert-butyl 4-ethyl 5-amino-3-methylthiophene-2,4-dicarboxylate (Example 1A) were dissolved in 500 ml of dichloromethane and 11.4 g (70.1 mmol) of N,N'-carbonyldiimidazole (CDI) and 19.6 ml (140 mmol) of triethylamine were added. The reaction mixture was stirred at RT for 2 days, after which 8.8 ml (70.1 mmol) of 2-phenethylamine were added. After stirring at RT for a further 2 h, the mixture was evaporated to dryness on a rotary evaporator. The remaining residue was purified by MPLC (silica gel, cyclohexane/ethyl acetate 20:1→10:1). After evaporation of the product fractions and drying of the residue under high vacuum, 14.4 g (95% of theory) of the title compound were obtained.

$^1$H-NMR (400 MHz, DMSO-d$_6$, δ/ppm): 10.54 (s, 1H), 8.17 (t, 1H), 7.33-7.29 (m, 2H), 7.26-7.19 (m, 3H), 4.30 (q, 2H), 3.36 (q, 2H), 2.77 (t, 2H), 2.62 (s, 3H), 1.50 (s, 9H), 1.32 (t, 3H).

LC/MS (Method 1, ESIpos): R$_t$=1.43 min, m/z=433 [M+H]$^+$.

Example 3A 2-tert-Butyl 4-ethyl 5-[(ethylcarbamoyl)amino]-3-methylthiophene-2,4-dicarboxylate

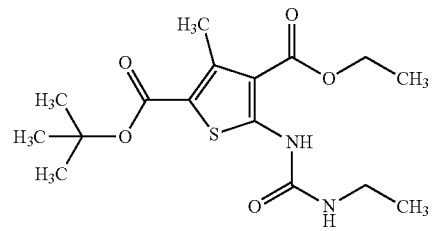 [SMILES: CCNC(=O)Nc1sc(C(=O)OC(C)(C)C)c(C)c1C(=O)OCC]

6.0 g (21.0 mmol) of 2-tert-butyl 4-ethyl 5-amino-3-methylthiophene-2,4-dicarboxylate (Example 1A) were dissolved in 300 ml of dichloromethane and 6.82 g (42.1 mmol) of CDI and 11.7 ml (84.1 mmol) of triethylamine were added. The reaction mixture was stirred at RT for 2 days, after which 42 ml (84.1 mmol) of a 2 M solution of ethylamine in THF were added. After stirring at RT for a further 2 h, the mixture was evaporated to dryness on a rotary evaporator. The remaining residue was purified by MPLC (Biotage cartridge with 340 g of silica gel, cyclohexane/ethyl acetate 10:1→5:1). After evaporation of the product fractions and drying of the residue under high vacuum, 6.98 g (93% of theory) of the title compound were obtained.

$^1$H-NMR (400 MHz, DMSO-d$_6$, δ/ppm): 10.52 (br. s, 1H), 8.06 (br. t, 1H), 4.31 (q, 2H), 3.13 (dq, 2H), 2.77 (t, 2H), 2.62 (s, 3H), 1.50 (s, 9H), 1.32 (t, 3H), 1.07 (t, 3H).

LC/MS (Method 1, ESIpos): R$_t$=1.26 min, m/z=357 [M+H]$^+$.

Example 4A 2-tert-Butyl 4-ethyl 5-{[(2,4-dimethoxybenzyl)carbamoyl]amino}-3-methylthiophene-2,4-dicarboxylate

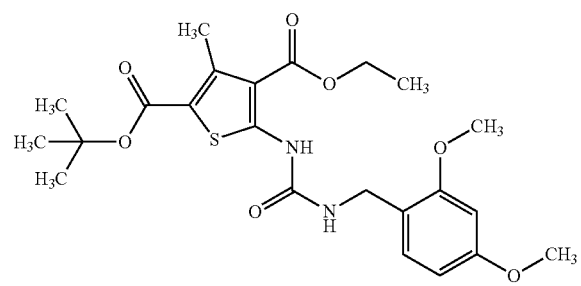 [SMILES: CCOC(=O)c1c(NC(=O)NCc2ccc(OC)cc2OC)sc(C(=O)OC(C)(C)C)c1C]

8.78 g (30.8 mmol) of 2-tert-butyl 4-ethyl 5-amino-3-methylthiophene-2,4-dicarboxylate (Example 1A) were dissolved in 300 ml of dichloromethane and 9.98 g (61.5 mmol) of CDI and 17.2 ml (123 mmol) of triethylamine were added. The reaction mixture was stirred at RT for 2 days, after which 9.3 ml (61.5 mmol) of 2,4-dimethoxybenzylamine were added. After stirring at RT for a further 2 h, the mixture was diluted with 200 ml of dichloromethane and washed successively with in each case about 200 ml of water and saturated sodium chloride solution. After drying over anhydrous magnesium sulphate, the mixture was filtered and the filtrate was evaporated. The remaining residue was taken up in dichloromethane, insolubles being removed by filtration. The filtrate was applied to silica gel and chromatographed on silica gel using cyclohexane/ethyl acetate 2:1→1:1 as eluent. After combination of the product fractions, evaporation and drying of the residue under high vacuum, 12.8 g (87% of theory) of the title compound were obtained.

$^1$H-NMR (400 MHz, DMSO-$d_6$, δ/ppm): 10.56 (s, 1H), 8.32 (t, 1H), 7.13 (d, 1H), 6.57 (d, 1H), 6.49 (dd, 1H), 4.30 (q, 2H), 4.19 (d, 2H), 3.80 (s, 3H), 3.75 (s, 3H), 2.62 (s, 3H), 1.50 (s, 9H), 1.32 (t, 3H).

LC/MS (Method 1, ESIpos): $R_t$=1.40 min, m/z=479 [M+H]$^+$.

Example 5A

Diethyl 5-[(ethylcarbamoyl)amino]-3-methylthiophene-2,4-dicarboxylate

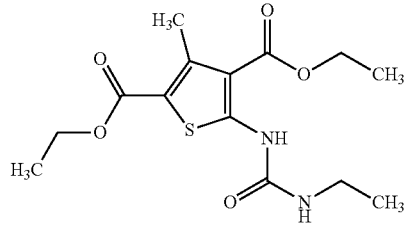 [SMILES: CCNC(=O)Nc1sc(C(=O)OCC)c(C)c1C(=O)OCC]

100 mg (0.377 mmol) of diethyl 2-amino-4-methylthiophene-2,5-dicarboxylate (commercially available) were dissolved in 0.4 ml of pyridine. 0.122 ml (1.51 mmol) of ethyl isocyanate were added to the solution and the mixture was stirred at 80° C. After 28 h, the mixture was cooled to RT and the pyridine was distilled off. The residue was taken up in dichloromethane and concentrated again. The title compound (135 mg, 98% of theory) was obtained as brown crystals.

$^1$H-NMR (400 MHz, DMSO-$d_6$, δ/ppm): 10.53 (s, 1H), 8.06 (br. s, 1H), 4.32 (q, 2H), 4.22 (q, 2H), 3.14 (qd, 2H), 2.65 (s, 3H), 1.33 (t, 3H), 1.27 (t, 3H), 1.07 (t, 3H).

LC/MS (Method 3): $R_t$=1.29 min, m/z=329 [M+H]$^+$.

Example 6A tert-Butyl 5-methyl-2,4-dioxo-3-(2-phenylethyl)-1,2,3,4-tetrahydrothieno[2,3-d]pyrimidine-6-carboxylate

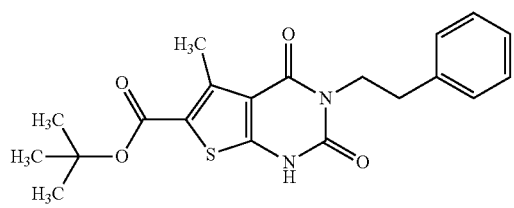 [SMILES: Cc1c(C(=O)OC(C)(C)C)sc2[nH]c(=O)n(CCc3ccccc3)c(=O)c12]

7.34 g (17.0 mmol) of the compound from Ex. 2A were dissolved in 145 ml of ethanol, and 9.5 ml (25.4 mmol) of a 20% solution of sodium ethoxide in ethanol were added. The reaction mixture was stirred at RT for 2 h. The mixture was then poured into about 400 ml of water and adjusted to a pH of about 5 using 5 M acetic acid. In the course of this, the product precipitated out. The product was filtered off with suction, washed neutral with water and dried under a high vacuum. 5.89 g (91% of theory) of the title compound were obtained.

$^1$H-NMR (400 MHz, DMSO-$d_6$, δ/ppm): 12.44 (s, 1H), 7.33-7.29 (m, 2H), 7.25-7.20 (m, 3H), 4.01 (m, 2H), 2.83 (m, 2H), 2.72 (s, 3H), 1.52 (s, 9H).

LC/MS (Method 1, ESIpos): $R_t$=1.28 min, m/z=387 [M+H]$^+$.

Example 7A tert-Butyl 3-ethyl-5-methyl-2,4-dioxo-1,2,3,4-tetrahydrothieno[2,3-d]pyrimidine-6-carboxylate

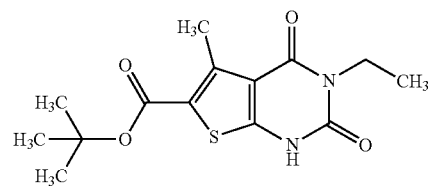 [SMILES: CCn1c(=O)[nH]c2sc(C(=O)OC(C)(C)C)c(C)c2c1=O]

6.98 g (19.6 mmol) of the compound from Ex. 3A were dissolved in 130 ml of ethanol, and 11 ml (29.4 mmol) of a 20% solution of sodium ethoxide in ethanol were added. The reaction mixture was stirred at RT for 2 h. The mixture was then poured into about 400 ml of water and adjusted to a pH of about 5 using 5 M acetic acid. In the course of this, the product precipitated out. The product was filtered off with suction, washed neutral with water and dried under a high vacuum. 5.89 g (97% of theory) of the title compound were obtained.

$^1$H-NMR (400 MHz, DMSO-$d_6$, δ/ppm): 12.39 (s, 1H), 3.85 (q, 2H), 2.71 (s, 3H), 1.51 (s, 9H), 1.11 (t, 3H).

LC/MS (Method 1, ESIpos): $R_t$=1.06 min, m/z=311 [M+H]$^+$.

Example 8A tert-Butyl 3-(2,4-dimethoxybenzyl)-5-methyl-2,4-dioxo-1,2,3,4-tetrahydrothieno[2,3-d]pyrimidine-6-carboxylate

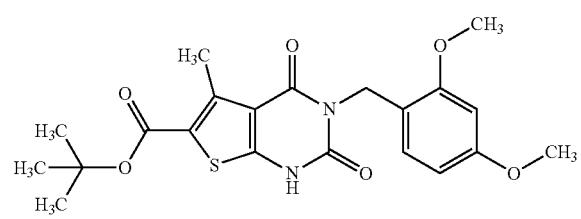 [SMILES: COc1ccc(Cn2c(=O)[nH]c3sc(C(=O)OC(C)(C)C)c(C)c3c2=O)c(OC)c1]

12.8 g (26.8 mmol) of the compound from Ex. 4A were dissolved in 250 ml of ethanol, and 15 ml (40.2 mmol) of a 20% solution of sodium ethoxide in ethanol were added. The reaction mixture was stirred at RT for about 16 h. The mixture was then poured into about 1.5 l of water and adjusted to a pH of about 5 using acetic acid. In the course of this, the product precipitated out. The product was filtered off with suction, washed neutral with water and dried under a high vacuum. 11.3 g (97% of theory) of the title compound were obtained.

$^1$H-NMR (400 MHz, DMSO-d$_6$, δ/ppm): 12.50 (s, 1H), 6.72 (d, 1H), 6.56 (d, 1H), 6.39 (dd, 1H), 4.89 (s, 2H), 3.82 (s, 3H), 3.72 (s, 3H), 2.69 (s, 3H), 1.52 (s, 9H).

LC/MS (Method 1, ESIpos): R$_t$=1.20 min, m/z=433 [M+H]$^+$.

Example 9A

Ethyl 3-ethyl-5-methyl-2,4-dioxo-1,2,3,4-tetrahydrothieno[2,3-d]pyrimidine-6-carboxylate

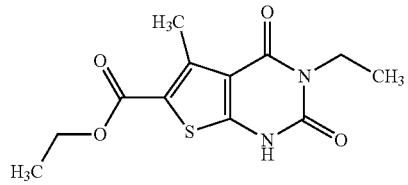 [SMILES: CCOC(=O)c1sc2[nH]c(=O)n(CC)c(=O)c2c1C]

470 mg (1.26 mmol) of the compound from Ex. 5A were dissolved in 7.5 ml of ethanol, and 0.94 ml of sodium ethoxide solution (21% by weight in ethanol) was added. The mixture was stirred at RT for 1 h and then 2.89 ml of 1 M hydrochloric acid were added. The ethanol was removed very substantially on a rotary evaporator. Water was added to the remaining residue, and the solids were filtered off, washed to neutrality with water and dried by suction. 386 mg (99% of theory) of the title compound were obtained.

$^1$H-NMR (400 MHz, DMSO-d$_6$, δ/ppm): 12.40 (br. s, 1H), 4.26 (q, 2H), 3.85 (q, 2H), 2.74 (s, 3H), 1.28 (t, 3H), 1.11 (t, 3H).

LC/MS (Method 3): R$_t$=1.08 min, m/z=283 [M+H]$^+$.

Example 10A tert-Butyl 1-(2-methoxyethyl)-5-methyl-2,4-dioxo-3-(2-phenylethyl)-1,2,3,4-tetrahydrothieno[2,3-d]pyrimidine-6-carboxylate

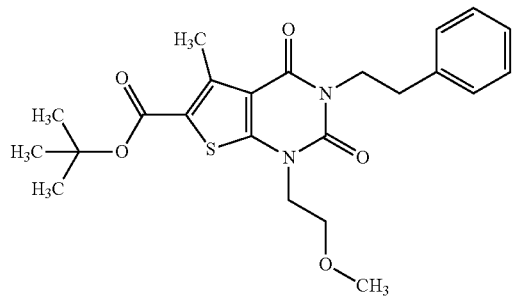 [SMILES: COCCn1c(=O)n(CCc2ccccc2)c(=O)c2c(C)c(C(=O)OC(C)(C)C)sc21]

1.85 g (5.69 mmol) of caesium carbonate were added to a solution of 2.0 g (5.18 mmol) of the compound from Ex. 6A in 60 ml of DMF, and the mixture was stirred at RT for 10 min. 863 mg (6.21 mmol) of 2-bromomethyl methyl ether were then added, and the mixture was heated to 100° C. for 30 min. The mixture was then evaporated to dryness on a rotary evaporator. The remaining residue was taken up in ethyl acetate and washed successively with water and saturated sodium chloride solution. After drying over anhydrous magnesium sulphate, the mixture was filtered and the filtrate was evaporated. The crude product was purified by MPLC (Puriflash column with 80 g of silica gel, cyclohexane/ethyl acetate 10:1). Filtration, evaporation and drying of the residue under high vacuum gave 2.22 g (96% of theory) of the title compound.

$^1$H-NMR (400 MHz, DMSO-d$_6$, δ/ppm): 7.32-7.28 (m, 2H), 7.24-7.20 (m, 3H), 4.09-4.04 (m, 4H), 3.61 (t, 2H), 3.24 (s, 3H), 2.84 (dd, 2H), 2.74 (s, 3H), 1.53 (s, 9H).

LC/MS (Method 1, ESIpos): R$_t$=1.40 min, m/z=445 [M+H]$^+$.

Example 11A tert-Butyl 3-ethyl-5-methyl-2,4-dioxo-1-(3,3,3-trifluoropropyl)-1,2,3,4-tetrahydrothieno[2,3-d]pyrimidine-6-carboxylate

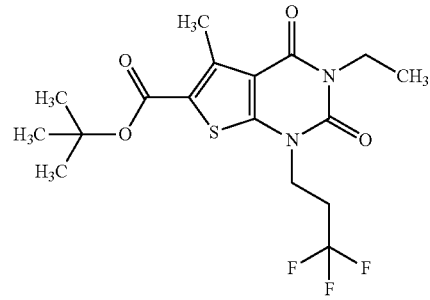 [SMILES: CCn1c(=O)c2c(C)c(C(=O)OC(C)(C)C)sc2n(CCC(F)(F)F)c1=O]

4.72 g (14.5 mmol) of caesium carbonate were added to a solution of 3.0 g (9.67 mmol) of the compound from Ex. 7A in 100 ml of DMF, and the mixture was stirred at RT for 20 min. 2.57 g (14.5 mmol) of 3,3,3-trifluoro-1-iodopropane were then added, and the mixture was heated to 100° C. for 5 h. The mixture was then evaporated to dryness on a rotary evaporator. The remaining residue was taken up in ethyl acetate and washed successively with water and saturated sodium chloride solution. After drying over anhydrous magnesium sulphate, the mixture was filtered and the filtrate was evaporated. The crude product was purified by MPLC (Puriflash column with 120 g of silica gel, cyclohexane/ethyl acetate 10:1). The product fractions were combined and concentrated, and the residue was dried under high vacuum. 3.24 g (76% of theory, 93% purity) of the title compound were obtained.

$^1$H-NMR (400 MHz, DMSO-d$_6$, δ/ppm): 4.15 (t, 2H), 3.90 (q, 2H), 2.84-2.74 (m, 2H), 2.76 (s, 3H), 1.53 (s, 9H), 1.13 (t, 3H).

LC/MS (Method 1, ESIpos): R$_t$=1.36 min, m/z=407 [M+H]$^+$.

Example 12A tert-Butyl 3-ethyl-1-(2-methoxyethyl)-5-methyl-2,4-dioxo-1,2,3,4-tetrahydrothieno[2,3-d]pyrimidine-6-carboxylate

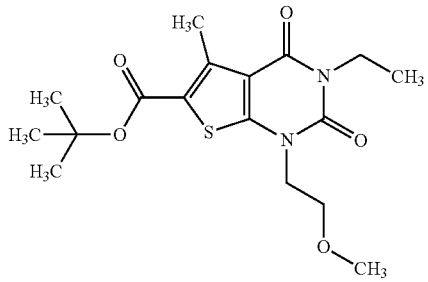 [SMILES: CCn1c(=O)c2c(C)c(C(=O)OC(C)(C)C)sc2n(CCOC)c1=O]

Analogously to the method described in Ex. 11A, 2.50 g (8.05 mmol) of the compound from Ex. 7A, 3.94 g (12.1 mmol) of caesium carbonate and 1.68 g (12.1 mmol) of 2-bromoethyl methyl ether were used to obtain 2.13 g (71% of theory) of the title compound. In a departure from the method described above, a Biotage cartridge containing 50 g of silica gel was used here for the MPLC purification, and the product was finally purified by stirring in a mixture of 60 ml of pentane and 0.5 ml of dichloromethane.

$^1$H-NMR (400 MHz, DMSO-$d_6$, δ/ppm): 4.07 (t, 2H), 3.90 (q, 2H), 3.65 (t, 2H), 3.25 (s, 3H), 2.74 (s, 3H), 1.53 (s, 9H), 1.13 (t, 3H).

LC/MS (Method 1, ESIpos): $R_t$=1.21 min, m/z=369 [M+H]$^+$.

Example 13A tert-Butyl 3-(2,4-dimethoxybenzyl)-1-(2-methoxyethyl)-5-methyl-2,4-dioxo-1,2,3,4-tetrahydrothieno[2,3-d]pyrimidine-6-carboxylate

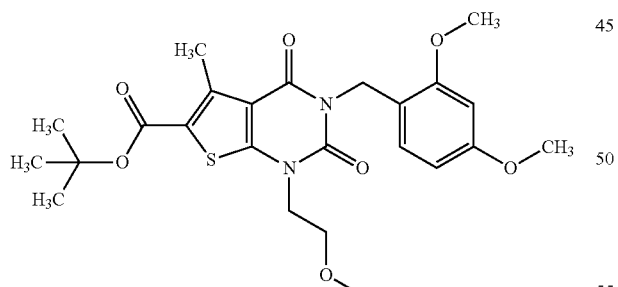

3.24 g (23.4 mmol) of potassium carbonate were added to a solution of 7.50 g (15.6 mmol) of the compound from Ex. 8A in 200 ml of acetonitrile, and the mixture was stirred at RT for 10 min. Then 6.63 g (23.4 mmol) of 2-bromomethyl methyl ether were added, and the mixture was heated under reflux for about 18 h. After cooling to RT, 300 ml of water were added, and then the product precipitated out. The product was filtered off with suction, washed with water and dried under high vacuum. 6.21 g (73% of theory, 90% purity) of the title compound were obtained.

$^1$H-NMR (300 MHz, DMSO-$d_6$, δ/ppm): 6.74 (d, 1H), 6.57 (d, 1H), 6.40 (dd, 1H), 4.95 (s, 2H), 4.09 (t, 2H), 3.81 (s, 3H), 3.72 (s, 3H), 3.66 (t, 2H), 3.25 (s, 3H), 2.72 (s, 3H), 1.54 (s, 9H).

Example 14A

Ethyl 3-ethyl-1-(3-fluoropropyl)-5-methyl-2,4-dioxo-1,2,3,4-tetrahydrothieno[2,3-d]pyrimidine-6-carboxylate

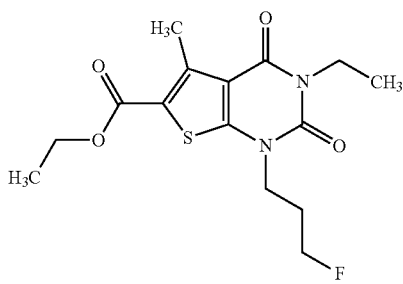 [SMILES: CCOC(=O)c1sc2c(c1C)c(=O)n(CC)c(=O)n2CCCF]

433 mg (3.14 mmol) of potassium carbonate were added to a solution of 385 mg (1.25 mmol) of the compound from Ex. 9A in 11 ml of DMF, and the mixture was stirred at RT for 15 min. Then 1.06 g (5.64 mmol) of 1-fluoro-3-iodopropane were added, and the mixture was stirred at 50° C. for 20 h. The DMF was very substantially removed and the remaining residue was partitioned between semisaturated sodium chloride solution (100 ml) and ethyl acetate (100 ml). The aqueous phase was extracted with ethyl acetate. The combined organic phases were dried over sodium sulphate, filtered and concentrated. 469 mg of the title compound were obtained.

$^1$H-NMR (400 MHz, DMSO-$d_6$, δ/ppm): 4.61 (t, 1H), 4.49 (t, 1H), 4.29 (q, 2H), 4.03 (t, 2H), 3.90 (q, 2H), 2.78 (s, 3H), 2.17-2.01 (m, 2H), 1.30 (t, 3H), 1.13 (t, 3H).

LC/MS (Method 3): $R_t$=1.29 min, m/z=343 [M+H]$^+$.

Example 15A 1-(2-Methoxyethyl)-5-methyl-2,4-dioxo-3-(2-phenylethyl)-1,2,3,4-tetrahydrothieno[2,3-d]pyrimidine-6-carboxylic acid

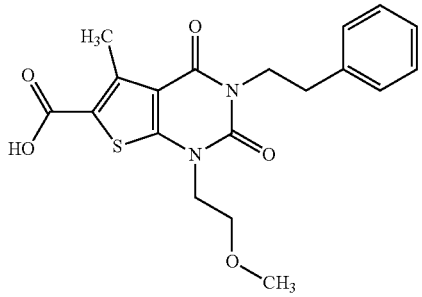 [SMILES: COCCn1c(=O)n(CCc2ccccc2)c(=O)c2c(C)c(C(=O)O)sc21]

75 ml of trifluoroacetic acid were added to a solution of 5.0 g (11.2 mmol) of the compound from Ex. 10A in 225 ml of dichloromethane, and the mixture was stirred at RT for 2 h. The reaction mixture was then concentrated to dryness on a rotary evaporator. The remaining residue was stirred in diethyl ether and filtered off with suction, and the solid was dried under high vacuum. 4.1 g (92% of theory) of the title compound were obtained.

¹H-NMR (400 MHz, DMSO-d₆, δ/ppm): 13.37 (br. s, 1H), 7.33-7.29 (m, 2H), 7.25-7.20 (m, 3H), 4.09-4.04 (m, 4H), 3.62 (t, 2H), 3.25 (s, 3H), 2.84 (dd, 2H), 2.75 (s, 3H).

LC/MS (Method 1, ESIpos): R$_t$=1.03 min, m/z=389 [M+H]⁺.

Example 16A

3-Ethyl-5-methyl-2,4-dioxo-1-(3,3,3-trifluoropropyl)-1,2,3,4-tetrahydrothieno[2,3-d]pyrimidine-6-carboxylic acid

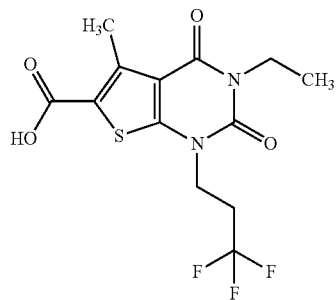 [SMILES: CCn1c(=O)c2c(C)c(C(=O)O)sc2n(CCC(F)(F)F)c1=O]

80 ml of trifluoroacetic acid were added to a solution of 6.89 g (16.9 mmol) of the compound from Ex. 11A in 240 ml of dichloromethane, and the mixture was stirred at RT for 2 h. The reaction mixture was then concentrated to dryness on a rotary evaporator. The remaining residue was stirred in diethyl ether and filtered off with suction, and the solid was dried under high vacuum. 5.13 g (86% of theory) of the title compound were obtained.

¹H-NMR (400 MHz, DMSO-d₆, δ/ppm): 13.46 (br. s, 1H), 4.15 (t, 2H), 3.91 (q, 2H), 2.85-2.73 (m, 2H), 2.76 (s, 3H), 1.13 (t, 3H).

LC/MS (Method 1, ESIpos): R$_t$=0.94 min, m/z=351 [M+H]⁺.

Example 17A

3-Ethyl-1-(2-methoxyethyl)-5-methyl-2,4-dioxo-1,2,3,4-tetrahydrothieno[2,3-d]pyrimidine-6-carboxylic acid

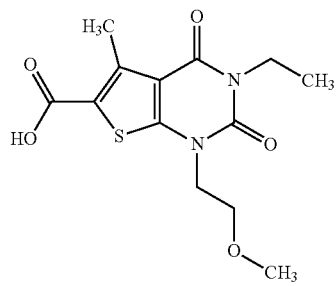 [SMILES: CCn1c(=O)c2c(C)c(C(=O)O)sc2n(CCOC)c1=O]

Analogously to the method described in Ex. 16A, 2.50 g (6.78 mmol) of the compound from Ex. 12A were used to obtain 1.82 g (85% of theory) of the title compound. The reaction time in this case was 1 h.

¹H-NMR (400 MHz, DMSO-d₆, δ/ppm): 13.32 (br. s, 1H), 4.07 (t, 2H), 3.90 (q, 2H), 3.65 (t, 2H), 3.25 (s, 3H), 2.75 (s, 3H), 1.13 (t, 3H).

LC/MS (Method 1, ESIpos): R$_t$=0.99 min, m/z=313 [M+H]⁺.

Example 18A 1-(2-Methoxyethyl)-5-methyl-2,4-dioxo-1,2,3,4-tetrahydrothieno[2,3-d]pyrimidine-6-carboxylic acid

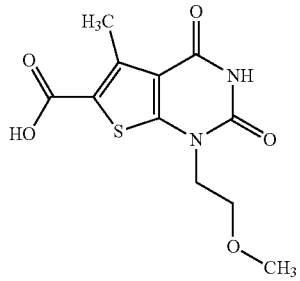 [SMILES: COCCn1c(=O)[nH]c(=O)c2c(C)c(C(=O)O)sc21]

13.5 g (27.5 mmol) of the compound from Ex. 13A were dissolved in 350 ml of toluene, and 22.0 g (165 mmol) of solid aluminium trichloride were added at RT. The reaction mixture was then stirred at 65° C. for 90 min. After cooling to RT, the mixture was cooled with an ice/water bath and about 200 g of ice were added. Once the ice had melted, the mixture was adjusted to a pH of about 1 by adding concentrated hydrochloric acid. In the course of this, the product precipitated out. The mixture was stirred at RT for 3 h, then the product was filtered off with suction, washed with a little acetonitrile and dried under high vacuum. 7.82 g (76% of theory, 86% purity) of the title compound were obtained.

¹H-NMR (400 MHz, DMSO-d₆, δ/ppm): 13.29 (broad, 1H), 11.52 (s, 1H), 4.02 (t, 2H), 3.63 (t, 2H), 3.24 (s, 3H), 2.71 (s, 3H).

LC/MS (Method 1, ESIpos): R$_t$=0.52 min, m/z=285 [M+H]⁺.

Example 19A

Methyl 1-(2-methoxyethyl)-5-methyl-2,4-dioxo-3-(2-phenylethyl)-1,2,3,4-tetrahydrothieno[2,3-d]pyrimidine-6-carboxylate

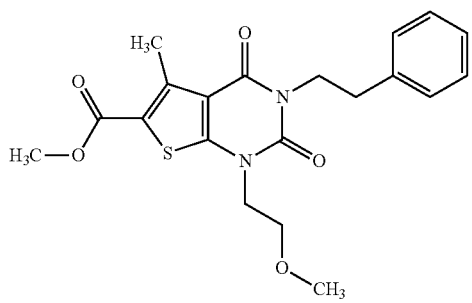 [SMILES: COCCn1c(=O)n(CCc2ccccc2)c(=O)c2c(C)c(C(=O)OC)sc21]

3.30 g (8.50 mmol) of the compound from Ex. 15A were suspended in 125 ml of dichloromethane, and 7.4 ml (85.0 mmol) of oxalyl chloride were added dropwise, as was one drop of DMF. After 2 h, the reaction mixture was concentrated to dryness. The residue obtained was dissolved again in 75 ml of dichloromethane, and 8.6 ml (212 mmol) of methanol were added. After the reaction mixture had been stirred at RT for about 18 h, it was concentrated to dryness again and the residue was chromatographed using a silica gel cartridge (Biotage, 100 g of silica gel, cyclohexane/ethyl acetate 5:1→1:1). After combination of the product fractions, concentration and drying under high vacuum, 3.35 g (97% of theory) of the title compound were obtained.

¹H-NMR (400 MHz, CDCl₃, δ/ppm): 7.33-7.28 (m, 4H), 7.26-7.20 (m, 1H), 4.21 (m, 2H), 4.13 (t, 2H), 3.88 (s, 3H), 3.71 (t, 2H), 3.35 (s, 3H), 2.95 (m, 2H), 2.89 (s, 3H).

LC/MS (Method 1, ESIpos): R$_t$=1.23 min, m/z=403 [M+H]⁺.

Example 20A

Methyl 1-(2-methoxyethyl)-3,5-dimethyl-2,4-dioxo-1,2,3,4-tetrahydrothieno[2,3-d]pyrimidine-6-carboxylate

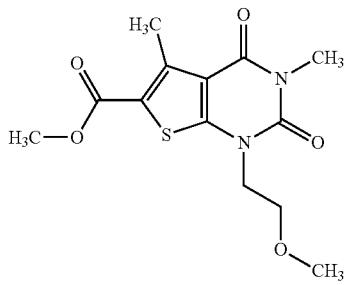

1.246 g (3.825 mmol) of caesium carbonate were added to a solution of 402 mg (1.25 mmol) of the compound from Ex. 18A in 12.3 ml of DMF, and the mixture was stirred at RT for 10 min. Then 452 mg (3.18 mmol) of iodomethane were added, and the mixture was stirred at RT for 22 h. The reaction mixture was then partitioned between water (75 ml) and dichloromethane (75 ml). The aqueous phase was extracted with dichloromethane. The combined organic phases were dried over sodium sulphate, filtered and concentrated. The residue obtained was chromatographed on silica gel (hexane/ethyl acetate eluent). 248 mg (59% of theory) of the title compound were obtained.

¹H-NMR (400 MHz, DMSO-d₆, δ/ppm): 4.08 (t, 2H), 3.81 (s, 3H), 3.65 (t, 2H), 3.24 (s, 3H), 3.23 (s, 3H), 2.77 (s, 3H).

LC/MS (Method 3): R$_t$=1.06 min, m/z=313 [M+H]⁺.

Example 21A

Methyl 3-ethyl-5-methyl-2,4-dioxo-1-(3,3,3-trifluoropropyl)-1,2,3,4-tetrahydrothieno[2,3-d]pyrimidine-6-carboxylate

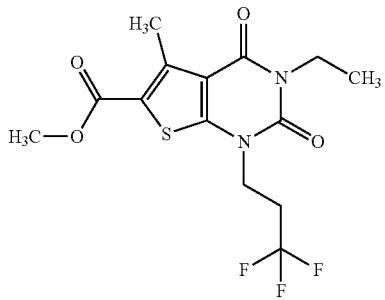 [SMILES: CCn1c(=O)c2c(C)c(C(=O)OC)sc2n(CCC(F)(F)F)c1=O]

Analogously to the method described in Ex. 19A, 10.0 g (28.5 mmol) of the compound from Ex. 16A were used to obtain 10.8 g (99% of theory, 96% purity) of the title compound. It was possible here to dispense with chromatographic purification of the product.

¹H-NMR (400 MHz, DMSO-d₆, δ/ppm): 4.16 (t, 2H), 3.91 (q, 2H), 3.83 (s, 3H), 2.90-2.70 (m, 2H), 2.79 (s, 3H), 1.13 (t, 3H).

LC/MS (Method 1, ESIpos): R$_t$=1.12 min, m/z=365 [M+H]⁺.

Example 22A

Methyl 3-ethyl-1-(2-methoxyethyl)-5-methyl-2,4-dioxo-1,2,3,4-tetrahydrothieno[2,3-d]pyrimidine-6-carboxylate

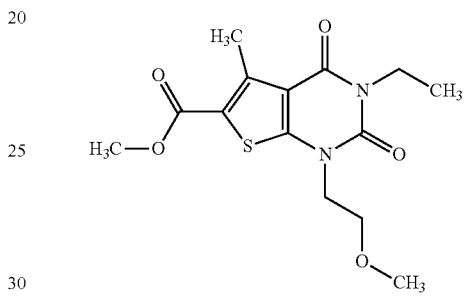

Analogously to the method described in Ex. 19A, 2.05 g (6.56 mmol) of the compound from Ex. 17A were used to obtain 2.11 g (98% of theory) of the title compound. It was possible here to dispense with chromatographic purification of the product.

¹H-NMR (400 MHz, DMSO-d₆, δ/ppm): 4.08 (t, 2H), 3.90 (q, 2H), 3.81 (s, 3H), 3.65 (t, 2H), 3.24 (s, 3H), 2.77 (s, 3H), 1.13 (t, 3H).

LC/MS (Method 1, ESIpos): R$_t$=0.99 min, m/z=327 [M+H]⁺.

Example 23A

2-Phenylethyl 1-(2-methoxyethyl)-5-methyl-2,4-dioxo-3-(2-phenylethyl)-1,2,3,4-tetrahydrothieno[2,3-d]pyrimidine-6-carboxylate

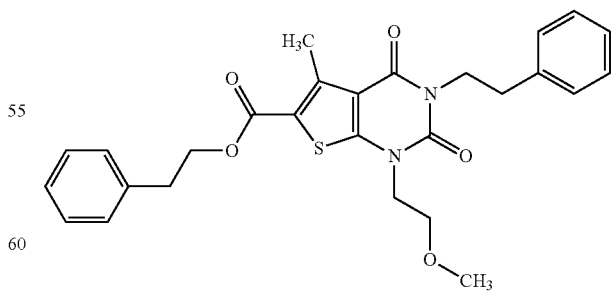

Analogously to the method described in Ex. 20A, 500 mg (1.583 mmol) of the compound from Ex. 18A and 879 mg (4.749 mmol) of phenethyl bromide were used to obtain 432 mg (54% of theory) of the title compound.

¹H-NMR (400 MHz, DMSO-d₆, δ/ppm): 7.34-7.27 (m, 6H), 7.27-7.19 (m, 4H), 4.45 (t, 2H), 4.09-4.02 (m, 4H), 3.62 (t, 2H), 3.25 (s, 3H), 3.00 (t, 2H), 2.88-2.79 (m, 2H), 2.70 (s, 3H).

LC/MS (Method 3): $R_t$=1.60 min, m/z=493 [M+H]⁺.

Example 24A

Propyl 1-(2-methoxyethyl)-5-methyl-2,4-dioxo-3-propyl-1,2,3,4-tetrahydrothieno[2,3-d]pyrimidine-6-carboxylate

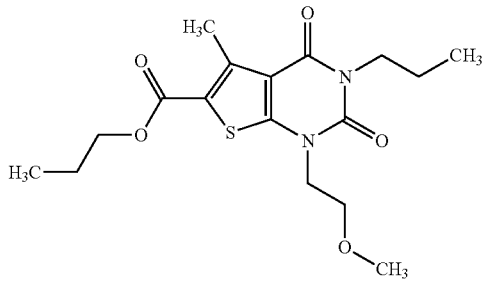 [SMILES: CCCOC(=O)c1sc2c(c1C)c(=O)n(CCC)c(=O)n2CCOC]

Analogously to the method described in Ex. 20A, 400 mg (1.266 mmol) of the compound from Ex. 18A and 538 mg (3.166 mmol) of 1-iodopropane were used to obtain 273 mg (57% of theory) of the title compound.

¹H-NMR (400 MHz, DMSO-d₆, δ/ppm): 4.20 (t, 2H), 4.08 (t, 2H), 3.85-3.79 (m, 2H), 3.65 (t, 2H), 3.24 (s, 3H), 2.77 (s, 3H), 1.69 (sext, 2H), 1.57 (sext, 2H), 0.95 (t, 3H), 0.87 (t, 3H).

LC/MS (Method 3): $R_t$=1.42 min, m/z=369 [M+H]⁺.

Example 25A

Allyl 3-allyl-1-(2-methoxyethyl)-5-methyl-2,4-dioxo-1,2,3,4-tetrahydrothieno[2,3-d]pyrimidine-6-carboxylate

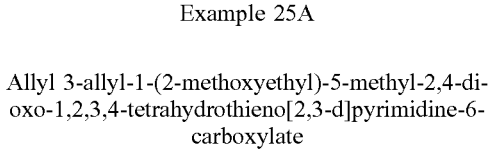

Analogously to the method described in Ex. 20A, 503 mg (1.592 mmol) of the compound from Ex. 18A and 481 mg (3.981 mmol) of allyl bromide were used to obtain 352 mg (59% of theory) of the title compound.

¹H-NMR (400 MHz, DMSO-d₆, δ/ppm): 6.02 (ddt, 1H), 5.85 (ddt, 1H), 5.38 (dq, 1H), 5.29 (dd, 1H), 5.14 (dd, 1H), 5.12-5.08 (m, 1H), 4.78 (dt, 2H), 4.47 (d, 2H), 4.10 (t, 2H), 3.65 (t, 2H), 3.24 (s, 3H), 2.77 (s, 3H).

LC/MS (Method 3): $R_t$=1.30 min, m/z=365 [M+H]⁺.

Example 26A

Isopropyl 3-isopropyl-1-(2-methoxyethyl)-5-methyl-2,4-dioxo-1,2,3,4-tetrahydrothieno[2,3-d]pyrimidine-6-carboxylate

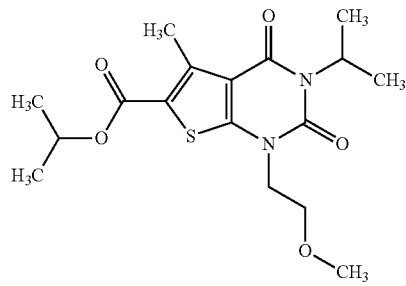 [SMILES: COCCn1c(=O)n(C(C)C)c(=O)c2c(C)c(C(=O)OC(C)C)sc21]

Analogously to the method described in Ex. 20A, 500 mg (1.583 mmol) of the compound from Ex. 18A and 949 mg (5.539 mmol) of 2-iodopropane were used to obtain 293 mg (49% of theory) of the title compound. The reaction time here was 28 h at a temperature of 50° C.

¹H-NMR (400 MHz, DMSO-d₆, δ/ppm): 5.18-5.03 (m, 2H), 4.05 (t, 2H), 3.64 (t, 2H), 3.25 (s, 3H), 2.75 (s, 3H), 1.40 (d, 6H), 1.30 (d, 6H).

LC/MS (Method 3): $R_t$=1.43 min, m/z=369 [M+H]⁺.

Example 27A sec-Butyl 3-sec-butyl-1-(2-methoxyethyl)-5-methyl-2,4-dioxo-1,2,3,4-tetrahydrothieno[2,3-d]pyrimidine-6-carboxylate (diastereomer mixture)

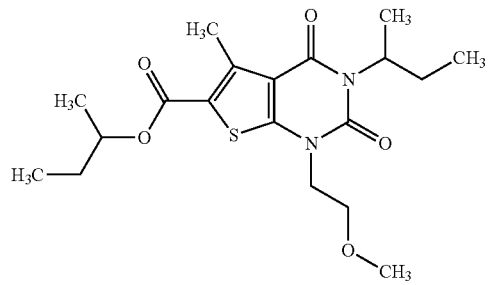 [SMILES: CCC(C)OC(=O)c1sc2c(c1C)c(=O)n(C(C)CC)c(=O)n2CCOC]

Analogously to the method described in Ex. 20A, 500 mg (1.583 mmol) of the compound from Ex. 18A and 685 mg (4.749 mmol) of 2-bromobutane were used to obtain 325 mg (49% of theory) of the title compound. The reaction time here was 19 h at a temperature of 70° C.

¹H-NMR (400 MHz, DMSO-d₆, δ/ppm): 5.00-4.84 (m, 1H), 4.13-3.99 (m, 1H), 3.63 (t, 1H), 3.23 (s, 1H), 2.76 (s, 1H), 2.07-1.94 (m, 1H), 1.80-1.69 (m, 1H), 1.68-1.59 (m, 2H), 1.41-1.35 (m, 3H), 1.27 (d, 3H), 0.90 (t, 3H), 0.76 (t, 3H).

LC/MS (Method 3): $R_t$=1.58 min, m/z=397 [M+H]⁺.

Example 28A

3-Methylbut-2-en-1-yl 1-(2-methoxyethyl)-5-methyl-3-(3-methylbut-2-en-1-yl)-2,4-dioxo-1,2,3,4-tetrahydrothieno[2,3-d]pyrimidine-6-carboxylate

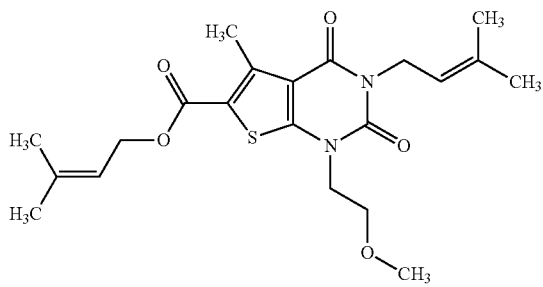 [SMILES: COCCn1c(=O)n(CC=C(C)C)c(=O)c2c(C)c(C(=O)OCC=C(C)C)sc21]

Analogously to the method described in Ex. 20A, 500 mg (1.583 mmol) of the compound from Ex. 18A and 786 mg (4.749 mmol) of 1-bromo-3-methylbut-2-ene were used to obtain 408 mg (58% of theory) of the title compound.

$^1$H-NMR (400 MHz, DMSO-$d_6$, δ/ppm): 5.44-5.36 (m, 1H), 5.20-5.12 (m, 1H), 4.74 (d, 2H), 4.44 (d, 2H), 4.07 (t, 2H), 3.64 (t, 2H), 3.24 (s, 3H), 2.75 (s, 3H), 1.75 (s, 6H), 1.72 (s, 3H), 1.66 (s, 3H).

LC/MS (Method 3): $R_t$=1.60 min, m/z=421 [M+H]$^+$.

Example 29A

Cyclopropylmethyl 3-(cyclopropylmethyl)-1-(2-methoxyethyl)-5-methyl-2,4-dioxo-1,2,3,4-tetrahydrothieno[2,3-d]pyrimidine-6-carboxylate

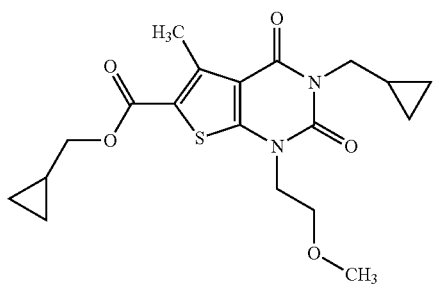 [SMILES: COCCn1c(=O)n(CC2CC2)c(=O)c2c(C)c(C(=O)OCC3CC3)sc21]

Analogously to the method described in Ex. 20A, 508 mg (1.608 mmol) of the compound from Ex. 18A and 542 mg (4.020 mmol) of cyclopropylmethyl bromide were used to obtain 357 mg (55% of theory) of the title compound.

$^1$H-NMR (400 MHz, DMSO-$d_6$, δ/ppm): 4.13-4.07 (m, 4H), 3.77 (d, 2H), 3.66 (t, 2H), 3.25 (s, 3H), 2.78 (s, 3H), 1.27-1.10 (m, 2H), 0.61-0.54 (m, 2H), 0.48-0.40 (m, 2H), 0.38-0.31 (m, 4H).

LC/MS (Method 3): $R_t$=1.45 min, m/z=393 [M+H]$^+$.

Example 30A

2-Fluoroethyl 3-(2-fluoroethyl)-1-(2-methoxyethyl)-5-methyl-2,4-dioxo-1,2,3,4-tetrahydrothieno-[2,3-d]pyrimidine-6-carboxylate

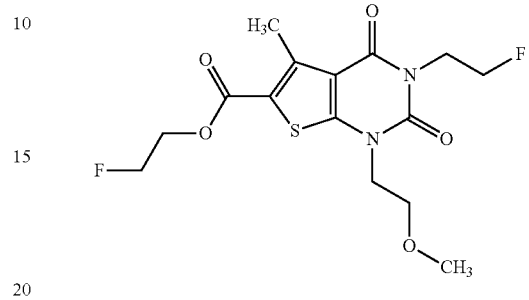

Analogously to the method described in Ex. 20A, 500 mg (1.583 mmol) of the compound from Ex. 18A and 507 mg (3.957 mmol) of 1-bromo-2-fluoroethane were used to obtain 317 mg (51% of theory) of the title compound. The reaction time here was 18 h at a temperature of 50° C.

$^1$H-NMR (400 MHz, DMSO-$d_6$, δ/ppm): 4.78 (dd, 1H), 4.70-4.63 (m, 2H), 4.58-4.51 (m, 2H), 4.47 (dd, 1H), 4.24 (t, 1H), 4.21-4.16 (m, 1H), 4.10 (t, 2H), 3.66 (t, 2H), 3.25 (s, 3H), 2.78 (s, 3H).

LC/MS (Method 3): $R_t$=1.09 min, m/z=377 [M+H]$^+$.

Example 31A 3,3,3-Trifluoropropyl 1-(2-methoxyethyl)-5-methyl-2,4-dioxo-3-(3,3,3-trifluoropropyl)-1,2,3,4-tetrahydrothieno[2,3-d]pyrimidine-6-carboxylate

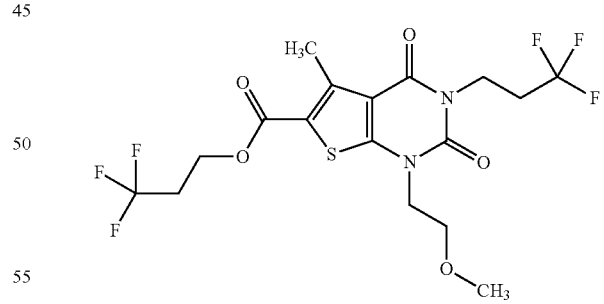

Analogously to the method described in Ex. 20A, 501 mg (1.586 mmol) of the compound from Ex. 18A and 888 mg (3.966 mmol) of 1-iodo-3-trifluoropropane were used to obtain 455 mg (57% of theory) of the title compound. The reaction time here was 44 h at a temperature of 50° C.

$^1$H-NMR (400 MHz, DMSO-$d_6$, δ/ppm): 4.47 (t, 2H), 4.14-4.06 (m, 4H), 3.65 (t, 2H), 3.24 (s, 3H), 2.86-2.73 (m, 5H), 2.65-2.54 (m, 2H).

LC/MS (Method 3): $R_t$=1.39 min, m/z=477 [M+H]$^+$.

Example 32A

3-Fluoropropyl 3-(3-fluoropropyl)-1-(2-methoxy-ethyl)-5-methyl-2,4-dioxo-1,2,3,4-tetrahydrothieno[2,3-d]pyrimidine-6-carboxylate

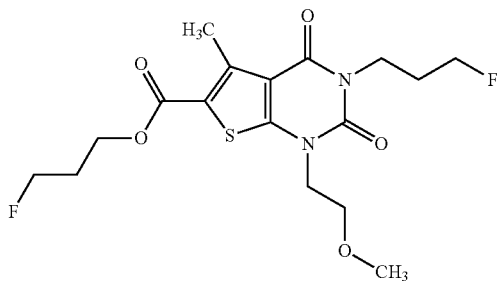 [SMILES: COCCn1c(=O)n(CCCF)c(=O)c2c(C)c(C(=O)OCCCF)sc21]

Analogously to the method described in Ex. 20A, 503 mg (1.594 mmol) of the compound from Ex. 18A and 898 mg (4.782 mmol) of 3-fluoro-1-iodopropane were used to obtain 310 mg (45% of theory) of the title compound. The reaction time here was 42 h.

$^1$H-NMR (400 MHz, DMSO-d$_6$, δ/ppm): 4.63 (t, 1H), 4.55 (t, 1H), 4.52 (t, 1H), 4.43 (t, 1H), 4.35 (t, 2H), 4.08 (t, 2H), 3.99 (t, 2H), 3.65 (t, 2H), 3.24 (s, 3H), 2.77 (s, 3H), 2.12 (quin, 1H), 2.05 (quin, 1H), 2.02-1.95 (m, 1H), 1.95-1.88 (m, 1H).

LC/MS (Method 3): R$_t$=1.22 min, m/z=405 [M+H]$^+$.

Example 33A

2-Methoxyethyl 1,3-bis(2-methoxyethyl)-5-methyl-2,4-dioxo-1,2,3,4-tetrahydrothieno[2,3-d]pyrimidine-6-carboxylate

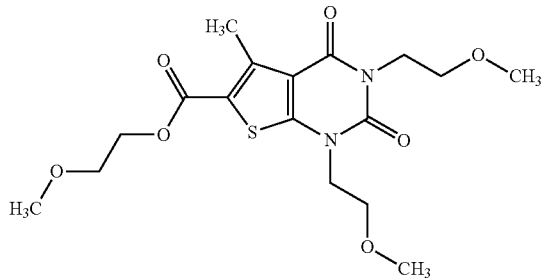

Analogously to the method described in Ex. 20A, 500 mg (1.583 mmol) of the compound from Ex. 18A and 550 mg (3.957 mmol) of 1-bromo-2-methoxyethane were used to obtain 297 mg (47% of theory) of the title compound.

$^1$H-NMR (400 MHz, DMSO-d$_6$, δ/ppm): 4.39-4.34 (m, 2H), 4.12-4.02 (m, 4H), 3.69-3.60 (m, 4H), 3.54-3.49 (m, 2H), 3.30 (s, 3H), 3.24 (d, 6H), 2.77 (s, 3H).

LC/MS (Method 3): R$_t$=1.08 min, m/z=401 [M+H]$^+$.

Example 34A

1-Methoxypropan-2-yl 1-(2-methoxyethyl)-3-(1-methoxypropan-2-yl)-5-methyl-2,4-dioxo-1,2,3,4-tetrahydrothieno[2,3-d]pyrimidine-6-carboxylate (diastereomer mixture)

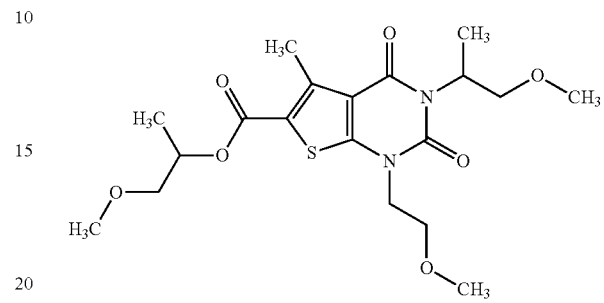

Analogously to the method described in Ex. 20A, 644 mg (2.038 mmol) of the compound from Ex. 18A and 985 mg (6.115 mmol) of 2-bromo-1-methoxypropane were used to obtain 391 mg (44% of theory) of the title compound. The reaction time here was 97 h at a temperature of 70° C.

$^1$H-NMR (400 MHz, DMSO-d$_6$, δ/ppm): 5.22-5.12 (m, 2H), 4.08-4.00 (m, 2H), 3.90 (dd, 1H), 3.63 (t, 2H), 3.57-3.52 (m, 1H), 3.51-3.43 (m, 2H), 3.29 (s, 3H), 3.24 (s, 3H), 3.21 (s, 3H), 2.75 (s, 3H), 1.34 (d, 3H), 1.25 (d, 3H).

LC/MS (Method 3): R$_t$=1.28 min, m/z=429 [M+H]$^+$.

Example 35A

2-Methoxypropyl 1-(2-methoxyethyl)-3-(2-methoxypropyl)-5-methyl-2,4-dioxo-1,2,3,4-tetrahydrothieno[2,3-d]pyrimidine-6-carboxylate (diastereomer mixture)

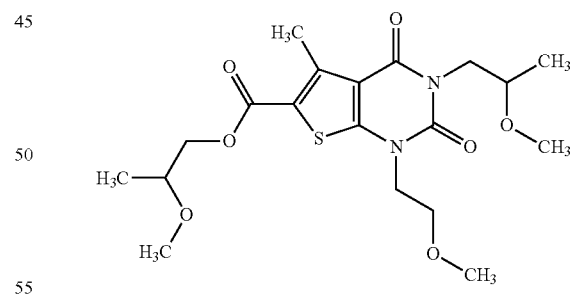

Analogously to the method described in Ex. 20A, 505 mg (1.599 mmol) of the compound from Ex. 18A and 773 mg (4.797 mmol) of 1-bromo-2-methoxypropane were used to obtain 381 mg (53% of theory) of the title compound. The reaction time here was 19 h at a temperature of 80° C.

$^1$H-NMR (400 MHz, DMSO-d$_6$, δ/ppm): 4.32-4.27 (m, 1H), 4.17 (dd, 1H), 4.12-4.01 (m, 3H), 3.76 (dd, 1H), 3.68-3.58 (m, 4H), 3.29 (s, 3H), 3.23 (s, 3H), 3.21 (s, 3H), 2.77 (s, 3H), 1.14 (d, 3H), 1.06 (d, 3H).

LC/MS (Method 3): R$_t$=1.22 min, m/z=429 [M+H]$^+$.

Example 36A

Ethyl 2-[(ethylcarbamoyl)amino]-4-methylthiophene-3-carboxylate

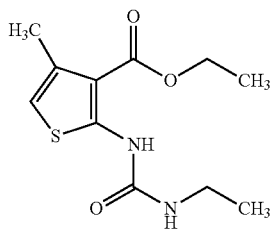 [SMILES: CCNC(=O)Nc1scc(C)c1C(=O)OCC]

Method A:

96 ml (1.21 mol) of ethyl isocyanate were added to a solution of 150 g (0.810 mol) of ethyl 2-amino-4-methylthiophene-3-carboxylate and 113 ml (0.810 mol) of triethylamine in 1.5 liters of THF. Subsequently, the reaction mixture was heated under reflux for 2 days. After cooling to RT, the mixture was poured into about 2 liters of water and extracted four times with a total of 1.1 liters of dichloromethane. The organic extract was dried over anhydrous sodium sulphate, filtered and concentrated to dryness. After the residue had been dried under high vacuum, 200 g (89% of theory, about 93% purity) of the title compound were obtained, which was used in the next step without further purification.

Method B:

To a solution of 440 g (2.37 mol) of ethyl 2-amino-4-methylthiophene-3-carboxylate in 4.4 liters of THF were added, at RT, 1.32 liters (9.50 mol) of triethylamine and 770 g (4.75 mol) of N,N'-carbonyldiimidazole (CDI). After 4 days, 4.75 liters (9.50 mol) of a 2 M solution of ethylamine in THF were added to the reaction mixture. After a reaction time of 2 h, the mixture was stirred into about 27 liters of water. The product which precipitated out was filtered off with suction, washed with a little water and dried under high vacuum. 578 g (95% of theory) of the title compound were obtained.

$^1$H-NMR (300 MHz, DMSO-$d_6$, δ/ppm): 10.28 (s, 1H), 7.83 (broad, 1H), 6.39 (s, 1H), 4.27 (q, 2H), 3.13 (m, 2H), 2.26 (s, 3H), 1.31 (t, 3H), 1.06 (t, 3H).

LC/MS (Method 1, ESIpos): $R_t$=0.92 min, m/z=257 [M+H]$^+$.

Example 37A

Ethyl 2-[(isopropylcarbamoyl)amino]-4-methylthiophene-3-carboxylate

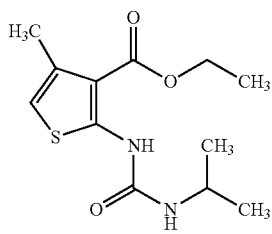 [SMILES: CCOC(=O)c1c(C)csc1NC(=O)NC(C)C]

To a solution of 10.0 g (54.0 mmol) of ethyl 2-amino-4-methylthiophene-3-carboxylate in 55 ml of pyridine were added 10.6 ml (108 mmol) of isopropyl isocyanate. The reaction mixture was then stirred at 55° C. for 95 h. Thereafter, the mixture was concentrated to dryness on a rotary evaporator and the remaining residue was purified by means of MPLC (Biotage cartridge, 340 g of silica gel, cyclohexane/ethyl acetate 3:1). After concentration of the product fractions and drying under high vacuum, 14.3 g (97% of theory) of the title compound were obtained.

$^1$H-NMR (400 MHz, CDCl$_3$, δ/ppm): 10.61 (br. s, 1H), 6.23 (s, 1H), 4.61 (d, 1H), 4.32 (q, 2H), 4.08-3.87 (m, 1H), 2.33 (s, 3H), 1.38 (t, 3H), 1.22 (d, 6H).

LC/MS (Method 5, ESIpos): $R_t$=1.34 min, m/z=271 [M+H]$^+$.

Example 38A

Ethyl 2-[(isobutylcarbamoyl)amino]-4-methylthiophene-3-carboxylate

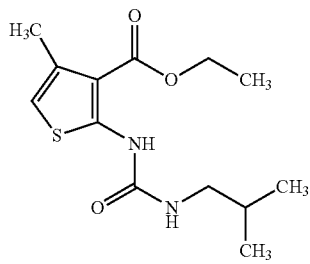 [SMILES: CCOC(=O)c1c(C)csc1NC(=O)NCC(C)C]

To a solution of 10.0 g (54.0 mmol) of ethyl 2-amino-4-methylthiophene-3-carboxylate in 55 ml of pyridine were added 12.3 ml (108 mmol) of isobutyl isocyanate. The reaction mixture was then stirred at 50° C. for 43 h. Thereafter, the mixture was concentrated to dryness on a rotary evaporator and the remaining residue was purified by means of MPLC (Biotage cartridge, 340 g of silica gel, cyclohexane/ethyl acetate 10:1). After concentration of the product fractions and drying under high vacuum, 12.35 g (80% of theory) of the title compound were obtained.

$^1$H-NMR (300 MHz, DMSO-$d_6$, δ/ppm): 10.32 (s, 1H), 7.87 (br. t, 1H), 6.41 (s, 1H), 4.28 (q, 2H), 2.93 (t, 2H), 2.26 (s, 3H), 1.70 (sept, 1H), 1.31 (t, 3H), 0.87 (d, 6H).

LC/MS (Method 1, ESIpos): $R_t$=1.14 min, m/z=285 [M+H]$^+$.

Example 39A

Ethyl 4-methyl-2-{[(2,2,2-trifluoroethyl)carbamoyl]amino}thiophene-3-carboxylate

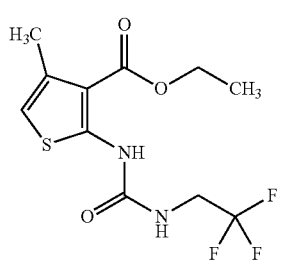 [SMILES: CCOC(=O)c1c(C)csc1NC(=O)NCC(F)(F)F]

To a solution of 1.5 g (7.854 mmol) of ethyl 2-amino-4-methylthiophene-3-carboxylate in 7.5 ml of pyridine were added 1.473 g (11.782 mmol) of 2,2,2-trifluoroethyl isocyanate. The reaction mixture was then stirred at 70° C. for 30 min. It was then concentrated to dryness on a rotary evaporator. The remaining residue was dissolved in dichloromethane and concentrated to dryness again. 2.84 g (89% of theory, at 77% purity) of the title compound were obtained.

$^1$H-NMR (400 MHz, DMSO-$d_6$, δ/ppm): 10.48 (s, 1H), 8.58 (t, 1H), 6.50 (s, 1H), 4.29 (q, 2H), 3.96 (qd, 2H), 2.28 (d, 3H), 1.32 (t, 3H).

LC/MS (Method 3): $R_t$=1.26 min, m/z=311 [M+H]$^+$.

Example 40A

Ethyl 2-{[(2,2-difluoroethyl)carbamoyl]amino}-4-methylthiophene-3-carboxylate

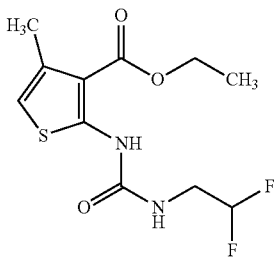 [SMILES: CCOC(=O)c1c(C)csc1NC(=O)NCC(F)F]

To a solution of 1.19 g (6.277 mmol) of ethyl 2-amino-4-methylthiophene-3-carboxylate in 5.8 ml of pyridine were added 1.4 g (9.415 mmol) of 1,1-difluoro-2-isocyanatoethane. The reaction mixture was then stirred at 50° C. for 1 h. It was then concentrated to dryness on a rotary evaporator. The remaining residue was dissolved in dichloromethane and concentrated to dryness again. 2.03 g of the title compound were obtained.

$^1$H-NMR (400 MHz, DMSO-$d_6$, δ/ppm): 10.41 (s, 1H), 8.30 (t, 1H), 6.47 (s, 1H), 6.23-5.92 (m, 1H), 4.29 (q, 2H), 3.54 (tdd, 2H), 2.27 (d, 3H), 1.31 (t, 3H).

LC/MS (Method 3): $R_t$=1.17 min, m/z=293 [M+H]$^+$.

Example 41A

Ethyl 2-{[(2-methoxyethyl)carbamoyl]amino}-4-methylthiophene-3-carboxylate

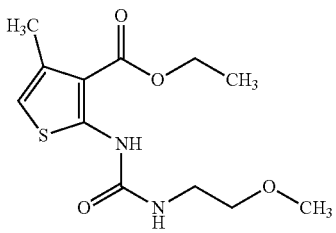 [SMILES: CCOC(=O)c1c(C)csc1NC(=O)NCCOC]

To a solution of 2 g (10.473 mmol) of ethyl 2-amino-4-methylthiophene-3-carboxylate in 10 ml of pyridine were added 2.12 g (20.945 mmol) of 1-isocyanato-2-methoxyethane. The reaction mixture was then stirred at 50° C. for 24 h. It was then concentrated to dryness on a rotary evaporator. The remaining residue was dissolved in dichloromethane and concentrated to dryness again. The material thus obtained was suspended in hexane and the solids were filtered off with suction and dried. 3.32 g of the title compound were obtained.

$^1$H-NMR (400 MHz, DMSO-$d_6$, δ/ppm): 10.30 (s, 1H), 8.02 (br. s, 1H), 6.42 (s, 1H), 4.27 (q, 2H), 3.39-3.36 (m, 2H), 3.28-3.23 (m, 5H), 2.26 (d, 3H), 1.31 (t, 3H).

LC/MS (Method 3): $R_t$=1.12 min, m/z=287 [M+H]$^+$.

Example 42A

3-Ethyl-5-methylthieno[2,3-d]pyrimidine-2,4(1H,3H)-dione

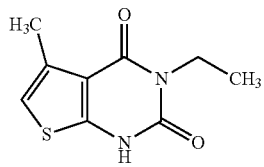

67 g (261 mmol) of the compound from Ex. 36A were dissolved in 1.6 liters of ethanol, and 141 ml (392 mmol) of a 21% solution of sodium ethoxide in ethanol were added. After the mixture had been stirred at RT for about 16 h, it was poured into about 500 ml of cold water and adjusted to a pH of about 5 by addition of glacial acetic acid. The resulting precipitate was filtered off with suction, washed with water until neutral and dried. 50 g (91% of theory) of the title compound were obtained.

$^1$H-NMR (300 MHz, DMSO-$d_6$, δ/ppm): 12.10 (br. s, 1H), 6.66 (s, 1H), 3.86 (q, 2H), 2.35 (s, 3H), 1.11 (t, 3H).

LC/MS (Method 1, ESIpos): $R_t$=0.67 min, m/z=211 [M+H]$^+$.

Example 43A

3-Isopropyl-5-methylthieno[2,3-d]pyrimidine-2,4(1H,3H)-dione

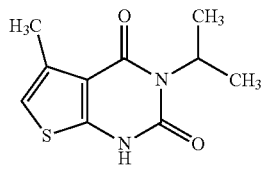

7.88 g (29.1 mmol) of the compound from Ex. 37A were dissolved in 80 ml of ethanol, and 22 ml (58.3 mmol) of a 21% solution of sodium ethoxide in ethanol were added. After the mixture had been stirred at 50° C. for 3 h, 67 ml (67 mmol) of 1 M hydrochloric acid were added at RT, and the product precipitated out. The heterogeneous mixture was first concentrated on a rotary evaporator to about half the original volume. After cooling to RT, the product was then filtered off with suction, washed to neutrality with water and dried under high vacuum. 5.87 g (89% of theory) of the title compound were obtained.

$^1$H-NMR (300 MHz, DMSO-$d_6$, δ/ppm): 11.95 (br. s, 1H), 6.65 (d, 1H), 5.10 (sept, 1H), 2.34 (d, 3H), 1.40 (d, 6H).

LC/MS (Method 6, ESIpos): $R_t$=1.44 min, m/z=225 [M+H]$^+$.

Example 44A

3-Isobutyl-5-methylthieno[2,3-d]pyrimidine-2,4(1H,3H)-dione

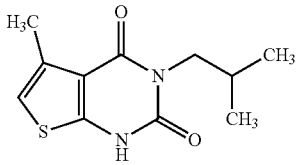 [SMILES: Cc1csc2[nH]c(=O)n(CC(C)C)c(=O)c12]

12.3 g (43.4 mmol) of the compound from Ex. 38A were dissolved in 120 ml of ethanol, and 32.4 ml (86.8 mmol) of a 21% solution of sodium ethoxide in ethanol were added. After the mixture had been stirred at RT for about 16 h, 99.8 ml (99.8 mmol) of 1 M hydrochloric acid were added at RT. The resulting precipitate was filtered off with suction, washed with water until neutral and dried. 10.1 g (97% of theory) of the title compound were obtained.

$^1$H-NMR (300 MHz, DMSO-$d_6$, δ/ppm): 12.09 (s, 1H), 6.68 (s, 1H), 3.67 (d, 2H), 2.35 (s, 3H), 2.04 (sept, 1H), 0.85 (d, 6H).

LC/MS (Method 1, ESIpos): $R_t$=0.84 min, m/z=239 [M+H]$^+$.

Example 45A

5-Methyl-3-(2,2,2-trifluoroethyl)thieno[2,3-d]pyrimidine-2,4(1H,3H)-dione

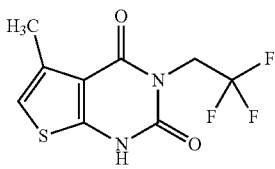 [SMILES: Cc1csc2[nH]c(=O)n(CC(F)(F)F)c(=O)c12]

2.78 g (8.33 mmol) of the compound from Ex. 39A were dissolved in 30 ml of ethanol, and 6.22 ml (16.66 mmol) of a 21% solution of sodium ethoxide in ethanol were added. After the mixture had been stirred at RT for about 14 h, 19 ml of 1 M hydrochloric acid were added at RT. The resulting precipitate was filtered off with suction, washed with water until neutral and dried. 2.15 g (89% of theory) of the title compound were obtained.

$^1$H-NMR (400 MHz, DMSO-$d_6$, δ/ppm): 12.42 (br. s, 1H), 6.76 (d, 1H), 4.64 (q, 2H), 2.35 (d, 3H).

LC/MS (Method 3): $R_t$=0.97 min, m/z=265 [M+H]$^+$.

Example 46A 3-(2,2-Difluoroethyl)-5-methylthieno[2,3-d]pyrimidine-2,4(1H,3H)-dione

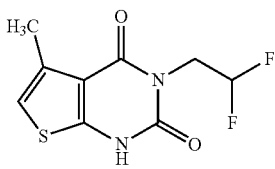 [SMILES: Cc1csc2[nH]c(=O)n(CC(F)F)c(=O)c12]

2.38 g (8 mmol) of the compound from Ex. 40A were dissolved in 23 ml of ethanol, and 5.97 ml (16.01 mmol) of a 21% solution of sodium ethoxide in ethanol were added. After the mixture had been stirred at RT for about 1 h, 18.4 ml of 1 M hydrochloric acid were added at RT. The resulting precipitate was filtered off with suction, washed with water until neutral and dried. 1.8 g (91% of theory) of the title compound were obtained.

$^1$H-NMR (400 MHz, DMSO-$d_6$, δ/ppm): 12.32 (br. s, 1H), 6.72 (d, 1H), 6.36-6.03 (m, 1H), 4.24 (td, 2H), 2.34 (d, 3H).

LC/MS (Method 3): $R_t$=0.89 min, m/z=211 [M+H]$^+$.

Example 47A 3-(2-Methoxyethyl)-5-methylthieno[2,3-d]pyrimidine-2,4(1H,3H)-dione

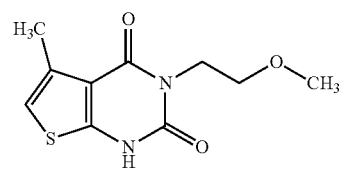 [SMILES: COCCn1c(=O)[nH]c2scc(C)c2c1=O]

3.26 g (11.38 mmol) of the compound from Ex. 41A were dissolved in 30 ml of ethanol, and 8.5 ml (22.76 mmol) of a 21% solution of sodium ethoxide in ethanol were added. After the mixture had been stirred at RT for about 2 h, 26.1 ml of 1 M hydrochloric acid were added at RT. The resulting precipitate was filtered off with suction, washed with water until neutral and dried. 2.44 g (89% of theory) of the title compound were obtained.

$^1$H-NMR (400 MHz, DMSO-$d_6$, δ/ppm): 12.14 (br. s, 1H), 6.69 (d, 1H), 4.01 (t, 2H), 3.48 (t, 2H), 3.24 (s, 3H), 2.34 (d, 3H).

LC/MS (Method 3): $R_t$=0.79 min, m/z=241 [M+H]$^+$.

Example 48A

3-Ethyl-5-methyl-2,4-dioxo-1,2,3,4-tetrahydrothieno[2,3-d]pyrimidine-6-carbaldehyde

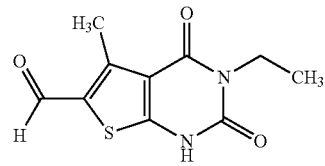 [SMILES: CCn1c(=O)[nH]c2sc(C=O)c(C)c2c1=O]

588 ml (6.31 mol) of phosphorus oxychloride were added cautiously to a solution of 442 g (2.10 mol) of the compound from Ex. 42A in 1.6 liters (21.0 mol) of DMF (strongly exothermic reaction). After half the amount of phosphorus oxychloride had been added, a solid precipitated out and was brought into solution by addition of a further liter of DMF. Then the addition of phosphorus oxychloride was continued. After the strongly exothermic reaction (temperature rise to 110° C.) had subsided, the mixture was stirred for a further 15 min. The reaction mixture was then stirred cautiously into 10 liters of ice-water. After stirring for 1 h, the precipitated product was filtered off with suction, washed with water until neutral and dried. 437 g (87% of theory) of the title compound were obtained.

$^1$H-NMR (400 MHz, DMSO-$d_6$, δ/ppm): 12.58 (broad, 1H), 10.06 (s, 1H), 3.86 (q, 2H), 2.76 (s, 3H), 1.12 (t, 3H).

LC/MS (Method 1, ESIpos): $R_t$=0.68 min, m/z=239 [M+H]$^+$.

Example 49A

3-Isopropyl-5-methyl-2,4-dioxo-1,2,3,4-tetrahydrothieno[2,3-d]pyrimidine-6-carbaldehyde

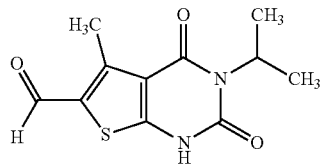 [SMILES: Cc1c(C=O)sc2[nH]c(=O)n(C(C)C)c(=O)c12]

11.4 ml (123 mmol) of phosphorus oxychloride were added cautiously to a solution of 6.90 g (30.8 mmol) of the compound from Ex. 43A in 28.4 ml (369 mmol) of DMF. After the strongly exothermic reaction had subsided, the mixture was stirred at RT for another 60 min. Since reactant was still detectable by HPLC analysis, the reaction mixture was heated to 90° C. for a further 30 min. Then the reaction mixture was stirred cautiously into 300 ml of water at RT, and the product precipitated out. The heterogeneous mixture was stirred at RT for about 18 h, then the product was filtered off with suction, washed to neutrality with water and dried. The crude product thus obtained was stirred with 30 ml acetonitrile at RT. The solids were filtered off with suction and gave a first fraction of the title compound. The mother liquor from the stirring was concentrated to about 10 ml and then 30 ml of pentane were added. This precipitated a second fraction of the product, which was filtered off with suction and combined with the first. A total of 7.25 g (93% of theory) of the title compound were thus obtained.

$^1$H-NMR (400 MHz, DMSO-$d_6$, δ/ppm): 12.44 (br. s, 1H), 10.06 (s, 1H), 5.07 (sept, 1H), 2.75 (s, 3H), 1.40 (d, 6H).

LC/MS (Method 1, ESIpos): $R_t$=0.76 min, m/z=253 [M+H]$^+$.

Example 50A

3-Isobutyl-5-methyl-2,4-dioxo-1,2,3,4-tetrahydrothieno[2,3-d]pyrimidine-6-carbaldehyde

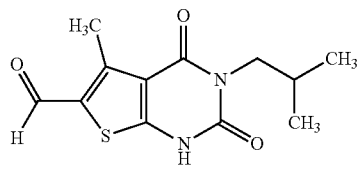 [SMILES: Cc1c(C=O)sc2[nH]c(=O)n(CC(C)C)c(=O)c12]

1.4 ml (15.1 mmol) of phosphorus oxychloride were added cautiously to a solution of 300 mg (1.26 mmol) of the compound from Ex. 44A in 1 ml (12.6 mol) of DMF. After the strongly exothermic reaction had subsided, the mixture was stirred for another 15 min. The reaction mixture was then stirred cautiously into 100 ml of ice-water. After stirring for 1 h, the precipitated product was filtered off with suction, washed with water until neutral and dried. 323 mg (96% of theory) of the title compound were obtained.

$^1$H-NMR (400 MHz, DMSO-$d_6$, δ/ppm): 12.58 (broad, 1H), 10.06 (s, 1H), 3.66 (d, 2H), 2.76 (s, 3H), 2.03 (sept, 1H), 0.86 (d, 6H).

LC/MS (Method 2, ESIpos): $R_t$=2.18 min, m/z=267 [M+H]$^+$.

Example 51A

5-Methyl-2,4-dioxo-3-(2,2,2-trifluoroethyl)-1,2,3,4-tetrahydrothieno[2,3-d]pyrimidine-6-carbaldehyde

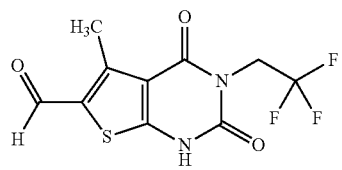 [SMILES: Cc1c(C=O)sc2[nH]c(=O)n(CC(F)(F)F)c(=O)c12]

14.33 ml (153.76 mmol) of phosphorus oxychloride were added cautiously, while cooling with an ice bath, to a solution of 4.67 g (15.37 mmol) of the compound from Ex. 45A in 143 ml of DMF. The mixture was stirred at 50° C. for 5 h. Then the reaction mixture was concentrated very substantially on a rotary evaporator. The remaining residue was added to ice-water and stirred. The precipitated product was filtered off with suction, washed to neutrality with water and dried. 4.52 g (99% of theory) of the title compound were obtained.

$^1$H-NMR (400 MHz, DMSO-$d_6$, δ/ppm): 12.93 (br. s, 1H), 10.08 (s, 1H), 4.64 (q, 2H), 2.76 (s, 3H).

LC/MS (Method 3): $R_t$=0.93 min, m/z=293 [M+H]$^+$.

Example 52A 3-(2,2-Difluoroethyl)-5-methyl-2,4-dioxo-1,2,3,4-tetrahydrothieno[2,3-d]pyrimidine-6-carbaldehyde

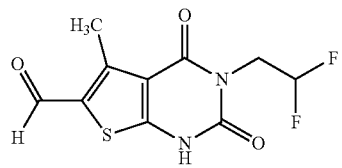 [SMILES: Cc1c(C=O)sc2[nH]c(=O)n(CC(F)F)c(=O)c12]

3.76 ml (40.4 mmol) of phosphorus oxychloride were added cautiously, while cooling with an ice bath, to a solution of 995 mg (4.04 mmol) of the compound from Ex. 46A in 37.7 ml of DMF. The mixture was stirred at 50° C. for 3 h. Then the reaction mixture was concentrated very substantially on a rotary evaporator. The remaining residue was added to ice-water and stirred. The precipitated product was filtered off with suction, washed to neutrality with water and dried. 1.06 g (95% of theory) of the title compound were obtained.

$^1$H-NMR (400 MHz, DMSO-$d_6$, δ/ppm): 12.84 (br. s, 1H), 10.07 (s, 1H), 6.37-6.04 (m, 1H), 4.24 (td, 2H), 2.76 (s, 3H).

LC/MS (Method 3): $R_t$=0.83 min, m/z=275 [M+H]$^+$.

95

Example 53A 3-(2-Methoxyethyl)-5-methyl-2,4-dioxo-1,2,3,4-tetrahydrothieno[2,3-d]pyrimidine-6-carbaldehyde

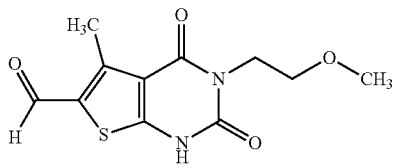 [SMILES: COCCn1c(=O)[nH]c2sc(C=O)c(C)c2c1=O]

1.94 ml (20.8 mmol) of phosphorus oxychloride were added cautiously, while cooling with an ice bath, to a solution of 500 mg (2.08 mmol) of the compound from Ex. 47A in 19.5 ml of DMF. The mixture was stirred at 50° C. for 3 h. Then the reaction mixture was concentrated very substantially on a rotary evaporator. The remaining residue was added to ice-water and stirred. The precipitated product was filtered off with suction, washed to neutrality with water and dried. 530 mg (93% of theory) of the title compound were obtained.

$^1$H-NMR (400 MHz, DMSO-$d_6$, δ/ppm): 12.64 (br. s, 1H), 10.06 (s, 1H), 4.00 (t, 2H), 3.49 (t, 2H), 3.24 (s, 3H), 2.75 (s, 3H).

LC/MS (Method 3): $R_t$=0.76 min, m/z=269 [M+H]$^+$.

Example 54A

3-Ethyl-5-methyl-1-(2,2,2-trifluoroethyl)thieno[2,3-d]pyrimidine-2,4(1H,3H)-dione

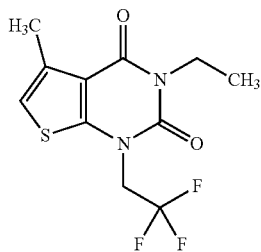 [SMILES: CCn1c(=O)c2c(C)csc2n(CC(F)(F)F)c1=O]

1.0 g (4.76 mmol) of the compound from Ex. 42A and 2.32 g (7.13 mmol) of caesium carbonate were stirred in 12 ml of anhydrous DMF at RT for 10 min, before 700 µl (7.13 mmol) of 1,1,1-trifluoro-2-iodoethane were added. Then the reaction mixture was heated in a microwave oven (Biotage Initiator with dynamic control of irradiation power) to 120° C. for 4 h. After cooling to RT, the mixture was diluted with ethyl acetate and washed successively with water and saturated sodium chloride solution. After drying over anhydrous magnesium sulphate, the mixture was filtered and concentrated to dryness. The residue obtained was purified by MPLC (Biotage cartridge, 100 g of silica gel, cyclohexane/ethyl acetate 3:1). After combination of the product fractions, concentration and drying under high vacuum, 592 mg (42% of theory) of the title compound were obtained.

$^1$H-NMR (400 MHz, DMSO-$d_6$, δ/ppm): 6.91 (s, 1H), 4.84 (q, 2H), 3.92 (q, 2H), 2.39 (s, 3H), 1.13 (t, 3H).

LC/MS (Method 1, ESIpos/neg): $R_t$=1.01 min, no ionization.

96

Example 55A

3-Ethyl-5-methyl-1-(3,3,3-trifluoropropyl)thieno[2,3-d]pyrimidine-2,4(1H,3H)-dione

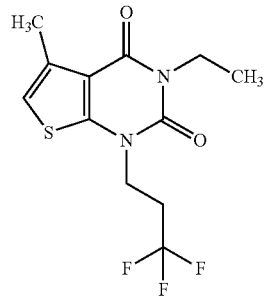 [SMILES: CCn1c(=O)c2c(C)csc2n(CCC(F)(F)F)c1=O]

2.0 g (9.51 mmol) of the compound from Ex. 42A and 3.29 g (23.8 mmol) of potassium carbonate were stirred in 50 ml of anhydrous DMF at RT for 15 min, before 3.3 ml (28.5 mmol) of 1,1,1-trifluoro-3-iodopropane were added. Since the conversion was still incomplete after stirring at RT overnight, a further 1.31 g (9.51 mmol) of potassium carbonate and 1.1 ml (9.51 mmol) of 1,1,1-trifluoro-3-iodopropane were added and the mixture was stirred at 60° C. for 2 h. After cooling to RT, the mixture was diluted with ethyl acetate and washed successively with water (twice) and saturated sodium chloride solution. After drying over anhydrous magnesium sulphate, the mixture was filtered and the filtrate was concentrated to dryness. The crude product was purified by chromatography using a Biotage cartridge (340 g of silica gel, eluent: cyclohexane/ethyl acetate 24:1→10:1). Concentration and drying of the product fractions gave 2.06 g (70% of theory) of the title compound.

$^1$H-NMR (400 MHz, DMSO-$d_6$, δ/ppm): 6.88 (s, 1H), 4.12 (t, 2H), 3.91 (q, 2H), 2.84-2.71 (m, 2H), 2.39 (s, 3H), 1.12 (t, 3H).

LC/MS (Method 1, ESIpos): $R_t$=1.02 min, m/z=307 [M+H]$^+$.

Example 56A

3-Ethyl-5-methyl-1-(4,4,4-trifluorobutyl)thieno[2,3-d]pyrimidine-2,4(1H,3H)-dione

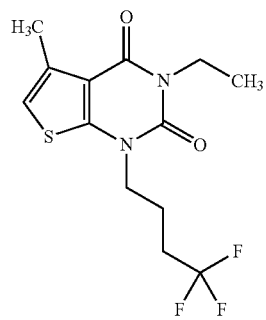 [SMILES: CCn1c(=O)c2c(C)csc2n(CCCC(F)(F)F)c1=O]

Analogously to the method described in Ex. 54A, 1.0 g (4.76 mmol) of the compound from Ex. 42A and 1.70 g (7.13 mmol) of 1,1,1-trifluoro-4-iodobutane were used to prepare 1.35 g (90% of theory) of the title compound. The reaction in the microwave was effected here at 100° C. and the reaction time was 1 h. The eluent gradient used in the MPLC purification was cyclohexane/ethyl acetate 20:1→10:1.

$^1$H-NMR (400 MHz, DMSO-d$_6$, δ/ppm): 6.85 (s, 1H), 3.98 (t, 2H), 3.90 (q, 2H), 2.46-2.36 (m, 2H), 2.39 (s, 3H), 1.91 (quin, 2H), 1.12 (t, 3H).

LC/MS (Method 1, ESIpos): R$_t$=1.07 min, m/z=321 [M+H]$^+$.

Example 57A

3-Ethyl-5-methyl-1-[2-(trifluoromethoxy)ethyl]thieno[2,3-d]pyrimidine-2,4(1H,3H)-dione

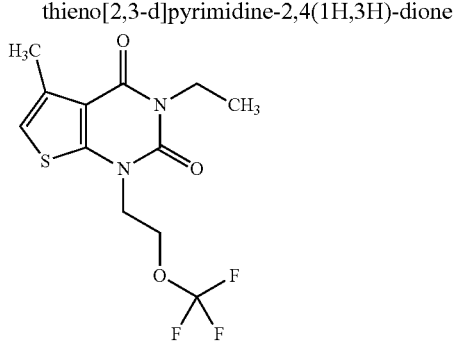

1.0 g (4.76 mmol) of the compound from Ex. 42A and 2.32 g (7.13 mmol) of caesium carbonate were stirred in 12 ml of anhydrous DMF at RT for 10 min, before 1.38 g (7.13 mmol) of 1-bromo-2-(trifluoromethoxy)ethane [commercially available; Lit.: P. E. Aldrich, W. A. Sheppard, *J. Org. Chem.* 1964, 29 (1), 11-15] were added. Then the reaction mixture was heated in a microwave oven (Biotage Initiator with dynamic control of irradiation power) to 100° C. for 1 h. After cooling to RT, the mixture was diluted with ethyl acetate and washed successively with water and saturated sodium chloride solution. After drying over anhydrous magnesium sulphate, the mixture was filtered and concentrated to dryness. The residue obtained was purified by MPLC (Biotage cartridge, 100 g of silica gel, cyclohexane/ethyl acetate 10:1). After combination of the product fractions, concentration and drying under high vacuum, 1.21 g (78% of theory) of the title compound were obtained.

$^1$H-NMR (400 MHz, DMSO-d$_6$, δ/ppm): 6.85 (s, 1H), 4.42 (t, 2H), 4.21 (t, 2H), 3.91 (q, 2H), 2.39 (s, 3H), 1.12 (t, 3H).

LC/MS (Method 1, ESIpos): R$_t$=1.04 min, m/z=323 [M+H]$^+$.

Example 58A

3-Ethyl-5-methyl-1-{2-[(trifluoromethyl)sulphanyl]ethyl}thieno[2,3-d]pyrimidine-2,4(1H,3H)-dione

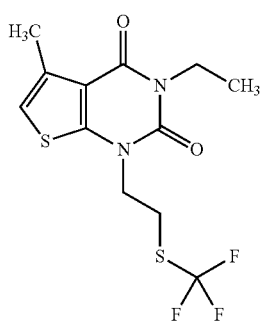 [SMILES: CCn1c(=O)c2c(C)csc2n(CCSC(F)(F)F)c1=O]

Analogously to the method described in Ex. 57A, 1.0 g (4.76 mmol) of the compound from Ex. 42A and 1.49 g (7.13 mmol) of 1-bromo-2-[(trifluoromethyl)sulphanyl]ethane were used to obtain 1.36 g (84% of theory) of the title compound. MPLC purification was effected here with an eluent gradient of cyclohexane/ethyl acetate 20:1→10:1. This gave a first, pure fraction of the title compound (932 mg) and a mixed fraction, from which a second fraction of pure title compound (427 mg) was subsequently obtained by means of preparative HPLC (Method 9).

$^1$H-NMR (400 MHz, DMSO-d$_6$, δ/ppm): 6.86 (s, 1H), 4.16 (t, 2H), 3.91 (q, 2H), 3.37 (t, 2H), 2.39 (s, 3H), 1.12 (t, 3H).

LC/MS (Method 1, ESIpos): R$_t$=1.11 min, m/z=339 [M+H]$^+$.

Example 59A

3-Ethyl-1-(2-methoxyethyl)-5-methylthieno[2,3-d]pyrimidine-2,4(1H,3H)-dione

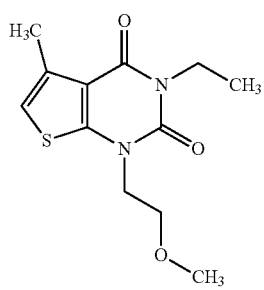 [SMILES: CCn1c(=O)c2c(C)csc2n(CCOC)c1=O]

7.5 g (35.7 mmol) of the compound from Ex. 42A and 12.3 g (89.2 mmol) of potassium carbonate were stirred in 200 ml of anhydrous DMF at RT for 15 min, before 10 ml (107 mmol) of 2-bromoethyl methyl ether were added. The reaction mixture was then stirred at 50° C. for 2 h. Thereafter, the majority of the DMF was removed on a rotary evaporator. The residue was diluted with about 800 ml of ethyl acetate, and the mixture was washed successively with water (twice) and saturated sodium chloride solution. After drying over anhydrous magnesium sulphate, the mixture was filtered and the filtrate was concentrated to dryness. The crude product was purified by chromatography using a Biotage cartridge (340 g of silica gel, eluent: cyclohexane/ethyl acetate 10:1→4:1). After the product fractions had been concentrated and dried, a first portion of 6.51 g of the title compound was obtained. A second portion of 0.91 g was obtained by concentrating the product-containing mixed fractions (1.4 g) and then stirring with 200 ml of pentane/dichloromethane (25:1). A total of 7.42 g (77% of theory) of the title compound were thus obtained.

$^1$H-NMR (400 MHz, CDCl$_3$, δ/ppm): 6.42 (s, 1H), 4.12 (t, 2H), 4.08 (q, 2H), 3.74 (t, 2H), 3.35 (s, 3H), 2.49 (s, 3H), 1.26 (t, 3H).

LC/MS (Method 1, ESIpos): R$_t$=0.87 min, m/z=269 [M+H]$^+$.

Example 60A

3-Ethyl-5-methyl-1-(tetrahydrofuran-2-ylmethyl)thieno[2,3-d]pyrimidine-2,4(1H,3H)-dione (racemate)

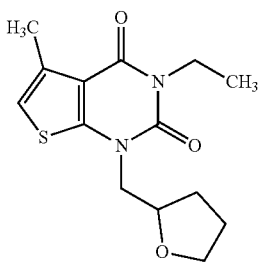 [SMILES: CCn1c(=O)c2c(C)csc2n(CC2CCCO2)c1=O]

1.0 g (4.76 mmol) of the compound from Ex. 42A and 2.32 g (7.13 mmol) of caesium carbonate were stirred in 12 ml of anhydrous DMF at RT for 10 min, before 1.18 ml (7.13 mmol) of racemic 2-(bromomethyl)tetrahydrofuran were added. Subsequently, the reaction mixture was heated in a microwave oven (Biotage Initiator with dynamic control of irradiation power) to 100° C. for 90 min. After cooling to RT, the mixture was diluted with ethyl acetate and washed successively with water and saturated sodium chloride solution. After drying over anhydrous magnesium sulphate, the mixture was filtered and concentrated to dryness. The residue obtained was first purified by MPLC (Biotage cartridge, 100 g of silica gel, cyclohexane/ethyl acetate 10:1→8:1). This gave a mixture of O- and N-alkylated product (1.27 g), which was separated into its components by means of preparative HPLC (Method 8). After combination of the product fractions, concentration and drying under high vacuum, 1.09 g (78% of theory) of the title compound were obtained.

$^1$H-NMR (400 MHz, DMSO-$d_6$, δ/ppm): 6.80 (s, 1H), 4.27-4.21 (m, 1H), 4.05 (dd, 1H), 3.91 (q, 2H), 3.78-3.70 (m, 2H), 3.62 (dd, 1H), 2.38 (s, 3H), 2.03-1.95 (m, 1H), 1.93-1.76 (m, 2H), 1.71-1.62 (m, 1H), 1.12 (t, 3H).

LC/MS (Method 1, ESIpos): $R_t$=0.93 min, m/z=295 [M+H]$^+$.

Example 61A

3-Ethyl-5-methyl-1-propylthieno[2,3-d]pyrimidine-2,4(1H,3H)-dione

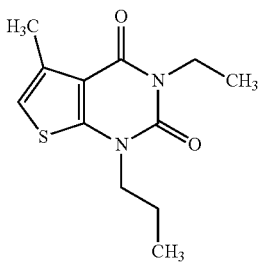 [SMILES: CCCn1c(=O)n(CC)c(=O)c2c(C)csc21]

Analogously to the method described in Ex. 54A, 1.0 g (4.76 mmol) of the compound from Ex. 42A and 696 μl (7.13 mmol) of 1-iodopropane were used to prepare 1.08 g (95% of theory) of the title compound. The reaction time here was 60 min at 100° C., and the MPLC purification was conducted with the eluent gradient of cyclohexane/ethyl acetate 20:1→10:1.

$^1$H-NMR (400 MHz, DMSO-$d_6$, δ/ppm): 6.83 (s, 1H), 3.91 (q, 2H), 3.85 (t, 2H), 2.38 (s, 3H), 1.71 (sext, 2H), 1.12 (t, 3H), 0.91 (t, 3H).

LC/MS (Method 1, ESIpos): $R_t$=1.02 min, m/z=253 [M+H]$^+$.

Example 62A

3-Isopropyl-5-methyl-1-(3,3,3-trifluoropropyl)thieno[2,3-d]pyrimidine-2,4(1H,3H)-dione

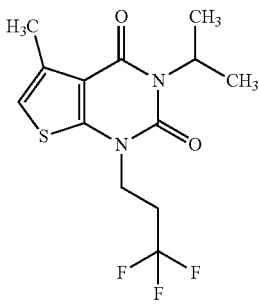 [SMILES: Cc1csc2c1c(=O)n(C(C)C)c(=O)n2CCC(F)(F)F]

500 mg (2.23 mmol) of the compound from Ex. 43A and 1.90 g (3.34 mmol) of caesium carbonate were stirred in 10 ml of anhydrous DMF at RT for 10 min, before 392 μl (3.34 mmol) of 1,1,1-trifluoro-3-iodopropane were added. Subsequently, the reaction mixture was heated in a microwave oven (Biotage Initiator with dynamic control of irradiation power), at first to 60° C. for 1 h and then to 100° C. for 1 h. Then the same amounts of caesium carbonate and 1,1,1-trifluoro-3-iodopropane were added once again and the heating to 100° C. was continued for 6 h. The same amounts of caesium carbonate and 1,1,1-trifluoro-3-iodopropane were added once more and, after a further 30 min at 100° C., the conversion was complete. After cooling to RT, the mixture was diluted with ethyl acetate and washed successively with water and saturated sodium chloride solution. After drying over anhydrous magnesium sulphate, the mixture was filtered and concentrated to dryness. The residue obtained was purified by means of preparative HPLC (Method 8). After combination of the product fractions, concentration and drying under high vacuum, 553 mg (77% of theory) of the title compound were obtained.

$^1$H-NMR (400 MHz, DMSO-$d_6$, δ/ppm): 6.85 (d, 1H), 5.14 (sept, 1H), 4.09 (t, 2H), 2.76 (qt, 2H), 2.38 (d, 3H), 1.40 (d, 6H).

LC/MS (Method 1, ESIpos): $R_t$=1.14 min, m/z=321 [M+H]$^+$.

Example 63A 1-(2-Fluoroethyl)-3-isopropyl-5-methylthieno[2,3-d]pyrimidine-2,4(1H,3H)-dione

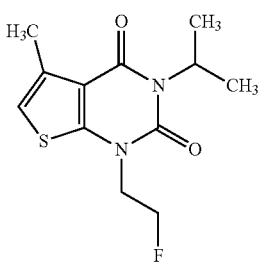 [SMILES: Cc1csc2c1c(=O)n(C(C)C)c(=O)n2CCF]

Analogously to the method described in Ex. 54A, 500 mg (2.23 mmol) of the compound from Ex. 43A and 277 µl (3.34 mmol) of 1-fluoro-2-iodoethane were used to prepare 462 mg (76% of theory) of the title compound. The reaction time here was 60 min at 60° C., and the product was purified by means of preparative HPLC (Method 8).

$^1$H-NMR (400 MHz, DMSO-$d_6$, δ/ppm): 6.80 (s, 1H), 5.14 (sept, 1H), 4.85-4.61 (dt, 2H), 4.28-4.07 (dt, 2H), 2.37 (s, 3H), 1.41 (d, 6H).

LC/MS (Method 1, ESIpos): $R_t$=0.94 min, m/z=271 [M+H]$^+$.

Example 64A

3-Isopropyl-5-methyl-1-(tetrahydrofuran-2-ylmethyl)thieno[2,3-d]pyrimidine-2,4(1H,3H)-dione (racemate)

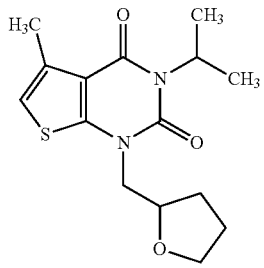 [SMILES: Cc1csc2c1c(=O)n(C(C)C)c(=O)n2CC1CCCO1]

500 mg (2.23 mmol) of the compound from Ex. 43A and 1.09 g (3.34 mmol) of caesium carbonate were stirred in 10 ml of anhydrous DMF at RT for 10 min, before 380 µl (3.34 mmol) of 2-(bromomethyl)tetrahydrofuran were added. Subsequently, the reaction mixture was heated in a microwave oven (Biotage Initiator with dynamic control of irradiation power) to 100° C. for 2 h. After cooling to RT, the mixture was diluted with ethyl acetate and washed successively with water and saturated sodium chloride solution. After drying over anhydrous magnesium sulphate, the mixture was filtered and concentrated to dryness. The residue obtained was stirred in an acetonitrile/water mixture. The undissolved material was filtered off with suction and dried under high vacuum, which gave a first fraction of the title compound (220 mg). The filtrate was purified by means of preparative HPLC (Method 8). After the product fractions had been concentrated and dried under high vacuum, a further portion of the title compound was obtained (213 mg). A total of 433 mg (57% of theory, 90% purity) of the title compound were thus obtained.

$^1$H-NMR (400 MHz, DMSO-$d_6$, δ/ppm): 6.77 (d, 1H), 5.15 (sept, 1H), 4.28-4.17 (m, 1H), 4.04 (dd, 1H), 3.80-3.56 (m, 3H), 2.37 (d, 3H), 2.06-1.73 (m, 3H), 1.71-1.60 (m, 1H), 1.40 (dd, 6H).

LC/MS (Method 5, ESIpos): $R_t$=1.34 min, m/z=309 [M+H]$^+$.

Example 65A

3-Isopropyl-1,5-dimethylthieno[2,3-d]pyrimidine-2,4(1H,3H)-dione

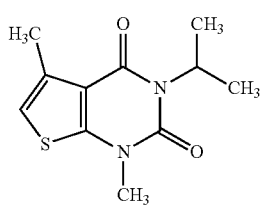 [SMILES: Cc1csc2c1c(=O)n(C(C)C)c(=O)n2C]

Analogously to the method described in Ex. 54A, 500 mg (2.23 mmol) of the compound from Ex. 43A and 316 µl (3.34 mmol) of dimethyl sulphate were used to prepare 439 mg (82% of theory) of the title compound. The reaction time here was 60 min at 100° C., and the eluent gradient used in the MPLC purification was cyclohexane/ethyl acetate 13:1→2:1.

$^1$H-NMR (400 MHz, DMSO-$d_6$, δ/ppm): 6.80 (d, 1H), 5.15 (sept, 1H), 3.40 (s, 3H), 2.38 (d, 3H), 1.40 (d, 6H).

LC/MS (Method 1, ESIpos): $R_t$=0.95 min, m/z=239 [M+H]$^+$.

Example 66A

3-Isobutyl-5-methyl-1-(3,3,3-trifluoropropyl)thieno[2,3-d]pyrimidine-2,4(1H,3H)-dione

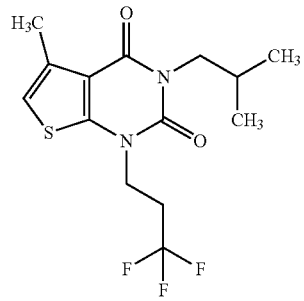 [SMILES: Cc1csc2c1c(=O)n(CC(C)C)c(=O)n2CCC(F)(F)F]

3.23 g (23.39 mmol) of potassium carbonate were added to a solution of 2.23 g (9.35 mmol) of the compound from Ex. 44A in 82.6 ml of DMF, and the mixture was stirred at RT for 15 min. Then 6.48 g (28.07 mmol) of 1,1,1-trifluoro-3-iodopropane were added, and the mixture was stirred at RT for 73 h. The DMF was then very substantially distilled off and the remaining residue was partitioned between semisaturated sodium chloride solution (200 ml) and ethyl acetate (100 ml). The aqueous phase was extracted with ethyl acetate. The combined organic phases were dried over sodium sulphate, filtered and concentrated. The residue obtained was chromatographed using a silica gel cartridge (Biotage, 340 g of silica gel, eluent: hexane/ethyl acetate). In this way, 2.67 g (84% of theory) of the title compound were obtained.

$^1$H-NMR (400 MHz, DMSO-$d_6$, δ/ppm): 6.88 (d, 1H), 4.13 (t, 2H), 3.71 (d, 2H), 2.84-2.70 (m, 2H), 2.38 (d, 3H), 2.11-1.96 (m, 1H), 0.85 (d, 6H).

LC/MS (Method 3): $R_t$=1.4 min, m/z=335 [M+H]$^+$.

Example 67A 1-(2-Fluoroethyl)-3-isobutyl-5-methylthieno[2,3-d]pyrimidine-2,4(1H,3H)-dione

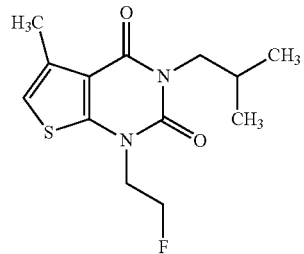 [SMILES: Cc1csc2c1c(=O)n(CC(C)C)c(=O)n2CCF]

Analogously to the method described in Ex. 54A, 500 mg (2.10 mmol) of the compound from Ex. 44A and 261 μl (3.15 mmol) of 1-fluoro-2-iodoethane were used to prepare 458 mg (76% of theory) of the title compound. The reaction time here was 60 min at 60° C., and the product was purified by means of preparative HPLC (Method 8).

$^1$H-NMR (400 MHz, DMSO-$d_6$, δ/ppm): 6.83 (d, 1H), 4.82-4.64 (dt, 2H), 4.27-4.14 (dt, 2H), 3.72 (d, 2H), 2.38 (d, 3H), 2.05 (m, 1H), 0.86 (d, 6H).

LC/MS (Method 1, ESIpos): $R_t$=1.10 min, m/z=285 [M+H]$^+$.

Example 68A

3-Isobutyl-1-(2-methoxyethyl)-5-methylthieno[2,3-d]pyrimidine-2,4(1H,3H)-dione

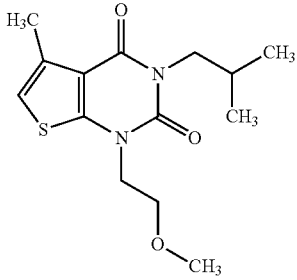 [SMILES: COCCn1c(=O)n(CC(C)C)c(=O)c2c(C)csc21]

3.23 g (23.39 mmol) of potassium carbonate were added to a solution of 2.23 g (9.35 mmol) of the compound from Ex. 44A in 80 ml of DMF, and the mixture was stirred at RT for 15 min. 3.9 g (28.07 mmol) of 2-bromoethyl methyl ether were then added, and the mixture was stirred at 50° C. for 3 h. The DMF was then very substantially distilled off and the remaining residue was partitioned between semi-saturated sodium chloride solution (300 ml) and ethyl acetate (150 ml). The aqueous phase was extracted with ethyl acetate. The combined organic phases were dried over sodium sulphate, filtered and concentrated. The residue obtained was chromatographed using a silica gel cartridge (Biotage, 340 g of silica gel, eluent: hexane/ethyl acetate). In this way, 2.37 g (85% of theory) of the title compound were obtained.

$^1$H-NMR (400 MHz, DMSO-$d_6$, δ/ppm): 6.81 (d, 1H), 4.04 (t, 2H), 3.71 (d, 2H), 3.64 (t, 2H), 3.23 (s, 3H), 2.37 (d, 3H), 2.03 (dquin, 1H), 0.85 (d, 6H).

LC/MS (Method 3): $R_t$=1.24 min, m/z=297 [M+H]$^+$.

Example 69A

3-Isobutyl-5-methyl-1-(tetrahydrofuran-2-ylmethyl)thieno[2,3-d]pyrimidine-2,4(1H,3H)-dione (racemate)

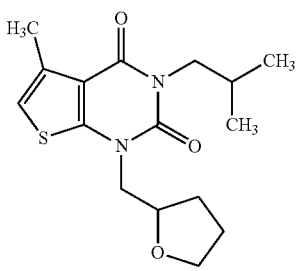 [SMILES: Cc1csc2c1c(=O)n(CC(C)C)c(=O)n2CC1CCCO1]

Analogously to the method described in Ex. 54A, 500 mg (2.10 mmol) of the compound from Ex. 44A and 358 μl (3.15 mmol) of racemic 2-(bromomethyl)tetrahydrofuran were used to prepare 516 mg (76% of theory) of the title compound. The reaction time here was 90 min at 100° C., and the product was purified by means of preparative HPLC (Method 8).

$^1$H-NMR (400 MHz, DMSO-$d_6$, δ/ppm): 6.81 (d, 1H), 4.28-4.19 (m, 1H), 4.04 (dd, 1H), 3.79-3.69 (m, 4H), 3.65-3.58 (m, 1H), 2.37 (d, 3H), 2.09-1.76 (m, 4H), 1.67 (m, 1H), 0.86 (d, 3H), 0.85 (d, 3H).

LC/MS (Method 1, ESIpos): $R_t$=1.17 min, m/z=323 [M+H]$^+$.

Example 70A

3-Isobutyl-1,5-dimethylthieno[2,3-d]pyrimidine-2,4(1H,3H)-dione

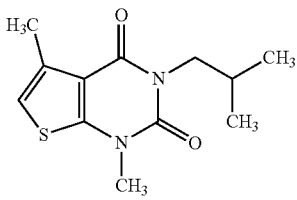 [SMILES: Cc1csc2c1c(=O)n(CC(C)C)c(=O)n2C]

Analogously to the method described in Ex. 54A, 500 mg (2.10 mmol) of the compound from Ex. 44A and 596 μl (3.30 mmol) of dimethyl sulphate were used to prepare 172 mg (32% of theory) of the title compound. The reaction time here was 8 h at 60° C., and the product was purified by means of preparative HPLC (Method 8).

$^1$H-NMR (400 MHz, DMSO-$d_6$, δ/ppm): 6.83 (d, 1H), 3.71 (d, 2H), 3.43 (s, 3H), 2.38 (d, 3H), 2.13-1.96 (m, 1H), 0.85 (d, 6H).

LC/MS (Method 1, ESIpos): $R_t$=0.99 min, m/z=253 [M+H]$^+$.

Example 71A 1-(3-Fluoropropyl)-5-methyl-3-(2,2,2-trifluoroethyl)thieno[2,3-d]pyrimidine-2,4(1H,3H)-dione

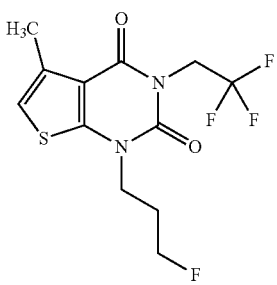 [SMILES: Cc1csc2c1c(=O)n(CC(F)(F)F)c(=O)n2CCCF]

1.19 g (8.63 mmol) of potassium carbonate were added to a solution of 1 g (3.45 mmol) of the compound from Ex. 45A in 30 ml of DMF, and the mixture was stirred at RT for 15 min. Then 1.94 g (10.35 mmol) of 1-fluoro-3-iodopropane were added, and the mixture was stirred at 50° C. for 96 h. The DMF was then very substantially distilled off and the remaining residue was partitioned between semisaturated sodium chloride solution (100 ml) and ethyl acetate (50 ml). The water phase was extracted with ethyl acetate. The combined organic phases were dried over sodium sulphate, filtered and concentrated. The residue obtained was chromatographed using a silica gel cartridge (Biotage, 100 g of silica gel, eluent: hexane/ethyl acetate). 1.05 g (94% of theory) of the title compound were obtained.

$^1$H-NMR (400 MHz, DMSO-$d_6$, δ/ppm): 6.92 (d, 1H), 4.69 (q, 2H), 4.60 (t, 1H), 4.48 (t, 1H), 4.03 (t, 2H), 2.39 (d, 3H), 2.17-2.01 (m, 2H).

LC/MS (Method 3): $R_t$=1.2 min, m/z=325 [M+H]$^+$.

Example 72A 1-(2-Methoxyethyl)-5-methyl-3-(2,2,2-trifluoroethyl)thieno[2,3-d]pyrimidine-2,4(1H,3H)-dione

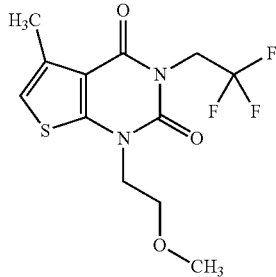 [SMILES: COCCn1c(=O)n(CC(F)(F)F)c(=O)c2c(C)csc21]

1.19 g (8.63 mmol) of potassium carbonate were added to a solution of 1 g (3.45 mmol) of the compound from Ex. 45A in 30 ml of DMF, and the mixture was stirred at RT for 15 min. 1.43 g (8.61 mmol) of 2-bromoethyl methyl ether were then added, and the mixture was stirred at 50° C. for 17 h. The DMF was then very substantially distilled off and the remaining residue was partitioned between semisaturated sodium chloride solution (100 ml) and ethyl acetate (50 ml). The aqueous phase was extracted with ethyl acetate. The combined organic phases were dried over sodium sulphate, filtered and concentrated. The residue obtained was chromatographed using a silica gel cartridge (Biotage, 100 g of silica gel, eluent: hexane/ethyl acetate). 946 mg (85% of theory) of the title compound were obtained.

$^1$H-NMR (400 MHz, DMSO-$d_6$, δ/ppm): 6.89 (d, 1H), 4.70 (q, 2H), 4.08 (t, 2H), 3.65 (t, 2H), 3.24 (s, 3H), 2.38 (d, 3H).

LC/MS (Method 3): $R_t$=1.16 min, m/z=323 [M+H]$^+$.

Example 73A

3-Ethyl-5-methyl-2,4-dioxo-1-(2,2,2-trifluoroethyl)-1,2,3,4-tetrahydrothieno[2,3-d]pyrimidine-6-carbaldehyde

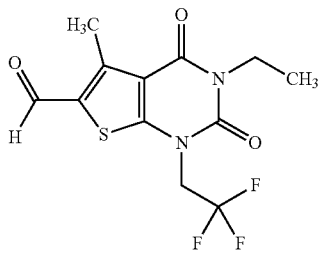 [SMILES: CCn1c(=O)c2c(C)c(C=O)sc2n(CC(F)(F)F)c1=O]

2.2 ml (23.8 mmol) of phosphorus oxychloride were added to a solution of 581 mg (1.99 mmol) of the compound from Ex. 54A in 1.5 ml (19.9 mmol) of DMF. After the strongly exothermic reaction had subsided, the mixture was stirred at RT for another 30 min. Subsequently, the reaction mixture was stirred cautiously into 100 ml of water. After stirring for 1 h, the precipitated product was filtered off with suction, washed with water until neutral and dried. 600 mg (94% of theory) of the title compound were obtained.

$^1$H-NMR (400 MHz, DMSO-$d_6$, δ/ppm): 10.12 (s, 1H), 4.94 (q, 2H), 3.92 (q, 2H), 2.80 (s, 3H), 1.15 (t, 3H).

LC/MS (Method 1, ESIpos): $R_t$=0.95 min, m/z=321 [M+H]$^+$.

Example 74A

3-Ethyl-5-methyl-2,4-dioxo-1-(3,3,3-trifluoropropyl)-1,2,3,4-tetrahydrothieno[2,3-d]pyrimidine-6-carbaldehyde

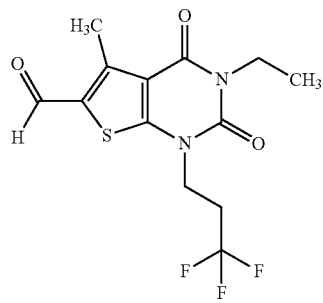 [SMILES: CCn1c(=O)c2c(C)c(C=O)sc2n(CCC(F)(F)F)c1=O]

Method A:

5.0 g (21.0 mmol) of the compound from Ex. 48A and 10.3 g (31.5 mmol) of caesium carbonate were stirred in 50 ml of DMF at RT for 15 min, before 3.7 ml (31.5 mmol) of 1,1,1-trifluoro-3-iodopropane were added. Subsequently, the reaction mixture was stirred at a temperature of 60° C. for about 18 h. After cooling to RT, the mixture was diluted with about 200 ml of ethyl acetate and washed successively with water and saturated sodium chloride solution. After drying over anhydrous magnesium sulphate, the mixture was filtered and the filtrate was concentrated to dryness. The crude product was purified by MPLC (Biotage cartridge, 80 g of silica gel, eluent: cyclohexane/ethyl acetate 3:1). Concentration and drying of the product fractions gave 4.8 g (62% of theory) of the title compound.

Method B:

12.6 ml (135 mmol) of phosphorus oxychloride were added rapidly to a solution of 13.8 g (45.0 mmol) of the compound from Ex. 55A in 52 ml (676 mmol) of DMF. After the strongly exothermic reaction had almost subsided, the mixture was stirred at 90° C. for a further 30 min. After cooling to RT, the reaction mixture was stirred cautiously into 300 ml of lukewarm water. After stirring for about 18 h, the precipitated product was filtered off with suction, washed to neutrality with water and dried. 13.9 g (92% of theory) of the title compound were obtained.

$^1$H-NMR (400 MHz, DMSO-$d_6$, δ/ppm): 10.11 (s, 1H), 4.18 (t, 2H), 3.91 (q, 2H), 2.86-2.74 (m, 2H), 2.80 (s, 3H), 1.14 (t, 3H).

LC/MS (Method 1, ESIpos): $R_t$=0.98 min, m/z=335 [M+H]$^+$.

Example 75A

3-Ethyl-5-methyl-2,4-dioxo-1-(4,4,4-trifluorobutyl)-1,2,3,4-tetrahydrothieno[2,3-d]pyrimidine-6-carbaldehyde

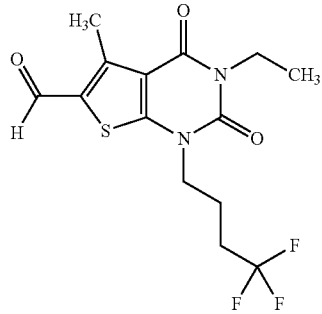 [SMILES: CCn1c(=O)c2c(C)c(C=O)sc2n(CCCC(F)(F)F)c1=O]

Analogously to the method described in Ex. 73A, 1.32 g (4.14 mmol) of the compound from Ex. 56A, 3.2 ml (41.3 mmol) of anhydrous DMF and 4.6 ml (49.6 mmol) of phosphorus oxychloride were used to prepare 1.38 mg (95% of theory) of the title compound.

$^1$H-NMR (400 MHz, DMSO-$d_6$, δ/ppm): 10.10 (s, 1H), 4.02 (t, 2H), 3.90 (q, 2H), 2.80 (s, 3H), 2.49-2.38 (m, 2H), 1.91 (quin, 2H), 1.14 (t, 3H).

LC/MS (Method 1, ESIpos): $R_t$=1.03 min, m/z=349 [M+H]$^+$.

Example 76A 1-(2,2-Difluoroethyl)-3-ethyl-5-methyl-2,4-dioxo-1,2,3,4-tetrahydrothieno[2,3-d]pyrimidine-6-carbaldehyde

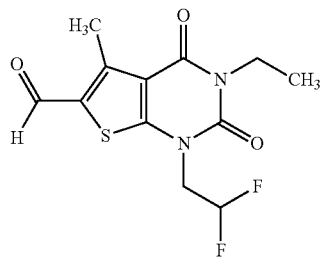 [SMILES: CCn1c(=O)c2c(C)c(C=O)sc2n(CC(F)F)c1=O]

601 mg (4.35 mmol) of potassium carbonate were added to a solution of 349 mg (1.45 mmol) of the compound from Ex. 48A in 13 ml of DMF, and the mixture was stirred at RT for 15 min. Then 1.11 g (5.8 mmol) of 1,1-difluoro-2-iodoethane were added, and the mixture was stirred at 80° C. for 90 h. The DMF was then very substantially distilled off and the remaining residue was partitioned between semi-saturated sodium chloride solution (40 ml) and ethyl acetate (25 ml). The aqueous phase was extracted with ethyl acetate. The combined organic phases were dried over sodium sulphate, filtered and concentrated. The residue obtained was chromatographed using a silica gel cartridge (Biotage, 25 g of silica gel, eluent: hexane/ethyl acetate). 235 mg (54% of theory) of the title compound were obtained.

$^1$H-NMR (400 MHz, DMSO-$d_6$, δ/ppm): 10.10 (s, 1H), 6.52-6.22 (m, 1H), 4.43 (td, 2H), 3.91 (q, 2H), 2.79 (s, 3H), 1.14 (t, 3H).

LC/MS (Method 3): $R_t$=1.05 min, m/z=303 [M+H]$^+$.

Example 77A

3-Ethyl-1-(2-fluoroethyl)-5-methyl-2,4-dioxo-1,2,3,4-tetrahydrothieno[2,3-d]pyrimidine-6-carbaldehyde

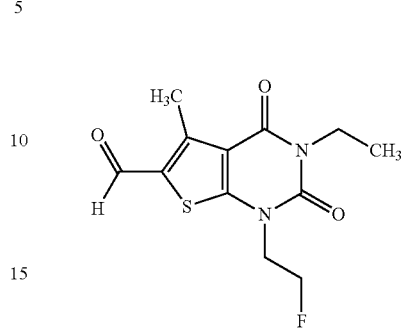

Analogously to the method described in Ex. 54A, 500 mg (2.10 mmol) of the compound from Ex. 48A and 547 mg (3.15 mmol) of 1-fluoro-2-iodoethane were used to prepare 258 mg (43% of theory) of the title compound. The reaction in the microwave was effected here at 60° C. with a reaction time of 3 h. The eluent used in the MPLC purification was cyclohexane/ethyl acetate 2:1.

$^1$H-NMR (400 MHz, DMSO-$d_6$, δ/ppm): 10.10 (s, 1H), 4.75 (dt, 2H), 4.28 (dt, 2H), 3.91 (q, 2H), 2.79 (s, 3H), 1.15 (t, 3H).

LC/MS (Method 1, ESIpos): $R_t$=0.80 min, m/z=285 [M+H]$^+$.

Example 78A

3-Ethyl-1-(3-fluoropropyl)-5-methyl-2,4-dioxo-1,2,3,4-tetrahydrothieno[2,3-d]pyrimidine-6-carbaldehyde

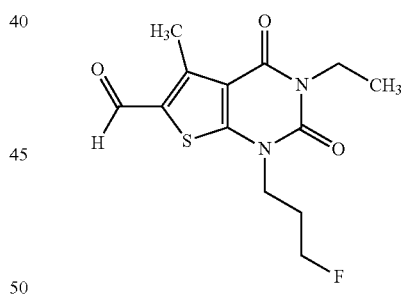

683 mg (4.92 mmol) of potassium carbonate were added to a solution of 471 mg (1.97 mmol) of the compound from Ex. 48A in 18 ml of DMF, and the mixture was stirred at RT for 15 min. Then 1.11 g (5.93 mmol) of 1-fluoro-3-iodopropane were added, and the mixture was stirred at 50° C. for 2.5 h. The DMF was then very substantially distilled off and the remaining residue was partitioned between semi-saturated sodium chloride solution (300 ml) and ethyl acetate (150 ml). The aqueous phase was extracted with ethyl acetate. The combined organic phases were dried over sodium sulphate, filtered and concentrated. 545 mg (90% of theory) of the title compound were obtained.

$^1$H-NMR (400 MHz, DMSO-$d_6$, δ/ppm): 10.10 (s, 1H), 4.61 (t, 1H), 4.49 (t, 1H), 4.05 (t, 2H), 3.90 (q, 2H), 2.79 (s, 3H), 2.17-2.09 (m, 1H), 2.05 (quin, 1H), 1.13 (t, 3H).

LC/MS (Method 3): $R_t$=1.03 min, m/z=299 [M+H]$^+$.

Example 79A

3-Ethyl-1-(4-fluorobutyl)-5-methyl-2,4-dioxo-1,2,3,4-tetrahydrothieno[2,3-d]pyrimidine-6-carbaldehyde

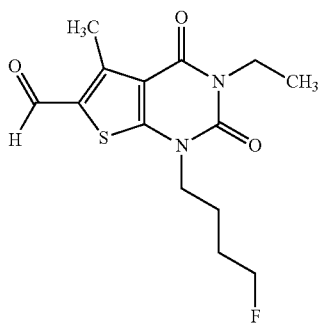 [SMILES: CCn1c(=O)c2c(C)c(C=O)sc2n(CCCCF)c1=O]

543 mg (3.93 mmol) of potassium carbonate were added to a solution of 446 mg (1.57 mmol) of the compound from Ex. 48A in 15 ml of DMF, and the mixture was stirred at RT for 15 min. Then 497 mg (3.14 mmol) of 1-bromo-4-fluorobutane were added, and the mixture was stirred at 50° C. for 21 h. The DMF was then very substantially distilled off and the remaining residue was partitioned between semisaturated sodium chloride solution (100 ml) and ethyl acetate (150 ml). The aqueous phase was extracted with ethyl acetate. The combined organic phases were dried over sodium sulphate, filtered and concentrated. The residue obtained was chromatographed using a silica gel cartridge (Biotage, 100 g of silica gel, eluent: hexane/ethyl acetate). 219 mg (44% of theory) of the title compound were obtained.

$^1$H-NMR (400 MHz, DMSO-$d_6$, δ/ppm): 10.10 (s, 1H), 4.53 (t, 1H), 4.42 (t, 1H), 3.97 (t, 2H), 3.90 (q, 2H), 2.79 (s, 3H), 1.84-1.74 (m, 3H), 1.74-1.65 (m, 1H), 1.13 (t, 3H).

LC/MS (Method 3): $R_t$=1.11 min, m/z=313 [M+H]$^+$.

Example 80A

3-Ethyl-5-methyl-2,4-dioxo-1-[2-(trifluoromethyl)prop-2-en-1-yl]-1,2,3,4-tetrahydrothieno[2,3-d]pyrimidine-6-carbaldehyde

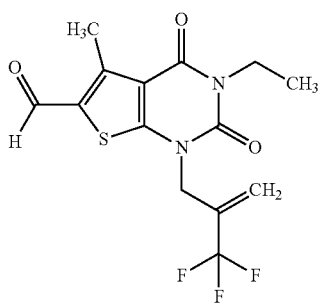 [SMILES: C=C(Cn1c(=O)n(CC)c(=O)c2c(C)c(C=O)sc21)C(F)(F)F]

Analogously to the method described in Ex. 54A, 500 mg (2.10 mmol) of the compound from Ex. 48A and 595 mg (3.15 mmol) of 2-bromomethyl-3,3,3-trifluoropropene were used to prepare 220 mg (30% of theory) of the title compound. The reaction in the microwave was effected here at 80° C. with a reaction time of 2 h. The eluent gradient used in the MPLC purification was cyclohexane/ethyl acetate 10:1→2:1.

$^1$H-NMR (400 MHz, DMSO-$d_6$, δ/ppm): 10.09 (s, 1H), 6.02 (s, 1H), 5.87 (s, 1H), 4.84 (s, 2H), 3.93 (q, 2H), 2.81 (s, 3H), 1.14 (t, 3H).

LC/MS (Method 1, ESIpos): $R_t$=0.96 min, m/z=347 [M+H]$^+$.

Example 81A

1-[(2,2-Difluorocyclopropyl)methyl]-3-ethyl-5-methyl-2,4-dioxo-1,2,3,4-tetrahydrothieno[2,3-d]pyrimidine-6-carbaldehyde (racemate)

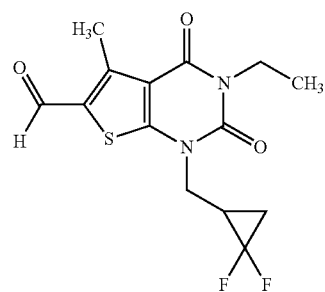 [SMILES: CCn1c(=O)c2c(C)c(C=O)sc2n(CC2CC2(F)F)c1=O]

Analogously to the method described in Ex. 54A, 500 mg (2.10 mmol) of the compound from Ex. 48A and 538 mg (3.15 mmol) of 2-bromomethyl-1,1-difluorocyclopropane were used to prepare 415 mg (60% of theory) of the title compound. The reaction in the microwave was effected here at 100° C. with a reaction time of 2 h. The product was purified by means of MPLC (Biotage cartridge, 50 g of silica gel, cyclohexane/ethyl acetate 2:1) and subsequent stirring with pentane.

$^1$H-NMR (400 MHz, DMSO-$d_6$, δ/ppm): 10.10 (s, 1H), 4.20 (ddd, 1H), 4.00 (dd, 1H), 3.91 (q, 2H), 2.80 (s, 3H), 2.30-2.18 (m, 1H), 1.76-1.67 (m, 1H), 1.54-1.46 (m, 1H), 1.14 (t, 3H).

LC/MS (Method 1, ESIpos): $R_t$=0.91 min, m/z=329 [M+H]$^+$.

Example 82A

3-Ethyl-5-methyl-2,4-dioxo-1-[2-(trifluoromethoxy)ethyl]-1,2,3,4-tetrahydrothieno[2,3-d]pyrimidine-6-carbaldehyde

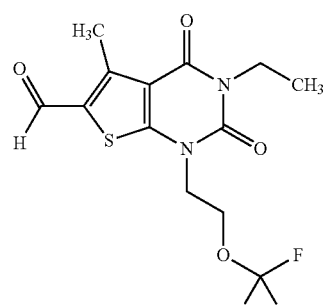

4 ml (43.4 mmol) of phosphorus oxychloride were added to a solution of 1.16 g (3.61 mmol) of the compound from Ex. 57A in 2.8 ml (36.1 mmol) of DMF. After the strongly exothermic reaction had subsided, the mixture was stirred without further supply of heat for another 30 min. Then the reaction mixture was stirred cautiously into 100 ml of ice-cold water. After stirring for 1 h, the precipitated product was filtered off with suction, washed with water until neutral and dried. 1.23 g (94% of theory, 97% purity) of the title compound were obtained.

$^1$H-NMR (400 MHz, DMSO-$d_6$, δ/ppm): 10.10 (s, 1H), 4.42 (t, 2H), 4.28 (t, 2H), 3.91 (q, 2H), 2.80 (s, 3H), 1.14 (t, 3H).

LC/MS (Method 1, ESIpos): $R_t$=0.99 min, m/z=351 [M+H]$^+$.

Example 83A

3-Ethyl-5-methyl-2,4-dioxo-1-{2-[(trifluoromethyl)sulphanyl]ethyl}-1,2,3,4-tetrahydrothieno[2,3-d]pyrimidine-6-carbaldehyde

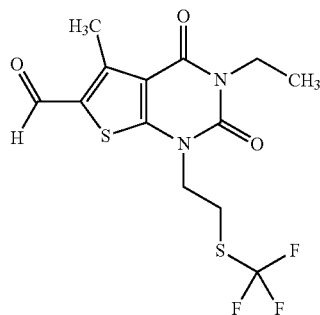 [SMILES: CCn1c(=O)c2c(C)c(C=O)sc2n(CCSC(F)(F)F)c1=O]

Analogously to the method described in Ex. 82A, 1.32 g (3.61 mmol) of the compound from Ex. 58A were used to obtain 1.39 g (97% of theory) of the title compound.

$^1$H-NMR (400 MHz, DMSO-$d_6$, δ/ppm): 10.10 (s, 1H), 4.21 (t, 2H), 3.91 (q, 2H), 3.37 (t, 2H), 2.80 (s, 3H), 1.13 (t, 3H).

LC/MS (Method 1, ESIpos): $R_t$=1.06 min, m/z=367 [M+H]$^+$.

Example 84A

3-Ethyl-1-(2-methoxyethyl)-5-methyl-2,4-dioxo-1,2,3,4-tetrahydrothieno[2,3-d]pyrimidine-6-carbaldehyde

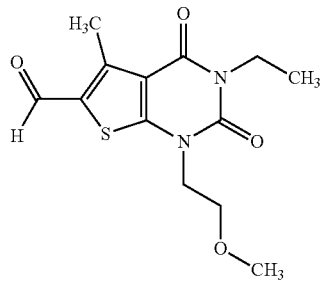 [SMILES: CCn1c(=O)c2c(C)c(C=O)sc2n(CCOC)c1=O]

Method A:

200 g (839 mmol) of the compound from Ex. 48A and 290 g (2.10 mol) of potassium carbonate were stirred in a mixture of 670 ml of DMF and 4 liters of acetonitrile at RT for 15 min, before 251 ml (2.52 mol) of 2-bromoethyl methyl ether were added. Subsequently, the reaction mixture was stirred at a temperature of 100° C. for about 18 h. After cooling to RT, the mixture was diluted with water and extracted with dichloromethane. After the extract had been dried over anhydrous magnesium sulphate, the mixture was filtered and the filtrate was evaporated to dryness. The crude product was dissolved in 1 liter of diethyl ether. After adding 400 ml of petroleum ether, the mixture was stirred for a while longer. Then the product was filtered off with suction and dried. 203 g (81% of theory) of the title compound were obtained.

Method B:

30.1 ml (323 mmol) of phosphorus oxychloride were added to a solution of 7.22 g (26.9 mmol) of the compound from Ex. 59A in 20.7 ml (269 mmol) of DMF. After the strongly exothermic reaction had subsided, the mixture was stirred without further supply of heat for another 60 min. Thereafter, the reaction mixture was stirred cautiously into 300 ml of ice-cold water. After stirring for 1 h, the precipitated product was filtered off with suction, washed with water until neutral and dried. 7.62 g (88% of theory, 93% purity) of the title compound were obtained.

$^1$H-NMR (400 MHz, CDCl$_3$, δ/ppm): 10.08 (s, 1H), 4.16 (t, 2H), 4.07 (q, 2H), 3.74 (t, 2H), 3.34 (s, 3H), 2.86 (s, 3H), 1.26 (t, 3H).

LC/MS (Method 1, ESIpos): $R_t$=0.85 min, m/z=297 [M+H]$^+$.

Example 85A 1-(2-Ethoxyethyl)-3-ethyl-5-methyl-2,4-dioxo-1,2,3,4-tetrahydrothieno[2,3-d]pyrimidine-6-carbaldehyde

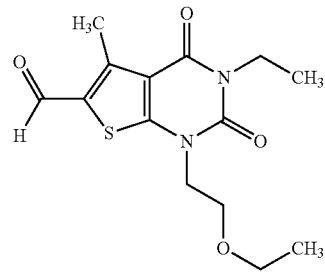 [SMILES: CCOCCn1c(=O)n(CC)c(=O)c2c(C)c(C=O)sc21]

437 mg (3.16 mmol) of potassium carbonate were added to a solution of 301 mg (1.26 mmol) of the compound from Ex. 48A in 11 ml of DMF, and the mixture was stirred at RT for 15 min. 653 mg (3.83 mmol) of 2-bromoethyl ethyl ether were then added, and the mixture was stirred at 50° C. for 68 h. The DMF was then very substantially distilled off and the remaining residue was partitioned between semisaturated sodium chloride solution (70 ml) and ethyl acetate (70 ml). The aqueous phase was extracted with ethyl acetate. The combined organic phases were dried over sodium sulphate, filtered and concentrated. The residue obtained was chromatographed using a silica gel cartridge (Biotage, 50 g of silica gel, eluent: hexane/ethyl acetate). 224 mg (56% of theory) of the title compound were obtained.

$^1$H-NMR (400 MHz, DMSO-$d_6$, δ/ppm): 10.09 (s, 1H), 4.09 (t, 2H), 3.91 (q, 2H), 3.69 (t, 2H), 3.44 (q, 2H), 2.79 (s, 3H), 1.14 (t, 3H), 1.03 (t, 3H).

LC/MS (Method 3): $R_t$=1.1 min, m/z=311 [M+H]$^+$.

Example 86A

3-Ethyl-1-(2-isopropoxyethyl)-5-methyl-2,4-dioxo-1,2,3,4-tetrahydrothieno[2,3-d]pyrimidine-6-carbaldehyde

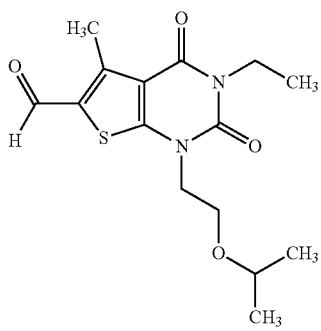 [SMILES: CCn1c(=O)c2c(C)c(C=O)sc2n(CCOC(C)C)c1=O]

412 mg (2.98 mmol) of potassium carbonate were added to a solution of 284 mg (1.19 mmol) of the compound from Ex. 48A in 10.6 ml of DMF, and the mixture was stirred at RT for 15 min. Then 705 mg (4.22 mmol) of 2-(2-bromoethoxy)propane were added, and the mixture was stirred at 50° C. for 38 h. The DMF was then very substantially distilled off and the remaining residue was partitioned between semisaturated sodium chloride solution (70 ml) and ethyl acetate (70 ml). The aqueous phase was extracted with ethyl acetate. The combined organic phases were dried over sodium sulphate, filtered and concentrated. The residue obtained was chromatographed using a silica gel cartridge (Biotage, 25 g of silica gel, eluent: hexane/ethyl acetate). 165 mg (41% of theory) of the title compound were obtained.

$^1$H-NMR (400 MHz, DMSO-d$_6$, δ/ppm): 10.09 (s, 1H), 4.06 (t, 2H), 3.91 (q, 2H), 3.68 (t, 2H), 3.55 (sept, 1H), 2.79 (s, 3H), 1.13 (t, 3H), 1.00 (d, 6H).

LC/MS (Method 3): R$_t$=1.16 min, m/z=325 [M+H]$^+$.

Example 87A

3-Ethyl-1-(2-methoxypropyl)-5-methyl-2,4-dioxo-1,2,3,4-tetrahydrothieno[2,3-d]pyrimidine-6-carbaldehyde (racemate)

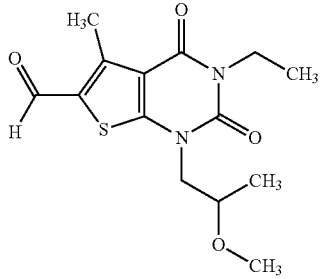 [SMILES: CCn1c(=O)c2c(C)c(C=O)sc2n(CC(C)OC)c1=O]

Analogously to the method described in Ex. 54A, 1.0 g (4.20 mmol) of the compound from Ex. 48A and 1.54 mg (6.30 mmol) of racemic 2-methoxypropyl 4-methylbenzenesulphonate were used to prepare 327 mg (25% of theory) of the title compound. The reaction in the microwave was effected here at 110° C. with a reaction time of 12 h. The eluent used in the MPLC purification was cyclohexane/ethyl acetate 4:1.

$^1$H-NMR (400 MHz, DMSO-d$_6$, δ/ppm): 10.09 (s, 1H), 4.03 (dd, 1H), 3.91 (q, 2H), 3.81 (dd, 1H), 3.78-3.71 (m, 1H), 3.18 (s, 3H), 2.79 (s, 3H), 1.16 (d, 3H), 1.14 (t, 3H).

LC/MS (Method 1, ESIpos): R$_t$=0.86 min, m/z=311 [M+H]$^+$.

Example 88A

3-Ethyl-5-methyl-1-(oxetan-2-ylmethyl)-2,4-dioxo-1,2,3,4-tetrahydrothieno[2,3-d]pyrimidine-6-carbaldehyde (racemate)

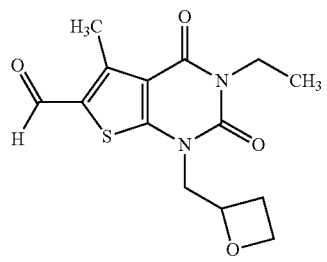 [SMILES: CCn1c(=O)c2c(C)c(C=O)sc2n(CC2CCO2)c1=O]

Analogously to the method described in Ex. 86A, 645 mg (2.46 mmol) of the compound from Ex. 48A and 1.48 g (9.48 mmol) of racemic 2-(bromomethyl)oxetane were used to prepare 759 mg (92% of theory) of the title compound. The conversion was conducted here at 80° C.

$^1$H-NMR (400 MHz, DMSO-d$_6$, δ/ppm): 10.09 (s, 1H), 5.06-4.98 (m, 1H), 4.52-4.42 (m, 2H), 4.28-4.16 (m, 2H), 3.91 (q, 2H), 2.78 (s, 3H), 2.74-2.66 (m, 1H), 1.14 (t, 3H).

LC/MS (Method 3): R$_t$=0.96 min, m/z=309 [M+H]$^+$.

Example 89A

3-Ethyl-5-methyl-2,4-dioxo-1-(tetrahydrofuran-2-ylmethyl)-1,2,3,4-tetrahydrothieno[2,3-d]pyrimidine-6-carbaldehyde (racemate)

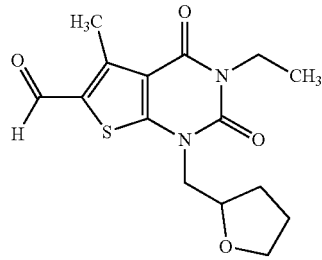 [SMILES: CCn1c(=O)c2c(C)c(C=O)sc2n(CC2CCCO2)c1=O]

Method A:
Analogously to the method described in Ex. 86A, 400 mg (1.66 mmol) of the compound from Ex. 48A and 1.44 g (8.31 mmol) of racemic 2-(bromomethyl)tetrahydrofuran were used to prepare 350 mg (53% of theory) of the title compound. The conversion was conducted here at 80° C.

Method B:
4.1 ml (44.2 mmol) of phosphorus oxychloride were added to a solution of 1.08 g (3.68 mmol) of the compound from Ex. 60A in 2.8 ml (36.8 mmol) of DMF. After the strongly exothermic reaction had subsided, the mixture was stirred without further supply of heat for another 15 min. Thereafter, the reaction mixture was stirred cautiously into 100 ml of ice-cold water. After stirring for 1 h, the precipitated product was filtered off with suction, washed with water until neutral and dried. 1.08 g (83% of theory, 92% purity) of the title compound were obtained.

$^1$H-NMR (400 MHz, DMSO-d$_6$, δ/ppm): 10.09 (s, 1H), 4.27-4.20 (m, 1H), 4.13 (dd, 1H), 3.91 (q, 2H), 3.80-3.72 (m, 2H), 3.62 (dd, 1H), 2.78 (s, 3H), 2.05-1.96 (m, 1H), 1.95-1.77 (m, 2H), 1.72-1.64 (m, 1H), 1.14 (t, 3H).

LC/MS (Method 1, ESIpos): R$_t$=0.89 min, m/z=323 [M+H]$^+$.

Example 90A

3-Ethyl-5-methyl-2,4-dioxo-1-(tetrahydro-2H-pyran-2-ylmethyl)-1,2,3,4-tetrahydrothieno[2,3-d]pyrimidine-6-carbaldehyde (racemate)

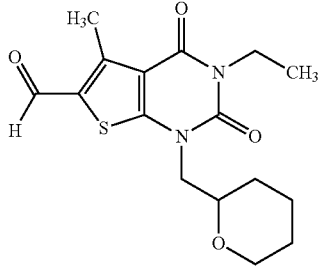 [SMILES: CCn1c(=O)c2c(C)c(C=O)sc2n(CC2CCCCO2)c1=O]

Analogously to the method described in Ex. 86A, 740 mg (2.86 mmol) of the compound from Ex. 48A and 2.08 g (11.43 mmol) of racemic 2-(bromomethyl)tetrahydro-2H-pyran were used to prepare 590 mg (61% of theory) of the title compound. The conversion was conducted here at 70° C. and the reaction time was 43 h.

$^1$H-NMR (400 MHz, DMSO-d$_6$, δ/ppm): 10.08 (s, 1H), 4.05 (dd, 1H), 3.90 (q, 2H), 3.84-3.74 (m, 2H), 3.72-3.64 (m, 1H), 3.26 (dt, 1H), 2.77 (s, 3H), 1.78 (d, 1H), 1.65 (d, 1H), 1.50-1.37 (m, 3H), 1.36-1.21 (m, 1H), 1.13 (t, 3H).

LC/MS (Method 3): R$_t$=1.21 min, m/z=337 [M+H]$^+$.

Example 91A

3-Ethyl-5-methyl-1-(oxetan-3-ylmethyl)-2,4-dioxo-1,2,3,4-tetrahydrothieno[2,3-d]pyrimidine-6-carbaldehyde

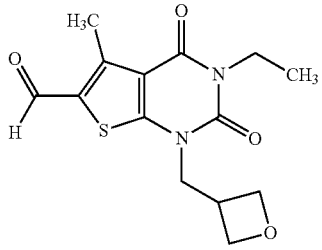 [SMILES: CCn1c(=O)c2c(C)c(C=O)sc2n(CC2COC2)c1=O]

Analogously to the method described in Ex. 54A, 500 mg (2.10 mmol) of the compound from Ex. 48A and 335 mg (3.15 mmol) of 3-(chloromethyl)oxetane were used to prepare 85 mg (13% of theory) of the title compound. The reaction in the microwave was effected here at 60° C. with a reaction time of 2 h. The MPLC purification was conducted with a 50 g silica gel cartridge and cyclohexane/ethyl acetate 2:1 as eluent.

$^1$H-NMR (400 MHz, DMSO-d$_6$, δ/ppm): 10.09 (s, 1H), 4.61 (dd, 2H), 4.45 (t, 2H), 4.27 (d, 2H), 3.89 (q, 2H), 3.45 (sept, 1H), 2.79 (s, 3H), 1.12 (t, 3H).

LC/MS (Method 1, ESIpos): R$_t$=0.70 min, m/z=309 [M+H]$^+$.

Example 92A

3-Ethyl-5-methyl-2,4-dioxo-1-(tetrahydrofuran-3-ylmethyl)-1,2,3,4-tetrahydrothieno[2,3-d]pyrimidine-6-carbaldehyde (racemate)

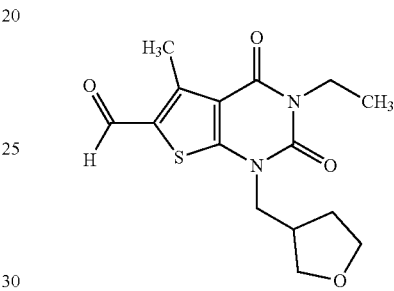

Analogously to the method described in Ex. 43A, 500 mg (2.10 mmol) of the compound from Ex. 48A and 519 mg (3.15 mmol) of racemic 3-(bromomethyl)tetrahydrofuran were used to prepare 188 mg (27% of theory) of the title compound. The reaction in the microwave was effected here first at 60° C. (1 h), then at 80° C. (5 h) and finally at 100° C. (3 h). The purification of the product was conducted by means of preparative HPLC (Method 8).

$^1$H-NMR (400 MHz, DMSO-d$_6$, δ/ppm): 10.10 (s, 1H), 3.95 (dd, 2H), 3.91 (q, 2H), 3.84-3.78 (m, 1H), 3.69-3.60 (m, 2H), 3.51 (dd, 1H), 2.80 (s, 3H), 2.79-2.70 (m, 1H), 2.02-1.93 (m, 1H), 1.71-1.63 (m, 1H), 1.14 (t, 3H).

LC/MS (Method 1, ESIpos): R$_t$=0.78 min, m/z=323 [M+H]$^+$.

Example 93A

3-Ethyl-1,5-dimethyl-2,4-dioxo-1,2,3,4-tetrahydrothieno[2,3-d]pyrimidine-6-carbaldehyde

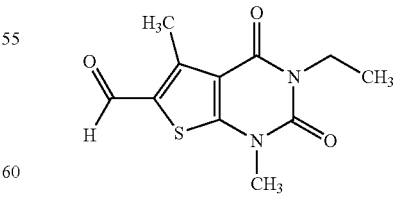

500 mg (2.10 mmol) of the compound from Ex. 48A and 1.03 g (3.15 mmol) of caesium carbonate were stirred in 10 ml of anhydrous DMF at RT for 8 min, before 300 μl (3.15 mmol) of dimethyl sulphate were added. Subsequently, the reaction mixture was heated in a microwave oven (Biotage Initiator with dynamic control of irradiation power) to 60° C. for 1 h. After cooling to RT, the mixture was diluted with ethyl acetate and washed successively with water and saturated sodium chloride solution. After drying over anhydrous magnesium sulphate, the mixture was filtered and concentrated to dryness. The residue obtained was stirred with pentane. After filtration with suction and drying under high vacuum, 467 mg (88% of theory) of the title compound were obtained.

$^1$H-NMR (400 MHz, DMSO-$d_6$, δ/ppm): 10.09 (s, 1H), 3.90 (q, 2H), 3.47 (s, 3H), 2.79 (s, 3H), 1.13 (t, 3H).

LC/MS (Method 1, ESIpos): $R_t$=0.76 min, m/z=253 [M+H]$^+$.

Example 94A 1,3-Diethyl-5-methyl-2,4-dioxo-1,2,3,4-tetrahydrothieno[2,3-d]pyrimidine-6-carbaldehyde

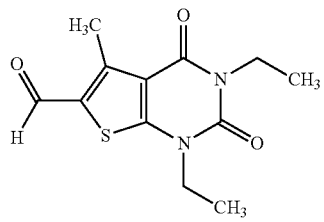 [SMILES: CCn1c(=O)c2c(C)c(C=O)sc2n(CC)c1=O]

Analogously to the method described in Ex. 54A, 500 mg (2.10 mmol) of the compound from Ex. 48A and 252 μl (3.15 mmol) of iodoethane were used to obtain 476 mg (85% of theory) of the title compound. The reaction in the microwave was effected here at 60° C. for 60 min, and the MPLC purification was conducted with a Biotage cartridge containing 50 g of silica gel and cyclohexane/ethyl acetate 5:1 as eluent.

$^1$H-NMR (400 MHz, DMSO-$d_6$, δ/ppm): 10.09 (s, 1H), 3.97 (q, 2H), 3.90 (q, 2H), 2.79 (s, 3H), 1.26 (t, 3H), 1.14 (t, 3H).

LC/MS (Method 1, ESIpos): $R_t$=0.87 min, m/z=267 [M+H]$^+$.

Example 95A

3-Ethyl-5-methyl-2,4-dioxo-1-propyl-1,2,3,4-tetrahydrothieno[2,3-d]pyrimidine-6-carbaldehyde

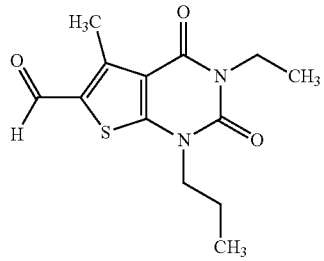 [SMILES: CCCn1c(=O)n(CC)c(=O)c2c(C)c(C=O)sc21]

Analogously to the method described in Ex. 89A (Method B), 1.04 g (4.12 mmol) of the compound from Ex. 61A were used to obtain 1.08 g (93% of theory) of the title compound.

$^1$H-NMR (400 MHz, DMSO-$d_6$, δ/ppm): 10.09 (s, 1H), 3.97-3.84 (m, 4H), 2.79 (s, 3H), 1.72 (sext, 2H), 1.13 (t, 3H), 0.93 (t, 3H).

LC/MS (Method 1, ESIpos): $R_t$=0.96 min, m/z=281 [M+H]$^+$.

Example 96A

1-Butyl-3-ethyl-5-methyl-2,4-dioxo-1,2,3,4-tetrahydrothieno[2,3-d]pyrimidine-6-carbaldehyde

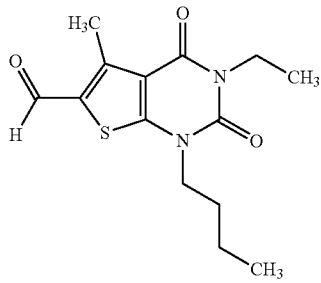 [SMILES: CCCCn1c(=O)n(CC)c(=O)c2c(C)c(C=O)sc21]

Analogously to the method described in Ex. 54A, 500 mg (2.10 mmol) of the compound from Ex. 48A and 362 μl (3.15 mmol) of 1-iodobutane were used to obtain 327 mg (52% of theory) of the title compound. The reaction in the microwave was effected here at 60° C. for 60 min, and the MPLC purification was conducted using a Biotage cartridge with 50 g of silica gel and cyclohexane/ethyl acetate 6:1 as eluent.

$^1$H-NMR (400 MHz, DMSO-$d_6$, δ/ppm): 10.09 (s, 1H), 3.93 (t, 2H), 3.90 (q, 2H), 2.79 (s, 3H), 1.67 (quin, 2H), 1.36 (sext, 2H), 1.13 (t, 3H), 0.92 (t, 3H).

LC/MS (Method 1, ESIpos): $R_t$=1.03 min, m/z=295 [M+H]$^+$.

Example 97A

3-Ethyl-5-methyl-1-(3-methylbutyl)-2,4-dioxo-1,2,3,4-tetrahydrothieno[2,3-d]pyrimidine-6-carbaldehyde

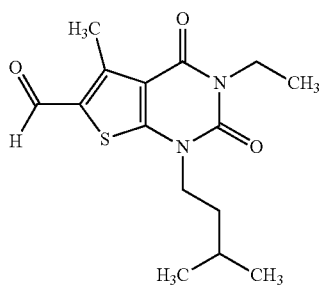 [SMILES: CCn1c(=O)c2c(C)c(C=O)sc2n(CCC(C)C)c1=O]

Analogously to the method described in Ex. 54A, 500 mg (2.10 mmol) of the compound from Ex. 48A and 414 μl (3.15 mmol) of 1-iodo-3-methylbutane were used to obtain 398 mg (59% of theory, 97% purity) of the title compound. The reaction in the microwave was effected here at 60° C. for 60 min, and the MPLC purification was conducted using a Biotage cartridge with 50 g of silica gel and cyclohexane/ethyl acetate 10:1→5:1 as eluent.

$^1$H-NMR (400 MHz, DMSO-$d_6$, δ/ppm): 10.09 (s, 1H), 3.93 (t, 2H), 3.90 (q, 2H), 2.79 (s, 3H), 1.72-1.61 (m, 1H), 1.61-1.52 (m, 2H), 1.13 (t, 3H), 0.95 (d, 6H).

LC/MS (Method 1, ESIpos): $R_t$=1.11 min, m/z=309 [M+H]$^+$.

Example 98A 1-(3,3-Dimethylbutyl)-3-ethyl-5-methyl-2,4-dioxo-1,2,3,4-tetrahydrothieno[2,3-d]pyrimidine-6-carbaldehyde

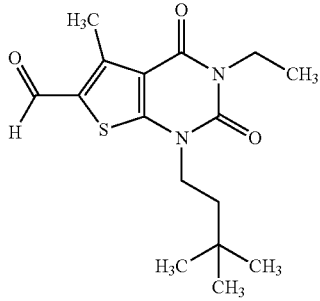 [SMILES: CCn1c(=O)c2c(C)c(C=O)sc2n(CCC(C)(C)C)c1=O]

Analogously to the method described in Ex. 86A, 300 mg (1.12 mmol) of the compound from Ex. 48A and 636 mg (3.77 mmol) of 1-bromo-3,3-dimethylbutane were used to prepare 273 mg (67% of theory) of the title compound. The conversion was conducted here at 80° C.

$^1$H-NMR (400 MHz, DMSO-d$_6$, δ/ppm): 10.09 (s, 1H), 3.96-3.87 (m, 4H), 2.79 (s, 3H), 1.60-1.53 (m, 2H), 1.13 (t, 3H), 0.98 (s, 9H).

LC/MS (Method 3): $R_t$=1.4 min, m/z=323 [M+H]$^+$.

Example 99A 1-(Cyclobutylmethyl)-3-ethyl-5-methyl-2,4-dioxo-1,2,3,4-tetrahydrothieno[2,3-d]pyrimidine-6-carbaldehyde

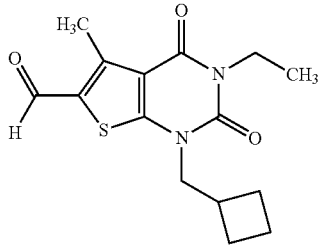 [SMILES: CCn1c(=O)c2c(C)c(C=O)sc2n(CC2CCC2)c1=O]

Analogously to the method described in Ex. 54A, 500 mg (2.10 mmol) of the compound from Ex. 48A and 469 mg (3.15 mmol) of (bromomethyl)cyclobutane were used to obtain 308 mg (47% of theory) of the title compound. The reaction in the microwave was effected here at 100° C. for 2 h, and the MPLC purification was conducted using a Biotage cartridge with 50 g of silica gel and cyclohexane/ethyl acetate 2:1 as eluent.

$^1$H-NMR (400 MHz, DMSO-d$_6$, δ/ppm): 10.09 (s, 1H), 4.00 (d, 2H), 3.90 (q, 2H), 2.84-2.73 (m, 1H), 2.79 (s, 3H), 2.04-1.92 (m, 2H), 1.90-1.75 (m, 4H), 1.13 (t, 3H).

LC/MS (Method 1, ESIpos): $R_t$=1.03 min, m/z=307 [M+H]$^+$.

Example 100A (3-Ethyl-6-formyl-5-methyl-2,4-dioxo-3,4-dihydrothieno[2,3-d]pyrimidin-1 (2H)-yl)acetonitrile

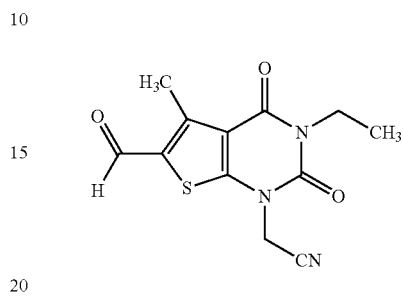

Analogously to the method described in Ex. 54A, 920 mg (3.86 mmol) of the compound from Ex. 48A and 1.39 g (11.6 mmol) of bromoacetonitrile were used to obtain 550 mg (51% of theory) of the title compound. The reaction in the microwave was effected here at 60° C. for 50 min, and the MPLC purification was conducted using a Biotage cartridge with 50 g of silica gel and cyclohexane/ethyl acetate 2:1 as eluent.

$^1$H-NMR (400 MHz, DMSO-d$_6$, δ/ppm): 10.12 (s, 1H), 5.22 (s, 2H), 3.91 (q, 2H), 2.80 (s, 3H), 1.15 (t, 3H).

LC/MS (Method 1, ESIpos): $R_t$=0.76 min, m/z=278 [M+H]$^+$.

Example 101A

3-Ethyl-5-methyl-1-[(4-methyl-1,2,5-oxadiazol-3-yl)methyl]-2,4-dioxo-1,2,3,4-tetrahydrothieno[2,3-d]pyrimidine-6-carbaldehyde

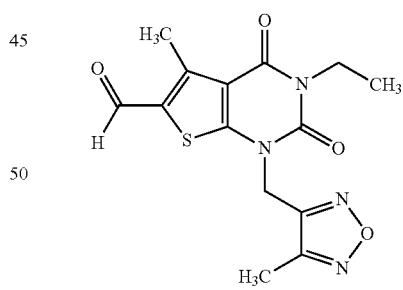

Analogously to the method described in Ex. 54A, 500 mg (2.10 mmol) of the compound from Ex. 48A and 417 mg (3.15 mmol) of 3-(chloromethyl)-4-methyl-1,2,5-oxadiazole were used to obtain 389 mg (55% of theory) of the title compound. The reaction in the microwave was effected here at 100° C. for 2 h, and the MPLC purification was conducted using a Biotage cartridge with 50 g of silica gel and cyclohexane/ethyl acetate 3:1 as eluent.

$^1$H-NMR (400 MHz, DMSO-d$_6$, δ/ppm): 10.09 (s, 1H), 5.42 (s, 2H), 3.92 (q, 2H), 2.80 (s, 3H), 2.44 (s, 3H), 1.14 (t, 3H).

Example 102A

1-[2-(Dimethylamino)ethyl]-3-ethyl-5-methyl-2,4-dioxo-1,2,3,4-tetrahydrothieno[2,3-d]pyrimidine-6-carbaldehyde

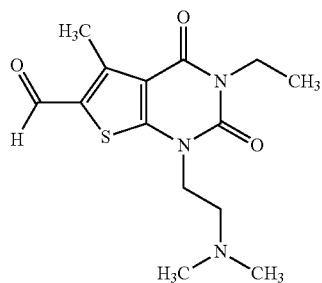 [SMILES: CCn1c(=O)c2c(C)c(C=O)sc2n(CCN(C)C)c1=O]

Analogously to the method described in Ex. 54A, 500 mg (2.10 mmol) of the compound from Ex. 48A and 733 mg (3.15 mmol) of 2-bromo-N,N-dimethylethanamine hydrobromide were used to obtain 453 mg (69% of theory) of the title compound. The reaction in the microwave was effected here at 100° C. for 2 h, and the MPLC purification was conducted using a Biotage cartridge with 50 g of silica gel and cyclohexane/ethyl acetate 1:1 as eluent.

$^1$H-NMR (400 MHz, DMSO-$d_6$, δ/ppm): 10.09 (s, 1H), 4.00 (t, 2H), 3.91 (q, 2H), 2.79 (s, 3H), 2.58 (t, 2H), 2.20 (s, 6H), 1.13 (t, 3H).

LC/MS (Method 1, ESIpos): $R_t$=0.39 min, m/z=310 [M+H]$^+$.

Example 103A

3-Isopropyl-5-methyl-2,4-dioxo-1-(3,3,3-trifluoropropyl)-1,2,3,4-tetrahydrothieno[2,3-d]pyrimidine-6-carbaldehyde

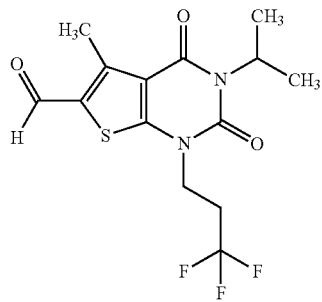 [SMILES: Cc1c(C=O)sc2c1c(=O)n(C(C)C)c(=O)n2CCC(F)(F)F]

Method A:

1.8 g (7.13 mmol) of the compound from Ex. 49A and 3.49 g (10.7 mmol) of caesium carbonate were stirred in 15 ml of DMF at RT for 10 min, before 1.3 ml (10.7 mmol) of 1,1,1-trifluoro-3-iodopropane were added. Subsequently, the reaction mixture was stirred at a temperature of 100° C. in a microwave oven (Biotage Initiator with dynamic control of irradiation power). After 2 h, a further 167 µl (1.43 mmol) of 1,1,1-trifluoro-3-iodopropane were added and the heating was continued for 30 min. After cooling to RT, the mixture was diluted with about 75 ml of ethyl acetate and washed successively with water and saturated sodium chloride solution. After drying over anhydrous magnesium sulphate, the mixture was filtered and the filtrate was evaporated to dryness. The crude product was purified by MPLC (Biotage cartridge, 100 g of SNAP KP-Sil silica gel, eluent: cyclohexane/ethyl acetate 1:2). After concentration and drying, a mixture of N- and O-alkylated product was obtained, from which it was possible to obtain the N-alkylated main product in solid form by stirring with a mixture of 30 ml of pentane and 2 ml of dichloromethane. Further N-alkylated product was obtained from the concentrated mother liquor from the stirring by means of preparative HPLC (Method 8). After concentration of the product fractions and drying under high vacuum, together with the solids from the stirring, 1.86 g (74% of theory) of the title compound were obtained.

Method B:

1.8 ml (19.0 mmol) of phosphorus oxychloride were added rapidly to a solution of 508 mg (1.59 mmol) of the compound from Ex. 62A in 1.2 ml (15.9 mmol) of DMF. After the strongly exothermic reaction had subsided, the mixture was stirred at RT for another 15 min. Then the reaction mixture was stirred cautiously into 100 ml of water. After stirring for 1 h, the precipitated product was filtered off with suction, washed with water until neutral and dried. 490 mg (88% of theory) of the title compound were obtained.

$^1$H-NMR (400 MHz, DMSO-$d_6$, δ/ppm): 10.10 (s, 1H), 5.11 (sept, 1H), 4.15 (t, 2H), 2.87-2.69 (m, 2H), 2.79 (s, 3H), 1.41 (d, 6H).

LC/MS (Method 1, ESIpos): $R_t$=1.04 min, m/z=349 [M+H]$^+$.

Example 104A 1-(2-Fluoroethyl)-3-isopropyl-5-methyl-2,4-dioxo-1,2,3,4-tetrahydrothieno[2,3-d]pyrimidine-6-carbaldehyde

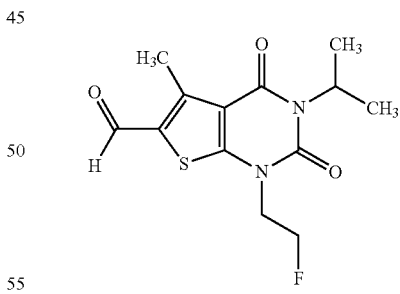

Analogously to the method described in Ex. 89A (Method B), 450 mg (1.66 mmol) of the compound from Ex. 61A were used to obtain 422 mg (85% of theory) of the title compound.

$^1$H-NMR (400 MHz, DMSO-$d_6$, δ/ppm): 10.09 (s, 1H), 5.12 (sept, 1H), 4.86-4.63 (dt, 2H), 4.37-4.15 (dt, 2H), 2.78 (s, 3H), 1.42 (d, 6H).

LC/MS (Method 1, ESIpos): $R_t$=0.93 min, m/z=299 [M+H]$^+$.

Example 105A

3-Isopropyl-1-(2-methoxyethyl)-5-methyl-2,4-dioxo-1,2,3,4-tetrahydrothieno[2,3-d]pyrimidine-6-carbaldehyde

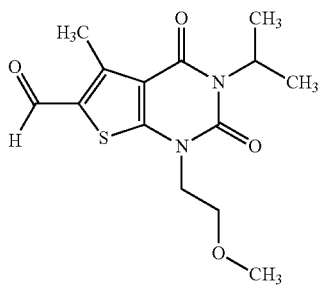 [SMILES: COCCn1c(=O)n(C(C)C)c(=O)c2c(C)c(C=O)sc21]

Analogously to the method described in Ex. 54A, 1.80 g (7.13 mmol) of the compound from Ex. 49A and 1.49 g (10.7 mmol) of 2-bromoethyl methyl ether were used to prepare 0.86 g (37% of theory, 97% purity) of the title compound. The reaction in the microwave was effected here at 100° C. for 2 h, and cyclohexane/ethyl acetate 1:2 was used as eluent in the MPLC purification.

$^1$H-NMR (400 MHz, DMSO-$d_6$, δ/ppm): 10.08 (s, 1H), 5.11 (sept, 1H), 4.07 (t, 2H), 3.64 (t, 2H), 3.31 (s, 3H), 2.77 (s, 3H), 1.41 (d, 6H).

LC/MS (Method 1, ESIpos): $R_t$=0.94 min, m/z=311 [M+H]$^+$.

Example 106A

3-Isopropyl-5-methyl-1-(oxetan-2-ylmethyl)-2,4-dioxo-1,2,3,4-tetrahydrothieno[2,3-d]pyrimidine-6-carbaldehyde (racemate)

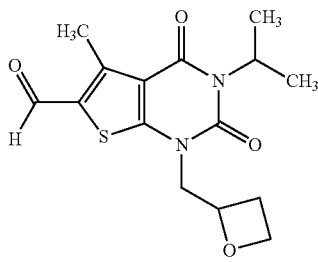 [SMILES: Cc1c(C=O)sc2c1c(=O)n(C(C)C)c(=O)n2CC1CCO1]

Analogously to the method described in Ex. 54A, 3.60 g (14.3 mmol) of the compound from Ex. 49A and 3.02 g (20.0 mmol) of racemic 2-(chloromethyl)oxetane were used to prepare 2.40 g (50% of theory, 97% purity) of the title compound. The reaction in the microwave was effected here at 100° C., and cyclohexane/ethyl acetate 1:2 was used as eluent in the MPLC purification.

$^1$H-NMR (400 MHz, DMSO-$d_6$, δ/ppm): 10.08 (s, 1H), 5.12 (sept, 1H), 5.05-4.97 (m, 1H), 4.53-4.39 (m, 2H), 4.22-4.16 (m, 2H), 2.77 (s, 3H), 2.75-2.65 (m, 1H), 2.50-2.43 (m, 1H, partially obscured by the DMSO signal), 1.41 (d, 6H).

LC/MS (Method 1, ESIpos): $R_t$=0.87 min, m/z=323 [M+H]$^+$.

Example 107A

3-Isopropyl-5-methyl-2,4-dioxo-1-(tetrahydrofuran-2-ylmethyl)-1,2,3,4-tetrahydrothieno[2,3-d]pyrimidine-6-carbaldehyde (racemate)

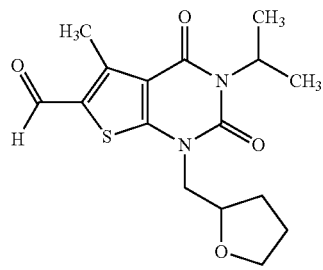 [SMILES: Cc1c(C=O)sc2c1c(=O)n(C(C)C)c(=O)n2CC1CCCO1]

Analogously to the method described in Ex. 89A (Method B), 431 mg (1.40 mmol) of the compound from Ex. 64A were used to obtain 358 mg (70% of theory, 93% purity) of the title compound.

$^1$H-NMR (400 MHz, DMSO-$d_6$, δ/ppm): 10.08 (s, 1H), 5.12 (sept, 1H), 4.28-4.18 (m, 1H), 4.12 (dd, 1H), 3.80-3.67 (m, 2H), 3.66-3.57 (m, 1H), 2.77 (s, 3H), 2.09-1.75 (m, 3H), 1.73-1.61 (m, 1H), 1.41 (dd, 6H).

LC/MS (Method 1, ESIpos): $R_t$=1.01 min, m/z=337 [M+H]$^+$.

Example 108A

3-Isopropyl-5-methyl-1-(oxetan-3-ylmethyl)-2,4-dioxo-1,2,3,4-tetrahydrothieno[2,3-d]pyrimidine-6-carbaldehyde

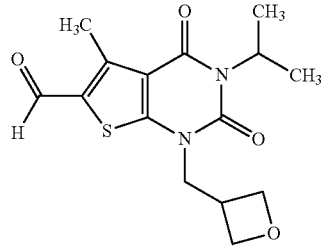 [SMILES: Cc1c(C=O)sc2c1c(=O)n(C(C)C)c(=O)n2CC1COC1]

119 mg (0.473 mmol) of the compound from Ex. 49A, 231 mg (0.709 mmol) of caesium carbonate and 39 mg (0.236 mmol) of potassium iodide were stirred in 2.1 ml of anhydrous DMF at RT for 10 min, before 65 µl (0.709 mmol) of 3-(chloromethyl)oxetane were added. Subsequently, the reaction mixture was heated in a microwave oven (Biotage Initiator with dynamic control of irradiation power) to 80° C. for 1.5 h. After cooling to RT, the mixture was diluted with ethyl acetate and washed successively with water and saturated sodium chloride solution. After drying over anhydrous magnesium sulphate, the mixture was filtered and concentrated to dryness. 149 mg (96% of theory, 98% purity) of the title compound were obtained.

$^1$H-NMR (400 MHz, DMSO-$d_6$, δ/ppm): 10.09 (s, 1H), 5.10 (sept, 1H), 4.61 (dd, 2H), 4.44 (t, 2H), 4.24 (d, 2H), 3.48-3.38 (m, 1H), 2.77 (s, 3H), 1.40 (d, 6H).

LC/MS (Method 1, ESIpos): $R_t$=0.87 min, m/z=323 [M+H]$^+$.

Example 109A

3-Isopropyl-1,5-dimethyl-2,4-dioxo-1,2,3,4-tetrahydrothieno[2,3-d]pyrimidine-6-carbaldehyde

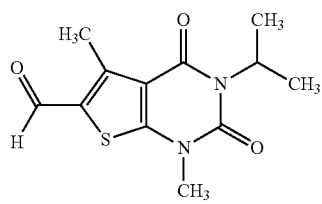 [SMILES: Cc1c(C=O)sc2c1c(=O)n(C(C)C)c(=O)n2C]

Analogously to the method described in Ex. 89A (Method B), 450 mg (1.89 mmol) of the compound from Ex. 65A were used to obtain 408 mg (81% of theory) of the title compound.

$^1$H-NMR (400 MHz, DMSO-d$_6$, δ/ppm): 10.08 (s, 1H), 5.13 (sept, 1H), 3.44 (s, 3H), 2.78 (s, 3H), 1.41 (d, 6H).

LC/MS (Method 1, ESIpos): R$_t$=0.86 min, m/z=267 [M+H]$^+$.

Example 110A

3-Isobutyl-5-methyl-2,4-dioxo-1-(3,3,3-trifluoropropyl)-1,2,3,4-tetrahydrothieno[2,3-d]pyrimidine-6-carbaldehyde

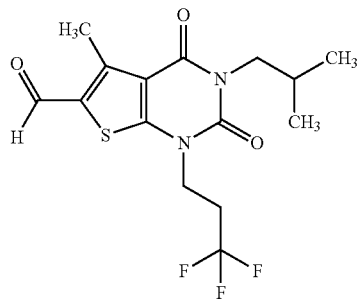 [SMILES: Cc1c(C=O)sc2c1c(=O)n(CC(C)C)c(=O)n2CCC(F)(F)F]

15.37 ml (164.92 mmol) of phosphorus oxychloride were added cautiously, while cooling with an ice bath, to a solution of 2.39 g (7.07 mmol) of the compound from Ex. 66A in 7.68 ml of DMF. After the exothermic reaction had subsided, the mixture was cooled to RT. Thereafter, the reaction mixture was concentrated very substantially on a rotary evaporator. The remaining residue was added to ice-water and stirred. The precipitated product was filtered off with suction, washed to neutrality with water and dried. 2.56 g (99% of theory) of the title compound were obtained.

$^1$H-NMR (400 MHz, DMSO-d$_6$, δ/ppm): 10.11 (s, 1H), 4.18 (t, 2H), 3.72 (d, 2H), 2.87-2.72 (m, 5H), 2.03 (dquin, 1H), 0.86 (d, 6H).

LC/MS (Method 3): R$_t$=1.33 min, m/z=363 [M+H]$^+$.

Example 111A 1-(2,2-Difluoroethyl)-3-isobutyl-5-methyl-2,4-dioxo-1,2,3,4-tetrahydrothieno[2,3-d]pyrimidine-6-carbaldehyde

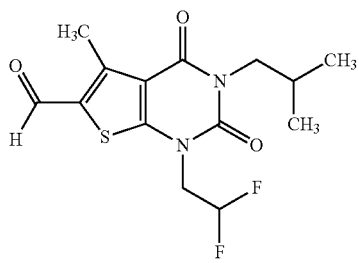 [SMILES: Cc1c(C=O)sc2c1c(=O)n(CC(C)C)c(=O)n2CC(F)F]

Analogously to the method described in Ex. 86A, 450 mg (1.69 mmol) of the compound from Ex. 50A and 1.29 g (6.76 mmol) of 1,1-difluoro-2-iodoethane were used to prepare 190 mg (34% of theory) of the title compound. The conversion was conducted here at 80° C. and the reaction time was 40 h.

$^1$H-NMR (400 MHz, DMSO-d$_6$, δ/ppm): 10.11 (s, 1H), 6.52-6.21 (m, 1H), 4.43 (td, 2H), 3.71 (d, 2H), 2.78 (s, 3H), 2.10-1.96 (m, 1H), 0.87 (d, 6H).

LC/MS (Method 3): R$_t$=1.23 min, m/z=331 [M+H]$^+$.

Example 112A 1-(2-Fluoroethyl)-3-isobutyl-5-methyl-2,4-dioxo-1,2,3,4-tetrahydrothieno[2,3-d]pyrimidine-6-carbaldehyde

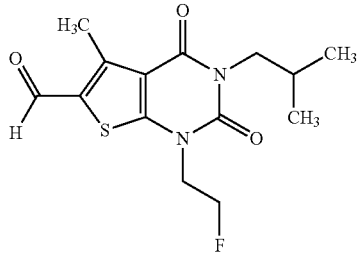 [SMILES: Cc1c(C=O)sc2c1c(=O)n(CC(C)C)c(=O)n2CCF]

Analogously to the method described in Ex. 89A (Method B), 443 mg (1.56 mmol) of the compound from Ex. 67A were used to obtain 462 mg (94% of theory) of the title compound.

$^1$H-NMR (400 MHz, DMSO-d$_6$, δ/ppm): 10.10 (s, 1H), 4.86-4.63 (dt, 2H), 4.36-4.18 (dt, 2H), 3.72 (d, 2H), 2.79 (s, 3H), 2.04 (m, 1H), 0.87 (d, 6H).

LC/MS (Method 1, ESIpos): R$_t$=0.98 min, m/z=313 [M+H]$^+$.

Example 113A 1-(3-Fluoropropyl)-3-isobutyl-5-methyl-2,4-dioxo-1,2,3,4-tetrahydrothieno[2,3-d]pyrimidine-6-carbaldehyde

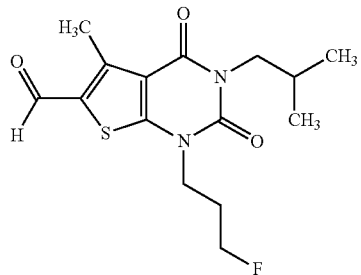 [SMILES: Cc1c(C=O)sc2c1c(=O)n(CC(C)C)c(=O)n2CCCF]

Analogously to the method described in Ex. 86A, 490 mg (1.84 mmol) of the compound from Ex. 50A and 1.03 g (5.52 mmol) of 1-fluoro-3-iodopropane were used to prepare 571 mg (91% of theory) of the title compound. The reaction time here was 17 h.

$^1$H-NMR (400 MHz, DMSO-$d_6$, δ/ppm): 10.10 (s, 1H), 4.60 (t, 1H), 4.48 (t, 1H), 4.05 (t, 2H), 3.71 (d, 2H), 2.78 (s, 3H), 2.16-2.09 (m, 1H), 2.09-1.97 (m, 2H), 0.86 (d, 6H).

LC/MS (Method 3): $R_t$=1.23 min, m/z=327 [M+H]$^+$.

Example 114A

3-Isobutyl-1-(2-methoxyethyl)-5-methyl-2,4-dioxo-1,2,3,4-tetrahydrothieno[2,3-d]pyrimidine-6-carbaldehyde

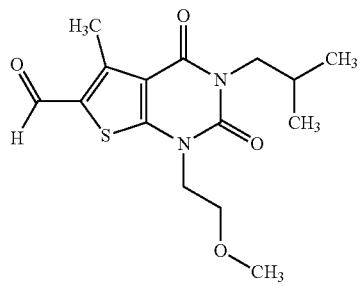 [SMILES: COCCn1c(=O)n(CC(C)C)c(=O)c2c(C)c(C=O)sc21]

17.07 ml (183.21 mmol) of phosphorus oxychloride were added cautiously, while cooling with an ice bath, to a solution of 2.33 g (7.86 mmol) of the compound from Ex. 68A in 8.53 ml of DMF. After the exothermic reaction had subsided, the mixture was cooled to RT. Thereafter, the reaction mixture was concentrated very substantially on a rotary evaporator. The remaining residue was added to ice-water and stirred. The precipitated product was filtered off with suction, washed to neutrality with water and dried. 2.51 g (95% of theory) of the title compound were obtained.

$^1$H-NMR (400 MHz, DMSO-$d_6$, δ/ppm): 10.09 (s, 1H), 4.10 (t, 2H), 3.71 (d, 2H), 3.65 (t, 2H), 3.23 (s, 3H), 2.78 (s, 3H), 2.03 (dquin, 1H), 0.86 (d, 6H).

LC/MS (Method 3): $R_t$=1.20 min, m/z=324 [M+H]$^+$.

Example 115A 1-(2-Ethoxyethyl)-3-isobutyl-5-methyl-2,4-dioxo-1,2,3,4-tetrahydrothieno[2,3-d]pyrimidine-6-carbaldehyde

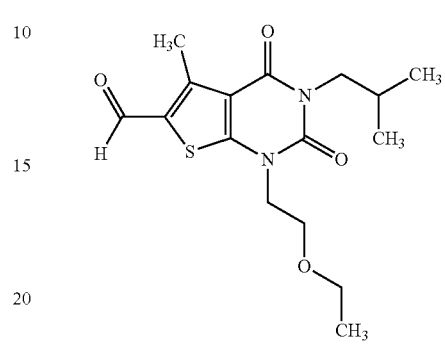

Analogously to the method described in Ex. 86A, 450 mg (1.69 mmol) of the compound from Ex. 50A and 862 mg (5.07 mmol) of 2-bromoethyl ethyl ether were used to prepare 362 mg (63% of theory) of the title compound. The reaction time here was 40 h.

$^1$H-NMR (400 MHz, DMSO-$d_6$, δ/ppm): 10.09 (s, 1H), 4.09 (t, 2H), 3.75-3.65 (m, 4H), 3.43 (q, 2H), 2.78 (s, 3H), 2.09-1.97 (m, 1H), 1.01 (t, 3H), 0.86 (d, 6H).

LC/MS (Method 3): $R_t$=1.28 min, m/z=339 [M+H]$^+$.

Example 116A

3-Isobutyl-5-methyl-1-(oxetan-2-ylmethyl)-2,4-dioxo-1,2,3,4-tetrahydrothieno[2,3-d]pyrimidine-6-carbaldehyde (racemate)

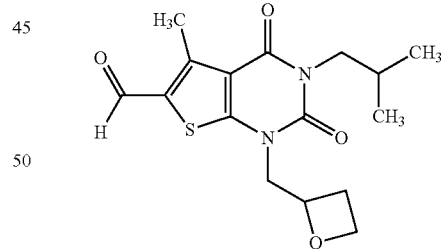

Analogously to the method described in Ex. 86A, 800 mg (3 mmol) of the compound from Ex. 50A and 1.84 g (12.01 mmol) of racemic 2-(bromomethyl)oxetane were used to prepare 849 mg (84% of theory) of the title compound. The conversion was conducted here at 80° C. and the reaction time was 21 h.

$^1$H-NMR (400 MHz, DMSO-$d_6$, δ/ppm): 10.09 (s, 1H), 5.06-4.97 (m, 1H), 4.51-4.40 (m, 2H), 4.28-4.15 (m, 2H), 3.71 (d, 2H), 2.77 (s, 3H), 2.75-2.65 (m, 1H), 2.09-1.97 (m, 1H), 0.86 (dd, 6H).

LC/MS (Method 3): $R_t$=1.15 min, m/z=337 [M+H]$^+$.

Example 117A

3-Isobutyl-5-methyl-2,4-dioxo-1-(tetrahydrofuran-2-ylmethyl)-1,2,3,4-tetrahydrothieno[2,3-d]pyrimidine-6-carbaldehyde (racemate)

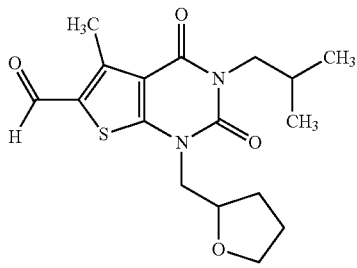 [SMILES: Cc1c(C=O)sc2c1c(=O)n(CC(C)C)c(=O)n2CC1CCCO1]

Analogously to the method described in Ex. 89A (Method B), 503 mg (1.56 mmol) of the compound from Ex. 69A were used to obtain 506 mg (92% of theory) of the title compound.

$^1$H-NMR (400 MHz, DMSO-$d_6$, δ/ppm): 10.09 (s, 1H), 4.28-4.19 (m, 1H), 4.12 (dd, 1H), 3.83-3.70 (m, 4H), 3.65-3.58 (m, 1H), 2.78 (s, 3H), 2.09-1.76 (m, 4H), 1.68 (m, 1H), 0.87 (d, 3H), 0.86 (d, 3H).

LC/MS (Method 1, ESIpos): $R_t$=1.14 min, m/z=351 [M+H]$^+$.

Example 118A

3-Isobutyl-5-methyl-1-(oxetan-3-ylmethyl)-2,4-dioxo-1,2,3,4-tetrahydrothieno[2,3-d]pyrimidine-6-carbaldehyde

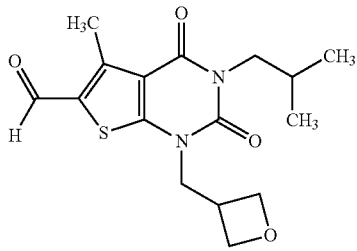 [SMILES: Cc1c(C=O)sc2c1c(=O)n(CC(C)C)c(=O)n2CC1COC1]

315 mg (1.18 mmol) of the compound from Ex. 50A and 578 mg (1.77 mmol) of caesium carbonate were stirred in 10 ml of anhydrous DMF at RT for 7 min, before 189 mg (1.77 mmol) of 3-(chloromethyl)oxetane were added. Subsequently, the reaction mixture was first heated in a microwave oven (Biotage Initiator with dynamic control of irradiation power) to 100° C. for 2 h. After this time, the same amounts of caesium carbonate and 3-(chloromethyl)oxetane once again were added. After a further 8 h at 100° C., the mixture was cooled down, diluted with ethyl acetate and washed successively with water and saturated sodium chloride solution. After drying over anhydrous magnesium sulphate, the mixture was filtered and concentrated to dryness. The residue obtained was purified by means of preparative HPLC (Method 8). After combination of the product fractions, concentration and drying under high vacuum, 75 mg (18% of theory) of the title compound were obtained.

LC/MS (Method 1, ESIpos): $R_t$=0.93 min, m/z=337 [M+H]$^+$.

Example 119A

3-Isobutyl-1,5-dimethyl-2,4-dioxo-1,2,3,4-tetrahydrothieno[2,3-d]pyrimidine-6-carbaldehyde

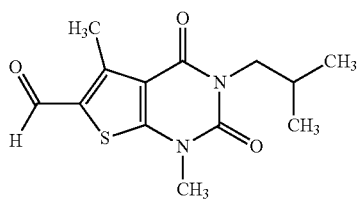 [SMILES: Cc1c(C=O)sc2c1c(=O)n(CC(C)C)c(=O)n2C]

Analogously to the method described in Ex. 89A (Method B), 168 mg (0.67 mmol) of the compound from Ex. 70A were used to obtain 173 mg (92% of theory) of the title compound.

$^1$H-NMR (400 MHz, DMSO-$d_6$, δ/ppm): 10.09 (s, 1H), 3.71 (d, 2H), 3.48 (s, 3H), 2.79 (s, 3H), 2.04 (m, 1H), 0.87 (d, 6H).

LC/MS (Method 1, ESIpos): $R_t$=0.94 min, m/z=281 [M+H]$^+$.

Example 120A

5-Methyl-2,4-dioxo-3-(2,2,2-trifluoroethyl)-1-(3,3,3-trifluoropropyl)-1,2,3,4-tetrahydrothieno[2,3-d]pyrimidine-6-carbaldehyde

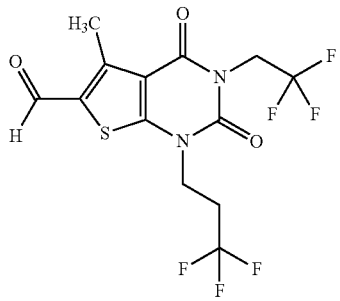 [SMILES: Cc1c(C=O)sc2c1c(=O)n(CC(F)(F)F)c(=O)n2CCC(F)(F)F]

Analogously to the method described in Ex. 86A, 450 mg (1.5 mmol) of the compound from Ex. 51A and 1.01 g (4.52 mmol) of 1,1,1-trifluoro-3-iodopropane were used to prepare 382 mg (65% of theory) of the title compound. The reaction time here was 21 h.

$^1$H-NMR (400 MHz, DMSO-$d_6$, δ/ppm): 10.12 (s, 1H), 4.72 (q, 2H), 4.21 (t, 2H), 2.88-2.73 (m, 5H).

LC/MS (Method 3): $R_t$=1.22 min, m/z=389 [M+H]$^+$.

Example 121A 1-(3-Fluoropropyl)-5-methyl-2,4-dioxo-3-(2,2,2-trifluoroethyl)-1,2,3,4-tetrahydrothieno[2,3-d]pyrimidine-6-carbaldehyde

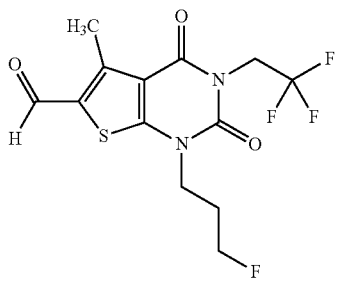 [SMILES: Cc1c(C=O)sc2c1c(=O)n(CC(F)(F)F)c(=O)n2CCCF]

2.87 ml (30.83 mmol) of phosphorus oxychloride were added cautiously, while cooling with an ice bath, to a solution of 1 g (3.08 mmol) of the compound from Ex. 71A in 28.7 ml of DMF. The mixture was then stirred in a microwave apparatus at 50° C. for 3 h. Thereafter, the reaction mixture was concentrated very substantially on a rotary evaporator. The remaining residue was added to ice-water and stirred. The precipitated product was filtered off with suction, washed to neutrality with water and dried. 1.02 g (94% of theory) of the title compound were obtained.

$^1$H-NMR (400 MHz, DMSO-$d_6$, δ/ppm): 10.11 (s, 1H), 4.70 (q, 2H), 4.61 (t, 1H), 4.49 (t, 1H), 4.08 (t, 2H), 2.79 (s, 3H), 2.17-2.02 (m, 2H).

LC/MS (Method 3): $R_t$=1.11 min, m/z=353 [M+H]$^+$.

Example 122A 1-(2-Methoxyethyl)-5-methyl-2,4-dioxo-3-(2,2,2-trifluoroethyl)-1,2,3,4-tetrahydrothieno[2,3-d]pyrimidine-6-carbaldehyde

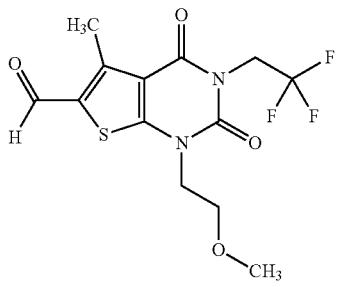 [SMILES: COCCn1c(=O)n(CC(F)(F)F)c(=O)c2c(C)c(C=O)sc21]

1.52 ml (16.28 mmol) of phosphorus oxychloride were added cautiously, while cooling with an ice bath, to a solution of 525 mg (1.63 mmol) of the compound from Ex. 72A in 15.2 ml of DMF. The mixture was then stirred in a microwave apparatus at 50° C. for 2 h. Thereafter, the reaction mixture was concentrated very substantially on a rotary evaporator. The remaining residue was added to ice-water and stirred. The precipitated product was filtered off with suction, washed to neutrality with water and dried. 540 mg (94% of theory) of the title compound were obtained.

$^1$H-NMR (400 MHz, DMSO-$d_6$, δ/ppm): 10.10 (s, 1H), 4.70 (q, 2H), 4.14 (t, 2H), 3.66 (t, 2H), 3.24 (s, 3H), 2.78 (s, 3H).

LC/MS (Method 3): $R_t$=1.09 min, m/z=351 [M+H]$^+$.

Example 123A 1-(2-Methoxyethyl)-5-methyl-2,4-dioxo-3-(2,2,2-trifluoroethyl)-1,2,3,4-tetrahydrothieno[2,3-d]pyrimidine-6-carbaldehyde

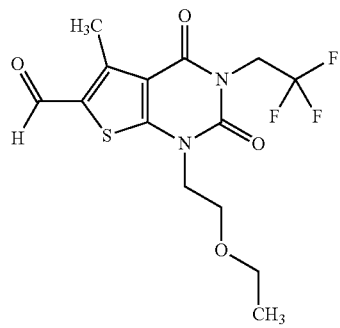 [SMILES: CCOCCn1c(=O)n(CC(F)(F)F)c(=O)c2c(C)c(C=O)sc21]

Analogously to the method described in Ex. 86A, 400 mg (1.37 mmol) of the compound from Ex. 51A and 628 mg (4.11 mmol) of 1-bromo-2-ethoxyethane were used to prepare 201 mg (40% of theory) of the title compound. The reaction time here was 70 h.

$^1$H-NMR (400 MHz, DMSO-$d_6$, δ/ppm): 10.11 (s, 1H), 4.71 (q, 2H), 4.13 (t, 2H), 3.69 (t, 2H), 3.44 (q, 2H), 2.78 (s, 3H), 1.02 (t, 3H).

LC/MS (Method 3): $R_t$=1.18 min, m/z=365 [M+H]$^+$.

Example 124A

5-Methyl-1-(oxetan-2-ylmethyl)-2,4-dioxo-3-(2,2,2-trifluoroethyl)-1,2,3,4-tetrahydrothieno[2,3-d]pyrimidine-6-carbaldehyde (racemate)

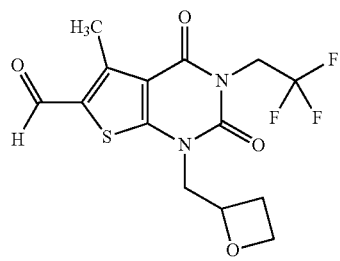 [SMILES: Cc1c(C=O)sc2c1c(=O)n(CC(F)(F)F)c(=O)n2CC1CCO1]

Analogously to the method described in Ex. 86A, 1.25 g (4.19 mmol) of the compound from Ex. 51A and 3.22 g (20.95 mmol) of racemic 2-(bromomethyl)oxetane were used to prepare 613 mg (39% of theory) of the title compound. The conversion was conducted here at 70° C. and the reaction time was 114 h.

$^1$H-NMR (400 MHz, DMSO-$d_6$, δ/ppm): 10.11 (s, 1H), 5.03 (ddt, 1H), 4.71 (q, 2H), 4.52-4.41 (m, 2H), 4.33-4.18 (m, 2H), 2.78 (s, 3H), 2.74-2.65 (m, 1H).

LC/MS (Method 3): $R_t$=1.06 min, m/z=363 [M+H]$^+$.

Example 125A

5-Methyl-2,4-dioxo-1-(tetrahydrofuran-2-ylmethyl)-3-(2,2,2-trifluoroethyl)-1,2,3,4-tetrahydrothieno[2,3-d]pyrimidine-6-carbaldehyde (racemate)

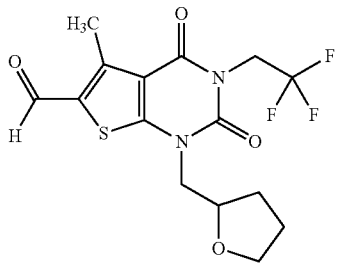 [SMILES: Cc1c(C=O)sc2c1c(=O)n(CC(F)(F)F)c(=O)n2CC1CCCO1]

Analogously to the method described in Ex. 86A, 1.25 g (4.19 mmol) of the compound from Ex. 51A and 3.84 g (20.96 mmol) of racemic 2-(bromomethyl)tetrahydrofuran were used to prepare 689 mg (43% of theory) of the title compound. The conversion was conducted here at 80° C.

$^1$H-NMR (400 MHz, DMSO-$d_6$, δ/ppm): 10.10 (s, 1H), 4.71 (q, 2H), 4.27-4.19 (m, 1H), 4.15 (dd, 1H), 3.82 (dd, 1H), 3.78-3.71 (m, 1H), 3.62 (td, 1H), 2.78 (s, 3H), 2.06-1.97 (m, 1H), 1.97-1.76 (m, 2H), 1.73-1.63 (m, 1H).

LC/MS (Method 3): $R_t$=1.16 min, m/z=377 [M+H]$^+$.

Example 126A

5-Methyl-1-(oxetan-3-ylmethyl)-2,4-dioxo-3-(2,2,2-trifluoroethyl)-1,2,3,4-tetrahydrothieno[2,3-d]pyrimidine-6-carbaldehyde

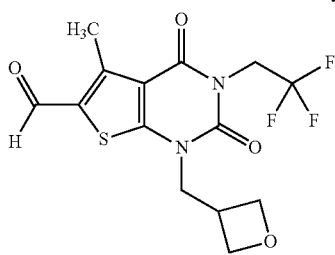

Analogously to the method described in Ex. 86A, 400 mg (1.34 mmol) of the compound from Ex. 51A and 810 mg (5.36 mmol) of 3-(bromomethyl)oxetane were used to prepare 156 mg (32% of theory) of the title compound. The reaction time here was 70 h.

$^1$H-NMR (400 MHz, DMSO-$d_6$, δ/ppm): 10.11 (s, 1H), 4.69 (q, 2H), 4.61 (dd, 2H), 4.44 (t, 2H), 4.30 (d, 2H), 3.51-3.41 (m, 1H), 2.78 (s, 3H).

LC/MS (Method 3): $R_t$=1.01 min, m/z=363 [M+H]$^+$.

Example 127A 1,5-Dimethyl-2,4-dioxo-3-(2,2,2-trifluoroethyl)-1,2,3,4-tetrahydrothieno[2,3-d]pyrimidine-6-carbaldehyde

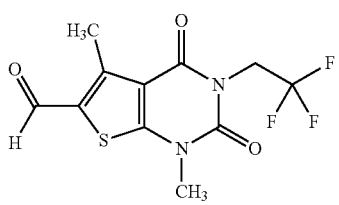 [SMILES: Cc1c(C=O)sc2c1c(=O)n(CC(F)(F)F)c(=O)n2C]

Analogously to the method described in Ex. 86A, 350 mg (1.17 mmol) of the compound from Ex. 51A and 505 mg (3.52 mmol) of iodomethane were used to prepare 401 mg of the title compound. The reaction time here was 24 h.

$^1$H-NMR (400 MHz, DMSO-$d_6$, δ/ppm): 10.10 (s, 1H), 4.70 (q, 2H), 3.51 (s, 3H), 2.79 (s, 3H).

LC/MS (Method 3): $R_t$=1.04 min, m/z=307 [M+H]$^+$.

Example 128A 3-(2,2-Difluoroethyl)-5-methyl-2,4-dioxo-1-(3,3,3-trifluoropropyl)-1,2,3,4-tetrahydrothieno[2,3-d]pyrimidine-6-carbaldehyde

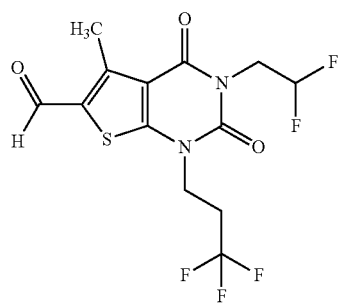 [SMILES: Cc1c(C=O)sc2c1c(=O)n(CC(F)F)c(=O)n2CCC(F)(F)F]

Analogously to the method described in Ex. 86A, 350 mg (1.26 mmol) of the compound from Ex. 52A and 857 mg (3.83 mmol) of 1,1,1-trifluoro-3-iodopropane were used to prepare 318 mg (67% of theory) of the title compound. The reaction time here was 45 h.

$^1$H-NMR (400 MHz, DMSO-$d_6$, δ/ppm): 10.12 (s, 1H), 6.38-6.05 (m, 1H), 4.31 (td, 2H), 4.20 (t, 2H), 2.88-2.73 (m, 5H).

LC/MS (Method 3): $R_t$=1.16 min, m/z=371 [M+H]$^+$.

Example 129A 3-(2,2-Difluoroethyl)-1-(3-fluoropropyl)-5-methyl-2,4-dioxo-1,2,3,4-tetrahydrothieno[2,3-d]pyrimidine-6-carbaldehyde

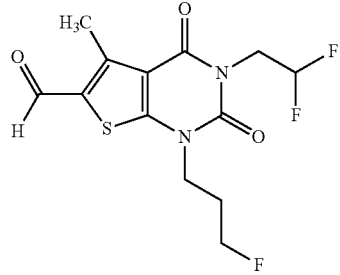 [SMILES: Cc1c(C=O)sc2c1c(=O)n(CC(F)F)c(=O)n2CCCF]

Analogously to the method described in Ex. 86A, 501 mg (1.79 mmol) of the compound from Ex. 52A and 1.01 g (5.37 mmol) of 1-fluoro-3-iodopropane were used to prepare 526 mg (86% of theory) of the title compound. The reaction time here was 16 h.

$^1$H-NMR (400 MHz, DMSO-$d_6$, δ/ppm): 10.11 (s, 1H), 6.37-6.05 (m, 1H), 4.61 (t, 1H), 4.49 (t, 1H), 4.30 (td, 2H), 4.07 (t, 2H), 2.79 (s, 3H), 2.17-2.01 (m, 2H).

LC/MS (Method 3): $R_t$=1.04 min, m/z=335 [M+H]$^+$.

Example 130A 3-(2,2-Difluoroethyl)-1-(2-methoxyethyl)-5-methyl-2,4-dioxo-1,2,3,4-tetrahydrothieno[2,3-d]pyrimidine-6-carbaldehyde

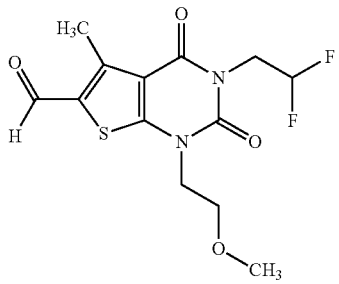 [SMILES: COCCn1c(=O)n(CC(F)F)c(=O)c2c(C)c(C=O)sc21]

Analogously to the method described in Ex. 86A, 527 mg (1.92 mmol) of the compound from Ex. 52A and 827 mg (5.77 mmol) of 2-bromoethyl methyl ether were used to prepare 468 mg (72% of theory) of the title compound. The reaction time here was 40 h.

$^1$H-NMR (400 MHz, DMSO-$d_6$, δ/ppm): 10.10 (s, 1H), 6.38-6.06 (m, 1H), 4.30 (td, 2H), 4.12 (t, 2H), 3.66 (t, 2H), 3.24 (s, 3H), 2.78 (s, 3H).

LC/MS (Method 3): $R_t$=1.0 min, m/z=333 [M+H]$^+$.

Example 131A 3-(2,2-Difluoroethyl)-1-(2-ethoxyethyl)-5-methyl-2,4-dioxo-1,2,3,4-tetrahydrothieno[2,3-d]pyrimidine-6-carbaldehyde

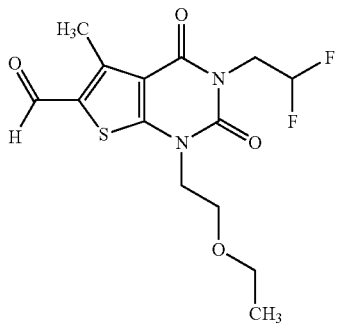 [SMILES: CCOCCn1c(=O)n(CC(F)F)c(=O)c2c(C)c(C=O)sc21]

Analogously to the method described in Ex. 86A, 350 mg (1.27 mmol) of the compound from Ex. 52A and 651 mg (3.83 mmol) of 2-bromoethyl ethyl ether were used to prepare 189 mg (41% of theory) of the title compound. The reaction time here was 116 h.

$^1$H-NMR (400 MHz, DMSO-$d_6$, δ/ppm): 10.10 (s, 1H), 6.38-6.06 (m, 1H), 4.30 (td, 2H), 4.11 (t, 2H), 3.69 (t, 2H), 3.44 (q, 2H), 2.78 (s, 3H), 1.03 (t, 3H).

LC/MS (Method 3): $R_t$=1.11 min, m/z=347 [M+H]$^+$.

Example 132A 3-(2,2-Difluoroethyl)-5-methyl-1-(oxetan-2-ylmethyl)-2,4-dioxo-1,2,3,4-tetrahydrothieno[2,3-d]pyrimidine-6-carbaldehyde (racemate)

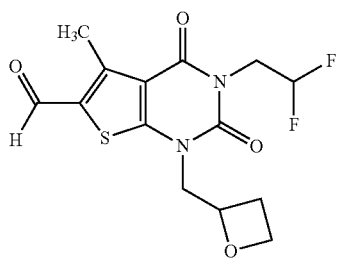 [SMILES: Cc1c(C=O)sc2c1c(=O)n(CC(F)F)c(=O)n2CC1CCO1]

Analogously to the method described in Ex. 86A, 543 mg (1.98 mmol) of the compound from Ex. 52A and 1.19 g (7.92 mmol) of racemic 2-(bromomethyl)oxetane were used to prepare 333 mg (47% of theory) of the title compound. The conversion was conducted here at 80° C. and the reaction time was 62 h.

$^1$H-NMR (400 MHz, DMSO-$d_6$, δ/ppm): 10.10 (s, 1H), 6.38-6.06 (m, 1H), 5.03 (ddt, 1H), 4.52-4.41 (m, 2H), 4.36-4.17 (m, 4H), 2.78 (s, 3H), 2.74-2.64 (m, 1H).

LC/MS (Method 3): $R_t$=0.98 min, m/z=345 [M+H]$^+$.

Example 133A 3-(2,2-Difluoroethyl)-5-methyl-2,4-dioxo-1-(tetrahydrofuran-2-ylmethyl)-1,2,3,4-tetrahydrothieno[2,3-d]pyrimidine-6-carbaldehyde (racemate)

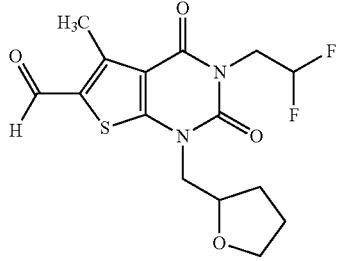 [SMILES: Cc1c(C=O)sc2c1c(=O)n(CC(F)F)c(=O)n2CC1CCCO1]

Analogously to the method described in Ex. 86A, 800 mg (2.92 mmol) of the compound from Ex. 52A and 2.53 g (14.58 mmol) of racemic 2-(bromomethyl)tetrahydrofuran were used to prepare 520 mg (49% of theory) of the title compound. The conversion was conducted here at 70° C.

$^1$H-NMR (400 MHz, DMSO-$d_6$, δ/ppm): 10.10 (s, 1H), 6.39-6.07 (m, 1H), 4.36-4.19 (m, 3H), 4.15 (dd, 1H), 3.84-3.70 (m, 2H), 3.62 (td, 1H), 2.78 (s, 3H), 2.07-1.96 (m, 1H), 1.96-1.86 (m, 1H), 1.86-1.76 (m, 1H), 1.73-1.63 (m, 1H).

LC/MS (Method 3): $R_t$=1.08 min, m/z=359 [M+H]$^+$.

Example 134A 3-(2,2-Difluoroethyl)-5-methyl-1-(oxetan-3-ylmethyl)-2,4-dioxo-1,2,3,4-tetrahydrothieno[2,3-d]pyrimidine-6-carbaldehyde

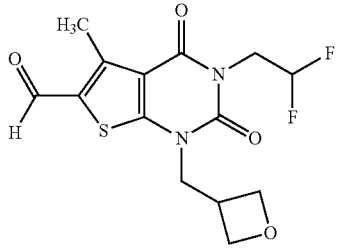 [SMILES: Cc1c(C=O)sc2c1c(=O)n(CC(F)F)c(=O)n2CC1COC1]

Analogously to the method described in Ex. 86A, 350 mg (1.27 mmol) of the compound from Ex. 52A and 771 mg (5.1 mmol) of 3-(bromomethyl)oxetane were used to prepare 133 mg (29% of theory) of the title compound. The reaction time here was 22 h.

$^1$H-NMR (400 MHz, DMSO-$d_6$, δ/ppm): 10.11 (s, 1H), 6.35-6.03 (m, 1H), 4.61 (dd, 2H), 4.45 (t, 2H), 4.34-4.23 (m, 4H), 3.51-3.39 (m, 1H), 2.78 (s, 3H).

LC/MS (Method 3): $R_t$=0.93 min, m/z=345 [M+H]$^+$.

Example 135A 3-(2,2-Difluoroethyl)-1,55-dimethyl-2,4-dioxo-1,2,3,4-tetrahydrothieno[2,3-d]pyrimidine-6-carbaldehyde

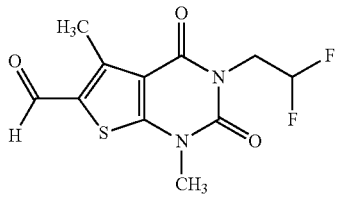 [SMILES: Cc1c(C=O)sc2c1c(=O)n(CC(F)F)c(=O)n2C]

Analogously to the method described in Ex. 86A, 350 mg (1.27 mmol) of the compound from Ex. 52A and 549 mg (3.83 mmol) of iodomethane were used to prepare 358 mg (88% of theory) of the title compound. The reaction time here was 18 h.

$^1$H-NMR (400 MHz, DMSO-$d_6$, δ/ppm): 10.10 (s, 1H), 6.37-6.05 (m, 1H), 4.30 (td, 2H), 3.50 (s, 3H), 2.79 (s, 3H).

LC/MS (Method 3): $R_t$=0.95 min, m/z=289 [M+H]$^+$.

Example 136A 1,3-Bis(2-methoxyethyl)-5-methyl-2,4-dioxo-1,2,3,4-tetrahydrothieno[2,3-d]pyrimidine-6-carbaldehyde

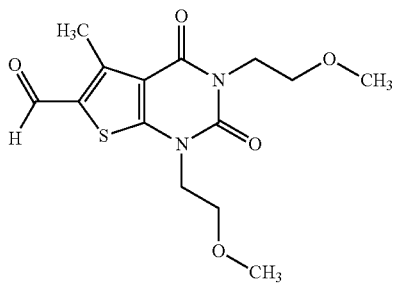 [SMILES: COCCn1c(=O)c2c(C)c(C=O)sc2n(CCOC)c1=O]

Analogously to the method described in Ex. 86A, 450 mg (1.66 mmol) of the compound from Ex. 53A and 692 mg (4.98 mmol) of 2-bromoethyl methyl ether were used to prepare 391 mg (71% of theory) of the title compound. The reaction time here was 18 h.

$^1$H-NMR (400 MHz, DMSO-$d_6$, δ/ppm): 10.09 (s, 1H), 4.10 (t, 2H), 4.06 (t, 2H), 3.65 (t, 2H), 3.51 (t, 2H), 3.24 (2s, 6H), 2.78 (s, 3H).

LC/MS (Method 3): $R_t$=0.93 min, m/z=327 [M+H]$^+$.

Example 137A 1-(2-Ethoxyethyl)-3-(2-methoxyethyl)-5-methyl-2,4-dioxo-1,2,3,4-tetrahydrothieno[2,3-d]pyrimidine-6-carbaldehyde

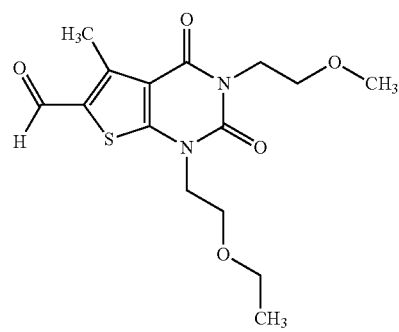 [SMILES: CCOCCn1c(=O)n(CCOC)c(=O)c2c(C)c(C=O)sc21]

Analogously to the method described in Ex. 86A, 475 mg (1.77 mmol) of the compound from Ex. 53A and 903 mg (5.31 mmol) of 2-bromoethyl ethyl ether were used to prepare 381 mg (61% of theory) of the title compound. The reaction time here was 24 h.

$^1$H-NMR (400 MHz, DMSO-$d_6$, δ/ppm): 10.09 (s, 1H), 4.12-4.02 (m, 4H), 3.68 (t, 2H), 3.51 (t, 2H), 3.44 (q, 2H), 3.24 (s, 3H), 2.78 (s, 3H), 1.02 (t, 3H).

LC/MS (Method 3): $R_t$=1.03 min, m/z=341 [M+H]$^+$.

Example 138A 6-(Hydroxymethyl)-1-(2-methoxyethyl)-5-methyl-3-(2-phenylethyl)thieno[2,3-d]pyrimidine-2,4(1H,3H)-dione

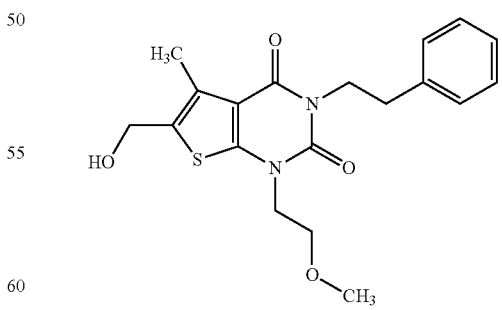

Method A:

At 0° C., 130 μl (0.129 mmol) of a 1 M solution of lithium aluminium hydride in THF were added dropwise to a solution of 100 mg (0.257 mmol) of the compound from Example 15A in 2 ml of dry THF. After 1 h at 0° C., the reaction was complete. Excess lithium aluminium hydride was destroyed by adding a little methanol. Subsequently, a sufficient amount of DMF was added to form a clear solution, which was then separated into its components by means of preparative HPLC (Method 8). After concentration of the product fractions and drying under high vacuum, 12 g (13% of theory) of the title compound were obtained.
Method B:
At 0° C., 2.5 ml (2.49 mmol) of a 1 M solution of lithium aluminium hydride in THF were added dropwise to a solution of 1.0 g (2.49 mmol) of the compound from Example 19A in 30 ml of dry THF. After 10 min at 0° C., excess lithium aluminium hydride was destroyed by adding 1 ml of water. Then 10 ml of 1 M sodium hydroxide solution were added. The undissolved material was filtered off with suction and the residue was washed thoroughly with THF. The filtrate was concentrated to dryness. The residue obtained was purified by MPLC (Biotage cartridge, 100 g of silica gel, cyclohexane/ethyl acetate 2:1→1:1). After concentration of the product fractions and drying under high vacuum, 572 mg (61% of theory) of the title compound were obtained.
Method C:
At −40° C., 0.847 ml (0.847 mmol) of a 1 M solution of lithium aluminium hydride in THF was added dropwise to a solution of 430 mg (0.847 mmol) of the compound from Example 23A in 23 ml of dry THF. After stirring at −40° C. for 30 min, 1 ml of 10% hydrochloric acid was added cautiously. The mixture was brought to RT and 100 ml of saturated sodium chloride solution were added. The aqueous phase was extracted with ethyl acetate. The combined organic phases were dried over sodium sulphate, filtered and concentrated. The residue obtained was chromatographed using a silica gel cartridge (Biotage, 25 g of silica gel, eluent: hexane/ethyl acetate). 235 mg (74% of theory) of the title compound were obtained.

$^1$H-NMR (400 MHz, DMSO-$d_6$, δ/ppm): 7.32-7.27 (m, 2H), 7.26-7.20 (m, 3H), 5.58 (t, 1H), 4.57 (d, 2H), 4.06 (dd, 2H), 4.03 (t, 2H), 3.61 (t, 2H), 3.24 (s, 3H), 2.84 (dd, 2H), 2.33 (s, 3H).

LC/MS (Method 1, ESIpos): $R_t$=0.97 min, m/z=375 [M+H]$^+$.

Example 139A 6-(Hydroxymethyl)-1-(2-methoxyethyl)-3,5-dimethylthieno[2,3-d]pyrimidine-2,4(1H,3H)-dione

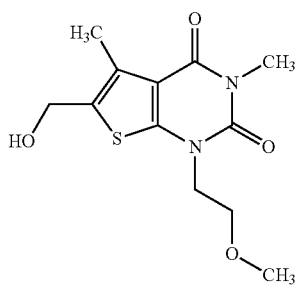 [SMILES: COCCn1c(=O)n(C)c(=O)c2c(C)c(CO)sc21]

At −40° C., 0.73 ml (0.73 mmol) of a 1 M solution of lithium aluminium hydride in THF was added dropwise to a solution of 240 mg (0.73 mmol) of the compound from Example 20A in 8.7 ml of dry THF. After stirring at −40° C. for 30 min, 10% hydrochloric acid was added cautiously until a clear solution was present. The mixture was brought to RT and 30 ml of saturated sodium chloride solution were added. The aqueous phase was extracted with ethyl acetate. The combined organic phases were dried over sodium sulphate, filtered and concentrated. The residue obtained was chromatographed using a silica gel cartridge (Biotage, 10 g of silica gel, eluent: hexane/ethyl acetate). 129 mg (61% of theory) of the title compound were obtained.

$^1$H-NMR (400 MHz, DMSO-$d_6$, δ/ppm): 5.56 (t, 1H), 4.57 (d, 2H), 4.04 (t, 2H), 3.64 (t, 2H), 3.24 (s, 3H), 3.22 (s, 3H), 2.32 (s, 3H).

LC/MS (Method 3): $R_t$=0.74 min, m/z=285 [M+H]$^+$.

Example 140A

3-Ethyl-6-(hydroxymethyl)-5-methyl-1-(3,3,3-trifluoropropyl)thieno[2,3-d]pyrimidine-2,4(1H,3H)-dione

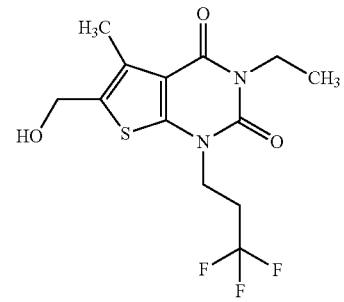 [SMILES: CCn1c(=O)c2c(C)c(CO)sc2n(CCC(F)(F)F)c1=O]

Method A:
At 0° C., 1.4 ml (2.75 mmol) of a 1 M solution of lithium aluminium hydride in THF were added dropwise to a solution of 1.0 g (2.75 mmol) of the compound from Example 21A in 30 ml of dry THF. After 15 min at 0° C., excess lithium aluminium hydride was destroyed by adding 1 ml of water. Then 10 ml of 1 M sodium hydroxide solution were added. Kieselguhr was added, undissolved material was filtered off with suction and the residue was washed thoroughly with THF. The filtrate was concentrated to dryness. The residue obtained was purified by MPLC (Interchim cartridge, 120 g of silica gel, cyclohexane/ethyl acetate 2:1→1:1). Since the product obtained in this manner was still not entirely pure, another purification was conducted by means of preparative HPLC (Method 10). After concentration of the product fractions and drying under high vacuum, 385 g (41% of theory) of the title compound were obtained.
Method B:
At −78° C., 3.4 ml (3.43 mmol) of a 1 M solution of lithium aluminium hydride in THF were added dropwise to a solution of 3.83 g (11.4 mmol) of the compound from Example 74A in 100 ml of dry THF. After 15 min at −78° C., excess lithium aluminium hydride was destroyed by adding 2.5 ml of water. Then 10 ml of 1 M sodium hydroxide solution were added. Kieselguhr was added, the mixture was allowed to come to RT, undissolved material was filtered off with suction and the residue was washed thoroughly with THF. The filtrate was first concentrated to dryness, then taken up in 100 ml of ethyl acetate and washed successively with water and saturated sodium chloride solution. The organic phase was dried over anhydrous magnesium sulphate and then concentrated. At RT, the residue obtained was stirred with a mixture of 10 ml each of cyclohexane and ethyl acetate. Filtration with suction and drying of the solid under high vacuum gave 3.12 g (78% of theory, 97% purity) of the title compound.

$^1$H-NMR (400 MHz, DMSO-$d_6$, δ/ppm): 5.61 (t, 1H), 4.59 (d, 2H), 4.12 (t, 2H), 3.91 (q, 2H), 2.83-2.71 (m, 2H), 2.34 (s, 3H), 1.12 (t, 3H).

LC/MS (Method 1, ESIpos): $R_t$=0.80 min, m/z=337 [M+H]$^+$.

Example 141A

3-Ethyl-1-(3-fluoropropyl)-6-(hydroxymethyl)-5-methylthieno[2,3-d]pyrimidine-2,4(1H,3H)-dione

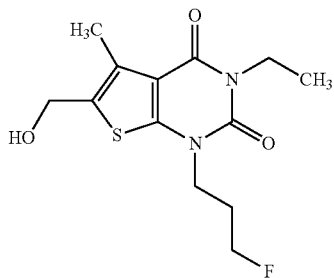 [SMILES: CCn1c(=O)c2c(C)c(CO)sc2n(CCCF)c1=O]

Method A:

Analogously to the method described in Ex. 138A (Method C), 465 mg (1.23 mmol) of the compound from Ex. 14A were used to prepare 210 mg (56% of theory) of the title compound.

$^1$H-NMR (400 MHz, DMSO-$d_6$, δ/ppm): 5.64-5.55 (m, 1H), 4.62-4.55 (m, 3H), 4.48 (t, 1H), 4.00 (t, 2H), 3.90 (q, 2H), 2.33 (s, 3H), 2.15-2.07 (m, 1H), 2.07-1.99 (m, 1H), 1.11 (t, 3H).

LC/MS (Method 3): $R_t$=0.90 min, m/z=301 [M+H]$^+$.

Method B:

At −78° C., 0.56 ml (0.56 mmol) of a 1 M solution of lithium aluminium hydride in THF were added dropwise to a solution of 580 mg (1.86 mmol) of the compound from Example 78A in 20 ml of dry THF. After stirring at −78° C. for 120 min, excess lithium aluminium hydride was destroyed by adding 1 ml of water. Then 1.66 ml of 1 M sodium hydroxide solution were added. Kieselguhr was added, undissolved material was filtered off with suction and the residue was washed thoroughly with THF. The filtrate was concentrated to dryness. The residue obtained was taken up in 100 ml of ethyl acetate. This solution was washed with water (100 ml) and saturated sodium chloride solution. The organic phase was dried over sodium sulphate, filtered and concentrated. 569 mg (91% of theory) of the title compound were obtained.

LC/MS (Method 3): $R_t$=0.88 min, m/z=301 [M+H]$^+$.

Example 142A

3-Ethyl-6-(hydroxymethyl)-5-methyl-1-[2-(trifluoromethoxy)ethyl]thieno[2,3-d]pyrimidine-2,4(1H,3H)-dione

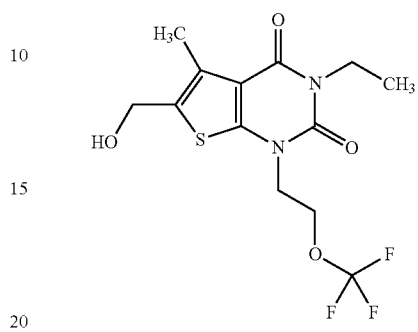

At RT, 16 mg (0.428 mmol) of sodium borohydride were added to a solution of 100 mg (0.285 mmol) of the compound from Ex. 82A in 2.8 ml of ethanol. After 1 h, about 1 ml of 1 M hydrochloric acid was added cautiously. Subsequently, undissolved material was filtered off with suction and the filtrate was separated into its components directly via preparative HPLC (Method 12). After concentration of the product fractions and drying under high vacuum, 82 mg (81% of theory) of the title compound were obtained.

$^1$H-NMR (400 MHz, DMSO-$d_6$, δ/ppm): 5.60 (t, 1H), 4.58 (d, 2H), 4.41 (t, 2H), 4.21 (t, 2H), 3.91 (q, 2H), 2.33 (s, 3H), 1.12 (t, 3H).

LC/MS (Method 1, ESIpos): $R_t$=0.88 min, m/z=353 [M+H]$^+$.

Example 143A

3-Ethyl-6-(hydroxymethyl)-1-(2-methoxyethyl)-5-methylthieno[2,3-d]pyrimidine-2,4(1H,3H)-dione

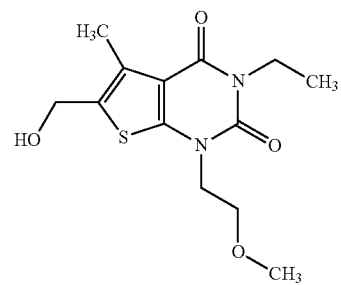 [SMILES: CCn1c(=O)c2c(C)c(CO)sc2n(CCOC)c1=O]

Method A:

Analogously to the method described in Ex. 138A (Method A), 100 mg (0.320 mmol) of the compound from Ex. 17A were used to obtain 22 mg (23% of theory) of the title compound. Preparative HPLC was effected here by Method 11.

Method B:

Analogously to the method described in Ex. 138A (Method B), 2.08 g (6.37 mmol) of the compound from Ex. 18A were used to obtain 1.04 g (52% of theory, 95% purity) of the title compound.

Method C:

At −78° C., 10.1 ml (10.1 mmol) of a 1 M solution of lithium aluminium hydride in THF were added dropwise to a solution of 10.0 g (33.7 mmol) of the compound from Example 84A in 300 ml of dry THF. After 2 h at −78° C., the reaction mixture was warmed briefly (<5 min) to about −30° C. and cooled down again to −78° C., then the excess lithium aluminium hydride was destroyed by adding 5 ml of water. Then 30 ml of 1 M sodium hydroxide solution were added. Kieselguhr was added, the mixture was allowed to come to RT, undissolved material was filtered off with suction and the residue was washed thoroughly with THF. The filtrate was first concentrated to dryness, then taken up in 400 ml of ethyl acetate and washed successively with water and saturated sodium chloride solution. The organic phase was dried over anhydrous sodium sulphate and then concentrated. Drying of the residue obtained under high vacuum gave 9.84 g (94% of theory, 97% purity) of the title compound.

$^1$H-NMR (400 MHz, DMSO-$d_6$, δ/ppm): 5.55 (t, 1H), 4.57 (d, 2H), 4.04 (t, 2H), 3.90 (q, 2H), 3.64 (t, 2H), 3.24 (s, 3H), 2.33 (s, 3H), 1.12 (t, 3H).

LC/MS (Method 1, ESIpos): $R_t$=0.63 min, m/z=299 [M+H]$^+$.

Example 144A 6-(Hydroxymethyl)-1-(2-methoxyethyl)-5-methyl-3-propylthieno[2,3-d]pyrimidine-2,4(1H,3H)-dione

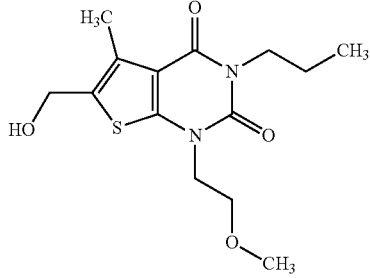 [SMILES: CCCn1c(=O)c2c(C)c(CO)sc2n(CCOC)c1=O]

Analogously to the method described in Ex. 138A (Method C), 260 mg (0.69 mmol) of the compound from Ex. 24A were used to prepare 97 mg (44% of theory) of the title compound. The conversion was effected here at −40° C.

$^1$H-NMR (400 MHz, DMSO-$d_6$, δ/ppm): 5.55 (br. s, 1H), 4.57 (s, 2H), 4.04 (t, 2H), 3.86-3.78 (m, 2H), 3.64 (t, 2H), 3.24 (s, 3H), 1.56 (sext, 2H), 0.86 (t, 3H).

LC/MS (Method 3): $R_t$=0.94 min, m/z=313 [M+H]$^+$.

Example 145A

3-Allyl-6-(hydroxymethyl)-1-(2-methoxyethyl)-5-methylthieno[2,3-d]pyrimidine-2,4(1H,3H)-dione

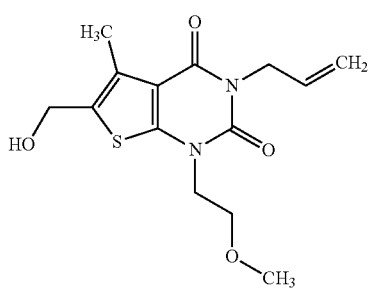 [SMILES: C=CCn1c(=O)c2c(C)c(CO)sc2n(CCOC)c1=O]

Analogously to the method described in Ex. 138A (Method C), 345 mg (0.92 mmol) of the compound from Ex. 25A were used to prepare 169 mg (59% of theory) of the title compound. The conversion was effected here at −40° C.

$^1$H-NMR (400 MHz, DMSO-$d_6$, δ/ppm): 5.84 (ddt, 1H), 5.59 (br. s, 1H), 5.13-5.02 (m, 2H), 4.57 (d, 2H), 4.46 (d, 2H), 4.04 (t, 2H), 3.63 (t, 2H), 3.23 (s, 3H), 2.32 (s, 3H).

LC/MS (Method 3): $R_t$=0.88 min, m/z=311 [M+H]$^+$.

Example 146A 6-(Hydroxymethyl)-3-isopropyl-1-(2-methoxyethyl)-5-methylthieno[2,3-d]pyrimidine-2,4(1H,3H)-dione

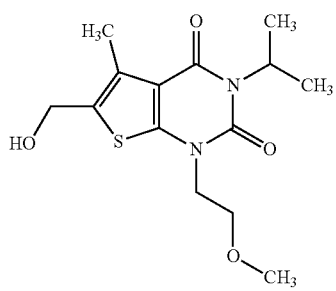 [SMILES: COCCn1c(=O)n(C(C)C)c(=O)c2c(C)c(CO)sc21]

Analogously to the method described in Ex. 138A (Method C), 280 mg (0.74 mmol) of the compound from Ex. 26A were used to prepare 113 mg (45% of theory) of the title compound. The conversion was effected here at −40° C.

$^1$H-NMR (400 MHz, DMSO-$d_6$, δ/ppm): 5.55 (t, 1H), 5.13 (sept, 1H), 4.56 (d, 2H), 4.00 (t, 2H), 3.62 (t, 2H), 3.26-3.23 (m, 3H), 2.31 (s, 3H), 1.40 (d, 6H).

LC/MS (Method 3): $R_t$=0.97 min, m/z=313 [M+H]$^+$.

Example 147A 3-sec-Butyl-6-(hydroxymethyl)-1-(2-methoxyethyl)-5-methylthieno[2,3-d]pyrimidine-2,4(1H,3H)-dione (racemate)

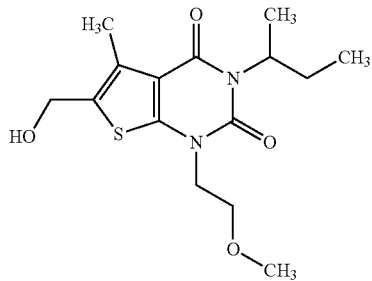 [SMILES: CCC(C)n1c(=O)c2c(C)c(CO)sc2n(CCOC)c1=O]

Analogously to the method described in Ex. 138A (Method C), 320 mg (0.77 mmol) of the compound from Ex. 27A were used to prepare 172 mg (69% of theory) of the title compound. The conversion was effected here at −40° C.

$^1$H-NMR (400 MHz, DMSO-$d_6$, δ/ppm): 5.56 (t, 1H), 4.91 (d, 1H), 4.56 (d, 2H), 4.08-3.95 (m, 2H), 3.62 (t, 2H), 3.23 (s, 3H), 2.31 (s, 3H), 2.09-1.97 (m, 1H), 1.73 (dquin, 1H), 1.37 (d, 3H), 0.75 (t, 3H).

LC/MS (Method 3): $R_t$=1.06 min, m/z=327 [M+H]$^+$.

Example 148A 6-(Hydroxymethyl)-3-isobutyl-1-(2-methoxyethyl)-5-methylthieno[2,3-d]pyrimidine-2,4(1H,3H)-dione

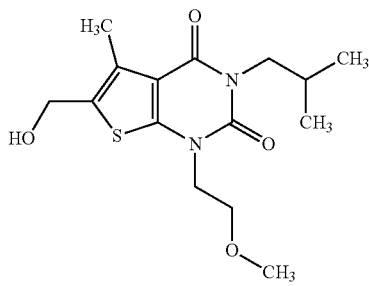 [SMILES: COCCn1c(=O)n(CC(C)C)c(=O)c2c(C)c(CO)sc21]

68.4 mg (1.81 mmol) of sodium borohydride (dissolved in 2 ml of ethanol) were added to a solution of 395 mg (1.2 mmol) of the compound from Ex. 114A in 12 ml of THF and 38 ml of ethanol, and the mixture was stirred at RT. After 22 h, excess sodium borohydride was destroyed by adding acetic acid. The reaction mixture was concentrated very substantially on a rotary evaporator. The remaining residue was taken up in ethyl acetate. It was washed with water, and the organic phase was dried over sodium sulphate, filtered and concentrated. The residue obtained was chromatographed using a silica gel cartridge (Biotage, 50 g of silica gel, eluent: hexane/ethyl acetate). 285 mg (72% of theory) of the title compound were obtained.

$^1$H-NMR (400 MHz, DMSO-$d_6$, δ/ppm): 5.55 (br. s, 1H), 4.57 (br. s, 2H), 4.04 (t, 2H), 3.71 (d, 2H), 3.63 (t, 2H), 3.23 (s, 3H), 2.32 (s, 3H), 2.09-1.98 (m, 1H), 0.85 (d, 6H).

LC/MS (Method 3): $R_t$=1.04 min, m/z=327 [M+H]$^+$.

Example 149A 6-(Hydroxymethyl)-1-(2-methoxyethyl)-5-methyl-3-(3-methylbut-2-en-1-yl)thieno[2,3-d]pyrimidine-2,4(1H,3H)-dione

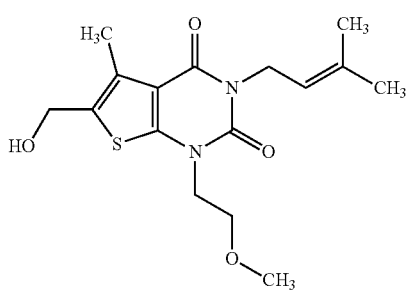 [SMILES: COCCn1c(=O)n(CC=C(C)C)c(=O)c2c(C)c(CO)sc21]

Analogously to the method described in Ex. 138A (Method C), 405 mg (0.92 mmol) of the compound from Ex. 28A were used to prepare 197 mg (59% of theory) of the title compound. The conversion was effected here at −40° C.

$^1$H-NMR (400 MHz, DMSO-$d_6$, δ/ppm): 5.58 (t, 1H), 5.15 (ddd, 1H), 4.57 (d, 2H), 4.44 (d, 2H), 4.03 (t, 2H), 3.63 (t, 2H), 3.24 (s, 3H), 2.32 (s, 3H), 1.75 (d, 3H), 1.66 (d, 3H).

LC/MS (Method 3): $R_t$=1.09 min, m/z=339 [M+H]$^+$.

Example 150A 3-(Cyclopropylmethyl)-6-(hydroxymethyl)-1-(2-methoxyethyl)-5-methylthieno[2,3-d]pyrimidine-2,4(1H,3H)-dione

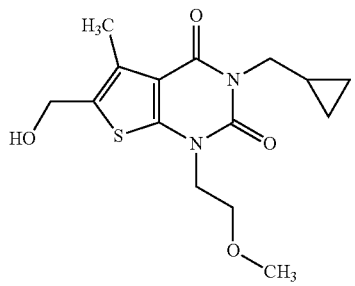 [SMILES: COCCn1c(=O)n(CC2CC2)c(=O)c2c(C)c(CO)sc21]

Analogously to the method described in Ex. 138A (Method C), 350 mg (0.86 mmol) of the compound from Ex. 29A were used to prepare 74 mg (26% of theory) of the title compound. The conversion was effected here at −40° C.

$^1$H-NMR (400 MHz, DMSO-$d_6$, δ/ppm): 5.56 (t, 1H), 4.57 (d, 2H), 4.05 (t, 2H), 3.76 (d, 2H), 3.65 (t, 2H), 3.24 (s, 3H), 2.33 (s, 3H), 1.23-1.11 (m, 1H), 0.45-0.39 (m, 2H), 0.36-0.30 (m, 2H).

LC/MS (Method 3): $R_t$=0.99 min, m/z=325 [M+H]$^+$.

Example 151A 3-(2-Fluoroethyl)-6-(hydroxymethyl)-1-(2-methoxyethyl)-5-methylthieno[2,3-d]pyrimidine-2,4(1H,3H)-dione

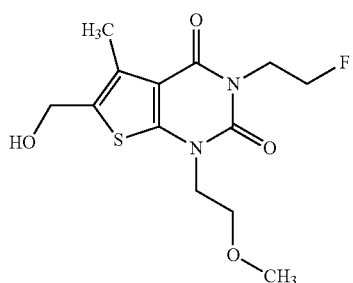

Analogously to the method described in Ex. 138A (Method C), 305 mg (0.78 mmol) of the compound from Ex. 30A were used to prepare 169 mg (66% of theory) of the title compound. The conversion was effected here at −40° C.

$^1$H-NMR (400 MHz, DMSO-$d_6$, δ/ppm): 5.57 (t, 1H), 4.66 (t, 1H), 4.58 (d, 2H), 4.54 (t, 1H), 4.24 (t, 1H), 4.20-4.16 (m, 1H), 4.05 (t, 2H), 3.64 (t, 2H), 3.24 (s, 3H), 2.32 (s, 3H).

LC/MS (Method 3): $R_t$=0.81 min, m/z=317 [M+H]$^+$.

Example 152A 6-(Hydroxymethyl)-1-(2-methoxyethyl)-5-methyl-3-(3,3,3-trifluoropropyl)thieno[2,3-d]pyrimidine-2,4(1H,3H)-dione

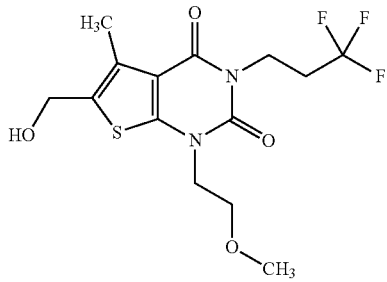 [SMILES: COCCn1c(=O)n(CCC(F)(F)F)c(=O)c2c(C)c(CO)sc21]

Analogously to the method described in Ex. 138A (Method C), 435 mg (0.86 mmol) of the compound from Ex. 31A were used to prepare 219 mg (68% of theory) of the title compound. The conversion was effected here at −40° C.

$^1$H-NMR (400 MHz, DMSO-d$_6$, δ/ppm): 5.60 (s, 1H), 4.57 (d, 2H), 4.11 (t, 2H), 4.04 (t, 2H), 3.64 (t, 2H), 3.24 (s, 3H), 2.58 (d, 2H), 2.32 (s, 3H).

LC/MS (Method 3): R$_t$=1.02 min, m/z=367 [M+H]$^+$.

Example 153A 6-(Hydroxymethyl)-1,3-bis(2-methoxyethyl)-5-methylthieno[2,3-d]pyrimidine-2,4(1H,3H)-dione

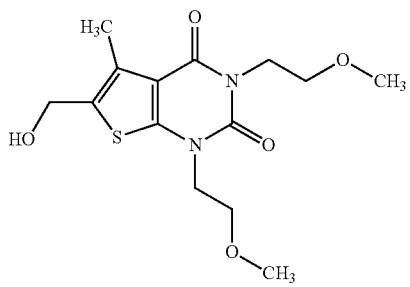 [SMILES: COCCn1c(=O)c2c(C)c(CO)sc2n(CCOC)c1=O]

At 0° C., a total of 0.936 ml (1.12 mmol) of a 1.2 M solution of diisobutylaluminium hydride in toluene was added to a solution of 100 mg (0.25 mmol) of the compound from Example 33A in 10 ml of dry THF. The reaction mixture was stirred at RT. On completion of reaction, 30 ml of 10% hydrochloric acid and 50 ml of saturated sodium chloride solution were added cautiously. This mixture was extracted with ethyl acetate. The combined organic phases were dried over sodium sulphate, filtered and concentrated. The residue obtained was purified by chromatography. 48 mg (55% of theory) of the title compound were obtained.

LC/MS (Method 3): R$_t$=0.8 min, m/z=329 [M+H]$^+$.

Example 154A 6-(Hydroxymethyl)-1-(2-methoxyethyl)-3-(1-methoxypropan-2-yl)-5-methylthieno[2,3-d]pyrimidine-2,4(1H,3H)-dione (racemate)

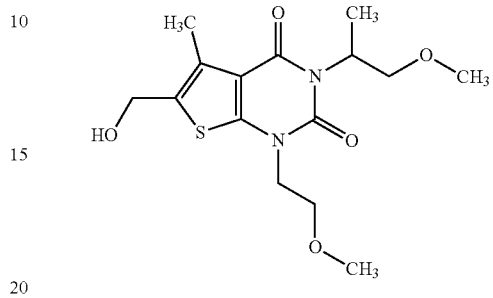

Analogously to the method described in Ex. 138A (Method C), 385 mg (0.89 mmol) of the compound from Ex. 34A were used to prepare 218 mg (68% of theory) of the title compound. The conversion was effected here initially at −40° C. for 45 min, then stirring was continued at RT until the reaction was complete.

$^1$H-NMR (400 MHz, DMSO-d$_6$, δ/ppm): 5.57 (t, 1H), 5.17 (d, 1H), 4.56 (d, 2H), 4.05-3.97 (m, 2H), 3.91 (dd, 1H), 3.62 (t, 2H), 3.54 (dd, 1H), 3.24 (s, 3H), 3.20 (s, 3H), 2.30 (s, 3H), 1.33 (d, 3H).

LC/MS (Method 3): R$_t$=0.91 min, m/z=343 [M+H]$^+$.

Example 155A 6-(Hydroxymethyl)-1-(2-methoxyethyl)-3-(2-methoxypropyl)-5-methylthieno[2,3-d]pyrimidine-2,4(1H,3H)-dione (racemate)

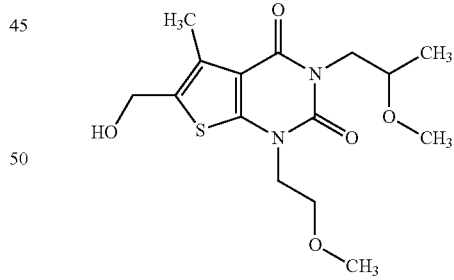

Analogously to the method described in Ex. 138A (Method C), 370 mg (0.83 mmol) of the compound from Ex. 35A were used to prepare 205 mg (67% of theory) of the title compound. The conversion was effected here initially at −40° C. for 30 min, then stirring was continued at RT until the reaction was complete.

$^1$H-NMR (400 MHz, DMSO-d$_6$, δ/ppm): 5.58 (t, 1H), 4.57 (d, 2H), 4.11-3.98 (m, 3H), 3.75 (dd, 1H), 3.68-3.60 (m, 3H), 3.23 (s, 3H), 3.21 (s, 3H), 2.32 (s, 3H), 1.05 (d, 3H).

LC/MS (Method 3): R$_t$=0.86 min, m/z=343 [M+H]$^+$.

Example 156A 3-(3-Fluoropropyl)-6-(hydroxymethyl)-1-(2-methoxyethyl)-5-methylthieno[2,3-d]pyrimidine-2,4(1H,3H)-dione

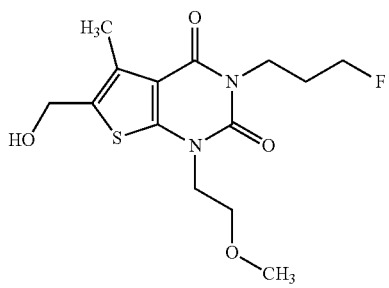 [SMILES: COCCn1c(=O)n(CCCF)c(=O)c2c(C)c(CO)sc21]

Analogously to the method described in Ex. 138A (Method C), 305 mg (0.7 mmol) of the compound from Ex. 32A were used to prepare 167 mg (71% of theory) of the title compound. The conversion was effected here initially at −40° C. for 30 min, then stirring was continued at RT until the reaction was complete.

$^1$H-NMR (400 MHz, DMSO-d$_6$, δ/ppm): 5.58 (t, 1H), 4.60-4.51 (m, 3H), 4.42 (t, 1H), 4.04 (t, 2H), 3.98 (t, 2H), 3.63 (t, 2H), 3.24 (s, 3H), 2.32 (s, 3H), 2.01-1.85 (m, 2H).

LC/MS (Method 3): R$_t$=0.87 min, m/z=331 [M+H]$^+$.

Example 157A 1-(2-Phenylethyl)pyrimidine-2,4,6(1H,3H,5H)-trione

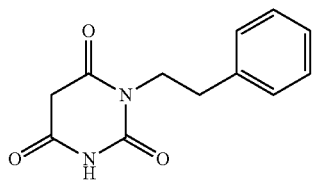 [SMILES: O=C1CC(=O)N(CCc2ccccc2)C(=O)N1]

20.0 g (122 mmol) of 2-phenethylurea [commercially available; lit. e.g.: L. De Luca, A. Porcheddu, G. Giacomelli, I. Murgia, *Synlett* 2010 (16), 2439-2442] and 18.5 ml (122 mmol) of diethyl malonate were dissolved in 70 ml of ethanol, and 45.5 ml (122 mmol) of a 20% strength solution of sodium ethoxide in ethanol were added. The mixture was heated under reflux for 16 h. Most of the solvent was then removed on a rotary evaporator, and about 100 ml of water were added to the remaining residue. Insolubles were filtered off and the filtrate was acidified to pH 3-4 with concentrated hydrochloric acid. This resulted in the precipitation of the product, which was filtered off with suction and washed first with water and then with hexane/diethyl ether 1:1. After drying under high vacuum, 20.9 g (72% of theory) of the title compound were obtained.

$^1$H-NMR (400 MHz, DMSO-d$_6$, δ/ppm): 11.36 (s, 1H), 7.33-7.29 (m, 2H), 7.25-7.20 (m, 3H), 3.86 (dd, 2H), 3.62 (s, 2H), 2.77 (dd, 2H).

LC/MS (Method 1, ESIpos): R$_t$=0.76 min, m/z=233 [M+H]$^+$.

Example 158A

1-Ethylpyrimidine-2,4,6(1H,3H,5H)-trione

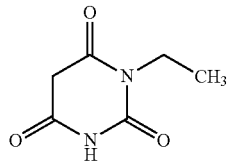

25.0 g (284 mmol) of ethylurea and 43 ml (284 mmol) of diethyl malonate were dissolved in 150 ml of ethanol, and 106 ml (284 mmol) of a 20% solution of sodium ethoxide in ethanol were added. The mixture was heated under reflux for 1 h, resulting in the formation of a precipitate. After cooling to RT, the precipitate was separated off and the filtrate was freed from most of the solvent on a rotary evaporator. About 500 ml of water were added to the remaining residue, and the mixture was acidified with 5 M hydrochloric acid to pH 3-4. The aqueous solution was then extracted three times with about 100 ml of ethyl acetate each time. Drying over anhydrous magnesium sulphate, filtration and evaporation of the combined organic extracts gave a first fraction of the title compound (14.1 g, 31% of theory). The aqueous phase left earlier was concentrated to a volume of about 250 ml and adjusted to pH 1 with 5 M hydrochloric acid, and solid sodium chloride was added to saturation. The mixture was once more extracted with ethyl acetate and the organic phase was dried over magnesium sulphate, filtered and concentrated. At RT, the product obtained in this manner was stirred with 200 ml of diethyl ether. The mixture was then filtered and the residue was dried under high vacuum. This gave a second fraction of the title compound (6.0 g, 13% of theory). A total of 20.1 g (45% of theory) of the title compound were thus obtained.

$^1$H-NMR (400 MHz, DMSO-d$_6$, δ/ppm): 11.30 (s, 1H), 3.70 (q, 2H), 3.59 (s, 2H), 1.06 (t, 3H).

GC/MS (method 7, ESIpos): R$_t$=4.28 min, m/z=156 [M]$^+$.

Example 159A

6-Chloro-3-(2-phenylethyl)pyrimidine-2,4(1H,3H)-dione

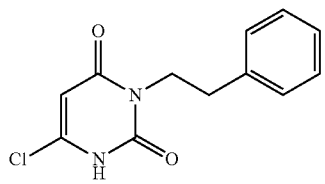 [SMILES: O=c1cc(Cl)[nH]c(=O)n1CCc1ccccc1]

31.0 g (133 mmol) of the compound from Ex. 157A were suspended in 7 ml of water and then 111 ml (1.19 mol) of phosphorus oxychloride were added dropwise over a period of about 45 min. After the addition had ended, the reaction mixture was first heated to 90° C. for 1 h. This formed a clear solution. Thereafter, the reaction mixture was heated to 150° C. for a further 30 min. After cooling, the majority of the unconsumed phosphorus oxychloride was removed on a rotary evaporator. The remaining brown oil was poured cautiously onto ice. After the ice had melted, the precipitated crude product was filtered off with suction, washed to neutrality with water, dried under high vacuum and then purified by stirring in dichloromethane. Another filtration with suction and drying gave 20.4 g (61% of theory) of the title compound.

$^1$H-NMR (400 MHz, DMSO-d$_6$, δ/ppm): 12.37 (s, 1H), 7.32-7.28 (m, 2H), 7.23-7.19 (m, 3H), 5.90 (s, ca. 1H), 3.93 (dd, 2H), 2.79 (dd, 2H).

LC/MS (Method 1, ESIpos): R$_t$=0.77 min, m/z=251/253 [M+H]$^+$.

Example 160A

6-Chloro-3-ethylpyrimidine-2,4(1H,3H)-dione

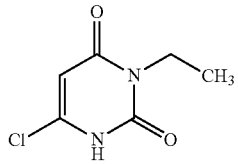

At a temperature of 0° C., 28.8 ml (309 mmol) of phosphorus oxychloride were added cautiously to 6.6 ml of 50% aqueous ethanol. Then, likewise at 0° C., 5.4 g (34.6 mmol) of the compound from Ex. 158A were added in portions. After the addition had ended, the reaction mixture was heated first for 30 min at 50° C. and then for 2 h at 100° C. After the mixture had cooled to RT, it was poured into about 100 ml of ice-water. The precipitated solid was filtered off with suction and washed with water. After drying under high vacuum, 2.78 g (46% of theory) of the title compound were obtained.

$^1$H-NMR (400 MHz, DMSO-d$_6$, δ/ppm): 12.34 (s, 1H), 5.89 (s, ca. 1H), 3.76 (q, 2H), 1.07 (t, 3H).

LC/MS (Method 1, ESIpos): R$_t$=0.42 min, m/z=175/177 [M+H]$^+$.

Example 161A

1-[2,6-Dioxo-1-(2-phenylethyl)-4-(pyridinium-1-yl)-1,6-dihydropyrimidin-5 (2H)-ylidene] 2,2,2-trifluoroethoxide

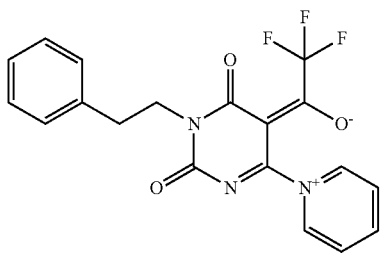 [SMILES: O=C1N=C([n+]2ccccc2)/C(=C(\[O-])C(F)(F)F)C(=O)N1CCc1ccccc1]

At RT, 16.1 ml (199 mmol) of pyridine were added to a suspension of 5.0 g (19.9 mmol) of the compound from Ex. 159A in 50 ml of acetonitrile. 11.3 ml (79.8 mmol) of trifluoroacetic anhydride were then slowly added dropwise. After the addition had ended, the mixture was stirred at RT for about another 45 min. Subsequently, about 500 ml of water were added and the mixture was extracted three times with about 500 ml of ethyl acetate. The organic extract was washed with saturated aqueous sodium chloride solution. Then the solid, which was finely suspended in the extract, was filtered off with suction and washed with a little ethyl acetate. The solid was dried under high vacuum and gave a first fraction of the title compound (4.22 g, 54% of theory). The filtrate obtained was dried over anhydrous magnesium sulphate, filtered and concentrated down to a residual volume of about 30 ml. The precipitated solid was filtered off with suction again and dried under high vacuum and gave a second fraction of the title compound (2.63 g, 33% of theory). A total of 6.85 g (88% of theory) of the title compound were thus obtained.

$^1$H-NMR (400 MHz, DMSO-d$_6$, δ/ppm): 9.29 (d, 2H), 8.81 (t, 1H), 8.27 (t, 2H), 7.36-7.28 (m, 4H), 7.26-7.22 (m, 1H), 4.02 (dd, 2H), 2.84 (dd, 2H).

LC/MS (Method 1, ESIpos): R$_t$=0.85 min, m/z=390 [M+H]$^+$.

Example 162A

1-[1-Ethyl-2,6-dioxo-4-(pyridinium-1-yl)-1,6-dihydropyrimidin-5(2H)-ylidene] 2,2,2-trifluoroethoxide

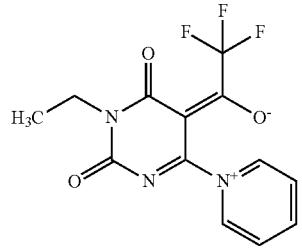 [SMILES: CCN1C(=O)N=C([n+]2ccccc2)/C(=C(\[O-])C(F)(F)F)C1=O]

At RT, 4.6 ml (57.3 mmol) of pyridine were added to a suspension of 1.0 g (5.73 mmol) of the compound from Ex. 160A in 15 ml of acetonitrile. 3.2 ml (22.9 mmol) of trifluoroacetic anhydride were then slowly added dropwise. After the addition had ended, stirring of the mixture was continued at RT for 1 h. About 100 ml of water were then added, and the mixture was extracted twice with about 100 ml of ethyl acetate each time. The organic extract was washed with saturated aqueous sodium chloride solution and then evaporated to dryness. The solid that remained was stirred in a mixture of 25 ml of diisopropyl ether and 5 ml of ethyl acetate at 40° C. for 30 min. After cooling to RT, the solid present was filtered off with suction and washed with a little pentane. After drying under high vacuum, 1.54 g (86% of theory) of the title compound were obtained.

$^1$H-NMR (400 MHz, DMSO-d$_6$, δ/ppm): 9.28 (d, 2H), 8.80 (t, 1H), 8.26 (t, 2H), 3.87 (q, 2H), 1.13 (t, 3H).

LC/MS (Method 1, ESIpos): R$_t$=0.56 min, m/z=314 [M+H]$^+$.

Example 163A

1-[1-Ethyl-2,6-dioxo-4-(pyridinium-1-yl)-1,6-dihydropyrimidin-5(2H)-ylidene] 2,2-difluoroethoxide

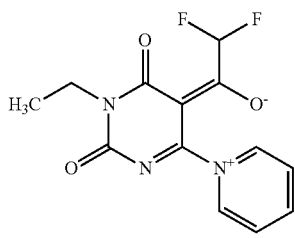 [SMILES: CCN1C(=O)N=C([n+]2ccccc2)/C(=C(\[O-])C(F)F)C1=O]

At RT, 35 ml (430 mmol) of pyridine were added to a suspension of 7.5 g (43.0 mmol) of the compound from Ex. 160A in 110 ml of acetonitrile. 21.4 ml (172 mmol) of difluoroacetic anhydride were then slowly added dropwise. After the addition had ended, the mixture was stirred at RT for another 1 h. About 300 ml of water were then added, and the mixture was extracted four times with about 100 ml of ethyl acetate each time. The organic extract was washed with saturated aqueous sodium chloride solution, dried over anhydrous magnesium sulphate and then concentrated to dryness. At RT, the solid that remained was stirred in a mixture of 50 ml of diisopropyl ether and 50 ml of diethyl ether. After filtration with suction and drying under high vacuum, 6.38 g (50% of theory) of the title compound were obtained.

$^1$H-NMR (400 MHz, DMSO-$d_6$, δ/ppm): 9.20 (d, 2H), 8.80 (t, 1H), 8.25 (t, 2H), 6.97 (t, 1H), 3.89 (q, 2H), 1.14 (t, 3H).

LC/MS (Method 1, ESIpos): $R_t$=0.46 min, m/z=296 [M+H]$^+$.

Example 164A

Ethyl 2,4-dioxo-3-(2-phenylethyl)-5-(trifluoromethyl)-1,2,3,4-tetrahydrothieno[2,3-d]pyrimidine-6-carboxylate

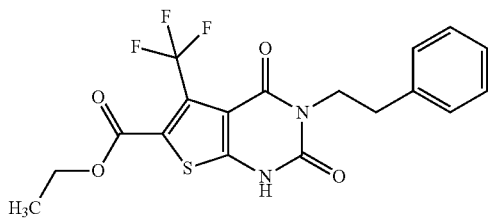

In a microwave oven (Biotage Initiator with dynamic control of irradiation power), divided between two reaction vessels, a mixture of 4.21 g (10.8 mmol) of the compound from Ex. 161A, 2.52 g (23.8 mmol) of sodium carbonate and 2.4 ml (21.7 mmol) of ethyl mercaptoacetate in 26 ml of ethanol was heated to 120° C. for 1 h. Subsequently, the two batches are combined and concentrated to dryness on a rotary evaporator. The remaining residue was taken up in about 700 ml of ethyl acetate and the mixture was washed successively with about 300 ml each of semisaturated aqueous sodium chloride solution, water and saturated sodium chloride solution. After drying over anhydrous magnesium sulphate, the mixture was filtered and the filtrate was evaporated. The crude product was purified by MPLC (Puriflash cartridge, 100 g of silica gel, cyclohexane/ethyl acetate 5:1→1:1). After combination and evaporation of the product fractions and drying of the residue under high vacuum, 3.2 g (71% of theory) of the title compound were obtained.

$^1$H-NMR (400 MHz, DMSO-$d_6$, δ/ppm): 12.61 (s, 1H), 7.33-7.29 (m, 2H), 7.26-7.20 (m, 3H), 4.33 (q, 2H), 4.02 (m, 2H), 2.83 (m, 2H), 1.29 (t, 3H).

LC/MS (Method 1, ESIpos): $R_t$=1.12 min, m/z=413 [M+H]$^+$.

Example 165A

Ethyl 3-ethyl-2,4-dioxo-5-(trifluoromethyl)-1,2,3,4-tetrahydrothieno[2,3-d]pyrimidine-6-carboxylate

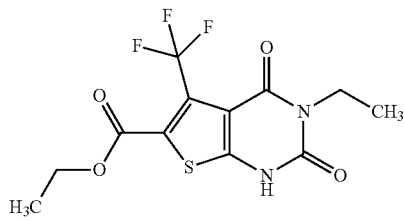 [SMILES: CCOC(=O)c1sc2[nH]c(=O)n(CC)c(=O)c2c1C(F)(F)F]

In a microwave oven (Biotage Initiator with dynamic control of irradiation power), a mixture of 4.75 g (15.2 mmol) of the compound from Ex. 162A, 3.54 g (33.4 mmol) of sodium carbonate and 3.3 ml (30.3 mmol) of ethyl mercaptoacetate in 39 ml of ethanol was heated to 120° C. for 1 h. Then the mixture was evaporated to dryness on a rotary evaporator. About 200 ml of water were added to the remaining residue, and the mixture was acidified slightly with acetic acid (about pH 4). The mixture was extracted three times with about 100 ml of dichloromethane each time. The combined organic phases were washed with saturated sodium chloride solution and dried over anhydrous magnesium sulphate and then filtered and evaporated. The crude product was purified by MPLC (Puriflash cartridge, 25 g of silica gel, cyclohexane/ethyl acetate 3:1→1:1). After combination and evaporation of the product fractions and drying of the residue under high vacuum, 2.78 g (54% of theory) of the title compound were obtained.

$^1$H-NMR (400 MHz, CDCl$_3$, δ/ppm): 11.38 (s, 1H), 4.40 (q, 2H), 4.10 (q, 2H), 1.39 (t, 3H), 1.29 (t, 3H).

LC/MS (Method 4, ESIpos): $R_t$=2.06 min, m/z=337 [M+H]$^+$.

Example 166A

Ethyl 5-(difluoromethyl)-3-ethyl-2,4-dioxo-1,2,3,4-tetrahydrothieno[2,3-d]pyrimidine-6-carboxylate

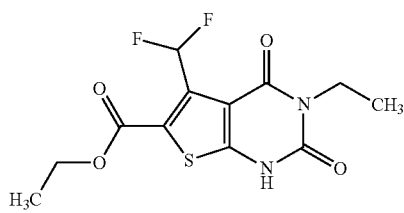 [SMILES: CCOC(=O)c1sc2[nH]c(=O)n(CC)c(=O)c2c1C(F)F]

1.5 ml (13.8 mmol) of ethyl mercaptoacetate were added to a suspension of 2.04 g (6.92 mmol) of the compound from Ex. 163A in 15 ml of ethanol, and the mixture was stirred at RT for 5 min. Then 1.61 g (15.2 mmol) of sodium carbonate were added, and the mixture was heated in a microwave oven (Biotage Initiator with dynamic control of irradiation power) to 120° C. for 1 h. Three such batches were combined and concentrated to dryness on a rotary evaporator. The remaining residue was taken up in about 300 ml of water, acidified slightly by addition of acetic acid and extracted three times with about 100 ml of dichloromethane each. The organic extract was washed with saturated aqueous sodium chloride solution, dried over anhydrous magnesium sulphate, filtered and concentrated. The solid that remained was chromatographed on a silica gel cartridge (Puriflash, cyclohexane/ethyl acetate 3:1→1:1). After evaporation of the product fractions and drying of the residue under high vacuum, 890 mg (12% of theory) of the title compound were obtained.

$^1$H-NMR (400 MHz, DMSO-d$_6$, δ/ppm): 12.59 (s, 1H), 7.71 (t, 1H), 4.32 (q, 2H), 3.87 (q, 2H), 1.30 (t, 3H), 1.13 (t, 3H).

LC/MS (Method 1, ESIpos): R$_t$=0.87 min, m/z=319 [M+H]$^+$.

Example 167A

Ethyl 1-(2-methoxyethyl)-2,4-dioxo-3-(2-phenyl-ethyl)-5-(trifluoromethyl)-1,2,3,4-tetrahydrothieno[2,3-d]pyrimidine-6-carboxylate

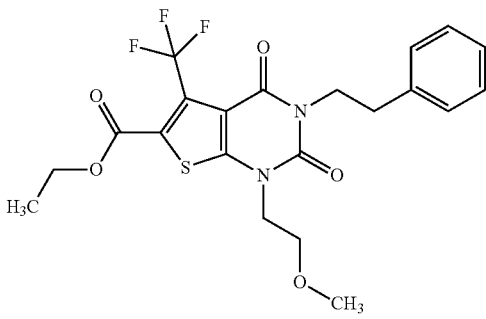 [SMILES: CCOC(=O)c1sc2c(c1C(F)(F)F)c(=O)n(CCc1ccccc1)c(=O)n2CCOC]

1.78 g (16.8 mmol) of caesium carbonate were added to a solution of 3.15 g (7.64 mmol) of the compound from Ex. 164A in 60 ml of DMF, and the mixture was stirred at RT for 15 min. Then 2.12 g (15.3 mmol) of 2-bromoethyl methyl ether were added, and the mixture was heated to 80° C. for 5.5 h. After cooling, the mixture was concentrated to dryness on a rotary evaporator. The residue obtained was slurried in 400 ml of ethyl acetate and washed successively with water and saturated aqueous sodium chloride solution. After drying over anhydrous magnesium sulphate, the mixture was filtered and concentrated. The crude product was purified by MPLC on a Biotage cartridge (100 g of silica gel, cyclohexane/ethyl acetate 5:1→1:1). The product fractions were combined, concentrated and dried under high vacuum. This gave a first portion of 2.28 g (63% of theory) of the title compound. In addition, a mixed fraction composed of N- and O-alkylated product was also obtained, which was separated by means of preparative HPLC (Method 8) and gave a second portion of 0.55 g (14% of theory) of the title compound. A total of 2.83 g (78% of theory) of the title compound were thus obtained.

$^1$H-NMR (400 MHz, DMSO-d$_6$, δ/ppm): 7.32-7.28 (m, 2H), 7.25-7.20 (m, 3H), 4.35 (q, 2H), 4.12-4.06 (m, 4H), 3.63 (t, 2H), 3.25 (s, 3H), 2.85 (m, 2H), 1.30 (t, 3H).

LC/MS (Method 1, ESIpos): R$_t$=1.24 min, m/z=471 [M+H]$^+$.

Example 168A

Ethyl 3-ethyl-2,4-dioxo-5-(trifluoromethyl)-1-(3,3,3-trifluoro9propyl)-1,2,3,4-tetrahydrothieno[2,3-d]pyrimidine-6-carboxylate

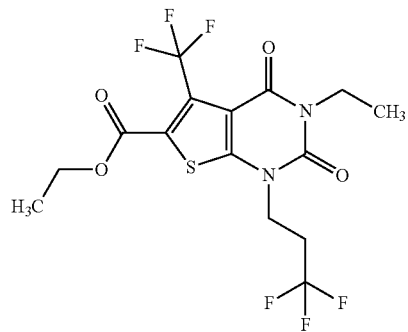 [SMILES: CCOC(=O)c1sc2c(c1C(F)(F)F)c(=O)n(CC)c(=O)n2CCC(F)(F)F]

1.39 g (13.1 mmol) of caesium carbonate were added to a solution of 2.0 g (5.95 mmol) of the compound from Ex. 165A in 40 ml of DMF, and the mixture was stirred at RT for 15 min. Then 2.66 g (11.9 mmol) of 3,3,3-trifluoro-1-iodopropane were added, and the mixture was heated at 60° C. After 1 h, a further 2.66 g (11.9 mmol) of 3,3,3-trifluoro-1-iodopropane were added. Stirring at 60° C. was continued for 16 h. After cooling to RT, about 160 ml of water were added and the mixture was extracted three times with about 80 ml of diethyl ether each time. The combined organic extracts were washed with saturated sodium chloride solution. After drying over anhydrous magnesium sulphate, the mixture was filtered and the filtrate was evaporated. The crude product was purified by MPLC on a Puriflash cartridge (100 g of silica gel, cyclohexane/ethyl acetate 7:1→1:1). The product fractions were combined and concentrated, and the residue was dried under high vacuum. 1.86 g (72% of theory) of the title compound were obtained.

$^1$H-NMR (400 MHz, CDCl$_3$, δ/ppm): 4.41 (q, 2H), 4.20 (t, 2H), 4.08 (q, 2H), 2.73-2.61 (m, 2H), 1.40 (t, 3H), 1.26 (t, 3H).

LC/MS (Method 1, ESIpos): R$_t$=1.15 min, m/z=433 [M+H]$^+$.

Example 169A

Ethyl 3-ethyl-1-(3-fluoropropyl)-2,4-dioxo-5-(trifluoromethyl)-1,2,3,4-tetrahydrothieno[2,3-d]pyrimidine-6-carboxylate

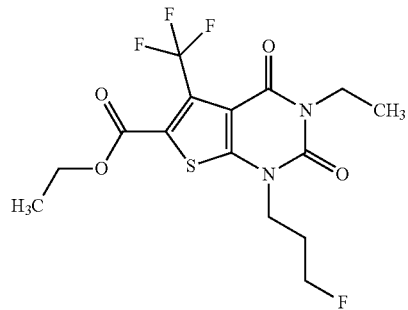 [SMILES: CCOC(=O)c1sc2c(c1C(F)(F)F)c(=O)n(CC)c(=O)n2CCCF]

Analogously to the method described in Ex. 86A, 500 mg (1.48 mmol) of the compound from Ex. 165A and 838 mg (4.46 mmol) of 1-fluoro-3-iodopropane were used to prepare 519 mg (84% of theory) of the title compound. The conversion was conducted here at RT and the reaction time was 24 h.

$^1$H-NMR (400 MHz, DMSO-d$_6$, δ/ppm): 4.62 (t, 1H), 4.50 (t, 1H), 4.35 (q, 2H), 4.06 (t, 2H), 3.91 (q, 2H), 2.17-2.02 (m, 2H), 1.30 (t, 3H), 1.13 (t, 3H).

LC/MS (Method 3): R$_t$=1.28 min, m/z=397 [M+H]$^+$.

Example 170A

Ethyl 5-(difluoromethyl)-3-ethyl-2,4-dioxo-1-(3,3,4,4,4-pentafluorobutyl)-1,2,3,4-tetrahydrothieno[2,3-d]pyrimidine-6-carboxylate

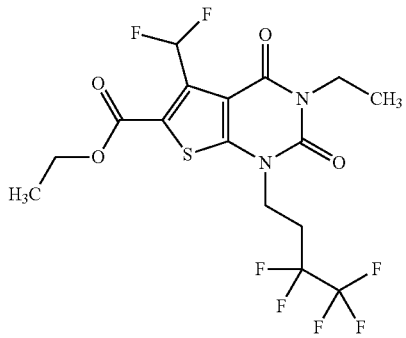 [SMILES: CCOC(=O)c1sc2c(c1C(F)F)c(=O)n(CC)c(=O)n2CCC(F)(F)C(F)(F)F]

Analogously to the method described in Ex. 86A, 294 mg (0.92 mmol) of the compound from Ex. 166A and 783 mg (2.77 mmol) of 1,1,1,2,2-pentafluoro-4-iodobutane were used to prepare 223 mg (48% of theory) of the title compound. The reaction time here was 17 h.

$^1$H-NMR (400 MHz, DMSO-d$_6$, δ/ppm): 7.91-7.58 (m, 1H), 4.39-4.30 (m, 2H), 4.28-4.20 (m, 2H), 3.92 (q, 2H), 2.83-2.65 (m, 2H), 1.32 (t, 3H), 1.14 (t, 3H).

LC/MS (Method 3): R$_t$=1.44 min, m/z=465 [M+H]$^+$.

Example 171A

Ethyl 3-ethyl-1-(2-methoxyethyl)-2,4-dioxo-5-(trifluoromethyl)-1,2,3,4-tetrahydrothieno[2,3-d]pyrimidine-6-carboxylate

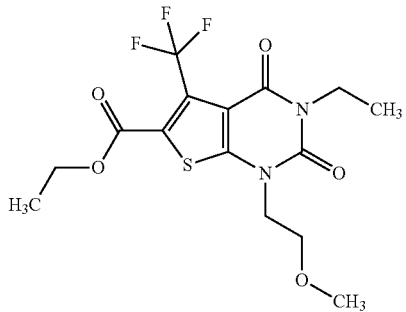 [SMILES: CCOC(=O)c1sc2c(c1C(F)(F)F)c(=O)n(CC)c(=O)n2CCOC]

Analogously to the method described in Ex. 168A, 1.77 g (5.26 mmol) of the compound from Ex. 165A and 1 ml (10.5 mmol) of 2-bromoethyl methyl ether were used to obtain 1.34 g (64% of theory) of the title compound. The reaction was conducted at 80° C. for 2 h, and the eluent used in the MPLC purification was cyclohexane/ethyl acetate 5:1. For final purification, the product was stirred once again in pentane/dichloromethane 20:1.

$^1$H-NMR (400 MHz, DMSO-d$_6$, δ/ppm): 4.34 (q, 2H), 4.11 (t, 2H), 3.91 (q, 2H), 3.66 (t, 2H), 3.25 (s, 3H), 1.30 (t, 3H), 1.14 (t, 3H).

LC/MS (Method 1, ESIpos): R$_t$=1.01 min, m/z=395 [M+H]$^+$.

Example 172A

Ethyl 5-(difluoromethyl)-3-ethyl-2,4-dioxo-1-(3,3,3-trifluoropropyl)-1,2,3,4-tetrahydrothieno[2,3-d]pyrimidine-6-carboxylate

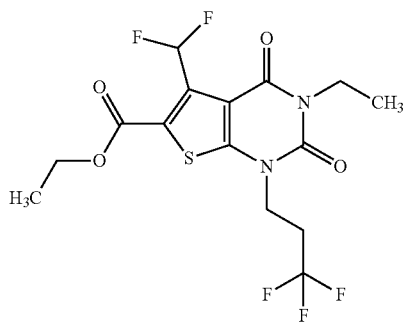 [SMILES: CCOC(=O)c1sc2c(c1C(F)F)c(=O)n(CC)c(=O)n2CCC(F)(F)F]

1.35 g (4.15 mmol) of caesium carbonate were added to a solution of 880 mg (2.76 mmol) of the compound from Ex. 166A in 12 ml of DMF, and the mixture was stirred at RT for 20 min. Then 929 mg (4.15 mmol) of 3,3,3-trifluoro-1-iodopropane were added, and the mixture was heated to 80° C. for 2 h. After cooling to RT, the mixture was diluted with about 100 ml of ethyl acetate and, in succession, washed twice with in each case about 100 ml of water and once with about 100 ml of saturated sodium chloride solution. After drying over anhydrous magnesium sulphate, the mixture was filtered and concentrated. The crude product was purified by preparative HPLC (Method 9). The product fractions were combined, concentrated and dried under high vacuum. 750 mg (63% of theory) of the title compound were obtained.

$^1$H-NMR (400 MHz, DMSO-d$_6$, δ/ppm): 7.74 (t, 1H), 4.36 (q, 2H), 4.20 (t, 2H), 3.92 (q, 2H), 2.88-2.76 (m, 2H), 1.32 (t, 3H), 1.14 (t, 3H).

LC/MS (Method 1, ESIpos): R$_t$=1.13 min, m/z=415 [M+H]$^+$.

Example 173A

Ethyl 5-(difluoromethyl)-3-ethyl-1-(2-methoxyethyl)-2,4-dioxo-1,2,3,4-tetrahydrothieno[2,3-d]pyrimidine-6-carboxylate

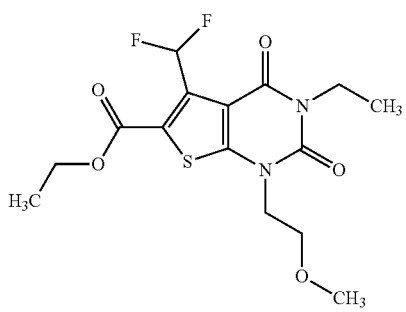 [SMILES: CCOC(=O)c1sc2c(c1C(F)F)c(=O)n(CC)c(=O)n2CCOC]

Analogously to the method described in Ex. 86A, 2 g (6.31 mmol) of the compound from Ex. 166A and 2.71 g (18.9 mmol) of 2-bromoethyl methyl ether were used to prepare 1.72 g (58% of theory) of the title compound. The reaction time here was 12 h.

$^1$H-NMR (400 MHz, DMSO-$d_6$, δ/ppm): 7.88-7.58 (m, 1H), 4.34 (q, 2H), 4.12 (t, 2H), 3.92 (q, 2H), 3.66 (t, 2H), 3.25 (s, 3H), 1.31 (t, 3H), 1.14 (t, 3H).

LC/MS (Method 3): $R_t$=1.22 min, m/z=377 [M+H]$^+$.

Example 174A 6-(Hydroxymethyl)-1-(2-methoxyethyl)-3-(2-phenylethyl)-5-(trifluoromethyl)thieno[2,3-d]pyrimidine-2,4(1H,3H)-dione

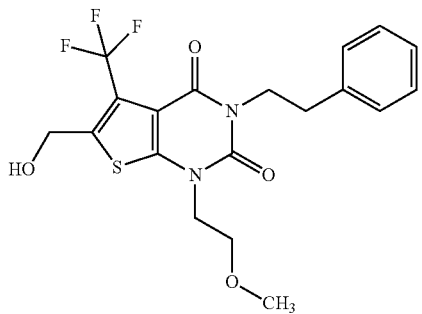 [SMILES: COCCn1c(=O)n(CCc2ccccc2)c(=O)c2c(C(F)(F)F)c(CO)sc21]

At 0° C., 5.6 ml (5.63 mmol) of a 1 M solution of lithium aluminium hydride in THF were added dropwise to a solution of 2.65 g (5.63 mmol) of the compound from Example 167A in 55 ml of dry THF. After 10 min at 0° C., excess lithium aluminium hydride was destroyed by adding 100 μl of water. Then 300 μl of 1 M sodium hydroxide solution were added. A little kieselguhr was added and, after 2 min, anhydrous magnesium sulphate. Subsequently, the undissolved material was filtered off with suction and the residue was washed thoroughly with THF. The filtrate was concentrated to dryness. The residue obtained was stirred with pentane/ethyl acetate. By filtering off the solids with suction and drying under high vacuum, a first portion of the title compound was obtained (1.35 g, 55% of theory). The filtrate was concentrated by evaporation and the residue was purified by MPLC (Biotage cartridge, 50 g of silica gel, cyclohexane/ethyl acetate 2:1). After the product fractions had been concentrated, the residue had been stirred with pentane, and the solids had been filtered off with suction and dried under high vacuum, a second portion of the title compound was obtained (0.56 g, 23% of theory). Thus, the total yield of the title compound was 1.91 g (78% of theory).

$^1$H-NMR (400 MHz, DMSO-$d_6$, δ/ppm): 7.32-7.28 (m, 2H), 7.24-7.20 (m, 3H), 6.46 (s, 1H), 4.82 (s, 2H), 4.10-4.05 (m, 4H), 3.62 (t, 2H), 3.25 (s, 3H), 2.84 (m, 2H).

LC/MS (Method 1, ESIpos): $R_t$=1.06 min, m/z=429 [M+H]$^+$.

Example 175A

3-Ethyl-6-(hydroxymethyl)-5-(trifluoromethyl)-1-(3,3,3-trifluoropropyl)thieno[2,3-d]pyrimidine-2,4(1H,3H)-dione

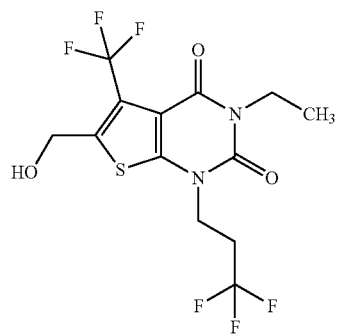 [SMILES: CCn1c(=O)c2c(C(F)(F)F)c(CO)sc2n(CCC(F)(F)F)c1=O]

Analogously to the method described in Ex. 138A (Method B), 607 mg (1.40 mmol) of the compound from Ex. 168A were used to obtain 456 mg (82% of theory) of the title compound. The MPLC purification was effected here using a Biotage cartridge with 50 g of silica gel and cyclohexane/ethyl acetate 3:1→1:1 as eluent.

$^1$H-NMR (400 MHz, CDCl$_3$, δ/ppm): 5.06 (m, 2H), 4.20 (dd, 2H), 4.08 (q, 2H), 2.72-2.60 (m, 2H), 2.53 (t, 1H), 1.26 (t, 3H).

LC/MS (Method 1, ESIpos): $R_t$=0.96 min, m/z=391 [M+H]$^+$.

Example 176A

3-Ethyl-1-(3-fluoropropyl)-6-(hydroxymethyl)-5-(trifluoromethyl)thieno[2,3-d]pyrimidine-2,4(1H,3H)-dione

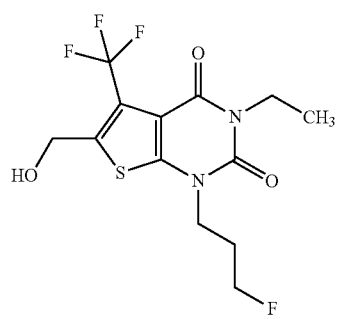 [SMILES: CCn1c(=O)c2c(C(F)(F)F)c(CO)sc2n(CCCF)c1=O]

Analogously to the method described in Ex. 138A (Method B), 540 mg (1.31 mmol) of the compound from Ex. 169A were used to prepare 360 mg (77% of theory) of the title compound.

$^1$H-NMR (400 MHz, DMSO-d$_6$, δ/ppm): 6.48 (s, 1H), 4.82 (br. s, 2H), 4.61 (t, 1H), 4.50 (t, 1H), 4.05 (t, 2H), 3.90 (q, 2H), 2.18-2.00 (m, 2H), 1.12 (t, 3H).

LC/MS (Method 3): R$_t$=1.01 min, m/z=355 [M+H]$^+$.

Example 177A 5-(Difluoromethyl)-3-ethyl-6-(hydroxymethyl)-1-(3,3,4,4,4-pentafluorobutyl)thieno[2,3-d]pyrimidine-2,4(1H,3H)-dione

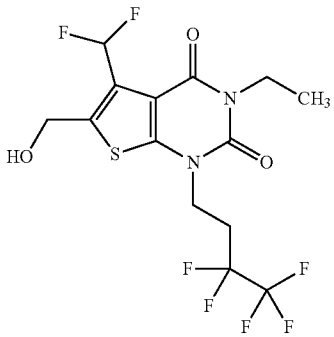 [SMILES: CCn1c(=O)c2c(C(F)F)c(CO)sc2n(CCC(F)(F)C(F)(F)F)c1=O]

Analogously to the method described in Ex. 138A (Method C), 337 mg (0.73 mmol) of the compound from Ex. 170A were used to prepare 218 mg (66% of theory) of the title compound.

$^1$H-NMR (400 MHz, DMSO-d$_6$, δ/ppm): 7.59-7.27 (m, 1H), 6.28 (s, 1H), 4.83 (br. s, 2H), 4.25-4.17 (m, 2H), 3.92 (q, 2H), 2.81-2.64 (m, 2H), 1.13 (t, 3H).

LC/MS (Method 3): R$_t$=1.23 min, m/z=423 [M+H]$^+$.

Example 178A

3-Ethyl-6-(hydroxymethyl)-1-(2-methoxyethyl)-5-(trifluoromethyl)thieno[2,3-d]pyrimidine-2,4(1H,3H)-dione

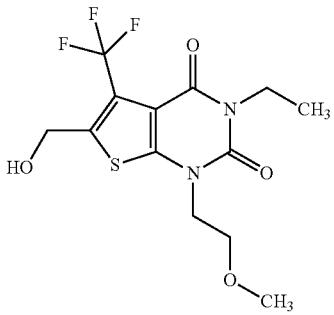 [SMILES: CCn1c(=O)c2c(C(F)(F)F)c(CO)sc2n(CCOC)c1=O]

Analogously to the method described in Ex. 138A (Method B), 600 mg (1.52 mmol) of the compound from Ex. 171A were used to obtain 420 mg (78% of theory) of the title compound. MPLC purification was effected here with the eluent gradient of cyclohexane/ethyl acetate 2:1→1:1.

$^1$H-NMR (400 MHz, DMSO-d$_6$, δ/ppm): 5.04 (dd, 2H), 4.14 (t, 2H), 4.08 (q, 2H), 3.74 (t, 2H), 3.35 (s, 3H), 2.53 (t, 1H), 1.26 (t, 3H).

LC/MS (Method 1, ESIpos): R$_t$=0.83 min, m/z=353 [M+H]$^+$.

Example 179A 5-(Difluoromethyl)-3-ethyl-6-(hydroxymethyl)-1-(3,3,3-trifluoropropyl)thieno[2,3-d]pyrimidine-2,4(1H,3H)-dione

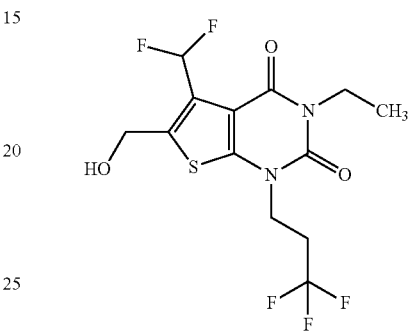

Analogously to the method described in Ex. 138A (Method C), 400 mg (0.96 mmol) of the compound from Ex. 172A were used to prepare 295 mg (82% of theory) of the title compound. The conversion was effected at −40° C.

$^1$H-NMR (400 MHz, DMSO-d$_6$, δ/ppm): 7.61-7.26 (m, 1H), 6.30 (t, 1H), 4.82 (d, 2H), 4.16 (t, 2H), 3.91 (q, 2H), 2.86-2.72 (m, 2H), 1.13 (t, 3H).

LC/MS (Method 3): R$_t$=1.09 min, m/z=373 [M+H]$^+$.

Example 180A 5-(Difluoromethyl)-3-ethyl-6-(hydroxymethyl)-1-(2-methoxyethyl)thieno[2,3-d]pyrimidine-2,4(1H,3H)-dione

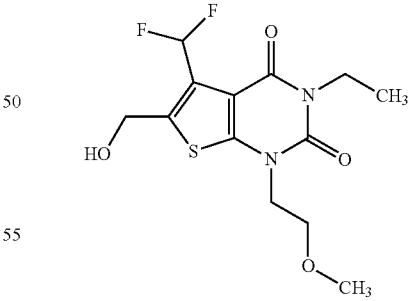

Analogously to the method described in Ex. 138A (Method C), 1.32 g (3.51 mmol) of the compound from Ex. 173A were used to prepare 1.03 g (86% of theory) of the title compound. The conversion was effected at −40° C.

$^1$H-NMR (400 MHz, DMSO-d$_6$, δ/ppm): 7.58-7.27 (m, 1H), 6.23 (t, 1H), 4.80 (br. s, 2H), 4.08 (t, 2H), 3.91 (q, 2H), 3.65 (t, 2H), 3.25 (s, 3H), 1.13 (t, 3H).

LC/MS (Method 3): R$_t$=0.95 min, m/z=335 [M+H]$^+$.

Example 181A 6-(Chloromethyl)-1-(2-methoxyethyl)-3-(2-phenylethyl)-5-(trifluoromethyl)thieno[2,3-d]pyrimidine-2,4(1H,3H)-dione

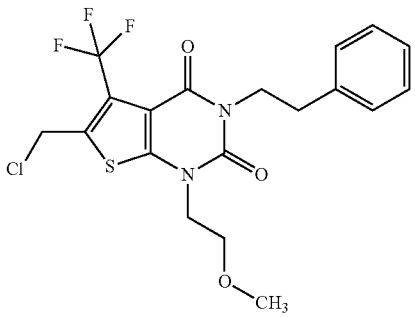 [SMILES: COCCn1c(=O)n(CCc2ccccc2)c(=O)c2c(C(F)(F)F)c(CCl)sc21]

1.30 g (3.03 mmol) of the compound from Ex. 174A were dissolved in 13 ml of chloroform, and 443 µl (6.07 mmol) of thionyl chloride were added. The reaction mixture was heated in a microwave oven (Biotage Initiator with dynamic control of irradiation power) to 80° C. for 30 min. All the volatile constituents were then removed on a rotary evaporator. The residue obtained was twice taken up with toluene and concentrated again each time. After drying under high vacuum, 1.34 g (99% of theory) of the title compound were obtained.

$^1$H-NMR (400 MHz, DMSO-d$_6$, δ/ppm): 7.33-7.28 (m, 2H), 7.25-7.20 (m, 3H), 5.15 (s, 2H), 4.09-4.04 (m, 4H), 3.63 (t, 2H), 3.25 (s, 3H), 2.84 (m, 2H).

LC/MS (Method 1, ESIpos): R$_t$=1.22 min, m/z=447/449 [M+H]$^+$.

Example 182A 6-(Chloromethyl)-3-ethyl-5-(trifluoromethyl)-1-(3,3,3-trifluoropropyl)thieno[2,3-d]pyrimidine-2,4(1H,3H)-dione

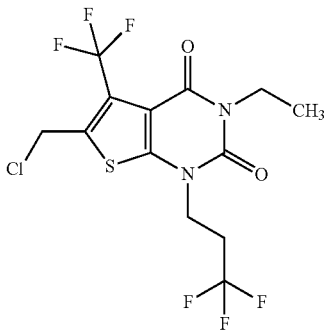 [SMILES: CCn1c(=O)c2c(C(F)(F)F)c(CCl)sc2n(CCC(F)(F)F)c1=O]

Analogously to the method described in Ex. 181A, 580 mg (1.48 mmol) of the compound from Ex. 175A and 217 µl (2.97 mmol) of thionyl chloride were used to obtain 505 mg (83% of theory) of the title compound. In addition, purification of the product was effected here by means of MPLC (Biotage cartridge, 50 g of silica gel, cyclohexane/ethyl acetate gradient 10:1→5:1).

$^1$H-NMR (400 MHz, CDCl$_3$, δ/ppm): 4.90 (s, 2H), 4.19 (dd, 2H), 4.08 (q, 2H), 2.73-2.60 (m, 2H), 1.26 (t, 3H).

LC/MS (Method 1, ESIpos): R$_t$=1.13 min, m/z=409/411 [M+H]$^+$.

Example 183A 6-(Chloromethyl)-3-ethyl-1-(3-fluoropropyl)-5-(trifluoromethyl)thieno[2,3-d]pyrimidine-2,4(1H,3H)-dione

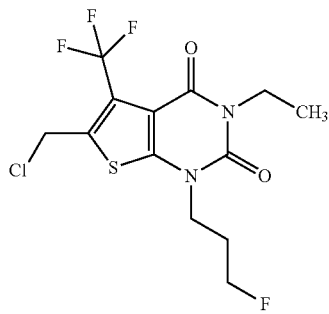 [SMILES: CCn1c(=O)c2c(C(F)(F)F)c(CCl)sc2n(CCCF)c1=O]

355 mg (1 mmol) of the compound from Example 176A were dissolved in 3.55 ml of chloroform, and 241 mg (2 mmol) of thionyl chloride were added. The mixture was stirred in a microwave apparatus at a temperature of 80° C. for 30 min. The solution, having been cooled to RT, was then concentrated on a rotary evaporator. The remaining residue was chromatographed using a silica gel cartridge (Biotage, 50 g of silica gel, eluent: cyclohexane/ethyl acetate). 343 mg (89% of theory) of the title compound were obtained.

$^1$H-NMR (400 MHz, DMSO-d$_6$, δ/ppm): 5.16 (d, 1H), 4.62 (t, 1H), 4.50 (t, 1H), 4.03 (t, 2H), 3.90 (q, 2H), 2.17-2.02 (m, 2H), 1.12 (t, 3H).

LC/MS (Method 3): R$_t$=1.24 min, m/z=373 [M+H]$^+$.

Example 184A 6-(Chloromethyl)-3-ethyl-1-(2-methoxyethyl)-5-(trifluoromethyl)thieno[2,3-d]pyrimidine-2,4(1H,3H)-dione

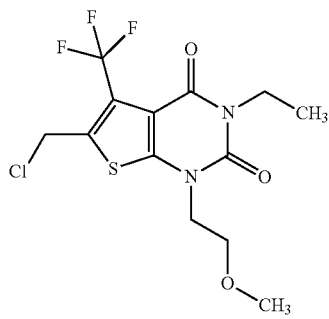 [SMILES: CCn1c(=O)c2c(C(F)(F)F)c(CCl)sc2n(CCOC)c1=O]

Analogously to the method described in Ex. 181A, 376 mg (10.7 mmol) of the compound from Ex. 178A and 234 µl (3.20 mmol) of thionyl chloride were used to obtain 395 mg (99% of theory) of the title compound.

¹H-NMR (400 MHz, DMSO-d₆, δ/ppm): 5.14 (s, 2H), 4.08 (t, 2H), 3.91 (q, 2H), 3.66 (t, 2H), 3.25 (s, 3H), 1.13 (t, 3H).

LC/MS (Method 1, ESIpos): $R_t$=0.97 min, m/z=371/373 [M+H]⁺.

Example 185A 5-(Difluoromethyl)-3-ethyl-2,4-dioxo-1-(3,3,3-trifluoropropyl)-1,2,3,4-tetrahydrothieno[2,3-d]-pyrimidine-6-carbaldehyde

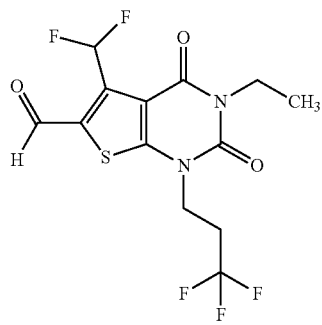 [SMILES: CCn1c(=O)c2c(C(F)F)c(C=O)sc2n(CCC(F)(F)F)c1=O]

1.48 g (3.65 mmol) of the compound from Example 179A were dissolved in 120 ml of chloroform, and 3.53 g (3.65 mmol) of manganese(IV) oxide were added. The mixture was stirred at RT for 16 h. Then it was filtered with suction through Celite and the filtrate was concentrated to dryness. The residue obtained was chromatographed using a silica gel cartridge (Biotage, 100 g of silica gel, eluent: hexane/ethyl acetate). 1.31 g (85% of theory) of the title compound were obtained.

¹H-NMR (400 MHz, DMSO-d₆, δ/ppm): 10.19 (s, 1H), 7.85-7.57 (m, 1H), 4.22 (t, 2H), 3.93 (q, 2H), 2.88-2.75 (m, 2H), 1.15 (t, 3H).

LC/MS (Method 3): $R_t$=1.25 min, m/z=371 [M+H]⁺.

Example 186A 5-(Difluoromethyl)-3-ethyl-1-(2-methoxyethyl)-2,4-dioxo-1,2,3,4-tetrahydrothieno[2,3-d]pyrimidine-6-carbaldehyde

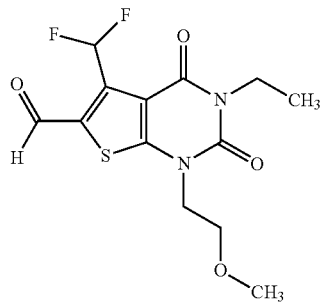 [SMILES: CCn1c(=O)c2c(C(F)F)c(C=O)sc2n(CCOC)c1=O]

1.02 g (3.03 mmol) of the compound from Example 180A were dissolved in 50 ml of chloroform, and 2.93 g (30.35 mmol) of manganese(IV) oxide were added. The mixture was stirred at RT for 22 h. Then it was filtered with suction through Celite and the filtrate was concentrated to dryness. 993 mg (97% of theory) of the title compound were obtained.

¹H-NMR (400 MHz, DMSO-d₆, δ/ppm): 10.18 (s, 1H), 7.86-7.54 (m, 1H), 4.15 (t, 2H), 3.92 (q, 2H), 3.67 (t, 2H), 3.25 (s, 3H), 1.15 (t, 3H).

LC/MS (Method 3): $R_t$=1.13 min, m/z=333 [M+H]⁺.

Example 187A

6-Bromo-3-ethyl-5-methyl-1-(3,3,3-trifluoropropyl)thieno[2,3-d]pyrimidine-2,4(1H,3H)-dione

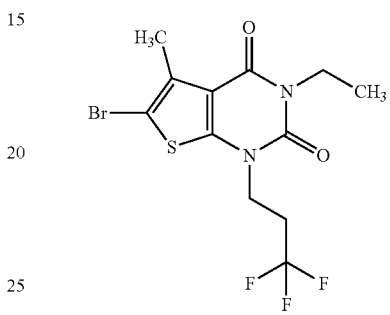

To a solution of 2.50 g (8.16 mmol) of the compound from Ex. 55A in 40 ml of chloroform were added in portions, at 0° C. and over a period of about 15 min, a total of 1.48 g (8.16 mmol) of N-bromosuccinimide (NBS). Subsequently, the cooling bath was removed and the stirring was continued at RT. After about 16 h, the mixture was diluted with dichloromethane and washed successively with water and saturated sodium chloride solution. After drying over anhydrous magnesium sulphate, the mixture was filtered and concentrated. The residue obtained was purified by means of filtration with suction through silica gel using 5:1 cyclohexane/ethyl acetate as eluent. Concentration of the product fractions and drying of the residue under high vacuum gave 2.92 g (92% of theory) of the title compound.

¹H-NMR (400 MHz, DMSO-d₆, δ/ppm): 4.09 (t, 2H), 3.91 (q, 2H), 2.88-2.69 (m, 2H), 2.37 (s, 3H), 1.12 (t, 3H).

LC/MS (Method 5, ESIpos): $R_t$=1.48 min, m/z=385/387 [M+H]⁺.

Example 188A tert-Butyl [3-ethyl-5-methyl-2,4-dioxo-1-(3,3,3-trifluoropropyl)-1,2,3,4-tetrahydrothieno[2,3-d]pyrimidin-6-yl]acetate

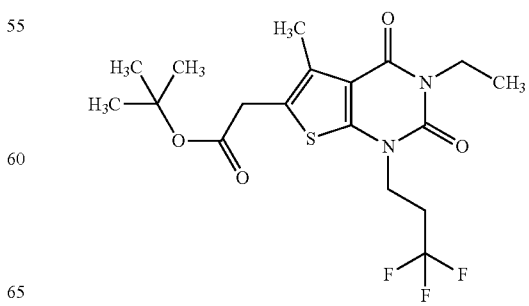

Preparation of 2-tert-butoxy-2-oxoethylzinc bromide: To an initial charge of 6.36 g (97.4 mmol) zinc dust in 97.5 ml of anhydrous diethyl ether were added dropwise, at RT, 235 µl (1.85 mmol) of chlorotrimethylsilane. After 15 min, the mixture was heated to reflux, and then 14.4 ml (97.4 mmol) of tert-butyl bromoacetate were added dropwise in such a way that the mixture remained at boiling without outside supply of heat. After the dropwise addition had ended, heating under reflux continued for a further 90 min. Cooling gave a solution which was used in the next step.

Coupling reaction to prepare the title compound: To a solution of 2.50 g (6.49 mmol) of the compound from Ex. 187A in 25 ml of anhydrous THF were added, at RT, 28 ml (about 26.0 mmol) of the previously prepared solution of 2-tert-butoxy-2-oxoethylzinc bromide. Then 346 mg (0.487 mmol) of Q-Phos and 297 mg (0.324 mmol) of tris(dibenzylideneacetone)dipalladium were added and the mixture was stirred at 60° C. for about 16 h. After cooling to RT, water was added and extraction was effected with ethyl acetate. The organic extract was washed with saturated sodium chloride solution, dried over anhydrous magnesium sulphate, filtered and concentrated. The remaining residue was purified by means of MPLC (Puriflash cartridge, 340 g of silica gel, cyclohexane/ethyl acetate 20:1→7:1). After concentration of the product fractions and drying under high vacuum, 1.95 g (71% of theory) of the title compound were obtained.

$^1$H-NMR (400 MHz, DMSO-$d_6$, δ/ppm): 4.11 (t, 2H), 3.91 (q, 2H), 3.77 (s, 2H), 2.85-2.70 (m, 2H), 2.33 (s, 3H), 1.42 (s, 9H), 1.12 (t, 3H).

LC/MS (Method 1, ESIpos): $R_t$=1.26 min, m/z=421 [M+H]$^+$.

Example 189A

[3-Ethyl-5-methyl-2,4-dioxo-1-(3,3,3-trifluoropropyl)-1,2,3,4-tetrahydrothieno[2,3-d]pyrimidin-6-yl]acetic acid

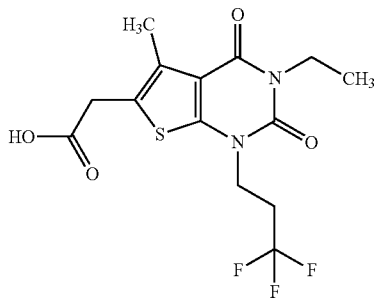 [SMILES: CCn1c(=O)c2c(C)c(CC(=O)O)sc2n(CCC(F)(F)F)c1=O]

1.74 g (4.14 mmol) of the compound from Example 188A were dissolved in 100 ml of dichloromethane, and 50 ml of trifluoroacetic acid were added. After the reaction mixture had been stirred at RT for 2 h, all volatile components were removed on a rotary evaporator. The remaining residue was stirred in a mixture of 20 ml of pentane and 5 ml of dichloromethane at RT for 90 min. Filtration with suction and drying of the solid under high vacuum gave 1.46 g (96% of theory) of the title compound.

$^1$H-NMR (400 MHz, DMSO-$d_6$, δ/ppm): 12.68 (br. s, 1H), 4.11 (t, 2H), 3.91 (q, 2H), 3.79 (s, 2H), 2.85-2.68 (m, 2H), 2.33 (s, 3H), 1.12 (t, 3H).

LC/MS (Method 1, ESIpos): $R_t$=0.86 min, m/z=365 [M+H]$^+$.

Example 190A

3-Ethyl-6-[(hydroxyimino)methyl]-5-methyl-1-(3,3,3-trifluoropropyl)thieno[2,3-d]pyrimidine-2,4(1H,3H)-dione

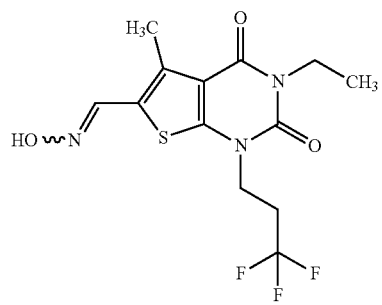 [SMILES: CCn1c(=O)c2c(C)c(C=NO)sc2n(CCC(F)(F)F)c1=O]

To a solution of 500 mg (1.42 mmol) of the compound from Ex. 74A in 4.2 ml of THF were added 261 µl (4.26 mmol) of hydroxylamine solution (50% in water). After the reaction mixture had been stirred at RT for about 16 h, 25 ml of water were added, and the product precipitated out. The product was filtered off with suction, washed with a little water and dried under high vacuum. 495 mg (99% of theory) of the title compound were obtained as an E/Z isomer mixture (about 9:1).

$^1$H-NMR (Major isomer; 400 MHz, DMSO-$d_6$, δ/ppm): 12.17 (s, 1H), 7.97 (s, 1H), 4.16 (t, 2H), 3.92 (q, 2H), 2.85-2.73 (m, 2H), 2.62 (s, 3H), 1.13 (t, 3H).

LC/MS (Major isomer; Method 6, ESIpos): $R_t$=1.62 min, m/z=350 [M+H]$^+$.

Example 191A

3-Ethyl-6-[(hydroxyimino)methyl]-1-(2-methoxyethyl)-5-methylthieno[2,3-d]pyrimidine-2,4(1H,3H)-dione

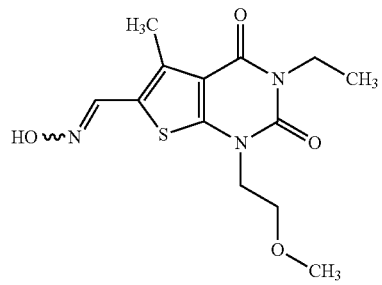 [SMILES: CCn1c(=O)c2c(C)c(C=NO)sc2n(CCOC)c1=O]

To a solution of 2.0 g (6.75 mmol) of the compound from Ex. 84A in 20 ml of THF were added 1.2 ml (20.2 mmol) of hydroxylamine solution (50% in water). After the reaction mixture had been stirred at RT for about 16 h, the precipitated solid was filtered off with suction, washed with a little water and dried under high vacuum. This gave a first fraction of 1.46 g of the title compound. The filtrate was diluted with about 20 ml of dichloromethane and washed successively with 10 ml each of saturated sodium hydrogencarbonate solution and saturated sodium chloride solution. After drying over anhydrous magnesium sulphate, the mixture was filtered, concentrated and dried under high vacuum. This gave a second fraction of 0.50 g of the title compound. In this way, a total of 1.96 g (90% of theory, 96% purity) of the title compound were obtained as an E/Z isomer mixture (about 8:1).

$^1$H-NMR (Major isomer; 400 MHz, DMSO-$d_6$, δ/ppm): 12.10 (s, 1H), 7.94 (s, 1H), 4.08 (t, 2H), 3.91 (q, 2H), 3.65 (t, 2H), 3.24 (s, 3H), 2.60 (s, 3H), 1.13 (t, 3H).

LC/MS (Major isomer; Method 5, ESIpos): $R_t$=0.99 min, m/z=312 [M+H]$^+$.

Example 192A 1-(2-Fluoroethyl)-6-[(hydroxyimino)methyl]-3-isopropyl-5-methylthieno[2,3-d]pyrimidine-2,4(1H,3H)-dione

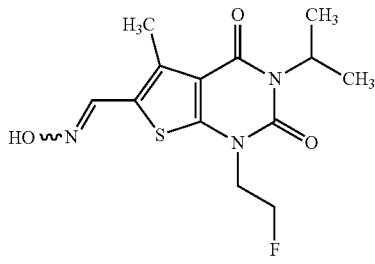 [SMILES: Cc1c(C=NO)sc2c1c(=O)n(C(C)C)c(=O)n2CCF]

Analogously to the method described in Ex. 191A, 420 mg (1.41 mmol) of the compound from Ex. 104A and 259 µl (4.22 mmol) of hydroxylamine solution (50% in water) were used to obtain 404 mg (92% of theory) of the title compound as an E/Z isomer mixture (about 9:1).

$^1$H-NMR (Major isomer; 400 MHz, DMSO-$d_6$, δ/ppm): 12.11 (s, 1H), 7.94 (s, 1H), 5.14 (sept, 1H), 4.84-4.64 (dt, 2H), 4.30-4.14 (dt, 2H), 2.60 (s, 3H), 1.42 (d, 6H).

LC/MS (Major isomer; Method 1, ESIpos): $R_t$=0.93 min, m/z=314 [M+H]$^+$.

Example 193A

6-[(Hydroxyimino)methyl]-3-isopropyl-5-methyl-1-(3,3,3-trifluoropropyl)thieno[2,3-d]pyrimidine-2,4(1H,3H)-dione

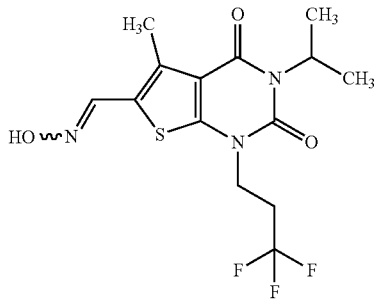 [SMILES: Cc1c(C=NO)sc2c1c(=O)n(C(C)C)c(=O)n2CCC(F)(F)F]

To a solution of 488 mg (1.40 mmol) of the compound from Ex. 103A in 4.2 ml of THF were added 257 µl (4.20 mmol) of hydroxylamine solution (50% in water). After stirring at RT for 1 h, the mixture was diluted with about 10 ml of dichloromethane and washed successively with about 10 ml each of saturated sodium hydrogencarbonate solution and saturated sodium chloride solution. After drying over anhydrous magnesium sulphate, the mixture was filtered, concentrated and dried under high vacuum. 486 mg (95% of theory) of the title compound were obtained as an E/Z isomer mixture (about 6:1).

$^1$H-NMR (Major isomer; 400 MHz, DMSO-$d_6$, δ/ppm): 12.15 (s, 1H), 7.96 (s, 1H), 5.14 (sept, 1H), 4.13 (t, 2H), 2.86-2.69 (m, 2H), 2.60 (s, 3H), 1.41 (d, 6H).

LC/MS (Major isomer; Method 1, ESIpos): $R_t$=1.01 min, m/z=364 [M+H]$^+$.

Example 194A

6-[(Hydroxyimino)methyl]-3-isopropyl-5-methyl-1-(oxetan-2-ylmethyl)thieno[2,3-d]pyrimidine-2,4(1H,3H)-dione (racemate)

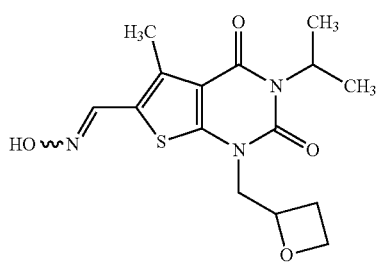 [SMILES: Cc1c(C=NO)sc2c1c(=O)n(C(C)C)c(=O)n2CC1CCO1]

Analogously to the method described in Ex. 191A, 400 mg (1.24 mmol) of the compound from Ex. 106A and 228 µl (3.72 mmol) of hydroxylamine solution (50% in water) were used to obtain 395 mg (95% of theory) of the title compound as an E/Z isomer mixture (about 5:1).

$^1$H-NMR (Major isomer; 400 MHz, DMSO-$d_6$, δ/ppm): 12.06 (s, 1H), 7.93 (s, 1H), 5.15 (sept, 1H), 5.07-4.96 (m, 1H), 4.54-4.34 (m, 2H), 4.25-4.07 (m, 2H), 2.75-2.63 (m, 1H), 2.59 (s, 3H), 2.50-2.43 (m, 1H, partially obscured by the DMSO signal), 1.41 (d, 6H).

LC/MS (Major isomer; Method 1, ESIpos): $R_t$=0.80 min, m/z=338 [M+H]$^+$.

Example 195A

6-[(Hydroxyimino)methyl]-3-isopropyl-5-methyl-1-(tetrahydrofuran-2-ylmethyl)thieno[2,3-d]pyrimidine-2,4(1H,3H)-dione (racemate)

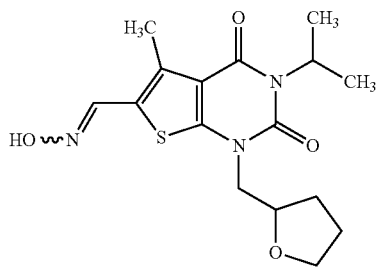 [SMILES: Cc1c(C=NO)sc2c1c(=O)n(C(C)C)c(=O)n2CC1CCCO1]

Analogously to the method described in Ex. 193A, 334 mg (0.925 mmol) of the compound from Ex. 107A and 170 µl (2.77 mmol) of hydroxylamine solution (50% in water) were used to obtain 328 mg (98% of theory, 97% purity) of the title compound as an E/Z isomer mixture (about 6:1). The reaction time here was 3.5 h.

$^1$H-NMR (Major isomer; 400 MHz, DMSO-$d_6$, δ/ppm): 12.05 (s, 1H), 7.93 (s, 1H), 5.15 (sept, 1H), 4.31-4.15 (m, 1H), 4.06 (dd, 1H), 3.83-3.70 (m, 2H), 3.67-3.55 (m, 1H), 2.59 (s, 3H), 2.08-1.73 (m, 3H), 1.72-1.59 (m, 1H), 1.41 (dd, 6H).

LC/MS (Major isomer; Method 1, ESIpos): $R_t$=0.92 min, m/z=352 [M+H]$^+$.

Example 196A

6-[(Hydroxyimino)methyl]-3-isopropyl-5-methyl-1-(oxetan-3-ylmethyl)thieno[2,3-d]pyrimidine-2,4(1H,3H)-dione

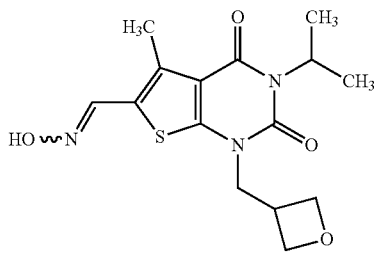 [SMILES: Cc1c(C=NO)sc2c1c(=O)n(C(C)C)c(=O)n2CC1COC1]

Analogously to the method described in Ex. 193A, 299 mg (0.863 mmol) of the compound from Ex. 108A and 159 µl (2.59 mmol) of hydroxylamine solution (50% in water) were used to obtain 290 mg (79% of theory, 80% purity) of the title compound as an E/Z isomer mixture (about 6:1). The reaction time here was about 16 h.

$^1$H-NMR (Major isomer; 400 MHz, DMSO-$d_6$, δ/ppm): 12.12 (s, 1H), 7.94 (s, 1H), 5.13 (sept, 1H), 4.63 (dd, 2H), 4.45 (t, 2H), 4.23 (d, 2H), 3.48-3.41 (m, 1H), 2.59 (s, 3H), 1.40 (d, 6H).

LC/MS (Major isomer; Method 1, ESIpos): $R_t$=0.81 min, m/z=338 [M+H]$^+$.

Example 197A

6-[(Hydroxyimino)methyl]-3-isopropyl-1,5-dimethylthieno[2,3-d]pyrimidine-2,4(1H,3H)-dione

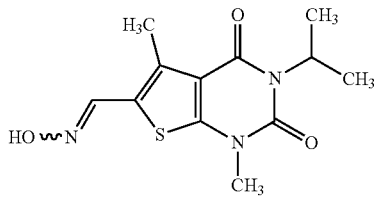 [SMILES: Cc1c(C=NO)sc2c1c(=O)n(C(C)C)c(=O)n2C]

Analogously to the method described in Ex. 191A, 407 mg (1.53 mmol) of the compound from Ex. 109A and 281 µl (4.59 mmol) of hydroxylamine solution (50% in water) were used to obtain 402 mg (86% of theory, 91% purity) of the title compound as an E/Z isomer mixture (about 13:1). The reaction time here was 1 h.

$^1$H-NMR (Major isomer; 400 MHz, DMSO-$d_6$, δ/ppm): 12.09 (s, 1H), 7.93 (s, 1H), 5.15 (sept, 1H), 3.43 (s, 3H), 2.60 (s, 3H), 1.41 (d, 6H).

LC/MS (Major isomer; Method 1, ESIpos): $R_t$=0.84 min, m/z=282 [M+H]$^+$.

Example 198A 6-(Azidomethyl)-3-ethyl-1-(2-methoxyethyl)-5-methylthieno[2,3-d]pyrimidine-2,4(1H,3H)-dione

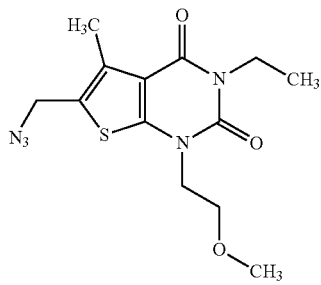 [SMILES: CCn1c(=O)c2c(C)c(CN=[N+]=[N-])sc2n(CCOC)c1=O]

600 mg (1.95 mmol) of the compound from Ex. 143A were dissolved in 9 ml of THF and cooled to 0° C. 767 ml (2.73 mmol) of diphenylphosphoryl azide were added and then the mixture was stirred at 0° C. for 5 min. Subsequently, 356 mg (2.34 mmol) of 1,8-diazabicyclo[5.4.0]undec-7-ene were added, and stirring of the reaction mixture was continued at RT for 67 h. The mixture was then admixed with water (75 ml) and extracted with ethyl acetate. The aqueous phase was once more extracted with ethyl acetate. The combined organic phases were dried over sodium sulphate, filtered and concentrated. The residue was chromatographed using a silica gel cartridge (Biotage, 25 g of silica gel, eluent: hexane/ethyl acetate). 541 mg of the title compound were obtained.

$^1$H-NMR (400 MHz, DMSO-$d_6$, δ/ppm): 4.67 (s, 2H), 4.04 (t, 2H), 3.90 (q, 2H), 3.64 (t, 2H), 3.24 (s, 3H), 2.41 (s, 3H), 1.12 (t, 3H).

LC/MS (Method 3): $R_t$=1.15 min, m/z=324 [M+H]$^+$.

Example 199A 6-(Aminomethyl)-3-ethyl-5-methyl-1-(3,3,3-trifluoropropyl)thieno[2,3-d]pyrimidine-2,4(1H,3H)-dione hydrochloride

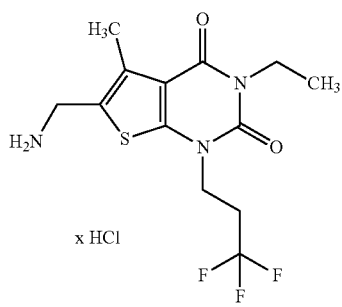 [SMILES: CCn1c(=O)c2c(C)c(CN)sc2n(CCC(F)(F)F)c1=O]

To a solution of 495 mg (1.42 mmol) of the compound from Ex. 190A in 35 ml of methanol were added 295 µl (3.54 mmol) of concentrated hydrochloric acid and 45 mg of palladium on charcoal (10%). Subsequently, hydrogenation was effected at RT at a hydrogen pressure of 1 bar for 2.5 h. This was followed by removal of the catalyst by filtration through a little kieselguhr and concentration of the filtrate on a rotary evaporator. Drying of the product under high vacuum gave 526 mg (89% of theory, 90% purity) of the title compound.

$^1$H-NMR (400 MHz, DMSO-d$_6$, δ/ppm): 8.29 (br. s, 3H), 4.21 (m, 2H), 4.13 (t, 2H), 3.92 (q, 2H), 2.88-2.71 (m, 2H), 2.46 (s, 3H), 1.13 (t, 3H).

LC/MS (Method 1, ESIpos): R$_t$=0.54 min, m/z=319 [M+H—NH$_3$]$^+$.

Example 200A 6-(Aminomethyl)-3-ethyl-1-(2-methoxyethyl)-5-methylthieno[2,3-d]pyrimidine-2,4(1H,3H)-dione

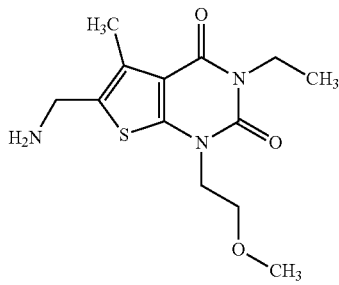 [SMILES: CCn1c(=O)c2c(C)c(CN)sc2n(CCOC)c1=O]

260 mg (0.710 mmol, 85% purity) of the compound from Ex. 191A, dissolved in 15 ml of methanol, were added to a solution of 169 mg (0.710 mmol) of nickel(II) chloride hexahydrate and 27 mg (0.710 mmol) of sodium borohydride in 10 ml of methanol. Subsequently, a further 146 mg (3.91 mmol) of solid sodium borohydride were added. After stirring at RT for 10 min, the solid constituents of the reaction mixture were removed by filtration with suction through a little kieselguhr. The filtrate was concentrated on a rotary evaporator. The remaining residue was admixed with aqueous ammonia and extracted with ethyl acetate. The organic extract was washed with saturated sodium chloride solution, dried over anhydrous magnesium sulphate, filtered and concentrated. After drying under high vacuum, 210 mg (79% of theory, 80% purity) of the title compound were obtained.

$^1$H-NMR (400 MHz, DMSO-d$_6$, δ/ppm): 4.04 (t, 2H), 3.90 (q, 2H), 3.82 (s, 2H), 3.64 (t, 2H), 3.24 (s, 3H), 2.31 (s, 3H), 1.11 (t, 3H).

LC/MS (Method 1, ESIpos): R$_t$=0.45 min, m/z=298 [M+H]$^+$.

Example 201A 6-(Aminomethyl)-3-ethyl-1-(2-methoxyethyl)-5-methylthieno[2,3-d]pyrimidine-2,4(1H,3H)-dione hydrochloride

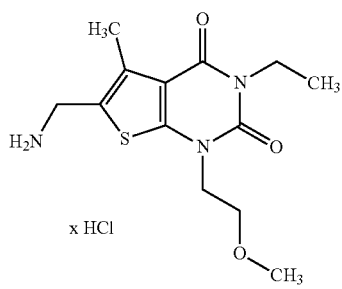

To a solution of 1.45 g (4.65 mmol) of the compound from Ex. 191A in 145 ml of methanol were added 970 µl (11.6 mmol) of concentrated hydrochloric acid and 145 mg of palladium on charcoal (10%). Subsequently, hydrogenation was effected at RT at a hydrogen pressure of about 1 bar for 4.5 h. This was followed by removal of the catalyst by filtration through a little kieselguhr and concentration of the filtrate on a rotary evaporator. After the product had been dried under high vacuum, 1.52 g (97% of theory) of the title compound were obtained.

$^1$H-NMR (400 MHz, DMSO-d$_6$, δ/ppm): 8.25 (br. s, 3H), 4.18 (br. s, 2H), 4.04 (t, 2H), 3.91 (q, 2H), 3.66 (t, 2H), 3.25 (s, 3H), 2.45 (s, 3H), 1.13 (t, 3H).

LC/MS (Method 5, ESIpos): R$_t$=0.58 min, m/z=298 [M+H]$^+$.

Example 202A 6-(Aminomethyl)-3-ethyl-1-(2-methoxyethyl)-5-methylthieno[2,3-d]pyrimidine-2,4(1H,3H)-dione formate

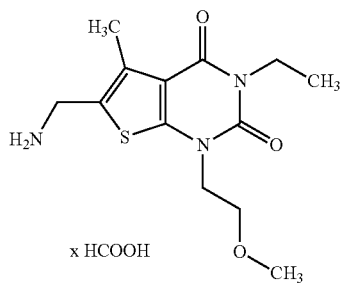 [SMILES: CCn1c(=O)c2c(C)c(CN)sc2n(CCOC)c1=O]

To a solution of 540 mg (1.6 mmol) of the compound from Ex. 198A in 28.3 ml of THF were added 272 mg (3.57 mmol) of trimethylphosphine, and the mixture was stirred at RT for 2 h. Then 3.56 ml of 25% aqueous ammonia solution were added and stirring was continued at RT for 3 h. The reaction mixture was then concentrated on a rotary evaporator. The residue was admixed with toluene and concentrated again. The material obtained was purified by means of preparative HPLC (Method 14). Combination of the product fractions and freeze-drying gave 359 mg (65% of theory) of the title compound.

¹H-NMR (400 MHz, DMSO-d₆, δ/ppm): 8.26 (s, 1H), 4.04 (t, 2H), 3.94-3.86 (m, 4H), 3.64 (t, 2H), 2.34 (s, 3H), 1.11 (t, 3H).

LC/MS (Method 3): $R_t$=0.59 min.

Example 203A 6-(Aminomethyl)-1-(2-fluoroethyl)-3-isopropyl-5-methylthieno[2,3-d]pyrimidine-2,4(1H,3H)-dione hydrochloride

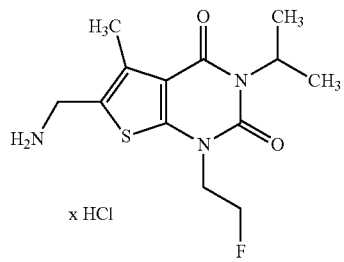 [SMILES: Cc1c(CN)sc2c1c(=O)n(C(C)C)c(=O)n2CCF]

Analogously to the method described in Ex. 201A, 401 mg (1.28 mmol) of the compound from Ex. 192A were used to obtain 379 mg (83% of theory, 94% purity) of the title compound. The reaction time here was 4 h; the product, after being concentrated by evaporation, was purified by stirring with cyclohexane/ethyl acetate (10:1).

¹H-NMR (400 MHz, DMSO-d₆, δ/ppm): 8.16 (br. s, 3H), 5.14 (sept, 1H), 4.88-4.62 (dt, 2H), 4.29-4.10 (dt, 2H), 4.19 (s, 2H), 2.43 (s, 3H), 1.41 (d, 6H).

LC/MS (Method 1, ESIpos): $R_t$=0.53 min, m/z=283 [M+H—NH₃]⁺.

Example 204A 6-(Aminomethyl)-3-isopropyl-5-methyl-1-(3,3,3-trifluoropropyl)thieno[2,3-d]pyrimidine-2,4(1H,3H)-dione hydrochloride

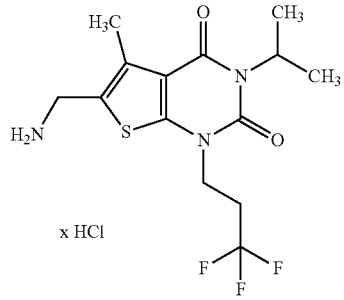 [SMILES: Cc1c(CN)sc2c1c(=O)n(C(C)C)c(=O)n2CCC(F)(F)F]

Analogously to the method described in Ex. 201A, 473 mg (1.30 mmol) of the compound from Ex. 193A were used to obtain 469 mg (98% of theory) of the title compound. The product, after being concentrated by evaporation, was purified by stirring with cyclohexane/ethyl acetate (10:1).

¹H-NMR (400 MHz, DMSO-d₆, δ/ppm): 8.14 (br. s, 3H), 5.13 (sept, 1H), 4.21 (br. s, 2H), 4.10 (t, 2H), 2.86-2.69 (m, 2H), 2.44 (s, 3H), 1.41 (d, 6H).

LC/MS (Method 1, ESIpos): $R_t$=0.57 min, m/z=333 [M+H—NH₃]⁺.

Example 205A 6-(Aminomethyl)-3-isopropyl-5-methyl-1-(oxetan-2-ylmethyl)thieno[2,3-d]pyrimidine-2,4(1H,3H)-dione (racemate)

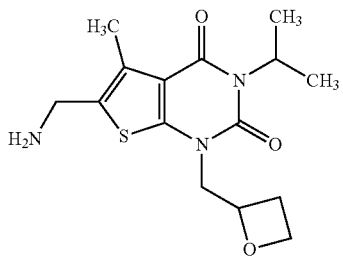 [SMILES: Cc1c(CN)sc2c1c(=O)n(C(C)C)c(=O)n2CC1CCO1]

Analogously to the method described in Ex. 200A, 372 mg (1.10 mmol) of the compound from Ex. 194A were used to obtain 290 mg (69% of theory, 85% purity) of the title compound.

¹H-NMR (400 MHz, DMSO-d₆, δ/ppm): 5.14 (sept, 1H), 5.05-4.93 (m, 1H), 4.53-4.36 (m, 2H), 4.12 (d, 2H), 2.75-2.63 (m, 1H), 2.52-2.43 (m, 1H, partially obscured by the DMSO signal), 2.29 (s, 3H), 1.39 (d, 6H).

LC/MS (Method 1, ESIpos): $R_t$=0.49 min, m/z=307 [M+H—NH₃]⁺.

Example 206A 6-(Aminomethyl)-3-isopropyl-5-methyl-1-(tetrahydrofuran-2-ylmethyl)thieno[2,3-d]pyrimidine-2,4 (1H,3H)-dione hydrochloride (racemate)

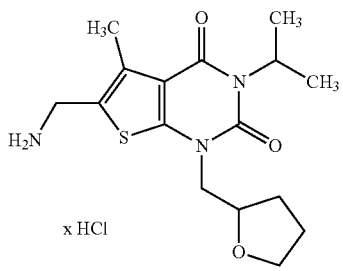 [SMILES: Cc1c(CN)sc2c1c(=O)n(C(C)C)c(=O)n2CC1CCCO1]

Analogously to the method described in Ex. 201A, 320 mg (0.883 mmol) of the compound from Ex. 195A were used to obtain 267 mg (71% of theory, 88% purity) of the title compound. The reaction time here was 5 h; the product, after being concentrated by evaporation, was purified by stirring with cyclohexane/ethyl acetate (10:1).

¹H-NMR (400 MHz, DMSO-d₆, δ/ppm): 8.13 (br. s, 3H), 5.14 (sept, 1H), 4.28-4.15 (m, 3H), 4.09 (dd, 1H), 3.83-3.72 (m, 1H), 3.69-3.56 (m, 2H), 2.43 (s, 3H), 2.06-1.95 (m, 1H), 1.94-1.76 (m, 2H), 1.74-1.59 (m, 1H), 1.41 (d, 6H).

LC/MS (Method 1, ESIpos): $R_t$=0.59 min, m/z=321 [M+H—NH₃]⁺.

Example 207A 6-(Aminomethyl)-3-isopropyl-5-methyl-1-(oxetan-3-ylmethyl)thieno[2,3-d]pyrimidine-2,4(1H,3H)-dione

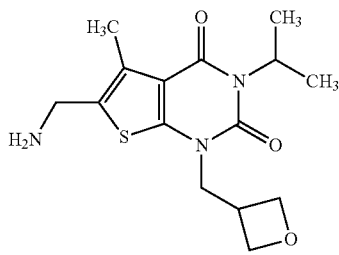 [SMILES: Cc1c(CN)sc2c1c(=O)n(C(C)C)c(=O)n2CC1COC1]

Analogously to the method described in Ex. 200A, 279 mg (0.663 mmol) of the compound from Ex. 196A were used to obtain 216 mg (70% of theory, 70% purity) of the title compound.

$^1$H-NMR (400 MHz, DMSO-d$_6$, δ/ppm): 5.12 (sept, 1H), 4.68-4.57 (m, 2H), 4.49-4.39 (m, 2H), 4.18 (d, 2H), 3.81 (s, 1H), 3.43 (dt, 1H), 2.29 (s, 3H), 1.39 (d, 6H).

LC/MS (Method 1, ESIpos): R$_t$=0.50 min, m/z=307 [M+H—NH$_3$]$^+$.

Example 208A 6-(Aminomethyl)-3-isopropyl-1,5-dimethylthieno[2,3-d]pyrimidine-2,4(1H,3H)-dione

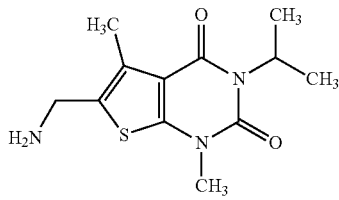 [SMILES: Cc1c(CN)sc2c1c(=O)n(C(C)C)c(=O)n2C]

Analogously to the method described in Ex. 200A, 20 mg (0.066 mmol) of the compound from Ex. 197A were used to obtain 16 mg (91% of theory) of the title compound.

LC/MS (Method 1, ESIpos): R$_t$=0.49 min, m/z=251 [M+H—NH$_3$]$^+$.

Example 209A

6-{[(2-Aminoethyl)amino]methyl}-3-ethyl-5-methyl-1-(2,2,2-trifluoroethyl)thieno[2,3-d]pyrimidine-2,4(1H,3H)-dione

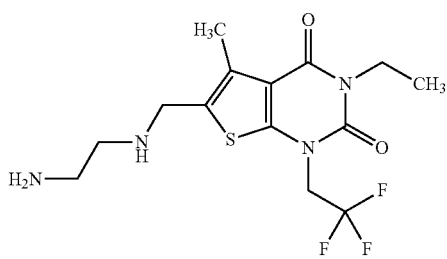 [SMILES: CCn1c(=O)c2c(C)c(CNCCN)sc2n(CC(F)(F)F)c1=O]

570 mg (1.71 mmol) of the compound from Ex. 73A were dissolved in a mixture of 10 ml of methanol and 4 ml of dichloromethane. Subsequently, at RT, 457 µl (6.83 mmol) of 1,2-diaminoethane, 391 µl (6.83 mmol) of acetic acid and, in portions distributed over about 2 h, 429 mg (6.83 mmol) of sodium cyanoborohydride were added. After the reaction mixture had been stirred at RT for 3 days, it was admixed with 2 M sodium hydroxide solution and extracted with ethyl acetate. The organic extract was washed with saturated sodium chloride solution, dried over anhydrous magnesium sulphate, filtered and concentrated on a rotary evaporator. The crude product thus obtained, after drying under high vacuum, gave 730 mg (83% of theory, 71% purity) of the title compound, which was used for subsequent reactions without further purification.

LC/MS (Method 1, ESIpos): R$_t$=0.41 min, m/z=365 [M+H]$^+$.

Example 210A

6-{[(2-Aminoethyl)amino]methyl}-3-ethyl-5-methyl-1-(3,3,3-trifluoropropyl)thieno[2,3-d]pyrimidine-2,4(1H,3H)-dione

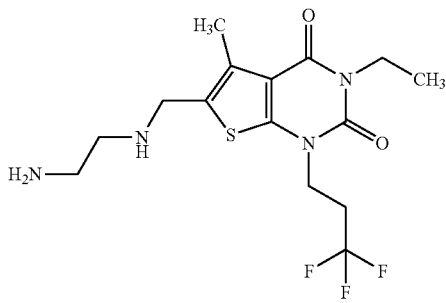 [SMILES: CCn1c(=O)c2c(C)c(CNCCN)sc2n(CCC(F)(F)F)c1=O]

330 mg (0.89 mmol) of the compound from Ex. 74A were dissolved in a mixture of 7.36 ml of methanol and 3.16 ml of dichloromethane. Then 240 µl (3.59 mmol) of 1,2-diaminoethane and 205 µl (3.59 mmol) of acetic acid were added at RT. The mixture was stirred at RT for 30 minutes, and then 237 mg (3.59 mmol) of sodium cyanoborohydride were added. After the reaction mixture had been stirred at 60° C. for 20 h, it was admixed with 30 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 369 mg (83% of theory, 77% purity) of the title compound and was used for subsequent reactions without further purification.

LC/MS (Method 3): R$_t$=0.57 min, m/z=319 [M+H—C$_2$H$_8$N$_2$]$^+$.

Example 211A

6-{[(2-Aminoethyl)amino]methyl}-3-ethyl-5-methyl-1-(4,4,4-trifluorobutyl)thieno[2,3-d]pyrimidine-2,4(1H,3H)-dione

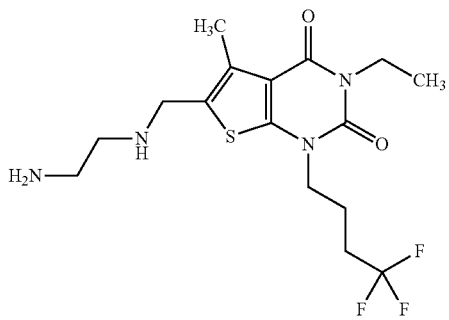 [SMILES: CCn1c(=O)c2c(C)c(CNCCN)sc2n(CCCC(F)(F)F)c1=O]

Analogously to the method described in Ex. 209A, 200 mg (2.30 mmol) of the compound from Ex. 75A and 1,2-diaminoethane were used to prepare 310 mg (96% of theory, 70% purity) of the title compound. The reaction time here was about 18 h.

LC/MS (Method 1, ESIpos): $R_t$=0.50 min, m/z=393 [M+H]$^+$.

Example 212A

6-{[(2-Aminoethyl)amino]methyl}-1-(2, 2-difluoroethyl)-3-ethyl-5-methylthieno[2,3-d]pyrimidine-2,4(1H,3H)-dione

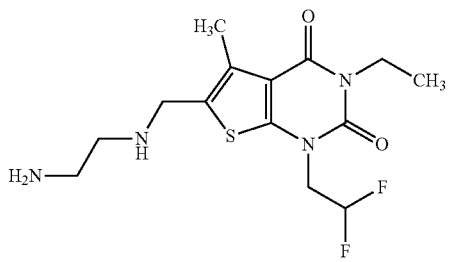 [SMILES: CCn1c(=O)c2c(C)c(CNCCN)sc2n(CC(F)F)c1=O]

235 mg (0.77 mmol) of the compound from Ex. 76A were dissolved in a mixture of 15.74 ml of methanol and 7.5 ml of dichloromethane. Then 520 µl (7.74 mmol) of 1,2-diaminoethane and 178 µl (3.11 mmol) of acetic acid were added at RT. The mixture was stirred at RT for 30 minutes, and then 206 mg (3.11 mmol) of sodium cyanoborohydride were added. After the reaction mixture had been stirred at 60° C. for 116 h, it was admixed with 50 ml of water (pH 9-10) and extracted with ethyl acetate. The organic extract was washed with saturated sodium chloride solution, dried over anhydrous sodium sulphate, filtered and concentrated. The crude product obtained, after drying under high vacuum, gave 353 mg (85% purity) of the title compound and was used for subsequent reactions without further purification.

LC/MS (Method 3): $R_t$=0.55 min, m/z=347 [M+H]$^+$.

Example 213A

6-{[(2-Aminoethyl)amino]methyl}-3-ethyl-1-(2-fluoroethyl)-5-methylthieno[2,3-d]pyrimidine-2,4(1H,3H)-dione

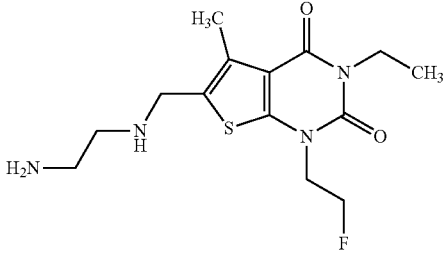 [SMILES: CCn1c(=O)c2c(C)c(CNCCN)sc2n(CCF)c1=O]

Analogously to the method described in Ex. 209A, 252 mg (0.886 mmol) of the compound from Ex. 77A and 1,2-diaminoethane were used to prepare 292 mg (86% of theory, 86% purity) of the title compound. The reaction time here was 2 days.

LC/MS (Method 1, ESIpos): $R_t$=0.26 min, m/z=329 [M+H]$^+$.

Example 214A

6-{[(2-Aminoethyl)amino]methyl}-3-ethyl-1-(3-fluoropropyl)-5-methylthieno[2,3-d]pyrimidine-2,4(1H,3H)-dione

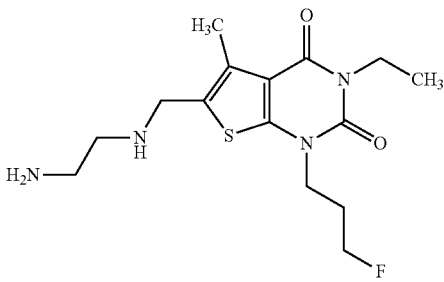 [SMILES: CCn1c(=O)c2c(C)c(CNCCN)sc2n(CCCF)c1=O]

150 mg (0.49 mmol) of the compound from Ex. 78A were dissolved in a mixture of 4.04 ml of methanol and 1.73 ml of dichloromethane. Then 132 µl (1.97 mmol) of 1,2-diaminoethane and 113 µl (1.97 mmol) of acetic acid were added at RT. The mixture was stirred at RT for 30 minutes, and then 130 mg (1.97 mmol) of sodium cyanoborohydride were added. After the reaction mixture had been stirred at 60° C. for 2 h, it was admixed with 5 ml of 2 M sodium hydroxide solution and extracted with ethyl acetate. The organic extract was washed with saturated sodium chloride solution, dried over anhydrous sodium sulphate, filtered and concentrated. The crude product obtained was purified by preparative HPLC (Method 14). Combination of the product fractions and freeze-drying gave 116 mg (62% of theory) of the title compound.

$^1$H-NMR (400 MHz, DMSO-d$_6$+D$_2$O, δ/ppm): 4.59 (t, 1H), 4.47 (t, 1H), 3.99 (t, 2H), 3.89 (q, 2H), 3.80 (s, 2H), 2.85-2.79 (m, 2H), 2.73-2.67 (m, 2H), 2.35 (s, 2H), 2.16-1.97 (m, 2H), 1.10 (t, 3H).

LC/MS (Method 3): R$_t$=0.52 min; m/z=343 [M+H]$^+$, 283 [M+H—C$_2$H$_8$N$_2$]$^+$.

Example 215A

6-{[(2-Aminoethyl)amino]methyl}-3-ethyl-1-(4-fluorobutyl)-5-methylthieno[2,3-d]pyrimidine-2,4(1H,3H)-dione

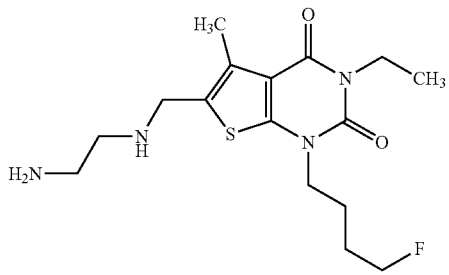 [SMILES: CCn1c(=O)c2c(C)c(CNCCN)sc2n(CCCCF)c1=O]

216 mg (0.68 mmol) of the compound from Ex. 79A were dissolved in a mixture of 13.86 ml of methanol and 6.6 ml of dichloromethane. Then 458 µl (6.85 mmol) of 1,2-diaminoethane and 157 µl (2.74 mmol) of acetic acid were added at RT. The mixture was stirred at RT for 30 min. Then 181 mg (2.74 mmol) of sodium cyanoborohydride were added. After the reaction mixture had been stirred at 60° C. for 92 h, it was admixed with 100 ml of water and extracted with ethyl acetate. The organic extract was washed with saturated sodium chloride solution, dried over anhydrous sodium sulphate, filtered and concentrated. The crude product obtained, after drying under high vacuum, gave 250 mg (47% of theory, 46% purity) of the title compound and was used for subsequent reactions without further purification.

LC/MS (Method 3): R$_t$=0.59 min, m/z=297 [M+H—C$_2$H$_8$N$_2$]$^+$.

Example 216A

6-{[(2-Aminoethyl)amino]methyl}-3-ethyl-5-methyl-1-[2-(trifluoromethyl)prop-2-en-1-yl]thieno[2,3-d]pyrimidine-2,4(1H,3H)-dione

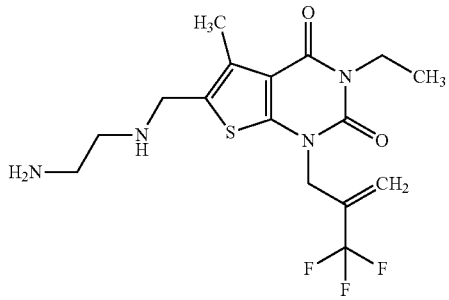 [SMILES: C=C(Cn1c(=O)n(CC)c(=O)c2c(C)c(CNCCN)sc21)C(F)(F)F]

Analogously to the method described in Ex. 209A, 215 mg (0.621 mmol) of the compound from Ex. 80A and 1,2-diaminoethane were used to prepare 246 mg (86% of theory, 84% purity) of the title compound.

LC/MS (Method 1, ESIpos): R$_t$=0.43 min, m/z=391 [M+H]$^+$.

Example 217A

6-{[(2-Aminoethyl)amino]methyl}-1-[(2,2-difluorocyclopropyl)methyl]-3-ethyl-5-methylthieno[2,3-d]pyrimidine-2,4(1H,3H)-dione

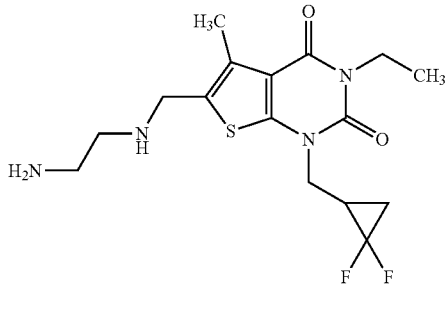 [SMILES: CCn1c(=O)c2c(C)c(CNCCN)sc2n(CC2CC2(F)F)c1=O]

Analogously to the method described in Ex. 209A, 408 mg (1.24 mmol) of the compound from Ex. 81A and 1,2-diaminoethane were used to prepare 548 mg (97% of theory, 82% purity) of the title compound.

LC/MS (Method 1, ESIpos): R$_t$=0.42 min, m/z=373 [M+H]$^+$.

Example 218A

6-{[(2-Aminoethyl)amino]methyl}-3-ethyl-5-methyl-1-[2-(trifluoromethoxy)ethyl]thieno[2,3-d]pyrimidine-2,4(1H,3H)-dione

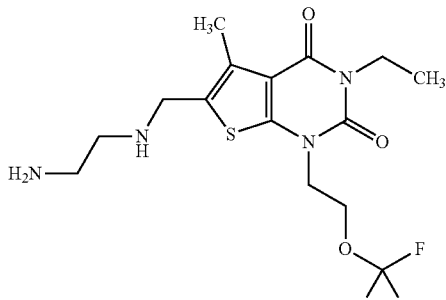

Analogously to the method described in Ex. 209A, 200 mg (0.571 mmol) of the compound from Ex. 82A and 1,2-diaminoethane were used to prepare 288 mg (99% of theory, 78% purity) of the title compound. The reaction time here was about 18 h.

LC/MS (Method 2, ESIpos): R$_t$=0.97 min, m/z=395 [M+H]$^+$.

Example 219A

6-{[(2-Aminoethyl)amino]methyl}-3-ethyl-5-methyl-1-{2-[(trifluoromethyl) sulphanyl]ethyl}thieno[2,3-d]pyrimidine-2,4(1H,3H)-dione

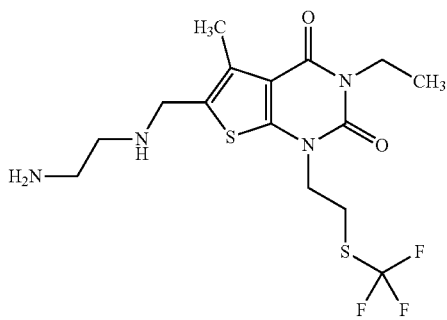 [SMILES: CCn1c(=O)c2c(C)c(CNCCN)sc2n(CCSC(F)(F)F)c1=O]

Analogously to the method described in Ex. 209A, 200 mg (0.546 mmol) of the compound from Ex. 83A and 1,2-diaminoethane were used to prepare 271 mg (96% of theory, 80% purity) of the title compound. The reaction time here was about 18 h.

LC/MS (Method 2, ESIpos): $R_t$=1.09 min, m/z=411 [M+H]$^+$.

Example 220A

6-{[(2-Aminoethyl)amino]methyl}-3-ethyl-1-(2-methoxyethyl)-5-methylthieno[2,3-d]pyrimidine-2,4(1H,3H)-dione

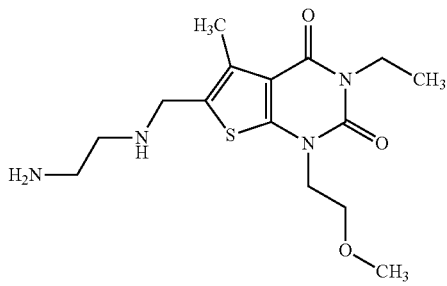 [SMILES: CCn1c(=O)c2c(C)c(CNCCN)sc2n(CCOC)c1=O]

40.0 g (135 mmol) of the compound from Ex. 84A were dissolved in a mixture of 1120 ml of methanol and 440 ml of dichloromethane. Subsequently, at RT, 54.1 ml (810 mmol) of 1,2-diaminoethane, 31 ml (540 mmol) of acetic acid and, in portions distributed over about 6 h, 33.9 g (540 mmol) of sodium cyanoborohydride were added. After the reaction mixture had been stirred at RT for 6 days, it was admixed with 1000 ml of 2 M sodium hydroxide solution and extracted four times with a total of 2800 ml of ethyl acetate. The organic extract was washed with saturated sodium chloride solution, dried over anhydrous magnesium sulphate, filtered and concentrated on a rotary evaporator. The crude product thus obtained, after drying under high vacuum, gave 45.9 g (69% of theory, 69% purity) of the title compound, which was used for subsequent reactions without further purification.

$^1$H-NMR (400 MHz, DMSO-d$_6$, δ/ppm): 4.04 (t, 2H), 3.90 (q, 2H), 3.79 (s, 2H), 3.64 (t, 2H), 3.24 (s, 3H), 2.69-2.62 (m, 2H), 2.59-2.56 (m, 2H), 2.34 (s, 3H), 1.11 (t, 3H).

LC/MS (Method 6, ESIpos): $R_t$=1.02 min, m/z=281 [M+H—C$_2$H$_8$N$_2$]$^+$.

Example 221A

6-{[(2-Aminoethyl)amino]methyl}-1-(2-ethoxyethyl)-3-ethyl-5-methylthieno[2,3-d]pyrimidine-2,4(1H,3H)-dione

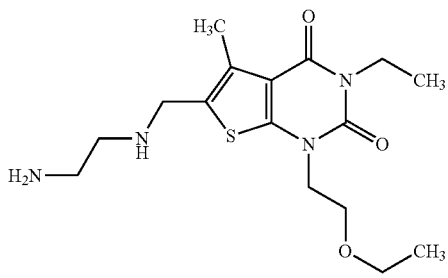

Analogously to the method described in Ex. 210A, 215 mg (0.686 mmol) of the compound from Ex. 85A and 1,2-diaminoethane were used to prepare 255 mg (82% of theory, 79% purity) of the title compound. The reaction time here was about 92 h.

LC/MS (Method 3): $R_t$=0.54 min, m/z=295 [M+H—C$_2$H$_8$N$_2$]$^+$.

Example 222A

6-{[(2-Aminoethyl)amino]methyl}-3-ethyl-1-(2-isopropoxyethyl)-5-methylthieno[2,3-d]pyrimidine-2,4(1H,3H)-dione

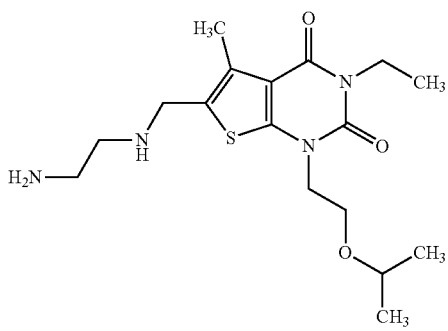 [SMILES: CCn1c(=O)c2c(C)c(CNCCN)sc2n(CCOC(C)C)c1=O]

Analogously to the method described in Ex. 210A, 169 mg (0.495 mmol) of the compound from Ex. 86A and 1,2-diaminoethane were used to prepare 206 mg (75% of theory, 67% purity) of the title compound. The reaction time here was about 64 h.

LC/MS (Method 3): $R_t$=0.59 min, m/z=369 [M+H]$^+$.

Example 223A

6-{[(2-Aminoethyl)amino]methyl}-3-ethyl-1-(2-methoxypropyl)-5-methylthieno[2,3-d]pyrimidine-2,4(1H,3H)-dione (racemate)

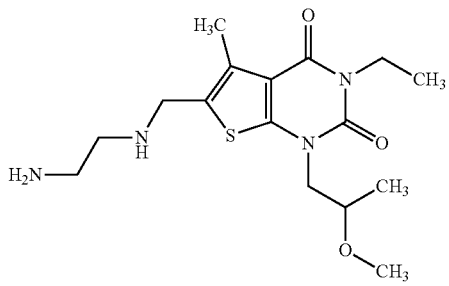 [SMILES: CCn1c(=O)c2c(C)c(CNCCN)sc2n(CC(C)OC)c1=O]

Analogously to the method described in Ex. 209A, 325 mg (1.05 mmol) of the compound from Ex. 87A and 1,2-diaminoethane were used to prepare 425 mg (98% of theory, 86% purity) of the title compound.

LC/MS (Method 1, ESIpos): $R_t$=0.37 min, m/z=295 [M+H—$C_2H_8N_2$]$^+$.

Example 224A

6-{[(2-Aminoethyl)amino]methyl}-3-ethyl-5-methyl-1-(oxetan-2-ylmethyl)thieno[2,3-d]pyrimidine-2,4(1H,3H)-dione (racemate)

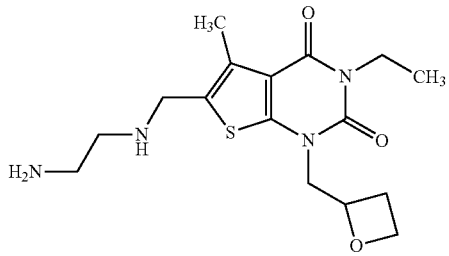 [SMILES: CCn1c(=O)c2c(C)c(CNCCN)sc2n(CC2CCO2)c1=O]

375 mg (1.1 mmol) of the compound from Ex. 88A were dissolved in a mixture of 18.15 ml of methanol and 7.83 ml of dichloromethane. Then 740 µl (11.06 mmol) of 1,2-diaminoethane and 253 µl (4.42 mmol) of acetic acid were added at RT. The mixture was stirred at RT for 30 min. Then 293 mg (4.42 mmol) of sodium cyanoborohydride were added. After the reaction mixture had been stirred at 60° C. for 65 h, it was admixed with 50 ml of water and extracted with ethyl acetate. The organic extract was washed with saturated sodium chloride solution, dried over anhydrous sodium sulphate, filtered and concentrated. The crude product obtained was purified by preparative HPLC (Method 14). Combination of the product fractions and freeze-drying gave 339 mg (64% of theory, 63% purity) of the title compound.

LC/MS (Method 3): $R_t$=0.48 min, m/z=293 [M+H—$C_2H_8N_2$]$^+$.

Example 225A

6-{[(2-Aminoethyl)amino]methyl}-3-ethyl-5-methyl-1-(tetrahydrofuran-2-ylmethyl)thieno[2,3-d]pyrimidine-2,4(1H,3H)-dione (racemate)

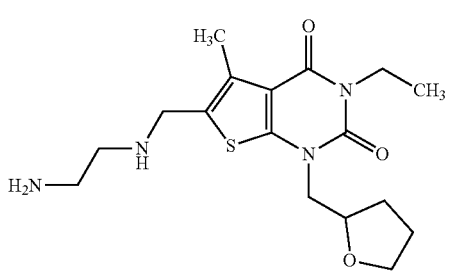 [SMILES: CCn1c(=O)c2c(C)c(CNCCN)sc2n(CC2CCCO2)c1=O]

1.36 g (4.20 mmol) of the compound from Ex. 89A were dissolved in a mixture of 40 ml of methanol and 15 ml of dichloromethane. Subsequently, at RT, 1.01 g (16.8 mmol) of 1,2-diaminoethane, 962 µl (16.8 mmol) of acetic acid and, in portions distributed over about 4 h, 1.06 g (16.8 mmol) of sodium cyanoborohydride were added. After the reaction mixture had been stirred at RT for 2 days, it was admixed with 2 M sodium hydroxide solution and extracted with ethyl acetate. The organic extract was washed with saturated sodium chloride solution, dried over anhydrous magnesium sulphate, filtered and concentrated on a rotary evaporator. The crude product thus obtained, after drying under high vacuum, gave 2.12 g (76% of theory, 75% purity) of the title compound, which was used for subsequent reactions without further purification.

LC/MS (Method 1, ESIpos): $R_t$=0.39 min, m/z=367 [M+H]$^+$.

Example 226A

6-{[(2-Aminoethyl)amino]methyl}-3-ethyl-5-methyl-1-(tetrahydro-2H-pyran-2-ylmethyl)thieno[2,3-d]pyrimidine-2,4(1H,3H)-dione (racemate)

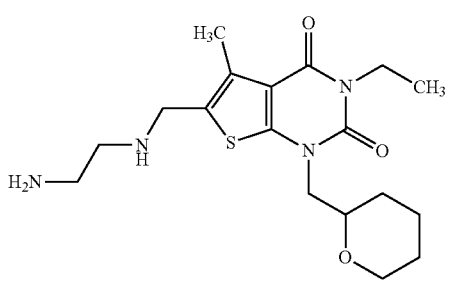 [SMILES: CCn1c(=O)c2c(C)c(CNCCN)sc2n(CC2CCCCO2)c1=O]

Analogously to the method described in Ex. 210A, 585 mg (1.739 mmol) of the compound from Ex. 90A and 1,2-diaminoethane were used to prepare 642 mg (84% of theory, 87% purity) of the title compound.

LC/MS (Method 3): $R_t$=0.59 min, m/z=381 [M+H]$^+$.

Example 227A

6-{[(2-Aminoethyl)amino]methyl}-3-ethyl-5-methyl-1-(oxetan-3-ylmethyl)thieno[2,3-d]pyrimidine-2,4(1H,3H)-dione

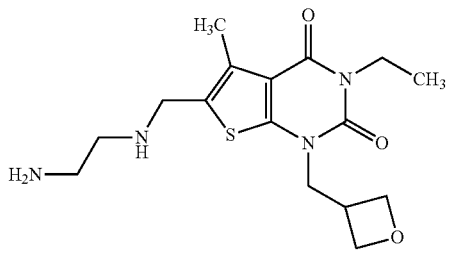 [SMILES: CCn1c(=O)c2c(C)c(CNCCN)sc2n(CC2COC2)c1=O]

82 mg (0.266 mmol) of the compound from Ex. 91A were dissolved in a mixture of 2.3 ml of methanol and 0.9 ml of dichloromethane. Subsequently, at RT, 71 µl (1.06 mmol) of 1,2-diaminoethane, 61 µl (1.06 mmol) of acetic acid and, in portions distributed over about 2 h, 67 mg (1.06 mmol) of sodium cyanoborohydride were added. After the reaction mixture had been stirred at RT for about 18 h, it was admixed with 2 M sodium hydroxide solution and extracted with ethyl acetate. The organic extract was washed with saturated sodium chloride solution, dried over anhydrous magnesium sulphate, filtered and concentrated on a rotary evaporator. The crude product thus obtained, after drying under high vacuum, gave 110 mg (93% of theory, 80% purity) of the title compound, which was used for subsequent reactions without further purification.

LC/MS (Method 1, ESIpos): $R_t$=0.26 min, m/z=353 $[M+H]^+$.

Example 228A

6-{[(2-Aminoethyl)amino]methyl}-3-ethyl-5-methyl-1-(tetrahydrofuran-3-ylmethyl)thieno[2,3-d]pyrimidine-2,4(1H,3H)-dione (racemate)

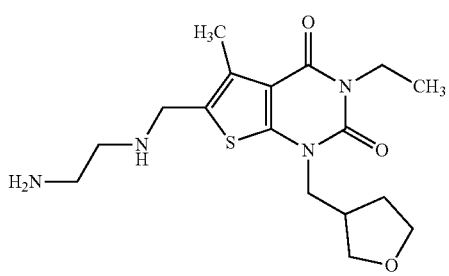 [SMILES: CCn1c(=O)c2c(C)c(CNCCN)sc2n(CC2CCOC2)c1=O]

Analogously to the method described in Ex. 209A, 182 mg (0.565 mmol) of the compound from Ex. 92A and 1,2-diaminoethane were used to prepare 215 mg (91% of theory, 87% purity) of the title compound.

LC/MS (Method 1, ESIpos): $R_t$=0.33 min, m/z=367 $[M+H]^+$.

Example 229A

6-{[(2-Aminoethyl)amino]methyl}-3-ethyl-1,5-dimethylthieno[2,3-d]pyrimidine-2,4(1H,3H)-dione

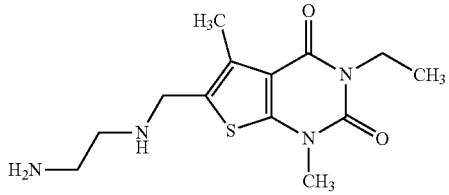 [SMILES: CCn1c(=O)c2c(C)c(CNCCN)sc2n(C)c1=O]

Analogously to the method described in Ex. 209A, 300 mg (1.19 mmol) of the compound from Ex. 93A and 1,2-diaminoethane were used to prepare 380 mg (82% of theory, 76% purity) of the title compound. The reaction time here was about 18 h.

LC/MS (Method 1, ESIpos): $R_t$=0.21 min, m/z=237 $[M+H-C_2H_8N_2]^+$.

Example 230A

6-{[(2-Aminoethyl)amino]methyl}-1,3-diethyl-5-methylthieno[2,3-d]pyrimidine-2,4(1H,3H)-dione

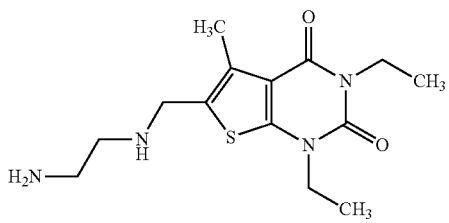 [SMILES: CCn1c(=O)c2c(C)c(CNCCN)sc2n(CC)c1=O]

Analogously to the method described in Ex. 209A, 300 mg (1.13 mmol) of the compound from Ex. 94A and 1,2-diaminoethane were used to prepare 380 mg (88% of theory, 81% purity) of the title compound. The reaction time here was about 18 h.

$^1$H-NMR (400 MHz, DMSO-$d_6$, δ/ppm): 3.92 (q, 2H), 3.90 (q, 2H), 3.80 (s, 2H), 2.72-2.63 (m, 2H), 2.62-2.56 (m, 2H), 2.35 (s, 3H), 1.25 (t, 3H), 1.12 (t, 3H).

LC/MS (Method 1, ESIpos): $R_t$=0.26 min, m/z=251 $[M+H-C_2H_8N_2]^+$.

Example 231A

6-{[(2-Aminoethyl)amino]methyl}-3-ethyl-5-methyl-1-propylthieno[2,3-d]pyrimidine-2,4(1H,3H)-dione

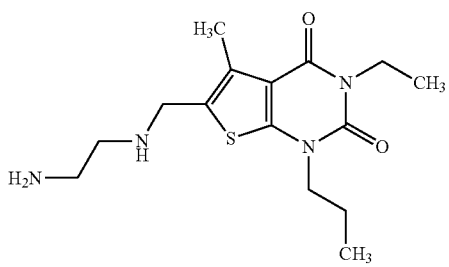 [SMILES: CCCn1c(=O)n(CC)c(=O)c2c(C)c(CNCCN)sc21]

Analogously to the method described in Ex. 209A, 198 mg (0.706 mmol) of the compound from Ex. 95A and 1,2-diaminoethane were used to prepare 287 mg (88% of theory, 70% purity) of the title compound.

$^{1}$H-NMR (400 MHz, DMSO-d$_{6}$, δ/ppm): 3.96-3.74 (m, 6H), 2.78-2.72 (m, 2H), 2.67-2.61 (m, 2H), 2.35 (s, 3H), 1.77-1.64 (m, 2H), 1.11 (t, 3H), 0.91 (t, 3H).

LC/MS (Method 1, ESIpos): R$_{t}$=0.41 min, m/z=325 [M+H]$^{+}$.

Example 232A

6-{[(2-Aminoethyl)amino]methyl}-1-butyl-3-ethyl-5-methylthieno[2,3-d]pyrimidine-2,4(1H,3H)-dione

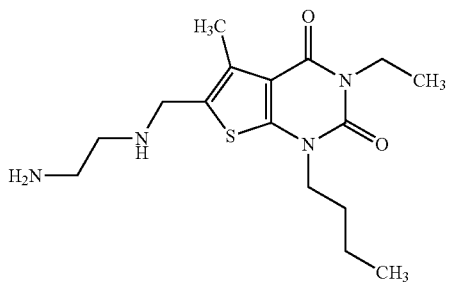 [SMILES: CCCCn1c(=O)n(CC)c(=O)c2c(C)c(CNCCN)sc21]

Analogously to the method described in Ex. 209A, 300 mg (1.02 mmol) of the compound from Ex. 96A and 1,2-diaminoethane were used to prepare 388 mg (73% of theory, 65% purity) of the title compound.

$^{1}$H-NMR (400 MHz, DMSO-d$_{6}$, δ/ppm): 3.89 (m, 4H), 3.80 (s, 2H), 2.73-2.65 (m, 2H), 2.61-2.58 (m, 2H), 2.35 (s, 3H), 1.72-1.59 (m, 2H), 1.39-1.30 (m, 2H), 1.11 (t, 3H), 0.92 (t, 3H).

LC/MS (Method 1, ESIpos): R$_{t}$=0.50 min, m/z=339 [M+H]$^{+}$.

Example 233A

6-{[(2-Aminoethyl)amino]methyl}-3-ethyl-5-methyl-1-(3-methylbutyl)thieno[2,3-d]pyrimidine-2,4(1H,3H)-dione

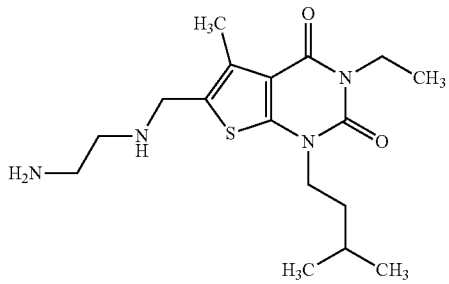 [SMILES: CCn1c(=O)c2c(C)c(CNCCN)sc2n(CCC(C)C)c1=O]

Analogously to the method described in Ex. 209A, 300 mg (0.973 mmol) of the compound from Ex. 97A and 1,2-diaminoethane were used to prepare 368 mg (96% of theory, 90% purity) of the title compound. The reaction time here was about 18 h.

LC/MS (Method 1, ESIpos): R$_{t}$=0.56 min, m/z=353 [M+H]$^{+}$.

Example 234A

6-{[(2-Aminoethyl)amino]methyl}-1-(3,3-dimethylbutyl)-3-ethyl-5-methylthieno[2,3-d]pyrimidine-2,4(1H,3H)-dione

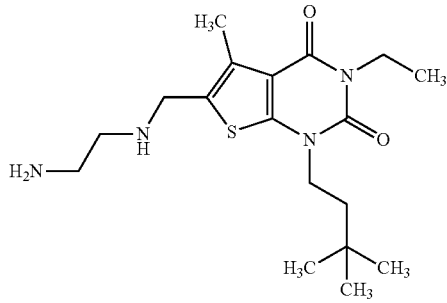 [SMILES: CCn1c(=O)c2c(C)c(CNCCN)sc2n(CCC(C)(C)C)c1=O]

Analogously to the method described in Ex. 210A, 272 mg (0.844 mmol) of the compound from Ex. 98A and 1,2-diaminoethane were used to prepare 370 mg (89% of theory, 75% purity) of the title compound.

LC/MS (Method 3): R$_{t}$=0.77 min, m/z=367 [M+H]$^{+}$.

Example 235A

6-{[(2-Aminoethyl)amino]methyl}-1-(cyclobutylmethyl)-3-ethyl-5-methylthieno[2,3-d]pyrimidine-2,4(1H,3H)-dione

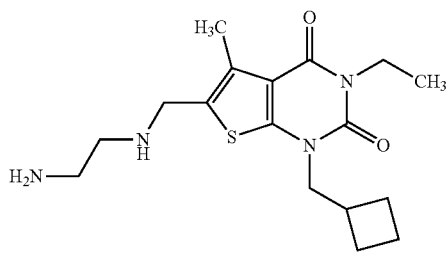 [SMILES: CCn1c(=O)c2c(C)c(CNCCN)sc2n(CC2CCC2)c1=O]

Analogously to the method described in Ex. 209A, 300 mg (0.979 mmol) of the compound from Ex. 99A and 1,2-diaminoethane were used to prepare 350 mg (92% of theory, 90% purity) of the title compound. The reaction time here was 4 days.

LC/MS (Method 1, ESIpos): R$_{t}$=0.44 min, m/z=291 [M+H—C$_{2}$H$_{8}$N$_{2}$]$^{+}$.

Example 236A

[6-{[(2-Aminoethyl)amino]methyl}-3-ethyl-5-methyl-2,4-dioxo-3,4-dihydrothieno[2,3-d]pyrimidine-1(2H)-yl]acetonitrile

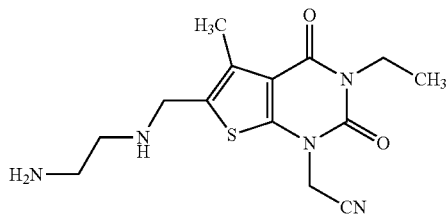 [SMILES: CCn1c(=O)c2c(C)c(CNCCN)sc2n(CC#N)c1=O]

Analogously to the method described in Ex. 209A, 300 mg (1.08 mmol) of the compound from Ex. 100A and 1,2-diaminoethane were used to prepare 289 mg (80% of theory, 80% purity) of the title compound. The reaction time here was 5 days.

LC/MS (Method 1, ESIpos): $R_t$=0.17 min, no ionization.

Example 237A

6-{[(2-Aminoethyl)amino]methyl}-3-ethyl-5-methyl-1-[(4-methyl-1,2,5-oxadiazol-3-yl)methyl]thieno[2,3-d]pyrimidine-2,4(1H,3H)-dione

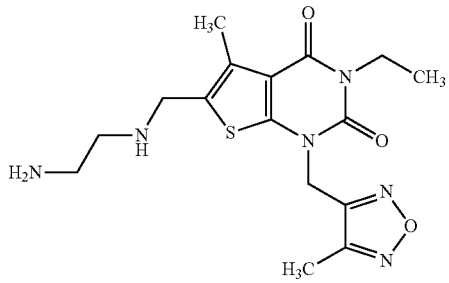 [SMILES: CCn1c(=O)c2c(C)c(CNCCN)sc2n(Cc2nonc2C)c1=O]

Analogously to the method described in Ex. 209A, 380 mg (1.34 mmol) of the compound from Ex. 101A and 1,2-diaminoethane were used to prepare 492 mg (94% of theory, 82% purity) of the title compound.

LC/MS (Method 1, ESIpos): $R_t$=0.42 min, m/z=379 [M+H]$^+$.

Example 238A

6-{[(2-Aminoethyl)amino]methyl}-1-[2-(dimethylamino)ethyl]-3-ethyl-5-methylthieno[2,3-d]pyrimidine-2,4(1H,3H)-dione

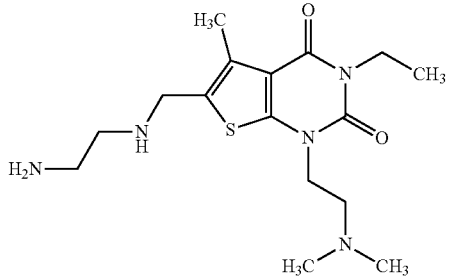 [SMILES: CCn1c(=O)c2c(C)c(CNCCN)sc2n(CCN(C)C)c1=O]

Analogously to the method described in Ex. 209A, 434 mg (1.40 mmol) of the compound from Ex. 102A and 1,2-diaminoethane were used to prepare 665 mg (99% of theory, 73% purity) of the title compound. The reaction time here was 5 days.

LC/MS (Method 1, ESIpos): $R_t$=0.15 min, no ionization.

Example 239A

6-{[(2-Aminoethyl)amino]methyl}-3-isobutyl-5-methyl-1-(3,3,3-trifluoropropyl)thieno[2,3-d]pyrimidine-2,4(1H,3H)-dione

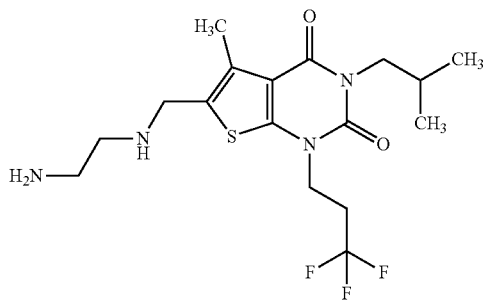 [SMILES: Cc1c(CNCCN)sc2c1c(=O)n(CC(C)C)c(=O)n2CCC(F)(F)F]

600 mg (1.65 mmol) of the compound from Ex. 110A were dissolved in a mixture of 13.59 ml of methanol and 5.84 ml of dichloromethane. Then 1.77 ml (26.49 mmol) of 1,2-diaminoethane and 569 µl (9.93 mmol) of acetic acid were added at RT. The mixture was stirred at RT for 30 min. Then 657 mg (9.93 mmol) of sodium cyanoborohydride were added. After the reaction mixture had been stirred at 70° C. for 24 h, it was admixed with 100 ml of water and extracted with ethyl acetate. The organic extract was washed with saturated sodium chloride solution, dried over anhydrous sodium sulphate, filtered and concentrated. The crude product obtained was purified by preparative HPLC (Method 14). Combination of the product fractions and freeze-drying gave 228 mg (32% of theory, 95% purity) of the title compound.

$^1$H-NMR (400 MHz, DMSO-d$_6$, δ/ppm): 8.56-8.24 (m, 1H), 4.12 (t, 2H), 3.82 (br. s, 3H), 3.71 (d, 3H), 2.84-2.64 (m, 6H), 2.35 (s, 3H), 2.03 (dquin, 1H), 0.84 (d, 6H).

LC/MS (Method 3): $R_t$=0.74 min, m/z=407 [M+H]$^+$.

Example 240A

6-{[(2-Aminoethyl)amino]methyl}-1-(2-fluoroethyl)-3-isobutyl-5-methylthieno[2,3-d]pyrimidine-2,4(1H,3H)-dione

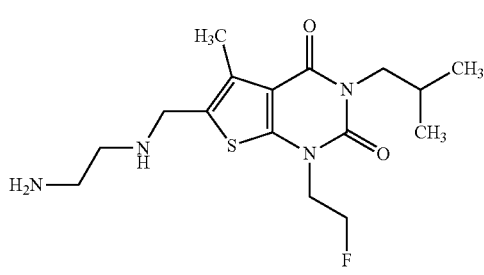 [SMILES: Cc1c(CNCCN)sc2c1c(=O)n(CC(C)C)c(=O)n2CCF]

Analogously to the method described in Ex. 209A, 465 mg (1.49 mmol) of the compound from Ex. 112A and 1,2-diaminoethane were used to prepare 528 mg (75% of theory, 75% purity) of the title compound. The reaction time here was 5 days.

LC/MS (Method 5, ESIpos): $R_t$=0.56 min, m/z=297 [M+H—C$_2$H$_8$N$_2$]$^+$.

Example 241A

6-{[(2-Aminoethyl)amino]methyl}-1-(3-fluoropropyl)-3-isobutyl-5-methylthieno[2,3-d]pyrimidine-2,4(1H,3H)-dione

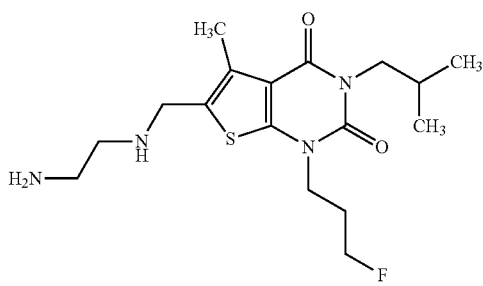 [SMILES: Cc1c(CNCCN)sc2c1c(=O)n(CC(C)C)c(=O)n2CCCF]

Analogously to the method described in Ex. 210A, 320 mg (0.941 mmol) of the compound from Ex. 113A and 1,2-diaminoethane were used to prepare 446 mg (74% of theory, 58% purity) of the title compound.

LC/MS (Method 3): $R_t$=0.64 min, m/z=371 [M+H]$^+$.

Example 242A

6-{[(2-Aminoethyl)amino]methyl}-3-isobutyl-1-(2-methoxyethyl)-5-methylthieno[2,3-d]pyrimidine-2,4(1H,3H)-dione

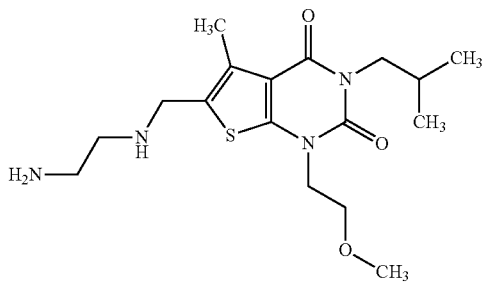 [SMILES: COCCn1c(=O)n(CC(C)C)c(=O)c2c(C)c(CNCCN)sc21]

500 mg (1.49 mmol) of the compound from Ex. 114A were dissolved in a mixture of 30.28 ml of methanol and 14.43 ml of dichloromethane. Then 999 µl (14.95 mmol) of 1,2-diaminoethane and 342 µl (5.98 mmol) of acetic acid were added at RT. The mixture was stirred at RT for 30 min. Then 395 mg (5.98 mmol) of sodium cyanoborohydride were added. After the reaction mixture had been stirred at 60° C. for 89 h, it was admixed with 100 ml of water and extracted with ethyl acetate. The organic extract was washed with saturated sodium chloride solution, dried over anhydrous sodium sulphate, filtered and concentrated. The crude product obtained, after drying under high vacuum, gave 580 mg (73% of theory, 70% purity) of the title compound and was used for subsequent reactions without further purification.

LC/MS (Method 3): $R_t$=0.63 min, m/z=369 [M+H]$^+$.

Example 243A

6-{[(2-Aminoethyl)amino]methyl}-3-isobutyl-5-methyl-1-(oxetan-2-ylmethyl)thieno[2,3-d]pyrimidine-2,4(1H,3H)-dione (racemate)

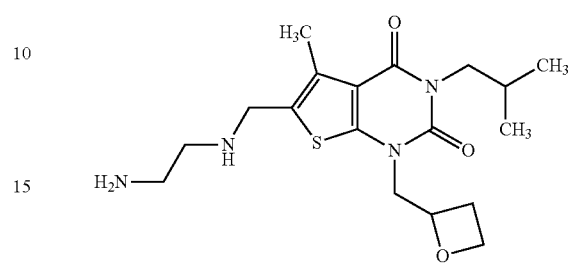

845 mg (2.51 mmol) of the compound from Ex. 116A were dissolved in a mixture of 50.87 ml of methanol and 24.24 ml of dichloromethane. Then 1.68 ml (25.12 mmol) of 1,2-diaminoethane and 575 µl (10.04 mmol) of acetic acid were added at RT. The mixture was stirred at RT for 30 min. Then 664 mg (10.04 mmol) of sodium cyanoborohydride were added. After the reaction mixture had been stirred at 60° C. for 65 h, it was admixed with 250 ml of water and extracted with ethyl acetate. The organic extract was washed with saturated sodium chloride solution, dried over anhydrous sodium sulphate, filtered and concentrated. The crude product obtained, after drying under high vacuum, gave 1.22 g (86% purity) of the title compound and was used for subsequent reactions without further purification.

LC/MS (Method 3): $R_t$=0.62 min, m/z=381 [M+H]$^+$.

Example 244A

6-{[(2-Aminoethyl)amino]methyl}-3-isobutyl-5-methyl-1-(tetrahydrofuran-2-ylmethyl)thieno[2,3-d]pyrimidine-2,4(1H,3H)-dione (racemate)

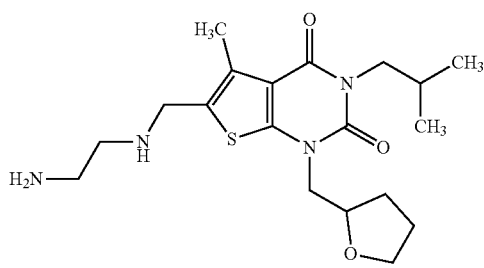 [SMILES: Cc1c(CNCCN)sc2c1c(=O)n(CC(C)C)c(=O)n2CC1CCCO1]

498 mg (1.42 mmol) of the compound from Ex. 117A were dissolved in a mixture of 13 ml of methanol and 5 ml of dichloromethane. Subsequently, at RT, 380 µl (5.68 mmol) of 1,2-diaminoethane, 325 µl (5.68 mmol) of acetic acid and, in portions distributed over about 4 h, 357 mg (5.68 mmol) of sodium cyanoborohydride were added. After the reaction mixture had been stirred at RT for 2 days, it was admixed with 2 M sodium hydroxide solution and extracted with ethyl acetate. The organic extract was washed with saturated sodium chloride solution, dried over anhydrous magnesium sulphate, filtered and concentrated on a rotary evaporator. The crude product thus obtained, after drying under high vacuum, gave 710 mg (98% of theory, 79% purity) of the title compound, which was used for subsequent reactions without further purification.

LC/MS (Method 1, ESIpos): $R_t$=0.50 min, m/z=395 [M+H]$^+$.

Example 245A

6-{[(2-Aminoethyl)amino]methyl}-3-isobutyl-5-methyl-1-methyl-1-(oxetan-3-ylmethyl)thieno[2,3d]pyrimidine-2,4(1H,3H)-dione

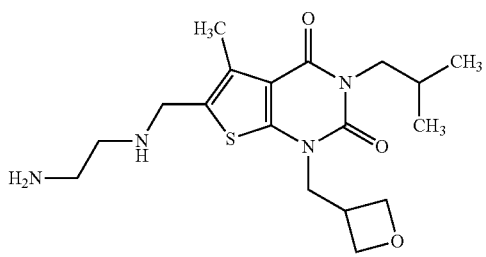 [SMILES: Cc1c(CNCCN)sc2c1c(=O)n(CC(C)C)c(=O)n2CC1COC1]

75 mg (0.223 mmol) of the compound from Ex. 118A were dissolved in a mixture of 2 ml of methanol and 0.8 ml of dichloromethane. Subsequently, at RT, 60 µl (0.892 mmol) of 1,2-diaminoethane, 51 µl (0.892 mmol) of acetic acid and, in portions distributed over about 2 h, 56 mg (0.892 mmol) of sodium cyanoborohydride were added. After the reaction mixture had been stirred at RT for 3 days, it was admixed with 2 M sodium hydroxide solution and extracted with ethyl acetate. The organic extract was washed with saturated sodium chloride solution, dried over anhydrous magnesium sulphate, filtered and concentrated on a rotary evaporator. The crude product thus obtained, after drying under high vacuum, gave 84 mg (70% of theory, 70% purity) of the title compound, which was used for subsequent reactions without further purification.

LC/MS (Method 1, ESIpos): $R_t$=0.47 min, m/z=381 [M+H]$^+$.

Example 246A

6-{[(2-Aminoethyl)amino]methyl}-3-isobutyl-1,5-dimethylthieno[2,3-d]pyrimidine-2,4(1H,3H)-dione

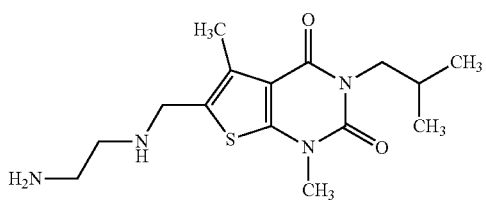 [SMILES: Cc1c(CNCCN)sc2c1c(=O)n(CC(C)C)c(=O)n2C]

Analogously to the method described in Ex. 209A, 170 mg (0.606 mmol) of the compound from Ex. 119A and 1,2-diaminoethane were used to prepare 195 mg (80% of theory, 80% purity) of the title compound. The reaction time here was 5 days.

LC/MS (Method 1, ESIpos): $R_t$=0.48 min, m/z=265 [M+H—C$_2$H$_8$N$_2$]$^+$.

Example 247A

6-{[(2-Aminoethyl)amino]methyl}-5-methyl-3-(2,2,2-trifluoroethyl)-1-(3,3,3-trifluoropropyl)thieno[2,3-d]pyrimidine-2,4(1H,3H)-dione

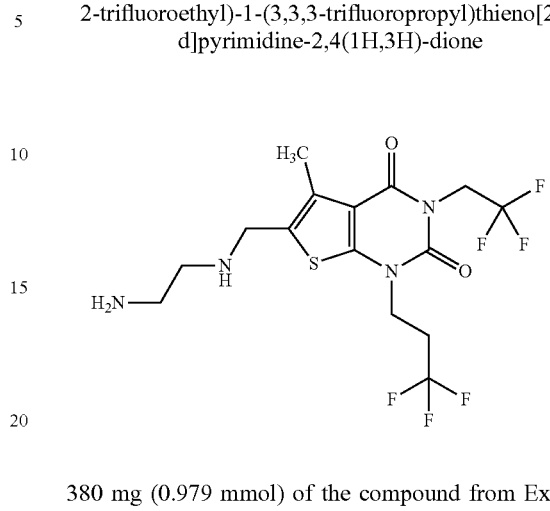

380 mg (0.979 mmol) of the compound from Ex. 120A were dissolved in a mixture of 19.82 ml of methanol and 9.44 ml of dichloromethane. Then 654 µl (9.78 mmol) of 1,2-diaminoethane and 224 µl (3.91 mmol) of acetic acid were added at RT. The mixture was stirred at RT for 30 min. Then 258 mg (3.91 mmol) of sodium cyanoborohydride were added. After the reaction mixture had been stirred at 60° C. for 89 h, it was admixed with 100 ml of water and extracted with ethyl acetate. The organic extract was washed with saturated sodium chloride solution, dried over anhydrous sodium sulphate, filtered and concentrated. The crude product obtained, after drying under high vacuum, gave 526 mg (about 80% purity) of the title compound and was used for subsequent reactions without further purification.

LC/MS (Method 3): $R_t$=0.68 min, m/z=433 [M+H]$^+$.

Example 248A

6-{[(2-Aminoethyl)amino]methyl}-1-(3-fluoropropyl)-5-methyl-3-(2,2,2-trifluoroethyl)thieno[2,3-d]pyrimidine-2,4(1H,3H)-dione

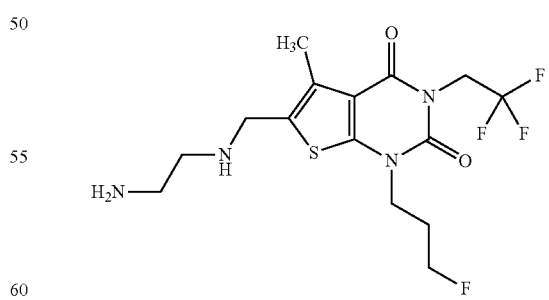

Analogously to the method described in Ex. 210A, 450 mg (1.27 mmol) of the compound from Ex. 121A and 1,2-diaminoethane were used to prepare 521 mg (74% of theory, 72% purity) of the title compound.

LC/MS (Method 3): $R_t$=0.64 min, m/z=397 [M+H]$^+$.

Example 249A

6-{[(2-Aminoethyl)amino]methyl}-1-(2-methoxy-ethyl)-5-methyl-3-(2,2,2-trifluoroethyl)thieno[2,3-d]pyrimidine-2,4(1H,3H)-dione

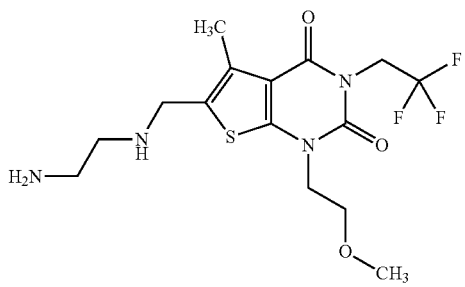 [SMILES: COCCn1c(=O)n(CC(F)(F)F)c(=O)c2c(C)c(CNCCN)sc21]

382 mg (1.09 mmol) of the compound from Ex. 122A were dissolved in a mixture of 18.11 ml of methanol and 7.71 ml of dichloromethane. Then 729 µl (10.9 mmol) of 1,2-diaminoethane and 250 µl (1.05 mmol) of acetic acid were added at RT. The mixture was stirred at RT for 30 min. Then 288 mg (4.36 mmol) of sodium cyanoborohydride were added. After the reaction mixture had been stirred at 60° C. for 112 h, it was admixed with 50 ml of water and extracted with ethyl acetate. The organic extract was washed with saturated sodium chloride solution, dried over anhydrous sodium sulphate, filtered and concentrated. The crude product obtained, after drying under high vacuum, gave 408 mg (62% of theory, 66% purity) of the title compound and was used for subsequent reactions without further purification.

LC/MS (Method 3): $R_t$=0.60 min, m/z=395 [M+H]$^+$.

Example 250A

6-{[(2-Aminoethyl)amino]methyl}-1-(2-ethoxy-ethyl)-5-methyl-3-(2,2,2-trifluoroethyl)thieno[2,3-d]pyrimidine-2,4(1H,3H)-dione

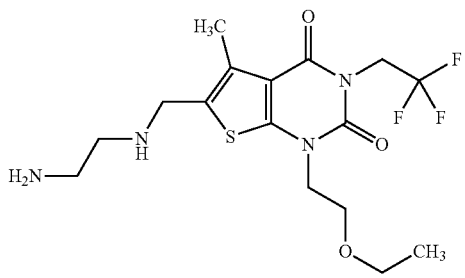 [SMILES: CCOCCn1c(=O)n(CC(F)(F)F)c(=O)c2c(C)c(CNCCN)sc21]

Analogously to the method described in Ex. 210A, 198 mg (0.538 mmol) of the compound from Ex. 123A and 1,2-diaminoethane were used to prepare 227 mg (69% of theory, 64% purity) of the title compound.

LC/MS (Method 3): $R_t$=0.64 min, m/z=409 [M+H]$^+$.

Example 251A

6-{[(2-Aminoethyl)amino]methyl}-5-methyl-1-(oxetan-2-ylmethyl)-3-(2,2,2-trifluoroethyl)thieno[2,3-d]pyrimidine-2,4(1H,3H)-dione (racemate)

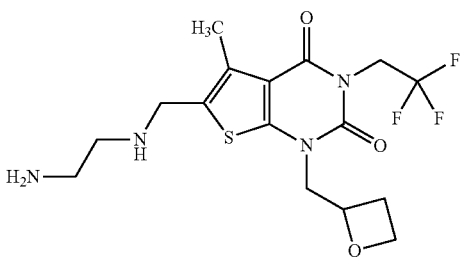 [SMILES: Cc1c(CNCCN)sc2c1c(=O)n(CC(F)(F)F)c(=O)n2CC1CCO1]

605 mg (1.67 mmol) of the compound from Ex. 124A were dissolved in a mixture of 33.82 ml of methanol and 16.11 ml of dichloromethane. Then 1.11 ml (16.69 mmol) of 1,2-diaminoethane and 382 µl (6.68 mmol) of acetic acid were added at RT. The mixture was stirred at RT for 30 min. Then 442 mg (6.68 mmol) of sodium cyanoborohydride were added. After the reaction mixture had been stirred at 60° C. for 89 h, it was admixed with 100 ml of water and extracted with ethyl acetate. The organic extract was washed with saturated sodium chloride solution, dried over anhydrous sodium sulphate, filtered and concentrated. The crude product obtained, after drying under high vacuum, gave 855 mg (about 75% purity) of the title compound and was used for subsequent reactions without further purification.

LC/MS (Method 3): $R_t$=0.55 min, m/z=407 [M+H]$^+$.

Example 252A

6-{[(2-Aminoethyl)amino]methyl}-5-methyl-1-(tetrahydrofuran-2-ylmethyl)-3-(2,2,2-trifluoroethyl)thieno[2,3-d]pyrimidine-2,4(1H,3H)-dione (racemate)

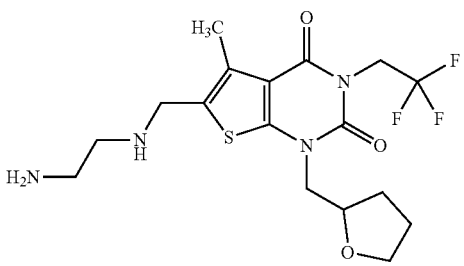 [SMILES: Cc1c(CNCCN)sc2c1c(=O)n(CC(F)(F)F)c(=O)n2CC1CCCO1]

685 mg (1.82 mmol) of the compound from Ex. 125A were dissolved in a mixture of 36.86 ml of methanol and 17.56 ml of dichloromethane. Then 1.217 ml (18.2 mmol) of 1,2-diaminoethane and 417 µl (7.28 mmol) of acetic acid were added at RT. The mixture was stirred at RT for 30 min. Then 481 mg (7.28 mmol) of sodium cyanoborohydride were added. After the reaction mixture had been stirred at 60° C. for 65 h, it was admixed with 100 ml of water and extracted with ethyl acetate. The organic extract was washed with saturated sodium chloride solution, dried over anhydrous sodium sulphate, filtered and concentrated. The crude product obtained, after drying under high vacuum, gave 855 mg (90% of theory, 81% purity) of the title compound and was used for subsequent reactions without further purification.

LC/MS (Method 3): $R_t$=0.63 min, m/z=421 [M+H]$^+$.

Example 253A

6-{[(2-Aminoethyl)amino]methyl}-5-methyl-1-(oxetan-3-ylmethyl)-3-(2,2,2-trifluoroethyl)thieno[2,3-d]pyrimidine-2,4(1H,3H)-dione

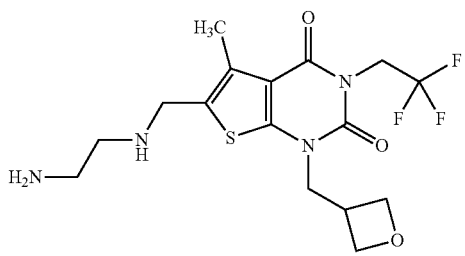 [SMILES: Cc1c(CNCCN)sc2c1c(=O)n(CC(F)(F)F)c(=O)n2CC1COC1]

209 mg (0.577 mmol) of the compound from Ex. 126A were dissolved in a mixture of 11.68 ml of methanol and 5.56 ml of dichloromethane. Then 386 µl (5.76 mmol) of 1,2-diaminoethane and 132 µl (2.31 mmol) of acetic acid were added at RT. The mixture was stirred at RT for 30 min. Then 152 mg (2.31 mmol) of sodium cyanoborohydride were added. After the reaction mixture had been stirred at 60° C. for 89 h, it was admixed with 100 ml of water and extracted with ethyl acetate. The organic extract was washed with saturated sodium chloride solution, dried over anhydrous sodium sulphate, filtered and concentrated. The crude product obtained, after drying under high vacuum, gave 218 mg (31% of theory, 34% purity) of the title compound and was used for subsequent reactions without further purification.

LC/MS (Method 3): $R_t$=0.58 min, m/z=407 [M+H]$^+$.

Example 254A

6-{[(2-Aminoethyl)amino]methyl}-1,5-dimethyl-3-(2,2,2-trifluoroethyl)thieno[2,3-d]pyrimidine-2,4(1H,3H)-dione

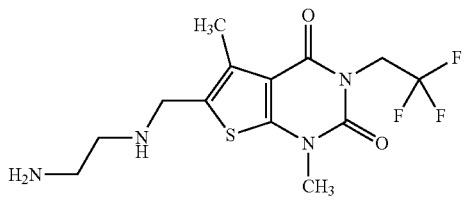 [SMILES: Cc1c(CNCCN)sc2c1c(=O)n(CC(F)(F)F)c(=O)n2C]

Analogously to the method described in Ex. 210A, 400 mg (1.28 mmol) of the compound from Ex. 127A and 1,2-diaminoethane were used to prepare 508 mg (49% of theory, 44% purity) of the title compound.

LC/MS (Method 3): $R_t$=0.53 min, m/z=351 [M+H]$^+$.

Example 255A

6-{[(2-Aminoethyl)amino]methyl}-3-(2,2-difluoroethyl)-5-methyl-1-(3,3,3-trifluoropropyl)thieno[2,3-d]pyrimidine-2,4(1H,3H)-dione

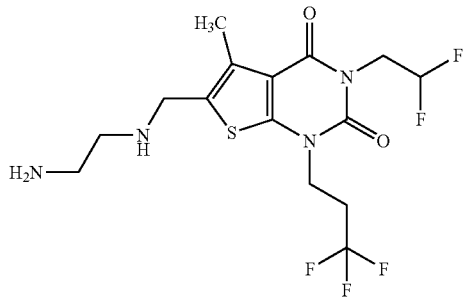 [SMILES: Cc1c(CNCCN)sc2c1c(=O)n(CC(F)F)c(=O)n2CCC(F)(F)F]

315 mg (0.815 mmol) of the compound from Ex. 128A were dissolved in a mixture of 17.23 ml of methanol and 8.21 ml of dichloromethane. Then 569 µl (8.5 mmol) of 1,2-diaminoethane and 195 µl (3.4 mmol) of acetic acid were added at RT. The mixture was stirred at RT for 30 min. Then 225 mg (3.4 mmol) of sodium cyanoborohydride were added. After the reaction mixture had been stirred at 60° C. for 90 h, it was admixed with 100 ml of water and extracted with ethyl acetate. The organic extract was washed with saturated sodium chloride solution, dried over anhydrous sodium sulphate, filtered and concentrated. The crude product obtained, after drying under high vacuum, gave 402 mg (81% of theory, 71% purity) of the title compound and was used for subsequent reactions without further purification.

LC/MS (Method 3): $R_t$=0.61 min, m/z=415 [M+H]$^+$.

Example 256A

6-{[(2-Aminoethyl)amino]methyl}-3-(2,2-difluoroethyl)-1-(3-fluoropropyl)-5-methylthieno[2,3-d]pyrimidine-2,4(1H,3H)-dione

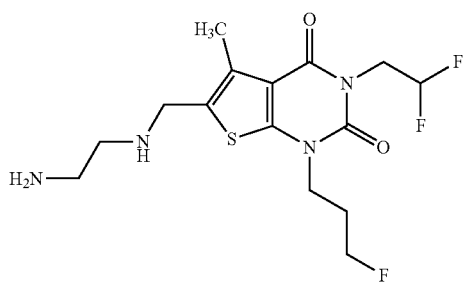 [SMILES: Cc1c(CNCCN)sc2c1c(=O)n(CC(F)F)c(=O)n2CCCF]

Analogously to the method described in Ex. 210A, 300 mg (0.879 mmol) of the compound from Ex. 129A and 1,2-diaminoethane were used to prepare 395 mg (99% of theory, 84% purity) of the title compound.

LC/MS (Method 3): $R_t$=0.54 min, m/z=379 [M+H]$^+$.

Example 257A

6-{[(2-Aminoethyl)amino]methyl}-3-(2,2-difluoro-ethyl)-1-(2-methoxyethyl)-5-methylthieno[2,3-d]pyrimidine-2,4(1H,3H)-dione

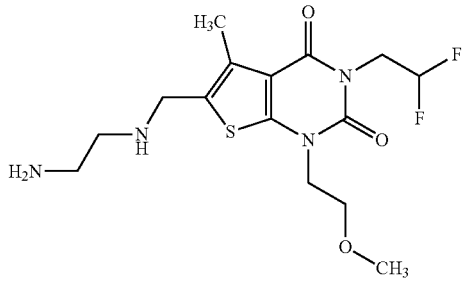 [SMILES: COCCn1c(=O)n(CC(F)F)c(=O)c2c(C)c(CNCCN)sc21]

300 mg (0.894 mmol) of the compound from Ex. 130A were dissolved in a mixture of 18.1 ml of methanol and 8.62 ml of dichloromethane. Then 597 µl (8.93 mmol) of 1,2-diaminoethane and 205 µl (3.57 mmol) of acetic acid were added at RT. The mixture was stirred at RT for 30 min. Then 236 mg (3.57 mmol) of sodium cyanoborohydride were added. After the reaction mixture had been stirred at 60° C. for 64 h, it was admixed with 100 ml of water and extracted with ethyl acetate. The organic extract was washed with saturated sodium chloride solution, dried over anhydrous sodium sulphate, filtered and concentrated. The crude product obtained, after drying under high vacuum, gave 356 mg (76% of theory, 72% purity) of the title compound and was used for subsequent reactions without further purification.

LC/MS (Method 3): $R_t$=0.48 min, m/z=377 [M+H]$^+$.

Example 258A

6-{[(2-Aminoethyl)amino]methyl}-3-(2,2-difluoro-ethyl)-1-(2-ethoxyethyl)-5-methylthieno[2,3-d]pyrimidine-2,4(1H,3H)-dione

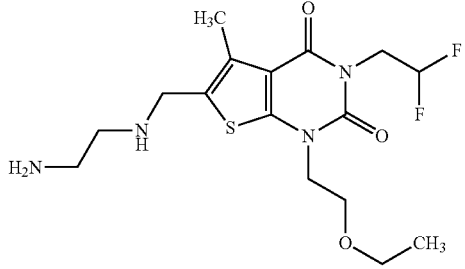 [SMILES: CCOCCn1c(=O)n(CC(F)F)c(=O)c2c(C)c(CNCCN)sc21]

Analogously to the method described in Ex. 210A, 185 mg (0.518 mmol) of the compound from Ex. 131A and 1,2-diaminoethane were used to prepare 240 mg (89% of theory, 75% purity) of the title compound.

LC/MS (Method 3): $R_t$=0.58 min, m/z=391 [M+H]$^+$.

Example 259A

6-{[(2-Aminoethyl)amino]methyl}-3-(2,2-difluoro-ethyl)-5-methyl-1-(oxetan-2-ylmethyl)thieno[2,3-d]pyrimidine-2,4(1H,3H)-dione (racemate)

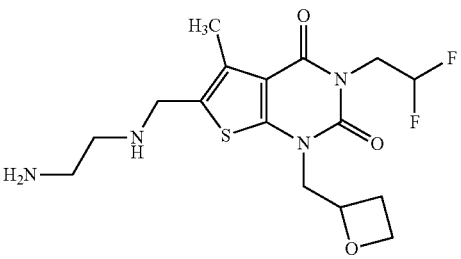 [SMILES: Cc1c(CNCCN)sc2c1c(=O)n(CC(F)F)c(=O)n2CC1CCO1]

330 mg (0.939 mmol) of the compound from Ex. 132A were dissolved in a mixture of 19 ml of methanol and 9 ml of dichloromethane. Then 628 µl (9.39 mmol) of 1,2-diaminoethane and 215 µl (3.75 mmol) of acetic acid were added at RT. The mixture was stirred at RT for 30 min. Then 248 mg (3.75 mmol) of sodium cyanoborohydride were added. After the reaction mixture had been stirred at 60° C. for 60 h, it was admixed with 100 ml of water and extracted with ethyl acetate. The organic extract was washed with saturated sodium chloride solution, dried over anhydrous sodium sulphate, filtered and concentrated. The crude product obtained, after drying under high vacuum, gave 446 mg (96% of theory, 79% purity) of the title compound and was used for subsequent reactions without further purification.

LC/MS (Method 3): $R_t$=0.51 min, m/z=389 [M+H]$^+$.

Example 260A

6-{[(2-Aminoethyl)amino]methyl}-3-(2,2-difluoro-ethyl)-5-methyl-1-(tetrahydrofuran-2-ylmethyl)thieno[2,3-d]pyrimidine-2,4(1H,3H)-dione (racemate)

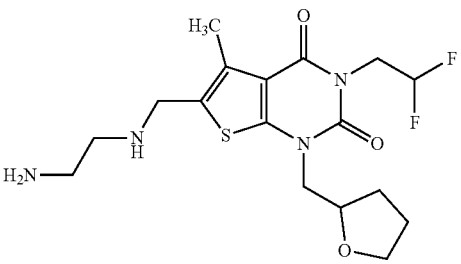 [SMILES: Cc1c(CNCCN)sc2c1c(=O)n(CC(F)F)c(=O)n2CC1CCCO1]

515 mg (1.437 mmol) of the compound from Ex. 133A were dissolved in a mixture of 29.1 ml of methanol and 13.87 ml of dichloromethane. Then 961 µl (14.37 mmol) of 1,2-diaminoethane and 329 µl (5.74 mmol) of acetic acid were added at RT. The mixture was stirred at RT for 30 min. Then 380 mg (5.74 mmol) of sodium cyanoborohydride were added. After the reaction mixture had been stirred at 60° C. for 67 h, it was admixed with 100 ml of water and extracted with ethyl acetate. The organic extract was washed with saturated sodium chloride solution, dried over anhydrous sodium sulphate, filtered and concentrated. The crude product obtained, after drying under high vacuum, gave 667 mg (72% of theory, 63% purity) of the title compound and was used for subsequent reactions without further purification.

LC/MS (Method 3): $R_t$=0.55 min, m/z=403 [M+H]$^+$.

Example 261A

6-{[(2-Aminoethyl)amino]methyl}-3-(2,2-difluoroethyl)-5-methyl-1-(oxetan-3-ylmethyl)thieno[2,3-d]pyrimidine-2,4(1H,3H)-dione

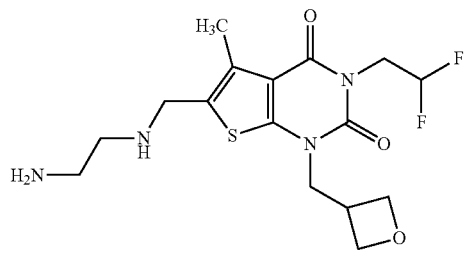 [SMILES: Cc1c(CNCCN)sc2c1c(=O)n(CC(F)F)c(=O)n2CC1COC1]

197 mg (0.571 mmol) of the compound from Ex. 134A were dissolved in a mixture of 11.56 ml of methanol and 5.51 ml of dichloromethane. Then 382 µl (5.71 mmol) of 1,2-diaminoethane and 131 µl (2.28 mmol) of acetic acid were added at RT. The mixture was stirred at RT for 30 min. Then 151 mg (2.28 mmol) of sodium cyanoborohydride were added. After the reaction mixture had been stirred at 60° C. for 63 h, it was admixed with 100 ml of water and extracted with ethyl acetate. The organic extract was washed with saturated sodium chloride solution, dried over anhydrous sodium sulphate, filtered and concentrated. The crude product obtained, after drying under high vacuum, gave 171 mg (51% of theory, 67% purity) of the title compound and was used for subsequent reactions without further purification.

LC/MS (Method 3): $R_t$=0.51 min, m/z=389 [M+H]$^+$.

Example 262A

6-{[(2-Aminoethyl)amino]methyl}-1,3-bis(2-methoxyethyl)-5-methylthieno[2,3-d]pyrimidine-2,4(1H,3H)-dione

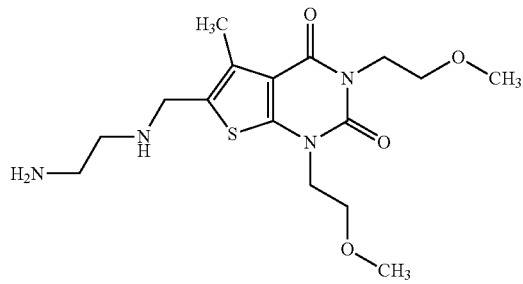 [SMILES: COCCn1c(=O)c2c(C)c(CNCCN)sc2n(CCOC)c1=O]

357 mg (1.08 mmol) of the compound from Ex. 136A were dissolved in a mixture of 21.93 ml of methanol and 10.45 ml of dichloromethane. Then 724 µl (10.83 mmol) of 1,2-diaminoethane and 248 µl (4.33 mmol) of acetic acid were added at RT. The mixture was stirred at RT for 30 min. Then 286 mg (4.33 mmol) of sodium cyanoborohydride were added. After the reaction mixture had been stirred at 60° C. for 112 h, it was admixed with 100 ml of water and extracted with ethyl acetate. The organic extract was washed with saturated sodium chloride solution, dried over anhydrous sodium sulphate, filtered and concentrated. The crude product obtained, after drying under high vacuum, gave 597 mg (73% of theory, 49% purity) of the title compound and was used for subsequent reactions without further purification.

LC/MS (Method 3): $R_t$=0.49 min, m/z=371 [M+H]$^+$.

Example 263A

6-{[(2-Aminoethyl)amino]methyl}-1-(2-ethoxyethyl)-3-(2-methoxyethyl)-5-methylthieno[2,3-d]pyrimidine-2,4(1H,3H)-dione

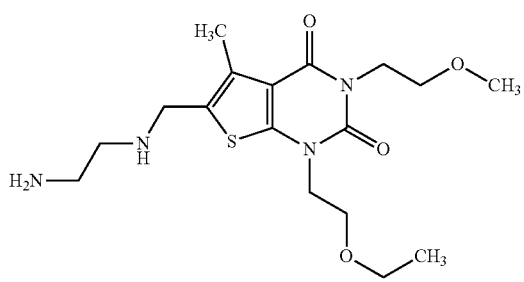 [SMILES: CCOCCn1c(=O)n(CCOC)c(=O)c2c(C)c(CNCCN)sc21]

Analogously to the method described in Ex. 210A, 355 mg (1.01 mmol) of the compound from Ex. 136A and 1,2-diaminoethane were used to prepare 287 mg (42% of theory, 58% purity) of the title compound.

LC/MS (Method 3): $R_t$=0.54 min, m/z=385 [M+H]$^+$.

Example 264A

6-{[(2-Aminoethyl)amino]methyl}-5-(difluoromethyl)-3-ethyl-1-(3,3,3-trifluoropropyl)thieno[2,3-d]pyrimidine-2,4(1H,3H)-dione

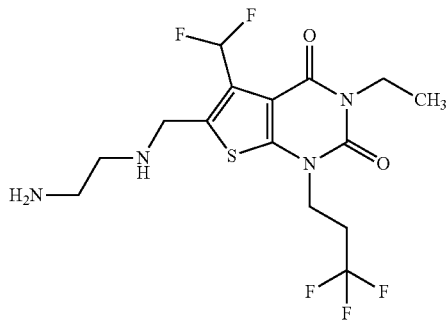 [SMILES: CCn1c(=O)c2c(C(F)F)c(CNCCN)sc2n(CCC(F)(F)F)c1=O]

Analogously to the method described in Ex. 210A, 300 mg (0.81 mmol) of the compound from Ex. 185A and 1,2-diaminoethane were used to prepare 370 mg (24% of theory, 22% purity) of the title compound.

LC/MS (Method 3): $R_t$=0.74 min, m/z=415 [M+H]$^+$.

Example 265A

6-{[(2-Aminoethyl)amino]methyl}-5-(difluoromethyl)-3-ethyl-4(2-methoxyethyl)thieno[2,3-d]pyrimidine-2,4(1H,3H)-dione

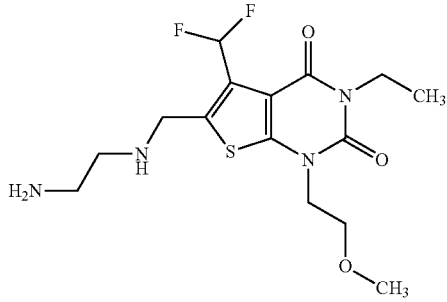 [SMILES: CCn1c(=O)c2c(C(F)F)c(CNCCN)sc2n(CCOC)c1=O]

Analogously to the method described in Ex. 210A, 300 mg (0.894 mmol) of the compound from Ex. 186A and 1,2-diaminoethane were used to prepare 345 mg (15% of theory, 15% purity) of the title compound.

LC/MS (Method 3): $R_t$=0.62 min, m/z=377 [M+H]$^+$.

Example 266A

6-{[(2-Aminopropyl)amino]methyl}-3-ethyl-1-(2-methoxyethyl)-5-methylthieno[2,3-d]pyrimidine-2,4(1H,3H)-dione (racemate)

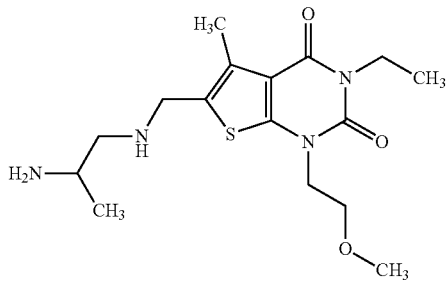 [SMILES: CCn1c(=O)c2c(C)c(CNCC(C)N)sc2n(CCOC)c1=O]

Analogously to the method described in Ex. 210A, 300 mg (0.894 mmol) of the compound from Ex. 84A and racemic 1,2-diaminopropane were used to prepare 411 mg (79% of theory, 69% purity) of the title compound.

LC/MS (Method 3): $R_t$=0.53 min, m/z=355 [M+H]$^+$.

Example 267A

6-{[(2,2-Dimethoxyethyl)amino]methyl}-3-ethyl-5-methyl-1-(3,3,3-trifluoropropyl)thieno[2,3-d]pyrimidine-2,4(1H,3H)-dione

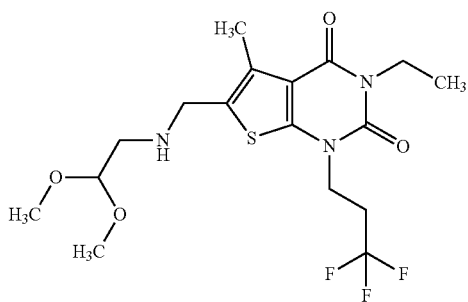 [SMILES: CCn1c(=O)c2c(C)c(CNCC(OC)OC)sc2n(CCC(F)(F)F)c1=O]

150 mg (0.413 mmol, 92% purity) of the compound from Ex. 74A were dissolved in 10 ml of methanol, and 65 mg (0.619 mmol) of 2,2-dimethoxyethanamine were added. Then the mixture was heated at 70° C. for 4 h. After cooling to RT, 276 mg (1.24 mmol) of sodium triacetoxyborohydride were added. Stirring was continued at RT. After 18 h, another 65 mg (0.619 mmol) of 2,2-dimethoxyethanamine and, 30 min later, a further 276 mg (1.24 mmol) of sodium triacetoxyborohydride were added. After a further 18 h and stirring at RT for 36 h, the same amounts of 2,2-dimethoxyethanamine and sodium triacetoxyborohydride were added once again. Lastly, the reaction mixture was heated under reflux for 3 h. After cooling to RT, the mixture was diluted with ethyl acetate and washed successively with saturated sodium hydrogencarbonate solution and saturated sodium chloride solution. After drying over anhydrous magnesium sulphate, the mixture was filtered and the filtrate was evaporated to dryness. The residue obtained was separated into its components by means of preparative HPLC (Method 8). After concentration of the product fractions and drying under high vacuum, 115 mg (62% of theory, 95% purity) of the title compound were obtained.

LC/MS (Method 1, ESIpos): $R_t$=0.63 min, m/z=424 [M+H]$^+$.

Example 268A

6-{[(2,2-Dimethoxyethyl)amino]methyl}-3-ethyl-1-(2-methoxyethyl)-5-methylthieno[2,3-d]pyrimidine-2,4(1H,3H)-dione

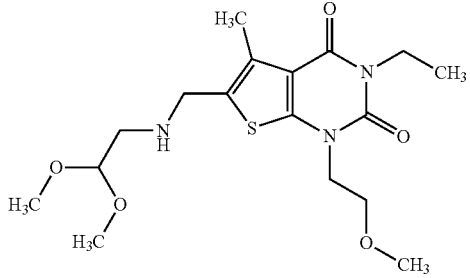 [SMILES: CCn1c(=O)c2c(C)c(CNCC(OC)OC)sc2n(CCOC)c1=O]

300 mg (0.922 mmol, 91% purity) of the compound from Ex. 84A were dissolved in 21 ml of dichloromethane, and 145 mg (1.38 mmol) of 2,2-dimethoxyethanamine were added. The mixture was heated to reflux for 1 h. After cooling to RT, 586 mg (2.76 mmol) of sodium triacetoxyborohydride were added. Stirring was continued at RT. After 18 h, the mixture was diluted with ethyl acetate and washed successively with saturated sodium hydrogencarbonate solution and saturated sodium chloride solution. After drying over anhydrous magnesium sulphate, the mixture was filtered and the filtrate was evaporated to dryness. The residue obtained was purified by means of chromatography on silica gel with cyclohexane/ethyl acetate 2:1 and then dichloromethane/methanol 20:1 as eluent. After concentration of the product fractions and drying under high vacuum, 300 mg (78% of theory, 93% purity) of the title compound were obtained.

$^1$H-NMR (400 MHz, DMSO-$d_6$, δ/ppm): 4.41 (t, 1H), 4.03 (t, 2H), 3.90 (q, 2H), 3.82 (s, 2H), 3.63 (t, 2H), 3.26 (s, 6H), 3.24 (s, 3H), 2.62 (d, 2H), 2.33 (s, 3H), 1.11 (t, 3H).

LC/MS (Method 1, ESIpos): $R_t$=0.53 min, m/z=281 [M+H—$C_4H_{11}NO_2$]$^+$.

Example 269A

6-{[(1,1-Dimethoxypropan-2-yl)amino]methyl}-3-ethyl-5-methyl-1-(3,3,3-trifluoropropyl)thieno[2,3-d]pyrimidine-2,4(1H,3H)-dione (racemate)

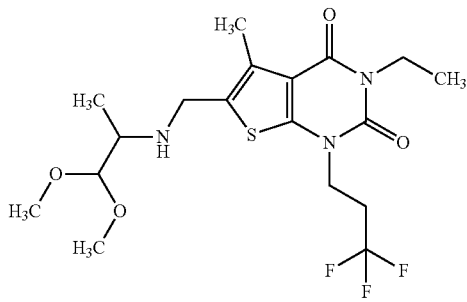 [SMILES: CCn1c(=O)c2c(C)c(CNC(C)C(OC)OC)sc2n(CCC(F)(F)F)c1=O]

Analogously to the method described in Ex. 268A, 250 mg (0.680 mmol, 91% purity) of the compound from Ex. 74A and 162 mg (1.36 mmol) of racemic 2-aminopropanal dimethyl acetal were used to prepare 214 mg (71% of theory) of the title compound. Chromatography was effected here using a Biotage Isolera One system with a Biotage cartridge (SNAP KP-Sil, 50 g of silica gel) and cyclohexane/ethyl acetate 1:2 as eluent.

$^1$H-NMR (400 MHz, DMSO-$d_6$, δ/ppm): 4.17-4.07 (m, 3H), 3.90 (q, 2H), 3.87 (s, 2H), 3.31 (s, 3H), 3.30 (s, 3H), 2.84-2.67 (m, 3H), 2.34 (s, 3H), 1.11 (t, 3H), 0.97 (d, 3H).

LC/MS (Method 6, ESIpos): $R_t$=1.88 min, m/z=438 [M+H]$^+$.

Example 270A

6-{[(1,1-Dimethoxypropan-2-yl)amino]methyl}-3-ethyl-1-(2-methoxyethyl)-5-methylthieno[2,3-d]pyrimidine-2,4(1H,3H)-dione (racemate)

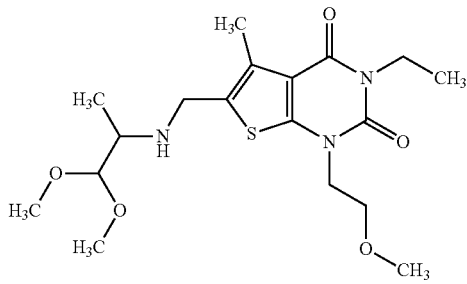 [SMILES: CCn1c(=O)c2c(C)c(CNC(C)C(OC)OC)sc2n(CCOC)c1=O]

Analogously to the method described in Ex. 268A, 250 mg (0.844 mmol) of the compound from Ex. 84A and 201 mg (1.69 mmol) of racemic 2-aminopropanal dimethyl acetal were used to prepare 154 mg (45% of theory) of the title compound. Chromatography was effected here using a Biotage Isolera One system with a Biotage cartridge (SNAP KP-Sil, 25 g of silica gel) and cyclohexane/ethyl acetate 1:2 as eluent.

$^1$H-NMR (400 MHz, DMSO-$d_6$, δ/ppm): 4.13 (d, 1H), 4.03 (t, 2H), 3.90 (q, 2H), 3.85 (s, 2H), 3.63 (t, 2H), 3.33 (s, 3H), 3.31 (s, 3H), 3.30 (s, 3H), 2.76-2.70 (m, 1H), 2.33 (s, 3H), 1.11 (t, 3H), 0.97 (d, 3H).

LC/MS (Method 6, ESIpos): $R_t$=1.58 min, m/z=400 [M+H]$^+$.

Example 271A

3-Ethyl-5-methyl-6-({[(2-methyl-1,3-dioxolan-2-yl)methyl]amino}methyl)-1-(3,3,3-trifluoropropyl)thieno[2,3-d]pyrimidine-2,4(1H,3H)-dione

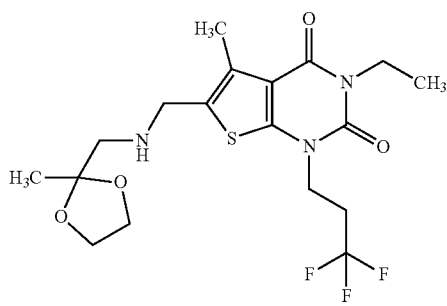 [SMILES: CCn1c(=O)c2c(C)c(CNCC3(C)OCCO3)sc2n(CCC(F)(F)F)c1=O]

Analogously to the method described in Ex. 268A, 250 mg (0.748 mmol) of the compound from Ex. 74A and 175 mg (1.50 mmol) of 2-(aminomethyl)-2-methyl-1,3-dioxolane were used to prepare 344 mg (85% of theory, 81% purity) of the title compound. Chromatographic purification was dispensed with here.

LC/MS (Method 1, ESIpos): $R_t$=0.61 min, m/z=436 [M+H]$^+$.

Example 272A

3-Ethyl-1-(2-methoxyethyl)-5-methyl-6-({[(2-methyl-1,3-dioxolan-2-yl)methyl]amino}methyl)thieno[2,3-d]pyrimidine-2,4(1H,3H)-dione

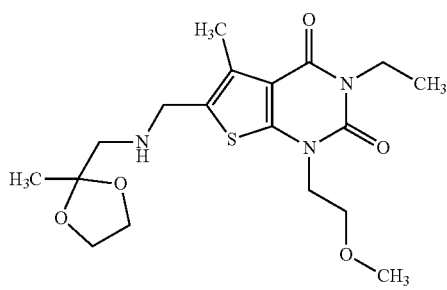 [SMILES: CCn1c(=O)c2c(C)c(CNCC3(C)OCCO3)sc2n(CCOC)c1=O]

Analogously to the method described in Ex. 268A, 250 mg (0.844 mmol) of the compound from Ex. 84A and 197 mg (1.69 mmol) of 2-(aminomethyl)-2-methyl-1,3-dioxolane were used to prepare 340 mg (84% of theory, 83% purity) of the title compound. Chromatographic purification was dispensed with here.

LC/MS (Method 1, ESIpos): $R_t$=0.51 min, m/z=398 [M+H]$^+$.

Example 273A 1-(2,2-Dimethoxyethyl)-1-{[3-ethyl-5-methyl-2,4-dioxo-1-(3,3,3-trifluoropropyl)-1,2,3,4-tetrahydrothieno[2,3-d]pyrimidin-6-yl]methyl}urea

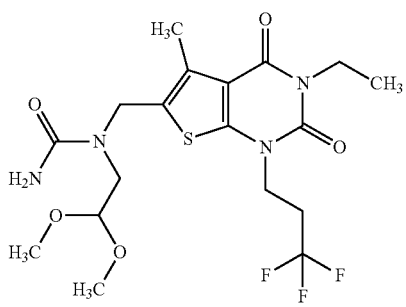 [SMILES: CCn1c(=O)c2c(C)c(CN(CC(OC)OC)C(N)=O)sc2n(CCC(F)(F)F)c1=O]

To a solution of 154 mg (0.364 mmol) of the compound from Ex. 267A in 6 ml of methanol were added, at RT, first 68 mg (0.836 mmol) of potassium cyanate and then 53 µl (0.618 mmol) of perchloric acid (70% in water). After 1 h, the reaction mixture was admixed with saturated aqueous sodium hydrogencarbonate solution and then extracted with ethyl acetate. The organic extract was washed successively with water and saturated sodium chloride solution, dried over anhydrous magnesium sulphate, filtered and concentrated. After the residue obtained had been dried under high vacuum, 103 mg (47% of theory, 78% purity) of the title compound were obtained, which was used for subsequent reactions without further purification.

LC/MS (Method 2, ESIpos): $R_t$=2.45 min, m/z=467 [M+H]$^+$.

Example 274A 1-(2,2-Dimethoxyethyl)-1-{[3-ethyl-1-(2-methoxyethyl)-5-methyl-2,4-dioxo-1,2,3,4-tetrahydrothieno[2,3-d]pyrimidin-6-yl]methyl}urea

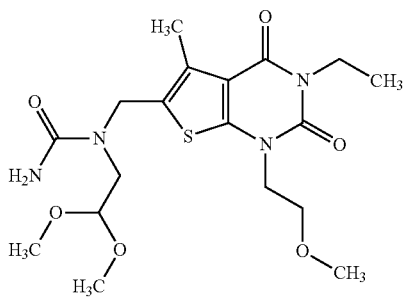 [SMILES: CCn1c(=O)c2c(C)c(CN(CC(OC)OC)C(N)=O)sc2n(CCOC)c1=O]

Analogously to the method described in Ex. 273A, 300 mg (0.724 mmol, 93% purity) of the compound from Ex. 268A, 135 mg (1.67 mmol) of potassium cyanate and 106 µl (1.23 mmol) of perchloric acid (70% in water) were used to prepare 200 mg (54% of theory, 84% purity) of the title compound. The reaction time here was 2 h.

$^1$H-NMR (400 MHz, DMSO-$d_6$, δ/ppm): 6.03 (s, 2H), 4.54 (s, 2H), 4.44 (t, 1H), 4.01 (t, 2H), 3.90 (q, 2H), 3.62 (t, 2H), 3.31 (s, 6H, partially obscured by the water signal), 3.23 (s, 3H), 3.16 (d, 2H), 2.39 (s, 3H), 1.11 (t, 3H).

LC/MS (Method 1, ESIpos): $R_t$=0.76 min, m/z=429 [M+H]$^+$.

Example 275A 1-(1,1-Dimethoxypropan-2-yl)-1-{[3-ethyl-5-methyl-2,4-dioxo-1-(3,3,3-trifluoropropyl)-1,2,3,4-tetrahydrothieno[2,3-d]pyrimidin-6-yl]methyl}urea (racemate)

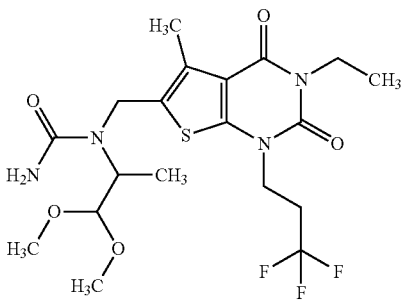 [SMILES: CCn1c(=O)c2c(C)c(CN(C(N)=O)C(C)C(OC)OC)sc2n(CCC(F)(F)F)c1=O]

Analogously to the method described in Ex. 273A, 202 mg (0.462 mmol) of the compound from Ex. 269A, 86 mg (1.06 mmol) of potassium cyanate and 68 µl (0.785 mmol) of perchloric acid (70% in water) were used to prepare 221 mg (64% of theory, 65% purity) of the title compound. The reaction time here was 3 h.

LC/MS (Method 1, ESIpos): $R_t$=0.91 min, m/z=481 [M+H]$^+$.

Example 276A 1-(1,1-Dimethoxypropan-2-yl)-1-{[3-ethyl-1-(2-methoxyethyl)-5-methyl-2,4-dioxo-1,2,3,4-tetrahydrothieno[2,3-d]pyrimidin-6-yl]methyl}urea (racemate)

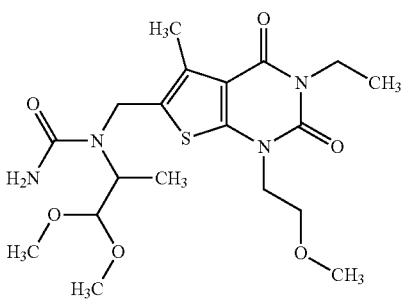 [SMILES: CCn1c(=O)c2c(C)c(CN(C(N)=O)C(C)C(OC)OC)sc2n(CCOC)c1=O]

Analogously to the method described in Ex. 273A, 145 mg (0.363 mmol) of the compound from Ex. 270A, 68 mg (0.835 mmol) of potassium cyanate and 53 µl (0.617 mmol) of perchloric acid (70% in water) were used to prepare 160 mg (59% of theory, 60% purity) of the title compound. The reaction time here was 3 h.

LC/MS (Method 1, ESIpos): $R_t$=0.77 min, m/z=443 [M+H]$^+$.

Example 277A

1-{[3-Ethyl-5-methyl-2,4-dioxo-1-(3,3,3-trifluoropropyl)-1,2,3,4-tetrahydrothieno[2,3-d]pyrimidin-6-yl]methyl}-1-[(2-methyl-1,3-dioxolan-2-yl)methyl]urea

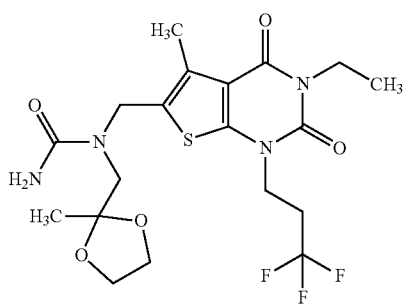 [SMILES: CCn1c(=O)c2c(C)c(CN(CC3(C)OCCO3)C(N)=O)sc2n(CCC(F)(F)F)c1=O]

Analogously to the method described in Ex. 273A, 344 mg (0.640 mmol, 81% purity) of the compound from Ex. 271A, 119 mg (1.42 mmol) of potassium cyanate and 94 µl (1.09 mmol) of perchloric acid (70% in water) were used to prepare 124 mg (34% of theory, 85% purity) of the title compound. The reaction time here was 2 h, and the product was isolated from the reaction mixture by means of preparative HPLC (Method 8).

$^1$H-NMR (400 MHz, DMSO-$d_6$, δ/ppm): 6.01 (s, 2H), 4.60 (s, 2H), 4.08 (t, 2H), 3.96-3.81 (m, 6H), 3.21 (s, 2H), 2.83-2.66 (m, 2H), 2.41 (s, 3H), 1.24 (s, 3H), 1.11 (t, 3H).

LC/MS (Method 1, ESIpos): $R_t$=0.90 min, m/z=479 [M+H]$^+$.

Example 278A

1-{[3-Ethyl-1-(2-methoxyethyl)-5-methyl-2,4-dioxo-1,2,3,4-tetrahydrothieno[2,3-d]pyrimidin-6-yl]methyl}-1-[(2-methyl-1,3-dioxolan-2-yl)methyl]urea

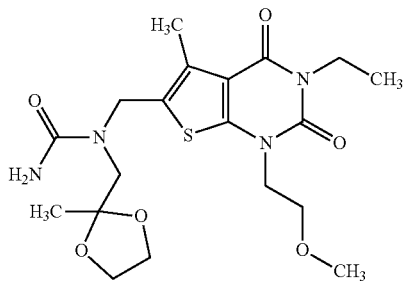 [SMILES: CCn1c(=O)c2c(C)c(CN(CC3(C)OCCO3)C(N)=O)sc2n(CCOC)c1=O]

Analogously to the method described in Ex. 273A, 339 mg (0.708 mmol, 83% purity) of the compound from Ex. 272A, 132 mg (1.63 mmol) of potassium cyanate and 104 µl (1.09 mmol) of perchloric acid (70% in water) were used to prepare 182 mg (58% of theory) of the title compound. The reaction time here was 2 h, and the product was isolated from the reaction mixture by means of preparative HPLC (Method 8).

$^1$H-NMR (400 MHz, DMSO-$d_6$, δ/ppm): 5.99 (s, 2H), 4.58 (s, 2H), 4.00 (t, 2H), 3.95-3.82 (m, 6H), 3.62 (t, 2H), 3.23 (s, 3H), 3.20 (s, 2H), 2.39 (s, 3H), 1.24 (s, 3H), 1.11 (t, 3H).

LC/MS (Method 1, ESIpos): $R_t$=0.80 min, m/z=441 [M+H]$^+$.

Example 279A

N-{[3-Ethyl-5-methyl-2,4-dioxo-1-(3,3,3-trifluoropropyl)-1,2,3,4-tetrahydrothieno[2,3-d]pyrimidin-6-yl]methyl}-2-formylhydrazinecarboxamide

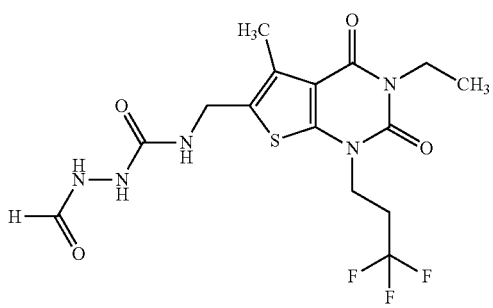 [SMILES: CCn1c(=O)c2c(C)c(CNC(=O)NNC=O)sc2n(CCC(F)(F)F)c1=O]

Preparation of the acid chloride: To a solution of 250 mg (0.686 mmol) of the compound from Ex. 189A in 12 ml of dichloromethane were added, at RT, first 78 µl (0.892 mmol) of oxalyl chloride and then a small drop of DMF. After the reaction mixture had been stirred at RT for 2 h, it was concentrated to dryness on a rotary evaporator. The remaining residue was dried under high vacuum and then converted further in the next step.

Preparation of the acid azide: The acid chloride obtained beforehand was dissolved in 12 ml of toluene, and 67 mg (1.03 mmol) of sodium azide were added. The reaction mixture was stirred at RT for about 18 h. In the course of this, a fine solid precipitated out, which was filtered off. The filtrate was converted further as such in the next step.

Preparation of the isocyanate: The filtrate obtained beforehand (solution of the acid azide) was heated under reflux for 1.5 h. After cooling to RT, the solution of isocyanate thus obtained was converted further as such in the next step.

Preparation of the urea: To the solution of isocyanate obtained beforehand were added a solution of 41 mg (0.686 mmol) of formylhydrazine in 3 ml of THF and 105 µl (0.755 mmol) of triethylamine. After the reaction mixture had been stirred at RT for about 18 h, 20 ml of saturated aqueous ammonium chloride solution were added. Extraction was effected four times with about 20 ml each time of ethyl acetate. The combined organic extract was washed with saturated sodium chloride solution, dried over anhydrous magnesium sulphate, filtered and concentrated. The remaining residue was separated into its components by means of preparative HPLC (Method 8). The product fractions were combined, concentrated and dried under high vacuum. 83 mg (28% of theory, 98% pure) of the title compound were obtained.

$^1$H-NMR (Major rotamer; 500 MHz, DMSO-$d_6$, δ/ppm): 9.61 (s, 1H), 8.05 (s, 1H), 7.97 (s, 1H), 7.10 (br. s, 1H), 4.35-4.25 (m, 2H), 4.09 (t, 2H), 3.90 (q, 2H), 2.84-2.68 (m, 2H), 2.39 (s, 3H), 1.11 (t, 3H).

LC/MS (Method 1, ESIpos): $R_t$=0.72 min, m/z=422 [M+H]$^+$.

Example 280A

Ethyl 2-{[(2,2-dimethylpropyl)carbamoyl]amino}-4-methylthiophene-3-carboxylate

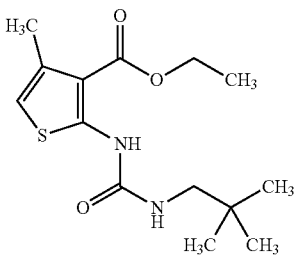 [SMILES: CCOC(=O)c1c(C)csc1NC(=O)NCC(C)(C)C]

To a solution of 2 g (10.5 mmol) of ethyl 2-amino-4-methylthiophene-3-carboxylate in 10 ml of pyridine were added 2.42 g (20.9 mmol) of 2,2-dimethylpropyl isocyanate. The reaction mixture was stirred at 50° C. for 21 h. Thereafter, another 1.18 g (10.5 mmol) of 2,2-dimethylpropyl isocyanate were added, and the mixture was stirred at 50° C. for a further 23 h. The reaction mixture was then concentrated to dryness on a rotary evaporator. The remaining residue was dissolved in dichloromethane and concentrated to dryness again. The material thus obtained was chromatographed using a silica gel cartridge (Biotage, 340 g of silica gel, eluent: hexane/ethyl acetate). 3.07 g (98% of theory) of the title compound were obtained.

$^1$H-NMR (400 MHz, DMSO-$d_6$, δ/ppm): 10.37 (s, 1H), 7.84 (t, 1H), 6.41 (s, 1H), 4.28 (q, 2H), 2.92 (d, 2H), 2.26 (d, 3H), 1.31 (t, 3H), 0.87 (s, 9H).

LC/MS (Method 3, ESIpos): $R_t$=1.39 min, m/z=299 [M+H]$^+$.

Example 281A

Ethyl 2-{[(2-fluoro-2-methylpropyl)carbamoyl]amino}-4-methylthiophene-3-carboxylate

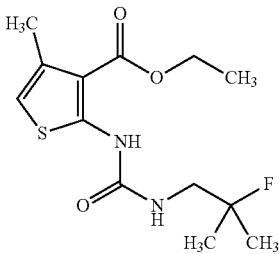 [SMILES: CCOC(=O)c1c(C)csc1NC(=O)NCC(C)(C)F]

To a solution of 5.49 g (28.7 mmol) of ethyl 2-amino-4-methylthiophene-3-carboxylate in 80 ml of THF were added 9.32 g (57.5 mmol) of 1,1'-carbonyldiimidazole (CDI) and 16 ml (115 mmol) of triethylamine, and the mixture was stirred at RT for 4 days. Then a solution of 5.50 g (43.1 mmol) of 2-fluoro-2-methylpropanamine hydrochloride [WO 2006/029115-A2, Example 43, Part A/B] and 8 ml (57 mmol) of triethylamine in 70 ml of THF were added to the mixture. Since the conversion was incomplete after 3 h at RT, stirring was continued at 50° C. for 1 h. Then the reaction mixture was stirred at RT for 2 days and subsequently at 50° C. for a further 4 h. Since the conversion was still incomplete, 50 ml of pyridine were added and the stirring was continued at 50° C. for 15 h. After cooling to RT, the precipitated solids were filtered off with suction and discarded. The filtrate was stirred into water. The precipitated solids were filtered off again and likewise discarded. The majority of the THF was removed from the filtrate on a rotary evaporator. The remaining aqueous phase was extracted with ethyl acetate. The organic extract was washed successively with water and saturated sodium chloride solution. After concentration by evaporation, the remaining residue was purified by means of flash chromatography (Combiflash, 100 g of silica gel, eluent: cyclohexane/ethyl acetate). After combination and concentration of the product fractions, 3.80 g (43% of theory) of the title compound were thus obtained.

$^1$H-NMR (400 MHz, DMSO-$d_6$, δ/ppm): 10.38 (s, 1H), 8.13 (t, 1H), 6.43 (s, 1H), 4.38-4.20 (m, 2H), 3.39-3.21 (m, 2H), 2.27 (s, 3H), 1.37-1.23 (m, 9H).

LC/MS (Method 17, ESIpos): $R_t$=1.97 min, m/z=303.12 [M+H]$^+$.

Example 282A

Ethyl 2-{[(2-methoxy-2-methylpropyl)carbamoyl]amino}-4-methylthiophene-3-carboxylate

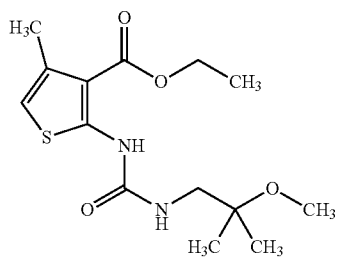 [SMILES: CCOC(=O)c1c(C)csc1NC(=O)NCC(C)(C)OC]

To a solution of 1.11 g (5.8 mmol) of ethyl 2-amino-4-methylthiophene-3-carboxylate in 6 ml of pyridine were added 1.5 g (11.6 mmol) of 1-isocyanato-2-methoxy-2-methylpropane. The reaction mixture was stirred at 50° C. for 72 h. The mixture was then concentrated to dryness on a rotary evaporator. The remaining residue was dissolved in dichloromethane and concentrated to dryness again. The material thus obtained was chromatographed using a silica gel cartridge (Biotage, 340 g of silica gel, eluent: hexane/ethyl acetate). 2.03 g of the title compound were obtained.

$^1$H-NMR (400 MHz, DMSO-$d_6$, δ/ppm): 10.37 (s, 1H), 7.90 (br. s, 1H), 6.41 (s, 1H), 4.28 (q, 2H), 3.15 (d, 2H), 3.11 (s, 3H), 2.26 (d, 3H), 1.31 (t, 3H), 1.08 (s, 6H).

LC/MS (Method 3, ESIpos): $R_t$=1.23 min, m/z=314 [M+H]$^+$.

Example 283A 3-(2,2-Dimethylpropyl)-5-methylthieno[2,3-d]pyrimidine-2,4(1H,3H)-dione

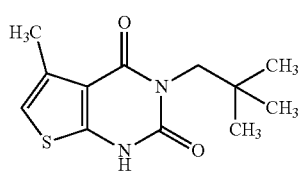 [SMILES: Cc1csc2[nH]c(=O)n(CC(C)(C)C)c(=O)c12]

1.51 g (5.07 mmol) of the compound from Ex. 280A were dissolved in 14 ml of ethanol, and 3.8 ml of sodium ethoxide solution (21% by weight in ethanol) were added. The mixture was stirred at 40° C. for 27 h and then 11.7 ml of 1 M hydrochloric acid were added. The ethanol was very substantially removed from the resultant suspension on a rotary evaporator. Water was added to the remaining residue, and the solids were filtered off, washed to neutrality with water and dried by suction. 1.28 g (98% of theory) of the title compound were obtained.

$^1$H-NMR (400 MHz, DMSO-$d_6$, δ/ppm): 12.05 (br. s, 1H), 6.68 (d, 1H), 3.76 (s, 2H), 2.34 (d, 3H), 0.89 (s, 9H).

LC/MS (Method 3): $R_t$=1.13 min, m/z=253 [M+H]$^+$.

Example 284A 3-(2-Fluoro-2-methylpropyl)-5-methylthieno[2,3-d]pyrimidine-2,4(1H,3H)-dione

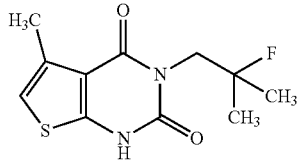 [SMILES: Cc1csc2[nH]c(=O)n(CC(C)(C)F)c(=O)c12]

3.70 g (12.2 mmol) of the compound from Ex. 281A were dissolved in 40 ml of ethanol, and 9.1 ml (24.5 mmol) of a 21% solution of sodium ethoxide in ethanol were added. After the mixture had been stirred at RT for 15 h, 28.1 ml (28.1 mmol) of 1 M hydrochloric acid were added, and the product precipitated out. The solids were filtered off with suction, washed to neutrality with water and dried under high vacuum. 2.60 g (82% of theory) of the title compound were obtained.

$^1$H-NMR (400 MHz, DMSO-$d_6$, δ/ppm): 12.13 (s, 1H), 6.70 (d, 1H), 4.10 (d, 2H), 2.35 (d, 3H), 1.41-1.23 (m, 6H).

LC/MS (Method 6, ESIneg): $R_t$=1.38 min, m/z=255 [M−H]$^-$.

Example 285A 3-(2-Methoxy-2-methylpropyl)-5-methylthieno[2,3-d]pyrimidine-2,4(1H,3H)-dione

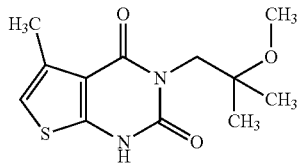 [SMILES: COC(C)(C)Cn1c(=O)[nH]c2scc(C)c2c1=O]

2.03 g (6.45 mmol) of the compound from Ex. 282A were dissolved in 18 ml of ethanol, and 4.8 ml of sodium ethoxide solution (21% by weight in ethanol) were added. The mixture was stirred at RT for 88 h and then 15 ml of 1 M hydrochloric acid were added. The ethanol was very substantially removed from the resultant suspension on a rotary evaporator. Water was added to the remaining residue, and the solids were filtered off, washed to neutrality with water and dried by suction. 1.7 g (98% of theory) of the title compound were obtained.

$^1$H-NMR (400 MHz, DMSO-$d_6$, δ/ppm): 12.07 (br. s, 1H), 6.68 (d, 1H), 3.95 (s, 2H), 3.15 (s, 3H), 2.34 (d, 3H), 1.08 (s, 6H).

LC/MS (Method 3, ESIpos): $R_t$=0.92 min, m/z=267 [M+H]$^+$.

Example 286A 3-(2,2-Dimethylpropyl)-5-methyl-2,4-dioxo-1,2,3,4-tetrahydrothieno[2,3-d]pyrimidine-6-carbaldehyde

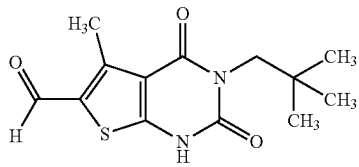 [SMILES: Cc1c(C=O)sc2[nH]c(=O)n(CC(C)(C)C)c(=O)c12]

4.7 ml (50.2 mmol) of phosphorus oxychloride were added cautiously, while cooling with an ice bath, to a solution of 1.26 g (5.02 mmol) of the compound from Ex. 283A in 47 ml of DMF. The mixture was then stirred at 70° C. for 4 h. Then the reaction mixture was concentrated very substantially on a rotary evaporator. The remaining residue was added to ice-water and stirred. The precipitated product was filtered off with suction, washed to neutrality with water and dried. 1.2 g (85% of theory) of the title compound were obtained.

$^1$H-NMR (400 MHz, DMSO-$d_6$, δ/ppm): 12.55 (br. s, 1H), 10.06 (s, 1H), 3.75 (s, 2H), 2.75 (s, 3H), 0.90 (s, 9H).

LC/MS (Method 3, ESIpos): $R_t$=1.10 min, m/z=281 [M+H]$^+$.

Example 287A 3-(2-Fluoro-2-methylpropyl)-5-methyl-2,4-dioxo-1,2,3,4-tetrahydrothieno[2,3-d]pyrimidine-6-carbaldehyde

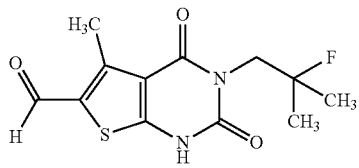 [SMILES: Cc1c(C=O)sc2[nH]c(=O)n(CC(C)(C)F)c(=O)c12]

11.1 ml (119 mmol) of phosphorus oxychloride were added carefully to a solution of 2.55 g (9.95 mmol) of the compound from Ex. 284A in 7.7 ml (99.5 mmol) of DMF. After the strongly exothermic reaction had subsided, the mixture was stirred for another 15 min. Then the reaction mixture was stirred cautiously into 350 ml of water. After stirring for 1 h, the precipitated product was filtered off with suction, washed with water until neutral and dried. 2.63 g (90% of theory, 97% purity) of the title compound were obtained.

$^1$H-NMR (400 MHz, DMSO-$d_6$, δ/ppm): 12.62 (s, 1H), 10.07 (s, 1H), 4.09 (d, 2H), 2.75 (s, 3H), 1.40-1.23 (m, 6H).

LC/MS (Method 17, ESIpos): R$_t$=1.84 min, m/z=285.07 [M+H]$^+$, 265.06 [M−F]$^+$.

Example 288A 3-(2-Methoxy-2-methylpropyl)-5-methyl-2,4-dioxo-1,2,3,4-tetrahydrothieno[2,3-d]pyrimidine-6-carbaldehyde

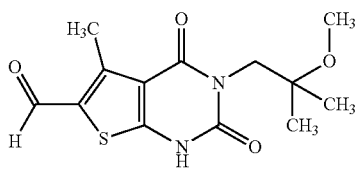 [SMILES: COC(C)(C)Cn1c(=O)[nH]c2sc(C=O)c(C)c2c1=O]

4.1 ml (44.0 mmol) of phosphorus oxychloride were added cautiously, while cooling with an ice bath, to a solution of 1.18 g (4.39 mmol) of the compound from Ex. 285A in 41 ml of DMF. The mixture was then stirred at 70° C. for 2 h. Then the reaction mixture was concentrated very substantially on a rotary evaporator. The remaining residue was added to ice-water and stirred. The precipitated product was filtered off with suction, washed to neutrality with water and dried. 1.06 g (77% of theory) of the title compound were obtained.

$^1$H-NMR (400 MHz, DMSO-d$_6$, δ/ppm): 12.56 (br. s, 1H), 10.06 (s, 1H), 3.94 (s, 2H), 3.15 (s, 3H), 2.75 (s, 3H), 1.09 (s, 6H).

LC/MS (Method 3, ESIpos): R$_t$=0.89 min, m/z=295 [M+H]$^+$.

Example 289A

Ethyl (6-formyl-5-methyl-2,4-dioxo-1,4-dihydrothieno[2,3-d]pyrimidin-3(2H)-yl)acetate

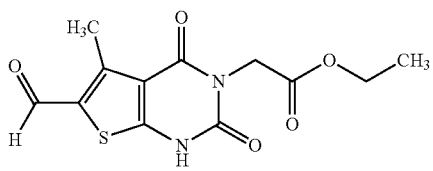 [SMILES: CCOC(=O)Cn1c(=O)[nH]c2sc(C=O)c(C)c2c1=O]

To a solution of 4.50 g (16.8 mmol) of ethyl (5-methyl-2,4-dioxo-1,4-dihydrothieno[2,3-d]pyrimidine-3(2H)-yl)acetate [U.S. Pat. No. 6,140,325, Reference Example 2 (2)] in 12.9 ml (168 mmol) of DMF were cautiously added 18.8 ml (201 mmol) of phosphorus oxychloride. After the strongly exothermic reaction had subsided, the mixture was stirred for another 15 min. Then the reaction mixture was stirred cautiously into 100 ml of water. After stirring for 1 h, the precipitated product was filtered off with suction, washed with water until neutral and dried under high vacuum. 4.88 g (98% of theory) of the title compound were obtained.

$^1$H-NMR (400 MHz, DMSO-d$_6$, δ/ppm): 12.86 (br. s, 1H), 10.08 (s, 1H), 4.58 (s, 2H), 4.15 (q, 2H), 2.75 (s, 3H), 1.21 (t, 3H).

LC/MS (Method 1, ESIpos): R$_t$=0.68 min, m/z=297 [M+H]$^+$.

Example 290A

1-[2-(Cyclopropyloxy)ethyl]-3-ethyl-5-methyl-2,4-dioxo-1,2,3,4-tetrahydrothieno[2,3-d]pyrimidine-6-carbaldehyde

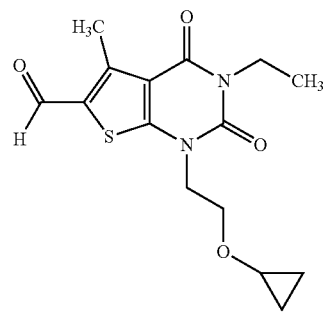 [SMILES: CCn1c(=O)c2c(C)c(C=O)sc2n(CCOC2CC2)c1=O]

948 mg (6.85 mmol) of potassium carbonate were added to a solution of 560 mg (2.28 mmol) of the compound from Ex. 48A in 22 ml of DMF, and the mixture was stirred at RT for 15 min. Then 827 mg (6.86 mmol) of (2-chloroethoxy)cyclopropane and 85 mg (0.57 mmol) of sodium iodide were added, and the mixture was stirred at 90° C. for 115 h. The DMF was then very substantially distilled off and the remaining residue was partitioned between semisaturated sodium chloride solution (40 ml) and ethyl acetate (25 ml). The aqueous phase was extracted with ethyl acetate. The combined organic phases were dried over sodium sulphate, filtered and concentrated. The residue obtained was chromatographed using a silica gel cartridge (Biotage, 100 g of silica gel, eluent: hexane/ethyl acetate). 390 mg (53% of theory) of the title compound were obtained.

$^1$H-NMR (400 MHz, DMSO-d$_6$, δ/ppm): 10.09 (s, 1H), 4.08 (t, 2H), 3.90 (q, 2H), 3.75 (t, 2H), 2.78 (s, 3H), 1.13 (t, 3H), 0.42-0.36 (m, 4H).

LC/MS (Method 3, ESIpos): R$_t$=1.14 min, m/z=323 [M+H]$^+$.

Example 291A 3-(2,2-Dimethylpropyl)-5-methyl-2,4-dioxo-1-(3,3,3-trifluoropropyl)-1,2,3,4-tetrahydrothieno[2,3-d]pyrimidine-6-carbaldehyde

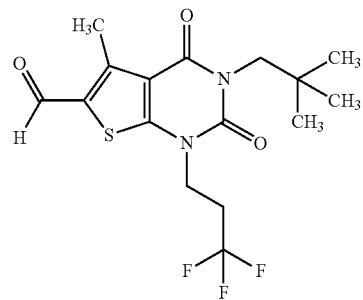 [SMILES: Cc1c(C=O)sc2c1c(=O)n(CC(C)(C)C)c(=O)n2CCC(F)(F)F]

554 mg (4.01 mmol) of potassium carbonate were added to a solution of 450 mg (1.6 mmol) of the compound from Ex. 286A in 17 ml of DMF, and the mixture was stirred at RT for 15 min. Then 1.11 g (4.81 mmol) of 1,1,1-trifluoro-

Example 292A 3-(2,2-Dimethylpropyl)-1-(3-fluoropropyl)-5-methyl-2,4-dioxo-1,2,3,4-tetrahydrothieno[2,3-d]pyrimidine-6-carbaldehyde

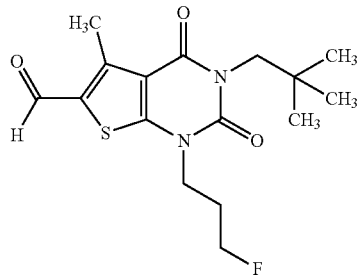 [SMILES: Cc1c(C=O)sc2c1c(=O)n(CC(C)(C)C)c(=O)n2CCCF]

3-iodopropane were added, and the mixture was stirred at 50° C. for 21 h. The DMF was then very substantially distilled off and the remaining residue was partitioned between semisaturated sodium chloride solution (100 ml) and ethyl acetate (50 ml). The aqueous phase was extracted with ethyl acetate. The combined organic phases were dried over sodium sulphate, filtered and concentrated. The residue obtained was chromatographed using a silica gel cartridge (Biotage, 100 g of silica gel, eluent: hexane/ethyl acetate). 491 mg (81% of theory) of the title compound were obtained.

$^1$H-NMR (400 MHz, DMSO-$d_6$, δ/ppm): 10.11 (s, 1H), 4.17 (t, 2H), 3.81 (br. s, 2H), 2.86-2.71 (m, 5H), 0.90 (s, 9H).

LC/MS (Method 3, ESIpos): $R_t$=1.40 min, m/z=377 [M+H]$^+$.

554 mg (4.01 mmol) of potassium carbonate were added to a solution of 450 mg (1.6 mmol) of the compound from Ex. 286A in 16 ml of DMF, and the mixture was stirred at RT for 15 min. Then 905 mg (4.81 mmol) of 1-fluoro-3-iodopropane were added, and the mixture was stirred at 50° C. for 21 h. The DMF was then very substantially distilled off and the remaining residue was partitioned between semisaturated sodium chloride solution (100 ml) and ethyl acetate (50 ml). The aqueous phase was extracted with ethyl acetate. The combined organic phases were dried over sodium sulphate, filtered and concentrated. The residue obtained was chromatographed using a silica gel cartridge (Biotage, 100 g of silica gel, eluent: hexane/ethyl acetate). 423 mg (77% of theory) of the title compound were obtained.

$^1$H-NMR (400 MHz, DMSO-$d_6$, δ/ppm): 10.10 (s, 1H), 4.60 (t, 1H), 4.48 (t, 1H), 4.05 (t, 2H), 3.81 (br. s, 2H), 2.78 (s, 3H), 2.11 (quin, 1H), 2.04 (t, 1H), 0.90 (s, 9H).

LC/MS (Method 3, ESIpos): $R_t$=1.32 min, m/z=341 [M+H]$^+$.

Example 293A 3-(2,2-Dimethylpropyl)-1-(2-methoxyethyl)-5-methyl-2,4-dioxo-1,2,3,4-tetrahydrothieno[2,3-d]pyrimidine-6-carbaldehyde

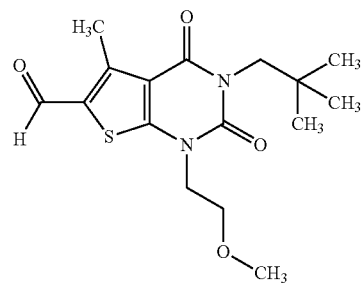 [SMILES: COCCn1c(=O)n(CC(C)(C)C)c(=O)c2c(C)c(C=O)sc21]

555 mg (4.01 mmol) of potassium carbonate were added to a solution of 450 mg (1.6 mmol) of the compound from Ex. 286A in 15 ml of DMF, and the mixture was stirred at RT for 15 min. 669 mg (4.81 mmol) of 2-bromoethyl methyl ether were then added, and the mixture was stirred at 50° C. for 16 h. The DMF was then very substantially distilled off and the remaining residue was partitioned between semisaturated sodium chloride solution (100 ml) and ethyl acetate (50 ml). The aqueous phase was extracted with ethyl acetate. The combined organic phases were dried over sodium sulphate, filtered and concentrated. The residue obtained was chromatographed using a silica gel cartridge (Biotage, 50 g of silica gel, eluent: hexane/ethyl acetate). 417 mg (76% of theory) of the title compound were obtained.

$^1$H-NMR (400 MHz, DMSO-$d_6$, δ/ppm): 10.09 (s, 1H), 4.10 (t, 2H), 3.81 (br. s, 2H), 3.64 (t, 2H), 3.33 (s, 3H), 2.77 (s, 3H), 0.89 (s, 9H).

LC/MS (Method 3, ESIpos): $R_t$=1.29 min, m/z=339 [M+H]$^+$.

Example 294A 3-(2-Fluoro-2-methylpropyl)-5-methyl-2,4-dioxo-1-(3,3,3-trifluoropropyl)-1,2,3,4-tetrahydrothieno[2,3-d]pyrimidine-6-carbaldehyde

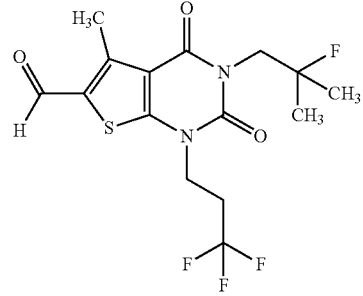 [SMILES: Cc1c(C=O)sc2c1c(=O)n(CC(C)(C)F)c(=O)n2CCC(F)(F)F]

1.30 g (4.57 mmol) of the compound from Ex. 287A were dissolved in 22 ml of DMF, and 1.26 μl (9.15 mmol) of potassium carbonate were added. The mixture was heated to 60° C. and, at this temperature, 1.02 g (4.57 mmol) of 1,1,1-trifluoro-3-iodopropane were added. After 2 h at 60°

C., the same amount of 1,1,1-trifluoro-3-iodopropane was added once again. After a further 3.5 h at 60° C., the reaction mixture was cooled to RT and then poured onto about 100 ml of ice-water. In the course of this, the product precipitated out. The product was filtered off with suction, washed with water and dried under high vacuum. 1.63 g (88% of theory, 94% purity) of the title compound were obtained.

$^1$H-NMR (400 MHz, DMSO-$d_6$, δ/ppm): 10.11 (s, 1H), 4.24-4.08 (m, 4H), 2.90-2.71 (m, 2H), 2.79 (s, 3H), 1.42-1.23 (m, 6H).

LC/MS (Method 17, ESIpos): $R_t$=1.88 min, m/z=381.09 [M+H]$^+$.

Example 295A 3-(2-Fluoro-2-methylpropyl)-1-(2-methoxyethyl)-5-methyl-2,4-dioxo-1,2,3,4-tetrahydrothieno[2,3-d]pyrimidine-6-carbaldehyde

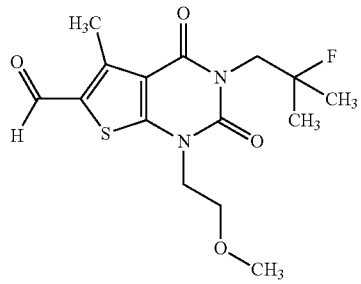 [SMILES: COCCn1c(=O)n(CC(C)(C)F)c(=O)c2c(C)c(C=O)sc21]

Analogously to the method described in Ex. 294A, 1.30 g (4.57 mmol) of the compound from Ex. 287A and a total of 1.27 g (9.14 mmol) of 2-bromoethyl methyl ether were used to obtain 1.36 g (86% of theory) of the title compound.

$^1$H-NMR (400 MHz, DMSO-$d_6$, δ/ppm): 10.09 (s, 1H), 4.21-4.06 (m, 4H), 3.65 (t, 2H), 3.24 (s, 3H), 2.78 (s, 3H), 1.40-1.26 (m, 6H).

LC/MS (Method 17, ESIpos): $R_t$=1.63 min, m/z=343.11 [M+H]$^+$.

Example 296A 3-(2-Methoxyethyl)-5-methyl-2,4-dioxo-1-(3,3,3-trifluoropropyl)-1,2,3,4-tetrahydrothieno[2,3-d]pyrimidine-6-carbaldehyde

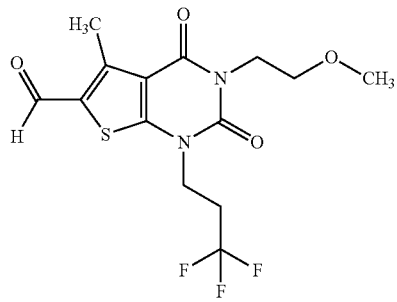 [SMILES: COCCn1c(=O)c2c(C)c(C=O)sc2n(CCC(F)(F)F)c1=O]

341 mg (2.47 mmol) of potassium carbonate were added to a solution of 285 mg (0.98 mmol) of the compound from Ex. 53A in 9 ml of DMF, and the mixture was stirred at RT for 15 min. Then 664 mg (2.96 mmol) of 1,1,1-trifluoro-3-iodopropane were added, and the mixture was stirred at 50° C. for 19 h. The DMF was then very substantially distilled off and the remaining residue was partitioned between semisaturated sodium chloride solution (200 ml) and ethyl acetate (100 ml). The aqueous phase was extracted with ethyl acetate. The combined organic phases were dried over sodium sulphate, filtered and concentrated. The residue obtained was chromatographed using a silica gel cartridge (Biotage, 50 g of silica gel, eluent: hexane/ethyl acetate). 254 mg (69% of theory) of the title compound were obtained.

$^1$H-NMR (400 MHz, DMSO-$d_6$, δ/ppm): 10.11 (s, 1H), 4.18 (t, 2H), 4.06 (t, 2H), 3.53-3.48 (m, 2H), 3.24 (s, 3H), 2.84-2.75 (m, 5H).

LC/MS (Method 3, ESIpos): $R_t$=1.10 min, m/z=365 [M+H]$^+$.

Example 297A 1-(3-Fluoropropyl)-3-(2-methoxyethyl)-5-methyl-2,4-dioxo-1,2,3,4-tetrahydrothieno[2,3-d]pyrimidine-6-carbaldehyde

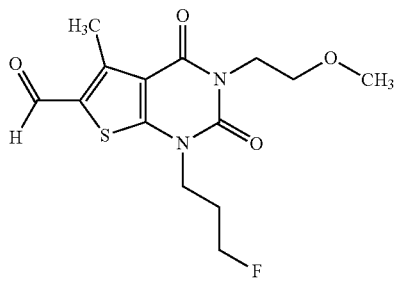 [SMILES: COCCn1c(=O)c2c(C)c(C=O)sc2n(CCCF)c1=O]

341 mg (2.47 mmol) of potassium carbonate were added to a solution of 285 mg (0.98 mmol) of the compound from Ex. 53A in 9 ml of DMF, and the mixture was stirred at RT for 15 min. Then 557 mg (2.96 mmol) of 1-fluoro-3-iodopropane were added, and the mixture was stirred at 50° C. for 19 h. The DMF was then very substantially distilled off and the remaining residue was partitioned between semisaturated sodium chloride solution (100 ml) and ethyl acetate (50 ml). The aqueous phase was extracted with ethyl acetate. The combined organic phases were dried over sodium sulphate, filtered and concentrated. The residue obtained was chromatographed using a silica gel cartridge (Biotage, 100 g of silica gel, eluent: hexane/ethyl acetate). 175 mg (52% of theory) of the title compound were obtained.

$^1$H-NMR (400 MHz, DMSO-$d_6$, δ/ppm): 10.10 (s, 1H), 4.60 (t, 1H), 4.48 (t, 1H), 4.09-4.01 (m, 4H), 3.53-3.47 (m, 2H), 3.24 (s, 3H), 2.79 (s, 3H), 2.15-2.08 (m, 1H), 2.08-2.00 (m, 1H).

LC/MS (Method 3, ESIpos): $R_t$=0.98 min, m/z=329 [M+H]$^+$.

Example 298A 3-(2-Methoxyethyl)-5-methyl-2,4-dioxo-1-(tetrahydrofuran-2-ylmethyl)-1,2,3,4-tetrahydrothieno[2,3-d]pyrimidine-6-carbaldehyde (racemate)

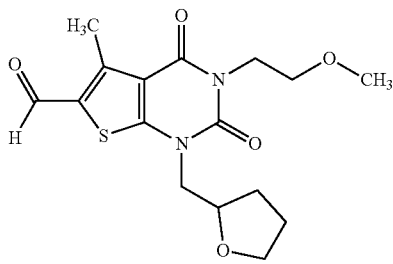 [SMILES: COCCn1c(=O)c2c(C)c(C=O)sc2n(CC2CCCO2)c1=O]

1.29 g (9.35 mmol) of potassium carbonate were added to a solution of 900 mg (3.12 mmol) of the compound from Ex. 53A in 30 ml of DMF, and the mixture was stirred at RT for 15 min. 2.86 g (15.6 mmol) of racemic 2-(bromomethyl)tetrahydrofuran were then added, and the mixture was stirred at 70° C. for 94 h. The DMF was then very substantially distilled off and the remaining residue was partitioned between semisaturated sodium chloride solution (200 ml) and ethyl acetate (100 ml). The aqueous phase was extracted with ethyl acetate. The combined organic phases were dried over sodium sulphate, filtered and concentrated. The residue obtained was chromatographed using a silica gel cartridge (Biotage, 340 g of silica gel, eluent: hexane/ethyl acetate). 440 mg (39% of theory) of the title compound were obtained.

$^1$H-NMR (400 MHz, DMSO-$d_6$, δ/ppm): 10.09 (s, 1H), 4.23 (dtd, 1H), 4.13 (dd, 1H), 4.06 (t, 2H), 3.81-3.70 (m, 2H), 3.62 (td, 1H), 3.54-3.48 (m, 2H), 3.24 (s, 3H), 2.78 (s, 3H), 2.06-1.95 (m, 1H), 1.95-1.75 (m, 2H), 1.73-1.62 (m, 1H).

LC/MS (Method 3, ESIpos): $R_t$=1.0 min, m/z=353 [M+H]$^+$.

Example 299A 3-(2-Methoxy-2-methylpropyl)-5-methyl-2,4-dioxo-1-(3,3,3-trifluoropropyl)-1,2,3,4-tetrahydrothieno[2,3-d]pyrimidine-6-carbaldehyde

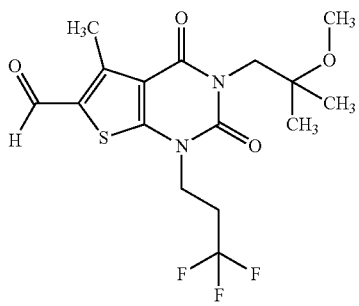 [SMILES: COC(C)(C)Cn1c(=O)c2c(C)c(C=O)sc2n(CCC(F)(F)F)c1=O]

498 mg (3.6 mmol) of potassium carbonate were added to a solution of 450 mg (1.44 mmol) of the compound from Ex. 288A in 15 ml of DMF, and the mixture was stirred at RT for 15 min. Then 969 mg (4.32 mmol) of 1,1,1-trifluoro-3-iodopropane were added, and the mixture was stirred at 50° C. for 18 h. The DMF was then very substantially distilled off and the remaining residue was partitioned between semisaturated sodium chloride solution (100 ml) and ethyl acetate (50 ml). The aqueous phase was extracted with ethyl acetate. The combined organic phases were dried over sodium sulphate, filtered and concentrated. The residue obtained was chromatographed using a silica gel cartridge (Biotage, 50 g of silica gel, eluent: hexane/ethyl acetate). 463 mg (79% of theory) of the title compound were obtained.

$^1$H-NMR (400 MHz, DMSO-$d_6$, δ/ppm): 10.11 (s, 1H), 4.17 (t, 2H), 4.00 (br. s, 2H), 3.15 (s, 3H), 2.86-2.71 (m, 5H), 1.09 (s, 6H).

LC/MS (Method 3, ESIpos): $R_t$=1.22 min, m/z=361 [M+H—CH$_3$OH]$^+$.

Example 300A 1-(3-Fluoropropyl)-3-(2-methoxy-2-methylpropyl)-5-methyl-2,4-dioxo-1,2,3,4-tetrahydrothieno[2,3-d]pyrimidine-6-carbaldehyde

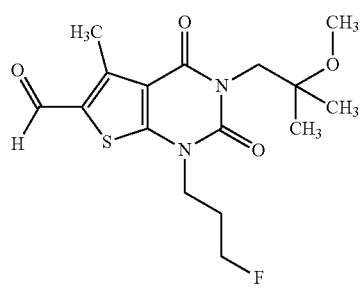 [SMILES: COC(C)(C)Cn1c(=O)c2c(C)c(C=O)sc2n(CCCF)c1=O]

498 mg (3.6 mmol) of potassium carbonate were added to a solution of 450 mg (1.44 mmol) of the compound from Ex. 288A in 15 ml of DMF, and the mixture was stirred at RT for 15 min. Then 814 mg (4.32 mmol) of 1-fluoro-3-iodopropane were added, and the mixture was stirred at 50° C. for 18 h. The DMF was then very substantially distilled off and the remaining residue was partitioned between semisaturated sodium chloride solution (100 ml) and ethyl acetate (50 ml). The aqueous phase was extracted with ethyl acetate. The combined organic phases were dried over sodium sulphate, filtered and concentrated. The residue obtained was chromatographed using a silica gel cartridge (Biotage, 50 g of silica gel, eluent: hexane/ethyl acetate). 456 mg (88% of theory) of the title compound were obtained.

$^1$H-NMR (400 MHz, DMSO-$d_6$, δ/ppm): 10.10 (s, 1H), 4.60 (t, 1H), 4.48 (t, 1H), 4.05 (t, 2H), 3.99 (br. s, 2H), 3.15 (s, 3H), 2.78 (s, 3H), 2.11 (quin, 1H), 2.04 (quin, 1H), 1.09 (s, 6H).

LC/MS (Method 3, ESIpos): $R_t$=1.11 min, m/z=325 [M+H—CH$_3$OH]$^+$.

Example 301A 1-(2-Methoxyethyl)-3-(2-methoxy-2-methylpropyl)-5-methyl-2,4-dioxo-1,2,3,4-tetrahydrothieno[2,3-d]pyrimidine-6-carbaldehyde

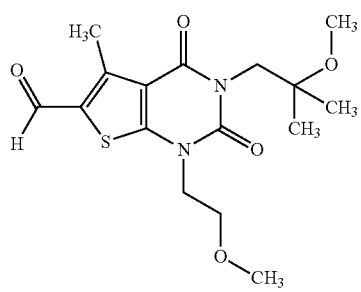 [SMILES: COCCn1c(=O)n(CC(C)(C)OC)c(=O)c2c(C)c(C=O)sc21]

520 mg (3.76 mmol) of potassium carbonate were added to a solution of 446 mg (1.5 mmol) of the compound from Ex. 288A in 14 ml of DMF, and the mixture was stirred at RT for 15 min. 628 mg (4.51 mmol) of 2-bromoethyl methyl ether were then added, and the mixture was stirred at 50° C. for 14 h. The DMF was then very substantially distilled off and the remaining residue was partitioned between semi-saturated sodium chloride solution (70 ml) and ethyl acetate (70 ml). The aqueous phase was extracted with ethyl acetate. The combined organic phases were dried over sodium sulphate, filtered and concentrated. The residue obtained was chromatographed using a silica gel cartridge (Biotage, 50 g of silica gel, eluent: hexane/ethyl acetate). 395 mg (71% of theory) of the title compound were obtained.

$^1$H-NMR (400 MHz, DMSO-$d_6$, δ/ppm): 10.09 (s, 1H), 4.10 (t, 2H), 4.00 (br. s, 2H), 3.64 (t, 2H), 3.23 (s, 3H), 3.15 (s, 3H), 2.77 (s, 3H), 1.09 (s, 6H).

LC/MS (Method 3, ESIpos): $R_t$=1.07 min, m/z=355 [M+H]$^+$.

Example 302A

Ethyl [6-formyl-5-methyl-2,4-dioxo-1-(3,3,3-trifluoropropyl)-1,4-dihydrothieno[2,3-d]pyrimidin-3(2H)-yl]acetate

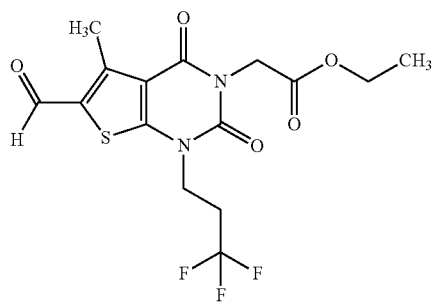 [SMILES: CCOC(=O)Cn1c(=O)c2c(C)c(C=O)sc2n(CCC(F)(F)F)c1=O]

1.0 g (3.37 mmol) of the compound from Ex. 289A and 1.65 g (5.06 mmol) of caesium carbonate were stirred in 17 ml of DMF at RT for 10 min, before 1.13 g (5.06 mmol) of 1,1,1-trifluoro-3-iodopropane were added. Subsequently, the reaction mixture was stirred at a temperature of 100° C. in a microwave oven (Biotage Initiator with dynamic control of irradiation power). After 1.5 h, the mixture was cooled to RT, diluted with about 75 ml of ethyl acetate and washed successively with water and saturated sodium chloride solution. After drying over anhydrous magnesium sulphate, the mixture was filtered and the filtrate was evaporated to dryness. The crude product was purified by preparative HPLC (Method 8). After concentration of the product fractions and drying under high vacuum, 938 g (70% of theory) of the title compound were obtained.

$^1$H-NMR (500 MHz, DMSO-$d_6$, δ/ppm): 10.12 (s, 1H), 4.64 (s, 2H), 4.22 (t, 2H), 4.15 (q, 2H), 2.89-2.74 (m, 2H), 2.79 (s, 3H), 1.21 (t, 3H).

LC/MS (Method 1, ESIpos): $R_t$=0.98 min, m/z=393 [M+H]$^+$.

Example 303A

Ethyl [6-formyl-1-(2-methoxyethyl)-5-methyl-2,4-dioxo-1,4-dihydrothieno[2,3-d]pyrimidin-3(2H)-yl]acetate

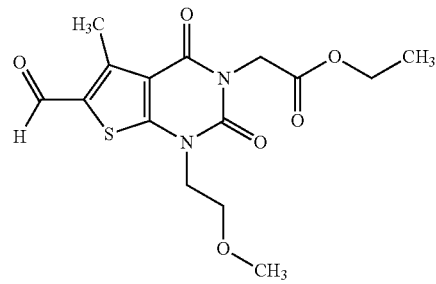 [SMILES: CCOC(=O)Cn1c(=O)c2c(C)c(C=O)sc2n(CCOC)c1=O]

Analogously to the method described in Ex. 302A, 1.0 g (3.37 mmol) of the compound from Ex. 289A and 704 mg (5.06 mmol) of 2-bromoethyl methyl ether were used to obtain 530 mg (43% of theory) of the title compound. The reaction was conducted in this case at a temperature of 80° C., and the preparative HPLC purification was effected according to Method 9.

$^1$H-NMR (500 MHz, DMSO-$d_6$, δ/ppm): 10.10 (s, 1H), 4.63 (s, 2H), 4.22-4.08 (m, 4H), 3.66 (t, 2H), 3.31 (s, 3H), 2.77 (s, 3H), 1.21 (t, 3H).

LC/MS (Method 1, ESIpos): $R_t$=0.87 min, m/z=355 [M+H]$^+$.

Example 304A 3-(2-Fluoro-2-methylpropyl)-6-(hydroxymethyl)-5-methyl-1-(3,3,3-trifluoropropyl)thieno[2,3-d]pyrimidine-2,4(1H,3H)-dione

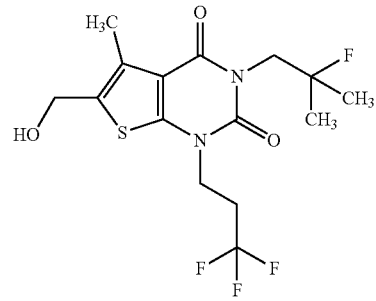 [SMILES: Cc1c(CO)sc2c1c(=O)n(CC(C)(C)F)c(=O)n2CCC(F)(F)F]

400 mg (1.05 mmol) of the compound from Ex. 294A were dissolved in 8.3 ml of anhydrous THF, and 315 μl (0.315 mmol) of a 1 M solution of lithium aluminium hydride in THF were added at −78° C. After the reaction mixture had been stirred at the same temperature for 20 min, 211 μl of water, 914 μl of 1 M sodium hydroxide solution and a little kieselguhr were added. Subsequently, the mixture was warmed to RT and then filtered. The filtrate was concentrated to dryness and then dissolved again in ethyl acetate. The mixture was washed successively with water and saturated sodium chloride solution. After drying over anhydrous magnesium sulphate and filtration, the mixture was concentrated to dryness again. 400 mg (93% of theory, 94% purity) of the title compound were obtained, which was used for subsequent reactions without further purification.

$^1$H-NMR (400 MHz, DMSO-d$_6$, δ/ppm): 5.62 (t, 1H), 4.60 (d, 2H), 4.21-4.07 (m, 4H), 2.87-2.68 (m, 2H), 2.33 (s, 3H), 1.39-1.23 (m, 6H).

LC/MS (Method 17, ESIpos): R$_t$=1.64 min, m/z=383.10 [M+H]$^+$, 365.09 [M−OH]$^+$, 363.10 [M−F]$^+$.

Example 305A 3-(2-Fluoro-2-methylpropyl)-6-(hydroxymethyl)-1-(2-methoxyethyl)-5-methylthieno[2,3-d]pyrimidine-2,4(1H,3H)-dione

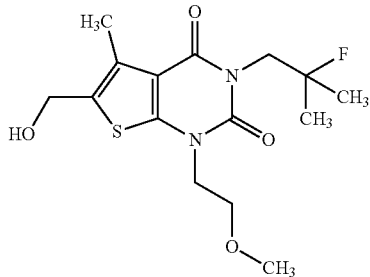 [SMILES: COCCn1c(=O)n(CC(C)(C)F)c(=O)c2c(C)c(CO)sc21]

Analogously to the method described in Ex. 304A, 360 mg (1.01 mmol) of the compound from Ex. 295A and 303 μl (0.303 mmol) of a 1 M solution of lithium aluminium hydride in THF were used to obtain 142 mg (40% of theory) of the title compound. The product in this case was purified by means of preparative HPLC (Method 8).

$^1$H-NMR (400 MHz, DMSO-d$_6$, δ/ppm): 5.56 (t, 1H), 4.57 (d, 2H), 4.15 (d, 2H), 4.05 (t, 2H), 3.64 (t, 2H), 3.24 (s, 3H), 2.32 (s, 3H), 1.40-1.21 (m, 6H).

LC/MS (Method 17, ESIpos): R$_t$=1.33 min, m/z=345.13 [M+H]$^+$, 327.12 [M−OH]$^+$, 325.12 [M−F]$^+$.

Example 306A

Ethyl [6-(hydroxymethyl)-5-methyl-2,4-dioxo-1-(3,3,3-trifluoropropyl)-1,4-dihydrothieno[2,3-d]pyrimidin-3(2H)-yl]acetate

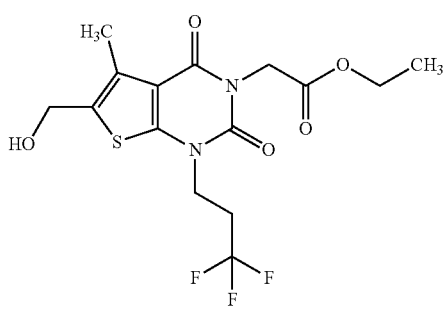 [SMILES: CCOC(=O)Cn1c(=O)c2c(C)c(CO)sc2n(CCC(F)(F)F)c1=O]

300 mg (0.765 mmol) of the compound from Example 302A were dissolved in 7.6 ml of ethanol, and 43 mg (1.15 mmol) of sodium borohydride were added at RT. After 1 h, about 1 ml each of water and 1 M hydrochloric acid were added to the reaction mixture. After concentration on a rotary evaporator, the remaining residue was taken up in ethyl acetate and washed successively with water and saturated sodium chloride solution. After drying over anhydrous magnesium sulphate, the mixture was filtered and concentrated again. Drying of the residue under high vacuum gave 279 mg (92% of theory) of the title compound.

$^1$H-NMR (500 MHz, DMSO-d$_6$, δ/ppm): 5.66 (t, 1H), 4.62 (s, 2H), 4.61 (d, 2H), 4.16 (t, 2H), 4.13 (q, 2H), 2.85-2.70 (m, 2H), 2.32 (s, 3H), 1.20 (t, 3H).

LC/MS (Method 1, ESIpos): R$_t$=0.85 min, m/z=395 [M+H]$^+$, 377 [M−OH]$^+$.

Example 307A

Ethyl [6-(hydroxymethyl)-1-(2-methoxyethyl)-5-methyl-2,4-dioxo-1,4-dihydrothieno[2,3-d]pyrimidin-3(2H)-yl]acetate

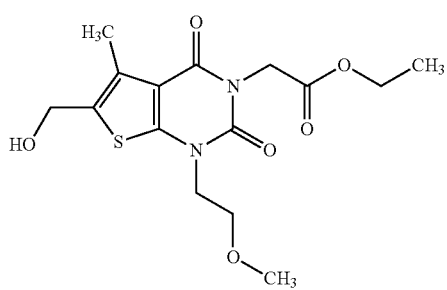 [SMILES: CCOC(=O)Cn1c(=O)c2c(C)c(CO)sc2n(CCOC)c1=O]

Analogously to the method described in Ex. 306A, 300 mg (0.847 mmol) of the compound from Ex. 303A and 48 mg (1.27 mmol) of sodium borohydride were used to obtain 268 mg (88% of theory) of the title compound.

$^1$H-NMR (400 MHz, DMSO-d$_6$, δ/ppm): 5.60 (t, 1H), 4.62 (s, 2H), 4.59 (d, 2H), 4.14 (q, 2H), 4.07 (t, 2H), 3.64 (t, 2H), 3.24 (s, 3H), 2.31 (s, 3H), 1.20 (t, 3H).

LC/MS (Method 1, ESIpos): R$_t$=0.72 min, m/z=357 [M+H]$^+$, 339 [M−OH]$^+$.

Example 308A

6-{[(2-Aminoethyl)amino]methyl}-1-[2-(cyclopropyloxy)ethyl]-3-ethyl-5-methylthieno[2,3-d]pyrimidine-2,4(1H,3H)-dione

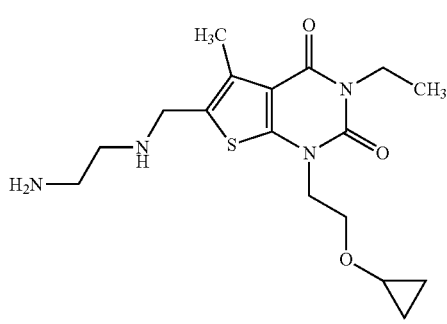 [SMILES: CCn1c(=O)c2c(C)c(CNCCN)sc2n(CCOC2CC2)c1=O]

388 mg (1.17 mmol) of the compound from Ex. 290A were dissolved in a mixture of 20 ml of methanol and 8 ml of dichloromethane. Then 788 µl (11.8 mmol) of 1,2-diaminoethane and 270 µl (4.72 mmol) of acetic acid were added at RT. The mixture was stirred at RT for 30 minutes, and then 312 mg (4.72 mmol) of sodium cyanoborohydride were added. After the reaction mixture had been stirred at 60° C. for 111 h, it was admixed with 50 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 385 mg (63% of theory, 71% purity) of the title compound, which was used for subsequent reactions without further purification.

LC/MS (Method 3, ESIpos): $R_t$=0.59 min, m/z=307 [M+H—$C_2H_8N_2$]$^+$.

Example 309A

6-{[(2-Aminoethyl)amino]methyl}-3-isopropyl-5-methyl-1-(3,3,3-trifluoropropyl)thieno[2,3-d]pyrimidine-2,4(1H,3H)-dione

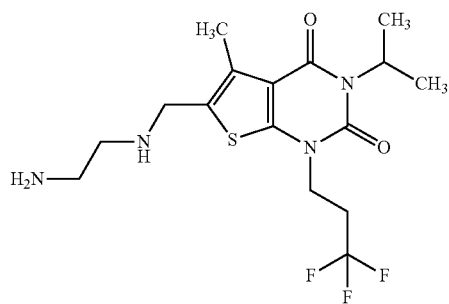 [SMILES: Cc1c(CNCCN)sc2c1c(=O)n(C(C)C)c(=O)n2CCC(F)(F)F]

300 mg (0.861 mmol) of the compound from Ex. 103A were dissolved in a mixture of 7.5 ml of methanol and 3 ml of dichloromethane, and 345 µl (5.17 mmol) of 1,2-diaminoethane and 197 µl (3.45 mmol) of acetic acid were added at RT. After 30 min, 216 mg (3.45 mmol) of sodium cyanoborohydride were added, and the reaction mixture was heated to 50° C. After 5 h, the reaction mixture was allowed to cool down to RT, and the stirring was continued at RT for 2 days. Since the conversion was still incomplete after this time, a further 100 mg (1.59 mmol) of sodium cyanoborohydride were added and the mixture was heated again to 50° C. After 2 h, the mixture was allowed to cool back down to RT. The mixture was then admixed with 50 ml of 2 M sodium hydroxide solution and extracted thoroughly with ethyl acetate. The organic extract was washed with saturated sodium chloride solution, dried over anhydrous magnesium sulphate, filtered and concentrated on a rotary evaporator. The crude product thus obtained, after drying under high vacuum, gave 360 mg (76% of theory, 72% purity) of the title compound, which was used for subsequent reactions without further purification.

LC/MS (Method 1, ESIpos): $R_t$=0.49 min, m/z=393 [M+H]$^+$, 333 [M+H—$C_2H_8N_2$]$^+$.

Example 310A

6-{[(2-Aminoethyl)amino]methyl}-3-isopropyl-1-(2-methoxyethyl)-5-methylthieno[2,3-d]pyrimidine-2,4(1H,3H)-dione

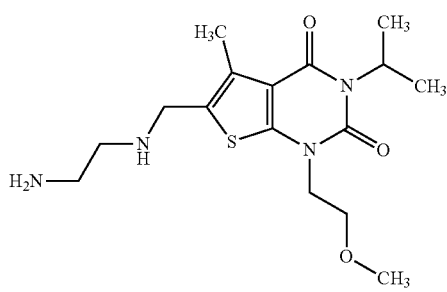 [SMILES: COCCn1c(=O)n(C(C)C)c(=O)c2c(C)c(CNCCN)sc21]

270 mg (0.870 mmol) of the compound from Ex. 105A were dissolved in a mixture of 7.5 ml of methanol and 3 ml of dichloromethane, and 349 µl (5.22 mmol) of 1,2-diaminoethane and 199 µl (3.48 mmol) of acetic acid were added at RT. After 30 min, 218 mg (3.48 mmol) of sodium cyanoborohydride were added, and the reaction mixture was heated to 50° C. After 5 h, the reaction mixture was allowed to cool down to RT, and the stirring was continued at RT for 2 days. Since the conversion was still incomplete after this time, a further 100 mg (1.59 mmol) of sodium cyanoborohydride were added and the mixture was heated again to 50° C. After 2 h, the mixture was allowed to cool back down to RT. The mixture was then admixed with 50 ml of 2 M sodium hydroxide solution and extracted thoroughly with ethyl acetate. The organic extract was washed with saturated sodium chloride solution, dried over anhydrous magnesium sulphate, filtered and concentrated on a rotary evaporator. The crude product thus obtained, after drying under high vacuum, gave 466 mg (90% of theory, 60% purity) of the title compound, which was used for subsequent reactions without further purification.

LC/MS (Method 1, ESIpos): $R_t$=0.39 min, m/z=295 [M+H—$C_2H_8N_2$]$^+$.

Example 311A

6-{[(2-Aminoethyl)amino]methyl}-3-isopropyl-5-methyl-1-(oxetan-2-ylmethyl)thieno[2,3-d]pyrimidine-2,4(1H,3H)-dione (racemate)

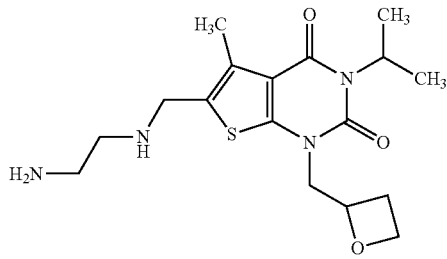 [SMILES: Cc1c(CNCCN)sc2c1c(=O)n(C(C)C)c(=O)n2CC1CCO1]

Analogously to the method described in Ex. 310A, 830 mg (2.57 mmol) of the compound from Ex. 106A, 1 ml (15.4 mmol) of 1,2-diaminoethane and a total of 747 mg (11.9 mmol) of sodium cyanoborohydride were used to obtain 880 mg (65% of theory, 70% purity) of the title compound.

LC/MS (Method 1, ESIpos): $R_t$=0.49 min, m/z=367 [M+H]$^+$, 307 [M+H—$C_2H_8N_2$]$^+$.

Example 312A

6-{[(2-Aminoethyl)amino]methyl}-3-isopropyl-5-methyl-1-(tetrahydrofuran-2-ylmethyl)thieno[2,3-d]pyrimidine-2,4(1H,3H)-dione (racemate)

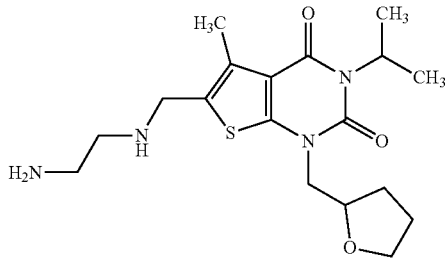 [SMILES: Cc1c(CNCCN)sc2c1c(=O)n(C(C)C)c(=O)n2CC1CCCO1]

900 mg (2.57 mmol) of the compound from Ex. 107A were dissolved in a mixture of 22 ml of methanol and 9 ml of dichloromethane, and 1 ml (15.4 mmol) of 1,2-diaminoethane and 588 µl (10.3 mmol) of acetic acid were added at RT. After 30 min, 645 mg (10.3 mmol) of sodium cyanoborohydride were added, and the reaction mixture was heated to 60° C. After about 15 h, the reaction mixture was allowed to cool down to RT. The majority of the solvent was removed on a rotary evaporator. The remaining residue was admixed with 50 ml of 2 M sodium hydroxide solution and extracted thoroughly with ethyl acetate. The organic extract was washed with saturated sodium chloride solution, dried over anhydrous magnesium sulphate, filtered and concentrated on a rotary evaporator. The crude product thus obtained, after drying under high vacuum, gave 937 mg (52% of theory, 55% purity) of the title compound, which was used for subsequent reactions without further purification.

LC/MS (Method 1, ESIpos): $R_t$=0.49 min, m/z=381 [M+H]$^+$, 321 [M+H—$C_2H_8N_2$]$^+$.

Example 313A

6-{[(2-Aminoethyl)amino]methyl}-1-(2,2-difluoroethyl)-3-isobutyl-5-methylthieno[2,3-d]pyrimidine-2,4(1H,3H)-dione

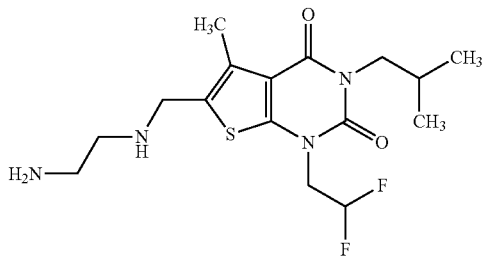 [SMILES: Cc1c(CNCCN)sc2c1c(=O)n(CC(C)C)c(=O)n2CC(F)F]

184 mg (0.55 mmol) of the compound from Ex. 111A were dissolved in a mixture of 11 ml of methanol and 5 ml of dichloromethane. Then 372 µl (5.57 mmol) of 1,2-diaminoethane and 127 µl (2.22 mmol) of acetic acid were added at RT. The mixture was stirred at RT for 30 minutes, and then 147 mg (2.23 mmol) of sodium cyanoborohydride were added. After the reaction mixture had been stirred at 60° C. for 93 h, it was admixed with 100 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 275 mg (100% of theory, 76% purity) of the title compound, which was used for subsequent reactions without further purification. 5 LC/MS (Method 3, ESIpos): $R_t$=0.72 min, m/z=315 [M+H—$C_2H_8N_2$]$^+$.

Example 314A

6-{[(2-Aminoethyl)amino]methyl}-1-(2-ethoxyethyl)-3-isobutyl-5-methylthieno[2,3-d]pyrimidine-2,4(1H,3H)-dione

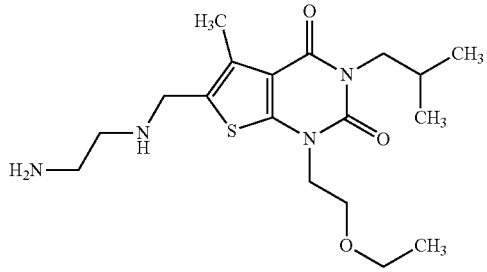 [SMILES: CCOCCn1c(=O)n(CC(C)C)c(=O)c2c(C)c(CNCCN)sc21]

357 mg (1.05 mmol) of the compound from Ex. 115A were dissolved in a mixture of 21 ml of methanol and 10 ml of dichloromethane. Then 705 µl (10.6 mmol) of 1,2-diaminoethane and 241 µl (4.22 mmol) of acetic acid were added at RT. The mixture was stirred at RT for 30 minutes, and then 279 mg (4.22 mmol) of sodium cyanoborohydride were added. After the reaction mixture had been stirred at 60° C. for 140 h, it was admixed with 100 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 585 mg (83% purity) of the title compound, which was used for subsequent reactions without further purification.

LC/MS (Method 3, ESIpos): $R_t$=0.72 min, m/z=323 [M+H—$C_2H_8N_2$]$^+$.

Example 315A

6-{[(2-Aminoethyl)amino]methyl}-3-(2,2-dimethylpropyl)-5-methyl-1-(3,3,3-trifluoropropyl)thieno[2,3-d]pyrimidine-2,4(1H,3H)-dione

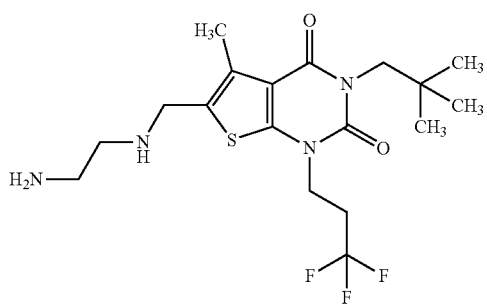 [SMILES: Cc1c(CNCCN)sc2c1c(=O)n(CC(C)(C)C)c(=O)n2CCC(F)(F)F]

386 mg (1.02 mmol) of the compound from Ex. 291A were dissolved in a mixture of 21 ml of methanol and 10 ml of dichloromethane. Then 686 µl (10.2 mmol) of 1,2-diaminoethane and 235 µl (4.1 mmol) of acetic acid were added at RT. The mixture was stirred at RT for 30 minutes, and then 271 mg (4.1 mmol) of sodium cyanoborohydride were added. After the reaction mixture had been stirred at 60° C. for 93 h, it was admixed with 100 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 610 mg (83% purity) of the title compound, which was used for subsequent reactions without further purification.

LC/MS (Method 3, ESIpos): $R_t$=0.75 min, m/z=421 [M+H]$^+$, 361 [M+H—C$_2$H$_8$N$_2$]$^+$.

Example 316A

6-{[(2-Aminoethyl)amino]methyl}-3-(2,2-dimethylpropyl)-1-(3-fluoropropyl)-5-methylthieno[2,3-d]pyrimidine-2,4(1H,3H)-dione

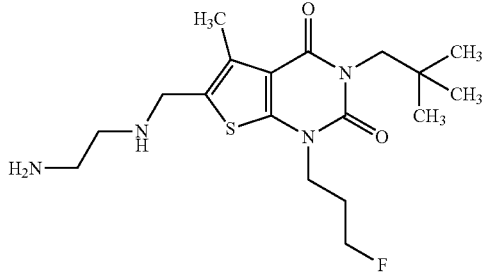 [SMILES: Cc1c(CNCCN)sc2c1c(=O)n(CC(C)(C)C)c(=O)n2CCCF]

321 mg (0.94 mmol) of the compound from Ex. 292A were dissolved in a mixture of 16 ml of methanol and 7 ml of dichloromethane. Then 630 µl (9.43 mmol) of 1,2-diaminoethane and 216 µl (3.77 mmol) of acetic acid were added at RT. The mixture was stirred at RT for 30 minutes, and then 249 mg (3.77 mmol) of sodium cyanoborohydride were added. After the reaction mixture had been stirred at 60° C. for 42 h, it was admixed with 100 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 396 mg (89% of theory, 82% purity) of the title compound, which was used for subsequent reactions without further purification.

LC/MS (Method 3, ESIpos): $R_t$=0.69 min, m/z=385 [M+H]$^+$, 325 [M+H—C$_2$H$_8$N$_2$]$^+$.

Example 317A

6-{[(2-Aminoethyl)amino]methyl}-3-(2,2-dimethylpropyl)-1-(2-methoxyethyl)-5-methylthieno[2,3-d]pyrimidine-2,4(1H,3H)-dione

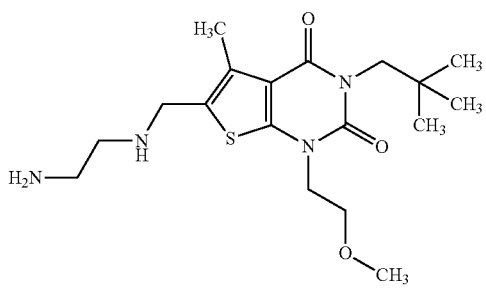 [SMILES: COCCn1c(=O)n(CC(C)(C)C)c(=O)c2c(C)c(CNCCN)sc21]

417 mg (1.23 mmol) of the compound from Ex. 293A were dissolved in a mixture of 25 ml of methanol and 12 ml of dichloromethane. Then 824 µl (12.3 mmol) of 1,2-diaminoethane and 282 µl (4.93 mmol) of acetic acid were added at RT. The mixture was stirred at RT for 30 minutes, and then 326 mg (4.93 mmol) of sodium cyanoborohydride were added. After the reaction mixture had been stirred at 60° C. for 66 h, it was admixed with 100 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 645 mg (81% purity) of the title compound, which was used for subsequent reactions without further purification.

LC/MS (Method 3, ESIpos): $R_t$=0.65 min, m/z=383 [M+H]$^+$, 323 [M+H—C$_2$H$_8$N$_2$]$^+$.

Example 318A

6-{[(2-Aminoethyl)amino]methyl}-3-(2,2-difluoroethyl)-1,5-dimethylthieno[2,3-d]pyrimidine-2,4(1H,3H)-dione

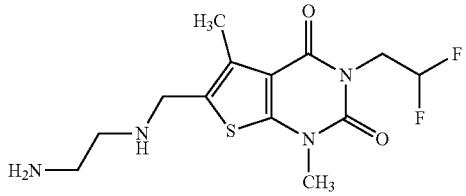 [SMILES: Cc1c(CNCCN)sc2c1c(=O)n(CC(F)F)c(=O)n2C]

355 mg (1.12 mmol) of the compound from Ex. 135A were dissolved in a mixture of 19 ml of methanol and 8 ml of dichloromethane. Then 749 µl (11.2 mmol) of 1,2-diaminoethane and 257 µl (4.48 mmol) of acetic acid were added at RT. The mixture was stirred at RT for 30 minutes, and then 296 mg (4.48 mmol) of sodium cyanoborohydride were added. After the reaction mixture had been stirred at 60° C. for 132 h, it was admixed with 50 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 350 mg (65% of theory, 70% purity) of the title compound, which was used for subsequent reactions without further purification.

LC/MS (Method 3, ESIpos): $R_t$=0.46 min, m/z=333 [M+H]$^+$, 273 [M+H—C$_2$H$_8$N$_2$]$^+$.

Example 319A

6-{[(2-Aminoethyl)amino]methyl}-3-(2-methoxyethyl)-5-methyl-1-(3,3,3-trifluoropropyl)thieno[2,3-d]pyrimidine-2,4(1H,3H)-dione

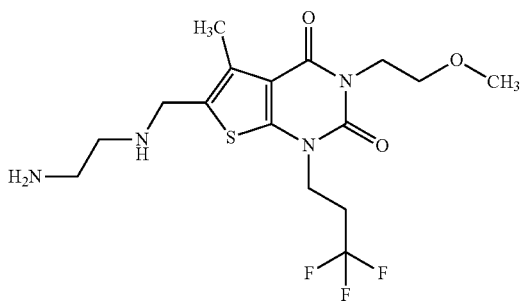 [SMILES: COCCn1c(=O)c2c(C)c(CNCCN)sc2n(CCC(F)(F)F)c1=O]

250 mg (0.67 mmol) of the compound from Ex. 296A were dissolved in a mixture of 11 ml of methanol and 5 ml of dichloromethane. Then 450 μl (6.72 mmol) of 1,2-diaminoethane and 154 μl (2.69 mmol) of acetic acid were added at RT. The mixture was stirred at RT for 30 minutes, and then 178 mg (2.69 mmol) of sodium cyanoborohydride were added. After the reaction mixture had been stirred at 60° C. for 118 h, it was admixed with 50 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 277 mg (81% of theory, 81% purity) of the title compound, which was used for subsequent reactions without further purification.

LC/MS (Method 3, ESIpos): $R_t$=0.57 min, m/z=409 [M+H]$^+$, 349 [M+H—$C_2H_8N_2$]$^+$.

Example 320A

6-{[(2-Aminoethyl)amino]methyl}-1-(3-fluoropropyl)-3-(2-methoxyethyl)-5-methylthieno[2,3-d]pyrimidine-2,4(1H,3H)-dione

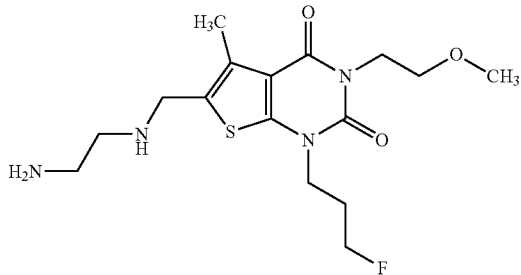 [SMILES: COCCn1c(=O)c2c(C)c(CNCCN)sc2n(CCCF)c1=O]

175 mg (0.52 mmol) of the compound from Ex. 297A were dissolved in a mixture of 9 ml of methanol and 4 ml of dichloromethane. Then 349 μl (5.22 mmol) of 1,2-diaminoethane and 120 μl (2.09 mmol) of acetic acid were added at RT. The mixture was stirred at RT for 30 minutes, and then 138 mg (2.09 mmol) of sodium cyanoborohydride were added. After the reaction mixture had been stirred at 60° C. for 92 h, it was admixed with 50 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 150 mg (49% of theory, 64% purity) of the title compound, which was used for subsequent reactions without further purification.

LC/MS (Method 3, ESIpos): $R_t$=0.49 min, m/z=373 [M+H]f, 313 [M+H—$C_2H_8N_2$]$^+$.

Example 321A

6-{[(2-Aminoethyl)amino]methyl}-3-(2-methoxyethyl)-5-methyl-1-(tetrahydrofuran-2-ylmethyl)thieno[2,3-d]pyrimidine-2,4(1H,3H)-dione (racemate)

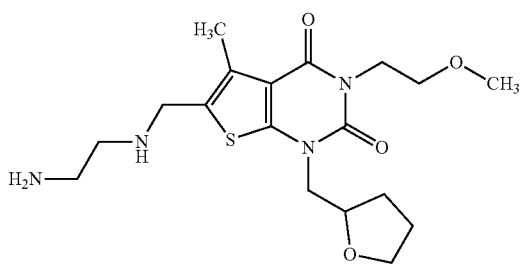 [SMILES: COCCn1c(=O)c2c(C)c(CNCCN)sc2n(CC2CCCO2)c1=O]

440 mg (1.22 mmol) of the compound from Ex. 298A were dissolved in a mixture of 20 ml of methanol and 9 ml of dichloromethane. Then 818 μl (12.2 mmol) of 1,2-diaminoethane and 280 μl (4.89 mmol) of acetic acid were added at RT. The mixture was stirred at RT for 30 minutes, and then 324 mg (4.89 mmol) of sodium cyanoborohydride were added. After the reaction mixture had been stirred at 60° C. for 117 h, it was admixed with 50 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 305 mg (41% of theory, 66% purity) of the title compound, which was used for subsequent reactions without further purification.

LC/MS (Method 3, ESIpos): $R_t$=0.53 min, m/z=397 [M+H]$^+$, 337 [M+H—$C_2H_8N_2$]$^+$.

Example 322A

6-{[(2-Aminoethyl)amino]methyl}-3-(2-methoxy-2-methylpropyl)-5-methyl-1-(3,3,3-trifluoropropyl)thieno[2,3-d]pyrimidine-2,4(1H,3H)-dione

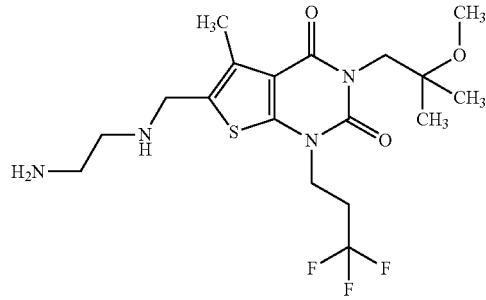 [SMILES: COC(C)(C)Cn1c(=O)c2c(C)c(CNCCN)sc2n(CCC(F)(F)F)c1=O]

463 mg (1.18 mmol) of the compound from Ex. 299A were dissolved in a mixture of 24 ml of methanol and 11 ml of dichloromethane. Then 789 μl (11.8 mmol) of 1,2-diaminoethane and 270 μl (4.72 mmol) of acetic acid were added at RT. The mixture was stirred at RT for 30 minutes, and then 312 mg (4.72 mmol) of sodium cyanoborohydride were added. After the reaction mixture had been stirred at 60° C. for 69 h, it was admixed with 100 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 630 mg (99% of theory, 81% purity) of the title compound, which was used for subsequent reactions without further purification.

LC/MS (Method 3, ESIpos): $R_t$=0.64 min, m/z=437 [M+H]$^+$, 377 [M+H—$C_2H_8N_2$]$^+$.

Example 323A

6-{[(2-Aminoethyl)amino]methyl}-1-(3-fluoropropyl)-3-(2-methoxy-2-methylpropyl)-5-methylthieno[2,3-d]pyrimidine-2,4(1H,3H)-dione

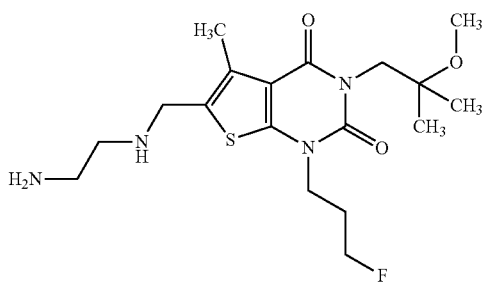 [SMILES: COC(C)(C)Cn1c(=O)c2c(C)c(CNCCN)sc2n(CCCF)c1=O]

456 mg (1.28 mmol) of the compound from Ex. 300A were dissolved in a mixture of 26 ml of methanol and 12 ml of dichloromethane. Then 855 µl (12.8 mmol) of 1,2-diaminoethane and 293 µl (5.12 mmol) of acetic acid were added at RT. The mixture was stirred at RT for 30 minutes, and then 338 mg (5.12 mmol) of sodium cyanoborohydride were added. After the reaction mixture had been stirred at 60° C. for 66 h, it was admixed with 100 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 730 mg (85% purity) of the title compound, which was used for subsequent reactions without further purification.

LC/MS (Method 3, ESIpos): $R_t$=0.56 min, m/z=401 [M+H]$^+$, 341 [M+H—C$_2$H$_8$N$_2$]$^+$.

Example 324A

6-{[(2-Aminoethyl)amino]methyl}-1-(2-methoxyethyl)-3-(2-methoxy-2-methylpropyl)-5-methylthieno[2,3-d]pyrimidine-2,4(1H,3H)-dione

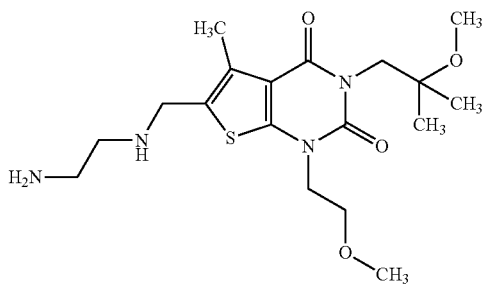 [SMILES: COCCn1c(=O)n(CC(C)(C)OC)c(=O)c2c(C)c(CNCCN)sc21]

390 mg (1.05 mmol) of the compound from Ex. 301A were dissolved in a mixture of 21 ml of methanol and 10 ml of dichloromethane. Then 706 µl (10.56 mmol) of 1,2-diaminoethane and 242 µl (4.22 mmol) of acetic acid were added at RT. The mixture was stirred at RT for 30 minutes, and then 279 mg (4.22 mmol) of sodium cyanoborohydride were added. After the reaction mixture had been stirred at 60° C. for 87 h, it was admixed with 100 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 355 mg (65% of theory, 78% purity) of the title compound, which was used for subsequent reactions without further purification.

LC/MS (Method 3, ESIpos): $R_t$=0.56 min, m/z=399 [M+H]$^+$, 339 [M+H—C$_2$H$_8$N$_2$]$^+$.

Example 325A

6-{[(2,2-Dimethoxyethyl)amino]methylaminomethyl}-3-ethyl-5-methyl-1-(tetrahydrofuran-2-ylmethyl)thieno[2,3-d]pyrimidine-2,4(1H,3H)-dione (racemate)

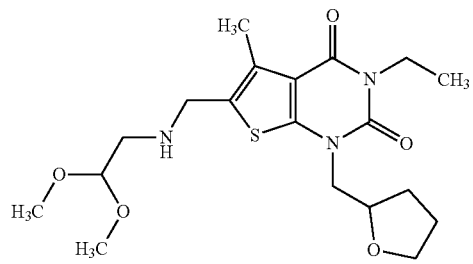 [SMILES: CCn1c(=O)c2c(C)c(CNCC(OC)OC)sc2n(CC2CCCO2)c1=O]

1.0 g (3.10 mmol) of the compound from Ex. 89A were dissolved in 70 ml of dichloromethane, and 326 mg (3.10 mmol) of 2,2-dimethoxyethanamine were added. The mixture was heated to reflux for 1 h. After cooling to RT, 1.31 g (6.20 mmol) of sodium triacetoxyborohydride were added, and stirring was continued at RT. Since the conversion was still incomplete after about 18 h, a further 163 mg (1.55 mmol) of 2,2-dimethoxyethanamine and 657 mg (3.10 mmol) of sodium triacetoxyborohydride were added. After stirring at RT for a further 20 h, the mixture was diluted with ethyl acetate and washed successively with saturated sodium hydrogencarbonate solution and saturated sodium chloride solution. After drying over anhydrous magnesium sulphate, the mixture was filtered and the filtrate was evaporated to dryness. The residue obtained was purified by means of chromatography (Biotage Isolera One, SNAP KP-Sil cartridge, 50 g of silica gel, eluent: cyclohexane/ethyl acetate 50:50→0:100). After concentration of the product fractions and drying under high vacuum, 1.22 g (94% of theory) of the title compound were obtained.

LC/MS (Method 17, ESIpos): $R_t$=0.82 min, m/z=307 [M+H—C$_4$H$_{11}$NO$_2$]$^+$.

Example 326A

6-{[(2,2-Dimethoxyethyl)amino]methyl}-3-isopropyl-5-methyl-1-(3,3,3-trifluoropropyl)thieno[2,3-d]pyrimidine-2,4(1H,3H)-dione

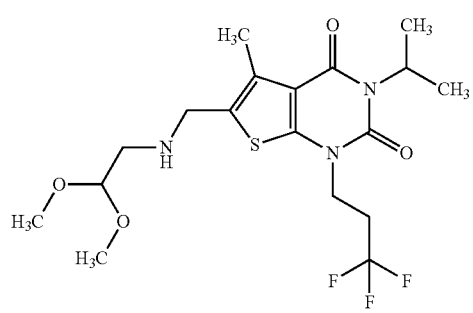 [SMILES: COC(CNCc1sc2c(c1C)c(=O)n(C(C)C)c(=O)n2CCC(F)(F)F)OC]

500 mg (1.43 mmol) of the compound from Ex. 103A were dissolved in 30 ml of dichloromethane, and 223 µl (2.15 mmol) of 2,2-dimethoxyethanamine were added. The mixture was heated to reflux for 1 h. After cooling to RT, 960 mg (4.31 mmol) of sodium triacetoxyborohydride were added, and stirring was continued at RT. After about 18 h, the mixture was diluted with ethyl acetate and washed successively with saturated sodium hydrogencarbonate solution and saturated sodium chloride solution. After drying over anhydrous magnesium sulphate, the mixture was filtered and the filtrate was evaporated to dryness. The residue obtained was purified by means of chromatography (Biotage Isolera One, SNAP KP-Sil cartridge, 50 g of silica gel, eluent: cyclohexane/ethyl acetate 2:1). After concentration of the product fractions and drying under high vacuum, 438 mg (68% of theory) of the title compound were obtained.

$^1$H-NMR (400 MHz, DMSO-d$_6$, δ/ppm): 5.13 (sept, 1H), 4.41 (t, 1H), 4.08 (t, 2H), 3.83 (s, 2H), 3.26 (s, 6H), 2.83-2.67 (m, 2H), 2.62 (d, 2H), 2.33 (s, 3H), 2.30 (broad, 1H), 1.40 (d, 6H).

LC/MS (Method 17, ESIpos): R$_t$=1.10 min, m/z=333.09 [M+H—C$_4$H$_{11}$NO$_2$]$^+$.

Example 327A

6-{[(2,2-Dimethoxyethyl)amino]methyl}-3-isopropyl-1-(2-methoxyethyl)-5-methylthieno[2,3-d]pyrimidine-2,4(1H,3H)-dione

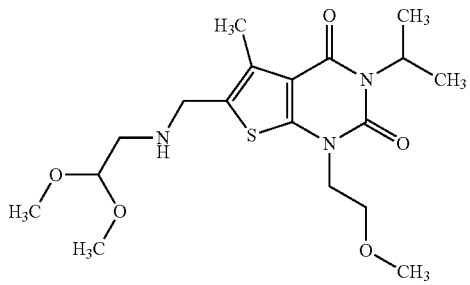 [SMILES: COCCn1c(=O)n(C(C)C)c(=O)c2c(C)c(CNCC(OC)OC)sc21]

500 mg (1.61 mmol) of the compound from Ex. 105A were dissolved in 30 ml of dichloromethane, and 261 µl (2.42 mmol) of 2,2-dimethoxyethanamine were added. The mixture was heated to reflux for 1 h. After cooling to RT, 1.02 g (4.83 mmol) of sodium triacetoxyborohydride were added, and stirring was continued at RT. After about 18 h, the mixture was diluted with ethyl acetate and washed successively with saturated sodium hydrogencarbonate solution and saturated sodium chloride solution. After drying over anhydrous magnesium sulphate, the mixture was filtered and the filtrate was evaporated to dryness. The residue obtained was purified by means of chromatography (Biotage Isolera One, SNAP KP-Sil cartridge, 50 g of silica gel, eluent: cyclohexane/ethyl acetate 2:1). After concentration of the product fractions and drying under high vacuum, 461 mg (70% of theory) of the title compound were obtained.

$^1$H-NMR (400 MHz, DMSO-d$_6$, δ/ppm): 5.13 (sept, 1H), 4.40 (t, 1H), 4.00 (t, 2H), 3.81 (br. s, 2H), 3.62 (t, 2H), 3.26 (s, 6H), 3.24 (s, 3H), 2.62 (br. s, 2H), 2.31 (s, 3H), 2.24 (broad, 1H), 1.40 (d, 6H).

LC/MS (Method 1, ESIpos): R$_t$=0.60 min, m/z=400 [M+H]$^+$, 295 [M+H—C$_4$H$_{11}$NO$_2$]$^+$.

Example 328A

6-{[(2,2-Dimethoxyethyl)amino]methyl}-3-isopropyl-5-methyl-1-(tetrahydrofuran-2-ylmethyl)thieno[2,3-d]pyrimidine-2,4(1H,3H)-dione (racemate)

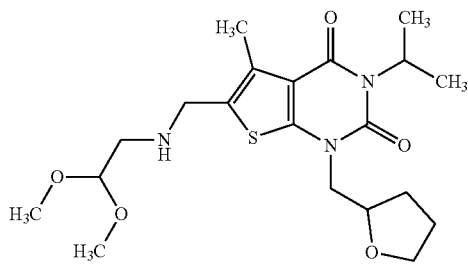 [SMILES: COC(CNCc1sc2c(c1C)c(=O)n(C(C)C)c(=O)n2CC1CCCO1)OC]

Analogously to the method described in Ex. 327A, 900 mg (2.67 mmol) of the compound from Ex. 107A, 434 µl (4.01 mmol) of 2,2-dimethoxyethanamine and 1.70 g (8.03 mmol) of sodium triacetoxyborohydride were used to obtain 1.01 g (88% of theory) of the title compound. Chromatography was effected here under the following conditions: Biotage Isolera One, SNAP KP-Sil cartridge, 100 g of silica gel, eluent: cyclohexane/ethyl acetate 50:50→0:100.

$^1$H-NMR (400 MHz, DMSO-d$_6$, δ/ppm): 5.14 (sept, 1H), 4.40 (t, 1H), 4.27-4.17 (m, 1H), 4.07-3.97 (m, 1H), 3.81 (s, 2H), 3.78-3.57 (m, 3H), 3.26 (s, 6H), 2.61 (d, 2H), 2.32 (s, 3H), 2.04-1.74 (m, 3H), 1.72-1.59 (m, 1H), 1.40 (d, 6H).

LC/MS (Method 17, ESIpos): R$_t$=0.98 min, m/z=321.13 [M+H—C$_4$H$_{11}$NO$_2$]$^+$.

Example 329A 1-(2,2-Dimethoxyethyl)-1-{[3-ethyl-5-methyl-2,4-dioxo-1-(tetrahydrofuran-2-ylmethyl)-1,2,3,4-tetrahydrothieno[2,3-d]pyrimidin-6-yl]methyl}urea (racemate)

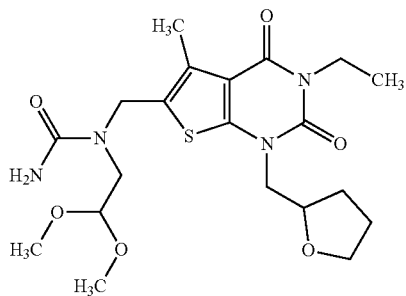 [SMILES: CCn1c(=O)c2c(C)c(CN(CC(OC)OC)C(N)=O)sc2n(CC2CCCO2)c1=O]

Analogously to the method described in Ex. 273A, 1.20 g (2.92 mmol) of the compound from Ex. 325A, 544 mg (6.71 mmol) of potassium cyanate and 428 µl (4.96 mmol) of perchloric acid (70% in water) were used to prepare 912 mg (61% of theory, 90% purity) of the title compound. The reaction time here was 3 h, and the isolated crude product was additionally stirred with ethyl acetate at RT.

$^1$H-NMR (400 MHz, DMSO-d$_6$, δ/ppm): 6.03 (s, 2H), 4.54 (s, 2H), 4.44 (t, 1H), 4.27-4.15 (m, 1H), 4.01 (dd, 1H), 3.90 (q, 2H), 3.78-3.66 (m, 2H), 3.64-3.56 (m, 1H), 3.31 (m, 7H), 3.16 (t, 1H), 2.39 (s, 3H), 2.04-1.73 (m, 3H), 1.71-1.59 (m, 1H), 1.11 (t, 3H).

LC/MS (Method 17, ESIpos): $R_t$=1.35 min, m/z=423.17 [M+H—CH$_3$OH]$^+$, 307.11 [M+H—C$_5$H$_{12}$N$_2$O$_3$]$^+$.

Example 330A 1-(2,2-Dimethoxyethyl)-1-{[3-isopropyl-5-methyl-2,4-dioxo-1-(3,3,3-trifluoropropyl)-1,2,3,4-tetrahydrothieno[2,3-d]pyrimidin-6-yl]methyl}urea

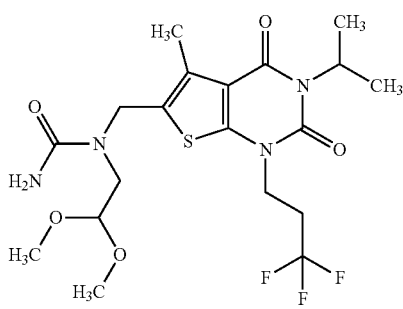 [SMILES: COC(CN(Cc1sc2c(c1C)c(=O)n(C(C)C)c(=O)n2CCC(F)(F)F)C(N)=O)OC]

To a solution of 425 mg (0.971 mmol) of the compound from Ex. 326A in 9 ml of methanol were added, at RT, first 181 mg (2.23 mmol) of potassium cyanate and then 142 µl (1.65 mmol) of perchloric acid (70% in water). After 6 days, the reaction mixture was admixed with saturated aqueous sodium hydrogencarbonate solution and then extracted with ethyl acetate. The organic extract was washed successively with water and saturated sodium chloride solution, dried over anhydrous magnesium sulphate, filtered and concentrated. After the residue obtained had been dried under high vacuum, 294 mg (62% of theory) of the title compound were obtained.

$^1$H-NMR (400 MHz, DMSO-d$_6$, δ/ppm): 6.04 (s, 2H), 5.13 (sept, 1H), 4.55 (s, 2H), 4.45 (t, 1H), 4.06 (t, 2H), 3.31 (s, 6H, partially obscured by the water signal), 3.16 (d, 2H), 2.84-2.65 (m, 2H), 2.39 (s, 3H), 1.39 (d, 6H).

LC/MS (Method 17, ESIpos): $R_t$=1.77 min, m/z=449.15 [M+H—CH$_3$OH]$^+$, 333.09 [M+H—C$_5$H$_{12}$N$_2$O$_3$]$^+$.

Example 331A 1-(2,2-Dimethoxyethyl)-1-{[3-isopropyl-1-(2-methoxyethyl)-5-methyl-2,4-dioxo-1,2,3,4-tetrahydrothieno[2,3-d]pyrimidin-6-yl]methyl}urea

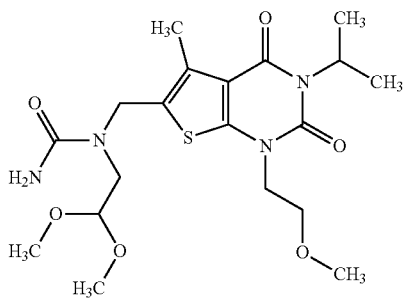 [SMILES: COCCn1c(=O)n(C(C)C)c(=O)c2c(C)c(CN(CC(OC)OC)C(N)=O)sc21]

To a solution of 450 mg (1.13 mmol) of the compound from Ex. 327A in 12 ml of methanol were added, at RT, first 210 mg (2.59 mmol) of potassium cyanate and then 165 µl (1.91 mmol) of perchloric acid (70% in water). After 6 days, the reaction mixture was admixed with saturated aqueous sodium hydrogencarbonate solution and then extracted with ethyl acetate. The organic extract was washed successively with water and saturated sodium chloride solution, dried over anhydrous magnesium sulphate, filtered and concentrated. After the residue obtained had been dried under high vacuum, 580 mg (76% of theory, 66% purity) of the title compound were obtained, which was used for subsequent reactions without further purification.

LC/MS (Method 1, ESIpos): $R_t$=0.86 min, m/z=443 [M+H]$^+$, 411 [M+H—CH$_3$OH]$^+$, 295 [M+H—C$_5$H$_{12}$N$_2$O$_3$]$^+$.

Example 332A 1-(2,2-Dimethoxyethyl)-1-{[3-ethyl-5-isopropyl-2,4-dioxo-1-(tetrahydrofuran-2-ylmethyl)-1,2,3,4-tetrahydrothieno[2,3-d]pyrimidin-6-yl]methyl}urea (racemate)

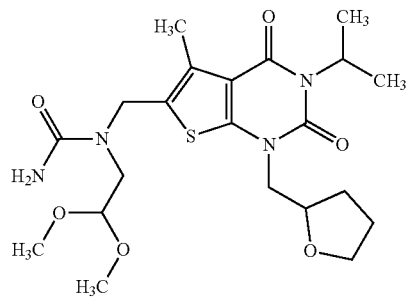 [SMILES: COC(CN(Cc1sc2c(c1C)c(=O)n(C(C)C)c(=O)n2CC1CCCO1)C(N)=O)OC]

Analogously to the method described in Ex. 273A, 985 mg (2.31 mmol) of the compound from Ex. 328A, 432 mg (5.32 mmol) of potassium cyanate and 339 µl (3.93 mmol) of perchloric acid (70% in water) were used to prepare 1.15 g (81% of theory, 77% purity) of the title compound, which was used for subsequent reactions without further purification. The reaction time here was about 18 h.

LC/MS (Method 1, ESIpos): $R_t$=0.85 min, m/z=469 [M+H]$^+$, 437 [M+H—CH$_3$OH]$^+$, 321 [M+H—C$_5$H$_{12}$N$_2$O$_3$]$^+$.

Example 333A tert-Butyl 2-{[3-ethyl-5-methyl-2,4-dioxo-1-(3,3,3-trifluoropropyl)-1,2,3,4-tetrahydrothieno[2,3-d]pyrimidin-6-yl]methylene}hydrazinecarboxylate

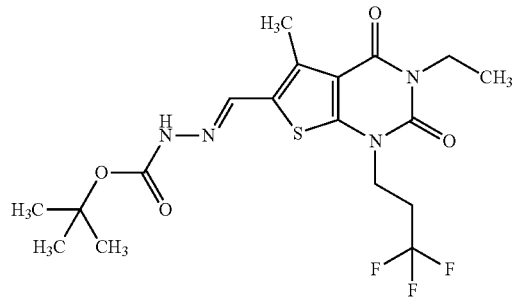 [SMILES: CCn1c(=O)c2c(C)c(/C=N/NC(=O)OC(C)(C)C)sc2n(CCC(F)(F)F)c1=O]

To a solution of 1.0 g (2.99 mmol) of the compound from Ex. 74A in 30 ml of ethanol were added first 395 mg (2.99 mmol) of tert-butyl hydrazinecarboxylate and then 5 drops of concentrated hydrochloric acid. After the reaction mixture had been stirred at RT for about 18 h, the majority of the ethanol was removed on a rotary evaporator. The remaining residue was diluted with 150 ml of water and neutralized by adding saturated aqueous sodium hydrogencarbonate solution. The precipitated solids were filtered off with suction, washed with a little water and dried under high vacuum. 1.25 g (93% of theory) of the title compound were obtained.

$^1$H-NMR (400 MHz, DMSO-$d_6$, δ/ppm): 10.88 (br. s, 1H), 8.30 (s, 1H), 4.15 (t, 2H), 3.90 (q, 2H), 2.88-2.71 (m, 2H), 2.46 (s, 3H), 1.46 (s, 9H), 1.12 (t, 3H).

LC/MS (Method 1, ESIpos): $R_t$=1.13 min, m/z=449 [M+H]$^+$.

Example 334A tert-Butyl 2-{[3-ethyl-1-(2-methoxyethyl)-5-methyl-2,4-dioxo-1,2,3,4-tetrahydrothieno[2,3-d]pyrimidin-6-yl]methylene}hydrazinecarboxylate

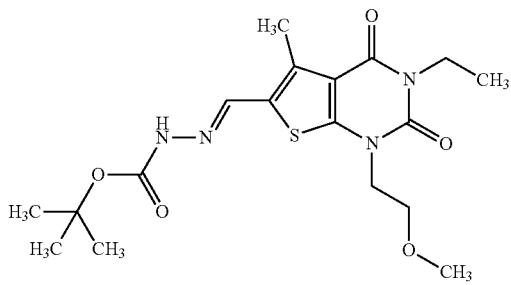 [SMILES: CCn1c(=O)c2c(C)c(/C=N/NC(=O)OC(C)(C)C)sc2n(CCOC)c1=O]

To a solution of 1.0 g (3.37 mmol) of the compound from Ex. 84A in 30 ml of ethanol were added first 669 mg (5.06 mmol) of tert-butyl hydrazinecarboxylate and then 5 drops of concentrated hydrochloric acid. After the reaction mixture had been stirred at RT for about 18 h, the majority of the ethanol was removed on a rotary evaporator. The remaining residue was diluted with 150 ml of water and neutralized by adding saturated aqueous sodium hydrogencarbonate solution. The precipitated solids were filtered off with suction, washed with a little water and dried under high vacuum. 1.34 g (96% of theory) of the title compound were obtained.

$^1$H-NMR (400 MHz, DMSO-$d_6$, δ/ppm): 10.85 (broad, 1H), 8.29 (s, 1H), 4.07 (t, 2H), 3.90 (q, 2H), 3.65 (t, 2H), 3.25 (s, 3H), 2.45 (s, 3H), 1.45 (s, 9H), 1.12 (t, 3H).

LC/MS (Method 1, ESIpos): $R_t$=1.00 min, m/z=411 [M+H]$^+$.

Example 335A tert-Butyl 2-{[3-ethyl-5-methyl-2,4-dioxo-1-(tetrahydrofuran-2-ylmethyl)-1,2,3,4-tetrahydrothieno[2,3-d]pyrimidin-6-yl]methylene}hydrazinecarboxylate (racemate)

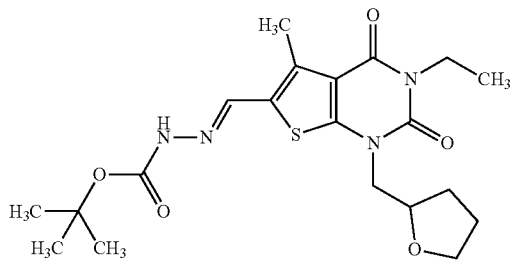 [SMILES: CCn1c(=O)c2c(C)c(/C=N/NC(=O)OC(C)(C)C)sc2n(CC2CCCO2)c1=O]

To a solution of 1.10 g (3.41 mmol) of the compound from Ex. 89A in 25 ml of ethanol were added first 676 mg (5.12 mmol) of tert-butyl hydrazinecarboxylate and then 5 drops of concentrated hydrochloric acid. After the reaction mixture had been stirred at RT for about 18 h, the majority of the ethanol was removed on a rotary evaporator. The remaining residue was diluted with 150 ml of water and neutralized by adding saturated aqueous sodium hydrogencarbonate solution. The precipitated solids were filtered off with suction, washed with a little water and dried under high vacuum. 1.49 g (99% of theory) of the title compound were obtained.

$^1$H-NMR (400 MHz, DMSO-$d_6$, δ/ppm): 10.85 (broad, 1H), 8.29 (s, 1H), 4.29-4.16 (m, 1H), 4.09 (dd, 1H), 3.90 (q, 2H), 3.81-3.71 (m, 2H), 3.67-3.57 (m, 1H), 2.45 (s, 3H), 2.08-1.77 (m, 3H), 1.72-1.59 (m, 1H), 1.45 (s, 9H), 1.12 (t, 3H).

LC/MS (Method 17, ESIpos): $R_t$=1.94 min, m/z=437.18 [M+H]$^+$.

Example 336A tert-Butyl 2-{[3-isopropyl-5-methyl-2,4-dioxo-1-(3,3,3-trifluoropropyl)-1,2,3,4-tetrahydrothieno[2,3-d]pyrimidin-6-yl]methylene}hydrazinecarboxylate

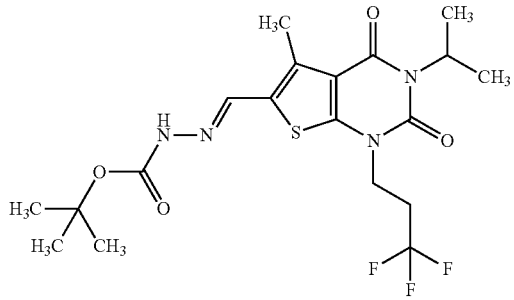 [SMILES: Cc1c(/C=N/NC(=O)OC(C)(C)C)sc2c1c(=O)n(C(C)C)c(=O)n2CCC(F)(F)F]

To a solution of 1.02 g (2.93 mmol) of the compound from Ex. 103A in 25 ml of ethanol were added first 580 mg (4.39 mmol) of tert-butyl hydrazinecarboxylate and then 5 drops of concentrated hydrochloric acid. After the reaction mixture had been stirred at RT for about 18 h, the majority of the ethanol was removed on a rotary evaporator. The remaining residue was diluted with 150 ml of water and neutralized by adding saturated aqueous sodium hydrogencarbonate solution. The precipitated solids were filtered off with suction, washed with a little water and dried under high vacuum. 1.27 g (93% of theory) of the title compound were obtained.

$^1$H-NMR (400 MHz, DMSO-$d_6$, δ/ppm): 10.87 (broad, 1H), 8.30 (s, 1H), 5.12 (sept, 1H), 4.12 (t, 2H), 2.89-2.69 (m, 2H), 2.45 (s, 3H), 1.45 (s, 9H), 1.40 (d, 6H).

LC/MS (Method 17, ESIpos): $R_t$=2.23 min, m/z=463.16 [M+H]$^+$.

Example 337A tert-Butyl 2-{[3-isopropyl-1-(2-methoxyethyl)-5-methyl-2,4-dioxo-1,2,3,4-tetrahydrothieno[2,3-d]pyrimidin-6-yl]methylene}hydrazinecarboxylate

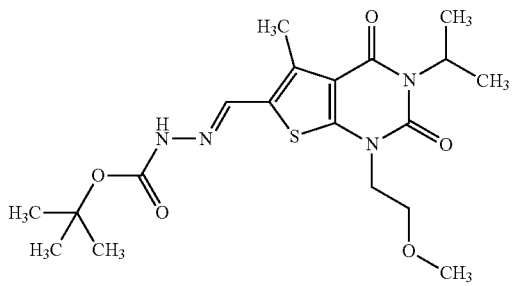 [SMILES: COCCn1c(=O)n(C(C)C)c(=O)c2c(C)c(/C=N/NC(=O)OC(C)(C)C)sc21]

Analogously to the method described in Ex. 333A, 650 mg (2.09 mmol) of the compound from Ex. 105A and 415 mg (3.14 mmol) of tert-butyl hydrazinecarboxylate were used to obtain 824 mg (92% of theory) of the title compound.

$^1$H-NMR (400 MHz, DMSO-$d_6$, δ/ppm): 10.84 (broad, 1H), 8.28 (s, 1H), 5.12 (sept, 1H), 4.04 (t, 2H), 3.64 (t, 2H), 3.26 (s, 3H), 2.44 (s, 3H), 1.45 (s, 9H), 1.40 (d, 6H).

LC/MS (Method 1, ESIpos): $R_t$=1.06 min, m/z=425 [M+H]$^+$.

Example 338A tert-Butyl 2-{[3-isopropyl-5-methyl-2,4-dioxo-1-(tetrahydrofuran-2-ylmethyl)-1,2,3,4-tetrahydrothieno[2,3-d]pyrimidin-6-yl]methylene}hydrazinecarboxylate (racemate)

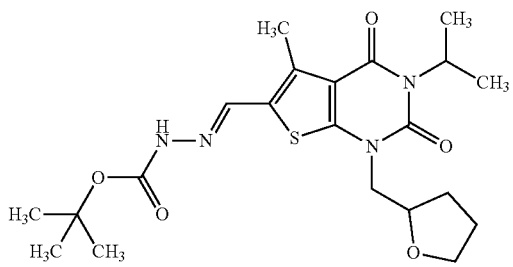 [SMILES: Cc1c(/C=N/NC(=O)OC(C)(C)C)sc2c1c(=O)n(C(C)C)c(=O)n2CC1CCCO1]

Analogously to the method described in Ex. 333A, 900 mg (2.67 mmol) of the compound from Ex. 107A and 530 mg (4.01 mmol) of tert-butyl hydrazinecarboxylate were used to obtain 1.17 g (87% of theory, 90% purity) of the title compound, which was used for subsequent reactions without further purification.

$^1$H-NMR (400 MHz, DMSO-$d_6$, δ/ppm): 10.84 (broad, 1H), 8.29 (s, 1H), 5.13 (sept, 1H), 4.27-4.17 (m, 1H), 4.08 (dd, 1H), 3.82-3.67 (m, 2H), 3.66-3.58 (m, 1H), 2.44 (s, 3H), 2.08-1.73 (m, 3H), 1.71-1.59 (m, 1H), 1.45 (s, 9H), 1.40 (d, 6H).

LC/MS (Method 1, ESIpos): $R_t$=1.11 min, m/z=451 [M+H]$^+$.

Example 339A tert-Butyl 2-{[3-ethyl-5-methyl-2,4-dioxo-1-(3,3,3-trifluoropropyl)-1,2,3,4-tetrahydrothieno[2,3-d]pyrimidin-6-yl]methyl}hydrazinecarboxylate

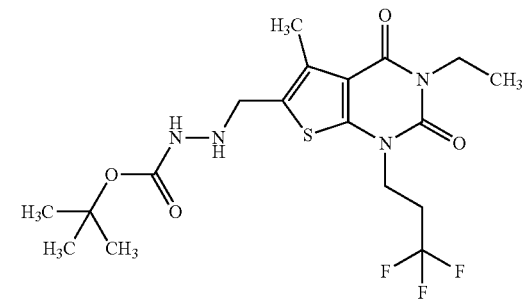 [SMILES: CCn1c(=O)c2c(C)c(CNNC(=O)OC(C)(C)C)sc2n(CCC(F)(F)F)c1=O]

To a solution of 6.50 g (14.5 mmol) of the compound from Ex. 333A in 150 ml of methanol were added 4.55 g (72.5 mmol) of sodium cyanoborohydride and a little Bromocresol Green. Subsequently, a sufficient amount of acetic acid was added by titration that the indicator colour just changed from blue to yellow. Then the reaction mixture was heated to 65° C. After 1 h, after 3 h and after 4 h, a further 2.28 g (36.2 mmol) of sodium cyanoborohydride were added in each case. Over the entire reaction time, by addition of further acetic acid, the pH was constantly regulated such that the indicator colour just remained yellow. After a total of 8 h, the volatile constituents of the reaction mixture were substantially removed on a rotary evaporator. The remaining residue was taken up in ethyl acetate and washed successively with saturated aqueous sodium hydrogencarbonate solution, water and saturated aqueous sodium chloride solution. After drying over anhydrous magnesium sulphate, the mixture was filtered and concentrated to dryness. The product was isolated by means of chromatography (Biotage Isolera One, SNAP KP-Sil cartridge, 340 g of silica gel, eluent: cyclohexane/ethyl acetate 2:1). The product fractions were combined and extracted by shaking with 1 M sodium hydroxide solution and, after phase separation, concentrated again. After drying under high vacuum, 5.23 g (80% of theory) of the title compound were obtained.

$^1$H-NMR (400 MHz, DMSO-$d_6$, δ/ppm): 8.25 (br. s, 1H), 5.07 (br. d, 1H), 4.13 (t, 2H), 3.99 (d, 2H), 3.91 (q, 2H), 2.86-2.68 (m, 2H), 2.33 (s, 3H), 1.39 (s, 9H), 1.11 (t, 3H).

LC/MS (Method 1, ESIpos): $R_t$=1.07 min, m/z=451 [M+H]$^+$.

Example 340A tert-Butyl 2-{[3-ethyl-1-(2-methoxyethyl)-5-methyl-2,4-dioxo-1,2,3,4-tetrahydrothieno[2,3-d]pyrimidin-6-yl]methyl}hydrazinecarboxylate

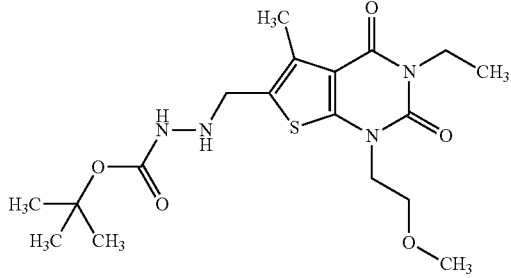 [SMILES: CCn1c(=O)c2c(C)c(CNNC(=O)OC(C)(C)C)sc2n(CCOC)c1=O]

To a solution of 1.34 g (3.26 mmol) of the compound from Ex. 334A in 33 ml of methanol were added 1.03 g (16.3 mmol) of sodium cyanoborohydride and a little Bromocresol Green. Subsequently, a sufficient amount of acetic acid was added by titration that the indicator colour just changed from blue to yellow. Then the reaction mixture was heated to 65° C. After 1 h, after 3 h and after 4 h, a further 0.52 g (8.2 mmol) of sodium cyanoborohydride were added in each case. Over the entire reaction time, by addition of further acetic acid, the pH was constantly regulated such that the indicator colour just remained yellow. After a total of 5 h, the volatile constituents of the reaction mixture were substantially removed on a rotary evaporator. The remaining residue was taken up in ethyl acetate and washed successively with saturated aqueous sodium hydrogencarbonate solution, water and saturated aqueous sodium chloride solution. After drying over anhydrous magnesium sulphate, the mixture was filtered and concentrated to dryness. The crude product was stirred with acetonitrile. The solid was filtered off with suction and dried under high vacuum. This gave a first fraction of 810 mg of the title compound. A further 166 mg of the product were obtained from the mother liquor from the stirring by means of preparative HPLC (Method 8). A total of 976 mg (72% of theory) of the title compound were thus obtained.

$^1$H-NMR (400 MHz, DMSO-$d_6$, δ/ppm): 8.25 (br. s, 1H), 4.99 (br. s, 1H), 4.04 (t, 2H), 3.97 (d, 2H), 3.90 (q, 2H), 3.65 (t, 2H), 3.25 (s, 3H), 2.33 (s, 3H), 1.39 (s, 9H), 1.11 (t, 3H).

LC/MS (Method 1, ESIpos): $R_t$=0.92 min, m/z=413 [M+H]$^+$, 281 [M+H—$C_5H_{12}N_2O_2$]$^+$.

Example 341A tert-Butyl 2-{[3-ethyl-5-methyl-2,4-dioxo-1-(tetrahydrofuran-2-ylmethyl)-1,2,3,4-tetrahydrothieno[2,3-d]pyrimidin-6-yl]methyl}hydrazinecarboxylate (racemate)

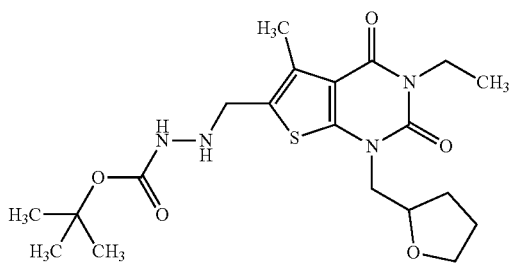 [SMILES: CCn1c(=O)c2c(C)c(CNNC(=O)OC(C)(C)C)sc2n(CC2CCCO2)c1=O]

To a solution of 1.40 g (3.21 mmol) of the compound from Ex. 335A in 32 ml of methanol were added 1.01 g (16.0 mmol) of sodium cyanoborohydride and a little Bromocresol Green. Subsequently, a sufficient amount of acetic acid was added by titration that the indicator colour just changed from blue to yellow. Then the reaction mixture was heated to 65° C. After 1 h, after 3 h and after 4 h, a further 0.50 g (8.0 mmol) of sodium cyanoborohydride were added in each case. Over the entire reaction time, by addition of further acetic acid, the pH was constantly regulated such that the indicator colour just remained yellow. After a total of 5 h, the volatile constituents of the reaction mixture were substantially removed on a rotary evaporator. The remaining residue was taken up in ethyl acetate and washed successively with saturated aqueous sodium hydrogencarbonate solution, water and saturated aqueous sodium chloride solution. After drying over anhydrous magnesium sulphate, the mixture was filtered and concentrated to dryness. The crude product was stirred with acetonitrile. The solid was filtered off with suction and dried under high vacuum. 900 mg (64% of theory) of the title compound were obtained.

$^1$H-NMR (400 MHz, DMSO-$d_6$, δ/ppm): 8.26 (br. s, 1H), 4.98 (br. s, 1H), 4.31-4.21 (m, 1H), 4.06-3.85 (m, 5H), 3.83-3.68 (m, 2H), 3.62 (q, 1H), 2.33 (s, 3H), 2.05-1.75 (m, 3H), 1.73-1.61 (m, 1H), 1.39 (s, 9H), 1.11 (t, 3H).

LC/MS (Method 1, ESIpos): $R_t$=0.95 min, m/z=307 [M+H—$C_5H_{12}N_2O_2$]$^+$.

Example 342A tert-Butyl 2-{[3-ethyl-5-isopropyl-2,4-dioxo-1-(3,3,3-trifluoropropyl)-1,2,3,4-tetrahydrothieno[2,3-d]pyrimidin-6-yl]methyl}hydrazinecarboxylate

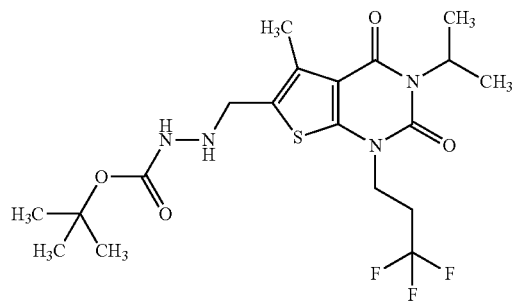 [SMILES: Cc1c(CNNC(=O)OC(C)(C)C)sc2c1c(=O)n(C(C)C)c(=O)n2CCC(F)(F)F]

To a solution of 1.24 g (2.68 mmol) of the compound from Ex. 336A in 25 ml of methanol were added 842 mg (13.4 mmol) of sodium cyanoborohydride and a little Bromocresol Green. Subsequently, a sufficient amount of acetic acid was added by titration that the indicator colour just changed from blue to yellow. Then the reaction mixture was heated to 65° C. After 1 h, after 3 h and after 4 h, a further 421 mg (6.7 mmol) of sodium cyanoborohydride were added in each case. Over the entire reaction time, by addition of further acetic acid, the pH was constantly regulated such that the indicator colour just remained yellow. After a total of 5 h, the volatile constituents of the reaction mixture were substantially removed on a rotary evaporator. The remaining residue was taken up in ethyl acetate and washed successively with saturated aqueous sodium hydrogencarbonate solution, water and saturated aqueous sodium chloride solution. After drying over anhydrous magnesium sulphate, the mixture was filtered and concentrated to dryness. The product was isolated by means of chromatography (Biotage Isolera One, SNAP KP-Sil cartridge, 100 g of silica gel, eluent: cyclohexane/ethyl acetate 2:1). After combination of the product fractions, concentration and drying under high vacuum, 1.07 g (85% of theory) of the title compound were obtained.

$^1$H-NMR (400 MHz, DMSO-d$_6$, δ/ppm): 8.24 (br. s, 1H), 5.13 (sept, 1H), 5.05 (br. s, 1H), 4.09 (t, 2H), 3.98 (d, 2H), 2.85-2.66 (m, 2H), 2.32 (s, 3H), 1.44-1.34 (m, 15H).

LC/MS (Method 1, ESIpos): R$_t$=1.12 min, m/z=333 [M+H—C$_5$H$_{12}$N$_2$O$_2$]$^+$.

Example 343A tert-Butyl 2-{[3-isopropyl-1-(2-methoxyethyl)-5-methyl-2,4-dioxo-1,2,3,4-tetrahydrothieno[2,3-d]pyrimidin-6-yl]methyl}hydrazinecarboxylate

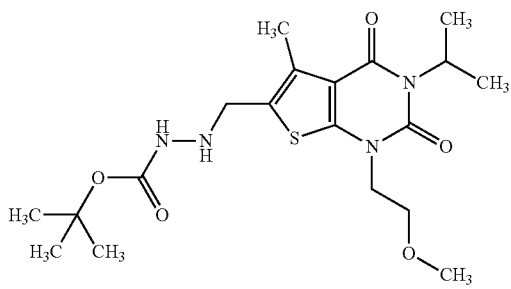 [SMILES: COCCn1c(=O)n(C(C)C)c(=O)c2c(C)c(CNNC(=O)OC(C)(C)C)sc21]

To a solution of 1.08 g (2.19 mmol) of the compound from Ex. 337A in 25 ml of methanol were added 687 mg (10.9 mmol) of sodium cyanoborohydride and a little Bromocresol Green. Subsequently, a sufficient amount of acetic acid was added by titration that the indicator colour just changed from blue to yellow. Then the reaction mixture was heated to 65° C. After 1 h, a further 343 mg (5.45 mmol) of sodium cyanoborohydride were added. Over the entire reaction time, by addition of further acetic acid, the pH was constantly regulated such that the indicator colour just remained yellow. After a total of 4 h, the volatile constituents of the reaction mixture were substantially removed on a rotary evaporator. The remaining residue was taken up in ethyl acetate and washed successively with saturated aqueous sodium hydrogencarbonate solution, water and saturated aqueous sodium chloride solution. After drying over anhydrous magnesium sulphate, the mixture was filtered and concentrated to dryness. The product was isolated by means of chromatography (Biotage Isolera One, SNAP KP-Sil cartridge, 100 g of silica gel, eluent: cyclohexane/ethyl acetate 1:1). After combination of the product fractions, concentration and drying under high vacuum, 800 mg (85% of theory) of the title compound were obtained.

$^1$H-NMR (400 MHz, DMSO-d$_6$, δ/ppm): 8.24 (br. s, 1H), 5.14 (sept, 1H), 4.97 (br. d, 1H), 4.00 (t, 2H), 3.96 (d, 2H), 3.63 (t, 2H), 3.26 (s, 3H, substantially concealed by the water signal), 2.31 (s, 3H), 1.46-1.34 (m, 15H).

LC/MS (Method 1, ESIpos): R$_t$=1.04 min, m/z=427 [M+H]$^+$, 295 [M+H—C$_5$H$_{12}$N$_2$O$_2$]$^+$.

Example 344A tert-Butyl 2-{[3-isopropyl-5-methyl-2,4-dioxo-1-(tetrahydrofuran-2-ylmethyl)-1,2,3,4-tetrahydrothieno[2,3-d]pyrimidin-6-yl]methyl}hydrazinecarboxylate (racemate)

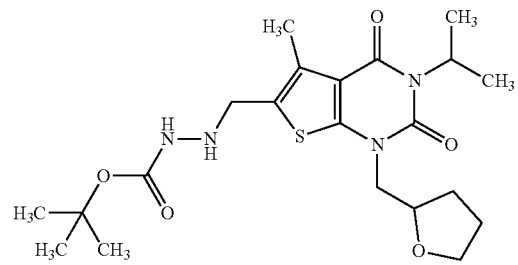 [SMILES: Cc1c(CNNC(=O)OC(C)(C)C)sc2c1c(=O)n(C(C)C)c(=O)n2CC1CCCO1]

Analogously to the method described in Ex. 343A, 1.15 g (2.55 mmol) of the compound from Ex. 338A and a total of 1.20 g (19.1 mmol) of sodium cyanoborohydride were used to obtain 876 mg (73% of theory, 97% purity) of the title compound. The reaction time here was 3 h.

$^1$H-NMR (400 MHz, DMSO-d$_6$, δ/ppm): 8.24 (br. s, 1H), 5.23-5.06 (sept, 1H), 4.95 (br. s, 1H), 4.31-4.18 (m, 1H), 4.04-3.92 (m, 3H), 3.82-3.74 (m, 1H), 3.72-3.55 (m, 2H), 2.32 (s, 3H), 2.06-1.76 (m, 3H), 1.72-1.60 (m, 1H), 1.43-1.34 (m, 15H).

LC/MS (Method 17, ESIpos): R$_t$=2.03 min, m/z=453.22 [M+H]$^+$, 321.13 [M+H—C$_5$H$_{12}$N$_2$O$_2$]$^+$.

Example 345A tert-Butyl 2-(3-ethoxyprop-2-enoyl)-2-{[3-ethyl-5-methyl-2,4-dioxo-1-(3,3,3-trifluoropropyl)-1,2,3,4-tetrahydrothieno[2,3-d]pyrimidin-6-yl]methyl}hydrazinecarboxylate

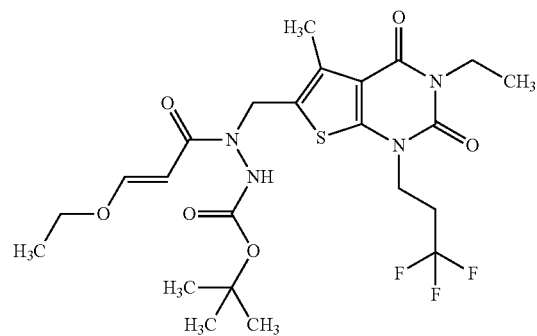 [SMILES: CCO/C=C/C(=O)N(Cc1sc2c(c1C)c(=O)n(CC)c(=O)n2CCC(F)(F)F)NC(=O)OC(C)(C)C]

To a solution of 100 mg (0.222 mmol) of the compound from Ex. 339A in 3 ml of dichloromethane were added, at 0° C., 50 µl (0.289 mmol) of N,N-diisopropylethylamine and 35 mg (0.222 mmol, content 85%) of 3-ethoxyacryloyl chloride. Then the cooling bath was removed and the reaction mixture was stirred at RT for about 18 h. After this time, a further 116 µl (0.667 mmol) of N,N-diisopropylethylamine and 105 mg (0.666 mmol, content 85%) of 3-ethoxyacryloyl chloride were added. After a further 3 h at RT, the reaction mixture was diluted with dichloromethane and washed with water. Drying of the organic phase over

251 anhydrous magnesium sulphate was followed by filtration and concentration. The product was isolated by means of preparative HPLC (Method 8). After concentration of the product fractions and drying under high vacuum, 108 mg (88% of theory) of the title compound were obtained.

LC/MS (Method 1, ESIneg): $R_t$=1.13 min, m/z=547 [M–H]⁻.

Example 346A tert-Butyl 2-(3-ethoxyprop-2-enoyl)-2-{[3-ethyl-1-(2-methoxyethyl)-5-methyl-2,4-dioxo-1,2,3,4-tetrahydrothieno[2,3-d]pyrimidin-6-yl]methyl}hydrazinecarboxylate

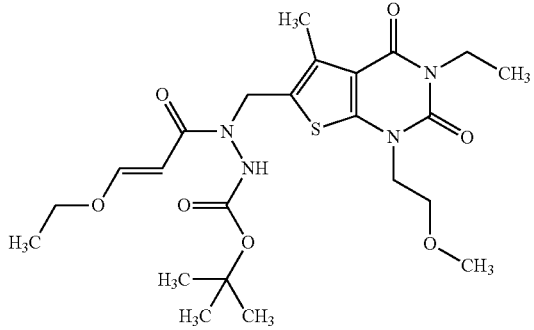 [SMILES: CCO/C=C/C(=O)N(Cc1sc2c(c1C)c(=O)n(CC)c(=O)n2CCOC)NC(=O)OC(C)(C)C]

To a solution of 300 mg (0.727 mmol) of the compound from Ex. 340A in 8 ml of dichloromethane were added, at 0° C., 165 µl (0.945 mmol) of N,N-diisopropylethylamine and 138 mg (0.873 mmol, content 85%) of 3-ethoxyacryloyl chloride. Then the cooling bath was removed and the reaction mixture was stirred at RT for about 18 h. The reaction mixture was then diluted with dichloromethane and washed with water. Drying of the organic phase over anhydrous magnesium sulphate was followed by filtration and concentration. The product was isolated by means of preparative HPLC (Method 8). After concentration of the product fractions and drying under high vacuum, 278 mg (73% of theory, 97% purity) of the title compound were obtained.

¹H-NMR (400 MHz, DMSO-d₆, δ/ppm): 9.48 (br. s, 1H), 7.50 (d, 1H), 5.57 (d, 1H), 5.04-4.34 (m, 2H), 4.03 (t, 2H), 3.97-3.84 (m, 4H), 3.63 (t, 2H), 3.24 (s, 3H), 2.36 (s, 3H), 1.39 (s, 9H), 1.23 (t, 3H), 1.11 (t, 3H).

LC/MS (Method 1, ESIneg): $R_t$=1.13 min, m/z=509 [M–H]⁻.

Example 347A tert-Butyl 2-(-3-ethoxyprop-2-enoyl)-2-{[3-ethyl-5-methyl-2,4-dioxo-1-(tetrahydrofuran-2-ylmethyl)-1,2,3,4-tetrahydrothieno[2,3-d]pyrimidin-6-yl]methyl}hydrazinecarboxylate (racemate)

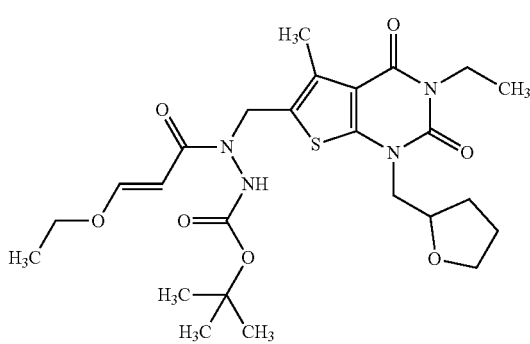 [SMILES: CCO/C=C/C(=O)N(Cc1sc2c(c1C)c(=O)n(CC)c(=O)n2CC1CCCO1)NC(=O)OC(C)(C)C]

252

To a solution of 500 mg (1.14 mmol) of the compound from Ex. 341A in 12 ml of dichloromethane were added, at 0° C., 258 µl (1.48 mmol) of N,N-diisopropylethylamine and 217 mg (1.37 mmol, content 85%) of 3-ethoxyacryloyl chloride. Then the cooling bath was removed and the reaction mixture was stirred at RT for about 18 h. The reaction mixture was then diluted with dichloromethane and washed with water. Drying of the organic phase over anhydrous magnesium sulphate was followed by filtration and concentration. The product was isolated by means of preparative HPLC (Method 8). After concentration of the product fractions and drying under high vacuum, 378 mg (61% of theory) of the title compound were obtained.

¹H-NMR (400 MHz, DMSO-d₆, δ/ppm): 9.48 (br. s, 1H), 7.49 (d, 1H), 5.57 (d, 1H), 5.07-4.32 (m, 2H), 4.28-4.19 (m, 1H), 4.06-3.83 (m, 5H), 3.81-3.67 (m, 2H), 3.66-3.53 (m, 1H), 2.36 (s, 3H), 2.02-1.75 (m, 3H), 1.73-1.61 (m, 1H), 1.39 (s, 9H), 1.23 (t, 3H), 1.11 (t, 3H).

LC/MS (Method 1, ESIneg): $R_t$=1.08 min, m/z=535 [M–H]⁻.

Example 348A tert-Butyl 2-(3-ethoxyprop-2-enoyl)-2-{[3-isopropyl-5-methyl-2,4-dioxo-1-(3,3,3-trifluoropropyl)-1,2,3,4-tetrahydrothieno[2,3-d]pyrimidin-6-yl]methyl}hydrazinecarboxylate

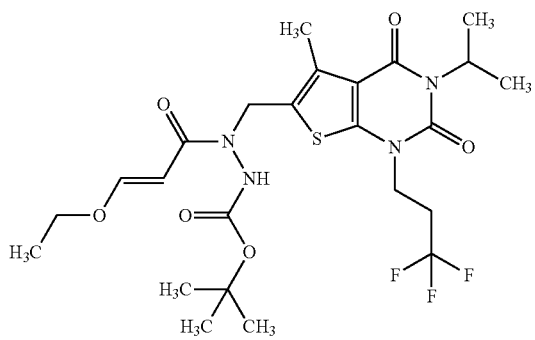 [SMILES: CCO/C=C/C(=O)N(Cc1sc2c(c1C)c(=O)n(C(C)C)c(=O)n2CCC(F)(F)F)NC(=O)OC(C)(C)C]

To a solution of 300 mg (0.646 mmol) of the compound from Ex. 342A in 7 ml of dichloromethane were added, at 0° C., 146 µl (0.840 mmol) of N,N-diisopropylethylamine and 123 mg (0.775 mmol, content 85%) of 3-ethoxyacryloyl chloride. Then the cooling bath was removed and the reaction mixture was stirred at RT for about 18 h. The reaction mixture was then diluted with dichloromethane and washed with water. Drying of the organic phase over anhydrous magnesium sulphate was followed by filtration and concentration. The product was isolated by means of preparative HPLC (Method 8). After concentration of the product fractions and drying under high vacuum, 278 mg (76% of theory) of the title compound were obtained.

¹H-NMR (400 MHz, DMSO-d₆, δ/ppm): 9.46 (br. s, 1H), 7.50 (d, 1H), 5.57 (d, 1H), 5.13 (sept, 1H), 5.00-4.34 (m, 2H), 4.09 (t, 2H), 3.93 (m, 2H), 2.83-2.62 (m, 2H), 2.36 (s, 3H), 1.43-1.35 (m, 15H), 1.23 (t, 3H).

LC/MS (Method 17, ESIneg): $R_t$=2.23 min, m/z=561.20 [M–H]⁻.

Example 349A tert-Butyl 2-(3-ethoxyprop-2-enoyl)-2-{[3-isopropyl-1-(2-methoxyethyl)-5-methyl-2,4-dioxo-1,2,3,4-tetrahydrothieno[2,3-d]pyrimidin-6-yl]methyl}hydrazinecarboxylate

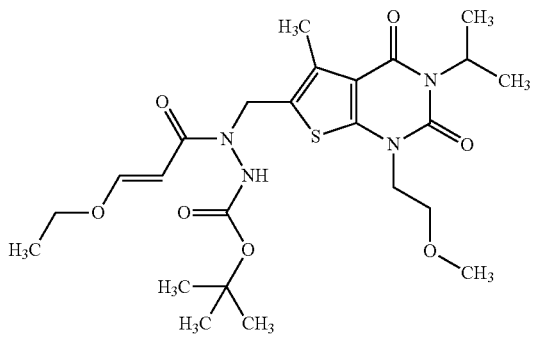 [SMILES: CCO/C=C/C(=O)N(Cc1sc2c(c1C)c(=O)n(C(C)C)c(=O)n2CCOC)NC(=O)OC(C)(C)C]

Analogously to the method described in Ex. 348A, 300 mg (0.703 mmol) of the compound from Ex. 343A and 134 mg (0.844 mmol, content 85%) of 3-ethoxyacryloyl chloride were used to obtain 293 mg (79% of theory) of the title compound.

$^1$H-NMR (400 MHz, DMSO-$d_6$, δ/ppm): 9.46 (br. s, 1H), 7.50 (d, 1H), 5.57 (d, 1H), 5.13 (sept, 1H), 5.02-4.33 (m, 2H), 3.99 (t, 2H), 3.93 (m, 2H), 3.62 (t, 2H), 3.24 (s, 3H), 2.34 (s, 3H), 1.39 (m, 15H), 1.23 (t, 3H).

LC/MS (Method 1, ESIneg): $R_t$=1.08 min, m/z=523 [M−H]$^−$.

Example 350A tert-Butyl 2-(3-ethoxyprop-2-enoyl)-2-{[3-isopropyl-5-methyl-2,4-dioxo-1-(tetrahydrofuran-2-ylmethyl)-1,2,3,4-tetrahydrothieno[2,3-d]pyrimidin-6-yl]methyl}hydrazinecarboxylate (racemate)

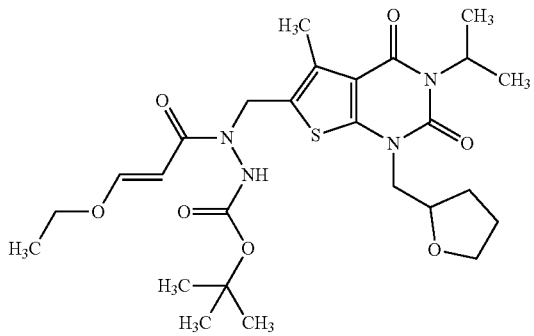 [SMILES: CCO/C=C/C(=O)N(Cc1sc2c(c1C)c(=O)n(C(C)C)c(=O)n2CC1CCCO1)NC(=O)OC(C)(C)C]

Analogously to the method described in Ex. 348A, 500 mg (1.11 mmol) of the compound from Ex. 344A and 210 mg (1.33 mmol, content 85%) of 3-ethoxyacryloyl chloride were used to obtain 514 mg (84% of theory) of the title compound.

$^1$H-NMR (400 MHz, DMSO-$d_6$, δ/ppm): 9.46 (br. s, 1H), 7.49 (d, 1H), 5.57 (d, 1H), 5.14 (sept, 1H), 5.07-4.32 (m, 2H), 4.28-4.15 (m, 1H), 4.06-3.86 (m, 3H), 3.82-3.53 (m, 3H), 2.34 (s, 3H), 2.04-1.75 (m, 3H), 1.73-1.58 (m, 1H), 1.39 (m, 15H), 1.23 (t, 3H).

LC/MS (Method 1, ESIneg): $R_t$=1.13 min, m/z=549 [M−H]$^−$.

Example 351A 6-(Hydrazinomethyl)-3-isopropyl-5-methyl-1-(3,3,3-trifluoropropyl)thieno[2,3-d]pyrimidine-2,4(1H,3H)-dione

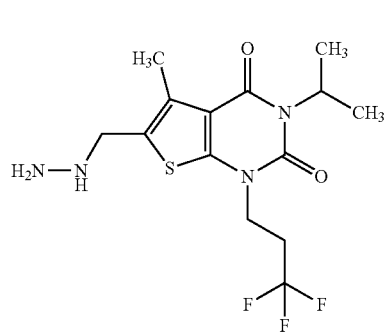 [SMILES: Cc1c(CNN)sc2c1c(=O)n(C(C)C)c(=O)n2CCC(F)(F)F]

1.55 g (3.34 mmol) of the compound from Example 342A were dissolved in 30 ml of dichloromethane, and 15 ml of trifluoroacetic acid were added at 0° C. The reaction mixture was stirred first at 0° C. for 90 min and then at RT for 60 min. Subsequently, all the volatile constituents were removed at RT on a rotary evaporator. The remaining residue was purified by means of preparative HPLC (Method 8). After concentration of the product fractions and drying under high vacuum, 647 mg (51% of theory, 96% purity) of the title compound were obtained.

$^1$H-NMR (400 MHz, DMSO-$d_6$, δ/ppm): 8.46-7.32 (m, 3H), 5.14 (sept, 1H), 4.11 (t, 2H), 4.10 (s, 2H), 2.86-2.67 (m, 2H), 2.39 (s, 3H), 1.40 (d, 6H).

LC/MS (Method 1, ESIpos): $R_t$=0.61 min, m/z=333 [M+H−N$_2$H$_4$]$^+$.

Example 352A 6-(Hydrazinomethyl)-3-isopropyl-1-(2-methoxyethyl)-5-methylthieno[2,3-d]pyrimidine-2,4(1H,3H)-dione

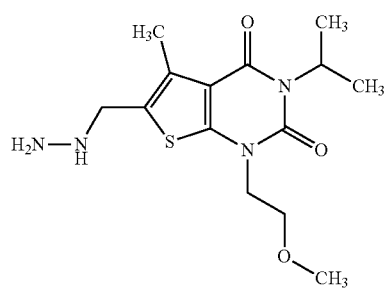 [SMILES: COCCn1c(=O)n(C(C)C)c(=O)c2c(C)c(CNN)sc21]

800 mg (1.88 mmol) of the compound from Example 343A were dissolved in 16 ml of dichloromethane, and 8 ml of trifluoroacetic acid were added at 0° C. The reaction mixture was stirred at 0° C. for 10 min. Then all the volatile constituents were removed at RT on a rotary evaporator. The remaining residue was purified by means of preparative HPLC (Method 8). After concentration of the product fractions and drying under high vacuum, 235 mg (38% of theory) of the title compound were obtained.

$^1$H-NMR (400 MHz, DMSO-$d_6$, δ/ppm): 9.09 (broad, 2H), 5.83 (broad, 1H), 5.14 (sept, 1H), 4.10 (broad, 2H), 4.02 (t, 2H), 3.64 (t, 2H), 3.25 (s, 3H), 2.38 (s, 3H), 1.40 (d, 6H).

LC/MS (Method 1, ESIpos): $R_t$=0.50 min, m/z=295 [M+H—$N_2H_4$]$^+$.

Example 353A ({[3-Isopropyl-5-methyl-2,4-dioxo-1-(3,33-trifluoropropyl)-1,2,3,4-tetrahydrothieno[2,3-d]pyrimidin-6-yl]methyl}hydrazono)acetic acid

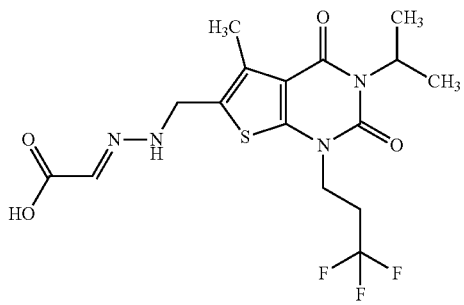 [SMILES: Cc1c(CN/N=C/C(=O)O)sc2c1c(=O)n(C(C)C)c(=O)n2CCC(F)(F)F]

At 0° C., 190 µl (1.72 mmol) of glyoxalic acid were added dropwise to a solution of 647 mg (1.72 mmol, 97% purity) of the compound from Ex. 351A in 13 ml of water and 2.6 ml (2.58 mmol) of 1 M hydrochloric acid. After the reaction mixture had been stirred at 10-20° C. for 1 h, the precipitated solids were filtered off with suction, washed with a little water and dried under high vacuum. This gave 495 mg (68% of theory) of the title compound.

$^1$H-NMR (400 MHz, DMSO-$d_6$, δ/ppm): 11.91 (broad, 1H), 8.97 (t, 1H), 6.73 (s, 1H), 5.13 (sept, 1H), 4.50 (d, 2H), 4.07 (t, 2H), 2.86-2.62 (m, 2H), 2.39 (s, 3H), 1.40 (d, 6H).

LC/MS (Method 1, ESIneg): $R_t$=0.91 min, m/z=419 [M−H]$^-$.

Example 354A ({[3-Isopropyl-1-(2-methoxyethyl)-5-methyl-2,4-dioxo-1,2,3,4-tetrahydrothieno[2,3-d]pyrimidin-6-yl]methyl}hydrazono)acetic acid

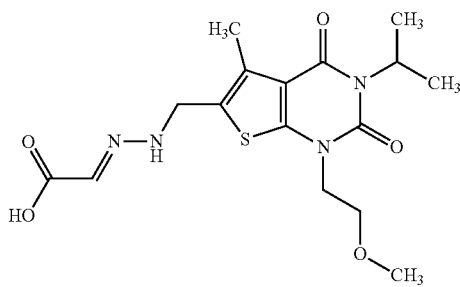 [SMILES: COCCn1c(=O)n(C(C)C)c(=O)c2c(C)c(CN/N=C/C(=O)O)sc21]

Analogously to the method described in Ex. 353A, 220 mg (0.674 mmol) of the compound from Ex. 352A and 74 µl (0.674 mmol) of glyoxalic acid were used to prepare 89 mg (34% of theory) of the title compound. In this case, the product was additionally purified by means of preparative HPLC (Method 8).

$^1$H-NMR (400 MHz, DMSO-$d_6$, δ/ppm): 11.82 (broad, 1H), 8.95 (t, 1H), 6.72 (s, 1H), 5.13 (sept, 1H), 4.47 (d, 2H), 3.99 (t, 2H), 3.62 (t, 2H), 3.23 (s, 3H), 2.37 (s, 3H), 1.40 (d, 6H).

LC/MS (Method 1, ESIneg): $R_t$=0.75 min, m/z=381 [M−H]$^-$.

Example 355A

Ethyl {5-methyl-2,4-dioxo-6-[(2-oxoimidazolidin-1-yl)methyl]-1-(3,3,3-trifluoropropyl)-1,4-dihydrothieno[2,3-d]pyrimidin-3(2H)-yl}acetate

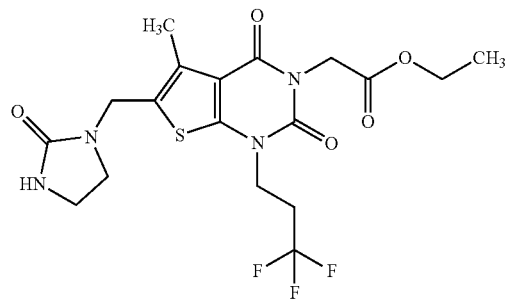 [SMILES: CCOC(=O)Cn1c(=O)c2c(C)c(CN3CCNC3=O)sc2n(CCC(F)(F)F)c1=O]

To a solution of 218 mg (2.54 mmol) of imidazolidin-2-one in 6 ml of DMF were added 101 mg (2.54 mmol) of sodium hydride (60% suspension in mineral oil), then the mixture was heated to 60° C. for 5 min and subsequently cooled back down to RT ("Solution 1"). To a solution of 250 mg (0.634 mmol) of the compound from Ex. 306A in 5 ml of dichloromethane in another reaction vessel were added, at 0° C., 221 µl (1.27 mmol) of N,N-diisopropylethylamine and 49 µl (0.666 mmol) of thionyl chloride. After stirring at 0° C. for 20 min, Solution 1 was added in portions and then the cooling bath was removed. The reaction mixture was stirred at RT for about 18 h. All the volatile constituents were then removed on a rotary evaporator. The remaining residue was separated into its components by means of preparative HPLC (Method 8). After concentration of the product fractions and drying under high vacuum, 87 mg (28% of theory, 97% purity) of the title compound were obtained.

$^1$H-NMR (400 MHz, DMSO-$d_6$, δ/ppm): 6.55 (s, 1H), 4.62 (s, 2H), 4.38 (s, 2H), 4.14 (q, 2H), 4.13 (t, 2H), 3.30-3.16 (m, 4H), 2.87-2.66 (m, 2H), 2.39 (s, 3H), 1.20 (t, 3H).

LC/MS (Method 1, ESIpos): $R_t$=0.85 min, m/z=463 [M+H]$^+$.

Example 356A

Ethyl [1-(2-methoxyethyl)-5-methyl-2,4-dioxo-6-[(2-oxoimidazolidin-1-yl)methyl]-1,4-dihydrothieno[2,3-d]pyrimidin-3(2H)-yl]acetate

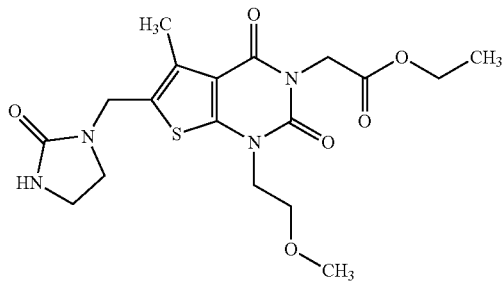 [SMILES: CCOC(=O)Cn1c(=O)c2c(C)c(CN3CCNC3=O)sc2n(CCOC)c1=O]

Analogously to the method described in Ex. 355A, 250 mg (0.701 mmol) of the compound from Ex. 307A and 242 mg (2.81 mmol) of imidazolidin-2-one were used to obtain 158 mg (50% of theory, 95% purity) of the title compound.

$^1$H-NMR (400 MHz, DMSO-$d_6$, δ/ppm): 6.54 (s, 1H), 4.61 (s, 2H), 4.36 (s, 2H), 4.14 (q, 2H), 4.05 (t, 2H), 3.63 (t, 2H), 3.29-3.16 (m, 4H), 3.23 (s, 3H), 2.38 (s, 3H), 1.20 (t, 3H).

LC/MS (Method 1, ESIpos): $R_t$=0.72 min, m/z=425 [M+H]$^+$.

Example 357A

Prop-2-yn-1-yl 1-(2-methoxyethyl)-5-methyl-2,4-dioxo-3-(prop-2-yn-1-yl)-1,2,3,4-tetrahydrothieno[2,3-d]pyrimidine-6-carboxylate

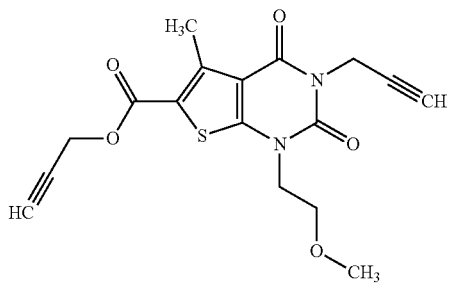 [SMILES: C#CCOC(=O)c1sc2c(c1C)c(=O)n(CC#C)c(=O)n2CCOC]

Analogously to the method described in Ex. 20A, 450 mg (1.43 mmol) of the compound from Ex. 18A and 635 mg (4.27 mmol) of propargyl bromide were used to obtain 321 mg (59% of theory) of the title compound. The reaction time here was 74 h.

$^1$H-NMR (400 MHz, DMSO-$d_6$, δ/ppm): 4.93 (d, 2H), 4.60 (d, 2H), 4.12 (t, 2H), 3.69-3.63 (m, 3H), 3.24 (s, 3H), 3.18-3.15 (m, 1H), 2.78 (s, 3H).

LC/MS (Method 3): $R_t$=1.13 min, m/z=361 [M+H]$^+$.

Example 358A

But-3-en-1-yl 3-(but-3-en-1-yl)-1-(2-methoxyethyl)-5-methyl-2,4-dioxo-1,2,3,4-tetrahydrothieno[2,3-d]pyrimidine-6-carboxylate

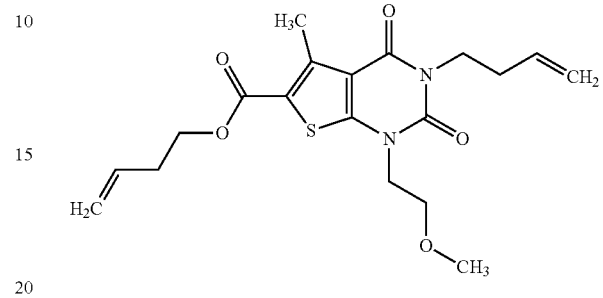

Analogously to the method described in Ex. 20A, 450 mg (1.43 mmol) of the compound from Ex. 18A and 594 mg (4.27 mmol) of 1-bromo-3-butene were used to obtain 335 mg (60% of theory) of the title compound. The reaction time here was 16 h.

$^1$H-NMR (400 MHz, DMSO-$d_6$, δ/ppm): 5.90-5.73 (m, 1H), 5.15 (dq, 1H), 5.11-5.07 (m, 1H), 5.06-4.97 (m, 2H), 4.30 (t, 2H), 4.07 (t, 2H), 3.93 (t, 2H), 3.64 (t, 2H), 3.23 (s, 3H), 2.76 (s, 3H), 2.44 (q, 2H), 2.36-2.27 (m, 2H).

LC/MS (Method 3): $R_t$=1.45 min, m/z=393 [M+H]$^+$.

Example 359A

But-2-yn-1-yl 3-(but-2-yn-1-yl)-1-(2-methoxyethyl)-5-methyl-2,4-dioxo-1,2,3,4-tetrahydrothieno[2,3-d]pyrimidine-6-carboxylate

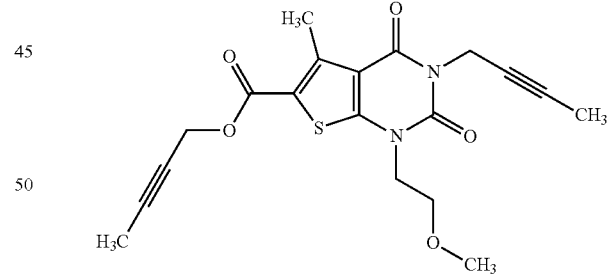

Analogously to the method described in Ex. 20A, 450 mg (1.43 mmol) of the compound from Ex. 18A and 574 mg (4.27 mmol) of 1-bromo-2-butyne were used to obtain 310 mg (57% of theory) of the title compound. The reaction time here was 74 h.

$^1$H-NMR (400 MHz, DMSO-$d_6$, δ/ppm): 4.89 (q, 2H), 4.56 (d, 2H), 4.11 (t, 2H), 3.66 (t, 2H), 3.24 (s, 3H), 2.77 (s, 3H), 1.86 (t, 3H), 1.75 (t, 3H).

LC/MS (Method 3): $R_t$=1.30 min, m/z=389 [M+H]$^+$.

Example 360A

But-3-yn-1-yl 3-(but-3-yn-1-yl)-1-(2-methoxyethyl)-5-methyl-2,4-dioxo-1,2,3,4-tetrahydrothieno[2,3-d]pyrimidine-6-carboxylate

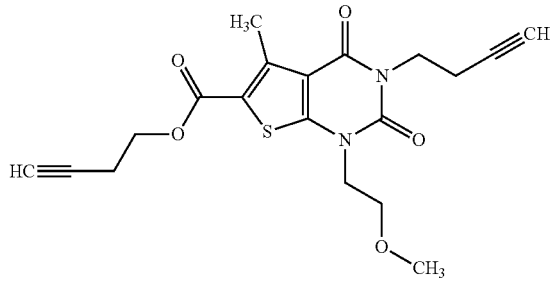 [SMILES: C#CCCOC(=O)c1sc2c(c1C)c(=O)n(CCC#C)c(=O)n2CCOC]

Analogously to the method described in Ex. 20A, 450 mg (1.43 mmol) of the compound from Ex. 18A and 586 mg (4.27 mmol) of 1-bromo-3-butyne were used to obtain 305 mg (50% of theory) of the title compound. The reaction time here was 113 h.

$^1$H-NMR (400 MHz, DMSO-$d_6$, δ/ppm): 4.31 (t, 2H), 4.08 (t, 2H), 4.00 (t, 2H), 3.65 (t, 2H), 3.24 (s, 3H), 2.92 (t, 1H), 2.88 (t, 1H), 2.78 (s, 3H), 2.63 (td, 2H), 2.48-2.43 (m, 2H).

LC/MS (Method 3): $R_t$=1.24 min, m/z=389 [M+H]$^+$.

Example 361A

3-Methylbut-3-en-1-yl 1-(2-methoxyethyl)-5-methyl-3-(3-methylbut-3-en-1-yl)-2,4-dioxo-1,2,3,4-tetrahydrothieno[2,3-d]pyrimidine-6-carboxylate

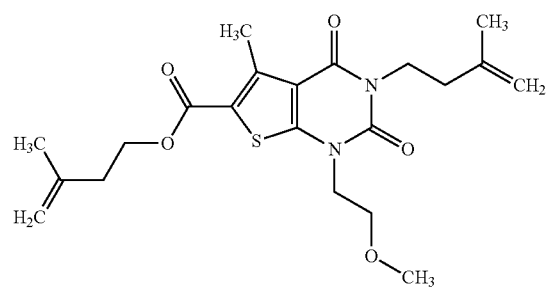 [SMILES: C=C(C)CCOC(=O)c1sc2c(c1C)c(=O)n(CCC(=C)C)c(=O)n2CCOC]

To a solution of 450 mg (1.43 mmol) of the compound from Ex. 18A in 15 ml of DMF were added 1.39 g (4.27 mmol) of caesium carbonate, and the mixture was stirred at RT for 15 min. Then 670 mg (4.27 mmol) of 4-bromo-2-methylbut-1-ene were added, and the mixture was stirred at RT for 113 h. The reaction mixture was then partitioned between semisaturated aqueous sodium chloride solution (70 ml) and ethyl acetate (70 ml). The aqueous phase was extracted with ethyl acetate. The combined organic phases were dried over sodium sulphate, filtered and concentrated. The residue obtained was chromatographed on silica gel (hexane/ethyl acetate eluent). 300 mg (47% of theory) of the title compound were obtained.

$^1$H-NMR (400 MHz, DMSO-$d_6$, δ/ppm): 4.79 (d, 2H), 4.75-4.62 (m, 2H), 4.36 (t, 2H), 4.07 (t, 2H), 4.01-3.94 (m, 2H), 3.64 (t, 2H), 3.23 (s, 3H), 2.75 (s, 3H), 2.40 (t, 2H), 2.25 (t, 2H), 1.75 (d, 6H).

LC/MS (Method 3): $R_t$=1.57 min, m/z=421 [M+H]$^+$.

Example 362A

4-Methylpent-3-en-1-yl 1-(2-methoxyethyl)-5-methyl-3-(4-methylpent-3-en-1-yl)-2,4-dioxo-1,2,3,4-tetrahydrothieno[2,3-d]pyrimidine-6-carboxylate

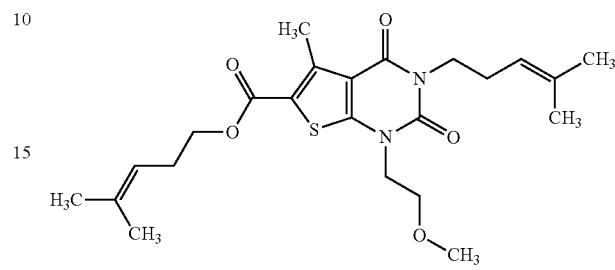

Analogously to the method described in Ex. 361A, 450 mg (1.43 mmol) of the compound from Ex. 18A and 718 mg (4.27 mmol) of 5-bromo-2-methylpent-2-ene were used to obtain 313 mg (49% of theory) of the title compound. The reaction time here was 16 h.

$^1$H-NMR (400 MHz, DMSO-$d_6$, δ/ppm): 5.18-5.09 (m, 2H), 4.20 (t, 2H), 4.07 (t, 2H), 3.86-3.78 (m, 2H), 3.64 (t, 2H), 3.24 (s, 3H), 2.75 (s, 3H), 2.37 (q, 2H), 2.23 (q, 2H), 1.68 (s, 3H), 1.64 (s, 3H), 1.61 (s, 3H), 1.54 (s, 3H).

LC/MS (Method 3): $R_t$=1.69 min, m/z=449 [M+H]$^+$.

Example 363A 3,4,4-Trifluorobut-3-en-1-yl 1-(2-methoxyethyl)-5-methyl-2,4-dioxo-3-(3,4,4-trifluorobut-3-en-1-yl)-1,2,3,4-tetrahydrothieno[2,3-d]pyrimidine-6-carboxylate

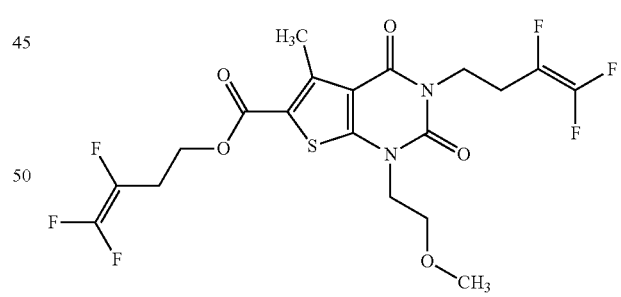

Analogously to the method described in Ex. 361A, 450 mg (1.43 mmol) of the compound from Ex. 18A and 824 mg (4.27 mmol) of 4-bromo-1,1,2-trifluorobut-1-ene were used to obtain 427 mg (55% of theory) of the title compound. The reaction time here was 74 h.

$^1$H-NMR (400 MHz, DMSO-$d_6$, δ/ppm): 4.42 (t, 1H), 4.12-4.04 (m, 4H), 3.64 (t, 1H), 3.22 (s, 3H), 2.87-2.80 (m, 1H), 2.80-2.73 (m, 4H), 2.72-2.66 (m, 1H), 2.66-2.59 (m, 1H).

LC/MS (Method 3): $R_t$=1.45 min, m/z=501 [M+H]$^+$.

Example 364A 4,4-Difluorobut-3-en-1-yl-3-(4,4-difluorobut-3-en-1-yl)-1-(2-methoxyethyl)-5-methyl-2,4-dioxo-1,2,3,4-tetrahydrothieno[2,3-d]pyrimidine-6-carboxylate

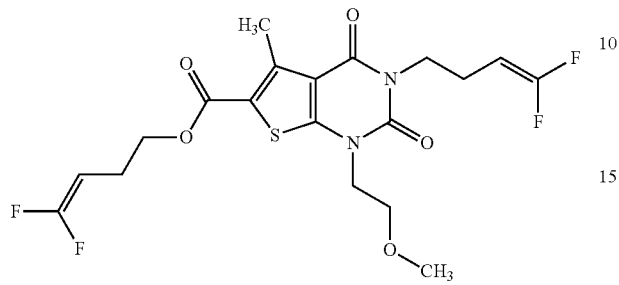

To a solution of 450 mg (1.43 mmol) of the compound from Ex. 18A in 13.5 ml of DMF were added 1.39 g (4.27 mmol) of caesium carbonate, and the mixture was stirred at RT for 15 min. Then 769 mg (4.27 mmol) of 4-bromo-1,1-difluorobut-1-ene were added, and the mixture was stirred at RT for 16 h. The reaction mixture was then partitioned between water (75 ml) and ethyl acetate (75 ml). The aqueous phase was extracted with ethyl acetate. The combined organic phases were dried over sodium sulphate, filtered and concentrated. The residue obtained was chromatographed on silica gel (hexane/ethyl acetate eluent). 350 mg (52% of theory) of the title compound were obtained.

$^1$H-NMR (400 MHz, DMSO-$d_6$, δ/ppm): 4.65-4.48 (m, 2H), 4.27 (t, 2H), 4.08 (t, 2H), 3.91 (t, 2H), 3.64 (t, 2H), 3.23 (s, 3H), 2.78-2.75 (m, 3H), 2.41-2.34 (m, 2H), 2.26 (q, 2H).

LC/MS (Method 3): $R_t$=1.47 min, m/z=465 [M+H]$^+$.

Example 365A (2,2-Difluorocyclopropyl)methyl 3-[(2,2-difluorocyclopropyl)methyl]-1-(2-methoxyethyl)-5-methyl-2,4-dioxo-1,2,3,4-tetrahydrothieno[2,3-d]pyrimidine-6-carboxylate (stereoisomer mixture)

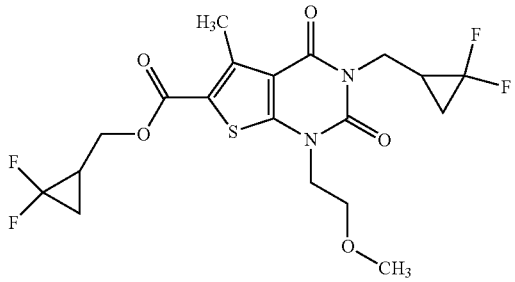 [SMILES: COCCn1c(=O)n(CC2CC2(F)F)c(=O)c2c(C)c(C(=O)OCC3CC3(F)F)sc21]

Analogously to the method described in Ex. 361A, 500 mg (1.58 mmol) of the compound from Ex. 18A and 812 mg (4.75 mmol) of 2-bromomethyl-1,1-difluorocyclopropane were used to obtain 437 mg (55% of theory) of the title compound. The reaction time here was 20 h at a temperature of 80° C.

$^1$H-NMR (400 MHz, DMSO-$d_6$, δ/ppm): 4.50-4.41 (m, 1H), 4.26-4.17 (m, 1H), 4.15-4.02 (m, 3H), 4.01-3.91 (m, 1H), 3.66 (t, 2H), 3.24 (s, 3H), 2.82-2.75 (m, 3H), 2.29-2.16 (m, 1H), 2.15-2.01 (m, 1H), 1.80-1.68 (m, 1H), 1.67-1.48 (m, 2H), 1.41-1.30 (m, 1H).

LC/MS (Method 3): $R_t$=1.38 min, m/z=465 [M+H]$^+$.

Example 366A

3-Methoxypropyl 1-(2-methoxyethyl)-3-(3-methoxypropyl)-5-methyl-2,4-dioxo-1,2,3,4-tetrahydrothieno[2,3-d]pyrimidine-6-carboxylate

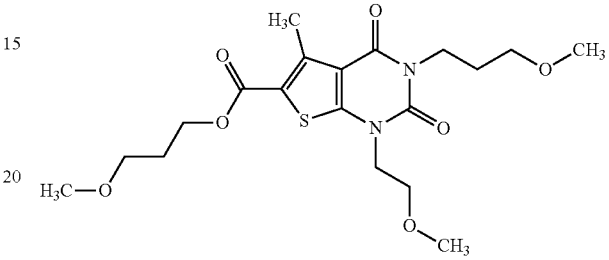

Analogously to the method described in Ex. 361A, 450 mg (1.43 mmol) of the compound from Ex. 18A and 654 mg (4.27 mmol) of 1-bromo-3-methoxypropane were used to obtain 316 mg (48% of theory) of the title compound. The reaction time here was 113 h.

$^1$H-NMR (400 MHz, DMSO-$d_6$, δ/ppm): 4.28 (t, 2H), 4.08 (t, 2H), 3.92 (t, 2H), 3.65 (t, 2H), 3.43 (t, 2H), 3.39-3.34 (m, 2H), 3.24 (d, 6H), 3.20 (s, 3H), 2.76 (s, 3H), 1.91 (quin, 2H), 1.78 (quin, 2H).

LC/MS (Method 3): $R_t$=1.20 min, m/z=429 [M+H]$^+$.

Example 367A

Tetrahydrofuran-2-ylmethyl 1-(2-methoxyethyl)-5-methyl-2,4-dioxo-3-(tetrahydrofuran-2-ylmethyl)-1,2,3,4-tetrahydrothieno[2,3-d]pyrimidine-6-carboxylate (stereoisomer mixture)

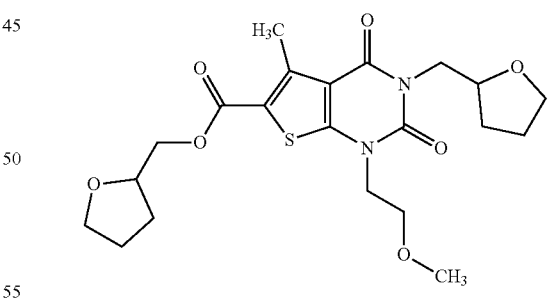

Analogously to the method described in Ex. 361A, 550 mg (1.74 mmol) of the compound from Ex. 18A and 907 mg (5.22 mmol) of racemic 2-(bromomethyl)tetrahydrofuran were used to obtain 433 mg (52% of theory) of the title compound. The reaction time here was 40 h at a temperature of 80° C.

$^1$H-NMR (400 MHz, DMSO-$d_6$, δ/ppm): 4.29-4.24 (m, 1H), 4.21-3.99 (m, 6H), 3.80-3.71 (m, 3H), 3.71-3.56 (m, 4H), 3.24 (s, 3H), 2.77 (s, 3H), 2.03-1.75 (m, 6H), 1.68-1.57 (m, 2H).

LC/MS (Method 3): $R_t$=1.21 min, m/z=453 [M+H]$^+$.

Example 368A

Oxetan-3-ylmethyl 1-(2-methoxyethyl)-5-methyl-3-(oxetan-3-ylmethyl)-2,4-dioxo-1,2,3,4-tetrahydrothieno[2,3-d]pyrimidine-6-carboxylate

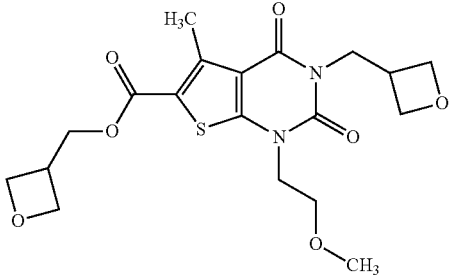 [SMILES: COCCn1c(=O)n(CC2COC2)c(=O)c2c(C)c(C(=O)OCC3COC3)sc21]

Analogously to the method described in Ex. 361A, 450 mg (1.43 mmol) of the compound from Ex. 18A and 645 mg (4.27 mmol) of 3-(bromomethyl)oxetane were used to obtain 349 mg (55% of theory) of the title compound. The reaction time here was 21 h.

$^1$H-NMR (400 MHz, DMSO-$d_6$, δ/ppm): 4.68 (dd, 1H), 4.58 (dd, 1H), 4.45 (d, 1H), 4.41 (td, 2H), 4.17 (d, 1H), 4.07 (t, 1H), 3.64 (t, 1H), 3.41-3.35 (m, 1H), 3.32-3.25 (m, 1H), 3.23 (s, 3H), 2.76 (s, 3H).

LC/MS (Method 3): $R_t$=0.97 min, m/z=425 [M+H]$^+$.

Example 369A

Ethyl 2-{[(2-ethoxyethyl)carbamoyl]amino}-4-methylthiophene-3-carboxylate

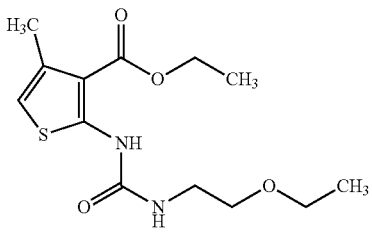 [SMILES: CCOCCNC(=O)Nc1scc(C)c1C(=O)OCC]

To a solution of 2.79 g (15.1 mmol) of ethyl 2-amino-4-methylthiophene-3-carboxylate in 15 ml of pyridine were added 2.6 g (22.6 mmol) of 1-ethoxy-2-isocyanatoethane. The reaction mixture was then stirred at 70° C. for 21 h. It was then concentrated to dryness on a rotary evaporator. The remaining residue was dissolved in dichloromethane and concentrated to dryness again. 4.68 g (quant.) of the title compound were obtained.

$^1$H-NMR (400 MHz, DMSO-$d_6$, δ/ppm): 10.30 (s, 1H), 8.00 (br. s, 1H), 6.42 (s, 1H), 4.28 (q, 2H), 3.48-3.38 (m, 4H), 3.24 (q, 2H), 2.26 (d, 3H), 1.31 (t, 3H), 1.12 (t, 3H).

LC/MS (Method 3): $R_t$=1.19 min, m/z=301 [M+H]$^+$.

Example 370A 3-(2-Ethoxyethyl)-5-methylthieno[2,3-d]pyrimidine-2,4(1H,3H)-dione

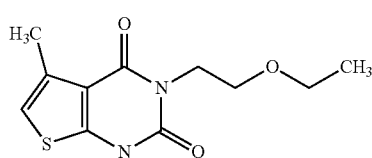

4.68 g (15.6 mmol) of the compound from Ex. 369A were dissolved in 42 ml of ethanol, and 11.6 ml (31.2 mmol) of a 21% solution of sodium ethoxide in ethanol were added. After the mixture had been stirred at RT for about 1 h, 35.8 ml of 1 M hydrochloric acid were added at RT. The resulting precipitate was filtered off with suction, washed with water until neutral and dried. 3.86 g (97% of theory) of the title compound were obtained.

$^1$H-NMR (400 MHz, DMSO-$d_6$, δ/ppm): 12.15 (br. s, 1H), 6.69 (d, 1H), 3.99 (t, 2H), 3.50 (t, 2H), 3.44 (q, 2H), 2.34 (d, 3H), 1.07 (t, 3H).

LC/MS (Method 3): $R_t$=0.88 min, m/z=255 [M+H]$^+$.

Example 371A 3-(2-Ethoxyethyl)-5-methyl-2,4-dioxo-1,2,3,4-tetrahydrothieno[2,3-d]pyrimidine-6-carbaldehyde

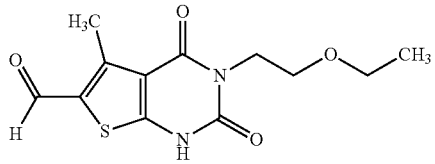 [SMILES: CCOCCn1c(=O)[nH]c2sc(C=O)c(C)c2c1=O]

10.5 ml (113 mmol) of phosphorus oxychloride were added cautiously, while cooling with an ice bath, to a solution of 2.87 g (11.3 mmol) of the compound from Ex. 370A in 105 ml of DMF. The mixture was stirred at 70° C. for 90 min. Then the reaction mixture was concentrated very substantially on a rotary evaporator. The remaining residue was added to ice-water and stirred. The precipitated product was filtered off with suction, washed to neutrality with water and dried. 3.08 g (96% of theory) of the title compound were obtained.

$^1$H-NMR (400 MHz, DMSO-$d_6$, δ/ppm): 12.64 (br. s, 1H), 10.06 (s, 1H), 3.99 (t, 2H), 3.51 (t, 2H), 3.44 (q, 2H), 2.75 (s, 3H), 1.07 (t, 3H).

LC/MS (Method 3): $R_t$=0.84 min, m/z=283 [M+H]$^+$.

Example 372A

3-Ethyl-1-(fluoromethyl)-5-methyl-2,4-dioxo-1,2,3,4-tetrahydrothieno[2,3-d]pyrimidine-6-carbaldehyde

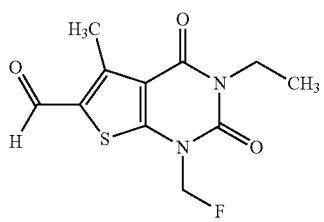 [SMILES: CCn1c(=O)c2c(C)c(C=O)sc2n(CF)c1=O]

1.2 g (8.68 mmol) of potassium carbonate were added to a solution of 690 mg (2.89 mmol) of the compound from Ex. 48A in 30 ml of DMF, and the mixture was stirred at RT for 15 min. Then 4.3 ml (8.68 mmol) of a 2 M solution of bromofluoromethane in DMF and 108 mg (0.724 mmol) of sodium iodide were added, and the mixture was stirred at 50° C. for 21 h. The DMF was then very substantially distilled off and the remaining residue was partitioned between semisaturated aqueous sodium chloride solution (100 ml) and ethyl acetate (150 ml). The aqueous phase was extracted with ethyl acetate. The combined organic phases were dried over sodium sulphate, filtered and concentrated. The residue obtained was chromatographed using a silica gel cartridge (Biotage, 50 g of silica gel, eluent: hexane/ethyl acetate). 332 mg (39% of theory) of the title compound were obtained.

$^1$H-NMR (400 MHz, DMSO-d$_6$, δ/ppm): 10.12 (s, 1H), 6.10 (d, 2H), 3.91 (q, 2H), 2.80 (s, 3H), 1.15 (t, 3H).

LC/MS (Method 3): R$_t$=1.0 min, m/z=271 [M+H]$^+$.

Example 373A

1-[2-(Cyclopentyloxy)ethyl]-3-ethyl-5-methyl-2,4-dioxo-1,2,3,4-tetrahydrothieno[2,3-d]pyrimidine-6-carbaldehyde

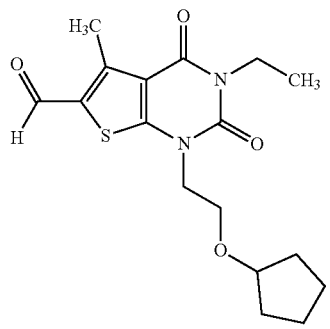 [SMILES: CCn1c(=O)c2c(C)c(C=O)sc2n(CCOC2CCCC2)c1=O]

933 mg (6.75 mmol) of potassium carbonate were added to a solution of 650 mg (2.7 mmol) of the compound from Ex. 48A in 24 ml of DMF, and the mixture was stirred at RT for 15 min. Then 1.66 g (8.2 mmol) of (2-bromoethoxy)cyclopentane were added, and the mixture was stirred at 50° C. for 20 h. The DMF was then very substantially distilled off and the remaining residue was partitioned between semisaturated aqueous sodium chloride solution (70 ml) and ethyl acetate (70 ml). The aqueous phase was extracted with ethyl acetate. The combined organic phases were dried over sodium sulphate, filtered and concentrated. The residue obtained was chromatographed using a silica gel cartridge (Biotage, 100 g of silica gel, eluent: hexane/ethyl acetate). 646 mg (68% of theory) of the title compound were obtained.

$^1$H-NMR (400 MHz, DMSO-d$_6$, δ/ppm): 10.09 (s, 1H), 4.06 (t, 2H), 3.94-3.85 (m, 3H), 3.65 (t, 2H), 2.78 (s, 3H), 1.61-1.49 (m, 2H), 1.49-1.37 (m, 7H), 1.13 (t, 3H).

LC/MS (Method 3): R$_t$=1.31 min, m/z=351 [M+H]$^+$.

Example 374A

3-Ethyl-5-methyl-1-[2-(methylsulphanyl)ethyl]-2,4-dioxo-1,2,3,4-tetrahydrothieno[2,3-d]pyrimidine-6-carbaldehyde

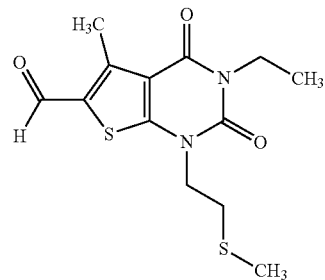 [SMILES: CCn1c(=O)c2c(C)c(C=O)sc2n(CCSC)c1=O]

718 mg (5.19 mmol) of potassium carbonate were added to a solution of 500 mg (2.08 mmol) of the compound from Ex. 48A in 19 ml of DMF, and the mixture was stirred at RT for 15 min. Then 644 mg (4.16 mmol) of 1-bromo-2-(methylsulphanyl)ethane were added, and the mixture was stirred at 50° C. for 16 h. The DMF was then very substantially distilled off and the remaining residue was partitioned between semisaturated aqueous sodium chloride solution (300 ml) and ethyl acetate (150 ml). The aqueous phase was extracted with ethyl acetate. The combined organic phases were dried over sodium sulphate, filtered and concentrated. The residue obtained was chromatographed using a silica gel cartridge (Biotage, 340 g of silica gel, eluent: hexane/ethyl acetate). 360 mg (51% of theory) of the title compound were obtained.

$^1$H-NMR (400 MHz, DMSO-d$_6$, δ/ppm): 10.10 (s, 1H), 4.12 (t, 2H), 3.91 (q, 2H), 2.87-2.81 (m, 2H), 2.79 (s, 3H), 2.14 (s, 3H), 1.13 (t, 3H).

LC/MS (Method 3): R$_t$=1.13 min, m/z=313 [M+H]$^+$.

Example 375A

3-Ethyl-1-[2-(ethylsulphanyl)ethyl]-5-methyl-2,4-dioxo-1,2,3,4-tetrahydrothieno[2,3-d]pyrimidine-6-carbaldehyde

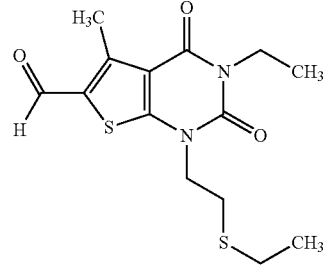 [SMILES: CCSCCn1c(=O)n(CC)c(=O)c2c(C)c(C=O)sc21]

1.08 g (7.79 mmol) of potassium carbonate were added to a solution of 750 mg (3.12 mmol) of the compound from Ex. 48A in 28 ml of DMF, and the mixture was stirred at RT for 15 min. Then 1.05 g (6.23 mmol) of 1-bromo-2-(ethylsulphanyl)ethane were added, and the mixture was stirred at 50° C. for 16 h. The DMF was then very substantially distilled off and the remaining residue was partitioned between semisaturated aqueous sodium chloride solution (300 ml) and ethyl acetate (150 ml). The aqueous phase was extracted with ethyl acetate. The combined organic phases were dried over sodium sulphate, filtered and concentrated. The residue obtained was chromatographed using a silica gel cartridge (Biotage, 340 g of silica gel, eluent: hexane/ethyl acetate). 666 mg (63% of theory) of the title compound were obtained.

$^1$H-NMR (400 MHz, DMSO-d$_6$, δ/ppm): 10.10 (s, 1H), 4.12-4.06 (m, 2H), 3.90 (q, 2H), 2.89-2.83 (m, 2H), 2.79 (s, 3H), 2.60 (q, 2H), 1.19 (t, 3H), 1.13 (t, 3H).

LC/MS (Method 3): R$_t$=1.22 min, m/z=327 [M+H]$^+$.

Example 376A

3-Ethyl-5-methyl-1-[2-(methylsulphonyl)ethyl]-2,4-dioxo-1,2,3,4-tetrahydrothieno[2,3-d]pyrimidine-6-carbaldehyde

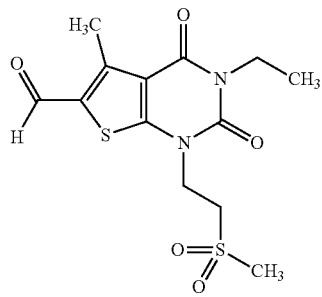 [SMILES: CCn1c(=O)c2c(C)c(C=O)sc2n(CCS(C)(=O)=O)c1=O]

To a solution of 375 mg (1.09 mmol) of the compound from Ex. 374A in 37 ml of dichloromethane were added, at 0° C., 592 mg (2.40 mmol) of 3-chloroperoxybenzoic acid (content 70%). The mixture was stirred at 0° C. for 30 min. Then the cooling bath was removed and the mixture was stirred at RT for a further 2 h. Subsequently added to the reaction mixture were 50 ml of water and 220 mg (2.62 mmol) of sodium hydrogencarbonate. The organic phase was removed and the aqueous phase was extracted with dichloromethane. The combined organic phases were dried over sodium sulphate, filtered and concentrated. The residue obtained was chromatographed using a silica gel cartridge (Biotage, 100 g of silica gel, eluent: hexane/ethyl acetate). 353 mg (92% of theory) of the title compound were obtained.

$^1$H-NMR (400 MHz, DMSO-d$_6$, δ/ppm): 10.11 (s, 1H), 4.37-4.31 (m, 2H), 3.91 (q, 2H), 3.60 (t, 2H), 3.12 (s, 3H), 2.80 (s, 3H), 1.14 (t, 3H).

LC/MS (Method 3): R$_t$=0.84 min, m/z=345 [M+H]$^+$.

Example 377A

3-Ethyl-1-(3-methoxypropyl)-5-methyl-2,4-dioxo-1,2,3,4-tetrahydrothieno[2,3-d]pyrimidine-6-carbaldehyde

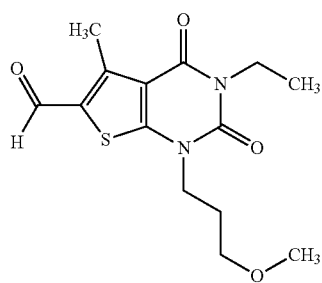 [SMILES: CCn1c(=O)c2c(C)c(C=O)sc2n(CCCOC)c1=O]

927 mg (6.71 mmol) of potassium carbonate were added to a solution of 639 mg (2.68 mmol) of the compound from Ex. 48A in 24 ml of DMF, and the mixture was stirred at RT for 15 min. Then 1.25 g (8.15 mmol) of 1-bromo-3-methoxypropane were added, and the mixture was stirred at 50° C. for 15 h. The DMF was then very substantially distilled off and the remaining residue was partitioned between semisaturated aqueous sodium chloride solution (70 ml) and ethyl acetate (70 ml). The aqueous phase was extracted with ethyl acetate. The combined organic phases were dried over sodium sulphate, filtered and concentrated. The residue obtained was chromatographed using a silica gel cartridge (Biotage, 100 g of silica gel, eluent: hexane/ethyl acetate). 521 mg (60% of theory) of the title compound were obtained.

$^1$H-NMR (400 MHz, DMSO-d$_6$, δ/ppm): 10.09 (s, 1H), 3.99 (t, 2H), 3.90 (q, 2H), 3.40 (t, 2H), 3.20 (s, 3H), 2.79 (s, 3H), 1.97-1.88 (m, 2H), 1.13 (t, 3H).

LC/MS (Method 3): R$_t$=1.05 min, m/z=311 [M+H]$^+$.

Example 378A 1-(Fluoromethyl)-3-isopropyl-5-methyl-2,4-dioxo-1,2,3,4-tetrahydrothieno[2,3-d]pyrimidine-6-carbaldehyde

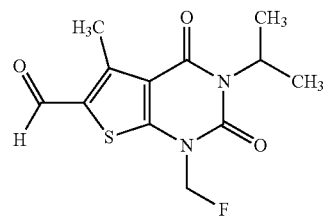 [SMILES: Cc1c(C=O)sc2c1c(=O)n(C(C)C)c(=O)n2CF]

1.31 g (9.51 mmol) of potassium carbonate were added to a solution of 800 mg (3.17 mmol) of the compound from Ex. 49A in 39 ml of DMF, and the mixture was stirred at RT for 15 min. Then 4.8 ml (9.51 mmol) of a 2 M solution of bromofluoromethane in DMF were added, and the mixture was stirred at 50° C. for 44 h. The DMF was then very substantially distilled off and the remaining residue was partitioned between semisaturated aqueous sodium chloride solution (100 ml) and ethyl acetate (150 ml). The aqueous phase was extracted with ethyl acetate. The combined organic phases were dried over sodium sulphate, filtered and concentrated. The residue obtained was chromatographed using a silica gel cartridge (Biotage, 100 g of silica gel, eluent: hexane/ethyl acetate). 488 mg (51% of theory) of the title compound were obtained.

$^1$H-NMR (400 MHz, DMSO-d$_6$, δ/ppm): 10.12 (s, 1H), 6.16-5.98 (m, 2H), 5.11 (quin, 1H), 2.79 (s, 3H), 1.42 (d, 6H).

LC/MS (Method 3): R$_t$=1.12 min, m/z=285 [M+H]$^+$.

Example 379A 1-(3-Fluoropropyl)-3-isopropyl-5-methyl-2,4-dioxo-1,2,3,4-tetrahydrothieno[2,3-d]pyrimidine-6-carbaldehyde

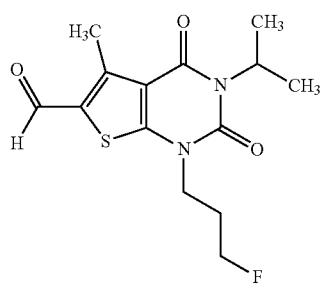 [SMILES: Cc1c(C=O)sc2c1c(=O)n(C(C)C)c(=O)n2CCCF]

1.09 g (7.93 mmol) of potassium carbonate were added to a solution of 800 mg (3.17 mmol) of the compound from Ex. 49A in 33 ml of DMF, and the mixture was stirred at RT for 15 min. Then 1.79 g (9.51 mmol) of 1-fluoro-3-iodopropane were added, and the mixture was stirred at 50° C. for 20 h. The DMF was then very substantially distilled off and the remaining residue was partitioned between semisaturated aqueous sodium chloride solution (100 ml) and ethyl acetate (50 ml). The aqueous phase was extracted with ethyl acetate. The combined organic phases were dried over sodium sulphate, filtered and concentrated. The residue obtained was chromatographed using a silica gel cartridge (Biotage, 100 g of silica gel, eluent: hexane/ethyl acetate). 796 mg (79% of theory) of the title compound were obtained.

$^1$H-NMR (400 MHz, DMSO-$d_6$, δ/ppm): 10.09 (s, 1H), 5.11 (sept, 1H), 4.61 (t, 1H), 4.49 (t, 1H), 4.02 (t, 2H), 2.78 (s, 3H), 2.15-2.07 (m, 1H), 2.07-1.99 (m, 1H), 1.40 (d, 6H).

LC/MS (Method 3): $R_t$=1.16 min, m/z=313 [M+H]$^+$.

Example 380A 3-(2-Methoxyethyl)-5-methyl-1-(oxetan-2-ylmethyl)-2,4-dioxo-1,2,3,4-tetrahydrothieno[2,3-d]pyrimidine-6-carbaldehyde (racemate)

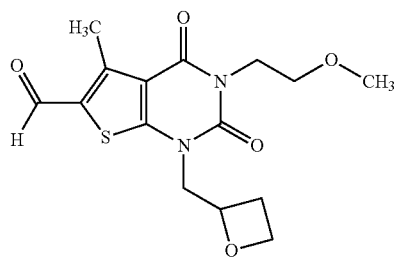 [SMILES: COCCn1c(=O)c2c(C)c(C=O)sc2n(CC2CCO2)c1=O]

In a closed reaction vessel, a mixture of 3.0 g (11.2 mmol) of the compound from Ex. 53A, 3.86 g (27.9 mmol) of potassium carbonate, 186 mg (1.12 mmol) of potassium iodide and 2.36 g (15.7 mmol) of racemic 2-(bromomethyl)oxetane in 15 ml of DMF was heated to 80° C. for 36 h. After cooling to RT, the reaction mixture was diluted with about 75 ml of water and extracted with ethyl acetate. The organic extract was washed successively with water and saturated sodium chloride solution. After drying over anhydrous magnesium sulphate, the mixture was filtered and concentrated. The residue obtained was stirred with diisopropyl ether to which a little ethyl acetate had been added. The solid was filtered off with suction and dried under high vacuum. This gave a first fraction of the title compound. The mother liquor from the stirring was concentrated again and the residue was purified by MPLC (340 g of silica gel, eluent: cyclohexane/ethyl acetate 88:12→0:100). The concentration of the product fractions gave a second portion of the title compound, which was combined with the first. A total of 2.33 g (60% of theory) of the title compound were thus obtained.

$^1$H-NMR (400 MHz, DMSO-$d_6$, δ/ppm): 10.09 (s, 1H), 5.09-4.96 (m, 1H), 4.54-4.38 (m, 2H), 4.31-4.14 (m, 2H), 4.06 (t, 2H), 3.52 (t, 2H), 3.31 (s, 3H), 2.78 (s, 3H), 2.76-2.64 (m, 1H), 2.55-2.46 (m, 1H).

LC/MS (Method 17, ESIpos): $R_t$=1.31 min, m/z=339.10 [M+H]$^+$.

Example 381A 3-(2-Ethoxyethyl)-5-methyl-2,4-dioxo-1-(3,3,3-trifluoropropyl)-1,2,3,4-tetrahydrothieno[2,3-d]pyrimidine-6-carbaldehyde

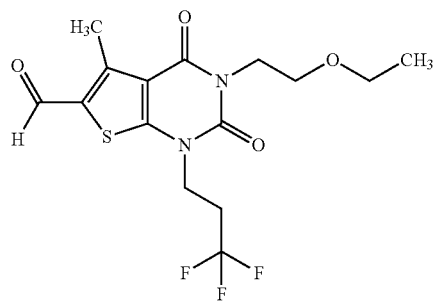 [SMILES: CCOCCn1c(=O)c2c(C)c(C=O)sc2n(CCC(F)(F)F)c1=O]

636 mg (4.6 mmol) of potassium carbonate were added to a solution of 520 mg (1.84 mmol) of the compound from Ex. 371A in 18 ml of DMF, and the mixture was stirred at RT for 15 min. Then 1.24 g (5.52 mmol) of 1-iodo-3,3,3-trifluoropropane were added, and the mixture was stirred at 50° C. for 19 h. The DMF was then very substantially distilled off and the remaining residue was partitioned between semisaturated aqueous sodium chloride solution (200 ml) and ethyl acetate (100 ml). The aqueous phase was extracted with ethyl acetate. The combined organic phases were dried over sodium sulphate, filtered and concentrated. The residue obtained was chromatographed using a silica gel cartridge (Biotage, 100 g of silica gel, eluent: hexane/ethyl acetate). 560 mg (80% of theory) of the title compound were obtained.

$^1$H-NMR (400 MHz, DMSO-$d_6$, δ/ppm): 10.11 (s, 1H), 4.18 (t, 2H), 4.05 (t, 2H), 3.53 (t, 2H), 3.44 (q, 2H), 2.85-2.74 (m, 5H), 1.06 (t, 3H).

LC/MS (Method 3): $R_t$=1.18 min, m/z=379 [M+H]$^+$.

Example 382A 3-(2-Ethoxyethyl)-1-(2-methoxyethyl)-5-methyl-2,4-dioxo-1,2,3,4-tetrahydrothieno[2,3-d]pyrimidine-6-carbaldehyde

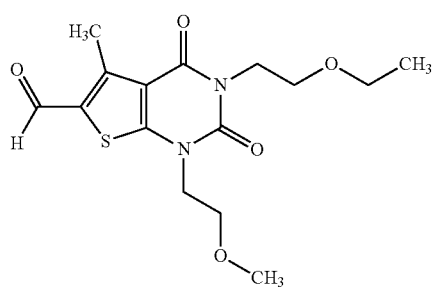 [SMILES: CCOCCn1c(=O)c2c(C)c(C=O)sc2n(CCOC)c1=O]

636 mg (4.6 mmol) of potassium carbonate were added to a solution of 520 mg (1.84 mmol) of the compound from Ex. 371A in 18 ml of DMF, and the mixture was stirred at RT for 15 min. Then 768 mg (5.52 mmol) of 1-bromo-2-methoxyethane were added, and the mixture was stirred at 50° C. for 25 h. The DMF was then very substantially distilled off and the remaining residue was partitioned between semisaturated aqueous sodium chloride solution (70 ml) and ethyl acetate (70 ml). The aqueous phase was extracted with ethyl acetate. The combined organic phases were dried over sodium sulphate, filtered and concentrated. The residue obtained was chromatographed using a silica gel cartridge (Biotage, 100 g of silica gel, eluent: hexane/ethyl acetate). 586 mg (71% of theory) of the title compound were obtained.

$^1$H-NMR (600 MHz, DMSO-$d_6$, δ/ppm): 10.09 (s, 1H), 4.10 (t, 2H), 4.05 (t, 2H), 3.65 (t, 2H), 3.53 (t, 2H), 3.45 (q, 2H), 3.24 (s, 3H), 2.78 (s, 3H), 1.06 (t, 3H).

LC/MS (Method 3): $R_t$=1.02 min, m/z=342 [M+H]$^+$.

Example 383A

3-Ethyl-1-(fluoromethyl)-6-(hydroxymethyl)-5-methylthieno[2,3-d]pyrimidine-2,4(1H,3H)-dione

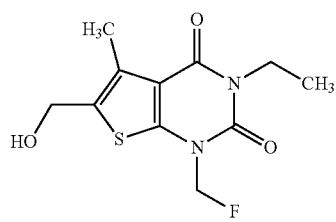 [SMILES: CCn1c(=O)c2c(C)c(CO)sc2n(CF)c1=O]

Analogously to the method described in Ex. 143A (Method C), 444 mg (1.65 mmol) of the compound from Ex. 372A were used to prepare 432 mg (93% of theory) of the title compound. The conversion was effected here at −78° C. for 2 h.

$^1$H-NMR (400 MHz, DMSO-$d_6$, δ/ppm): 6.03 (d, 2H), 5.67 (t, 1H), 4.60 (d, 2H), 3.91 (q, 2H), 2.33 (s, 3H), 1.13 (t, 3H).

LC/MS (Method 3): $R_t$=0.86 min, m/z=273 [M+H]$^+$.

Example 384A

3-Ethyl-6-(hydroxymethyl)-1-(3-methoxypropyl)-5-methylthieno[2,3-d]pyrimidine-2,4(1H,3H)-dione

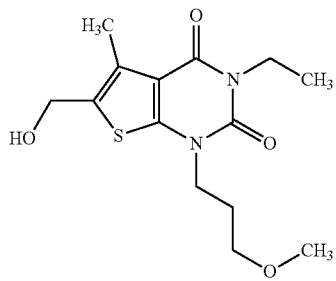 [SMILES: CCn1c(=O)c2c(C)c(CO)sc2n(CCCOC)c1=O]

Analogously to the method described in Ex. 143A (Method C), 121 mg (0.378 mmol) of the compound from Ex. 377A were used to prepare 106 mg (87% of theory) of the title compound. The conversion was effected here at −78° C. for 2 h.

$^1$H-NMR (400 MHz, DMSO-$d_6$, δ/ppm): 5.58 (t, 1H), 4.57 (d, 2H), 3.96-3.86 (m, 4H), 3.39 (t, 2H), 3.21 (s, 3H), 2.33 (s, 3H), 1.94-1.87 (m, 2H), 1.11 (t, 3H).

LC/MS (Method 3): $R_t$=0.89 min, m/z=313 [M+H]$^+$.

Example 385A 6-(Hydroxymethyl)-1-(2-methoxyethyl)-5-methyl-3-(prop-2-yn-1-yl)thieno[2,3-d]pyrimidine-2,4(1H,3H)-dione

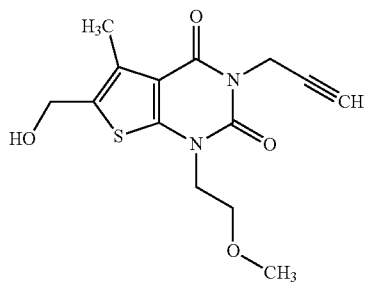 [SMILES: C#CCn1c(=O)c2c(C)c(CO)sc2n(CCOC)c1=O]

Analogously to the method described in Ex. 138A (Method C), 312 mg (0.82 mmol) of the compound from Ex. 357A were used to prepare 162 mg (64% of theory) of the title compound. The conversion was effected here at −40° C.

$^1$H-NMR (400 MHz, DMSO-$d_6$, δ/ppm): 5.62 (t, 1H), 4.61-4.56 (m, 4H), 4.06 (t, 2H), 3.65 (t, 2H), 3.24 (s, 3H), 3.14-3.12 (m, 1H), 2.33 (s, 3H).

LC/MS (Method 3): $R_t$=0.82 min, m/z=309 [M+H]$^+$.

Example 386A 3-(But-3-en-1-yl)-6-(hydroxymethyl)-1-(2-methoxyethyl)-5-methylthieno[2,3-d]pyrimidine-2,4(1H,3H)-dione

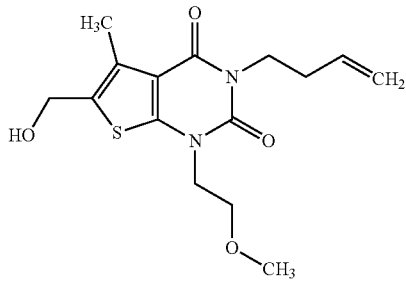

Analogously to the method described in Ex. 138A (Method C), 330 mg (0.84 mmol) of the compound from Ex. 358A were used to prepare 178 mg (65% of theory) of the title compound. The conversion was effected here at −40° C.

$^1$H-NMR (400 MHz, DMSO-d$_6$, δ/ppm): 5.78 (ddt, 1H), 5.57 (t, 1H), 5.06-4.95 (m, 2H), 4.57 (d, 2H), 4.04 (t, 2H), 3.93 (t, 2H), 3.63 (t, 2H), 3.23 (s, 3H), 2.36-2.27 (m, 5H).

LC/MS (Method 3): R$_t$=1.0 min, m/z=325 [M+H]$^+$.

Example 387A 3-(But-2-yn-1-yl)-6-(hydroxymethyl)-1-(2-methoxyethyl)-5-methylthieno[2,3-d]pyrimidine-2,4(1H,3H)-dione

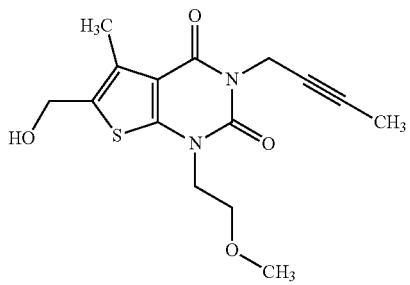 [SMILES: CC#CCn1c(=O)c2c(C)c(CO)sc2n(CCOC)c1=O]

Analogously to the method described in Ex. 138A (Method C), 305 mg (0.652 mmol) of the compound from Ex. 359A were used to prepare 122 mg (58% of theory) of the title compound. The conversion was effected here at RT.

$^1$H-NMR (400 MHz, DMSO-d$_6$, δ/ppm): 5.61 (t, 1H), 4.60-4.53 (m, 4H), 4.06 (t, 2H), 3.64 (t, 2H), 3.24 (s, 3H), 2.32 (s, 3H), 1.74 (t, 3H).

LC/MS (Method 3): R$_t$=0.89 min, m/z=323 [M+H]$^+$.

Example 388A 3-(But-3-yn-1-yl)-6-(hydroxymethyl)-1-(2-methoxyethyl)-5-methylthieno[2,3-d]pyrimidine-2,4(1H,3H)-dione

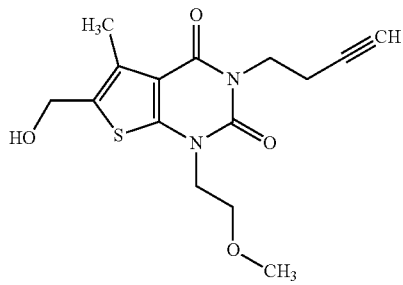 [SMILES: C#CCCn1c(=O)c2c(C)c(CO)sc2n(CCOC)c1=O]

Analogously to the method described in Ex. 138A (Method C), 300 mg (0.703 mmol) of the compound from Ex. 360A were used to prepare 134 mg (58% of theory) of the title compound. The conversion was effected here at RT.

$^1$H-NMR (400 MHz, DMSO-d$_6$, δ/ppm): 5.58 (t, 1H), 4.57 (d, 2H), 4.06-4.02 (m, 2H), 4.00 (t, 2H), 3.63 (t, 2H), 3.24 (s, 3H), 2.85 (t, 1H), 2.48-2.43 (m, 2H), 2.32 (s, 3H).

LC/MS (Method 3): R$_t$=0.86 min, m/z=323 [M+H]$^+$.

Example 389A 6-(Hydroxymethyl)-1-(2-methoxyethyl)-5-methyl-3-(3-methylbut-3-en-1-yl)thieno[2,3-d]pyrimidine-2,4(1H,3H)-dione

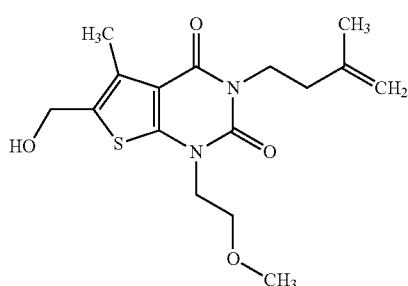

At −40° C., 666 μl (0.666 mmol) of a 1 M solution of lithium aluminium hydride in THF were added dropwise to a solution of 295 mg (0.666 mmol) of the compound from Example 361A in 18 ml of dry THF. On completion of addition, stirring was continued at RT for 2 h. Then 1 ml of 10% hydrochloric acid was added cautiously. 100 ml of saturated sodium chloride solution were added to the mixture, and the aqueous phase was extracted with ethyl acetate. The combined organic phases were dried over sodium sulphate, filtered and concentrated. The residue obtained was purified by means of preparative HPLC (Method 14). 151 mg (65% of theory) of the title compound were obtained.

$^1$H-NMR (400 MHz, DMSO-d$_6$, δ/ppm): 5.57 (t, 1H), 4.72 (s, 1H), 4.63 (d, 1H), 4.57 (d, 2H), 4.03 (t, 2H), 4.01-3.94 (m, 2H), 3.63 (t, 2H), 3.23 (s, 3H), 2.32 (s, 3H), 2.24 (t, 2H), 1.76 (s, 3H).

LC/MS (Method 3): R$_t$=1.05 min, m/z=339 [M+H]$^+$.

Example 390A 6-(Hydroxymethyl)-1-(2-methoxyethyl)-5-methyl-3-(4-methylpent-3-en-1-yl)thieno[2,3-d]pyrimidine-2,4(1H,3H)-dione

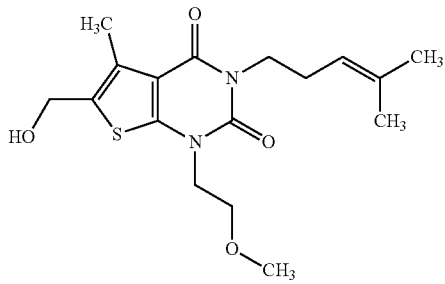 [SMILES: COCCn1c(=O)n(CCC=C(C)C)c(=O)c2c(C)c(CO)sc21]

Analogously to the method described in Ex. 138A (Method C), 310 mg (0.691 mmol) of the compound from Ex. 362A were used to prepare 125 mg (48% of theory) of the title compound. The conversion was effected here at RT for 1 h.

$^1$H-NMR (400 MHz, DMSO-$d_6$, δ/ppm): 5.57 (t, 1H), 5.16-5.08 (m, 1H), 4.57 (d, 2H), 4.03 (t, 2H), 3.86-3.79 (m, 2H), 3.63 (t, 2H), 3.25-3.22 (m, 3H), 2.32 (s, 3H), 2.27-2.17 (m, 2H), 1.63 (s, 3H), 1.54 (s, 3H).

LC/MS (Method 3): $R_t$=1.17 min, m/z=353 [M+H]$^+$.

Example 391A 6-(Hydroxymethyl)-1-(2-methoxyethyl)-5-methyl-3-(3,4,4-trifluorobut-3-en-1-yl)thieno[2,3-d]pyrimidine-2,4(1H,3H)-dione

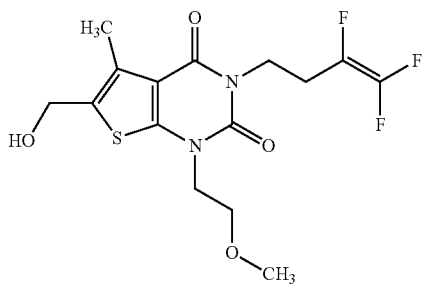 [SMILES: COCCn1c(=O)n(CCC(F)=C(F)F)c(=O)c2c(C)c(CO)sc21]

At −40° C., 737 μl (0.737 mmol) of a 1 M solution of lithium aluminium hydride in THF were added dropwise to a solution of 424 mg (0.737 mmol) of the compound from Example 363A in 17 ml of dry THF. On completion of addition, stirring was continued at RT for 1 h. Then 1 ml of 10% hydrochloric acid was added cautiously. 100 ml of saturated sodium chloride solution were added to the mixture, and the aqueous phase was extracted with ethyl acetate. The combined organic phases were dried over sodium sulphate, filtered and concentrated. The residue obtained was purified by means of preparative HPLC (Method 14). 199 mg (70% of theory) of the title compound were obtained.

$^1$H-NMR (400 MHz, DMSO-$d_6$, δ/ppm): 5.59 (t, 1H), 4.57 (d, 2H), 4.08 (t, 2H), 4.05 (t, 2H), 3.63 (t, 2H), 3.22 (s, 3H), 2.72-2.65 (m, 1H), 2.65-2.59 (m, 1H), 2.32 (s, 3H).

LC/MS (Method 3): $R_t$=1.04 min, m/z=379 [M+H]$^+$.

Example 392A 3-(4,4-Difluorobut-3-en-1-yl)-6-(hydroxymethyl)-1-(2-methoxyethyl)-5-methylthieno[2,3-d]pyrimidine-2,4(1H,3H)-dione

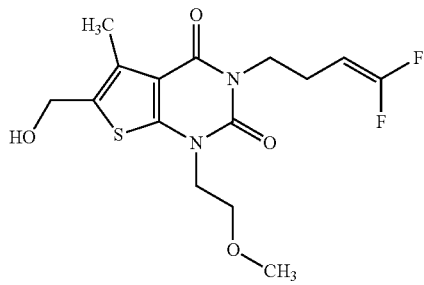 [SMILES: COCCn1c(=O)n(CCC=C(F)F)c(=O)c2c(C)c(CO)sc21]

At −40° C., 735 μl (0.735 mmol) of a 1 M solution of lithium aluminium hydride in THF were added dropwise to a solution of 345 mg (0.735 mmol) of the compound from Example 364A in 17 ml of dry THF. On completion of addition, stirring was continued at RT for 1 h. Then 1 ml of 10% hydrochloric acid was added cautiously. 100 ml of saturated sodium chloride solution were added to the mixture, and the aqueous phase was extracted with ethyl acetate. The combined organic phases were dried over sodium sulphate, filtered and concentrated. The residue obtained was chromatographed using a silica gel cartridge (Biotage, 25 g of silica gel, eluent: hexane/ethyl acetate). 133 mg (49% of theory) of the title compound were obtained.

$^1$H-NMR (400 MHz, DMSO-$d_6$, δ/ppm): 5.58 (t, 1H), 4.60-4.44 (m, 3H), 4.04 (t, 2H), 3.92 (t, 2H), 3.63 (t, 2H), 3.23 (s, 3H), 2.32 (s, 3H), 2.26 (q, 2H).

LC/MS (Method 3): $R_t$=1.05 min, m/z=361 [M+H]$^+$.

Example 393A

3-[(2,2-Difluorocyclopropyl)methyl]-6-(hydroxymethyl)-1-(2-methoxyethyl)-5-methylthieno[2,3-d]pyrimidine-2,4(1H,3H)-dione (racemate)

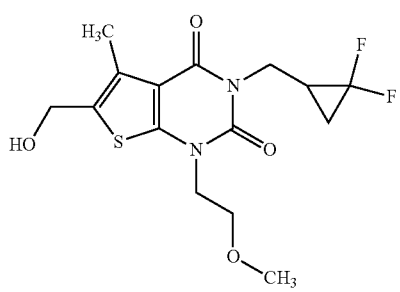 [SMILES: COCCn1c(=O)n(CC2CC2(F)F)c(=O)c2c(C)c(CO)sc21]

Analogously to the method described in Ex. 138A (Method C), 430 mg (0.870 mmol) of the compound from Ex. 365A were used to prepare 171 mg (53% of theory) of the title compound. The conversion was effected here at RT for 1 h.

¹H-NMR (400 MHz, DMSO-d₆, δ/ppm): 5.59 (t, 1H), 4.58 (d, 2H), 4.12-4.02 (m, 3H), 3.98 (d, 1H), 3.65 (t, 2H), 3.24 (s, 3H), 2.33 (s, 3H), 2.16-2.02 (m, 1H), 1.59 (tdd, 1H), 1.39-1.28 (m, 1H).

LC/MS (Method 3): R$_t$=1.0 min, m/z=361 [M+H]⁺.

Example 394A 6-(Hydroxymethyl)-1-(2-methoxyethyl)-3-(3-methoxypropyl)-5-methylthieno[2,3-d]pyrimidine-2,4(1H,3H)-dione

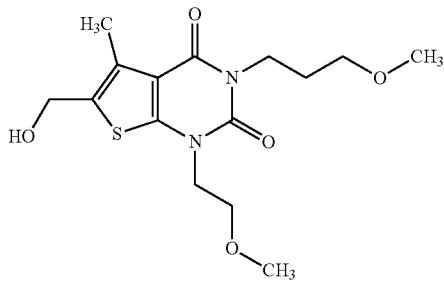 [SMILES: COCCCn1c(=O)c2c(C)c(CO)sc2n(CCOC)c1=O]

Analogously to the method described in Ex. 138A (Method C), 310 mg (0.673 mmol) of the compound from Ex. 366A were used to prepare 146 mg (60% of theory) of the title compound. The conversion was effected here at RT for 2 h.

¹H-NMR (400 MHz, DMSO-d₆, δ/ppm): 5.57 (t, 1H), 4.57 (d, 2H), 4.03 (t, 2H), 3.92 (t, 2H), 3.63 (t, 2H), 3.38-3.34 (m, 2H), 3.24 (s, 3H), 3.20 (s, 3H), 2.32 (s, 3H), 1.76 (m, 2H).

LC/MS (Method 3): R$_t$=0.83 min, m/z=343 [M+H]⁺.

Example 395A 6-(Hydroxymethyl)-1-(2-methoxyethyl)-5-methyl-3-(tetrahydrofuran-2-ylmethyl)thieno[2,3-d]pyrimidine-2,4(1H,3H)-dione (racemate)

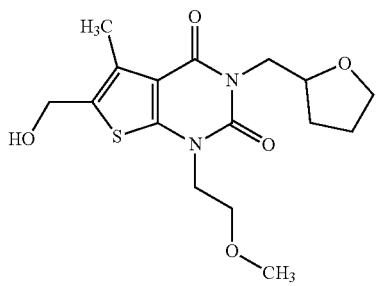 [SMILES: COCCn1c(=O)n(CC2CCCO2)c(=O)c2c(C)c(CO)sc21]

Analogously to the method described in Ex. 138A (Method C), 430 mg (0.912 mmol) of the compound from Ex. 367A were used to prepare 178 mg (54% of theory) of the title compound. The conversion was effected here at RT for 2 h.

¹H-NMR (400 MHz, DMSO-d₆, δ/ppm): 5.57 (t, 1H), 4.57 (d, 2H), 4.18-4.09 (m, 1H), 4.09-3.97 (m, 3H), 3.80-3.71 (m, 2H), 3.67-3.56 (m, 3H), 3.24 (s, 3H), 2.32 (s, 3H), 1.94-1.73 (m, 3H), 1.67-1.57 (m, 1H).

LC/MS (Method 3): R$_t$=0.87 min, m/z=355 [M+H]⁺.

Example 396A 6-(Hydroxymethyl)-1-(2-methoxyethyl)-5-methyl-3-(oxetan-3-ylmethyl)thieno[2,3-d]pyrimidine-2,4(1H,3H)-dione

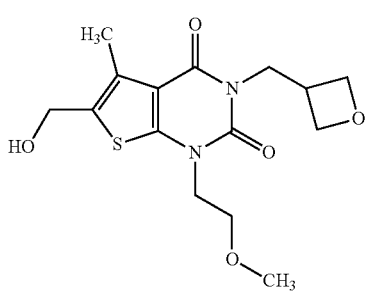 [SMILES: COCCn1c(=O)n(CC2COC2)c(=O)c2c(C)c(CO)sc21]

Analogously to the method described in Ex. 138A (Method C), 349 mg (0.789 mmol) of the compound from Ex. 368A were used to prepare 76 mg (28% of theory) of the title compound. The conversion was effected here at RT for 1 h.

¹H-NMR (400 MHz, DMSO-d₆, δ/ppm): 5.58 (t, 1H), 4.60-4.55 (m, 4H), 4.40 (t, 2H), 4.16 (d, 2H), 4.03 (t, 2H), 3.63 (t, 2H), 3.30-3.24 (m, 1H), 3.23 (s, 3H), 2.31 (s, 3H).

LC/MS (Method 3): R$_t$=0.76 min, m/z=341 [M+H]⁺.

Example 397A

6-{[(2-Aminoethyl)amino]methyl}-3-ethyl-1-(fluoromethyl)-5-methylthieno[2,3-d]pyrimidine-2,4(1H,3H)-dione

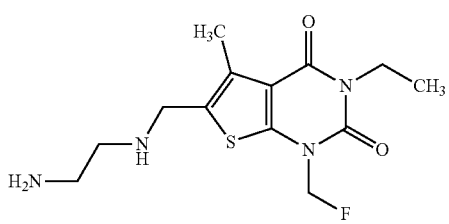 [SMILES: CCn1c(=O)c2c(C)c(CNCCN)sc2n(CF)c1=O]

Analogously to the method described in Ex. 210A, 332 mg (1.15 mmol) of the compound from Ex. 372A and 1,2-diaminoethane were used to prepare 440 mg (95% of theory, 79% purity) of the title compound. The reaction time here was 66 h.

LC/MS (Method 3): R$_t$=0.48 min, m/z=315 [M+H]⁺.

Example 398A

6-{[(2-Aminoethyl)amino]methyl}-1-[2-(cyclopentyloxy)ethyl]-3-ethyl-5-methylthieno[2,3-d]pyrimidine-2,4(1H,3H)-dione

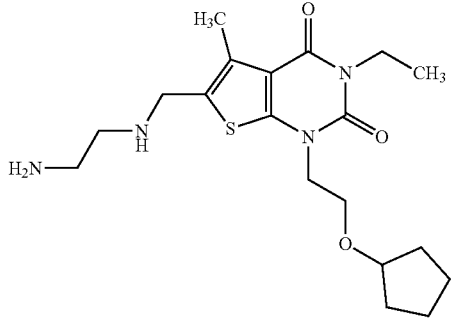 [SMILES: CCn1c(=O)c2c(C)c(CNCCN)sc2n(CCOC2CCCC2)c1=O]

Analogously to the method described in Ex. 210A, 380 mg (1.08 mmol) of the compound from Ex. 373A and 1,2-diaminoethane were used to prepare 510 mg (97% of theory, 82% purity) of the title compound. The reaction time here was 89 h.

LC/MS (Method 3): $R_t$=0.70 min, m/z=395 [M+H]$^+$.

Example 399A

6-{[(2-Aminoethyl)amino]methyl}-3-ethyl-1-[2-(ethylsulphanyl)ethyl]-5-methylthieno[2,3-d]pyrimidine-2,4(1H,3H)-dione

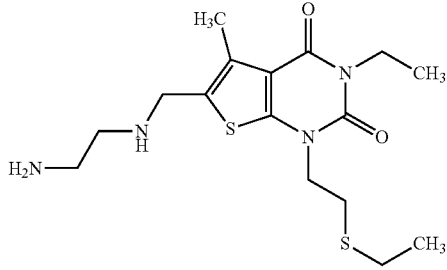 [SMILES: CCSCCn1c(=O)n(CC)c(=O)c2c(C)c(CNCCN)sc21]

Analogously to the method described in Ex. 210A, 300 mg (0.891 mmol) of the compound from Ex. 375A and 1,2-diaminoethane were used to prepare 512 mg of the title compound. The reaction time here was 65 h.

LC/MS (Method 3): $R_t$=0.61 min, m/z=311 [M+H—$C_2H_8N_2$]$^+$.

Example 400A

6-{[(2-Aminoethyl)amino]methyl}-3-ethyl-5-methyl-1-[2-(methylsulphonyl)ethyl]thieno[2,3-d]pyrimidine-2,4(1H,3H)-dione

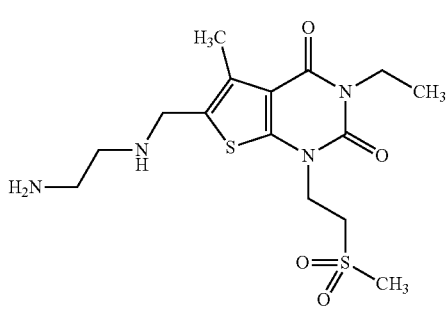 [SMILES: CCn1c(=O)c2c(C)c(CNCCN)sc2n(CCS(C)(=O)=O)c1=O]

Analogously to the method described in Ex. 210A, 346 mg (1 mmol) of the compound from Ex. 376A and 1,2-diaminoethane were used to prepare 470 mg (42% of theory, 35% purity) of the title compound. The reaction time here was 90 h.

LC/MS (Method 3): $R_t$=0.73 min, m/z=389 [M+H]$^+$.

Example 401A

6-{[(2-Aminoethyl)amino]methyl}-3-ethyl-1-(3-methoxypropyl)-5-methylthieno[2,3-d]pyrimidine-2,4(1H,3H)-dione

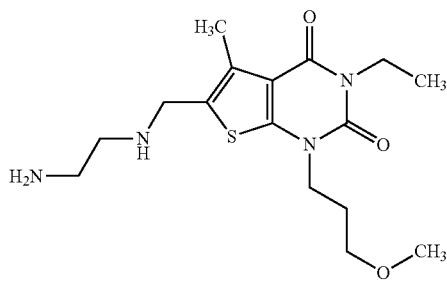 [SMILES: CCn1c(=O)c2c(C)c(CNCCN)sc2n(CCCOC)c1=O]

Analogously to the method described in Ex. 210A, 360 mg (1.13 mmol) of the compound from Ex. 377A and 1,2-diaminoethane were used to prepare 310 mg (65% of theory, 83% purity) of the title compound. The reaction time here was 93 h.

LC/MS (Method 3): $R_t$=0.55 min, m/z=355 [M+H]$^+$.

Example 402A

6-{[(2-Aminoethyl)amino]methyl}-3-isopropyl-1,5-dimethylthieno[2,3-d]pyrimidine-2,4(1H,3H)-dione

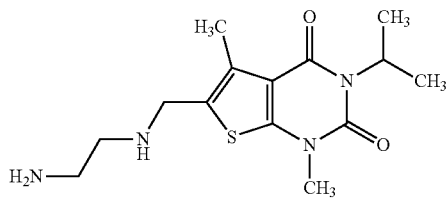 [SMILES: Cc1c(CNCCN)sc2c1c(=O)n(C(C)C)c(=O)n2C]

Analogously to the method described in Ex. 210A, 260 mg (0.976 mmol) of the compound from Ex. 109A and 1,2-diaminoethane were used to prepare 266 mg (83% of theory, 95% purity) of the title compound. The reaction time here was 97 h.

LC/MS (Method 3): $R_t$=0.50 min, m/z=251 [M+H—$C_2H_8N_2$]$^+$.

Example 403A

6-{[(2-Aminoethyl)amino]methyl}-1-(fluoromethyl)-3-isopropyl-5-methylthieno[2,3-d]pyrimidine-2,4(1H,3H)-dione

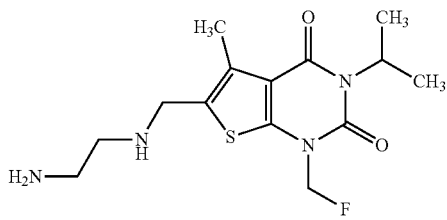 [SMILES: Cc1c(CNCCN)sc2c1c(=O)n(C(C)C)c(=O)n2CF]

Analogously to the method described in Ex. 210A, 170 mg (0.562 mmol) of the compound from Ex. 378A and 1,2-diaminoethane were used to prepare 119 mg (55% of theory, 86% purity) of the title compound. The reaction time here was 97 h.

LC/MS (Method 3): $R_t$=0.57 min, m/z=269 [M+H—$C_2H_8N_2$]$^+$.

Example 404A

6-{[(2-Aminoethyl)amino]methyl}-1-(3-fluoropropyl)-3-isopropyl-5-methylthieno[2,3-d]pyrimidine-2,4(1H,3H)-dione

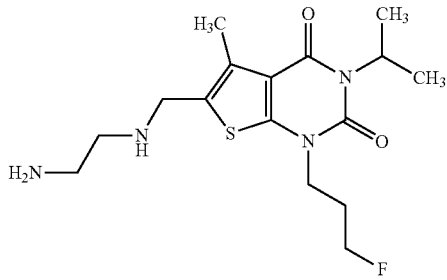 [SMILES: Cc1c(CNCCN)sc2c1c(=O)n(C(C)C)c(=O)n2CCCF]

340 mg (1.08 mmol) of the compound from Ex. 379A were dissolved in a mixture of 18 ml of methanol and 8 ml of dichloromethane. Then 720 μl (10.8 mmol) of 1,2-diaminoethane and 247 μl (4.31 mmol) of acetic acid were added at RT. The mixture was stirred at RT for 30 minutes, and then 285 mg (4.31 mmol) of sodium cyanoborohydride were added. After the reaction mixture had been stirred at 60° C. for 44 h, it was admixed with 80 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 406 mg (70% of theory, 67% purity) of the title compound, which was used for subsequent reactions without further purification.

LC/MS (Method 3): $R_t$=0.64 min, m/z=357 [M+H]$^+$.

Example 405A

6-{[(2-Aminoethyl)amino]methyl}-3-(2-methoxyethyl)-5-methyl-1-(oxetan-2-ylmethyl)thieno[2,3-d]pyrimidine-2,4(1H,3H)-dione (racemate)

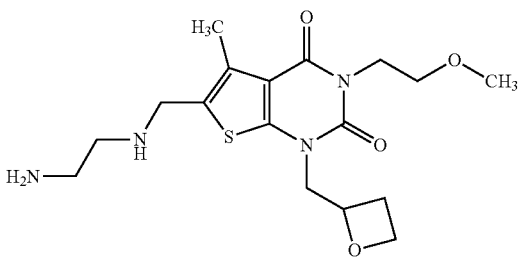 [SMILES: COCCn1c(=O)c2c(C)c(CNCCN)sc2n(CC2CCO2)c1=O]

Analogously to the method described in Ex. 245A, 1.30 g (3.76 mmol) of the compound from Ex. 380A and 1.36 g (22.6 mmol) of 1,2-diaminoethane were used to prepare 956 mg (66% of theory) of the title compound. The reaction time here was about 18 h.

LC/MS (Method 6, ESIpos): $R_t$=0.96 min, m/z=383 [M+H]$^+$.

Example 406A

6-{[(2-Aminoethyl)amino]methyl}-3-(2-ethoxyethyl)-5-methyl-1-(3,3,3-trifluoropropyl)thieno[2,3-d]pyrimidine-2,4(1H,3H)-dione

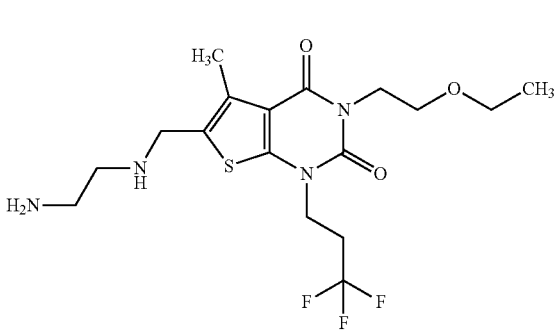 [SMILES: CCOCCn1c(=O)c2c(C)c(CNCCN)sc2n(CCC(F)(F)F)c1=O]

430 mg (1.14 mmol) of the compound from Ex. 381A were dissolved in a mixture of 19 ml of methanol and 8 ml of dichloromethane. Then 760 μl (11.4 mmol) of 1,2-diaminoethane and 260 μl (4.54 mmol) of acetic acid were added at RT. The mixture was stirred at RT for 30 minutes, and then 301 mg (4.54 mmol) of sodium cyanoborohydride were added. After the reaction mixture had been stirred at 60° C. for 72 h, it was admixed with 50 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 486 mg (90% of theory, 89% purity) of the title compound, which was used for subsequent reactions without further purification.

LC/MS (Method 3): $R_t$=0.62 min, m/z=423 [M+H]$^+$.

Example 407A

6-{[(2-Aminoethyl)amino]methyl}-3-(2-ethoxy-ethyl)-1-(2-methoxyethyl)-5-methylthieno[2,3-d]pyrimidine-2,4(1H,3H)-dione

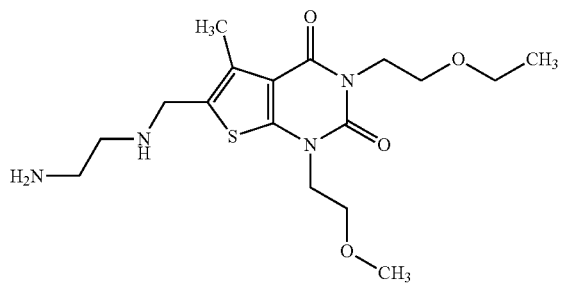 [SMILES: CCOCCn1c(=O)c2c(C)c(CNCCN)sc2n(CCOC)c1=O]

Analogously to the method described in Ex. 210A, 345 mg (0.983 mmol) of the compound from Ex. 382A and 1,2-diaminoethane were used to prepare 185 mg (33% of theory, 68% purity) of the title compound. The reaction time here was 72 h.

LC/MS (Method 3): $R_t$=0.53 min, m/z=385 [M+H]$^+$.

Example 408A

6-{[(2,2-Dimethoxyethyl)amino]methyl}-5-methyl-3-(2,2,2-trifluoroethyl)-1-(3,3,3-trifluoropropyl)thieno[2,3-d]pyrimidine-2,4(1H,3H)-dione

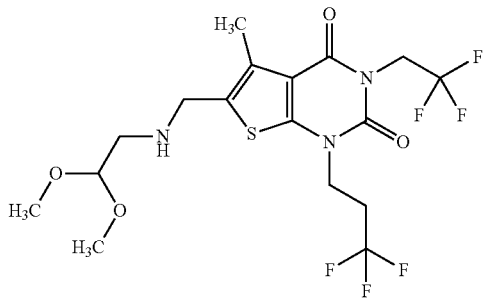 [SMILES: COC(CNCc1sc2c(c1C)c(=O)n(CC(F)(F)F)c(=O)n2CCC(F)(F)F)OC]

470 mg (1.21 mmol) of the compound from Ex. 120A and 191 mg (1.82 mmol) of 2,2-dimethoxyethanamine were dissolved in 25 ml of dichloromethane and heated to reflux for 1 h. After cooling to RT, 770 mg (3.63 mmol) of sodium triacetoxyborohydride were added. The reaction mixture was stirred at RT for about 18 h. Since the conversion was still incomplete after this time, a further 64 mg (0.605 mmol) of 2,2-dimethoxyethanamine and 257 mg (1.21 mmol) of sodium triacetoxyborohydride were added. After further stirring at RT for about 24 h, the reaction mixture was diluted with ethyl acetate and washed successively with saturated aqueous sodium hydrogencarbonate solution, water and saturated sodium chloride solution. After drying over anhydrous magnesium sulphate, the mixture was filtered and concentrated. The remaining residue was purified by means of MPLC (Isolera One with Biotage SNAP KP-Sil cartridge, 25 g of silica gel, eluent: cyclohexane/ethyl acetate 1:1). After combination of the product fractions, concentration and drying under high vacuum, 433 mg (74% of theory) of the title compound were obtained.

$^1$H-NMR (400 MHz, DMSO-d$_6$, δ/ppm): 4.70 (q, 2H), 4.42 (t, 1H), 4.15 (t, 2H), 3.85 (s, 2H), 3.31 (s, 3H), 2.87-2.70 (m, 2H), 2.64 (d, 2H), 2.54 (s, 3H), 2.34 (s, 3H).

LC/MS (Method 17, ESIpos): $R_t$=1.12 min, m/z=478.12 [M+H]$^+$.

Example 409A

6-{[(2,2-Dimethoxyethyl)amino]methyl}-1-(2-methoxyethyl)-5-methyl-3-(2,2,2-trifluoroethyl)thieno[2,3-d]pyrimidine-2,4(1H,3H)-dione

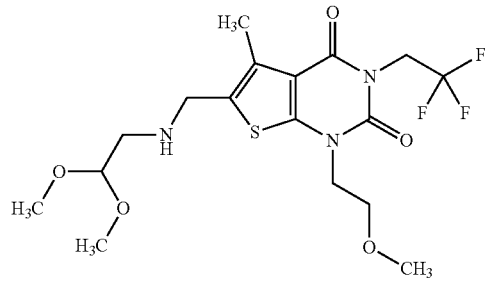 [SMILES: COCCn1c(=O)n(CC(F)(F)F)c(=O)c2c(C)c(CNCC(OC)OC)sc21]

500 mg (1.43 mmol) of the compound from Ex. 122A and 225 mg (2.14 mmol) of 2,2-dimethoxyethanamine were dissolved in 25 ml of dichloromethane and heated to reflux for 1 h. After cooling to RT, 907 mg (4.28 mmol) of sodium triacetoxyborohydride were added. The reaction mixture was stirred at RT for about 18 h. Then the mixture was diluted with ethyl acetate and washed successively with saturated aqueous sodium hydrogencarbonate solution, water and saturated sodium chloride solution. After drying over anhydrous magnesium sulphate, the mixture was filtered and concentrated. The remaining residue was purified by means of MPLC (Isolera One with Biotage SNAP KP-Sil cartridge, 25 g of silica gel, eluent: cyclohexane/ethyl acetate 1:1). After combination of the product fractions, concentration and drying under high vacuum, 460 mg (73% of theory) of the title compound were obtained.

$^1$H-NMR (400 MHz, DMSO-d$_6$, δ/ppm): 4.69 (q, 2H), 4.41 (t, 1H), 4.07 (t, 2H), 3.83 (s, 2H), 3.64 (t, 2H), 3.27 (s, 6H), 3.24 (s, 3H), 2.63 (d, 2H), 2.32 (s, 3H).

LC/MS (Method 17, ESIpos): $R_t$=0.96 min, m/z=440.15 [M+H]$^+$.

Example 410A

6-{[(2,2-Dimethoxyethyl)amino]methyl}-5-methyl-1-(tetrahydrofuran-2-ylmethyl)-3-(2,2,2-trifluoroethyl)thieno[2,3-d]pyrimidine-2,4(1H,3H)-dione (racemate)

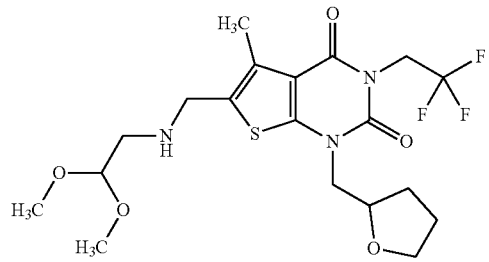 [SMILES: COC(CNCc1sc2c(c1C)c(=O)n(CC(F)(F)F)c(=O)n2CC1CCCO1)OC]

Analogously to the method described in Ex. 268A, 600 mg (1.59 mmol) of the compound from Ex. 125A and 251 mg (2.39 mmol) of 2,2-dimethoxyethanamine were used to prepare 638 mg (85% of theory) of the title compound. Chromatography was effected here using a Biotage Isolera One system with a Biotage cartridge (SNAP KP-Sil, 50 g of silica gel) and cyclohexane/ethyl acetate 1:1 as eluent.

$^1$H-NMR (400 MHz, DMSO-$d_6$, δ/ppm): 4.70 (q, 2H), 4.41 (t, 1H), 4.29-4.18 (m, 1H), 4.10-4.00 (m, 1H), 3.83 (s, 2H), 3.81-3.70 (m, 2H), 3.66-3.56 (m, 1H), 3.27 (s, 6H), 2.63 (d, 2H), 2.33 (s, 3H), 2.03-1.79 (m, 3H), 1.71-1.63 (m, 1H).

LC/MS (Method 1, ESIpos): $R_t$=0.63 min, m/z=466 [M+H]$^+$.

Example 411A

6-{[(2,2-Dimethoxyethyl)amino]methyl}-3-(2-methoxyethyl)-5-methyl-1-(3,3,3-trifluoropropyl)thieno[2,3-d]pyrimidine-2,4(1H,3H)-dione

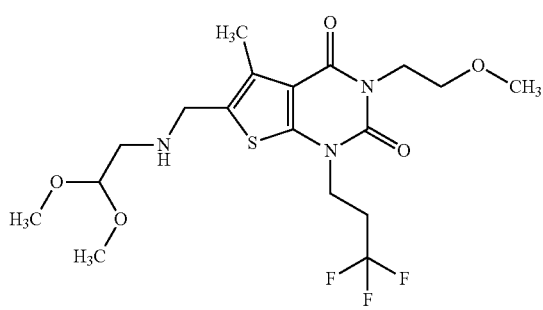

500 mg (1.37 mmol) of the compound from Ex. 296A and 216 mg (2.06 mmol) of 2,2-dimethoxyethanamine were dissolved in 30 ml of dichloromethane and heated to reflux for 1 h. After cooling to RT, 872 mg (4.12 mmol) of sodium triacetoxyborohydride were added. The reaction mixture was stirred at RT for 2.5 days. Then the mixture was diluted with ethyl acetate and washed successively with saturated aqueous sodium hydrogencarbonate solution, water and saturated sodium chloride solution. After drying over anhydrous magnesium sulphate, the mixture was filtered and concentrated. The remaining residue was purified by means of MPLC (Isolera One with Biotage SNAP KP-Sil cartridge, 50 g of silica gel, eluent: cyclohexane/ethyl acetate 1:1). After combination of the product fractions, concentration and drying under high vacuum, 455 mg (73% of theory) of the title compound were obtained.

$^1$H-NMR (400 MHz, DMSO-$d_6$, δ/ppm): 4.41 (t, 1H), 4.11 (t, 2H), 4.05 (t, 2H), 3.84 (s, 2H), 3.49 (t, 2H), 3.27 (s, 6H), 3.24 (s, 3H), 2.84-2.68 (m, 2H), 2.63 (d, 2H), 2.33 (s, 3H).

LC/MS (Method 17, ESIneg): $R_t$=0.93 min, m/z=498.15 [M−H+HCOOH]$^-$.

Example 412A

6-{[(2,2-Dimethoxyethyl)amino]methyl}-1,3-bis(2-methoxyethyl)-5-methylthieno[2,3-d]pyrimidine-2,4(1H,3H)-dione

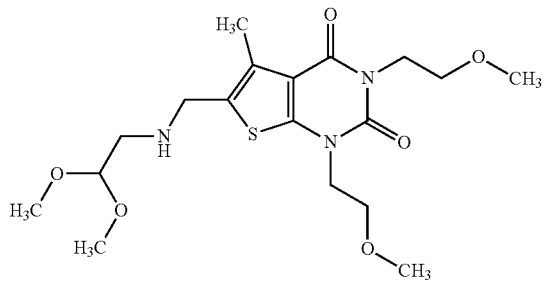

Analogously to the method described in Ex. 268A, 500 mg (1.53 mmol) of the compound from Ex. 136A and 241 mg (2.30 mmol) of 2,2-dimethoxyethanamine were used to prepare 533 mg (83% of theory) of the title compound. Chromatography was effected here using a Biotage Isolera One system with a Biotage cartridge (SNAP KP-Sil, 50 g of silica gel) and cyclohexane/ethyl acetate (33:67→0:100) as eluent.

$^1$H-NMR (400 MHz, DMSO-$d_6$, δ/ppm): 4.41 (t, 1H), 4.05 (t, 2H), 4.03 (t, 2H), 3.82 (s, 2H), 3.63 (t, 2H), 3.49 (t, 2H), 3.26 (s, 6H), 3.24 (2s, 6H), 2.62 (d, 2H), 2.32 (s, 3H).

LC/MS (Method 17, ESIpos): $R_t$=0.77 min, m/z=311.11 [M+H—$C_4H_{11}NO_2$]$^+$.

Example 413A

6-{[(2,2-Dimethoxyethyl)amino]methyl}-3-(2-methoxyethyl)-5-methyl-1-(tetrahydrofuran-2-ylmethyl)thieno[2,3-d]pyrimidine-2,4(1H,3H)-dione (racemate)

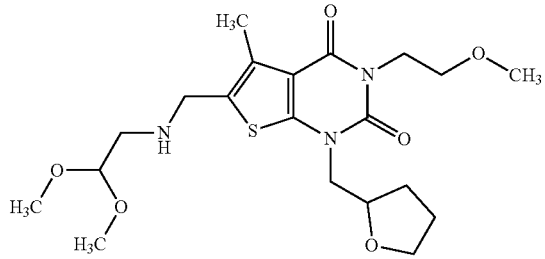

Analogously to the method described in Ex. 268A, 900 mg (2.55 mmol) of the compound from Ex. 298A and 403 mg (3.83 mmol) of 2,2-dimethoxyethanamine were used to prepare 745 mg (66% of theory) of the title compound. Chromatography was effected here using a Biotage Isolera One system with a Biotage cartridge (SNAP KP-Sil, 100 g of silica gel) and cyclohexane/ethyl acetate (50:50→0:100) as eluent.

$^1$H-NMR (400 MHz, DMSO-$d_6$, δ/ppm): 4.41 (t, 1H), 4.27-4.17 (m, 1H), 4.10-3.97 (m, 3H), 3.82 (s, 2H), 3.79-3.68 (m, 2H), 3.66-3.57 (m, 1H), 3.50 (t, 2H), 3.26 (s, 6H), 3.24 (s, 3H), 2.62 (d, 2H), 2.32 (s, 3H), 2.03-1.75 (m, 3H), 1.72-1.60 (m, 1H).

LC/MS (Method 1, ESIneg): $R_t$=0.53 min, m/z=486 [M−H+HCOOH]⁻.

Example 414A 1-(2,2-Dimethoxyethyl)-1-{[3-(2-methoxyethyl)-5-isopropyl-2,4-dioxo-1-(tetrahydrofuran-2-ylmethyl)-1,2,3,4-tetrahydrothieno[2,3-d]pyrimidin-6-yl]methyl}urea (racemate)

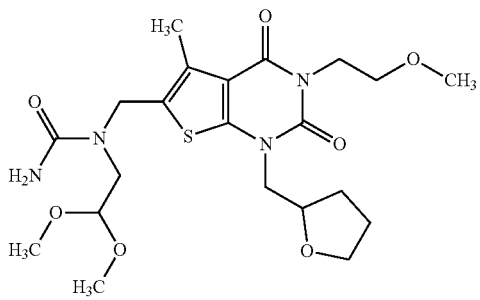 [SMILES: COCCn1c(=O)c2c(C)c(CN(CC(OC)OC)C(N)=O)sc2n(CC2CCCO2)c1=O]

To a solution of 735 mg (1.66 mmol) of the compound from Ex. 413A in 17 ml of methanol were added, at RT, first 311 mg (3.83 mmol) of potassium cyanate and then 244 µl (2.83 mmol) of perchloric acid (70% in water). After stirring at RT for 2.5 days, the same amounts of potassium cyanate and perchloric acid once again were added, and the stirring was continued for a further 3 days. Thereafter, the reaction mixture was admixed with saturated aqueous sodium hydrogencarbonate solution and then extracted with ethyl acetate. The organic extract was washed successively with water and saturated sodium chloride solution, dried over anhydrous magnesium sulphate, filtered and concentrated. After the residue obtained had been dried under high vacuum, 905 mg (97% of theory, 87% purity) of the title compound were obtained, which was used for subsequent reactions without further purification.

LC/MS (Method 1, ESIpos): $R_t$=0.72 min, m/z=485 [M+H]⁺.

Example 415A tert-Butyl 2-{[5-methyl-2,4-dioxo-3-(2,2,2-trifluoroethyl)-1-(3,3,3-trifluoropropyl)-1,2,3,4-tetrahydrothieno[2,3-d]pyrimidin-6-yl]methylene}hydrazinecarboxylate

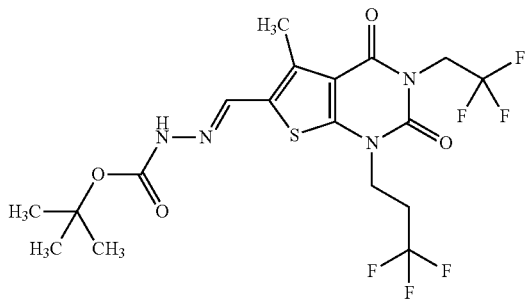 [SMILES: Cc1c(/C=N/NC(=O)OC(C)(C)C)sc2c1c(=O)n(CC(F)(F)F)c(=O)n2CCC(F)(F)F]

Analogously to the method described in Ex. 333A, 500 mg (1.29 mmol) of the compound from Ex. 120A and 255 mg (1.93 mmol) of tert-butyl hydrazinecarboxylate were used to obtain 603 mg (93% of theory) of the title compound.

¹H-NMR (400 MHz, DMSO-d₆, δ/ppm): 10.92 (broad, 1H), 8.31 (s, 1H), 4.70 (q, 2H), 4.19 (t, 2H), 2.93-2.71 (m, 2H), 2.46 (s, 3H), 1.46 (s, 9H).

LC/MS (Method 17, ESIneg): $R_t$=2.13 min, m/z=501.10 [M−H]⁻.

Example 416A tert-Butyl 2-{[1-(2-methoxyethyl)-5-methyl-2,4-dioxo-3-(2,2,2-trifluoroethyl)-1,2,3,4-tetrahydrothieno[2,3-d]pyrimidin-6-yl]methylene}hydrazinecarboxylate

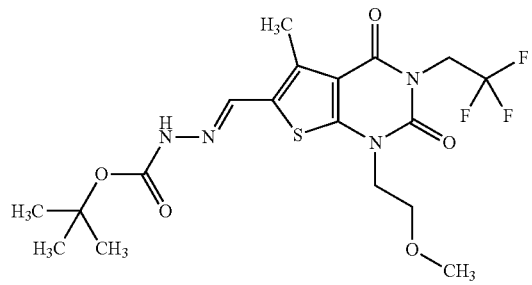 [SMILES: COCCn1c(=O)n(CC(F)(F)F)c(=O)c2c(C)c(/C=N/NC(=O)OC(C)(C)C)sc21]

Analogously to the method described in Ex. 333A, 600 mg (1.71 mmol) of the compound from Ex. 122A and 339 mg (2.57 mmol) of tert-butyl hydrazinecarboxylate were used to obtain 735 mg (92% of theory) of the title compound.

¹H-NMR (400 MHz, DMSO-d₆, δ/ppm): 10.89 (broad, 1H), 8.29 (s, 1H), 4.69 (q, 2H), 4.11 (t, 2H), 3.66 (t, 2H), 3.25 (s, 3H), 2.45 (s, 3H), 1.46 (s, 9H).

LC/MS (Method 1, ESIpos): $R_t$=1.11 min, m/z=465 [M+H]⁺.

Example 417A tert-Butyl 2-{[5-methyl-2,4-dioxo-1-(tetrahydrofuran-2-ylmethyl)-3-(2,2,2-trifluoroethyl)-1,2,3,4-tetrahydrothieno[2,3-d]pyrimidin-6-yl]methylene}hydrazinecarboxylate (racemate)

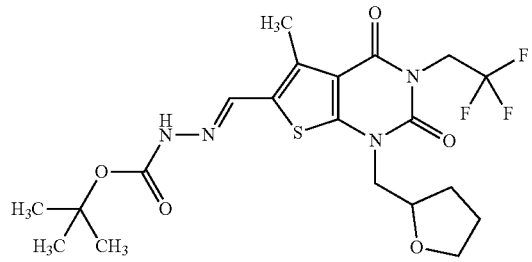 [SMILES: Cc1c(/C=N/NC(=O)OC(C)(C)C)sc2c1c(=O)n(CC(F)(F)F)c(=O)n2CC1CCCO1]

Analogously to the method described in Ex. 333A, 1.11 g (2.96 mmol) of the compound from Ex. 125A and 587 mg (4.44 mmol) of tert-butyl hydrazinecarboxylate were used to obtain 1.39 g (95% of theory) of the title compound.

¹H-NMR (400 MHz, DMSO-d₆, δ/ppm): 10.89 (broad, 1H), 8.30 (s, 1H), 4.70 (q, 2H), 4.29-4.17 (m, 1H), 4.12 (dd, 1H), 3.88-3.71 (m, 2H), 3.68-3.57 (m, 1H), 2.45 (s, 3H), 2.09-1.75 (m, 3H), 1.73-1.59 (m, 1H), 1.46 (s, 9H).

LC/MS (Method 17, ESIneg): $R_t$=2.08 min, m/z=489.14 [M−H]⁻.

Example 418A tert-Butyl 2-{[3-(2-methoxyethyl)-5-methyl-2,4-dioxo-1-(3,3,3-trifluoropropyl)-1,2,3,4-tetrahydrothieno[2,3-d]pyrimidin-6-yl]methylene}hydrazinecarboxylate

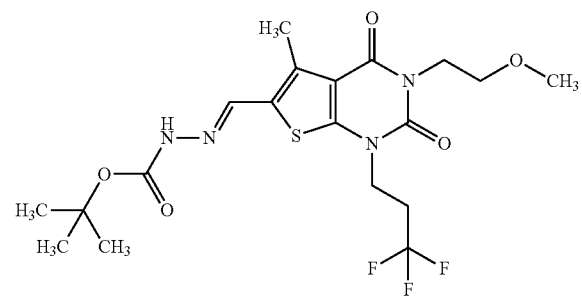 [SMILES: COCCn1c(=O)c2c(C)c(/C=N/NC(=O)OC(C)(C)C)sc2n(CCC(F)(F)F)c1=O]

Analogously to the method described in Ex. 333A, 600 mg (1.65 mmol) of the compound from Ex. 296A and 326 mg (2.47 mmol) of tert-butyl hydrazinecarboxylate were used to obtain 741 mg (94% of theory) of the title compound.

¹H-NMR (400 MHz, DMSO-$d_6$, δ/ppm): 10.88 (broad, 1H), 8.30 (s, 1H), 4.15 (t, 2H), 4.05 (t, 2H), 3.50 (t, 2H), 3.24 (s, 3H), 2.87-2.69 (m, 2H), 2.46 (s, 3H), 1.46 (s, 9H).

LC/MS (Method 1, ESIpos): $R_t$=1.11 min, m/z=479 [M+H]⁺.

Example 419A tert-Butyl 2-{[1,3-bis(2-methoxyethyl)-5-methyl-2,4-dioxo-1,2,3,4-tetrahydrothieno[2,3-d]pyrimidin-6-yl]methylene}hydrazinecarboxylate

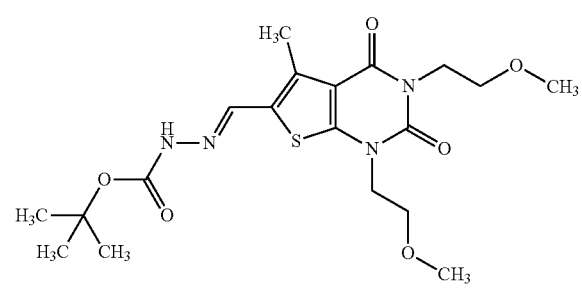 [SMILES: COCCn1c(=O)c2c(C)c(/C=N/NC(=O)OC(C)(C)C)sc2n(CCOC)c1=O]

Analogously to the method described in Ex. 333A, 600 mg (1.84 mmol) of the compound from Ex. 136A and 364 mg (2.76 mmol) of tert-butyl hydrazinecarboxylate were used to obtain 753 mg (92% of theory) of the title compound.

¹H-NMR (400 MHz, DMSO-$d_6$, δ/ppm): 10.86 (broad, 1H), 8.29 (s, 1H), 4.11-4.01 (m, 4H), 3.65 (t, 2H), 3.50 (t, 2H), 3.25 (s, 3H), 3.24 (s, 3H), 2.44 (s, 3H), 1.46 (s, 9H).

LC/MS (Method 1, ESIpos): $R_t$=0.99 min, m/z=441 [M+H]⁺.

Example 420A tert-Butyl 2-{[3-(2-methoxyethyl)-5-methyl-2,4-dioxo-1-(tetrahydrofuran-2-ylmethyl)-1,2,3,4-tetrahydrothieno[2,3-d]pyrimidin-6-yl]methylene}hydrazinecarboxylate (racemate)

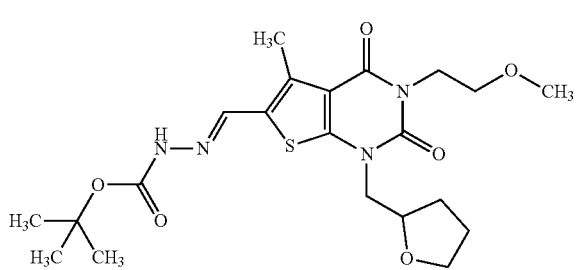 [SMILES: COCCn1c(=O)c2c(C)c(/C=N/NC(=O)OC(C)(C)C)sc2n(CC2CCCO2)c1=O]

Analogously to the method described in Ex. 333A, 1.11 g (3.12 mmol) of the compound from Ex. 298A and 619 mg (4.68 mmol) of tert-butyl hydrazinecarboxylate were used to obtain 1.34 g (92% of theory) of the title compound.

¹H-NMR (400 MHz, DMSO-$d_6$, δ/ppm): 10.86 (broad, 1H), 8.29 (s, 1H), 4.28-4.16 (m, 1H), 4.14-4.01 (m, 3H), 3.82-3.72 (m, 2H), 3.67-3.57 (m, 1H), 3.54-3.47 (m, 2H), 3.24 (s, 3H), 2.45 (s, 3H), 2.07-1.76 (m, 3H), 1.72-1.61 (m, 1H), 1.45 (s, 9H).

LC/MS (Method 17, ESIneg): $R_t$=1.86 min, m/z=465.18 [M−H]⁻.

Example 421A tert-Butyl 2-{[5-methyl-2,4-dioxo-3-(2,2,2-trifluoroethyl)-1-(3,3,3-trifluoropropyl)-1,2,3,4-tetrahydrothieno[2,3-d]pyrimidin-6-yl]methyl}hydrazinecarboxylate

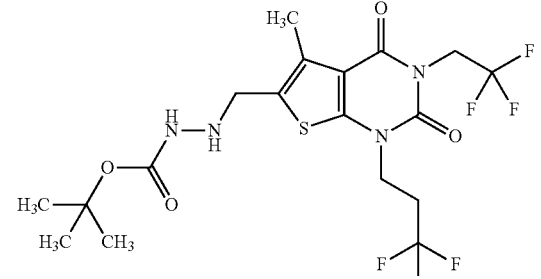

Analogously to the method described in Ex. 343A, 600 mg (1.19 mmol) of the compound from Ex. 415A and a total of 750 mg (11.9 mmol) of sodium cyanoborohydride were used to obtain 415 mg (68% of theory) of the title compound.

¹H-NMR (400 MHz, DMSO-$d_6$, δ/ppm): 8.27 (broad, 1H), 5.12 (broad, 1H), 4.70 (q, 2H), 4.17 (t, 2H), 4.00 (d, 2H), 2.87-2.69 (m, 2H), 2.33 (s, 3H), 1.38 (s, 9H).

LC/MS (Method 17, ESIpos): $R_t$=2.03 min, m/z=373.04 [M+H−$C_5H_{12}N_2O_2$]⁺.

Example 422A tert-Butyl 2-{[1-(2-methoxyethyl)-5-methyl-2,4-dioxo-3-(2,2,2-trifluoroethyl)-1,2,3,4-tetrahydrothieno[2,3-d]pyrimidin-6-yl]methyl}hydrazinecarboxylate

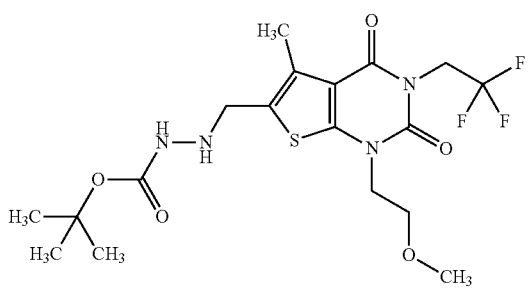 [SMILES: COCCn1c(=O)n(CC(F)(F)F)c(=O)c2c(C)c(CNNC(=O)OC(C)(C)C)sc21]

Analogously to the method described in Ex. 343A, 730 mg (1.57 mmol) of the compound from Ex. 416A and a total of 988 mg (15.7 mmol) of sodium cyanoborohydride were used to obtain 665 mg (90% of theory) of the title compound.

$^1$H-NMR (400 MHz, DMSO-$d_6$, δ/ppm): 8.27 (broad, 1H), 5.04 (broad, 1H), 4.70 (q, 2H), 4.07 (t, 2H), 3.98 (d, 2H), 3.66 (t, 2H), 3.25 (s, 3H), 2.32 (s, 3H), 1.38 (s, 9H).

LC/MS (Method 1, ESIpos): $R_t$=1.05 min, m/z=335 [M+H—$C_5H_{12}N_2O_2$]$^+$.

Example 423A tert-Butyl 2-{[5-methyl-2,4-dioxo-1-(tetrahydrofuran-2-ylmethyl)-3-(2,2,2-trifluoroethyl)-1,2,3,4-tetrahydrothieno[2,3-d]pyrimidin-6-yl]methyl}hydrazinecarboxylate (racemate)

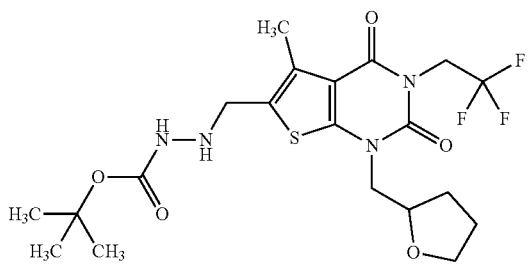 [SMILES: Cc1c(CNNC(=O)OC(C)(C)C)sc2c1c(=O)n(CC(F)(F)F)c(=O)n2CC1CCCO1]

Analogously to the method described in Ex. 343A, 1.39 g (2.83 mmol) of the compound from Ex. 417A and a total of 1.33 g (21.2 mmol) of sodium cyanoborohydride were used to obtain 1.27 g (91% of theory) of the title compound.

$^1$H-NMR (400 MHz, DMSO-$d_6$, δ/ppm): 8.27 (broad, 1H), 5.03 (broad, 1H), 4.71 (q, 2H), 4.36-4.20 (m, 1H), 4.09-3.89 (m, 3H), 3.85-3.72 (m, 2H), 3.68-3.56 (m, 1H), 2.32 (s, 3H), 2.07-1.76 (m, 3H), 1.74-1.61 (m, 1H), 1.38 (s, 9H).

LC/MS (Method 17, ESIneg): $R_t$=1.98 min, m/z=491.16 [M−H]$^-$.

Example 424A tert-Butyl 2-{[3-(2-methoxyethyl)-5-methyl-2,4-dioxo-1-(3,3,3-trifluoropropyl)-1,2,3,4-tetrahydrothieno[2,3-d]pyrimidin-6-yl]methyl}hydrazinecarboxylate

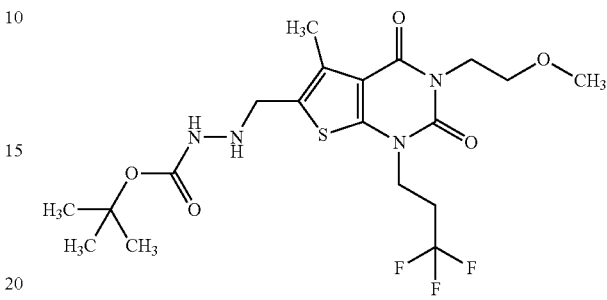

Analogously to the method described in Ex. 343A, 740 mg (1.55 mmol) of the compound from Ex. 418A and a total of 972 mg (15.5 mmol) of sodium cyanoborohydride were used to obtain 652 mg (87% of theory) of the title compound.

$^1$H-NMR (400 MHz, DMSO-$d_6$, δ/ppm): 8.26 (broad, 1H), 5.08 (broad, 1H), 4.13 (t, 2H), 4.06 (t, 2H), 3.99 (d, 2H), 3.49 (t, 2H), 3.31 (s, 3H), 2.86-2.68 (m, 2H), 2.33 (s, 3H), 1.39 (s, 9H).

LC/MS (Method 17, ESIneg): $R_t$=1.87 min, m/z=525.16 [M−H+HCOOH]$^-$.

Example 425A tert-Butyl 2-{[1,3-bis(2-methoxyethyl)-5-methyl-2,4-dioxo-1,2,3,4-tetrahydrothieno[2,3-d]pyrimidin-6-yl]methyl}hydrazinecarboxylate

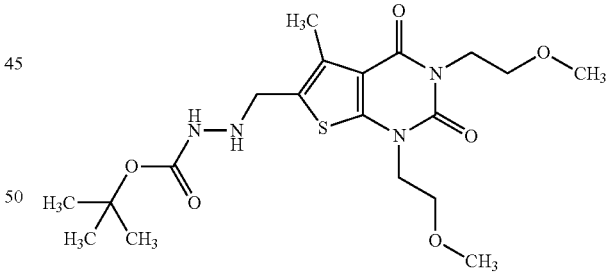

Analogously to the method described in Ex. 343A, 750 mg (1.70 mmol) of the compound from Ex. 419A and a total of 1.07 g (17.0 mmol) of sodium cyanoborohydride were used to obtain 571 mg (75% of theory) of the title compound. Instead of the MPLC purification, a first fraction of the title compound was obtained here by stirring the crude product with acetonitrile at RT. A second fraction of the product was isolated by preparative HPLC (Method 8) of the mother liquor.

$^1$H-NMR (400 MHz, DMSO-$d_6$, δ/ppm): 8.25 (broad, 1H), 4.99 (broad, 1H), 4.06 (t, 2H), 4.03 (t, 2H), 3.97 (d, 2H), 3.64 (t, 2H), 3.49 (t, 2H), 3.26 (s, 3H), 3.24 (s, 3H), 2.32 (s, 3H), 1.39 (s, 9H).

LC/MS (Method 1, ESIpos): R$_t$=0.85 min, m/z=443 [M+H]$^+$.

Example 426A tert-Butyl 2-{[3-(2-methoxyethyl)-5-methyl-2,4-dioxo-1-(tetrahydrofuran-2-ylmethyl)-1,2,3,4-tetrahydrothieno[2,3-d]pyrimidin-6-yl]methyl}hydrazinecarboxylate (racemate)

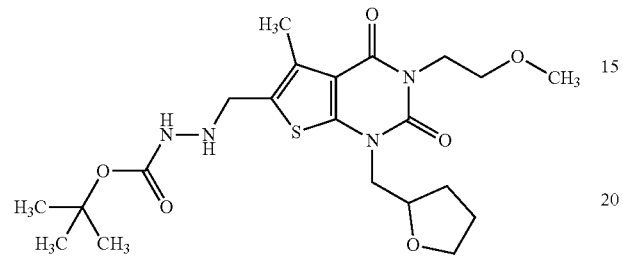

Analogously to the method described in Ex. 343A, 1.05 g (2.24 mmol) of the compound from Ex. 420A and a total of 1.06 g (16.8 mmol) of sodium cyanoborohydride were used to obtain 750 mg (71% of theory) of the title compound.

$^1$H-NMR (400 MHz, DMSO-d$_6$, δ/ppm): 8.26 (broad, 1H), 4.98 (broad, 1H), 4.31-4.20 (m, 1H), 4.10-3.93 (m, 5H), 3.83-3.69 (m, 2H), 3.66-3.57 (m, 1H), 3.50 (t, 2H), 3.24 (s, 3H), 2.32 (s, 3H), 2.05-1.75 (m, 3H), 1.73-1.61 (m, 1H), 1.39 (s, 9H).

LC/MS (Method 2, ESIpos): R$_t$=2.70 min, m/z=469 [M+H]$^+$.

Example 427A tert-Butyl 2-(3-ethoxyprop-2-enoyl)-2-{[5-methyl-2,4-dioxo-3-(2,2,2-trifluoroethyl)-1-(3,3,3-trifluoropropyl)-1,2,3,4-tetrahydrothieno[2,3-d]pyrimidin-6-yl]methyl}hydrazinecarboxylate

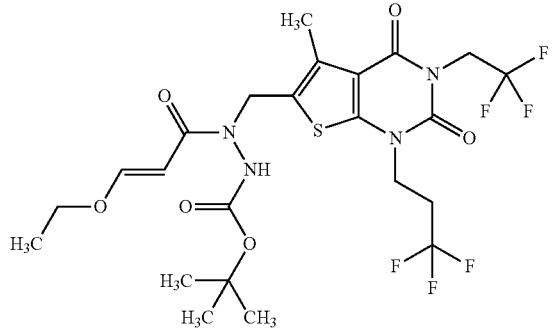 [SMILES: CCO/C=C/C(=O)N(Cc1sc2c(c1C)c(=O)n(CC(F)(F)F)c(=O)n2CCC(F)(F)F)NC(=O)OC(C)(C)C]

Analogously to the method described in Ex. 348A, 400 mg (0.793 mmol) of the compound from Ex. 421A and 151 mg (0.952 mmol, content 85%) of 3-ethoxyacryloyl chloride were used to obtain 381 mg (79% of theory) of the title compound.

$^1$H-NMR (400 MHz, DMSO-d$_6$, δ/ppm): 9.50 (broad, 1H), 7.51 (d, 1H), 5.57 (d, 1H), 4.91 (broad, 1H), 4.72 (q, 2H), 4.52 (broad, 1H), 4.16 (t, 2H), 4.04-3.80 (m, 2H), 2.86-2.66 (m, 2H), 2.37 (s, 3H), 1.38 (s, 9H), 1.23 (t, 3H).

LC/MS (Method 17, ESIneg): R$_t$=2.16 min, m/z=601.16 [M−H]$^-$.

Example 428A tert-Butyl 2-(3-ethoxyprop-2-enoyl)-2-{[1-(2-methoxyethyl)-5-methyl-2,4-dioxo-3-(2,2,2-trifluoroethyl)-1,2,3,4-tetrahydrothieno[2,3-d]pyrimidin-6-yl]methyl}hydrazinecarboxylate

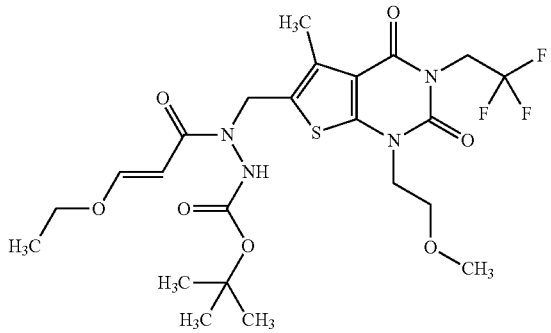 [SMILES: CCO/C=C/C(=O)N(Cc1sc2c(c1C)c(=O)n(CC(F)(F)F)c(=O)n2CCOC)NC(=O)OC(C)(C)C]

Analogously to the method described in Ex. 348A, 396 mg (0.849 mmol) of the compound from Ex. 422A and 161 mg (1.02 mmol, content 85%) of 3-ethoxyacryloyl chloride were used to obtain 377 mg (78% of theory) of the title compound.

$^1$H-NMR (400 MHz, DMSO-d$_6$, δ/ppm): 9.49 (broad, 1H), 7.50 (d, 1H), 5.57 (d, 1H), 5.02-4.80 (m, 1H), 4.71 (q, 3H), 4.60-4.38 (m, 1H), 4.06 (t, 2H), 3.98-3.85 (m, 2H), 3.64 (t, 2H), 3.23 (s, 3H), 2.36 (s, 3H), 1.38 (s, 9H), 1.23 (t, 3H).

LC/MS (Method 17, ESIneg): R$_t$=2.01 min, m/z=563.18 [M−H]$^-$.

Example 429A tert-Butyl 2-(3-ethoxyprop-2-enoyl)-2-{[5-methyl-2,4-dioxo-1-(tetrahydrofuran-2-ylmethyl)-3-(2,2,2-trifluoroethyl)-1,2,3,4-tetrahydrothieno[2,3-d]pyrimidin-6-yl]methyl}hydrazinecarboxylate (racemate)

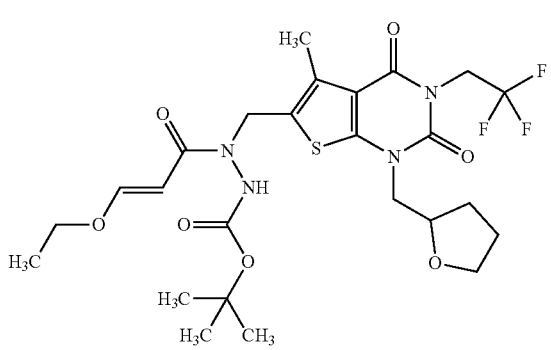 [SMILES: CCO/C=C/C(=O)N(Cc1sc2c(c1C)c(=O)n(CC(F)(F)F)c(=O)n2CC1CCCO1)NC(=O)OC(C)(C)C]

Analogously to the method described in Ex. 348A, 600 mg (1.22 mmol) of the compound from Ex. 423A and 231 mg (1.46 mmol, content 85%) of 3-ethoxyacryloyl chloride were used to obtain 700 mg (97% of theory) of the title compound.

¹H-NMR (400 MHz, DMSO-d₆, δ/ppm): 9.49 (broad, 1H), 7.50 (d, 1H), 5.57 (d, 1H), 5.07-4.79 (m, 1H), 4.72 (q, 2H), 4.62-4.33 (m, 1H), 4.27-4.20 (m, 1H), 4.10-3.85 (m, 3H), 3.83-3.68 (m, 2H), 3.66-3.53 (m, 1H), 2.36 (s, 3H), 2.04-1.74 (m, 3H), 1.73-1.60 (m, 1H), 1.38 (s, 9H), 1.23 (t, 3H).

LC/MS (Method 17, ESIneg): R$_t$=2.10 min, m/z=589.19 [M−H]⁻.

Example 430A tert-Butyl 2-(3-ethoxyprop-2-enoyl)-2-{[3-(2-methoxyethyl)-5-methyl-2,4-dioxo-1-(3,3,3-trifluoropropyl)-1,2,3,4-tetrahydrothieno[2,3-d]pyrimidin-6-yl]methyl}hydrazinecarboxylate

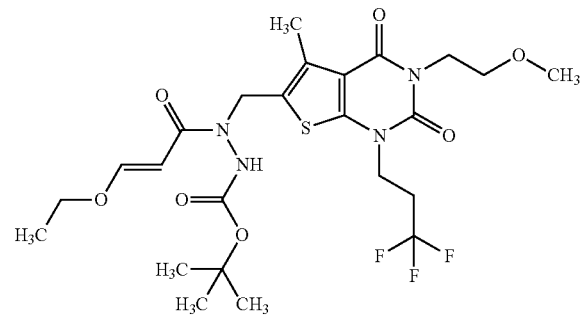 [SMILES: CCO/C=C/C(=O)N(Cc1sc2c(c1C)c(=O)n(CCOC)c(=O)n2CCC(F)(F)F)NC(=O)OC(C)(C)C]

Analogously to the method described in Ex. 348A, 300 mg (0.624 mmol) of the compound from Ex. 424A and 119 mg (0.749 mmol, content 85%) of 3-ethoxyacryloyl chloride were used to obtain 277 mg (76% of theory) of the title compound.

¹H-NMR (400 MHz, DMSO-d₆, δ/ppm): 9.49 (broad, 1H), 7.50 (d, 1H), 5.57 (d, 1H), 4.94 (broad, 1H), 4.48 (broad, 1H), 4.12 (t, 2H), 4.06 (t, 2H), 3.93 (broad, 2H), 3.49 (t, 2H), 3.23 (s, 3H), 2.87-2.64 (m, 2H), 2.37 (s, 3H), 1.39 (s, 9H), 1.23 (t, 3H).

LC/MS (Method 17, ESIneg): R$_t$=1.99 min, m/z=577.19 [M−H]⁻.

Example 431A tert-Butyl 2-{[1,3-bis(2-methoxyethyl)-5-methyl-2,4-dioxo-1,2,3,4-tetrahydrothieno[2,3-d]pyrimidin-6-yl]methyl}-2-(3-ethoxyprop-2-enoyl)hydrazinecarboxylate

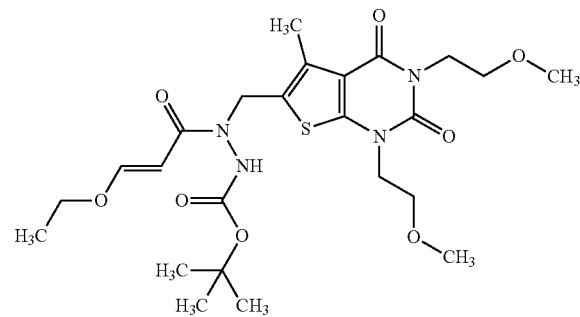 [SMILES: CCO/C=C/C(=O)N(Cc1sc2c(c1C)c(=O)n(CCOC)c(=O)n2CCOC)NC(=O)OC(C)(C)C]

Analogously to the method described in Ex. 348A, 300 mg (0.678 mmol) of the compound from Ex. 425A and 129 mg (0.813 mmol, content 85%) of 3-ethoxyacryloyl chloride were used to obtain 292 mg (79% of theory) of the title compound.

¹H-NMR (400 MHz, DMSO-d₆, δ/ppm): 9.49 (broad, 1H), 7.50 (d, 1H), 5.57 (d, 1H), 4.93 (broad, 1H), 4.45 (broad, 1H), 4.06 (t, 2H), 4.02 (t, 2H), 3.92 (m, 2H), 3.63 (t, 2H), 3.49 (t, 2H), 3.23 (s, 6H), 2.35 (s, 3H), 1.39 (s, 9H), 1.23 (t, 3H).

LC/MS (Method 17, ESIpos): R$_t$=1.78 min, m/z=541.23 [M+H]⁺.

Example 432A tert-Butyl 2-(3-ethoxyprop-2-enoyl)-2-{[3-(2-methoxyethyl)-5-methyl-2,4-dioxo-1-(tetrahydrofuran-2-ylmethyl)-1,2,3,4-tetrahydrothieno[2,3-d]pyrimidin-6-yl]methyl}hydrazinecarboxylate (racemate)

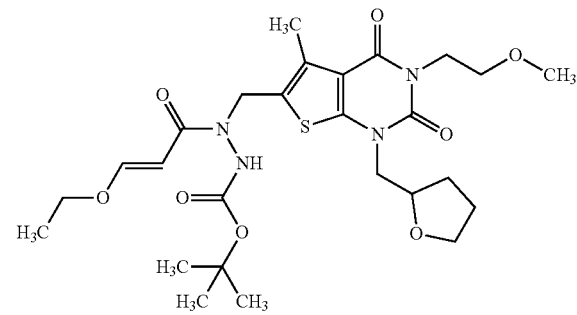 [SMILES: CCO/C=C/C(=O)N(Cc1sc2c(c1C)c(=O)n(CCOC)c(=O)n2CC1CCCO1)NC(=O)OC(C)(C)C]

Analogously to the method described in Ex. 348A, 600 mg (1.28 mmol) of the compound from Ex. 426A and 243 mg (1.54 mmol, content 85%) of 3-ethoxyacryloyl chloride were used to obtain 450 mg (62% of theory) of the title compound.

¹H-NMR (500 MHz, DMSO-d₆, δ/ppm): 9.49 (broad, 1H), 7.49 (d, 1H), 5.57 (d, 1H), 5.08-4.84 (m, 1H), 4.54-4.31 (m, 1H), 4.28-4.17 (m, 1H), 4.07 (t, 2H), 4.04-3.97 (m, 1H), 3.93 (d, 2H), 3.82-3.69 (m, 2H), 3.61 (q, 1H), 3.49 (t, 2H), 3.23 (s, 3H), 2.35 (s, 3H), 2.04-1.75 (m, 3H), 1.72-1.60 (m, 1H), 1.39 (s, 9H), 1.23 (t, 3H).

LC/MS (Method 1, ESIpos): R$_t$=0.99 min, m/z=567 [M+H]⁺.

Example 433A tert-Butyl 3-(2,4-dimethoxybenzyl)-5-methyl-2,4-dioxo-1-(3,3,3-trifluoropropyl)-1,2,3,4-tetrahydrothieno[2,3-d]pyrimidine-6-carboxylate

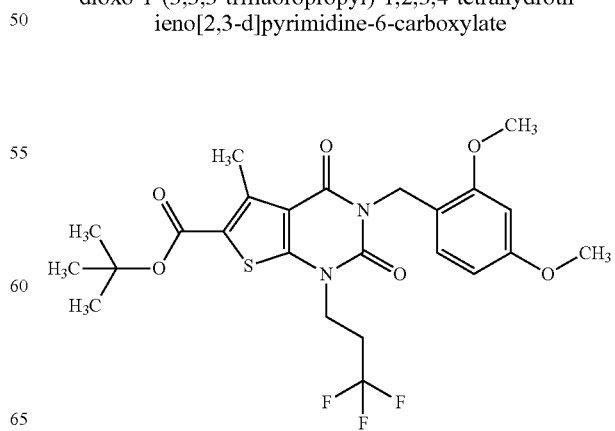

1.71 g (5.25 mmol) of caesium carbonate were added to a solution of 3.18 g (7.35 mmol) of the compound from Ex. 8A in 70 ml of DMF, and the mixture was stirred at RT for 15 min. Then 1.65 g (7.35 mmol) of 1,1,1-trifluoro-3-iodopropane were added and the mixture was stirred at 70° C. for a total of 11 h, with addition of 1.65 g (7.35 mmol) of 1,1,1-trifluoro-3-iodopropane once again after 6 h of reaction time. After cooling to RT, water was added, and then the product precipitated out. After briefly stirring, the product was filtered off with suction, washed with water and dried under high vacuum. The product thus obtained was purified by stirring with pentane/dichloromethane at RT. 3.56 g (91% of theory) of the title compound were obtained.

$^1$H-NMR (400 MHz, DMSO-d$_6$, δ/ppm): 6.75 (d, 1H), 6.57 (d, 1H), 6.39 (dd, 1H), 4.95 (s, 2H), 4.17 (t, 2H), 3.81 (s, 3H), 3.72 (s, 3H), 2.95-2.62 (m, 2H), 2.74 (s, 3H), 1.54 (s, 9H).

LC/MS (Method 1, ESIpos): R$_t$=1.40 min, m/z=529 [M+H]$^+$.

Example 434A

Ethyl 3-ethyl-1-(2-methoxyethyl)-5-methyl-2,4-dioxo-1,2,3,4-tetrahydrothieno[2,3-d]pyrimidine-6-carboxylate

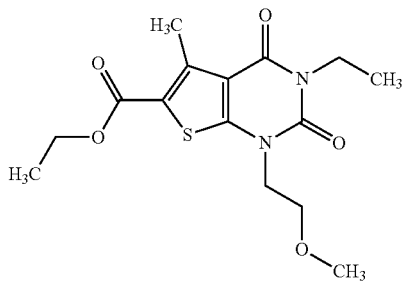 [SMILES: CCOC(=O)c1sc2c(c1C)c(=O)n(CC)c(=O)n2CCOC]

1.73 g (5.31 mmol) of caesium carbonate were added to a solution of 1.0 g (3.54 mmol) of the compound from Ex. 9A in 10 ml of DMF, and the mixture was stirred at RT for 10 min. Then 739 mg (5.31 mmol) of 2-bromoethyl methyl ether were added, and the mixture was stirred in a microwave oven (Biotage Initiator with dynamic control of irradiation power) at 100° C. for 2 h. After cooling to RT, the mixture was diluted with ethyl acetate and admixed with water. The precipitated product was filtered off with suction and dried. The organic phase of the filtrate was removed and the aqueous phase was extracted three times more with ethyl acetate. The combined organic phases were washed with saturated aqueous sodium chloride solution, dried over anhydrous magnesium sulphate, filtered and concentrated. The residue was combined with the product filtered off with suction at the start and then purified by means of MPLC (Isolera, Biotage SNAP-KP-Sil cartridge with 100 g of silica gel, cyclohexane/ethyl acetate 92:8→33:66). The product fractions were combined, concentrated and dried under high vacuum. 953 mg (78% of theory) of the title compound were obtained.

$^1$H-NMR (400 MHz, DMSO-d$_6$, δ/ppm): 4.28 (q, 2H), 4.09 (t, 2H), 3.91 (q, 2H), 3.65 (t, 2H), 3.24 (s, 3H), 2.77 (s, 3H), 1.30 (t, 3H), 1.13 (t, 3H).

LC/MS (Method 17, ESIpos): R$_t$=1.99 min, m/z=341.12 [M+H]$^+$.

Example 435A

5-Methyl-2,4-dioxo-1-(3,3,3-trifluoropropyl)-1,2,3,4-tetrahydrothieno[2,3-d]pyrimidine-6-carboxylic acid

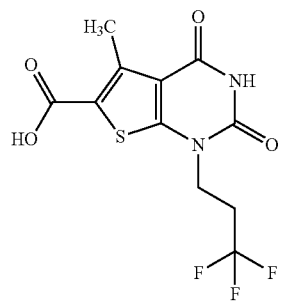 [SMILES: Cc1c(C(=O)O)sc2c1c(=O)[nH]c(=O)n2CCC(F)(F)F]

5.46 g (10.3 mmol) of the compound from Ex. 433A were dissolved in 200 ml of toluene, and 8.27 g (62.0 mmol) of solid aluminium trichloride were added. The reaction mixture was then stirred at 50° C. for 90 min. After cooling to RT, 120 ml of water and about 180 ml of ethyl acetate were added successively. After phase separation, the organic phase was washed successively with water and saturated aqueous sodium chloride solution. It was dried over anhydrous magnesium sulphate. After filtration, the mixture was concentrated to dryness. The remaining residue was stirred with 100 ml of pentane/dichloromethane (20:1) at RT. Filtration and drying of the solids under high vacuum gave 2.98 g (83% of theory, 93% purity) of the title compound.

$^1$H-NMR (400 MHz, DMSO-d$_6$, δ/ppm): 13.41 (br. s, 1H), 11.63 (s, 1H), 4.09 (t, 2H), 2.91-2.61 (m, 2H), 2.72 (s, 3H).

LC/MS (Method 1, ESIpos): R$_t$=0.65 min, m/z=323 [M+H]$^+$.

Example 436A

2-Methoxypropyl 3-(2-methoxypropyl)-5-methyl-2,4-dioxo-1-(3,3,3-trifluoropropyl)-1,2,3,4-tetrahydrothieno[2,3-d]pyrimidine-6-carboxylate (stereoisomer mixture)

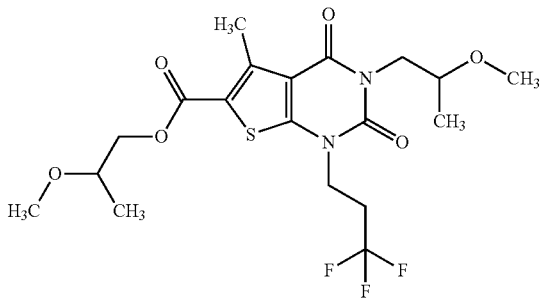

To a solution of 510 mg (1.38 mmol) of the compound from Ex. 435A in 15 ml of DMF were added 1.35 g (4.13 mmol) of caesium carbonate, and the mixture was stirred at RT for 10 min. Then 665 mg (4.13 mmol) of racemic 1-bromo-2-methoxypropane were added, and the mixture was stirred at 80° C. for 66 h. The DMF was then very substantially distilled out of the reaction mixture. The remaining residue was partitioned between water (75 ml) and dichloromethane (75 ml). The aqueous phase was extracted with dichloromethane. The combined organic phases were dried over sodium sulphate, filtered and concentrated. The residue obtained was chromatographed on silica gel (hexane/ethyl acetate eluent). 483 mg (71% of theory) of the title compound were obtained.

$^1$H-NMR (400 MHz, DMSO-$d_6$, δ/ppm): 4.31 (dd, 1H), 4.24-4.11 (m, 3H), 4.09-4.01 (m, 1H), 3.76 (dd, 1H), 3.68-3.58 (m, 2H), 3.31-3.27 (m, 3H), 3.21 (s, 3H), 2.87-2.72 (m, 5H), 1.15 (d, 3H), 1.06 (d, 3H).

LC/MS (Method 3): $R_t$=1.34 min, m/z=467 [M+H]$^+$.

Example 437A

Ethyl 4-methyl-2-{[(1,1,1-trifluoropropan-2-yl)carbamoyl]amino}thiophene-3-carboxylate (racemate)

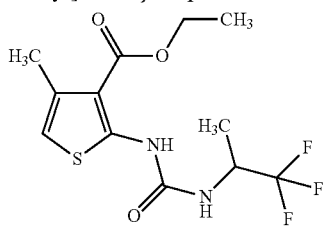

To a solution of 7.0 g (37.8 mmol) of ethyl 2-amino-4-methylthiophene-3-carboxylate in 200 ml of dichloromethane were added 12.3 g (75.6 mmol) of 1,1'-carbonyldiimidazole (CDI) and 16 ml (113 mmol) of triethylamine, and the mixture was stirred at RT for 2 days. Then 8.55 g (75.6 mmol) of racemic 2-amino-1,1,1-trifluoropropane were added to the mixture and the mixture was stirred at RT for a further 2 days. This was followed by extraction by shaking successively with 300 ml each of water and saturated aqueous sodium chloride solution. Drying over anhydrous magnesium sulphate and filtration were followed by concentration to dryness and purification of the remaining residue by means of MPLC (Isolera, Biotage cartridge with 340 g of silica gel, cyclohexane/ethyl acetate 5:1). This gave, after concentration of the product fractions and drying under high vacuum, 9.21 g (75% of theory) of the title compound.

$^1$H-NMR (500 MHz, DMSO-$d_6$, δ/ppm): 10.46 (s, 1H), 8.50 (d, 1H), 6.50 (s, 1H), 4.49 (dq, 1H), 4.30 (q, 2H), 2.28 (d, 3H), 1.32 (t, 3H), 1.28 (d, 3H).

LC/MS (Method 1, ESIpos): $R_t$=1.13 min, m/z=325 [M+H]$^+$.

Example 438A

Ethyl 2-{[(2-methoxypropyl)carbamoyl]amino}-4-methylthiophene-3-carboxylate

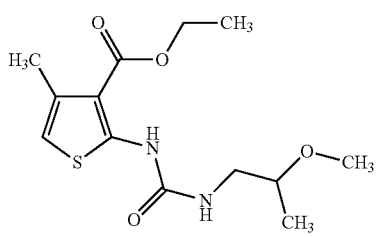

To a solution of 7.6 g (39.8 mmol, 97% purity) of ethyl 2-amino-4-methylthiophene-3-carboxylate in 150 ml of dichloromethane were added 12.9 g (79.6 mmol) of 1,1'-carbonyldiimidazole (CDI) and 22 ml (159 mmol) of triethylamine, and the mixture was stirred at RT for 2 days. Then 10 g (79.6 mmol) of racemic 1-amino-2-methoxypropane hydrochloride were added to the mixture and the mixture was stirred at RT for 1 h. This was followed by extraction by shaking successively with 80 ml each of water (twice) and saturated aqueous sodium chloride solution. Drying over anhydrous magnesium sulphate and filtration were followed by concentration to dryness and purification of the remaining residue by means of MPLC (Isolera, Biotage cartridge with 340 g of silica gel, cyclohexane/ethyl acetate 90:10→20:80). After concentration of the product fractions and drying under high vacuum, 11.3 g (94% of theory) of the title compound were obtained.

$^1$H-NMR (400 MHz, DMSO-$d_6$, δ/ppm): 10.32 (s, 1H), 7.95 (br. s, 1H), 6.42 (s, 1H), 4.28 (q, 2H), 3.41-3.33 (m, 1H), 3.31 (s, 3H), 3.22-3.05 (m, 2H), 2.26 (s, 3H), 1.31 (t, 3H), 1.06 (d, 3H).

LC/MS (Method 17, ESIpos): $R_t$=1.80 min, m/z=301.12 [M+H]$^+$.

Example 439A

5-Methyl-3-(1,1,1-trifluoropropan-2-yl)thieno[2,3-d]pyrimidine-2,4(1H,3H)-dione (racemate)

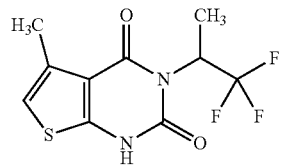 [SMILES: Cc1csc2[nH]c(=O)n(C(C)C(F)(F)F)c(=O)c12]

Analogously to the method described in Ex. 44A, 9.15 g (28.2 mmol) of the compound from Ex. 437A were used to prepare 7.39 g (94% of theory) of the title compound. The conversion was effected here at 50° C., and the reaction time was 5 h.

$^1$H-NMR (400 MHz, DMSO-$d_6$, δ/ppm): 12.67-12.01 (m, 1H), 6.74 (d, 1H), 5.81-5.42 (m, 1H), 2.34 (d, 3H), 1.73-1.57 (m, 3H).

LC/MS (Method 17, ESIpos): $R_t$=1.61 min, m/z=279.04 [M+H]$^+$.

Example 440A 3-(2-Methoxypropyl)-5-methylthieno[2,3-d]pyrimidine-2,4(1H,3H)-dione (racemate)

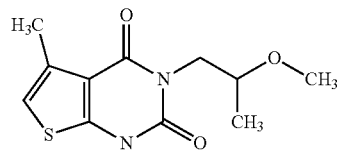

11.2 g (37.3 mmol) of the compound from Ex. 438A were dissolved in 350 ml of ethanol, and 20.9 ml (55.9 mmol) of a 21% solution of sodium ethoxide in ethanol were added.

After the mixture had been stirred at RT for 4 h, 74.6 ml (74.6 mmol) of 1 M hydrochloric acid were added at RT. The solid that precipitated out was filtered off with suction, washed to neutrality with water and dried under high vacuum. This gave a first fraction of the title compound (6.1 g). Further product precipitated out of the mother liquor overnight, which was likewise filtered off with suction, washed and dried (fraction 2, 1.7 g). The two fractions were combined. Thus, a total of 7.8 g (82% of theory) of the title compound was obtained.

$^1$H-NMR (400 MHz, DMSO-d$_6$, δ/ppm): 12.11 (s, 1H), 6.69 (d, 1H), 4.01 (dd, 1H), 3.77-3.59 (m, 2H), 3.22 (s, 3H), 2.35 (d, 3H), 1.05 (d, 3H).

LC/MS (Method 17, ESIpos): R$_t$=1.18 min, m/z=255.08 [M+H]$^+$.

Example 441A

5-Methyl-2,4-dioxo-3-(1,1,1-trifluoropropan-2-yl)-1,2,3,4-tetrahydrothieno[2,3-d]pyrimidine-6-carbaldehyde (racemate)

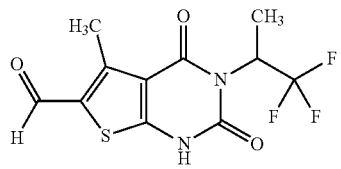 [SMILES: Cc1c(C=O)sc2[nH]c(=O)n(C(C)C(F)(F)F)c(=O)c12]

Analogously to the method described in Ex. 50A, 7.38 g (26.5 mmol) of the compound from Ex. 439A, 20 ml (265 mmol) of DMF and 30 ml (318 mmol) of phosphorus oxychloride were used to prepare 7.60 g (93% of theory) of the title compound.

$^1$H-NMR (400 MHz, DMSO-d$_6$, δ/ppm): 12.79 (br. s, 1H), 10.08 (s, 1H), 5.80-5.37 (m, 1H), 2.82-2.67 (m, 3H), 1.76-1.55 (m, 3H).

LC/MS (Method 17, ESIpos): R$_t$=1.55 min, m/z=307.04 [M+H]$^+$.

Example 442A 3-(2-Methoxypropyl)-5-methyl-2,4-dioxo-1,2,3,4-tetrahydrothieno[2,3-d]pyrimidine-6-carbaldehyde (racemate)

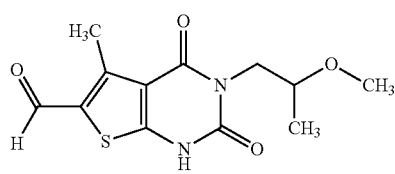 [SMILES: COC(C)Cn1c(=O)[nH]c2sc(C=O)c(C)c2c1=O]

7.82 g (30.7 mmol) of the compound from Example 440A were dissolved in 236 ml (3075 mmol) of DMF, and 28.7 ml (307 mmol) of phosphorus oxychloride were added gradually at 0° C. The reaction mixture was then stirred at 70° C. for 1 h. After cooling to RT, 1500 ml of water were added. The product precipitated out, and the heterogeneous mixture was stirred at RT overnight. Then the product was filtered off with suction, washed with water and dried under high vacuum. 7.75 g (89% of theory) of the title compound were obtained.

$^1$H-NMR (400 MHz, DMSO-d$_6$, δ/ppm): 12.60 (br. s, 1H), 10.07 (s, 1H), 4.00 (dd, 1H), 3.75-3.68 (m, 1H), 3.63 (sext, 1H), 3.22 (s, 3H), 2.76 (s, 3H), 1.07 (d, 3H).

LC/MS (Method 1, ESIpos): R$_t$=0.65 min, m/z=283 [M+H]$^+$.

Example 443A 3-(2,2-Dimethylpropyl)-5-methyl-2,4-dioxo-1-(tetrahydrofuran-2-ylmethyl)-1,2,3,4-tetrahydrothieno[2,3-d]pyrimidine-6-carbaldehyde (racemate)

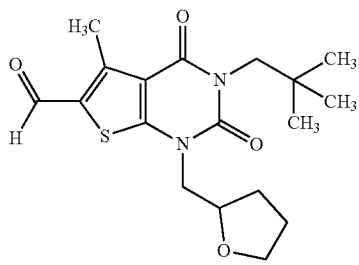 [SMILES: Cc1c(C=O)sc2c1c(=O)n(CC(C)(C)C)c(=O)n2CC1CCCO1]

3.08 g (22.3 mmol) of potassium carbonate were added to a solution of 2.5 g (8.92 mmol) of the compound from Ex. 286A in 80 ml of DMF, and the mixture was stirred at RT for 15 min. Then 2 ml (17.8 mmol) of 2-(bromomethyl)tetrahydrofuran were added, and the mixture was first stirred at 50° C. for 18 h. After this time, another 1 ml (8.92 mmol) of 2-(bromomethyl)tetrahydrofuran was added and the stirring was continued at 50° C. for two days. Then water was added to the reaction mixture at RT, and then the product precipitated out. The product was filtered off with suction, washed with water and dried under high vacuum. 2.96 g (91% of theory) of the title compound were obtained.

$^1$H-NMR (400 MHz, DMSO-d$_6$, δ/ppm): 10.09 (s, 1H), 4.26-4.20 (m, 1H), 4.11 (dd, 1H), 3.88-3.69 (m, 2H), 3.82 (s, 2H), 3.67-3.57 (m, 1H), 2.77 (s, 3H), 2.07-1.75 (m, 3H), 1.74-1.61 (m, 1H), 0.90 (s, 9H).

LC/MS (Method 17, ESIpos): R$_t$=2.16 min, m/z=365.15 [M+H]$^+$.

Example 444A

5-Methyl-2,4-dioxo-3-(1,1,1-trifluoropropan-2-yl)-1-(3,3,3-trifluoropropyl)-1,2,3,4-tetrahydrothieno[2,3-d]pyrimidine-6-carbaldehyde (racemate)

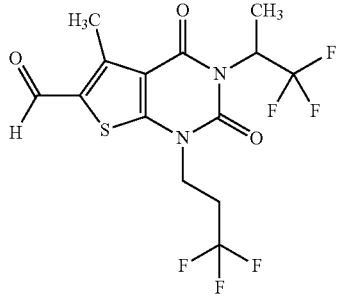 [SMILES: Cc1c(C=O)sc2c1c(=O)n(C(C)C(F)(F)F)c(=O)n2CCC(F)(F)F]

2.26 g (16.3 mmol) of potassium carbonate were added to a solution of 2.0 g (6.53 mmol) of the compound from Ex.

441A in 40 ml of DMF, and the mixture was stirred at RT for 15 min. Then 4.39 g (19.6 mmol) of 1,1,1-trifluoro-3-iodopropane were added, and the mixture was stirred at 50° C. for about 18 h. After cooling to RT, about 200 ml of water were added and the product was extracted with ethyl acetate. The organic extract was washed with saturated aqueous sodium chloride solution, dried over anhydrous magnesium sulphate, filtered and concentrated. The remaining residue was purified by MPLC (Isolera, Biotage cartridge with 340 g of silica gel, cyclohexane/ethyl acetate 5:1). The product fractions were combined, concentrated by evaporation and dried under high vacuum. In this way, 2.25 g (85% of theory) of the title compound were obtained.

$^1$H-NMR (400 MHz, DMSO-$d_6$, δ/ppm): 10.12 (s, 1H), 5.87-5.40 (m, 1H), 4.29-4.07 (m, 2H), 2.91-2.72 (m, 2H), 2.79 (s, 3H), 1.78-1.55 (m, 3H).

LC/MS (Method 1, ESIpos): $R_t$=1.10 min, m/z=403 [M+H]$^+$.

Example 445A 1-(2-Methoxyethyl)-5-methyl-2,4-dioxo-3-(1,1,1-trifluoropropan-2-yl)-1,2,3,4-tetrahydrothieno[2,3-d]pyrimidine-6-carbaldehyde (racemate)

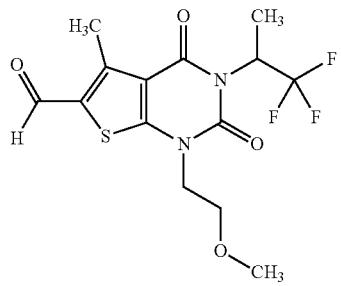 [SMILES: COCCn1c(=O)n(C(C)C(F)(F)F)c(=O)c2c(C)c(C=O)sc21]

2.82 g (20.4 mmol) of potassium carbonate were added to a solution of 2.5 g (8.16 mmol) of the compound from Ex. 441A in 50 ml of DMF, and the mixture was stirred at RT for 15 min. Then 2.27 g (16.3 mmol) of 2-bromoethyl methyl ether were added, and the mixture was stirred at 50° C. After about 18 h, a further 1.13 g (8.16 mmol) of 2-bromoethyl methyl ether were added and the stirring was continued at 50° C. for 2 days. After cooling to RT, about 250 ml of water were added and the product was extracted with ethyl acetate. The organic extract was washed with saturated aqueous sodium chloride solution, dried over anhydrous magnesium sulphate, filtered and concentrated. The remaining residue was purified by MPLC (Isolera, Biotage cartridge with 100 g of silica gel, cyclohexane/ethyl acetate 5:1). The product fractions were combined, concentrated by evaporation and dried under high vacuum. 1.46 g (48% of theory) of the title compound were obtained.

$^1$H-NMR (400 MHz, DMSO-$d_6$, δ/ppm): 10.10 (s, 1H), 5.84-5.42 (m, 1H), 4.14-4.08 (m, 2H), 3.69-3.62 (m, 2H), 3.25 (s, 3H), 2.78 (s, 3H), 1.77-1.58 (m, 3H).

LC/MS (Method 17, ESIpos): $R_t$=1.84 min, m/z=365.08 [M+H]$^+$.

Example 446A 3-(2-Ethoxyethyl)-1-(3-fluoropropyl)-5-methyl-2,4-dioxo-1,2,3,4-tetrahydrothieno[2,3-d]pyrimidine-6-carbaldehyde

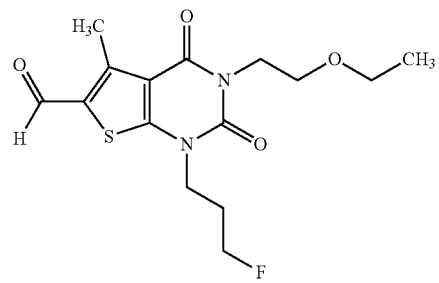 [SMILES: CCOCCn1c(=O)c2c(C)c(C=O)sc2n(CCCF)c1=O]

1.1 g (7.97 mmol) of potassium carbonate were added to a solution of 900 mg (3.19 mmol) of the compound from Ex. 371A in 29 ml of DMF, and the mixture was stirred at RT for 15 min. Then 1.79 g (9.56 mmol) of 1-fluoro-3-iodopropane were added, and the mixture was stirred at 50° C. for 18 h. The DMF was then very substantially distilled off and the remaining residue was partitioned between semisaturated sodium chloride solution (100 ml) and ethyl acetate (50 ml). The aqueous phase was extracted with ethyl acetate. The combined organic phases were dried over sodium sulphate, filtered and concentrated. 977 mg (87% of theory) of the title compound were obtained.

$^1$H-NMR (400 MHz, DMSO-$d_6$, δ/ppm): 10.10 (s, 1H), 4.60 (t, 1H), 4.48 (t, 1H), 4.04 (td, 4H), 3.52 (t, 2H), 3.45 (q, 2H), 2.78 (s, 3H), 2.15-2.00 (m, 2H), 1.07 (t, 3H).

LC/MS (Method 3, ESIpos): $R_t$=1.06 min, m/z=343 [M+H]$^+$.

Example 447A 3-(2-Methoxypropyl)-5-methyl-2,4-dioxo-1-(3,3,3-trifluoropropyl)-1,2,3,4-tetrahydrothieno[2,3-d]pyrimidino-6-carbaldehyde (racemate)

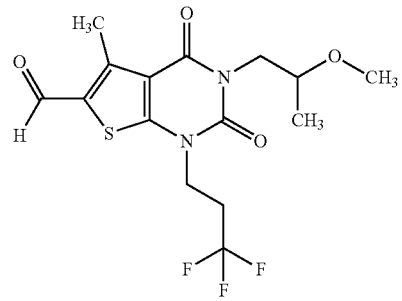 [SMILES: COC(C)Cn1c(=O)c2c(C)c(C=O)sc2n(CCC(F)(F)F)c1=O]

4.33 g (13.3 mmol) of caesium carbonate were added to a solution of 2.5 g (8.86 mmol) of the compound from Ex. 442A in 18 ml of DMF, and the mixture was stirred at RT for 10 min. Then 2.98 g (13.3 mmol) of 1,1,1-trifluoro-3-iodopropane were added, and the mixture was stirred in a microwave oven (Biotage Initiator with dynamic control of irradiation power), first at 100° C. for 3 h, then at 80° C. for 3 h. After cooling to RT, about 90 ml of water were added and the product was extracted with ethyl acetate. The organic extract was washed with saturated aqueous sodium chloride solution, dried over anhydrous magnesium sulphate, filtered and concentrated. The remaining residue was purified by MPLC (Isolera, Biotage cartridge with 340 g of silica gel, cyclohexane/ethyl acetate 90:10→10:90). The product fractions were combined, concentrated by evaporation and dried under high vacuum. 2.8 g (83% of theory) of the title compound were obtained.

$^1$H-NMR (400 MHz, DMSO-$d_6$, δ/ppm): 10.11 (s, 1H), 4.30-4.11 (m, 2H), 4.05 (dd, 1H), 3.77 (dd, 1H), 3.63 (sext, 1H), 3.22 (s, 3H), 2.91-2.72 (m, 2H), 2.79 (s, 3H), 1.07 (d, 3H).

LC/MS (Method 1, ESIpos): $R_t$=0.94 min, m/z=379 [M+H]$^+$.

Example 448A

3-Ethyl-N-methoxy-N,5-dimethyl-2,4-dioxo-1-(3,3,3-trifluoropropyl)-1,2,3,4-tetrahydrothieno[2,3-d]pyrimidine-6-carboxamide

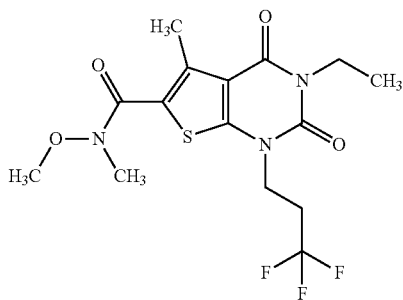 [SMILES: CCn1c(=O)c2c(C)c(C(=O)N(C)OC)sc2n(CCC(F)(F)F)c1=O]

Preparation of the acid chloride: At RT, first 1.2 ml (14.3 mmol) of oxalyl chloride and then a drop of DMF were added to a solution of 1.0 g (2.86 mmol) of the compound from Ex. 16A in 30 ml of dichloromethane. After the reaction mixture had been stirred at RT for 2 h, it was concentrated to dryness on a rotary evaporator. The remaining residue of the acid chloride was dried under high vacuum and then converted further in the next step.

Preparation of the amide: The acid chloride obtained beforehand was dissolved in 30 ml of anhydrous THF, and 334 mg (3.43 mmol) of N,O-dimethylhydroxylamine hydrochloride and 1.2 ml (7.14 mmol) of N,N-diisopropylethylamine were added. The reaction mixture was then stirred at RT. After about 18 h, the mixture was diluted with about 300 ml of ethyl acetate, and the mixture was washed successively with water (twice) and saturated aqueous sodium chloride solution. After drying over anhydrous magnesium sulphate, the mixture was filtered and concentrated. After drying under high vacuum, 1.11 g (99% of theory) of the title compound were obtained.

$^1$H-NMR (400 MHz, DMSO-$d_6$, δ/ppm): 4.16 (t, 2H), 3.92 (q, 2H), 3.70 (s, 3H), 3.26 (s, 3H), 2.89-2.69 (m, 2H), 2.74 (s, 3H), 1.13 (t, 3H).

LC/MS (Method 1, ESIpos): $R_t$=0.99 min, m/z=394 [M+H]$^+$.

Example 449A

6-Acetyl-3-ethyl-5-methyl-1-(3,3,3-trifluoropropyl)thieno[2,3-d]pyrimidine-2,4(1H,3H)-dione

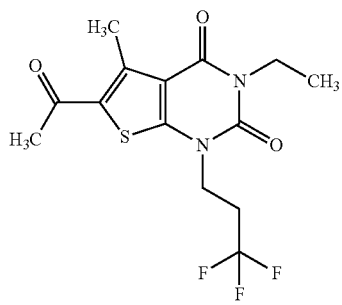 [SMILES: CCn1c(=O)c2c(C)c(C(C)=O)sc2n(CCC(F)(F)F)c1=O]

1.0 g (2.54 mmol) of the compound from Ex. 448A were dissolved in 25 ml of anhydrous THF, and 1.7 ml (5.08 mmol) of a 3 M solution of methylmagnesium chloride in THF were added dropwise at −78° C. When the dropwise addition had ended, the reaction mixture was stirred at 0° C. for a further 1 h. Then a small volume of saturated aqueous ammonium chloride solution was added. The mixture was diluted with ethyl acetate, and sufficient anhydrous solid magnesium sulphate was added that the aqueous phase was taken up completely. The mixture was filtered and the filtrate was concentrated. The remaining residue was purified by MPLC (Isolera, Biotage cartridge with 50 g of silica gel, cyclohexane/ethyl acetate 2:1). The product fractions were combined, concentrated by evaporation and dried under high vacuum. 775 mg (87% of theory) of the title compound were obtained.

$^1$H-NMR (400 MHz, DMSO-$d_6$, δ/ppm): 4.17 (t, 2H), 3.91 (q, 2H), 2.88-2.73 (m, 2H), 2.83 (s, 3H), 2.56 (s, 3H), 1.13 (t, 3H).

LC/MS (Method 1, ESIpos): $R_t$=0.99 min, m/z=349 [M+H]$^+$.

Example 450A 1-(Fluoromethyl)-6-(hydroxymethyl)-3-isopropyl-5-methylthieno[2,3-d]pyrimidine-2,4(1H,3H)-dione

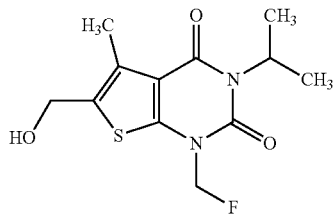 [SMILES: Cc1c(CO)sc2c1c(=O)n(C(C)C)c(=O)n2CF]

Analogously to the method described in Ex. 143A (Method C), 312 mg (1.03 mmol) of the compound from Ex. 378A were used to prepare 338 mg of the title compound. The conversion was effected here at −78° C. for 2 h.

$^1$H-NMR (400 MHz, DMSO-$d_6$, δ/ppm): 6.08-5.92 (m, 1H), 5.65 (t, 1H), 5.13 (quin, 1H), 4.59 (d, 2H), 2.32 (s, 3H), 1.41 (d, 6H).

LC/MS (Method 3): $R_t$=0.96 min, m/z=287 [M+H]$^+$.

Example 451A 1-(3-Fluoropropyl)-6-(hydroxymethyl)-3-isopropyl-5-methylthieno[2,3-d]pyrimidine-2,4(1H,3H)-dione

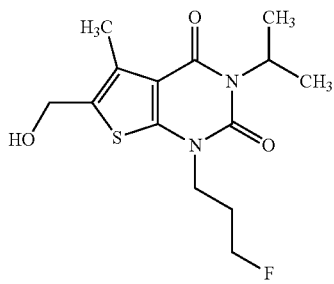 [SMILES: Cc1c(CO)sc2c1c(=O)n(C(C)C)c(=O)n2CCCF]

Analogously to the method described in Ex. 143A (Method C), 455 mg (1.44 mmol) of the compound from Ex. 379A were used to prepare 458 mg (99% of theory) of the title compound. The conversion was effected here at −78° C. for 2 h.

$^1$H-NMR (400 MHz, DMSO-d$_6$, δ/ppm): 5.59 (t, 1H), 5.14 (sept, 1H), 4.62-4.55 (m, 3H), 4.48 (t, 1H), 3.97 (t, 2H), 2.32 (s, 3H), 2.14-1.98 (m, 2H), 1.40 (d, 6H).

LC/MS (Method 3): R$_t$=1.01 min, m/z=315 [M+H]$^+$.

Example 452A 6-(Hydroxymethyl)-3-(2-methoxypropyl)-5-methyl-1-(3,3,3-trifluoropropyl)thieno[2,3-d]pyrimidine-2,4(1H,3H)-dione (racemate)

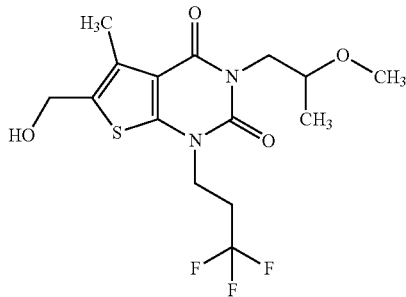 [SMILES: COC(C)Cn1c(=O)c2c(C)c(CO)sc2n(CCC(F)(F)F)c1=O]

Analogously to the method described in Ex. 138A (Method C), 562 mg (0.735 mmol) of the compound from Ex. 436A were used to prepare 199 mg (71% of theory) of the title compound. The conversion was effected here at −78° C. for 30 min.

$^1$H-NMR (400 MHz, DMSO-d$_6$, δ/ppm): 5.63 (t, 1H), 4.59 (d, 2H), 4.20-4.00 (m, 3H), 3.76 (dd, 1H), 3.63 (sext, 1H), 3.21 (s, 3H), 2.84-2.70 (m, 2H), 2.33 (s, 3H), 1.05 (d, 3H).

LC/MS (Method 3): R$_t$=1.01 min, m/z=381 [M+H]$^+$.

Example 453A

6-[Dideutero(hydroxy)methyl]-3-ethyl-1-(2-methoxyethyl)-5-methylthieno[2,3-d]pyrimidine-2,4(1H,3H)-dione

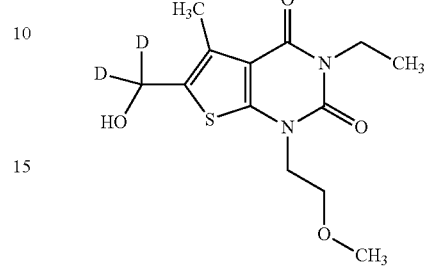

At −78° C., 1.8 ml (1.75 mmol) of a 1 M solution of lithium aluminium deuteride in THF were added dropwise to a solution of 660 mg (1.94 mmol) of the compound from Example 434A in 17 ml of THF. The reaction mixture was then stirred at 0° C. for 1 h. Thereafter, 0.6 ml of water and 4.5 ml of 1 M sodium hydroxide solution were added and the cooling bath was removed. The precipitate formed was filtered off with suction and washed thoroughly with THF. The filtrate combined with the wash liquid was concentrated to dryness. The remaining residue was taken up in ethyl acetate and washed successively with water and saturated aqueous sodium chloride solution. After drying over anhydrous magnesium sulphate, the mixture was filtered and concentrated. The crude product was purified by MPLC (Isolera, Biotage SNAP KP-Sil cartridge, cyclohexane/ethyl acetate 100:0→0:100). The product fractions were combined, concentrated by evaporation and dried under high vacuum. 298 mg (49% of theory, 98% purity) of the title compound were obtained.

$^1$H-NMR (400 MHz, DMSO-d$_6$, δ/ppm): 5.50 (s, 1H), 4.04 (t, 2H), 3.90 (q, 2H), 3.64 (t, 2H), 3.24 (s, 3H), 2.33 (s, 3H), 1.12 (t, 3H).

LC/MS (Method 17, ESIpos): R$_t$=1.20 min, m/z=301.12 [M+H]$^+$.

Example 454A

6-{[(2-Aminoethyl)amino]methyl}-3-(2,2-dimethylpropyl)-5-methyl-1-(tetrahydrofuran-2-ylmethyl)thieno[2,3-d]pyrimidine-2,4(1H,3H)-dione (racemate)

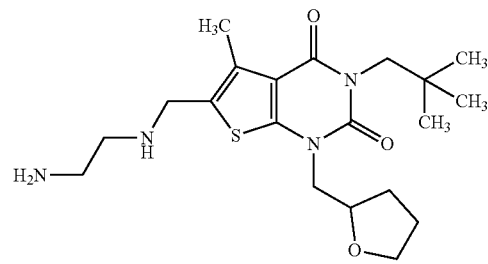 [SMILES: Cc1c(CNCCN)sc2c1c(=O)n(CC(C)(C)C)c(=O)n2CC1CCCO1]

To a solution of 2.0 mg (5.49 mmol) of the compound from Ex. 443A in a mixture of 50 ml of methanol and 20 ml of dichloromethane were first added 2.2 ml (32.9 mmol) of 1,2-diaminoethane and 1.3 ml (21.9 mmol) of acetic acid. After 30 min, 1.38 g (21.9 mmol) of sodium cyanoborohydride were added, and the reaction mixture was stirred at 60° C. for about 18 h. After cooling to RT, 2 M sodium hydroxide solution was added and extraction was effected with ethyl acetate. The organic extract was washed with saturated aqueous sodium chloride solution, dried over anhydrous magnesium sulphate, filtered and concentrated. The remaining residue was dried under high vacuum and thus gave 2.25 g (85% of theory, 85% purity) of the title compound, which was used for subsequent reactions without further purification.

LC/MS (Method 1, ESIpos): $R_t$=0.54 min, m/z=409 [M+H]$^+$.

Example 455A

6-{[(2-Aminoethyl)amino]methyl}-5-methyl-3-(1,1,1-trifluoropropan-2-yl)-1-(3,3,3-trifluoropropyl)thieno[2,3-d]pyrimidine-2,4(1H,3H)-dione (racemate)

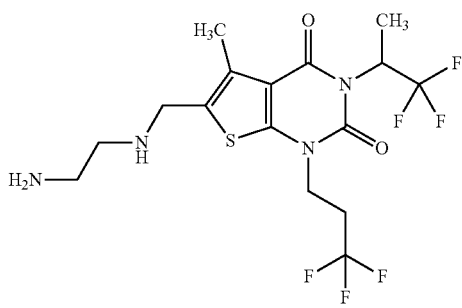 [SMILES: Cc1c(CNCCN)sc2c1c(=O)n(C(C)C(F)(F)F)c(=O)n2CCC(F)(F)F]

Analogously to the method described in Ex. 312A, 1.80 g (4.47 mmol) of the compound from Ex. 444A and 1.61 g (26.8 mmol) of 1,2-diaminoethane were used to prepare 2.37 g (99% of theory, 84% purity) of the title compound, which was used for subsequent reactions without further purification.

LC/MS (Method 1, ESIpos): $R_t$=0.62 min, m/z=447 [M+H]$^+$.

Example 456A

6-{[(2-Aminoethyl)amino]methyl}-1-(2-methoxyethyl)-5-methyl-3-(1,1,1-trifluoropropan-2-yl)thieno[2,3-d]pyrimidine-2,4(1H,3H)-dione (racemate)

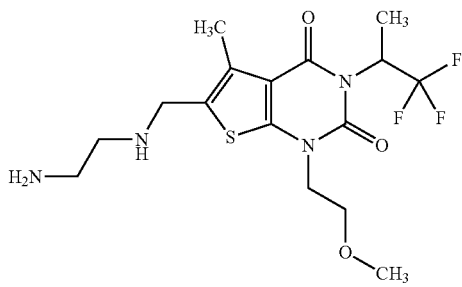 [SMILES: COCCn1c(=O)n(C(C)C(F)(F)F)c(=O)c2c(C)c(CNCCN)sc21]

Analogously to the method described in Ex. 312A, 1.01 g (2.77 mmol) of the compound from Ex. 445A and 1.0 g (16.6 mmol) of 1,2-diaminoethane were used to prepare 1.19 g (85% of theory, 82% purity) of the title compound, which was used for subsequent reactions without further purification.

LC/MS (Method 1, ESIpos): $R_t$=0.48 min, m/z=409 [M+H]$^+$.

Example 457A

6-{[(2-Aminoethyl)amino]methyl}-3-(2-ethoxyethyl)-1-(3-fluoropropyl)-5-methylthieno[2,3-d]pyrimidine-2,4(1H,3H)-dione

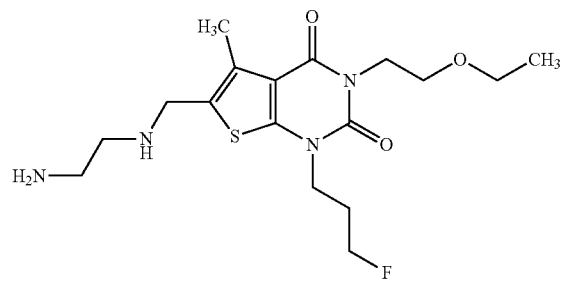 [SMILES: CCOCCn1c(=O)c2c(C)c(CNCCN)sc2n(CCCF)c1=O]

975 mg (2.79 mmol) of the compound from Ex. 446A were dissolved in a mixture of 43 ml of methanol and 20 ml of dichloromethane. Then 1.86 ml (27.9 mmol) of 1,2-diaminoethane and 639 µl (11.2 mmol) of acetic acid were added at RT. The mixture was stirred at RT for 30 min. Then 738 mg (11.2 mmol) of sodium cyanoborohydride were added. After the reaction mixture had been stirred at 60° C. for 72 h, it was admixed with 80 ml of water (pH about 9) and extracted with ethyl acetate. The organic extract was washed with saturated sodium chloride solution, dried over anhydrous sodium sulphate, filtered and concentrated. The crude product obtained, after drying under high vacuum, gave 890 mg (62% of theory, 75% purity) of the title compound, which was used for subsequent reactions without further purification.

LC/MS (Method 3, ESIpos): $R_t$=0.55 min, m/z=387 [M+H]$^+$.

Example 458A

6-{[(2-Aminoethyl)amino]methyl}-3-(2-methoxypropyl)-5-methyl-1-(3,3,3-trifluoropropyl)thieno[2,3-d]pyrimidine-2,4(1H,3H)-dione (racemate)

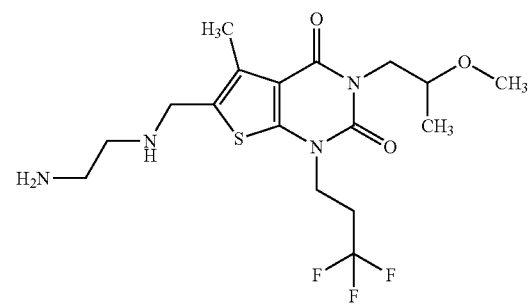 [SMILES: COC(C)Cn1c(=O)c2c(C)c(CNCCN)sc2n(CCC(F)(F)F)c1=O]

2.8 g (7.10 mmol) of the compound from Ex. 447A were dissolved in a mixture of 50 ml of methanol and 25 ml of dichloromethane, and 2.8 ml (42.6 mmol) of 1,2-diaminoethane and 1.6 ml (28.4 mmol) of acetic acid were added at RT. After 30 min, 1.79 g (28.4 mmol) of sodium cyanoborohydride were added, and the reaction mixture was heated to 60° C. After about 15 h, the reaction mixture was allowed to cool down to RT. The majority of the solvent was removed on a rotary evaporator. The remaining residue was admixed with 50 ml of 2 M sodium hydroxide solution and extracted thoroughly with ethyl acetate. The organic extract was washed with saturated sodium chloride solution, dried over anhydrous magnesium sulphate, filtered and concentrated on a rotary evaporator. The crude product thus obtained, after drying under high vacuum, gave 3.15 g (99% of theory, 95% purity) of the title compound, which was used for subsequent reactions without further purification.

LC/MS (Method 6, ESIpos): $R_t$=2.01 min, m/z=361 [M+H−62]$^+$.

Example 459A

3-Ethyl-6-(N-hydroxyethanimidoyl)-5-methyl-1-(3,3,3-trifluoropropyl)thieno[2,3-d]pyrimidine-2,4(1H,3H)-dione

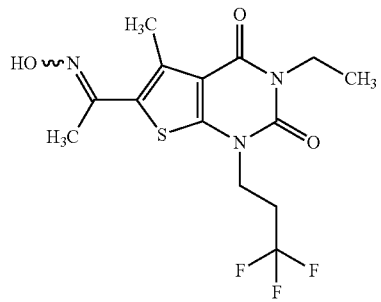 [SMILES: CCn1c(=O)c2c(C)c(C(C)=NO)sc2n(CCC(F)(F)F)c1=O]

To a solution of 665 mg (1.91 mmol) of the compound from Ex. 449A in 20 ml of ethanol were added 351 µl (5.73 mmol) of hydroxylamine (50% solution in water) and the mixture was heated under reflux for about 18 h. After cooling to RT, water was added, and the product precipitated out. The product was filtered off with suction, washed with a little cold water and dried under high vacuum. 673 mg (97% of theory) of the title compound were obtained in the form of an E/Z isomer mixture (ratio about 3:1, no attribution).

$^1$H-NMR (400 MHz, DMSO-d$_6$, δ/ppm; Major isomer): 11.42 (s, 1H), 4.12 (t, 2H), 3.91 (q, 2H), 2.85-2.69 (m, 2H), 2.59 (s, 3H), 2.23 (s, 3H), 1.12 (t, 3H).

LC/MS (Method 17, ESIpos; Major isomer): $R_t$=1.82 min, m/z=364.09 [M+H]$^+$.

Example 460A 6-(Aminomethyl)-3-ethyl-5-methyl-1-(3,3,3-trifluoropropyl)thieno[2,3-d]pyrimidine-2,4(1H,3H)-dione

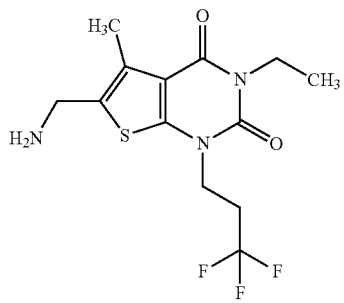 [SMILES: CCn1c(=O)c2c(C)c(CN)sc2n(CCC(F)(F)F)c1=O]

To a solution of 990 mg (2.83 mmol) of the compound from Ex. 190A in 70 ml of methanol were added 590 µl (7.08 mmol) of concentrated hydrochloric acid and 100 mg of palladium on charcoal (10%). Subsequently, hydrogenation was effected at RT at a hydrogen pressure of 1 bar for 2 h. This was followed by removal of the catalyst by filtration through a little kieselguhr and concentration of the filtrate on a rotary evaporator. The remaining residue was dissolved in 50 ml of ethyl acetate and washed successively with saturated aqueous sodium hydrogencarbonate solution (twice) and saturated aqueous sodium chloride solution. Drying over anhydrous magnesium sulphate, filtration, concentration and drying of the product under high vacuum gave 920 mg (96% of theory) of the title compound.

$^1$H-NMR (400 MHz, DMSO-d$_6$, δ/ppm): 4.12 (t, 2H), 3.90 (q, 2H), 2.83-2.71 (m, 2H), 2.32 (s, 3H), 2.19 (br. s, 2H), 1.11 (t, 3H).

LC/MS (Method 6, ESIpos): $R_t$=1.27 min, m/z=319 [M+H—NH$_3$]$^+$.

Example 461A 6-(1-Aminoethyl)-3-ethyl-5-methyl-1-(3,3,3-trifluoropropyl)thieno[2,3-d]pyrimidine-2,4(1H,3H)-dione (racemate)

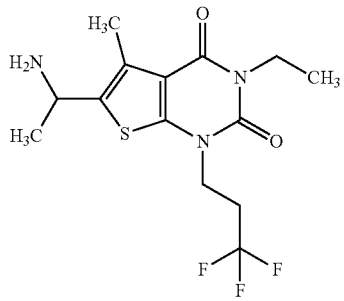 [SMILES: CCn1c(=O)c2c(C)c(C(C)N)sc2n(CCC(F)(F)F)c1=O]

To a solution of 235 mg (0.991 mmol) of nickel(II) chloride hexahydrate and 37 mg (0.991 mmol) of sodium borohydride in 10 ml of methanol was added a solution of 360 mg (0.991 mmol) of the compound from Ex. 459A in 30 ml of methanol. Subsequently, a further 206 mg (5.45 mmol) of sodium borohydride were added with significant evolution of gas. After stirring at RT for 3 h, another 118 mg (0.496 mmol) of nickel(II) chloride hexahydrate and 115 mg (3.17 mmol) of sodium borohydride were added. After a further 3 h at RT, the reaction mixture was filtered through kieselguhr and the filtrate was concentrated to dryness on a rotary evaporator. The remaining residue was dissolved in 20 ml of water, aqueous ammonia was added, and the mixture was extracted three times with ethyl acetate. The combined organic extract was washed successively with water and saturated aqueous sodium chloride solution, dried over anhydrous magnesium sulphate, filtered and concentrated. Drying under high vacuum gave 314 mg (72% of theory, 80% purity) of the title compound, which were used for subsequent reactions without further purification.

LC/MS (Method 17, ESIpos): $R_t$=0.92 min, m/z=333.09 [M+H—NH$_3$]$^+$.

Example 462A tert-Butyl 2-{[3-(2,2-dimethylpropyl)-5-methyl-2,4-dioxo-1-(3,3,3-trifluoropropyl)-1,2,3,4-tetrahydrothieno[2,3-d]pyrimidin-6-yl]methylene}hydrazinecarboxylate

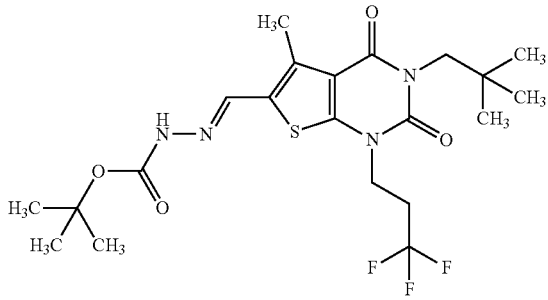 [SMILES: Cc1c(/C=N/NC(=O)OC(C)(C)C)sc2c1c(=O)n(CC(C)(C)C)c(=O)n2CCC(F)(F)F]

Analogously to the method described in Ex. 333A, 500 mg (1.33 mmol) of the compound from Ex. 291A and 263 mg (1.99 mmol) of tert-butyl hydrazinecarboxylate were used to obtain 649 mg (99% of theory) of the title compound.

$^1$H-NMR (400 MHz, DMSO-d$_6$, δ/ppm): 10.88 (br. s, 1H), 8.30 (s, 1H), 4.15 (t, 2H), 3.81 (s, 2H), 2.90-2.71 (m, 2H), 2.45 (s, 3H), 1.46 (s, 9H), 0.90 (s, 9H).

LC/MS (Method 17, ESIneg): $R_t$=2.41 min, m/z=489.18 [M–H]$^-$.

Example 463A tert-Butyl 2-{[3-(2,2-dimethylpropyl)-1-(2-methoxyethyl)-5-methyl-2,4-dioxo-1,2,3,4-tetrahydrothieno[2,3-d]pyrimidin-6-yl]methylene}hydrazinecarboxylate

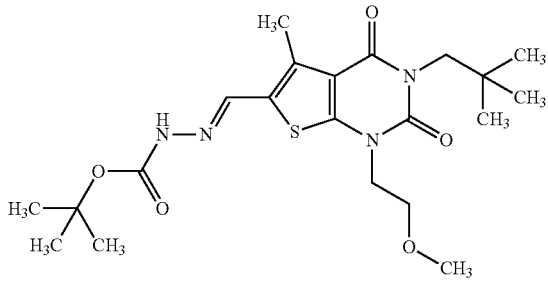 [SMILES: COCCn1c(=O)n(CC(C)(C)C)c(=O)c2c(C)c(/C=N/NC(=O)OC(C)(C)C)sc21]

Analogously to the method described in Ex. 333A, 220 mg (0.650 mmol) of the compound from Ex. 293A and 129 mg (0.975 mmol) of tert-butyl hydrazinecarboxylate were used to obtain 270 mg (91% of theory) of the title compound.

$^1$H-NMR (400 MHz, DMSO-d$_6$, δ/ppm): 10.85 (br. s, 1H), 8.29 (s, 1H), 4.07 (t, 2H), 3.81 (s, 2H), 3.64 (t, 2H), 3.24 (s, 3H), 2.44 (s, 3H), 1.46 (s, 9H), 0.89 (s, 9H).

LC/MS (Method 17, ESIneg): $R_t$=2.25 min, m/z=451.20 [M–H]$^-$.

Example 464A tert-Butyl 2-{[3-(2,2-dimethylpropyl)-5-methyl-2,4-dioxo-1-(tetrahydrofuran-2-ylmethyl)-1,2,3,4-tetrahydrothieno[2,3-d]pyrimidin-6-yl]methylene}hydrazinecarboxylate (racemate)

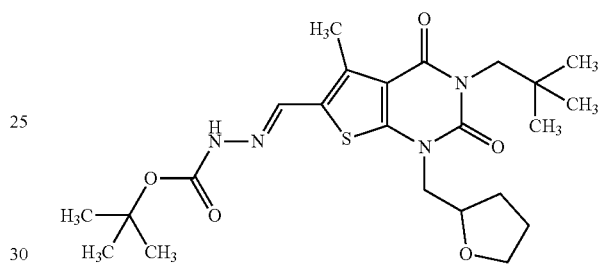

Analogously to the method described in Ex. 333A, 350 mg (0.960 mmol) of the compound from Ex. 443A and 190 mg (1.44 mmol) of tert-butyl hydrazinecarboxylate were used to obtain 360 mg (76% of theory, 97% purity) of the title compound.

$^1$H-NMR (400 MHz, DMSO-d$_6$, δ/ppm): 10.85 (br. s, 1H), 8.29 (s, 1H), 4.29-4.16 (m, 1H), 4.07 (dd, 1H), 3.88-3.70 (m, 4H), 3.67-3.56 (m, 1H), 2.44 (s, 3H), 2.07-1.75 (m, 3H), 1.73-1.58 (m, 1H), 1.45 (s, 9H), 0.90 (s, 9H).

LC/MS (Method 17, ESIneg): $R_t$=2.36 min, m/z=477.22 [M–H]$^-$.

Example 465A tert-Butyl 2-{[5-methyl-2,4-dioxo-3-(1,1,1-trifluoropropan-2-yl)-1-(3,3,3-trifluoropropyl)-1,2,3,4-tetrahydrothieno[2,3-d]pyrimidin-6-yl]methylene}hydrazinecarboxylate (racemate)

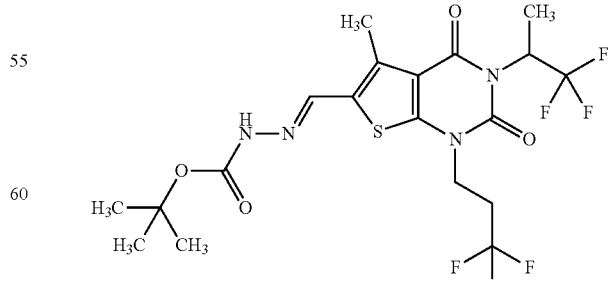

Analogously to the method described in Ex. 333A, 400 mg (0.994 mmol) of the compound from Ex. 444A and 197 mg (1.49 mmol) of tert-butyl hydrazinecarboxylate were used to obtain 493 mg (96% of theory) of the title compound.

$^1$H-NMR (400 MHz, DMSO-$d_6$, δ/ppm): 10.91 (br. s, 1H), 8.31 (s, 1H), 5.86-5.42 (m, 1H), 4.24-4.06 (m, 2H), 2.85-2.74 (m, 2H), 2.48-2.41 (m, 3H), 1.72-1.59 (m, 3H), 1.46 (s, 9H).

LC/MS (Method 17, ESIneg): $R_t$=2.24 min, m/z=515.12 [M−H]$^−$.

Example 466A tert-Butyl 2-{[1-(2-methoxyethyl)-5-methyl-2,4-dioxo-3-(1,1,1-trifluoropropan-2-yl)-1,2,3,4-tetrahydrothieno[2,3-d]pyrimidin-6-yl]methylene}hydrazinecarboxylate (racemate)

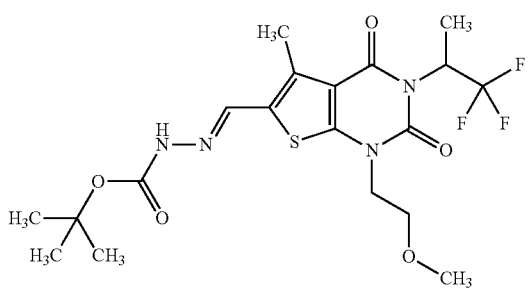 [SMILES: COCCn1c(=O)n(C(C)C(F)(F)F)c(=O)c2c(C)c(/C=N/NC(=O)OC(C)(C)C)sc21]

Analogously to the method described in Ex. 333A, 400 mg (1.10 mmol) of the compound from Ex. 445A and 218 mg (1.65 mmol) of tert-butyl hydrazinecarboxylate were used to obtain 509 mg (96% of theory) of the title compound.

$^1$H-NMR (400 MHz, DMSO-$d_6$, δ/ppm): 10.88 (br. s, 1H), 8.29 (s, 1H), 5.85-5.46 (m, 1H), 4.12-4.05 (m, 2H), 3.68-3.61 (m, 2H), 3.26 (s, 3H), 2.47-2.38 (m, 3H), 1.74-1.58 (m, 3H), 1.46 (s, 9H).

LC/MS (Method 17, ESIneg): $R_t$=2.09 min, m/z=477.14 [M−H]$^−$.

Example 467A tert-Butyl 2-{[3-(2-methoxypropyl)-5-methyl-2,4-dioxo-1-(3,3,3-trifluoropropyl)-1,2,3,4-tetrahydrothieno[2,3-d]pyrimidin-6-yl]methylene}hydrazinecarboxylate (racemate)

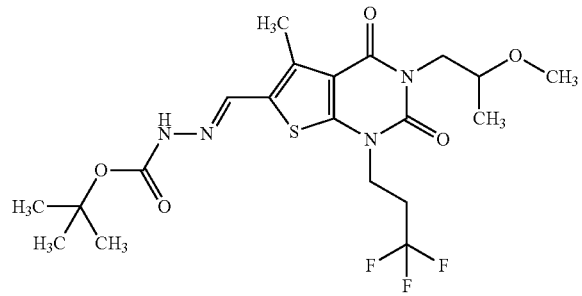 [SMILES: COC(C)Cn1c(=O)c2c(C)c(/C=N/NC(=O)OC(C)(C)C)sc2n(CCC(F)(F)F)c1=O]

To a solution of 1.1 g (2.91 mmol) of the compound from Ex. 447A in 35 ml of ethanol were added first 576 mg (4.36 mmol) of tert-butyl hydrazinecarboxylate and then 5 drops of concentrated hydrochloric acid. After the reaction mixture had been stirred at RT for about 18 h, the majority of the ethanol was removed on a rotary evaporator. The remaining residue was diluted with 150 ml of water and neutralized by adding saturated aqueous sodium hydrogencarbonate solution. The precipitated solids were filtered off with suction, washed with a little water and dried under high vacuum. 1.38 g (91% of theory, 95% purity) of the title compound were obtained.

$^1$H-NMR (400 MHz, DMSO-$d_6$, δ/ppm): 10.88 (br. s, 1H), 8.30 (s, 1H), 4.23-4.08 (m, 2H), 4.04 (dd, 1H), 3.76 (dd, 1H), 3.63 (sext, 1H), 3.22 (s, 3H), 2.88-2.71 (m, 2H), 2.46 (s, 3H), 1.46 (s, 9H), 1.06 (d, 3H).

LC/MS (Method 1, ESIpos): $R_t$=1.08 min, m/z=493 [M+H]$^+$.

Example 468A tert-Butyl 2-{[3-(2,2-dimethylpropyl)-5-methyl-2,4-dioxo-1-(3,3,3-trifluoropropyl)-1,2,3,4-tetrahydrothieno[2,3-d]pyrimidin-6-yl]methyl}hydrazinecarboxylate

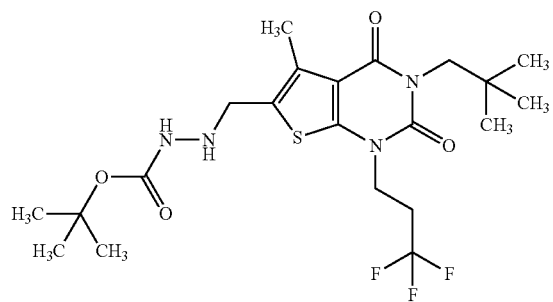 [SMILES: Cc1c(CNNC(=O)OC(C)(C)C)sc2c1c(=O)n(CC(C)(C)C)c(=O)n2CCC(F)(F)F]

Analogously to the method described in Ex. 342A, 650 mg (1.33 mmol) of the compound from Ex. 462A were used to obtain 590 mg (85% of theory, 94% purity) of the title compound.

$^1$H-NMR (400 MHz, DMSO-$d_6$, δ/ppm): 8.27 (br. s, 1H), 5.06 (br. s, 1H), 4.13 (t, 2H), 3.98 (br. d, 2H), 3.82 (br. s, 2H), 2.87-2.69 (m, 2H), 2.32 (s, 3H), 1.38 (s, 9H), 0.89 (s, 9H).

LC/MS (Method 17, ESIneg): $R_t$=2.35 min, m/z=491.19 [M−H]$^−$.

Example 469A tert-Butyl 2-{[3-(2,2-dimethylpropyl)-1-(2-methoxyethyl)-5-methyl-2,4-dioxo-1,2,3,4-tetrahydrothieno[2,3-d]pyrimidin-6-yl]methyl}hydrazinecarboxylate

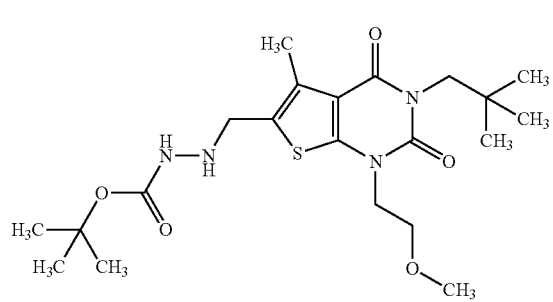 [SMILES: COCCn1c(=O)n(CC(C)(C)C)c(=O)c2c(C)c(CNNC(=O)OC(C)(C)C)sc21]

Analogously to the method described in Ex. 342A, 268 mg (0.592 mmol) of the compound from Ex. 463A were used to obtain 216 mg (78% of theory, 98% purity) of the title compound. The total reaction time here was about 20 h.

¹H-NMR (400 MHz, DMSO-d₆, δ/ppm): 8.27 (br. s, 1H), 4.99 (br. s, 1H), 4.08-4.00 (m, 2H), 3.96 (br. d, 2H), 3.82 (br. s, 2H), 3.64 (t, 2H), 3.24 (s, 3H), 2.32 (s, 3H), 1.38 (s, 9H), 0.89 (s, 9H).

LC/MS (Method 17, ESIneg): $R_t$=2.15 min, m/z=453.22 [M−H]⁻.

Example 470A tert-Butyl 2-{[3-(2,2-dimethylpropyl)-5-methyl-2,4-dioxo-1-(tetrahydrofuran-2-ylmethyl)-1,2,3,4-tetrahydrothieno[2,3-d]pyrimidin-6-yl]methyl}hydrazinecarboxylate (racemate)

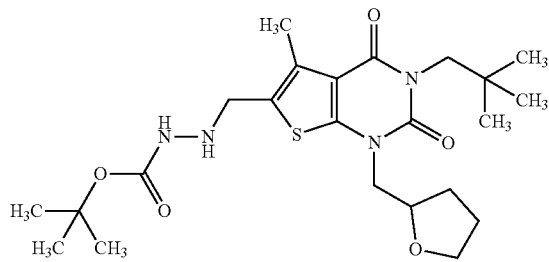 [SMILES: Cc1c(CNNC(=O)OC(C)(C)C)sc2c1c(=O)n(CC(C)(C)C)c(=O)n2CC1CCCO1]

Analogously to the method described in Ex. 342A, 360 mg (0.752 mmol) of the compound from Ex. 464A were used to obtain 402 mg (100% of theory, 90% purity) of the title compound, which was used for subsequent reactions without further purification (a chromatographic purification was dispensed with here).

¹H-NMR (400 MHz, DMSO-d₆, δ/ppm): 8.27 (br. s, 1H), 4.98 (br. s, 1H), 4.29-4.22 (m, 1H), 4.08-3.89 (m, 3H), 3.88-3.69 (m, 4H), 3.67-3.56 (m, 1H), 2.32 (s, 3H), 2.01-1.76 (m, 3H), 1.74-1.60 (m, 1H), 1.38 (s, 9H), 0.89 (s, 9H).

LC/MS (Method 17, ESIneg): $R_t$=2.26 min, m/z=479.23 [M−H]⁻.

Example 471A tert-Butyl 2-{[5-methyl-2,4-dioxo-3-(1,1,1-trifluoropropan-2-yl)-1-(3,3,3-trifluoropropyl)-1,2,3,4-tetrahydrothieno[2,3-d]pyrimidin-6-yl]methyl}hydrazinecarboxylate (racemate)

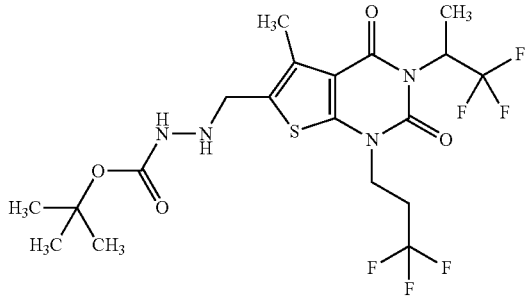 [SMILES: Cc1c(CNNC(=O)OC(C)(C)C)sc2c1c(=O)n(C(C)C(F)(F)F)c(=O)n2CCC(F)(F)F]

Analogously to the method described in Ex. 342A, 490 mg (0.949 mmol) of the compound from Ex. 465A were used to obtain 444 mg (90% of theory) of the title compound.

¹H-NMR (400 MHz, DMSO-d₆, δ/ppm): 8.26 (br. s, 1H), 5.85-5.46 (m, 1H), 5.11 (br. s, 1H), 4.13 (t, 2H), 4.02-3.94 (m, 2H), 2.89-2.68 (m, 2H), 2.38-2.28 (m, 3H), 1.72-1.59 (m, 3H), 1.38 (s, 9H).

LC/MS (Method 17, ESIneg): $R_t$=2.21 min, m/z=517.14 [M−H]⁻.

Example 472A tert-Butyl 2-{[1-(2-methoxyethyl)-5-methyl-2,4-dioxo-3-(1,1,1-trifluoropropan-2-yl)-1,2,3,4-tetrahydrothieno[2,3-d]pyrimidin-6-yl]methyl}hydrazinecarboxylate (racemate)

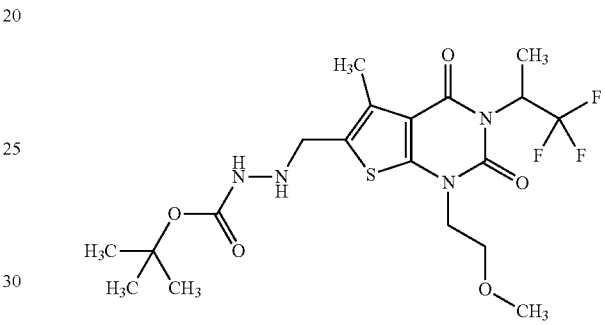

Analogously to the method described in Ex. 342A, 500 mg (1.05 mmol) of the compound from Ex. 466A were used to obtain 454 mg (86% of theory, 95% purity) of the title compound.

¹H-NMR (400 MHz, DMSO-d₆, δ/ppm): 8.26 (br. s, 1H), 5.86-5.46 (m, 1H), 5.03 (br. s, 1H), 4.14-3.84 (m, 4H), 3.72-3.57 (m, 2H), 3.25 (s, 3H), 2.36-2.24 (m, 3H), 1.73-1.58 (m, 3H), 1.38 (br. s, 9H).

LC/MS (Method 17, ESIneg): $R_t$=2.00 min, m/z=479.16 [M−H]⁻.

Example 473A tert-Butyl 2-{[3-(2-methoxypropyl)-5-methyl-2,4-dioxo-1-(3,3,3-trifluoropropyl)-1,2,3,4-tetrahydrothieno[2,3-d]pyrimidin-6-yl]methyl}hydrazinecarboxylate (racemate)

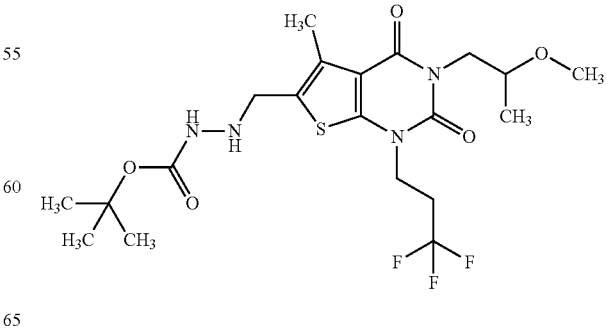

To a solution of 1.37 g (2.64 mmol, 95% purity) of the compound from Ex. 467A in 25 ml of methanol were added 830 mg (13.2 mmol) of sodium cyanoborohydride and a little Bromocresol Green (as indicator). Subsequently, a sufficient amount of acetic acid was added by titration that the indicator colour just changed from blue to yellow. Then the reaction mixture was heated to 65° C. After 1 h, after 3 h and after 4 h, a further 415 mg (6.61 mmol) of sodium cyanoborohydride were added in each case. Over the entire reaction time, by further addition of acetic acid, the pH was constantly regulated such that the indicator colour just remained yellow. After a total of 5 h, the volatile constituents of the reaction mixture were substantially removed on a rotary evaporator. The remaining residue was taken up in ethyl acetate and washed successively with saturated aqueous sodium hydrogencarbonate solution, water and saturated aqueous sodium chloride solution. After drying over anhydrous magnesium sulphate, the mixture was filtered and concentrated to dryness. The product was isolated by means of chromatography (Biotage Isolera One, SNAP KP-Sil cartridge, 100 g of silica gel, eluent: cyclohexane/ethyl acetate 2:1). After combination of the product fractions, concentration and drying under high vacuum, 890 mg (67% of theory) of the title compound were thus obtained.

$^1$H-NMR (400 MHz, DMSO-$d_6$, δ/ppm): 8.27 (br. s, 1H), 5.08 (br. m, 1H), 4.20-4.08 (m, 2H), 4.08-4.01 (m, 1H), 3.99 (br. d, 2H), 3.76 (dd, 1H), 3.63 (sext, 1H), 3.21 (s, 3H), 2.85-2.70 (m, 2H), 2.33 (s, 3H), 1.38 (s, 9H), 1.05 (d, 3H).

LC/MS (Method 1, ESIpos): $R_t$=1.02 min, m/z=495 [M+H]$^+$.

Example 474A tert-Butyl 2-carbamoyl-2-{[3-ethyl-5-methyl-2,4-dioxo-1-(3,3,3-trifluoropropyl)-1,2,3,4-tetrahydrothieno[2,3-d]pyrimidin-6-yl]methyl}hydrazinecarboxylate

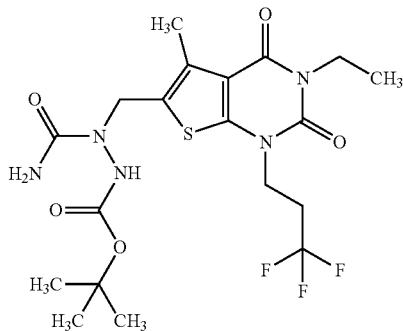 [SMILES: CCn1c(=O)c2c(C)c(CN(NC(=O)OC(C)(C)C)C(N)=O)sc2n(CCC(F)(F)F)c1=O]

To a solution of 16.56 g (36.8 mmol) of the compound from Ex. 339A in 700 ml of isopropanol were added 15.1 ml (110 mmol) of trimethylsilyl isocyanate, and the mixture was stirred at 50° C. for 3 h. Thereafter, the reaction mixture was concentrated to dryness. The residue was taken up in ethyl acetate and washed successively with saturated aqueous sodium hydrogencarbonate solution and saturated aqueous sodium chloride solution. After drying over anhydrous magnesium sulphate, the mixture was filtered and concentrated. The remaining residue was purified in three portions by means of MPLC (Biotage Isolera, cartridge with 340 g of silica gel, cyclohexane/ethyl acetate 1:1). The product fractions, which were sufficiently clean, were combined, concentrated and dried under high vacuum. This gave a first fraction of the title compound (10.38 g). The mixed fractions obtained from the MPLC were likewise combined and concentrated and then purified once more by means of MPLC. In this way, a second fraction of the title compound was obtained (2.53 g). A total of 12.91 g (66% of theory, 94% purity) of the title compound was thus obtained.

$^1$H-NMR (400 MHz, DMSO-$d_6$, δ/ppm): 8.92 (br. s, 1H), 6.21 (s, 2H), 4.59 (br. s, 2H), 4.13 (t, 2H), 3.91 (q, 2H), 2.87-2.68 (m, 2H), 2.35 (s, 3H), 1.38 (br. s, 9H), 1.11 (t, 3H).

LC/MS (Method 17, ESIneg): $R_t$=1.67 min, m/z=492.15 [M−H]$^-$.

Example 475A tert-Butyl 2-carbamoyl-2-{[3-ethyl-5-methyl-2,4-dioxo-1-(tetrahydrofuran-2-ylmethyl)-1,2,3,4-tetrahydrothieno[2,3-d]pyrimidin-6-yl]methyl}hydrazinecarboxylate (racemate)

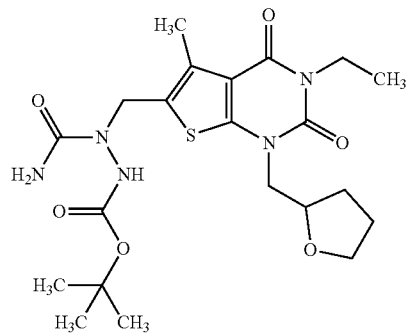 [SMILES: CCn1c(=O)c2c(C)c(CN(NC(=O)OC(C)(C)C)C(N)=O)sc2n(CC2CCCO2)c1=O]

To a solution of 214 mg (0.488 mmol) of the compound from Ex. 341A in 11 ml of isopropanol were added 131 μl (0.976 mmol) of trimethylsilyl isocyanate, and the mixture was stirred at RT. After 24 h, a further 50 μl (0.373 mmol) of trimethylsilyl isocyanate were added and the stirring was continued at RT. After a further 2 days, the conversion was still incomplete. Therefore, another 131 μl (0.976 mmol) of trimethylsilyl isocyanate were added, and the reaction mixture was heated to 50° C. After a further 24 h, the reaction mixture was concentrated to dryness. The remaining residue was purified by MPLC (Biotage Isolera, cartridge with 100 g of silica gel, cyclohexane/ethyl acetate 1:1→dichloromethane/methanol 20:1). The product fractions, which were sufficiently clean, were combined, concentrated and dried under high vacuum. 238 mg (85% of theory, 84% purity) of the title compound were obtained, which was used for subsequent reactions without further purification.

$^1$H-NMR (400 MHz, DMSO-$d_6$, δ/ppm): 9.70 (s, 1H), 7.36-6.95 (m, 2H), 4.58 (br. s, 1H), 4.30-4.19 (m, 1H), 4.02-3.96 (m, 1H), 3.91 (q, 2H), 3.82-3.70 (m, 2H), 3.66-3.56 (m, 1H), 2.34 (s, 3H), 2.03-1.75 (m, 3H), 1.73-1.59 (m, 1H), 1.39 (br. s, 9H), 1.11 (t, 3H).

LC/MS (Method 17, ESIneg): $R_t$=1.52 min, m/z=480.19 [M−H]$^-$.

Example 476A tert-Butyl 2-carbamoyl-2-{[3-isopropyl-5-methyl-2,4-dioxo-1-(tetrahydrofuran-2-ylmethyl)-1,2,3,4-tetrahydrothieno[2,3-d]pyrimidin-6-yl]methyl}hydrazinecarboxylate (racemate)

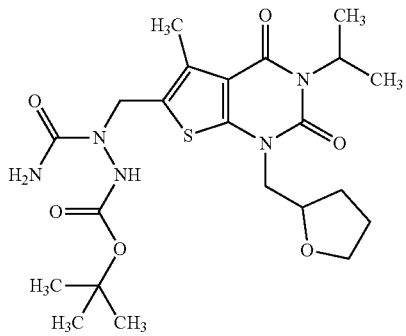 [SMILES: Cc1c(CN(NC(=O)OC(C)(C)C)C(N)=O)sc2c1c(=O)n(C(C)C)c(=O)n2CC1CCCO1]

To a solution of 372 mg (0.822 mmol) of the compound from Ex. 344A in 18 ml of isopropanol were added 220 μl (1.64 mmol) of trimethylsilyl isocyanate, and the mixture was stirred at RT. After 24 h, a further 10 μl (0.075 mmol) of trimethylsilyl isocyanate were added and the stirring was continued at RT. After a further 2 days, the reaction mixture was concentrated to dryness. The remaining residue was purified by MPLC (Biotage Isolera, cartridge with 100 g of silica gel, cyclohexane/ethyl acetate 1:1→dichloromethane/methanol 20:1). The product fractions, which were sufficiently clean, were combined, concentrated and dried under high vacuum. 366 mg (74% of theory, 83% purity) of the title compound were obtained, which was used for subsequent reactions without further purification.

$^1$H-NMR (400 MHz, DMSO-$d_6$, δ/ppm): 8.91 (br. s, 1H), 6.17 (s, 2H), 5.15 (sept, 1H), 5.03-4.29 (broad, 2H), 4.28-4.18 (m, 1H), 4.02-3.95 (m, 1H), 3.81-3.66 (m, 2H), 3.65-3.57 (m, 1H), 2.32 (s, 3H), 2.02-1.75 (m, 3H), 1.73-1.59 (m, 1H), 1.40 (broad, 15H).

LC/MS (Method 17, ESIneg): $R_t$=1.68 min, m/z=494.21 [M−H]$^-$.

Example 477A tert-Butyl 2-carbamoyl-2-{[3-(2,2-dimethylpropyl)-5-methyl-2,4-dioxo-1-(3,3,3-trifluoropropyl)-1,2,3,4-tetrahydrothieno[2,3-d]pyrimidin-6-yl]methyl}hydrazinecarboxylate

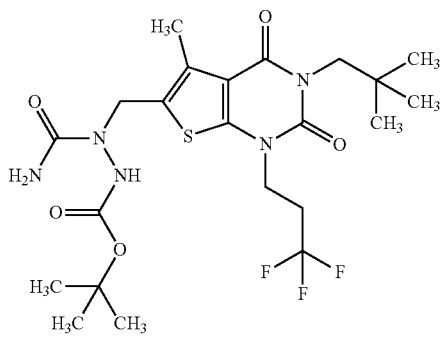 [SMILES: Cc1c(CN(NC(=O)OC(C)(C)C)C(N)=O)sc2c1c(=O)n(CC(C)(C)C)c(=O)n2CCC(F)(F)F]

To a solution of 150 mg (0.286 mmol, 94% purity) of the compound from Ex. 468A in 10 ml of isopropanol were added 115 μl (0.859 mmol) of trimethylsilyl isocyanate, and the mixture was stirred at 50° C. for 5 h. Thereafter, the reaction mixture was concentrated to dryness. The remaining residue was purified by MPLC (Biotage Isolera, cartridge with 25 g of silica gel, cyclohexane/ethyl acetate 1:1→dichloromethane/methanol 20:1). The product fractions, which were sufficiently clean, were combined, concentrated and dried under high vacuum. 154 mg (91% of theory, 91% purity) of the title compound were obtained, which was used for subsequent reactions without further purification.

$^1$H-NMR (400 MHz, DMSO-$d_6$, δ/ppm): 11.94 (br. s, 1H), 6.20 (br. s, 2H), 5.12-4.25 (m, 2H), 4.13 (t, 2H), 3.82 (br. s, 2H), 2.84-2.65 (m, 2H), 2.34 (s, 3H), 1.37 (br. s, 9H), 0.88 (s, 9H).

LC/MS (Method 17, ESIneg): $R_t$=2.05 min, m/z=534.20 [M−H]$^-$.

Example 478A tert-Butyl 2-carbamoyl-2-{[3-(2,2-dimethylpropyl)-1-(2-methoxyethyl)-5-methyl-2,4-dioxo-1,2,3,4-tetrahydrothieno[2,3-d]pyrimidin-6-yl]methyl}hydrazinecarboxylate

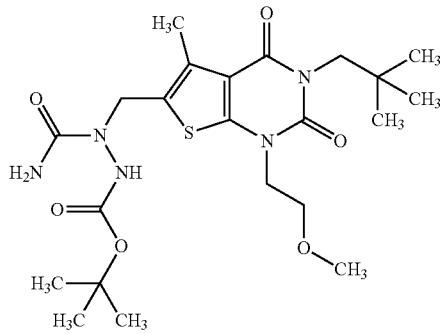 [SMILES: COCCn1c(=O)n(CC(C)(C)C)c(=O)c2c(C)c(CN(NC(=O)OC(C)(C)C)C(N)=O)sc21]

To a solution of 214 mg (0.471 mmol) of the compound from Ex. 469A in 14 ml of isopropanol were added 193 μl (1.41 mmol) of trimethylsilyl isocyanate, and the mixture was stirred at 50° C. for about 18 h. Thereafter, the reaction mixture was concentrated to dryness. The residue was taken up in ethyl acetate and washed successively with saturated aqueous sodium hydrogencarbonate solution and saturated aqueous sodium chloride solution. After drying over anhydrous magnesium sulphate, the mixture was filtered and concentrated. 299 mg (100% of theory, 80% purity) of the title compound were obtained, which was used for subsequent reactions without further purification.

$^1$H-NMR (400 MHz, DMSO-$d_6$, δ/ppm): 8.94 (br. s, 1H), 6.18 (br. s, 2H), 4.92-4.24 (m, 2H), 4.03 (q, 2H), 3.83 (br. s, 2H), 3.63 (t, 2H), 3.23 (s, 3H), 2.33 (s, 3H), 1.38 (br. s, 9H), 0.88 (s, 9H).

LC/MS (Method 17, ESIneg): $R_t$=1.80 min, m/z=496.22 [M−H]$^-$.

Example 479A tert-Butyl 2-carbamoyl-2-{[3-(2,2-dimethylpropyl)-5-methyl-2,4-dioxo-1-(tetrahydrofuran-2-ylmethyl)-1,2,3,4-tetrahydrothieno[2,3-d]pyrimidin-6-yl]methyl}hydrazinecarboxylate (racemate)

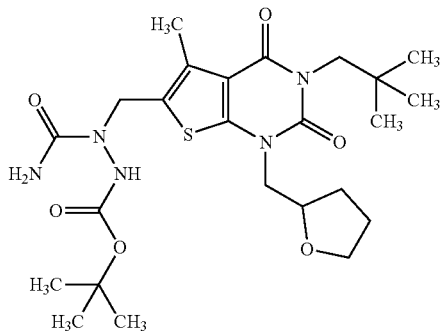 [SMILES: Cc1c(CN(NC(=O)OC(C)(C)C)C(N)=O)sc2c1c(=O)n(CC(C)(C)C)c(=O)n2CC1CCCO1]

Analogously to the method described in Ex. 478A, 402 mg (0.769 mmol, 90% purity) of the compound from Ex. 470A and 316 µl (2.31 mmol) of trimethylsilyl isocyanate were used to obtain 534 mg (100% of theory, 76% purity) of the title compound, which was used for subsequent reactions without further purification.

LC/MS (Method 17, ESIneg): $R_t$=1.90 min, m/z=522.24 [M−H]⁻.

Example 480A tert-Butyl 2-carbamoyl-2-{[5-methyl-2,4-dioxo-3-(2,2,2-trifluoroethyl)-1-(3,3,3-trifluoropropyl)-1,2,3,4-tetrahydrothieno[2,3-d]pyrimidin-6-yl]methyl}hydrazinecarboxylate

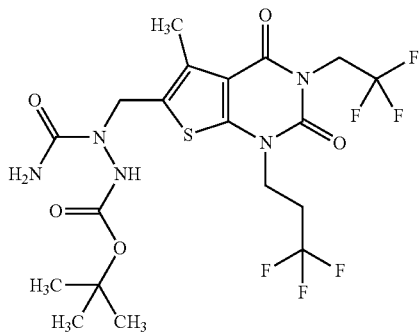 [SMILES: Cc1c(CN(NC(=O)OC(C)(C)C)C(N)=O)sc2c1c(=O)n(CC(F)(F)F)c(=O)n2CCC(F)(F)F]

To a solution of 400 mg (0.793 mmol) of the compound from Ex. 421A in 10 ml of isopropanol were added 213 µl (1.59 mmol) of trimethylsilyl isocyanate, and the mixture was stirred at 50° C. for about 18 h. Thereafter, the reaction mixture was concentrated to dryness. The residue was taken up in ethyl acetate and washed successively with saturated aqueous sodium hydrogencarbonate solution and saturated aqueous sodium chloride solution. After drying over anhydrous magnesium sulphate, the mixture was filtered and concentrated. The remaining residue was purified by MPLC (Biotage Isolera, cartridge with 25 g of silica gel, cyclohexane/ethyl acetate 1:1→dichloromethane/methanol 20:1). The product fractions, which were sufficiently clean, were combined, concentrated and dried under high vacuum. 378 mg (82% of theory, 95% purity) of the title compound were obtained, which was used for subsequent reactions without further purification.

¹H-NMR (400 MHz, DMSO-$d_6$, δ/ppm): 8.94 (br. s, 1H), 6.22 (br. s, 2H), 5.22-4.33 (m, 2H), 4.72 (q, 2H), 4.17 (t, 2H), 2.86-2.68 (m, 2H), 2.35 (s, 3H), 1.38 (br. s, 9H).

LC/MS (Method 17, ESIneg): $R_t$=1.78 min, m/z=546.13 [M−H]⁻.

Example 481A tert-Butyl 2-carbamoyl-2-{[1-(2-methoxyethyl)-5-methyl-2,4-dioxo-3-(2,2,2-trifluoroethyl)-1,2,3,4-tetrahydrothieno[2,3-d]pyrimidin-6-yl]methyl}hydrazinecarboxylate

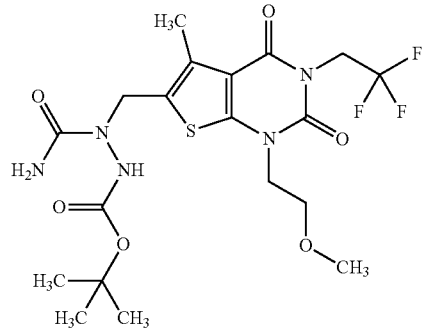 [SMILES: COCCn1c(=O)n(CC(F)(F)F)c(=O)c2c(C)c(CN(NC(=O)OC(C)(C)C)C(N)=O)sc21]

To a solution of 210 mg (0.450 mmol) of the compound from Ex. 422A in 8 ml of isopropanol were added 185 µl (1.35 mmol) of trimethylsilyl isocyanate, and the mixture was stirred at 50° C. for about 18 h. Thereafter, a further 93 µl (0.676 mmol) of trimethylsilyl isocyanate were added and the stirring was continued at 50° C. for another 3 h. Subsequently, the reaction mixture was left to stand at RT overnight. In the course of this, a portion of the product precipitated out, which was filtered off with suction and dried. The mother liquor was concentrated to dryness and the residue was purified by preparative HPLC (Method 8). The product fractions were combined and concentrated, then combined with the precipitate filtered off with suction beforehand, and dried under high vacuum. 180 mg (73% of theory, 94% purity) of the title compound were obtained, which was used for subsequent reactions without further purification.

¹H-NMR (500 MHz, DMSO-$d_6$, δ/ppm): 8.95 (br. s, 1H), 6.20 (br. s, 2H), 5.14-4.24 (m, 2H), 4.71 (q, 2H), 4.07 (t, 2H), 3.65 (t, 2H), 3.24 (s, 3H), 2.33 (s, 3H), 1.38 (br. s, 9H).

LC/MS (Method 17, ESIneg): $R_t$=1.57 min, m/z=508.15 [M−H]⁻.

Example 482A tert-Butyl 2-carbamoyl-2-{[5-methyl-2,4-dioxo-1-(tetrahydrofuran-2-ylmethyl)-3-(2,2,2-trifluoroethyl)-1,2,3,4-tetrahydrothieno[2,3-d]pyrimidin-6-yl]methyl}hydrazinecarboxylate (racemate)

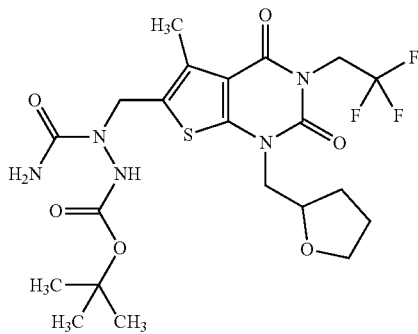 [SMILES: Cc1c(CN(NC(=O)OC(C)(C)C)C(N)=O)sc2c1c(=O)n(CC(F)(F)F)c(=O)n2CC1CCCO1]

To a solution of 1.12 g (2.27 mmol) of the compound from Ex. 423A in 50 ml of isopropanol were added 610 µl (4.55 mmol) of trimethylsilyl isocyanate, and the mixture was stirred at RT for about 18 h. Then a further 305 µl (2.27 mmol) of trimethylsilyl isocyanate were added and the stirring was continued at RT for 2 days. Thereafter, the reaction mixture was concentrated to dryness. The remaining residue was purified by MPLC (Biotage Isolera, cartridge with 100 g of silica gel, cyclohexane/ethyl acetate 1:1→dichloromethane/methanol 20:1). The product fractions were combined, concentrated by evaporation and dried under high vacuum. 810 mg (66% of theory) of the title compound were obtained.

$^1$H-NMR (400 MHz, DMSO-$d_6$, δ/ppm): 8.95 (br. s, 1H), 6.20 (s, 2H), 5.23-4.31 (broad, 2H), 4.72 (q, 2H), 4.30-4.19 (m, 1H), 4.03 (dd, 1H), 3.87-3.71 (m, 2H), 3.67-3.56 (m, 1H), 2.33 (s, 3H), 2.03-1.75 (m, 3H), 1.74-1.60 (m, 1H), 1.49-1.15 (br. s, 9H).

LC/MS (Method 17, ESIneg): $R_t$=1.66 min, m/z=534.16 [M–H]$^-$.

Example 483A tert-Butyl 2-carbamoyl-2-{[5-methyl-2,4-dioxo-3-(1,1,1-trifluoropropan-2-yl)-1-(3,3,3-trifluoropropyl)-1,2,3,4-tetrahydrothieno[2,3-d]pyrimidin-6-yl]methyl}hydrazinecarboxylate (racemate)

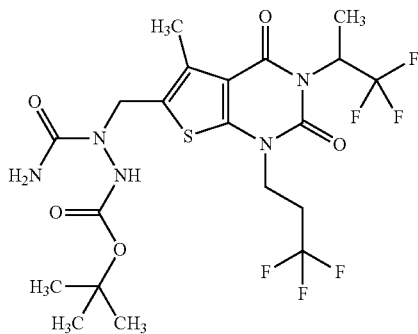 [SMILES: Cc1c(CN(NC(=O)OC(C)(C)C)C(N)=O)sc2c1c(=O)n(C(C)C(F)(F)F)c(=O)n2CCC(F)(F)F]

To a solution of 440 mg (0.849 mmol) of the compound from Ex. 471A in 20 ml of isopropanol were added 228 µl (1.697 mmol) of trimethylsilyl isocyanate, and the mixture was stirred at RT for about 18 h. Thereafter, the reaction mixture was concentrated to dryness. The remaining residue was purified by MPLC (Biotage Isolera, cartridge with 100 g of silica gel, ethyl acetate). The product fractions, which were sufficiently clean, were combined, concentrated and dried under high vacuum. 397 mg (79% of theory, 96% purity) of the title compound were obtained.

$^1$H-NMR (400 MHz, DMSO-$d_6$, δ/ppm): 8.92 (br. s, 1H), 6.22 (br. s, 2H), 5.83-5.48 (m, 1H), 4.60 (br. s, 2H), 4.14 (t, 2H), 4.03 (q, 1H), 2.85-2.69 (m, 2H), 2.39-2.27 (m, 3H), 1.71-1.59 (m, 3H), 1.38 (br. s, 9H).

LC/MS (Method 17, ESIneg): $R_t$=1.90 min, m/z=560.14 [M–H]$^-$.

Example 484A tert-Butyl 2-carbamoyl-2-{[1-(2-methoxyethyl)-5-methyl-2,4-dioxo-3-(1,1,1-trifluoropropan-2-yl)-1,2,3,4-tetrahydrothieno[2,3-d]pyrimidin-6-yl]methyl}hydrazinecarboxylate (racemate)

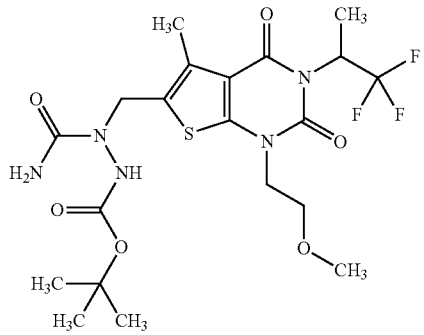 [SMILES: COCCn1c(=O)n(C(C)C(F)(F)F)c(=O)c2c(C)c(CN(NC(=O)OC(C)(C)C)C(N)=O)sc21]

Analogously to the method described in Ex. 483A, 450 mg (0.937 mmol) of the compound from Ex. 472A and 251 µl (1.87 mmol) of trimethylsilyl isocyanate were used to obtain 413 mg (80% of theory, 96% purity) of the title compound.

$^1$H-NMR (400 MHz, DMSO-$d_6$, δ/ppm): 8.92 (br. s, 1H), 6.20 (br. s, 2H), 5.86-5.47 (m, 1H), 5.12-4.20 (br. m, 2H), 4.14-3.95 (m, 2H), 3.67-3.60 (m, 2H), 3.31 (s, 3H), 2.33 (br. s, 3H), 1.73-1.59 (m, 3H), 1.38 (br. s, 9H).

LC/MS (Method 17, ESIneg): $R_t$=1.72 min, m/z=522.16 [M–H]$^-$.

Example 485A tert-Butyl 2-carbamoyl-2-{[3-(2-methoxyethyl)-5-methyl-2,4-dioxo-1-(3,3,3-trifluoropropyl)-1,2,3,4-tetrahydrothieno[2,3-d]pyrimidin-6-yl]methyl}hydrazinecarboxylate

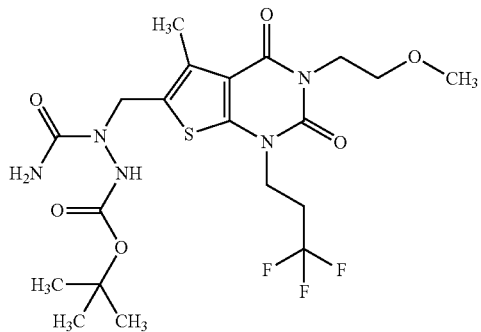 [SMILES: COCCn1c(=O)c2c(C)c(CN(NC(=O)OC(C)(C)C)C(N)=O)sc2n(CCC(F)(F)F)c1=O]

To a solution of 200 mg (0.404 mmol, 97% purity) of the compound from Ex. 424A in 5 ml of isopropanol were added 108 µl (0.807 mmol) of trimethylsilyl isocyanate, and the mixture was stirred at RT for 2 days. Thereafter, the reaction mixture was concentrated to dryness. The remaining residue was purified by MPLC (Biotage Isolera, cartridge with 10 g of silica gel, cyclohexane/ethyl acetate 1:1→dichloromethane/methanol 20:1). The product fractions, which were sufficiently clean, were combined, concentrated and dried under high vacuum. 187 mg (85% of theory, 97% purity) of the title compound were obtained.

$^1$H-NMR (400 MHz, DMSO-$d_6$, δ/ppm): 8.93 (br. s, 1H), 6.21 (s, 2H), 4.59 (br. s, 2H), 4.13 (t, 2H), 4.07 (t, 2H), 3.49 (t, 2H), 3.23 (s, 3H), 2.83-2.68 (m, 2H), 2.34 (s, 3H), 1.39 (br. s, 9H).

LC/MS (Method 17, ESIneg): $R_t$=1.56 min, m/z=522.16 [M−H]$^-$.

Example 486A tert-Butyl 2-carbamoyl-2-{[3-(2-methoxypropyl)-5-methyl-2,4-dioxo-1-(3,3,3-trifluoropropyl)-1,2,3,4-tetrahydrothieno[2,3-d]pyrimidin-6-yl]methyl}hydrazinecarboxylate (racemate)

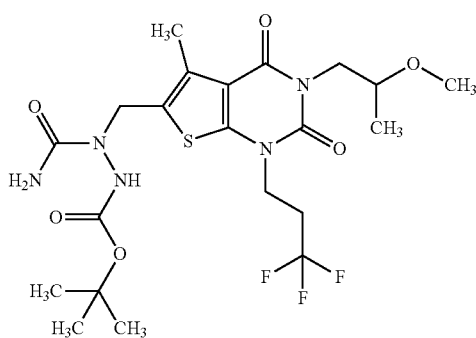 [SMILES: COC(C)Cn1c(=O)c2c(C)c(CN(NC(=O)OC(C)(C)C)C(N)=O)sc2n(CCC(F)(F)F)c1=O]

To a solution of 400 mg (785 mmol, 97% purity) of the compound from Ex. 473A in 10 ml of isopropanol were added 210 µl (1.57 mmol) of trimethylsilyl isocyanate, and the mixture was stirred at RT for 2 days. Thereafter, the reaction mixture was concentrated to dryness. The remaining residue was purified by MPLC (Biotage Isolera, cartridge with 100 g of silica gel, dichloromethane/methanol 98:2→80:20). The product fractions were combined, concentrated and dried under high vacuum. 387 mg (91% of theory) of the title compound were obtained.

$^1$H-NMR (400 MHz, DMSO-$d_6$, δ/ppm): 8.94 (br. s, 1H), 6.21 (br. s, 2H), 5.12-4.23 (m, 2H), 4.22-4.10 (m, 2H), 4.06 (dd, 1H), 3.76 (dd, 1H), 3.63 (sext, 1H), 3.20 (s, 3H), 2.83-2.68 (m, 2H), 2.35 (s, 3H), 1.38 (br. s, 9H), 1.04 (d, 3H).

LC/MS (Method 17, ESIpos): $R_t$=1.63 min, m/z=538.19 [M+H]$^+$.

Example 487A

2-Chloro-N-{[3-ethyl-5-methyl-2,4-dioxo-1-(3,3,3-trifluoropropyl)-1,2,3,4-tetrahydrothieno[2,3-d]pyrimidin-6-yl]methyl}acetamide

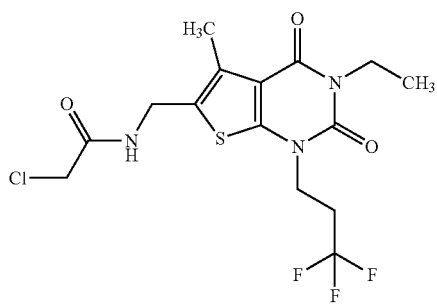 [SMILES: CCn1c(=O)c2c(C)c(CNC(=O)CCl)sc2n(CCC(F)(F)F)c1=O]

To a solution of 588 mg (1.75 mmol) of the compound from Ex. 460A and 733 µl (5.26 mmol) of triethylamine in 25 ml of dichloromethane were added dropwise, at 0° C., 209 µl (2.63 mmol) of chloroacetyl chloride. After 10 min, the cooling bath was removed, and stirring was continued at RT. After a total reaction time of 2 h, the reaction mixture was separated directly into its components by means of MPLC (Biotage Isolera, cartridge with 50 g of silica gel, cyclohexane/ethyl acetate 90:10→0:100). The product fractions were combined, concentrated and dried under high vacuum. 563 mg (77% of theory) of the title compound were obtained.

$^1$H-NMR (400 MHz, DMSO-$d_6$, δ/ppm): 8.85 (t, 1H), 4.39 (d, 2H), 4.10 (t, 2H), 4.10 (s, 2H), 3.90 (q, 2H), 2.83-2.68 (m, 2H), 2.41 (s, 3H), 1.11 (t, 3H).

LC/MS (Method 1, ESIpos): $R_t$=0.88 min, m/z=412 [M+H]$^+$.

Example 488A

N-{[3-Ethyl-5-methyl-2,4-dioxo-1-(3,3,3-trifluoropropyl)-1,2,3,4-tetrahydrothieno[2,3-d]pyrimidin-6-yl]methyl}glycinamide

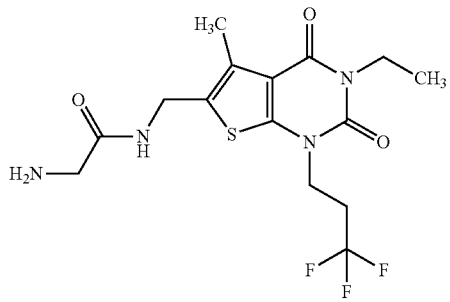 [SMILES: CCn1c(=O)c2c(C)c(CNC(=O)CN)sc2n(CCC(F)(F)F)c1=O]

562 mg (1.36 mmol) of the compound from Ex. 487A were dissolved in 20 ml of DMF, and 23 mg (0.136 mmol) of potassium iodide and 9.5 ml (68.2 mmol) of concentrated aqueous ammonia were added. The reaction mixture was stirred at 50° C. for 7 h and then left to stand at RT for 18 h. This was followed by concentration to dryness on a rotary evaporator and addition of 20 ml of water to the residue. The undissolved material was filtered off with suction, and the solids were discarded. The filtrate was concentrated a little, and then the product precipitated out. The solids were filtered off with suction and purified by means of HPLC (Method 8). 307 mg (54% yield, 95% purity) of the title compound were isolated.

$^1$H-NMR (400 MHz, DMSO-d$_6$, δ/ppm): 8.97 (t, 1H), 8.06 (br. s, 2H), 4.44 (d, 2H), 4.09 (t, 2H), 3.91 (q, 2H), 3.56 (s, 2H), 2.84-2.69 (m, 2H), 2.43 (s, 3H), 1.12 (t, 3H).

LC/MS (Method 17, ESIneg): R$_t$=0.91 min, m/z=437.11 [M−H+HCO$_2$H]$^-$.

Example 489A

N$^2$-(Chloroacetyl)-N-{[3-ethyl-5-methyl-2,4-dioxo-1-(3,3,3-trifluoropropyl)-1,2,3,4-tetrahydrothieno[2,3-d]pyrimidin-6-yl]methyl}glycinamide

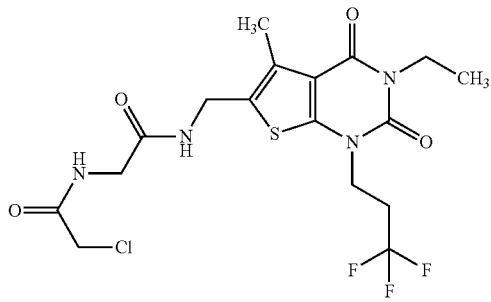 [SMILES: CCn1c(=O)c2c(C)c(CNC(=O)CNC(=O)CCl)sc2n(CCC(F)(F)F)c1=O]

To a solution of 305 mg (0.622 mmol, 80% purity) of the compound from Ex. 488A and 260 µl (1.87 mmol) of triethylamine in 10 ml of dichloromethane were added dropwise, at 0° C., 74 µl (0.933 mmol) of chloroacetyl chloride. After 10 min, the cooling bath was removed, and stirring was continued at RT. After a total reaction time of 2 h, the reaction mixture was admixed with water and then extracted with ethyl acetate. The organic extract was washed with saturated aqueous sodium chloride solution, dried over anhydrous magnesium sulphate, filtered and concentrated. After drying under high vacuum, 295 mg (99% of theory, 98% purity) of the title compound were obtained.

$^1$H-NMR (400 MHz, DMSO-d$_6$, δ/ppm): 8.56 (t, 1H), 8.45 (t, 1H), 4.36 (d, 2H), 4.13 (s, 2H), 4.09 (t, 2H), 3.90 (q, 2H), 3.74 (d, 2H), 2.83-2.68 (m, 2H), 2.41 (s, 3H), 1.11 (t, 3H).

LC/MS (Method 17, ESIneg): R$_t$=1.45 min, m/z=467.08 [M−H]$^-$.

Example 490A

Diethyl 5-[(isopropylcarbamoyl)amino]-3-methylthiophene-2,4-dicarboxylate

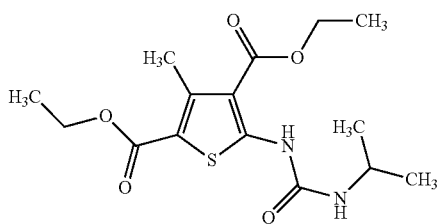 [SMILES: CCOC(=O)c1sc(NC(=O)NC(C)C)c(C(=O)OCC)c1C]

3.0 g (11.7 mmol) of diethyl 5-amino-3-methylthiophene-2,4-dicarboxylate were dissolved in 50 ml of dichloromethane and 3.78 g (23.3 mmol) of CDI and 3.3 ml (23.3 mmol) of triethylamine were added. The reaction mixture was stirred at RT for 3 days, after which 4.0 ml (46.6 mmol) of isopropylamine were added. After stirring at RT for a further hour, 100 ml of water were added to the reaction mixture and then extraction was effected with ethyl acetate. The organic extract was concentrated by evaporation and the residue was taken up again in 50 ml of dichloromethane. This left an undissolved portion, which was filtered off with suction and dried under high vacuum. This gave a first, contaminated fraction of the title compound (3.59 g, 80% of theory, 89% purity, remainder: N,N'-diisopropylurea), which was used as such for further reactions. The portion of the crude product dissolved in dichloromethane was purified by means of MPLC (Biotage cartridge with 100 g of silica gel, cyclohexane/ethyl acetate 2:1). Concentration of the product fractions and drying of the residue under high vacuum thus gave a second, pure fraction of the title compound (0.46 g, 11% of theory). A total of 4.05 g (92% of theory, 90% purity) of the title compound was thus obtained.

$^1$H-NMR (400 MHz, DMSO-d$_6$, δ/ppm): 10.51 (s, 1H), 8.02 (br. d, 1H), 4.32 (q, 2H), 4.22 (q, 2H), 3.75 (sept, 1H), 2.65 (s, 3H), 1.33 (t, 3H), 1.27 (t, 3H), 1.11 (d, 6H).

LC/MS (Method 17, ESIpos): R$_t$=2.20 min, m/z=343.13 [M+H]$^+$.

Example 491A

Diethyl 3-methyl-5-{[(2,2,2-trifluoroethyl)carbamoyl]amino}thiophene-2,4-dicarboxylate 3.0 g (11.7 mmol) of diethyl 5-amino-3-methylthiophene-2,4-dicarboxylate were dissolved in 50 ml of dichloromethane, and 3.78 g (23.3 mmol) of CDI and 3.3 ml (23.3 mmol) of triethylamine were added. The reaction mixture was stirred at RT for 2 days, before 3.7 ml (46.6 mmol) of 2,2,2-trifluoroethylamine were added. After stirring at RT for a further day, 100 ml of water were added to the mixture and then extraction was effected with dichloromethane. The organic extract was washed with saturated sodium chloride solution, dried over anhydrous magnesium sulphate, filtered and concentrated. The residue obtained was purified by MPLC (Biotage Isolera, cartridge with 340 g of silica gel, cyclohexane/ethyl acetate 2:1). After concentration of the product fractions and drying of the residue under high vacuum, 3.93 g (82% of theory, 95% purity) of the title compound were obtained.

$^1$H-NMR (600 MHz, DMSO-d$_6$, δ/ppm): 10.75 (s, 1H), 8.81 (t, 1H), 4.33 (q, 2H), 4.23 (q, 2H), 4.07-3.95 (m, 2H), 2.66 (s, 3H), 1.34 (t, 3H), 1.28 (t, 3H).

LC/MS (Method 17, ESIpos): R$_t$=2.16 min, m/z=383.09 [M+H]$^+$.

Example 492A

Diethyl 3-methyl-5-({[(2R)-1,1,1-trifluoropropan-2-yl]carbamoyl}amino)thiophene-2,4-dicarboxylate

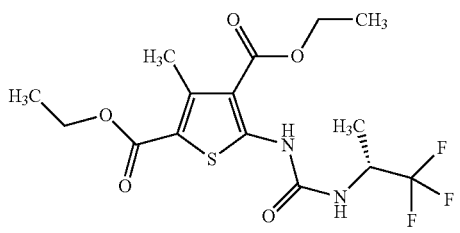 [SMILES: CCOC(=O)c1sc(NC(=O)N[C@H](C)C(F)(F)F)c(C(=O)OCC)c1C]

5.0 g (19.4 mmol) of diethyl 5-amino-3-methylthiophene-2,4-dicarboxylate were dissolved in 83 ml of dichloromethane, and 6.3 g (38.9 mmol) of CDI and 13.5 ml (97.2 mmol) of triethylamine were added. The reaction mixture was stirred at RT for 2 days, before 5.81 g (38.9 mmol) of (2R)-1,1,1-trifluoropropan-2-amine hydrochloride were added. After stirring at RT for a further 6 days, 100 ml of water were added to the mixture and then extraction was effected with dichloromethane. The organic extract was washed with saturated sodium chloride solution, dried over anhydrous magnesium sulphate, filtered and concentrated almost to dryness on a rotary evaporator. The precipitated solids were filtered off with suction, washed with a little dichloromethane and dried under high vacuum. This gave a first fraction of the product (2.43 g). The filtrate and the wash liquid were combined and concentrated further until even more product precipitated out. This was filtered off with suction again and dried under high vacuum. A second fraction of the product was thus obtained (1.68 g). The filtrate was then concentrated to dryness. The remaining residue was purified by MPLC (Isolera, 340 g of silica gel, cyclohexane/ethyl acetate 2:1). The product fractions were combined, concentrated and dried under high vacuum. This gave a third fraction of the product (5.25 g). A total of 9.36 g (85% of theory, 70% purity) of the title compound was thus obtained, which was used for subsequent reactions without further purification.

$^1$H-NMR (400 MHz, DMSO-d$_6$, δ/ppm): 10.72 (s, 1H), 8.73 (d, 1H), 4.57-4.42 (m, 1H), 4.33 (q, 2H), 4.23 (q, 2H), 2.67 (s, 3H), 1.34 (t, 3H), 1.29 (d, 3H), 1.27 (t, 3H).

LC/MS (Method 1, ESIpos): R$_t$=1.18 min, m/z=397 [M+H]$^+$.

Example 493A

Diethyl 3-methyl-5-({[(2S)-1,1,1-trifluoropropan-2-yl]carbamoyl}amino)thiophene-2,4-dicarboxylate

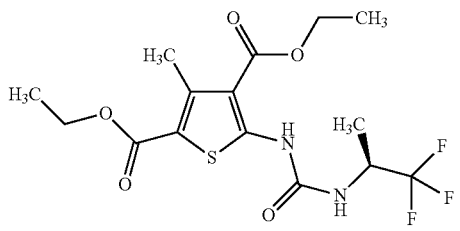 [SMILES: CCOC(=O)c1sc(NC(=O)N[C@@H](C)C(F)(F)F)c(C(=O)OCC)c1C]

4.0 g (15.5 mmol) of diethyl 5-amino-3-methylthiophene-2,4-dicarboxylate were dissolved in 67 ml of dichloromethane, and 5.04 g (31.1 mmol) of CDI and 10.8 ml (77.7 mmol) of triethylamine were added. The reaction mixture was stirred at RT for 2 days, before 4.65 g (31.1 mmol) of (2S)-1,1,1-trifluoropropan-2-amine hydrochloride were added. After stirring at RT for a further 2 days, 100 ml of water were added to the mixture and then extraction was effected with dichloromethane. The organic extract was washed with saturated sodium chloride solution, dried over anhydrous magnesium sulphate, filtered and concentrated to dryness on a rotary evaporator. The remaining residue was first prepurified by MPLC (Isolera, 340 g of silica gel, cyclohexane/ethyl acetate 2:1). The product fractions were combined, concentrated and then purified further by means of preparative HPLC (Method 8). The product fractions were again combined and concentrated. The remaining residue was then taken up in ethyl acetate and washed successively with water, 1 M hydrochloric acid and saturated sodium chloride solution. Drying over anhydrous magnesium sulphate, filtration and concentration gave 6.28 g (81% of theory, 80% purity) of the title compound, which was used for subsequent reactions without further purification.

$^1$H-NMR (400 MHz, DMSO-d$_6$, δ/ppm): 10.72 (s, 1H), 8.73 (d, 1H), 4.57-4.42 (m, 1H), 4.33 (q, 2H), 4.23 (q, 2H), 2.67 (s, 3H), 1.34 (t, 3H), 1.29 (d, 3H), 1.27 (t, 3H).

LC/MS (Method 1, ESIpos): R$_t$=1.18 min, m/z=397 [M+H]$^+$.

Example 494A

Ethyl 3-isopropyl-5-methyl-2,4-dioxo-1,2,3,4-tetrahydrothieno[2,3-d]pyrimidine-6-carboxylate

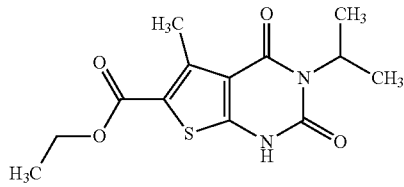 [SMILES: CCOC(=O)c1sc2[nH]c(=O)n(C(C)C)c(=O)c2c1C]

4.05 g (10.6 mmol, 90% purity) of the compound from Ex. 490A were dissolved in 85 ml of ethanol, and 6.6 ml (17.7 mmol) of a 21% solution of sodium ethoxide in ethanol were added. The mixture was stirred first at RT for 18 h, then at 50° C. for 6 h and lastly at RT again for 18 h. Thereafter, the mixture was concentrated to about half the original volume. The precipitate formed was filtered off with suction and stirred with diisopropyl ether with a little added ethyl acetate at RT. After another filtration with suction and drying under high vacuum, 2.67 g (85% of theory) of the title compound were obtained.

$^1$H-NMR (400 MHz, DMSO-d$_6$, δ/ppm): 12.29 (s, 1H), 5.08 (sept, 1H), 4.26 (q, 2H), 2.74 (s, 3H), 1.40 (d, 6H), 1.28 (t, 3H).

LC/MS (Method 17, ESIpos): R$_t$=1.80 min, m/z=297.09 [M+H]$^+$.

Example 495A

Ethyl 5-methyl-2,4-dioxo-3-(2,2,2-trifluoroethyl)-1,2,3,4-tetrahydrothieno[2,3-d]pyrimidine-6-carboxylate

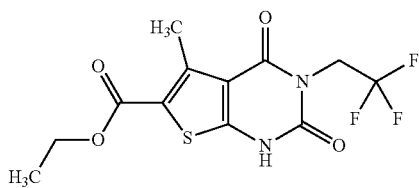 [SMILES: CCOC(=O)c1sc2[nH]c(=O)n(CC(F)(F)F)c(=O)c2c1C]

3.93 g (9.76 mmol, 95% purity) of the compound from Ex. 491A were dissolved in 95 ml of ethanol, and 7.3 ml (19.5 mmol) of a 21% solution of sodium ethoxide in ethanol were added. The reaction mixture was stirred at 50° C. for 2 h. Thereafter, the mixture was concentrated to about half the original volume. Then 22.5 ml (22.5 mmol) of 1 M hydrochloric acid were added. The resulting precipitate was filtered off with suction, washed with water until neutral and dried. The solids were finally stirred with diisopropyl ether with a little added ethyl acetate at RT. After another filtration with suction and drying under high vacuum, 3.20 g (97% of theory) of the title compound were obtained.

$^1$H-NMR (400 MHz, DMSO-d$_6$, δ/ppm): 12.76 (br. s, 1H), 4.65 (q, 2H), 4.27 (q, 2H), 2.74 (s, 3H), 1.29 (t, 3H).

LC/MS (Method 17, ESIpos): R$_t$=1.77 min, m/z=337.05 [M+H]$^+$.

Example 496A

Ethyl 5-methyl-2,4-dioxo-3-[(2R)-1,1,1-trifluoropropan-2-yl]-1,2,3,4-tetrahydrothieno[2,3-d]pyrimidine-6-carboxylate

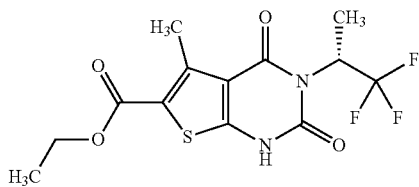 [SMILES: CCOC(=O)c1sc2[nH]c(=O)n([C@H](C)C(F)(F)F)c(=O)c2c1C]

9.35 g (16.5 mmol, 70% purity) of the compound from Ex. 492A were dissolved in 120 ml of ethanol, and 12.3 ml (33.0 mmol) of a 21% solution of sodium ethoxide in ethanol were added. The reaction mixture was stirred at 50° C. for about 16 h. Thereafter, 38 ml (38.0 mmol) of 1 M hydrochloric acid and saturated sodium chloride solution were added and then extraction was effected with diethyl ether. The organic extract was concentrated, and the remaining residue was prepurified by means of MPLC (Isolera, 100 g of silica gel, cyclohexane/ethyl acetate 100:0→40:60). The product fractions were combined, concentrated and purified by means of preparative HPLC [column: XBridge C18, 5 μm, 100 mm×30 mm; eluent A: water; eluent B: acetonitrile; eluent C: aqueous ammonia (1% NH$_3$); gradient: 0.0-1.0 min A:B:C 75:20:5, 1.0-6.0 min A:B:C 75:20:5→25:70:5, 6.0-6.2 min A:B:C 25:70:5→75:20:5, 6.2-7.2 min A:B:C 75:20:5; flow rate: 75 ml/min; temperature: 40° C.; detection: 210 nm]. After concentration of the product fractions and drying under high vacuum, 2.91 g (50% of theory) of the title compound were obtained (>99% ee, chiral analytical HPLC).

$^1$H-NMR (400 MHz, DMSO-d$_6$, δ/ppm): 12.65 (br. s, 1H), 5.78-5.62 and 5.57-5.44 (2 m, tog. 1H), 4.27 (q, 2H), 2.74 and 2.72 (2 s, tog. 3H), 1.67 and 1.64 (2 d, tog. 3H), 1.29 (t, 3H).

LC/MS (Method 17, ESIpos): R$_t$=1.90 min, m/z=351.06 [M+H]$^+$.

Chiral analytical HPLC [column: Daicel Chiralcel IC-3, 3 μm, 50 mm×4.6 mm; eluent: isohexane/isopropanol 4:1; flow rate: 1 ml/min; temperature: 25° C.; detection: 220 nm]: R$_t$=1.38 min.

Specific optical rotation: $[\alpha]_D^{20}$=+15.1°·ml·dm$^{-1}$·g$^{-1}$ (methanol).

Example 497A

Ethyl 5-methyl-2,4-dioxo-3-[(2S)-1,1,1-trifluoropropan-2-yl]-1,2,3,4-tetrahydrothieno[2,3-d]pyrimidine-6-carboxylate

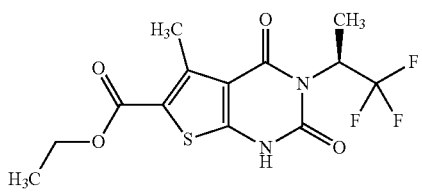 [SMILES: CCOC(=O)c1sc2[nH]c(=O)n([C@@H](C)C(F)(F)F)c(=O)c2c1C]

6.0 g (12.1 mmol, 80% purity) of the compound from Ex. 493A were dissolved in 100 ml of ethanol, and 9 ml (24.2 mmol) of a 21% solution of sodium ethoxide in ethanol were added. The reaction mixture was stirred at 50° C. for about 16 h. Thereafter, 28 ml (28.0 mmol) of 1 M hydrochloric acid were added. The precipitated solids were filtered off with suction, while the filtrate was extracted with ethyl acetate. The concentrated organic extract was combined with the precipitate removed beforehand and purified by means of preparative HPLC (Method 8). After concentration of the product fractions and drying under high vacuum, 2.75 g (64% of theory) of the title compound were obtained (>99% ee, chiral analytical HPLC).

$^1$H-NMR (600 MHz, DMSO-d$_6$, δ/ppm): 12.67 (br. s, 1H), 5.74-5.66 and 5.54-5.47 (2 m, tog. 1H), 4.27 (q, 2H), 2.74 and 2.72 (2 s, tog. 3H), 1.67 and 1.64 (2 d, tog. 3H), 1.29 (t, 3H).

LC/MS (Method 17, ESIpos): R$_t$=1.92 min, m/z=351.06 [M+H]$^+$.

Chiral analytical HPLC [column: Daicel Chiralcel IC-3, 3 μm, 50 mm×4.6 mm; eluent: isohexane/isopropanol 4:1; flow rate: 1 ml/min; temperature: 25° C.; detection: 220 nm]: R$_t$=1.67 min.

Specific optical rotation: $[\alpha]_D^{20}$=−13.9°·ml·dm$^{-1}$·g$^{-1}$ (methanol).

Example 498A

Ethyl 3-isopropyl-1-(2-methoxyethyl)-5-methyl-2,4-dioxo-1,2,3,4-tetrahydrothieno[2,3-d]pyrimidine-6-carboxylate

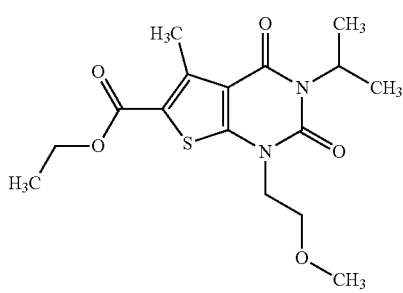 [SMILES: CCOC(=O)c1sc2c(c1C)c(=O)n(C(C)C)c(=O)n2CCOC]

1.05 g (7.59 mmol) of potassium carbonate were added to a solution of 900 mg (3.04 mmol) of the compound from Ex. 494A in 22 ml of DMF, and the mixture was stirred at RT for 15 min. Then 844 mg (6.07 mmol) of 2-bromoethyl methyl ether were added. The mixture was stirred first at RT for 4 days and then at 60° C. for 2 h. Thereafter, about 125 ml of water were added to the reaction mixture at RT. In the course of this, the product precipitated out. The mixture was stirred at RT for another 30 min, before the product was then filtered off with suction. The residue obtained was stirred once again with water. After the water phase had been decanted off, the product was dried under high vacuum. 1.03 g (86% of theory, 90% purity) of the title compound were obtained, which was used for subsequent reactions without further purification.

$^1$H-NMR (400 MHz, DMSO-$d_6$, δ/ppm): 5.12 (sept, 1H), 4.28 (q, 2H), 4.05 (t, 2H), 3.64 (t, 2H), 3.25 (s, 3H), 2.76 (s, 3H), 1.41 (d, 6H), 1.29 (t, 3H).

LC/MS (Method 17, ESIpos): $R_t$=2.17 min, m/z=355.13 [M+H]$^+$.

Example 499A

Ethyl 1-(2-methoxyethyl)-5-methyl-2,4-dioxo-3-(2,2,2-trifluoroethyl)-1,2,3,4-tetrahydrothieno[2,3-d]pyrimidine-6-carboxylate

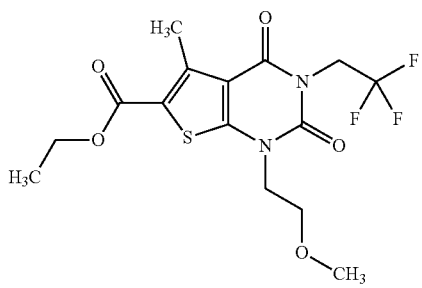 [SMILES: CCOC(=O)c1sc2c(c1C)c(=O)n(CC(F)(F)F)c(=O)n2CCOC]

1.64 g (11.9 mmol) of potassium carbonate were added to a solution of 1.60 g (4.76 mmol) of the compound from Ex. 495A in 35 ml of DMF, and the mixture was stirred at RT for 15 min. Then 1.32 g (9.52 mmol) of 2-bromoethyl methyl ether were added. The mixture was stirred first at RT for 3 days and then at 60° C. for 24 h. Thereafter, about 175 ml of water were added to the reaction mixture at RT. In the course of this, the product precipitated out. The mixture was stirred at RT for another 30 min, before the product was then filtered off with suction and washed with water. Drying under high vacuum gave 1.93 g (94% of theory, 92% purity) of the title compound, which was used for subsequent reactions without further purification.

$^1$H-NMR (400 MHz, DMSO-$d_6$, δ/ppm): 4.70 (q, 2H), 4.30 (q, 2H), 4.12 (t, 2H), 3.66 (t, 2H), 3.24 (s, 3H), 2.77 (s, 3H), 1.30 (t, 3H).

LC/MS (Method 17, ESIpos): $R_t$=2.07 min, m/z=395.09 [M+H]$^+$.

Example 500A

Ethyl 1-(2-methoxyethyl)-5-methyl-2,4-dioxo-3-[(2R)-1,1,1-trifluoropropan-2-yl]-1,2,3,4-tetrahydrothieno[2,3-d]pyrimidine-6-carboxylate

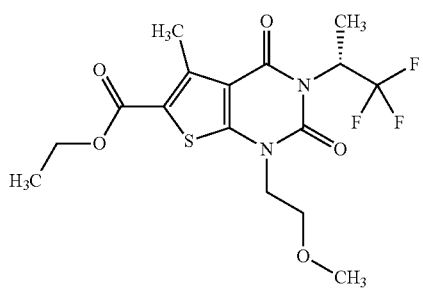 [SMILES: CCOC(=O)c1sc2c(c1C)c(=O)n([C@H](C)C(F)(F)F)c(=O)n2CCOC]

690 mg (5.0 mmol) of potassium carbonate were added to a solution of 1.0 g (2.85 mmol) of the compound from Ex. 496A in 15 ml of DMF, and the mixture was stirred at RT for 15 min. Then 555 mg (4.0 mmol) of 2-bromoethyl methyl ether were added. The mixture was stirred at 60° C. for about 18 h. Thereafter, about 75 ml of water were added to the reaction mixture at RT and extraction was effected with ethyl acetate. The organic extract was washed with sodium chloride solution, dried over anhydrous magnesium sulphate, filtered and concentrated. The remaining residue was purified by means of preparative HPLC (Method 8). After concentration of the product fractions and drying under high vacuum, 690 mg (59% of theory, 98% purity) of the title compound were obtained (>99% ee, chiral analytical HPLC).

$^1$H-NMR (400 MHz, DMSO-$d_6$, δ/ppm): 5.80-5.68 and 5.61-5.50 (2 m, tog. 1H), 4.29 (q, 2H), 4.13-4.06 (m, 2H), 3.68-3.62 (m, 2H), 3.25 (s, 3H), 2.77 (s, 3H), 1.69 and 1.64 (2 d, tog. 3H), 1.30 (t, 3H).

LC/MS (Method 1, ESIpos): $R_t$=1.16 min, m/z=409 [M+H]$^+$.

Chiral analytical HPLC [column: Daicel Chiralpak AZ-3, 3 μm, 50 mm×4.6 mm; eluent: heptane/ethanol 9:1; flow rate: 1 ml/min; temperature: 25° C.; detection: 220 nm]: $R_t$=1.05 min.

Specific optical rotation: $[\alpha]_D^{20}$=+14.5°·ml·dm$^{-1}$·g$^{-1}$ (methanol).

Example 501A

Ethyl 1-(2-methoxyethyl)-5-methyl-2,4-dioxo-3-[(2S)-1,1,1-trifluoropropan-2-yl]-1,2,3,4-tetrahydrothieno[2,3-d]pyrimidine-6-carboxylate

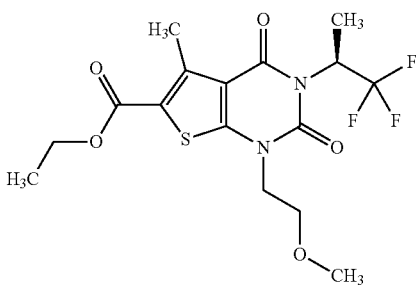 [SMILES: CCOC(=O)c1sc2c(c1C)c(=O)n([C@@H](C)C(F)(F)F)c(=O)n2CCOC]

493 mg (3.57 mmol) of potassium carbonate were added to a solution of 500 mg (1.43 mmol) of the compound from Ex. 497A in 10 ml of DMF, and the mixture was stirred at RT for 15 min. Then 397 mg (2.85 mmol) of 2-bromoethyl methyl ether were added. The mixture was stirred at 60° C. for about 18 h. Thereafter, about 50 ml of water were added to the reaction mixture at RT and extraction was effected with ethyl acetate. The organic extract was washed with sodium chloride solution, dried over anhydrous magnesium sulphate, filtered and concentrated. The remaining residue was purified by means of preparative HPLC (Method 8). After concentration of the product fractions and drying under high vacuum, 270 mg (46% of theory) of the title compound were obtained (>99% ee, chiral analytical HPLC).

$^1$H-NMR (400 MHz, DMSO-$d_6$, δ/ppm): 5.80-5.68 and 5.60-5.49 (2 m, tog. 1H), 4.29 (q, 2H), 4.13-4.06 (m, 2H), 3.68-3.62 (m, 2H), 3.25 (s, 3H), 2.76 (s, 3H), 1.69 and 1.64 (2 d, tog. 3H), 1.30 (t, 3H).

LC/MS (Method 17, ESIpos): $R_t$=2.23 min, m/z=409.10 [M+H]$^+$.

Chiral analytical HPLC [column: Daicel Chiralpak AZ-3, 3 μm, 50 mm×4.6 mm; eluent: heptane/ethanol 9:1; flow rate: 1 ml/min; temperature: 25° C.; detection: 220 nm]: $R_t$=1.10 min.

Specific optical rotation: $[α]_D^{20}$=−13.6°·ml·dm$^{-1}$·g$^{-1}$ (methanol).

Example 502A

Ethyl 4-methyl-2-{[(1,1,1-trifluoropropan-2-yl)carbamoyl]amino}thiophene-3-carboxylate
(Enantiomer 1)

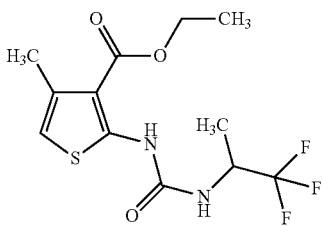 [SMILES: CCOC(=O)c1c(C)csc1NC(=O)NC(C)C(F)(F)F]

4.36 g (13.4 mmol) of the racemic compound from Ex. 437A were dissolved in 135 ml of isopropanol and, in 190 portions, separated into the enantiomers by preparative SFC-HPLC on a chiral phase [column: Daicel Chiralpak OX-H, 5 μm, 250 mm×30 mm; eluent: carbon dioxide/isopropanol 90:10; flow rate: 175 ml/min; temperature: 38° C.; detection: 210 nm]. After concentration of the product fractions and drying of the solids under high vacuum, 2.10 g (96% of theory) of Enantiomer 1 were obtained (>99% ee, chiral analytical HPLC).

$^1$H-NMR (400 MHz, DMSO-$d_6$, δ/ppm): 10.45 (s, 1H), 8.50 (d, 1H), 6.50 (s, 1H), 4.58-4.39 (m, 1H), 4.29 (q, 2H), 2.28 (d, 3H), 1.32 (t, 3H), 1.28 (d, 3H).

Chiral analytical SFC HPLC [column: Daicel Chiralcel QX, 3 μm, 50 mm×5 mm; eluent: carbon dioxide/isopropanol 95:5→50:50; flow rate: 3 ml/min; temperature: 40° C.; detection: 210 nm]: $R_t$=0.80 min.

Specific optical rotation: $[α]_D^{20}$=−8.29°·ml·dm$^{-1}$·g$^{-1}$ (methanol).

Example 503A

Ethyl 4-methyl-2-{[(1,1,1-trifluoropropan-2-yl)carbamoyl]amino}thiophene-3-carboxylate
(Enantiomer 2)

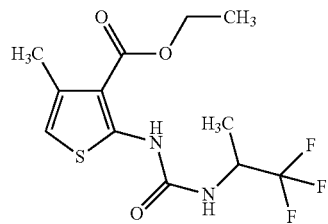 [SMILES: CCOC(=O)c1c(C)csc1NC(=O)NC(C)C(F)(F)F]

4.36 g (13.4 mmol) of the racemic compound from Ex. 437A were dissolved in 135 ml of isopropanol and, in 190 portions, separated into the enantiomers by preparative SFC-HPLC on a chiral phase [column: Daicel Chiralpak OX-H, 5 μm, 250 mm×30 mm; eluent: carbon dioxide/isopropanol 90:10; flow rate: 175 ml/min; temperature: 38° C.; detection: 210 nm]. After concentration of the product fractions and drying of the solids under high vacuum, 2.10 g (96% of theory) of Enantiomer 2 were obtained (>99% ee, chiral analytical HPLC).

$^1$H-NMR (400 MHz, DMSO-$d_6$, δ/ppm): 10.45 (s, 1H), 8.50 (d, 1H), 6.50 (s, 1H), 4.56-4.42 (m, 1H), 4.29 (q, 2H), 2.28 (s, 3H), 1.32 (t, 3H), 1.28 (d, 3H).

Chiral analytical SFC HPLC [column: Daicel Chiralcel QX, 3 μm, 50 mm×5 mm; eluent: carbon dioxide/isopropanol 95:5→50:50; flow rate: 3 ml/min; temperature: 40° C.; detection: 210 nm]: $R_t$=1.37 min.

Specific optical rotation: $[α]_D^{20}$=+7.40°·ml·dm$^{-1}$·g$^{-1}$ (methanol).

Example 504A

5-Methyl-3-(1,1,1-trifluoropropan-2-yl)thieno[2,3-d]pyrimidine-2,4(1H,3H)-dione (Enantiomer 1)

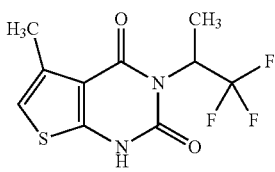 [SMILES: Cc1csc2[nH]c(=O)n(C(C)C(F)(F)F)c(=O)c12]

2.09 g (6.44 mmol) of the compound from Ex. 502A were dissolved in 20 ml of ethanol, and 4.8 ml (12.9 mmol) of a 21% solution of sodium ethoxide in ethanol were added. After the mixture had been stirred at 50° C. for 5 h, 14.8 ml (14.8 mmol) of 1 M hydrochloric acid were added. The resulting precipitate was filtered off with suction, washed with water until neutral and dried. 1.75 g (97% of theory) of the enantiomerically pure title compound were obtained (>99% ee, chiral analytical HPLC).

$^1$H-NMR (400 MHz, DMSO-$d_6$, δ/ppm): 12.40 and 12.26 (2 br. s, tog. 1H), 6.74 (2 s, tog. 1H), 5.78-5.66 and 5.58-5.46 (2 m, tog. 1H), 2.35 and 2.34 (2 s, tog. 3H), 1.67 and 1.64 (2 d, tog. 3H).

LC/MS (Method 17, ESIpos): $R_t$=1.60 min, m/z=279.04 [M+H]$^+$.

Chiral analytical HPLC [column: Daicel Chiralpak AS-3, 3 μm, 50 mm×4.6 mm; eluent: heptane/isopropanol 4:1; flow rate: 1 ml/min; temperature: 30° C.; detection: 220 nm]: $R_t$=1.07 min.

Specific optical rotation: $[α]_D^{20}$=−15.7°·ml·dm$^{-1}$·g$^{-1}$ (methanol).

Example 505A

5-Methyl-3-(1,1,1-trifluoropropan-2-yl)thieno[2,3-d]pyrimidine-2,4(1H,3H)-dione (Enantiomer 2)

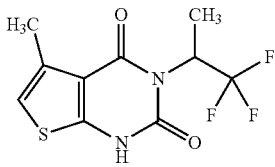 [SMILES: Cc1csc2[nH]c(=O)n(C(C)C(F)(F)F)c(=O)c12]

2.09 g (6.44 mmol) of the compound from Ex. 503A were dissolved in 20 ml of ethanol, and 4.8 ml (12.9 mmol) of a 21% solution of sodium ethoxide in ethanol were added. After the mixture had been stirred at 50° C. for 5 h, 14.8 ml (14.8 mmol) of 1 M hydrochloric acid were added. The resulting precipitate was filtered off with suction, washed with water until neutral and dried. 1.75 g (97% of theory) of the enantiomerically pure title compound were obtained (>99% ee, chiral analytical HPLC).

$^1$H-NMR (400 MHz, DMSO-$d_6$, δ/ppm): 12.40 and 12.27 (2 br. s, tog. 1H), 6.74 (2 s, tog. 1H), 5.78-5.66 and 5.58-5.46 (2 m, tog. 1H), 2.35 and 2.34 (2 s, tog. 3H), 1.67 and 1.64 (2 d, tog. 3H).

LC/MS (Method 17, ESIpos): $R_t$=1.60 min, m/z=279.04 [M+H]$^+$.

Chiral analytical HPLC [column: Daicel Chiralpak AS-3, 3 μm, 50 mm×4.6 mm; eluent: heptane/isopropanol 4:1; flow rate: 1 ml/min; temperature: 30° C.; detection: 220 nm]: $R_t$=1.00 min.

Specific optical rotation: $[α]_D^{20}$=+19.5°·ml·dm$^{-1}$·g$^{-1}$ (methanol).

Example 506A

5-Methyl-2,4-dioxo-3-(1,1,1-trifluoropropan-2-yl)-1,2,3,4-tetrahydrothieno[2,3-d]pyrimidine-6-carbaldehyde (Enantiomer 1)

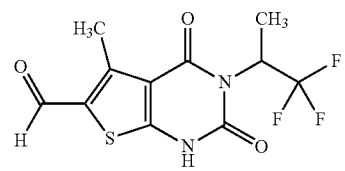 [SMILES: Cc1c(C=O)sc2[nH]c(=O)n(C(C)C(F)(F)F)c(=O)c12]

7.0 ml (75.0 mmol) of phosphorus oxychloride were added carefully to a solution of 1.74 g (6.25 mmol) of the compound from Ex. 504A in 4.8 ml (62.5 mmol) of DMF. After the strongly exothermic reaction had subsided, the mixture was stirred for another 15 min. The reaction mixture was then stirred cautiously into 250 ml of ice-water. After stirring for 1 h, the precipitated product was filtered off with suction, washed with water until neutral and dried. 1.79 g (93% of theory) of the enantiomerically pure title compound were obtained (>99% ee, chiral analytical HPLC).

$^1$H-NMR (400 MHz, DMSO-$d_6$, δ/ppm): 12.80 (br. s, 1H), 10.08 (s, 1H), 5.75-5.63 and 5.56-5.43 (2 m, tog. 1H), 2.76 and 2.75 (2 s, tog. 3H), 1.67 and 1.64 (2 d, tog. 3H).

LC/MS (Method 17, ESIpos): $R_t$=1.54 min, m/z=307.04 [M+H]$^+$.

Chiral analytical HPLC [column: Daicel Chiralpak IC-3, 3 μm, 50 mm×4.6 mm; eluent: heptane/ethanol 4:1; flow rate: 1 ml/min; temperature: 30° C.; detection: 220 nm]: $R_t$=1.99 min.

Specific optical rotation: $[α]_D^{20}$=−18.5°·ml·dm$^{-1}$·g$^{-1}$ (methanol).

Example 507A

5-Methyl-2,4-dioxo-3-(1,1,1-trifluoropropan-2-yl)-1,2,3,4-tetrahydrothieno[2,3-d]pyrimidine-6-carbaldehyde (Enantiomer 2)

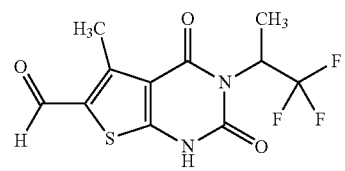 [SMILES: Cc1c(C=O)sc2[nH]c(=O)n(C(C)C(F)(F)F)c(=O)c12]

7.0 ml (75.0 mmol) of phosphorus oxychloride were added carefully to a solution of 1.74 g (6.25 mmol) of the compound from Ex. 505A in 4.8 ml (62.5 mmol) of DMF. After the strongly exothermic reaction had subsided, the mixture was stirred for another 15 min. The reaction mixture was then stirred cautiously into 250 ml of ice-water. After stirring for 1 h, the precipitated product was filtered off with suction, washed with water until neutral and dried. 1.78 g (92% of theory) of the enantiomerically pure title compound were obtained (>99% ee, chiral analytical HPLC).

$^1$H-NMR (400 MHz, DMSO-d$_6$, δ/ppm): 12.79 (br. s, 1H), 10.08 (s, 1H), 5.75-5.63 and 5.56-5.43 (2 m, tog. 1H), 2.76 and 2.75 (2 s, tog. 3H), 1.67 and 1.64 (2 d, tog. 3H).

LC/MS (Method 17, ESIpos): R$_t$=1.54 min, m/z=307.04 [M+H]$^+$.

Chiral analytical HPLC [column: Daicel Chiralpak IC-3, 3 μm, 50 mm×4.6 mm; eluent: heptane/ethanol 4:1; flow rate: 1 ml/min; temperature: 30° C.; detection: 220 nm]: R$_t$=1.58 min.

Specific optical rotation: $[α]_D^{20}$=+19.0°·ml·dm$^{-1}$·g$^{-1}$ (methanol).

Example 508A 1-(2-Methoxyethyl)-5-methyl-2,4-dioxo-3-(1,1,1-trifluoropropan-2-yl)-1,2,3,4-tetrahydrothieno[2,3-d]pyrimidine-6-carbaldehyde (Enantiomer 1)

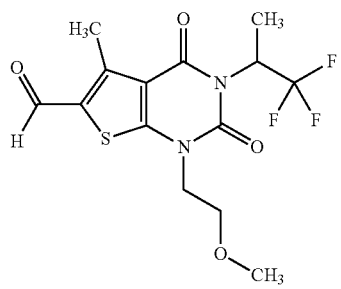 [SMILES: COCCn1c(=O)n(C(C)C(F)(F)F)c(=O)c2c(C)c(C=O)sc21]

2.01 g (14.5 mmol) of potassium carbonate were added to a solution of 1.78 g (5.81 mmol) of the compound from Ex. 506A in 35 ml of DMF, and the mixture was stirred at RT for 15 min. Then 1.62 g (11.6 mmol) of 2-bromoethyl methyl ether were added, and the mixture was stirred at 50° C. After about 18 h, a further 0.81 g (5.81 mmol) of 2-bromoethyl methyl ether were added and the stirring was continued at 50° C. for 2 days. After cooling to RT, about 200 ml of water were added and the mixture was then extracted with ethyl acetate. The organic extract was washed with saturated aqueous sodium chloride solution, dried over anhydrous magnesium sulphate, filtered and concentrated. The remaining residue was purified by MPLC (Biotage Isolera, cartridge with 100 g of silica gel, cyclohexane/ethyl acetate 5:1). The product fractions were combined, concentrated and dried under high vacuum. 1.32 g (62% of theory) of the enantiomerically pure title compound were obtained (>99% ee, chiral analytical HPLC).

$^1$H-NMR (400 MHz, DMSO-d$_6$, δ/ppm): 10.10 (s, 1H), 5.79-5.67 and 5.60-5.48 (2 m, tog. 1H), 4.15-4.07 (m, 2H), 3.68-3.62 (m, 2H), 3.25 (s, 3H), 2.78 (s, 3H), 1.69 and 1.65 (2 d, tog. 3H).

LC/MS (Method 1, ESIpos): R$_t$=0.97 min, m/z=365 [M+H]$^+$.

Chiral analytical HPLC [column: Daicel Chiralpak OJ-3, 3 μm, 50 mm×4.6 mm; eluent: heptane/ethanol 1:1; flow rate: 1 ml/min; temperature: 30° C.; detection: 220 nm]: R$_t$=1.82 min.

Specific optical rotation: $[α]_D^{20}$=−17.9°·ml·dm$^{-1}$·g$^{-1}$ (methanol).

Example 509A 1-(2-Methoxyethyl)-5-methyl-2,4-dioxo-3-(1,1,1-trifluoropropan-2-yl)-1,2,3,4-tetrahydrothieno[2,3-d]pyrimidine-6-carbaldehyde (Enantiomer 2)

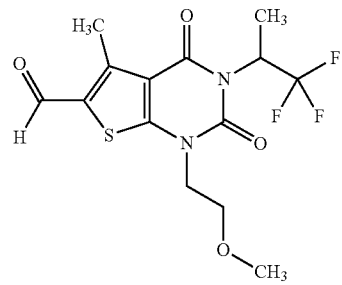 [SMILES: COCCn1c(=O)n(C(C)C(F)(F)F)c(=O)c2c(C)c(C=O)sc21]

2.0 g (14.4 mmol) of potassium carbonate were added to a solution of 1.77 g (5.78 mmol) of the compound from Ex. 507A in 35 ml of DMF, and the mixture was stirred at RT for 15 min. Then 1.61 g (11.6 mmol) of 2-bromoethyl methyl ether were added, and the mixture was stirred at 50° C. After about 18 h, a further 0.81 g (5.81 mmol) of 2-bromoethyl methyl ether were added and the stirring was continued at 50° C. for 2 days. After cooling to RT, about 200 ml of water were added and the mixture was then extracted with ethyl acetate. The organic extract was washed with saturated aqueous sodium chloride solution, dried over anhydrous magnesium sulphate, filtered and concentrated. The remaining residue was purified by MPLC (Biotage Isolera, cartridge with 100 g of silica gel, cyclohexane/ethyl acetate 5:1). The product fractions were combined, concentrated and dried under high vacuum. 1.42 g (67% of theory) of the enantiomerically pure title compound were obtained (>99% ee, chiral analytical HPLC).

$^1$H-NMR (400 MHz, DMSO-d$_6$, δ/ppm): 10.10 (s, 1H), 5.79-5.67 and 5.60-5.48 (2 m, tog. 1H), 4.16-4.07 (m, 2H), 3.70-3.61 (m, 2H), 3.25 (s, 3H), 2.78 (s, 3H), 1.69 and 1.65 (2 d, tog. 3H).

LC/MS (Method 1, ESIpos): R$_t$=0.97 min, m/z=365 [M+H]$^+$.

Chiral analytical HPLC [column: Daicel Chiralpak OJ-3, 3 μm, 50 mm×4.6 mm; eluent: heptane/ethanol 1:1; flow rate: 1 ml/min; temperature: 30° C.; detection: 220 nm]: R$_t$=1.65 min.

Specific optical rotation: $[α]_D^{20}$=+18.8°·ml·dm$^{-1}$·g$^{-1}$ (methanol).

Example 510A

6-[Dideutero(hydroxy)methyl]-3-isopropyl-1-(2-methoxyethyl)-5-methylthieno[2,3-d]pyrimidine-2,4(1H,3H)-dione

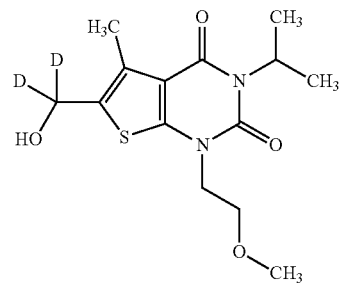 [SMILES: [2H]C([2H])(O)c1sc2c(c1C)c(=O)n(C(C)C)c(=O)n2CCOC]

At -78° C., 2.4 ml (2.35 mmol) of a 1 M solution of lithium aluminium deuteride in THF were added dropwise to a solution of 1.03 g (2.61 mmol, 90% purity) of the compound from Example 498A in 28 ml of THF. Subsequently, the reaction mixture was stirred at 0° C. for 1 h, before 1.2 ml of water, 9 ml of 1 M sodium hydroxide solution and a little kieselguhr were added and the cooling bath was removed. The precipitate formed was filtered off with suction and washed thoroughly with THF. The filtrate combined with the wash liquid was concentrated to dryness. The remaining residue was taken up in ethyl acetate and washed successively with water and saturated aqueous sodium chloride solution. After drying over anhydrous magnesium sulphate, the mixture was filtered and concentrated. The crude product was purified by MPLC (Biotage Isolera, SNAP KP-Sil cartridge with 50 g of silica gel, cyclohexane/ethyl acetate 90:10→30:70). The product fractions were combined and concentrated, and the residue was dried under high vacuum. 680 mg (80% of theory, 98% purity) of the title compound were obtained.

$^1$H-NMR (400 MHz, DMSO-d$_6$, δ/ppm): 5.49 (s, 1H), 5.14 (sept, 1H), 4.01 (t, 2H), 3.63 (t, 2H), 3.31 (s, 3H), 2.31 (s, 3H), 1.40 (d, 6H).

LC/MS (Method 1, ESIpos): R$_t$=0.75 min, m/z=315 [M+H]$^+$.

Example 511A

6-[Dideutero(hydroxy)methyl]-1-(2-methoxyethyl)-5-methyl-3-(2,2,2-trifluoroethyl)thieno[2,3-d]pyrimidine-2,4(1H,3H)-dione

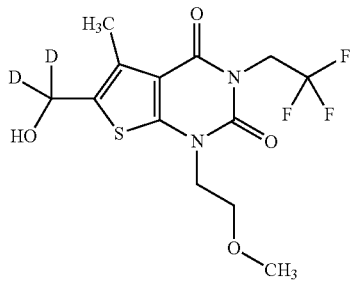 [SMILES: [2H]C([2H])(O)c1sc2c(c1C)c(=O)n(CC(F)(F)F)c(=O)n2CCOC]

At -78° C., 4 ml (4.03 mmol) of a 1 M solution of lithium aluminium deuteride in THF were added dropwise to a solution of 1.92 g (4.48 mmol, 92% purity) of the compound from Example 499A in 47 ml of THF. Subsequently, the reaction mixture was stirred at 0° C. for 1 h, before 1.2 ml of water, 9 ml of 1 M sodium hydroxide solution and a little kieselguhr were added and the cooling bath was removed. The precipitate formed was filtered off with suction and washed thoroughly with THF. The filtrate combined with the wash liquid was concentrated to dryness. The remaining residue was taken up in ethyl acetate and washed successively with water and saturated aqueous sodium chloride solution. After drying over anhydrous magnesium sulphate, the mixture was filtered and concentrated. The crude product was first prepurified by means of MPLC (Biotage Isolera, SNAP KP-Sil cartridge with 100 g of silica gel, cyclohexane/ethyl acetate 90:10→30:70). The product-containing fractions were concentrated and the residue was purified further by means of preparative HPLC (Method 8). Reconcentration of the product fractions and drying under high vacuum gave 620 mg (34% of theory, 88% purity) of the title compound, which was used for subsequent reactions without further purification.

$^1$H-NMR (400 MHz, DMSO-d$_6$, δ/ppm): 5.57 (s, 1H), 4.70 (q, 2H), 4.08 (t, 2H), 3.65 (t, 2H), 3.24 (s, 3H), 2.32 (s, 3H).

LC/MS (Method 1, ESIpos): R$_t$=0.76 min, m/z=355 [M+H]$^+$.

Example 512A

6-[Dideutero(hydroxy)methyl]-1-(2-methoxyethyl)-5-methyl-3-[(2R)-1,1,1-trifluoropropan-2-yl]thieno[2,3-d]pyrimidine-2,4(1H,3H)-dione

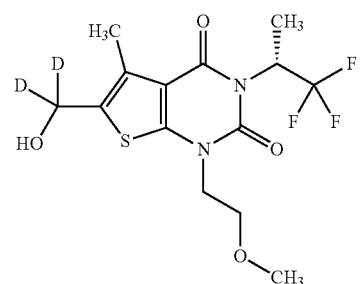

At -78° C., 1.5 ml (1.5 mmol) of a 1 M solution of lithium aluminium deuteride in THF were added dropwise to a solution of 680 mg (1.67 mmol) of the compound from Example 500A in 20 ml of THF. Subsequently, the reaction mixture was stirred at 0° C. for 1 h, before 0.8 ml of water, 5 ml of 1 M sodium hydroxide solution and a little kieselguhr were added and the cooling bath was removed. The precipitate formed was filtered off with suction and washed thoroughly with THF. The filtrate combined with the wash liquid was concentrated to dryness. The remaining residue was taken up in ethyl acetate and washed successively with water and saturated aqueous sodium chloride solution. After drying over anhydrous magnesium sulphate, the mixture was filtered and concentrated. The crude product was purified by MPLC (Biotage Isolera, SNAP KP-Sil cartridge with 50 g of silica gel, cyclohexane/ethyl acetate 1:1). After concentration of the product fractions and drying under high vacuum, 462 mg (75% of theory) of the title compound were obtained (>99% ee, chiral analytical HPLC).

$^1$H-NMR (400 MHz, DMSO-d$_6$, δ/ppm): 5.81-5.69 and 5.62-5.51 (2 m, tog. 1H), 5.55 (s, 1H), 4.10-3.98 (m, 2H), 3.69-3.59 (m, 2H), 3.24 (s, 3H), 2.32 and 2.30 (2 s, tog. 3H), 1.68 and 1.64 (2 d, tog. 3H).

LC/MS (Method 17, ESIpos): R$_t$=1.59 min, m/z=369.11 [M+H]$^+$.

Chiral analytical HPLC [column: Daicel Chiralpak AS-3, 3 μm, 50 mm×4.6 mm; eluent: heptane/isopropanol 4:1; flow rate: 1 ml/min; temperature: 25° C.; detection: 220 nm]: R$_t$=2.52 min.

Specific optical rotation: [α]$_D^{20}$=+12.4°·ml·dm$^{-1}$·g$^{-1}$ (methanol).

Example 513A

6-[Dideutero(hydroxy)methyl]-1-(2-methoxyethyl)-5-methyl-3-[(2S)-1,1,1-trifluoropropan-2-yl]thieno[2,3-d]pyrimidine-2,4(1H,3H)-dione

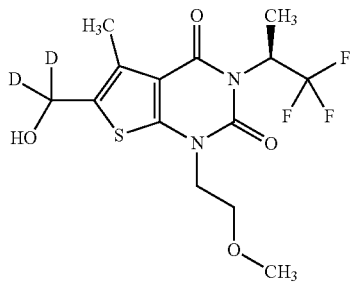 [SMILES: [2H]C([2H])(O)c1sc2c(c1C)c(=O)n([C@@H](C)C(F)(F)F)c(=O)n2CCOC]

At −78° C., 542 µl (0.542 mmol) of a 1 M solution of lithium aluminium deuteride in THF were added dropwise to a solution of 246 mg (0.602 mmol) of the compound from Example 501A in 7 ml of THF. Subsequently, the reaction mixture was stirred at 0° C. for 1 h, before 1.2 ml of water, 9 ml of 1 M sodium hydroxide solution and a little kieselguhr were added and the cooling bath was removed. The precipitate formed was filtered off with suction and washed thoroughly with THF. The filtrate combined with the wash liquid was concentrated to dryness. The remaining residue was taken up in ethyl acetate and washed successively with water and saturated aqueous sodium chloride solution. After drying over anhydrous magnesium sulphate, the mixture was filtered and concentrated. The crude product was purified by MPLC (Biotage Isolera, SNAP KP-Sil cartridge with 25 g of silica gel, cyclohexane/ethyl acetate 90:10→0:100). After concentration of the product fractions and drying under high vacuum, 164 mg (73% of theory) of the title compound were obtained (>99% ee, chiral analytical HPLC).

$^1$H-NMR (400 MHz, DMSO-$d_6$, δ/ppm): 5.81-5.69 and 5.62-5.52 (2 m, tog. 1H), 5.55 (s, 1H), 4.08-4.01 (m, 2H), 3.67-3.61 (m, 2H), 3.24 (s, 3H), 2.32 and 2.30 (2 s, tog. 3H), 1.68 and 1.64 (2 d, tog. 3H).

LC/MS (Method 17, ESIpos): $R_t$=1.59 min, m/z=369.11 [M+H]$^+$.

Chiral analytical HPLC [column: Daicel Chiralpak AS-3, 3 µm, 50 mm×4.6 mm; eluent: heptane/isopropanol 4:1; flow rate: 1 ml/min; temperature: 25° C.; detection: 220 nm]: $R_t$=1.79 min.

Specific optical rotation: $[\alpha]_D^{20}$=−7.1°·ml·dm$^{-1}$·g$^{-1}$ (methanol).

Example 514A

6-{[(2-Aminoethyl)amino]methyl}-1-(2-methoxyethyl)-5-methyl-3-(1,1,1-trifluoropropan-2-yl)thieno[2,3-d]pyrimidine-2,4(1H,3H)-dione (Enantiomer 1)

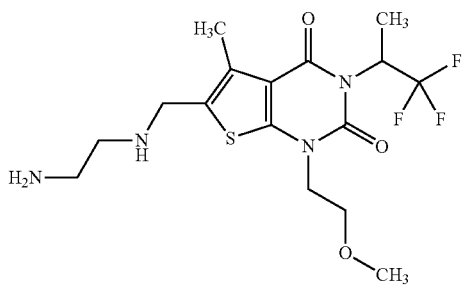 [SMILES: COCCn1c(=O)n(C(C)C(F)(F)F)c(=O)c2c(C)c(CNCCN)sc21]

650 mg (1.78 mmol) of the compound from Ex. 508A were dissolved in a mixture of 18 ml of methanol and 6 ml of dichloromethane, and 716 µl (10.7 mmol) of 1,2-diaminoethane and 409 µl (7.14 mmol) of acetic acid were added at RT. After 30 min, 448 mg (7.14 mmol) of sodium cyanoborohydride were added, and the reaction mixture was heated to 60° C. After about 15 h, the reaction mixture was allowed to cool down again to RT. Subsequently, about 50 ml of 2 M sodium hydroxide solution were added and thorough extraction was effected with ethyl acetate. The organic extract was washed with saturated sodium chloride solution, dried over anhydrous magnesium sulphate, filtered and concentrated on a rotary evaporator. The crude product thus obtained, after drying under high vacuum, gave 910 mg (99% of theory, 80% purity) of the enantiomerically pure title compound (>99% ee, chiral analytical HPLC), which was used for subsequent reactions without further purification.

LC/MS (Method 2, ESIpos): $R_t$=0.92 min, m/z=409 [M+H]$^+$.

Chiral analytical HPLC [column: Daicel Chiralpak IC-3, 3 µm, 50 mm×4.6 mm; eluent: heptane/isopropanol 80:20+0.2% diethylamine; flow rate: 1 ml/min; temperature: 30° C.; detection: 220 nm]: $R_t$=2.86 min.

Example 515A

6-{[(2-Aminoethyl)amino]methyl}-1-(2-methoxyethyl)-5-methyl-3-(1,1,1-trifluoropropan-2-yl)thieno[2,3-d]pyrimidine-2,4(1H,3H)-dione (Enantiomer 2)

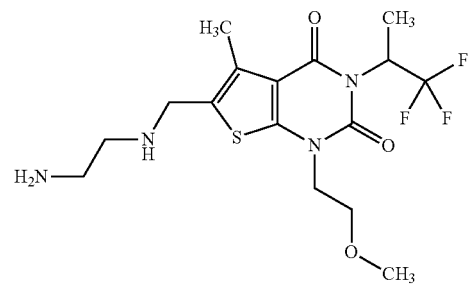 [SMILES: COCCn1c(=O)n(C(C)C(F)(F)F)c(=O)c2c(C)c(CNCCN)sc21]

700 mg (1.92 mmol) of the compound from Ex. 509A were dissolved in a mixture of 18 ml of methanol and 6 ml of dichloromethane, and 771 µl (11.5 mmol) of 1,2-diaminoethane and 440 µl (7.68 mmol) of acetic acid were added at RT. After 30 min, 483 mg (7.68 mmol) of sodium cyanoborohydride were added, and the reaction mixture was heated to 60° C. After about 15 h, the reaction mixture was allowed to cool down again to RT. Subsequently, about 50 ml of 2 M sodium hydroxide solution were added and thorough extraction was effected with ethyl acetate. The organic extract was washed with saturated sodium chloride solution, dried over anhydrous magnesium sulphate, filtered and concentrated on a rotary evaporator. The crude product thus obtained, after drying under high vacuum, gave 920 mg (93% of theory, 80% purity) of the enantiomerically pure title compound (>99% ee, chiral analytical HPLC), which was used for subsequent reactions without further purification.

LC/MS (Method 2, ESIpos): $R_t$=0.96 min, m/z=409 [M+H]$^+$.

Chiral analytical HPLC [column: Daicel Chiralpak IC-3, 3 µm, 50 mm×4.6 mm; eluent: heptane/isopropanol 80:20+

0.2% diethylamine; flow rate: 1 ml/min; temperature: 30° C.; detection: 220 nm]: $R_t$=2.62 min.

Example 516A

6-{[(2,2-Dimethoxyethyl)amino]methyl}-3-(2,2-dimethylpropyl)-5-methyl-1-(3,3,3-trifluoropropyl)thieno[2,3-d]pyrimidine2,4(1H,3H)-dione

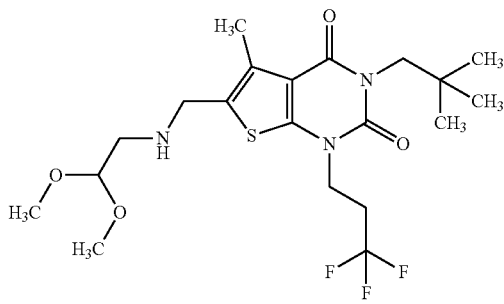 [SMILES: COC(CNCc1sc2c(c1C)c(=O)n(CC(C)(C)C)c(=O)n2CCC(F)(F)F)OC]

100 mg (0.255 mmol, 96% purity) of the compound from Ex. 291A were dissolved in 6 ml of dichloromethane, and 42 µl (0.383 mmol) of 2,2-dimethoxyethanamine were added. The mixture was heated to 35° C. for 1 h. After cooling to RT, 162 mg (0.765 mmol) of sodium triacetoxyborohydride were added, and stirring of the mixture was continued at RT. After 18 h, the reaction mixture was diluted with dichloromethane and washed successively with saturated sodium hydrogencarbonate solution and saturated sodium chloride solution. After drying over anhydrous magnesium sulphate, the mixture was filtered and the filtrate was concentrated to dryness. 95 mg (62% of theory, 77% purity) of the title compound were obtained, which was used for subsequent reactions without further purification.

LC/MS (Method 1, ESIpos): $R_t$=0.78 min, m/z=466 [M+H]$^+$.

Example 517A

6-{[(2,2-Dimethoxyethyl)amino]methyl}-3-(2,2-dimethylpropyl)-1-(2-methoxyethyl)-5-methylthieno[2,3-d]pyrimidine-2,4(1H,3H)-dione

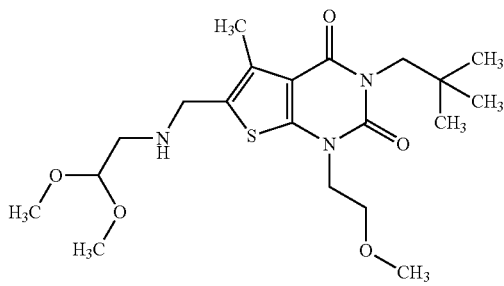 [SMILES: COCCn1c(=O)n(CC(C)(C)C)c(=O)c2c(C)c(CNCC(OC)OC)sc21]

100 mg (0.269 mmol, 91% purity) of the compound from Ex. 293A were dissolved in 6 ml of dichloromethane, and 44 µl (0.403 mmol) of 2,2-dimethoxyethanamine were added. The mixture was heated to 35° C. for 1 h. After cooling to RT, 171 mg (0.807 mmol) of sodium triacetoxyborohydride were added, and stirring of the mixture was continued at RT. After 18 h, the reaction mixture was diluted with dichloromethane and washed successively with saturated sodium hydrogencarbonate solution and saturated sodium chloride solution. After drying over anhydrous magnesium sulphate, the mixture was filtered and the filtrate was evaporated to dryness. 108 mg (78% of theory, 83% purity) of the title compound were obtained, which was used for subsequent reactions without further purification.

LC/MS (Method 1, ESIpos): $R_t$=0.70 min, m/z=324 [M+H—$C_4H_{11}NO_2$]$^+$.

Example 518A

6-{[(2,2-Dimethoxyethyl)amino]methyl}-3-(2,2-dimethylpropyl)-5-methyl-1-(tetrahydrofuran-2-ylmethyl)thieno[2,3-d]pyrimidine-2,4(1H,3H)-dione (racemate)

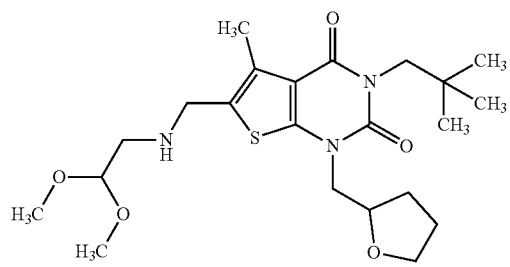 [SMILES: COC(CNCc1sc2c(c1C)c(=O)n(CC(C)(C)C)c(=O)n2CC1CCCO1)OC]

100 mg (0.230 mmol, 84% purity) of the compound from Ex. 443A were dissolved in 5 ml of dichloromethane, and 37 µl (0.346 mmol) of 2,2-dimethoxyethanamine were added. The mixture was heated to 35° C. for 1 h. After cooling to RT, 146 mg (0.691 mmol) of sodium triacetoxyborohydride were added, and stirring of the mixture was continued at RT. After 18 h, the reaction mixture was diluted with dichloromethane and washed successively with saturated sodium hydrogencarbonate solution and saturated sodium chloride solution. After drying over anhydrous magnesium sulphate, the mixture was filtered and the filtrate was evaporated to dryness. 107 mg (83% of theory, 81% purity) of the title compound were obtained, which was used for subsequent reactions without further purification.

LC/MS (Method 1, ESIpos): $R_t$=0.71 min, m/z=350 [M+H—$C_4H_{11}NO_2$]$^+$.

Example 519A 1-(2,2-Dimethoxyethyl)-1-{[3-(2,2-dimethylpropyl)-5-methyl-2,4-dioxo-1-(3,3,3-trifluoropropyl)-1,2,3,4-tetrahydrothieno[2,3-d]pyrimidin-6-yl]methyl}urea

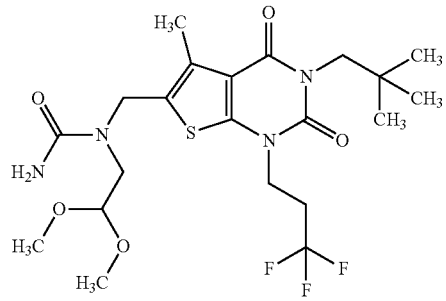 [SMILES: COC(CN(Cc1sc2c(c1C)c(=O)n(CC(C)(C)C)c(=O)n2CCC(F)(F)F)C(N)=O)OC]

To a solution of 93 mg (0.157 mmol, 78% purity) of the compound from Ex. 516A in 1.6 ml of methanol were added, at RT, first 29 mg (0.360 mmol) of potassium cyanate and then 23 µl (0.266 mmol) of perchloric acid (70% in water). After 1 h, the reaction mixture was admixed with water and with aqueous sodium hydrogencarbonate solution and then extracted with ethyl acetate. The organic extract was washed successively with saturated sodium hydrogencarbonate solution and saturated sodium chloride solution, dried over anhydrous magnesium sulphate, filtered and concentrated. After the residue obtained had been dried under high vacuum, 80 mg (79% of theory, 79% purity) of the title compound were obtained, which was used for subsequent reactions without further purification.

LC/MS (Method 17, ESIneg): $R_t$=1.97 min, m/z=553.19 [M−H+HCO$_2$H]$^-$.

Example 520A 1-(2,2-Dimethoxyethyl)-1-{[3-(2,2-dimethylpropyl)-1-(2-methoxyethyl)-5-methyl-2,4-dioxo-1,2,3,4-tetrahydrothieno[2,3-d]pyrimidin-6-yl]methyl}urea

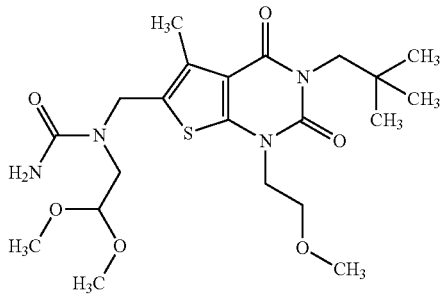 [SMILES: COCCn1c(=O)n(CC(C)(C)C)c(=O)c2c(C)c(CN(CC(OC)OC)C(N)=O)sc21]

To a solution of 106 mg (0.193 mmol, 78% purity) of the compound from Ex. 517A in 2 ml of methanol were added, at RT, first 36 mg (0.445 mmol) of potassium cyanate and then 28 µl (0.329 mmol) of perchloric acid (70% in water). After 1 h, the reaction mixture was admixed with water and with saturated sodium hydrogencarbonate solution and then extracted with ethyl acetate. The organic extract was washed with saturated sodium chloride solution, dried over anhydrous magnesium sulphate, filtered and concentrated. After the residue obtained had been dried under high vacuum, 95 mg (74% of theory, 71% purity) of the title compound were obtained, which was used for subsequent reactions without further purification.

LC/MS (Method 17, ESIneg): $R_t$=1.74 min, m/z=515.22 [M−H+HCO$_2$H]$^-$.

Example 521A 1-(2,2-Dimethoxyethyl)-1-{[3-(2,2-dimethylpropyl)-5-isopropyl-2,4-dioxo-1-(tetrahydrofuran-2-ylmethyl)-1,2,3,4-tetrahydrothieno[2,3-d]pyrimidin-6-yl]methyl}urea (racemate)

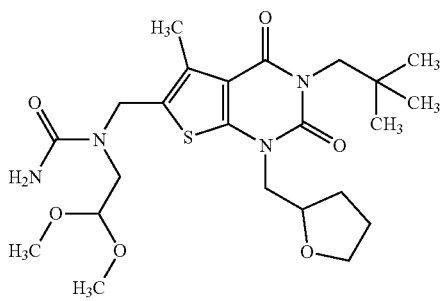 [SMILES: COC(CN(Cc1sc2c(c1C)c(=O)n(CC(C)(C)C)c(=O)n2CC1CCCO1)C(N)=O)OC]

To a solution of 106 mg (0.189 mmol, 81% purity) of the compound from Ex. 518A in 2 ml of methanol were added, at RT, first 35 mg (0.435 mmol) of potassium cyanate and then 28 µl (0.322 mmol) of perchloric acid (70% in water). After 1 h, the reaction mixture was admixed with water and with saturated sodium hydrogencarbonate solution and then extracted with ethyl acetate. The organic extract was washed successively with saturated sodium hydrogencarbonate solution and saturated sodium chloride solution, dried over anhydrous magnesium sulphate, filtered and concentrated. After the residue obtained had been dried under high vacuum, 93 mg (81% of theory, 82% purity) of the title compound were obtained, which was used for subsequent reactions without further purification.

LC/MS (Method 1, ESIneg): $R_t$=1.83 min, m/z=541.23 [M−H+HCO$_2$H]$^-$.

Example 522A

1-{[3-Ethyl-5-methyl-2,4-dioxo-1-(3,3,3-trifluoropropyl)-1,2,3,4-tetrahydrothieno[2,3-d]pyrimidin-6-yl]methyl}hydrazinecarboxamide

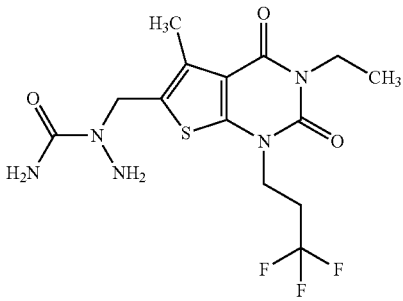 [SMILES: CCn1c(=O)c2c(C)c(CN(N)C(N)=O)sc2n(CCC(F)(F)F)c1=O]

1.22 g (2.47 mmol) of the compound from Example 474A were dissolved in 20 ml of chloroform, and 10 ml of trifluoroacetic acid were added at 0° C. After the reaction mixture had been stirred at RT for 1 h, it was concentrated to dryness. The remaining residue was taken up in ethyl acetate and extracted by shaking with saturated aqueous sodium carbonate solution. After the organic phase had been concentrated and the residue had been dried under high vacuum, 1.09 g (89% of theory) of the title compound were obtained.

$^1$H-NMR (400 MHz, DMSO-d$_6$, δ/ppm): 6.16 (br. s, 2H), 4.63 (s, 2H), 4.41 (s, 2H), 4.11 (t, 2H), 3.91 (q, 2H), 2.84-2.68 (m, 3H), 2.43 (s, 3H), 1.12 (t, 3H).

LC/MS (Method 1, ESIpos): $R_t$=0.73 min, m/z=394 [M+H]$^+$.

Example 523A

2-Acetyl-1-{[3-ethyl-5-methyl-2,4-dioxo-1-(3,3,3-trifluoropropyl)-1,2,3,4-tetrahydrothieno[2,3-d]pyrimidin-6-yl]methyl}hydrazinecarboxamide

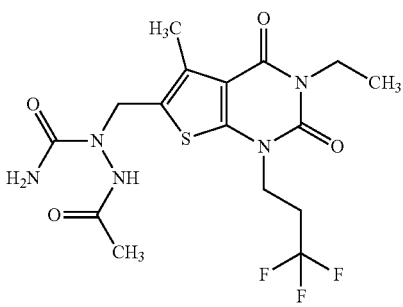 [SMILES: CCn1c(=O)c2c(C)c(CN(NC(C)=O)C(N)=O)sc2n(CCC(F)(F)F)c1=O]

70 mg (0.179 mmol) of the compound from Ex. 522A were dissolved in 5 ml of dichloromethane, and 30 μl (0.215 mmol) of triethylamine and 13 μl (0.179 mmol) of acetyl chloride were added. After stirring at RT for 4 h, a further 50 μl (0.358 mmol) of triethylamine and 19 μl (0.268 mmol) of acetyl chloride were added. After stirring at RT for a further 16 h, the reaction mixture was diluted with dichloromethane and washed with water. The organic phase was concentrated, and the product was isolated by means of preparative HPLC (Method 8). After concentration of the product fractions and drying under high vacuum, 12 mg (15% of theory) of the title compound were obtained.

$^1$H-NMR (400 MHz, DMSO-$d_6$, δ/ppm): 9.78 (s, 1H), 6.28 (s, 2H), 5.19-4.20 (broad, 2H), 4.13 (t, 2H), 3.91 (q, 2H), 2.85-2.68 (m, 2H), 2.32 (s, 3H), 1.82 (s, 3H), 1.12 (t, 3H).

LC/MS (Method 17, ESIneg): $R_t$=1.22 min, m/z=434.11 [M−H]$^-$.

WORKING EXAMPLES

Example 1

1-(2-Methoxyethyl)-5-methyl-6-[(2-oxoazetidin-1-yl)methyl]-3-(2-phenylethyl)thieno[2,3-d]pyrimidine-2,4(1H,3H)-dione

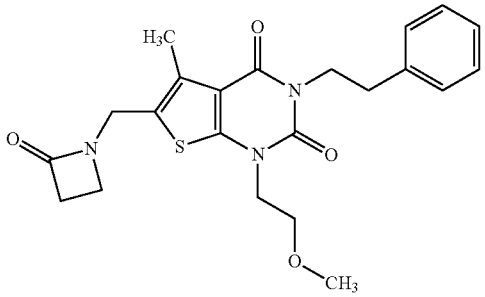 [SMILES: COCCn1c(=O)n(CCc2ccccc2)c(=O)c2c(C)c(CN3CCC3=O)sc21]

To a solution of 80 mg (0.214 mmol) of the compound from Ex. 138A in 1.6 ml of dichloromethane were added, at 0° C., 74 μl (0.427 mmol) of N,N-diisopropylethylamine and 16 μl (0.224 mmol) of thionyl chloride. After 20 min, a solution of 46 mg (0.641 mmol) of 2-azetidinone in 1.6 ml of THF, to which 27 mg (0.641 mmol) of sodium hydride (60% suspension in mineral oil) had been added and which had been stirred at RT for 30 min beforehand, was added. Subsequently, the reaction mixture was stirred at RT for 2 h. All the volatile constituents were then removed on a rotary evaporator. The remaining residue was separated into its components by means of preparative HPLC (Method 8). After concentration of the product fractions and drying under high vacuum, 33 mg (34% of theory, 95% purity) of the title compound were obtained.

$^1$H-NMR (400 MHz, DMSO-$d_6$, δ/ppm): 7.35-7.27 (m, 2H), 7.26-7.17 (m, 3H), 4.45 (s, 2H), 4.13-3.97 (m, 4H), 3.61 (t, 2H), 3.24 (s, 3H), 3.16 (t, 2H), 2.88 (t, 2H), 2.86-2.78 (m, 2H), 2.39 (s, 3H).

LC/MS (Method 1, ESIpos): $R_t$=1.02 min, m/z=428 [M+H]$^+$.

Example 2

3-Ethyl-5-methyl-6-[(2-oxoazetidin-1-yl)methyl]-1-(3,3,3-trifluoropropyl)thieno[2,3-d]pyrimidine-2,4(1H,3H)-dione

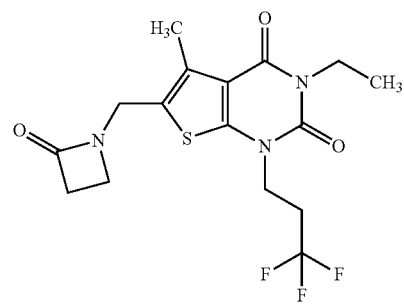 [SMILES: CCn1c(=O)c2c(C)c(CN3CCC3=O)sc2n(CCC(F)(F)F)c1=O]

To a solution of 85 mg (1.19 mmol) of 2-azetidinone in 1.6 ml of THF were added 48 mg (1.19 mmol) of sodium hydride (60% suspension in mineral oil), then the mixture was heated to 60° C. for 60 min and subsequently cooled back down to RT ("Solution 1"). To a solution of 80 mg (0.238 mmol) of the compound from Ex. 140A in 1.6 ml of dichloromethane in another reaction vessel were added, at 0° C., 83 μl (0.476 mmol) of N,N-diisopropylethylamine and 18 μl (0.250 mmol) of thionyl chloride. After 20 min at 0° C., Solution 1 was added and the cooling bath was removed. The reaction mixture was stirred at RT for about 18 h. All the volatile constituents were then removed on a rotary evaporator. The remaining residue was separated into its components by means of preparative HPLC (Method 10). After concentration of the product fractions and drying under high vacuum, 5 mg (5% of theory, 92% purity) of the title compound were obtained.

$^1$H-NMR (500 MHz, DMSO-$d_6$, δ/ppm): 4.46 (s, 2H), 4.11 (t, 2H), 3.91 (q, 2H), 3.16 (t, 2H), 2.87 (t, 2H), 2.83-2.71 (m, 2H), 2.40 (s, 3H), 1.12 (t, 3H).

LC/MS (Method 1, ESIpos): $R_t$=0.93 min, m/z=390 [M+H]$^+$.

Example 3

1-(2-Methoxyethyl)-5-methyl-6-[(2-oxopyrrolidin-1-yl)methyl]-3-(2-phenylethyl)thieno[2,3-d]pyrimidine-2,4(1H,3H)-dione

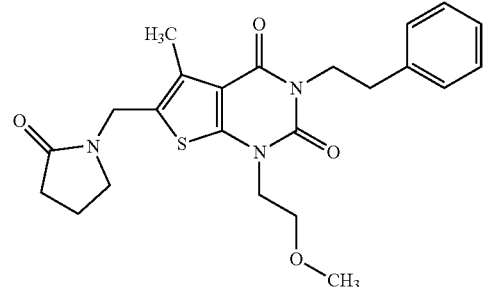

Analogously to the method described in Ex. 1, 100 mg (0.267 mmol) of the compound from Ex. 138A and 113 mg (1.34 mmol) of 2-pyrrolidinone were used to obtain 55 mg (47% of theory) of the title compound.

$^1$H-NMR (400 MHz, DMSO-d$_6$, δ/ppm): 7.35-7.27 (m, 2H), 7.26-7.17 (m, 3H), 4.48 (s, 2H), 4.12-4.03 (m, 2H), 4.01 (t, 2H), 3.60 (t, 2H), 3.29 (t, 2H, partially obscured by the water signal), 3.24 (s, 3H), 2.88-2.78 (m, 2H), 2.41 (s, 3H), 2.25 (t, 2H), 1.95-1.87 (m, 2H).

LC/MS (Method 1, ESIpos): R$_t$=1.03 min, m/z=442 [M+H]$^+$.

Example 4

3-Ethyl-5-methyl-6-[(2-oxopyrrolidin-1-yl)methyl]-1-(3,3,3-trifluoropropyl)thieno[2,3-d]pyrimidine-2,4(1H,3H)-dione

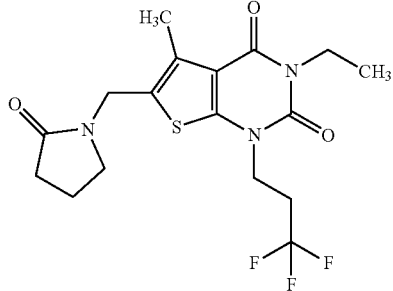

Analogously to the method described in Ex. 2, 80 mg (0.238 mmol) of the compound from Ex. 140A and a total of 170 mg (2.00 mmol) of 2-pyrrolidinone were used to obtain 28 mg (29% of theory) of the title compound. In a departure from the method described above, the solution of the deprotonated 2-pyrrolidinone was added here in two portions: the first portion as described above and the second portion after 18 h of reaction time. Thereafter, the reaction mixture was stirred at RT for a further 2 days.

$^1$H-NMR (400 MHz, DMSO-d$_6$, δ/ppm): 4.49 (s, 2H), 4.09 (t, 2H), 3.90 (q, 2H), 3.29 (t, 2H), 2.87-2.68 (m, 2H), 2.42 (s, 3H), 2.25 (t, 2H), 1.94-1.87 (m, 2H), 1.11 (t, 3H).

LC/MS (Method 1, ESIpos): R$_t$=0.91 min, m/z=404 [M+H]$^+$.

Example 5

1-(2-Methoxyethyl)-6-[(2-oxopyrrolidin-1-yl)methyl]-3-(2-phenylethyl)-5-(trifluoromethyl)thieno[2,3-d]pyrimidine-2,4(1H,3H)-dione

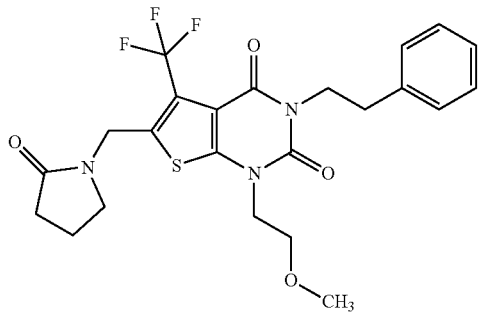

99 mg (1.16 mmol) of 2-pyrrolidinone were dissolved in 2 ml of DMF, 45 mg (1.12 mmol) of sodium hydride (60% suspension in mineral oil) were added and the mixture was stirred at RT for 25 min ("Mixture 1"). In another reaction vessel, 100 mg (0.224 mmol) of the compound from Example 181A were dissolved in 1.5 ml of DMF, and 1 ml of Mixture 1 was added dropwise at 0° C. After 30 min at RT, the reaction mixture was separated into its components directly by means of preparative HPLC (Method 9). Concentration of the product fractions, stirring of the residue with pentane and filtration with suction and drying of the solids under high vacuum gave 53 mg (47% of theory) of the title compound.

$^1$H-NMR (400 MHz, DMSO-d$_6$, δ/ppm): 7.35-7.27 (m, 2H), 7.26-7.16 (m, 3H), 4.70 (s, 2H), 4.14-3.98 (m, 4H), 3.60 (t, 2H), 3.40 (t, 2H), 3.24 (s, 3H), 2.89-2.77 (m, 2H), 2.31 (t, 2H), 2.03-1.95 (m, 2H).

LC/MS (Method 1, ESIpos): R$_t$=1.07 min, m/z=496 [M+H]$^+$.

Example 6

3-Ethyl-5-methyl-6-[(3-methyl-2-oxopyrrolidin-1-yl)methyl]-1-(3,3,3-trifluoropropyl)thieno[2,3-d]pyrimidine-2,4(1H,3H)-dione (racemate)

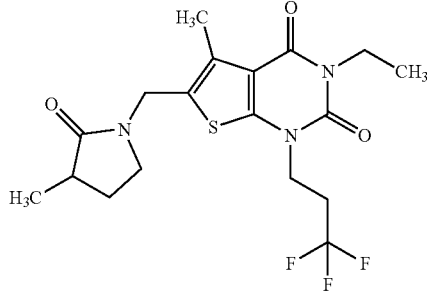 [SMILES: CCn1c(=O)c2c(C)c(CN3CCC(C)C3=O)sc2n(CCC(F)(F)F)c1=O]

Analogously to the method described in Ex. 2, 80 mg (0.238 mmol) of the compound from Ex. 140A and 122 mg (1.24 mmol) of racemic 3-methylpyrrolidin-2-one were used to obtain 57 mg (56% of theory) of the title compound. In a departure from the method described above, the 3-methylpyrrolidin-2-one was deprotonated here with sodium hydride at 60° C. for 2.5 h.

$^1$H-NMR (400 MHz, DMSO-d$_6$, δ/ppm): 4.50 (s, 2H), 4.09 (t, 2H), 3.90 (q, 2H), 3.30-3.14 (m, 2H), 2.85-2.68 (m, 2H), 2.41 (s, 3H), 2.40-2.30 (m, 1H), 2.22-2.11 (m, 1H), 1.51 (dq, 1H), 1.11 (t, 3H), 1.06 (d, 3H).

LC/MS (Method 1, ESIpos): R$_t$=0.98 min, m/z=418 [M+H]$^+$.

Example 7

3-Ethyl-6-{[(3R)-3-hydroxy-2-oxopyrrolidin-1-yl]methyl}-1-(2-methoxyethyl)-5-methylthieno[2,3-d]pyrimidine-2,4(1H,3H)-dione

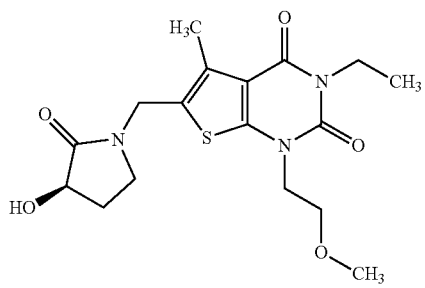 [SMILES: CCn1c(=O)c2c(C)c(CN3CC[C@@H](O)C3=O)sc2n(CCOC)c1=O]

To a solution of 106 mg (0.673 mmol) of [(4R)-2,2-dimethyl-5-oxo-1,3-dioxolan-4-yl]acetaldehyde [Int. Pat. Appl. WO 2012/037393-A1, Preparation B/Step B] in 6.7 ml of 1,2-dichloroethane were added 200 mg (0.673 mmol) of the compound from Ex. 200A and 23 µl (0.404 mmol) of acetic acid. After 15 min, at RT, a total of 225 mg (1.01 mmol) of sodium triacetoxyborohydride was added in three portions. After the reaction mixture had been stirred at RT for about 18 h, it was admixed with saturated sodium hydrogencarbonate solution and extracted with dichloromethane. The organic extract was washed with saturated sodium chloride solution, dried over anhydrous magnesium sulphate, filtered and concentrated. The remaining residue was purified by means of preparative HPLC (Method 8). After concentration of the product fractions and drying under high vacuum, 63 mg (24% of theory, 98% purity, >99% ee) of the title compound were obtained.

$^1$H-NMR (500 MHz, DMSO-$d_6$, δ/ppm): 5.59 (d, 1H), 4.48 (s, 2H), 4.10 (td, 1H), 4.01 (t, 2H), 3.90 (q, 2H), 3.63 (t, 2H), 3.27-3.20 (m, 1H), 3.23 (s, 3H), 3.17-3.09 (m, 1H), 2.40 (s, 3H), 2.28-2.21 (m, 1H), 1.70-1.63 (m, 1H), 1.11 (t, 3H).

LC/MS (Method 1, ESIpos): $R_t$=0.67 min, m/z=382 [M+H]$^+$.

Chiral analytical HPLC [column: Daicel Chiralpak AS-3, 3 µm, 50 mm×4.6 mm; eluent: isohexane/ethanol 1:1; flow rate: 1 ml/min; temperature: 30° C.; detection: 220 nm]: $R_t$=1.23 min [(S) enantiomer under the same conditions: $R_t$=2.23 min].

Example 8 tert-Butyl (1-{[3-ethyl-5-methyl-2,4-dioxo-1-(3,3,3-trifluoropropyl)-1,2,3,4-tetrahydrothieno[2,3-d]pyrimidin-6-yl]methyl}-5-oxopyrrolidin-3-yl)carbamate (racemate)

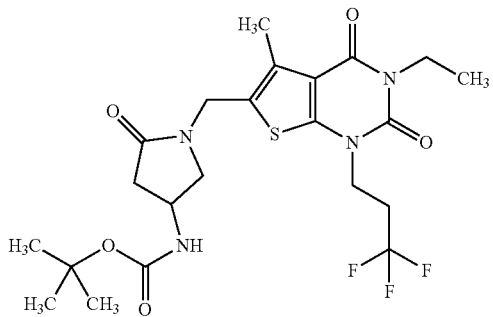 [SMILES: CCn1c(=O)c2c(C)c(CN3CC(NC(=O)OC(C)(C)C)CC3=O)sc2n(CCC(F)(F)F)c1=O]

Step 1: Preparation of racemic tert-butyl (5-oxopyrrolidin-3-yl)carbamate: 100 mg (0.732 mmol) of racemic 4-aminopyrrolidin-2-one hydrochloride were dissolved in a mixture of 1.2 ml of water and 3.7 ml of 1,4-dioxane, and 185 mg (2.20 mmol) of sodium hydrogencarbonate and 168 mg (0.769 mmol) of di-tert-butyl dicarbonate were added successively. After the reaction mixture had been stirred at RT for about 18 h, it was diluted with water and extracted with ethyl acetate. The combined organic extract was dried over anhydrous sodium sulphate, filtered and concentrated. Drying under high vacuum gave 121 mg (82% of theory) of racemic tert-butyl (5-oxopyrrolidin-3-yl)carbamate.

$^1$H-NMR (400 MHz, DMSO-$d_6$, δ/ppm): 7.56 (br. s, 1H), 7.25 (br. d, 1H), 4.24-3.97 (m, 1H), 3.43 (dd, 1H), 2.99 (dd, 1H), 2.36 (dd, 1H), 2.04 (dd, 1H), 1.38 (s, 9H). LC/MS (Method 1, ESIpos): $R_t$=0.50 min, m/z=201 [M+H]$^+$.

Step 2: Preparation of the title compound: Analogously to the method described in Ex. 2, 70 mg (0.208 mmol) of the compound from Ex. 140A and 167 mg (0.833 mmol) of racemic tert-butyl (5-oxopyrrolidin-3-yl)carbamate (see Step 1) were used to obtain 42 mg (38% of theory) of the title compound. In a departure from the method described above, the tert-butyl (5-oxopyrrolidin-3-yl)carbamate was deprotonated here with sodium hydride at 60° C. for 2.5 h.

$^1$H-NMR (400 MHz, DMSO-$d_6$, δ/ppm): 7.26 (br. d, 1H), 4.49 (s, 2H), 4.10 (t, 2H), 4.08-3.97 (m, 1H), 3.90 (q, 2H), 3.51 (dd, 1H), 3.09 (dd, 1H), 2.87-2.68 (m, 2H), 2.40 (s, 3H), 2.21 (dd, 1H), 1.35 (s, 9H), 1.11 (t, 3H).

LC/MS (Method 1, ESIpos): $R_t$=1.04 min, m/z=519 [M+H]$^+$.

Example 9

6-[(4-Amino-2-oxopyrrolidin-1-yl)methyl]-3-ethyl-5-methyl-1-(3,3,3-trifluoropropyl)thieno[2,3-d]pyrimidine-2,4(1H,3H)-dione (racemate)

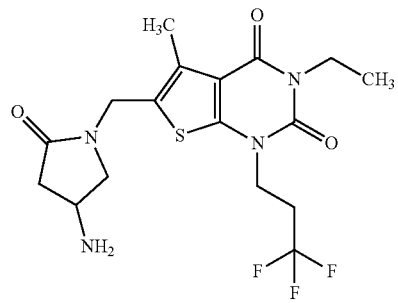 [SMILES: CCn1c(=O)c2c(C)c(CN3CC(N)CC3=O)sc2n(CCC(F)(F)F)c1=O]

38 mg (0.073 mmol) of the compound from Ex. 8 were dissolved in about 5 ml of dichloromethane/trifluoroacetic acid (3:1) and stirred at RT for 45 min. All the volatile constituents were then removed on a rotary evaporator. The remaining residue was admixed with ethyl acetate and extracted by shaking with saturated aqueous sodium hydrogencarbonate solution. Drying of the organic phase over anhydrous sodium sulphate was followed by filtration and concentration. The residue obtained was dried under high vacuum and gave 30 mg (94% of theory, 97% purity) of the title compound.

$^1$H-NMR (500 MHz, DMSO-$d_6$, δ/ppm): 4.48 (d, 2H), 4.09 (t, 2H), 3.90 (q, 2H), 3.53-3.45 (m, 1H), 3.42 (dd, 1H), 2.89 (dd, 1H), 2.83-2.67 (m, 2H), 2.45 (dd, 1H), 2.41 (s, 3H), 1.96 (dd, 1H), 1.72 (broad, 2H), 1.12 (t, 3H).

LC/MS (Method 1, ESIpos): $R_t$=0.60 min, m/z=419 [M+H]$^+$.

Example 10

3-Ethyl-5-methyl-6-[(2-methyl-5-oxopyrrolidin-1-yl)methyl]-1-(3,3,3-trifluoropropyl)thieno[2,3-d]pyrimidine-2,4(1H,3H)-dione (racemate)

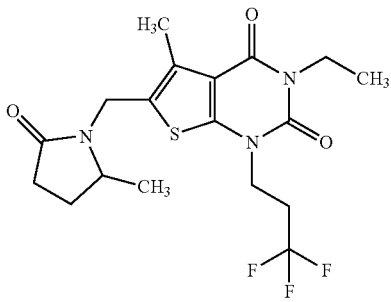 [SMILES: CCn1c(=O)c2c(C)c(CN3C(=O)CCC3C)sc2n(CCC(F)(F)F)c1=O]

Analogously to the method described in Ex. 2, 80 mg (0.238 mmol) of the compound from Ex. 140A and 296 mg (2.85 mmol) of racemic 5-methylpyrrolidin-2-one were used to obtain 10 mg (10% of theory) of the title compound. In a departure from the method described above, the deprotonated 5-methylpyrrolidin-2-one was added here to the reaction mixture in three portions over a period of about 42 h. The total reaction time was 4.5 days.

$^1$H-NMR (400 MHz, DMSO-d$_6$, δ/ppm): 4.69 (d, 1H), 4.29 (d, 1H), 4.08 (td, 2H), 3.90 (q, 2H), 3.59-3.52 (m, 1H), 2.84-2.68 (m, 2H), 2.42 (s, 3H), 2.39-2.28 (m, 1H), 2.27-2.16 (m, 1H), 2.15-2.03 (m, 1H), 1.59-1.44 (m, 1H), 1.16 (d, 3H), 1.11 (t, 3H).

LC/MS (Method 1, ESIpos): R$_t$=0.97 min, m/z=418 [M+H]$^+$.

Example 11

3-Ethyl-5-methyl-6-[(1-oxo-1,3-dihydro-2H-isoindol-2-yl)methyl]-1-(3,3,3-trifluoropropyl)thieno[2,3-d]pyrimidine-2,4(1H,3H)-dione

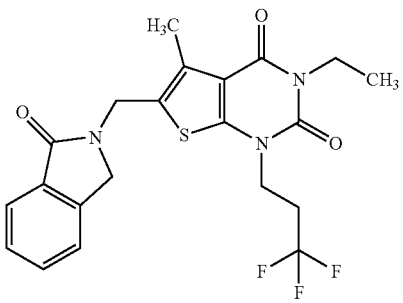 [SMILES: CCn1c(=O)c2c(C)c(CN3Cc4ccccc4C3=O)sc2n(CCC(F)(F)F)c1=O]

Analogously to the method described in Ex. 2, 80 mg (0.238 mmol) of the compound from Ex. 140A and 253 mg (1.90 mmol) of isoindolin-1-one were used to obtain 22 mg (20% of theory) of the title compound. In a departure from the method described above, the deprotonated isoindolin-1-one was added here to the reaction mixture in two portions over a period of about 18 h. The total reaction time was 1.5 days.

$^1$H-NMR (400 MHz, DMSO-d$_6$, δ/ppm): 7.72 (d, 1H), 7.65-7.55 (m, 2H), 7.53-7.45 (m, 1H), 4.88 (s, 2H), 4.45 (s, 2H), 4.08 (t, 2H), 3.90 (q, 2H), 2.83-2.63 (m, 2H), 1.11 (t, 3H).

LC/MS (Method 1, ESIpos): R$_t$=1.07 min, m/z=452 [M+H]$^+$.

Example 12

3-Ethyl-5-methyl-6-[(2-oxopiperidin-1-yl)methyl]-1-(3,3,3-trifluoropropyl)thieno[2,3-d]pyrimidine-2,4(1H,3H)-dione

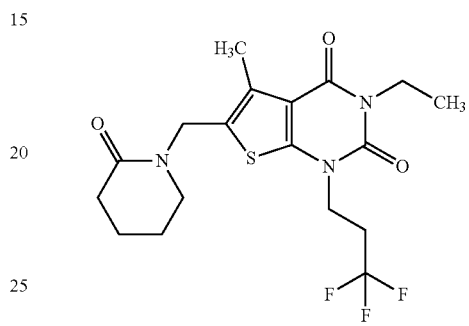

Analogously to the method described in Ex. 2, 50 mg (0.149 mmol) of the compound from Ex. 140A and 124 mg (1.25 mmol) of piperidin-2-one were used to obtain 34 mg (54% of theory) of the title compound. In a departure from the method described above, the deprotonated piperidin-2-one was added here to the reaction mixture in two portions over a period of about 18 h. The total reaction time was 24 h.

$^1$H-NMR (400 MHz, DMSO-d$_6$, δ/ppm): 4.58 (s, 2H), 4.08 (t, 2H), 3.90 (q, 2H), 3.26 (t, 2H), 2.88-2.68 (m, 2H), 2.44 (s, 3H), 2.26 (t, 2H), 1.78-1.59 (m, 4H), 1.11 (t, 3H).

LC/MS (Method 1, ESIpos): R$_t$=0.96 min, m/z=418 [M+H]$^+$.

Example 13

1-(2-Methoxyethyl)-5-methyl-6-[(3-oxomorpholin-4-yl)methyl]-3-(2-phenylethyl)thieno[2,3-d]pyrimidine-2,4(1H,3H)-dione

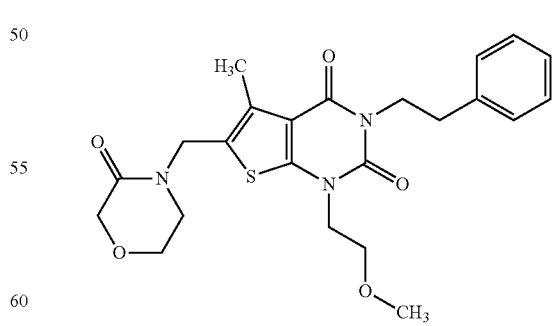

To a solution of 80 mg (0.214 mmol) of the compound from Ex. 138A in 1.3 ml of dichloromethane were added, at 0° C., 74 µl (0.427 mmol) of N,N-diisopropylethylamine and 16 µl (0.224 mmol) of thionyl chloride. After stirring at 0° C. for 20 min, a solution of 65 mg (0.641 mmol) of morpholin-3-one in 2 ml of THF, to which 26 mg (0.641 mmol) of sodium hydride (60% suspension in mineral oil) had been added beforehand, was then added at RT. The reaction mixture was stirred at RT for about 18 h. Then the same amount of deprotonated morpholin-3-one was added once again. After stirring for a further about 2 h, all the volatile constituents were removed on a rotary evaporator. The remaining residue was separated into its components by means of preparative HPLC (Method 8). After concentration of the product fractions and drying under high vacuum, 13 g (14% of theory) of the title compound were obtained.

$^1$H-NMR (400 MHz, CDCl$_3$, δ/ppm): 7.38-7.16 (m, 5H, partially obscured by the CHCl$_3$ signal), 4.69 (s, 2H), 4.22 (s, 2H), 4.28-4.16 (m, 2H), 4.10 (t, 2H), 3.87 (t, 2H), 3.69 (t, 2H), 3.37 (t, 2H), 3.34 (s, 3H), 3.00-2.88 (m, 2H), 2.53 (s, 3H).

LC/MS (Method 1, ESIpos): R$_t$=1.01 min, m/z=458 [M+H]$^+$.

Example 14

3-Ethyl-5-methyl-6-[(3-oxomorpholin-4-yl)methyl]-1-(3,3,3-trifluoropropyl)thieno[2,3-d]pyrimidine-2,4(1H,3H)-dione

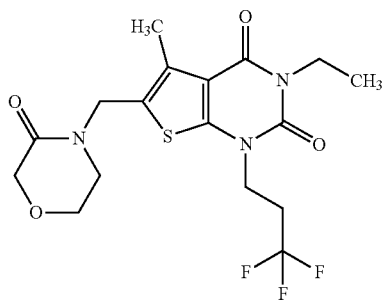 [SMILES: CCn1c(=O)c2c(C)c(CN3CCOCC3=O)sc2n(CCC(F)(F)F)c1=O]

To a solution of 80 mg (0.238 mmol) of the compound from Ex. 140A in 1.6 ml of dichloromethane were added, at 0° C., 83 µl (0.476 mmol) of N,N-diisopropylethylamine and 18 µl (0.250 mmol) of thionyl chloride. After stirring at 0° C. for 20 min, a solution of 72 mg (0.714 mmol) of morpholin-3-one in 1.6 ml of THF, to which 29 mg (0.714 mmol) of sodium hydride (60% suspension in mineral oil) had been added and which had been stirred at RT for 30 min beforehand, was added. The reaction mixture was stirred at RT for about 18 h. Since the conversion was incomplete, another 72 mg (0.714 mmol) of morpholin-3-one were dissolved in 1.6 ml of THF and admixed with 550 µl (1.10 mmol) of a 2 M solution of lithium diisopropylamide (LDA) in THF. After 10 min, this solution was added to the reaction mixture. Thereafter, the mixture was stirred first at RT for 30 min, then at 80° C. for 5 h and finally at RT for 2 days. All the volatile constituents were then removed on a rotary evaporator. The remaining residue was separated into its components by means of preparative HPLC (Method 10). After concentration of the product fractions and drying under high vacuum, 47 mg (47% of theory, 96% purity) of the title compound were obtained.

$^1$H-NMR (400 MHz, DMSO-d$_6$, δ/ppm): 4.66 (s, 2H), 4.09 (t, 2H), 4.08 (s, 2H), 3.90 (q, 2H), 3.80 (t, 2H), 2.85-2.69 (m, 2H), 2.45 (s, 3H), 1.11 (t, 3H).

LC/MS (Method 1, ESIpos): R$_t$=0.88 min, m/z=420 [M+H]$^+$.

Example 15

6-[(1,1-Dioxido-1,2-thiazolidin-2-yl)methyl]-1-(2-methoxyethyl)-5-methyl-3-(2-phenylethyl)thieno[2,3-d]pyrimidine-2,4(1H,3H)-dione

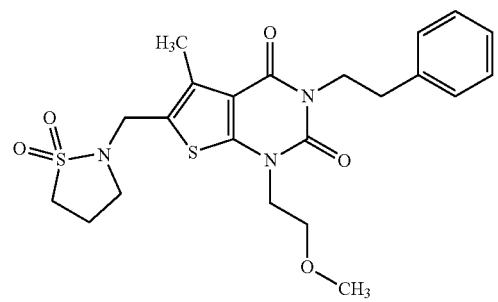 [SMILES: COCCn1c(=O)n(CCc2ccccc2)c(=O)c2c(C)c(CN3CCCS3(=O)=O)sc21]

To a solution of 49 µl (0.668 mmol) of propane sultam in 1.5 ml of DMF were added 27 mg (0.668 mmol) of sodium hydride (60% suspension in mineral oil) and then the mixture was stirred at RT for 25 min ("Solution 1"). To a solution of 50 mg (0.134 mmol) of the compound from Ex. 138A in 1.3 ml of dichloromethane in another reaction vessel were added, at 0° C., 47 µl (0.267 mmol) of N,N-diisopropylethylamine and 10 µl (0.140 mmol) of thionyl chloride. After 20 min, one third of Solution 1 was added at 0° C. The reaction mixture was stirred at 0° C., with addition of a further third of Solution 1 after 20 min and after 40 min of reaction time. After the last addition, the cooling bath was removed and the reaction mixture was stirred at RT for about 18 h. All the volatile constituents were then removed on a rotary evaporator. The remaining residue was separated into its components by means of preparative HPLC (Method 8). After concentration of the product fractions and drying under high vacuum, 41 mg (64% of theory) of the title compound were obtained.

$^1$H-NMR (400 MHz, CDCl$_3$, δ/ppm): 7.41-7.16 (m, 5H, partially obscured by the CHCl$_3$ signal), 4.30 (s, 2H), 4.25-4.17 (m, 2H), 4.11 (t, 2H), 3.70 (t, 2H), 3.35 (s, 3H), 3.26-3.15 (m, 4H), 2.99-2.88 (m, 2H), 2.50 (s, 3H), 2.44-2.28 (m, 2H).

LC/MS (Method 1, ESIpos): R$_t$=1.03 min, m/z=478 [M+H]$^+$.

Example 16

6-[(1,1-Dioxido-1,2-thiazolidin-2-yl)methyl]-3-ethyl-5-methyl-1-(3,3,3-trifluoropropyl)thieno[2,3-d]pyrimidine-2,4(1H,3H)-dione

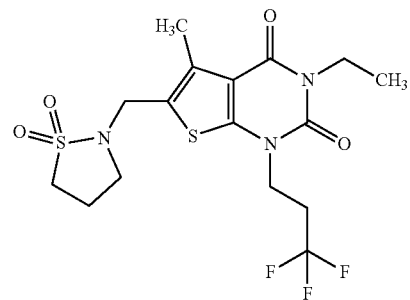 [SMILES: CCn1c(=O)c2c(C)c(CN3CCCS3(=O)=O)sc2n(CCC(F)(F)F)c1=O]

Analogously to the method described in Ex. 2, 90 mg (0.268 mmol) of the compound from Ex. 140A and 130 mg (1.07 mmol) of propane sultam were used to obtain 63 mg (54% of theory) of the title compound. In a departure from the method described above, the propane sultam was deprotonated here with sodium hydride at 60° C. for 2 h.

¹H-NMR (400 MHz, DMSO-d₆, δ/ppm): 4.26 (s, 2H), 4.12 (t, 2H), 3.90 (q, 2H), 3.29-3.21 (m, 2H), 3.17 (t, 2H), 2.86-2.69 (m, 2H), 2.41 (s, 3H), 2.29-2.16 (m, 2H), 1.12 (t, 3H).

LC/MS (Method 1, ESIpos): $R_t$=0.96 min, m/z=440 [M+H]⁺.

Example 17

6-[(1,1-Dioxido-1,2-thiazolidin-2-yl)methyl]-3-ethyl-1-(2-methoxyethyl)-5-methylthieno[2,3-d]pyrimidine-2,4(1H,3H)-dione

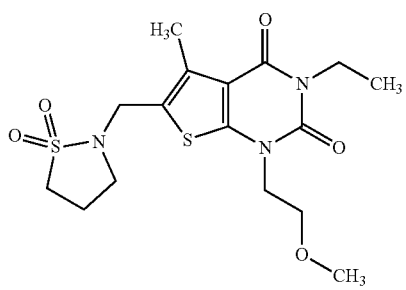 [SMILES: CCn1c(=O)c2c(C)c(CN3CCCS3(=O)=O)sc2n(CCOC)c1=O]

Analogously to the method described in Ex. 2, 90 mg (0.287 mmol, 95% purity) of the compound from Ex. 143A and 139 mg (1.15 mmol) of propane sultam were used to obtain 48 mg (41% of theory) of the title compound. In a departure from the method described above, the propane sultam was deprotonated here with sodium hydride at 60° C. for 2 h. Preparative HPLC purification was effected by Method 8.

¹H-NMR (400 MHz, DMSO-d₆, δ/ppm): 4.24 (s, 2H), 4.03 (t, 2H), 3.90 (q, 2H), 3.64 (t, 2H), 3.27-3.20 (m, 2H), 3.24 (s, 3H), 3.17 (t, 2H), 2.39 (s, 3H), 2.27-2.14 (m, 2H), 1.12 (t, 3H).

LC/MS (Method 1, ESIpos): $R_t$=0.82 min, m/z=402 [M+H]⁺.

Example 18

6-[(1,1-Dioxido-1,2-thiazolidin-2-yl)methyl]-1-(2-methoxyethyl)-3-(2-phenylethyl)-5-(trifluoromethyl)thieno[2,3-d]pyrimidine-2,4(1H,3H)-dione

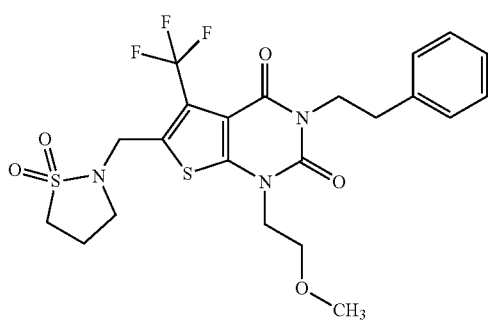 [SMILES: COCCn1c(=O)n(CCc2ccccc2)c(=O)c2c(C(F)(F)F)c(CN3CCCS3(=O)=O)sc21]

Analogously to the method described in Ex. 5, 100 mg (0.224 mmol) of the compound from Ex. 181A and 141 mg (1.16 mmol) of propane sultam were used to obtain 102 mg (85% of theory) of the title compound. It was possible here to dispense with the final stirring with pentane.

¹H-NMR (400 MHz, DMSO-d₆, δ/ppm): 7.37-7.27 (m, 2H), 7.25-7.20 (m, 3H), 4.54 (d, 2H), 4.16-3.99 (m, 4H), 3.62 (t, 2H), 3.37 (t, 2H), 3.33 (s, 3H), 3.31 (t, 3H), 2.91-2.78 (m, 2H), 2.37-2.22 (m, 2H).

LC/MS (Method 1, ESIpos): $R_t$=1.07 min, m/z=532 [M+H]⁺.

Example 19

6-[(1,1-Dioxido-1,2-thiazolidin-2-yl)methyl]-3-ethyl-5-(trifluoromethyl)-1-(3,3,3-trifluoropropyl)thieno[2,3-d]pyrimidine-2,4(1H,3H)-dione

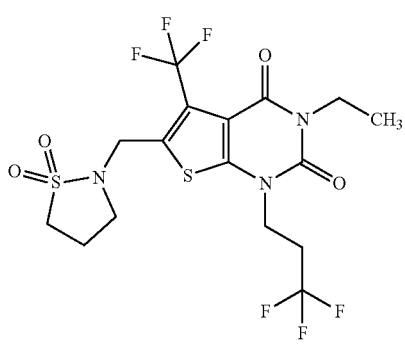 [SMILES: CCn1c(=O)c2c(C(F)(F)F)c(CN3CCCS3(=O)=O)sc2n(CCC(F)(F)F)c1=O]

74 mg (0.612 mmol) of propane sultam were dissolved in 1.5 ml of DMF, 24 mg (0.612 mmol) of sodium hydride (60% suspension in mineral oil) were added and the mixture was stirred at RT for 25 min. This was followed by dilution with 0.25 ml of THF ("Mixture 1"). In another reaction vessel, 50 mg (0.122 mmol) of the compound from Example 182A were dissolved in 1 ml of DMF, and 350 µl of Mixture 1 were added dropwise at 0° C. After 2.5 h at 0° C., a further 350 µl of Mixture 1 were added. After a further 30 min at 0° C., the reaction mixture was separated directly into its components by means of preparative HPLC (Method 8). Concentration of the product fractions and drying under high vacuum gave 42 mg (69% of theory) of the title compound.

¹H-NMR (400 MHz, CDCl₃, δ/ppm): 4.57 (d, 2H), 4.23-4.14 (m, 2H), 4.08 (q, 2H), 3.40 (t, 2H), 3.31-3.19 (m, 2H), 2.74-2.57 (m, 2H), 2.53-2.38 (m, 2H), 1.26 (t, 3H).

LC/MS (Method 1, ESIpos): $R_t$=0.98 min, m/z=494 [M+H]⁺.

Example 20

1-(2-Methoxyethyl)-5-methyl-6-[(2-oxo-,3-oxazolidin-3-yl)methyl]-3-(2-phenylethyl)thieno[2,3-d]pyrimidine-2,4(1H,3H)-dione

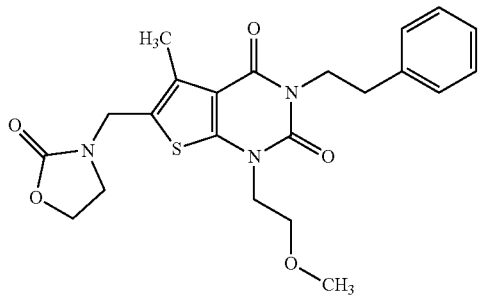

To a solution of 80 mg (0.214 mmol) of the compound from Ex. 138A in 1.3 ml of dichloromethane were added, at 0° C., 74 μl (0.427 mmol) of N,N-diisopropylethylamine and 16 μl (0.224 mmol) of thionyl chloride. After stirring at 0° C. for 20 min, a solution of 56 mg (0.641 mmol) of oxazolidin-2-one in 1.6 ml of THF, to which 26 mg (0.641 mmol) of sodium hydride (60% suspension in mineral oil) had been added and which had been stirred at RT for 30 min beforehand, was added. Subsequently, the cooling bath was removed and the reaction mixture was stirred at RT for about 18 h. Since the conversion was incomplete, the same amount of deprotonated oxazolidin-2-one once again was added. After 2 h at RT, all the volatile constituents were then removed on a rotary evaporator. The remaining residue was separated into its components by means of preparative HPLC (Method 8). After concentration of the product fractions and drying under high vacuum, 44 mg (47% of theory) of the title compound were obtained.

$^1$H-NMR (400 MHz, DMSO-d$_6$, δ/ppm): 7.36-7.27 (m, 2H), 7.26-7.18 (m, 3H), 4.49 (s, 2H), 4.31-4.21 (m, 2H), 4.13-3.98 (m, 4H), 3.61 (t, 2H), 3.53-3.44 (m, 2H), 3.24 (s, 3H), 2.89-2.78 (m, 2H), 2.42 (s, 3H).

LC/MS (Method 1, ESIpos): R$_t$=1.02 min, m/z=444 [M+H]$^+$.

Example 21

3-Ethyl-5-methyl-6-[(2-oxo-1,3-oxazolidin-3-yl)methyl]-1-(3,3,3-trifluoropropyl)thieno[2,3-d]pyrimidine-2,4(1H,3H)-dione

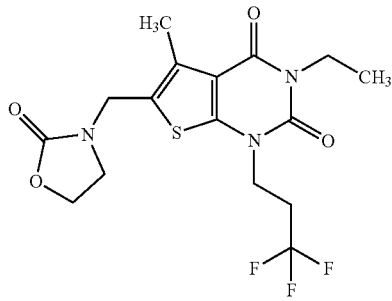

Analogously to the method described in Ex. 2, 80 mg (0.238 mmol) of the compound from Ex. 140A and 108 mg (1.24 mmol) of oxazolidin-2-one were used to obtain 46 mg (48% of theory) of the title compound.

$^1$H-NMR (400 MHz, DMSO-d$_6$, δ/ppm): 4.51 (s, 2H), 4.31-4.21 (m, 2H), 4.11 (t, 2H), 3.90 (q, 2H), 3.53-3.44 (m, 2H), 2.89-2.69 (m, 2H), 2.42 (s, 3H), 1.12 (t, 3H).

LC/MS (Method 1, ESIpos): R$_t$=0.90 min, m/z=406 [M+H]$^+$.

Example 22

1-(2-Methoxyethyl)-6-[(2-oxo-1,3-oxazolidin-3-yl)methyl]-3-(2-phenylethyl)-5-(trifluoromethyl)thieno[2,3-d]pyrimidine-2,4(1H,3H)-dione

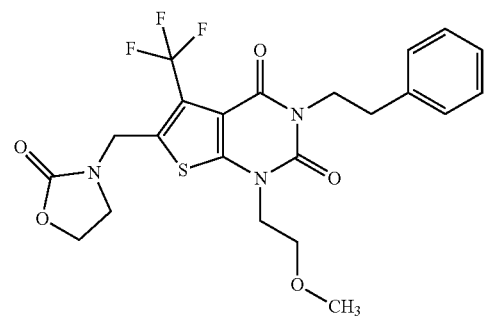 [SMILES: COCCn1c(=O)n(CCc2ccccc2)c(=O)c2c(C(F)(F)F)c(CN3CCOC3=O)sc21]

Analogously to the method described in Ex. 5, 100 mg (0.224 mmol) of the compound from Ex. 181A and 101 mg (1.16 mmol) of oxazolidin-2-one were used to obtain 82 mg (72% of theory) of the title compound. The final stirring with pentane was dispensed with here.

$^1$H-NMR (400 MHz, DMSO-d$_6$, δ/ppm): 7.36-7.27 (m, 2H), 7.26-7.17 (m, 3H), 4.71 (d, 2H), 4.35 (t, 2H), 4.13-4.00 (m, 4H), 3.66-3.53 (m, 4H), 3.24 (s, 3H), 2.91-2.78 (m, 2H).

LC/MS (Method 1, ESIpos): R$_t$=1.06 min, m/z=498 [M+H]$^+$.

Example 23

3-Ethyl-6-[(2-oxo-1,3-oxazolidin-3-yl)methyl]-5-(trifluoromethyl)-1-(3,3,3-trifluoropropyl)thieno[2,3-d]pyrimidine-2,4(1H,3H)-dione

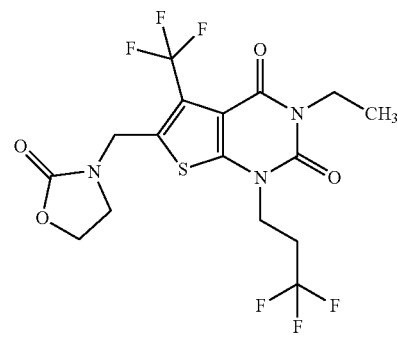 [SMILES: CCn1c(=O)c2c(C(F)(F)F)c(CN3CCOC3=O)sc2n(CCC(F)(F)F)c1=O]

Analogously to the method described in Ex. 19, 70 mg (0.171 mmol) of the compound from Ex. 182A and 74 mg (0.856 mmol) of oxazolidin-2-one were used to obtain 61 mg (77% of theory) of the title compound.

$^{1}$H-NMR (400 MHz, CDCl$_3$, δ/ppm): 4.77 (d, 2H), 4.47-4.35 (m, 2H), 4.23-4.14 (m, 2H), 4.08 (q, 2H), 3.70-3.55 (m, 2H), 2.76-2.54 (m, 2H), 1.26 (t, 3H).

LC/MS (Method 1, ESIpos): R$_t$=0.98 min, m/z=460 [M+H]$^+$.

Example 24

6-[(4,4-Dimethyl-2-oxo-1,3-oxazolidin-3-yl)methyl]-3-ethyl-5-methyl-1-(3,3,3-trifluoropropyl)thieno[2,3-d]pyrimidine-2,4(1H,3H)-dione

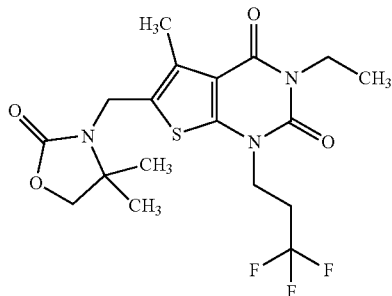 [SMILES: CCn1c(=O)c2c(C)c(CN3C(=O)OCC3(C)C)sc2n(CCC(F)(F)F)c1=O]

Analogously to the method described in Ex. 2, 80 mg (0.238 mmol) of the compound from Ex. 140A and 110 mg (0.951 mmol) of 4,4-dimethyl-1,3-oxazolidin-2-one were used to obtain 27 mg (26% of theory) of the title compound.

$^{1}$H-NMR (400 MHz, DMSO-d$_6$, δ/ppm): 4.45 (s, 2H), 4.10 (t, 2H), 4.02 (s, 2H), 3.90 (q, 2H), 2.86-2.69 (m, 2H), 2.45 (s, 3H), 1.23 (s, 6H), 1.12 (t, 3H).

LC/MS (Method 1, ESIpos): R$_t$=1.02 min, m/z=434 [M+H]$^+$.

Example 25

3-Ethyl-5-methyl-6-[(2-oxo-1,3-oxazinan-3-yl)methyl]-1-(3,3,3-trifluoropropyl)thieno[2,3-d]pyrimidine-2,4(1H,3H)-dione

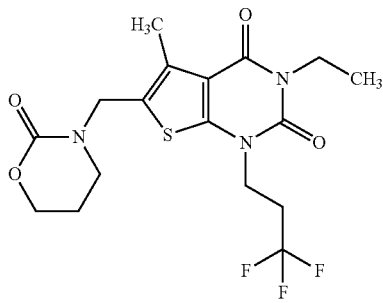 [SMILES: CCn1c(=O)c2c(C)c(CN3CCCOC3=O)sc2n(CCC(F)(F)F)c1=O]

Analogously to the method described in Ex. 2, 80 mg (0.238 mmol) of the compound from Ex. 140A and a total of 168 mg (1.66 mmol) of 1,3-oxazin-2-one were used to obtain 21 mg (20% of theory, 97% purity) of the title compound. In a departure from the method described above, the deprotonated 1,3-oxazin-2-one was added here in two portions separated by about 20 h. The total reaction time was 4 days.

$^{1}$H-NMR (400 MHz, DMSO-d$_6$, δ/ppm): 4.56 (s, 2H), 4.21-4.14 (m, 2H), 4.10 (t, 2H), 3.90 (q, 2H), 3.28 (t, 2H), 2.87-2.69 (m, 2H), 2.44 (s, 3H), 1.91 (quin, 2H), 1.12 (t, 3H).

LC/MS (Method 1, ESIpos): R$_t$=0.89 min, m/z=420 [M+H]$^+$.

Example 26 tert-Butyl 5-{[3-ethyl-5-methyl-2,4-dioxo-1-(3,3,3-trifluoropropyl)-1,2,3,4-tetrahydrothieno[2,3-d]pyrimidin-6-yl]methyl}-1,2,5-thiadiazolidine-2-carboxylate 1,1-dioxide

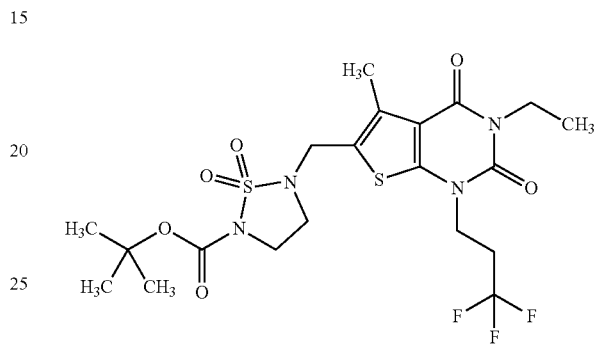

Analogously to the method described in Ex. 2, 100 mg (0.282 mmol, 95% purity) of the compound from Ex. 140A and 188 mg (0.847 mmol) of tert-butyl 1,2,5-thiadiazolidine-2-carboxylate 1,1-dioxide [S. J. Kim et al., *Eur. J. Med. Chem.* 2007, 42 (9), 1176-1183] were used to obtain 22 mg (14% of theory) of the title compound. Preparative HPLC purification was effected here by Method 8.

$^{1}$H-NMR (400 MHz, CDCl$_3$, δ/ppm): 4.32 (s, 2H), 4.21-4.12 (m, 2H), 4.06 (q, 2H), 3.79 (t, 2H), 3.32 (t, 2H), 2.72-2.56 (m, 2H), 2.52 (s, 3H), 1.56 (s, 9H), 1.25 (t, 3H).

LC/MS (Method 1, ESIpos): R$_t$=1.17 min, m/z=319 [M+H—C$_7$H$_{14}$N$_2$O$_4$S]$^+$.

Example 27

6-[(1,1-Dioxido-1,2,5-thiadiazolidin-2-yl)methyl]-3-ethyl-5-methyl-1-(3,3,3-trifluoropropyl)thieno[2,3-d]pyrimidine-2,4(1H,3H)-dione

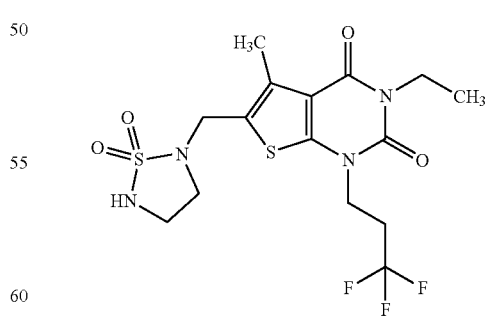

18 mg (0.033 mmol) of the compound from Ex. 26 were dissolved in 1.5 ml of dichloromethane, and 1 ml of trifluoroacetic acid were added. After 1 h, all the volatile constituents were removed by rotary evaporator and the remaining residue was separated into its components by means of preparative HPLC (Method 8). After concentration of the product fractions and drying under high vacuum, 5.5 g (37% of theory) of the title compound were obtained.

$^1$H-NMR (400 MHz, CDCl$_3$, δ/ppm): 4.38 (t, 1H), 4.30 (s, 2H), 4.21-4.12 (m, 2H), 4.06 (q, 2H), 3.53 (q, 2H), 3.43-3.33 (m, 2H), 2.73-2.54 (m, 2H), 2.51 (s, 3H), 1.25 (t, 3H).

LC/MS (Method 1, ESIpos): R$_t$=0.91 min, m/z=441 [M+H]$^+$.

Example 28

3-Ethyl-5-methyl-6-[(2-thioxoimidazolidin-1-yl)methyl]-1-(3,3,3-trifluoropropyl)thieno[2,3-d]pyrimidine-2,4(1H,3H)-dione

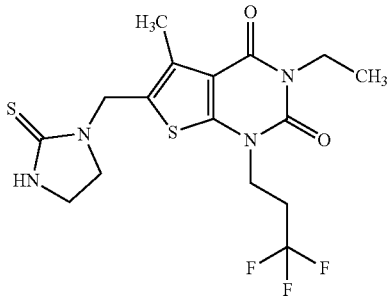 [SMILES: CCn1c(=O)c2c(C)c(CN3CCNC3=S)sc2n(CCC(F)(F)F)c1=O]

369 mg (0.751 mmol) of the compound from Ex. 210A were dissolved in 14 ml of dioxane, and 211 mg (1.12 mmol) of 1,1'-thiocarbonyldiimidazole were added. The mixture was stirred at RT for 17 h. The reaction solution was then concentrated on a rotary evaporator. The resulting residue was taken up in 20 ml of ethyl acetate and washed with 10 ml of 5% hydrochloric acid. The organic phase was washed with saturated sodium chloride solution, dried over sodium sulphate, filtered and concentrated. The material thus obtained was purified by means of preparative HPLC (Method 14). Combination of the product fractions and freeze-drying gave 168 mg (50% of theory) of the title compound.

$^1$H-NMR (400 MHz, DMSO-d$_6$, δ/ppm): 8.34 (s, 1H), 4.85 (s, 2H), 4.09 (t, 2H), 3.90 (q, 2H), 3.57-3.50 (m, 2H), 3.45-3.37 (m, 2H), 2.83-2.69 (m, 2H), 2.45 (s, 3H), 1.12 (t, 3H).

LC/MS (Method 3): R$_t$=1.11 min, m/z=421 [M+H]$^+$.

Example 29

3-Ethyl-1-(3-fluoropropyl)-5-methyl-6-[(2-thioxoimidazolidin-1-yl)methyl]thieno[2,3-d]pyrimidine-2,4(1H,3H)-dione

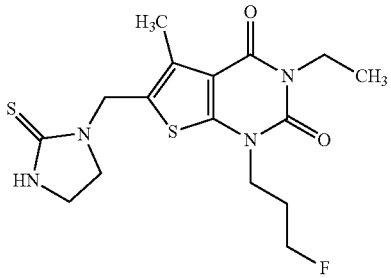 [SMILES: CCn1c(=O)c2c(C)c(CN3CCNC3=S)sc2n(CCCF)c1=O]

55 mg (0.145 mmol) of the compound from Ex. 214A were dissolved in 3 ml of DMSO, and 40.6 mg (0.217 mmol) of 1,1'-thiocarbonyldiimidazole were added. The mixture was stirred at RT for 116 h. The reaction mixture was then purified directly by means of preparative HPLC (Method 14). Combination of the product fractions and freeze-drying gave 12.4 mg (22% of theory) of the title compound.

$^1$H-NMR (400 MHz, DMSO-d$_6$, δ/ppm): 8.32 (s, 1H), 4.84 (s, 2H), 4.59 (t, 1H), 4.47 (t, 1H), 3.97 (t, 2H), 3.90 (q, 2H), 3.57-3.50 (m, 2H), 3.44-3.37 (m, 2H), 2.44 (s, 3H), 2.14-1.98 (m, 2H), 1.11 (t, 3H).

LC/MS (Method 3): R$_t$=1.0 min, m/z=385 [M+H]$^+$.

Example 30

3-Ethyl-1-(4-fluorobutyl)-5-methyl-6-[(2-thioxoimidazolidin-1-yl)methyl]thieno[2,3-d]pyrimidine-2,4(1H,3H)-dione

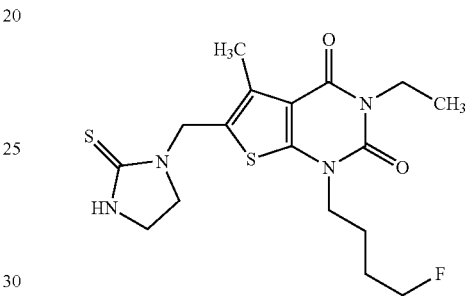

125 mg (0.145 mmol) of the compound from Ex. 215A were dissolved in 4 ml of dioxane, and 45.6 mg (0.243 mmol) of 1,1'-thiocarbonyldiimidazole were added. The mixture was stirred at RT for 19 h. The reaction solution was then concentrated on a rotary evaporator. The residue was dissolved in 3 ml of DMSO and this solution was purified by means of preparative HPLC (Method 14). Combination of the product fractions and freeze-drying gave 46 mg (68% of theory) of the title compound.

$^1$H-NMR (400 MHz, DMSO-d$_6$, δ/ppm): 8.33 (s, 1H), 4.83 (s, 2H), 4.51 (t, 1H), 4.42 (t, 1H), 3.94-3.86 (m, 4H), 3.58-3.48 (m, 2H), 3.45-3.37 (m, 2H), 2.44 (s, 3H), 1.81-1.64 (m, 4H), 1.11 (t, 3H).

LC/MS (Method 3): R$_t$=1.07 min, m/z=399 [M+H]$^+$.

Example 31

3-Ethyl-1-(2-methoxyethyl)-5-methyl-6-[(2-thioxoimidazolidin-1-yl)methyl]thieno[2,3-d]pyrimidine-2,4(1H,3H)-dione

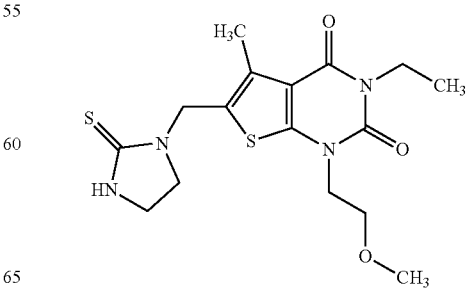

100 mg (0.164 mmol) of the compound from Ex. 220A were dissolved in 3.5 ml of dioxane, and 46.3 mg (0.247 mmol) of 1,1'-thiocarbonyldiimidazole were added. The mixture was stirred at RT for 1 h. The reaction solution was then concentrated, and the residue obtained was chromatographed using a silica gel cartridge (Biotage, 10 g of silica gel, eluent: hexane/ethyl acetate). 26 mg (41% of theory) of the title compound were obtained.

$^1$H-NMR (400 MHz, DMSO-$d_6$, δ/ppm): 8.32 (s, 1H), 4.82 (s, 2H), 4.01 (t, 2H), 3.90 (q, 2H), 3.63 (t, 2H), 3.57-3.49 (m, 2H), 3.44-3.37 (m, 2H), 3.24 (s, 3H), 2.43 (s, 3H), 1.12 (t, 3H).

LC/MS (Method 3): $R_t$=0.96 min, m/z=383 [M+H]$^+$.

Example 32

1-(2-Ethoxyethyl)-3-ethyl-5-methyl-6-[(2-thioxoimidazolidin-1-yl)methyl]thieno[2,3-d]pyrimidine-2,4(1H,3H)-dione

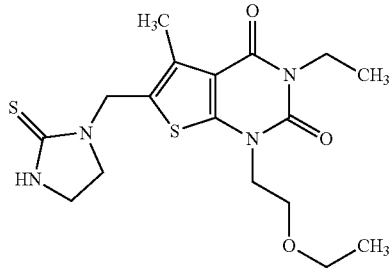 [SMILES: CCOCCn1c(=O)n(CC)c(=O)c2c(C)c(CN3CCNC3=S)sc21]

255 mg (0.568 mmol) of the compound from Ex. 221A were dissolved in 14 ml of dioxane, and 160 mg (0.852 mmol) of 1,1'-thiocarbonyldiimidazole were added. The mixture was stirred at RT for 18 h. The reaction solution was then concentrated on a rotary evaporator. The residue was dissolved in 6 ml of DMSO and this solution was purified by means of preparative HPLC (Method 14). Combination of the product fractions and freeze-drying gave 144 mg (64% of theory) of the title compound.

$^1$H-NMR (400 MHz, DMSO-$d_6$, δ/ppm): 8.33 (s, 1H), 4.83 (s, 2H), 4.00 (t, 2H), 3.90 (q, 2H), 3.65 (t, 2H), 3.57-3.49 (m, 2H), 3.47-3.36 (m, 4H), 2.44 (s, 3H), 1.12 (t, 3H), 1.03 (t, 3H).

LC/MS (Method 3): $R_t$=1.04 min, m/z=397 [M+H]$^+$.

Example 33

3-Ethyl-1-(2-isopropoxyethyl)-5-methyl-6-[(2-thioxoimidazolidin-1-yl)methyl]thieno[2,3-d]pyrimidine-2,4(1H,3H)-dione

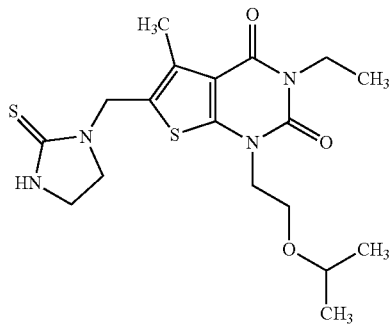 [SMILES: CCn1c(=O)c2c(C)c(CN3CCNC3=S)sc2n(CCOC(C)C)c1=O]

206 mg (0.375 mmol) of the compound from Ex. 222A were dissolved in 9 ml of dioxane, and 105 mg (0.562 mmol) of 1,1'-thiocarbonyldiimidazole were added. The mixture was stirred at RT for 64 h. The reaction solution was then concentrated on a rotary evaporator. The residue was dissolved in 6 ml of DMSO and this solution was purified by means of preparative HPLC (Method 14). Combination of the product fractions and freeze-drying gave 79 mg (50% of theory) of the title compound.

$^1$H-NMR (400 MHz, DMSO-$d_6$, δ/ppm): 8.34 (s, 1H), 4.82 (s, 2H), 3.96 (t, 2H), 3.90 (q, 2H), 3.64 (t, 2H), 3.58-3.47 (m, 3H), 3.43-3.36 (m, 2H), 2.43 (s, 3H), 1.11 (t, 3H), 1.00 (d, 6H).

LC/MS (Method 3): $R_t$=1.11 min, m/z=411 [M+H]$^+$.

Example 34

3-Ethyl-5-methyl-1-(oxetan-2-ylmethyl)-6-[(2-thioxoimidazolidin-1-yl)methyl]thieno[2,3-d]pyrimidine-2,4(1H,3H)-dione (racemate)

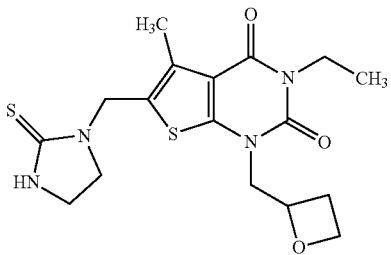 [SMILES: CCn1c(=O)c2c(C)c(CN3CCNC3=S)sc2n(CC2CCO2)c1=O]

399 mg (1.132 mmol) of the compound from Ex. 224A were dissolved in 20 ml of dioxane, and 318 mg (1.692 mmol) of 1,1'-thiocarbonyldiimidazole were added. The mixture was stirred at RT for 21 h. The reaction solution was then concentrated on a rotary evaporator. The residue was dissolved in 6 ml of DMSO and this solution was purified by means of preparative HPLC (Method 14). Combination of the product fractions and freeze-drying gave 54 mg (12% of theory) of the title compound.

$^1$H-NMR (400 MHz, DMSO-$d_6$, δ/ppm): 8.32 (s, 1H), 5.05-4.96 (m, 1H), 4.82 (s, 2H), 4.51-4.38 (m, 2H), 4.13 (d, 2H), 3.90 (q, 2H), 3.57-3.48 (m, 2H), 3.45-3.35 (m, 2H), 2.74-2.63 (m, 1H), 2.44 (s, 3H), 1.12 (t, 3H).

LC/MS (Method 3): $R_t$=0.94 min, m/z=395 [M+H]$^+$.

Example 35

3-Ethyl-5-methyl-1-(tetrahydrofuran-2-ylmethyl)-6-[(2-thioxoimidazolidin-1-yl)methyl]thieno[2,3-d]pyrimidine-2,4(1H,3H)-dione (racemate)

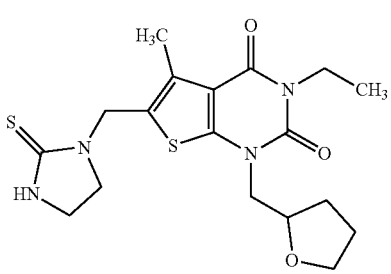 [SMILES: CCn1c(=O)c2c(C)c(CN3CCNC3=S)sc2n(CC2CCCO2)c1=O]

582 mg (1.175 mmol) of the compound from Ex. 225A were dissolved in 28.9 ml of dioxane, and 330.6 mg (1.763 mmol) of 1,1'-thiocarbonyldiimidazole were added. The mixture was stirred at RT for 19 h. The reaction solution was then concentrated on a rotary evaporator. The residue was dissolved in 12 ml of DMSO and this solution was purified by means of preparative HPLC (Method 14). Combination of the product fractions and freeze-drying gave 281 mg (58% of theory) of the title compound.

$^1$H-NMR (400 MHz, DMSO-$d_6$, δ/ppm): 8.35 (s, 1H), 4.82 (s, 2H), 4.26-4.18 (m, 1H), 4.02 (dd, 1H), 3.90 (q, 2H), 3.78-3.65 (m, 2H), 3.64-3.57 (m, 1H), 3.56-3.49 (m, 2H), 3.44-3.37 (m, 2H), 2.43 (s, 3H), 2.02-1.76 (m, 3H), 1.71-1.61 (m, 1H), 1.11 (t, 3H).

LC/MS (Method 3): $R_t$=1.02 min, m/z=409 [M+H]$^+$.

Example 36

3-Ethyl-5-methyl-1-(tetrahydro-2H-pyran-2-ylmethyl)-6-[(2-thioxoimidazolidin-1-yl)methyl]thieno[2,3-d]pyrimidine-2,4(1H,3H)-dione (racemate)

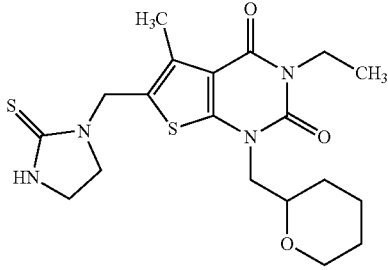 [SMILES: CCn1c(=O)c2c(C)c(CN3CCNC3=S)sc2n(CC2CCCCO2)c1=O]

320 mg (0.732 mmol) of the compound from Ex. 226A were dissolved in 14 ml of dioxane, and 206 mg (1.097 mmol) of 1,1'-thiocarbonyldiimidazole were added. The mixture was stirred at RT for 18 h. The reaction solution was then concentrated on a rotary evaporator. The residue was dissolved in 9 ml of DMSO and this solution was purified by means of preparative HPLC (Method 14). Combination of the product fractions and freeze-drying gave 191 mg (61% of theory) of the title compound.

$^1$H-NMR (400 MHz, DMSO-$d_6$, δ/ppm): 8.34 (s, 1H), 4.88-4.75 (m, 2H), 4.01-3.93 (m, 1H), 3.90 (q, 2H), 3.81 (dd, 1H), 3.72-3.63 (m, 2H), 3.58-3.46 (m, 2H), 3.44-3.35 (m, 2H), 3.30-3.21 (m, 1H), 2.43 (s, 3H), 1.78 (d, 1H), 1.61 (d, 1H), 1.52-1.38 (m, 3H), 1.32-1.19 (m, 1H), 1.11 (t, 3H).

LC/MS (Method 3): $R_t$=1.13 min, m/z=423 [M+H]$^+$.

Example 37

1-(3,3-Dimethylbutyl)-3-ethyl-5-methyl-6-[(2-thioxoimidazolidin-1-yl)methyl]thieno[2,3-d]pyrimidine-2,4(1H,3H)-dione

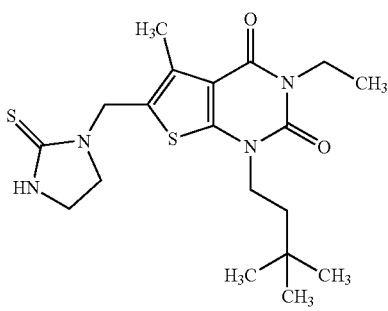 [SMILES: CCn1c(=O)c2c(C)c(CN3CCNC3=S)sc2n(CCC(C)(C)C)c1=O]

180 mg (0.368 mmol) of the compound from Ex. 234A were dissolved in 9.2 ml of dioxane, and 104 mg (0.552 mmol) of 1,1'-thiocarbonyldiimidazole were added. The mixture was stirred at RT for 19 h. The reaction solution was then concentrated on a rotary evaporator. The residue was dissolved in 6 ml of DMSO and this solution was purified by means of preparative HPLC (Method 14). Combination of the product fractions and freeze-drying gave 78 mg (52% of theory) of the title compound.

$^1$H-NMR (400 MHz, DMSO-$d_6$, δ/ppm): 8.34 (s, 1H), 4.82 (s, 2H), 3.93-3.80 (m, 4H), 3.57-3.49 (m, 2H), 2.43 (s, 3H), 1.57-1.50 (m, 2H), 1.11 (t, 3H), 0.96 (s, 9H).

LC/MS (Method 3): $R_t$=1.30 min, m/z=409 [M+H]$^+$.

Example 38

3-Isobutyl-5-methyl-6-[(2-thioxoimidazolidin-1-yl)methyl]-1-(3,3,3-trifluoropropyl)thieno[2,3-d]pyrimidine-2,4(1H,3H)-dione

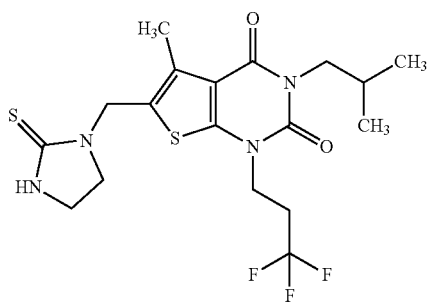 [SMILES: Cc1c(CN2CCNC2=S)sc2c1c(=O)n(CC(C)C)c(=O)n2CCC(F)(F)F]

115 mg (0.269 mmol) of the compound from Ex. 239A were dissolved in 5 ml of dioxane, and 75.6 mg (0.4 mmol) of 1,1'-thiocarbonyldiimidazole were added. The mixture was stirred at RT for 67 h. The reaction solution was then concentrated on a rotary evaporator. The residue was dissolved in 3 ml of DMSO and this solution was purified by means of preparative HPLC (Method 14). Combination of the product fractions and freeze-drying gave 13 mg (11% of theory) of the title compound.

$^1$H-NMR (400 MHz, DMSO-$d_6$, δ/ppm): 8.36 (s, 1H), 4.84 (s, 2H), 4.10 (t, 2H), 3.71 (d, 2H), 3.59-3.50 (m, 2H), 3.46-3.37 (m, 2H), 2.83-2.69 (m, 2H), 2.44 (s, 3H), 2.09-1.97 (m, 1H), 0.85 (d, 6H).

LC/MS (Method 3): $R_t$=1.27 min, m/z=449 [M+H]$^+$.

Example 39

3-Isobutyl-1-(2-methoxyethyl)-5-methyl-6-[(2-thioxoimidazolidin-1-yl)methyl]thieno[2,3-d]pyrimidine-2,4(1H,3H)-dione

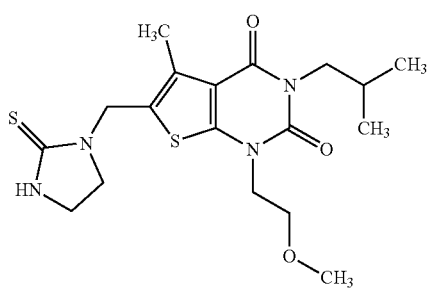 [SMILES: COCCn1c(=O)n(CC(C)C)c(=O)c2c(C)c(CN3CCNC3=S)sc21]

103 mg (0.204 mmol) of the compound from Ex. 242A were dissolved in 5 ml of dioxane, and 57.4 mg (0.306 mmol) of 1,1'-thiocarbonyldiimidazole were added. The mixture was stirred at RT for 18 h. The reaction mixture was then purified directly by means of preparative HPLC (Method 14). Combination of the product fractions and freeze-drying gave 11 mg (11% of theory) of the title compound and 18 mg of the N-formyl derivative (see Example 46).

$^1$H-NMR (400 MHz, DMSO-$d_6$, δ/ppm): 8.32 (s, 1H), 4.82 (s, 2H), 4.01 (t, 2H), 3.71 (d, 2H), 3.62 (t, 2H), 3.58-3.49 (m, 2H), 3.45-3.36 (m, 2H), 3.23 (s, 3H), 2.43 (s, 3H), 2.09-1.97 (m, 1H), 0.85 (d, 6H).

LC/MS (Method 3): $R_t$=1.13 min, m/z=411 [M+H]$^+$.

Example 40

1-(3-Fluoropropyl)-5-methyl-6-[(2-thioxoimidazolidin-1-yl)methyl]-3-(2,2,2-trifluoroethyl)thieno[2,3-d]pyrimidine-2,4(1H,3H)-dione

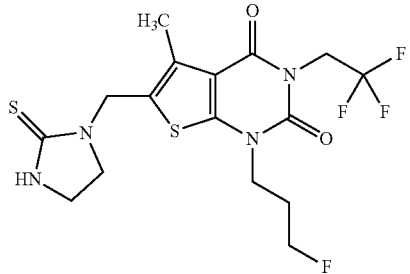 [SMILES: Cc1c(CN2CCNC2=S)sc2c1c(=O)n(CC(F)(F)F)c(=O)n2CCCF]

140 mg (0.254 mmol) of the compound from Ex. 248A were dissolved in 5 ml of dioxane, and 71.5 mg (0.381 mmol) of 1,1'-thiocarbonyldiimidazole were added. The mixture was stirred at RT for 20 h. The reaction mixture was then purified directly by means of preparative HPLC (Method 14). Combination of the product fractions and freeze-drying gave 77 mg (67% of theory) of the title compound.

$^1$H-NMR (400 MHz, DMSO-$d_6$, δ/ppm): 8.36 (s, 1H), 4.85 (s, 2H), 4.69 (q, 2H), 4.59 (t, 1H), 4.47 (t, 1H), 4.01 (t, 2H), 3.59-3.51 (m, 2H), 3.46-3.37 (m, 2H), 2.44 (s, 3H), 2.15-1.99 (m, 2H).

LC/MS (Method 3): $R_t$=1.10 min, m/z=439 [M+H]$^+$.

Example 41

1-(2-Methoxyethyl)-5-methyl-6-[(2-thioxoimidazolidin-1-yl)methyl]-3-(2,2,2-trifluoroethyl)thieno[2,3-d]pyrimidine-2,4(1H,3H)-dione

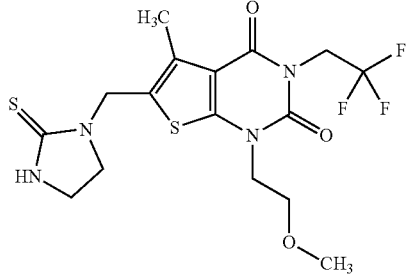 [SMILES: COCCn1c(=O)n(CC(F)(F)F)c(=O)c2c(C)c(CN3CCNC3=S)sc21]

140 mg (0.234 mmol) of the compound from Ex. 249A were dissolved in 5 ml of dioxane, and 65.9 mg (0.351 mmol) of 1,1'-thiocarbonyldiimidazole were added. The mixture was stirred at RT for 18 h. The reaction solution was then concentrated on a rotary evaporator. The residue was dissolved in 6 ml of DMSO and this solution was purified by means of preparative HPLC (Method 14). Combination of the product fractions and freeze-drying gave 46 mg (45% of theory) of the title compound.

$^1$H-NMR (400 MHz, DMSO-$d_6$, δ/ppm): 8.36 (s, 1H), 4.84 (s, 2H), 4.69 (q, 2H), 4.04 (t, 2H), 3.63 (t, 2H), 3.59-3.50 (m, 2H), 3.44-3.38 (m, 2H), 3.23 (s, 3H), 2.43 (s, 3H).

LC/MS (Method 3): $R_t$=1.05 min, m/z=437 [M+H]$^+$.

Example 42

3-(2,2-Difluoroethyl)-1-(3-fluoropropyl)-5-methyl-6-[(2-thioxoimidazolidin-1-yl)methyl]thieno[2,3-d]pyrimidine-2,4(1H,3H)-dione

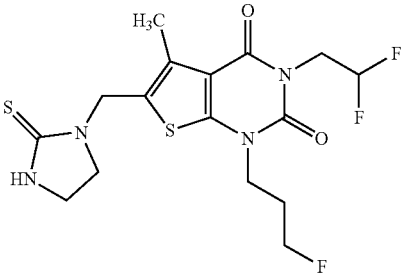 [SMILES: Cc1c(CN2CCNC2=S)sc2c1c(=O)n(CC(F)F)c(=O)n2CCCF]

195 mg (0.433 mmol) of the compound from Ex. 256A were dissolved in 8.8 ml of dioxane, and 121.8 mg (0.649 mmol) of 1,1'-thiocarbonyldiimidazole were added. The mixture was stirred at RT for 17 h. The reaction solution was then concentrated on a rotary evaporator. The residue was dissolved in 6 ml of DMSO and this solution was purified by means of preparative HPLC (Method 14). Combination of the product fractions and freeze-drying gave 73 mg (40% of theory) of the title compound.

$^1$H-NMR (400 MHz, DMSO-$d_6$, δ/ppm): 8.34 (s, 1H), 6.36-6.04 (m, 1H), 4.85 (s, 2H), 4.59 (t, 1H), 4.47 (t, 1H), 4.29 (td, 2H), 4.00 (t, 2H), 3.58-3.50 (m, 2H), 3.46-3.37 (m, 2H), 2.44 (s, 3H), 2.14-2.00 (m, 2H).

LC/MS (Method 3): $R_t$=1.04 min, m/z=421 [M+H]$^+$.

Example 43

3-(2,2-Difluoroethyl)-1-(2-methoxy ethyl)-6-[(2-thioxoimidazolidin-1-yl)methyl]thieno[2,3-d]pyrimidine-2,4(1H,3H)-dione

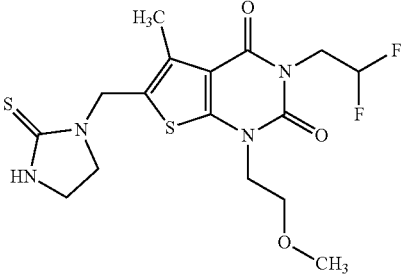 [SMILES: COCCn1c(=O)n(CC(F)F)c(=O)c2c(C)c(CN3CCNC3=S)sc21]

178 mg (0.34 mmol) of the compound from Ex. 257A were dissolved in 7.36 ml of dioxane, and 95.8 mg (0.511 mmol) of 1,1'-thiocarbonyldiimidazole were added. The mixture was stirred at RT for 16 h. Then another 31.9 mg (0.17 mmol) of 1,1'-thiocarbonyldiimidazole were added, and the mixture was stirred at RT for a further 7 h. The reaction solution was then concentrated on a rotary evaporator. The residue was dissolved in 6 ml of DMSO and this solution was purified by means of preparative HPLC (Method 14). Combination of the product fractions and freeze-drying gave 59 mg (40% of theory) of the title compound.

$^1$H-NMR (400 MHz, DMSO-$d_6$, δ/ppm): 8.34 (s, 1H), 6.38-6.05 (m, 1H), 4.84 (s, 2H), 4.29 (td, 2H), 4.03 (t, 2H), 3.63 (t, 2H), 3.58-3.49 (m, 2H), 3.46-3.37 (m, 2H), 3.24 (s, 3H), 2.43 (s, 3H).

LC/MS (Method 3): $R_t$=0.99 min, m/z=419 [M+H]$^+$.

Example 44

5-(Difluoromethyl)-3-ethyl-6-[(2-thioxoimidazolidin-1-yl)methyl]-1-(3,3,3-trifluoropropyl)thieno[2,3-d]pyrimidine-2,4(1H,3H)-dione

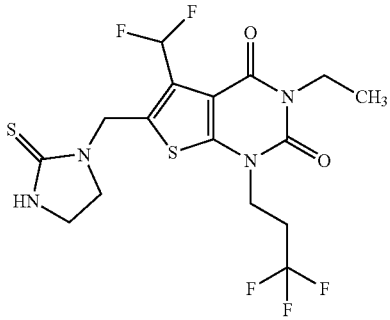 [SMILES: CCn1c(=O)c2c(C(F)F)c(CN3CCNC3=S)sc2n(CCC(F)(F)F)c1=O]

354 mg (0.854 mmol) of the compound from Ex. 264A were dissolved in 18 ml of dioxane, and 240 mg (1.28 mmol) of 1,1'-thiocarbonyldiimidazole were added. The mixture was stirred at RT for 17 h. The reaction solution was then concentrated on a rotary evaporator. The residue was dissolved in 6 ml of DMSO and this solution was purified by means of preparative HPLC (Method 14). Combination of the product fractions and freeze-drying gave 79 mg (19% of theory) of the title compound.

$^1$H-NMR (400 MHz, DMSO-$d_6$, δ/ppm): 8.55 (s, 1H), 7.74-7.43 (m, 1H), 5.05 (s, 2H), 4.12 (t, 2H), 3.92 (q, 2H), 3.65-3.57 (m, 2H), 3.50-3.42 (m, 2H), 2.85-2.71 (m, 2H), 1.13 (t, 3H).

LC/MS (Method 3): $R_t$=1.18 min, m/z=457 [M+H]$^+$.

Example 45

5-(Difluoromethyl)-3-ethyl-1-(2-methoxyethyl)-6-[(2-thioxoimidazolidin-1-yl)methyl]thieno[2,3-d]pyrimidine-2,4(1H,3H)-dione

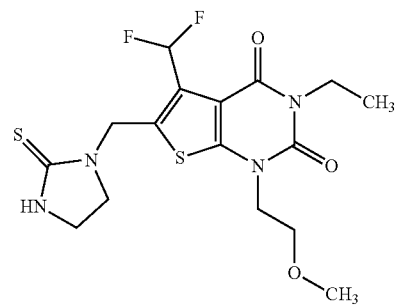 [SMILES: CCn1c(=O)c2c(C(F)F)c(CN3CCNC3=S)sc2n(CCOC)c1=O]

335 mg (0.89 mmol) of the compound from Ex. 265A were dissolved in 18 ml of dioxane, and 250.4 mg (1.33 mmol) of 1,1'-thiocarbonyldiimidazole were added. The mixture was stirred at RT for 17 h. The reaction solution was then concentrated on a rotary evaporator. The residue was dissolved in 6 ml of DMSO and this solution was purified by means of preparative HPLC (Method 14). Combination of the product fractions and freeze-drying gave 42 mg (10% of theory) of the title compound.

$^1$H-NMR (400 MHz, DMSO-$d_6$, δ/ppm): 8.58-8.49 (m, 1H), 7.72-7.42 (m, 1H), 5.02 (s, 2H), 4.04 (t, 2H), 3.91 (q, 2H), 3.68-3.55 (m, 4H), 3.50-3.41 (m, 2H), 3.24 (s, 3H), 1.13 (t, 3H).

LC/MS (Method 3): $R_t$=1.05 min, m/z=419 [M+H]$^+$.

Example 46

3-{[3-Isobutyl-1-(2-methoxyethyl)-5-methyl-2,4-dioxo-1,2,3,4-tetrahydrothieno[2,3-d]pyrimidin-6-yl]methyl}-2-thioxoimidazolidine-1-carbaldehyde

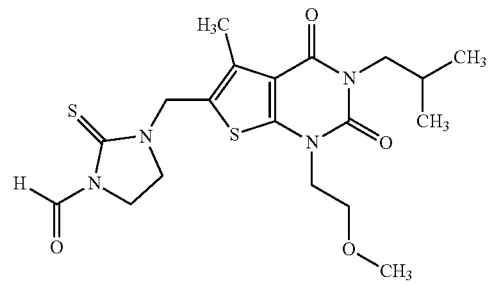 [SMILES: COCCn1c(=O)n(CC(C)C)c(=O)c2c(C)c(CN3CCN(C=O)C3=S)sc21]

The title compound (18 mg) was obtained as a by-product of the preparation and purification of the compound described in Example 39.

$^1$H-NMR (400 MHz, DMSO-$d_6$, δ/ppm): 9.29 (s, 1H), 5.05 (s, 2H), 4.05-3.99 (m, 2H), 3.87-3.80 (m, 2H), 3.77-3.68 (m, 4H), 3.62 (t, 2H), 3.22 (s, 3H), 2.47 (s, 3H), 2.09-1.99 (m, 1H), 0.84 (d, 6H).

LC/MS (Method 3): $R_t$=1.25 min, m/z=439 [M+H]$^+$.

Example 47

3-Ethyl-5-methyl-6-[(2-oxoimidazolidin-1-yl)methyl]-1-(2,2,2-trifluoroethyl)thieno[2,3-d]pyrimidine-2,4(1H,3H)-dione

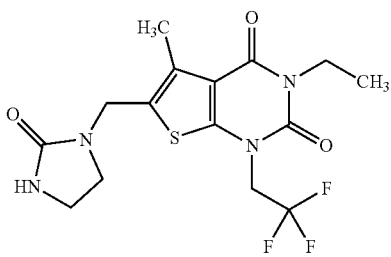 [SMILES: CCn1c(=O)c2c(C)c(CN3CCNC3=O)sc2n(CC(F)(F)F)c1=O]

To a solution of 720 mg (1.42 mmol, 72% purity) of the compound from Ex. 209A and 297 µl (2.13 mmol) of triethylamine in 14 ml of THF were added 277 mg (1.71 mmol) of CDI, and the mixture was stirred at RT for about 18 h. Subsequently, the mixture was concentrated to dryness. The remaining residue was taken up in ethyl acetate and washed successively with 1 M hydrochloric acid, water and saturated sodium chloride solution. After drying over anhydrous magnesium sulphate, the mixture was filtered and concentrated. The solid residue was stirred in a little acetonitrile at RT. Filtration and drying of the solid under high vacuum gave 276 mg (49% of theory) of the title compound.

$^1$H-NMR (400 MHz, DMSO-d$_6$, δ/ppm): 6.54 (br. s, 1H), 4.81 (q, 2H), 4.37 (s, 2H), 3.91 (q, 2H), 3.29-3.14 (m, 4H), 2.41 (s, 3H), 1.13 (t, 3H).

LC/MS (Method 1, ESIpos): R$_t$=0.79 min, m/z=391 [M+H]$^+$.

Example 48

3-Ethyl-5-methyl-6-[(2-oxoimidazolidin-1-yl)methyl]-1-(3,3,3-trifluoropropyl)thieno[2,3-d]pyrimidine-2,4(1H,3H)-dione

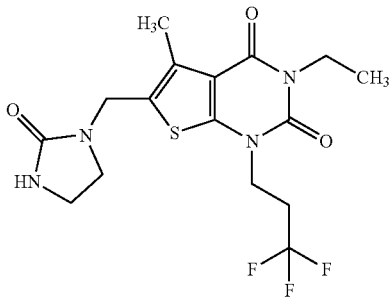

To a solution of 92 mg (1.07 mmol) of imidazolidin-2-one in 2.8 ml of THF were added 43 mg (1.07 mmol) of sodium hydride (60% suspension in mineral oil), and the mixture was heated to 60° C. for 2 h and subsequently cooled back down to RT ("Solution 1"). To a solution of 90 mg (0.268 mmol) of the compound from Ex. 140A in 1.8 ml of dichloromethane in another reaction vessel were added, at 0° C., 93 µl (0.535 mmol) of N,N-diisopropylethylamine and 20 µl (0.281 mmol) of thionyl chloride. After 20 min at 0° C., Solution 1 was added dropwise and then the cooling bath was removed. The reaction mixture was stirred at RT for 4 days. Then all the volatile constituents were removed on a rotary evaporator. The remaining residue was separated into its components by means of preparative HPLC (Method 10). After concentration of the product fractions and drying under high vacuum, 55 mg (51% of theory) of the title compound were obtained.

$^1$H-NMR (400 MHz, DMSO-d$_6$, δ/ppm): 6.55 (br. s, 1H), 4.37 (s, 2H), 4.10 (t, 2H), 3.90 (q, 2H), 3.33-3.13 (m, 4H), 2.87-2.67 (m, 2H), 2.41 (s, 3H), 1.12 (t, 3H).

LC/MS (Method 1, ESIpos): R$_t$=0.86 min, m/z=405 [M+H]$^+$.

Example 49

3-Ethyl-5-methyl-6-[(2-oxoimidazolidin-1-yl)methyl]-1-(4,4,4-trifluorobutyl)thieno[2,3-d]pyrimidine-2,4(1H,3H)-dione

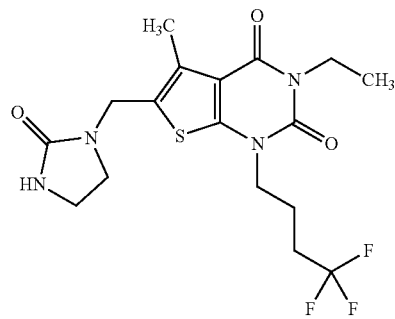 [SMILES: CCn1c(=O)c2c(C)c(CN3CCNC3=O)sc2n(CCCC(F)(F)F)c1=O]

Analogously to the method described in Ex. 47, 300 mg (0.573 mmol, 75% purity) of the compound from Ex. 211A and 112 mg (0.688 mmol) of CDI were used to prepare 140 mg (58% of theory) of the title compound. It was possible here to dispense with the aqueous workup prior to the stirring with acetonitrile.

$^1$H-NMR (400 MHz, DMSO-d$_6$, δ/ppm): 6.52 (s, 1H), 4.36 (s, 2H), 3.95 (t, 2H), 3.90 (q, 2H), 3.28-3.16 (m, 4H), 2.47-2.33 (m, 2H), 2.40 (s, 3H), 1.89 (quin, 2H), 1.12 (t, 3H).

LC/MS (Method 1, ESIpos): R$_t$=0.90 min, m/z=419 [M+H]$^+$.

Example 50

3-Ethyl-1-(2-fluoroethyl)-5-methyl-6-[(2-oxoimidazolidin-1-yl)methyl]thieno[2,3-d]pyrimidine-2,4(1H,3H)-dione

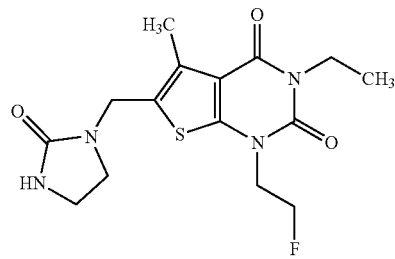 [SMILES: CCn1c(=O)c2c(C)c(CN3CCNC3=O)sc2n(CCF)c1=O]

Analogously to the method described in Ex. 47, 286 mg (0.749 mmol, 86% purity) of the compound from Ex. 213A and 146 mg (0.899 mmol) of CDI were used to prepare 135 mg (50% of theory) of the title compound.

$^1$H-NMR (400 MHz, DMSO-$d_6$, δ/ppm): 6.52 (s, 1H), 4.73 (dt, 2H), 4.35 (s, 2H), 4.18 (dt, 2H), 3.91 (q, 2H), 3.29-3.15 (m, 4H), 2.40 (s, 3H), 1.13 (t, 3H).

LC/MS (Method 1, ESIpos): $R_t$=0.65 min, m/z=355 [M+H]$^+$.

Example 51

3-Ethyl-1-(3-fluoropropyl)-5-methyl-6-[(2-oxoimidazolidin-1-yl)methyl]thieno[2,3-d]pyrimidine-2,4(1H,3H)-dione

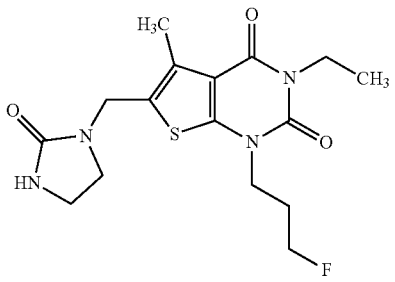

55 mg (0.154 mmol) of the compound from Example 214A were dissolved in 3 ml of DMSO, and 36.2 mg (0.217 mmol) of CDI were added. The mixture was stirred at RT for 116 h. The reaction mixture was then purified directly by means of preparative HPLC (Method 14). Combination of the product fractions and freeze-drying gave 9 mg (17% of theory) of the title compound.

$^1$H-NMR (400 MHz, DMSO-$d_6$, δ/ppm): 6.51 (s, 1H), 4.59 (t, 1H), 4.47 (t, 1H), 4.35 (s, 2H), 3.98 (t, 2H), 3.90 (q, 2H), 3.28-3.17 (m, 4H), 2.40 (s, 3H), 2.14-1.98 (m, 2H), 1.11 (t, 3H).

LC/MS (Method 3): $R_t$=0.9 min, m/z=369 [M+H]$^+$.

Example 52

3-Ethyl-1-(4-fluorobutyl)-5-methyl-6-[(2-oxoimidazolidin-1-yl)methyl]thieno[2,3-d]pyrimidine-2,4(1H,3H)-dione

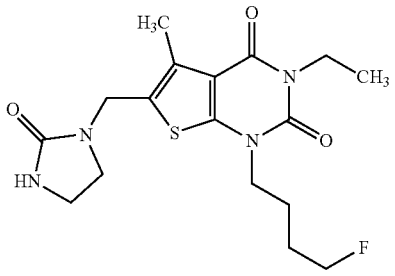

125 mg (0.162 mmol) of the compound from Example 215A were dissolved in 4 ml of dioxane, and 40.6 mg (0.243 mmol) of CDI were added. The mixture was stirred at RT for 19 h. The reaction solution was then concentrated on a rotary evaporator. The residue was dissolved in 3 ml of DMSO and this solution was purified by means of preparative HPLC (Method 14). Combination of the product fractions and freeze-drying gave 44 mg (62% of theory) of the title compound.

$^1$H-NMR (400 MHz, DMSO-$d_6$, δ/ppm): 6.52 (s, 1H), 4.51 (t, 1H), 4.42 (t, 1H), 4.35 (s, 2H), 3.93-3.86 (m, 4H), 3.28-3.18 (m, 4H), 2.40 (s, 3H), 1.80-1.64 (m, 4H), 1.11 (t, 3H).

LC/MS (Method 3): $R_t$=0.97 min, m/z=383 [M+H]$^+$.

Example 53

3-Ethyl-5-methyl-6-[(2-oxoimidazolidin-1-yl)methyl]-1-[2-(trifluoromethyl)prop-2-en-1-yl]thieno[2,3-d]pyrimidine-2,4(1H,3H)-dione

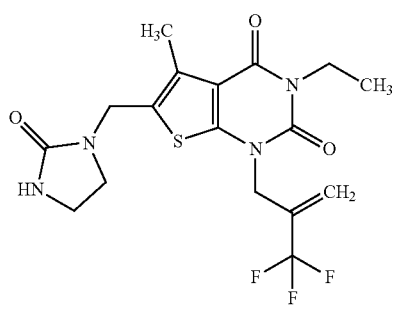 [SMILES: C=C(Cn1c(=O)n(CC)c(=O)c2c(C)c(CN3CCNC3=O)sc21)C(F)(F)F]

Analogously to the method described in Ex. 47, 238 mg (0.518 mmol, 85% purity) of the compound from Ex. 216A and 101 mg (0.622 mmol) of CDI were used to prepare 98 mg (43% of theory) of the title compound.

$^1$H-NMR (400 MHz, DMSO-$d_6$, δ/ppm): 6.52 (s, 1H), 5.98 (s, 1H), 5.70 (s, 1H), 4.74 (s, 2H), 4.35 (s, 2H), 3.92 (q, 2H), 3.28-3.12 (m, 4H), 2.41 (s, 3H), 1.13 (t, 3H).

LC/MS (Method 1, ESIpos): $R_t$=0.87 min, m/z=417 [M+H]$^+$.

Example 54

1-[(2,2-Difluorocyclopropyl)methyl]-3-ethyl-5-methyl-6-[(2-oxoimidazolidin-1-yl)methyl]thieno[2,3-d]pyrimidine-2,4(1H,3H)-dione (racemate)

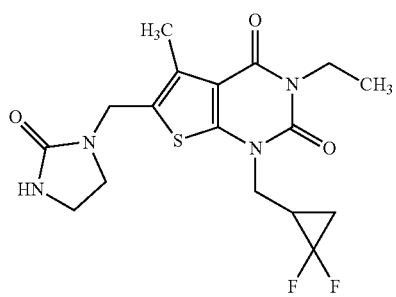 [SMILES: CCn1c(=O)c2c(C)c(CN3CCNC3=O)sc2n(CC2CC2(F)F)c1=O]

Analogously to the method described in Ex. 47, 540 mg (1.19 mmol, 82% purity) of the compound from Ex. 217A and 231 mg (1.43 mmol) of CDI were used to prepare 300 mg (63% of theory) of the title compound.

$^1$H-NMR (400 MHz, DMSO-d$_6$, δ/ppm): 6.53 (s, 1H), 4.36 (s, 2H), 4.17-4.04 (m, 1H), 4.01-3.92 (m, 1H), 3.91 (q, 2H), 3.29-3.17 (m, 4H), 2.41 (s, 3H), 2.28-2.10 (m, 1H), 1.79-1.62 (m, 1H), 1.54-1.39 (m, 1H), 1.12 (t, 3H).

LC/MS (Method 1, ESIpos): R$_t$=0.83 min, m/z=399 [M+H]$^+$.

Example 55

1-[(2,2-Difluorocyclopropyl)methyl]-3-ethyl-5-methyl-6-[(2-oxoimidazolidin-1-yl)methyl]thieno[2,3-d]pyrimidine-2,4(1H,3H)-dione (Enantiomer 1)

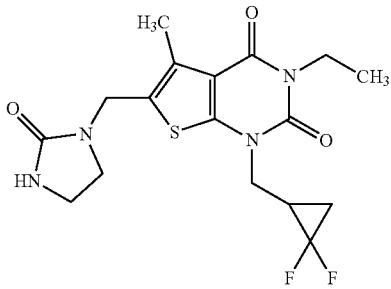 [SMILES: CCn1c(=O)c2c(C)c(CN3CCNC3=O)sc2n(CC2CC2(F)F)c1=O]

291 mg (0.730 mmol) of the racemic compound from Ex. 54 were dissolved in 20 ml of methanol and, in 24 portions, separated into the enantiomers by preparative HPLC on a chiral phase [column: Daicel Chiralpak IA, 5 µm, 250 mm×20 mm; eluent: tert-butyl methyl ether/methanol 50:50; flow rate: 20 ml/min; temperature: 20° C.; detection: 210 nm]. After concentration of the product fractions and drying under high vacuum, 122 mg (83% of theory) of Enantiomer 1 were obtained (99.0% ee, chiral analytical HPLC).

$^1$H-NMR (400 MHz, DMSO-d$_6$, δ/ppm): 6.53 (s, 1H), 4.36 (s, 2H), 4.19-4.03 (m, 1H), 4.01-3.92 (m, 1H), 3.91 (q, 2H), 3.29-3.16 (m, 4H), 2.41 (s, 3H), 2.27-2.11 (m, 1H), 1.80-1.63 (m, 1H), 1.53-1.39 (m, 1H), 1.12 (t, 3H).

Chiral analytical HPLC [column: Daicel Chiralpak IA, 5 µm, 250 mm×4.6 mm; eluent: tert-butyl methyl ether/methanol 50:50; flow rate: 3 ml/min; temperature: 30° C.; detection: 210 nm]: R$_t$=5.26 min.

Example 56

1-[(2,2-Difluorocyclopropyl)methyl]-3-ethyl-5-methyl-6-[(2-oxoimidazolidin-1-yl)methyl]thieno[2,3-d]pyrimidine-2,4(1H,3H)-dione (Enantiomer 2)

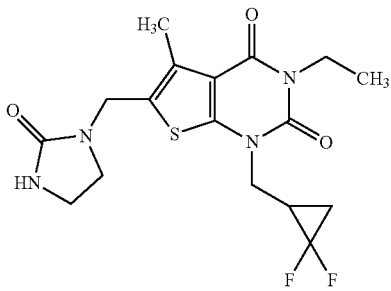 [SMILES: CCn1c(=O)c2c(C)c(CN3CCNC3=O)sc2n(CC2CC2(F)F)c1=O]

291 mg (0.730 mmol) of the racemic compound from Ex. 54 were dissolved in 20 ml of methanol and, in 24 portions, separated into the enantiomers by preparative HPLC on a chiral phase [column: Daicel Chiralpak IA, 5 µm, 250 mm×20 mm; eluent: tert-butyl methyl ether/methanol 50:50; flow rate: 20 ml/min; temperature: 20° C.; detection: 210 nm]. After concentration of the product fractions and drying under high vacuum, 126 mg (86% of theory) of Enantiomer 2 were obtained (99.9% ee, chiral analytical HPLC).

$^1$H-NMR (400 MHz, DMSO-d$_6$, δ/ppm): 6.53 (s, 1H), 4.36 (s, 2H), 4.17-4.03 (m, 1H), 4.01-3.92 (m, 1H), 3.91 (q, 2H), 3.29-3.15 (m, 4H), 2.41 (s, 3H), 2.29-2.11 (m, 1H), 1.82-1.61 (m, 1H), 1.55-1.40 (m, 1H), 1.12 (t, 3H).

Chiral analytical HPLC [column: Daicel Chiralpak IA, 5 µm, 250 mm×4.6 mm; eluent: tert-butyl methyl ether/methanol 50:50; flow rate: 3 ml/min; temperature: 30° C.; detection: 210 nm]: R$_t$=4.55 min.

Example 57

3-Ethyl-5-methyl-6-[(2-oxoimidazolidin-1-yl)methyl]-1-[2-(trifluoromethoxy)ethyl]thieno[2,3-d]pyrimidine-2,4(1H,3H)-dione

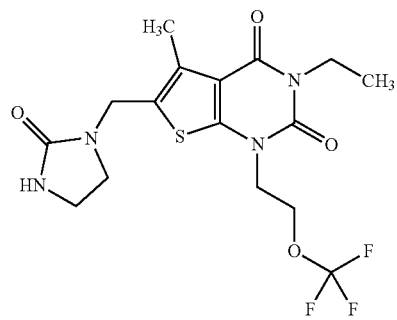

To a solution of 288 mg (0.570 mmol, 78% purity) of the compound from Ex. 218A and 119 µl (0.854 mmol) of triethylamine in 5.5 ml of THF were added 111 mg (0.683 mmol) of CDI, and the mixture was stirred at RT for about 18 h. The reaction mixture was then separated into its components directly by means of preparative HPLC (Method 8). After concentration of the product fractions and drying under high vacuum, 79 mg (32% of theory, 97% purity) of the title compound were obtained.

$^1$H-NMR (400 MHz, DMSO-d$_6$, δ/ppm): 6.53 (s, 1H), 4.43-4.37 (m, 2H), 4.36 (s, 2H), 4.19 (t, 2H), 3.91 (q, 2H), 3.28-3.15 (m, 4H), 2.40 (s, 3H), 1.12 (t, 3H).

LC/MS (Method 1, ESIpos): R$_t$=0.87 min, m/z=421 [M+H]$^+$.

Example 58

3-Ethyl-5-methyl-6-[(2-oxoimidazolidin-1-yl)methyl]-1-{2-[(trifluoromethyl) sulphanyl]ethyl}thieno[2,3-d]pyrimidine-2,4(1H,3H)-dione

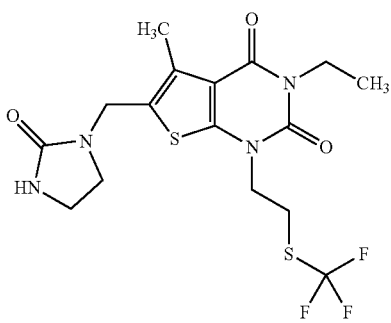

Analogously to the method described in Ex. 57, 270 mg (0.526 mmol, 80% purity) of the compound from Ex. 219A and 102 mg (0.631 mmol) of CDI were used to prepare 140 mg (60% of theory) of the title compound.

$^1$H-NMR (400 MHz, DMSO-$d_6$, δ/ppm): 6.53 (s, 1H), 4.36 (s, 2H), 4.14 (t, 2H), 3.90 (q, 2H), 3.35 (t, 2H, partially obscured by the water signal), 3.28-3.17 (m, 4H), 2.40 (s, 3H), 1.12 (t, 3H).

LC/MS (Method 1, ESIpos): $R_t$=0.92 min, m/z=437 [M+H]$^+$.

Example 59

3-Ethyl-1-(2-methoxyethyl)-5-methyl-6-[(2-oxoimidazolidin-1-yl)methyl]thieno[2,3-d]pyrimidine-2,4(1H,3H)-dione

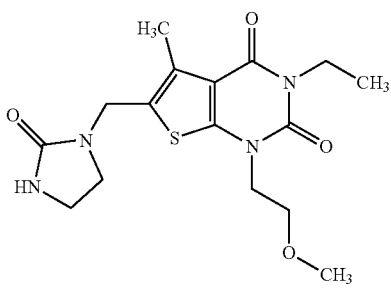

Method A:

To a solution of 99 mg (1.15 mmol) of imidazolidin-2-one in 3 ml of THF were added 46 mg (1.15 mmol) of sodium hydride (60% suspension in mineral oil), and the mixture was heated to 60° C. for 2 h and subsequently cooled back down to RT ("Solution 1"). To a solution of 90 mg (0.287 mmol) of the compound from Ex. 143A in 2 ml of dichloromethane in another reaction vessel were added, at 0° C., 100 µl (0.573 mmol) of N,N-diisopropylethylamine and 22 µl (0.301 mmol) of thionyl chloride. After 20 min at 0° C., Solution 1 was added dropwise and then the cooling bath was removed. The reaction mixture was stirred at RT for about 18 h. Then all the volatile constituents were removed on a rotary evaporator. The remaining residue was separated into its components by means of preparative HPLC (Method 8). After concentration of the product fractions and drying under high vacuum, 63 mg (60% of theory) of the title compound were obtained.

Method B:

To a solution of 45.95 g (135 mmol) of the compound from Ex. 220A and 28.2 ml (202 mmol) of triethylamine in 1.12 liters of THF were added 26.26 g (162 mmol) of CDI, and the mixture was stirred at RT for about 18 h. Subsequently, the mixture was concentrated to dryness. The remaining residue was taken up in 1.5 liters of ethyl acetate and washed successively with 1 M hydrochloric acid, water, saturated sodium carbonate solution and saturated sodium chloride solution. After drying over anhydrous magnesium sulphate, the mixture was filtered and concentrated. In this way, a first fraction of 37.5 g of the crude product was obtained. The combined aqueous phases were extracted once again with ethyl acetate. After concentration of the organic extract, a second fraction of 9.5 g of the crude product was obtained. The first crude product fraction was suspended in 200 ml of ethyl acetate and stirred at RT for 5 min, before 100 ml of cyclohexane were added. After the heterogeneous mixture had been stirred at RT overnight, the solids were filtered off with suction and dried under high vacuum. This gave a first pure fraction of the title compound (19.62 g). The same procedure was followed with the second crude product fraction, using 100 ml of ethyl acetate and 50 ml of cyclohexane. This gave the second pure fraction of the title compound (2.75 g). The ethyl acetate/cyclohexane filtrates obtained above were combined and concentrated to dryness. The remaining residue (17.64 g) was purified by means of preparative HPLC (Method 15). Concentration of the product fractions and drying under high vacuum gave a third pure product fraction (5.02 g). A total of 27.39 g (55% of theory) of the title compound were thus obtained.

Method C:

1.43 g (4.25 mmol) of the compound from Ex. 201A were dissolved in methanol and passed through a hydrogencarbonate cartridge (from Polymerlabs, Stratospheres SPE, PL-HCO$_3$ MP SPE). After concentration of the solution, 1.25 g of the free amine (compound from Ex. 200A) were obtained. The amine was dissolved in a mixture of 29 ml of DMF and 14 ml of THF, and 380 µl (4.46 mmol) of 2-chloroethyl isocyanate were added. After stirring for 2 h, 715 mg (6.37 mmol) of potassium tert-butoxide were added to the reaction mixture. After a further 30 min, the mixture was diluted with n-hexane and washed successively with saturated sodium hydrogencarbonate solution and saturated sodium chloride solution. The organic phase was dried over anhydrous magnesium sulphate, filtered and concentrated. This gave a first fraction of the crude product. The combined aqueous phases were extracted once again with ethyl acetate. Drying of the extract over anhydrous magnesium sulphate, filtration and concentration gave a second crude product fraction. The crude products were purified by means of preparative HPLC (Method 8). After combination of the product fractions and drying under high vacuum, 514 mg (31% of theory, 95% purity) of the title compound were obtained.

Crystallization of the Title Compound:

6.5 g of the title compound were admixed with 135 ml of water/ethanol (95:5) and heated until commencement of reflux. Once everything had gone into solution, the oil bath temperature was turned down to 70° C. At this time, the compound began to precipitate out. The mixture was stirred gently at 70° C. overnight. The next morning, the oil bath temperature was turned down to 50° C. and the mixture was stirred at this temperature for 3 h. Then the heating was switched off and the mixture was allowed to come gradually to RT in the oil bath while stirring. After about 4 h, RT had been attained, and the mixture was then left to stand at RT without stirring for a further 2.5 days. The compound was then filtered off with suction, washed with a little water/ethanol (95:5) and then dried at 4 mbar and 50° C. In this way, 6.02 g (93% of theory) of the title compound were obtained as a white crystalline solid. Melting point: 165-167° C.

$^1$H-NMR (500 MHz, DMSO-d$_6$, δ/ppm): 6.53 (s, 1H), 4.35 (s, 2H), 4.02 (t, 2H), 3.90 (q, 2H), 3.63 (t, 2H), 3.28-3.17 (m, 4H), 3.24 (s, 3H), 2.39 (s, 3H), 1.12 (t, 3H).

LC/MS (Method 1, ESIpos): R$_t$=0.65 min, m/z=367 [M+H]$^+$.

Example 60

1-(2-Ethoxyethyl)-3-ethyl-5-methyl-6-[(2-oxoimidazolidin-1-yl)methyl]thieno[2,3-d]pyrimidine-2,4(1H,3H)-dione

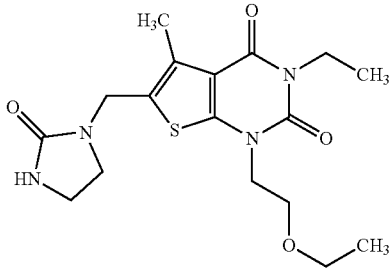

164 mg (0.333 mmol) of the compound from Example 221A were dissolved in 7 ml of dioxane, and 83.5 mg (0.5 mmol) of CDI were added. The mixture was stirred at RT for 20 h. The reaction solution was then concentrated on a rotary evaporator. The residue was dissolved in 3 ml of DMSO and this solution was purified by means of preparative HPLC (Method 14). Combination of the product fractions and freeze-drying gave 92 mg (72% of theory) of the title compound.

$^1$H-NMR (400 MHz, DMSO-d$_6$, δ/ppm): 6.53 (s, 1H), 4.35 (s, 2H), 4.01 (t, 2H), 3.90 (q, 2H), 3.65 (t, 2H), 3.43 (q, 2H), 3.27-3.16 (m, 4H), 2.39 (s, 3H), 1.11 (t, 3H), 1.03 (t, 3H).

LC/MS (Method 3): R$_t$=0.93 min, m/z=381 [M+H]$^+$.

Example 61

3-Ethyl-1-(2-isopropoxyethyl)-5-methyl-6-[(2-oxoimidazolidin-1-yl)methyl]thieno[2,3-d]pyrimidine-2,4(1H,3H)-dione

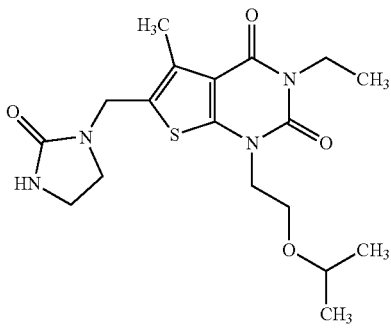

208 mg (0.344 mmol) of the compound from Example 222A were dissolved in 7 ml of dioxane, and 86.3 mg (0.516 mmol) of CDI were added. The mixture was stirred at RT for 16 h. The reaction solution was then concentrated on a rotary evaporator. The residue was dissolved in 6 ml of DMSO and this solution was purified by means of preparative HPLC (Method 14). Combination of the product fractions and freeze-drying gave 72 mg (52% of theory) of the title compound.

$^1$H-NMR (400 MHz, DMSO-d$_6$, δ/ppm): 6.51 (s, 1H), 4.35 (s, 2H), 3.97 (t, 2H), 3.90 (q, 2H), 3.65 (t, 2H), 3.54 (sept, 1H), 3.26-3.16 (m, 4H), 2.39 (s, 3H), 1.11 (t, 3H), 1.00 (d, 6H).

LC/MS (Method 3): R$_t$=0.99 min, m/z=395 [M+H]$^+$.

Example 62

3-Ethyl-1-(2-methoxypropyl)-5-methyl-6-[(2-oxoimidazolidin-1-yl)methyl]thieno[2,3-d]pyrimidine-2,4(1H,3H)-dione (racemate)

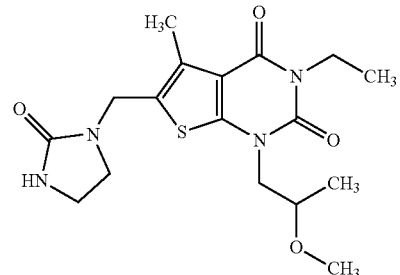

To a solution of 420 mg (1.02 mmol, 86% purity) of the compound from Ex. 223A and 248 µl (1.78 mmol) of triethylamine in 12 ml of THF were added 230 mg (1.42 mmol) of CDI, and the mixture was stirred at RT for about 18 h. Subsequently, the mixture was concentrated to dryness. The remaining residue was taken up in ethyl acetate and washed successively with 1 M hydrochloric acid, water and saturated sodium chloride solution. After drying over anhydrous magnesium sulphate, the mixture was filtered and concentrated. The remaining residue was purified by means of preparative HPLC (Method 8). After combination of the product fractions, concentration and drying under high vacuum, 219 mg (55% of theory) of the title compound were obtained.

$^1$H-NMR (400 MHz, DMSO-d$_6$, δ/ppm): 6.52 (s, 1H), 4.34 (d, 2H), 4.00-3.84 (m, 3H), 3.79-3.66 (m, 2H), 3.27-3.19 (m, 4H), 3.18 (s, 3H), 2.39 (s, 3H), 1.20-1.03 (m, 6H).

LC/MS (Method 1, ESIpos): R$_t$=0.73 min, m/z=381 [M+H]$^+$.

Example 63

3-Ethyl-1-(2-methoxypropyl)-5-methyl-6-[(2-ox-oimidazolidin-1-yl)methyl]thieno[2,3-d]pyrimidine-2,4(1H,3H)-dione (Enantiomer 1)

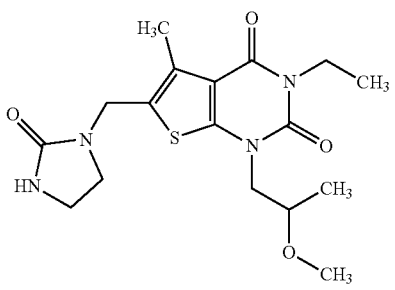 [SMILES: CCn1c(=O)c2c(C)c(CN3CCNC3=O)sc2n(CC(C)OC)c1=O]

207 mg (0.544 mmol) of the racemic compound from Ex. 62 were dissolved in 5 ml of ethanol and, in 10 portions, separated into the enantiomers by preparative HPLC on a chiral phase [column: Daicel Chiralpak AD-H, 5 µm, 250 mm×20 mm; eluent: isohexane/ethanol 1:1; flow rate: 15 ml/min; temperature: 25° C.; detection: 210 nm]. After concentration of the product fractions and drying under high vacuum, 58 mg (56% of theory) of Enantiomer 1 were obtained (90.9% ee, chiral analytical HPLC).

$^1$H-NMR (400 MHz, DMSO-$d_6$, δ/ppm): 6.52 (s, 1H), 4.34 (d, 2H), 4.00-3.84 (m, 3H), 3.81-3.65 (m, 2H), 3.27-3.19 (m, 4H), 3.18 (s, 3H), 2.39 (s, 3H), 1.19-0.98 (m, 6H).

LC/MS (Method 1, ESIpos): $R_t$=0.76 min, m/z=381 [M+H]$^+$.

Chiral analytical HPLC [column: Daicel Chiralpak AD-H, 5 µm, 250 mm×4.6 mm; eluent: isohexane/ethanol 1:1; flow rate: 1 ml/min; temperature: 40° C.; detection: 220 nm]: $R_t$=9.02 min.

Example 64

3-Ethyl-1-(2-methoxypropyl)-5-methyl-6-[(2-ox-oimidazolidin-1-yl)methyl]thieno[2,3-d]pyrimidine-2,4(1H,3H)-dione (Enantiomer 2)

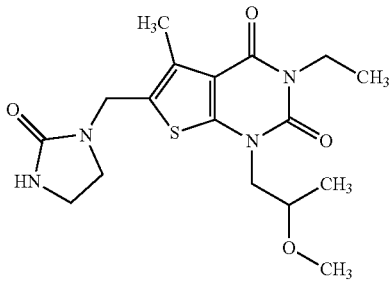 [SMILES: CCn1c(=O)c2c(C)c(CN3CCNC3=O)sc2n(CC(C)OC)c1=O]

207 mg (0.544 mmol) of the racemic compound from Ex. 62 were dissolved in 5 ml of ethanol and, in 10 portions, separated into the enantiomers by preparative HPLC on a chiral phase [column: Daicel Chiralpak AD-H, 5 µm, 250 mm×20 mm; eluent: isohexane/ethanol 1:1; flow rate: 15 ml/min; temperature: 25° C.; detection: 210 nm]. After concentration of the product fractions and drying under high vacuum, 86 mg (83% of theory) of Enantiomer 2 were obtained (>99% ee, chiral analytical HPLC).

$^1$H-NMR (400 MHz, DMSO-$d_6$, δ/ppm): 6.52 (s, 1H), 4.34 (d, 2H), 4.01-3.85 (m, 3H), 3.81-3.67 (m, 2H), 3.28-3.19 (m, 4H), 3.18 (s, 3H), 2.39 (s, 3H), 1.19-1.06 (m, 6H).

LC/MS (Method 1, ESIpos): $R_t$=0.76 min, m/z=381 [M+H]$^+$.

Chiral analytical HPLC [column: Daicel Chiralpak AD-H, 5 µm, 250 mm×4.6 mm; eluent: isohexane/ethanol 1:1; flow rate: 1 ml/min; temperature: 40° C.; detection: 220 nm]: $R_t$=6.55 min.

Example 65

3-Ethyl-5-methyl-1-(oxetan-2-ylmethyl)-6-[(2-ox-oimidazolidin-1-yl)methyl]thieno[2,3-d]pyrimidine-2,4(1H,3H)-dione (racemate)

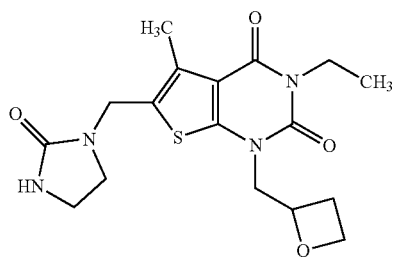 [SMILES: CCn1c(=O)c2c(C)c(CN3CCNC3=O)sc2n(CC2CCO2)c1=O]

358 mg (1.016 mmol) of the compound from Example 224A were dissolved in 18 ml of dioxane, and 254 mg (1.524 mmol) of CDI were added. The mixture was stirred at RT for 18 h. The reaction solution was then concentrated on a rotary evaporator. The residue was dissolved in 6 ml of DMSO and this solution was purified by means of preparative HPLC (Method 14). Combination of the product fractions and freeze-drying gave 140 mg (36% of theory) of the title compound.

$^1$H-NMR (400 MHz, DMSO-$d_6$, δ/ppm): 6.51 (s, 1H), 5.05-4.96 (m, 1H), 4.52-4.38 (m, 2H), 4.34 (s, 2H), 4.13 (d, 2H), 3.90 (q, 2H), 3.28-3.17 (m, 4H), 2.74-2.64 (m, 1H), 2.39 (s, 3H), 1.12 (t, 3H).

LC/MS (Method 3): $R_t$=0.85 min, m/z=379 [M+H]$^+$.

Example 66

3-Ethyl-5-methyl-1-(oxetan-2-ylmethyl)-6-[(2-ox-oimidazolidin-1-yl)methyl]thieno[2,3-d]pyrimidine-2,4(1H,3H)-dione (Enantiomer 1)

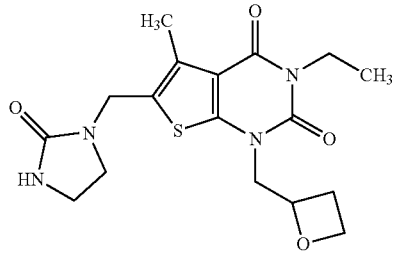 [SMILES: CCn1c(=O)c2c(C)c(CN3CCNC3=O)sc2n(CC2CCO2)c1=O]

110 mg of the racemic compound from Ex. 65 were dissolved in 1 ml of methanol and 1 ml of dichloromethane and separated into the enantiomers by preparative SFC-HPLC on a chiral phase [column: Chiralpak IB, 5 µm, 250 mm×30 mm; eluent: carbon dioxide/ethanol 85:15; buffer: 0.2% diethylamine; flow rate: 100 ml/min; pressure (outlet): 150 bar; temperature: 40° C.; DAD 254 nm]. The respective product fractions were concentrated on a rotary evaporator, admixed with tert-butanol and freeze-dried. 46 mg (41% of theory) of the Enantiomer 1 and 46 mg (41% of theory) of Enantiomer 2 (see Example 67) were obtained.

$^1$H-NMR (400 MHz, DMSO-d$_6$, δ/ppm): 6.51 (s, 1H), 5.04-4.96 (m, 1H), 4.52-4.38 (m, 2H), 4.34 (s, 2H), 4.13 (d, 2H), 3.90 (q, 2H), 3.28-3.17 (m, 4H), 2.69 (dtd, 1H), 2.39 (s, 3H), 1.15-1.08 (m, 3H).

Chiral analytical SFC-HPLC [column: Chiralpak IB, 5 µm, 100 mm×4.6 mm; eluent: carbon dioxide/ethanol 85:15; buffer: 0.2% diethylamine; flow rate: 1 ml/min; temperature: 40° C.; detection: 220 nm]: R$_t$=3.12 min.

Example 67

3-Ethyl-5-methyl-1-(oxetan-2-ylmethyl)-6-[(2-oxoimidazolidin-1-yl)methyl]thieno[2,3-d]pyrimidine-2,4(1H,3H)-dione (Enantiomer 2)

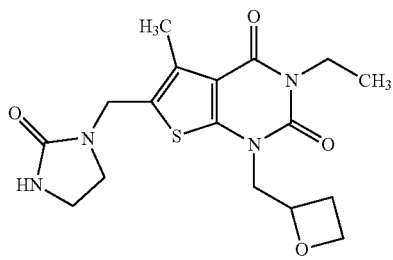

The title compound (46 mg) was obtained as the second enantiomer in the racemate separation of Ex. 65 described in Example 66 by means of preparative SFC-HPLC.

$^1$H-NMR (400 MHz, DMSO-d$_6$, δ/ppm): 6.52 (s, 1H), 5.05-4.95 (m, 1H), 4.52-4.38 (m, 2H), 4.34 (s, 2H), 4.13 (d, 2H), 3.90 (q, 2H), 3.29-3.17 (m, 4H), 2.69 (dtd, 1H), 2.39 (s, 3H), 1.16-1.07 (m, 4H).

Chiral analytical SFC-HPLC [column: Chiralpak IB, 5 µm, 100 mm×4.6 mm; eluent: carbon dioxide/ethanol 85:15; buffer: 0.2% diethylamine; flow rate: 1 ml/min; temperature: 40° C.; detection: 220 nm]: R$_t$=3.74 min.

Example 68

3-Ethyl-5-methyl-6-[(2-oxoimidazolidin-1-yl)methyl]-1-(tetrahydrofuran-2-ylmethyl)thieno[2,3-d]pyrimidine-2,4(1H,3H)-dione (racemate)

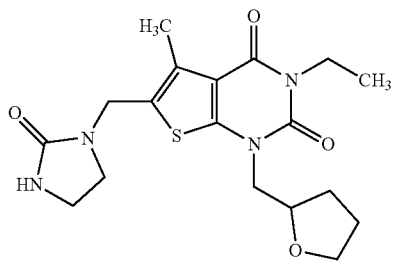

To a solution of 220 mg (0.450 mmol, 75% purity) of the compound from Ex. 225A and 125 µl (0.90 mmol) of triethylamine in 6 ml of THF were added 117 mg (0.720 mmol) of CDI, and the mixture was stirred at RT for about 18 h. Subsequently, the mixture was concentrated to dryness. The remaining residue was taken up in ethyl acetate and washed successively with 1 M hydrochloric acid, water and saturated sodium chloride solution. After drying over anhydrous magnesium sulphate, the mixture was filtered and concentrated. The solid residue was stirred in a little acetonitrile at RT. After filtration and drying of the solids under high vacuum, a first fraction of the title compound (554 mg) was obtained. The filtrate was concentrated to dryness and separated into its components by means of preparative HPLC (Method 8). After the product fractions had been concentrated and dried under high vacuum, a second fraction of the title compound was obtained (405 mg). A total of 959 mg (56% of theory) of the title compound were thus obtained.

$^1$H-NMR (400 MHz, DMSO-d$_6$, δ/ppm): 6.51 (s, 1H), 4.34 (s, 2H), 4.27-4.16 (m, 1H), 4.03 (dd, 1H), 3.90 (q, 2H), 3.79-3.66 (m, 2H), 3.61 (q, 1H), 3.28-3.14 (m, 4H), 2.39 (s, 3H), 2.05-1.74 (m, 3H), 1.72-1.59 (m, 1H), 1.12 (t, 3H).

LC/MS (Method 1, ESIpos): R$_t$=0.73 min, m/z=393 [M+H]$^+$.

Example 69

3-Ethyl-5-methyl-6-[(2-oxoimidazolidin-1-yl)methyl]-1-(tetrahydrofuran-2-ylmethyl)thieno[2,3-d]pyrimidine-2,4(1H,3H)-dione (Enantiomer 1)

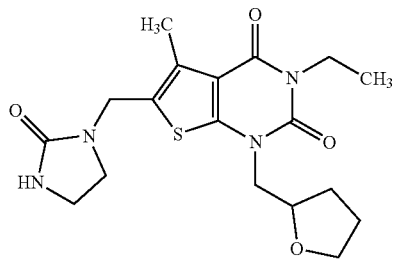 [SMILES: CCn1c(=O)c2c(C)c(CN3CCNC3=O)sc2n(CC2CCCO2)c1=O]

955 mg (2.43 mmol) of the racemic compound from Ex. 68 were dissolved in a mixture of 8 ml of ethanol and 3 ml of formic acid and, in 22 portions, separated into the enantiomers by preparative HPLC on a chiral phase [column: Daicel Chiralcel OX-H, 5 µm, 250 mm×20 mm; eluent: ethanol; flow rate: 15 ml/min; temperature: 25° C.; detection: 210 nm]. After concentration of the product fractions and drying under high vacuum, 320 mg (67% of theory) of Enantiomer 1 were obtained (>99% ee, chiral analytical HPLC).

$^1$H-NMR (400 MHz, DMSO-d$_6$, δ/ppm): 6.52 (s, 1H), 4.34 (s, 2H), 4.27-4.17 (m, 1H), 4.03 (dd, 1H), 3.90 (q, 2H), 3.79-3.66 (m, 2H), 3.65-3.57 (m, 1H), 3.28-3.15 (m, 4H), 2.39 (s, 3H), 2.04-1.74 (m, 3H), 1.71-1.59 (m, 1H), 1.12 (t, 3H).

Chiral analytical HPLC [column: Daicel Chiralcel OX-H, 3 µm, 50 mm×4.6 mm; eluent: ethanol; flow rate: 1 ml/min; temperature: 40° C.; detection: 220 nm]: R$_t$=2.85 min.

Example 70

3-Ethyl-5-methyl-6-[(2-oxoimidazolidin-1-yl)methyl]-1-(tetrahydrofuran-2-ylmethyl)thieno[2,3-d]pyrimidine-2,4(1H,3H)-dione (Enantiomer 2)

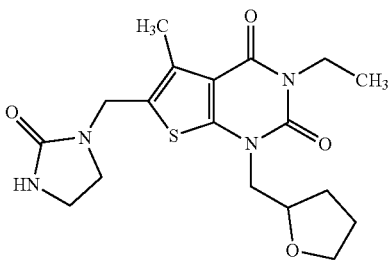

955 mg (2.43 mmol) of the racemic compound from Ex. 68 were dissolved in a mixture of 8 ml of ethanol and 3 ml of formic acid and, in 22 portions, separated into the enantiomers by preparative HPLC on a chiral phase [column: Daicel Chiralcel OX-H, 5 µm, 250 mm×20 mm; eluent: ethanol; flow rate: 15 ml/min; temperature: 25° C.; detection: 210 nm]. After concentration of the product fractions and drying under high vacuum, 194 mg (40% of theory) of Enantiomer 2 were obtained (>99% ee, chiral analytical HPLC).

$^1$H-NMR (400 MHz, DMSO-$d_6$, δ/ppm): 6.52 (s, 1H), 4.34 (s, 2H), 4.27-4.17 (m, 1H), 4.03 (dd, 1H), 3.90 (q, 2H), 3.79-3.66 (m, 2H), 3.65-3.56 (m, 1H), 3.28-3.15 (m, 4H), 2.39 (s, 3H), 2.05-1.73 (m, 3H), 1.70-1.61 (m, 1H), 1.12 (t, 3H).

Chiral analytical HPLC [column: Daicel Chiralcel OX-H, 3 µm, 50 mm×4.6 mm; eluent: ethanol; flow rate: 1 ml/min; temperature: 40° C.; detection: 220 nm]: $R_t$=3.17 min.

Example 71

3-Ethyl-5-methyl-6-[(2-oxoimidazolidin-1-yl)methyl]-1-(tetrahydro-2H-pyran-2-ylmethyl)thieno[2,3-d]pyrimidine-2,4(1H,3H)-dione (racemate)

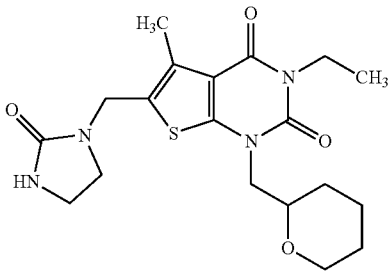

320 mg (0.732 mmol) of the compound from Example 226A were dissolved in 14 ml of dioxane, and 178 mg (1.097 mmol) of CDI were added. The mixture was stirred at RT for 18 h. The reaction solution was then concentrated on a rotary evaporator. The residue was dissolved in 9 ml of DMSO and this solution was purified by means of preparative HPLC (Method 14). Combination of the product fractions and freeze-drying gave 226 mg (79% of theory) of the title compound.

$^1$H-NMR (400 MHz, DMSO-$d_6$, δ/ppm): 6.53 (s, 1H), 4.38-4.28 (m, 2H), 4.02-3.93 (m, 1H), 3.89 (q, 2H), 3.80 (dd, 1H), 3.73-3.63 (m, 2H), 3.29-3.17 (m, 5H), 2.38 (s, 3H), 1.78 (d, 1H), 1.61 (d, 1H), 1.51-1.38 (m, 3H), 1.31-1.19 (m, 1H), 1.11 (t, 3H).

LC/MS (Method 3): $R_t$=1.02 min, m/z=407 [M+H]$^+$.

Example 72

3-Ethyl-5-methyl-1-(oxetan-3-ylmethyl)-6-[(2-oxoimidazolidin-1-yl)methyl]thieno[2,3-d]pyrimidine-2,4(1H,3H)-dione

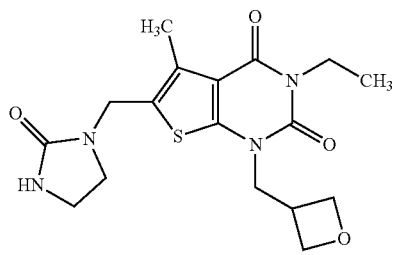 [SMILES: CCn1c(=O)c2c(C)c(CN3CCNC3=O)sc2n(CC2COC2)c1=O]

Analogously to the method described in Ex. 62, 105 mg (0.238 mmol, 80% purity) of the compound from Ex. 227A and 58 mg (0.357 mmol) of CDI were used to prepare 16 mg (17% of theory) of the title compound.

$^1$H-NMR (400 MHz, DMSO-$d_6$, δ/ppm): 6.53 (s, 1H), 4.62 (dd, 2H), 4.44 (t, 2H), 4.35 (s, 2H), 4.19 (d, 2H), 3.89 (q, 2H), 3.49-3.37 (m, 1H), 3.27-3.16 (m, 4H), 2.39 (s, 3H), 1.11 (t, 3H).

LC/MS (Method 1, ESIpos): $R_t$=0.68 min, m/z=379 [M+H]$^+$.

Example 73

3-Ethyl-5-methyl-6-[(2-oxoimidazolidin-1-yl)methyl]-1-(tetrahydrofuran-3-ylmethyl)thieno[2,3-d]pyrimidine-2,4(1H,3H)-dione (racemate)

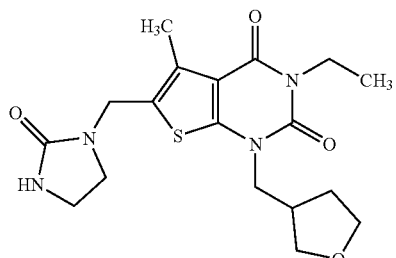

Analogously to the method described in Ex. 68, 211 mg (0.504 mmol, 87% purity) of the compound from Ex. 228A and 98 mg (0.605 mmol) of CDI were used to obtain 131 mg (66% of theory) of the title compound.

$^1$H-NMR (400 MHz, DMSO-$d_6$, δ/ppm): 6.53 (s, 1H), 4.36 (s, 2H), 3.97-3.84 (m, 4H), 3.80 (td, 1H), 3.70-3.57 (m, 2H), 3.51 (dd, 1H), 3.28-3.16 (m, 4H), 2.80-2.69 (m, 1H), 2.40 (s, 3H), 2.03-1.87 (m, 1H), 1.73-1.59 (m, 1H), 1.12 (t, 3H).

LC/MS (Method 1, ESIpos): $R_t$=0.67 min, m/z=393 [M+H]$^+$.

Example 74

3-Ethyl-5-methyl-6-[(2-oxoimidazolidin-1-yl)methyl]-1-(tetrahydrofuran-3-ylmethyl)thieno[2,3-d]pyrimidine-2,4(1H,3H)-dione (Enantiomer 1)

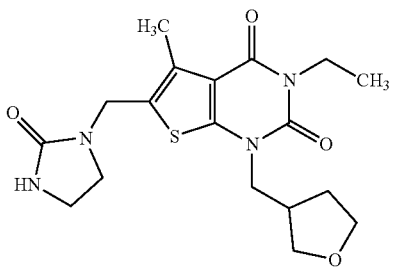 [SMILES: CCn1c(=O)c2c(C)c(CN3CCNC3=O)sc2n(CC2CCOC2)c1=O]

124 mg (0.316 mmol) of the racemic compound from Ex. 73 were dissolved in 22 ml of ethanol and, in 55 portions, separated into the enantiomers by preparative SFC-HPLC on a chiral phase [column: Daicel Chiralcel OJ-H, 5 μm, 250 mm×20 mm; eluent: carbon dioxide/ethanol 80:20; flow rate: 80 ml/min; temperature: 40° C.; detection: 210 nm]. After concentration of the product fractions and drying under high vacuum, 52 mg (83% of theory) of Enantiomer 1 were obtained (>99% ee, chiral analytical HPLC).

$^1$H-NMR (400 MHz, DMSO-d$_6$, δ/ppm): 6.53 (s, 1H), 4.36 (s, 2H), 3.96-3.85 (m, 4H), 3.80 (td, 1H), 3.70-3.57 (m, 2H), 3.51 (dd, 1H), 3.28-3.16 (m, 4H), 2.81-2.67 (m, 1H), 2.40 (s, 3H), 2.03-1.88 (m, 1H), 1.72-1.58 (m, 1H), 1.12 (t, 3H).

Chiral analytical HPLC [column: Daicel Chiralcel OJ-3, 3 μm, 50 mm×4.6 mm; eluent: carbon dioxide/ethanol, ethanol gradient 5%→60% in 6 min; flow rate: 3 ml/min; temperature: 40° C.; detection: 220 nm]: R$_t$=2.36 min.

Example 75

3-Ethyl-5-methyl-6-[(2-oxoimidazolidin-1-yl)methyl]-1-(tetrahydrofuran-3-ylmethyl)thieno[2,3-d]pyrimidine-2,4(1H,3H)-dione (Enantiomer 2)

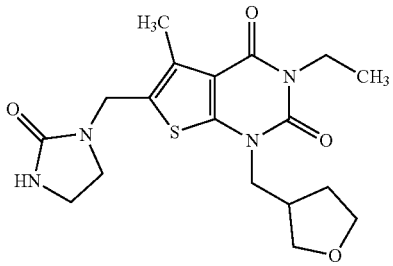 [SMILES: CCn1c(=O)c2c(C)c(CN3CCNC3=O)sc2n(CC2CCOC2)c1=O]

124 mg (0.316 mmol) of the racemic compound from Ex. 73 were dissolved in 22 ml of ethanol and, in 55 portions, separated into the enantiomers by preparative SFC-HPLC on a chiral phase [column: Daicel Chiralcel OJ-H, 5 μm, 250 mm×20 mm; eluent: carbon dioxide/ethanol 80:20; flow rate: 80 ml/min; temperature: 40° C.; detection: 210 nm]. After concentration of the product fractions and drying under high vacuum, 50 mg (80% of theory) of Enantiomer 2 were obtained (>99% ee, chiral analytical HPLC).

$^1$H-NMR (400 MHz, DMSO-d$_6$, δ/ppm): 6.53 (s, 1H), 4.36 (s, 2H), 3.96-3.85 (m, 4H), 3.80 (td, 1H), 3.69-3.58 (m, 2H), 3.51 (dd, 1H), 3.29-3.15 (m, 4H), 2.81-2.68 (m, 1H), 2.40 (s, 3H), 2.01-1.87 (m, 1H), 1.73-1.57 (m, 1H), 1.12 (t, 3H).

Chiral analytical SFC HPLC [column: Daicel Chiralcel OJ-3, 3 μm, 50 mm×4.6 mm; eluent: carbon dioxide/ethanol, ethanol gradient 5%→60% in 6 min; flow rate: 3 ml/min; temperature: 40° C.; detection: 220 nm]: R$_t$=2.21 min.

Example 76

3-Ethyl-1,5-dimethyl-6-[(2-oxoimidazolidin-1-yl)methyl]thieno[2,3-d]pyrimidine-2,4(1H,3H)-dione

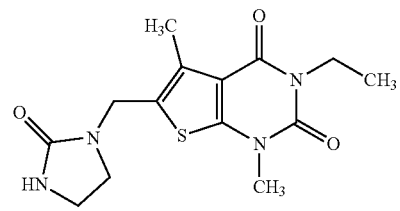 [SMILES: CCn1c(=O)c2c(C)c(CN3CCNC3=O)sc2n(C)c1=O]

Analogously to the method described in Ex. 68, 370 mg (0.949 mmol, 76% purity) of the compound from Ex. 229A and 185 mg (1.14 mmol) of CDI were used to obtain 174 mg (56% of theory) of the title compound.

$^1$H-NMR (400 MHz, DMSO-d$_6$, δ/ppm): 6.52 (br. s, 1H), 4.36 (s, 2H), 3.90 (q, 2H), 3.41 (s, 3H), 3.28-3.15 (m, 4H), 2.40 (s, 3H), 1.11 (t, 3H).

LC/MS (Method 1, ESIpos): R$_t$=0.66 min, m/z=323 [M+H]$^+$.

Example 77

3-Ethyl-5-methyl-6-[(2-oxoimidazolidin-1-yl)methyl]-1-propylthieno[2,3-d]pyrimidine-2,4(1H,3H)-dione

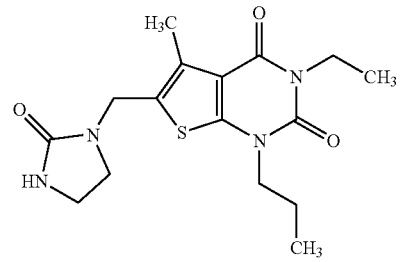 [SMILES: CCCn1c(=O)n(CC)c(=O)c2c(C)c(CN3CCNC3=O)sc21]

To a solution of 280 mg (0.604 mmol, 70% purity) of the compound from Ex. 231A and 126 μl (0.906 mmol) of triethylamine in 5 ml of THF were added 117 mg (0.725 mmol) of CDI, and the mixture was stirred at RT for about 18 h. The reaction mixture was then separated into its components directly by means of preparative HPLC (Method 8). After concentration of the product fractions and drying under high vacuum, a crude product was obtained, which was stirred with a little acetonitrile at RT. After filtration with suction and drying under high vacuum, the solids gave a first fraction of the title compound (25 mg).

The filtrate was concentrated and purified once again by means of preparative HPLC (Method 8). This gave a second fraction of the title compound (35 mg). A total of 60 mg (28% of theory) of the title compound were thus obtained.

$^1$H-NMR (400 MHz, DMSO-$d_6$, δ/ppm): 6.52 (s, 1H), 4.35 (s, 2H), 3.90 (q, 2H), 3.85-3.78 (m, 2H), 3.29-3.16 (m, 4H), 2.40 (s, 3H), 1.69 (sext, 2H), 1.11 (t, 3H), 0.91 (t, 3H).

LC/MS (Method 1, ESIpos): $R_t$=0.82 min, m/z=351 [M+H]$^+$.

Example 78

1-Butyl-3-ethyl-5-methyl-6-[(2-oxoimidazolidin-1-yl)methyl]thieno[2,3-d]pyrimidine-2,4(1H,3H)-dione

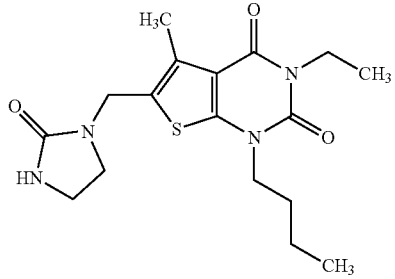

Analogously to the method described in Ex. 57, 380 mg (0.730 mmol, 65% purity) of the compound from Ex. 232A and 218 mg (1.35 mmol) of CDI were used to prepare 30 mg (7% of theory) of the title compound. The purification of the product was effected here by preparative HPLC twice according to Method 8.

$^1$H-NMR (400 MHz, DMSO-$d_6$, δ/ppm): 6.52 (s, 1H), 4.35 (s, 2H), 3.97-3.80 (m, 4H), 3.28-3.16 (m, 4H), 2.40 (s, 3H), 1.65 (quin, 2H), 1.34 (sext, 2H), 1.11 (t, 3H), 0.91 (t, 3H).

LC/MS (Method 1, ESIpos): $R_t$=0.86 min, m/z=365 [M+H]$^+$.

Example 79

3-Ethyl-5-methyl-1-(3-methylbutyl)-6-[(2-oxoimidazolidin-1-yl)methyl]thieno[2,3-d]pyrimidine-2,4(1H,3H)-dione

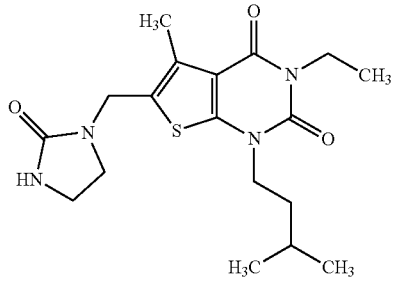 [SMILES: CCn1c(=O)c2c(C)c(CN3CCNC3=O)sc2n(CCC(C)C)c1=O]

Analogously to the method described in Ex. 47, 360 mg (0.919 mmol, 90% purity) of the compound from Ex. 233A and 179 mg (1.10 mmol) of CDI were used to prepare 154 mg (44% of theory) of the title compound.

$^1$H-NMR (400 MHz, DMSO-$d_6$, δ/ppm): 6.52 (s, 1H), 4.35 (s, 2H), 3.90 (q, 2H), 3.86 (t, 2H), 3.28-3.15 (m, 4H), 2.40 (s, 3H), 1.68-1.59 (m, 1H), 1.57-1.52 (m, 2H), 1.11 (t, 3H), 0.94 (d, 6H).

LC/MS (Method 1, ESIpos): $R_t$=0.89 min, m/z=379 [M+H]$^+$.

Example 80

1-(Cyclobutylmethyl)-3-ethyl-5-methyl-6-[(2-oxoimidazolidin-1-yl)methyl]thieno[2,3-d]pyrimidine-2,4(1H,3H)-dione

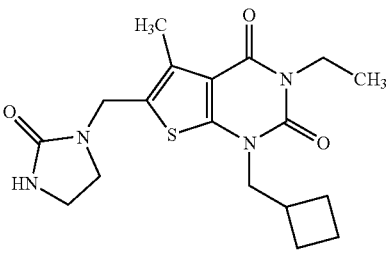 [SMILES: CCn1c(=O)c2c(C)c(CN3CCNC3=O)sc2n(CC2CCC2)c1=O]

Analogously to the method described in Ex. 47, 350 mg (0.909 mmol, 90% purity) of the compound from Ex. 235A and 177 mg (1.09 mmol) of CDI were used to prepare 234 mg (68% of theory) of the title compound.

$^1$H-NMR (400 MHz, DMSO-$d_6$, δ/ppm): 6.53 (s, 1H), 4.35 (s, 2H), 3.96-3.84 (m, 4H), 3.28-3.14 (m, 4H), 2.84-2.69 (m, 1H), 2.39 (s, 3H), 2.04-1.89 (m, 2H), 1.89-1.74 (m, 4H), 1.11 (t, 3H).

LC/MS (Method 1, ESIpos): $R_t$=0.90 min, m/z=377 [M+H]$^+$.

Example 81

{3-Ethyl-5-methyl-2,4-dioxo-6-[(2-oxoimidazolidin-1-yl)methyl]-3,4-dihydrothieno[2,3-d]pyrimidin-1(2H)-yl}acetonitrile

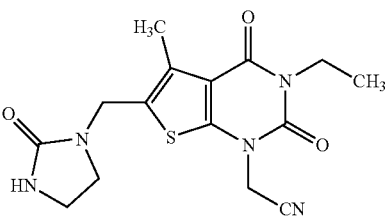 [SMILES: CCn1c(=O)c2c(C)c(CN3CCNC3=O)sc2n(CC#N)c1=O]

Analogously to the method described in Ex. 57, 289 mg (0.719 mmol, 80% purity) of the compound from Ex. 236A and 175 mg (1.08 mmol) of CDI were used to prepare 15 mg (4% of theory, 87% purity) of the title compound. For further purification of the product after the preparative HPLC, flash chromatography was also effected here using silica gel with ethyl acetate as the eluent.

$^1$H-NMR (400 MHz, DMSO-$d_6$, δ/ppm): 6.56 (s, 1H), 5.12 (s, 2H), 4.39 (s, 2H), 3.90 (q, 2H), 3.28-3.16 (m, 4H), 2.41 (s, 3H), 1.13 (t, 3H).

LC/MS (Method 1, ESIpos): $R_t$=0.70 min, m/z=695 [2M+H]$^+$.

Example 82

3-Ethyl-5-methyl-1-[(4-methyl-1,2,5-oxadiazol-3-yl)methyl]-6-[(2-oxoimidazolidin-1-yl)methyl]thieno[2,3-d]pyrimidine-2,4(1H,3H)-dione

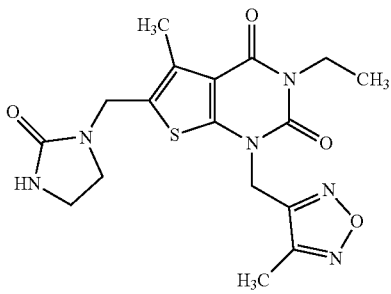 [SMILES: CCn1c(=O)c2c(C)c(CN3CCNC3=O)sc2n(Cc2nonc2C)c1=O]

Analogously to the method described in Ex. 62, 490 mg (1.06 mmol, 82% purity) of the compound from Ex. 237A and 207 mg (1.27 mmol) of CDI were used to prepare 162 mg (37% of theory) of the title compound.

$^1$H-NMR (400 MHz, DMSO-$d_6$, δ/ppm): 6.52 (s, 1H), 5.33 (s, 2H), 4.35 (s, 2H), 3.91 (q, 2H), 3.28-3.15 (m, 4H), 2.42 (s, 3H), 2.41 (s, 3H), 1.12 (t, 3H).

LC/MS (Method 1, ESIpos): $R_t$=0.77 min, m/z=405 [M+H]$^+$.

Example 83

1-[2-(Dimethylamino)ethyl]-3-ethyl-5-methyl-6-[(2-oxoimidazolidin-1-yl)methyl]thieno[2,3-d]pyrimidine-2,4(1H,3H)-dione

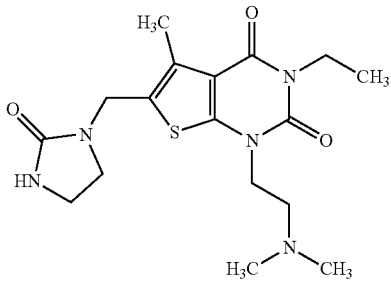 [SMILES: CCn1c(=O)c2c(C)c(CN3CCNC3=O)sc2n(CCN(C)C)c1=O]

Analogously to the method described in Ex. 47, 650 mg (1.34 mmol, 73% purity) of the compound from Ex. 238A and 304 mg (1.88 mmol) of CDI were used to prepare 212 mg (41% of theory) of the title compound.

$^1$H-NMR (400 MHz, DMSO-$d_6$, δ/ppm): 6.52 (s, 1H), 4.35 (s, 2H), 3.98-3.83 (m, 4H), 3.28-3.15 (m, 4H), 2.57-2.52 (m, 2H, partially obscured by the DMSO signal), 2.40 (s, 3H), 2.19 (s, 6H), 1.11 (t, 3H).

LC/MS (Method 1, ESIpos): $R_t$=0.46 min, m/z=380 [M+H]$^+$.

Example 84

1-(2-Methoxyethyl)-5-methyl-6-[(2-oxoimidazolidin-1-yl)methyl]-3-propylthieno[2,3-d]pyrimidine-2,4(1H,3H)-dione

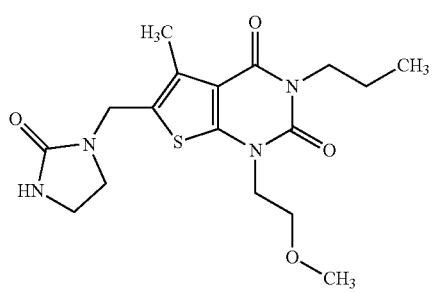 [SMILES: CCCn1c(=O)c2c(C)c(CN3CCNC3=O)sc2n(CCOC)c1=O]

To a solution of 106 mg (1.179 mmol) of 2-imidazolidinone in 4.2 ml of THF were added 47 mg (1.179 mmol) of sodium hydride (60% suspension in mineral oil) and the mixture was stirred at RT for 3 h ("Solution 1"). To a solution of 93 mg (0.295 mmol) of the compound from Ex. 144A in 2 ml of dichloromethane in another reaction vessel were added, at 0° C., 154 µl (0.884 mmol) of N,N-diisopropylethylamine and 32 µl (0.442 mmol) of thionyl chloride, and the mixture was stirred for 75 min. Subsequently, Solution 1 was added in portions and the mixture was stirred at RT for 66 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 10 g of silica gel, eluent: hexane/ethyl acetate). 48 mg (42% of theory) of the title compound were obtained.

$^1$H-NMR (400 MHz, DMSO-$d_6$, δ/ppm): 6.51 (s, 1H), 4.34 (s, 2H), 4.01 (t, 2H), 3.81 (dd, 2H), 3.62 (t, 2H), 3.28-3.17 (m, 7H), 2.39 (s, 3H), 1.55 (sext, 2H), 0.86 (t, 3H).

LC/MS (Method 3): $R_t$=0.95 min, m/z=381 [M+H]$^+$.

Example 85

3-Allyl-1-(2-methoxyethyl)-5-methyl-6-[(2-oxoimidazolidin-1-yl)methyl]thieno[2,3-d]pyrimidine-2,4(1H,3H)-dione

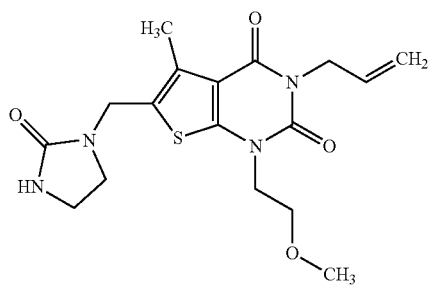 [SMILES: C=CCn1c(=O)c2c(C)c(CN3CCNC3=O)sc2n(CCOC)c1=O]

To a solution of 191 mg (2.126 mmol) of 2-imidazolidinone in 7.6 ml of THF were added 85 mg (2.126 mmol) of sodium hydride (60% suspension in mineral oil) and the mixture was stirred at RT for 3 h ("Solution 1"). To a solution of 165 mg (0.532 mmol) of the compound from Ex.

145A in 3.7 ml of dichloromethane in another reaction vessel were added, at 0° C., 278 µl (1.595 mmol) of N,N-diisopropylethylamine and 58 µl (0.797 mmol) of thionyl chloride, and the mixture was stirred for 75 min. Subsequently, Solution 1 was added in portions and the mixture was stirred at RT for 18 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 10 g of silica gel, eluent: hexane/ethyl acetate). 33 mg (16% of theory) of the title compound were obtained.

$^1$H-NMR (400 MHz, DMSO-d$_6$, δ/ppm): 6.55 (s, 1H), 5.89-5.78 (m, 1H), 5.13-5.04 (m, 2H), 4.46 (d, 2H), 4.35 (s, 2H), 4.02 (t, 2H), 3.62 (t, 2H), 3.29-3.17 (m, 7H), 2.38 (s, 3H).

LC/MS (Method 3): R$_t$=0.90 min, m/z=379 [M+H]$^+$.

Example 86

3-Isopropyl-1-(2-methoxyethyl)-5-methyl-6-[(2-oxoimidazolidin-1-yl)methyl]thieno[2,3-d]pyrimidine-2,4(1H,3H)-dione

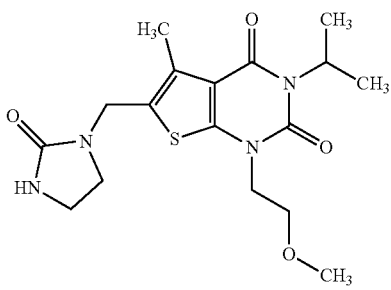

To a solution of 113 mg (1.264 mmol) of 2-imidazolidinone in 4.5 ml of THF were added 50 mg (1.264 mmol) of sodium hydride (60% suspension in mineral oil) and the mixture was stirred at RT for 3 h ("Solution 1"). To a solution of 105 mg (0.316 mmol) of the compound from Ex. 146A in 2.2 ml of dichloromethane in another reaction vessel were added, at 0° C., 165 µl (0.948 mmol) of N,N-diisopropylethylamine and 34.5 µl (0.474 mmol) of thionyl chloride, and the mixture was stirred for 75 min. Subsequently, Solution 1 was added in portions and the mixture was stirred at RT for 20 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 10 g of silica gel, eluent: hexane/ethyl acetate). 62 mg (50% of theory) of the title compound were obtained.

$^1$H-NMR (400 MHz, DMSO-d$_6$, δ/ppm): 6.52 (s, 1H), 5.13 (sept, 1H), 4.33 (s, 2H), 3.98 (t, 2H), 3.61 (t, 2H), 3.28-3.16 (m, 7H), 2.37 (s, 3H), 1.40 (d, 6H).

LC/MS (Method 3): R$_t$=0.98 min, m/z=381 [M+H]$^+$.

Example 87

3-Isobutyl-5-methyl-6-[(2-oxoimidazolidin-1-yl)methyl]-1-(3,3,3-trifluoropropyl)thieno[2,3-d]pyrimidine-2,4(1H,3H)-dione

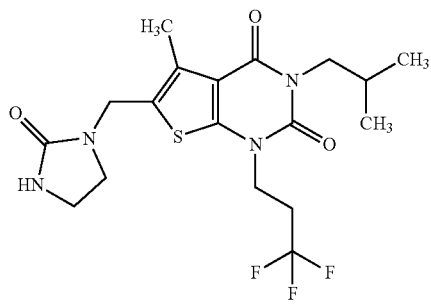 [SMILES: Cc1c(CN2CCNC2=O)sc2c1c(=O)n(CC(C)C)c(=O)n2CCC(F)(F)F]

115 mg (0.269 mmol) of the compound from Example 239A were dissolved in 5 ml of dioxane, and 67 mg (0.403 mmol) of CDI were added. The mixture was stirred at RT for 67 h. The reaction solution was then concentrated on a rotary evaporator. The residue was dissolved in 3 ml of DMSO and this solution was purified by means of preparative HPLC (Method 14). Combination of the product fractions and freeze-drying gave 16 mg (13% of theory) of the title compound.

$^1$H-NMR (400 MHz, DMSO-d$_6$, δ/ppm): 6.54 (s, 1H), 4.36 (s, 2H), 4.10 (t, 2H), 3.70 (d, 2H), 3.30-3.18 (m, 4H), 2.82-2.69 (m, 2H), 2.40 (s, 3H), 2.09-1.97 (m, 1H), 0.84 (d, 6H).

LC/MS (Method 3): R$_t$=1.19 min, m/z=433 [M+H]$^+$.

Example 88

1-(2-Fluoroethyl)-3-isobutyl-5-methyl-6-[(2-oxoimidazolidin-1-yl)methyl]thieno[2,3-d]pyrimidine-2,4(1H,3H)-dione

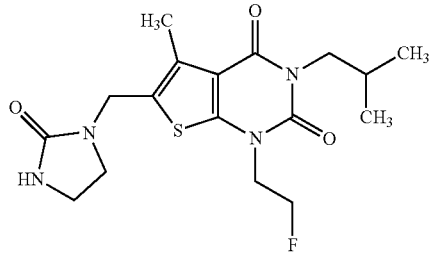 [SMILES: Cc1c(CN2CCNC2=O)sc2c1c(=O)n(CC(C)C)c(=O)n2CCF]

Analogously to the method described in Ex. 62, 528 mg (1.11 mmol, 75% purity) of the compound from Ex. 240A and 288 mg (1.78 mmol) of CDI were used to prepare 265 mg (62% of theory) of the title compound.

$^1$H-NMR (400 MHz, DMSO-d$_6$, δ/ppm): 6.52 (s, 1H), 4.72 (dt, 2H), 4.35 (s, 2H), 4.18 (dt, 2H), 3.72 (d, 2H), 3.29-3.16 (m, 4H), 2.39 (s, 3H), 2.11-1.95 (m, 1H), 0.85 (d, 6H).

LC/MS (Method 1, ESIpos): R$_t$=0.84 min, m/z=383 [M+H]$^+$.

Example 89

3-Isobutyl-1-(2-methoxyethyl)-5-methyl-6-[(2-oxoimidazolidin-1-yl)methyl]thieno[2,3-d]pyrimidine-2,4(1H,3H)-dione

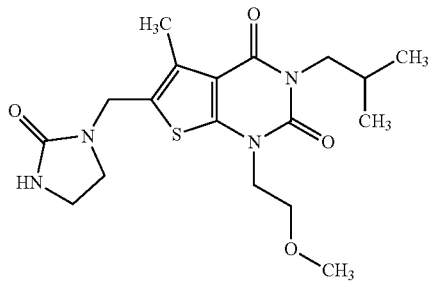

350 mg (0.665 mmol) of the compound from Example 242A were dissolved in 15 ml of dioxane, and 167 mg (0.997 mmol) of CDI were added. The mixture was stirred at RT for 20 h. The reaction solution was then concentrated on a rotary evaporator. The residue was dissolved in 9 ml of DMSO and this solution was purified by means of preparative HPLC (Method 14). Combination of the product fractions and freeze-drying gave 190 mg (72% of theory) of the title compound.

$^1$H-NMR (400 MHz, DMSO-$d_6$, δ/ppm): 6.53 (s, 1H), 4.34 (s, 2H), 4.02 (t, 2H), 3.71 (d, 2H), 3.62 (t, 2H), 3.29-3.17 (m, 7H), 2.38 (s, 3H), 2.03 (dquin, 1H), 0.85 (d, 6H).

LC/MS (Method 3): $R_t$=1.04 min, m/z=395 [M+H]$^+$.

Example 90

3-Isobutyl-5-methyl-6-[(2-oxoimidazolidin-1-yl)methyl]-1-(tetrahydrofuran-3-ylmethyl)thieno[2,3-d]pyrimidine-2,4(1H,3H)-dione (racemate)

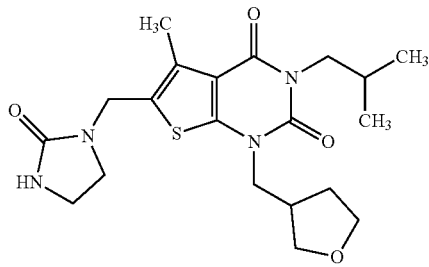 [SMILES: Cc1c(CN2CCNC2=O)sc2c1c(=O)n(CC(C)C)c(=O)n2CC1CCOC1]

To a solution of 705 mg (1.38 mmol, 79% purity) of the compound from Ex. 244A and 310 μl (2.23 mmol) of triethylamine in 15 ml of THF were added 289 mg (1.78 mmol) of CDI, and the mixture was stirred at RT for about 18 h. Subsequently, the mixture was concentrated to dryness. The remaining residue was taken up in ethyl acetate and washed successively with 1 M hydrochloric acid, water and saturated sodium chloride solution. After drying over anhydrous magnesium sulphate, the mixture was filtered and concentrated. The remaining residue was purified by means of preparative HPLC (Method 8). After combination of the product fractions, concentration and drying under high vacuum, 352 mg (59% of theory) of the title compound were obtained.

$^1$H-NMR (400 MHz, DMSO-$d_6$, δ/ppm): 6.52 (s, 1H), 4.34 (s, 2H), 4.27-4.16 (m, 1H), 4.01 (dd, 1H), 3.78-3.67 (m, 4H), 3.66-3.56 (m, 1H), 3.29-3.16 (m, 4H), 2.39 (s, 3H), 2.11-1.73 (m, 4H), 1.72-1.59 (m, 1H), 0.85 (dd, 6H).

LC/MS (Method 1, ESIpos): $R_t$=0.88 min, m/z=421 [M+H]$^+$.

Example 91

3-Isobutyl-1,5-dimethyl-6-[(2-oxoimidazolidin-1-yl)methyl]thieno[2,3-d]pyrimidine-2,4(1H,3H)-dione

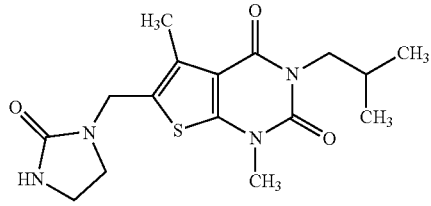 [SMILES: Cc1c(CN2CCNC2=O)sc2c1c(=O)n(CC(C)C)c(=O)n2C]

Analogously to the method described in Ex. 62, 195 mg (0.480 mmol, 80% purity) of the compound from Ex. 246A and 117 mg (0.720 mmol) of CDI were used to prepare 85 mg (50% of theory) of the title compound.

$^1$H-NMR (400 MHz, DMSO-$d_6$, δ/ppm): 6.52 (s, 1H), 4.36 (s, 2H), 3.71 (d, 2H), 3.41 (s, 3H), 3.28-3.14 (m, 4H), 2.40 (s, 3H), 2.09-1.99 (m, 1H), 0.85 (d, 6H).

LC/MS (Method 1, ESIpos): $R_t$=0.78 min, m/z=351 [M+H]$^+$.

Example 92

3-(Cyclopropylmethyl)-1-(2-methoxy ethyl-6-[(2-oxoimidazolidin-1-yl)methyl]thieno[2,3-d]pyrimidine-2,4(1H,3H)-dione

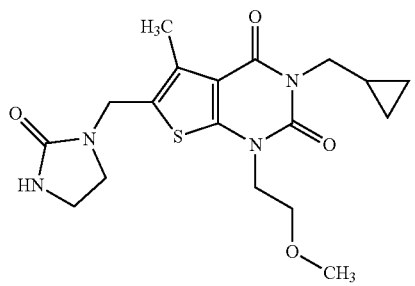 [SMILES: COCCn1c(=O)n(CC2CC2)c(=O)c2c(C)c(CN3CCNC3=O)sc21]

To a solution of 77 mg (0.854 mmol) of 2-imidazolidinone in 3 ml of THF were added 34 mg (0.854 mmol) of sodium hydride (60% suspension in mineral oil) and the mixture was stirred at RT for 3 h ("Solution 1"). To a solution of 70 mg (0.214 mmol) of the compound from Ex. 150A in 1.5 ml of dichloromethane in another reaction vessel were added, at 0° C., 111 μl (0.641 mmol) of N,N-diisopropylethylamine and 23.3 μl (0.32 mmol) of thionyl chloride, and the mixture was stirred for 75 min. Subsequently, Solution 1 was added in portions and the mixture was stirred at RT for 18 h. Thereafter, 70 ml of water were added to the reaction mixture. The mixture was extracted with ethyl acetate. The combined organic phases were dried over sodium sulphate, filtered and concentrated.

Example 93

1-(3-Fluoropropyl)-5-methyl-6-[(2-oxoimidazolidin-1-yl)methyl]-3-(2,2,2-trifluoroethyl)thieno[2,3-d]pyrimidine-2,4(1H,3H)-dione

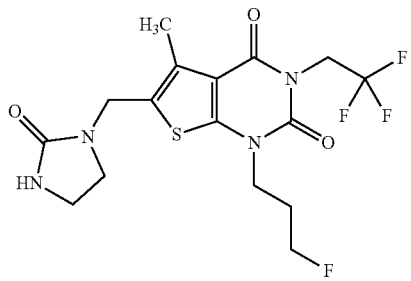 [SMILES: Cc1c(CN2CCNC2=O)sc2c1c(=O)n(CC(F)(F)F)c(=O)n2CCCF]

170 mg (0.309 mmol) of the compound from Example 248A were dissolved in 6.5 ml of dioxane, and 77 mg (0.463 mmol) of CDI were added. The mixture was stirred at RT for 20 h. The reaction mixture was then purified directly by means of preparative HPLC (Method 14). Combination of the product fractions and freeze-drying gave 74 mg (57% of theory) of the title compound.

$^1$H-NMR (400 MHz, DMSO-$d_6$, δ/ppm): 6.55 (s, 1H), 4.69 (q, 2H), 4.59 (t, 1H), 4.47 (t, 1H), 4.37 (s, 2H), 4.01 (t, 2H), 3.29-3.18 (m, 4H), 2.40 (s, 3H), 2.14-2.00 (m, 2H).

LC/MS (Method 3): $R_t$=1.01 min, m/z=423 [M+H]$^+$.

Example 94

1-(2-Methoxyethyl)-5-methyl-6-[(2-oxoimidazolidin-1-yl)methyl]-3-(2,2,2-trifluoroethyl)thieno[2,3-d]pyrimidine-2,4(1H,3H)-dione

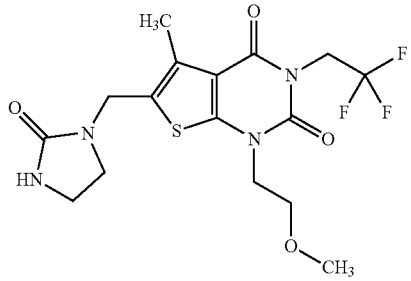

160 mg (0.268 mmol) of the compound from Example 249A were dissolved in 5.4 ml of dioxane, and 67 mg (0.402 mmol) of CDI were added. The mixture was stirred at RT for 15 h. The reaction solution was then concentrated on a rotary evaporator. The residue was dissolved in 6 ml of DMSO and this solution was purified by means of preparative HPLC (Method 14). Combination of the product fractions and freeze-drying gave 37 mg (31% of theory) of the title compound.

$^1$H-NMR (400 MHz, DMSO-$d_6$, δ/ppm): 6.53 (s, 1H), 4.69 (q, 2H), 4.36 (s, 2H), 4.05 (t, 2H), 3.64 (t, 2H), 3.29-3.19 (m, 7H), 2.39 (s, 3H).

LC/MS (Method 3): $R_t$=0.95 min, m/z=421 [M+H]$^+$.

Example 95

3-(2,2-Difluoroethyl)-1-(3-fluoropropyl)-5-methyl-6-[(2-oxoimidazolidin-1-yl)methyl]thieno[2,3-d]pyrimidine-2,4(1H,3H)-dione

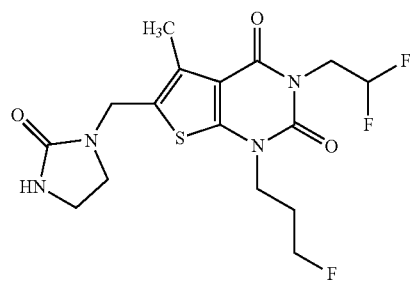 [SMILES: Cc1c(CN2CCNC2=O)sc2c1c(=O)n(CC(F)F)c(=O)n2CCCF]

195 mg (0.433 mmol) of the compound from Example 256A were dissolved in 8.8 ml of dioxane, and 108 mg (0.649 mmol) of CDI were added. The mixture was stirred at RT for 17 h. The reaction solution was then concentrated on a rotary evaporator. The residue was dissolved in 6 ml of DMSO and this solution was purified by means of preparative HPLC (Method 14). Combination of the product fractions and freeze-drying gave 105 mg (60% of theory) of the title compound.

$^1$H-NMR (400 MHz, DMSO-$d_6$, δ/ppm): 6.55 (s, 1H), 6.38-6.03 (m, 1H), 4.60 (t, 1H), 4.48 (t, 1H), 4.37 (s, 2H), 4.29 (td, 2H), 4.00 (t, 2H), 3.29-3.17 (m, 4H), 2.40 (s, 3H), 2.14-2.00 (m, 2H).

LC/MS (Method 3): $R_t$=0.92 min, m/z=405 [M+H]$^+$.

Example 96

3-(2,2-Difluoroethyl)-1-(2-methoxyethyl)-5-methyl-6-[(2-oxoimidazolidin-1-yl)methyl]thieno[2,3-d]pyrimidine-2,4(1H,3H)-dione

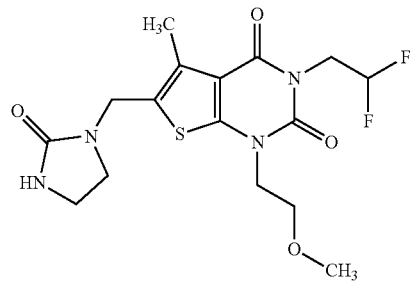 [SMILES: COCCn1c(=O)n(CC(F)F)c(=O)c2c(C)c(CN3CCNC3=O)sc21]

178 mg (0.340 mmol) of the compound from Example 257A were dissolved in 6.9 ml of dioxane, and 85 mg (0.511 mmol) of CDI were added. The mixture was stirred at RT for

---

The residue obtained was chromatographed using a silica gel cartridge (Biotage, 10 g of silica gel, eluent: hexane/ethyl acetate). 32 mg (38% of theory) of the title compound were obtained.

$^1$H-NMR (400 MHz, DMSO-$d_6$, δ/ppm): 6.52 (s, 1H), 4.35 (s, 2H), 4.03 (t, 2H), 3.76 (d, 2H), 3.63 (t, 2H), 3.28-3.18 (m, 7H), 2.39 (s, 3H), 1.21-1.11 (m, 1H), 0.45-0.38 (m, 2H), 0.36-0.30 (m, 2H).

LC/MS (Method 3): $R_t$=0.99 min, m/z=393 [M+H]$^+$.

16 h. The reaction solution was then concentrated on a rotary evaporator. The residue was dissolved in 6 ml of DMSO and this solution was purified by means of preparative HPLC (Method 14). Combination of the product fractions and freeze-drying gave 126 mg (92% of theory) of the title compound.

$^1$H-NMR (400 MHz, DMSO-$d_6$, δ/ppm): 6.53 (s, 1H), 6.39-6.05 (m, 1H), 4.36 (s, 2H), 4.29 (td, 2H), 4.04 (t, 2H), 3.64 (t, 2H), 3.29-3.18 (m, 7H), 2.39 (s, 3H).

LC/MS (Method 3): $R_t$=0.89 min, m/z=403 [M+H]$^+$.

Example 97

3-(2-Fluoroethyl)-1-(2-methoxyethyl)-5-methyl-6-[(2-oxoimidazolidin-1-yl)methyl]thieno[2,3-d]pyrimidine-2,4(1H,3H)-dione

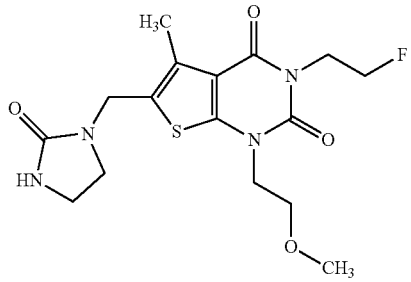 [SMILES: COCCn1c(=O)n(CCF)c(=O)c2c(C)c(CN3CCNC3=O)sc21]

To a solution of 176 mg (1.962 mmol) of 2-imidazolidinone in 7 ml of THF were added 78 mg (1.962 mmol) of sodium hydride (60% suspension in mineral oil) and the mixture was stirred at RT for 4 h ("Solution 1"). To a solution of 160 mg (0.491 mmol) of the compound from Ex. 151A in 3.4 ml of dichloromethane in another reaction vessel were added, at 0° C., 256 μl (1.472 mmol) of N,N-diisopropylethylamine and 53.7 μl (0.736 mmol) of thionyl chloride, and the mixture was stirred for 90 min. Subsequently, Solution 1 was added in portions and the mixture was stirred at RT for 18 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 10 g of silica gel, eluent: hexane/ethyl acetate). 88 mg (46% of theory) of the title compound were obtained.

$^1$H-NMR (400 MHz, DMSO-$d_6$, δ/ppm): 6.52 (s, 1H), 4.66 (t, 1H), 4.54 (t, 1H), 4.35 (s, 2H), 4.23 (t, 1H), 4.20-4.14 (m, 1H), 4.02 (t, 2H), 3.63 (t, 2H), 3.28-3.18 (m, 7H), 2.39 (s, 3H).

LC/MS (Method 3): $R_t$=0.82 min, m/z=385 [M+H]$^+$.

Example 98

1-(2-Methoxyethyl)-5-methyl-6-[(2-oxoimidazolidin-1-yl)methyl]-3-(3,3,3-trifluoropropyl)thieno[2,3-d]pyrimidine-2,4(1H,3H)-dione

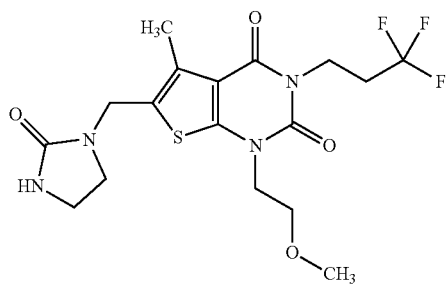 [SMILES: COCCn1c(=O)n(CCC(F)(F)F)c(=O)c2c(C)c(CN3CCNC3=O)sc21]

To a solution of 205 mg (2.293 mmol) of 2-imidazolidinone in 8.2 ml of THF were added 92 mg (2.293 mmol) of sodium hydride (60% suspension in mineral oil) and the mixture was stirred at RT for 3 h ("Solution 1"). To a solution of 210 mg (0.573 mmol) of the compound from Ex. 152A in 4 ml of dichloromethane in another reaction vessel were added, at 0° C., 299 μl (1.72 mmol) of N,N-diisopropylethylamine and 62.7 μl (0.86 mmol) of thionyl chloride, and the mixture was stirred for 90 min. Subsequently, Solution 1 was added in portions and the mixture was stirred at RT for 18 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 10 g of silica gel, eluent: hexane/ethyl acetate). 95 mg (37% of theory) of the title compound were obtained.

$^1$H-NMR (400 MHz, DMSO-$d_6$, δ/ppm): 6.55 (s, 1H), 4.35 (s, 2H), 4.11 (t, 2H), 4.02 (t, 2H), 3.62 (t, 2H), 3.27-3.18 (m, 7H), 2.64-2.53 (m, 2H), 2.39 (s, 3H).

LC/MS (Method 3): $R_t$=1.02 min, m/z=435 [M+H]$^+$.

Example 99

1-(2-Methoxyethyl)-3-(2-methoxypropyl)-5-methyl-6-[(2-oxoimidazolidin-1-yl)methyl]thieno[2,3-d]pyrimidine-2,4(1H,3H)-dione (racemate)

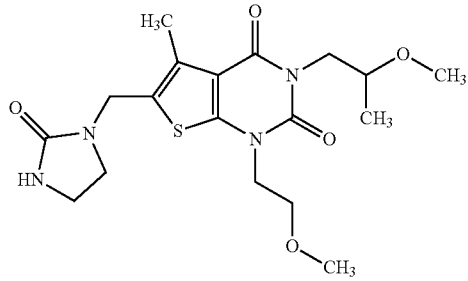 [SMILES: COCCn1c(=O)n(CC(C)OC)c(=O)c2c(C)c(CN3CCNC3=O)sc21]

To a solution of 195 mg (2.173 mmol) of 2-imidazolidinone in 7.8 ml of THF were added 87 mg (2.173 mmol) of sodium hydride (60% suspension in mineral oil) and the mixture was stirred at RT for 3 h ("Solution 1"). To a solution of 200 mg (0.543 mmol) of the compound from Ex.

155A in 3.8 ml of dichloromethane in another reaction vessel were added, at 0° C., 284 µl (1.63 mmol) of N,N-diisopropylethylamine and 59.4 µl (0.815 mmol) of thionyl chloride, and the mixture was stirred for 75 min. Subsequently, Solution 1 was added in portions and the mixture was stirred at RT for 18 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 10 g of silica gel, eluent: hexane/ethyl acetate). 102 mg (45% of theory) of the title compound were obtained.

$^1$H-NMR (400 MHz, DMSO-$d_6$, δ/ppm): 6.55 (s, 1H), 4.34 (s, 2H), 4.09-3.99 (m, 3H), 3.75 (dd, 1H), 3.68-3.59 (m, 3H), 3.29-3.17 (m, 10H), 2.38 (s, 3H), 1.05 (d, 3H).

LC/MS (Method 3): $R_t$=0.88 min, m/z=411 [M+H]$^+$.

Example 100

5-(Difluoromethyl)-3-ethyl-6-[(2-oxoimidazolidin-1-yl)methyl]-1-(3,3,3-trifluoropropyl)thieno[2,3-d]pyrimidine-2,4(1H,3H)-dione

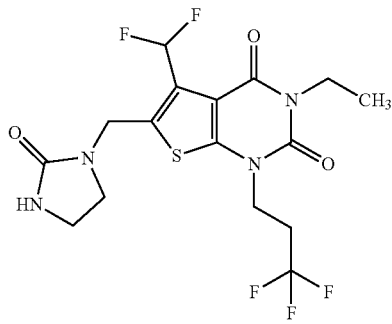

370 mg (0.893 mmol) of the compound from Example 264A were dissolved in 18 ml of dioxane, and 223 mg (1.339 mmol) of CDI were added. The mixture was stirred at RT for 17 h. The reaction solution was then concentrated on a rotary evaporator. The residue was dissolved in 6 ml of DMSO and this solution was purified by means of preparative HPLC (Method 14). Combination of the product fractions and freeze-drying gave 38 mg (10% of theory) of the title compound.

$^1$H-NMR (400 MHz, DMSO-$d_6$, δ/ppm): 7.68-7.39 (m, 1H), 6.72 (s, 1H), 4.57 (s, 2H), 4.13 (t, 2H), 3.91 (q, 2H), 2.86-2.71 (m, 2H), 1.13 (t, 3H).

LC/MS (Method 3): $R_t$=1.08 min, m/z=441 [M+H]$^+$.

Example 101

5-(Difluoromethyl)-3-ethyl-1-(2-methoxyethyl)-6-[(2-oxoimidazolidin-1-yl)methyl]thieno[2,3-d]pyrimidine-2,4(1H,3H)-dione

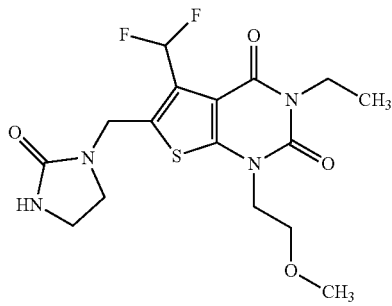

298 mg (0.792 mmol) of the compound from Example 265A were dissolved in 16 ml of dioxane, and 198 mg (1.187 mmol) of CDI were added. The mixture was stirred at RT for 17 h. The reaction solution was then concentrated on a rotary evaporator. The residue was dissolved in 6 ml of DMSO and this solution was purified by means of preparative HPLC (Method 14). Combination of the product fractions and freeze-drying gave 31 mg (9% of theory) of the title compound.

$^1$H-NMR (400 MHz, DMSO-$d_6$, δ/ppm): 7.68-7.38 (m, 1H), 6.70 (s, 1H), 4.55 (s, 2H), 4.05 (t, 2H), 3.91 (q, 2H), 3.64 (t, 2H), 3.36-3.24 (m, 4H), 3.24 (s, 3H), 1.13 (t, 3H).

LC/MS (Method 3): $R_t$=0.94 min, m/z=403 [M+H]$^+$.

Example 102

1-(2-Methoxyethyl)-5-methyl-6-[(3-methyl-2-oxoimidazolidin-1-yl)methyl]-3-(2-phenylethyl)thieno[2,3-d]pyrimidine-2,4(1H,3H)-dione

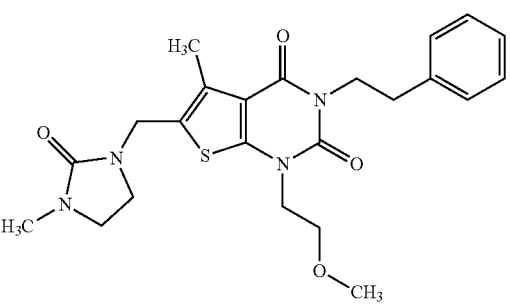 [SMILES: COCCn1c(=O)n(CCc2ccccc2)c(=O)c2c(C)c(CN3CCN(C)C3=O)sc21]

Analogously to the method described in Ex. 1, 80 mg (0.214 mmol) of the compound from Ex. 138A and 64 mg (0.641 mmol) of 1-methylimidazolidin-2-one were used to obtain 44 mg (45% of theory) of the title compound. The 1-methylimidazolidin-2-one was stirred here with sodium hydride in THF only for 2 min.

$^1$H-NMR (400 MHz, DMSO-$d_6$, δ/ppm): 7.35-7.27 (m, 2H), 7.26-7.17 (m, 3H), 4.38 (s, 2H), 4.08-4.04 (m, 2H), 4.01 (t, 2H), 3.60 (t, 2H), 3.26-3.16 (m, 4H), 3.23 (s, 3H), 2.89-2.76 (m, 2H), 2.67 (s, 3H), 2.40 (s, 3H).

LC/MS (Method 1, ESIpos): $R_t$=1.04 min, m/z=457 [M+H]$^+$.

Example 103

3-Ethyl-5-methyl-6-[(3-methyl-2-oxoimidazolidin-1-yl)methyl]-1-(3,3,3-trifluoropropyl)thieno[2,3-d]pyrimidine-2,4(1H,3H)-dione

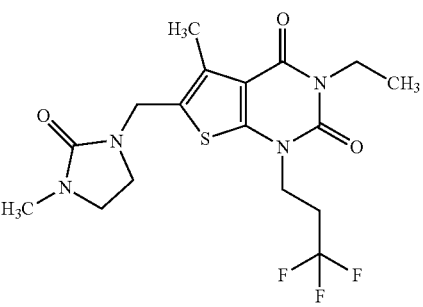 [SMILES: CCn1c(=O)c2c(C)c(CN3CCN(C)C3=O)sc2n(CCC(F)(F)F)c1=O]

Analogously to the method described in Ex. 2, 90 mg (0.268 mmol) of the compound from Ex. 140A and 107 mg (1.07 mmol) of 1-methylimidazolidin-2-one were used to obtain 58 mg (51% of theory) of the title compound. In a departure from the method described above, the 1-methyl-imidazolidin-2-one was deprotonated here with sodium hydride at 60° C. for 2 h, and the reaction time in the last reaction step was 4 days.

$^1$H-NMR (400 MHz, DMSO-$d_6$, δ/ppm): 4.39 (s, 2H), 4.09 (t, 2H), 3.90 (q, 2H), 3.27-3.16 (m, 4H), 2.83-2.69 (m, 2H), 2.67 (s, 3H), 2.41 (s, 3H), 1.11 (t, 3H).

LC/MS (Method 2, ESIpos): $R_t$=2.63 min, m/z=419 [M+H]$^+$.

Example 104

6-[(3-Acetyl-2-oxoimidazolidin-1-yl)methyl]-3-ethyl-1-(2-methoxyethyl)-5-methylthieno[2,3-d]pyrimidine-2,4(1H,3H)-dione

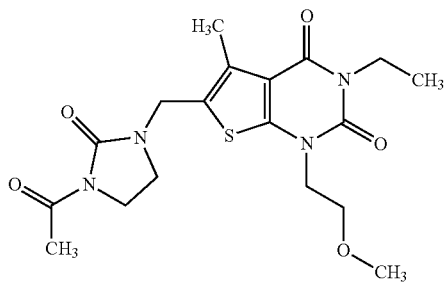 [SMILES: CCn1c(=O)c2c(C)c(CN3CCN(C(C)=O)C3=O)sc2n(CCOC)c1=O]

To a solution of 95 mg (0.161 mmol) of the compound from Ex. 59 in 5 ml of THF were added 7.7 mg (0.192 mmol) of sodium hydride (60% suspension in mineral oil), and the mixture was stirred at 0° C. for 1 h. Subsequently, 15 mg (0.193 mmol) of acetyl chloride were added, and the mixture was stirred at 0° C. for 80 min. Then the reaction mixture was partitioned between saturated aqueous ammonium chloride solution (20 ml) and THF (30 ml). The organic phase was washed with saturated aqueous sodium hydrogencarbonate solution, dried over sodium sulphate, filtered and concentrated. The residue obtained was purified by means of preparative HPLC (Method 14). Combination of the product fractions and freeze-drying gave 29 mg (44% of theory) of the title compound.

$^1$H-NMR (400 MHz, DMSO-$d_6$, δ/ppm): 4.51 (s, 2H), 4.02 (t, 2H), 3.90 (q, 2H), 3.70-3.61 (m, 4H), 3.23 (s, 3H), 2.42 (s, 3H), 2.37 (s, 3H), 1.11 (t, 3H).

LC/MS (Method 3): $R_t$=0.97 min, m/z=409 [M+H]$^+$.

Example 105

1-(2-Methoxyethyl)-6-[(3-methyl-2-oxoimidazolidin-1-yl)methyl]-3-(2-phenylethyl)-5-(trifluoromethyl)thieno[2,3-d]pyrimidine-2,4(1H,3H)-dione

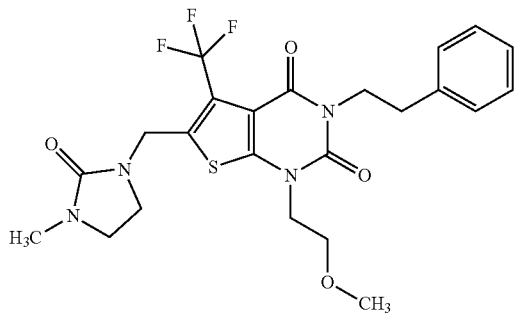 [SMILES: COCCn1c(=O)n(CCc2ccccc2)c(=O)c2c(C(F)(F)F)c(CN3CCN(C)C3=O)sc21]

Analogously to the method described in Ex. 5, 100 mg (0.224 mmol) of the compound from Ex. 181A and 116 mg (1.16 mmol) of 1-methylimidazolidin-2-one were used to obtain 24 mg (21% of theory) of the title compound.

$^1$H-NMR (400 MHz, DMSO-$d_6$, δ/ppm): 7.34-7.27 (m, 2H), 7.25-7.19 (m, 3H), 4.59 (d, 2H), 4.12-4.00 (m, 4H), 3.60 (t, 2H), 3.35 (m, 4H), 3.23 (s, 3H), 2.89-2.79 (m, 2H), 2.72 (s, 3H).

LC/MS (Method 1, ESIpos): $R_t$=1.07 min, m/z=511 [M+H]$^+$.

Example 106

6-[(2,5-Dioxoimidazolidin-1-yl)methyl]-3-ethyl-5-methyl-1-[2-(trifluoromethoxy)ethyl]thieno[2,3-d]pyrimidine-2,4(1H,3H)-dione

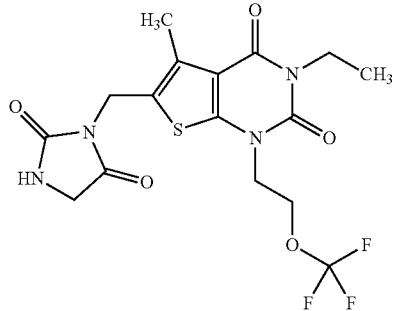 [SMILES: CCn1c(=O)c2c(C)c(CN3C(=O)CNC3=O)sc2n(CCOC(F)(F)F)c1=O]

To a solution of 60 mg (0.170 mmol) of the compound from Ex. 142A, 17 mg (0.170 mmol) of hydantoin and 54 mg (0.204 mmol) of triphenylphosphine in 1.2 ml of THF were added, at 0° C., 41 mg (0.204 mmol) of diisopropyl azodicarboxylate (DIAD). The reaction mixture was stirred first at 0° C. for 1 h and then at RT for 1 h. Subsequently, the mixture was concentrated to dryness. The remaining residue was first prepurified by means of preparative HPLC (Method 13). The product-containing fractions were concentrated and the residue was repurified once again by means of preparative HPLC (Method 16). 2.7 mg (3.5% of theory, 97% purity) of the title compound were obtained.

$^1$H-NMR (500 MHz, DMSO-$d_6$, δ/ppm): 8.18 (s, 1H), 4.63 (s, 2H), 4.39 (t, 2H), 4.17 (t, 2H), 3.94 (s, 2H), 3.90 (q, 2H), 2.48 (s, 3H), 1.11 (t, 3H).

Example 107

3-Ethyl-5-methyl-6-[(2-oxotetrahydropyrimidin-1(2H)-yl)methyl]-1-(3,3,3-trifluoropropyl)thieno[2,3-d]pyrimidine-2,4(1H,3H)-dione

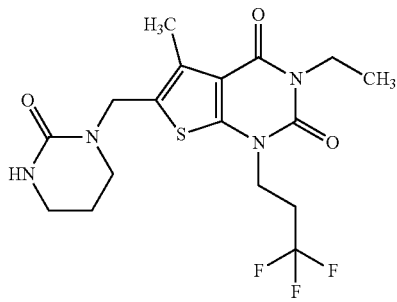 [SMILES: CCn1c(=O)c2c(C)c(CN3CCCNC3=O)sc2n(CCC(F)(F)F)c1=O]

Analogously to the method described in Ex. 2, 100 mg (0.297 mmol) of the compound from Ex. 140A and 37 mg (1.19 mmol) of tetrahydropyrimidin-2(1H)-one were used to obtain 19 mg (15% of theory) of the title compound. In a departure from the method described above, the tetrahydropyrimidin-2(1H)-one was deprotonated here with sodium hydride at 60° C. for 2 h, and the reaction time in the last reaction step was 7 days.

$^1$H-NMR (500 MHz, DMSO-d$_6$, δ/ppm): 6.40 (br. s, 1H), 4.51 (s, 2H), 4.09 (t, 2H), 3.90 (q, 2H), 3.18 (t, 2H), 3.09 (t, 2H), 2.82-2.69 (m, 2H), 2.42 (s, 3H), 1.77 (quin, 2H), 1.11 (t, 3H).

LC/MS (Method 2, ESIpos): R$_t$=2.42 min, m/z=419 [M+H]$^+$.

Example 108

3-Ethyl-5-methyl-6-[(3-methyl-2-oxotetrahydropyrimidin-1(2H)-yl)methyl]-1-(3,3,3-trifluoropropyl)thieno[2,3-d]pyrimidine-2,4(1H,3H)-dione

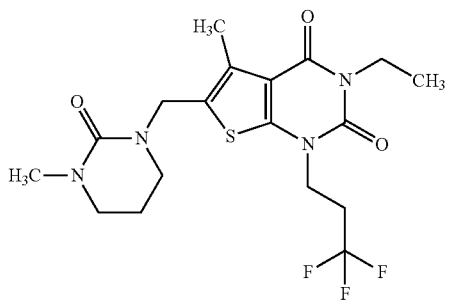 [SMILES: CCn1c(=O)c2c(C)c(CN3CCCN(C)C3=O)sc2n(CCC(F)(F)F)c1=O]

Analogously to the method described in Ex. 2, 90 mg (0.268 mmol) of the compound from Ex. 140A and 122 mg (1.07 mmol) of 1-methyltetrahydropyrimidin-2(1H)-one were used to obtain 78 mg (67% of theory) of the title compound. In a departure from the method described above, the 1-methyltetrahydropyrimidin-2(1H)-one was deprotonated here with sodium hydride at 60° C. for 2 h, and the reaction time in the last reaction step was 7 days.

$^1$H-NMR (400 MHz, DMSO-d$_6$, δ/ppm): 4.52 (s, 2H), 4.09 (t, 2H), 3.90 (q, 2H), 3.22-3.17 (m, 4H), 2.81 (s, 3H), 2.81-2.72 (m, 2H), 2.41 (s, 3H), 1.86 (quin, 2H), 1.11 (t, 3H).

LC/MS (Method 1, ESIpos): R$_t$=0.96 min, m/z=433 [M+H]$^+$.

Example 109

3-Ethyl-1-(2-methoxyethyl)-5-methyl-6-[(2-oxo-2,3-dihydro-1H-imidazol-1-yl)methyl]thieno[2,3-d]pyrimidine-2,4(1H,3H)-dione

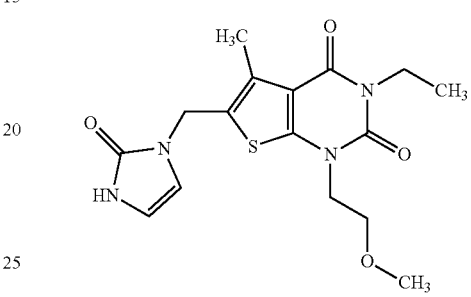

To a solution of 47 mg (0.110 mmol) of the compound from Ex. 274A in a mixture of 800 μl of water and 220 μl of methanol were added 217 μl (0.109 mmol) of 0.5 M hydrochloric acid. After the reaction mixture had been stirred at RT for 3 days, it was separated into its components directly by means of preparative HPLC (Method 8). Concentration and drying of the product fraction under high vacuum gave 20 mg (47% of theory, 95% purity) of the title compound.

$^1$H-NMR (400 MHz, DMSO-d$_6$, δ/ppm): 9.99 (br. s, 1H), 6.43 (dd, 1H), 6.34 (t, 1H), 4.79 (s, 2H), 4.00 (t, 2H), 3.89 (q, 2H), 3.62 (t, 2H), 3.22 (s, 3H), 2.46 (s, 3H), 1.11 (t, 3H).

LC/MS (Method 1, ESIpos): R$_t$=0.67 min, m/z=365 [M+H]$^+$.

Example 110

6-[(4-Allyl-5-oxo-4,5-dihydro-H-1,2,4-triazol-1-yl)methyl]-3-ethyl-5-methyl-1-(3,3,3-trifluoropropyl)thieno[2,3-d]pyrimidine-2,4(1H,3H)-dione

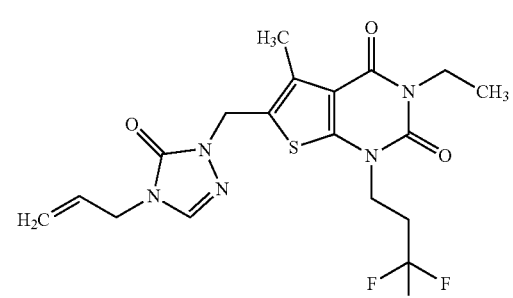

6.16 g (18.3 mmol) of the compound from Ex. 140A and 2.75 g (22.0 mmol) of 4-allyl-2,4-dihydro-3H-1,2,4-triazol-3-one were dissolved in 300 ml of dichloromethane, and 12.2 g (46.5 mmol) of polymer-bound triphenylphosphine LC/MS (Method 1, ESIpos): R$_t$=0.85 min, m/z=435 [M+H]$^+$.

were added. After 10 min, 5.4 ml (27.5 mmol) of diisopropyl azodicarboxylate (DIAD) were added dropwise. The reaction mixture was stirred at RT. After about 18 h, a further 5 g (19.1 mmol) of polymer-bound triphenylphosphine and 1 g (4.95 mmol) of DIAD were added. After a further 2 h, the reaction mixture was filtered and the residue was washed with dichloromethane. The filtrate was washed successively with water and saturated sodium chloride solution. After drying over anhydrous magnesium sulphate, filtration and concentration, the remaining residue was purified by means of suction filtration through silica gel with cyclohexane/ethyl acetate (1:1) as eluent. The product fractions were combined, concentrated by evaporation and dried under high vacuum. 2.72 g (30% of theory, 92% purity) of the title compound were obtained.

$^1$H-NMR (400 MHz, DMSO-$d_6$, δ/ppm): 7.96 (s, 1H), 5.96-5.84 (m, 1H), 5.19 (dd, 1H), 5.11-5.03 (m, 1H), 5.02 (s, 2H), 4.21 (dt, 2H), 4.08 (t, 2H), 3.90 (q, 2H), 2.81-2.66 (m, 2H), 2.47 (s, 3H), 1.11 (t, 3H).

LC/MS (Method 1, ESIpos): $R_t$=0.93 min, m/z=444 [M+H]$^+$.

Example 111

6-[(4-Allyl-5-oxo-4,5-dihydro-1H-1,2,4-triazol-1-yl) methyl]-3-ethyl-5-methyl-1-[2-(trifluoromethoxy) ethyl]thieno[2,3-d]pyrimidine-2,4(1H,3H)-dione

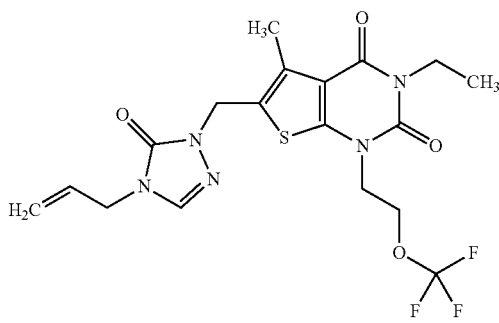 [SMILES: C=CCn1cnn(Cc2sc3c(c2C)c(=O)n(CC)c(=O)n3CCOC(F)(F)F)c1=O]

To a solution of 75 mg (0.213 mmol) of the compound from Ex. 142A, 27 mg (0.213 mmol) of 4-allyl-2,4-dihydro-3H-1,2,4-triazol-3-one and 56 mg (0.213 mmol) of triphenylphosphine in 2.1 ml of THF were added, at 0° C., 43 mg (0.213 mmol) of diisopropyl azodicarboxylate (DIAD). The reaction mixture was stirred at RT for 2 h. Subsequently, the mixture was concentrated to dryness. The remaining residue was purified by means of preparative HPLC (Method 13). The product-containing fractions were concentrated and dried under high vacuum. 14 mg (14% of theory, 98% purity) of the title compound were obtained.

$^1$H-NMR (500 MHz, DMSO-$d_6$, δ/ppm): 7.96 (s, 1H), 5.89 (ddt, 1H), 5.18 (dd, 1H), 5.09-5.02 (m, 1H), 5.01 (s, 2H), 4.38 (t, 2H), 4.23-4.14 (m, 4H), 3.90 (q, 2H), 2.46 (s, 3H), 1.11 (t, 3H).

LC/MS (Method 1, ESIpos): $R_t$=0.93 min, m/z=460 [M+H]$^+$.

Example 112

6-[(4-Allyl-5-oxo-4,5-dihydro-1H-1,2,4-triazol-1-yl) methyl]-3-ethyl-1-(2-methoxyethyl)-5-methylthieno [2,3-d]pyrimidine-2,4(1H,3H)-dione

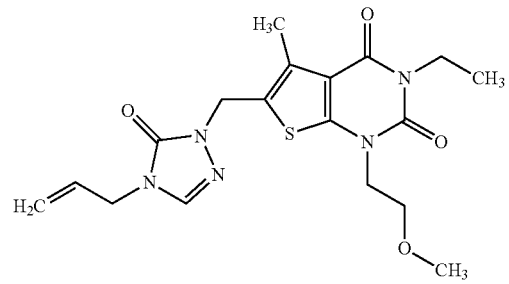 [SMILES: C=CCn1cnn(Cc2sc3c(c2C)c(=O)n(CC)c(=O)n3CCOC)c1=O]

To a solution of 839 mg (6.70 mmol) of 4-allyl-2,4-dihydro-3H-1,2,4-triazol-3-one in 12 ml of DMF were added 268 mg (6.70 mmol) of sodium hydride (60% suspension in mineral oil), then the mixture was heated to 60° C. for 5 min and subsequently cooled back down to RT ("Solution 1"). To a solution of 500 mg (1.68 mmol) of the compound from Ex. 143A in 10 ml of dichloromethane in another reaction vessel were added, at 0° C., 584 µl (3.35 mmol) of N,N-diisopropylethylamine and 128 µl (1.76 mmol) of thionyl chloride. After 20 min at 0° C., Solution 1 was added dropwise and the cooling bath was removed. The reaction mixture was stirred at RT for 2.5 days. Thereafter, the mixture was admixed with 100 ml of water and extracted three times with dichloromethane. The combined organic extracts were washed successively with water and saturated sodium chloride solution. After drying over anhydrous magnesium sulphate, the mixture was filtered and concentrated. The remaining residue was purified by means of preparative HPLC (Method 8). After concentration of the product fractions and drying under high vacuum, 196 mg (28% of theory) of the title compound were obtained.

$^1$H-NMR (400 MHz, DMSO-$d_6$, δ/ppm): 7.96 (s, 1H), 5.90 (ddt, 1H), 5.19 (dd, 1H), 5.07 (dq, 1H), 4.99 (s, 2H), 4.21 (dt, 2H), 4.00 (t, 2H), 3.89 (q, 2H), 3.62 (t, 2H), 3.22 (s, 3H), 2.45 (s, 3H), 1.11 (t, 3H).

LC/MS (Method 1, ESIpos): $R_t$=0.78 min, m/z=406 [M+H]$^+$.

Example 113

3-Ethyl-5-methyl-6-[(5-oxo-4,5-dihydro-1H-1,2,4-triazol-1-yl)methyl]-1-(3,3,3-trifluoropropyl)thieno [2,3-d]pyrimidine-2,4(1H,3H)-dione

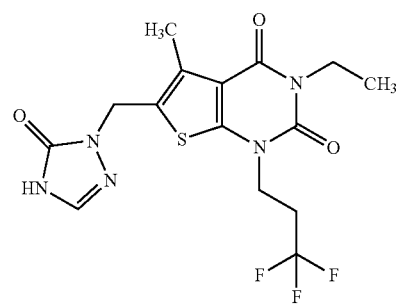 [SMILES: CCn1c(=O)c2c(C)c(Cn3nc[nH]c3=O)sc2n(CCC(F)(F)F)c1=O]

Method A:

407 mg (0.685 mmol, 75% purity) of the compound from Ex. 110 were dissolved in 8 ml of 1,4-dioxane, and 54 µl (1.44 mmol) of formic acid, 239 µl (1.71 mmol) of triethylamine and 79 mg (0.068 mmol) of tetrakis(triphenylphosphine)palladium(0) were added. The mixture was heated to 100° C. in a microwave oven (Biotage Initiator with dynamic control of irradiation power) for 28 h, with addition of the same amounts of palladium catalyst once again after 12 h and after 16 h of reaction time. Then the reaction mixture was filtered and the filtrate was concentrated to dryness. The remaining residue was taken up in ethyl acetate and washed successively with water and saturated sodium chloride solution. After drying over anhydrous magnesium sulphate and filtration, the mixture was concentrated again. Preparative HPLC purification of the residue (Method 8), after concentration and drying of the product fractions under high vacuum, gave 100 mg (36% of theory) of the title compound.

Method B:

7.31 g (14.8 mmol) of the compound from Ex. 474A were dissolved in a mixture of 412 ml of methanol and 412 ml of trimethyl orthoformate, and 37 ml (148 mmol) of a 4 M solution of hydrogen chloride in dioxane were first added at RT. After 5 h of reaction time, a further 7.4 ml (29.6 mmol) of the 4 M solution of hydrogen chloride in dioxane were added and the stirring was continued at RT. After a total reaction time of about 20 h, the reaction mixture was concentrated to about half its original volume on a rotary evaporator. Then it was diluted with water and extracted with ethyl acetate. The organic extract was concentrated on a rotary evaporator to such an extent that the product began to precipitate out. After cooling to RT, the product was filtered off with suction, washed with a little cold ethyl acetate and dried under high vacuum. This gave a first fraction of the title compound (4.95 g). The mother liquor combined with the wash solution was concentrated, and the remaining residue was purified by means of preparative HPLC (Method 8). After the product fractions had been concentrated and dried under high vacuum, a second fraction of the title compound was thus obtained (0.25 g). A total of 5.2 g (85% of theory, 98% purity) of the title compound was thus obtained.

$^1$H-NMR (400 MHz, DMSO-$d_6$, δ/ppm): 11.60 (br. s, 1H), 7.84 (s, 1H), 4.95 (s, 2H), 4.08 (t, 2H), 3.90 (q, 2H), 2.82-2.68 (m, 2H), 2.47 (s, 3H), 1.11 (t, 3H).

LC/MS (Method 1, ESIpos): $R_t$=0.79 min, m/z=404 [M+H]$^+$.

Example 114

3-Ethyl-1-(2-methoxyethyl)-5-methyl-6-[(5-oxo-4,5-dihydro-1H-1,2,4-triazol-1-yl)methyl]thieno[2,3-d]pyrimidine-2,4(1H,3H)-dione

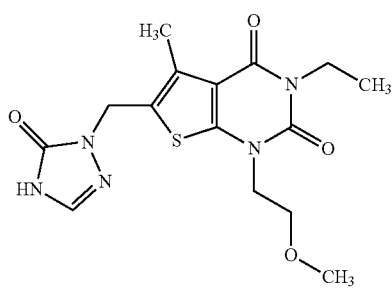

Analogously to the method described in Ex. 113, 189 mg (0.466 mmol) of the compound from Ex. 112 were used to prepare 32 mg (18% of theory) of the title compound. The product was stirred here with pentane for further purification after the preparative HPLC.

$^1$H-NMR (400 MHz, DMSO-$d_6$, δ/ppm): 11.60 (br. s, 1H), 7.84 (s, 1H), 4.93 (s, 2H), 4.01 (t, 2H), 3.89 (q, 2H), 3.62 (t, 2H), 3.23 (s, 3H), 2.45 (s, 3H), 1.11 (t, 3H).

LC/MS (Method 1, ESIpos): $R_t$=0.65 min, m/z=366 [M+H]$^+$.

Example 115

6-{[4-(2,3-Dihydroxypropyl)-5-oxo-4,5-dihydro-1H-1,2,4-triazol-1-yl]methyl}-3-ethyl-5-methyl-1-[2-(trifluoromethoxy)ethyl]thieno[2,3-d]pyrimidine-2,4(1H,3H)-dione (racemate)

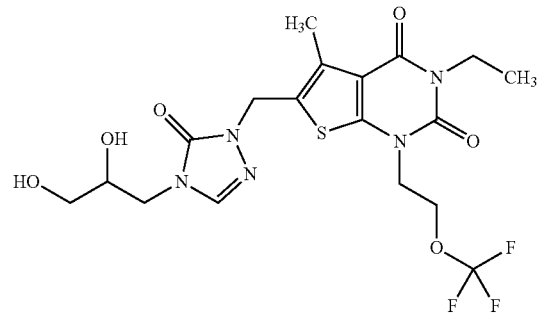 [SMILES: CCn1c(=O)c2c(C)c(Cn3ncn(CC(O)CO)c3=O)sc2n(CCOC(F)(F)F)c1=O]

To a solution of 10 mg (0.022 mmol) of the compound from Ex. 111 in 220 µl of acetone were added 3.8 mg (0.033 mmol) of N-methylmorpholine N-oxide (NMO) and 4 µl (0.001 mmol) of osmium tetroxide solution (4% in water), and the mixture was stirred at RT for about 18 h. Then about 100 µl each of sodium thiosulphate solution (20% in water) and 1 M hydrochloric acid solution were added. Undissolved material was filtered off and the filtrate was separated into its components by means of preparative HPLC (Method 12). Concentration of the product fraction and drying under high vacuum gave 7 mg (65% of theory) of the title compound.

$^1$H-NMR (500 MHz, DMSO-$d_6$, δ/ppm): 7.85 (s, 1H), 4.99 (s, 2H), 4.41-4.36 (m, 2H), 4.18 (t, 2H), 3.90 (q, 2H), 3.71 (dd, 1H), 3.67-3.60 (m, 1H), 3.43 (dd, 2H), 2.47 (s, 3H), 1.11 (t, 3H) [further signals are concealed by the water signal].

LC/MS (Method 1, ESIpos): $R_t$=0.76 min, m/z=494 [M+H]$^+$.

Example 116

3-Ethyl-5-methyl-6-[(5-oxo-1,5-dihydro-4H-1,2,4-triazol-4-yl)methyl]-1-(3,3,3-trifluoropropyl)thieno[2,3-d]pyrimidine-2,4(1H,3H)-dione

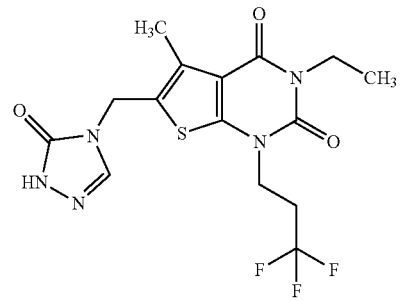 [SMILES: CCn1c(=O)c2c(C)c(Cn3cn[nH]c3=O)sc2n(CCC(F)(F)F)c1=O]

106 mg (0.253 mmol) of the compound from Ex. 279A were dissolved in 11 ml of methanol, 13 mg (0.317 mmol) of solid sodium hydroxide were added and the mixture was heated to 55° C. After 40 h, the reaction mixture was concentrated to dryness. The remaining residue was purified by means of preparative HPLC (Method 8). After concentration, the product fraction was dissolved again in methanol and the solution was passed through a hydrogencarbonate cartridge (from Polymerlabs, Stratospheres SPE, PL-HCO$_3$ MP SPE). Concentration once again and drying under high vacuum gave 68 mg (66% of theory) of the title compound.

$^1$H-NMR (400 MHz, DMSO-d$_6$, δ/ppm): 7.84 (s, 1H), 4.86 (s, 2H), 4.08 (t, 2H), 3.90 (q, 2H), 2.83-2.67 (m, 2H), 2.48 (s, 3H), 1.11 (t, 3H).

LC/MS (Method 1, ESIpos): R$_t$=0.74 min, m/z=404 [M+H]$^+$.

Example 117

[1-{[3-Ethyl-1-(2-methoxyethyl)-5-methyl-2,4-dioxo-1,2,3,4-tetrahydrothieno[2,3-d]pyrimidin-6-yl]methyl}imidazolidin-2-ylidene]cyanamide (with Unknown E/Z isomer Ratio)

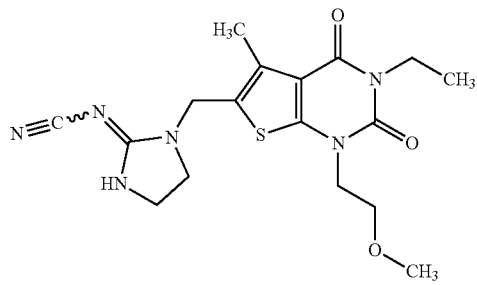 [SMILES: CCn1c(=O)c2c(C)c(CN3CCNC3=NC#N)sc2n(CCOC)c1=O]

60 mg (0.127 mmol, 72% purity) of the compound from Ex. 220A were dissolved in 5 ml of DMF, and 28 mg (0.190 mmol) of dimethyl N-cyanodithioiminocarbonate and 35 mg (0.254 mmol) of potassium carbonate were added. The mixture was stirred at 80° C. in a microwave oven (Biotage Initiator with dynamic control of irradiation power) for 4 h. Thereafter, the reaction mixture was diluted with ethyl acetate and washed successively with saturated sodium hydrogencarbonate solution, water and saturated sodium chloride solution. After drying over anhydrous magnesium sulphate, the mixture was filtered and concentrated. The product obtained after drying under high vacuum was stirred in pentane/dichloromethane (10:1). Filtration with suction again and drying of the solid under high vacuum gave 25 mg (49% of theory, 95% purity) of the title compound.

$^1$H-NMR (400 MHz, DMSO-d$_6$, δ/ppm): 8.07 (s, 1H), 4.47 (s, 2H), 4.03 (t, 2H), 3.90 (q, 2H), 3.64 (t, 2H), 3.49-3.37 (m, 4H), 3.24 (s, 3H), 2.41 (s, 3H), 1.12 (t, 3H).

LC/MS (Method 1, ESIpos): R$_t$=0.73 min, m/z=391 [M+H]$^+$.

Example 118

Methyl [1-{[3-ethyl-1-(2-methoxyethyl)-5-methyl-2,4-dioxo-1,2,3,4-tetrahydrothieno[2,3-d]pyrimidin-6-yl]methyl}imidazolidin-2-ylidene]carbamate (Isomer 1, pure E or Z isomer)

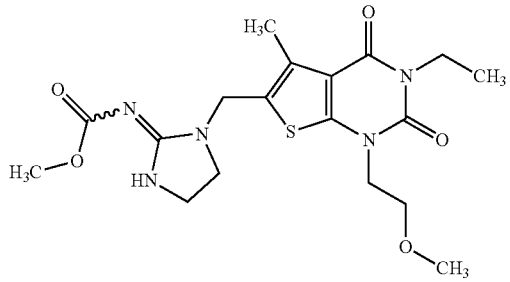 [SMILES: CCn1c(=O)c2c(C)c(CN3CCNC3=NC(=O)OC)sc2n(CCOC)c1=O]

121 mg (0.214 mmol, 60% purity) of the compound from Ex. 220A and 60 μl (0.428 mmol) of triethylamine were dissolved in 6 ml of dichloromethane, and a solution of 34 mg (0.214 mmol) of methyl (dichloromethylene)carbamate [DE 1 900 755 (1970); DE 2 036 171 (1972); K. Findeisen et al., *Synthesis* 1972, 599-605] in 4 ml of dichloromethane was added. After the reaction mixture had been stirred at RT for 3 h, it was diluted with ethyl acetate and washed successively with saturated sodium hydrogencarbonate solution, water and saturated sodium chloride solution. After drying over anhydrous magnesium sulphate, the mixture was filtered and concentrated. The remaining residue was separated into its components by means of preparative HPLC (Method 8). This gave the two E/Z isomers of the target product as separate fractions (see also Ex. 119). Concentration of the first product fraction and drying of the residue under high vacuum gave 15 mg (16% of theory, 95% pure) of the title compound.

$^1$H-NMR (400 MHz, DMSO-d$_6$, δ/ppm): 8.34 (br. s, 1H), 4.63 (s, 2H), 4.01 (t, 2H), 3.90 (q, 2H), 3.69 (t, 2H), 3.61 (s, 3H), 3.56-3.47 (m, 2H), 3.44-3.36 (m, 2H), 3.23 (s, 3H), 2.42 (s, 3H), 1.12 (t, 3H).

LC/MS (Method 1, ESIpos): R$_t$=0.63 min, m/z=424 [M+H]$^+$.

Example 119

Methyl [1-{[3-ethyl-1-(2-methoxyethyl)-5-methyl-2,4-dioxo-1,2,3,4-tetrahydrothieno[2,3-d]pyrimidin-6-yl]methyl}imidazolidin-2-ylidene]carbamate (Isomer 2, pure E or Z isomer)

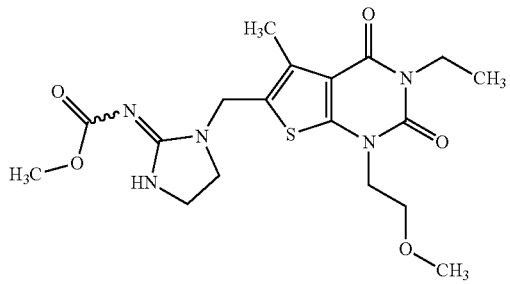 [SMILES: CCn1c(=O)c2c(C)c(CN3CCNC3=NC(=O)OC)sc2n(CCOC)c1=O]

121 mg (0.214 mmol, 60% purity) of the compound from Ex. 220A and 60 μl (0.428 mmol) of triethylamine were dissolved in 6 ml of dichloromethane, and a solution of 34 mg (0.214 mmol) of methyl (dichloromethylene)carbamate [DE 1 900 755 (1970); DE 2 036 171 (1972); K. Findeisen et al., *Synthesis* 1972, 599-605] in 4 ml of dichloromethane was added. After the reaction mixture had been stirred at RT for 3 h, it was diluted with ethyl acetate and washed successively with saturated sodium hydrogencarbonate solution, water and saturated sodium chloride solution. After drying over anhydrous magnesium sulphate, the mixture was filtered and concentrated. The remaining residue was separated into its components by means of preparative HPLC (Method 8). This gave the two E/Z isomers of the target product as separate fractions (cf Ex. 118). Concentration of the second product fraction and drying of the residue under high vacuum gave 16 mg (17% of theory, 95% pure) of the title compound.

$^1$H-NMR (400 MHz, DMSO-d$_6$, δ/ppm): 8.93 (br. s, 1H), 4.76 (s, 2H), 4.03 (t, 2H), 3.91 (q, 2H), 3.76 (s, 3H), 3.67-3.57 (m, 4H), 3.55-3.47 (m, 2H), 3.23 (s, 3H), 2.42 (s, 3H), 1.12 (t, 3H).

LC/MS (Method 1, ESIpos): R$_t$=0.64 min, m/z=424 [M+H]$^+$.

Example 120

6-[(2,3-Dioxopiperazin-1-yl)methyl]-3-ethyl-1-(2-methoxyethyl)-5-methylthieno[2,3-d]pyrimidine-2,4 (1H,3H)-dione

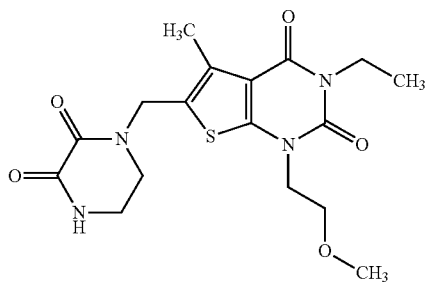 [SMILES: CCn1c(=O)c2c(C)c(CN3CCNC(=O)C3=O)sc2n(CCOC)c1=O]

523 mg (about 22% purity, 0.338 mmol) of the compound from Example 220A were dissolved in 5 ml of ethanol, and 100 mg (0.676 mmol) of diethyl oxalate were added. The mixture was stirred at 80° C. for 22 h. The reaction solution was then concentrated on a rotary evaporator. The residue was dissolved in 9 ml of DMSO and this solution was purified by means of preparative HPLC (Method 14). Combination of the product fractions and freeze-drying gave 170 mg of the title compound.

$^1$H-NMR (400 MHz, DMSO-d$_6$, δ/ppm): 8.64 (br. s, 1H), 4.69 (s, 2H), 4.02 (t, 2H), 3.89 (q, 2H), 3.62 (t, 2H), 3.50-3.45 (m, 2H), 3.33-3.29 (m, 2H), 3.23 (s, 3H), 2.43 (s, 3H), 1.11 (t, 3H).

LC/MS (Method 3): R$_t$=0.78 min, m/z=395 [M+H]$^+$.

Example 121

6-[(2,3-Dioxopiperazin-1-yl)methyl]-1-(3-fluoropropyl)-3-isobutyl-5-methylthieno[2,3-d]pyrimidine-2,4 (1H,3H)-dione

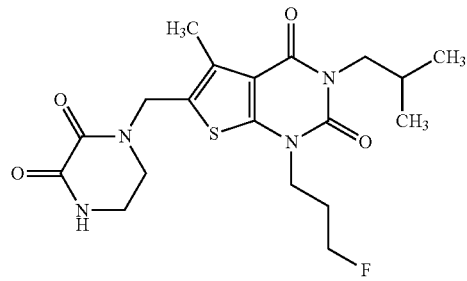 [SMILES: Cc1c(CN2CCNC(=O)C2=O)sc2c1c(=O)n(CC(C)C)c(=O)n2CCCF]

106 mg (0.166 mmol) of the compound from Example 241A were dissolved in 3 ml of ethanol, and 49 mg (0.332 mmol) of diethyl oxalate were added. The mixture was stirred at 80° C. for 26 h. The reaction solution was then concentrated on a rotary evaporator. The residue was dissolved in 3 ml of DMSO and this solution was purified by means of preparative HPLC (Method 14). Combination of the product fractions and freeze-drying gave 27 mg (70% of theory) of the title compound.

$^1$H-NMR (400 MHz, DMSO-d$_6$, δ/ppm): 8.64 (br. s, 1H), 4.70 (s, 2H), 4.58 (t, 1H), 4.46 (t, 1H), 3.98 (t, 2H), 3.70 (d, 2H), 3.49 (dd, 2H), 2.43 (s, 3H), 2.13-1.96 (m, 3H), 0.84 (d, 6H).

LC/MS (Method 3): R$_t$=0.99 min, m/z=425 [M+H]$^+$.

Example 122

6-[(2,3-Dioxopiperazin-1-yl)methyl]-5-methyl-3-(2,2,2-trifluoroethyl)-1-(3,3,3-trifluoropropyl)thieno[2,3-d]pyrimidine-2,4(1H,3H)-dione

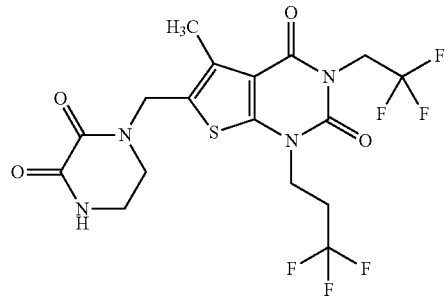 [SMILES: Cc1c(CN2CCNC(=O)C2=O)sc2c1c(=O)n(CC(F)(F)F)c(=O)n2CCC(F)(F)F]

126 mg (0.271 mmol) of the compound from Example 247A were dissolved in 4 ml of ethanol, and 80 mg (0.332 mmol) of diethyl oxalate were added. The mixture was stirred at 80° C. for 68 h. The reaction solution was then concentrated on a rotary evaporator. The residue was dissolved in 3 ml of DMSO and this solution was purified by means of preparative HPLC (Method 14). Combination of the product fractions and freeze-drying gave 48 mg (36% of theory) of the title compound.

$^1$H-NMR (400 MHz, DMSO-d$_6$, δ/ppm): 8.65 (br. s, 1H), 4.75-4.65 (m, 4H), 4.14 (t, 2H), 3.51 (dd, 2H), 2.84-2.70 (m, 2H), 2.44 (s, 3H).

LC/MS (Method 3): R$_t$=1.01 min, m/z=487 [M+H]$^+$.

Example 123

6-[(2,3-Dioxopiperazin-1-yl)methyl]-5-methyl-1-(oxetan-2-ylmethyl)-3-(2,2,2-trifluoroethyl)thieno[2,3-d]pyrimidine-2,4(1H,3H)-dione (racemate)

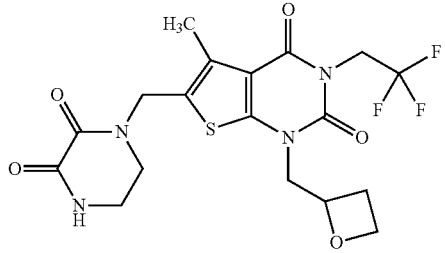 [SMILES: Cc1c(CN2CCNC(=O)C2=O)sc2c1c(=O)n(CC(F)(F)F)c(=O)n2CC1CCO1]

73 mg (0.158 mmol) of the compound from Example 251A were dissolved in 4 ml of ethanol, and 43 mg (0.292 mmol) of diethyl oxalate were added. The mixture was stirred in a microwave apparatus at 80° C. for 26 h. The reaction solution was then concentrated on a rotary evaporator. The residue was dissolved in 3 ml of DMSO and this solution was purified by means of preparative HPLC (Method 14). Combination of the product fractions and freeze-drying gave 29 mg (39% of theory) of the title compound.

$^1$H-NMR (400 MHz, DMSO-d$_6$, δ/ppm): 8.64 (br. s, 1H), 5.05-4.97 (m, 1H), 4.74-4.65 (m, 4H), 4.52-4.37 (m, 2H), 4.22-4.11 (m, 2H), 3.51-3.47 (m, 2H), 2.74-2.64 (m, 2H), 2.43 (s, 3H).

LC/MS (Method 3): R$_t$=0.87 min, m/z=461 [M+H]$^+$.

Example 124

6-[(2,3-Dioxopiperazin-1-yl)methyl]-1,5-dimethyl-3-(2,2,2-trifluoroethyl)thieno[2,3-d]pyrimidine-2,4(1H,3H)-dione

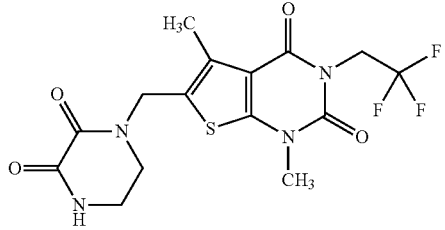 [SMILES: Cc1c(CN2CCNC(=O)C2=O)sc2c1c(=O)n(CC(F)(F)F)c(=O)n2C]

128 mg (44% purity, 0.161 mmol) of the compound from Example 254A were dissolved in 3 ml of ethanol, and 47 mg (0.321 mmol) of diethyl oxalate were added. The mixture was stirred in a microwave apparatus at 80° C. for 26 h. Thereafter, the reaction solution was purified directly by means of preparative HPLC (Method 14). Combination of the product fractions and freeze-drying gave 15 mg (23% of theory) of the title compound.

$^1$H-NMR (400 MHz, DMSO-d$_6$, δ/ppm): 8.65 (br. s, 1H), 4.75-4.64 (m, 4H), 3.50 (dd, 2H), 3.45 (s, 3H), 2.44 (s, 3H).

Example 125

3-(2,2-Difluoroethyl)-6-[(2,3-dioxopiperazin-1-yl)methyl]-5-methyl-1-(3,3,3-trifluoropropyl)thieno[2,3-d]pyrimidine-2,4(1H,3H)-dione

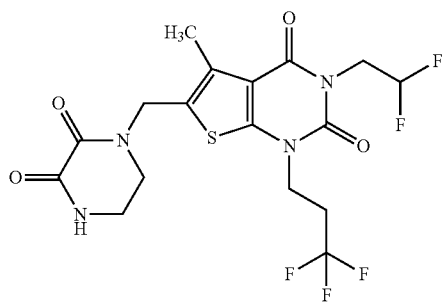 [SMILES: Cc1c(CN2CCNC(=O)C2=O)sc2c1c(=O)n(CC(F)F)c(=O)n2CCC(F)(F)F]

100 mg (0.171 mmol) of the compound from Example 255A were dissolved in 4 ml of ethanol, and 50 mg (0.343 mmol) of diethyl oxalate were added. The mixture was stirred in a microwave apparatus at 80° C. for 18 h. Thereafter, the reaction solution was concentrated on a rotary evaporator. The residue was dissolved in 3 ml of DMSO and this solution was purified by means of preparative HPLC (Method 14). Combination of the product fractions and freeze-drying gave 42 mg (51% of theory) of the title compound.

$^1$H-NMR (400 MHz, DMSO-d$_6$, δ/ppm): 8.65 (br. s, 1H), 6.38-6.03 (m, 1H), 4.72 (s, 2H), 4.34-4.24 (m, 2H), 4.12 (t, 2H), 3.50 (dd, 2H), 2.84-2.70 (m, 2H), 2.44 (s, 3H).

LC/MS (Method 3): R$_t$=0.95 min, m/z=469 [M+H]$^+$.

Example 126

3-Ethyl-6-{[(3R)-3-hydroxy-2-oxopyrrolidin-1-yl]methyl}-5-methyl-1-(3,3,3-trifluoropropyl)thieno[2,3-d]pyrimidine-2,4(1H,3H)-dione

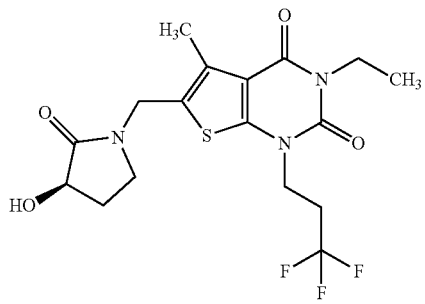 [SMILES: CCn1c(=O)c2c(C)c(CN3CC[C@@H](O)C3=O)sc2n(CCC(F)(F)F)c1=O]

250 mg (0.672 mmol) of the compound from Ex. 199A were dissolved in 2 ml of methanol and passed through a hydrogencarbonate cartridge (from Polymerlabs, Stratospheres SPE, PL-HCO$_3$ MP SPE). After the solution had been concentrated, the free amine 6-(aminomethyl)-3-ethyl-5-methyl-1-(3,3,3-trifluoropropyl)thieno[2,3-d]pyrimidine-2,4(1H,3H)-dione was thus obtained, which was reacted analogously to the method described in Ex. 7 with 101 mg (0.639 mmol) of [(4R)-2,2-dimethyl-5-oxo-1,3-dioxolan-4-yl]acetaldehyde [Int. Pat. Appl. WO 2012/037393-A1, Preparation B/Step B] to give 128 mg (45% of theory) of the title compound.

¹H-NMR (400 MHz, DMSO-d₆, δ/ppm): 5.59 (d, 1H), 4.50 (s, 2H), 4.16-4.03 (m, 3H), 3.90 (q, 2H), 3.29-3.21 (m, 1H), 3.19-3.09 (m, 1H), 2.85-2.69 (m, 2H), 2.42 (s, 3H), 2.30-2.18 (m, 1H), 1.67 (m, 1H), 1.11 (t, 3H).

LC/MS (Method 1, ESIpos): $R_t$=0.82 min, m/z=420 [M+H]⁺.

Example 127

3-Ethyl-5-methyl-6-[(5-oxo-2,5-dihydro-1H-pyrazol-1-yl)methyl]-1-(3,3,3-trifluoropropyl)thieno[2,3-d]pyrimidine-2,4(1H,3H)-dione

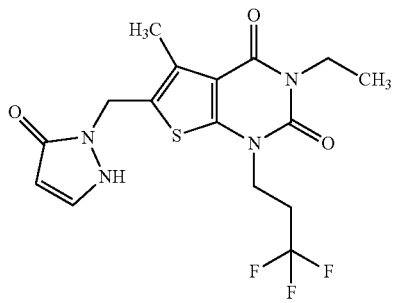 [SMILES: CCn1c(=O)c2c(C)c(Cn3[nH]ccc3=O)sc2n(CCC(F)(F)F)c1=O]

100 mg (0.182 mmol) of the compound from Ex. 345A were dissolved in 2 ml of concentrated sulphuric acid and stirred at RT for 30 min. Thereafter, the reaction mixture was introduced cautiously into a little ice-water. The precipitated solids were filtered off with suction, washed to neutrality with water and then purified by means of preparative HPLC (Method 8). After concentration of the product fractions and drying under high vacuum, 30 mg (41% of theory) of the title compound were obtained.

¹H-NMR (400 MHz, DMSO-d₆, δ/ppm): 11.16 (broad, 1H), 7.17 (d, 1H), 5.32 (d, 1H), 5.16 (s, 2H), 4.07 (t, 2H), 3.89 (q, 2H), 2.86-2.62 (m, 2H), 2.48 (s, 3H), 1.11 (t, 3H).

LC/MS (Method 1, ESIneg): $R_t$=0.81 min, m/z=401 [M−H]⁻.

Example 128

3-Ethyl-1-(2-methoxyethyl)-5-methyl-6-[(5-oxo-2,5-dihydro-1H-pyrazol-1-yl)methyl]thieno[2,3-d]pyrimidine-2,4(1H,3H)-dione

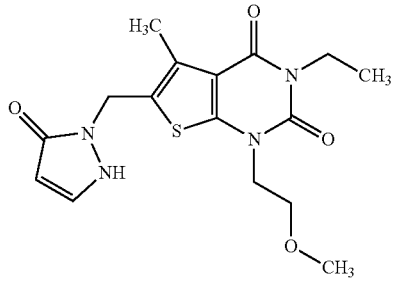 [SMILES: CCn1c(=O)c2c(C)c(Cn3[nH]ccc3=O)sc2n(CCOC)c1=O]

223 mg (0.437 mmol) of the compound from Ex. 346A were dissolved in 5 ml of dichloromethane and one drop of concentrated sulphuric acid was added. After the reaction mixture had been stirred at RT for 30 min, it was cautiously poured onto ice-water. The organic phase was removed, washed with saturated sodium chloride solution and dried over anhydrous magnesium sulphate. After filtration and concentration, the remaining solids were stirred with acetonitrile at RT. After filtration with suction again and drying under high vacuum, 96 mg (60% of theory) of the title compound were obtained.

¹H-NMR (400 MHz, DMSO-d₆, δ/ppm): 11.12 (broad, 1H), 7.16 (s, 1H), 5.32 (d, 1H), 5.14 (s, 2H), 3.99 (t, 2H), 3.89 (q, 2H), 3.60 (t, 2H), 3.22 (s, 3H), 2.47 (s, 3H), 1.11 (t, 3H).

LC/MS (Method 17, ESIneg): $R_t$=1.11 min, m/z=363.11 [M−H]⁻.

Example 129

3-Ethyl-5-methyl-6-[(5-oxo-2,5-dihydro-1H-pyrazol-1-yl)methyl]-1-(tetrahydrofuran-2-ylmethyl)thieno[2,3-d]pyrimidine-2,4(1H,3H)-dione (racemate)

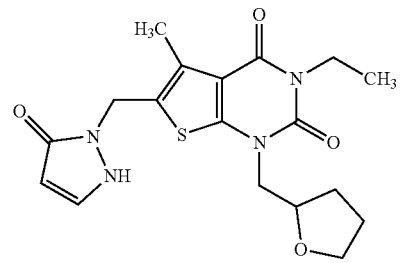 [SMILES: CCn1c(=O)c2c(C)c(Cn3[nH]ccc3=O)sc2n(CC2CCCO2)c1=O]

370 mg (0.689 mmol) of the compound from Ex. 347A were dissolved in 7 ml of dichloromethane and two drops of concentrated sulphuric acid was added. After the reaction mixture had been stirred at RT for 30 min, it was cautiously poured onto ice-water. The organic phase was removed, washed with saturated sodium chloride solution and dried over anhydrous magnesium sulphate. After filtration and concentration, the remaining solids were stirred with acetonitrile at RT. After filtration with suction again and drying under high vacuum, 155 mg (57% of theory) of the title compound were obtained.

¹H-NMR (400 MHz, DMSO-d₆, δ/ppm): 11.11 (br. s, 1H), 7.15 (s, 1H), 5.32 (s, 1H), 5.13 (s, 2H), 4.27-4.13 (m, 1H), 4.01 (dd, 1H), 3.89 (q, 2H), 3.77-3.52 (m, 3H), 2.47 (s, 3H), 2.04-1.72 (m, 3H), 1.70-1.58 (m, 1H), 1.10 (t, 3H).

LC/MS (Method 1, ESIneg): $R_t$=0.72 min, m/z=389 [M−H]⁻.

Example 130

3-Ethyl-5-methyl-6-[(5-oxo-2,5-dihydro-1H-pyrazol-1-yl)methyl]-1-(tetrahydrofuran-2-ylmethyl)thieno[2,3-d]pyrimidine-2,4(1H,3H)-dione (Enantiomer 1)

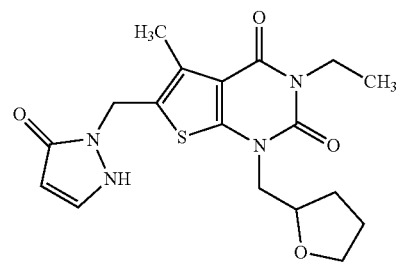 [SMILES: CCn1c(=O)c2c(C)c(Cn3[nH]ccc3=O)sc2n(CC2CCCO2)c1=O]

135 mg (0.346 mmol) of the racemic compound from Ex. 129 were dissolved in 6 ml of ethanol and, in 20 portions, separated into the enantiomers by preparative HPLC on a chiral phase [column: Daicel Chiralcel OX-H, 5 µm, 250 mm×20 mm; eluent: ethanol; flow rate: 15 ml/min; temperature: 40° C.; detection: 220 nm]. After concentration of the product fractions and drying under high vacuum, 49 mg (72% of theory) of Enantiomer 1 were obtained (99% ee, chiral analytical HPLC).

$^1$H-NMR (400 MHz, DMSO-$d_6$, δ/ppm): 11.10 (br. s, 1H), 7.14 (s, 1H), 5.27 (s, 1H), 5.12 (s, 2H), 4.25-4.14 (m, 1H), 4.01 (dd, 1H), 3.89 (q, 2H), 3.77-3.53 (m, 3H), 2.47 (s, 3H), 2.03-1.73 (m, 3H), 1.70-1.57 (m, 1H), 1.10 (t, 3H).

Chiral analytical HPLC [column: Daicel Chiralcel OX-H, 5 µm, 250 mm×4.6 mm; eluent: ethanol+0.2% TFA+1% water; flow rate: 1 ml/min; temperature: 40° C.; detection: 260 nm]: $R_t$=5.65 min.

Example 131

3-Ethyl-5-methyl-6-[(5-oxo-2,5-dihydro-1H-pyrazol-1-yl)methyl]-1-(tetrahydrofuran-2-ylmethyl)thieno[2,3-d]pyrimidine-2,4(1H,3H)-dione (Enantiomer 2)

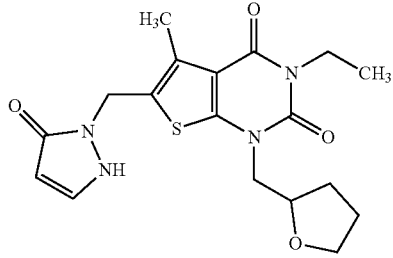 [SMILES: CCn1c(=O)c2c(C)c(Cn3[nH]ccc3=O)sc2n(CC2CCCO2)c1=O]

135 mg (0.346 mmol) of the racemic compound from Ex. 129 were dissolved in 6 ml of ethanol and, in 20 portions, separated into the enantiomers by preparative HPLC on a chiral phase [column: Daicel Chiralcel OX-H, 5 µm, 250 mm×20 mm; eluent: ethanol; flow rate: 15 ml/min; temperature: 40° C.; detection: 220 nm]. After concentration of the product fractions and drying under high vacuum, 52 mg (77% of theory) of Enantiomer 2 were obtained (99% ee, chiral analytical HPLC).

$^1$H-NMR (400 MHz, DMSO-$d_6$, δ/ppm): 11.16 (br. s, 1H), 7.14 (s, 1H), 5.29 (s, 1H), 5.12 (s, 2H), 4.25-4.14 (m, 1H), 4.01 (dd, 1H), 3.89 (q, 2H), 3.76-3.54 (m, 3H), 2.47 (s, 3H), 2.04-1.74 (m, 3H), 1.71-1.58 (m, 1H), 1.10 (t, 3H).

Chiral analytical HPLC [column: Daicel Chiralcel OX-H, 5 µm, 250 mm×4.6 mm; eluent: ethanol+0.2% TFA+1% water; flow rate: 1 ml/min; temperature: 40° C.; detection: 260 nm]: $R_t$=6.96 min.

Example 132

3-Isopropyl-5-methyl-6-[(5-oxo-2,5-dihydro-1H-pyrazol-1-yl)methyl]-1-(3,3,3-trifluoropropyl)thieno[2,3-d]pyrimidine-2,4(1H,3H)-dione

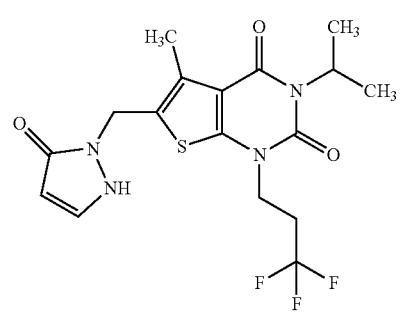 [SMILES: Cc1c(Cn2[nH]ccc2=O)sc2c1c(=O)n(C(C)C)c(=O)n2CCC(F)(F)F]

270 mg (0.480 mmol) of the compound from Ex. 348A were dissolved in 5 ml of dichloromethane and one drop of concentrated sulphuric acid was added. After the reaction mixture had been stirred at RT for 30 min, it was cautiously poured onto ice-water. The organic phase was removed, washed with saturated sodium chloride solution and dried over anhydrous magnesium sulphate. After filtration and concentration, the remaining solids were stirred with acetonitrile at RT. After filtration with suction again and drying, a first fraction of 92 mg of the title compound was obtained. The mother liquor from the stirring was purified by means of preparative HPLC (Method 8) and gave a second fraction of 54 mg of the product. A total of 146 mg (73% of theory) of the title compound were thus obtained.

$^1$H-NMR (400 MHz, DMSO-$d_6$, δ/ppm): 11.13 (s, 1H), 7.15 (d, 1H), 5.32 (d, 1H), 5.15 (s, 2H), 5.11 (sept, 1H), 4.03 (t, 2H), 2.82-2.61 (m, 2H), 2.47 (s, 3H), 1.39 (d, 6H).

LC/MS (Method 17, ESIneg): $R_t$=1.62 min, m/z=415.11 [M−H]$^-$.

Example 133

3-Isopropyl-1-(2-methoxyethyl)-5-methyl-6-[(5-oxo-2,5-dihydro-1H-pyrazol-1-yl)methyl]thieno[2,3-d]pyrimidine-2,4(1H,3H)-dione

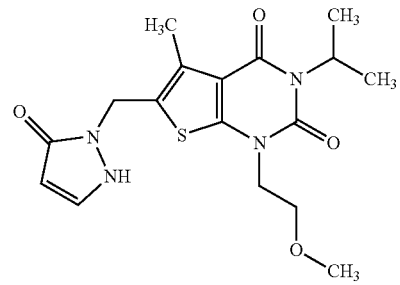 [SMILES: COCCn1c(=O)n(C(C)C)c(=O)c2c(C)c(Cn3[nH]ccc3=O)sc21]

288 mg (0.549 mmol) of the compound from Ex. 349A were dissolved in 6 ml of dichloromethane and two drops of concentrated sulphuric acid were added. After the reaction mixture had been stirred at RT for 30 min, it was cautiously poured onto ice-water. The organic phase was removed, washed with saturated sodium chloride solution and dried over anhydrous magnesium sulphate. After filtration and concentration, the remaining crude product was purified by means of preparative HPLC (Method 8). After combination of the product fractions, concentration and drying under high vacuum, 105 mg (50% of theory) of the title compound were obtained.

¹H-NMR (400 MHz, DMSO-d₆, δ/ppm): 11.11 (s, 1H), 7.14 (d, 1H), 5.32 (d, 1H), 5.13 (s, 2H), 5.12 (sept, 1H), 3.95 (t, 2H), 3.59 (t, 2H), 3.22 (s, 3H), 2.45 (s, 3H), 1.39 (d, 6H).

LC/MS (Method 1, ESIneg): $R_t$=0.72 min, m/z=377 [M−H]⁻.

Example 134

3-Isopropyl-5-methyl-6-[(5-oxo-2,5-dihydro-1H-pyrazol-1-yl)methyl]-1-(tetrahydrofuran-2-ylmethyl)thieno[2,3-d]pyrimidine-2,4(1H,3H)-dione (racemate)

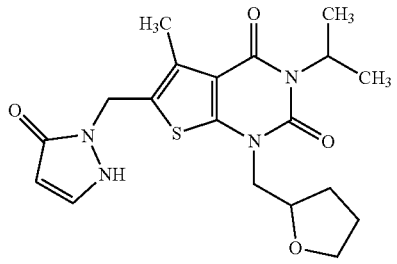

Analogously to the method described in Ex. 133, 508 mg (0.922 mmol) of the compound from Ex. 350A were used to prepare 150 mg (39% of theory, 97% purity) of the title compound. The reaction time here was 1 h.

¹H-NMR (400 MHz, DMSO-d₆, δ/ppm): 11.10 (br. s, 1H), 7.15 (s, 1H), 5.31 (d, 1H), 5.13 (sept, 1H), 5.12 (s, 2H), 4.24-4.13 (m, 1H), 4.01 (dd, 1H), 3.76-3.67 (m, 1H), 3.65-3.54 (m, 2H), 2.45 (s, 3H), 2.03-1.74 (m, 3H), 1.70-1.57 (m, 1H), 1.39 (d, 6H).

LC/MS (Method 1, ESIneg): $R_t$=0.77 min, m/z=403 [M−H]⁻.

Example 135

3-Isopropyl-5-methyl-6-[(5-oxo-2,5-dihydro-1H-pyrazol-1-yl)methyl]-1-(tetrahydrofuran-2-ylmethyl)thieno[2,3-d]pyrimidine-2,4(1H,3H)-dione (Enantiomer 1)

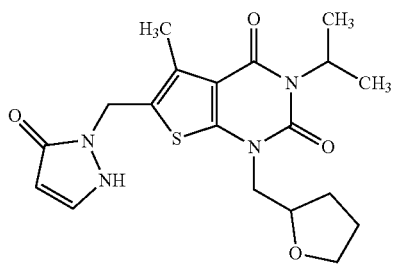

130 mg (0.321 mmol) of the racemic compound from Ex. 134 were dissolved in 6 ml of ethanol and, in 12 portions, separated into the enantiomers by preparative HPLC on a chiral phase [column: Daicel Chiralcel OX-H, 5 μm, 250 mm×20 mm; eluent: isohexane/ethanol 1:1; flow rate: 15 ml/min; temperature: 40° C.; detection: 220 nm]. After concentration of the product fractions and drying under high vacuum, 50 mg (76% of theory) of Enantiomer 1 were obtained (99% ee, chiral analytical HPLC).

¹H-NMR (400 MHz, DMSO-d₆, δ/ppm): 11.18 (br. s, 1H), 7.15 (s, 1H), 5.30 (s, 1H), 5.13 (sept, 1H), 5.12 (s, 2H), 4.24-4.12 (m, 1H), 4.00 (dd, 1H), 3.71 (q, 1H), 3.64-3.54 (m, 2H), 2.45 (s, 3H), 2.04-1.74 (m, 3H), 1.70-1.57 (m, 1H), 1.39 (d, 6H).

Chiral analytical HPLC [column: Daicel Chiralcel OX-H, 5 μm, 250 mm×4.6 mm; eluent: isohexane/ethanol 1:1+0.2% TFA+1% water; flow rate: 1 ml/min; temperature: 40° C.; detection: 220 nm]: $R_t$=5.59 min.

Example 136

3-Isopropyl-5-methyl-6-[(5-oxo-2,5-dihydro-1H-pyrazol-1-yl)methyl]-1-(tetrahydrofuran-2-ylmethyl)thieno[2,3-d]pyrimidine-2,4(1H,3H)-dione (Enantiomer 2)

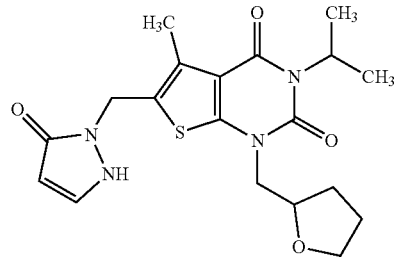 [SMILES: Cc1c(Cn2[nH]ccc2=O)sc2c1c(=O)n(C(C)C)c(=O)n2CC1CCCO1]

130 mg (0.321 mmol) of the racemic compound from Ex. 134 were dissolved in 6 ml of ethanol and, in 12 portions, separated into the enantiomers by preparative HPLC on a chiral phase [column: Daicel Chiralcel OX-H, 5 μm, 250 mm×20 mm; eluent: isohexane/ethanol 1:1; flow rate: 15 ml/min; temperature: 40° C.; detection: 220 nm]. After concentration of the product fractions and drying under high vacuum, 50 mg (76% of theory) of Enantiomer 2 were obtained (99% ee, chiral analytical HPLC).

¹H-NMR (400 MHz, DMSO-d₆, δ/ppm): 11.11 (br. s, 1H), 7.14 (d, 1H), 5.31 (d, 1H), 5.13 (sept, 1H), 5.13 (s, 2H), 4.23-4.13 (m, 1H), 4.01 (dd, 1H), 3.76-3.67 (m, 1H), 3.65-3.54 (m, 2H), 2.45 (s, 3H), 2.03-1.73 (m, 3H), 1.70-1.58 (m, 1H), 1.39 (d, 6H).

Chiral analytical HPLC [column: Daicel Chiralcel OX-H, 5 μm, 250 mm×4.6 mm; eluent: isohexane/ethanol 1:1+0.2% TFA+1% water; flow rate: 1 ml/min; temperature: 40° C.; detection: 220 nm]: $R_t$=6.46 min.

Example 137

1-(2,2-Difluoroethyl)-3-ethyl-5-methyl-6-[(2-thiox-oimidazolidin-1-yl)methyl]thieno[2,3-d]pyrimidine-2,4(1H,3H)-dione

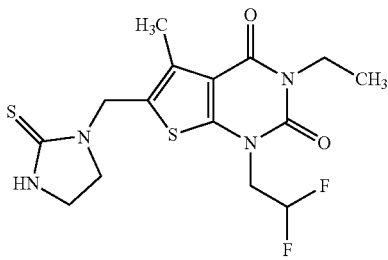 [SMILES: CCn1c(=O)c2c(C)c(CN3CCNC3=S)sc2n(CC(F)F)c1=O]

191 mg (0.48 mmol) of the compound from Ex. 212A were dissolved in 10 ml of dioxane, and 135 mg (0.72 mmol) of 1,1'-thiocarbonyldiimidazole were added. The mixture was stirred at RT for 16 h. The reaction solution was then concentrated on a rotary evaporator. The residue was dissolved in 6 ml of DMSO and this solution was purified by means of preparative HPLC (Method 14). Combination of the product fractions and freeze-drying gave 31.8 mg (16% of theory) of the title compound.

$^1$H-NMR (400 MHz, DMSO-$d_6$, δ/ppm): 8.37 (s, 1H), 6.51-6.19 (m, 1H), 4.84 (s, 2H), 4.30 (td, 2H), 3.90 (q, 2H), 3.57-3.48 (m, 2H), 3.43-3.37 (m, 2H), 2.46-2.42 (m, 3H), 1.12 (t, 3H).

LC/MS (Method 3, ESIpos): $R_t$=1.02 min, m/z=389 [M+H]$^+$.

Example 138

1-[2-(Cyclopropyloxy)ethyl]-3-ethyl-5-methyl-6-[(2-thioxoimidazolidin-1-yl)methyl]thieno[2,3-d]pyrimidine-2,4(1H,3H)-dione

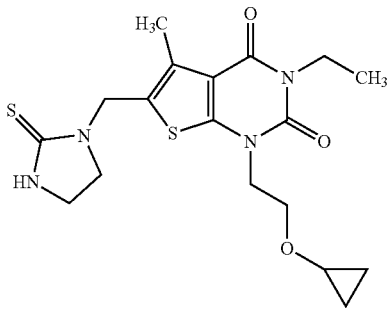 [SMILES: CCn1c(=O)c2c(C)c(CN3CCNC3=S)sc2n(CCOC2CC2)c1=O]

140 mg (0.271 mmol) of the compound from Ex. 308A were dissolved in 15 ml of dioxane, and 76 mg (0.407 mmol) of 1,1'-thiocarbonyldiimidazole were added. The mixture was stirred at RT for 18 h. The reaction solution was then concentrated on a rotary evaporator. The residue was dissolved in 6 ml of DMSO and this solution was purified by means of preparative HPLC (Method 14). Combination of the product fractions and freeze-drying gave 76 mg (68% of theory) of the title compound.

$^1$H-NMR (400 MHz, DMSO-$d_6$, δ/ppm): 8.36 (s, 1H), 4.82 (s, 2H), 3.99 (t, 2H), 3.89 (q, 2H), 3.72 (t, 2H), 3.57-3.47 (m, 2H), 3.44-3.37 (m, 2H), 3.33-3.29 (m, 1H), 2.43 (s, 3H), 1.11 (t, 3H), 0.41-0.36 (m, 4H).

LC/MS (Method 3, ESIpos): $R_t$=1.08 min, m/z=409 [M+H]$^+$.

Example 139

3-Ethyl-5-methyl-1-(tetrahydrofuran-2-ylmethyl)-6-[(2-thioxoimidazolidin-1-yl)methyl]thieno[2,3-d]pyrimidine-2,4(1H,3H)-dione (Enantiomer 1)

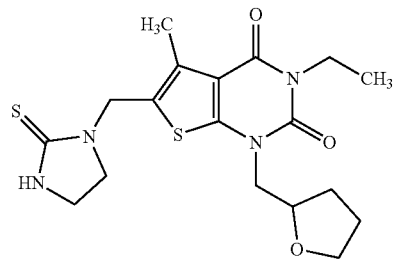 [SMILES: CCn1c(=O)c2c(C)c(CN3CCNC3=S)sc2n(CC2CCCO2)c1=O]

230 mg of the racemic compound from Ex. 35 were dissolved in 8 ml of a methanol/dichloromethane mixture (1:1 v/v) and separated into the enantiomers by means of preparative HPLC on a chiral phase [column: Daicel Chiralpak IC, 5 μm, 250 mm×30 mm; eluent: methanol; flow rate: 60 ml/min; temperature: RT; UV detection: 254 nm]. The product fractions were concentrated on a rotary evaporator, admixed with tert-butanol and freeze-dried. 88 mg (37% of theory) of the title compound (Enantiomer 1) and 90 mg (38% of theory) of Enantiomer 2 (see Example 140) were obtained.

$^1$H-NMR (400 MHz, DMSO-$d_6$, δ/ppm): 8.35 (s, 1H), 4.86-4.77 (m, 2H), 4.26-4.18 (m, 1H), 4.02 (dd, 1H), 3.90 (q, 2H), 3.77-3.72 (m, 1H), 3.69 (dd, 1H), 3.61 (td, 1H), 3.56-3.50 (m, 2H), 3.43-3.37 (m, 2H), 2.43 (s, 3H), 2.02-1.92 (m, 1H), 1.92-1.76 (m, 2H), 1.66 (ddt, 1H), 1.14-1.08 (m, 3H).

Chiral analytical HPLC [column: Daicel Chiralpak IC, 3 μm, 100 mm×4.6 mm; eluent: methanol; flow rate: 1.0 ml/min; temperature: 25° C.; injection: 5 μl; DAD 254 nm]: $R_t$=8.73 min.

Example 140

3-Ethyl-5-methyl-1-(tetrahydrofuran-2-ylmethyl)-6-[(2-thioxoimidazolidin-1-yl)methyl]thieno[2,3-d]pyrimidine-2,4(1H,3H)-dione (Enantiomer 2)

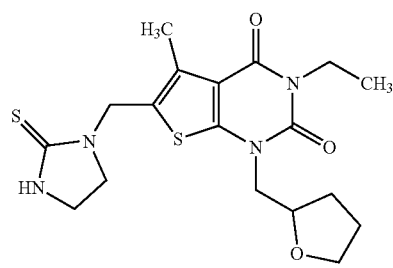 [SMILES: CCn1c(=O)c2c(C)c(CN3CCNC3=S)sc2n(CC2CCCO2)c1=O]

The title compound (90 mg) was obtained as the second enantiomer in the preparative HPLC separation of the racemate from Ex. 35 described in Ex. 139.

$^1$H-NMR (400 MHz, DMSO-d$_6$, δ/ppm): 8.35 (s, 1H), 4.86-4.77 (m, 2H), 4.26-4.18 (m, 1H), 4.02 (dd, 1H), 3.90 (q, 2H), 3.77-3.72 (m, 1H), 3.69 (dd, 1H), 3.64-3.58 (m, 1H), 3.56-3.50 (m, 2H), 3.43-3.37 (m, 2H), 2.43 (s, 3H), 2.02-1.93 (m, 1H), 1.93-1.76 (m, 2H), 1.66 (ddt, 1H), 1.14-1.08 (m, 3H).

Chiral analytical HPLC [column: Daicel Chiralpak IC, 3 μm, 100 mm×4.6 mm; eluent: methanol; flow rate: 1.0 ml/min; temperature: 25° C.; injection: 5 μl; DAD 254 nm]: R$_t$=10.25 min.

Example 141

3-Ethyl-5-methyl-1-(tetrahydro-2H-pyran-2-ylmethyl)-6-[(2-thioxoimidazolidin-1-yl)methyl]thieno[2,3-d]pyrimidine-2,4(1H,3H)-dione (Enantiomer 1)

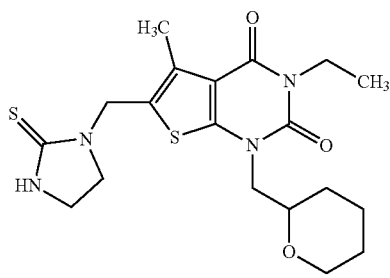 [SMILES: CCn1c(=O)c2c(C)c(CN3CCNC3=S)sc2n(CC2CCCCO2)c1=O]

158 mg of the racemic compound from Ex. 36 were dissolved in 6 ml of a methanol/dichloromethane mixture (1:1 v/v) and separated into the enantiomers by means of preparative HPLC on a chiral phase [column: Daicel Chiralpak IC, 5 μm, 250 mm×30 mm; eluent: methanol; flow rate: 60 ml/min; temperature: RT; UV detection: 254 nm]. The product fractions were concentrated on a rotary evaporator, admixed with tert-butanol and freeze-dried. 65 mg (42% of theory) of the title compound (Enantiomer 1) and 66 mg (42% of theory) of Enantiomer 2 (see Example 142) were obtained.

$^1$H-NMR (400 MHz, DMSO-d$_6$, δ/ppm): 8.35 (s, 1H), 4.88-4.75 (m, 2H), 4.01-3.93 (m, 1H), 3.89 (q, 2H), 3.84-3.77 (m, 1H), 3.72-3.63 (m, 2H), 3.58-3.46 (m, 2H), 3.44-3.36 (m, 2H), 3.30-3.21 (m, 1H), 2.43 (s, 3H), 1.78 (d, 1H), 1.61 (d, 1H), 1.52-1.38 (m, 3H), 1.32-1.19 (m, 1H), 1.14-1.08 (m, 3H).

Chiral analytical HPLC [column: Daicel Chiralpak IC, 3 μm, 100 mm×4.6 mm; eluent: methanol; flow rate: 1.0 ml/min; temperature: 25° C.; injection: 5 μl; DAD 254 nm]: R$_t$=7.03 min.

Example 142

3-Ethyl-5-methyl-1-(tetrahydro-2H-pyran-2-ylmethyl)-6-[(2-thioxoimidazolidin-1-yl)methyl]thieno[2,3-d]pyrimidine-2,4(1H,3H)-dione (Enantiomer 2)

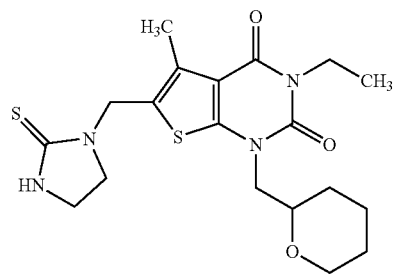 [SMILES: CCn1c(=O)c2c(C)c(CN3CCNC3=S)sc2n(CC2CCCCO2)c1=O]

The title compound (66 mg) was obtained as the second enantiomer in the preparative HPLC separation of the racemate from Ex. 36 described in Ex. 141.

$^1$H-NMR (400 MHz, DMSO-d$_6$, δ/ppm): 8.35 (s, 1H), 4.88-4.75 (m, 2H), 4.01-3.93 (m, 1H), 3.89 (q, 2H), 3.84-3.77 (m, 1H), 3.72-3.63 (m, 2H), 3.58-3.46 (m, 2H), 3.44-3.36 (m, 2H), 3.29-3.21 (m, 1H), 2.43 (s, 3H), 1.78 (d, 1H), 1.61 (d, 1H), 1.52-1.38 (m, 3H), 1.32-1.19 (m, 1H), 1.14-1.08 (m, 3H).

Chiral analytical HPLC [column: Daicel Chiralpak IC, 3 μm, 100 mm×4.6 mm; eluent: methanol; flow rate: 1.0 ml/min; temperature: 25° C.; injection: 5 μl; DAD 254 nm]: R$_t$=8.43 min.

Example 143

1-(2,2-Difluoroethyl)-3-isobutyl-5-methyl-6-[(2-thioxoimidazolidin-methyl]thieno[2,3-d]pyrimidine-2,4(1H,3H)-dione

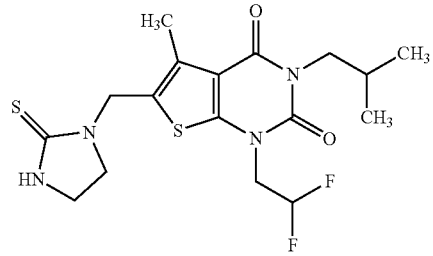 [SMILES: Cc1c(CN2CCNC2=S)sc2c1c(=O)n(CC(C)C)c(=O)n2CC(F)F]

138 mg (0.28 mmol) of the compound from Ex. 313A were dissolved in 15 ml of dioxane, and 79 mg (0.42 mmol) of 1,1'-thiocarbonyldiimidazole were added. The mixture was stirred at RT for 18 h. The reaction solution was then concentrated on a rotary evaporator. The residue was dissolved in 6 ml of DMSO and this solution was purified by means of preparative HPLC (Method 14). Combination of the product fractions and freeze-drying gave 41 mg (35% of theory) of the title compound.

$^1$H-NMR (400 MHz, DMSO-d$_6$, δ/ppm): 8.35 (s, 1H), 6.53-6.17 (m, 1H), 4.84 (s, 2H), 4.31 (td, 2H), 3.71 (d, 2H), 3.59-3.49 (m, 2H), 3.46-3.37 (m, 2H), 2.44 (s, 3H), 2.06-1.97 (m, 1H), 0.85 (d, 6H).

LC/MS (Method 3, ESIpos): R$_t$=1.18 min, m/z=417 [M+H]$^+$.

Example 144

1-(3-Fluoropropyl)-3-isobutyl-5-methyl-6-[(2-thiox-oimidazolidin-1-yl)methyl]thieno[2,3-d]pyrimidine-2,4(1H,3H)-dione

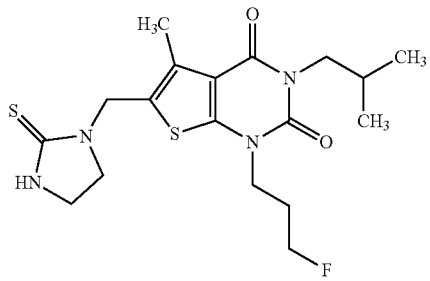 [SMILES: Cc1c(CN2CCNC2=S)sc2c1c(=O)n(CC(C)C)c(=O)n2CCCF]

170 mg (0.266 mmol) of the compound from Ex. 241A were dissolved in 15 ml of dioxane, and 75 mg (0.399 mmol) of 1,1'-thiocarbonyldiimidazole were added. The mixture was stirred at RT for 18 h. The reaction solution was then concentrated on a rotary evaporator. The residue was dissolved in 3 ml of DMSO and this solution was purified by means of preparative HPLC (Method 14). Combination of the product fractions and freeze-drying gave 49 mg (44% of theory) of the title compound.

$^1$H-NMR (400 MHz, DMSO-d$_6$, δ/ppm): 8.36 (s, 1H), 4.83 (s, 2H), 4.58 (t, 1H), 4.46 (t, 1H), 3.97 (t, 2H), 3.70 (d, 2H), 3.58-3.49 (m, 2H), 3.45-3.37 (m, 2H), 2.43 (s, 3H), 2.13-1.97 (m, 3H), 0.84 (d, 6H).

LC/MS (Method 3, ESIpos): R$_t$=1.17 min, m/z=413 [M+H]$^+$.

Example 145

1-(2-Ethoxyetyl)-3-isobutyl-5-methyl-6-[(2-thiox-oimidazolidin-1-yl)methyl]thieno[2,3-d]pyrimidine-2,4(1H,3H)-dione

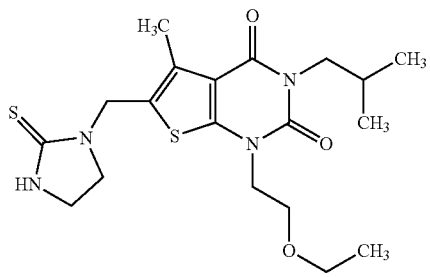 [SMILES: CCOCCn1c(=O)n(CC(C)C)c(=O)c2c(C)c(CN3CCNC3=S)sc21]

158 mg (0.343 mmol) of the compound from Ex. 314A were dissolved in 15 ml of dioxane, and 97 mg (0.514 mmol) of 1,1'-thiocarbonyldiimidazole were added. The mixture was stirred at RT for 18 h. The reaction solution was then concentrated on a rotary evaporator. The residue was dissolved in 6 ml of DMSO and this solution was purified by means of preparative HPLC (Method 14). Combination of the product fractions and freeze-drying gave 63 mg (43% of theory) of the title compound.

$^1$H-NMR (400 MHz, DMSO-d$_6$, δ/ppm): 8.34 (s, 1H), 4.82 (s, 2H), 4.00 (t, 2H), 3.70 (d, 2H), 3.65 (t, 2H), 3.57-3.49 (m, 2H), 3.46-3.36 (m, 4H), 2.43 (s, 3H), 2.09-1.96 (m, 1H), 1.02 (t, 3H), 0.84 (d, 6H).

LC/MS (Method 3, ESIpos): R$_t$=1.21 min, m/z=425 [M+H]$^+$.

Example 146

3-Isobutyl-5-methyl-1-(oxetan-2-ylmethyl)-6-[(2-thioxoimidazolidin-1-yl)methyl]thieno[2,3-d]pyrimidine-2,4(1H,3H)-dione (racemate)

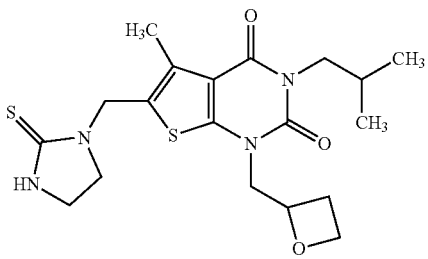 [SMILES: Cc1c(CN2CCNC2=S)sc2c1c(=O)n(CC(C)C)c(=O)n2CC1CCO1]

406 mg (0.918 mmol) of the compound from Ex. 243A were dissolved in 20 ml of dioxane, and 258 mg (1.38 mmol) of 1,1'-thiocarbonyldiimidazole were added. The mixture was stirred at RT for 16 h. The reaction solution was then concentrated on a rotary evaporator. The residue was dissolved in 9 ml of DMSO and this solution was purified by means of preparative HPLC (Method 14). Combination of the product fractions and freeze-drying gave 186 mg (47% of theory) of the title compound.

$^1$H-NMR (400 MHz, DMSO-d$_6$, δ/ppm): 8.35 (s, 1H), 5.04-4.96 (m, 1H), 4.82 (s, 2H), 4.51-4.44 (m, 1H), 4.39 (dt, 1H), 4.17-4.08 (m, 2H), 3.71 (d, 2H), 3.58-3.49 (m, 2H), 3.45-3.36 (m, 2H), 2.68 (dtd, 1H), 2.43 (s, 2H), 2.03 (m, 1H), 0.85 (dd, 6H).

LC/MS (Method 3, ESIpos): R$_t$=1.11 min, m/z=423 [M+H]$^+$.

Example 147

3-Isobutyl-5-methyl-1-(oxetan-2-ylmethyl)-6-[(2-thioxoimidazolidin-1-yl)methyl]thieno[2,3-d]pyrimidine-2,4(1H,3H)-dione (Enantiomer 1)

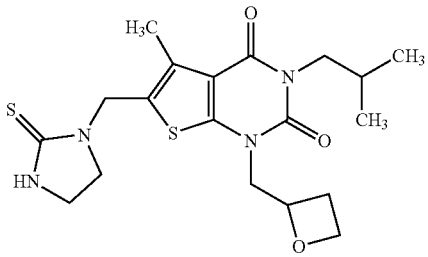 [SMILES: Cc1c(CN2CCNC2=S)sc2c1c(=O)n(CC(C)C)c(=O)n2CC1CCO1]

154 mg of the racemic compound from Ex. 146 were dissolved in 4 ml of a methanol/dichloromethane mixture (1:1 v/v) and separated into the enantiomers by means of preparative HPLC on a chiral phase [column: Daicel Chiralpak IC, 5 μm, 250 mm×20 mm; eluent: acetonitrile; flow rate: 15 ml/min; temperature: RT; UV detection: 232 nm]. The product fractions were concentrated on a rotary evaporator, admixed with tert-butanol and freeze-dried. 65 mg (42% of theory) of the title compound (Enantiomer 1) and 65 mg (42% of theory) of Enantiomer 2 (see Example 148) were obtained.

$^1$H-NMR (400 MHz, DMSO-$d_6$, δ/ppm): 8.35 (s, 1H), 5.04-4.95 (m, 1H), 4.87-4.76 (m, 2H), 4.51-4.44 (m, 1H), 4.39 (dt, 1H), 4.18-4.07 (m, 2H), 3.71 (d, 2H), 3.58-3.49 (m, 2H), 3.44-3.37 (m, 2H), 2.73-2.63 (m, 1H), 2.43 (s, 3H), 2.08-1.97 (m, 1H), 0.84 (dd, 6H).

Chiral analytical HPLC [column: Daicel Chiralpak IC, 3 μm, 100 mm×4.6 mm; eluent: acetonitrile; flow rate: 1.0 ml/min; temperature: 25° C.; injection: 5 μl; DAD 254 nm]: $R_t$=3.22 min.

Example 148

3-Isobutyl-5-methyl-1-(oxetan-2-ylmethyl)-6-[(2-thioxoimidazolidin-1-yl)methyl]thieno[2,3-d]pyrimidine-2,4(1H,3H)-dione (Enantiomer 2)

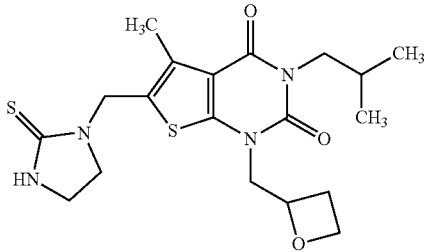 [SMILES: Cc1c(CN2CCNC2=S)sc2c1c(=O)n(CC(C)C)c(=O)n2CC1CCO1]

The title compound (65 mg) was obtained as the second enantiomer in the preparative HPLC separation of the racemate from Ex. 146 described in Ex. 147.

$^1$H-NMR (400 MHz, DMSO-$d_6$, δ/ppm): 8.35 (s, 1H), 5.00 (dt, 1H), 4.86-4.77 (m, 2H), 4.51-4.44 (m, 1H), 4.39 (dt, 1H), 4.18-4.07 (m, 2H), 3.71 (d, 2H), 3.58-3.49 (m, 2H), 3.44-3.36 (m, 2H), 2.73-2.63 (m, 1H), 2.45-2.40 (m, 3H), 2.07-1.96 (m, 1H), 0.85 (dd, 6H).

Chiral analytical HPLC [column: Daicel Chiralpak IC, 3 μm, 100 mm×4.6 mm; eluent: acetonitrile; flow rate: 1.0 ml/min; temperature: 25° C.; injection: 5 μl; DAD 254 nm]: $R_t$=3.97 min.

Example 149

3-(2,2-Dimethylpropyl)-5-methyl-6-[(2-thioxoimidazolidin-1-yl)methyl]-1-(3,3,3-trifluoropropyl)thieno[2,3-d]pyrimidine-2,4(1H,3H)-dione

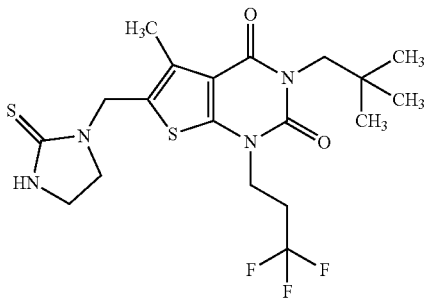 [SMILES: Cc1c(CN2CCNC2=S)sc2c1c(=O)n(CC(C)(C)C)c(=O)n2CCC(F)(F)F]

160 mg (0.316 mmol) of the compound from Ex. 315A were dissolved in 15 ml of dioxane, and 89 mg (0.474 mmol) of 1,1'-thiocarbonyldiimidazole were added. The mixture was stirred at RT for 21 h. The reaction solution was then concentrated on a rotary evaporator. The residue was dissolved in 3 ml of DMSO and this solution was purified by means of preparative HPLC (Method 14). Combination of the product fractions and freeze-drying gave 46 mg (31% of theory) of the title compound.

$^1$H-NMR (400 MHz, DMSO-$d_6$, δ/ppm): 8.37 (s, 1H), 4.84 (s, 2H), 4.09 (t, 2H), 3.81 (br. s, 2H), 3.60-3.51 (m, 2H), 3.45-3.36 (m, 2H), 2.82-2.69 (m, 2H), 2.43 (s, 3H), 0.89 (s, 9H).

LC/MS (Method 3, ESIpos): $R_t$=1.35 min, m/z=463 [M+H]$^+$.

Example 150

3-(2,2-Dimethylpropyl)-1-(3-fluoropropyl)-5-methyl-6-[(2-thioxoimidazolidin-1-yl)methyl]thieno[2,3-d]pyrimidine-2,4(1H,3H)-dione

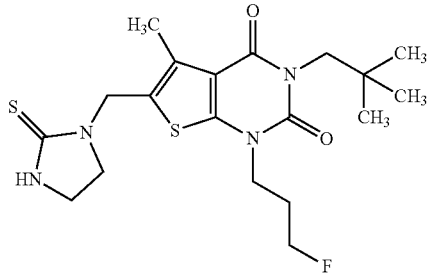 [SMILES: Cc1c(CN2CCNC2=S)sc2c1c(=O)n(CC(C)(C)C)c(=O)n2CCCF]

103 mg (0.22 mmol) of the compound from Ex. 316A were dissolved in 10 ml of dioxane, and 62 mg (0.329 mmol) of 1,1'-thiocarbonyldiimidazole were added. The mixture was stirred at RT for 19 h. The reaction solution was then concentrated on a rotary evaporator. The residue was dissolved in 3 ml of DMSO and this solution was purified by means of preparative HPLC (Method 14). Combination of the product fractions and freeze-drying gave 66 mg (70% of theory) of the title compound.

$^1$H-NMR (400 MHz, DMSO-$d_6$, δ/ppm): 8.35 (s, 1H), 4.83 (s, 2H), 4.58 (t, 1H), 4.46 (t, 1H), 3.97 (t, 2H), 3.80 (br. s, 2H), 3.60-3.51 (m, 2H), 3.45-3.37 (m, 2H), 2.43 (s, 3H), 2.13-2.05 (m, 1H), 2.05-1.97 (m, 1H), 0.88 (s, 9H).

LC/MS (Method 3, ESIpos): $R_t$=1.25 min, m/z=427 [M+H]$^+$.

Example 151

3-(2,2-Dimethylpropyl)-1-(2-methoxyethyl)-5-methyl-6-[(2-thioxoimidazolidin-1-yl)methyl]thieno[2,3-d]pyrimidine-2,4(1H,3H)-dione

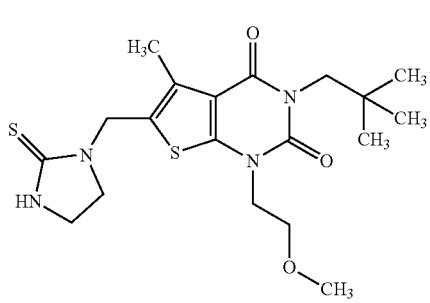 [SMILES: COCCn1c(=O)n(CC(C)(C)C)c(=O)c2c(C)c(CN3CCNC3=S)sc21]

172 mg (0.364 mmol) of the compound from Ex. 317A were dissolved in 15 ml of dioxane, and 102 mg (0.546 mmol) of 1,1'-thiocarbonyldiimidazole were added. The mixture was stirred at RT for 18 h. The reaction solution was then concentrated on a rotary evaporator. The residue was dissolved in 6 ml of DMSO and this solution was purified by means of preparative HPLC (Method 14). Combination of the product fractions and freeze-drying gave 84 mg (54% of theory) of the title compound.

$^1$H-NMR (400 MHz, DMSO-$d_6$, δ/ppm): 8.36 (s, 1H), 4.82 (s, 2H), 4.01 (t, 2H), 3.81 (br. s, 2H), 3.62 (t, 2H), 3.59-3.50 (m, 2H), 3.46-3.36 (m, 2H), 3.22 (s, 3H), 2.42 (s, 3H), 0.89 (s, 9H).

LC/MS (Method 3, ESIpos): $R_t$=1.22 min, m/z=425 [M+H]$^+$.

Example 152

5-Methyl-6-[(2-thioxoimidazolidin-1-yl)methyl]-3-(2,2,2-trifluoroethyl)-1-(3,3,3-trifluoropropyl)thieno[2,3-d]pyrimidine-2,4(1H,3H)-dione

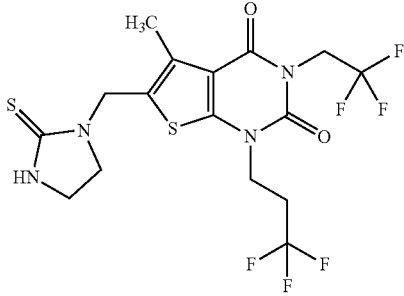 [SMILES: Cc1c(CN2CCNC2=S)sc2c1c(=O)n(CC(F)(F)F)c(=O)n2CCC(F)(F)F]

200 mg (0.43 mmol) of the compound from Ex. 247A were dissolved in 15 ml of dioxane, and 121 mg (0.645 mmol) of 1,1'-thiocarbonyldiimidazole were added. The mixture was stirred at RT for 17 h. The reaction solution was then concentrated on a rotary evaporator. The residue was dissolved in 6 ml of DMSO and this solution was purified by means of preparative HPLC (Method 14). Combination of the product fractions and freeze-drying gave 103 mg (50% of theory) of the title compound.

$^1$H-NMR (400 MHz, DMSO-$d_6$, δ/ppm): 8.40 (s, 1H), 4.86 (s, 2H), 4.70 (q, 2H), 4.13 (t, 2H), 3.60-3.51 (m, 2H), 3.46-3.37 (m, 2H), 2.84-2.70 (m, 2H), 2.45 (s, 3H).

LC/MS (Method 3, ESIpos): $R_t$=1.19 min, m/z=475 [M+H]$^+$.

Example 153

1-(2-Ethoxyethyl)-5-methyl-6-[(2-thioxoimidazolidin-1-yl)methyl]-3-(2,2,2-trifluoroethyl)thieno[2,3-d]pyrimidine-2,4(1H,3H)-dione

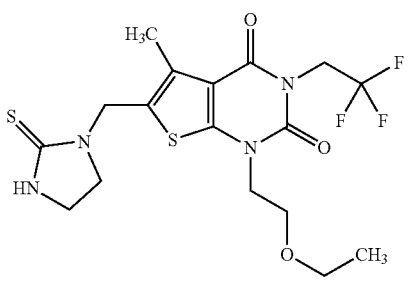 [SMILES: CCOCCn1c(=O)n(CC(F)(F)F)c(=O)c2c(C)c(CN3CCNC3=S)sc21]

113 mg (0.177 mmol) of the compound from Ex. 250A were dissolved in 10 ml of dioxane, and 50 mg (0.266 mmol) of 1,1'-thiocarbonyldiimidazole were added. The mixture was stirred at RT for 18 h. The reaction solution was then concentrated on a rotary evaporator. The residue was dissolved in 3 ml of DMSO and this solution was purified by means of preparative HPLC (Method 14). Combination of the product fractions and freeze-drying gave 63 mg (78% of theory) of the title compound.

$^1$H-NMR (400 MHz, DMSO-$d_6$, δ/ppm): 8.38 (s, 1H), 4.84 (s, 2H), 4.69 (q, 2H), 4.04 (t, 2H), 3.66 (t, 2H), 3.57-3.50 (m, 2H), 3.46-3.37 (m, 4H), 2.43 (s, 3H), 1.02 (t, 3H).

LC/MS (Method 3, ESIpos): $R_t$=1.13 min, m/z=451 [M+H]$^+$.

Example 154

5-Methyl-1-(oxetan-2-ylmethyl)-6-[(2-thioxoimidazolidin-1-yl)methyl]-3-(2,2,2-trifluoroethyl)thieno[2,3-d]pyrimidine-2,4(1H,3H)-dione (racemate)

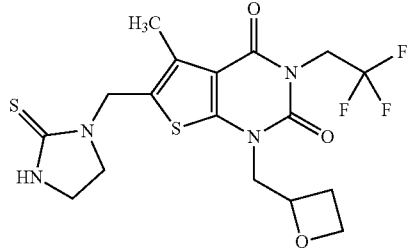 [SMILES: Cc1c(CN2CCNC2=S)sc2c1c(=O)n(CC(F)(F)F)c(=O)n2CC1CCO1]

260 mg (0.563 mmol) of the compound from Ex. 251A were dissolved in 13 ml of dioxane, and 158 mg (0.844 mmol) of 1,1'-thiocarbonyldiimidazole were added. The mixture was stirred at RT for 18 h. The reaction solution was then concentrated on a rotary evaporator. The residue was dissolved in 6 ml of DMSO and this solution was purified by means of preparative HPLC (Method 14). Combination of the product fractions and freeze-drying gave 116 mg (45% of theory) of the title compound.

$^1$H-NMR (400 MHz, DMSO-$d_6$, δ/ppm): 8.37 (s, 1H), 5.06-4.97 (m, 1H), 4.84 (s, 2H), 4.70 (q, 2H), 4.52-4.44 (m, 1H), 4.40 (dt, 1H), 4.22-4.10 (m, 2H), 3.59-3.49 (m, 2H), 3.44-3.37 (m, 2H), 2.73-2.64 (m, 1H), 2.43 (s, 3H).

LC/MS (Method 3, ESIpos): $R_t$=1.04 min, m/z=449 [M+H]$^+$.

Example 155

5-Methyl-1-(oxetan-2-ylmethyl)-6-[(2-thioxoimidazolidin-1-yl)methyl]-3-(2,2,2-trifluoroethyl)thieno[2,3-d]pyrimidine-2,4(1H,3H)-dione (Enantiomer 1)

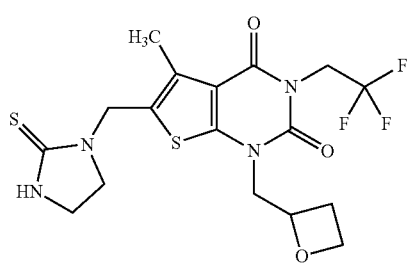 [SMILES: Cc1c(CN2CCNC2=S)sc2c1c(=O)n(CC(F)(F)F)c(=O)n2CC1CCO1]

106 mg of the racemic compound from Ex. 154 were dissolved in 6 ml of a methanol/dichloromethane mixture (1:1 v/v) and separated into the enantiomers by means of preparative HPLC on a chiral phase [column: Daicel Chiralpak IC, 5 µm, 250 mm×30 mm; eluent: methanol/ethanol/ diethylamine 50:50:0.1; flow rate: 20 ml/min; temperature: RT; UV detection: 254 nm]. The product fractions were concentrated on a rotary evaporator, admixed with tert-butanol and freeze-dried. 45 mg (42% of theory) of the title compound (Enantiomer 1) and 49 mg (45% of theory) of Enantiomer 2 (see Example 156) were obtained.

$^1$H-NMR (400 MHz, DMSO-$d_6$, δ/ppm): 8.37 (s, 1H), 5.01 (dt, 1H), 4.88-4.79 (m, 2H), 4.70 (q, 2H), 4.52-4.44 (m, 1H), 4.40 (dt, 1H), 4.23-4.10 (m, 2H), 3.59-3.49 (m, 2H), 3.44-3.37 (m, 2H), 2.74-2.64 (m, 1H), 2.43 (s, 3H).

Chiral analytical HPLC [column: Daicel Chiralpak IC, 5 µm, 100 mm×4.6 mm; eluent: methanol/ethanol/diethylamine 50:50:0.1 v/v; flow rate: 1.0 ml/min; temperature: RT; injection: 5 µl; DAD 254 nm]: $R_t$=3.76 min.

Example 156

5-Methyl-1-(oxetan-2-ylmethyl)-6-[(2-thioxoimidazolidin-1-yl)methyl]-3-(2,2,2-trifluoroethyl)thieno[2,3-d]pyrimidine-2,4(1H,3H)-dione (Enantiomer 2)

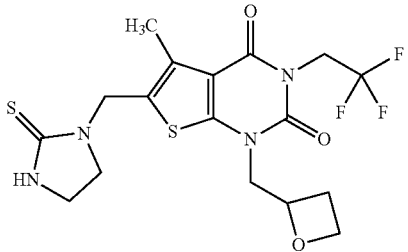 [SMILES: Cc1c(CN2CCNC2=S)sc2c1c(=O)n(CC(F)(F)F)c(=O)n2CC1CCO1]

The title compound (49 mg) was obtained as the second enantiomer in the preparative HPLC separation of the racemate from Ex. 154 described in Ex. 155.

$^1$H-NMR (400 MHz, DMSO-$d_6$, δ/ppm): 8.37 (s, 1H), 5.06-4.96 (m, 1H), 4.83 (s, 2H), 4.70 (q, 2H), 4.52-4.44 (m, 1H), 4.40 (dt, 1H), 4.23-4.09 (m, 2H), 3.59-3.49 (m, 2H), 3.44-3.37 (m, 2H), 2.74-2.64 (m, 1H), 2.43 (s, 3H).

Chiral analytical HPLC [column: Daicel Chiralpak IC, 5 µm, 100 mm×4.6 mm; eluent: methanol/ethanol/diethylamine 50:50:0.1 v/v; flow rate: 1.0 ml/min; temperature: RT; injection: 5 µl; DAD 254 nm]: $R_t$=4.35 min.

Example 157

5-Methyl-1-(tetrahydrofuran-2-ylmethyl)-6-[(2-thioxoimidazolidin-1-yl)methyl]-3-(2,2,2-trifluoroethyl) thieno[2,3-d]pyrimidine-2,4(1H,3H)-dione (racemate)

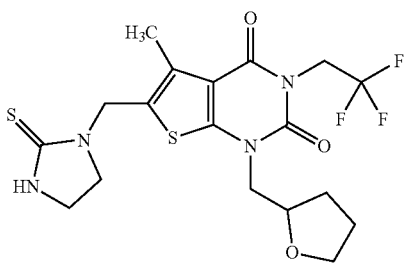 [SMILES: Cc1c(CN2CCNC2=S)sc2c1c(=O)n(CC(F)(F)F)c(=O)n2CC1CCCO1]

285 mg (0.549 mmol) of the compound from Ex. 252A were dissolved in 15 ml of dioxane, and 154 mg (0.824 mmol) of 1,1'-thiocarbonyldiimidazole were added. The mixture was stirred at RT for 17 h. The reaction solution was then concentrated on a rotary evaporator. The residue was dissolved in 9 ml of DMSO and this solution was purified by means of preparative HPLC (Method 14). Combination of the product fractions and freeze-drying gave 180 mg (70% of theory) of the title compound.

$^1$H-NMR (400 MHz, DMSO-$d_6$, δ/ppm): 8.37 (s, 1H), 4.83 (s, 2H), 4.70 (q, 2H), 4.26-4.18 (m, 1H), 4.05 (dd, 1H), 3.79-3.68 (m, 2H), 3.64-3.58 (m, 1H), 3.58-3.51 (m, 2H), 3.44-3.37 (m, 2H), 2.43 (s, 3H), 2.03-1.93 (m, 1H), 1.93-1.76 (m, 2H), 1.71-1.62 (m, 1H).

LC/MS (Method 3, ESIpos): $R_t$=1.12 min, m/z=463 [M+H]$^+$.

Example 158

5-Methyl-1-(oxetan-3-ylmethyl)-6-[(2-thioxoimidazolidin-1-yl)methyl]-3-(2,2,2-trifluoroethyl)thieno[2,3-d]pyrimidine-2,4(1H,3H)-dione

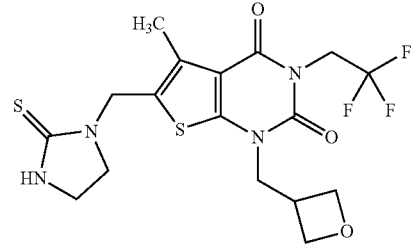 [SMILES: Cc1c(CN2CCNC2=S)sc2c1c(=O)n(CC(F)(F)F)c(=O)n2CC1COC1]

109 mg (0.091 mmol) of the compound from Ex. 253A were dissolved in 10 ml of dioxane, and 26 mg (0.137 mmol) of 1,1'-thiocarbonyldiimidazole were added. The mixture was stirred at RT for 17 h. The reaction solution was then concentrated on a rotary evaporator. The residue was dissolved in 3 ml of DMSO and this solution was purified by means of preparative HPLC (Method 14). Combination of the product fractions and freeze-drying gave 72 mg (76% of theory) of the title compound.

$^1$H-NMR (400 MHz, DMSO-$d_6$, δ/ppm): 8.39 (s, 1H), 4.85 (s, 2H), 4.68 (q, 2H), 4.61 (dd, 2H), 4.43 (t, 2H), 4.23 (d, 2H), 3.58-3.51 (m, 2H), 3.46-3.37 (m, 3H), 2.43 (s, 3H).

LC/MS (Method 3, ESIpos): $R_t$=1.03 min, m/z=449 [M+H]$^+$.

Example 159

1,5-Dimethyl-6-[(2-thioxoimidazolidin-1-yl) methyl]-3-(2,22-trifluoroethyl)thieno[2,3-d]pyrimidine-2,4(1H,3H)-dione

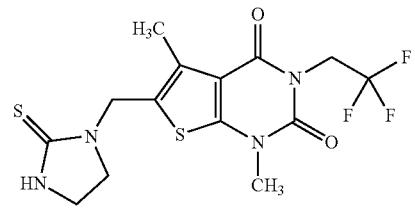 [SMILES: Cc1c(CN2CCNC2=S)sc2c1c(=O)n(CC(F)(F)F)c(=O)n2C]

190 mg (0.239 mmol) of the compound from Ex. 254A were dissolved in 15 ml of dioxane, and 67 mg (0.358 mmol) of 1,1'-thiocarbonyldiimidazole were added. The mixture was stirred at RT for 17 h. The reaction solution was then concentrated on a rotary evaporator. The residue was dissolved in 3 ml of DMSO and this solution was purified by means of preparative HPLC (Method 14). Combination of the product fractions and freeze-drying gave 48 mg (51% of theory) of the title compound.

$^1$H-NMR (400 MHz, DMSO-$d_6$, δ/ppm): 8.38 (s, 1H), 4.85 (s, 2H), 4.69 (q, 2H), 3.58-3.50 (m, 2H), 3.45-3.38 (m, 5H), 2.44 (s, 3H).

LC/MS (Method 3, ESIpos): $R_t$=1.03 min, m/z=393 [M+H]$^+$.

Example 160

3-(2,2-Difluoroethyl)-5-methyl-6-[(2-thioxoimidazolidin-1-yl)methyl]-1-(3,3,3-trifluoropropyl)thieno[2,3-d]pyrimidine-2,4(1H,3H)-dione

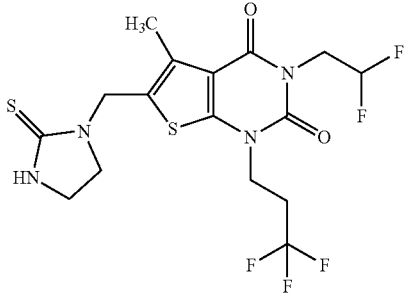 [SMILES: Cc1c(CN2CCNC2=S)sc2c1c(=O)n(CC(F)F)c(=O)n2CCC(F)(F)F]

150 mg (0.257 mmol) of the compound from Ex. 255A were dissolved in 15 ml of dioxane, and 72 mg (0.385 mmol) of 1,1'-thiocarbonyldiimidazole were added. The mixture was stirred at RT for 17 h. The reaction solution was then concentrated on a rotary evaporator. The residue was dissolved in 3 ml of DMSO and this solution was purified by means of preparative HPLC (Method 14). Combination of the product fractions and freeze-drying gave 53 mg (45% of theory) of the title compound.

$^1$H-NMR (400 MHz, DMSO-$d_6$, δ/ppm): 8.39 (s, 1H), 6.37-6.04 (m, 1H), 4.86 (s, 2H), 4.29 (td, 2H), 4.11 (t, 2H), 3.59-3.49 (m, 2H), 3.45-3.38 (m, 2H), 2.84-2.70 (m, 2H), 2.45 (s, 3H).

LC/MS (Method 3, ESIpos): $R_t$=1.13 min, m/z=457 [M+H]$^+$.

Example 161

3-(2,2-Difluoroethyl)-1-(2-ethoxyethyl)-5-methyl-6-[(2-thioxoimidazolidin-1-yl)methyl]thieno[2,3-d]pyrimidine-2,4(1H,3H)-dione

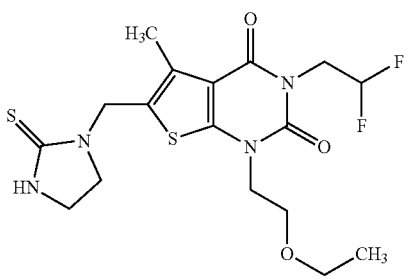 [SMILES: CCOCCn1c(=O)n(CC(F)F)c(=O)c2c(C)c(CN3CCNC3=S)sc21]

120 mg (0.206 mmol) of the compound from Ex. 258A were dissolved in 10 ml of dioxane, and 58 mg (0.309 mmol) of 1,1'-thiocarbonyldiimidazole were added. The mixture was stirred at RT for 17 h. The reaction solution was then concentrated on a rotary evaporator. The residue was dissolved in 3 ml of DMSO and this solution was purified by means of preparative HPLC (Method 14). Combination of the product fractions and freeze-drying gave 61 mg (68% of theory) of the title compound.

$^1$H-NMR (400 MHz, DMSO-$d_6$, δ/ppm): 8.38 (s, 1H), 6.38-6.05 (m, 1H), 4.84 (s, 2H), 4.29 (td, 2H), 4.02 (t, 2H), 3.66 (t, 2H), 3.57-3.48 (m, 2H), 3.47-3.36 (m, 4H), 2.43 (s, 3H), 1.03 (t, 3H).

LC/MS (Method 3, ESIpos): $R_t$=1.09 min, m/z=433 [M+H]$^+$.

Example 162

3-(2,2-Difluoroethyl)-5-methyl-1-(tetrahydrofuran-2-ylmethyl)-6-[(2-thioxoimidazolidin-1-yl)methyl]thieno[2,3-d]pyrimidine-2,4(1H,3H)-dione (racemate)

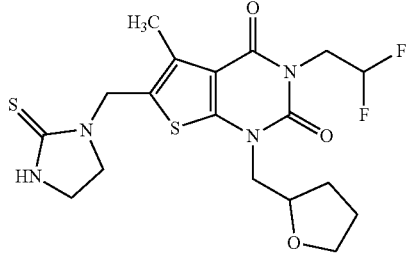 [SMILES: Cc1c(CN2CCNC2=S)sc2c1c(=O)n(CC(F)F)c(=O)n2CC1CCCO1]

222 mg (0.348 mmol) of the compound from Ex. 260A were dissolved in 8 ml of dioxane, and 98 mg (0.521 mmol) of 1,1'-thiocarbonyldiimidazole were added. The mixture was stirred at RT for 18 h. The reaction solution was then concentrated on a rotary evaporator. The residue was dissolved in 6 ml of DMSO and this solution was purified by means of preparative HPLC (Method 14). Combination of the product fractions and freeze-drying gave 75 mg (48% of theory) of the title compound.

$^1$H-NMR (400 MHz, DMSO-$d_6$, δ/ppm): 8.37 (s, 1H), 6.37-6.06 (m, 1H), 4.83 (s, 2H), 4.38-4.18 (m, 3H), 4.04 (dd, 1H), 3.78-3.67 (m, 2H), 3.64-3.57 (m, 1H), 3.57-3.49 (m, 2H), 3.44-3.37 (m, 2H), 2.43 (s, 3H), 2.03-1.93 (m, 1H), 1.93-1.76 (m, 2H), 1.72-1.62 (m, 1H).

LC/MS (Method 3, ESIpos): $R_t$=1.05 min, m/z=445 [M+H]$^+$.

Example 163

3-(2,2-Difluoroethyl)-5-methyl-1-(tetrahydrofuran-2-ylmethyl)-6-[(2-thioxoimidazolidin-1-yl)methyl]thieno[2,3-d]pyrimidine-2,4(1H,3H)-dione (Enantiomer 1)

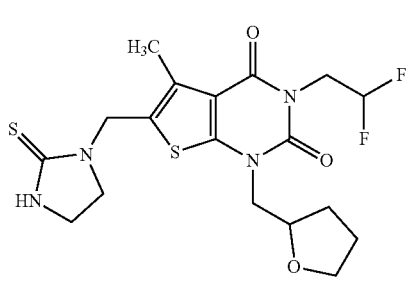 [SMILES: Cc1c(CN2CCNC2=S)sc2c1c(=O)n(CC(F)F)c(=O)n2CC1CCCO1]

66 mg of the racemic compound from Ex. 162 were dissolved in 3.4 ml of a methanol/dichloromethane mixture (1:1 v/v) and separated into the enantiomers by means of preparative HPLC on a chiral phase [column: Daicel Chiralpak IC, 5 μm, 250 mm×30 mm; eluent: methanol/ethanol/diethylamine 50:50:0.1; flow rate: 30 ml/min; temperature: RT; UV detection: 254 nm]. The product fractions were concentrated on a rotary evaporator, admixed with tert-butanol and freeze-dried. 26 mg (38% of theory) of the title compound (Enantiomer 1) and 28 mg (41% of theory) of Enantiomer 2 (see Example 164) were obtained.

$^1$H-NMR (400 MHz, DMSO-$d_6$, δ/ppm): 8.37 (s, 1H), 6.38-6.06 (m, 1H), 4.89-4.78 (m, 2H), 4.30 (td, 2H), 4.25-4.18 (m, 1H), 4.04 (dd, 1H), 3.78-3.67 (m, 2H), 3.65-3.57 (m, 1H), 3.57-3.49 (m, 2H), 3.44-3.37 (m, 2H), 2.43 (s, 3H), 2.03-1.93 (m, 1H), 1.93-1.75 (m, 2H), 1.72-1.62 (m, 1H).

Chiral analytical HPLC [column: Daicel Chiralpak IC, 5 μm, 100 mm×4.6 mm; eluent: methanol/ethanol/diethylamine 50:50:0.1 v/v; flow rate: 1.0 ml/min; temperature: RT; injection: 5 μl; DAD 254 nm]: $R_t$=4.43 min.

Example 164

3-(2,2-Difluoroethyl)-5-methyl-1-(tetrahydrofuran-2-ylmethyl)-6-[(2-thioxoimidazolidin-1-yl)methyl]thieno[2,3-d]pyrimidine-2,4(1H,3H)-dione (Enantiomer 2)

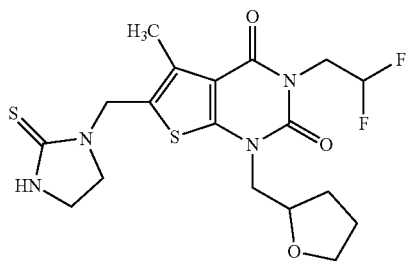 [SMILES: Cc1c(CN2CCNC2=S)sc2c1c(=O)n(CC(F)F)c(=O)n2CC1CCCO1]

The title compound (28 mg) was obtained as the second enantiomer in the preparative HPLC separation of the racemate from Ex. 162 described in Ex. 163.

$^1$H-NMR (400 MHz, DMSO-$d_6$, δ/ppm): 8.37 (s, 1H), 6.38-6.06 (m, 1H), 4.89-4.78 (m, 2H), 4.30 (td, 2H), 4.25-4.18 (m, 1H), 4.04 (dd, 1H), 3.78-3.67 (m, 2H), 3.65-3.57 (m, 1H), 3.57-3.49 (m, 2H), 3.44-3.37 (m, 2H), 2.43 (s, 3H), 2.03-1.93 (m, 1H), 1.93-1.75 (m, 2H), 1.67 (ddt, 1H).

Chiral analytical HPLC [column: Daicel Chiralpak IC, 5 μm, 100 mm×4.6 mm; eluent: methanol/ethanol/diethylamine 50:50:0.1 v/v; flow rate: 1.0 ml/min; temperature: RT; injection: 5 μl; DAD 254 nm]: $R_t$=5.22 min.

Example 165

3-(2, 2-Difluoroethyl)-5-methyl-1-(oxetan-3-ylmethyl)-6-[(2-thioxoimidazolidin-1-yl)methyl]thieno[2,3-d]pyrimidine-2,4(1H,3H)-dione

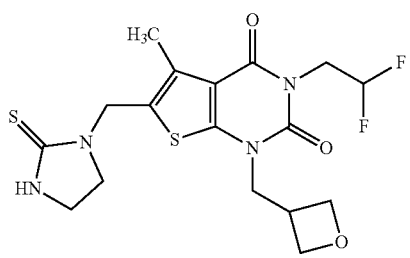 [SMILES: Cc1c(CN2CCNC2=S)sc2c1c(=O)n(CC(F)F)c(=O)n2CC1COC1]

85 mg (0.147 mmol) of the compound from Ex. 261A were dissolved in 10 ml of dioxane, and 41 mg (0.22 mmol) of 1,1'-thiocarbonyldiimidazole were added. The mixture was stirred at RT for 17 h. The reaction solution was then concentrated on a rotary evaporator. The residue was dissolved in 3 ml of DMSO and this solution was purified by means of preparative HPLC (Method 14). Combination of the product fractions and freeze-drying gave 47 mg (72% of theory) of the title compound.

$^1$H-NMR (400 MHz, DMSO-$d_6$, δ/ppm): 8.38 (s, 1H), 6.35-6.03 (m, 1H), 4.84 (s, 2H), 4.62 (dd, 2H), 4.43 (t, 2H), 4.28 (td, 2H), 4.21 (d, 2H), 3.57-3.49 (m, 2H), 3.46-3.37 (m, 3H), 2.43 (s, 3H).

LC/MS (Method 3, ESIpos): $R_t$=0.94 min, m/z=431 [M+H]$^+$.

Example 166

3-(2,2-Difluoroethyl)-1,5-dimethyl-6-[(2-thioxoimidazolidin-1-yl)methyl]thieno[2,3-d]pyrimidine-2,4 (1H,3H)-dione

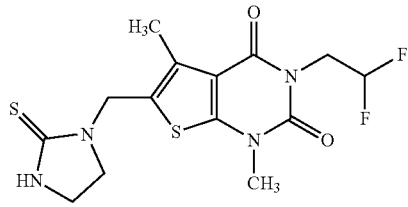 [SMILES: Cc1c(CN2CCNC2=S)sc2c1c(=O)n(CC(F)F)c(=O)n2C]

110 mg (0.232 mmol) of the compound from Ex. 318A were dissolved in 10.1 ml of dioxane, and 65 mg (0.347 mmol) of 1,1'-thiocarbonyldiimidazole were added. The mixture was stirred at RT for 13 h. The reaction solution was then concentrated on a rotary evaporator. The residue was dissolved in 3 ml of DMSO and this solution was purified by means of preparative HPLC (Method 14). Combination of the product fractions and freeze-drying gave 40 mg (45% of theory) of the title compound.

$^1$H-NMR (400 MHz, DMSO-$d_6$, δ/ppm): 8.38 (s, 1H), 6.37-6.04 (m, 1H), 4.85 (s, 2H), 4.29 (td, 2H), 3.56-3.49 (m, 2H), 3.44-3.37 (m, 5H), 2.44 (s, 3H).

LC/MS (Method 3, ESIpos): $R_t$=0.96 min, m/z=375 [M+H]$^+$.

Example 167

3-(2-Methoxyethyl)-5-methyl-6-[(2-thioxoimidazolidin-1-yl)methyl]-1-(3,3,3-trifluoropropyl)thieno[2,3-d]pyrimidine-2,4(1H,3H)-dione

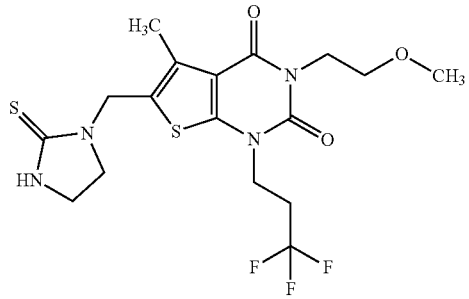 [SMILES: COCCn1c(=O)c2c(C)c(CN3CCNC3=S)sc2n(CCC(F)(F)F)c1=O]

100 mg (0.198 mmol) of the compound from Ex. 319A were dissolved in 15 ml of dioxane, and 56 mg (0.347 mmol) of 1,1'-thiocarbonyldiimidazole were added. The mixture was stirred at RT for 18 h. The reaction solution was then concentrated on a rotary evaporator. The residue was dissolved in 3 ml of DMSO and this solution was purified by means of preparative HPLC (Method 14). Combination of the product fractions and freeze-drying gave 56 mg (62% of theory) of the title compound.

$^1$H-NMR (400 MHz, DMSO-$d_6$, δ/ppm): 8.36 (s, 1H), 4.85 (s, 2H), 4.09 (t, 2H), 4.05 (t, 2H), 3.58-3.46 (m, 4H), 3.45-3.37 (m, 2H), 3.24 (s, 3H), 2.82-2.69 (m, 2H), 2.44 (s, 3H).

LC/MS (Method 3, ESIpos): $R_t$=1.05 min, m/z=451 [M+H]$^+$.

Example 168

1,3-Bis(2-methoxyethyl)-5-methyl-6-[(2-thioxoimidazolidin-1-yl)methyl]thieno[2,3-d]pyrimidine-2,4(1H,3H)-dione

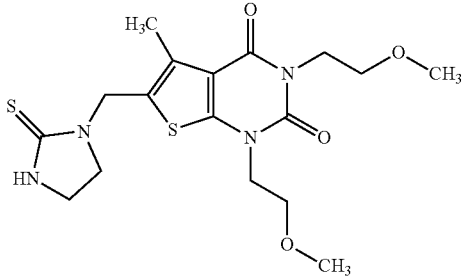 [SMILES: COCCn1c(=O)c2c(C)c(CN3CCNC3=S)sc2n(CCOC)c1=O]

155 mg (0.18 mmol) of the compound from Ex. 262A were dissolved in 5 ml of dioxane, and 51 mg (0.27 mmol) of 1,1'-thiocarbonyldiimidazole were added. The mixture was stirred at RT for 16 h. The reaction solution was then concentrated on a rotary evaporator. The residue was dissolved in 3 ml of DMSO and this solution was purified by means of preparative HPLC (Method 14). Combination of the product fractions and freeze-drying gave 42 mg (56% of theory) of the title compound.

$^1$H-NMR (400 MHz, DMSO-$d_6$, δ/ppm): 8.36 (s, 1H), 4.82 (s, 2H), 4.05 (t, 2H), 4.01 (t, 2H), 3.62 (t, 2H), 3.57-3.47 (m, 4H), 3.44-3.37 (m, 2H), 3.24 (s, 3H), 3.23 (s, 3H), 2.43 (s, 3H).

LC/MS (Method 3, ESIpos): $R_t$=0.91 min, m/z=413 [M+H]$^+$.

Example 169

1-(2-Ethoxyethyl)-3-(2-methoxyethyl)-5-methyl-6-[(2-thioxoimidazolidin-1-yl)methyl]thieno[2,3-d]pyrimidine-2,4(1H,3H)-dione

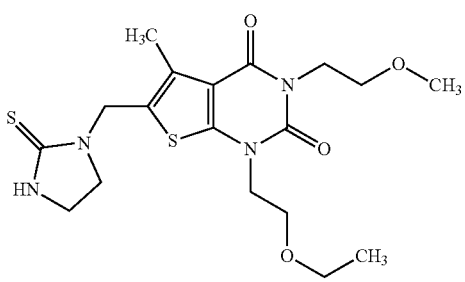 [SMILES: CCOCCn1c(=O)n(CCOC)c(=O)c2c(C)c(CN3CCNC3=S)sc21]

143 mg (0.216 mmol) of the compound from Ex. 263A were dissolved in 10 ml of dioxane, and 61 mg (0.324 mmol) of 1,1'-thiocarbonyldiimidazole were added. The mixture was stirred at RT for 17 h. The reaction solution was then concentrated on a rotary evaporator. The residue was dissolved in 3 ml of DMSO and this solution was purified by means of preparative HPLC (Method 14). Combination of the product fractions and freeze-drying gave 68 mg (73% of theory) of the title compound.

$^1$H-NMR (400 MHz, DMSO-$d_6$, δ/ppm): 8.36 (s, 1H), 4.83 (s, 2H), 4.05 (t, 2H), 4.00 (t, 2H), 3.65 (t, 2H), 3.56-3.47 (m, 4H), 3.46-3.36 (m, 4H), 3.24 (s, 3H), 2.43 (s, 3H), 1.03 (t, 3H).

LC/MS (Method 3, ESIpos): $R_t$=0.98 min, m/z=427 [M+H]$^+$.

Example 170

3-(2-Methoxy-2-methylpropyl)-5-methyl-6-[(2-thioxoimidazolidin-1-yl)methyl]-1-(3,3,3-trifluoropropyl)thieno[2,3-d]pyrimidine-2,4(1H,3H)-dione

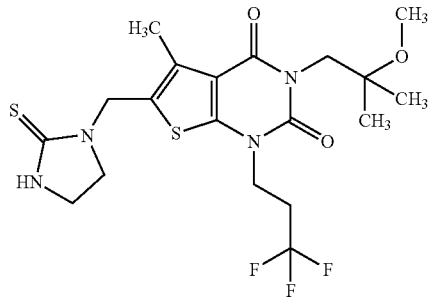 [SMILES: COC(C)(C)Cn1c(=O)c2c(C)c(CN3CCNC3=S)sc2n(CCC(F)(F)F)c1=O]

160 mg (0.297 mmol) of the compound from Ex. 322A were dissolved in 15 ml of dioxane, and 84 mg (0.445 mmol) of 1,1'-thiocarbonyldiimidazole were added. The mixture was stirred at RT for 19 h. The reaction solution was then concentrated on a rotary evaporator. The residue was dissolved in 3 ml of DMSO and this solution was purified by means of preparative HPLC (Method 14). Combination of the product fractions and freeze-drying gave 66 mg (46% of theory) of the title compound.

$^1$H-NMR (400 MHz, DMSO-$d_6$, δ/ppm): 8.37 (s, 1H), 4.84 (s, 2H), 4.09 (t, 2H), 4.00 (br. s, 2H), 3.59-3.51 (m, 2H), 3.45-3.37 (m, 2H), 3.15 (s, 3H), 2.82-2.68 (m, 2H), 2.43 (s, 3H), 1.08 (s, 6H).

LC/MS (Method 3, ESIpos): $R_t$=1.17 min, m/z=479 [M+H]$^+$.

Example 171

1-(3-Fluoropropyl)-3-(2-methoxy-2-methylpropyl)-5-methyl-6-[(2-thioxoimidazolidin-1-yl)methyl]thieno[2,3-d]pyrimidine-2,4(1H,3H)-dione

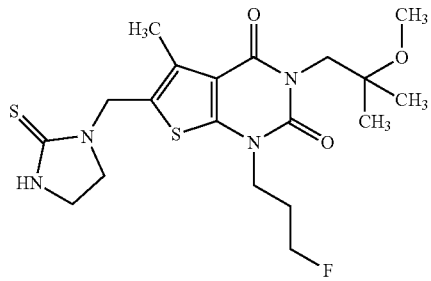 [SMILES: COC(C)(C)Cn1c(=O)c2c(C)c(CN3CCNC3=S)sc2n(CCCF)c1=O]

200 mg (0.424 mmol) of the compound from Ex. 323A were dissolved in 20 ml of dioxane, and 119 mg (0.637 mmol) of 1,1'-thiocarbonyldiimidazole were added. The mixture was stirred at RT for 17 h. The reaction solution was then concentrated on a rotary evaporator. The residue was dissolved in 6 ml of DMSO and this solution was purified by means of preparative HPLC (Method 14). Combination of the product fractions and freeze-drying gave 90 mg (47% of theory) of the title compound.

$^1$H-NMR (400 MHz, DMSO-$d_6$, δ/ppm): 8.36 (s, 1H), 4.84 (s, 2H), 4.58 (t, 1H), 4.46 (t, 1H), 4.03-3.93 (m, 4H), 3.59-3.51 (m, 2H), 3.44-3.37 (m, 2H), 3.15 (s, 3H), 2.43 (s, 3H), 2.12-2.05 (m, 2H), 2.01 (quin, 1H), 1.08 (s, 6H).

LC/MS (Method 3, ESIpos): $R_t$=1.07 min, m/z=443 [M+H]$^+$.

Example 172

1-(2-Methoxyethyl)-3-(2-methoxy-2-methylpropyl)-5-methyl-6-[(2-thioxoimidazolidin-1-yl)methyl]thieno[2,3-d]pyrimidine-2,4(1H,3H)-dione

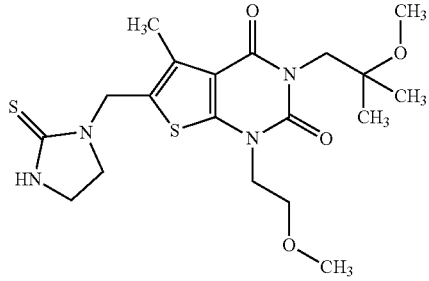 [SMILES: COCCn1c(=O)n(CC(C)(C)OC)c(=O)c2c(C)c(CN3CCNC3=S)sc21]

100 mg (0.196 mmol) of the compound from Ex. 324A were dissolved in 15 ml of dioxane, and 55 mg (0.324 mmol) of 1,1'-thiocarbonyldiimidazole were added. The mixture was stirred at RT for 20 h. The reaction solution was then concentrated on a rotary evaporator. The residue was dissolved in 3 ml of DMSO and this solution was purified by means of preparative HPLC (Method 14). Combination of the product fractions and freeze-drying gave 53 mg (61% of theory) of the title compound.

$^1$H-NMR (400 MHz, DMSO-$d_6$, δ/ppm): 8.35 (s, 1H), 4.82 (s, 2H), 4.06-3.94 (m, 4H), 3.61 (t, 2H), 3.58-3.50 (m, 2H), 3.44-3.37 (m, 2H), 3.22 (s, 3H), 3.15 (s, 3H), 2.42 (s, 3H), 1.08 (s, 6H).

LC/MS (Method 3, ESIpos): $R_t$=1.03 min, m/z=441 [M+H]$^+$.

Example 173

1-(3-Fluoropropyl)-5-methyl-6-[(3-methyl-2-thioxoimidazolidin-1-yl)methyl]-3-(2,2,2-trifluoroethyl)thieno[2,3-d]pyrimidine-2,4(1H,3H)-dione

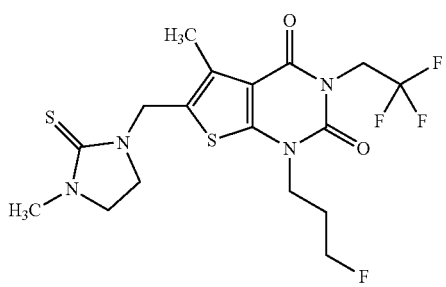 [SMILES: Cc1c(CN2CCN(C)C2=S)sc2c1c(=O)n(CC(F)(F)F)c(=O)n2CCCF]

To a solution of 40 mg (0.082 mmol) of the compound from Ex. 40 in 2 ml of DMF were added 80 mg (0.246 mmol) of caesium carbonate, and the mixture was stirred for 10 min. Subsequently, 29 mg (0.205 mmol) of iodomethane were added, and the mixture was stirred at RT for 66 h. Then the reaction mixture was partitioned between ethyl acetate (50 ml) and water (50 ml). The aqueous phase was extracted with ethyl acetate. The combined organic phases were dried over sodium sulphate, filtered and concentrated. The residue obtained was purified by means of preparative HPLC (Method 14). Combination of the product fractions and freeze-drying gave 20 mg (53% of theory) of the title compound.

$^1$H-NMR (400 MHz, DMSO-$d_6$, δ/ppm): 4.69 (q, 2H), 4.59 (t, 1H), 4.47 (t, 1H), 4.40 (s, 2H), 4.02 (t, 2H), 3.64-3.58 (m, 2H), 3.33-3.26 (m, 2H), 2.44 (s, 3H), 2.39 (s, 3H), 2.15-2.07 (m, 1H), 2.07-2.00 (m, 1H).

LC/MS (Method 3, ESIpos): $R_t$=0.8 min, m/z=453 [M+H]$^+$.

Example 174

3-Ethyl-6-[(3-isopropyl-2-thioxoimidazolidin-1-yl)methyl]-1-(2-methoxyethyl)-5-methylthieno[2,3-d]pyrimidine-2,4(1H,3H)-dione

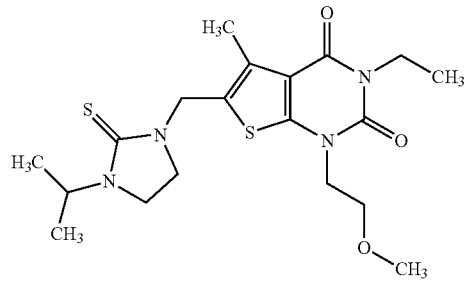 [SMILES: CCn1c(=O)c2c(C)c(CN3CCN(C(C)C)C3=S)sc2n(CCOC)c1=O]

The title compound (56 mg) was obtained as a by-product of the preparation and purification of the compound described in Example 31.

$^1$H-NMR (400 MHz, DMSO-$d_6$, δ/ppm): 4.87 (s, 1H), 4.61 (sept, 1H), 4.00 (t, 2H), 3.89 (q, 2H), 3.62 (t, 2H), 3.50-3.40 (m, 4H), 3.22 (s, 3H), 2.44 (s, 3H), 1.14-1.06 (m, 9H).

LC/MS (Method 3, ESIpos): $R_t$=1.24 min, m/z=425 [M+H]$^+$.

Example 175

3-Ethyl-6-[(3-isopropyl-2-thioxoimidazolidin-1-yl)methyl]-5-methyl-1-(tetrahydrofuran-2-ylmethyl)thieno[2,3-d]pyrimidine-2,4(1H,3H)-dione (racemate)

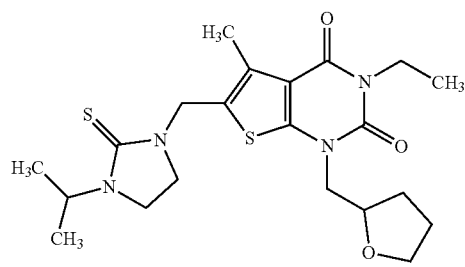 [SMILES: CCn1c(=O)c2c(C)c(CN3CCN(C(C)C)C3=S)sc2n(CC2CCCO2)c1=O]

The title compound (28 mg) was obtained as a by-product of the preparation and purification of the compound described in Example 35.

¹H-NMR (400 MHz, DMSO-d₆, δ/ppm): 4.92-4.81 (m, 2H), 4.66-4.54 (m, 1H), 4.25-4.17 (m, 1H), 4.02 (dd, 1H), 3.90 (q, 2H), 3.77-3.56 (m, 4H), 3.45 (br. s, 3H), 2.44 (s, 3H), 2.02-1.75 (m, 4H), 1.70-1.61 (m, 1H), 1.14-1.06 (m, 9H).

LC/MS (Method 3, ESIpos): R$_t$=1.28 min, m/z=451 [M+H]⁺.

Example 176

1-(2-Methoxyethyl)-5-methyl-6-[(2-oxoimidazolidin-1-yl)methyl]-3-(2-phenylethyl)thieno[2,3-d]pyrimidine-2,4(1H,3H)-dione

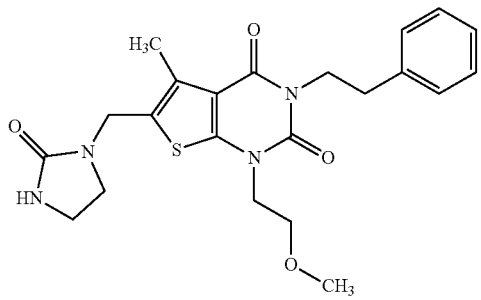 [SMILES: COCCn1c(=O)n(CCc2ccccc2)c(=O)c2c(C)c(CN3CCNC3=O)sc21]

To a solution of 215 mg (2.40 mmol) of 2-imidazolidinone in 9 ml of THF were added 96 mg (2.40 mmol) of sodium hydride (60% suspension in mineral oil) and the mixture was stirred at RT for 3 h ("Solution 1"). To a solution of 225 mg (0.601 mmol) of the compound from Ex. 138A in 4 ml of dichloromethane in another reaction vessel were added, at 0° C., 314 µl (1.80 mmol) of N,N-diisopropylethylamine and 66 µl (0.901 mmol) of thionyl chloride, and the mixture was stirred for 75 min. Subsequently, Solution 1 was added in portions and the mixture was stirred at RT for 18 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 151 mg (56% of theory) of the title compound were obtained.

¹H-NMR (400 MHz, DMSO-d₆, δ/ppm): 7.34-7.27 (m, 1H), 7.26-7.19 (m, 1H), 6.55 (s, 1H), 4.35 (s, 2H), 4.09-4.03 (m, 2H), 4.01 (t, 2H), 3.60 (t, 2H), 3.28-3.18 (m, 7H), 2.86-2.79 (m, 2H), 2.39 (s, 3H).

LC/MS (Method 3, ESIpos): R$_t$=1.12 min, m/z=443 [M+H]⁺.

Example 177

1-(2,2-Difluoroethyl)-3-ethyl-5-methyl-6-[(2-oxoimidazolidin-1-yl)methyl]thieno[2,3-d]pyrimidine-2,4(1H,3H)-dione

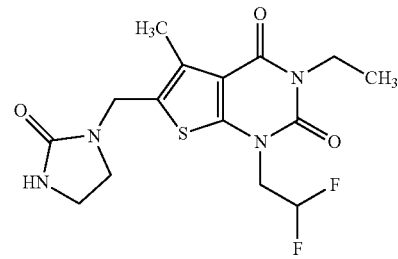 [SMILES: CCn1c(=O)c2c(C)c(CN3CCNC3=O)sc2n(CC(F)F)c1=O]

353 mg (0.866 mmol) of the compound from Example 212A were dissolved in 16 ml of dioxane, and 217 mg (1.299 mmol) of CDI were added. The mixture was stirred at RT for 16 h. The reaction solution was then concentrated on a rotary evaporator. The residue was dissolved in 3 ml of DMSO and this solution was purified by means of preparative HPLC (Method 14). Combination of the product fractions and freeze-drying gave 171 mg (53% of theory) of the title compound.

¹H-NMR (400 MHz, DMSO-d₆, δ/ppm): 6.56 (s, 1H), 6.50-6.19 (m, 1H), 4.40-4.25 (m, 4H), 3.90 (q, 2H), 3.28-3.17 (m, 4H), 2.40 (s, 3H), 1.12 (t, 3H).

LC/MS (Method 3, ESIpos): R$_t$=0.92 min, m/z=373 [M+H]⁺.

Example 178

1-[2-(Cyclopropyloxy)ethyl]-3-ethyl-5-methyl-6-[(2-oxoimidazolidin-1-yl)methyl]thieno[2,3-d]pyrimidine-2,4(1H,3H)-dione

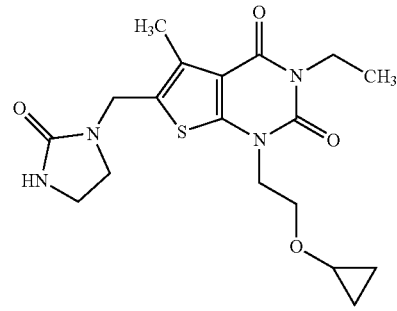 [SMILES: CCn1c(=O)c2c(C)c(CN3CCNC3=O)sc2n(CCOC2CC2)c1=O]

140 mg (0.271 mmol) of the compound from Example 308A were dissolved in 15 ml of dioxane, and 68 mg (0.407 mmol) of CDI were added. The mixture was stirred at RT for 18 h. The reaction solution was then concentrated on a rotary evaporator. The residue was dissolved in 6 ml of DMSO and this solution was purified by means of preparative HPLC (Method 14). Combination of the product fractions and freeze-drying gave 84 mg (78% of theory) of the title compound.

$^1$H-NMR (400 MHz, DMSO-$d_6$, δ/ppm): 6.54 (s, 1H), 4.34 (s, 2H), 3.99 (t, 2H), 3.90 (q, 2H), 3.72 (t, 2H), 3.33-3.29 (m, 1H), 3.27-3.16 (m, 4H), 2.39 (s, 3H), 1.11 (t, 3H), 0.43-0.33 (m, 4H).

LC/MS (Method 3, ESIpos): $R_t$=0.98 min, m/z=393 [M+H]$^+$.

Example 179

3-Ethyl-5-methyl-6-[(2-oxoimidazolidin-1-yl)methyl]-1-(tetrahydro-2H-pyran-2-ylmethyl)thieno[2,3-d]pyrimidine-2,4(1H,3H)-dione (Enantiomer 1)

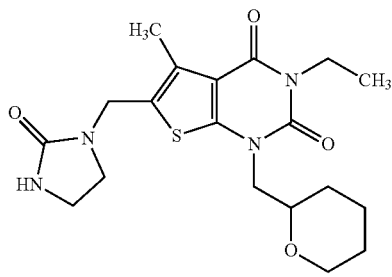

189 mg of the racemic compound from Ex. 71 were dissolved in 6 ml of a methanol/dichloromethane mixture (1:1 v/v) and separated into the enantiomers by means of preparative HPLC on a chiral phase [column: Daicel Chiralpak IC, 5 µm, 250 mm×30 mm; eluent A: acetonitrile+0.1% diethylamine, eluent B: ethanol; isocratic 90% A+10% B; flow rate: 50 ml/min; temperature: RT; detection: DAD 254 nm]. The product fractions were concentrated on a rotary evaporator, admixed with tert-butanol and freeze-dried. 80 mg (41% of theory) of the title compound (Enantiomer 1) and 81 mg (42% of theory) of Enantiomer 2 (see Example 180) were obtained.

$^1$H-NMR (400 MHz, DMSO-$d_6$, δ/ppm): 6.54 (s, 1H), 4.39-4.28 (m, 2H), 4.02-3.93 (m, 1H), 3.89 (q, 2H), 3.84-3.75 (m, 1H), 3.73-3.62 (m, 2H), 3.29-3.16 (m, 5H), 2.38 (s, 3H), 1.77 (br. s, 1H), 1.61 (d, 1H), 1.52-1.37 (m, 3H), 1.31-1.19 (m, 1H), 1.11 (t, 3H).

Chiral analytical HPLC [column: Daicel Chiralpak IC, 3 µm, 100 mm×4.6 mm; eluent A: acetonitrile+0.1% diethylamine, eluent B: ethanol; isocratic 90% A+10% B; flow rate: 1.0 ml/min; temperature: 25° C.; injection: 5 µl; DAD 254 nm]: $R_t$=8.06 min.

Example 180

3-Ethyl-5-methyl-6-[(2-oxoimidazolidin-1-yl)methyl]-1-(tetrahydro-2H-pyran-2-ylmethyl)thieno[2,3-d]pyrimidine-2,4(1H,3H)-dione (Enantiomer 2)

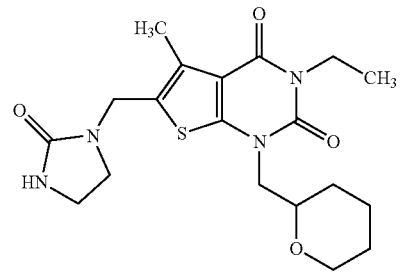 [SMILES: CCn1c(=O)c2c(C)c(CN3CCNC3=O)sc2n(CC2CCCCO2)c1=O]

The title compound (81 mg) was obtained as the second enantiomer in the preparative HPLC separation of the racemate from Ex. 71 described in Ex. 179.

$^1$H-NMR (400 MHz, DMSO-$d_6$, δ/ppm): 6.54 (s, 1H), 4.39-4.28 (m, 2H), 4.02-3.93 (m, 1H), 3.89 (q, 2H), 3.84-3.76 (m, 1H), 3.73-3.63 (m, 2H), 3.30-3.17 (m, 5H), 2.38 (s, 3H), 1.77 (br. s, 1H), 1.61 (d, 1H), 1.51-1.38 (m, 3H), 1.31-1.19 (m, 1H), 1.11 (t, 3H).

Chiral analytical HPLC [column: Daicel Chiralpak IC, 3 µm, 100 mm×4.6 mm; eluent A: acetonitrile+0.1% diethylamine, eluent B: ethanol; isocratic 90% A+10% B; flow rate: 1.0 ml/min; temperature: 25° C.; injection: 5 µl; DAD 254 nm]: $R_t$=9.39 min.

Example 181

3-Isopropyl-5-methyl-6-[(2-oxoimidazolidin-1-yl)methyl]-1-(3,3,3-trifluoropropyl)thieno[2,3-d]pyrimidine-2,4(1H,3H)-dione 495 mg (1.28 mmol) of the compound from Ex. 204A were dissolved in about 10 ml of methanol and passed through a hydrogencarbonate cartridge (from Polymerlabs, Stratospheres SPE, PL-HCO$_3$ MP SPE). After concentration of the solution, the free amine 6-(aminomethyl)-3-isopropyl-5-methyl-1-(3,3,3-trifluoropropyl)thieno[2,3-d]pyrimidine-2,4(1H,3H)-dione was thus obtained, which was then dissolved in a mixture of 8.7 ml of DMF and 4.2 ml of THF, and 115 µl (1.35 mmol) of 2-chloroethyl isocyanate were added at RT. After the reaction mixture had been stirred at RT for 40 min, 216 mg (1.92 mmol) of potassium tert-butoxide were added. After a further 60 min at RT, the reaction mixture was diluted with ethyl acetate and washed successively with saturated sodium hydrogencarbonate solution and saturated sodium chloride solution. After drying over anhydrous magnesium sulphate, the mixture was filtered and concentrated. The crude product thus obtained was purified by means of MPLC (instrument: Biotage Isolera One, SNAP KP-Sil cartridge, 50 g of silica gel, eluent: cyclohexane/ethyl acetate 15:85→0:100). After combination of the product fractions and concentration, the product was stirred in pentane/dichloromethane (10:1) at RT for 30 min. Removal of the solids by filtration with suction and drying under high vacuum gave 183 mg (34% of theory) of the title compound.

$^1$H-NMR (400 MHz, DMSO-$d_6$, δ/ppm): 6.53 (s, 1H), 5.13 (sept, 1H), 4.36 (s, 2H), 4.06 (t, 2H), 3.28-3.16 (m, 4H), 2.86-2.62 (m, 2H), 2.39 (s, 3H), 1.40 (d, 6H).

LC/MS (Method 1, ESIpos): $R_t$=0.94 min, m/z=419 [M+H]$^+$.

Example 182

1-(2-Fluoroethyl)-3-isopropyl-5-methyl-6-[(2-oxoimidazolidin-1-yl)methyl]thieno[2,3-d]pyrimidine-2,4(1H,3H)-dione

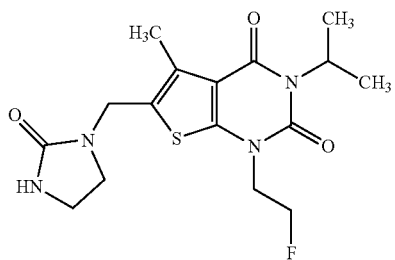 [SMILES: Cc1c(CN2CCNC2=O)sc2c1c(=O)n(C(C)C)c(=O)n2CCF]

379 mg (1.06 mmol, 94% purity) of the compounds from Ex. 203A were dissolved in about 10 ml of methanol and passed through a hydrogencarbonate cartridge (from Polymerlabs, Stratospheres SPE, PL-HCO$_3$ MP SPE). After concentration of the solution, the free amine 6-(aminomethyl)-1-(2-fluoroethyl)-3-isopropyl-5-methylthieno[2,3-d]pyrimidine-2,4(1H,3H)-dione was thus obtained, which was then dissolved in a mixture of 7.2 ml of DMF and 3.5 ml of THF, and 95 µl (1.11 mmol) of 2-chloroethyl isocyanate were added at RT. After the reaction mixture had been stirred at RT for 50 min, 179 mg (1.59 mmol) of potassium tert-butoxide were added. After a further 60 min at RT, the reaction mixture was diluted with ethyl acetate and washed successively with saturated sodium hydrogencarbonate solution and saturated sodium chloride solution. After drying over anhydrous magnesium sulphate, the mixture was filtered and concentrated. The crude product thus obtained was purified by means of MPLC (instrument: Biotage Isolera One, SNAP KP-Sil cartridge, 50 g of silica gel, eluent: cyclohexane/ethyl acetate 15:85→0:100). After combination and concentration of the product fractions and drying under high vacuum, 185 mg (45% of theory, 96% purity) of the title compound were obtained.

$^1$H-NMR (400 MHz, DMSO-$d_6$, δ/ppm): 6.51 (s, 1H), 5.13 (sept, 1H), 4.71 (dt, 2H), 4.34 (s, 2H), 4.15 (dt, 2H), 3.27-3.16 (m, 4H), 2.38 (s, 3H), 1.41 (d, 6H).

LC/MS (Method 1, ESIpos): $R_t$=0.82 min, m/z=369 [M+H]$^+$.

Example 183

3-Isopropyl-5-methyl-1-(oxetan-2-ylmethyl)-6-[(2-oxoimidazolidin-1-yl)methyl]thieno[2,3-d]pyrimidine-2,4(1H,3H)-dione (racemate)

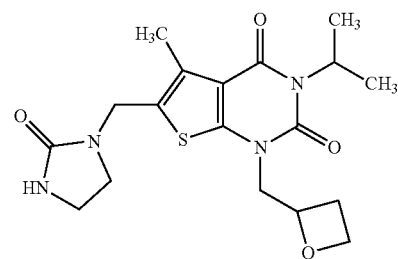 [SMILES: Cc1c(CN2CCNC2=O)sc2c1c(=O)n(C(C)C)c(=O)n2CC1CCO1]

284 mg (0.746 mmol, 85% purity) of the compound from Ex. 205A were dissolved in a mixture of 5 ml of DMF and 2.4 ml of THF, and 67 µl (0.783 mmol) of 2-chloroethyl isocyanate were added at RT. After the reaction mixture had been stirred at RT for 20 min, 126 mg (1.12 mmol) of potassium tert-butoxide were added. After a further 60 min at RT, the reaction mixture was diluted with ethyl acetate and washed successively with saturated sodium hydrogencarbonate solution and saturated sodium chloride solution. After drying over anhydrous magnesium sulphate, the mixture was filtered and concentrated. The crude product thus obtained was first purified by means of MPLC (instrument: Biotage Isolera One, SNAP KP-Sil cartridge, 50 g of silica gel, eluent: cyclohexane/ethyl acetate 15:85→0:100). The product fractions were combined and concentrated. The material thus obtained was then purified further by means of preparative HPLC (Method 8). After concentration of the product fractions, the product was stirred in pentane/dichloromethane (10:1) at RT for 30 min. Removal of the solids by filtration with suction and drying under high vacuum gave 108 g (36% of theory) of the title compound.

$^1$H-NMR (400 MHz, DMSO-$d_6$, δ/ppm): 6.51 (s, 1H), 5.14 (sept, 1H), 4.99 (quin, 1H), 4.53-4.37 (m, 2H), 4.33 (s, 2H), 4.15-4.04 (m, 2H), 3.27-3.15 (m, 4H), 2.76-2.62 (m, 1H), 2.53-2.44 (m, 1H, mostly obscured by the DMSO signal), 2.38 (s, 3H), 1.40 (d, 6H).

LC/MS (Method 6, ESIpos): $R_t$=1.39 min, m/z=393 [M+H]$^+$.

Example 184

3-Isopropyl-5-methyl-1-(oxetan-2-ylmethyl)-6-[(2-oxoimidazolidin-1-yl)methyl]thieno[2,3-d]pyrimidine-2,4(1H,3H)-dione (Enantiomer 1)

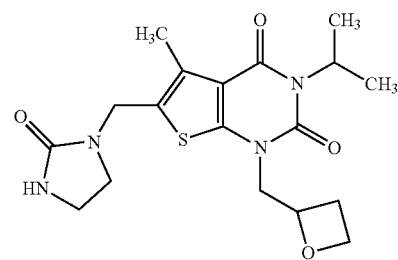 [SMILES: Cc1c(CN2CCNC2=O)sc2c1c(=O)n(C(C)C)c(=O)n2CC1CCO1]

106 mg (0.270 mmol) of the racemic compound from Ex. 183 were dissolved in 5 ml of ethanol and, in 10 portions, separated into the enantiomers by preparative HPLC on a chiral phase [column: Daicel Chiralcel OD-H, 5 μm, 250 mm×20 mm; eluent: isohexane/ethanol 1:1; flow rate: 15 ml/min; temperature: 25° C.; detection: 210 nm]. After concentration of the product fractions, the residue was stirred in pentane/dichloromethane (10:1) at RT for 60 min. The solid was filtered off with suction and dried under high vacuum. 22 g (42% of theory) of Enantiomer 1 were obtained (99% ee, chiral analytical HPLC).

$^1$H-NMR (400 MHz, DMSO-$d_6$, δ/ppm): 6.51 (s, 1H), 5.13 (sept, 1H), 5.05-4.93 (m, 1H), 4.53-4.37 (m, 2H), 4.33 (s, 2H), 4.15-4.05 (m, 2H), 3.26-3.14 (m, 4H), 2.77-2.63 (m, 1H), 2.53-2.44 (m, 1H, mostly obscured by the DMSO signal), 2.38 (s, 3H), 1.40 (d, 6H).

Chiral analytical HPLC [column: Daicel Chiralpak OX-3, 3 μm, 50 mm×4.6 mm; eluent: isohexane/ethanol 1:1; flow rate: 1 ml/min; temperature: 40° C.; detection: 220 nm]: $R_t$=2.77 min.

Example 185

3-Isopropyl-5-methyl-1-(oxetan-2-ylmethyl)-6-[(2-oxoimidazolidin-1-yl)methyl]thieno[2,3-d]pyrimidine-2,4(1H,3H)-dione (Enantiomer 2)

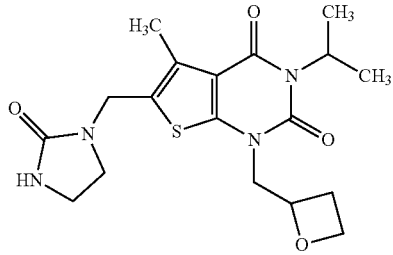

106 mg (0.270 mmol) of the racemic compound from Ex. 183 were dissolved in 5 ml of ethanol and, in 10 portions, separated into the enantiomers by preparative HPLC on a chiral phase [column: Daicel Chiralcel OD-H, 5 μm, 250 mm×20 mm; eluent: isohexane/ethanol 1:1; flow rate: 15 ml/min; temperature: 25° C.; detection: 210 nm]. After concentration of the product fractions, the residue was stirred in pentane/dichloromethane (10:1) at RT for 60 min. The solid was filtered off with suction and dried under high vacuum. 33 g (63% of theory) of Enantiomer 2 were obtained (99% ee, chiral analytical HPLC).

$^1$H-NMR (400 MHz, DMSO-$d_6$, δ/ppm): 6.51 (s, 1H), 5.14 (sept, 1H), 5.05-4.94 (m, 1H), 4.54-4.37 (m, 2H), 4.33 (s, 2H), 4.16-4.02 (m, 2H), 3.26-3.18 (m, 4H), 2.76-2.62 (m, 1H), 2.53-2.44 (m, 1H, mostly obscured by the DMSO signal), 2.38 (s, 3H), 1.40 (d, 6H).

Chiral analytical HPLC [column: Daicel Chiralpak OX-3, 3 μm, 50 mm×4.6 mm; eluent: isohexane/ethanol 1:1; flow rate: 1 ml/min; temperature: 40° C.; detection: 220 nm]: $R_t$=3.38 min.

Example 186

3-Isopropyl-5-methyl-6-[(2-oxoimidazolidin-1-yl)methyl]-1-(tetrahydrofuran-2-ylmethyl)thieno[2,3-d]pyrimidine-2,4(1H,3H)-dione (racemate)

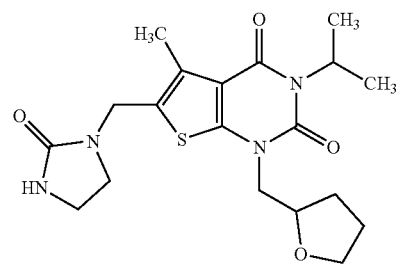 [SMILES: Cc1c(CN2CCNC2=O)sc2c1c(=O)n(C(C)C)c(=O)n2CC1CCCO1]

262 mg (0.619 mmol, 88% purity) of the compounds from Ex. 206A were dissolved in about 10 ml of methanol and passed through a hydrogencarbonate cartridge (from Polymerlabs, Stratospheres SPE, PL-HCO$_3$ MP SPE). After concentration of the solution, the free amine 6-(aminomethyl)-3-isopropyl-5-methyl-1-(tetrahydrofuran-2-ylmethyl)thieno[2,3-d]pyrimidine-2,4(1H,3H)-dione was thus obtained, which was then dissolved in a mixture of 4.2 ml of DMF and 2.0 ml of THF, and 55 μl (0.649 mmol) of 2-chloroethyl isocyanate were added at RT. After the reaction mixture had been stirred at RT for 30 min, 104 mg (0.928 mmol) of potassium tert-butoxide were added. After a further 50 min at RT, the reaction mixture was diluted with ethyl acetate and washed successively with saturated sodium hydrogencarbonate solution and saturated sodium chloride solution. After drying over anhydrous magnesium sulphate, the mixture was filtered and concentrated. The crude product thus obtained was purified by means of suction filtration through silica gel with ethyl acetate as eluent. After concentration of the product fractions and drying under high vacuum, 112 mg (44% of theory) of the title compound were obtained.

$^1$H-NMR (400 MHz, DMSO-$d_6$, δ/ppm): 6.51 (s, 1H), 5.14 (sept, 1H), 4.33 (s, 2H), 4.26-4.16 (m, 1H), 4.02 (dd, 1H), 3.74 (q, 1H), 3.69-3.57 (m, 2H), 3.27-3.14 (m, 4H), 2.38 (s, 3H), 2.05-1.74 (m, 3H), 1.71-1.59 (m, 1H), 1.40 (d, 6H).

LC/MS (Method 1, ESIpos): $R_t$=0.85 min, m/z=407 [M+H]$^+$.

Example 187

3-Isopropyl-5-methyl-6-[(2-oxoimidazolidin-1-yl)methyl]-1-(tetrahydrofuran-2-ylmethyl)thieno[2,3-d]pyrimidine-2,4(1H,3H)-dione (Enantiomer 1)

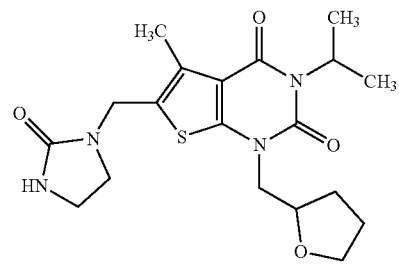 [SMILES: Cc1c(CN2CCNC2=O)sc2c1c(=O)n(C(C)C)c(=O)n2CC1CCCO1]

96 mg (0.236 mmol) of the racemic compound from Ex. 186 were dissolved in 5 ml of isopropanol and, in 5 portions, separated into the enantiomers by preparative HPLC on a chiral phase [column: Daicel Chiralcel OD-H, 5 μm, 250 mm×20 mm; eluent: isohexane/isopropanol 1:1; flow rate: 15 ml/min; temperature: 25° C.; detection: 210 nm]. After concentration of the product fractions, the residue was stirred in pentane/dichloromethane (10:1) at RT for 60 min. The solid was filtered off with suction and dried under high vacuum. 16 mg (33% of theory) of Enantiomer 1 were obtained (>99% ee, chiral analytical HPLC).

$^1$H-NMR (400 MHz, DMSO-d$_6$, δ/ppm): 6.51 (s, 1H), 5.14 (sept, 1H), 4.33 (s, 2H), 4.26-4.16 (m, 1H), 4.02 (dd, 1H), 3.74 (q, 1H), 3.69-3.57 (m, 2H), 3.26-3.16 (m, 4H), 2.38 (s, 3H), 2.04-1.76 (m, 3H), 1.71-1.59 (m, 1H), 1.40 (dd, 6H).

Chiral analytical HPLC [column: Daicel Chiralpak OX-3, 3 μm, 50 mm×4.6 mm; eluent: isohexane/isopropanol 1:1; flow rate: 1 ml/min; temperature: 40° C.; detection: 220 nm]: R$_t$=2.48 min.

Example 188

3-Isopropyl-5-methyl-6-[(2-oxoimidazolidin-1-yl)methyl]-1-(tetrahydrofuran-2-ylmethyl)thieno[2,3-d]pyrimidine-2,4(1H,3H)-dione (Enantiomer 2)

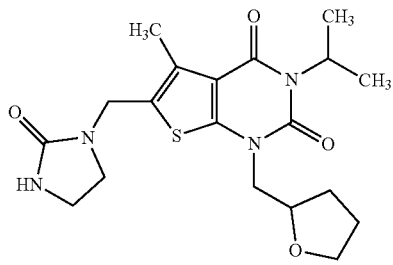

96 mg (0.236 mmol) of the racemic compound from Ex. 186 were dissolved in 5 ml of isopropanol and, in 5 portions, separated into the enantiomers by preparative HPLC on a chiral phase [column: Daicel Chiralcel OD-H, 5 μm, 250 mm×20 mm; eluent: isohexane/isopropanol 1:1; flow rate: 15 ml/min; temperature: 25° C.; detection: 210 nm]. After concentration of the product fractions, the residue was stirred in pentane/dichloromethane (10:1) at RT for 60 min. The solid was filtered off with suction and dried under high vacuum. 19 mg (39% of theory) of Enantiomer 2 were obtained (>99% ee, chiral analytical HPLC).

$^1$H-NMR (400 MHz, DMSO-d$_6$, δ/ppm): 6.51 (s, 1H), 5.14 (sept, 1H), 4.33 (s, 2H), 4.27-4.15 (m, 1H), 4.02 (dd, 1H), 3.79-3.70 (m, 1H), 3.69-3.56 (m, 2H), 3.26-3.16 (m, 4H), 2.38 (s, 3H), 2.04-1.76 (m, 3H), 1.70-1.59 (m, 1H), 1.40 (dd, 6H).

Chiral analytical HPLC [column: Daicel Chiralpak OX-3, 3 μm, 50 mm×4.6 mm; eluent: isohexane/isopropanol 1:1; flow rate: 1 ml/min; temperature: 40° C.; detection: 220 nm]: R$_t$=3.33 min.

Example 189

3-Isopropyl-5-methyl-1-(oxetan-3-ylmethyl)-6-[(2-oxoimidazolidin-1-yl)methyl]thieno[2,3-d]pyrimidine-2,4(1H,3H)-dione

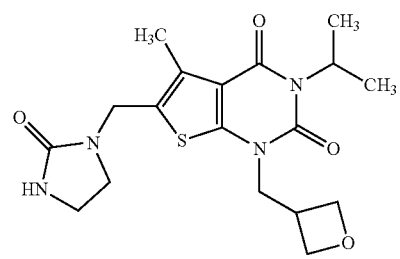 [SMILES: Cc1c(CN2CCNC2=O)sc2c1c(=O)n(C(C)C)c(=O)n2CC1COC1]

212 mg (0.459 mmol, 70% purity) of the compound from Ex. 207A were dissolved in a mixture of 3.1 ml of DMF and 1.5 ml of THF, and 41 μl (0.482 mmol) of 2-chloroethyl isocyanate were added at RT. After the reaction mixture had been stirred at RT for 30 min, 77 mg (0.688 mmol) of potassium tert-butoxide were added. After a further 60 min at RT, the reaction mixture was diluted with ethyl acetate and washed successively with saturated sodium hydrogencarbonate solution and saturated sodium chloride solution. After drying over anhydrous magnesium sulphate, the mixture was filtered and concentrated. The crude product thus obtained was first prepurified by means of preparative HPLC (Method 8). The resulting product was then stirred in pentane/dichloromethane (10:1) at RT for 30 min. This achieved further, but inadequate purification. After another preparative HPLC (Method 8), 26 mg (14% of theory) of the title compound were obtained.

$^1$H-NMR (400 MHz, DMSO-d$_6$, δ/ppm): 6.52 (s, 1H), 5.12 (sept, 1H), 4.62 (dd, 2H), 4.43 (t, 2H), 4.34 (s, 2H), 4.16 (d, 2H), 3.47-3.36 (m, 1H), 3.27-3.17 (m, 4H), 2.38 (s, 3H), 1.39 (d, 6H).

LC/MS (Method 1, ESIpos): R$_t$=0.77 min, m/z=393 [M+H]$^+$.

Example 190

3-sec-Butyl-1-(2-methoxyethyl)-5-methyl-6-[(2-oxoimidazolidin-1-yl)methyl]thieno[2,3-d]pyrimidine-2,4(1H,3H)-dione (racemate)

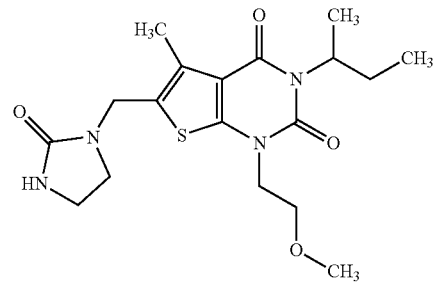 [SMILES: CCC(C)n1c(=O)c2c(C)c(CN3CCNC3=O)sc2n(CCOC)c1=O]

To a solution of 375 mg (4.18 mmol) of 2-imidazolidinone in 15 ml of THF were added 167 mg (4.18 mmol) of sodium hydride (60% suspension in mineral oil) and the mixture was stirred at RT for 3 h ("Solution 1"). To a solution of 341 mg (1.05 mmol) of the compound from Ex. 147A in 7.3 ml of dichloromethane in another reaction vessel were added, at 0° C., 546 µl (3.13 mmol) of N,N-diisopropylethylamine and 114 µl (1.57 mmol) of thionyl chloride, and the mixture was stirred for 75 min. Subsequently, Solution 1 was added in portions and the mixture was stirred at RT for 18 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 210 mg (51% of theory) of the title compound were obtained.

$^1$H-NMR (400 MHz, DMSO-$d_6$, δ/ppm): 6.54 (s, 1H), 4.90 (d, 1H), 4.33 (s, 2H), 4.06-3.92 (m, 2H), 3.61 (t, 2H), 3.28-3.17 (m, 7H), 2.37 (s, 3H), 2.09-1.95 (m, 1H), 1.73 (dquin, 1H), 1.37 (d, 3H), 0.75 (t, 3H).

LC/MS (Method 3, ESIpos): $R_t$=1.04 min, m/z=395 [M+H]$^+$.

Example 191

1-(2,2-Difluoroethyl)-3-isobutyl-5-methyl-6-[(2-oxoimidazolidin-1-yl)methyl]thieno[2,3-d]pyrimidine-2,4(1H,3H)-dione

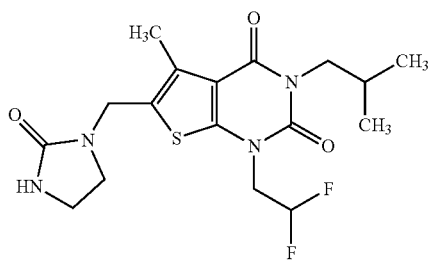 [SMILES: Cc1c(CN2CCNC2=O)sc2c1c(=O)n(CC(C)C)c(=O)n2CC(F)F]

138 mg (0.28 mmol) of the compound from Example 313A were dissolved in 15 ml of dioxane, and 70 mg (0.42 mmol) of CDI were added. The mixture was stirred at RT for 18 h. The reaction solution was then concentrated on a rotary evaporator. The residue was dissolved in 6 ml of DMSO and this solution was purified by means of preparative HPLC (Method 14). Combination of the product fractions and freeze-drying gave 57 mg (50% of theory) of the title compound.

$^1$H-NMR (400 MHz, DMSO-$d_6$, δ/ppm): 6.54 (s, 1H), 6.50-6.18 (m, 1H), 4.40-4.24 (m, 4H), 3.71 (d, 2H), 3.29-3.18 (m, 4H), 2.39 (s, 3H), 2.09-1.97 (m, 1H), 0.85 (d, 6H).

LC/MS (Method 3, ESIpos): $R_t$=1.09 min, m/z=401 [M+H]$^+$.

Example 192

1-(3-Fluoropropyl)-3-isobutyl-5-methyl-6-[(2-oxoimidazolidin-1-yl)methyl]thieno[2,3-d]pyrimidine-2,4(1H,3H)-dione

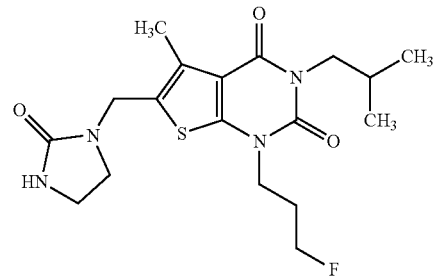 [SMILES: Cc1c(CN2CCNC2=O)sc2c1c(=O)n(CC(C)C)c(=O)n2CCCF]

170 mg (0.266 mmol) of the compound from Example 241A were dissolved in 15 ml of dioxane, and 67 mg (0.399 mmol) of CDI were added. The mixture was stirred at RT for 18 h. The reaction solution was then concentrated on a rotary evaporator. The residue was dissolved in 3 ml of DMSO and this solution was purified by means of preparative HPLC (Method 14). Combination of the product fractions and freeze-drying gave 57 mg (54% of theory) of the title compound.

$^1$H-NMR (400 MHz, DMSO-$d_6$, δ/ppm): 6.55 (s, 1H), 4.58 (t, 1H), 4.47 (t, 1H), 4.35 (s, 2H), 3.98 (t, 2H), 3.70 (d, 2H), 3.29-3.17 (m, 4H), 2.39 (s, 3H), 2.13-1.96 (m, 3H), 0.84 (d, 6H).

LC/MS (Method 3, ESIpos): $R_t$=1.08 min, m/z=397 [M+H]$^+$.

Example 193

1-(2-Ethoxyethyl)-3-isobutyl-5-methyl-6-[(2-oxoimidazolidin-1-yl)methyl]thieno[2,3-d]pyrimidine-2,4(1H,3H)-dione

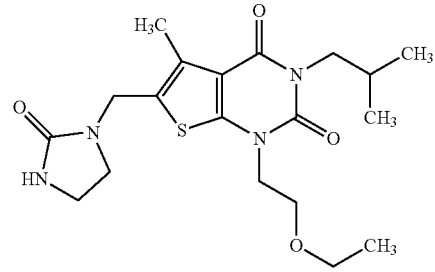 [SMILES: CCOCCn1c(=O)n(CC(C)C)c(=O)c2c(C)c(CN3CCNC3=O)sc21]

260 mg (0.564 mmol) of the compound from Example 314A were dissolved in 20 ml of dioxane, and 141 mg (0.846 mmol) of CDI were added. The mixture was stirred at RT for 18 h. The reaction solution was then concentrated on a rotary evaporator. The residue was dissolved in 6 ml of DMSO and this solution was purified by means of preparative HPLC (Method 14). Combination of the product fractions and freeze-drying gave 98 mg (42% of theory) of the title compound.

$^1$H-NMR (400 MHz, DMSO-$d_6$, δ/ppm): 6.53 (s, 1H), 4.35 (s, 2H), 4.01 (t, 2H), 3.71 (d, 2H), 3.65 (t, 2H), 3.42 (q, 2H), 3.28-3.16 (m, 4H), 2.38 (s, 3H), 2.09-1.97 (m, 1H), 1.02 (t, 3H), 0.85 (d, 6H).

LC/MS (Method 3, ESIpos): $R_t$=1.11 min, m/z=409 [M+H]$^+$.

Example 194

3-Isobutyl-5-methyl-1-(oxetan-2-ylmethyl)-6-[(2-oxoimidazolidin-1-yl)methyl]thieno[2,3-d]pyrimidine-2,4(1H,3H)-dione (racemate)

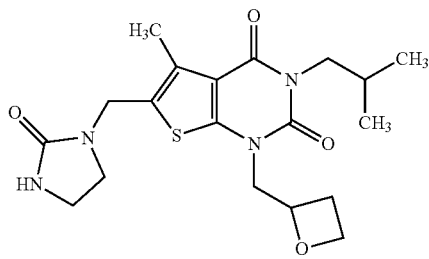

813 mg (1.84 mmol) of the compound from Example 243A were dissolved in 40 ml of dioxane, and 461 mg (2.76 mmol) of CDI were added. The mixture was stirred at RT for 16 h. The reaction solution was then concentrated on a rotary evaporator. The residue was dissolved in 15 ml of DMSO and this solution was purified by means of preparative HPLC (Method 14). Combination of the product fractions and freeze-drying gave 383 mg (42% of theory) of the title compound.

$^1$H-NMR (400 MHz, DMSO-d$_6$, δ/ppm): 6.54 (s, 1H), 5.05-4.95 (m, 1H), 4.52-4.37 (m, 2H), 4.34 (s, 2H), 4.13 (d, 2H), 3.71 (d, 2H), 3.28-3.16 (m, 4H), 2.74-2.62 (m, 1H), 2.38 (s, 2H), 2.03 (dquin, 1H), 0.85 (dd, 6H).

LC/MS (Method 3, ESIpos): $R_t$=1.02 min, m/z=407 [M+H]$^+$.

Example 195

3-Isobutyl-5-methyl-1-(oxetan-2-ylmethyl)-6-[(2-oxoimidazolidin-1-yl)methyl]thieno[2,3-d]pyrimidine-2,4(1H,3H)-dione (Enantiomer 1)

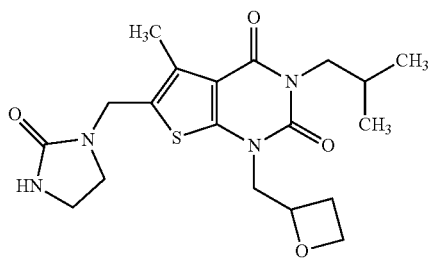

348 mg of the racemic compound from Ex. 194 were dissolved in 5.4 ml of a methanol/acetonitrile mixture (1:1 v/v) and separated into the enantiomers by means of preparative HPLC on a chiral phase [column: Daicel Chiralpak IC, 5 μm, 250 mm×30 mm; eluent: acetonitrile/ethanol/diethylamine 90:10:0.1; flow rate: 50 ml/min; temperature: RT; detection: 254 nm]. The product fractions were concentrated on a rotary evaporator, admixed with tert-butanol and freeze-dried. 70 mg (20% of theory) of the title compound (Enantiomer 1) and 67 mg (19% of theory) of Enantiomer 2 (see Example 196) were obtained.

$^1$H-NMR (400 MHz, DMSO-d$_6$, δ/ppm): 6.55 (s, 1H), 5.04-4.96 (m, 1H), 4.51-4.44 (m, 1H), 4.40 (dt, 1H), 4.34 (s, 2H), 4.16-4.09 (m, 2H), 3.70 (d, 2H), 3.28-3.16 (m, 4H), 2.68 (dtd, 1H), 2.38 (s, 3H), 2.02 (dquin, 1H), 0.84 (dd, 6H).

Chiral analytical HPLC [column: Daicel Chiralpak IC, 5 μm, 100 mm×4.6 mm; eluent: acetonitrile+0.1% diethylamine/ethanol 90:10; flow rate: 1.0 ml/min; temperature: RT; injection: 5 μl; DAD 254 nm; solution: 1.0 mg/ml of methanol]: $R_t$=8.11 min.

Example 196

3-Isobutyl-5-methyl-1-(oxetan-2-ylmethyl)-6-[(2-oxoimidazolidin-1-yl)methyl]thieno[2,3-d]pyrimidine-2,4(1H,3H)-dione (Enantiomer 2)

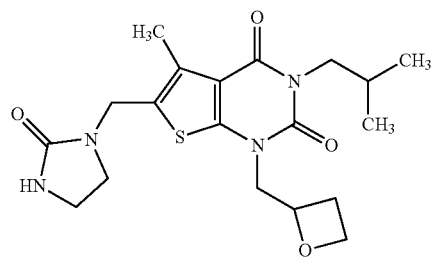 [SMILES: Cc1c(CN2CCNC2=O)sc2c1c(=O)n(CC(C)C)c(=O)n2CC1CCO1]

The title compound (67 mg) was obtained as the second enantiomer in the preparative HPLC separation of the racemate from Ex. 194 described in Ex. 195.

$^1$H-NMR (400 MHz, DMSO-d$_6$, δ/ppm): 6.54 (s, 1H), 5.04-4.95 (m, 1H), 4.52-4.44 (m, 1H), 4.40 (dt, 1H), 4.34 (s, 2H), 4.13 (d, 2H), 3.71 (d, 2H), 3.28-3.18 (m, 4H), 2.73-2.63 (m, 1H), 2.38 (s, 3H), 2.03 (dquin, 1H), 0.84 (dd, 6H).

Chiral analytical HPLC [column: Daicel Chiralpak IC, 5 μm, 100 mm×4.6 mm; eluent: acetonitrile+0.1% diethylamine/ethanol 90:10; flow rate: 1.0 ml/min; temperature: RT; injection: 5 μl; DAD 254 nm; solution: 1.0 mg/ml of methanol]: $R_t$=9.99 min.

Example 197

3-Isobutyl-5-methyl-6-[(2-oxoimidazolidin-1-yl)methyl]-1-(tetrahydrofuran-2-ylmethyl)thieno[2,3-d]pyrimidine-2,4(1H,3H)-dione (Enantiomer 1)

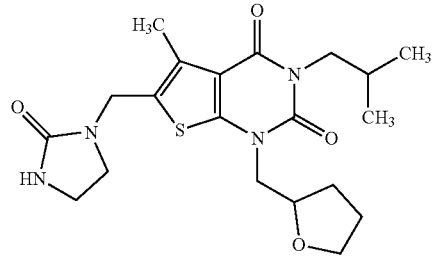 [SMILES: Cc1c(CN2CCNC2=O)sc2c1c(=O)n(CC(C)C)c(=O)n2CC1CCCO1]

346 mg (0.823 mmol) of the racemic compound from Ex. 90 were dissolved in 8 ml of isopropanol and, in 32 portions, separated into the enantiomers by preparative HPLC on a chiral phase [column: Daicel Chiralpak ID, 5 μm, 250 mm×20 mm; eluent: isohexane/isopropanol 1:1; flow rate: 15 ml/min; temperature: 25° C.; detection: 210 nm]. After the product fractions had been concentrated, a further preparative HPLC was conducted on an achiral phase (Method 8), in order to remove impurities. After recombination of the product fractions, concentration and drying under high vacuum, 112 mg (68% of theory) of Enantiomer 1 were obtained (>99% ee, chiral analytical HPLC).

$^1$H-NMR (400 MHz, DMSO-$d_6$, δ/ppm): 6.52 (s, 1H), 4.34 (s, 2H), 4.27-4.17 (m, 1H), 4.01 (dd, 1H), 3.79-3.66 (m, 4H), 3.65-3.57 (m, 1H), 3.28-3.15 (m, 4H), 2.39 (s, 3H), 2.11-1.75 (m, 4H), 1.72-1.59 (m, 1H), 0.85 (dd, 6H).

Chiral analytical HPLC [column: Daicel Chiralpak ID-3, 3 μm, 50 mm×4.6 mm; eluent: isohexane/isopropanol 1:1; flow rate: 1 ml/min; temperature: 40° C.; detection: 220 nm]: $R_t$=2.04 min.

Example 198

3-Isobutyl-5-methyl-6-[(2-oxoimidazolidin-1-yl)methyl]-1-(tetrahydrofuran-2-ylmethyl)thieno[2,3-d]pyrimidine-2,4(1H,3H)-dione (Enantiomer 2)

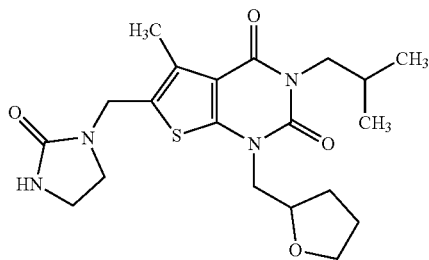 [SMILES: Cc1c(CN2CCNC2=O)sc2c1c(=O)n(CC(C)C)c(=O)n2CC1CCCO1]

346 mg (0.823 mmol) of the racemic compound from Ex. 90 were dissolved in 8 ml of isopropanol and, in 32 portions, separated into the enantiomers by preparative HPLC on a chiral phase [column: Daicel Chiralpak ID, 5 μm, 250 mm×20 mm; eluent: isohexane/isopropanol 1:1; flow rate: 15 ml/min; temperature: 25° C.; detection: 210 nm]. After the product fractions had been concentrated, a further preparative HPLC was conducted on an achiral phase (Method 8), in order to remove impurities. After recombination of the product fractions, concentration and drying under high vacuum, 88 mg (50% of theory) of Enantiomer 2 were obtained (>99% ee, chiral analytical HPLC).

$^1$H-NMR (400 MHz, DMSO-$d_6$, δ/ppm): 6.52 (s, 1H), 4.34 (s, 2H), 4.27-4.17 (m, 1H), 4.01 (dd, 1H), 3.79-3.67 (m, 4H), 3.65-3.55 (m, 1H), 3.28-3.15 (m, 4H), 2.39 (s, 3H), 2.10-1.74 (m, 4H), 1.71-1.57 (m, 1H), 0.85 (dd, 6H).

Chiral analytical HPLC [column: Daicel Chiralpak ID-3, 3 μm, 50 mm×4.6 mm; eluent: isohexane/isopropanol 1:1; flow rate: 1 ml/min; temperature: 40° C.; detection: 220 nm]: $R_t$=2.54 min.

Example 199

3-Isobutyl-5-methyl-1-(oxetan-3-ylmethyl)-6-[(2-oxoimidazolidin-1-yl)methyl]thieno[2,3-d]pyrimidine-2,4(1H,3H)-dione

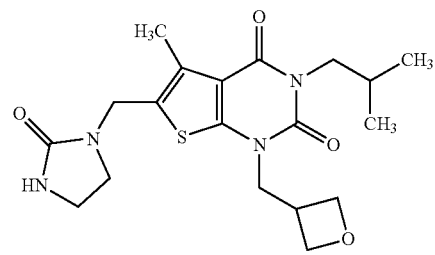 [SMILES: Cc1c(CN2CCNC2=O)sc2c1c(=O)n(CC(C)C)c(=O)n2CC1COC1]

To a solution of 84 mg (0.221 mmol) of the compound from Ex. 245A and 46 μl (0.331 mmol) of triethylamine in 2.5 ml of THF were added 43 mg (0.265 mmol) of CDI, and the mixture was stirred at RT for about 18 h. Subsequently, the mixture was concentrated to dryness. The remaining residue was taken up in ethyl acetate and washed successively with 1 M hydrochloric acid, water and saturated sodium chloride solution. After drying over anhydrous magnesium sulphate, the mixture was filtered and concentrated. The solid residue was purified twice in succession by means of preparative HPLC (Method 8 each time). After concentration of the product fractions and drying of the solids under high vacuum, 14 mg (15% of theory) of the title compound were obtained.

$^1$H-NMR (400 MHz, DMSO-$d_6$, δ/ppm): 6.53 (s, 1H), 4.61 (dd, 2H), 4.43 (t, 2H), 4.35 (s, 2H), 4.20 (d, 2H), 3.70 (d, 2H), 3.48-3.36 (m, 1H), 3.28-3.17 (m, 4H), 2.39 (s, 3H), 1.07-1.97 (m, 1H), 0.84 (d, 6H).

LC/MS (Method 1, ESIpos): $R_t$=0.78 min, m/z=407 [M+H]$^+$.

Example 200

3-(2,2-Dimethylpropyl)-5-methyl-6-[(2-oxoimidazolidin-1-yl)methyl]-1-(3,3,3-trifluoropropyl)thieno[2,3-d]pyrimidine-2,4(1H,3H)-dione

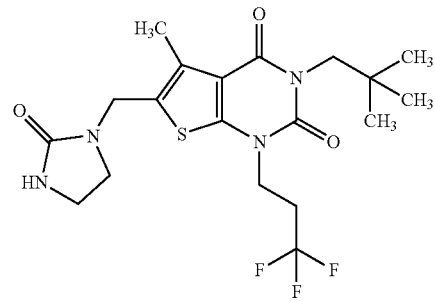

290 mg (0.572 mmol) of the compound from Example 315A were dissolved in 30 ml of dioxane, and 143 mg (0.859 mmol) of CDI were added. The mixture was stirred at RT for 21 h. The reaction solution was then concentrated on a rotary evaporator. The residue was dissolved in 6 ml of DMSO and this solution was purified by means of preparative HPLC (Method 14). Combination of the product fractions and freeze-drying gave 128 mg (49% of theory) of the title compound.

$^1$H-NMR (400 MHz, DMSO-d$_6$, δ/ppm): 6.56 (s, 1H), 4.36 (s, 2H), 4.09 (t, 2H), 3.81 (br. s, 2H), 3.31-3.17 (m, 4H), 2.82-2.69 (m, 2H), 2.39 (s, 3H), 0.89 (s, 9H).

LC/MS (Method 3, ESIpos): R$_t$=1.25 min, m/z=447 [M+H]$^+$.

Example 201

3-(2,2-Dimethylpropyl)-1-(3-fluoropropyl)-5-methyl-6-[(2-oxoimidazolidin-1-yl)methyl]thieno[2,3-d]pyrimidine-2,4(1H,3H)-dione

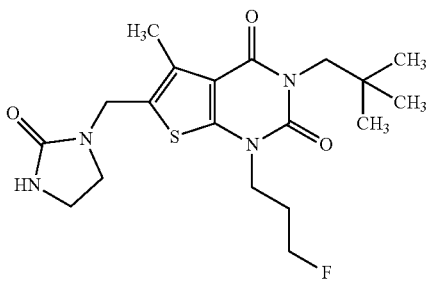 [SMILES: Cc1c(CN2CCNC2=O)sc2c1c(=O)n(CC(C)(C)C)c(=O)n2CCCF]

190 mg (0.405 mmol) of the compound from Example 316A were dissolved in 20 ml of dioxane, and 101 mg (0.608 mmol) of CDI were added. The mixture was stirred at RT for 20 h. The reaction solution was then concentrated on a rotary evaporator. The residue was dissolved in 6 ml of DMSO and this solution was purified by means of preparative HPLC (Method 14). Combination of the product fractions and freeze-drying gave 120 mg (71% of theory) of the title compound.

$^1$H-NMR (400 MHz, DMSO-d$_6$, δ/ppm): 6.55 (s, 1H), 4.59 (t, 1H), 4.47 (t, 1H), 4.35 (s, 2H), 3.97 (t, 2H), 3.81 (br. s, 2H), 3.30-3.17 (m, 4H), 2.38 (s, 3H), 2.12-2.05 (m, 1H), 2.01 (t, 1H), 0.89 (s, 9H).

LC/MS (Method 3, ESIpos): R$_t$=1.15 min, m/z=411 [M+H]$^+$.

Example 202

3-(2,2-Dimethylpropyl)-1-(2-methoxyethyl)-5-methyl-6-[(2-oxoimidazolidin-1-yl)methyl]thieno[2,3-d]pyrimidine-2,4(1H,3H)-dione

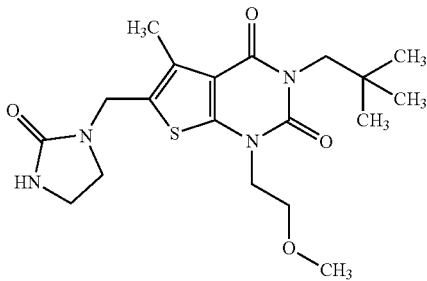 [SMILES: COCCn1c(=O)n(CC(C)(C)C)c(=O)c2c(C)c(CN3CCNC3=O)sc21]

300 mg (0.635 mmol) of the compound from Example 317A were dissolved in 30 ml of dioxane, and 159 mg (0.953 mmol) of CDI were added. The mixture was stirred at RT for 18 h. The reaction solution was then concentrated on a rotary evaporator. The residue was dissolved in 6 ml of DMSO and this solution was purified by means of preparative HPLC (Method 14). Combination of the product fractions and freeze-drying gave 117 mg (43% of theory) of the title compound.

$^1$H-NMR (400 MHz, DMSO-d$_6$, δ/ppm): 6.54 (s, 1H), 4.34 (s, 2H), 4.01 (t, 2H), 3.81 (br. s, 2H), 3.61 (d, 1H), 3.30-3.17 (m, 7H), 2.37 (s, 3H), 0.89 (s, 9H).

LC/MS (Method 3, ESIpos): R$_t$=1.13 min, m/z=409 [M+H]$^+$.

Example 203

1-(2-Methoxyethyl)-5-methyl-3-(3-methylbut-2-en-1-yl)-6-[(2-oxoimidazolidin-1-yl)methyl]thieno[2,3-d]pyrimidine-2,4(1H,3H)-dione

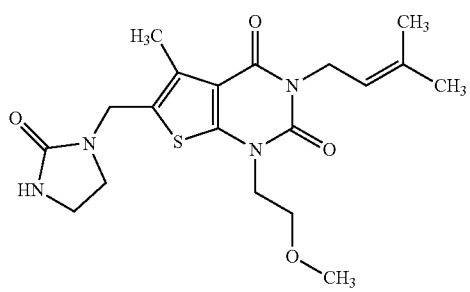 [SMILES: COCCn1c(=O)n(CC=C(C)C)c(=O)c2c(C)c(CN3CCNC3=O)sc21]

To a solution of 190 mg (2.12 mmol) of 2-imidazolidinone in 7.6 ml of THF were added 85 mg (2.12 mmol) of sodium hydride (60% suspension in mineral oil) and the mixture was stirred at RT for 3 h ("Solution 1"). To a solution of 189 mg (0.531 mmol) of the compound from Ex. 149A in 3.7 ml of dichloromethane in another reaction vessel were added, at 0° C., 277 μl (1.59 mmol) of N,N-diisopropylethylamine and 58 μl (0.796 mmol) of thionyl chloride, and the mixture was stirred for 75 min. Subsequently, Solution 1 was added in portions and the mixture was stirred at RT for 18 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 99 mg (45% of theory) of the title compound were obtained.

$^1$H-NMR (400 MHz, DMSO-d$_6$, δ/ppm): 6.54 (s, 1H), 5.14 (ddd, 1H), 4.44 (d, 2H), 4.34 (s, 2H), 4.01 (t, 2H), 3.62 (t, 2H), 3.27-3.17 (m, 7H), 2.38 (s, 3H), 1.75 (d, 3H), 1.66 (d, 3H).

LC/MS (Method 3, ESIpos): R$_t$=1.08 min, m/z=407 [M+H]$^+$.

Example 204

5-Methyl-6-[(2-oxoimidazolidin-1-yl)methyl]-3-(2,2,2-trifluoroethyl)-1-(3,3,3-trifluoropropyl)thieno[2,3-d]pyrimidine-2,4(1H,3H)-dione

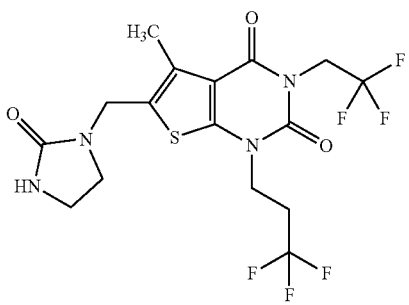

200 mg (0.43 mmol) of the compound from Example 247A were dissolved in 15 ml of dioxane, and 108 mg (0.645 mmol) of CDI were added. The mixture was stirred at RT for 17 h. The reaction solution was then concentrated on a rotary evaporator. The residue was dissolved in 6 ml of DMSO and this solution was purified by means of preparative HPLC (Method 14). Combination of the product fractions and freeze-drying gave 125 mg (63% of theory) of the title compound.

$^1$H-NMR (400 MHz, DMSO-$d_6$, δ/ppm): 6.58 (s, 1H), 4.70 (q, 2H), 4.38 (s, 2H), 4.13 (t, 2H), 3.30-3.18 (m, 4H), 2.84-2.70 (m, 2H), 2.40 (s, 3H).

LC/MS (Method 3, ESIpos): $R_t$=1.10 min, m/z=459 [M+H]$^+$.

Example 205

1-(2-Ethoxyethyl)-5-methyl-6-[(2-oxoimidazolidin-1-yl)methyl]-3-(2,2,2-trifluoroethyl)thieno[2,3-d]pyrimidine-2,4(1H,3H)-dione

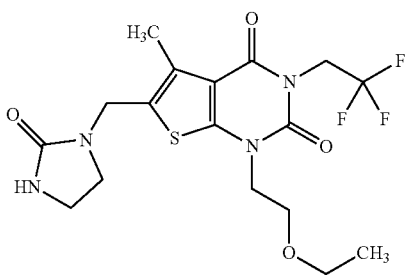 [SMILES: CCOCCn1c(=O)n(CC(F)(F)F)c(=O)c2c(C)c(CN3CCNC3=O)sc21]

113 mg (0.177 mmol) of the compound from Example 250A were dissolved in 10 ml of dioxane, and 44 mg (0.266 mmol) of CDI were added. The mixture was stirred at RT for 18 h. The reaction solution was then concentrated on a rotary evaporator. The residue was dissolved in 3 ml of DMSO and this solution was purified by means of preparative HPLC (Method 14). Combination of the product fractions and freeze-drying gave 58 mg (75% of theory) of the title compound.

$^1$H-NMR (400 MHz, DMSO-$d_6$, δ/ppm): 6.56 (s, 1H), 4.69 (q, 2H), 4.36 (s, 2H), 4.04 (t, 2H), 3.66 (t, 2H), 3.43 (q, 2H), 3.28-3.17 (m, 4H), 2.39 (s, 3H), 1.02 (t, 3H).

LC/MS (Method 3, ESIpos): $R_t$=1.04 min, m/z=435 [M+H]$^+$.

Example 206

5-Methyl-1-(oxetan-2-ylmethyl)-6-[(2-oxoimidazolidin-1-yl)methyl]-3-(2,2,2-trifluoroethyl)thieno[2,3-d]pyrimidine-2,4(1H,3H)-dione (racemate)

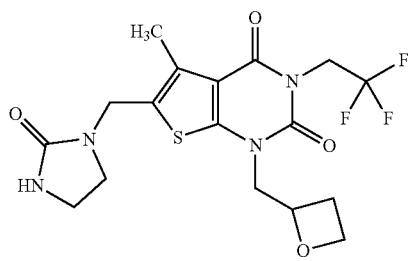 [SMILES: Cc1c(CN2CCNC2=O)sc2c1c(=O)n(CC(F)(F)F)c(=O)n2CC1CCO1]

520 mg (1.13 mmol) of the compound from Example 251A were dissolved in 25 ml of dioxane, and 282 mg (1.69 mmol) of CDI were added. The mixture was stirred at RT for 18 h. The reaction solution was then concentrated on a rotary evaporator. The residue was dissolved in 12 ml of DMSO and this solution was purified by means of preparative HPLC (Method 14). Combination of the product fractions and freeze-drying gave 286 mg (58% of theory) of the title compound.

$^1$H-NMR (400 MHz, DMSO-$d_6$, δ/ppm): 6.56 (s, 1H), 5.05-4.96 (m, 1H), 4.70 (q, 2H), 4.51-4.38 (m, 2H), 4.36 (s, 2H), 4.22-4.10 (m, 2H), 3.29-3.18 (m, 4H), 2.74-2.64 (m, 1H), 2.39 (s, 3H).

LC/MS (Method 3, ESIpos): $R_t$=0.95 min, m/z=433 [M+H]$^+$.

Example 207

5-Methyl-1-(oxetan-2-ylmethyl)-6-[(2-oxoimidazolidin-1-yl)methyl]-3-(2,2,2-trifluoroethyl)thieno[2,3-d]pyrimidine-2,4(1H,3H)-dione (Enantiomer 1)

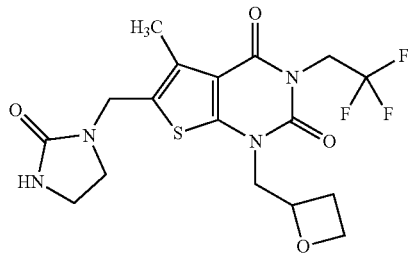 [SMILES: Cc1c(CN2CCNC2=O)sc2c1c(=O)n(CC(F)(F)F)c(=O)n2CC1CCO1]

253 mg of the racemic compound from Ex. 206 were dissolved in 7 ml of a methanol/acetonitrile mixture (1:1 v/v) and separated into the enantiomers by means of preparative HPLC on a chiral phase [column: Daicel Chiralpak IC, 5 μm, 250 mm×30 mm; eluent: ethanol/methanol/diethylamine 50:50:0.1; flow rate: 30 ml/min; temperature: RT; detection: 254 nm]. The product fractions were concentrated on a rotary evaporator, admixed with tert-butanol and freeze-dried. 100 mg (39% of theory) of the title compound (Enantiomer 1) and 120 mg (47% of theory) of Enantiomer 2 (see Example 208) were obtained.

¹H-NMR (400 MHz, DMSO-$d_6$, δ/ppm): 6.56 (s, 1H), 5.05-4.96 (m, 1H), 4.70 (q, 2H), 4.51-4.45 (m, 1H), 4.41 (dt, 1H), 4.35 (s, 2H), 4.19-4.14 (m, 2H), 3.28-3.19 (m, 4H), 2.69 (dtd, 1H), 2.39 (s, 3H).

Chiral analytical HPLC [column: Daicel Chiralpak IC, 5 µm, 100 mm×4.6 mm; eluent: methanol+0.1% diethylamine/ ethanol 50:50; flow rate: 1.0 ml/min; temperature: RT; injection: 5 µl; DAD 254 nm; solution: 1.0 mg/ml of methanol]: $R_t$=7.94 min.

Example 208

5-Methyl-1-(oxetan-2-ylmethyl)-6-[(2-oxoimidazolidin-1-yl)methyl]-3-(2,2,2-trifluoroethyl)thieno[2,3-d]pyrimidine-2,4(1H,3H)-dione (Enantiomer 2)

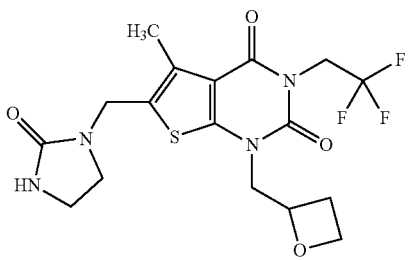 [SMILES: Cc1c(CN2CCNC2=O)sc2c1c(=O)n(CC(F)(F)F)c(=O)n2CC1CCO1]

The title compound (120 mg) was obtained as the second enantiomer in the preparative HPLC separation of the racemate from Ex. 206 described in Ex. 207.

¹H-NMR (400 MHz, DMSO-$d_6$, δ/ppm): 6.56 (s, 1H), 5.05-4.96 (m, 1H), 4.70 (q, 2H), 4.51-4.45 (m, 1H), 4.41 (dt, 1H), 4.35 (s, 2H), 4.21-4.11 (m, 2H), 3.29-3.17 (m, 4H), 2.69 (dtd, 1H), 2.39 (s, 3H).

Chiral analytical HPLC [column: Daicel Chiralpak IC, 5 µm, 100 mm×4.6 mm; eluent: methanol+0.1% diethylamine/ ethanol 50:50; flow rate: 1.0 ml/min; temperature: RT; injection: 5 µl; DAD 254 nm; solution: 1.0 mg/ml of methanol]: $R_t$=9.15 min.

Example 209

5-Methyl-6-[(2-oxoimidazolidin-1-yl)methyl]-1-(tetrahydrofuran-2-ylmethyl)-3-(2,2,2-trifluoroethyl) thieno[2,3-d]pyrimidine-2,4(1H,3H)-dione (racemate)

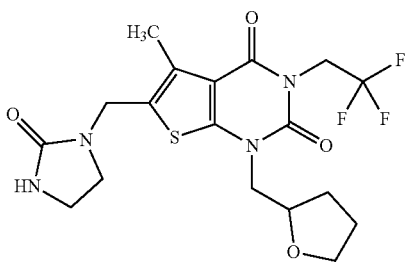

570 mg (1.1 mmol) of the compound from Example 252A were dissolved in 25 ml of dioxane, and 275 mg (1.65 mmol) of CDI were added. The mixture was stirred at RT for 17 h. The reaction solution was then concentrated on a rotary evaporator. The residue was dissolved in 12 ml of DMSO and this solution was purified by means of preparative HPLC (Method 14). Combination of the product fractions and freeze-drying gave 232 mg (71% of theory) of the title compound.

¹H-NMR (400 MHz, DMSO-$d_6$, δ/ppm): 6.56 (s, 1H), 4.70 (q, 2H), 4.36 (s, 2H), 4.26-4.18 (m, 1H), 4.05 (dd, 1H), 3.79-3.70 (m, 2H), 3.65-3.57 (m, 1H), 3.29-3.17 (m, 4H), 2.39 (s, 3H), 2.04-1.94 (m, 1H), 1.94-1.75 (m, 2H), 1.71-1.61 (m, 1H).

LC/MS (Method 3, ESIpos): $R_t$=1.02 min, m/z=447 [M+H]⁺.

Example 210

5-Methyl-6-[(2-oxoimidazolidin-1-yl)methyl]-1-(tetrahydrofuran-2-ylmethyl)-3-(2,2,2-trifluoroethyl) thieno[2,3-d]pyrimidine-2,4(1H,3H)-dione (Enantiomer 1)

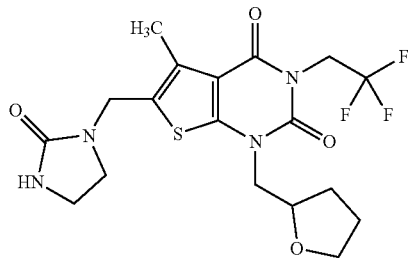 [SMILES: Cc1c(CN2CCNC2=O)sc2c1c(=O)n(CC(F)(F)F)c(=O)n2CC1CCCO1]

253 mg of the racemic compound from Ex. 209 were dissolved in 6 ml of a methanol/acetonitrile mixture (1:1 v/v) and separated into the enantiomers by means of preparative HPLC on a chiral phase [column: Daicel Chiralpak IC, 5 µm, 250 mm×30 mm; eluent: ethanol/methanol/diethylamine 50:50:0.1; flow rate: 30 ml/min; temperature: RT; detection: 254 nm]. The product fractions were concentrated on a rotary evaporator, admixed with tert-butanol and freeze-dried. 100 mg (39% of theory) of the title compound (Enantiomer 1) and 100 mg (39% of theory) of Enantiomer 2 (see Example 211) were obtained.

¹H-NMR (400 MHz, DMSO-$d_6$, δ/ppm): 6.56 (s, 1H), 4.70 (q, 2H), 4.36 (s, 2H), 4.27-4.17 (m, 1H), 4.05 (dd, 1H), 3.78-3.70 (m, 2H), 3.61 (td, 1H), 3.29-3.18 (m, 4H), 2.39 (s, 3H), 2.03-1.93 (m, 1H), 1.93-1.75 (m, 2H), 1.71-1.61 (m, 1H).

Chiral analytical HPLC [column: Daicel Chiralpak IC, 5 µm, 100 mm×4.6 mm; eluent: methanol+0.1% diethylamine/ ethanol 50:50; flow rate: 1.0 ml/min; temperature: RT; injection: 5 µl; DAD 254 nm; solution: 1.0 mg/ml of methanol]: $R_t$=6.04 min.

Example 211

5-Methyl-6-[(2-oxoimidazolidin-1-yl)methyl]-1-(tetrahydrofuran-2-ylmethyl)-3-(2,2,2-trifluoroethyl)thieno[2,3-d]pyrimidine-2,4(1H,3H)-dione (Enantiomer 2)

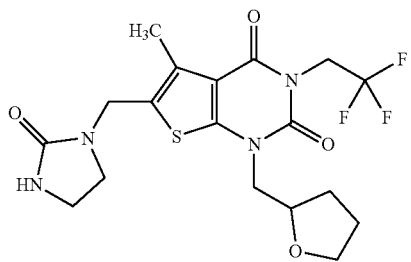 [SMILES: Cc1c(CN2CCNC2=O)sc2c1c(=O)n(CC(F)(F)F)c(=O)n2CC1CCCO1]

The title compound (100 mg) was obtained as the second enantiomer in the preparative HPLC separation of the racemate from Ex. 209 described in Ex. 210.

$^1$H-NMR (400 MHz, DMSO-$d_6$, δ/ppm): 6.56 (s, 1H), 4.70 (q, 2H), 4.36 (s, 2H), 4.26-4.18 (m, 1H), 4.05 (dd, 1H), 3.74 (dd, 2H), 3.61 (td, 1H), 3.28-3.18 (m, 4H), 2.39 (s, 3H), 2.03-1.93 (m, 1H), 1.93-1.76 (m, 2H), 1.71-1.61 (m, 1H).

Chiral analytical HPLC [column: Daicel Chiralpak IC, 5 µm, 100 mm×4.6 mm; eluent: methanol+0.1% diethylamine/ethanol 50:50; flow rate: 1.0 ml/min; temperature: RT; injection: 5 µl; DAD 254 nm; solution: 1.0 mg/ml of methanol]: $R_t$=8.09 min.

Example 212

5-Methyl-1-(oxetan-3-ylmethyl)-6-[(2-oxoimidazolidin-1-yl)methyl]-3-(2,2,2-trifluoroethyl)thieno[2,3-d]pyrimidine-2,4(1H,3H)-dione

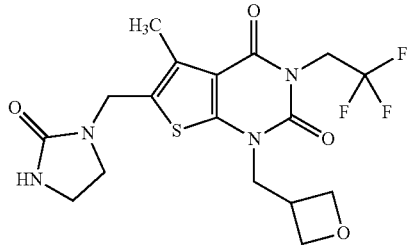 [SMILES: Cc1c(CN2CCNC2=O)sc2c1c(=O)n(CC(F)(F)F)c(=O)n2CC1COC1]

109 mg (0.091 mmol) of the compound from Example 253A were dissolved in 10 ml of dioxane, and 23 mg (0.137 mmol) of CDI were added. The mixture was stirred at RT for 17 h. The reaction solution was then concentrated on a rotary evaporator. The residue was dissolved in 3 ml of DMSO and this solution was purified by means of preparative HPLC (Method 14). Combination of the product fractions and freeze-drying gave 64 mg (39% of theory) of the title compound.

$^1$H-NMR (400 MHz, DMSO-$d_6$, δ/ppm): 6.57 (s, 1H), 4.68 (q, 2H), 4.61 (dd, 2H), 4.43 (t, 2H), 4.37 (s, 2H), 4.23 (d, 2H), 3.48-3.37 (m, 1H), 3.30-3.17 (m, 4H), 2.39 (s, 3H).

LC/MS (Method 3, ESIpos): $R_t$=0.94 min, m/z=433 [M+H]$^+$.

Example 213

1,5-Dimethyl-6-[(2-oxoimidazolidin-1-yl)methyl]-3-(2,2,2-trifluoroethyl)thieno[2,3-d]pyrimidine-2,4(1H,3H)-dione

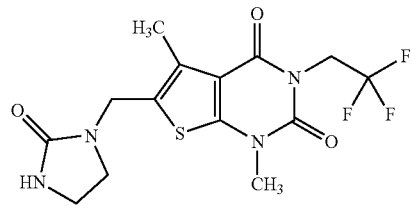 [SMILES: Cc1c(CN2CCNC2=O)sc2c1c(=O)n(CC(F)(F)F)c(=O)n2C]

190 mg (0.239 mmol) of the compound from Example 254A were dissolved in 15 ml of dioxane, and 60 mg (0.358 mmol) of CDI were added. The mixture was stirred at RT for 20 h. The reaction solution was then concentrated on a rotary evaporator. The residue was dissolved in 3 ml of DMSO and this solution was purified by means of preparative HPLC (Method 14). Combination of the product fractions and freeze-drying gave 48 mg (52% of theory) of the title compound.

$^1$H-NMR (400 MHz, DMSO-$d_6$, δ/ppm): 6.56 (s, 1H), 4.69 (q, 2H), 4.37 (s, 2H), 3.44 (s, 3H), 3.28-3.18 (m, 4H), 2.40 (s, 3H).

LC/MS (Method 3, ESIpos): $R_t$=0.93 min, m/z=377 [M+H]$^+$.

Example 214

3-(2,2-Difluoroethyl)-5-methyl-6-[(2-oxoimidazolidin-1-yl)methyl]-1-(3,3,3-trifluoropropyl)thieno[2,3-d]pyrimidine-2,4(1H,3H)-dione

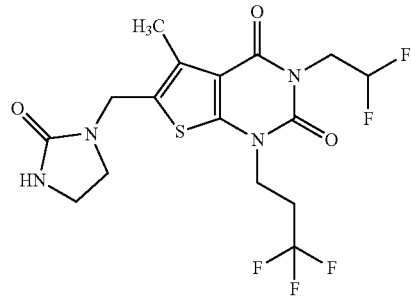 [SMILES: Cc1c(CN2CCNC2=O)sc2c1c(=O)n(CC(F)F)c(=O)n2CCC(F)(F)F]

150 mg (0.257 mmol) of the compound from Example 255A were dissolved in 10 ml of dioxane, and 64 mg (0.385 mmol) of CDI were added. The mixture was stirred at RT for 17 h. The reaction solution was then concentrated on a rotary evaporator. The residue was dissolved in 3 ml of DMSO and this solution was purified by means of preparative HPLC (Method 14). Combination of the product fractions and freeze-drying gave 92 mg (81% of theory) of the title compound.

$^1$H-NMR (400 MHz, DMSO-$d_6$, δ/ppm): 6.58 (s, 1H), 6.37-6.04 (m, 1H), 4.38 (s, 2H), 4.29 (td, 2H), 4.11 (t, 2H), 3.29-3.18 (m, 4H), 2.84-2.70 (m, 2H), 2.40 (s, 3H).

LC/MS (Method 3, ESIpos): $R_t$=1.04 min, m/z=441 [M+H]$^+$.

Example 215

3-(2,2-Difluoroethyl)-1-(2-ethoxyethyl)-5-methyl-6-[(2-oxoimidazolidin-1-yl)methyl]thieno[2,3-d]pyrimidine-2,4(1H,3H)-dione

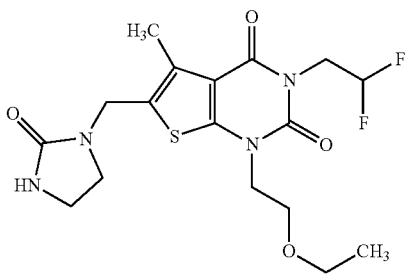

120 mg (0.231 mmol) of the compound from Example 258A were dissolved in 10 ml of dioxane, and 58 mg (0.346 mmol) of CDI were added. The mixture was stirred at RT for 17 h. The reaction solution was then concentrated on a rotary evaporator. The residue was dissolved in 3 ml of DMSO and this solution was purified by means of preparative HPLC (Method 14). Combination of the product fractions and freeze-drying gave 55 mg (56% of theory) of the title compound.

$^1$H-NMR (400 MHz, DMSO-$d_6$, δ/ppm): 6.56 (s, 1H), 6.38-6.05 (m, 1H), 4.36 (s, 2H), 4.29 (td, 2H), 4.03 (t, 2H), 3.66 (t, 2H), 3.43 (q, 2H), 3.28-3.16 (m, 4H), 2.39 (s, 3H), 1.03 (t, 3H).

LC/MS (Method 3, ESIpos): $R_t$=0.99 min, m/z=417 [M+H]$^+$.

Example 216

3-(2,2-Difluoroethyl)-5-methyl-1-(oxetan-2-ylmethyl)-6-[(2-oxoimidazolidin-1-yl)methyl]thieno[2,3-d]pyrimidine-2,4(1H,3H)-dione (racemate)

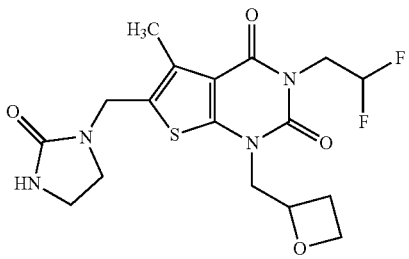 [SMILES: Cc1c(CN2CCNC2=O)sc2c1c(=O)n(CC(F)F)c(=O)n2CC1CCO1]

446 mg (0.907 mmol) of the compound from Example 259A were dissolved in 16 ml of dioxane, and 227 mg (1.36 mmol) of CDI were added. The mixture was stirred at RT for 17 h. The reaction solution was then concentrated on a rotary evaporator. The residue was dissolved in 9 ml of DMSO and this solution was purified by means of preparative HPLC (Method 14). Combination of the product fractions and freeze-drying gave 210 mg (55% of theory) of the title compound.

$^1$H-NMR (400 MHz, DMSO-$d_6$, δ/ppm): 6.55 (s, 1H), 6.37-6.06 (m, 1H), 5.05-4.97 (m, 1H), 4.51-4.38 (m, 2H), 4.35 (s, 2H), 4.29 (td, 2H), 4.15 (d, 2H), 3.28-3.17 (m, 4H), 2.74-2.64 (m, 1H), 2.39 (s, 3H).

LC/MS (Method 3, ESIpos): $R_t$=0.88 min, m/z=415 [M+H]$^+$.

Example 217

3-(2,2-Difluoroethyl)-5-methyl-1-(oxetan-2-ylmethyl)-6-[(2-oxoimidazolidin-1-yl)methyl]thieno[2,3-d]pyrimidine-2,4(1H,3H)-dione (Enantiomer 1)

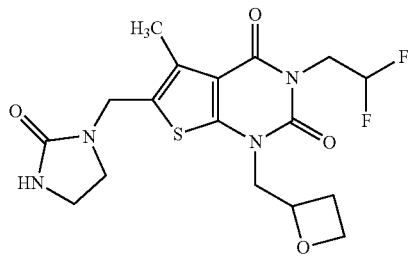 [SMILES: Cc1c(CN2CCNC2=O)sc2c1c(=O)n(CC(F)F)c(=O)n2CC1CCO1]

179 mg of the racemic compound from Ex. 216 were dissolved in 6.5 ml of DMSO and separated into the enantiomers by means of preparative HPLC on a chiral phase [column: Daicel Chiralpak IB, 5 µm, 250 mm×20 mm; eluent A: hexane, eluent B: ethanol; isocratic 58% A, 42% B; flow rate: 15 ml/min; temperature: RT; detection: 254 nm]. The product fractions were concentrated on a rotary evaporator, admixed with tert-butanol and freeze-dried. 75 mg (41% of theory) of the title compound (Enantiomer 1) and 58 mg (31% of theory) of Enantiomer 2 (see Example 218) were obtained.

$^1$H-NMR (400 MHz, DMSO-$d_6$, δ/ppm): 6.55 (s, 1H), 6.37-6.04 (m, 1H), 5.05-4.96 (m, 1H), 4.51-4.38 (m, 2H), 4.35 (s, 2H), 4.29 (td, 2H), 4.15 (d, 2H), 3.28-3.17 (m, 4H), 2.69 (dtd, 1H), 2.39 (s, 3H).

Chiral analytical HPLC [column: Daicel Chiralpak IB, 3 µm, 100 mm×4.6 mm; eluent A: hexane, eluent B: ethanol; isocratic 58% A, 42% B; flow rate: 1.0 ml/min; temperature: 25° C.; injection: 5 µl; DAD 254 nm]: $R_t$=4.63 min.

Example 218

3-(2,2-Difluoroethyl)-5-methyl-1-(oxetan-2-ylmethyl)-6-[(2-oxoimidazolidin-1-yl)methyl]thieno[2,3-d]pyrimidine-2,4(1H,3H)-dione (Enantiomer 2)

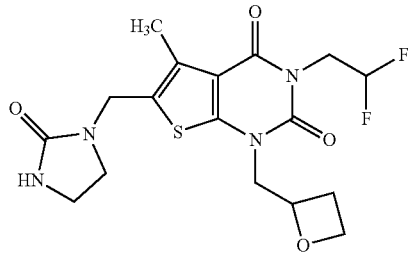 [SMILES: Cc1c(CN2CCNC2=O)sc2c1c(=O)n(CC(F)F)c(=O)n2CC1CCO1]

The title compound (58 mg) was obtained as the second enantiomer in the preparative HPLC separation of the racemate from Ex. 216 described in Ex. 217.

¹H-NMR (400 MHz, DMSO-d₆, δ/ppm): 6.55 (s, 1H), 6.38-6.06 (m, 1H), 5.05-4.96 (m, 1H), 4.52-4.38 (m, 2H), 4.35 (s, 2H), 4.29 (td, 2H), 4.15 (d, 2H), 3.28-3.18 (m, 4H), 2.69 (dtd, 1H), 2.39 (s, 3H).

Chiral analytical HPLC [column: Daicel Chiralpak IB, 3 µm, 100 mm×4.6 mm; eluent A: hexane, eluent B: ethanol; isocratic 58% A, 42% B; flow rate: 1.0 ml/min; temperature: 25° C.; injection: 5 µl; DAD 254 nm]: $R_t$=5.70 min.

Example 219

3-(2,2-Difluoroethyl)-5-methyl-6-[(2-oxoimidazolidin-1-yl)methyl]-1-(tetrahydrofuran-2-ylmethyl)thieno[2,3-d]pyrimidine-2,4(1H,3H)-dione (racemate)

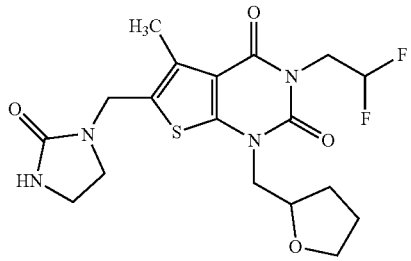 [SMILES: Cc1c(CN2CCNC2=O)sc2c1c(=O)n(CC(F)F)c(=O)n2CC1CCCO1]

444 mg (0.695 mmol) of the compound from Example 260A were dissolved in 15 ml of dioxane, and 174 mg (1.04 mmol) of CDI were added. The mixture was stirred at RT for 18 h. The reaction solution was then concentrated on a rotary evaporator. The residue was dissolved in 9 ml of DMSO and this solution was purified by means of preparative HPLC (Method 14). Combination of the product fractions and freeze-drying gave 156 mg (52% of theory) of the title compound.

¹H-NMR (400 MHz, DMSO-d₆, δ/ppm): 6.55 (s, 1H), 6.38-6.04 (m, 1H), 4.35 (s, 2H), 4.30 (td, 2H), 4.22 (td, 1H), 4.05 (dd, 1H), 3.78-3.68 (m, 2H), 3.65-3.58 (m, 1H), 3.28-3.17 (m, 4H), 2.39 (s, 3H), 2.04-1.94 (m, 1H), 1.93-1.77 (m, 2H), 1.71-1.61 (m, 1H).

LC/MS (Method 3, ESIpos): $R_t$=0.95 min, m/z=429 [M+H]⁺.

Example 220

3-(2, 2-Difluoroethyl)-5-methyl-6-[(2-oxoimidazolidin-1-yl)methyl]-1-(tetrahydrofuran-2-ylmethyl)thieno[2,3-d]pyrimidine-2,4(1H,3H)-dione (Enantiomer 1)

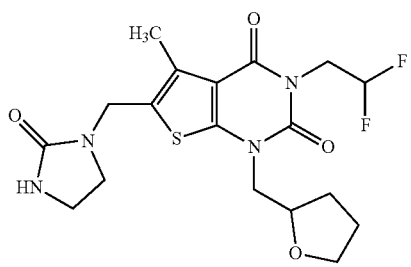

135 mg of the racemic compound from Ex. 219 were dissolved in 3 ml of a dichloromethane/methanol mixture (1:1 v/v) and separated into the enantiomers by means of preparative HPLC on a chiral phase [column: Daicel Chiralpak IC, 5 µm, 250 mm×30 mm; eluent: ethanol/methanol/diethylamine 50:50:0.1; flow rate: 30 ml/min; temperature: RT; detection: 254 nm]. The product fractions were concentrated on a rotary evaporator, admixed with tert-butanol and freeze-dried. 60 mg (43% of theory) of the title compound (Enantiomer 1) and 60 mg (43% of theory) of Enantiomer 2 (see Example 221) were obtained.

¹H-NMR (400 MHz, DMSO-d₆, δ/ppm): 6.57 (s, 1H), 6.38-6.06 (m, 1H), 4.35 (s, 2H), 4.29 (td, 2H), 4.24-4.18 (m, 1H), 4.05 (dd, 1H), 3.78-3.67 (m, 2H), 3.65-3.57 (m, 1H), 3.27-3.16 (m, 4H), 2.39 (s, 3H), 2.03-1.93 (m, 1H), 1.93-1.75 (m, 2H), 1.71-1.60 (m, 1H).

Chiral analytical HPLC [column: Daicel Chiralpak IC, 5 µm, 100 mm×4.6 mm; eluent: methanol+0.1% diethylamine/ethanol 50:50; flow rate: 1.0 ml/min; temperature: RT; injection: 5 µl; DAD 254 nm; solution: 1.0 mg/ml of methanol]: $R_t$=9.31 min.

Example 221

3-(2, 2-Difluoroethyl)-5-methyl-6-[(2-oxoimidazolidin-1-yl)methyl]-1-(tetrahydrofuran-2-ylmethyl)thieno[2,3-d]pyrimidine-2,4(1H,3H)-dione (Enantiomer 2)

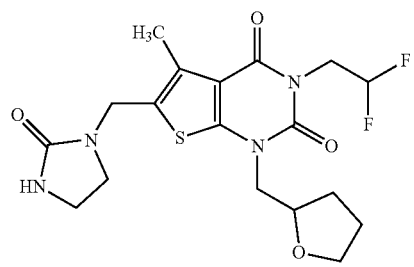 [SMILES: Cc1c(CN2CCNC2=O)sc2c1c(=O)n(CC(F)F)c(=O)n2CC1CCCO1]

The title compound (60 mg) was obtained as the second enantiomer in the preparative HPLC separation of the racemate from Ex. 219 described in Ex. 220.

¹H-NMR (400 MHz, DMSO-d₆, δ/ppm): 6.55 (s, 1H), 6.38-6.05 (m, 1H), 4.35 (s, 2H), 4.29 (td, 2H), 4.25-4.18 (m, 1H), 4.05 (dd, 1H), 3.78-3.68 (m, 2H), 3.65-3.57 (m, 1H), 3.28-3.17 (m, 4H), 2.39 (s, 3H), 2.03-1.93 (m, 1H), 1.93-1.75 (m, 2H), 1.71-1.61 (m, 1H).

Chiral analytical HPLC [column: Daicel Chiralpak IC, 5 µm, 100 mm×4.6 mm; eluent: methanol+0.1% diethylamine/ethanol 50:50; flow rate: 1.0 ml/min; temperature: RT; injection: 5 µl; DAD 254 nm; solution: 1.0 mg/ml of methanol]: $R_t$=12.96 min.

Example 222

3-(2,2-Difluoroethyl)-5-methyl-1-(oxetan-3-ylmethyl)-6-[(2-oxoimidazolidin-1-yl)methyl]thieno[2,3-d]pyrimidine-2,4(1H,3H)-dione

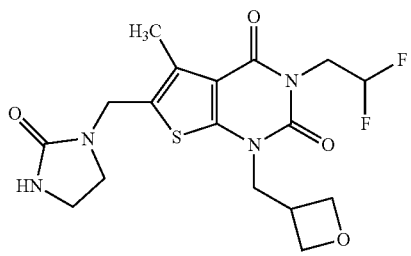

85 mg (0.147 mmol) of the compound from Example 261A were dissolved in 10 ml of dioxane, and 37 mg (1.36 mmol) of CDI were added. The mixture was stirred at RT for 17 h. The reaction solution was then concentrated on a rotary evaporator. The residue was dissolved in 3 ml of DMSO and this solution was purified by means of preparative HPLC (Method 14). Combination of the product fractions and freeze-drying gave 55 mg (60% of theory) of the title compound.

$^1$H-NMR (400 MHz, DMSO-$d_6$, δ/ppm): 6.57 (s, 1H), 6.35-6.02 (m, 1H), 4.62 (dd, 2H), 4.43 (t, 2H), 4.36 (s, 2H), 4.28 (td, 2H), 4.22 (d, 2H), 3.41 (d, 1H), 3.28-3.18 (m, 4H), 2.39 (s, 3H).

LC/MS (Method 3, ESIpos): $R_t$=0.86 min, m/z=415 [M+H]$^+$.

Example 223

3-(2,2-Difluoroethyl)-1,5-dimethyl-6-[(2-oxoimidazolidin-1-yl)methyl]thieno[2,3-d]pyrimidine-2,4(1H,3H)-dione

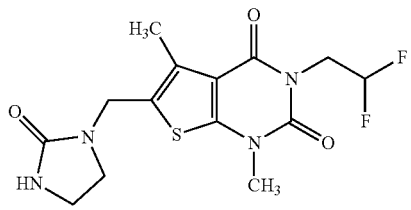 [SMILES: Cc1c(CN2CCNC2=O)sc2c1c(=O)n(CC(F)F)c(=O)n2C]

110 mg (0.232 mmol) of the compound from Example 318A were dissolved in 12 ml of dioxane, and 58 mg (0.347 mmol) of CDI were added. The mixture was stirred at RT for 13 h. The reaction solution was then concentrated on a rotary evaporator. The residue was dissolved in 3 ml of DMSO and this solution was purified by means of preparative HPLC (Method 14). Combination of the product fractions and freeze-drying gave 53 mg (63% of theory) of the title compound.

$^1$H-NMR (400 MHz, DMSO-$d_6$, δ/ppm): 6.54 (s, 1H), 6.37-6.04 (m, 1H), 4.37 (s, 2H), 4.29 (td, 2H), 3.43 (s, 3H), 3.28-3.18 (m, 4H), 2.40 (s, 3H).

LC/MS (Method 3, ESIpos): $R_t$=0.86 min, m/z=359 [M+H]$^+$.

Example 224

3-(3-Fluoropropyl)-1-(2-methoxyethyl)-5-methyl-6-[(2-oxoimidazolidin-1-yl)methyl]thieno[2,3-d]pyrimidine-2,4(1H,3H)-dione

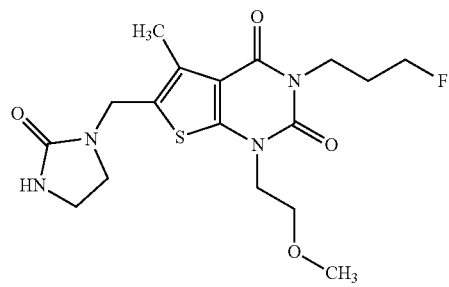 [SMILES: COCCn1c(=O)n(CCCF)c(=O)c2c(C)c(CN3CCNC3=O)sc21]

To a solution of 172 mg (1.92 mmol) of 2-imidazolidinone in 7 ml of THF were added 77 mg (1.92 mmol) of sodium hydride (60% suspension in mineral oil) and the mixture was stirred at RT for 3 h ("Solution 1"). To a solution of 160 mg (0.479 mmol) of the compound from Ex. 156A in 3.3 ml of dichloromethane in another reaction vessel were added, at 0° C., 250 µl (1.44 mmol) of N,N-diisopropylethylamine and 52 µl (0.719 mmol) of thionyl chloride, and the mixture was stirred for 75 min. Subsequently, Solution 1 was added in portions and the mixture was stirred at RT for 19 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 113 mg (58% of theory) of the title compound were obtained.

$^1$H-NMR (400 MHz, DMSO-$d_6$, δ/ppm): 6.54 (s, 1H), 4.54 (t, 1H), 4.42 (t, 1H), 4.34 (s, 2H), 4.04-3.94 (m, 4H), 3.62 (t, 2H), 3.28-3.17 (m, 7H), 2.39 (s, 3H), 2.01-1.85 (m, 2H).

LC/MS (Method 3, ESIpos): $R_t$=0.88 min, m/z=399 [M+H]$^+$.

Example 225

3-(2-Fluoro-2-methylpropyl)-5-methyl-6-[(2-oxoimidazolidin-1-yl)methyl]-1-(3,3,3-trifluoropropyl)thieno[2,3-d]pyrimidine-2,4(1H,3H)-dione

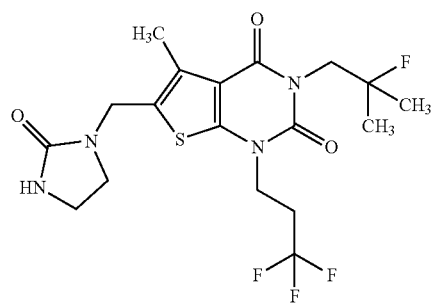 [SMILES: Cc1c(CN2CCNC2=O)sc2c1c(=O)n(CC(C)(C)F)c(=O)n2CCC(F)(F)F]

To a solution of 150 mg (1.75 mmol) of imidazolidin-2-one in 4.5 ml of DMF were added 70 mg (1.75 mmol) of sodium hydride (60% suspension in mineral oil), then the mixture was heated to 60° C. for 5 min and subsequently cooled back down to RT ("Solution 1"). To a solution of 180 mg (0.438 mmol) of the compound from Ex. 304A in 3.3 ml of dichloromethane in another reaction vessel were added, at 0° C., 153 µl (0.876 mmol) of N,N-diisopropylethylamine and 34 µl (0.460 mmol) of thionyl chloride. After 20 min at 0° C., Solution 1 was added in portions and then the cooling bath was removed. The reaction mixture was stirred at RT for about 18 h. All the volatile constituents were then removed on a rotary evaporator. The remaining residue was separated into its components by means of preparative HPLC (Method 8). The product fractions were combined and concentrated and the residue was stirred in a little diisopropyl ether at RT. After the solids had been filtered off with suction and dried under high vacuum, 75 mg (37% of theory) of the title compound were obtained.

$^1$H-NMR (400 MHz, DMSO-$d_6$, δ/ppm): 6.54 (s, 1H), 4.37 (s, 2H), 4.21-4.05 (m, 4H), 3.30-3.16 (m, 4H, partially obscured by the water signal), 2.86-2.68 (m, 2H), 2.40 (s, 3H), 1.32 (d, 6H).

LC/MS (Method 17, ESIpos): $R_t$=1.60 min, m/z=451.14 [M+H]$^+$.

Example 226

3-(2-Fluoro-2-methylpropyl)-1-(2-methoxyethyl)-5-methyl-6-[(2-oxoimidazolidin-1-yl)methyl]thieno[2,3-d]pyrimidine-2,4(1H,3H)-dione

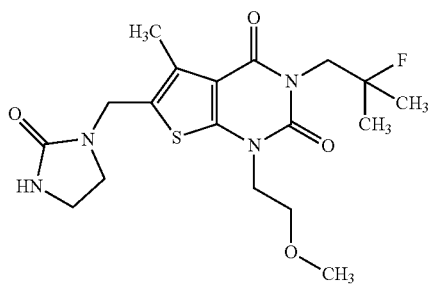 [SMILES: COCCn1c(=O)n(CC(C)(C)F)c(=O)c2c(C)c(CN3CCNC3=O)sc21]

Analogously to the method described in Ex. 225, 135 mg (0.392 mmol) of the compound from Ex. 305A and 135 mg (1.57 mmol) of imidazolidin-2-one were used to obtain 46 mg (28% of theory) of the title compound.

$^1$H-NMR (400 MHz, DMSO-$d_6$, δ/ppm): 6.53 (s, 1H), 4.35 (s, 2H), 4.15 (d, 2H), 4.03 (t, 2H), 3.62 (t, 2H), 3.29-3.15 (m, 4H, partially obscured by the water signal), 3.23 (s, 3H), 2.38 (s, 3H), 1.31 (d, 6H).

LC/MS (Method 1, ESIpos): $R_t$=0.74 min, m/z=413 [M+H]$^+$.

Example 227

3-(2-Hydroxy-2-methylpropyl)-5-methyl-6-[(2-oxoimidazolidin-1-yl)methyl]-1-(3,3,3-trifluoropropyl)thieno[2,3-d]pyrimidine-2,4(1H,3H)-dione

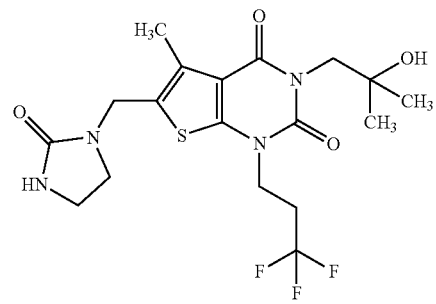 [SMILES: Cc1c(CN2CCNC2=O)sc2c1c(=O)n(CC(C)(C)O)c(=O)n2CCC(F)(F)F]

To a solution of 70 mg (0.151 mmol) of the compound from Ex. 355A in 2 ml of THF were added 50 µl (0.150 mmol) of a 3 M solution of methylmagnesium chloride in THF. After stirring at RT for 30 min, a further 100 µl (0.300 mmol) of the methylmagnesium chloride solution were added. After a further 45 min at RT, the reaction mixture was admixed with saturated aqueous ammonium chloride solution and extracted with ethyl acetate. The organic extract was dried over anhydrous magnesium sulphate, filtered and concentrated. The remaining, highly contaminated residue was purified by means of preparative HPLC twice in succession (Method 8 each time). The still slightly contaminated product thus obtained was then purified by means of preparative HPLC for a third time [column: Kinetex C18, 5 µm, 100 mm×30 mm; eluent A: water+0.07% formic acid; eluent B: acetonitrile; gradient: 0.0-2.2 min 10% B, 2.2-7.0 min 20% B, 7.0-7.5 min 60% B, 7.5-9.0 min 92% B; flow rate: 70 ml/min; temperature: 25° C.; detection: 210 nm]. After concentration of the product fractions and drying under high vacuum, 5 mg (7% of theory) of the title compound were obtained.

$^1$H-NMR (400 MHz, CDCl$_3$, δ/ppm): 4.47 (s, 2H), 4.39 (br. s, 1H), 4.23-4.12 (m, 4H), 3.64 (s, 1H), 3.50-3.33 (m, 4H), 2.72-2.53 (m, 2H), 2.48 (s, 3H), 1.26 (s, 6H).

LC/MS (Method 1, ESIpos): $R_t$=0.76 min, m/z=449 [M+H]$^+$.

Example 228

3-(2-Hydroxy-2-methylpropyl)-1-(2-methoxyethyl)-5-methyl-6-[(2-oxoimidazolidin-1-yl)methyl]thieno[2,3-d]pyrimidine-2,4(1H,3H)-dione

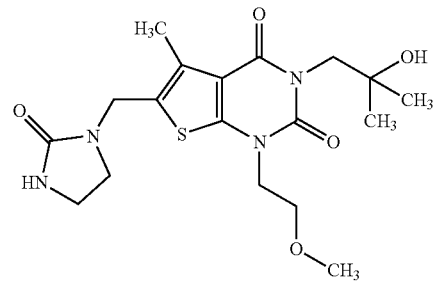 [SMILES: COCCn1c(=O)n(CC(C)(C)O)c(=O)c2c(C)c(CN3CCNC3=O)sc21]

To a solution of 137 mg (0.323 mmol) of the compound from Ex. 356A in 5 ml of THF were added, at −78° C., 333 μl (1.0 mmol) of a 3 M solution of methylmagnesium chloride in THF. After stirring at −78° C. for 60 min, the cooling bath was removed and the stirring was continued at RT. After a further 60 min, the reaction mixture was admixed with a little saturated aqueous ammonium chloride solution and diluted with ethyl acetate. Anhydrous magnesium sulphate was added, and the mixture was stirred for a few minutes, then filtered and concentrated. The remaining, highly contaminated residue was purified by means of preparative HPLC twice in succession (Method 8 each time). The still slightly contaminated product thus obtained was then purified by means of preparative HPLC for a third time [column: Kinetex C18, 5 μm, 100 mm×30 mm; eluent A: water+0.07% formic acid; eluent B: acetonitrile; gradient: 0.0-2.2 min 10% B, 2.2-7.0 min 20% B, 7.0-7.5 min 60% B, 7.5-9.0 min 92% B; flow rate: 70 ml/min; temperature: 25° C.; detection: 210 nm]. After concentration of the product fractions and drying under high vacuum, 3 g (2% of theory) of the title compound were obtained.

$^1$H-NMR (400 MHz, CDCl$_3$, δ/ppm): 4.46 (s, 2H), 4.37 (br. s, 1H), 4.18 (s, 2H), 4.12 (t, 2H), 3.90 (s, 1H), 3.71 (t, 2H), 3.47-3.35 (m, 4H), 3.33 (s, 3H), 2.47 (s, 3H), 1.26 (s, 6H).

LC/MS (Method 1, ESIpos): R$_t$=0.68 min, m/z=441 [M+H]$^+$.

Example 229

3-(2-Methoxyethyl)-5-methyl-6-[(2-oxoimidazolidin-1-yl)methyl]-1-(3,3,3-trifluoropropyl)thieno[2,3-d]pyrimidine-2,4(1H,3H)-dione

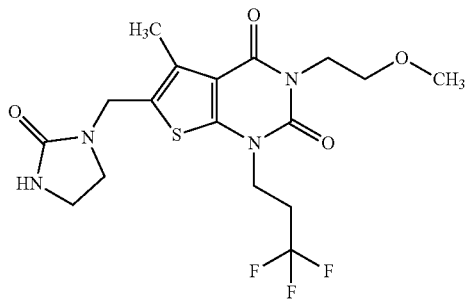 [SMILES: COCCn1c(=O)c2c(C)c(CN3CCNC3=O)sc2n(CCC(F)(F)F)c1=O]

100 mg (0.198 mmol) of the compound from Example 319A were dissolved in 11 ml of dioxane, and 50 mg (0.297 mmol) of CDI were added. The mixture was stirred at RT for 18 h. The reaction solution was then concentrated on a rotary evaporator. The residue was dissolved in 3 ml of DMSO and this solution was purified by means of preparative HPLC (Method 14). Combination of the product fractions and freeze-drying gave 66 mg (73% of theory) of the title compound.

$^1$H-NMR (400 MHz, DMSO-d$_6$, δ/ppm): 6.55 (s, 1H), 4.37 (s, 2H), 4.10 (t, 2H), 4.05 (t, 2H), 3.49 (t, 2H), 3.29-3.18 (m, 7H), 2.82-2.69 (m, 2H), 2.40 (s, 3H).

LC/MS (Method 3, ESIpos): R$_t$=0.96 min, m/z=435 [M+H]$^+$.

Example 230

1-(3-Fluoropropyl)-3-(2-methoxyethyl)-5-methyl-6-[(2-oxoimidazolidin-1-yl)methyl]thieno[2,3-d]pyrimidine-2,4(1H,3H)-dione

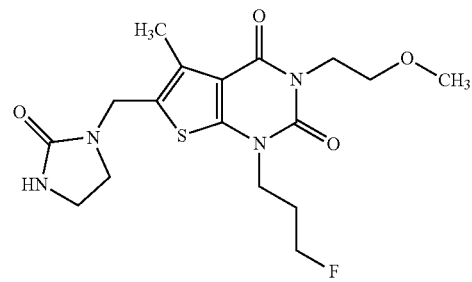 [SMILES: COCCn1c(=O)c2c(C)c(CN3CCNC3=O)sc2n(CCCF)c1=O]

80 mg (0.137 mmol) of the compound from Example 320A were dissolved in 10 ml of dioxane, and 34 mg (0.206 mmol) of CDI were added. The mixture was stirred at RT for 18 h. The reaction solution was then concentrated on a rotary evaporator. The residue was dissolved in 3 ml of DMSO and this solution was purified by means of preparative HPLC (Method 14). Combination of the product fractions and freeze-drying gave 43 mg (54% of theory) of the title compound.

$^1$H-NMR (400 MHz, DMSO-d$_6$, δ/ppm): 6.55 (s, 1H), 4.59 (t, 1H), 4.47 (t, 1H), 4.36 (s, 2H), 4.05 (t, 2H), 3.97 (t, 2H), 3.49 (t, 2H), 3.30-3.16 (m, 7H), 2.39 (s, 3H), 2.13-2.05 (m, 1H), 2.05-1.97 (m, 1H).

LC/MS (Method 3, ESIpos): R$_t$=0.86 min, m/z=399 [M+H]$^+$.

Example 231

1,3-Bis(2-methoxyethyl)-5-methyl-6-[(2-oxoimidazolidin-1-yl)methyl]thieno[2,3-d]pyrimidine-2,4(1H,3H)-dione

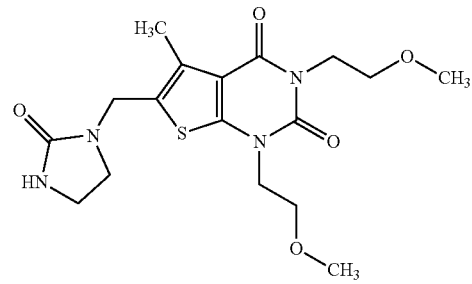 [SMILES: COCCn1c(=O)c2c(C)c(CN3CCNC3=O)sc2n(CCOC)c1=O]

155 mg (0.18 mmol) of the compound from Example 262A were dissolved in 5 ml of dioxane, and 45 mg (0.27 mmol) of CDI were added. The mixture was stirred at RT for 16 h. The reaction solution was then concentrated on a rotary evaporator. The residue was dissolved in 3 ml of DMSO and this solution was purified by means of preparative HPLC (Method 14). Combination of the product fractions and freeze-drying gave 60 mg (71% of theory) of the title compound.

$^1$H-NMR (400 MHz, DMSO-d$_6$, δ/ppm): 6.55 (s, 1H), 4.34 (s, 2H), 4.05 (t, 2H), 4.01 (t, 2H), 3.62 (t, 2H), 3.49 (t, 2H), 3.28-3.17 (m, 10H), 2.38 (s, 3H).

LC/MS (Method 3, ESIpos): $R_t$=0.82 min, m/z=397 [M+H]$^+$.

Example 232

1-(2-Ethoxyethyl)-3-(2-methoxyethyl)-5-methyl-6-[(2-oxoimidazolidin-1-yl)methyl]thieno[2,3-d]pyrimidine-2,4(1H,3H)-dione

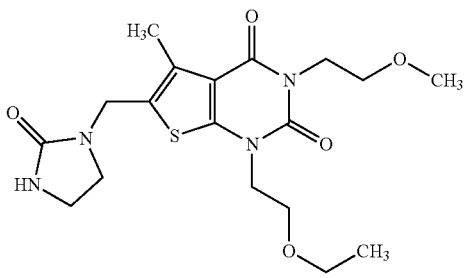 [SMILES: CCOCCn1c(=O)n(CCOC)c(=O)c2c(C)c(CN3CCNC3=O)sc21]

143 mg (0.216 mmol) of the compound from Example 263A were dissolved in 10 ml of dioxane, and 54 mg (0.324 mmol) of CDI were added. The mixture was stirred at RT for 17 h. The reaction solution was then concentrated on a rotary evaporator. The residue was dissolved in 3 ml of DMSO and this solution was purified by means of preparative HPLC (Method 14). Combination of the product fractions and freeze-drying gave 59 mg (66% of theory) of the title compound.

$^1$H-NMR (400 MHz, DMSO-d$_6$, δ/ppm): 6.54 (s, 1H), 4.35 (s, 2H), 4.05 (t, 2H), 4.00 (t, 2H), 3.65 (t, 2H), 3.49 (t, 2H), 3.43 (q, 2H), 3.27-3.17 (m, 7H), 2.38 (s, 3H), 1.03 (t, 3H).

LC/MS (Method 3, ESIpos): $R_t$=0.88 min, m/z=411 [M+H]$^+$.

Example 233

3-(2-Methoxyethyl)-5-methyl-6-[(2-oxoimidazolidin-1-yl)methyl]-1-(tetrahydrofuran-2-ylmethyl)thieno[2,3-d]pyrimidine-2,4(1H,3H)-dione (racemate)

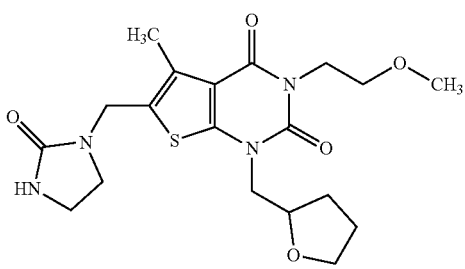 [SMILES: COCCn1c(=O)c2c(C)c(CN3CCNC3=O)sc2n(CC2CCCO2)c1=O]

200 mg (0.333 mmol) of the compound from Example 321A were dissolved in 15 ml of dioxane, and 84 mg (0.499 mmol) of CDI were added. The mixture was stirred at RT for 18 h. The reaction solution was then concentrated on a rotary evaporator. The residue was dissolved in 3 ml of DMSO and this solution was purified by means of preparative HPLC (Method 14). Combination of the product fractions and freeze-drying gave 109 mg (77% of theory) of the title compound.

$^1$H-NMR (400 MHz, DMSO-d$_6$, δ/ppm): 6.54 (s, 1H), 4.34 (s, 2H), 4.26-4.17 (m, 1H), 4.09-3.99 (m, 3H), 3.78-3.65 (m, 2H), 3.64-3.57 (m, 1H), 3.49 (t, 2H), 3.28-3.16 (m, 7H), 2.38 (s, 3H), 2.03-1.75 (m, 3H), 1.70-1.60 (m, 1H).

LC/MS (Method 3, ESIpos): $R_t$=0.86 min, m/z=423 [M+H]$^+$.

Example 234

1-(2-Methoxyethyl)-3-(2-methoxypropyl)-5-methyl-6-[(2-oxoimidazolidin-1-yl)methyl]thieno[2,3-d]pyrimidine-2,4(1H,3H)-dione (Enantiomer 1)

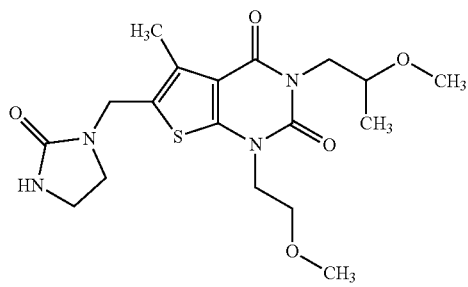 [SMILES: COCCn1c(=O)n(CC(C)OC)c(=O)c2c(C)c(CN3CCNC3=O)sc21]

81 mg of the racemic compound from Ex. 99 were dissolved in 4 ml of an acetonitrile/dichloromethane mixture (1:1 v/v) and separated into the enantiomers by means of preparative HPLC on a chiral phase [column: Daicel Chiralpak IC, 5 µm, 250 mm×30 mm; eluent A: acetonitrile, eluent B: ethanol; isocratic 90% A+10% B; flow rate: 60 ml/min; temperature: RT; DAD 254 nm]. The product fractions were concentrated on a rotary evaporator, admixed with tert-butanol and freeze-dried. 35 mg (41% of theory) of the title compound (Enantiomer 1) and 35 mg (41% of theory) of Enantiomer 2 (see Example 235) were obtained.

$^1$H-NMR (400 MHz, DMSO-d$_6$, δ/ppm): 6.55 (s, 1H), 4.34 (s, 2H), 4.09-3.99 (m, 3H), 3.75 (dd, 1H), 3.68-3.59 (m, 3H), 3.29-3.17 (m, 10H), 2.38 (s, 3H), 1.05 (d, 3H).

Chiral analytical HPLC [column: Daicel Chiralpak IC, 3 µm, 100 mm×4.6 mm; eluent A: acetonitrile, eluent B: ethanol; isocratic 90% A, 10% B; flow rate: 1.0 ml/min; temperature: 25° C.; injection: 5 µl; DAD 220 nm]: $R_t$=7.13 min.

Example 235

1-(2-Methoxyethyl)-3-(2-methoxypropyl)-5-methyl-6-[(2-oxoimidazolidin-1-yl)methyl]thieno[2,3-d]pyrimidine-2,4(1H,3H)-dione (Enantiomer 2)

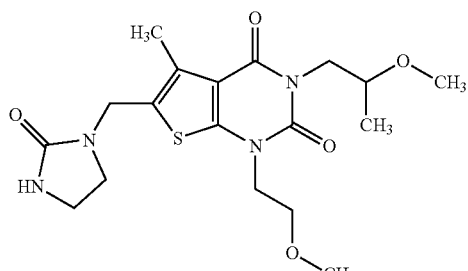

The title compound (35 mg) was obtained as the second enantiomer in the preparative HPLC separation of the racemate from Ex. 99 described in Ex. 234.

¹H-NMR (400 MHz, DMSO-d₆, δ/ppm): 6.55 (s, 1H), 4.34 (s, 2H), 4.09-3.98 (m, 3H), 3.75 (dd, 1H), 3.68-3.59 (m, 3H), 3.29-3.18 (m, 10H), 2.38 (s, 3H), 1.05 (d, 3H).

Chiral analytical HPLC [column: Daicel Chiralpak IC, 3 μm, 100 mm×4.6 mm; eluent A: acetonitrile, eluent B: ethanol; isocratic 90% A, 10% B; flow rate: 1.0 ml/min; temperature: 25° C.; injection: 5 μl; DAD 220 nm]: R$_t$=9.16 min.

Example 236

3-(2-Methoxy-2-methylpropyl)-5-methyl-6-[(2-oxoimidazolidin-1-yl)methyl]-1-(3,3,3-trifluoropropyl)thieno[2,3-d]pyrimidine-2,4(1H,3H)-dione

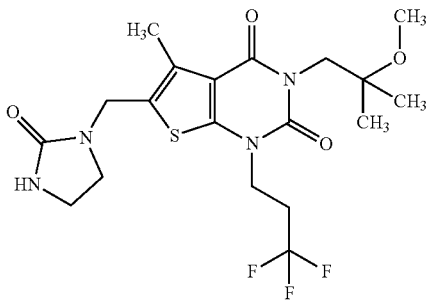

310 mg (0.575 mmol) of the compound from Example 322A were dissolved in 30 ml of dioxane, and 144 mg (0.863 mmol) of CDI were added. The mixture was stirred at RT for 19 h. The reaction solution was then concentrated on a rotary evaporator. The residue was dissolved in 6 ml of DMSO and this solution was purified by means of preparative HPLC (Method 14). Combination of the product fractions and freeze-drying gave 172 mg (62% of theory) of the title compound.

¹H-NMR (400 MHz, DMSO-d₆, δ/ppm): 6.56 (s, 1H), 4.36 (s, 2H), 4.09 (t, 2H), 3.99 (br. s, 2H), 3.30-3.18 (m, 4H), 3.15 (s, 3H), 2.82-2.68 (m, 2H), 2.39 (s, 3H), 1.08 (s, 6H).

LC/MS (Method 3, ESIpos): R$_t$=1.07 min, m/z=463 [M+H]⁺.

Example 237

1-(3-Fluoropropyl)-3-(2-methoxy-2-methylpropyl)-5-methyl-6-[(2-oxoimidazolidin-1-yl)methyl]thieno[2,3-d]pyrimidine-2,4(1H,3H)-dione

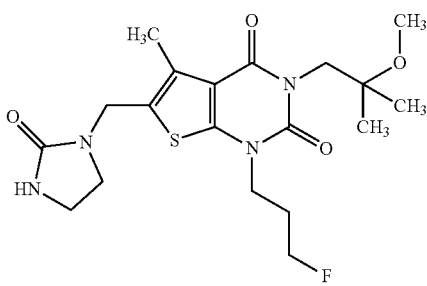 [SMILES: COC(C)(C)Cn1c(=O)c2c(C)c(CN3CCNC3=O)sc2n(CCCF)c1=O]

330 mg (0.7 mmol) of the compound from Example 323A were dissolved in 30 ml of dioxane, and 176 mg (1.05 mmol) of CDI were added. The mixture was stirred at RT for 18 h. The reaction solution was then concentrated on a rotary evaporator. The residue was dissolved in 6 ml of DMSO and this solution was purified by means of preparative HPLC (Method 14). Combination of the product fractions and freeze-drying gave 139 mg (45% of theory) of the title compound.

¹H-NMR (400 MHz, DMSO-d6, δ/ppm): 6.55 (s, 1H), 4.59 (t, 1H), 4.47 (t, 1H), 4.36 (s, 2H), 4.03-3.94 (m, 4H), 3.30-3.17 (m, 4H), 3.15 (s, 3H), 2.39 (s, 3H), 2.13-2.05 (m, 1H), 2.05-1.97 (m, 1H), 1.08 (s, 6H).

LC/MS (Method 3, ESIpos): R$_t$=0.97 min, m/z=427 [M+H]⁺.

Example 238

1-(2-Methoxyethyl)-3-(2-methoxy-2-methylpropyl)-5-methyl-6-[(2-oxoimidazolidin-1-yl)methyl]thieno[2,3-d]pyrimidine-2,4(1H,3H)-dione

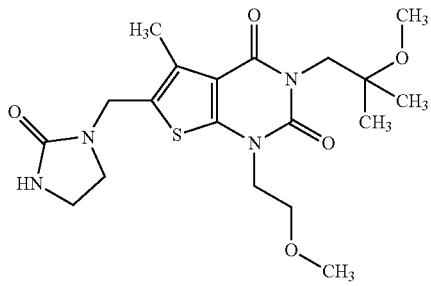 [SMILES: COCCn1c(=O)n(CC(C)(C)OC)c(=O)c2c(C)c(CN3CCNC3=O)sc21]

155 mg (0.303 mmol) of the compound from Example 324A were dissolved in 15 ml of dioxane, and 76 mg (0.455 mmol) of CDI were added. The mixture was stirred at RT for 20 h. The reaction solution was then concentrated on a rotary evaporator. The residue was dissolved in 6 ml of DMSO and this solution was purified by means of preparative HPLC (Method 14). Combination of the product fractions and freeze-drying gave 86 mg (66% of theory) of the title compound.

¹H-NMR (400 MHz, DMSO-d₆, δ/ppm): 6.54 (s, 1H), 4.34 (s, 2H), 4.06-3.94 (m, 4H), 3.61 (t, 2H), 3.30-3.17 (m, 7H), 3.15 (s, 3H), 2.37 (s, 3H), 1.08 (s, 6H).

LC/MS (Method 3, ESIpos): R$_t$=0.93 min, m/z=425 [M+H]⁺.

Example 239

6-[(3-Ethyl-2-oxoimidazolidin-1-yl)methyl]-1-(2-methoxyethyl)-5-methyl-3-(2-phenylethyl)thieno[2,3-d]pyrimidine-2,4(1H,3H)-dione

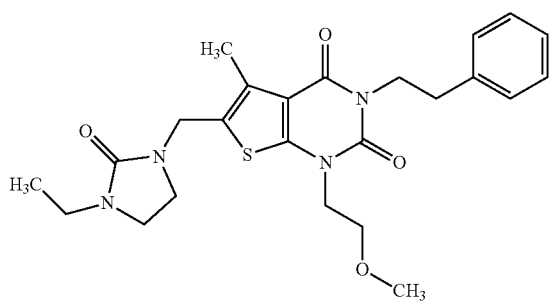 [SMILES: CCN1CCN(Cc2sc3c(c2C)c(=O)n(CCc2ccccc2)c(=O)n3CCOC)C1=O]

To a solution of 45 mg (0.102 mmol) of the compound from Ex. 176 in 3 ml of THF were added, at 0° C., 5 mg (0.122 mmol) of sodium hydride (60% suspension in mineral oil), and the mixture was stirred for 1 h. Subsequently, 19 mg (0.122 mmol) of iodoethane were added, and the mixture was stirred at 0° C. for 1 h. Then the reaction mixture was partitioned between saturated aqueous ammonium chloride solution (20 ml) and THF (30 ml). The organic phase was washed with saturated aqueous sodium hydrogencarbonate solution, dried over sodium sulphate, filtered and concentrated. The residue obtained was purified by means of preparative HPLC (Method 14). Combination of the product fractions and freeze-drying gave 11.6 mg (23% of theory) of the title compound.

$^1$H-NMR (400 MHz, DMSO-d$_6$, δ/ppm): 7.34-7.27 (m, 2H), 7.26-7.19 (m, 3H), 4.37 (s, 2H), 4.09-4.03 (m, 2H), 4.01 (t, 2H), 3.59 (t, 2H), 3.27-3.16 (m, 7H), 3.12 (q, 2H), 2.86-2.79 (m, 2H), 2.39 (s, 3H), 1.01 (t, 3H).

LC/MS (Method 3, ESIpos): R$_t$=1.26 min, m/z=471 [M+H]$^+$.

Example 240

1-(2-Methoxyethyl)-5-methyl-6-[(2-oxo-3-propylimidazolidin-1-yl)methyl]-3-(2-phenylethyl)thieno[2,3-d]pyrimidine-2,4(1H,3H)-dione

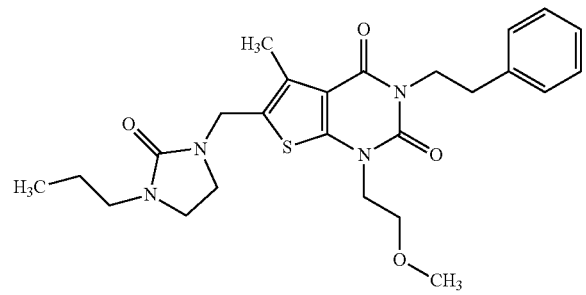 [SMILES: CCCN1CCN(Cc2sc3c(c2C)c(=O)n(CCc2ccccc2)c(=O)n3CCOC)C1=O]

To a solution of 45 mg (0.102 mmol) of the compound from Ex. 176 in 3 ml of THF were added, at 0° C., 5 mg (0.122 mmol) of sodium hydride (60% suspension in mineral oil), and the mixture was stirred for 1 h. Subsequently, 21 mg (0.122 mmol) of iodopropane were added, and the mixture was stirred at RT for 92 h. Then the reaction mixture was partitioned between saturated aqueous ammonium chloride solution (20 ml) and THF (30 ml). The organic phase was washed with saturated aqueous sodium hydrogencarbonate solution, dried over sodium sulphate, filtered and concentrated. The residue obtained was purified by means of preparative HPLC (Method 14). Combination of the product fractions and freeze-drying gave 17 mg (34% of theory) of the title compound.

$^1$H-NMR (400 MHz, DMSO-d$_6$, δ/ppm): 7.33-7.27 (m, 2H), 7.26-7.18 (m, 3H), 4.38 (s, 2H), 4.08-4.02 (m, 2H), 4.00 (t, 2H), 3.59 (t, 2H), 3.27-3.15 (m, 7H), 3.05 (t, 2H), 2.86-2.79 (m, 2H), 2.39 (s, 3H), 1.44 (sext, 2H), 0.82 (t, 3H).

LC/MS (Method 3, ESIpos): R$_t$=1.32 min, m/z=485 [M+H]$^+$.

Example 241

3-Ethyl-5-methyl-6-[(2-oxo-2,3-dihydro-1H-imidazol-1-yl)methyl]-1-(3,3,3-trifluoropropyl)thieno[2,3-d]pyrimidine-2,4(1H,3H)-dione

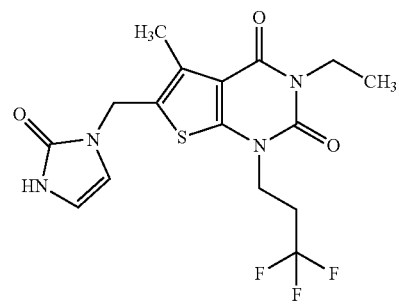 [SMILES: CCn1c(=O)c2c(C)c(Cn3cc[nH]c3=O)sc2n(CCC(F)(F)F)c1=O]

100 mg (0.178 mmol, 83% purity) of the compound from Ex. 273A were dissolved in a mixture of 2 ml of methanol and 0.4 ml of water. Then 353 μl (0.353 mmol) of 1 M hydrochloric acid were added and the mixture was stirred at RT for 2.5 days. Since the conversion was still incomplete after this time, another 1 ml (1.0 mmol) of hydrochloric acid was added. After stirring at RT for a further 18 h, the reaction mixture was separated into its components directly by means of preparative HPLC (Method 8). After concentration of the product fractions and drying under high vacuum, 55 mg (76% of theory) of the title compound were obtained.

$^1$H-NMR (400 MHz, DMSO-d$_6$, δ/ppm): 10.00 (br. s, 1H), 6.44 (t, 1H), 6.34 (t, 1H), 4.81 (s, 2H), 4.08 (t, 2H), 3.90 (q, 2H), 2.86-2.64 (m, 2H), 2.47 (s, 3H), 1.11 (t, 3H).

LC/MS (Method 1, ESIpos): R$_t$=0.79 min, m/z=403 [M+H]$^+$.

Example 242

3-Ethyl-5-methyl-6-[(2-oxo-2,3-dihydro-1H-imidazol-1-yl)methyl]-1-(tetrahydrofuran-2-ylmethyl)thieno[2,3-d]pyrimidine-2,4(1H,3H)-dione (racemate)

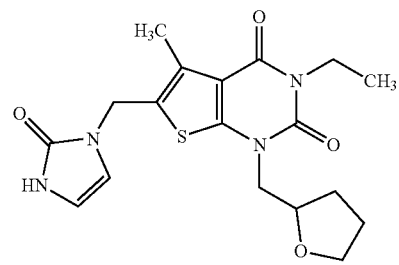 [SMILES: CCn1c(=O)c2c(C)c(Cn3cc[nH]c3=O)sc2n(CC2CCCO2)c1=O]

900 mg (1.78 mmol, 90% purity) of the compound from Ex. 329A were dissolved in a mixture of 13 ml of methanol and 4 ml of water. Then 3.5 ml (3.56 mmol) of 1 M hydrochloric acid were added and the mixture was stirred at RT for 2.5 days. Thereafter, the product was precipitated by adding water. The product was filtered off with suction, washed with a little water and dried under high vacuum. 472 mg (67% of theory) of the title compound were obtained.

¹H-NMR (400 MHz, DMSO-d$_6$, δ/ppm): 9.99 (br. s, 1H), 6.42 (t, 1H), 6.34 (t, 1H), 4.78 (s, 2H), 4.27-4.14 (m, 1H), 4.02 (dd, 1H), 3.90 (q, 2H), 3.79-3.51 (m, 3H), 2.46 (s, 3H), 2.05-1.73 (m, 3H), 1.71-1.58 (m, 1H), 1.11 (t, 3H).

LC/MS (Method 17, ESIneg): R$_t$=1.23 min, m/z=389.13 [M–H]⁻.

Example 243

3-Ethyl-5-methyl-6-[(2-oxo-2,3-dihydro-1H-imidazol-1-yl)methyl]-1-(tetrahydrofuran-2-ylmethyl)thieno[2,3-d]pyrimidine-2,4(1H,3H)-dione (Enantiomer 1)

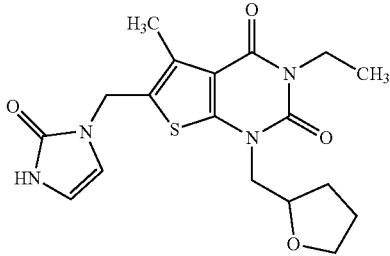

434 mg (1.11 mmol) of the racemic compound from Ex. 242 were dissolved in 25 ml of methanol/acetonitrile (1:1) and, in 17 portions, separated into the enantiomers by preparative SFC on a chiral phase [column: Daicel Chiralcel OX-H, 5 μm, SFC, 250 mm×30 mm; eluent: carbon dioxide/methanol 70:30; flow rate: 100 ml/min; temperature: 40° C.; detection: 210 nm]. After concentration of the product fractions and drying under high vacuum, 199 mg (91% of theory) of Enantiomer 1 were obtained (>99% ee, chiral analytical HPLC).

¹H-NMR (400 MHz, DMSO-d$_6$, δ/ppm): 9.99 (br. s, 1H), 6.45-6.40 (m, 1H), 6.37-6.30 (m, 1H), 4.78 (s, 2H), 4.26-4.15 (m, 1H), 4.02 (dd, 1H), 3.90 (q, 2H), 3.78-3.55 (m, 3H), 2.46 (s, 3H), 2.05-1.75 (m, 3H), 1.71-1.58 (m, 1H), 1.11 (t, 3H).

Chiral analytical SFC [column: Daicel Chiralcel OX-H, 5 μm, 250 mm×4.6 mm; eluent: carbon dioxide/methanol 60:40; flow rate: 3 ml/min; temperature: 40° C.; detection: 210 nm]: R$_t$=4.23 min.

Example 244

3-Ethyl-5-methyl-6-[(2-oxo-2,3-dihydro-1H-imidazol-1-yl)methyl]-1-(tetrahydrofuran-2-ylmethyl)thieno[2,3-d]pyrimidine-2,4(1H,3H)-dione (Enantiomer 2)

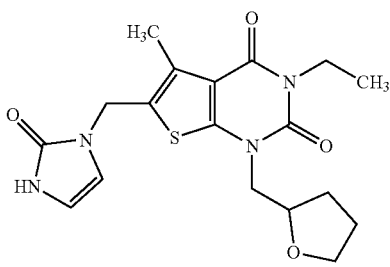

434 mg (1.11 mmol) of the racemic compound from Ex. 242 were dissolved in 25 ml of methanol/acetonitrile (1:1) and, in 17 portions, separated into the enantiomers by preparative SFC on a chiral phase [column: Daicel Chiralcel OX-H, 5 μm, SFC, 250 mm×30 mm; eluent: carbon dioxide/methanol 70:30; flow rate: 100 ml/min; temperature: 40° C.; detection: 210 nm]. After concentration of the product fractions and drying under high vacuum, 194 mg (89% of theory) of Enantiomer 2 were obtained (>99% ee, chiral analytical HPLC).

¹H-NMR (400 MHz, DMSO-d$_6$, δ/ppm): 9.99 (br. s, 1H), 6.42 (t, 1H), 6.34 (t, 1H), 4.78 (s, 2H), 4.27-4.15 (m, 1H), 4.02 (dd, 1H), 3.90 (q, 2H), 3.78-3.54 (m, 3H), 2.46 (s, 3H), 2.04-1.72 (m, 3H), 1.71-1.58 (m, 1H), 1.11 (t, 3H).

Chiral analytical SFC [column: Daicel Chiralcel OX-H, 5 μm, 250 mm×4.6 mm; eluent: carbon dioxide/methanol 60:40; flow rate: 3 ml/min; temperature: 40° C.; detection: 210 nm]: R$_t$=6.22 min.

Example 245

3-Isopropyl-5-methyl-6-[(2-oxo-2,3-dihydro-1H-imidazol-1-yl)methyl]-1-(3,3,3-trifluoropropyl)thieno[2,3-d]pyrimidine-2,4(1H,3H)-dione

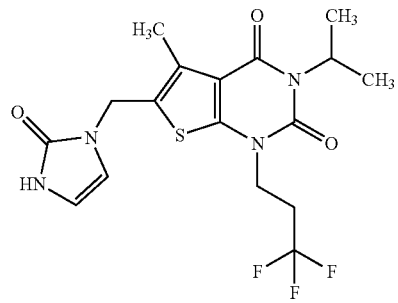 [SMILES: Cc1c(Cn2cc[nH]c2=O)sc2c1c(=O)n(C(C)C)c(=O)n2CCC(F)(F)F]

290 mg (0.604 mmol) of the compound from Ex. 330A were dissolved in a mixture of 6 ml of methanol and 1.2 ml of water. Then 1.2 ml (1.21 mmol) of 1 M hydrochloric acid were added and the mixture was stirred at RT for 6 days. Thereafter, the product was precipitated by adding water. The product was filtered off with suction, washed with a little water and dried under high vacuum. 210 mg (83% of theory) of the title compound were obtained.

¹H-NMR (400 MHz, DMSO-d$_6$, δ/ppm): 9.99 (br. s, 1H), 6.47-6.40 (m, 1H), 6.34 (t, 1H), 5.12 (sept, 1H), 4.80 (s, 2H), 4.05 (t, 2H), 2.84-2.64 (m, 2H), 2.46 (s, 3H), 1.39 (d, 6H).

LC/MS (Method 17, ESIneg): R$_t$=1.59 min, m/z=415.10 [M–H]⁻.

Example 246

3-Isopropyl-1-(2-methoxyethyl)-5-methyl-6-[(2-oxo-2,3-dihydro-1H-imidazol-1-yl)methyl]thieno[2,3-d]pyrimidine-2,4(1H,3H)-dione

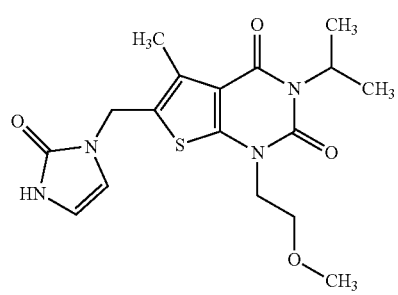 [SMILES: COCCn1c(=O)n(C(C)C)c(=O)c2c(C)c(Cn3cc[nH]c3=O)sc21]

580 mg (0.865 mmol, 66% purity) of the compound from Ex. 331A were dissolved in a mixture of 10 ml of methanol and 1.7 ml of water. Then 1.7 ml (1.73 mmol) of 1 M hydrochloric acid were added and the mixture was stirred at RT for 2.5 days. Thereafter, some of the product was precipitated by adding water. The product was filtered off with suction, washed with a little water and dried under high vacuum. The filtrate was extracted with ethyl acetate. The organic extract was washed with saturated sodium chloride solution, dried over anhydrous magnesium sulphate, filtered and concentrated. The remaining residue was combined with the product precipitated at the start and stirred with acetonitrile at RT. Removal of the solids again by filtration with suction and drying under high vacuum gave 163 mg (49% of theory) of the title compound.

$^1$H-NMR (400 MHz, DMSO-d$_6$, δ/ppm): 9.99 (br. s, 1H), 6.42 (t, 1H), 6.34 (t, 1H), 5.12 (sept, 1H), 4.78 (s, 2H), 3.97 (t, 2H), 3.60 (t, 2H), 3.31 (s, 3H), 2.44 (s, 3H), 1.39 (d, 6H).

LC/MS (Method 17, ESIneg): R$_t$=1.33 min, m/z=377.13 [M−H]$^-$.

Example 247

3-Isopropyl-5-methyl-6-[(2-oxo-2,3-dihydro-1H-imidazol-1-yl)methyl]-1-(tetrahydrofuran-2-ylmethyl)thieno[2,3-d]pyrimidine-2,4(1H,3H)-dione (racemate)

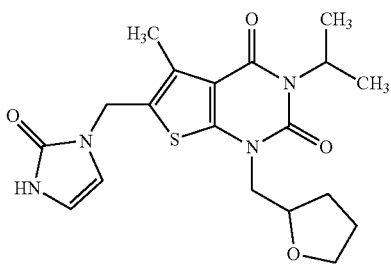

1.15 g (1.89 mmol, 77% purity) of the compound from Ex. 332A were dissolved in a mixture of 20 ml of methanol and 3.8 ml of water. Then 3.8 ml (3.78 mmol) of 1 M hydrochloric acid were added and the mixture was stirred at RT for 2.5 days. Then it was diluted with water and extracted with ethyl acetate. The extract was washed with saturated sodium chloride solution, dried over anhydrous magnesium sulphate, filtered and concentrated. The remaining residue was stirred with acetonitrile at RT. Removal of the solids by filtration with suction and drying under high vacuum gave 418 mg (54% of theory) of the title compound.

$^1$H-NMR (400 MHz, DMSO-d$_6$, δ/ppm): 9.98 (br. s, 1H), 6.41 (t, 1H), 6.34 (t, 1H), 5.13 (sept, 1H), 4.77 (s, 2H), 4.25-4.13 (m, 1H), 4.02 (dd, 1H), 3.80-3.68 (m, 1H), 3.66-3.52 (m, 2H), 2.44 (s, 3H), 2.04-1.72 (m, 3H), 1.70-1.57 (m, 1H), 1.39 (d, 6H).

LC/MS (Method 1, ESIpos): R$_t$=0.77 min, m/z=405 [M+H]$^+$.

Example 248

3-Isopropyl-5-methyl-6-[(2-oxo-2,3-dihydro-1H-imidazol-1-yl)methyl]-1-(tetrahydrofuran-2-ylmethyl)thieno[2,3-d]pyrimidine-2,4(1H,3H)-dione (Enantiomer 1)

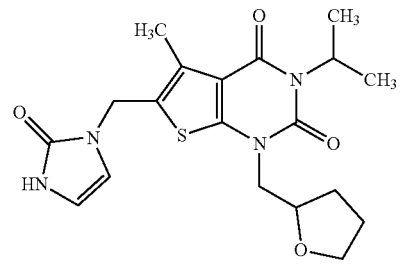 [SMILES: Cc1c(Cn2cc[nH]c2=O)sc2c1c(=O)n(C(C)C)c(=O)n2CC1CCCO1]

382 mg (0.944 mmol) of the racemic compound from Ex. 247 were dissolved in a mixture of 9 ml of ethanol and 1 ml of acetonitrile and, in 29 portions, separated into the enantiomers by preparative HPLC on a chiral phase [column: Daicel Chiralcel OX-H, 5 μm, 250 mm×20 mm; eluent: ethanol; flow rate: 15 ml/min; temperature: 40° C.; detection: 220 nm]. After concentration of the product fractions and drying under high vacuum, 155 mg (81% of theory) of Enantiomer 1 were obtained (>99% ee, chiral analytical HPLC).

$^1$H-NMR (400 MHz, DMSO-d$_6$, δ/ppm): 9.98 (br. s, 1H), 6.44-6.38 (m, 1H), 6.34 (t, 1H), 5.13 (sept, 1H), 4.77 (s, 2H), 4.25-4.13 (m, 1H), 4.02 (dd, 1H), 3.78-3.68 (m, 1H), 3.66-3.56 (m, 2H), 2.44 (s, 3H), 2.06-1.74 (m, 3H), 1.70-1.56 (m, 1H), 1.39 (dd, 6H).

Chiral analytical HPLC [column: Daicel Chiralcel OX-H, 5 μm, 250 mm×4.6 mm; eluent: ethanol; flow rate: 1 ml/min; temperature: 45° C.; detection: 260 nm]: R$_t$=6.19 min.

Example 249

3-Isopropyl-5-methyl-6-[(2-oxo-2,3-dihydro-1H-imidazol-1-yl)methyl]-1-(tetrahydrofuran-2-ylmethyl)thieno[2,3-d]pyrimidine-2,4(1H,3H)-dione (Enantiomer 2)

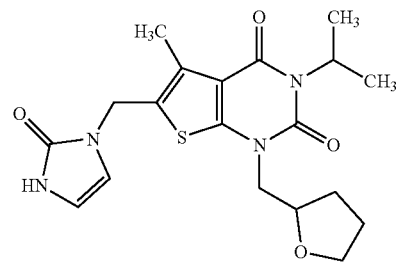 [SMILES: Cc1c(Cn2cc[nH]c2=O)sc2c1c(=O)n(C(C)C)c(=O)n2CC1CCCO1]

382 mg (0.944 mmol) of the racemic compound from Ex. 247 were dissolved in a mixture of 9 ml of ethanol and 1 ml of acetonitrile and, in 29 portions, separated into the enantiomers by preparative HPLC on a chiral phase [column: Daicel Chiralcel OX-H, 5 μm, 250 mm×20 mm; eluent: ethanol; flow rate: 15 ml/min; temperature: 40° C.; detection: 220 nm]. After concentration of the product fractions and drying under high vacuum, 165 mg (86% of theory) of Enantiomer 2 were obtained (>99% ee, chiral analytical HPLC).

$^1$H-NMR (400 MHz, DMSO-d$_6$, δ/ppm): 9.98 (br. s, 1H), 6.45-6.38 (m, 1H), 6.34 (t, 1H), 5.13 (sept, 1H), 4.77 (s, 2H), 4.25-4.13 (m, 1H), 4.02 (dd, 1H), 3.78-3.68 (m, 1H), 3.66-3.53 (m, 2H), 2.44 (s, 3H), 2.04-1.74 (m, 3H), 1.70-1.56 (m, 1H), 1.43-1.35 (dd, 6H).

Chiral analytical HPLC [column: Daicel Chiralcel OX-H, 5 μm, 250 mm×4.6 mm; eluent: ethanol; flow rate: 1 ml/min; temperature: 45° C.; detection: 260 nm]: R$_t$=8.19 min.

Example 250

3-Ethyl-5-methyl-6-[(4-methyl-2-oxo-2,3-dihydro-1H-imidazol-1-yl)methyl]-1-(3,3,3-trifluoropropyl)thieno[2,3-d]pyrimidine-2,4(1H,3H)-dione

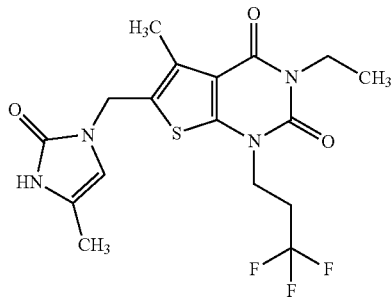 [SMILES: CCn1c(=O)c2c(C)c(Cn3cc(C)[nH]c3=O)sc2n(CCC(F)(F)F)c1=O]

122 mg (0.191 mmol, 75% purity) of the compound from Ex. 271A were dissolved in 3 ml of methanol, and 0.6 ml of 1 M hydrochloric acid was added. Since the conversion was still incomplete after stirring at RT for 18 hours, 0.6 ml of concentrated hydrochloric acid was added. After stirring at RT for a further 24 h, the reaction mixture was separated into its components directly by means of preparative HPLC (Method 8). The product fractions were combined and concentrated, and the residue was dried under high vacuum. 54 mg (67% of theory) of the title compound were obtained.

$^1$H-NMR (400 MHz, DMSO-d$_6$, δ/ppm): 9.94 (s, 1H), 6.09 (s, 1H), 4.74 (s, 2H), 4.08 (t, 2H), 3.90 (q, 2H), 2.85-2.66 (m, 2H), 2.46 (s, 3H), 1.87 (s, 3H), 1.11 (t, 3H).

LC/MS (Method 1, ESIpos): R$_t$=0.86 min, m/z=417 [M+H]$^+$.

Example 251

3-Ethyl-5-methyl-6-[(5-methyl-2-oxo-2,3-dihydro-1H-imidazol-1-yl)methyl]-1-(3,3,3-trifluoropropyl)thieno[2,3-d]pyrimidine-2,4(1H,3H)-dione

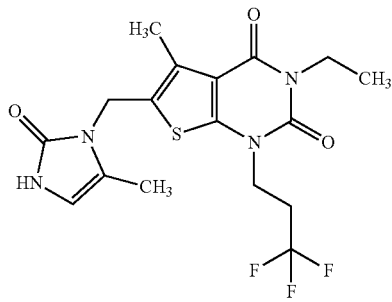 [SMILES: CCn1c(=O)c2c(C)c(Cn3c(C)c[nH]c3=O)sc2n(CCC(F)(F)F)c1=O]

215 mg (0.291 mmol, 65% purity) of the compound from Ex. 275A were dissolved in a mixture of 2.1 ml of methanol and 0.6 ml of water, and 0.6 ml (0.291 mmol) of 0.5 M hydrochloric acid was added. After the reaction mixture had been stirred at RT for 2.5 days, it was separated into its components directly by means of preparative HPLC (Method 8). The product fractions were combined and concentrated and the residue was stirred with a little acetonitrile at RT. After the solids had been filtered off with suction and dried under high vacuum, 61 mg (50% of theory) of the title compound were obtained.

$^1$H-NMR (400 MHz, DMSO-d$_6$, δ/ppm): 9.79 (s, 1H), 6.09 (s, 1H), 4.84 (s, 2H), 4.06 (t, 2H), 3.89 (q, 2H), 2.83-2.63 (m, 2H), 2.48 (s, 3H), 1.96 (s, 3H), 1.11 (t, 3H).

LC/MS (Method 1, ESIpos): R$_t$=0.86 min, m/z=417 [M+H]$^+$.

Example 252

3-Ethyl-1-(2-methoxyethyl)-5-methyl-6-[(5-oxo-2,3-dihydro-1H-imidazol-1-yl)methyl]thieno[2,3-d]pyrimidine-2,4(1H,3H)-dione

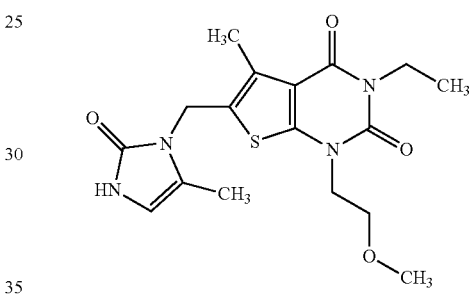

Analogously to the method described in Ex. 251, 155 mg (0.210 mmol, 60% purity) of the compound from Ex. 276A were used to obtain 52 mg (65% of theory) of the title compound.

$^1$H-NMR (400 MHz, DMSO-d$_6$, δ/ppm): 9.78 (s, 1H), 6.09 (s, 1H), 4.82 (s, 2H), 3.98 (t, 2H), 3.89 (q, 2H), 3.60 (t, 2H), 3.31 (s, 3H), 2.46 (s, 3H), 1.96 (s, 3H), 1.11 (t, 3H).

LC/MS (Method 1, ESIpos): R$_t$=0.75 min, m/z=379 [M+H]$^+$.

Example 253

3-Isopropyl-5-methyl-6-[(5-oxo-4,5-dihydro-1H-1,2,4-triazol-1-yl)methyl]-1-(3,3,3-trifluoropropyl)thieno[2,3-d]pyrimidine-2,4(1H,3H)-dione

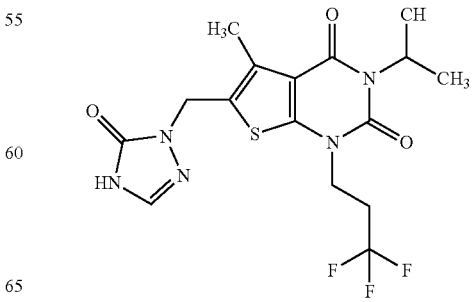

To a suspension of 490 mg (1.17 mmol) of the compound from Ex. 353A in 30 ml of toluene were added 162 µl (1.17 mmol) of triethylamine and 251 µl (1.17 mmol) of diphenylphosphoryl azide. Subsequently, the reaction mixture was heated first to 80° C. for 1 h and then to 100° C. for 1 h. All the volatile constituents were then removed on a rotary evaporator. The remaining residue was diluted with ethyl acetate and washed successively with water and saturated sodium chloride solution. After drying over anhydrous magnesium sulphate, the mixture was filtered and concentrated. The crude product was purified by preparative HPLC (Method 8). The product fractions were combined and concentrated, and the residue was dried under high vacuum. 75 mg (15% of theory) of the title compound were obtained.

$^1$H-NMR (400 MHz, DMSO-d$_6$, δ/ppm): 11.59 (br. s, 1H), 7.84 (s, 1H), 5.12 (sept, 1H), 4.94 (s, 2H), 4.05 (t, 2H), 2.82-2.64 (m, 2H), 2.45 (s, 3H), 1.39 (d, 6H).

LC/MS (Method 1, ESIpos): R$_t$=0.84 min, m/z=418 [M+H]$^+$.

Example 254

3-Isopropyl-1-(2-methoxyethyl)-5-methyl-6-[(5-oxo-4,5-dihydro-1H-1,2,4-triazol-1-yl)methyl]thieno[2,3-d]pyrimidine-2,4(1H,3H)-dione

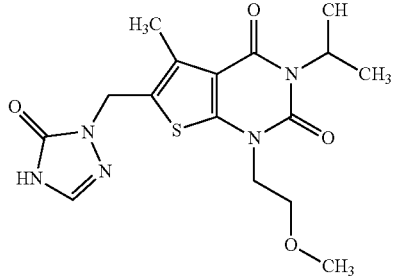

Analogously to the method described in Ex. 253, 85 mg (0.222 mmol) of the compound from Ex. 354A and 48 µl (0.222 mmol) of diphenylphosphoryl azide were used to obtain 3 mg (3% of theory) of the title compound. After the preparative HPLC, the product was repurified here once again by means of preparative TLC (eluent: dichloromethane/methanol 10:1).

$^1$H-NMR (400 MHz, DMSO-d$_6$, δ/ppm): 11.59 (br. s, 1H), 7.83 (s, 1H), 5.12 (sept, 1H), 4.92 (s, 2H), 3.97 (t, 2H), 3.60 (t, 2H), 3.23 (s, 3H), 2.44 (s, 3H), 1.39 (d, 6H).

LC/MS (Method 1, ESIpos): R$_t$=0.71 min, m/z=380 [M+H]$^+$.

Example 255

[1-{[3-Ethyl-5-methyl-2,4-dioxo-1-(3,3,3-trifluoropropyl)-1,2,3,4-tetrahydrothieno[2,3-d]pyrimidin-6-yl]methyl}imidazolidin-2-ylidene]cyanamide

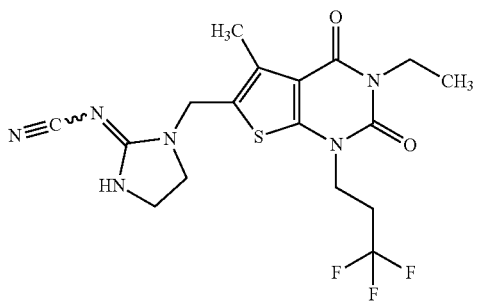 [SMILES: CCn1c(=O)c2c(C)c(CN3CCNC3=NC#N)sc2n(CCC(F)(F)F)c1=O]

Analogously to the method described in Ex. 117, 396 mg (0.889 mmol, 85% purity) of the compound from Ex. 210A and 195 mg (1.33 mmol) of dimethyl N-cyanodithioiminocarbonate were used to obtain 150 mg (39% of theory) of the title compound. The reaction time in this case was 3 h, and the crude product was purified by stirring with an acetonitrile/water mixture.

$^1$H-NMR (400 MHz, DMSO-d$_6$, δ/ppm): 8.08 (s, 1H), 4.50 (s, 2H), 4.11 (t, 2H), 3.90 (q, 2H), 3.53-3.37 (m, 4H), 2.87-2.68 (m, 2H), 2.42 (s, 3H), 1.12 (t, 3H).

LC/MS (Method 17, ESIpos): R$_t$=1.59 min, m/z=429.13 [M+H]$^+$.

Example 256

[1-{[3-Ethyl-5-methyl-1-(oxetan-2-ylmethyl)-2,4-dioxo-1,2,3,4-tetrahydrothieno[2,3-d]pyrimidin-6-yl]methyl}imidazolidin-2-ylidene]cyanamide (racemate)

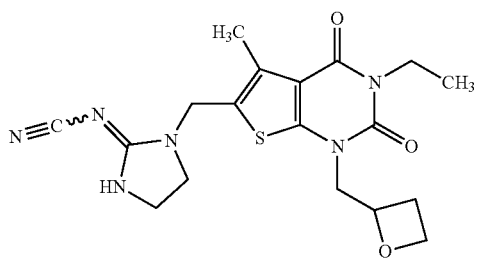 [SMILES: CCn1c(=O)c2c(C)c(CN3CCNC3=NC#N)sc2n(CC2CCO2)c1=O]

300 mg (0.783 mmol, 92% purity) of the compound from Ex. 224A were dissolved in 3.6 ml of DMF, and 172 mg (1.17 mmol) of dimethyl N-cyanodithioiminocarbonate and 216 mg (1.57 mmol) of potassium carbonate were added. The mixture was stirred at 80° C. in a microwave oven (Biotage Initiator with dynamic control of irradiation power) for 8.5 h. Thereafter, the reaction mixture was poured onto water. The solid which precipitated out was filtered off with suction and dissolved in ethyl acetate, and the solution was washed successively with saturated sodium hydrogencarbonate solution, water and saturated sodium chloride solution. After drying over anhydrous magnesium sulphate, the mixture was filtered and the crude product solution was concentrated. In the same way, a second reaction was conducted, proceeding from 350 mg (0.516 mmol, 52% purity) of the compound from Ex. 224A. The crude products from the first and second reactions were combined and stirred with a water/acetonitrile mixture. The solids were filtered off with suction and dried under high vacuum. This gave a first fraction of the title compound. The mother liquor from the stirring was purified by means of preparative HPLC (Method 8). This gave a second fraction of the product, which was combined with the first. A total of 275 mg (51% of theory, 97% purity) of the title compound was thus obtained.

$^1$H-NMR (400 MHz, DMSO-d$_6$, δ/ppm): 8.06 (s, 1H), 5.01 (quin, 1H), 4.54-4.36 (m, 2H), 4.47 (s, 2H), 4.14 (d, 2H), 3.90 (q, 2H), 3.51-3.36 (m, 4H), 2.76-2.63 (m, 1H), 2.55-2.45 (m, 1H, mostly obscured by the DMSO signal), 2.41 (s, 3H), 1.12 (t, 3H).

LC/MS (Method 17, ESIpos): R$_t$=1.26 min, m/z=403.15 [M+H]$^+$.

Example 257

[1-{[3-Ethyl-5-methyl-1-(oxetan-2-ylmethyl)-2,4-dioxo-1,2,3,4-tetrahydrothieno[2,3-d]pyrimidin-6-yl]methyl}imidazolidin-2-ylidene]cyanamide (Enantiomer 1)

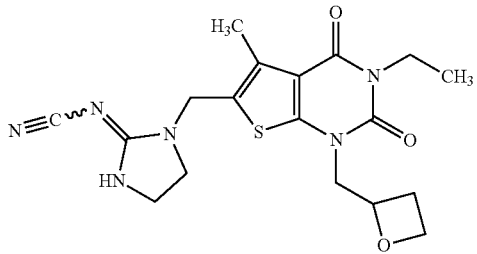 [SMILES: CCn1c(=O)c2c(C)c(CN3CCNC3=NC#N)sc2n(CC2CCO2)c1=O]

251 mg (0.624 mmol) of the racemic compound from Ex. 256 were dissolved in 25 ml of methanol/acetonitrile (1:1) and, in 50 portions, separated into the enantiomers by preparative SFC on a chiral phase [column: Daicel Chiralcel OJ-H, 5 µm, SFC, 250 mm×30 mm; eluent: carbon dioxide/methanol 90:10; flow rate: 100 ml/min; temperature: 40° C.; detection: 210 nm]. After the product fractions had been concentrated, the material obtained was stirred with diisopropyl ether at RT. Removal of the solids with suction and drying under high vacuum gave 65 mg (51% of theory) of Enantiomer 1 (90% ee, chiral analytical HPLC).

$^1$H-NMR (400 MHz, DMSO-d$_6$, δ/ppm): 8.06 (s, 1H), 5.01 (quin, 1H), 4.54-4.36 (m, 2H), 4.47 (s, 2H), 4.14 (d, 2H), 3.90 (q, 2H), 3.51-3.36 (m, 4H), 2.76-2.63 (m, 1H), 2.55-2.45 (m, 1H, mostly obscured by the DMSO signal), 2.41 (s, 3H), 1.12 (t, 3H).

Chiral analytical SFC [column: Daicel Chiralcel OJ-H, 5 µm, 250 mm×4.6 mm; eluent: carbon dioxide/methanol 80:20; flow rate: 3 ml/min; temperature: 40° C.; detection: 210 nm]: R$_t$=1.60 min.

Example 258

[1-{[3-Ethyl-5-methyl-1-(oxetan-2-ylmethyl)-2,4-dioxo-1,2,3,4-tetrahydrothieno[2,3-d]pyrimidin-6-yl]methyl}imidazolidin-2-ylidene]cyanamide (Enantiomer 2)

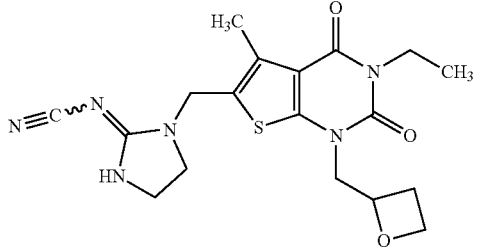 [SMILES: CCn1c(=O)c2c(C)c(CN3CCNC3=NC#N)sc2n(CC2CCO2)c1=O]

251 mg (0.624 mmol) of the racemic compound from Ex. 256 were dissolved in 25 ml of methanol/acetonitrile (1:1) and, in 50 portions, separated into the enantiomers by preparative SFC on a chiral phase [column: Daicel Chiralcel OJ-H, 5 µm, SFC, 250 mm×30 mm; eluent: carbon dioxide/methanol 90:10; flow rate: 100 ml/min; temperature: 40° C.; detection: 210 nm]. After the product fractions had been concentrated, the material obtained was stirred with diisopropyl ether at RT. Removal of the solids with suction and drying under high vacuum gave 48 mg (38% of theory) of Enantiomer 2 (>99% ee, chiral analytical HPLC).

$^1$H-NMR (400 MHz, DMSO-d$_6$, δ/ppm): 8.06 (s, 1H), 5.07-4.95 (m, 1H), 4.54-4.37 (m, 2H), 4.47 (s, 2H), 4.14 (d, 2H), 3.90 (q, 2H), 3.52-3.36 (m, 4H), 2.77-2.62 (m, 1H), 2.55-2.45 (m, 1H, mostly obscured by the DMSO signal), 2.41 (s, 3H), 1.12 (t, 3H).

Chiral analytical SFC [column: Daicel Chiralcel OJ-H, 5 µm, 250 mm×4.6 mm; eluent: carbon dioxide/methanol 80:20; flow rate: 3 ml/min; temperature: 40° C.; detection: 210 nm]: R$_t$=1.43 min.

Example 259

[1-{[3-Ethyl-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]cyanamide (racemate)

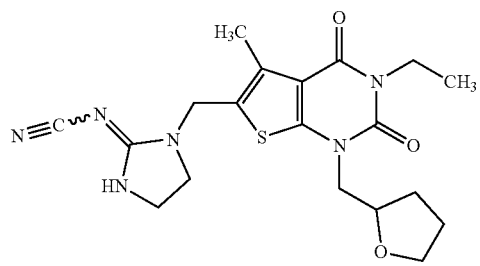 [SMILES: CCn1c(=O)c2c(C)c(CN3CCNC3=NC#N)sc2n(CC2CCCO2)c1=O]

1.0 g (2.05 mmol, 75% purity) of the compound from Ex. 225A was dissolved in 17 ml of DMF, and 449 mg (3.07 mmol) of dimethyl N-cyanodithioiminocarbonate and 566 mg (4.09 mmol) of potassium carbonate were added. The mixture was stirred at 80° C. in a microwave oven (Biotage Initiator with dynamic control of irradiation power) for 3 h. Thereafter, the reaction mixture was diluted with ethyl acetate and washed successively with saturated sodium hydrogencarbonate solution, water and saturated sodium chloride solution. After drying over anhydrous magnesium sulphate, the mixture was filtered and concentrated. The crude product was stirred with a water/acetonitrile mixture. The solids were filtered off with suction and dried under high vacuum. This gave a first fraction of the title compound (90 mg). The mother liquor from the stirring was purified by means of preparative HPLC (Method 8). This gave a second fraction of the product (142 mg), which was combined with the first. A total of 232 mg (27% of theory) of the title compound were thus obtained.

$^1$H-NMR (400 MHz, DMSO-d$_6$, δ/ppm): 8.07 (s, 1H), 4.47 (s, 2H), 4.29-4.16 (m, 1H), 4.05 (dd, 1H), 3.90 (q, 2H), 3.81-3.57 (m, 3H), 3.49-3.36 (m, 4H), 2.41 (s, 3H), 2.05-1.74 (m, 3H), 1.73-1.60 (m, 1H), 1.12 (t, 3H).

LC/MS (Method 1, ESIpos): R$_t$=0.78 min, m/z=417 [M+H]$^+$.

Example 260

[1-{[3-Ethyl-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]cyanamide (Enantiomer 1)

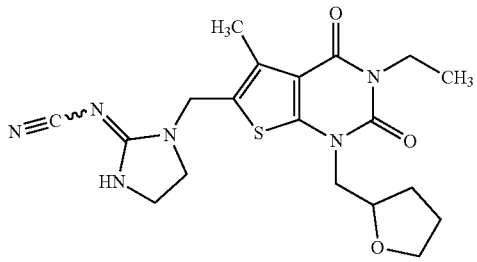 [SMILES: CCn1c(=O)c2c(C)c(CN3CCNC3=NC#N)sc2n(CC2CCCO2)c1=O]

201 mg (0.482 mmol) of the racemic compound from Ex. 259 were dissolved in a mixture of 30 ml of ethanol and 7 ml of acetonitrile and, in 125 portions, separated into the enantiomers by preparative HPLC on a chiral phase [column: Daicel Chiralcel OX-H, 5 μm, 250 mm×20 mm; eluent: ethanol; flow rate: 15 ml/min; temperature: 50° C.; detection: 220 nm]. After concentration of the product fractions and drying under high vacuum, 73 mg (72% of theory) of Enantiomer 1 were obtained (>99% ee, chiral analytical HPLC).

$^1$H-NMR (400 MHz, DMSO-$d_6$, δ/ppm): 8.07 (s, 1H), 4.47 (s, 2H), 4.28-4.18 (m, 1H), 4.05 (dd, 1H), 3.90 (q, 2H), 3.81-3.57 (m, 3H), 3.51-3.36 (m, 4H), 2.41 (s, 3H), 2.05-1.75 (m, 3H), 1.72-1.60 (m, 1H), 1.12 (t, 3H).

Chiral analytical HPLC [column: Daicel Chiralcel OX-H, 5 μm, 250 mm×4.6 mm; eluent: ethanol; flow rate: 1 ml/min; temperature: 50° C.; detection: 220 nm]: $R_t$=9.62 min.

Example 261

[1-{[3-Ethyl-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]cyanamide (Enantiomer 2)

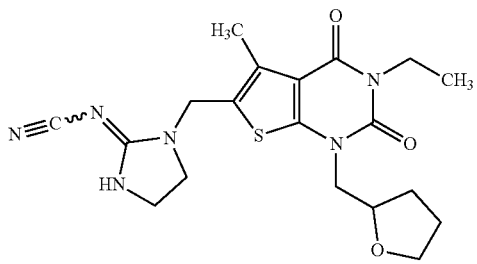 [SMILES: CCn1c(=O)c2c(C)c(CN3CCNC3=NC#N)sc2n(CC2CCCO2)c1=O]

201 mg (0.482 mmol) of the racemic compound from Ex. 259 were dissolved in a mixture of 30 ml of ethanol and 7 ml of acetonitrile and, in 125 portions, separated into the enantiomers by preparative HPLC on a chiral phase [column: Daicel Chiralcel OX-H, 5 μm, 250 mm×20 mm; eluent: ethanol; flow rate: 15 ml/min; temperature: 50° C.; detection: 220 nm]. After concentration of the product fractions and drying under high vacuum, 80 mg (79% of theory) of Enantiomer 2 were obtained (>99% ee, chiral analytical HPLC).

$^1$H-NMR (400 MHz, DMSO-$d_6$, δ/ppm): 8.07 (s, 1H), 4.47 (s, 2H), 4.28-4.16 (m, 1H), 4.05 (dd, 1H), 3.90 (q, 2H), 3.81-3.57 (m, 3H), 3.50-3.36 (m, 4H), 2.41 (s, 3H), 2.05-1.75 (m, 3H), 1.73-1.60 (m, 1H), 1.12 (t, 3H).

Chiral analytical HPLC [column: Daicel Chiralcel OX-H, 5 μm, 250 mm×4.6 mm; eluent: ethanol; flow rate: 1 ml/min; temperature: 50° C.; detection: 220 nm]: $R_t$=12.32 min.

Example 262

[1-{[3-Isopropyl-5-methyl-2,4-dioxo-1-(3,3,3-trifluoropropyl)-1,2,3,4-tetrahydrothieno[2,3-d]pyrimidin-6-yl]methyl}imidazolidin-2-ylidene]cyanamide

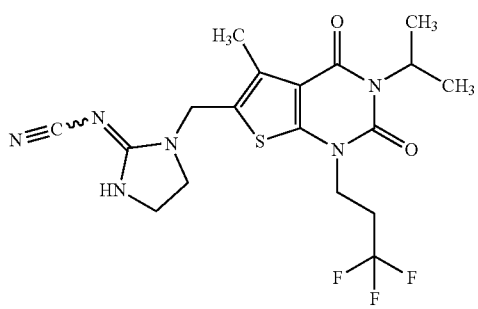 [SMILES: Cc1c(CN2CCNC2=NC#N)sc2c1c(=O)n(C(C)C)c(=O)n2CCC(F)(F)F]

360 mg (0.660 mmol, 72% purity) of the compound from Ex. 309A were dissolved in 5 ml of DMF, and 145 mg (0.991 mmol) of dimethyl N-cyanodithioiminocarbonate and 183 mg (1.32 mmol) of potassium carbonate were added. The mixture was stirred at 80° C. in a microwave oven (Biotage Initiator with dynamic control of irradiation power) for 4.5 h. Thereafter, the reaction mixture was filtered through a little silica gel and then separated into its components directly by means of preparative HPLC (Method 8). Concentration of the product fractions and drying under high vacuum gave 130 g (44% of theory) of the title compound.

$^1$H-NMR (400 MHz, DMSO-$d_6$, δ/ppm): 8.08 (s, 1H), 5.13 (sept, 1H), 4.49 (s, 2H), 4.08 (t, 2H), 3.53-3.35 (m, 4H), 2.85-2.68 (m, 2H), 2.41 (s, 3H), 1.40 (d, 6H).

LC/MS (Method 17, ESIpos): $R_t$=1.79 min, m/z=443.15 [M+H]$^+$.

Example 263

[1-{[3-Isoprpyl-1-(2-methoxyethyl)-5-methyl-2,4-dioxo-1,2,3,4-tetrahydrothieno[2,3-d]pyrimidin-6-yl]methyl}imidazolidin-2-ylidene]cyanamide

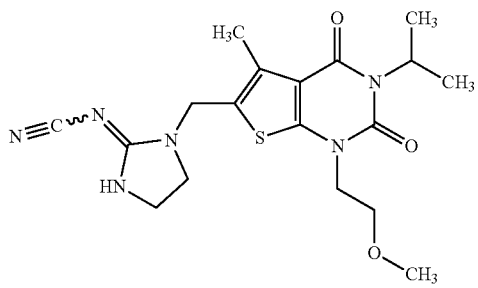 [SMILES: COCCn1c(=O)n(C(C)C)c(=O)c2c(C)c(CN3CCNC3=NC#N)sc21]

466 mg (1.05 mmol, 80% purity) of the compound from Ex. 310A were dissolved in 6 ml of DMF, and 231 mg (1.58 mmol) of dimethyl N-cyanodithioiminocarbonate and 291 mg (2.10 mmol) of potassium carbonate were added. The mixture was stirred at 80° C. in a microwave oven (Biotage Initiator with dynamic control of irradiation power) for 4.5 h. Thereafter, the reaction mixture was filtered through a little silica gel and then separated into its components directly by means of preparative HPLC (Method 8). Because of inadequate purity of the material thus obtained, the preparative HPLC was repeated twice more (the first time by Method 8 again, the second time by the following method: column: Kinetex C18, 5 µm, 100 mm×30 mm; eluent A: water+0.07% formic acid; eluent B: acetonitrile; gradient: 0.0-2.2 min 10% B, 2.2-7.0 min 20% B, 7.0-7.5 min 60% B, 7.5-9.0 min 92% B; flow rate: 70 ml/min; temperature: 25° C.; detection: 210 nm). Concentration of the product fractions and drying of the residue under high vacuum gave 61 mg (14% of theory) of the title compound.

$^1$H-NMR (400 MHz, DMSO-$d_6$, δ/ppm): 8.06 (s, 1H), 5.13 (sept, 1H), 4.46 (s, 2H), 3.99 (t, 2H), 3.62 (t, 2H), 3.50-3.35 (m, 4H), 3.25 (s, 3H), 2.39 (s, 3H), 1.40 (d, 6H).

LC/MS (Method 17, ESIpos): $R_t$=1.54 min, m/z=405.17 [M+H]$^+$.

Example 264

[1-{[3-Isopropyl-5-methyl-1-(oxetan-2-ylmethyl)-2,4-dioxo-1,2,3,4-tetrahydrothieno[2,3-d]pyrimidin-6-yl]methyl}imidazolidin-2-ylidene]cyanamide (racemate)

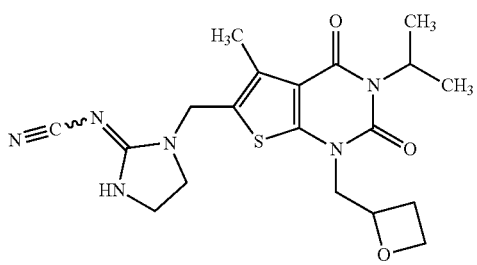

880 mg (1.68 mmol, 70% purity) of the compound from Ex. 311A were dissolved in 10 ml of DMF, and 369 mg (2.52 mmol) of dimethyl N-cyanodithioiminocarbonate and 465 mg (3.36 mmol) of potassium carbonate were added. The mixture was stirred at 80° C. in a microwave oven (Biotage Initiator with dynamic control of irradiation power) for 4.5 h. Thereafter, the reaction mixture was filtered through a little silica gel and then separated into its components directly by means of preparative HPLC (Method 8). Concentration of the product fractions and drying under high vacuum gave 140 mg (19% of theory) of the title compound.

$^1$H-NMR (400 MHz, DMSO-$d_6$, δ/ppm): 8.06 (s, 1H), 5.13 (sept, 1H), 5.05-4.93 (m, 1H), 4.54-4.36 (m, 2H), 4.46 (s, 2H), 4.11 (d, 2H), 3.51-3.35 (m, 4H), 2.76-2.62 (m, 1H), 2.53-2.44 (m, 1H, mostly obscured by the DMSO signal), 2.39 (s, 3H), 1.40 (d, 6H).

LC/MS (Method 17, ESIpos): $R_t$=1.48 min, m/z=417.17 [M+H]$^+$.

Example 265

[1-{[3-Isopropyl-5-methyl-1-(oxetan-2-ylmethyl)-2,4-dioxo-1,2,3,4-tetrahydrothieno[2,3-d]pyrimidin-6-yl]methyl}imidazolidin-2-ylidene]cyanamide (Enantiomer 1)

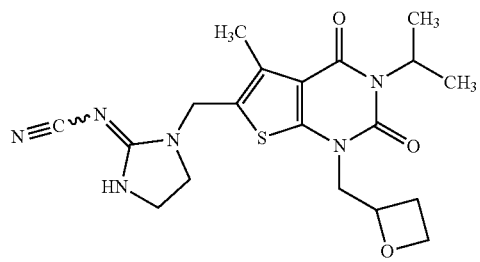 [SMILES: Cc1c(CN2CCNC2=NC#N)sc2c1c(=O)n(C(C)C)c(=O)n2CC1CCO1]

140 mg (0.336 mmol) of the racemic compound from Ex. 264 were dissolved in 20 ml of methanol/acetonitrile (1:1) and, in 20 portions, separated into the enantiomers by preparative SFC on a chiral phase [column: Daicel Chiralcel OX-H, 5 µm, SFC, 250 mm×30 mm; eluent: carbon dioxide/methanol 70:30; flow rate: 100 ml/min; temperature: 40° C.; detection: 210 nm]. After concentration of the product fractions and drying under high vacuum, 49 mg (70% of theory) of Enantiomer 1 were obtained (>99% ee, chiral analytical HPLC).

$^1$H-NMR (400 MHz, DMSO-$d_6$, δ/ppm): 8.06 (s, 1H), 5.13 (sept, 1H), 5.00 (quin, 1H), 4.54-4.37 (m, 2H), 4.46 (s, 2H), 4.11 (d, 2H), 3.53-3.35 (m, 4H), 2.76-2.62 (m, 1H), 2.53-2.44 (m, 1H, mostly obscured by the DMSO signal), 2.39 (s, 3H), 1.40 (d, 6H).

Chiral analytical SFC [column: Daicel Chiralcel OX-H, 5 µm, 250 mm×4.6 mm; eluent: carbon dioxide/methanol 70:30; flow rate: 3 ml/min; temperature: 40° C.; detection: 210 nm]: $R_t$=6.10 min.

Example 266

[1-{[3-Isopropyl-5-methyl-1-(oxetan-2-ylmethyl)-2,4-dioxo-1,2,3,4-tetrahydrothieno[2,3-d]pyrimidin-6-yl]methyl}imidazolidin-2-ylidene]cyanamide (Enantiomer 2)

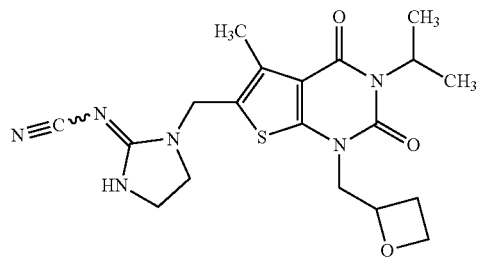 [SMILES: Cc1c(CN2CCNC2=NC#N)sc2c1c(=O)n(C(C)C)c(=O)n2CC1CCO1]

140 mg (0.336 mmol) of the racemic compound from Ex. 264 were dissolved in 20 ml of methanol/acetonitrile (1:1) and, in 20 portions, separated into the enantiomers by preparative SFC on a chiral phase [column: Daicel Chiralcel OX-H, 5 µm, SFC, 250 mm×30 mm; eluent: carbon dioxide/methanol 70:30; flow rate: 100 ml/min; temperature: 40° C.; detection: 210 nm]. After concentration of the product fractions and drying under high vacuum, 50 mg (71% of theory) of Enantiomer 2 were obtained (98.6% ee, chiral analytical HPLC).

¹H-NMR (400 MHz, DMSO-d₆, δ/ppm): 8.06 (s, 1H), 5.13 (sept, 1H), 5.05-4.93 (m, 1H), 4.54-4.35 (m, 2H), 4.46 (s, 2H), 4.11 (d, 2H), 3.50-3.36 (m, 4H), 2.76-2.62 (m, 1H), 2.54-2.44 (m, 1H, mostly obscured by the DMSO signal), 2.39 (s, 3H), 1.40 (d, 6H).

Chiral analytical SFC [column: Daicel Chiralcel OX-H, 5 μm, 250 mm×4.6 mm; eluent: carbon dioxide/methanol 70:30; flow rate: 3 ml/min; temperature: 40° C.; detection: 210 nm]: $R_t$=8.36 min.

Example 267

[1-{[3-Isopropyl-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]cyanamide (racemate)

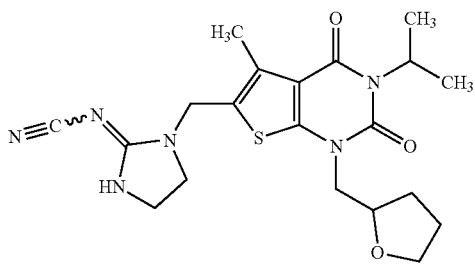 [SMILES: Cc1c(CN2CCNC2=NC#N)sc2c1c(=O)n(C(C)C)c(=O)n2CC1CCCO1]

900 mg (1.18 mmol, 50% purity) of the compound from Ex. 312A were dissolved in 12 ml of DMF, and 259 mg (1.77 mmol) of dimethyl N-cyanodithioiminocarbonate and 327 mg (2.36 mmol) of potassium carbonate were added. The mixture was stirred at 80° C. in a microwave oven (Biotage Initiator with dynamic control of irradiation power) for 4.5 h. Thereafter, the reaction mixture was diluted with ethyl acetate and washed successively with saturated sodium hydrogencarbonate solution, water and saturated sodium chloride solution. After drying over anhydrous magnesium sulphate, the mixture was filtered and concentrated. The crude product was stirred with diisopropyl ether with a few added drops of ethyl acetate. The solids were filtered off with suction and dried under high vacuum. This gave a first fraction of the title compound (290 mg). The mother liquor from the stirring was purified by means of preparative HPLC (Method 8). This gave a second fraction of the product (54 mg), which was combined with the first. A total of 344 mg (67% of theory) of the title compound were thus obtained.

¹H-NMR (400 MHz, DMSO-d₆, δ/ppm): 8.06 (s, 1H), 5.14 (sept, 1H), 4.46 (s, 2H), 4.29-4.15 (m, 1H), 4.04 (dd, 1H), 3.75 (q, 1H), 3.69-3.57 (m, 2H), 3.50-3.36 (m, 4H), 2.39 (s, 3H), 2.06-1.74 (m, 3H), 1.72-1.59 (m, 1H), 1.40 (d, 6H).

LC/MS (Method 17, ESIpos): $R_t$=1.63 min, m/z=431.18 [M+H]⁺.

Example 268

[1-{[1-(2-Methoxyethyl)-5-methyl-2,4-dioxo-3-(2,2,2-trifluoroethyl)-1,2,3,4-tetrahydrothieno[2,3-d]pyrimidin-6-yl]methyl}imidazolidin-2-ylidene]cyanamide

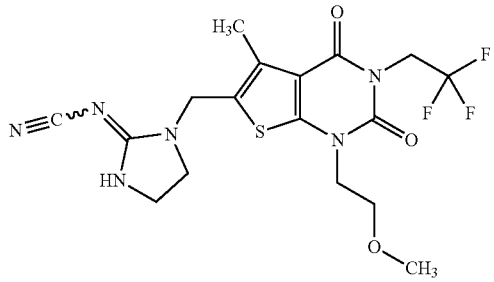 [SMILES: COCCn1c(=O)n(CC(F)(F)F)c(=O)c2c(C)c(CN3CCNC3=NC#N)sc21]

300 mg (0.761 mmol) of the compound from Ex. 249A were dissolved in 4.4 ml of DMF, and 167 mg (1.14 mmol) of dimethyl N-cyanodithioiminocarbonate and 210 mg (1.52 mmol) of potassium carbonate were added. The mixture was stirred at 80° C. in a microwave oven (Biotage Initiator with dynamic control of irradiation power) for 3.75 h. Thereafter, the reaction mixture was diluted with ethyl acetate and washed successively with saturated sodium hydrogencarbonate solution, water and saturated sodium chloride solution. After drying over anhydrous magnesium sulphate, the mixture was filtered and concentrated. The crude product was purified by preparative HPLC (Method 8). This gave 154 mg (45% of theory) of the title compound.

¹H-NMR (400 MHz, DMSO-d₆, δ/ppm): 8.09 (s, 1H), 4.70 (q, 2H), 4.49 (s, 2H), 4.06 (t, 2H), 3.64 (t, 2H), 3.53-3.36 (m, 4H), 3.24 (s, 3H), 2.41 (s, 3H).

LC/MS (Method 6, ESIpos): $R_t$=1.51 min, m/z=445 [M+H]⁺.

Example 269

[1-{[5-Methyl-2,4-dioxo-1-(tetrahydrofuran-2-ylmethyl)-3-(2,2,2-trifluoroethyl)-1,2,3,4-tetrahydrothieno[2,3-d]pyrimidin-6-yl]methyl}imidazolidin-2-ylidene]cyanamide (racemate)

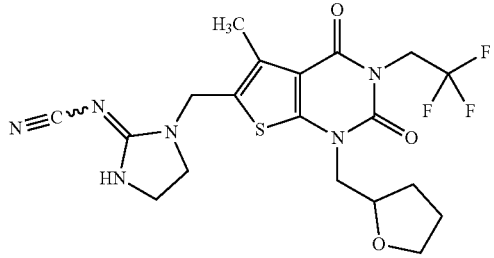 [SMILES: Cc1c(CN2CCNC2=NC#N)sc2c1c(=O)n(CC(F)(F)F)c(=O)n2CC1CCCO1]

890 mg (1.78 mmol, 84% purity) of the compound from Ex. 252A were dissolved in 14.5 ml of DMF, and 390 mg (2.67 mmol) of dimethyl N-cyanodithioiminocarbonate and 491 mg (3.56 mmol) of potassium carbonate were added. The mixture was stirred at 80° C. in a microwave oven (Biotage Initiator with dynamic control of irradiation power) for 4.5 h. Thereafter, the reaction mixture was diluted with ethyl acetate and washed successively with saturated sodium hydrogencarbonate solution, water and saturated sodium chloride solution. After drying over anhydrous magnesium sulphate, the mixture was filtered and concentrated. The crude product was purified by preparative HPLC (Method 8). After concentration of the product fractions and drying under high vacuum, 210 mg (25% of theory) of the title compound were obtained.

$^1$H-NMR (400 MHz, DMSO-$d_6$, δ/ppm): 8.09 (s, 1H), 4.70 (q, 2H), 4.49 (s, 2H), 4.28-4.18 (m, 1H), 4.07 (dd, 1H), 3.81-3.70 (m, 2H), 3.67-3.58 (m, 1H), 3.51-3.37 (m, 4H), 2.41 (s, 3H), 2.06-1.75 (m, 3H), 1.73-1.61 (m, 1H).

LC/MS (Method 1, ESIpos): $R_t$=0.87 min, m/z=471 [M+H]$^+$.

Example 270

1-[2-(Cyclopropyloxy)ethyl]-6-[(2,3-dioxopiperazin-1-yl)methyl]-3-ethyl-5-methylthieno[2,3-d]pyrimidine-2,4(1H,3H)-dione

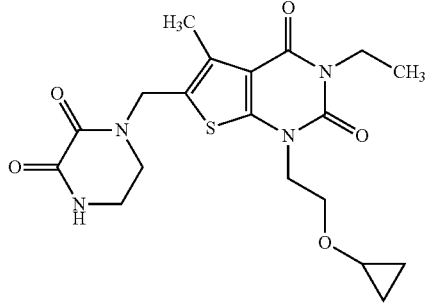 [SMILES: CCn1c(=O)c2c(C)c(CN3CCNC(=O)C3=O)sc2n(CCOC2CC2)c1=O]

105 mg (0.203 mmol) of the compound from Example 308A were dissolved in 4.5 ml of ethanol, and 300 mg (2.03 mmol) of diethyl oxalate were added. The mixture was stirred in a microwave apparatus at 80° C. for 18 h. Thereafter, the reaction solution was concentrated on a rotary evaporator. The residue was dissolved in 6 ml of DMSO and this solution was purified by means of preparative HPLC (Method 14). Combination of the product fractions and freeze-drying gave 55 mg (64% of theory) of the title compound.

$^1$H-NMR (400 MHz, DMSO-$d_6$, δ/ppm): 8.64 (br. s, 1H), 4.68 (s, 2H), 4.00 (t, 2H), 3.89 (q, 2H), 3.72 (t, 2H), 3.50-3.44 (m, 2H), 3.34-3.28 (m, 3H), 2.42 (s, 3H), 1.11 (t, 3H), 0.42-0.33 (m, 4H).

LC/MS (Method 3, ESIpos): $R_t$=0.89 min, m/z=421 [M+H]$^+$.

Example 271

6-[(2,3-Dioxopiperazin-1-yl)methyl]-1-(2-ethoxyethyl)-3-isobutyl-5-methylthieno[2,3-d]pyrimidine-2,4(1H,3H)-dione

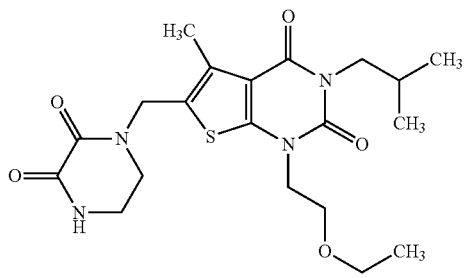 [SMILES: CCOCCn1c(=O)n(CC(C)C)c(=O)c2c(C)c(CN3CCNC(=O)C3=O)sc21]

158 mg (0.343 mmol) of the compound from Example 314A were dissolved in 5 ml of ethanol, and 101 mg (0.686 mmol) of diethyl oxalate were added. The mixture was stirred in a microwave apparatus at 80° C. for 18 h. Thereafter, the reaction solution was concentrated on a rotary evaporator. The residue was dissolved in 6 ml of DMSO and this solution was purified by means of preparative HPLC (Method 14). Combination of the product fractions and freeze-drying gave 45 mg (30% of theory) of the title compound.

$^1$H-NMR (400 MHz, DMSO-$d_6$, δ/ppm): 8.62 (br. s, 1H), 4.69 (s, 2H), 4.01 (t, 2H), 3.71 (d, 2H), 3.65 (t, 2H), 3.52-3.46 (m, 2H), 3.42 (q, 2H), 2.42 (s, 3H), 2.09-1.97 (m, 1H), 1.01 (t, 3H), 0.84 (d, 6H).

LC/MS (Method 3, ESIpos): $R_t$=1.02 min, m/z=437 [M+H]$^+$.

Example 272

3-(2,2-Dimethylpropyl)-6-[(2,3-dioxopiperazin-1-yl)methyl]-5-methyl-1-(3,3,3-trifluoropropyl)thieno[2,3-d]pyrimidine-2,4(1H,3H)-dione

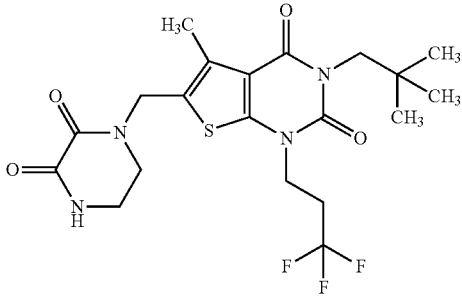 [SMILES: Cc1c(CN2CCNC(=O)C2=O)sc2c1c(=O)n(CC(C)(C)C)c(=O)n2CCC(F)(F)F]

160 mg (0.316 mmol) of the compound from Example 315A were dissolved in 5 ml of ethanol, and 466 mg (3.15 mmol) of diethyl oxalate were added. The mixture was stirred at 80° C. for 21 h. Thereafter, the reaction solution was concentrated on a rotary evaporator. The residue was dissolved in 3 ml of DMSO and this solution was purified by means of preparative HPLC (Method 14). Combination of the product fractions and freeze-drying gave 76 mg (50% of theory) of the title compound.

$^1$H-NMR (400 MHz, DMSO-$d_6$, δ/ppm): 8.64 (br. s, 1H), 4.71 (s, 2H), 4.10 (t, 2H), 3.81 (br. s, 2H), 3.55-3.46 (m, 2H), 2.84-2.68 (m, 2H), 2.43 (s, 3H), 0.89 (s, 9H).

LC/MS (Method 3, ESIneg): $R_t$=1.16 min, m/z=519 [M−H+HCOOH]$^-$.

Example 273

3-(2,2-Dimethylpropyl)-6-[(2,3-dioxopiperazin-1-yl)methyl]-1-(3-fluoropropyl)-5-methylthieno[2,3-d]pyrimidine-2,4(1H,3H)-dione

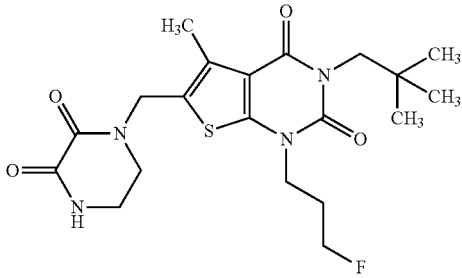 [SMILES: Cc1c(CN2CCNC(=O)C2=O)sc2c1c(=O)n(CC(C)(C)C)c(=O)n2CCCF]

103 mg (0.22 mmol) of the compound from Example 316A were dissolved in 3.5 ml of ethanol, and 324 mg (2.19 mmol) of diethyl oxalate were added. The mixture was stirred at 80° C. for 21 h. Thereafter, the reaction solution was concentrated on a rotary evaporator. The residue was dissolved in 3 ml of DMSO and this solution was purified by means of preparative HPLC (Method 14). Combination of the product fractions and freeze-drying gave 55 mg (55% of theory) of the title compound.

$^1$H-NMR (400 MHz, DMSO-d$_6$, δ/ppm): 8.64 (br. s, 1H), 4.70 (s, 2H), 4.59 (t, 1H), 4.47 (t, 1H), 3.98 (t, 2H), 3.80 (br. s, 2H), 3.54-3.47 (m, 2H), 2.42 (s, 3H), 2.12-2.05 (m, 1H), 2.02 (t, 1H), 0.89 (s, 9H).

LC/MS (Method 3, ESIneg): R$_t$=1.06 min, m/z=483 [M−H+HCOOH]$^-$.

Example 274

3-(2,2-Dimethylpropyl)-6-[(2,3-dioxopiperazin-1-yl)methyl]-1-(2-methoxyethyl)-5-methylthieno[2,3-d]pyrimidine-2,4(1H,3H)-dione

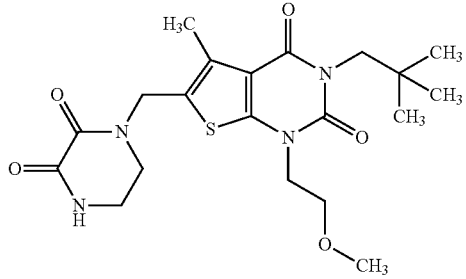 [SMILES: COCCn1c(=O)n(CC(C)(C)C)c(=O)c2c(C)c(CN3CCNC(=O)C3=O)sc21]

172 mg (0.364 mmol) of the compound from Example 317A were dissolved in 5 ml of ethanol, and 537 mg (3.64 mmol) of diethyl oxalate were added. The mixture was stirred at 80° C. for 18 h. Thereafter, the reaction solution was concentrated on a rotary evaporator. The residue was dissolved in 3 ml of DMSO and this solution was purified by means of preparative HPLC (Method 14). Combination of the product fractions and freeze-drying gave 84 mg (52% of theory) of the title compound.

$^1$H-NMR (400 MHz, DMSO-d$_6$, δ/ppm): 8.64 (br. s, 1H), 4.68 (s, 2H), 4.02 (t, 2H), 3.81 (br. s, 2H), 3.61 (t, 2H), 3.53-3.46 (m, 2H), 3.22 (s, 3H), 2.41 (s, 3H), 0.88 (s, 9H).

LC/MS (Method 3, ESIpos): R$_t$=1.03 min, m/z=437 [M+H]$^+$.

Example 275

3-(2,2-Difluoroethyl)-6-[(2,3-dioxopiperazin-1-yl)methyl]-1,5-dimethylthieno[2,3-d]pyrimidine-2,4(1H,3H)-dione

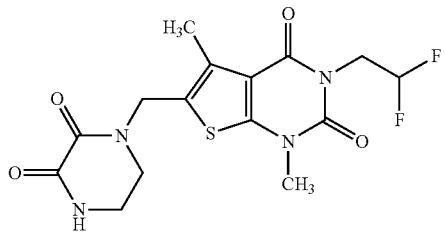 [SMILES: Cc1c(CN2CCNC(=O)C2=O)sc2c1c(=O)n(CC(F)F)c(=O)n2C]

65 mg (0.137 mmol) of the compound from Example 318A were dissolved in 2.5 ml of ethanol, and 202 mg (1.37 mmol) of diethyl oxalate were added. The mixture was stirred in a microwave apparatus at 80° C. for 18 h. Thereafter, the reaction solution was concentrated on a rotary evaporator. The residue was dissolved in 3 ml of DMSO and this solution was purified by means of preparative HPLC (Method 14). Combination of the product fractions and freeze-drying gave 32 mg (61% of theory) of the title compound.

$^1$H-NMR (400 MHz, DMSO-d$_6$, δ/ppm): 8.65 (br. s, 1H), 6.36-6.05 (m, 1H), 4.71 (s, 2H), 4.29 (td, 2H), 3.53-3.46 (m, 2H), 3.43 (s, 3H), 2.44 (s, 3H).

LC/MS (Method 3, ESIpos): R$_t$=0.77 min, m/z=387 [M+H]$^+$.

Example 276

6-[(2,3-Dioxopiperazin-1-yl)methyl]-3-(2-methoxyethyl)-5-methyl-1-(3,3,3-trifluoropropyl)thieno[2,3-d]pyrimidine-2,4(1H,3H)-dione

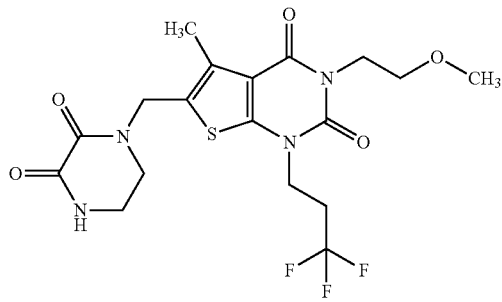 [SMILES: COCCn1c(=O)c2c(C)c(CN3CCNC(=O)C3=O)sc2n(CCC(F)(F)F)c1=O]

77 mg (0.153 mmol) of the compound from Example 319A were dissolved in 3 ml of ethanol, and 112 mg (0.764 mmol) of diethyl oxalate were added. The mixture was stirred in a microwave apparatus at 80° C. for 18 h. Thereafter, the reaction solution was concentrated on a rotary evaporator. The residue was dissolved in 3 ml of DMSO and this solution was purified by means of preparative HPLC (Method 14). Combination of the product fractions and freeze-drying gave 41 mg (58% of theory) of the title compound.

$^1$H-NMR (400 MHz, DMSO-d$_6$, δ/ppm): 8.63 (br. s, 1H), 4.71 (s, 2H), 4.10 (t, 2H), 4.05 (t, 2H), 3.49 (t, 4H), 3.23 (s, 3H), 2.82-2.69 (m, 2H), 2.44 (s, 3H).

LC/MS (Method 3, ESIpos): R$_t$=0.87 min, m/z=463 [M+H]$^+$.

Example 277

6-[(2,3-Dioxopiperazin-1-yl)methyl]-1-(3-fluoropropyl)-3-(2-methoxyethyl)-5-methylthieno[2,3-d]pyrimidine-2,4(1H,3H)-dione

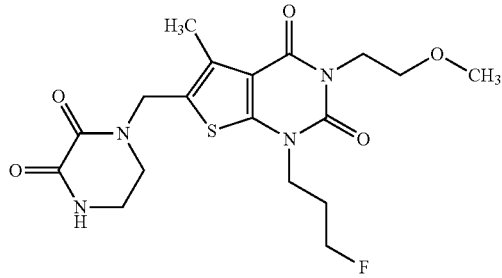 [SMILES: COCCn1c(=O)c2c(C)c(CN3CCNC(=O)C3=O)sc2n(CCCF)c1=O]

65 mg (0.112 mmol) of the compound from Example 320A were dissolved in 5 ml of ethanol, and 165 mg (1.12 mmol) of diethyl oxalate were added. The mixture was stirred at 80° C. for 18 h. Thereafter, the reaction solution was concentrated on a rotary evaporator. The residue was dissolved in 3 ml of DMSO and this solution was purified by means of preparative HPLC (Method 14). Combination of the product fractions and freeze-drying gave 25 mg (47% of theory) of the title compound.

$^1$H-NMR (400 MHz, DMSO-d$_6$, δ/ppm): 8.64 (br. s, 1H), 4.70 (s, 2H), 4.59 (t, 1H), 4.47 (t, 1H), 4.05 (t, 2H), 3.98 (t, 2H), 3.49 (d, 2H), 3.31 (br. s, 2H), 3.24 (s, 3H), 2.43 (s, 3H), 2.13-2.05 (m, 1H), 2.05-1.98 (m, 1H).

LC/MS (Method 3, ESIpos): R$_t$=0.77 min, m/z=427 [M+H]$^+$.

Example 278

6-[(2,3-Dioxopiperazin-1-yl)methyl]-3-(2-methoxy-ethyl)-5-methyl-1-(tetrahydrofuran-2-ylmethyl) thieno[2,3-d]pyrimidine-2,4(1H,3H)-dione (racemate)

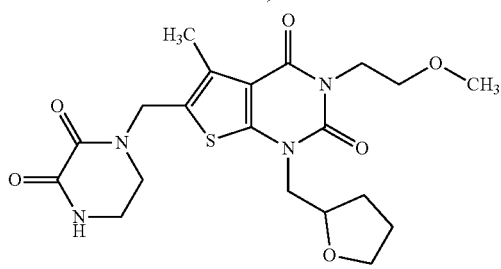

100 mg (0.166 mmol) of the compound from Example 321A were dissolved in 5 ml of ethanol, and 245 mg (1.66 mmol) of diethyl oxalate were added. The mixture was stirred at 80° C. for 18 h. Thereafter, the reaction solution was concentrated on a rotary evaporator. The residue was dissolved in 3 ml of DMSO and this solution was purified by means of preparative HPLC (Method 14). Combination of the product fractions and freeze-drying gave 43 mg (56% of theory) of the title compound.

$^1$H-NMR (400 MHz, DMSO-d$_6$, δ/ppm): 8.64 (br. s, 1H), 4.74-4.64 (m, 2H), 4.25-4.17 (m, 1H), 4.09-3.99 (m, 3H), 3.77-3.66 (m, 2H), 3.64-3.57 (m, 1H), 3.49 (q, 4H), 3.32-3.28 (m, 2H), 3.23 (s, 3H), 2.42 (s, 3H), 2.02-1.93 (m, 1H), 1.93-1.75 (m, 2H), 1.70-1.60 (m, 1H).

LC/MS (Method 3, ESIpos): R$_t$=0.79 min, m/z=451 [M+H]$^+$.

Example 279

6-[(2,3-Dioxopiperazin-1-yl)methyl]-3-(2-methoxy-2-methylpropyl)-5-methyl-1-(3,3,3-trifluoropropyl) thieno[2,3-d]pyrimidine-2,4(1H,3H)-dione

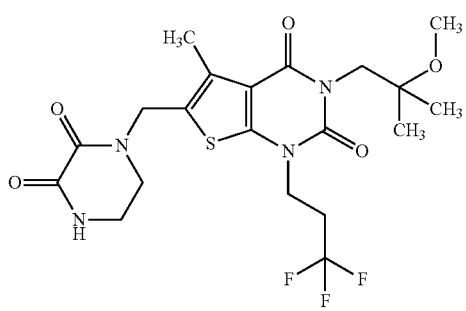 [SMILES: COC(C)(C)Cn1c(=O)c2c(C)c(CN3CCNC(=O)C3=O)sc2n(CCC(F)(F)F)c1=O]

160 mg (0.297 mmol) of the compound from Example 322A were dissolved in 5 ml of ethanol, and 438 mg (2.97 mmol) of diethyl oxalate were added. The mixture was stirred at 80° C. for 19 h. Thereafter, the reaction solution was concentrated on a rotary evaporator. The residue was dissolved in 3 ml of DMSO and this solution was purified by means of preparative HPLC (Method 14). Combination of the product fractions and freeze-drying gave 64 mg (40% of theory) of the title compound.

$^1$H-NMR (400 MHz, DMSO-d$_6$, δ/ppm): 8.64 (br. s, 1H), 4.71 (s, 2H), 4.10 (t, 2H), 3.99 (br. s, 2H), 3.54-3.47 (m, 2H), 3.15 (s, 3H), 2.82-2.68 (m, 2H), 2.43 (s, 3H), 1.08 (s, 6H).

LC/MS (Method 3, ESIpos): R$_t$=0.98 min, m/z=491 [M+H]$^+$.

Example 280

6-[(2,3-Dioxopiperazin-1-yl)methyl]-1-(3-fluoropropyl)-3-(2-methoxy-2-methylpropyl)-5-methylthieno [2,3-d]pyrimidine-2,4(1H,3H)-dione

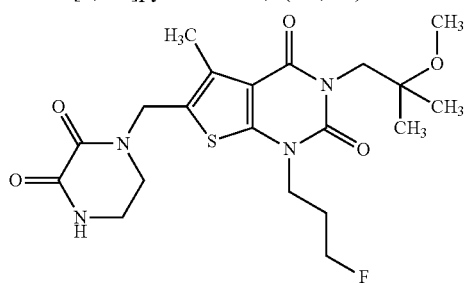

200 mg (0.424 mmol) of the compound from Example 323A were dissolved in 5 ml of ethanol, and 626 mg (4.24 mmol) of diethyl oxalate were added. The mixture was stirred at 80° C. for 18 h. Thereafter, the reaction solution was concentrated on a rotary evaporator. The residue was dissolved in 3 ml of DMSO and this solution was purified by means of preparative HPLC (Method 14). Combination of the product fractions and freeze-drying gave 91 mg (47% of theory) of the title compound.

$^1$H-NMR (400 MHz, DMSO-d$_6$, δ/ppm): 8.64 (br. s, 1H), 4.70 (s, 2H), 4.58 (t, 1H), 4.47 (t, 1H), 4.07-3.90 (m, 4H), 3.54-3.46 (m, 2H), 3.15 (s, 3H), 2.43 (s, 3H), 2.13-2.05 (m, 1H), 2.02 (quin, 1H), 1.08 (s, 6H).

LC/MS (Method 3, ESIpos): R$_t$=0.89 min, m/z=455 [M+H]$^+$.

Example 281

6-[(2,3-Dioxopiperazin-1-yl)methyl]-1-(2-methoxy-ethyl)-3-(2-methoxy-2-methylpropyl)-5-methylth-ieno[2,3-d]pyrimidine-2,4(1H,3H)-dione

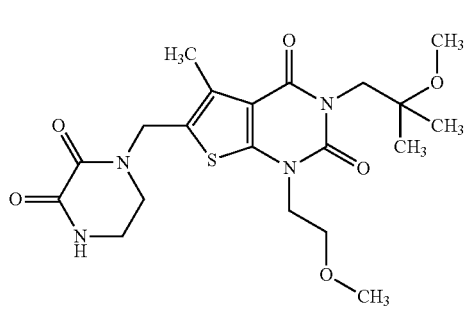 [SMILES: COCCn1c(=O)n(CC(C)(C)OC)c(=O)c2c(C)c(CN3CCNC(=O)C3=O)sc21]

100 mg (0.196 mmol) of the compound from Example 324A were dissolved in 5 ml of ethanol, and 289 mg (1.96 mmol) of diethyl oxalate were added. The mixture was stirred in a microwave apparatus at 80° C. for 18 h. Thereafter, the reaction solution was concentrated on a rotary evaporator. The residue was dissolved in 3 ml of DMSO and this solution was purified by means of preparative HPLC (Method 14). Combination of the product fractions and freeze-drying gave 58 mg (62% of theory) of the title compound.

$^1$H-NMR (400 MHz, DMSO-d$_6$, δ/ppm): 8.64 (br. s, 1H), 4.69 (s, 2H), 4.08-3.94 (m, 4H), 3.61 (t, 2H), 3.50 (dd, 2H), 3.22 (s, 3H), 3.15 (s, 3H), 2.42 (s, 3H), 1.08 (s, 6H).

LC/MS (Method 3, ESIpos): R$_t$=0.85 min, m/z=453 [M+H]$^+$.

Example 282

5-Methyl-6-[(5-oxo-2,5-dihydro-1H-pyrazol-1-yl)methyl]-3-(2,2,2-trifluoroethyl)-1-(3,3,3-trifluoropropyl)thieno[2,3-d]pyrimidine-2,4(1H,3H)-dione

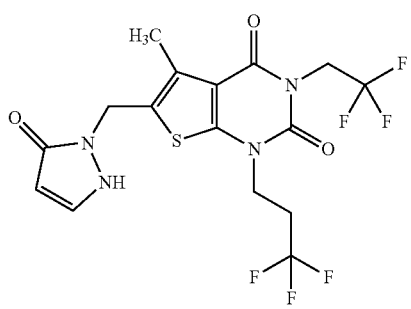 [SMILES: Cc1c(Cn2[nH]ccc2=O)sc2c1c(=O)n(CC(F)(F)F)c(=O)n2CCC(F)(F)F]

Analogously to the method described in Ex. 133, 365 mg (0.606 mmol) of the compound from Ex. 427A were used to prepare 164 mg (59% of theory) of the title compound.

$^1$H-NMR (400 MHz, DMSO-d$_6$, δ/ppm): 11.17 (s, 1H), 7.16 (d, 1H), 5.33 (d, 1H), 5.18 (s, 2H), 4.69 (q, 2H), 4.10 (t, 2H), 2.84-2.64 (m, 2H), 2.54 (s, 3H).

LC/MS (Method 17, ESIneg): R$_t$=1.61 min, m/z=455.06 [M-H]$^-$.

Example 283

1-(2-Methoxyethyl)-5-methyl-6-[(5-oxo-2,5-dihydro-1H-pyrazol-1-yl)methyl]-3-(2,2,2-trifluoroethyl)thieno[2,3-d]pyrimidine-2,4(1H,3H)-dione

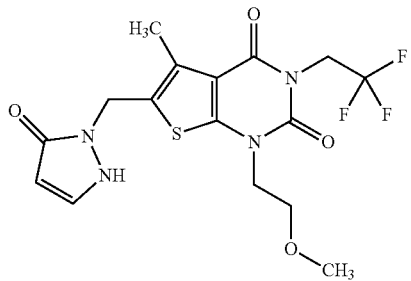 [SMILES: COCCn1c(=O)n(CC(F)(F)F)c(=O)c2c(C)c(Cn3[nH]ccc3=O)sc21]

Analogously to the method described in Ex. 133, 370 mg (0.655 mmol) of the compound from Ex. 428A were used to prepare 180 mg (65% of theory) of the title compound.

$^1$H-NMR (400 MHz, DMSO-d$_6$, δ/ppm): 11.15 (br. s, 1H), 7.17 (s, 1H), 5.33 (d, 1H), 5.16 (s, 2H), 4.69 (q, 2H), 4.02 (t, 2H), 3.61 (t, 2H), 3.21 (s, 3H), 2.46 (s, 3H).

LC/MS (Method 17, ESIneg): R$_t$=1.35 min, m/z=417.09 [M-H]$^-$.

Example 284

5-Methyl-6-[(5-oxo-2,5-dihydro-1H-pyrazol-1-yl)methyl]-1-(tetrahydrofuran-2-ylmethyl)-3-(2,2,2-trifluoroethyl)thieno[2,3-d]pyrimidine-2,4(1H,3H)-dione (racemate)

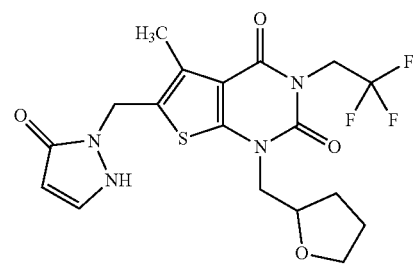 [SMILES: Cc1c(Cn2[nH]ccc2=O)sc2c1c(=O)n(CC(F)(F)F)c(=O)n2CC1CCCO1]

Analogously to the method described in Ex. 133, 695 mg (1.18 mmol) of the compound from Ex. 429A were used to prepare 230 mg (43% of theory) of the title compound.

$^1$H-NMR (400 MHz, DMSO-d$_6$, δ/ppm): 11.14 (s, 1H), 7.15 (d, 1H), 5.33 (d, 1H), 5.16 (s, 2H), 4.69 (q, 2H), 4.26-4.14 (m, 1H), 4.04 (dd, 1H), 3.77-3.65 (m, 2H), 3.64-3.53 (m, 1H), 2.46 (s, 3H), 2.04-1.74 (m, 3H), 1.71-1.59 (m, 1H).

LC/MS (Method 17, ESIneg): R$_t$=1.46 min, m/z=443.10 [M-H]$^-$.

Example 285

5-Methyl-6-[(5-oxo-2,5-dihydro-1H-pyrazol-1-yl)methyl]-1-(tetrahydrofuran-2-ylmethyl)-3-(2,2,2-trifluoroethyl)thieno[2,3-d]pyrimidine-2,4(1H,3H)-dione (Enantiomer 1)

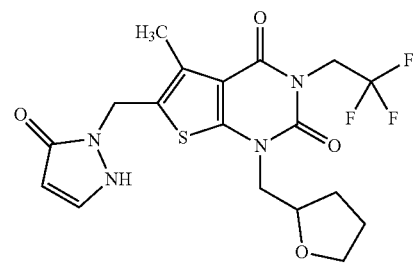 [SMILES: Cc1c(Cn2[nH]ccc2=O)sc2c1c(=O)n(CC(F)(F)F)c(=O)n2CC1CCCO1]

199 mg (0.448 mmol) of the racemic compound from Ex. 284 were dissolved in a mixture of 8 ml of ethanol and 1 ml of acetonitrile and, in 36 portions, separated into the enantiomers by preparative HPLC on a chiral phase [column: Daicel Chiralcel OZ-H, 5 μm, 250 mm×20 mm; eluent: isohexane/ethanol 1:1, with 0.2% acetic acid in the ethanol; flow rate: 15 ml/min; temperature: 35° C.; detection: 220 nm]. After concentration of the product fractions and drying under high vacuum, 88 mg (88% of theory) of Enantiomer 1 were obtained (>99% ee, chiral analytical HPLC).

¹H-NMR (400 MHz, DMSO-d₆, δ/ppm): 11.17 (br. s, 1H), 7.15 (s, 1H), 5.32 (s, 1H), 5.15 (s, 2H), 4.69 (q, 2H), 4.25-4.14 (m, 1H), 4.04 (dd, 1H), 3.77-3.65 (m, 2H), 3.63-3.54 (m, 1H), 2.46 (s, 3H), 2.05-1.75 (m, 3H), 1.71-1.59 (m, 1H).

Chiral analytical HPLC [column: Daicel Chiralcel OZ-H, 5 µm, 250 mm×4.6 mm; eluent: isohexane/ethanol 1:1, with 0.2% TFA and 1% water in the ethanol; flow rate: 1 ml/min; temperature: 40° C.; detection: 220 nm]: $R_t$=5.61 min.

Example 286

5-Methyl-6-[(5-oxo-2,5-dihydro-1H-pyrazol-1-yl) methyl]-1-(tetrahydrofuran-2-ylmethyl)-3-(2,2,2-trifluoroethyl)thieno[2,3-d]pyrimidine-2,4(1H,3H)-dione (Enantiomer 2)

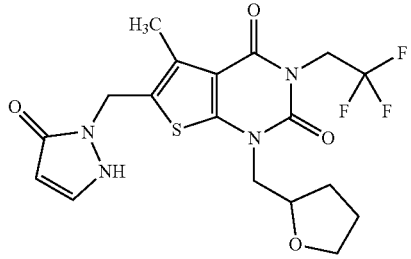 [SMILES: Cc1c(Cn2[nH]ccc2=O)sc2c1c(=O)n(CC(F)(F)F)c(=O)n2CC1CCCO1]

199 mg (0.448 mmol) of the racemic compound from Ex. 284 were dissolved in a mixture of 8 ml of ethanol and 1 ml of acetonitrile and, in 36 portions, separated into the enantiomers by preparative HPLC on a chiral phase [column: Daicel Chiralcel OZ-H, 5 µm, 250 mm×20 mm; eluent: isohexane/ethanol 1:1, with 0.2% acetic acid in the ethanol; flow rate: 15 ml/min; temperature: 35° C.; detection: 220 nm]. After concentration of the product fractions and drying under high vacuum, 80 mg (80% of theory) of Enantiomer 2 were obtained (95% ee, chiral analytical HPLC).

¹H-NMR (400 MHz, DMSO-d₆, δ/ppm): 11.18 (br. s, 1H), 7.16 (s, 1H), 5.32 (s, 1H), 5.15 (s, 2H), 4.69 (q, 2H), 4.25-4.13 (m, 1H), 4.04 (dd, 1H), 3.77-3.65 (m, 2H), 3.63-3.53 (m, 1H), 2.46 (s, 3H), 2.04-1.75 (m, 3H), 1.71-1.59 (m, 1H).

Chiral analytical HPLC [column: Daicel Chiralcel OZ-H, 5 µm, 250 mm×4.6 mm; eluent: isohexane/ethanol 1:1, with 0.2% TFA and 1% water in the ethanol; flow rate: 1 ml/min; temperature: 40° C.; detection: 220 nm]: $R_t$=6.36 min.

Example 287

3-(2-Methoxyethyl)-5-methyl-6-[(5-oxo-2,5-dihydro-1H-pyrazol-1-yl)methyl]-1-(3,3,3-trifluoropropyl)thieno[2,3-d]pyrimidine-2,4(1H,3H)-dione

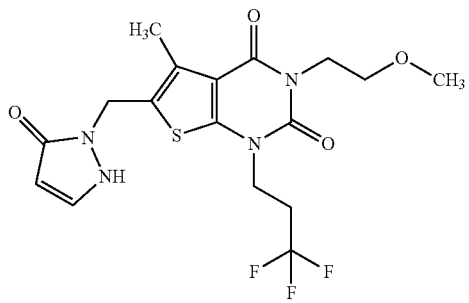 [SMILES: COCCn1c(=O)c2c(C)c(Cn3[nH]ccc3=O)sc2n(CCC(F)(F)F)c1=O]

Analogously to the method described in Ex. 133, 270 mg (0.467 mmol) of the compound from Ex. 430A were used to prepare 90 mg (44% of theory) of the title compound. The reaction time here was 15 min.

¹H-NMR (400 MHz, DMSO-d₆, δ/ppm): 11.19 (broad, 1H), 7.16 (br. s, 1H), 5.31 (d, 1H), 5.16 (s, 2H), 4.06 (t, 2H), 4.05 (t, 2H), 3.48 (t, 2H), 3.23 (s, 3H), 2.83-2.64 (m, 2H), 2.48 (s, 3H).

LC/MS (Method 17, ESIneg): $R_t$=1.35 min, m/z=431.10 [M−H]⁻.

Example 288

1,3-Bis(2-methoxyethyl)-5-methyl-6-[(5-oxo-2,5-dihydro-1H-pyrazol-1-yl)methyl]thieno[2,3-d]pyrimidine-2,4(1H,3H)-dione

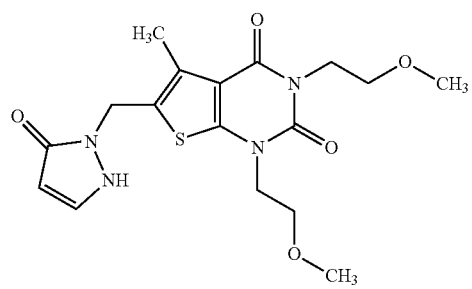 [SMILES: COCCn1c(=O)c2c(C)c(Cn3[nH]ccc3=O)sc2n(CCOC)c1=O]

Analogously to the method described in Ex. 133, 285 mg (0.527 mmol) of the compound from Ex. 431A were used to prepare 109 mg (52% of theory) of the title compound. The reaction time here was 15 min.

¹H-NMR (400 MHz, DMSO-d₆, δ/ppm): 7.19 (d, 1H), 5.34 (d, 1H), 5.15 (s, 2H), 4.05 (t, 2H), 3.98 (t, 2H), 3.60 (t, 2H), 3.48 (t, 2H), 3.23 (s, 3H), 3.21 (s, 3H), 2.46 (s, 3H).

LC/MS (Method 17, ESIneg): $R_t$=1.05 min, m/z=393.12 [M−H]⁻.

Example 289

3-(2-Methoxyethyl)-5-methyl-6-[(5-oxo-2,5-dihydro-1H-pyrazol-1-yl)methyl]-1-(tetrahydrofuran-2-ylmethyl)thieno[2,3-d]pyrimidine-2,4(1H,3H)-dione (racemate)

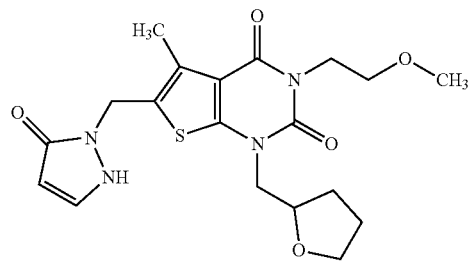 [SMILES: COCCn1c(=O)c2c(C)c(Cn3[nH]ccc3=O)sc2n(CC2CCCO2)c1=O]

Analogously to the method described in Ex. 133, 450 mg (0.794 mmol) of the compound from Ex. 432A were used to prepare 156 mg (46% of theory) of the title compound.

¹H-NMR (400 MHz, DMSO-d₆, δ/ppm): 11.12 (s, 1H), 7.14 (d, 1H), 5.32 (d, 1H), 5.14 (s, 2H), 4.24-4.13 (m, 1H), 4.09-3.97 (m, 3H), 3.76-3.54 (m, 3H), 3.48 (t, 2H), 3.23 (s, 3H), 2.46 (s, 3H), 2.02-1.73 (m, 3H), 1.70-1.58 (m, 1H).

LC/MS (Method 17, ESIneg): $R_t$=1.11 min, m/z=419.14 [M−H]⁻.

Example 290

3-(2-Methoxyethyl)-5-methyl-6-[(5-oxo-2,5-dihydro-1H-pyrazol-1-yl)methyl]-1-(tetrahydrofuran-2-ylmethyl)thieno[2,3-d]pyrimidine-2,4(1H,3H)-dione (Enantiomer 1)

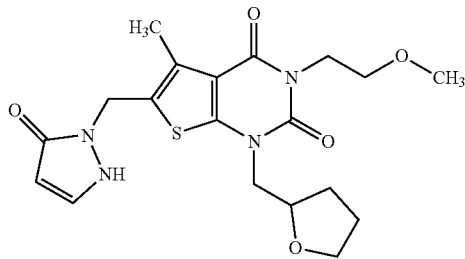 [SMILES: COCCn1c(=O)c2c(C)c(Cn3[nH]ccc3=O)sc2n(CC2CCCO2)c1=O]

150 mg (0.357 mmol) of the racemic compound from Ex. 289 were dissolved in a mixture of 8 ml of ethanol and 2 ml of acetonitrile and, in 20 portions, separated into the enantiomers by preparative HPLC on a chiral phase [column: Daicel Chiralcel OX-H, 5 µm, 250 mm×20 mm; eluent: isohexane/ethanol 1:1; flow rate: 15 ml/min; temperature: 50° C.; detection: 220 nm]. After concentration of the product fractions and drying under high vacuum, 72 mg (96% of theory) of Enantiomer 1 were obtained (>99% ee, chiral analytical HPLC).

¹H-NMR (400 MHz, DMSO-d₆, δ/ppm): 11.14 (br. s, 1H), 7.15 (s, 1H), 5.32 (s, 1H), 5.14 (s, 2H), 4.24-4.13 (m, 1H), 4.09-3.97 (m, 3H), 3.77-3.54 (m, 3H), 3.48 (t, 2H), 3.23 (s, 3H), 2.46 (s, 3H), 2.03-1.73 (m, 3H), 1.70-1.57 (m, 1H).

Chiral analytical HPLC [column: Daicel Chiralpak IC, 5 µm, 250 mm×4.6 mm; eluent: isohexane/ethanol 2:3; flow rate: 1 ml/min; temperature: 35° C.; detection: 220 nm]: $R_t$=10.00 min.

Example 291

3-(2-Methoxyethyl)-5-methyl-6-[(5-oxo-2,5-dihydro-1H-pyrazol-1-yl)methyl]-1-(tetrahydrofuran-2-ylmethyl)thieno[2,3-d]pyrimidine-2,4(1H,3H)-dione (Enantiomer 2)

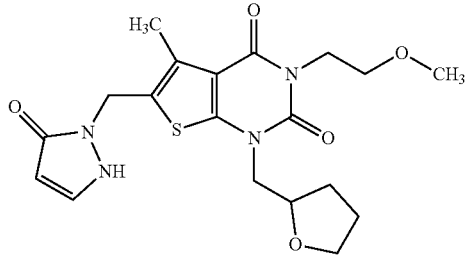 [SMILES: COCCn1c(=O)c2c(C)c(Cn3[nH]ccc3=O)sc2n(CC2CCCO2)c1=O]

150 mg (0.357 mmol) of the racemic compound from Ex. 289 were dissolved in a mixture of 8 ml of ethanol and 2 ml of acetonitrile and, in 20 portions, separated into the enantiomers by preparative HPLC on a chiral phase [column: Daicel Chiralcel OX-H, 5 µm, 250 mm×20 mm; eluent: isohexane/ethanol 1:1; flow rate: 15 ml/min; temperature: 50° C.; detection: 220 nm]. After concentration of the product fractions and drying under high vacuum, 73 mg (97% of theory) of Enantiomer 2 were obtained (98% ee, chiral analytical HPLC).

¹H-NMR (400 MHz, DMSO-d₆, δ/ppm): 11.15 (broad, 1H), 7.15 (br. s, 1H), 5.32 (s, 1H), 5.14 (s, 2H), 4.23-4.13 (m, 1H), 4.09-3.96 (m, 3H), 3.76-3.54 (m, 3H), 3.48 (t, 2H), 3.23 (s, 3H), 2.46 (s, 3H), 2.03-1.74 (m, 3H), 1.71-1.58 (m, 1H).

Chiral analytical HPLC [column: Daicel Chiralpak IC, 5 µm, 250 mm×4.6 mm; eluent: isohexane/ethanol 2:3; flow rate: 1 ml/min; temperature: 35° C.; detection: 220 nm]: $R_t$=12.03 min.

Example 292

3-Ethyl-1-(fluoromethyl)-5-methyl-6-[(2-thioxoimidazolidin-1-yl)methyl]thieno[2,3-d]pyrimidine-2,4(1H,3H)-dione

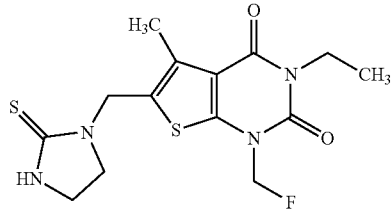 [SMILES: CCn1c(=O)c2c(C)c(CN3CCNC3=S)sc2n(CF)c1=O]

110 mg (0.276 mmol) of the compound from Ex. 397A were dissolved in 15 ml of dioxane, and 78 mg (0.415 mmol) of 1,1'-thiocarbonyldiimidazole were added. The mixture was stirred at RT for 17 h. The reaction solution was then concentrated on a rotary evaporator. The residue was dissolved in 3 ml of DMSO and this solution was purified by means of preparative HPLC (Method 14). Combination of the product fractions and freeze-drying gave 43 mg (39% of theory) of the title compound.

¹H-NMR (400 MHz, DMSO-d₆, δ/ppm): 8.40 (s, 1H), 6.00 (d, 2H), 4.85 (s, 2H), 3.90 (q, 2H), 3.58-3.50 (m, 2H), 3.45-3.37 (m, 2H), 2.45 (s, 3H), 1.13 (d, 3H).

LC/MS (Method 3, ESIpos): $R_t$=0.98 min, m/z=357 [M+H]⁺.

Example 293

1-[2-(Cyclopentyloxy)ethyl]-3-ethyl-5-methyl-6-[(2-thioxoimidazolidin-1-yl)methyl]thieno[2,3-d]pyrimidine-2,4(1H,3H)-dione

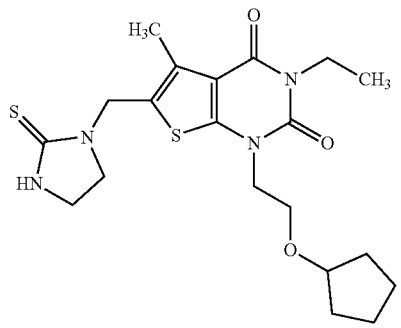 [SMILES: CCn1c(=O)c2c(C)c(CN3CCNC3=S)sc2n(CCOC2CCCC2)c1=O]

127 mg (0.264 mmol) of the compound from Ex. 398A were dissolved in 15 ml of dioxane, and 74 mg (0.396 mmol) of 1,1'-thiocarbonyldiimidazole were added. The mixture was stirred at RT for 19 h. The reaction solution was then concentrated on a rotary evaporator. The residue was dissolved in 3 ml of DMSO and this solution was purified by means of preparative HPLC (Method 14). Combination of the product fractions and freeze-drying gave 51 mg (43% of theory) of the title compound.

$^1$H-NMR (400 MHz, DMSO-$d_6$, δ/ppm): 8.35 (s, 1H), 4.82 (s, 2H), 3.97 (t, 2H), 3.94-3.83 (m, 3H), 3.61 (t, 2H), 3.54-3.46 (m, 2H), 3.43-3.35 (m, 2H), 2.43 (s, 3H), 1.61-1.49 (m, 2H), 1.49-1.36 (m, 6H), 1.11 (t, 3H).

LC/MS (Method 3, ESIpos): $R_t$=1.20 min, m/z=437 [M+H]$^+$.

Example 294

3-Ethyl-1-[2-(ethylsulphanyl)ethyl]-5-methyl-6-[(2-thioxoimidazolidin-1-yl)methyl]thieno[2,3-d]pyrimidine-2,4(1H,3H)-dione

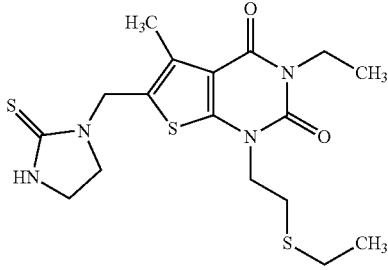 [SMILES: CCSCCn1c(=O)n(CC)c(=O)c2c(C)c(CN3CCNC3=S)sc21]

256 mg (0.573 mmol) of the compound from Ex. 399A were dissolved in 25 ml of dioxane, and 161 mg (0.86 mmol) of 1,1'-thiocarbonyldiimidazole were added. The mixture was stirred at RT for 19 h. The reaction solution was then concentrated on a rotary evaporator. The residue was dissolved in 6 ml of DMSO and this solution was purified by means of preparative HPLC (Method 14). Combination of the product fractions and freeze-drying gave 63 mg (26% of theory) of the title compound.

$^1$H-NMR (400 MHz, DMSO-$d_6$, δ/ppm): 8.37 (s, 1H), 4.83 (s, 2H), 4.05-3.96 (m, 2H), 3.90 (q, 2H), 3.58-3.49 (m, 2H), 3.44-3.36 (m, 2H), 2.87-2.79 (m, 2H), 2.58 (q, 2H), 2.44 (s, 3H), 1.19 (t, 3H), 1.11 (t, 3H).

LC/MS (Method 3, ESIpos): $R_t$=1.14 min, m/z=413 [M+H]$^+$.

Example 295

3-Ethyl-5-methyl-1-[2-(methylsulphonyl)ethyl]-6-[(2-thioxoimidazolidin-1-yl)methyl]thieno[2,3-d]pyrimidine-2,4(1H,3H)-dione

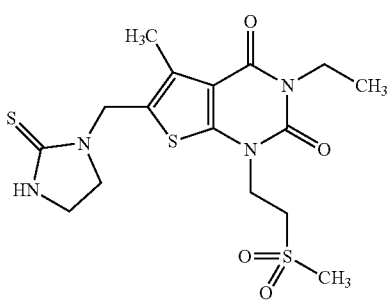 [SMILES: CCn1c(=O)c2c(C)c(CN3CCNC3=S)sc2n(CCS(C)(=O)=O)c1=O]

188 mg (0.377 mmol) of the compound from Ex. 400A were dissolved in 10 ml of dioxane, and 106 mg (0.566 mmol) of 1,1'-thiocarbonyldiimidazole were added. The mixture was stirred at RT for 15 h. The reaction solution was then concentrated on a rotary evaporator. The residue was dissolved in 6 ml of DMSO and this solution was purified by means of preparative HPLC (Method 14). Combination of the product fractions and freeze-drying gave 32 mg (19% of theory) of the title compound.

$^1$H-NMR (400 MHz, DMSO-$d_6$, δ/ppm): 8.35 (s, 1H), 4.85 (s, 2H), 4.27 (t, 2H), 3.90 (q, 2H), 3.60-3.50 (m, 4H), 3.45-3.37 (m, 2H), 3.11 (s, 3H), 2.45 (s, 3H), 1.12 (t, 3H).

LC/MS (Method 3, ESIpos): $R_t$=0.86 min, m/z=431 [M+H]$^+$.

Example 296

3-Ethyl-1-(3-methoxypropyl)-5-methyl-6-[(2-thioxoimidazolidin-1-yl)methyl]thieno[2,3-d]pyrimidine-2,4(1H,3H)-dione

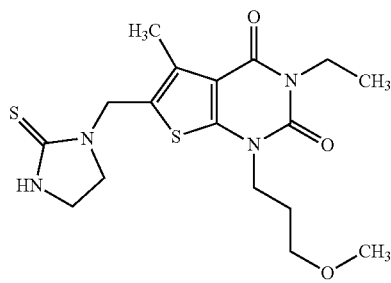 [SMILES: CCn1c(=O)c2c(C)c(CN3CCNC3=S)sc2n(CCCOC)c1=O]

90 mg (0.211 mmol) of the compound from Ex. 401A were dissolved in 10 ml of dioxane, and 59 mg (0.316 mmol) of 1,1'-thiocarbonyldiimidazole were added. The mixture was stirred at RT for 16 h. The reaction solution was then concentrated on a rotary evaporator. The residue was dissolved in 3 ml of DMSO and this solution was purified by means of preparative HPLC (Method 14). Combination of the product fractions and freeze-drying gave 42 mg (50% of theory) of the title compound.

$^1$H-NMR (400 MHz, DMSO-$d_6$, δ/ppm): 8.35 (s, 1H), 4.83 (s, 2H), 3.94-3.85 (m, 4H), 3.56-3.48 (m, 2H), 3.42-3.35 (m, 4H), 3.20 (s, 3H), 2.44 (s, 3H), 1.93-1.85 (m, 2H), 1.11 (t, 3H).

LC/MS (Method 3, ESIpos): $R_t$=1.0 min, m/z=397 [M+H]$^+$.

Example 297

3-Isopropyl-1,5-dimethyl-6-[(2-thioxoimidazolidin-1-yl)methyl]thieno[2,3-d]pyrimidine-2,4(1H,3H)-dione

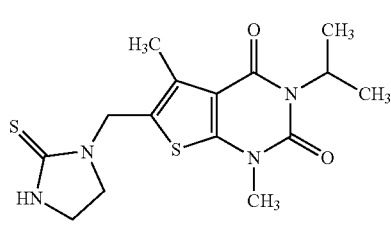 [SMILES: Cc1c(CN2CCNC2=S)sc2c1c(=O)n(C(C)C)c(=O)n2C]

133 mg (0.407 mmol) of the compound from Ex. 402A were dissolved in 16 ml of dioxane, and 115 mg (0.611 mmol) of 1,1'-thiocarbonyldiimidazole were added. The mixture was stirred at RT for 15 h. The reaction solution was then concentrated on a rotary evaporator. The residue was dissolved in 3 ml of DMSO and this solution was purified by means of preparative HPLC (Method 14). Combination of the product fractions and freeze-drying gave 83 mg (55% of theory) of the title compound.

$^1$H-NMR (400 MHz, DMSO-$d_6$, δ/ppm): 8.35 (s, 1H), 5.14 (sept, 1H), 4.82 (s, 2H), 3.56-3.48 (m, 2H), 3.44-3.36 (m, 5H), 2.42 (s, 3H), 1.39 (d, 6H).

LC/MS (Method 3, ESIpos): $R_t$=1.02 min, m/z=353 [M+H]$^+$.

Example 298

1-(3-Fluoropropyl)-3-isopropyl-5-methyl-6-[(2-thioxoimidazolidin-1-yl)methyl]thieno[2,3-d]pyrimidine-2,4(1H,3H)-dione

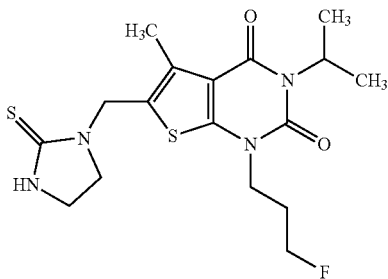 [SMILES: Cc1c(CN2CCNC2=S)sc2c1c(=O)n(C(C)C)c(=O)n2CCCF]

203 mg (0.382 mmol) of the compound from Ex. 404A were dissolved in 15 ml of dioxane, and 107 mg (0.572 mmol) of 1,1'-thiocarbonyldiimidazole were added. The mixture was stirred at RT for 17 h. The reaction solution was then concentrated on a rotary evaporator. The residue was dissolved in 6 ml of DMSO and this solution was purified by means of preparative HPLC (Method 14). Combination of the product fractions and freeze-drying gave 113 mg (74% of theory) of the title compound.

$^1$H-NMR (400 MHz, DMSO-$d_6$, δ/ppm): 8.35 (s, 1H), 5.13 (sept, 1H), 4.83 (s, 2H), 4.58 (t, 1H), 4.47 (t, 1H), 3.94 (t, 2H), 3.57-3.48 (m, 2H), 3.44-3.36 (m, 2H), 2.43 (s, 3H), 2.12-1.96 (m, 2H), 1.39 (d, 6H).

LC/MS (Method 3, ESIpos): $R_t$=1.10 min, m/z=397 [M+H]$^+$.

Example 299

5-Methyl-1-(tetrahydrofuran-2-ylmethyl)-6-[(2-thioxoimidazolidin-1-yl)methyl]-3-(2,2,2-trifluoroethyl)thieno[2,3-d]pyrimidine-2,4(1H,3H)-dione
(Enantiomer 1)

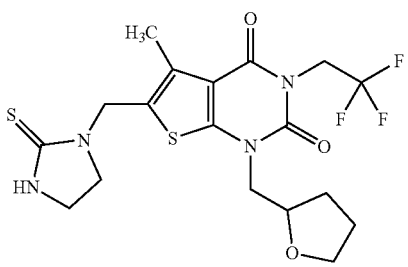 [SMILES: Cc1c(CN2CCNC2=S)sc2c1c(=O)n(CC(F)(F)F)c(=O)n2CC1CCCO1]

156 mg of the racemic compound from Ex. 157 were dissolved in 3.5 ml of a methanol/dichloromethane mixture (1:1 v/v) and separated into the enantiomers by means of preparative HPLC on a chiral phase [column: Daicel Chiralpak IA, 5 μm, 250 mm×30 mm; eluent: methanol/ethanol/diethylamine 50:50:0.1 (v/v/v); flow rate: 30 ml/min; temperature: RT; UV detection: 254 nm]. The product fractions were concentrated on a rotary evaporator, admixed with tert-butanol and freeze-dried. 62 mg of the title compound (Enantiomer 1) and 76 mg of Enantiomer 2 (see Example 300) were obtained.

$^1$H-NMR (500 MHz, DMSO-$d_6$, δ/ppm): 8.37 (s, 1H), 4.83 (s, 2H), 4.70 (q, 2H), 4.26-4.18 (m, 1H), 4.05 (dd, 1H), 3.79-3.69 (m, 2H), 3.65-3.58 (m, 1H), 3.58-3.50 (m, 2H), 3.44-3.37 (m, 2H), 2.43 (s, 3H), 2.03-1.93 (m, 1H), 1.93-1.76 (m, 2H), 1.67 (ddt, 1H).

Chiral analytical HPLC [column: Daicel Chiralpak IA, 5 μm, 100 mm×4.6 mm; eluent: methanol/ethanol/diethylamine 50:50:0.1 (v/v/v); flow rate: 1.0 ml/min; temperature: RT; injection: 5 μl; DAD 254 nm]: $R_t$=2.45 min.

Example 300

5-Methyl-1-(tetrahydrofuran-2-ylmethyl)-6-[(2-thioxoimidazolidin-1-yl)methyl]-3-(2,2,2-trifluoroethyl)thieno[2,3-d]pyrimidine-2,4(1H,3H)-dione
(Enantiomer 2)

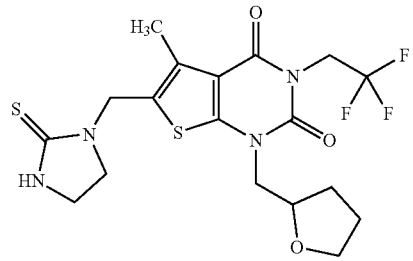 [SMILES: Cc1c(CN2CCNC2=S)sc2c1c(=O)n(CC(F)(F)F)c(=O)n2CC1CCCO1]

The title compound (76 mg) was obtained as the second enantiomer in the preparative HPLC separation of the racemate from Ex. 157 described in Ex. 299.

$^1$H-NMR (500 MHz, DMSO-$d_6$, δ/ppm): 8.37 (s, 1H), 4.83 (s, 2H), 4.70 (q, 2H), 4.22 (br. t, 1H), 4.05 (dd, 1H), 3.79-3.69 (m, 2H), 3.65-3.58 (m, 1H), 3.58-3.50 (m, 2H), 3.44-3.37 (m, 2H), 2.43 (s, 3H), 2.03-1.93 (m, 1H), 1.93-1.76 (m, 2H), 1.71-1.62 (m, 1H).

Chiral analytical HPLC [column: Daicel Chiralpak IA, 5 μm, 100 mm×4.6 mm; eluent: methanol/ethanol/diethylamine 50:50:0.1 (v/v/v); flow rate: 1.0 ml/min; temperature: RT; injection: 5 μl; DAD 254 nm]: $R_t$=3.13 min.

Example 301

3-(2-Ethoxyethyl)-5-methyl-6-[(2-thioxoimidazolidin-1-yl)methyl]-1-(3,3,3-trifluoropropyl)thieno[2,3-d]pyrimidine-2,4(1H,3H)-dione

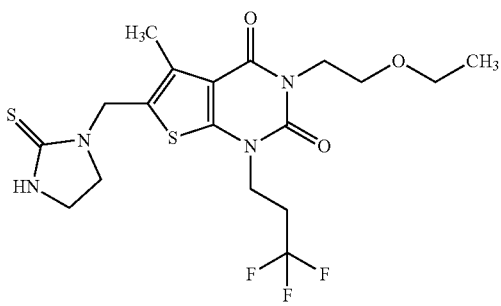 [SMILES: CCOCCn1c(=O)c2c(C)c(CN3CCNC3=S)sc2n(CCC(F)(F)F)c1=O]

120 mg (0.253 mmol) of the compound from Ex. 406A were dissolved in 15 ml of dioxane, and 71 mg (0.379 mmol) of 1,1'-thiocarbonyldiimidazole were added. The mixture was stirred at RT for 17 h. The reaction solution was then concentrated on a rotary evaporator. The residue was dissolved in 3 ml of DMSO and this solution was purified by means of preparative HPLC (Method 14). Combination of the product fractions and freeze-drying gave 71 mg (59% of theory) of the title compound.

$^1$H-NMR (400 MHz, DMSO-$d_6$, δ/ppm): 8.37 (s, 1H), 4.85 (s, 2H), 4.09 (t, 2H), 4.04 (t, 2H), 3.57-3.48 (m, 4H), 3.47-3.37 (m, 4H), 2.81-2.70 (m, 2H), 2.44 (s, 3H), 1.06 (t, 3H).

LC/MS (Method 3, ESIpos): $R_t$=1.13 min, m/z=465 [M+H]$^+$.

Example 302

3-(2-Ethoxyethyl)-1-(2-methoxyethyl)-5-methyl-6-[(2-thioxoimidazolidin-1-yl)methyl]thieno[2,3-d]pyrimidine-2,4(1H,3H)-dione

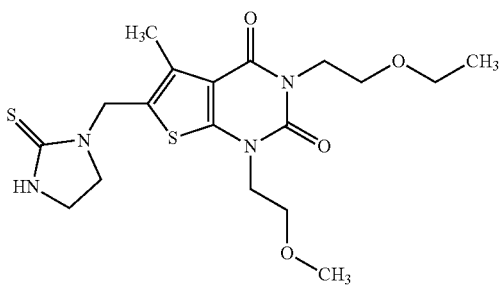 [SMILES: CCOCCn1c(=O)c2c(C)c(CN3CCNC3=S)sc2n(CCOC)c1=O]

85 mg (0.15 mmol) of the compound from Ex. 407A were dissolved in 7 ml of dioxane, and 42 mg (0.225 mmol) of 1,1'-thiocarbonyldiimidazole were added. The mixture was stirred at RT for 14 h. The reaction solution was then concentrated on a rotary evaporator. The residue was dissolved in 3 ml of DMSO and this solution was purified by means of preparative HPLC (Method 14). Combination of the product fractions and freeze-drying gave 33 mg (64% of theory) of the title compound.

$^1$H-NMR (400 MHz, DMSO-$d_6$, δ/ppm): 8.36 (s, 1H), 4.82 (s, 2H), 4.08-3.97 (m, 4H), 3.62 (t, 2H), 3.57-3.48 (m, 4H), 3.47-3.37 (m, 4H), 3.23 (s, 3H), 2.43 (s, 3H), 1.06 (t, 3H).

LC/MS (Method 3, ESIpos): $R_t$=0.98 min, m/z=427 [M+H]$^+$.

Example 303

3-Ethyl-1-(2-methoxyethyl)-5-methyl-6-[(4-methyl-2-thioxoimidazolidin-1-yl)methyl]thieno[2,3-d]pyrimidine-2,4(1H,3H)-dione (racemate)

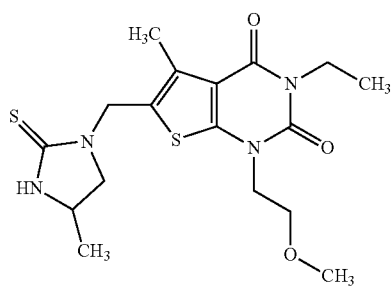 [SMILES: CCn1c(=O)c2c(C)c(CN3CC(C)NC3=S)sc2n(CCOC)c1=O]

205 mg (0.399 mmol) of the compound from Ex. 266A were dissolved in 15 ml of dioxane, and 112 mg (0.599 mmol) of 1,1'-thiocarbonyldiimidazole were added. The mixture was stirred at RT for 14 h. The reaction solution was then concentrated on a rotary evaporator. The residue was dissolved in 3 ml of DMSO and this solution was purified by means of preparative HPLC (Method 14). Combination of the product fractions and freeze-drying gave 100 mg (53% of theory) of the title compound.

$^1$H-NMR (400 MHz, DMSO-$d_6$, δ/ppm): 8.50 (s, 1H), 4.88-4.75 (m, 2H), 4.08-3.96 (m, 2H), 3.89 (q, 2H), 3.84-3.74 (m, 1H), 3.69-3.59 (m, 3H), 3.23 (s, 3H), 3.06 (dd, 1H), 2.46-2.40 (m, 3H), 1.22-1.06 (m, 6H).

LC/MS (Method 3, ESIpos): $R_t$=1.03 min, m/z=397 [M+H]$^+$.

Example 304

1-(3-Fluoropropyl)-3-isobutyl-6-[(3-isopropyl-2-thioxoimidazolidin-1-yl)methyl]-5-methylthieno[2,3-d]pyrimidine-2,4(1H,3H)-dione

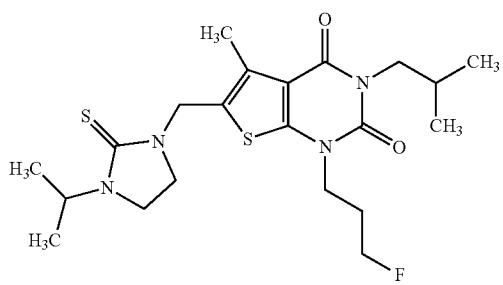 [SMILES: Cc1c(CN2CCN(C(C)C)C2=S)sc2c1c(=O)n(CC(C)C)c(=O)n2CCCF]

The title compound (11 mg) was obtained as a by-product of the preparation and purification of the compound described in Example 144.

¹H-NMR (400 MHz, DMSO-d₆, δ/ppm): 4.88 (s, 2H), 4.65-4.54 (m, 2H), 4.47 (t, 1H), 3.97 (t, 2H), 3.70 (d, 2H), 3.46 (s, 4H), 2.44 (s, 3H), 2.11-1.97 (m, 3H), 1.09 (d, 6H), 0.84 (d, 6H).

LC/MS (Method 3, ESIpos): R$_t$=1.39 min, m/z=455 [M+H]⁺.

Example 305

6-[(3-Isopropyl-2-thioxoimidazolidin-1-yl)methyl]-1,5-dimethyl-3-(2,2,2-trifluoroethyl)thieno[2,3-d]pyrimidine-2,4(1H,3H)-dione

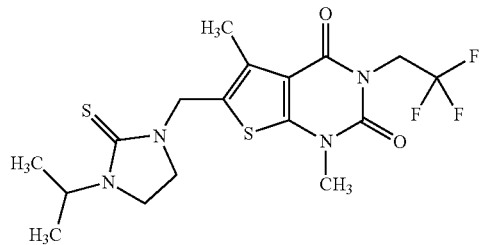 [SMILES: Cc1c(CN2CCN(C(C)C)C2=S)sc2c1c(=O)n(CC(F)(F)F)c(=O)n2C]

The title compound (16 mg) was obtained as a by-product of the preparation and purification of the compound described in Example 159.

¹H-NMR (400 MHz, DMSO-d₆, δ/ppm): 4.90 (s, 2H), 4.69 (q, 2H), 4.60 (dt, 1H), 3.46 (s, 4H), 3.43 (s, 3H), 2.45 (s, 3H), 1.09 (d, 6H).

LC/MS (Method 3, ESIpos): R$_t$=1.03 min, m/z=435 [M+H]⁺.

Example 306

5-Methyl-6-[(3-methyl-2-thioxoimidazolidin-1-yl)methyl]-3-(2,2,2-trifluoroethyl)-1-(3,3,3-trifluoropropyl)thieno[2,3-d]pyrimidine-2,4(1H,3H)-dione

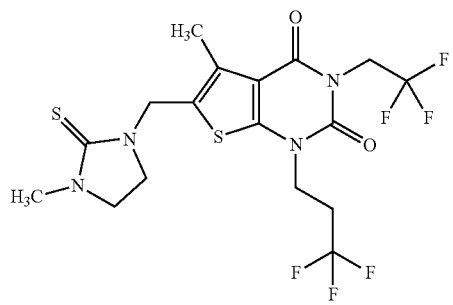 [SMILES: Cc1c(CN2CCN(C)C2=S)sc2c1c(=O)n(CC(F)(F)F)c(=O)n2CCC(F)(F)F]

To a solution of 50 mg (0.105 mmol) of the compound from Ex. 152 in 3.3 ml of THF were added, at 0° C., 5 mg (0.126 mmol) of sodium hydride (60% suspension in mineral oil), and the mixture was stirred for 1 h. Subsequently, 18 mg (0.126 mmol) of iodomethane were added, and the mixture was stirred at RT for 16 h. Then the reaction mixture was partitioned between saturated aqueous ammonium chloride solution (20 ml) and THF (30 ml). The organic phase was washed with saturated aqueous sodium hydrogencarbonate solution, dried over sodium sulphate, filtered and concentrated. The residue obtained was purified by means of preparative HPLC (Method 14). Combination of the product fractions and freeze-drying gave 32 mg (59% of theory) of the title compound.

¹H-NMR (400 MHz, DMSO-d₆, δ/ppm): 4.69 (q, 2H), 4.43 (s, 2H), 4.14 (t, 2H), 3.60 (d, 2H), 3.37-3.29 (m, 2H), 2.82-2.69 (m, 2H), 2.45 (s, 3H), 2.38 (s, 3H).

LC/MS (Method 3, ESIpos): R$_t$=0.92 min, m/z=489 [M+H]⁺.

Example 307

3-Ethyl-1-(fluoromethyl)-5-methyl-6-[(2-oxoimidazolidin-1-yl)methyl]thieno[2,3-d]pyrimidine-2,4(1H,3H)-dione

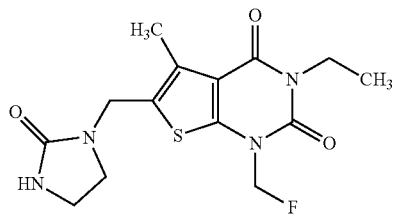 [SMILES: CCn1c(=O)c2c(C)c(CN3CCNC3=O)sc2n(CF)c1=O]

220 mg (0.553 mmol) of the compound from Example 397A were dissolved in 25 ml of dioxane, and 139 mg (0.829 mmol) of CDI were added. The mixture was stirred at RT for 17 h. The reaction solution was then concentrated on a rotary evaporator. The residue was dissolved in 6 ml of DMSO and this solution was purified by means of preparative HPLC (Method 14). Combination of the product fractions and freeze-drying gave 136 mg (71% of theory) of the title compound.

¹H-NMR (400 MHz, DMSO-d₆, δ/ppm): 6.57 (s, 1H), 6.01 (d, 2H), 4.37 (s, 2H), 3.90 (q, 2H), 3.29-3.18 (m, 4H), 2.40 (s, 3H), 1.13 (t, 3H).

LC/MS (Method 3, ESIpos): R$_t$=0.88 min, m/z=341 [M+H]⁺.

Example 308

1-[2-(Cyclopentyloxy)ethyl]-3-ethyl-5-methyl-6-[(2-oxoimidazolidin-1-yl)methyl]thieno[2,3-d]pyrimidine-2,4(1H,3H)-dione

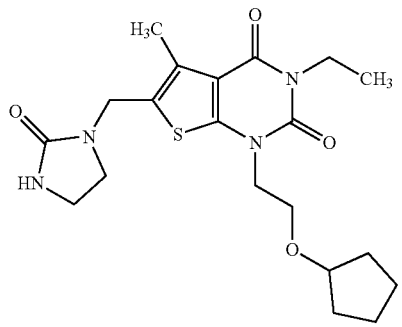 [SMILES: CCn1c(=O)c2c(C)c(CN3CCNC3=O)sc2n(CCOC2CCCC2)c1=O]

256 mg (0.532 mmol) of the compound from Example 398A were dissolved in 25 ml of dioxane, and 133 mg (0.798 mmol) of CDI were added. The mixture was stirred at RT for 19 h. The reaction solution was then concentrated on a rotary evaporator. The residue was dissolved in 6 ml of DMSO and this solution was purified by means of preparative HPLC (Method 14). Combination of the product fractions and freeze-drying gave 146 mg (64% of theory) of the title compound.

$^1$H-NMR (400 MHz, DMSO-$d_6$, δ/ppm): 6.54 (s, 1H), 4.34 (s, 2H), 3.97 (t, 2H), 3.94-3.83 (m, 3H), 3.61 (t, 2H), 3.26-3.15 (m, 4H), 2.39 (s, 3H), 1.54 (dd, 2H), 1.48-1.35 (m, 6H), 1.11 (t, 3H).

LC/MS (Method 3, ESIpos): $R_t$=1.09 min, m/z=421 [M+H]$^+$.

Example 309

3-Ethyl-1-[2-(ethylsulphanyl)ethyl]-5-methyl-6-[(2-oxoimidazolidin-1-yl)methyl]thieno[2,3-d]pyrimidine-2,4(1H,3H)-dione

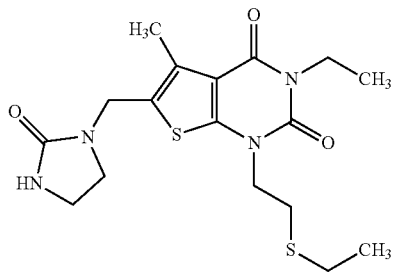

256 mg (0.573 mmol) of the compound from Example 399A were dissolved in 25 ml of dioxane, and 144 mg (0.86 mmol) of CDI were added. The mixture was stirred at RT for 19 h. The reaction solution was then concentrated on a rotary evaporator. The residue was dissolved in 6 ml of DMSO and this solution was purified by means of preparative HPLC (Method 14). Combination of the product fractions and freeze-drying gave 77 mg (32% of theory) of the title compound.

$^1$H-NMR (400 MHz, DMSO-$d_6$, δ/ppm): 6.55 (s, 1H), 4.35 (s, 2H), 4.05-3.97 (m, 2H), 3.90 (q, 2H), 3.28-3.16 (m, 4H), 2.87-2.79 (m, 2H), 2.58 (q, 2H), 2.40 (s, 3H), 1.19 (t, 3H), 1.11 (t, 3H).

LC/MS (Method 3, ESIpos): $R_t$=1.03 min, m/z=397 [M+H]$^+$.

Example 310

3-Ethyl-5-methyl-1-[2-(methylsulphonyl)ethyl]-6-[(2-oxoimidazolidin-1-yl)methyl]thieno[2,3-d]pyrimidine-2,4(1H,3H)-dione

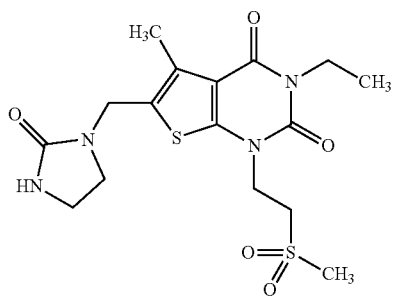

470 mg (0.423 mmol, 35% purity) of the compound from Example 400A were dissolved in 25 ml of dioxane, and 103 mg (0.635 mmol) of CDI were added. The mixture was stirred at RT for 20 h. The reaction solution was then concentrated on a rotary evaporator. The residue was dissolved in 6 ml of DMSO and this solution was purified by means of preparative HPLC (Method 14). Combination of the product fractions and freeze-drying gave 42 mg (24% of theory) of the title compound.

$^1$H-NMR (400 MHz, DMSO-$d_6$, δ/ppm): 6.56 (s, 1H), 4.37 (s, 2H), 4.31-4.23 (m, 2H), 3.90 (q, 2H), 3.56 (t, 2H), 3.30-3.17 (m, 4H), 3.11 (s, 3H), 2.40 (s, 3H), 1.12 (t, 3H).

LC/MS (Method 3, ESIpos): $R_t$=0.77 min, m/z=415 [M+H]$^+$.

Example 311

3-Ethyl-1-(3-methoxypropyl)-5-methyl-6-[(2-oxoimidazolidin-1-yl)methyl]thieno[2,3-d]pyrimidine-2,4(1H,3H)-dione

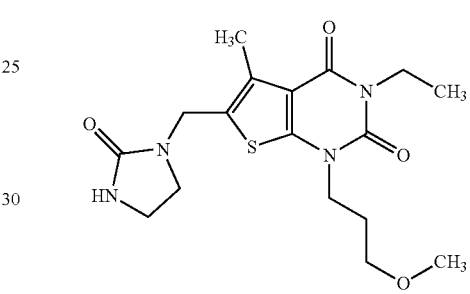

130 mg (0.304 mmol) of the compound from Example 401A were dissolved in 15 ml of dioxane, and 76 mg (0.457 mmol) of CDI were added. The mixture was stirred at RT for 16 h. The reaction solution was then concentrated on a rotary evaporator. The residue was dissolved in 3 ml of DMSO and this solution was purified by means of preparative HPLC (Method 14). Combination of the product fractions and freeze-drying gave 93 mg (78% of theory) of the title compound.

$^1$H-NMR (400 MHz, DMSO-$d_6$, δ/ppm): 6.54 (s, 1H), 4.35 (s, 2H), 3.94-3.85 (m, 4H), 3.37 (t, 2H), 3.28-3.17 (m, 7H), 2.39 (s, 3H), 1.93-1.85 (m, 2H), 1.11 (t, 3H).

LC/MS (Method 3, ESIpos): $R_t$=0.89 min, m/z=381 [M+H]$^+$.

Example 312

3-Isopropyl-1,5-dimethyl-6-[(2-oxoimidazolidin-1-yl)methyl]thieno[2,3-d]pyrimidine-2,4(1H,3H)-dione

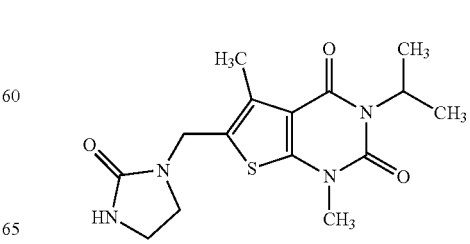

133 mg (0.407 mmol) of the compound from Example 402A were dissolved in 16 ml of dioxane, and 102 mg (0.611 mmol) of CDI were added. The mixture was stirred at RT for 15 h. The reaction solution was then concentrated on a rotary evaporator. The residue was dissolved in 3 ml of DMSO and this solution was purified by means of preparative HPLC (Method 14). Combination of the product fractions and freeze-drying gave 90 mg (65% of theory) of the title compound.

$^1$H-NMR (400 MHz, DMSO-$d_6$, δ/ppm): 6.54 (s, 1H), 5.14 (sept, 1H), 4.34 (s, 2H), 3.38 (s, 3H), 3.27-3.17 (m, 4H), 2.38 (s, 3H), 1.39 (d, 6H).

LC/MS (Method 3, ESIpos): $R_t$=0.92 min, m/z=336 [M+H]$^+$.

Example 313

1-(Fluoromethyl)-3-isopropyl-5-methyl-6-[(2-oxoimidazolidin-1-yl)methyl]thieno[2,3-d]pyrimidine-2,4(1H,3H)-dione

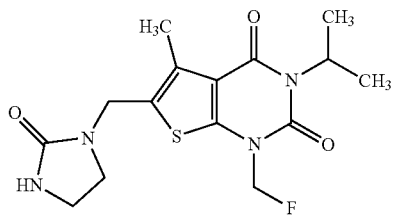 [SMILES: Cc1c(CN2CCNC2=O)sc2c1c(=O)n(C(C)C)c(=O)n2CF]

119 mg (0.312 mmol) of the compound from Example 403A were dissolved in 12 ml of dioxane, and 78 mg (0.467 mmol) of CDI were added. The mixture was stirred at RT for 15 h. The reaction solution was then concentrated on a rotary evaporator. The residue was dissolved in 3 ml of DMSO and this solution was purified by means of preparative HPLC (Method 14). Combination of the product fractions and freeze-drying gave 43 mg (37% of theory) of the title compound.

$^1$H-NMR (400 MHz, DMSO-$d_6$, δ/ppm): 6.57 (s, 1H), 5.98 (d, 2H), 5.12 (sept, 1H), 4.36 (s, 2H), 3.28-3.17 (m, 4H), 2.39 (s, 3H), 1.41 (d, 6H).

LC/MS (Method 3, ESIpos): $R_t$=0.98 min, m/z=355 [M+H]$^+$.

Example 314

1-(3-Fluoropropyl)-3-isopropyl-5-methyl-6-[(2-oxoimidazolidin-1-yl)methyl]thieno[2,3-d]pyrimidine-2,4(1H,3H)-dione

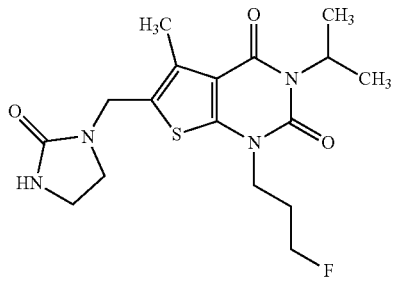 [SMILES: Cc1c(CN2CCNC2=O)sc2c1c(=O)n(C(C)C)c(=O)n2CCCF]

203 mg (0.382 mmol) of the compound from Example 404A were dissolved in 15 ml of dioxane, and 96 mg (0.572 mmol) of CDI were added. The mixture was stirred at RT for 17 h. The reaction solution was then concentrated on a rotary evaporator. The residue was dissolved in 6 ml of DMSO and this solution was purified by means of preparative HPLC (Method 14). Combination of the product fractions and freeze-drying gave 141 mg (97% of theory) of the title compound.

$^1$H-NMR (400 MHz, DMSO-$d_6$, δ/ppm: 6.54 (s, 1H), 5.13 (sept, 1H), 4.59 (t, 1H), 4.47 (t, 1H), 4.34 (s, 2H), 3.94 (t, 2H), 3.28-3.16 (m, 4H), 2.38 (s, 3H), 2.12-1.96 (m, 2H), 1.39 (d, 6H).

LC/MS (Method 3, ESIpos): $R_t$=1.0 min, m/z=383 [M+H]$^+$.

Example 315

1-(2-Methoxyethyl)-5-methyl-6-[(2-oxoimidazolidin-1-yl)methyl]-3-(prop-2-yn-1-yl)thieno[2,3-d]pyrimidine-2,4(1H,3H)-dione

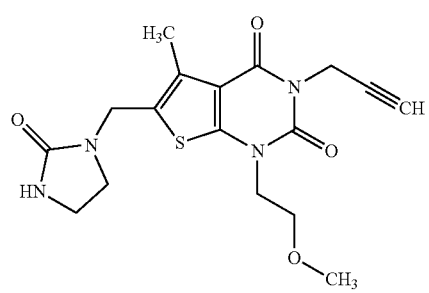 [SMILES: C#CCn1c(=O)c2c(C)c(CN3CCNC3=O)sc2n(CCOC)c1=O]

To a solution of 168 mg (1.87 mmol) of 2-imidazolidinone in 7 ml of THF were added 75 mg (1.87 mmol) of sodium hydride (60% suspension in mineral oil) and the mixture was stirred at RT for 3 h ("Solution 1"). To a solution of 144 mg (0.468 mmol) of the compound from Ex. 385A in 3 ml of dichloromethane in another reaction vessel were added, at 0° C., 244 μl (1.4 mmol) of N,N-diisopropylethylamine and 51 μl (0.702 mmol) of thionyl chloride, and the mixture was stirred for 90 min. Subsequently, Solution 1 was added in portions and the mixture was stirred at RT for 20 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 23 mg (13% of theory) of the title compound were obtained.

$^1$H-NMR (400 MHz, DMSO-$d_6$, δ/ppm): 6.55 (s, 1H), 4.59 (d, 2H), 4.35 (s, 2H), 4.04 (t, 2H), 3.63 (t, 2H), 3.29-3.17 (m, 7H), 3.15-3.11 (m, 1H), 2.39 (s, 3H).

LC/MS (Method 3, ESIpos): $R_t$=0.84 min, m/z=377 [M+H]$^+$.

Example 316

3-(But-3-en-1-yl)-1-(2-methoxyethyl)-5-methyl-6-[(2-oxoimidazolidin-1-yl)methyl]thieno[2,3-d]pyrimidine-2,4(1H,3H)-dione

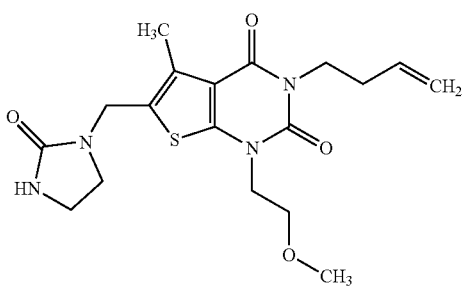 [SMILES: C=CCCn1c(=O)c2c(C)c(CN3CCNC3=O)sc2n(CCOC)c1=O]

To a solution of 188 mg (2.09 mmol) of 2-imidazolidinone in 7.5 ml of THF were added 84 mg (2.09 mmol) of sodium hydride (60% suspension in mineral oil) and the mixture was stirred at RT for 3 h ("Solution 1"). To a solution of 170 mg (0.524 mmol) of the compound from Ex. 386A in 3.6 ml of dichloromethane in another reaction vessel were added, at 0° C., 51 µl (0.702 mmol) of thionyl chloride, and the mixture was stirred for 75 min. Subsequently, Solution 1 was added in portions and the mixture was stirred at RT for 21 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 113 mg (53% of theory) of the title compound were obtained.

$^1$H-NMR (400 MHz, DMSO-d$_6$, δ/ppm): 6.55 (s, 1H), 5.79 (ddt, 1H), 5.06-4.96 (m, 2H), 4.34 (s, 2H), 4.01 (t, 2H), 3.92 (t, 2H), 3.62 (t, 2H), 3.28-3.17 (m, 7H), 2.38 (s, 3H), 2.35-2.26 (m, 2H).

LC/MS (Method 3, ESIpos): R$_t$=0.98 min, m/z=393 [M+H]$^+$.

Example 317

3-(But-2-yn-1-yl)-1-(2-methoxyethyl)-5-methyl-6-[(2-oxoimidazolidin-1-yl)methyl]thieno[2,3-d]pyrimidine-2,4(1H,3H)-dione

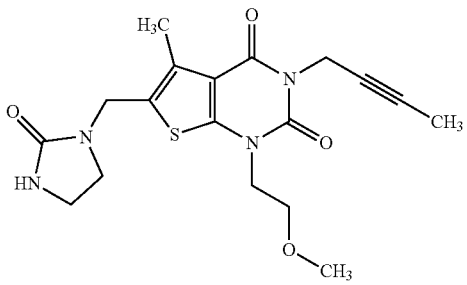 [SMILES: CC#CCn1c(=O)c2c(C)c(CN3CCNC3=O)sc2n(CCOC)c1=O]

To a solution of 128 mg (1.43 mmol) of 2-imidazolidinone in 5 ml of THF were added 57 mg (1.43 mmol) of sodium hydride (60% suspension in mineral oil) and the mixture was stirred at RT for 3 h ("Solution 1"). To a solution of 115 mg (0.357 mmol) of the compound from Ex. 387A in 2.5 ml of dichloromethane in another reaction vessel were added, at 0° C., 186 µl (1.07 mmol) of N,N-diisopropylethylamine and 64 µl (0.535 mmol) of thionyl chloride, and the mixture was stirred for 90 min. Subsequently, Solution 1 was added in portions and the mixture was stirred at RT for 20 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 23 mg (15% of theory) of the title compound were obtained.

$^1$H-NMR (400 MHz, DMSO-d$_6$, δ/ppm): 6.55 (s, 1H), 4.55 (d, 2H), 4.35 (s, 2H), 4.03 (t, 2H), 3.63 (t, 2H), 3.28-3.17 (m, 7H), 2.39 (s, 3H), 1.74 (t, 3H).

LC/MS (Method 3, ESIpos): R$_t$=0.9 min, m/z=391 [M+H]$^+$.

Example 318

3-(But-3-yn-1-yl)-1-(2-methoxyethyl)-5-methyl-6-[(2-oxoimidazolidin-1-yl)methyl]thieno[2,3-d]pyrimidine-2,4(1H,3H)-dione

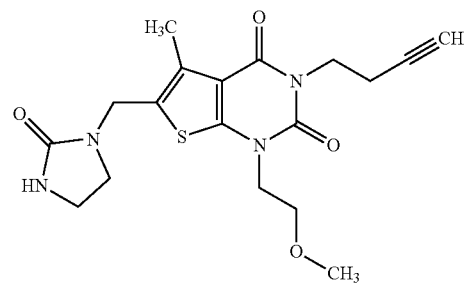 [SMILES: C#CCCn1c(=O)c2c(C)c(CN3CCNC3=O)sc2n(CCOC)c1=O]

To a solution of 139 mg (1.56 mmol) of 2-imidazolidinone in 6 ml of THF were added 62 mg (1.56 mmol) of sodium hydride (60% suspension in mineral oil) and the mixture was stirred at RT for 3 h ("Solution 1"). To a solution of 128 mg (0.389 mmol) of the compound from Ex. 388A in 3 ml of dichloromethane in another reaction vessel were added, at 0° C., 203 µl (1.17 mmol) of N,N-diisopropylethylamine and 42 µl (0.584 mmol) of thionyl chloride, and the mixture was stirred for 90 min. Subsequently, Solution 1 was added in portions and the mixture was stirred at RT for 115 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 70 mg (45% of theory) of the title compound were obtained.

$^1$H-NMR (400 MHz, DMSO-d$_6$, δ/ppm): 6.55 (s, 1H), 4.34 (s, 2H), 4.05-3.95 (m, 4H), 3.62 (t, 2H), 3.28-3.17 (m, 7H), 2.86 (t, 1H), 2.46 (td, 2H), 2.39 (s, 3H).

LC/MS (Method 3, ESIpos): R$_t$=0.88 min, m/z=391 [M+H]$^+$.

Example 319

1-(2-Methoxyethyl)-5-methyl-3-(3-methylbut-3-en-1-yl)-6-[(2-oxoimidazolidin-1-yl)methyl]thieno[2,3-d]pyrimidine-2,4(1H,3H)-dione

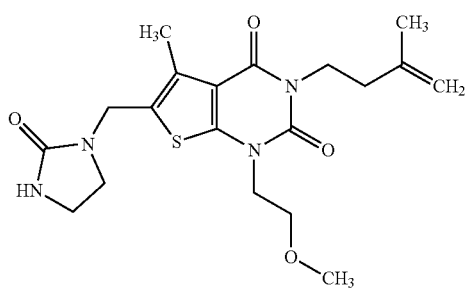 [SMILES: C=C(C)CCn1c(=O)c2c(C)c(CN3CCNC3=O)sc2n(CCOC)c1=O]

To a solution of 151 mg (1.68 mmol) of 2-imidazolidinone in 6 ml of THF were added 67 mg (1.68 mmol) of sodium hydride (60% suspension in mineral oil) and the mixture was stirred at RT for 3 h ("Solution 1"). To a solution of 145 mg (0.420 mmol) of the compound from Ex. 389A in 3 ml of dichloromethane in another reaction vessel were added, at 0° C., 219 µl (1.26 mmol) of N,N-diisopropylethylamine and 45 µl (0.63 mmol) of thionyl chloride, and the mixture was stirred for 90 min. Subsequently, Solution 1 was added in portions and the mixture was stirred at RT for 18 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 89 mg (51% of theory) of the title compound were obtained.

$^1$H-NMR (400 MHz, DMSO-d$_6$, δ/ppm): 6.54 (s, 1H), 4.75-4.62 (m, 2H), 4.34 (s, 2H), 4.05-3.93 (m, 4H), 3.62 (t, 2H), 3.29-3.16 (m, 7H), 2.38 (s, 3H), 2.24 (t, 2H), 1.76 (s, 3H).

LC/MS (Method 3, ESIpos): R$_t$=1.06 min, m/z=407 [M+H]$^+$.

Example 320

1-(2-Methoxyethyl)-5-methyl-3-(4-methylpent-3-en-1-yl)-6-[(2-oxoimidazolidin-1-yl)methyl]thieno[2,3-d]pyrimidine-2,4(1H,3H)-dione

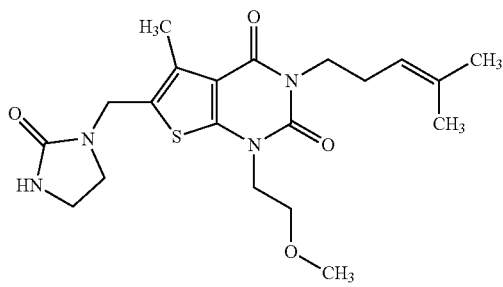 [SMILES: COCCn1c(=O)n(CCC=C(C)C)c(=O)c2c(C)c(CN3CCNC3=O)sc21]

To a solution of 111 mg (1.24 mmol) of 2-imidazolidinone in 4.5 ml of THF were added 49 mg (1.24 mmol) of sodium hydride (60% suspension in mineral oil) and the mixture was stirred at RT for 3 h ("Solution 1"). To a solution of 115 mg (0.31 mmol) of the compound from Ex. 390A in 2 ml of dichloromethane in another reaction vessel were added, at 0° C., 34 µl (0.465 mmol) of thionyl chloride, and the mixture was stirred for 90 min. Subsequently, Solution 1 was added in portions and the mixture was stirred at RT for 21 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 68 mg (51% of theory) of the title compound were obtained.

$^1$H-NMR (400 MHz, DMSO-d$_6$, δ/ppm): 6.55 (s, 1H), 5.16-5.09 (m, 1H), 4.34 (s, 2H), 4.01 (t, 2H), 3.86-3.77 (m, 2H), 3.62 (t, 2H), 3.28-3.17 (m, 7H), 2.38 (s, 3H), 2.22 (q, 2H), 1.64 (s, 3H), 1.55 (d, 3H).

LC/MS (Method 3, ESIpos): R$_t$=1.13 min, m/z=421 [M+H]$^+$.

Example 321

1-(2-Methoxyethyl)-5-methyl-6-[(2-oxoimidazolidin-1-yl)methyl]-3-(3,4,4-trifluorobut-3-en-1-yl)thieno[2,3-d]pyrimidine-2,4(1H,3H)-dione

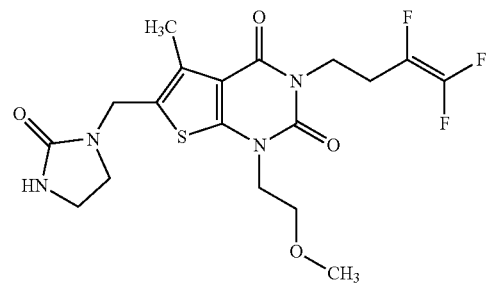 [SMILES: COCCn1c(=O)n(CCC(F)=C(F)F)c(=O)c2c(C)c(CN3CCNC3=O)sc21]

To a solution of 178 mg (1.99 mmol) of 2-imidazolidinone in 7 ml of THF were added 80 mg (1.99 mmol) of sodium hydride (60% suspension in mineral oil) and the mixture was stirred at 60° C. for 3 h ("Solution 1"). To a solution of 190 mg (0.497 mmol) of the compound from Ex. 391A in 3.5 ml of dichloromethane in another reaction vessel were added, at 0° C., 260 µl (1.49 mmol) of N,N-diisopropylethylamine and 54 µl (0.746 mmol) of thionyl chloride, and the mixture was stirred for 90 min. Subsequently, Solution 1 was added in portions and the mixture was stirred at RT for 20 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 92 mg (41% of theory) of the title compound were obtained.

$^1$H-NMR (400 MHz, DMSO-d$_6$, δ/ppm): 6.55 (s, 1H), 4.35 (s, 2H), 4.08 (t, 2H), 4.03 (t, 2H), 3.62 (t, 2H), 3.29-3.17 (m, 7H), 2.71-2.65 (m, 1H), 2.65-2.58 (m, 1H), 2.38 (s, 3H).

LC/MS (Method 3, ESIpos): R$_t$=1.03 min, m/z=447 [M+H]$^+$.

Example 322

3-(4,4-Difluorobut-3-en-1-yl)-1-(2-methoxyethyl)-5-methyl-6-[(2-oxoimidazolidin-1-yl)methyl]thieno[2,3-d]pyrimidine-2,4(1H,3H)-dione

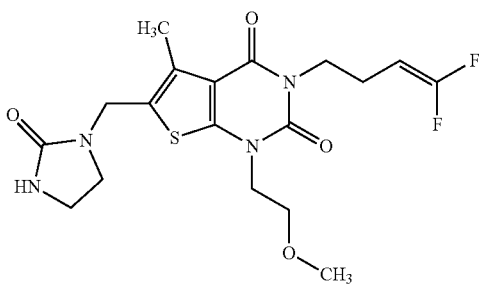 [SMILES: COCCn1c(=O)n(CCC=C(F)F)c(=O)c2c(C)c(CN3CCNC3=O)sc21]

To a solution of 119 mg (1.33 mmol) of 2-imidazolidinone in 5 ml of THF were added 53 mg (1.33 mmol) of sodium hydride (60% suspension in mineral oil) and the mixture was stirred at 60° C. for 3 h ("Solution 1"). To a solution of 121 mg (0.332 mmol) of the compound from Ex. 392A in 2 ml of dichloromethane in another reaction vessel were added, at 0° C., 174 µl (0.997 mmol) of N,N-diisopropylethylamine and 36 µl (0.499 mmol) of thionyl chloride, and the mixture was stirred for 90 min. Subsequently, Solution 1 was added in portions and the mixture was stirred at RT for 21 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 101 mg (69% of theory) of the title compound were obtained.

$^1$H-NMR (400 MHz, DMSO-$d_6$, δ/ppm): 6.55 (s, 1H), 4.60-4.46 (m, 1H), 4.34 (s, 2H), 4.02 (t, 2H), 3.91 (t, 2H), 3.62 (t, 2H), 3.29-3.17 (m, 7H), 2.39 (s, 3H), 2.25 (q, 2H).

LC/MS (Method 3, ESIpos): $R_t$=1.02 min, m/z=429 [M+H]$^+$.

Example 323

3-[(2,2-Difluorocyclopropyl)methyl]-1-(2-methoxyethyl)-5-methyl-6-[(2-oxoimidazolidin-1-yl)methyl]thieno[2,3-d]pyrimidine-2,4(1H,3H)-dione (racemate)

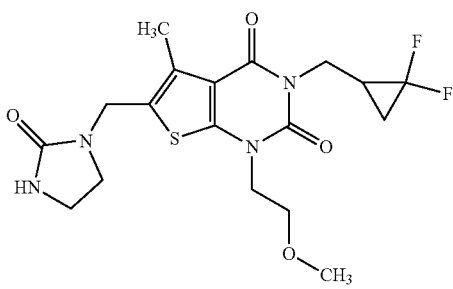 [SMILES: COCCn1c(=O)n(CC2CC2(F)F)c(=O)c2c(C)c(CN3CCNC3=O)sc21]

To a solution of 153 mg (1.7 mmol) of 2-imidazolidinone in 6 ml of THF were added 68 mg (1.7 mmol) of sodium hydride (60% suspension in mineral oil) and the mixture was stirred at 60° C. for 3 h ("Solution 1"). To a solution of 158 mg (0.425 mmol) of the compound from Ex. 393A in 3 ml of dichloromethane in another reaction vessel were added, at 0° C., 46 µl (0.638 mmol) of thionyl chloride, and the mixture was stirred for 75 min. Subsequently, Solution 1 was added in portions and the mixture was stirred at RT for 20 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 77 mg (41% of theory) of the title compound were obtained.

$^1$H-NMR (400 MHz, DMSO-$d_6$, δ/ppm): 6.55 (s, 1H), 4.35 (s, 2H), 4.11-3.91 (m, 4H), 3.63 (t, 2H), 3.29-3.17 (m, 7H), 2.39 (s, 3H), 2.15-2.01 (m, 1H), 1.59 (tdd, 1H), 1.40-1.28 (m, 1H).

LC/MS (Method 3, ESIpos): $R_t$=0.99 min, m/z=429 [M+H]$^+$.

Example 324

3-(2-Methoxyethyl)-5-methyl-6-[(2-oxoimidazolidin-1-yl)methyl]-1-(tetrahydrofuran-2-ylmethyl)thieno[2,3-d]pyrimidine-2,4(1H,3H)-dione (Enantiomer 1)

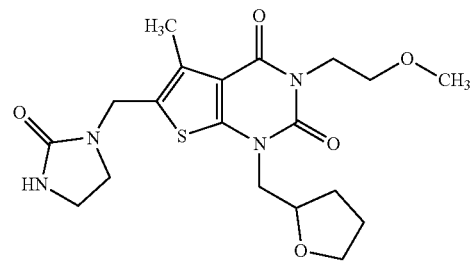 [SMILES: COCCn1c(=O)c2c(C)c(CN3CCNC3=O)sc2n(CC2CCCO2)c1=O]

94 mg of the racemic compound from Ex. 233 were dissolved in 3.5 ml of a methanol/dichloromethane mixture (1:1 v/v) and separated into the enantiomers by means of preparative HPLC on a chiral phase [column: Daicel Chiralpak IA, 5 µm, 250 mm×30 mm; eluent: ethanol+0.1% diethylamine (isocratic); flow rate: 60 ml/min; UV detection: 280 nm]. The product fractions were concentrated on a rotary evaporator, admixed with tert-butanol and freeze-dried. 15 mg of the title compound (Enantiomer 1) and 26 mg of Enantiomer 2 (see Example 325) were obtained.

$^1$H-NMR (400 MHz, DMSO-$d_6$, δ/ppm): 6.54 (s, 1H), 4.34 (s, 2H), 4.25-4.16 (m, 1H), 4.10-3.99 (m, 3H), 3.78-3.65 (m, 2H), 3.65-3.57 (m, 1H), 3.49 (t, 2H), 3.28-3.15 (m, 7H), 2.38 (s, 3H), 2.03-1.75 (m, 4H), 1.71-1.59 (m, 1H).

Chiral analytical HPLC [column: Daicel Chiralpak IA, 3 µm, 100 mm×4.6 mm; eluent: ethanol+0.1% diethylamine (isocratic); flow rate: 1.0 ml/min; temperature: 25° C.; DAD 280 nm]: $R_t$=4.32 min.

Example 325

3-(2-Methoxyethyl)-5-methyl-6-[(2-oxoimidazolidin-1-yl)methyl]-1-(tetrahydrofuran-2-ylmethyl)thieno[2,3-d]pyrimidine-2,4(1H,3H)-dione (Enantiomer 2)

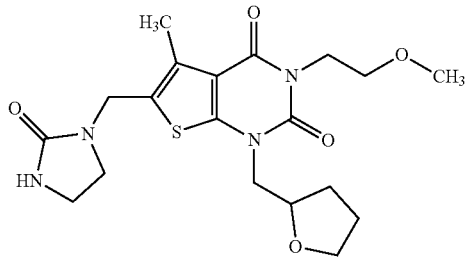

The title compound (26 mg) was obtained as the second enantiomer in the preparative HPLC separation of the racemate from Ex. 233 described in Ex. 324.

$^1$H-NMR (500 MHz, DMSO-$d_6$, δ/ppm): 6.54 (s, 1H), 4.34 (s, 2H), 4.25-4.17 (m, 1H), 4.08-3.99 (m, 3H), 3.78-3.65 (m, 2H), 3.64-3.56 (m, 1H), 3.49 (t, 2H), 3.28-3.16 (m, 7H), 2.38 (s, 3H), 2.03-1.75 (m, 4H), 1.65 (ddt, 1H).

Chiral analytical HPLC [column: Daicel Chiralpak IA, 3 μm, 100 mm×4.6 mm; eluent: ethanol+0.1% diethylamine (isocratic); flow rate: 1.0 ml/min; temperature: 25° C.; DAD 280 nm]: $R_t$=4.91 min.

Example 326

3-(2-Ethoxyethyl)-5-methyl-6-[(2-oxoimidazolidin-1-yl)methyl]-1-(3,3,3-trifluoropropyl)thieno[2,3-d]pyrimidine-2,4(1H,3H)-dione

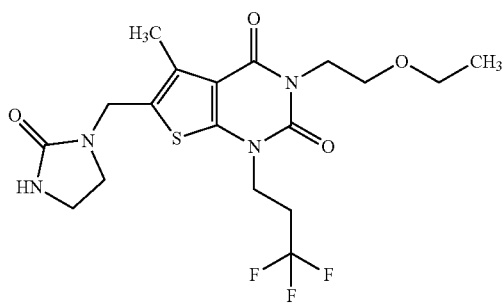

246 mg (0.518 mmol) of the compound from Example 406A were dissolved in 25 ml of dioxane, and 130 mg (0.777 mmol) of CDI were added. The mixture was stirred at RT for 17 h. The reaction solution was then concentrated on a rotary evaporator. The residue was dissolved in 6 ml of DMSO and this solution was purified by means of preparative HPLC (Method 14). Combination of the product fractions and freeze-drying gave 156 mg (65% of theory) of the title compound.

$^1$H-NMR (400 MHz, DMSO-$d_6$, δ/ppm): 6.56 (s, 1H), 4.37 (s, 2H), 4.09 (t, 2H), 4.04 (t, 2H), 3.51 (t, 2H), 3.44 (q, 2H), 3.29-3.18 (m, 4H), 2.82-2.69 (m, 2H), 2.40 (s, 3H), 1.06 (t, 3H).

LC/MS (Method 3, ESIpos): $R_t$=1.03 min, m/z=449 [M+H]$^+$.

Example 327

3-(2-Ethoxyethyl)-1-(2-methoxyethyl)-5-methyl-6-[(2-oxoimidazolidin-1-yl)methyl]thieno[2,3-d]pyrimidine-2,4(1H,3H)-dione

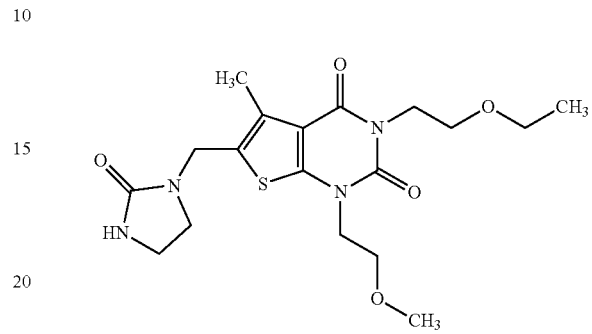

100 mg (0.177 mmol) of the compound from Example 407A were dissolved in 9 ml of dioxane, and 44.3 mg (0.265 mmol) of CDI were added. The mixture was stirred at RT for 14 h. The reaction solution was then concentrated on a rotary evaporator. The residue was dissolved in 3 ml of DMSO and this solution was purified by means of preparative HPLC (Method 14). Combination of the product fractions and freeze-drying gave 55 mg (75% of theory) of the title compound.

$^1$H-NMR (400 MHz, DMSO-$d_6$, δ/ppm): 6.54 (s, 1H), 4.34 (s, 2H), 4.08-3.96 (m, 4H), 3.62 (t, 2H), 3.51 (t, 2H), 3.44 (q, 2H), 3.28-3.16 (m, 7H), 2.38 (s, 3H), 1.06 (t, 3H).

LC/MS (Method 3, ESIpos): $R_t$=0.88 min, m/z=411 [M+H]$^+$.

Example 328

1-(2-Methoxyethyl)-3-(3-methoxypropyl)-5-methyl-6-[(2-oxoimidazolidin-1-yl)methyl]thieno[2,3-d]pyrimidine-2,4(1H,3H)-dione

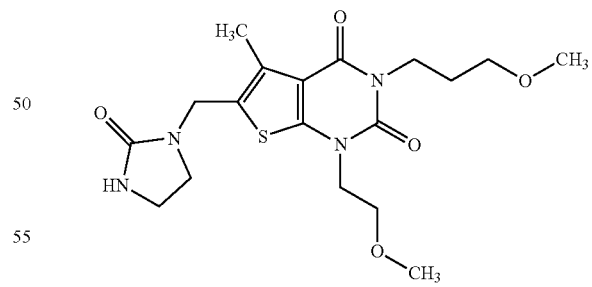

To a solution of 139 mg (1.55 mmol) of 2-imidazolidinone in 6 ml of THF were added 62 mg (1.55 mmol) of sodium hydride (60% suspension in mineral oil) and the mixture was stirred at 60° C. for 3 h ("Solution 1"). To a solution of 140 mg (0.388 mmol) of the compound from Ex. 394A in 3 ml of dichloromethane in another reaction vessel were added, at 0° C., 203 μl (1.165 mmol) of N,N-diisopropylethylamine and 42 μl (0.583 mmol) of thionyl chloride, and the mixture was stirred for 90 min. Subsequently, Solution 1 was added in portions and the mixture was stirred at RT for 18 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 86 mg (52% of theory) of the title compound were obtained.

$^1$H-NMR (400 MHz, DMSO-$d_6$, δ/ppm): 6.54 (s, 1H), 4.34 (s, 2H), 4.01 (t, 2H), 3.91 (t, 2H), 3.62 (t, 2H), 3.38-3.35 (m, 2H), 3.28-3.17 (m, 10H), 2.38 (s, 3H), 1.76 (quin, 2H).

LC/MS (Method 3, ESIpos): $R_t$=0.85 min, m/z=411 [M+H]$^+$.

Example 329

1-(2-Methoxyethyl)-3-(1-methoxypropan-2-yl)-5-methyl-6-[(2-oxoimidazolidin-1-yl)methyl]thieno[2,3-d]pyrimidine-2,4(1H,3H)-dione (racemate)

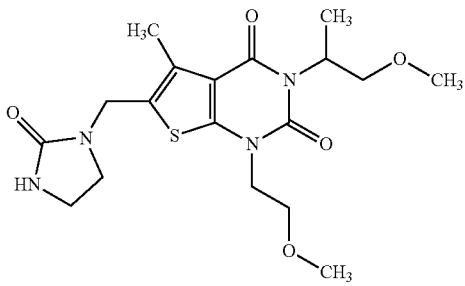 [SMILES: COCCn1c(=O)n(C(C)COC)c(=O)c2c(C)c(CN3CCNC3=O)sc21]

To a solution of 206 mg (2.3 mmol) of 2-imidazolidinone in 8 ml of THF were added 92 mg (2.3 mmol) of sodium hydride (60% suspension in mineral oil) and the mixture was stirred at 60° C. for 3 h ("Solution 1"). To a solution of 205 mg (0.575 mmol) of the compound from Ex. 154A in 4 ml of dichloromethane in another reaction vessel were added, at 0° C., 300 µl (1.72 mmol) of N,N-diisopropylethylamine and 63 µl (0.862 mmol) of thionyl chloride, and the mixture was stirred for 90 min. Subsequently, Solution 1 was added in portions and the mixture was stirred at RT for 17 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 134 mg (56% of theory) of the title compound were obtained.

$^1$H-NMR (400 MHz, DMSO-$d_6$, δ/ppm): 6.54 (s, 1H), 5.17 (br. d, 1H), 4.34 (s, 2H), 4.02-3.96 (m, 2H), 3.91 (dd, 1H), 3.61 (t, 2H), 3.54 (dd, 1H), 3.28-3.16 (m, 10H), 2.37 (s, 3H), 1.32 (d, 3H).

LC/MS (Method 3, ESIpos): $R_t$=0.92 min, m/z=411 [M+H]$^+$.

Example 330

1-(2-Methoxyethyl)-3-(1-methoxypropan-2-yl)-5-methyl-6-[(2-oxoimidazolidin-1-yl)methyl]thieno[2,3-d]pyrimidine-2,4(1H,3H)-dione (Enantiomer 1)

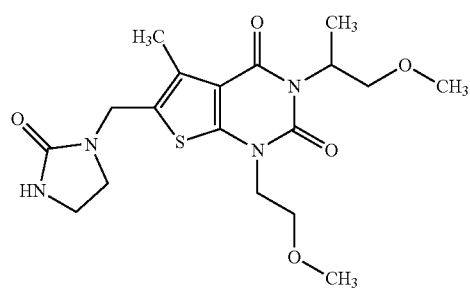 [SMILES: COCCn1c(=O)n(C(C)COC)c(=O)c2c(C)c(CN3CCNC3=O)sc21]

115 mg of the racemic compound from Ex. 329 were dissolved in 3.5 ml of a methanol/dichloromethane mixture (1:1 v/v) and separated into the enantiomers by means of preparative HPLC on a chiral phase [column: Daicel Chiralpak IA, 5 µm, 250 mm×30 mm; eluent: methanol/ethanol/diethylamine 50:50:0.1 (v/v/v); flow rate: 30 ml/min; temperature: RT; UV detection: 254 nm]. The product fractions were concentrated on a rotary evaporator, admixed with tert-butanol and freeze-dried. 47 mg of the title compound (Enantiomer 1) and 48 mg of Enantiomer 2 (see Example 331) were obtained.

$^1$H-NMR (600 MHz, DMSO-$d_6$, δ/ppm): 6.51 (s, 1H), 5.17 (br. s, 1H), 4.34 (s, 2H), 4.02-3.95 (m, 2H), 3.94-3.88 (m, 1H), 3.61 (t, 2H), 3.54 (dd, 1H), 3.27-3.17 (m, 10H), 2.37 (s, 3H), 1.33 (d, 3H).

Chiral analytical HPLC [column: Daicel Chiralpak IA, 5 µm, 100 mm×4.6 mm; eluent: methanol/ethanol/diethylamine 50:50:0.1 v/v/v; flow rate: 1.0 ml/min; temperature: RT; injection: 5 µl; DAD 254 nm]: $R_t$=2.19 min.

Example 331

1-(2-Methoxyethyl)-3-(1-methoxypropan-2-yl)-5-methyl-6-[(2-oxoimidazolidin-1-yl)methyl]thieno[2,3-d]pyrimidine-2,4(1H,3H)-dione (Enantiomer 2)

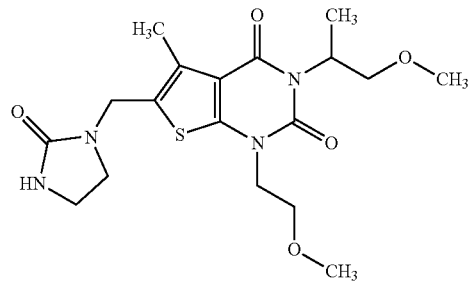 [SMILES: COCCn1c(=O)n(C(C)COC)c(=O)c2c(C)c(CN3CCNC3=O)sc21]

The title compound (48 mg) was obtained as the second enantiomer in the preparative HPLC separation of the racemate from Ex. 329 described in Ex. 330.

$^1$H-NMR (600 MHz, DMSO-$d_6$, δ/ppm): 6.51 (s, 1H), 5.17 (br. s, 1H), 4.34 (s, 2H), 4.03-3.95 (m, 2H), 3.91 (t, 1H), 3.61 (t, 2H), 3.54 (dd, 1H), 3.28-3.17 (m, 10H), 2.37 (s, 3H), 1.33 (d, 3H).

Chiral analytical HPLC [column: Daicel Chiralpak IA, 5 µm, 100 mm×4.6 mm; eluent: methanol/ethanol/diethylamine 50:50:0.1 v/v/v; flow rate: 1.0 ml/min; temperature: RT; injection: 5 µl; DAD 254 nm]: $R_t$=2.99 min.

Example 332

1-(2-Methoxyethyl)-5-methyl-6-[(2-oxoimidazolidin-1-yl)methyl]-3-(tetrahydrofuran-2-ylmethyl)thieno[2,3-d]pyrimidine-2,4(1H,3H)-dione (racemate)

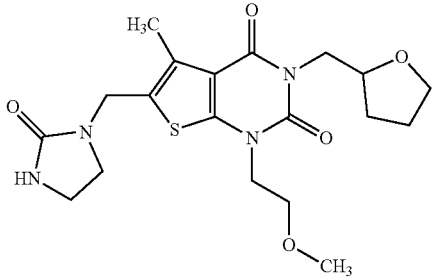

To a solution of 163 mg (1.82 mmol) of 2-imidazolidinone in 7 ml of THF were added 73 mg (1.82 mmol) of sodium hydride (60% suspension in mineral oil) and the mixture was stirred at 60° C. for 3 h ("Solution 1"). To a solution of 163 mg (0.455 mmol) of the compound from Ex. 395A in 3 ml of dichloromethane in another reaction vessel were added, at 0° C., 50 µl (0.683 mmol) of thionyl chloride, and the mixture was stirred for 90 min. Subsequently, Solution 1 was added in portions and the mixture was stirred at RT for 20 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 103 mg (53% of theory) of the title compound were obtained.

$^1$H-NMR (400 MHz, DMSO-d$_6$, δ/ppm): 6.55 (s, 1H), 4.35 (s, 2H), 4.18-4.10 (m, 1H), 4.08-3.95 (m, 3H), 3.79-3.70 (m, 2H), 3.65-3.55 (m, 3H), 3.28-3.17 (m, 7H), 2.38 (s, 3H), 1.95-1.73 (m, 3H), 1.67-1.56 (m, 1H).

LC/MS (Method 3, ESIpos): $R_t$=0.87 min, m/z=423 [M+H]$^+$.

Example 333

1-(2-Methoxyethyl)-5-methyl-6-[(2-oxoimidazolidin-1-yl)methyl]-3-(tetrahydrofuran-2-ylmethyl)thieno[2,3-d]pyrimidine-2,4(1H,3H)-dione (Enantiomer 1)

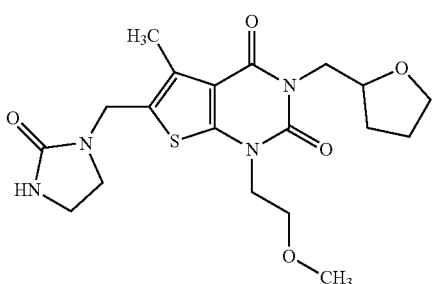

86 mg of the racemic compound from Ex. 332 were dissolved in 3.6 ml of methanol and separated into the enantiomers by means of preparative HPLC on a chiral phase [column: Daicel Chiralpak IC, 5 µm, 250 mm×30 mm; eluent A: acetonitrile+0.1% diethylamine, eluent B: methanol; isocratic 50% A+50% B; flow rate: 50.0 ml/min; UV detection: 254 nm]. The product fractions were concentrated on a rotary evaporator, admixed with tert-butanol and freeze-dried. 34 mg of the title compound (Enantiomer 1) and 35 mg of Enantiomer 2 (see Example 334) were obtained.

$^1$H-NMR (400 MHz, DMSO-d$_6$, δ/ppm): 6.54 (s, 1H), 4.34 (s, 2H), 4.18-4.10 (m, 1H), 4.08-3.95 (m, 3H), 3.79-3.71 (m, 2H), 3.65-3.55 (m, 3H), 3.28-3.17 (m, 7H), 2.38 (s, 3H), 1.95-1.72 (m, 3H), 1.68-1.57 (m, 1H).

Chiral analytical HPLC [column: Daicel Chiralpak IC, 3 µm, 100 mm×4.6 mm; eluent A: acetonitrile+0.1% diethylamine, eluent B: methanol; isocratic 50% A+50% B; flow rate: 1.4 ml/min; temperature: 25° C.; DAD 254 nm]: $R_t$=3.07 min.

Example 334

1-(2-Methoxyethyl)-5-methyl-6-[(2-oxoimidazolidin-1-yl)methyl]-3-(tetrahydrofuran-2-ylmethyl)thieno[2,3-d]pyrimidine-2,4(1H,3H)-dione (Enantiomer 2)

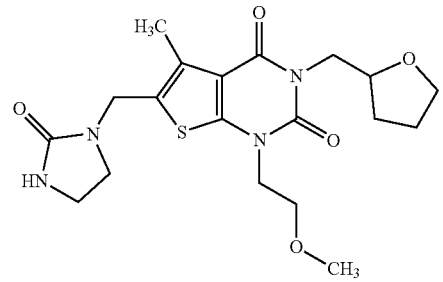 [SMILES: COCCn1c(=O)n(CC2CCCO2)c(=O)c2c(C)c(CN3CCNC3=O)sc21]

The title compound (35 mg) was obtained as the second enantiomer in the preparative HPLC separation of the racemate from Ex. 332 described in Ex. 333.

$^1$H-NMR (400 MHz, DMSO-d$_6$, δ/ppm): 6.55 (s, 1H), 4.34 (s, 2H), 4.18-4.09 (m, 1H), 4.08-3.95 (m, 3H), 3.79-3.70 (m, 2H), 3.65-3.55 (m, 3H), 3.28-3.17 (m, 7H), 2.38 (s, 3H), 1.95-1.72 (m, 3H), 1.68-1.56 (m, 1H).

Chiral analytical HPLC [column: Daicel Chiralpak IC, 3 µm, 100 mm×4.6 mm; eluent A: acetonitrile+0.1% diethylamine, eluent B: methanol; isocratic 50% A+50% B; flow rate: 1.4 ml/min; temperature: 25° C.; DAD 254 nm]: $R_t$=3.56 min.

Example 335

1-(2-Methoxyethyl)-5-methyl-3-(oxetan-3-ylmethyl)-6-[(2-oxoimidazolidin-1-yl)methyl]thieno[2,3-d]pyrimidine-2,4(1H,3H)-dione

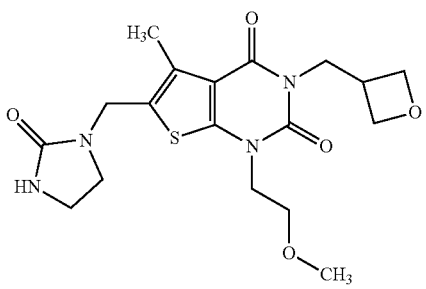 [SMILES: COCCn1c(=O)n(CC2COC2)c(=O)c2c(C)c(CN3CCNC3=O)sc21]

To a solution of 73 mg (0.811 mmol) of 2-imidazolidinone in 3 ml of THF were added 32 mg (0.811 mmol) of sodium hydride (60% suspension in mineral oil) and the mixture was stirred at 60° C. for 3 h ("Solution 1"). To a solution of 69 mg (0.203 mmol) of the compound from Ex. 396A in 1.4 ml of dichloromethane in another reaction vessel were added, at 0° C., 106 µl (0.608 mmol) of N,N-diisopropylethylamine and 22 µl (0.304 mmol) of thionyl chloride, and the mixture was stirred for 90 min. Subsequently, Solution 1 was added in portions and the mixture was stirred at RT for 17 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 25 g of silica gel, eluent: ethyl acetate/methanol). 15 mg (17% of theory) of the title compound were obtained.

$^1$H-NMR (400 MHz, DMSO-$d_6$, δ/ppm): 6.55 (s, 1H), 4.57 (dd, 2H), 4.40 (t, 2H), 4.34 (s, 2H), 4.16 (d, 2H), 4.00 (t, 2H), 3.63-3.59 (m, 2H), 3.28-3.18 (m, 8H), 2.38 (s, 3H).

LC/MS (Method 3, ESIpos): $R_t$=0.77 min, m/z=409 [M+H]$^+$.

Example 336

5-Methyl-6-[(3-methyl-2-oxoimidazolidin-1-yl)methyl]-3-(2,2,2-trifluoroethyl)-1-(3,3,3-trifluoropropyl)thieno[2,3-d]pyrimidine-2,4(1H,3H)-dione

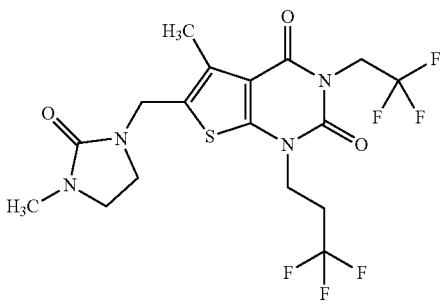 [SMILES: Cc1c(CN2CCN(C)C2=O)sc2c1c(=O)n(CC(F)(F)F)c(=O)n2CCC(F)(F)F]

To a solution of 60 mg (0.131 mmol) of the compound from Ex. 204 in 4 ml of THF were added, at 0° C., 6.3 mg (0.157 mmol) of sodium hydride (60% suspension in mineral oil), and the mixture was stirred for 1 h. Subsequently, 22.5 mg (0.157 mmol) of iodomethane were added, and the mixture was stirred at RT for 16 h. Then the reaction mixture was partitioned between saturated aqueous ammonium chloride solution (20 ml) and THF (30 ml). The organic phase was washed with saturated aqueous sodium hydrogencarbonate solution, dried over sodium sulphate, filtered and concentrated. The residue obtained was purified by means of preparative HPLC (Method 14). Combination of the product fractions and freeze-drying gave 25 mg (40% of theory) of the title compound.

$^1$H-NMR (400 MHz, DMSO-$d_6$, δ/ppm): 4.70 (q, 2H), 4.41 (s, 2H), 4.13 (t, 2H), 3.27-3.17 (m, 4H), 2.85-2.70 (m, 2H), 2.67 (s, 3H), 2.40 (s, 3H).

LC/MS (Method 3, ESIpos): $R_t$=1.20 min, m/z=473 [M+H]$^+$.

Example 337

1-(2-Methoxyethyl)-5-methyl-6-[(3-methyl-2-oxoimidazolidin-1-yl)methyl]-3-(3,3,3-trifluoropropyl)thieno[2,3-d]pyrimidine-2,4(1H,3H)-dione

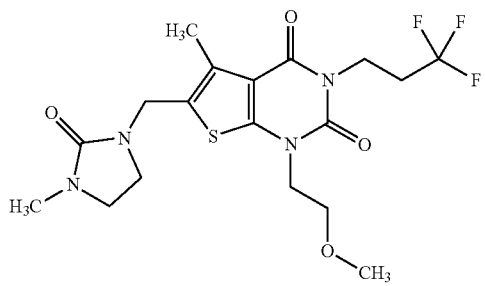 [SMILES: COCCn1c(=O)n(CCC(F)(F)F)c(=O)c2c(C)c(CN3CCN(C)C3=O)sc21]

To a solution of 62 mg (0.14 mmol) of the compound from Ex. 98 in 8 ml of THF were added, at 0° C., 6.7 mg (0.168 mmol) of sodium hydride (60% suspension in mineral oil), and the mixture was stirred for 1 h. Subsequently, 24 mg (0.168 mmol) of iodomethane were added, and the mixture was stirred at RT for 3 h. Thereafter, another 6.7 mg (0.168 mmol) of sodium hydride (60% suspension in mineral oil) and 24 mg (0.168 mmol) of iodomethane were added and the mixture was stirred at RT for a further 63 h. Then the reaction mixture was partitioned between saturated aqueous ammonium chloride solution (20 ml), THF (30 ml) and ethyl acetate (40 ml). The organic phase was washed with saturated aqueous sodium hydrogencarbonate solution, dried over sodium sulphate, filtered and concentrated. The residue obtained was purified by means of preparative HPLC (Method 14). Combination of the product fractions and freeze-drying gave 42 mg (64% of theory) of the title compound.

$^1$H-NMR (500 MHz, DMSO-$d_6$, δ/ppm): 4.38 (s, 2H), 4.10 (t, 2H), 4.01 (t, 2H), 3.62 (t, 2H), 3.26-3.15 (m, 7H), 2.67 (s, 3H), 2.63-2.52 (m, 2H), 2.39 (s, 3H).

LC/MS (Method 3, ESIpos): $R_t$=1.09 min, m/z=449 [M+H]$^+$.

Example 338

3-(2-Methoxy-2-methylpropyl)-5-methyl-6-[(3-methyl-2-oxoimidazolidin-1-yl)methyl]-1-(3,3,3-trifluoropropyl)thieno[2,3-d]pyrimidine-2,4(1H,3H)-dione

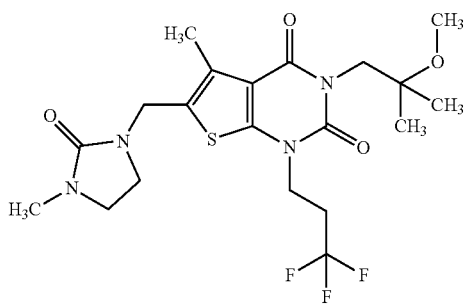

To a solution of 45 mg (0.093 mmol) of the compound from Ex. 236 in 5 ml of THF were added, at 0° C., 4.5 mg (0.112 mmol) of sodium hydride (60% suspension in mineral oil), and the mixture was stirred for 1 h. Subsequently, 16 mg (0.112 mmol) of iodomethane were added, and the mixture was stirred at RT for 2 h. Then the reaction mixture was partitioned between saturated aqueous ammonium chloride solution (20 ml), THF (30 ml) and ethyl acetate (40 ml). The organic phase was washed with saturated aqueous sodium hydrogencarbonate solution, dried over sodium sulphate, filtered and concentrated. The residue obtained was purified by means of preparative HPLC (Method 14). Combination of the product fractions and freeze-drying gave 32 mg (69% of theory) of the title compound.

$^1$H-NMR (400 MHz, DMSO-$d_6$, δ/ppm): 4.39 (s, 2H), 4.09 (br. t, 2H), 3.99 (br. s, 2H), 3.26-3.17 (m, 4H), 3.15 (s, 3H), 2.81-2.69 (m, 2H), 2.67 (s, 3H), 2.39 (s, 3H), 1.08 (s, 6H).

LC/MS (Method 3, ESIpos): $R_t$=1.15 min, m/z=477 [M+H]$^+$.

Example 339

5-Methyl-6-[(2-oxo-2,3-dihydro-1H-imidazol-1-yl)methyl]-3-(2,2,2-trifluoroethyl)-1-(3,3,3-trifluoropropyl)thieno[2,3-d]pyrimidine-2,4(1H,3H)-dione

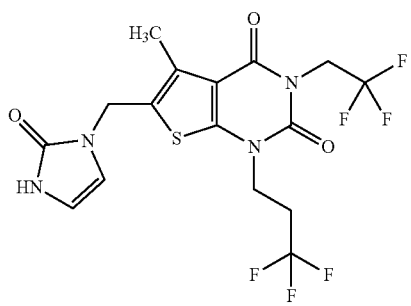 [SMILES: Cc1c(Cn2cc[nH]c2=O)sc2c1c(=O)n(CC(F)(F)F)c(=O)n2CCC(F)(F)F]

To a solution of 417 mg (0.873 mmol) of the compound from Ex. 408A in 9 ml of methanol were added first 163 mg (2.01 mmol) of potassium cyanate and then, dropwise, 128 μl (1.49 mmol) of perchloric acid (70% in water). After the reaction mixture had been stirred at RT for 5 days, it was admixed with semisaturated aqueous sodium hydrogencarbonate solution and extracted with ethyl acetate. The organic extract was washed with saturated sodium chloride solution, dried over anhydrous magnesium sulphate, filtered and concentrated. HPLC analysis of the crude product thus obtained showed that it was a mixture of reactant and desired product. The crude product was therefore dissolved once again in the same amount of methanol and the same amounts of potassium cyanate and perchloric acid as stated above were added. After stirring for about 18 h, a further 163 mg (2.01 mmol) of potassium cyanate were added. After about a further 24 h and after about a further 48 h, 1.7 ml (1.75 mmol) of 1 M hydrochloric acid were added. After stirring for another 2.5 days, the reaction mixture was diluted with water. The solid precipitated out was filtered off with suction, washed with a little water and dried. Subsequently, the solids were purified by means of preparative HPLC (Method 8). The product fractions were concentrated and stirred with a little acetonitrile at RT. After isolating the solids again and drying under high vacuum, 100 mg (25% of theory) of the title compound were obtained.

$^1$H-NMR (400 MHz, DMSO-$d_6$, δ/ppm): 10.01 (br. s, 1H), 6.46 (t, 1H), 6.35 (t, 1H), 4.83 (s, 2H), 4.70 (q, 2H), 4.11 (t, 2H), 2.85-2.67 (m, 2H), 2.47 (s, 3H).

LC/MS (Method 1, ESIpos): $R_t$=0.84 min, m/z=457 [M+H]$^+$.

Example 340

1-(2-Methoxyethyl)-5-methyl-6-[(2-oxo-2,3-dihydro-1H-imidazol-1-yl)methyl]-3-(2,2,2-trifluoroethyl)thieno[2,3-d]pyrimidine-2,4(1H,3H)-dione

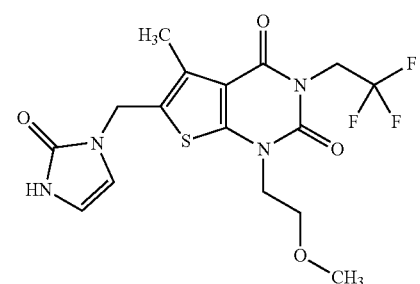

Analogously to the process described in Ex. 339, 454 mg (1.03 mmol) of the compound from Ex. 409A gave 140 mg (32% of theory) of the title compound. It was possible here to dispense with the purification by means of preparative HPLC; the product precipitated on dilution with water, after being filtered off with suction, was stirred with a little acetonitrile at RT, filtered off with suction again and dried.

$^1$H-NMR (400 MHz, DMSO-$d_6$, δ/ppm): 10.01 (br. s, 1H), 6.45 (br. s, 1H), 6.38-6.30 (m, 1H), 4.81 (s, 2H), 4.69 (q, 2H), 4.03 (t, 2H), 3.62 (t, 2H), 3.22 (s, 3H), 2.46 (s, 3H).

LC/MS (Method 17, ESIneg): $R_t$=1.33 min, m/z=417.08 [M−H]$^-$.

Example 341

5-Methyl-6-[(2-oxo-2,3-dihydro-1H-imidazol-1-yl)methyl]-1-(tetrahydrofuran-2-ylmethyl)-3-(2,2,2-trifluoroethyl)thieno[2,3-d]pyrimidine-2,4(1H,3H)-dione (racemate)

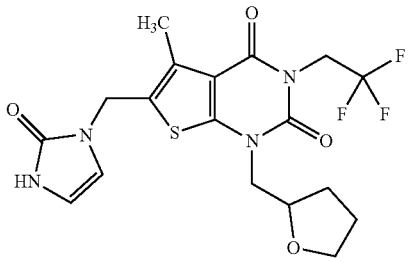 [SMILES: Cc1c(Cn2cc[nH]c2=O)sc2c1c(=O)n(CC(F)(F)F)c(=O)n2CC1CCCO1]

To a solution of 605 mg (1.30 mmol) of the compound from Ex. 410A in 13 ml of methanol were added first 242 mg (2.99 mmol) of potassium cyanate and then, dropwise, 190 µl (2.21 mmol) of perchloric acid (70% in water). After the reaction mixture had been stirred at RT for about 42 h, the same amounts of potassium cyanate and perchloric acid again were added. After stirring for a further 4 days, the reaction mixture was admixed with semisaturated aqueous sodium hydrogencarbonate solution and extracted with ethyl acetate. The organic extract was washed with saturated sodium chloride solution, dried over anhydrous magnesium sulphate, filtered and concentrated. The crude product was purified by preparative HPLC (Method 8). The product fractions were concentrated and the residue was dried under high vacuum. 275 mg (47% of theory) of the title compound were obtained.

$^1$H-NMR (400 MHz, DMSO-$d_6$, δ/ppm): 10.00 (br. s, 1H), 6.45 (dd, 1H), 6.35 (t, 1H), 4.80 (s, 2H), 4.70 (q, 2H), 4.26-4.15 (m, 1H), 4.05 (dd, 1H), 3.78-3.67 (m, 2H), 3.65-3.55 (m, 1H), 2.46 (s, 3H), 2.05-1.75 (m, 3H), 1.72-1.59 (m, 1H).

LC/MS (Method 17, ESIneg): $R_t$=1.41 min, m/z=443.10 [M−H]$^-$.

Example 342

5-Methyl-6-[(2-oxo-2,3-dihydro-1H-imidazol-1-yl)methyl]-1-(tetrahydrofuran-2-ylmethyl)-3-(2,2,2-trifluoroethyl)thieno[2,3-d]pyrimidine-2,4(1H,3H)-dione (Enantiomer 1)

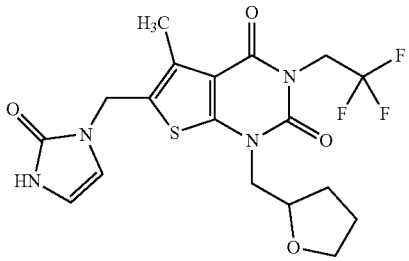 [SMILES: Cc1c(Cn2cc[nH]c2=O)sc2c1c(=O)n(CC(F)(F)F)c(=O)n2CC1CCCO1]

220 mg (0.495 mmol) of the racemic compound from Ex. 341 were dissolved in 20 ml of ethanol and, in 67 portions, separated into the enantiomers by preparative SFC on a chiral phase [column: Daicel Chiralpak AZ-H, 5 µm, 250 mm×30 mm; eluent: carbon dioxide/ethanol 82:18; flow rate: 100 ml/min; temperature: 40° C.; detection: 210 nm]. After concentration of the product fractions and drying under high vacuum, 74 mg (67% of theory) of Enantiomer 1 were obtained (>99% ee, chiral analytical HPLC).

$^1$H-NMR (400 MHz, DMSO-$d_6$, δ/ppm): 10.00 (br. s, 1H), 6.45 (dd, 1H), 6.35 (t, 1H), 4.80 (s, 2H), 4.70 (q, 2H), 4.26-4.14 (m, 1H), 4.05 (dd, 1H), 3.79-3.66 (m, 2H), 3.64-3.55 (m, 1H), 2.46 (s, 3H), 2.05-1.74 (m, 3H), 1.71-1.59 (m, 1H).

Chiral analytical SFC [column: Daicel Chiralpak AZ-H, 3 µm, 50 mm×4.6 mm; eluent: carbon dioxide/ethanol 80:20; flow rate: 3 ml/min; temperature: 40° C.; detection: 210 nm]: $R_t$=2.83 min.

Example 343

5-Methyl-6-[(2-oxo-2,3-dihydro-1H-imidazol-1-yl)methyl]-1-(tetrahydrofuran-2-ylmethyl)-3-(2,2,2-trifluoroethyl)thieno[2,3-d]pyrimidine-2,4(1H,3H)-dione (Enantiomer 2)

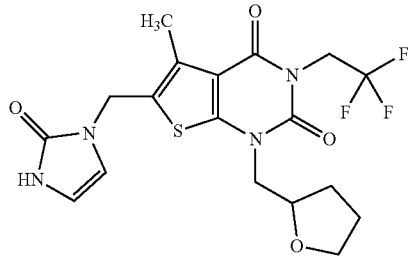 [SMILES: Cc1c(Cn2cc[nH]c2=O)sc2c1c(=O)n(CC(F)(F)F)c(=O)n2CC1CCCO1]

220 mg (0.495 mmol) of the racemic compound from Ex. 341 were dissolved in 20 ml of ethanol and, in 67 portions, separated into the enantiomers by preparative SFC on a chiral phase [column: Daicel Chiralpak AZ-H, 5 µm, 250 mm×30 mm; eluent: carbon dioxide/ethanol 82:18; flow rate: 100 ml/min; temperature: 40° C.; detection: 210 nm]. After concentration of the product fractions and drying under high vacuum, 50 mg (45% of theory) of Enantiomer 2 were obtained (>99% ee, chiral analytical HPLC).

$^1$H-NMR (400 MHz, DMSO-$d_6$, δ/ppm): 10.01 (br. s, 1H), 6.45 (dd, 1H), 6.35 (t, 1H), 4.80 (s, 2H), 4.70 (q, 2H), 4.26-4.15 (m, 1H), 4.05 (dd, 1H), 3.77-3.67 (m, 2H), 3.65-3.55 (m, 1H), 2.46 (s, 3H), 2.06-1.74 (m, 3H), 1.70-1.61 (m, 1H).

Chiral analytical SFC [column: Daicel Chiralpak AZ-H, 3 µm, 50 mm×4.6 mm; eluent: carbon dioxide/ethanol 80:20; flow rate: 3 ml/min; temperature: 40° C.; detection: 210 nm]: $R_t$=4.42 min.

Example 344

3-(2-Methoxyethyl)-5-methyl-6-[(2-oxo-2,3-dihydro-1H-imidazol-1-yl)methyl]-1-(3,3,3-trifluoropropyl)thieno[2,3-d]pyrimidine-2,4(1H,3H)-dione

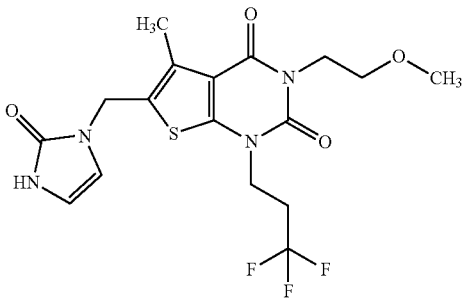 [SMILES: COCCn1c(=O)c2c(C)c(Cn3cc[nH]c3=O)sc2n(CCC(F)(F)F)c1=O]

To a solution of 450 mg (0.992 mmol) of the compound from Ex. 411A in 10 ml of methanol were added first 185 mg (2.28 mmol) of potassium cyanate and then, dropwise, 145 µl (1.68 mmol) of perchloric acid (70% in water). The mixture was stirred at RT. After 18 h and after 3 days, the same amounts of potassium cyanate and perchloric acid were added once again. After the reaction mixture had been stirred at RT for 4 further days, it was admixed with semisaturated aqueous sodium hydrogencarbonate solution and extracted with ethyl acetate. The organic extract was washed with saturated sodium chloride solution, dried over anhydrous magnesium sulphate, filtered and concentrated. The title compound was isolated from the remaining residue by means of preparative HPLC [column: Kinetex C18, 5 µm, 100 mm×30 mm; eluent A: water+0.07% formic acid; eluent B: acetonitrile; gradient: 0.0-2.0 min 10% B, 2.2 min 20% B, 7.0 min 60% B, 7.5-9.0 min 92% B; flow rate: 70 ml/min; temperature: 25° C.; detection: 210 nm]. This gave, after concentration of the product fractions and drying of the residue under high vacuum, 123 mg (28% of theory) of the title compound.

$^1$H-NMR (400 MHz, DMSO-$d_6$, δ/ppm): 10.00 (br. s, 1H), 6.48-6.41 (m, 1H), 6.35 (t, 1H), 4.81 (s, 2H), 4.08 (q, 2H), 4.05 (t, 2H), 3.49 (t, 2H), 3.31 (s, 3H), 2.82-2.65 (m, 2H), 2.47 (s, 3H).

LC/MS (Method 1, ESIpos): $R_t$=0.78 min, m/z=433 [M+H]$^+$.

Example 345

1,3-Bis(2-methoxyethyl)-5-methyl-6-[(2-oxo-2,3-dihydro-1H-imidazol-1-yl)methyl]thieno[2,3-d]pyrimidine-2,4(1H,3H)-dione

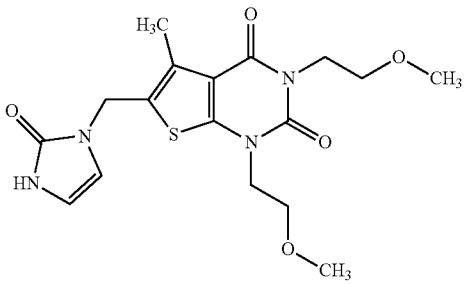 [SMILES: COCCn1c(=O)c2c(C)c(Cn3cc[nH]c3=O)sc2n(CCOC)c1=O]

To a solution of 520 mg (1.25 mmol) of the compound from Ex. 412A in 13 ml of methanol were added first 233 mg (2.88 mmol) of potassium cyanate and then, dropwise, 183 µl (2.13 mmol) of perchloric acid (70% in water). After stirring at RT for 6.5 days, the reaction mixture was admixed with semisaturated aqueous sodium hydrogencarbonate solution and extracted with ethyl acetate. The organic extract was washed with saturated sodium chloride solution, dried over anhydrous magnesium sulphate, filtered and concentrated. The remaining residue was purified by means of preparative HPLC (Method 8). Concentration of the product fractions gave a product that was still slightly contaminated and was purified further by preparative HPLC again [column: Kinetex C18, 5 µm, 100 mm×30 mm; eluent A: water+0.07% formic acid; eluent B: acetonitrile; gradient: 0.0-2.0 min 10% B, 2.2 min 20% B, 7.0 min 60% B, 7.5-9.0 min 92% B; flow rate: 70 ml/min; temperature: 25° C.; detection: 210 nm]. This gave, after concentration of the product fractions and drying of the residue under high vacuum, 87 mg (17% of theory) of the title compound.

$^1$H-NMR (400 MHz, DMSO-$d_6$, δ/ppm): 10.00 (br. s, 1H), 6.43 (dd, 1H), 6.34 (t, 1H), 4.79 (s, 2H), 4.05 (t, 2H), 4.00 (t, 2H), 3.61 (t, 2H), 3.49 (t, 2H), 3.24 (s, 3H), 3.22 (s, 3H), 2.45 (s, 3H).

LC/MS (Method 1, ESIpos): $R_t$=0.66 min, m/z=395 [M+H]$^+$.

Example 346

3-(2-Methoxyethyl)-5-methyl-6-[(2-oxo-2,3-dihydro-1H-imidazol-1-yl)methyl]-1-(tetrahydrofuran-2-ylmethyl)thieno[2,3-d]pyrimidine-2,4(1H,3H)-dione (racemate)

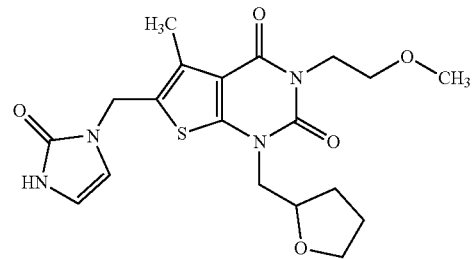 [SMILES: COCCn1c(=O)c2c(C)c(Cn3cc[nH]c3=O)sc2n(CC2CCCO2)c1=O]

Analogously to the process described in Ex. 247, 900 mg (1.67 mmol) of the compound from Ex. 414A gave 302 mg (42% of theory) of the title compound.

$^1$H-NMR (400 MHz, DMSO-$d_6$, δ/ppm): 9.99 (br. s, 1H), 6.46-6.40 (m, 1H), 6.34 (t, 1H), 4.79 (s, 2H), 4.26-4.14 (m, 1H), 4.10-3.97 (m, 3H), 3.78-3.54 (m, 3H), 3.49 (t, 2H), 3.23 (s, 3H), 2.45 (s, 3H), 2.04-1.74 (m, 3H), 1.71-1.57 (m, 1H).

LC/MS (Method 6, ESIpos): $R_t$=1.19 min, m/z=421 [M+H]$^+$.

Example 347

3-(2-Methoxyethyl)-5-methyl-6-[(2-oxo-2,3-di-hydro-1H-imidazol-1-yl)methyl]-1-(tetrahydrofuran-2-ylmethyl)thieno[2,3-d]pyrimidine-2,4(1H,3H)-dione (Enantiomer 1)

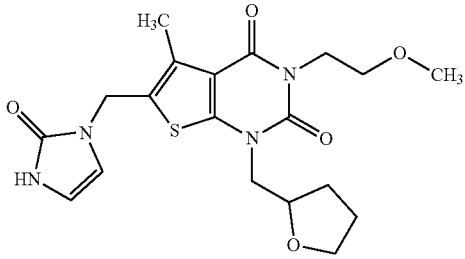 [SMILES: COCCn1c(=O)c2c(C)c(Cn3cc[nH]c3=O)sc2n(CC2CCCO2)c1=O]

274 mg (0.652 mmol) of the racemic compound from Ex. 346 were dissolved in 27 ml of methanol and, in 54 portions, separated into the enantiomers by preparative SFC on a chiral phase [column: Daicel Chiralcel OJ-H, 5 μm, 250 mm×30 mm; eluent: carbon dioxide/methanol 90:10; flow rate: 100 ml/min; temperature: 40° C.; detection: 210 nm]. After concentration of the product fractions and drying under high vacuum, 99 mg (72% of theory) of Enantiomer 1 were obtained (>99% ee, chiral analytical HPLC).

$^1$H-NMR (400 MHz, DMSO-$d_6$, δ/ppm): 9.99 (br. s, 1H), 6.43 (dd, 1H), 6.34 (t, 1H), 4.79 (s, 2H), 4.25-4.15 (m, 1H), 4.10-3.97 (m, 3H), 3.78-3.55 (m, 3H), 3.49 (t, 2H), 3.31 (s, 3H), 2.45 (s, 3H), 2.03-1.75 (m, 3H), 1.71-1.58 (m, 1H).

Chiral analytical SFC [column: Daicel Chiralcel OJ-H, 3 μm, 50 mm×4.6 mm; eluent: carbon dioxide/methanol 80:20; flow rate: 3 ml/min; temperature: 40° C.; detection: 210 nm]: $R_t$=0.93 min.

Example 348

3-(2-Methoxyethyl)-5-methyl-6-[(2-oxo-2,3-di-hydro-1H-imidazol-1-yl)methyl]-1-(tetrahydrofuran-2-ylmethyl)thieno[2,3-d]pyrimidine-2,4(1H,3H)-dione (Enantiomer 2)

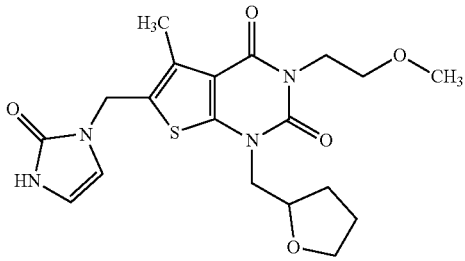 [SMILES: COCCn1c(=O)c2c(C)c(Cn3cc[nH]c3=O)sc2n(CC2CCCO2)c1=O]

274 mg (0.652 mmol) of the racemic compound from Ex. 346 were dissolved in 27 ml of methanol and, in 54 portions, separated into the enantiomers by preparative SFC on a chiral phase [column: Daicel Chiralcel OJ-H, 5 μm, 250 mm×30 mm; eluent: carbon dioxide/methanol 90:10; flow rate: 100 ml/min; temperature: 40° C.; detection: 210 nm]. After concentration of the product fractions and drying under high vacuum, 89 mg (64% of theory) of Enantiomer 2 were obtained (>99% ee, chiral analytical HPLC).

$^1$H-NMR (400 MHz, DMSO-$d_6$, δ/ppm): 9.99 (br. s, 1H), 6.43 (t, 1H), 6.34 (t, 1H), 4.79 (s, 2H), 4.25-4.14 (m, 1H), 4.12-3.97 (m, 3H), 3.79-3.55 (m, 3H), 3.49 (t, 2H), 3.23 (s, 3H), 2.45 (s, 3H), 2.03-1.75 (m, 3H), 1.72-1.58 (m, 1H).

Chiral analytical SFC [column: Daicel Chiralcel OJ-H, 3 μm, 50 mm×4.6 mm; eluent: carbon dioxide/methanol 80:20; flow rate: 3 ml/min; temperature: 40° C.; detection: 210 nm]: $R_t$=1.03 min.

Example 349

6-[(4-Allyl-5-oxo-4,5-dihydro-1H-1,2,4-triazol-1-yl)methyl]-3-ethyl-1-(fluoromethyl)-5-methylthieno[2,3-d]pyrimidine-2,4(1H,3H)-dione

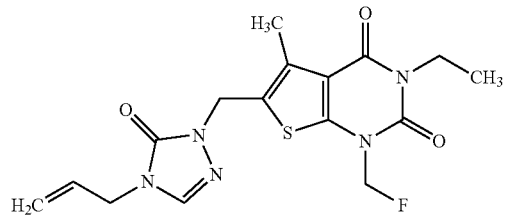 [SMILES: C=CCn1cnn(Cc2sc3c(c2C)c(=O)n(CC)c(=O)n3CF)c1=O]

300 mg (1.07 mmol) of the compound from Ex. 383A and 171 mg (1.28 mmol) of 4-allyl-2,4-dihydro-3H-1,2,4-triazol-3-one were dissolved in 20 ml of dichloromethane, and 462 mg (2.14 mmol) of tri-n-butylphosphine were added. After 30 min, 318 μl (1.6 mmol) of diisopropyl azodicarboxylate (DIAD) were added dropwise. The reaction mixture was stirred at RT for 1 h. Subsequently, the mixture was concentrated to dryness. The residue obtained was chromatographed using a silica gel cartridge (Biotage, 50 g of silica gel, eluent: hexane/ethyl acetate). 205 mg (47% of theory) of the title compound were obtained.

$^1$H-NMR (400 MHz, DMSO-$d_6$, δ/ppm): 7.97 (s, 1H), 6.06 (s, 1H), 5.96-5.84 (m, 2H), 5.19 (dd, 1H), 5.07 (dd, 1H), 5.03 (s, 2H), 4.20 (dt, 2H), 3.90 (q, 2H), 2.47 (s, 3H), 1.12 (t, 3H).

LC/MS (Method 1, ESIpos): $R_t$=0.98 min, m/z=380 [M+H]$^+$.

Example 350

6-[(4-Allyl-5-oxo-4,5-dihydro-1H-1,2,4-triazol-1-yl)methyl]-3-ethyl-1-(3-fluoropropyl)-5-methylthieno[2,3-d]pyrimidine-2,4(1H,3H)-dione

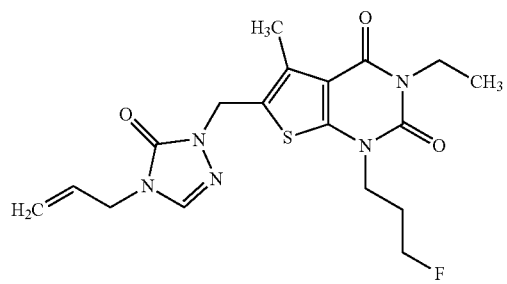 [SMILES: C=CCn1cnn(Cc2sc3c(c2C)c(=O)n(CC)c(=O)n3CCCF)c1=O]

255 mg (0.807 mmol) of the compound from Ex. 141A and 128 mg (0.968 mmol) of 4-allyl-2,4-dihydro-3H-1,2,4- triazol-3-one were dissolved in 14 ml of dichloromethane, and 349 mg (1.61 mmol) of tri-n-butylphosphine were added. After 30 min, 240 µl (1.613 mmol) of diisopropyl azodicarboxylate (DIAD) were added dropwise. The reaction mixture was stirred at RT for 3 h. Subsequently, the mixture was concentrated to dryness. The residue obtained was chromatographed using a silica gel cartridge (Biotage, 100 g of silica gel, eluent: hexane/ethyl acetate). 113 mg (32% of theory) of the title compound were obtained.

¹H-NMR (400 MHz, DMSO-d₆, δ/ppm): 7.96 (s, 1H), 5.90 (ddt, 1H), 5.19 (dq, 1H), 5.06 (dq, 1H), 5.00 (s, 2H), 4.58 (t, 1H), 4.46 (t, 1H), 4.20 (dt, 2H), 3.96 (t, 2H), 3.89 (q, 2H), 2.46 (s, 3H), 2.07 (quin, 1H), 2.04-1.96 (m, 1H), 1.10 (t, 3H).

LC/MS (Method 1, ESIpos): $R_t$=0.99 min, m/z=408 [M+H]⁺.

Example 351

6-[(4-Allyl-5-oxo-4,5-dihydro-1H-1,2,4-triazol-1-yl)methyl]-3-ethyl-1-(3-methoxypropyl)-5-methylthieno[2,3-d]pyrimidine-2,4(1H,3H)-dione

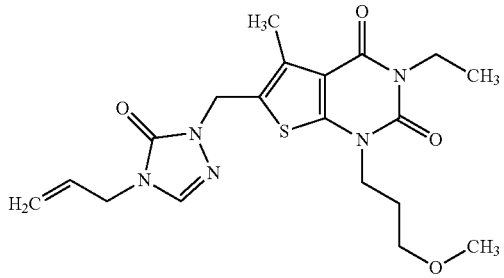 [SMILES: C=CCn1cnn(Cc2sc3c(c2C)c(=O)n(CC)c(=O)n3CCCOC)c1=O]

101 mg (0.314 mmol) of the compound from Ex. 384A and 58 mg (0.433 mmol) of 4-allyl-2,4-dihydro-3H-1,2,4-triazol-3-one were dissolved in 4 ml of dichloromethane, and 136 mg (0.627 mmol) of tri-n-butylphosphine were added. After 30 min, 93 µl (0.47 mmol) of diisopropyl azodicarboxylate (DIAD) were added dropwise. The reaction mixture was stirred at RT for 18 h. Subsequently, the mixture was concentrated to dryness. The residue was dissolved in 3 ml of DMSO and this solution was purified by means of preparative HPLC (Method 14). Combination of the product fractions and freeze-drying gave 49 mg (35% of theory) of the title compound.

¹H-NMR (500 MHz, DMSO-d₆, δ/ppm): 7.96 (s, 1H), 5.90 (ddt, 1H), 5.19 (dq, 1H), 5.06 (dq, 1H), 5.00 (s, 2H), 4.20 (dt, 2H), 3.92-3.85 (m, 4H), 3.38-3.34 (m, 2H), 3.18 (s, 3H), 2.46 (s, 3H), 1.91-1.84 (m, 2H), 1.10 (t, 3H).

LC/MS (Method 1, ESIpos): $R_t$=1.0 min, m/z=420 [M+H]⁺.

Example 352

3-Ethyl-1-(fluoromethyl)-5-methyl-6-[(5-oxo-4,5-dihydro-1H-1,2,4-triazol-1-yl)methyl]thieno[2,3-d]pyrimidine-2,4(1H,3H)-dione

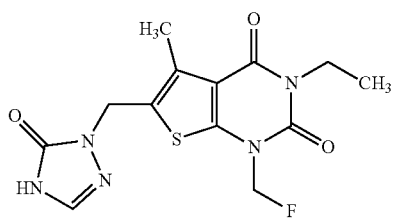 [SMILES: CCn1c(=O)c2c(C)c(Cn3nc[nH]c3=O)sc2n(CF)c1=O]

200 mg (0.495 mmol) of the compound from Example 349 were dissolved in 5 ml of 1,4-dioxane, and 79 mg (0.297 mmol) of triphenylphosphine were added. Then 39 µl (1.04 mmol) of formic acid, 173 µl (1.24 mmol) of triethylamine and 86 mg (0.074 mmol) of tetrakis(triphenylphosphine)palladium(0) were added. The mixture was heated to 125° C. in a microwave oven (Biotage Initiator with dynamic control of irradiation power) for 18 h. Thereafter, the reaction mixture was added to semisaturated aqueous sodium chloride solution (70 ml). The mixture was extracted with ethyl acetate. The combined organic phases were dried over sodium sulphate, filtered and concentrated. The residue was dissolved in 6 ml of DMSO and this solution was purified by means of preparative HPLC (Method 14). Combination of the product fractions and freeze-drying gave 73 mg (41% of theory) of the title compound.

¹H-NMR (400 MHz, DMSO-d₆, δ/ppm): 11.65 (br. s, 1H), 7.85 (s, 1H), 6.09-5.91 (m, 2H), 4.97 (s, 2H), 3.90 (q, 2H), 2.46 (s, 3H), 1.12 (t, 3H).

LC/MS (Method 1, ESIpos): $R_t$=0.8 min, m/z=340 [M+H]⁺.

Example 353

3-Ethyl-1-(3-fluoropropyl)-5-methyl-6-[(5-oxo-4,5-dihydro-1H-1,2,4-triazol-1-yl)methyl]thieno[2,3-d]pyrimidine-2,4(1H,3H)-dione

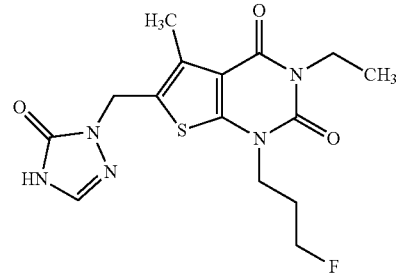 [SMILES: CCn1c(=O)c2c(C)c(Cn3nc[nH]c3=O)sc2n(CCCF)c1=O]

113 mg (0.263 mmol) of the compound from Example 350 were dissolved in 5 ml of 1,4-dioxane, and 41 mg (0.158 mmol) of triphenylphosphine were added. Then 21 µl (0.553 mmol) of formic acid, 92 µl (0.659 mmol) of triethylamine and 46 mg (0.04 mmol) of tetrakis(triphenylphosphine)palladium(0) were added. The mixture was heated to 120° C. in a microwave oven (Biotage Initiator with dynamic control of irradiation power) for 22 h. Thereafter, the reaction mixture was added to semisaturated aqueous sodium chloride solution (70 ml). The mixture was extracted with ethyl acetate. The combined organic phases were dried over sodium sulphate, filtered and concentrated. The residue was dissolved in 3 ml of DMSO and this solution was purified by means of preparative HPLC (Method 14). Combination of the product fractions and freeze-drying gave 61 mg (62% of theory) of the title compound.

¹H-NMR (400 MHz, DMSO-d₆, δ/ppm): 11.62 (br. s, 1H), 7.84 (s, 1H), 4.94 (s, 2H), 4.58 (t, 1H), 4.46 (t, 1H), 3.96 (t, 2H), 3.89 (q, 2H), 2.46 (s, 3H), 2.12-2.04 (m, 1H), 2.01 (quin, 1H), 1.10 (t, 3H).

LC/MS (Method 1, ESIpos): $R_t$=0.84 min, m/z=368 [M+H]⁺.

Example 354

3-Ethyl-1-(3-methoxypropyl)-5-methyl-6-[(5-oxo-4,5-dihydro-1H-1,2,4-triazol-1-yl)methyl]thieno[2,3-d]pyrimidine-2,4(1H,3H)-dione

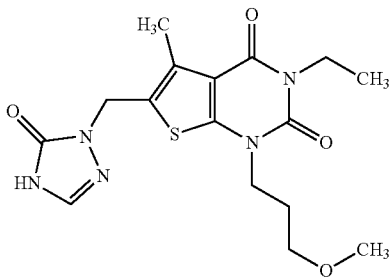 [SMILES: CCn1c(=O)c2c(C)c(Cn3nc[nH]c3=O)sc2n(CCCOC)c1=O]

49 mg (0.111 mmol) of the compound from Example 351 were dissolved in 3 ml of 1,4-dioxane, and 18 mg (0.067 mmol) of triphenylphosphine were added. Then 9 µl (0.223 mmol) of formic acid, 39 µl (0.277 mmol) of triethylamine and 19 mg (0.017 mmol) of tetrakis(triphenylphosphine)palladium(0) were added. The mixture was heated to 125° C. in a microwave oven (Biotage Initiator with dynamic control of irradiation power) for 18 h. Thereafter, the reaction mixture was added to semisaturated aqueous sodium chloride solution (40 ml). The mixture was extracted with ethyl acetate. The combined organic phases were dried over sodium sulphate, filtered and concentrated. The residue was dissolved in 3 ml of DMSO and this solution was purified by means of preparative HPLC (Method 14). Combination of the product fractions and freeze-drying gave 12 mg (27% of theory) of the title compound.

$^1$H-NMR (400 MHz, DMSO-$d_6$, δ/ppm): 11.61 (br. s, 1H), 7.84 (s, 1H), 4.94 (s, 2H), 3.95-3.84 (m, 4H), 3.19 (s, 3H), 2.46 (s, 3H), 1.88 (quin, 2H), 1.10 (t, 3H).

LC/MS (Method 1, ESIpos): $R_t$=0.84 min, m/z=380 [M+H]$^+$.

Example 355

3-Ethyl-5-methyl-6-[(5-oxo-4-propyl-4,5-dihydro-1H-H-1,2,4-triazol-1-yl)methyl]-1-(3,3,3-trifluoropropyl)thieno[2,3-d]pyrimidine-2,4(1H,3H)-dione

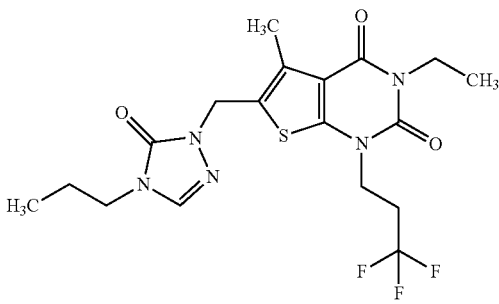 [SMILES: CCCn1cnn(Cc2sc3c(c2C)c(=O)n(CC)c(=O)n3CCC(F)(F)F)c1=O]

176 mg (0.393 mmol) of the compound from Ex. 110 were dissolved in 10 ml of 1,4-dioxane, and 32 µl (0.825 mmol) of formic acid, 137 µl (0.982 mmol) of triethylamine and 45 mg (0.039 mmol) of tetrakis(triphenylphosphine)palladium(0) were added. The mixture was heated under reflux for 15 h. Subsequently, a further 22 µl (0.589 mmol) of formic acid were added. After a total reaction time of 72 h, the reaction mixture was added to semisaturated aqueous sodium chloride solution (40 ml). The mixture was extracted with ethyl acetate. The combined organic phases were dried over sodium sulphate, filtered and concentrated. The residue was dissolved in 3 ml of DMSO and this solution was purified by means of preparative HPLC (Method 14). Combination of the product fractions and freeze-drying gave 75 mg (43% of theory) of the title compound.

$^1$H-NMR (400 MHz, DMSO-$d_6$, δ/ppm): 8.00 (s, 1H), 5.00 (s, 2H), 4.07 (t, 2H), 3.89 (q, 2H), 3.52 (t, 2H), 2.82-2.66 (m, 2H), 2.46 (s, 3H), 1.61 (sext, 2H), 1.10 (t, 3H), 0.81 (t, 3H).

LC/MS (Method 3, ESIneg): $R_t$=1.14 min, m/z=490 [M−H+HCOOH]$^+$.

Example 356

[1-{[3-Isopropyl-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]cyanamide (Enantiomer 1)

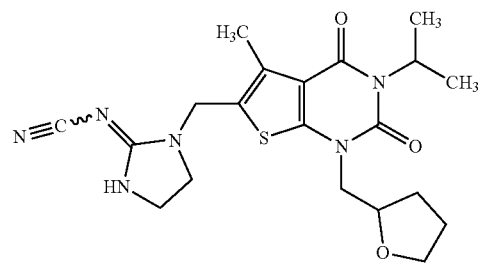 [SMILES: Cc1c(CN2CCNC2=NC#N)sc2c1c(=O)n(C(C)C)c(=O)n2CC1CCCO1]

320 mg (0.743 mmol) of the racemic compound from Ex. 267 were dissolved in 20 ml of methanol and, in 40 portions, separated into the enantiomers by preparative SFC on a chiral phase [column: Daicel Chiralcel OX-H, 5 µm, 250 mm×20 mm; eluent: carbon dioxide/methanol 65:35; flow rate: 80 ml/min; temperature: 40° C.; detection: 210 nm]. After concentration of the product fractions and drying under high vacuum, 127 mg (79% of theory) of Enantiomer 1 were obtained (>99% ee, chiral analytical HPLC).

$^1$H-NMR (400 MHz, DMSO-$d_6$, δ/ppm): 8.06 (s, 1H), 5.14 (sept, 1H), 4.46 (s, 2H), 4.27-4.16 (m, 1H), 4.04 (dd, 1H), 3.80-3.71 (m, 1H), 3.69-3.57 (m, 2H), 3.51-3.36 (m, 4H), 2.39 (s, 3H), 2.05-1.75 (m, 3H), 1.72-1.59 (m, 1H), 1.40 (d, 6H).

Chiral analytical SFC [column: Daicel Chiralcel OX-H, 3 µm, 50 mm×4.6 mm; eluent: carbon dioxide/methanol 60:40; flow rate: 3 ml/min; temperature: 40° C.; detection: 210 nm]: $R_t$=3.61 min.

Example 357

[1-{[3-Isopropyl-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]cyanamide (Enantiomer 2)

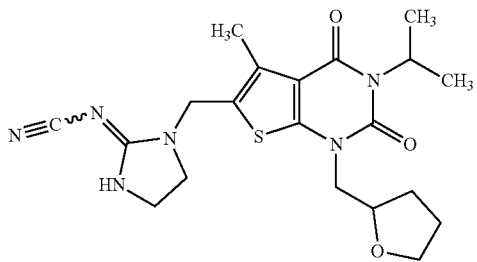 [SMILES: Cc1c(CN2CCNC2=NC#N)sc2c1c(=O)n(C(C)C)c(=O)n2CC1CCCO1]

320 mg (0.743 mmol) of the racemic compound from Ex. 267 were dissolved in 20 ml of methanol and, in 40 portions, separated into the enantiomers by preparative SFC on a chiral phase [column: Daicel Chiralcel OX-H, 5 μm, 250 mm×20 mm; eluent: carbon dioxide/methanol 65:35; flow rate: 80 ml/min; temperature: 40° C.; detection: 210 nm]. After concentration of the product fractions and drying under high vacuum, 109 mg (68% of theory) of Enantiomer 2 were obtained (>99% ee, chiral analytical HPLC).

$^1$H-NMR (400 MHz, DMSO-$d_6$, δ/ppm): 8.06 (s, 1H), 5.14 (sept, 1H), 4.46 (s, 2H), 4.27-4.15 (m, 1H), 4.04 (dd, 1H), 3.81-3.71 (m, 1H), 3.69-3.57 (m, 2H), 3.51-3.35 (m, 4H), 2.39 (s, 3H), 2.07-1.74 (m, 3H), 1.72-1.59 (m, 1H), 1.40 (d, 6H).

Chiral analytical SFC [column: Daicel Chiralcel OX-H, 3 μm, 50 mm×4.6 mm; eluent: carbon dioxide/methanol 60:40; flow rate: 3 ml/min; temperature: 40° C.; detection: 210 nm]: $R_t$=6.55 min.

Example 358

[1-{[5-Methyl-2,4-dioxo-3-(2,2,2-trifluoroethyl)-1-(3,3,3-trifluoropropyl)-1,2,3,4-tetrahydrothieno[2,3-d]pyrimidin-6-yl]methyl}imidazolidin-2-ylidene]cyanamide

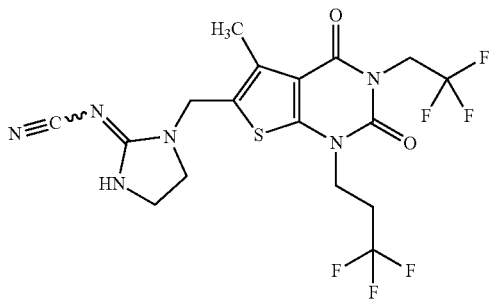 [SMILES: Cc1c(CN2CCNC2=NC#N)sc2c1c(=O)n(CC(F)(F)F)c(=O)n2CCC(F)(F)F]

361 mg (0.417 mmol, 50% purity) of the compound from Ex. 247A were dissolved in 2.4 ml of DMF, and 92 mg (0.626 mmol) of dimethyl N-cyanodithioiminocarbonate and 115 mg (0.835 mmol) of potassium carbonate were added. The mixture was stirred at 80° C. in a microwave oven (Biotage Initiator with dynamic control of irradiation power) for 3 h. Thereafter, the reaction mixture was diluted with ethyl acetate and washed successively with saturated sodium hydrogencarbonate solution, water and saturated sodium chloride solution. After drying over anhydrous magnesium sulphate, the mixture was filtered and concentrated. The crude product was prepurified by means of a first preparative HPLC (Method 8). The title compound was isolated in pure form from the combined product fractions by means of a second preparative HPLC [column: XBridge C18, 5 μm, 100 mm×30 mm; eluent A: water+0.07% formic acid; eluent B: acetonitrile; gradient: 0.0-2.0 min 10% B, 2.2 min 30% B, 7.0 min 60% B, 7.5-9.0 min 92% B; flow rate: 70 ml/min; temperature: 25° C.; detection: 210 nm]. After concentration of the product fractions and drying under high vacuum, 73 g (36% of theory) of the title compound were obtained.

$^1$H-NMR (400 MHz, DMSO-$d_6$, δ/ppm): 8.10 (s, 1H), 4.70 (q, 2H), 4.52 (s, 2H), 4.15 (t, 2H), 3.56-3.36 (m, 4H), 2.89-2.68 (m, 2H), 2.42 (s, 3H).

LC/MS (Method 17, ESIpos): $R_t$=1.63 min, m/z=483.10 [M+H]$^+$.

Example 359

[1-{[5-Methyl-1-(oxetan-2-ylmethyl)-2,4-dioxo-3-(2,2,2-trifluoroethyl)-1,2,3,4-tetrahydrothieno[2,3-d]pyrimidin-6-yl]methyl}imidazolidin-2-ylidene]cyanamide (stereoisomer mixture)

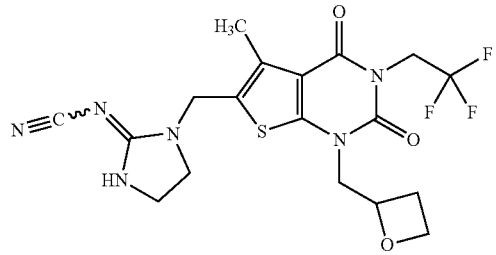 [SMILES: Cc1c(CN2CCNC2=NC#N)sc2c1c(=O)n(CC(F)(F)F)c(=O)n2CC1CCO1]

400 mg (0.817 mmol, 83% purity) of the compound from Ex. 251A were dissolved in 7.4 ml of DMF, and 179 mg (1.23 mmol) of dimethyl N-cyanodithioiminocarbonate and 226 mg (1.63 mmol) of potassium carbonate were added. The mixture was stirred at 80° C. in a closed vessel for about 18 h. Thereafter, the reaction mixture was diluted with ethyl acetate and washed successively with saturated sodium hydrogencarbonate solution, water and saturated sodium chloride solution. After drying over anhydrous magnesium sulphate, the mixture was filtered and concentrated. The crude product was stirred in a water/acetonitrile mixture at RT. The solids were filtered off with suction and dried under high vacuum. This gave a first portion of the title compound. The mother liquor from the stirring was concentrated and the residue was purified by means of preparative HPLC (Method 8). The product fractions were combined, concentrated, dried and combined with the first portion of the title compound. A total of 210 mg (55% of theory) of the title compound were thus obtained.

$^1$H-NMR (400 MHz, DMSO-$d_6$, δ/ppm): 8.08 (s, 1H), 5.08-4.95 (m, 1H), 4.70 (q, 2H), 4.54-4.36 (m, 2H), 4.49 (s, 2H), 4.26-4.09 (m, 2H), 3.53-3.36 (m, 4H), 2.77-2.62 (m, 1H), 2.53-2.44 (m, 1H, partially obscured by the DMSO signal), 2.41 (s, 3H).

LC/MS (Method 17, ESIpos): $R_t$=1.49 min, m/z=457.13 [M+H]$^+$.

Example 360

[1-{[5-Methyl-2,4-dioxo-1-(tetrahydrofuran-2-ylmethyl)-3-(2,2,2-trifluoroethyl)-1,2,3,4-tetrahydrothieno[2,3-d]pyrimidin-6-yl]methyl}imidazolidin-2-ylidene]cyanamide (Enantiomer 1)

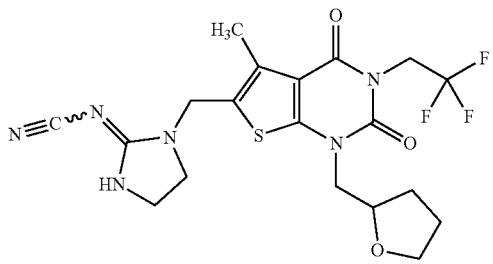 [SMILES: Cc1c(CN2CCNC2=NC#N)sc2c1c(=O)n(CC(F)(F)F)c(=O)n2CC1CCCO1]

199 mg (0.423 mmol) of the racemic compound from Ex. 269 were dissolved in 8 ml of ethanol and, in 32 portions, separated into the enantiomers by preparative HPLC on a chiral phase [column: Daicel Chiralcel OX-H, 5 μm, 250 mm×20 mm; eluent: isohexane/ethanol 2:3; flow rate: 15 ml/min; temperature: 25° C.; detection: 210 nm]. After the product fractions had been concentrated, the remaining solids were stirred with a little diisopropyl ether at RT. After the solids had been filtered off with suction and dried, 59 mg (59% of theory) of Enantiomer 1 were obtained (>99% ee, chiral analytical HPLC).

$^1$H-NMR (400 MHz, DMSO-d$_6$, δ/ppm): 8.09 (s, 1H), 4.70 (q, 2H), 4.49 (s, 2H), 4.28-4.17 (m, 1H), 4.07 (dd, 1H), 3.81-3.69 (m, 2H), 3.67-3.56 (m, 1H), 3.53-3.37 (m, 4H), 2.41 (s, 3H), 2.05-1.76 (m, 3H), 1.74-1.59 (m, 1H).

Chiral analytical HPLC [column: Daicel Chiralcel OX-H, 3 μm, 50 mm×4.6 mm; eluent: isohexane/ethanol 1:1; flow rate: 1 ml/min; temperature: 40° C.; detection: 220 nm]: $R_t$=2.62 min.

Example 361

[1-{[5-Methyl-2,4-dioxo-1-(tetrahydrofuran-2-ylmethyl)-3-(2,2,2-trifluoroethyl)-1,2,3,4-tetrahydrothieno[2,3-d]pyrimidin-6-yl]methyl}imidazolidin-2-ylidene]cyanamide (Enantiomer 2)

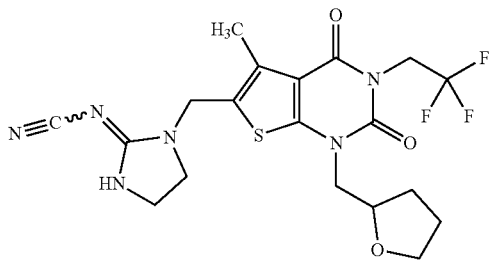 [SMILES: Cc1c(CN2CCNC2=NC#N)sc2c1c(=O)n(CC(F)(F)F)c(=O)n2CC1CCCO1]

199 mg (0.423 mmol) of the racemic compound from Ex. 269 were dissolved in 8 ml of ethanol and, in 32 portions, separated into the enantiomers by preparative HPLC on a chiral phase [column: Daicel Chiralcel OX-H, 5 μm, 250 mm×20 mm; eluent: isohexane/ethanol 2:3; flow rate: 15 ml/min; temperature: 25° C.; detection: 210 nm]. After the product fractions had been concentrated, the remaining solids were stirred with a little diisopropyl ether at RT. After the solids had been filtered off with suction and dried, 58 mg (58% of theory) of Enantiomer 2 were obtained (>99% ee, chiral analytical HPLC).

$^1$H-NMR (400 MHz, DMSO-d$_6$, δ/ppm): 8.09 (s, 1H), 4.70 (q, 2H), 4.49 (s, 2H), 4.29-4.17 (m, 1H), 4.07 (dd, 1H), 3.81-3.69 (m, 2H), 3.67-3.56 (m, 1H), 3.52-3.37 (m, 4H), 2.41 (s, 3H), 2.05-1.76 (m, 3H), 1.73-1.61 (m, 1H).

Chiral analytical HPLC [column: Daicel Chiralcel OX-H, 3 μm, 50 mm×4.6 mm; eluent: isohexane/ethanol 1:1; flow rate: 1 ml/min; temperature: 40° C.; detection: 220 nm]: $R_t$=3.46 min.

Example 362

[1-{[3-(2-Methoxyethyl)-5-methyl-2,4-dioxo-1-(3,3,3-trifluoropropyl)-1,2,3,4-tetrahydrothieno[2,3-d]pyrimidin-6-yl]methyl}imidazolidin-2-ylidene]cyanamide

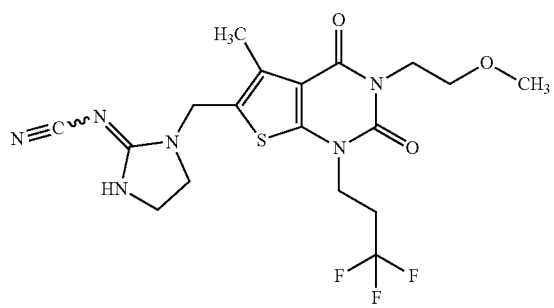 [SMILES: COCCn1c(=O)c2c(C)c(CN3CCNC3=NC#N)sc2n(CCC(F)(F)F)c1=O]

770 mg (1.72 mmol, 91% purity) of the compound from Ex. 319A were dissolved in 17 ml of DMF, and 376 mg (2.57 mmol) of dimethyl N-cyanodithioiminocarbonate and 474 mg (3.43 mmol) of potassium carbonate were added. The mixture was stirred at 80° C. in a microwave oven (Biotage Initiator with dynamic control of irradiation power) for 3.75 h. Thereafter, the reaction mixture was diluted with ethyl acetate and washed successively with saturated sodium hydrogencarbonate solution, water and saturated sodium chloride solution. After drying over anhydrous magnesium sulphate, the mixture was filtered and concentrated. The crude product was stirred with a water/acetonitrile mixture at RT. The solids were filtered off with suction and dried under high vacuum. This gave a first portion of the title compound (139 mg). The mother liquor from the stirring was concentrated and the residue was purified by means of preparative HPLC (Method 8). The product fractions were combined, concentrated by evaporation and dried. This gave a second portion of the title compound (141 mg). A total of 280 mg (35% of theory) of the title compound were thus obtained.

$^1$H-NMR (400 MHz, DMSO-d$_6$, δ/ppm): 8.08 (s, 1H), 4.50 (s, 2H), 4.11 (t, 2H), 4.06 (t, 2H), 3.49 (t, 2H), 3.49-3.37 (m, 4H), 3.24 (s, 3H), 2.90-2.64 (m, 2H), 2.42 (s, 3H).

LC/MS (Method 17, ESIpos): $R_t$=1.50 min, m/z=459.14 [M+H]$^+$.

Example 363

[1-{[1,3-Bis(2-methoxyethyl)-5-methyl-2,4-dioxo-1,2,3,4-tetrahydrothieno[2,3-d]pyrimidin-6-yl]methyl}imidazolidin-2-ylidene]cyanamide

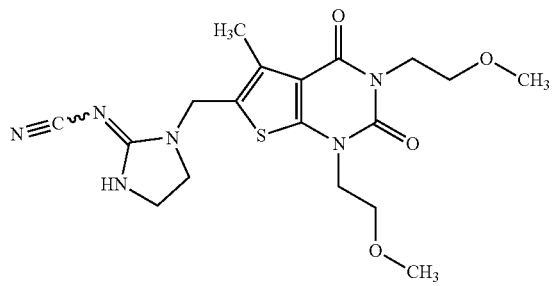 [SMILES: COCCn1c(=O)c2c(C)c(CN3CCNC3=NC#N)sc2n(CCOC)c1=O]

Analogously to the method described in Ex. 268, 713 mg (1.48 mmol, 77% purity) of the compound from Ex. 262A and 325 mg (2.22 mmol) of dimethyl N-cyanodithioiminocarbonate were used to obtain 255 mg (40% of theory) of the title compound. The reaction time here was 5.75 h.

$^1$H-NMR (400 MHz, DMSO-$d_6$, δ/ppm): 8.07 (s, 1H), 4.48 (s, 2H), 4.05 (t, 2H), 4.03 (t, 2H), 3.63 (t, 2H), 3.50 (t, 2H), 3.46-3.41 (m, 4H), 3.24 (s, 6H), 2.40 (s, 3H).

LC/MS (Method 5, ESIpos): $R_t$=0.95 min, m/z=421 [M+H]$^+$.

Example 364

[1-{[3-(2-Methoxyethyl)-5-methyl-1-(oxetan-2-ylmethyl)-2,4-dioxo-1,2,3,4-tetrahydrothieno[2,3-d]pyrimidin-6-yl]methyl}imidazolidin-2-ylidene]cyanamide (non-racemic enantiomer mixture)

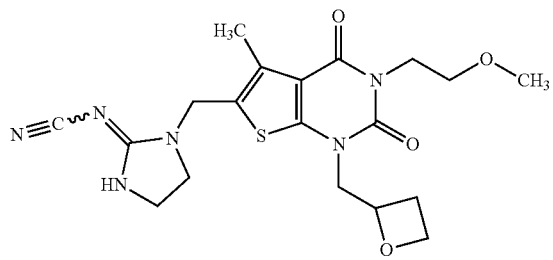 [SMILES: COCCn1c(=O)c2c(C)c(CN3CCNC3=NC#N)sc2n(CC2CCO2)c1=O]

Analogously to the method described in Ex. 359, 350 mg (0.824 mmol, 90% purity) of the compound from Ex. 405A and 181 mg (1.23 mmol) of dimethyl N-cyanodithioiminocarbonate were used to obtain 148 mg (41% of theory) of the title compound.

$^1$H-NMR (400 MHz, DMSO-$d_6$, δ/ppm): 8.07 (s, 1H), 5.00 (dt, 1H), 4.53-4.37 (m, 2H), 4.47 (s, 2H), 4.17-4.11 (m, 2H), 4.06 (t, 2H), 3.50 (t, 2H), 3.49-3.39 (m, 4H), 3.24 (s, 3H), 2.76-2.63 (m, 1H), 2.54-2.45 (m, 1H, partially obscured by the DMSO signal), 2.40 (s, 3H).

LC/MS (Method 17, ESIpos): $R_t$=1.17 min, m/z=433.16 [M+H]$^+$.

Example 365

[1-{[3-Methoxyethyl-5-methyl-1-(oxetan-2-ylmethyl)-2,4-dioxo-1,2,3,4-tetrahydrothieno[2,3-d]pyrimidin-6-yl]methyl}imidazolidin-2-ylidene]cyanamide (Enantiomer 1)

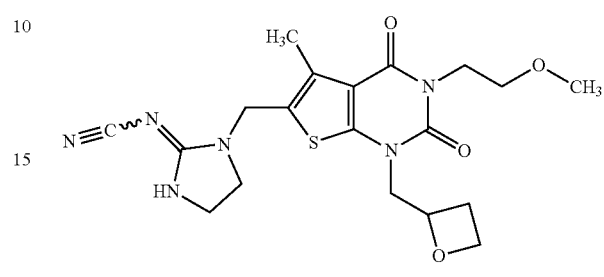

135 mg (0.312 mmol) of the enantiomer mixture from Ex. 364 were dissolved in a mixture of 15 ml of ethanol and 15 ml of dichloromethane and, in 30 portions, separated into the enantiomers by preparative HPLC on a chiral phase [column: Daicel Chiralpak IC, 5 μm, 250 mm×20 mm; eluent: ethanol; flow rate: 15 ml/min; temperature: 55° C.; detection: 220 nm]. After concentration of the product fractions and drying under high vacuum, 107 mg (79% of theory) of Enantiomer 1 were obtained (>99% ee, chiral analytical HPLC).

$^1$H-NMR (400 MHz, DMSO-$d_6$, δ/ppm): 8.07 (s, 1H), 5.00 (quin, 1H), 4.53-4.37 (m, 2H), 4.47 (s, 2H), 4.18-4.10 (m, 2H), 4.06 (t, 2H), 3.50 (t, 2H), 3.47-3.37 (m, 4H), 3.24 (s, 3H), 2.75-2.62 (m, 1H), 2.53-2.45 (m, 1H, partially obscured by the DMSO signal), 2.40 (s, 3H).

Chiral analytical HPLC [column: Daicel Chiralpak IC, 5 μm, 250 mm×4.6 mm; eluent: ethanol; flow rate: 1 ml/min; temperature: 50° C.; detection: 220 nm]: $R_t$=13.79 min.

Example 366

[1-{[3-Methoxyethyl-5-methyl-1-(oxetan-2-ylmethyl)-2,4-dioxo-1,2,3,4-tetrahydrothieno[2,3-d]pyrimidin-6-yl]methyl}imidazolidin-2-ylidene]cyanamide (Enantiomer 2)

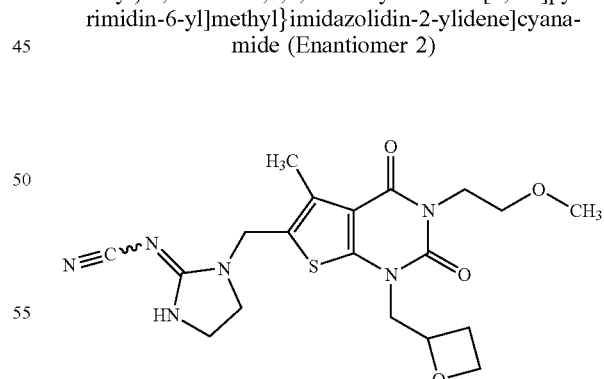

135 mg (0.312 mmol) of the enantiomer mixture from Ex. 364 were dissolved in a mixture of 15 ml of ethanol and 15 ml of dichloromethane and, in 30 portions, separated into the enantiomers by preparative HPLC on a chiral phase [column: Daicel Chiralpak IC, 5 μm, 250 mm×20 mm; eluent: ethanol; flow rate: 15 ml/min; temperature: 55° C.; detection: 220 nm]. After concentration of the product fractions, stirring in pentane (with 1 drop of dichloromethane), filtration with suction and drying under high vacuum, 13 mg (9% of theory) of Enantiomer 2 were obtained (98% ee, chiral analytical HPLC).

$^1$H-NMR (400 MHz, DMSO-d$_6$, δ/ppm): 8.07 (s, 1H), 5.01 (quin, 1H), 4.52-4.36 (m, 2H), 4.47 (s, 2H), 4.17-4.10 (m, 2H), 4.06 (t, 2H), 3.50 (t, 2H), 3.47-3.37 (m, 4H), 3.24 (s, 3H), 2.75-2.63 (m, 1H), 2.55-2.45 (m, 1H, partially obscured by the DMSO signal), 2.40 (s, 3H).

Chiral analytical HPLC [column: Daicel Chiralpak IC, 5 μm, 250 mm×4.6 mm; eluent: ethanol; flow rate: 1 ml/min; temperature: 50° C.; detection: 220 nm]: R$_t$=17.29 min.

Example 367

[1-{[3-(2-Methoxyethyl)-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]cyanamide (racemate)

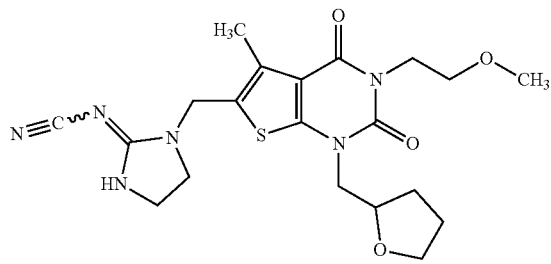 [SMILES: COCCn1c(=O)c2c(C)c(CN3CCNC3=NC#N)sc2n(CC2CCCO2)c1=O]

Analogously to the method described in Ex. 362, 875 mg (1.99 mmol, 90% purity) of the compound from Ex. 321A and 436 mg (2.98 mmol) of dimethyl N-cyanodithioiminocarbonate were used to obtain 332 mg (36% of theory) of the title compound.

$^1$H-NMR (400 MHz, DMSO-d$_6$, δ/ppm): 8.07 (s, 1H), 4.47 (s, 2H), 4.27-4.17 (m, 1H), 4.11-3.98 (m, 3H), 3.81-3.57 (m, 3H), 3.50 (t, 2H), 3.47-3.37 (m, 4H), 3.31 (s, 3H), 2.40 (s, 3H), 2.04-1.76 (m, 3H), 1.73-1.61 (m, 1H).

LC/MS (Method 1, ESIpos): R$_t$=0.73 min, m/z=447 [M+H]$^+$.

Example 368

[1-{[3-(2-Methoxyethyl)-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]cyanamide (Enantiomer 1)

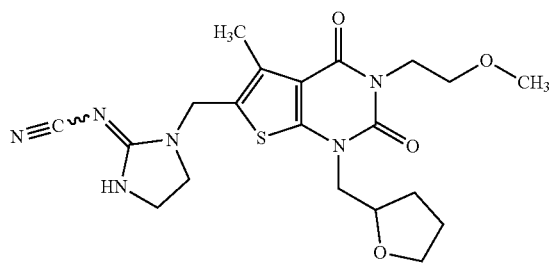

314 mg (0.703 mmol) of the racemic compound from Ex. 367 were dissolved in 45 ml of methanol and, in 45 portions, separated into the enantiomers by preparative SFC on a chiral phase [column: Daicel Chiralcel OJ-H, 5 μm, 250 mm×30 mm; eluent: carbon dioxide/methanol 90:10; flow rate: 100 ml/min; temperature: 40° C.; detection: 210 nm]. After concentration of the product fractions, stirring of the solids with a mixture of 10 ml of pentane and 0.5 ml of dichloromethane, filtration with suction and drying under high vacuum, 114 mg (72% of theory) of Enantiomer 1 were obtained (>99% ee, chiral analytical HPLC).

$^1$H-NMR (400 MHz, DMSO-d$_6$, δ/ppm): 8.07 (s, 1H), 4.47 (s, 2H), 4.28-4.16 (m, 1H), 4.12-3.98 (m, 3H), 3.82-3.56 (m, 3H), 3.50 (t, 2H), 3.47-3.37 (m, 4H), 3.24 (s, 3H), 2.40 (s, 3H), 2.05-1.76 (m, 3H), 1.73-1.60 (m, 1H).

Chiral analytical SFC [column: Daicel Chiralcel OJ-H, 3 μm, 50 mm×4.6 mm; eluent: carbon dioxide/methanol 90:10; flow rate: 3 ml/min; temperature: 40° C.; detection: 210 nm]: R$_t$=1.31 min.

Example 369

[1-{[3-(2-Methoxyethyl)-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]cyanamide (Enantiomer 2)

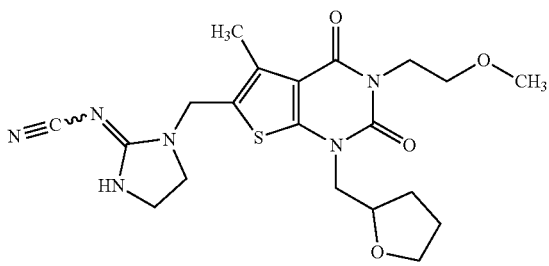 [SMILES: COCCn1c(=O)c2c(C)c(CN3CCNC3=NC#N)sc2n(CC2CCCO2)c1=O]

314 mg (0.703 mmol) of the racemic compound from Ex. 367 were dissolved in 45 ml of methanol and, in 45 portions, separated into the enantiomers by preparative SFC on a chiral phase [column: Daicel Chiralcel OJ-H, 5 μm, 250 mm×30 mm; eluent: carbon dioxide/methanol 90:10; flow rate: 100 ml/min; temperature: 40° C.; detection: 210 nm]. After concentration of the product fractions, stirring of the solids with a mixture of 10 ml of pentane and 0.5 ml of dichloromethane, filtration with suction and drying under high vacuum, 116 mg (73% of theory) of Enantiomer 2 were obtained (96% ee, chiral analytical HPLC).

$^1$H-NMR (400 MHz, DMSO-d$_6$, δ/ppm): 8.07 (s, 1H), 4.47 (s, 2H), 4.27-4.17 (m, 1H), 4.11-4.00 (m, 3H), 3.82-3.56 (m, 3H), 3.50 (t, 2H), 3.46-3.36 (m, 4H), 3.24 (s, 3H), 2.40 (s, 3H), 2.04-1.75 (m, 3H), 1.73-1.61 (m, 1H).

Chiral analytical SFC [column: Daicel Chiralcel OJ-H, 3 μm, 50 mm×4.6 mm; eluent: carbon dioxide/methanol 90:10; flow rate: 3 ml/min; temperature: 40° C.; detection: 210 nm]: R$_t$=1.48 min.

Example 370

Methyl [1-{[3-ethyl-5-methyl-2,4-dioxo-1-(3,3,3-trifluoropropyl)-1,2,3,4-tetrahydrothieno[2,3-d]pyrimidin-6-yl]methyl}imidazolidin-2-ylidene]carbamate

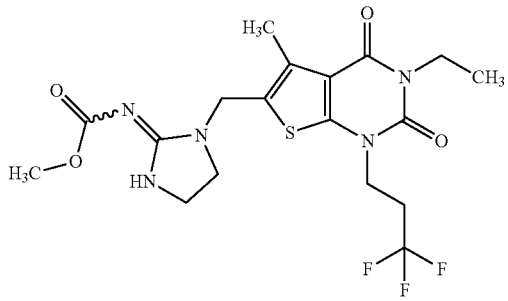 [SMILES: CCn1c(=O)c2c(C)c(CN3CCNC3=NC(=O)OC)sc2n(CCC(F)(F)F)c1=O]

290 mg (0.697 mmol, 91% purity) of the compound from Ex. 210A and 194 µl (1.40 mmol) of triethylamine were dissolved in 15 ml of dichloromethane, and a solution of 109 mg (0.697 mmol) of methyl (dichloromethylene)carbamate in 15 ml of dichloromethane was added. After the reaction mixture had been stirred at RT for 2.5 days, it was diluted with ethyl acetate and washed successively with saturated sodium hydrogencarbonate solution, water and saturated sodium chloride solution. After drying over anhydrous magnesium sulphate, the mixture was filtered and concentrated. The remaining residue was first prepurified by MPLC (Isolera, 50 g of silica gel, cyclohexane/ethyl acetate 80:20→0:100). The product-containing fractions were combined and then repurified by means of preparative HPLC (Method 11). Concentration of the product fraction and drying of the residue under high vacuum gave 194 mg (59% of theory) of the title compound.

$^1$H-NMR (400 MHz, DMSO-$d_6$, δ/ppm): 8.03 (s, 1H), 4.58 (s, 2H), 4.09 (t, 2H), 3.90 (q, 2H), 3.53 (s, 3H), 3.50-3.42 (m, 2H), 3.38-3.28 (m, 2H, partially obscured by the water signal), 2.85-2.66 (m, 2H), 2.43 (s, 3H), 1.11 (t, 3H).

LC/MS (Method 17, ESIpos): $R_t$=1.53 min, m/z=462.14 [M+H]$^+$.

Example 371

Methyl [1-{[3-ethyl-5-methyl-1-(oxetan-2-ylmethyl)-2,4-dioxo-1,2,3,4-tetrahydrothieno[2,3-d]pyrimidin-6-yl]methyl}imidazolidin-2-ylidene]carbamate (racemate)

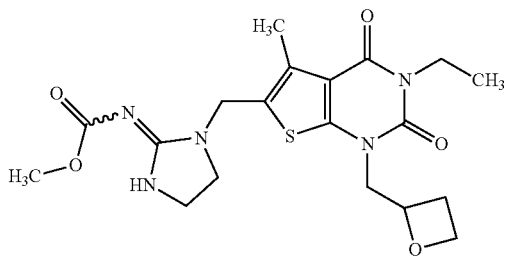 [SMILES: CCn1c(=O)c2c(C)c(CN3CCNC3=NC(=O)OC)sc2n(CC2CCO2)c1=O]

1.07 g (2.34 mmol, 77% purity) of the compound from Ex. 224A and 651 µl (4.67 mmol) of triethylamine were dissolved in 15 ml of dichloromethane, and a solution of 365 mg (2.34 mmol) of methyl (dichloromethylene)carbamate in 15 ml of dichloromethane was added. After the reaction mixture had been stirred at RT for about 16 h, it was diluted with ethyl acetate and washed successively with saturated sodium hydrogencarbonate solution, water and saturated sodium chloride solution. After drying over anhydrous magnesium sulphate, the mixture was filtered and concentrated. The remaining residue was first prepurified by MPLC (Isolera, 100 g of silica gel, dichloromethane/methanol 98:2→80:20). The product-containing fractions were combined, concentrated and then stirred with an acetonitrile/water mixture. The solids were filtered off with suction and dried under high vacuum and thus gave a first portion of the title compound. The concentrated mother liquor from the stirring was purified by means of preparative HPLC (Method 8). Concentration of the product fraction, drying of the residue under high vacuum and combination with the first portion gave a total of 205 mg (20% of theory) of the title compound.

$^1$H-NMR (400 MHz, DMSO-$d_6$, δ/ppm): 8.02 (s, 1H), 5.05-4.94 (m, 1H), 4.55 (s, 2H), 4.51-4.34 (m, 2H), 4.13 (d, 2H), 3.90 (q, 2H), 3.53 (s, 3H), 3.49-3.40 (m, 2H), 3.37-3.27 (m, 2H, partially obscured by the water signal), 2.76-2.62 (m, 1H), 2.53-2.44 (m, 1H, partially obscured by the DMSO signal), 2.42 (s, 3H), 1.11 (t, 3H).

LC/MS (Method 17, ESIpos): $R_t$=1.09 min, m/z=436.16 [M+H]$^+$.

Example 372

Methyl [1-{[3-ethyl-5-methyl-1-(oxetan-2-ylmethyl)-2,4-dioxo-1,2,3,4-tetrahydrothieno[2,3-d]pyrimidin-6-yl]methyl}imidazolidin-2-ylidene]carbamate (Enantiomer 1)

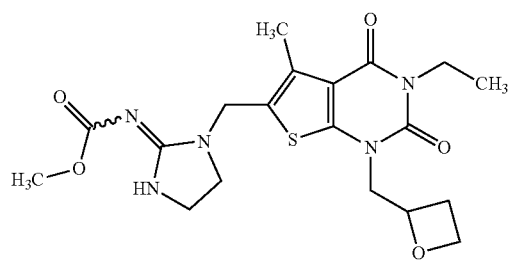 [SMILES: CCn1c(=O)c2c(C)c(CN3CCNC3=NC(=O)OC)sc2n(CC2CCO2)c1=O]

195 mg (0.448 mmol) of the racemic compound from Ex. 371 were dissolved in 40 ml of methanol and, in 50 portions, separated into the enantiomers by preparative SFC on a chiral phase [column: Daicel Chiralcel OD-H, 5 µm, 250 mm×20 mm; eluent: carbon dioxide/methanol 82:18; flow rate: 80 ml/min; temperature: 40° C.; detection: 210 nm]. After concentration of the product fractions and drying under high vacuum, 79 mg (81% of theory) of Enantiomer 1 were obtained (>99% ee, chiral analytical HPLC).

$^1$H-NMR (400 MHz, DMSO-$d_6$, δ/ppm): 8.02 (s, 1H), 5.06-4.92 (m, 1H), 4.55 (s, 2H), 4.51-4.35 (m, 2H), 4.13 (d, 2H), 3.90 (q, 2H), 3.53 (s, 3H), 3.49-3.41 (m, 2H), 3.37-3.28 (m, 2H, partially obscured by the water signal), 2.75-2.63 (m, 1H), 2.53-2.45 (m, 1H, partially obscured by the DMSO signal), 2.42 (s, 3H), 1.11 (t, 3H).

Chiral analytical SFC [column: Daicel Chiralcel OD-H, 3 μm, 50 mm×4.6 mm; eluent: carbon dioxide/methanol 80:20; flow rate: 3 ml/min; temperature: 40° C.; detection: 210 nm]: $R_t$=3.10 min.

Example 373

Methyl [1-{[3-ethyl-5-methyl-1-(oxetan-2-ylmethyl)-2,4-dioxo-1,2,3,4-tetrahydrothieno[2,3-d]pyrimidin-6-yl]methyl}imidazolidin-2-ylidene]carbamate (Enantiomer 2)

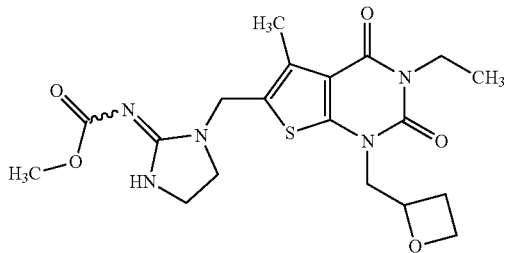 [SMILES: CCn1c(=O)c2c(C)c(CN3CCNC3=NC(=O)OC)sc2n(CC2CCO2)c1=O]

195 mg (0.448 mmol) of the racemic compound from Ex. 371 were dissolved in 40 ml of methanol and, in 50 portions, separated into the enantiomers by preparative SFC on a chiral phase [column: Daicel Chiralcel OD-H, 5 μm, 250 mm×20 mm; eluent: carbon dioxide/methanol 82:18; flow rate: 80 ml/min; temperature: 40° C.; detection: 210 nm]. After concentration of the product fractions and drying under high vacuum, 82 mg (84% of theory) of Enantiomer 2 were obtained (>99% ee, chiral analytical HPLC).

$^1$H-NMR (400 MHz, DMSO-$d_6$, δ/ppm): 8.02 (s, 1H), 5.05-4.94 (m, 1H), 4.55 (s, 2H), 4.51-4.36 (m, 2H), 4.13 (d, 2H), 3.90 (q, 2H), 3.53 (s, 3H), 3.49-3.41 (m, 2H), 3.37-3.28 (m, 2H, partially obscured by the water signal), 2.77-2.63 (m, 1H), 2.53-2.45 (m, 1H, partially obscured by the DMSO signal), 2.42 (s, 3H), 1.11 (t, 3H).

Chiral analytical SFC [column: Daicel Chiralcel OD-H, 3 μm, 50 mm×4.6 mm; eluent: carbon dioxide/methanol 80:20; flow rate: 3 ml/min; temperature: 40° C.; detection: 210 nm]: $R_t$=3.68 min.

Example 374

Methyl [1-{[3-ethyl-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]carbamate (racemate)

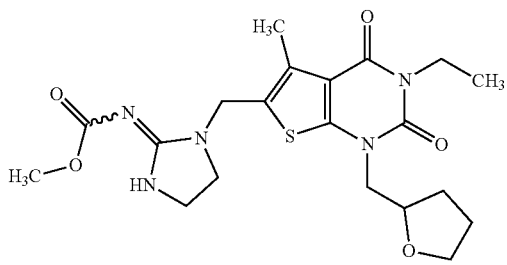 [SMILES: CCn1c(=O)c2c(C)c(CN3CCNC3=NC(=O)OC)sc2n(CC2CCCO2)c1=O]

1.14 g (2.18 mmol, 70% purity) of the compound from Ex. 225A and 607 μl (4.36 mmol) of triethylamine were dissolved in 50 ml of dichloromethane, and a solution of 340 mg (2.18 mmol) of methyl (dichloromethylene)carbamate in 50 ml of dichloromethane was added. After the reaction mixture had been stirred at RT for about 16 h, it was diluted with ethyl acetate and washed successively with saturated sodium hydrogencarbonate solution, water and saturated sodium chloride solution. After drying over anhydrous magnesium sulphate, the mixture was filtered and concentrated. The remaining residue was first prepurified by MPLC (Isolera, 100 g of silica gel, dichloromethane/methanol 98:2→90:10). The product-containing fractions were combined and then repurified by means of preparative HPLC (Method 8). Concentration of the product fraction and drying of the residue under high vacuum gave 247 mg (25% of theory) of the title compound.

$^1$H-NMR (400 MHz, DMSO-$d_6$, δ/ppm): 8.02 (s, 1H), 4.55 (s, 2H), 4.27-4.16 (m, 1H), 4.03 (dd, 1H), 3.90 (q, 2H), 3.77-3.55 (m, 3H), 3.53 (s, 3H), 3.49-3.41 (m, 2H), 3.36-3.29 (m, 2H, partially obscured by the water signal), 2.42 (s, 3H), 2.06-1.74 (m, 3H), 1.70-1.62 (m, 1H), 1.11 (t, 3H).

LC/MS (Method 1, ESIpos): $R_t$=0.67 min, m/z=450 [M+H]$^+$.

Example 375

Methyl [1-{[3-ethyl-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]carbamate (Enantiomer 1)

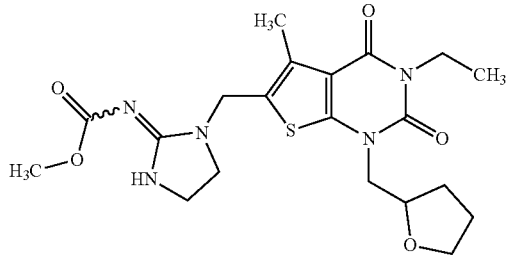 [SMILES: CCn1c(=O)c2c(C)c(CN3CCNC3=NC(=O)OC)sc2n(CC2CCCO2)c1=O]

325 mg (0.523 mmol) of the racemic compound from Ex. 374 were dissolved in 30 ml of methanol and, in 15 portions, separated into the enantiomers by preparative SFC on a chiral phase [column: Daicel Chiralcel OX-H, 5 μm, 250 mm×30 mm; eluent: carbon dioxide/methanol 60:40; flow rate: 100 ml/min; temperature: 40° C.; detection: 210 nm]. After concentration of the product fractions and drying under high vacuum, 90 mg (55% of theory) of Enantiomer 1 were obtained (>99% ee, chiral analytical HPLC).

$^1$H-NMR (400 MHz, DMSO-$d_6$, δ/ppm): 8.02 (s, 1H), 4.55 (s, 2H), 4.27-4.17 (m, 1H), 4.03 (dd, 1H), 3.90 (q, 2H), 3.78-3.56 (m, 3H), 3.53 (s, 3H), 3.49-3.41 (m, 2H), 3.36-3.29 (m, 2H, partially obscured by the water signal), 2.42 (s, 3H), 2.03-1.74 (m, 3H), 1.72-1.60 (m, 1H), 1.11 (t, 3H).

Chiral analytical SFC [column: Daicel Chiralcel OX-H, 3 μm, 50 mm×4.6 mm; eluent: carbon dioxide/methanol 60:40; flow rate: 3 ml/min; temperature: 40° C.; detection: 210 nm]: $R_t$=5.49 min.

Example 376

Methyl [1-{[3-ethyl-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]carbamate (Enantiomer 2)

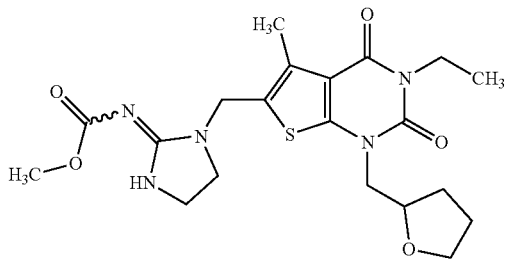 [SMILES: CCn1c(=O)c2c(C)c(CN3CCNC3=NC(=O)OC)sc2n(CC2CCCO2)c1=O]

325 mg (0.523 mmol) of the racemic compound from Ex. 374 were dissolved in 30 ml of methanol and, in 15 portions, separated into the enantiomers by preparative SFC on a chiral phase [column: Daicel Chiralcel OX-H, 5 μm, 250 mm×30 mm; eluent: carbon dioxide/methanol 60:40; flow rate: 100 ml/min; temperature: 40° C.; detection: 210 nm]. After concentration of the product fractions and drying under high vacuum, 88 mg (54% of theory) of Enantiomer 2 were obtained (>99% ee, chiral analytical HPLC).

$^1$H-NMR (400 MHz, DMSO-d$_6$, δ/ppm): 8.02 (s, 1H), 4.55 (s, 2H), 4.28-4.15 (m, 1H), 4.03 (dd, 1H), 3.90 (q, 2H), 3.77-3.55 (m, 3H), 3.53 (s, 3H), 3.49-3.41 (m, 2H), 3.36-3.29 (m, 2H, partially obscured by the water signal), 2.42 (s, 3H), 2.06-1.75 (m, 3H), 1.72-1.60 (m, 1H), 1.11 (t, 3H).

Chiral analytical SFC [column: Daicel Chiralcel OX-H, 3 μm, 50 mm×4.6 mm; eluent: carbon dioxide/methanol 60:40; flow rate: 3 ml/min; temperature: 40° C.; detection: 210 nm]: R$_t$=8.67 min.

Example 377

Methyl [1-{[3-isopropyl-5-methyl-2,4-dioxo-1-(3,3,3-trifluoropropyl)-1,2,3,4-tetrahydrothieno[2,3-d]pyrimidin-6-yl]methyl}imidazolidin-2-ylidene]carbamate

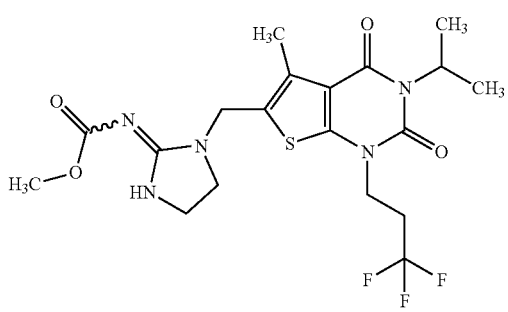 [SMILES: COC(=O)N=C1NCCN1Cc1sc2c(c1C)c(=O)n(C(C)C)c(=O)n2CCC(F)(F)F]

289 mg (0.368 mmol, 50% purity) of the compound from Ex. 309A and 103 μl (0.736 mmol) of triethylamine were dissolved in 10 ml of dichloromethane, and a solution of 115 mg (0.736 mmol) of methyl (dichloromethylene)carbamate in 10 ml of dichloromethane was added. After the reaction mixture had been stirred at RT for 2.5 days, it was diluted with ethyl acetate and washed successively with saturated sodium hydrogencarbonate solution, water and saturated sodium chloride solution. After drying over anhydrous magnesium sulphate, the mixture was filtered and concentrated. The remaining residue was first prepurified by means of preparative HPLC (Method 8). The product-containing fractions were combined, concentrated and then repurified by preparative HPLC once again [column: Kinetex C18, 5 μm, 100 mm×30 mm; eluent A: water+0.07% formic acid; eluent B: acetonitrile; gradient: 0.0-2.0 min 10% B, 2.2 min 20% B, 7.0 min 60% B, 7.5-9.0 min 92% B; flow rate: 70 ml/min; temperature: 25° C.; detection: 210 nm]. After the product fractions had been concentrated, the material obtained was stirred with pentane/dichloromethane (20:1). The solids were filtered off with suction and dried under high vacuum. This gave 63 mg (35% of theory) of the title compound.

$^1$H-NMR (400 MHz, DMSO-d$_6$, δ/ppm): 8.02 (s, 1H), 5.13 (sept, 1H), 4.57 (s, 2H), 4.06 (t, 2H), 3.53 (s, 3H), 3.50-3.44 (m, 2H), 3.36-3.29 (m, 2H, partially obscured by the water signal), 2.83-2.64 (m, 2H), 2.42 (s, 3H), 1.39 (d, 6H).

LC/MS (Method 1, ESIpos): R$_t$=0.93 min, m/z=476 [M+H]$^+$.

Example 378

Methyl [1-{[3-isopropyl-1-(2-methoxyethyl)-5-methyl-2,4-dioxo-1,2,3,4-tetrahydrothieno[2,3-d]pyrimidin-6-yl]methyl}imidazolidin-2-ylidene]carbamate

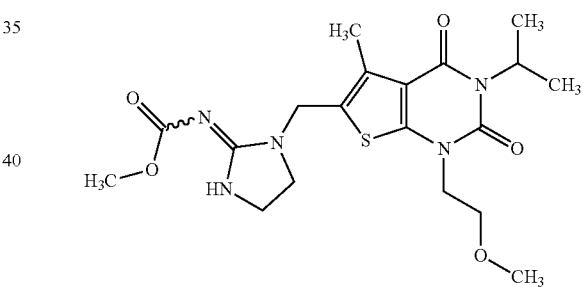

236 mg (0.573 mmol, 86% purity) of the compound from Ex. 310A and 160 μl (1.145 mmol) of triethylamine were dissolved in 15 ml of dichloromethane, and a solution of 179 mg (1.15 mmol) of methyl (dichloromethylene)carbamate in 15 ml of dichloromethane was added. After the reaction mixture had been stirred at RT for 2.5 days, it was diluted with ethyl acetate and washed successively with saturated sodium hydrogencarbonate solution, water and saturated sodium chloride solution. After drying over anhydrous magnesium sulphate, the mixture was filtered and concentrated. The remaining residue was purified by means of preparative HPLC (Method 8). Concentration of the product fractions and drying under high vacuum gave 127 mg (50% of theory) of the title compound.

$^1$H-NMR (400 MHz, DMSO-d$_6$, δ/ppm): 8.08 (br. s, 1H), 5.13 (sept, 1H), 4.56 (s, 2H), 3.97 (t, 2H), 3.61 (t, 2H), 3.55 (s, 3H), 3.50-3.42 (m, 2H), 3.37-3.29 (m, 2H, partially obscured by the water signal), 3.23 (s, 3H), 2.40 (s, 3H), 1.40 (d, 6H).

LC/MS (Method 17, ESIpos): R$_t$=1.40 min, m/z=438.18 [M+H]$^+$.

Example 379

Methyl [1-{[3-isopropyl-5-methyl-1-(oxetan-2-ylmethyl)-2,4-dioxo-1,2,3,4-tetrahydrothieno[2,3-d]pyrimidin-6-yl]methyl}imidazolidin-2-ylidene]carbamate (racemate)

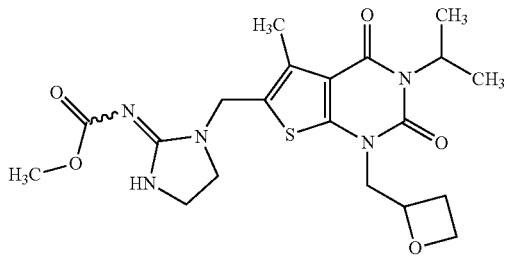 [SMILES: COC(=O)N=C1NCCN1Cc1sc2c(c1C)c(=O)n(C(C)C)c(=O)n2CC1CCO1]

350 mg (0.802 mmol, 84% purity) of the compound from Ex. 311A and 224 µl (1.60 mmol) of triethylamine were dissolved in 20 ml of dichloromethane, and a solution of 250 mg (1.60 mmol) of methyl (dichloromethylene)carbamate in 20 ml of dichloromethane was added. After the reaction mixture had been stirred at RT for 2.5 days, it was diluted with ethyl acetate and washed successively with saturated sodium hydrogencarbonate solution, water and saturated sodium chloride solution. After drying over anhydrous magnesium sulphate, the mixture was filtered and concentrated. The remaining residue was first prepurified by means of preparative HPLC (Method 8). The product-containing fractions were combined and concentrated, and the residue was stirred with pentane/dichloromethane (20:1). The solids thus obtained were repurified by preparative HPLC once again [column: Kinetex C18, 5 µm, 100 mm×30 mm; eluent A: water+0.07% formic acid; eluent B: acetonitrile; gradient: 0.0-2.0 min 10% B, 2.2 min 20% B, 7.0 min 60% B, 7.5-9.0 min 92% B; flow rate: 70 ml/min; temperature: 25° C.; detection: 210 nm]. After concentration of the product fractions and drying under high vacuum, 111 mg (30% of theory) of the title compound were obtained.

$^1$H-NMR (400 MHz, DMSO-$d_6$, δ/ppm): 8.02 (s, 1H), 5.13 (sept, 1H), 5.03-4.93 (m, 1H), 4.55 (s, 2H), 4.51-4.35 (m, 2H), 4.15-4.01 (m, 2H), 3.53 (s, 3H), 3.50-3.40 (m, 2H), 3.35-3.29 (m, 2H, partially obscured by the water signal), 2.76-2.62 (m, 1H), 2.52-2.42 (m, 1H, partially obscured by the DMSO signal), 2.40 (s, 3H), 1.39 (d, 6H).

LC/MS (Method 17, ESIpos): $R_t$=1.31 min, m/z=450.18 [M+H]$^+$.

Example 380

Methyl [1-{[3-isopropyl-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]carbamate (racemate)

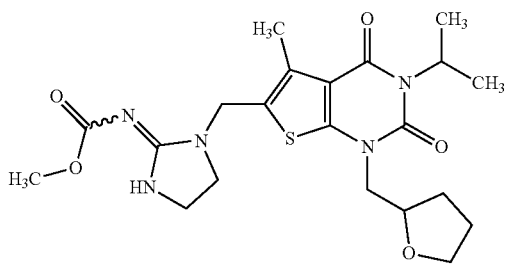 [SMILES: COC(=O)N=C1NCCN1Cc1sc2c(c1C)c(=O)n(C(C)C)c(=O)n2CC1CCCO1]

429 mg (0.970 mmol, 86% purity) of the compound from Ex. 312A and 270 µl (1.94 mmol) of triethylamine were dissolved in 25 ml of dichloromethane, and a solution of 302 mg (1.94 mmol) of methyl (dichloromethylene)carbamate in 25 ml of dichloromethane was added. After the reaction mixture had been stirred at RT for about 16 h, it was diluted with ethyl acetate and washed successively with saturated sodium hydrogencarbonate solution, water and saturated sodium chloride solution. After drying over anhydrous magnesium sulphate, the mixture was filtered and concentrated. The remaining residue was purified by means of preparative HPLC (Method 8). After concentration of the product fractions and drying under high vacuum, 200 mg (42% of theory) of the title compound were obtained.

$^1$H-NMR (400 MHz, DMSO-$d_6$, δ/ppm): 9.86 (broad, 1H), 5.14 (sept, 1H), 4.76 (br. s, 2H), 4.27-4.14 (m, 1H), 4.05 (dd, 1H), 2.41 (s, 3H), 2.06-1.76 (m, 3H), 1.71-1.59 (m, 1H), 1.40 (dd, 6H) [further signals concealed by broad water signal].

LC/MS (Method 6, ESIpos): $R_t$=1.63 min, m/z=464 [M+H]$^+$.

Example 381

Methyl [1-{[5-methyl-2,4-dioxo-3-(2,2,2-trifluoroethyl)-1-(3,3,3-trifluoropropyl)-1,2,3,4-tetrahydrothieno[2,3-d]pyrimidin-6-yl]methyl}imidazolidin-2-ylidene]carbamate

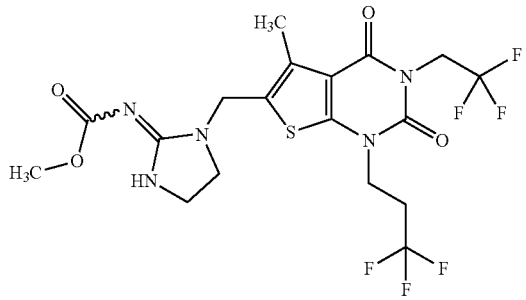 [SMILES: COC(=O)N=C1NCCN1Cc1sc2c(c1C)c(=O)n(CC(F)(F)F)c(=O)n2CCC(F)(F)F]

250 mg (0.405 mmol, 70% purity) of the compound from Ex. 247A and 113 µl (0.809 mmol) of triethylamine were dissolved in 10 ml of dichloromethane, and a solution of 126 mg (0.809 mmol) of methyl (dichloromethylene)carbamate in 10 ml of dichloromethane was added. After the reaction mixture had been stirred at RT for about 16 h, it was diluted with ethyl acetate and washed successively with saturated sodium hydrogencarbonate solution, water and saturated sodium chloride solution. After drying over anhydrous magnesium sulphate, the mixture was filtered and concentrated. The remaining residue was purified by means of preparative HPLC (Method 8). The product fractions were concentrated, and the residue was stirred with pentane/dichloromethane (20:1). After the solids had been filtered off with suction and dried under high vacuum, 89 mg (41% of theory) of the title compound were obtained.

$^1$H-NMR (400 MHz, DMSO-$d_6$, δ/ppm): 8.12 (br. s, 1H), 4.70 (q, 2H), 4.62 (s, 2H), 4.13 (t, 2H), 3.56 (s, 3H), 3.52-3.44 (m, 2H), 3.41-3.35 (m, 2H, partially obscured by the water signal), 2.90-2.65 (m, 2H), 2.43 (s, 3H).

LC/MS (Method 17, ESIpos): $R_t$=1.66 min, m/z=516.11 [M+H]$^+$.

Example 382

Methyl [1-{[1-(2-methoxyethyl)-5-methyl-2,4-di-oxo-3-(2,2,2-trifluoroethyl)-1,2,3,4-tetrahydrothieno[2,3-d]pyrimidin-6-yl]methyl}imidazolidin-2-ylidene]carbamate

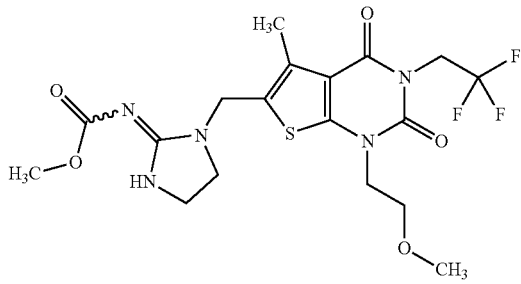 [SMILES: COCCn1c(=O)n(CC(F)(F)F)c(=O)c2c(C)c(CN3CCNC3=NC(=O)OC)sc21]

343 mg (0.696 mmol, 80% purity) of the compound from Ex. 249A and 194 μl (1.39 mmol) of triethylamine were dissolved in 15 ml of dichloromethane, and a solution of 217 mg (1.39 mmol) of methyl (dichloromethylene)carbamate in 15 ml of dichloromethane was added. After the reaction mixture had been stirred at RT for 2.5 days, it was diluted with ethyl acetate and washed successively with saturated sodium hydrogencarbonate solution, water and saturated sodium chloride solution. After drying over anhydrous magnesium sulphate, the mixture was filtered and concentrated. The remaining residue was purified by preparative HPLC twice (first by Method 8, then by Method 11). The product fractions were concentrated and the residue was dried under high vacuum. 91 mg (26% of theory) of the title compound were obtained.

$^1$H-NMR (400 MHz, DMSO-d$_6$, δ/ppm): 8.03 (s, 1H), 4.69 (q, 2H), 4.57 (s, 2H), 4.04 (t, 2H), 3.63 (t, 2H), 3.53 (s, 3H), 3.50-3.42 (m, 2H), 3.38-3-32 (m, 2H, partially obscured by the water signal), 3.23 (s, 3H), 2.42 (s, 3H).

LC/MS (Method 17, ESIpos): R$_t$=1.41 min, m/z=478.14 [M+H]$^+$.

Example 383

Methyl [1-{[5-methyl-1-(oxetan-2-ylmethyl)-2,4-dioxo-3-(2,2,2-trifluoroethyl)-1,2,3,4-tetrahydrothieno[2,3-d]pyrimidin-6-yl]methyl}imidazolidin-2-ylidene]carbamate (racemate)

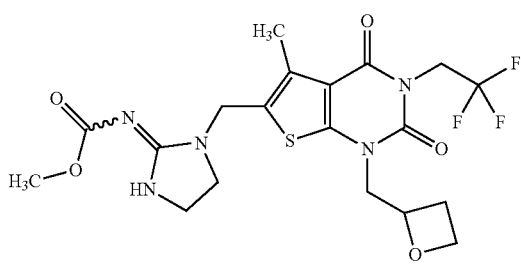 [SMILES: COC(=O)N=C1NCCN1Cc1sc2c(c1C)c(=O)n(CC(F)(F)F)c(=O)n2CC1CCO1]

400 mg (0.817 mmol, 83% purity) of the compound from Ex. 251A and 228 μl (1.63 mmol) of triethylamine were dissolved in 10 ml of dichloromethane, and a solution of 255 mg (1.63 mmol) of methyl (dichloromethylene)carbamate in 10 ml of dichloromethane was added. After the reaction mixture had been stirred at RT for about 16 h, it was diluted with ethyl acetate and washed successively with saturated sodium hydrogencarbonate solution, water and saturated sodium chloride solution. After drying over anhydrous magnesium sulphate, the mixture was filtered and concentrated. The remaining residue was first prepurified by means of preparative HPLC (Method 8). The product-containing fractions were combined and concentrated and then repurified by another preparative HPLC [column: Chromatorex C18, 10 μm, 125 mm×30 mm; eluent A: water, eluent B: acetonitrile, eluent C: 1% formic acid in water; A/B/C gradient programme; flow rate: 100 ml/min; temperature: 25° C.; detection: 210 nm]. After concentration of the product fractions and drying under high vacuum, 52 mg (11% of theory, 90% purity) of the title compound were obtained.

$^1$H-NMR (400 MHz, DMSO-d$_6$, δ/ppm): 8.03 (s, 1H), 5.05-4.94 (m, 1H), 4.70 (q, 2H), 4.57 (s, 2H), 4.51-4.35 (m, 2H), 4.19-4.12 (m, 2H), 3.53 (s, 3H), 3.50-3.42 (m, 2H), 3.38-3.30 (m, 2H, partially obscured by the water signal), 2.76-2.63 (m, 1H), 2.53-2.45 (m, 1H, partially obscured by the DMSO signal), 2.42 (s, 3H).

LC/MS (Method 17, ESIpos): R$_t$=1.33 min, m/z=490.14 [M+H]$^+$.

Example 384

Methyl [1-{[5-methyl-2,4-dioxo-1-(tetrahydrofuran-2-ylmethyl)-3-(2,2,2-trifluoroethyl)-1,2,3,4-tetrahydrothieno[2,3-d]pyrimidin-6-yl]methyl}imidazolidin-2-ylidene]carbamate (racemate)

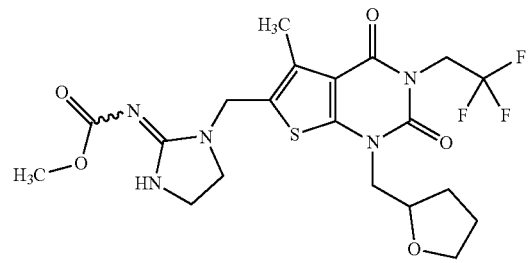 [SMILES: COC(=O)N=C1NCCN1Cc1sc2c(c1C)c(=O)n(CC(F)(F)F)c(=O)n2CC1CCCO1]

270 mg (0.578 mmol, 90% purity) of the compound from Ex. 252A and 161 μl (1.16 mmol) of triethylamine were dissolved in 15 ml of dichloromethane, and a solution of 180 mg (1.16 mmol) of methyl (dichloromethylene)carbamate in 15 ml of dichloromethane was added. After the reaction mixture had been stirred at RT for about 16 h, it was diluted with ethyl acetate and washed successively with saturated sodium hydrogencarbonate solution, water and saturated sodium chloride solution. After drying over anhydrous magnesium sulphate, the mixture was filtered and concentrated. The remaining residue was purified by means of preparative HPLC (Method 8). After concentration of the product fractions and drying under high vacuum, 186 mg (63% of theory) of the title compound were obtained.

$^1$H-NMR (400 MHz, DMSO-d$_6$, δ/ppm): 8.19 (br. s, 1H), 4.70 (q, 2H), 4.61 (s, 2H), 4.27-4.17 (m, 1H), 4.06 (dd, 1H), 3.78-3.66 (m, 2H), 3.64-3.54 (m, 1H), 3.58 (s, 3H), 3.53-3.44 (m, 2H), 3.42-3.34 (m, 2H, partially obscured by the water signal), 2.42 (s, 3H), 2.05-1.76 (m, 3H), 1.73-1.61 (m, 1H).

LC/MS (Method 6, ESIpos): R_t=1.63 min, m/z=504 [M+H]+.

Example 385

Methyl [1-{[3-(2-methoxyethyl)-5-methyl-2,4-di-oxo-1-(3,3,3-trifluoropropyl)-1,2,3,4-tetrahydroth-ieno[2,3-d]pyrimidin-6-yl]methyl}imidazolidin-2-ylidene]carbamate

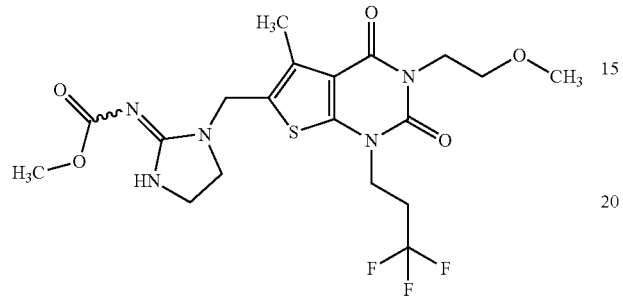

368 mg (0.820 mmol, 91% purity) of the compound from Ex. 319A and 229 μl (1.64 mmol) of triethylamine were dissolved in 15 ml of dichloromethane, and a solution of 256 mg (1.64 mmol) of methyl (dichloromethylene)carbamate in 15 ml of dichloromethane was added. After the reaction mixture had been stirred at RT for 2.5 days, it was diluted with ethyl acetate and washed successively with saturated sodium hydrogencarbonate solution, water and saturated sodium chloride solution. After drying over anhydrous magnesium sulphate, the mixture was filtered and concentrated. The remaining residue was purified by preparative HPLC twice (by Method 8 each time). Concentration of the product fractions and drying of the residue under high vacuum gave 89 mg (22% of theory) of the title compound.

$^1$H-NMR (400 MHz, DMSO-d$_6$, δ/ppm): 8.08 (br. s, 1H), 4.60 (s, 2H), 4.08 (q, 2H), 4.05 (t, 2H), 3.56 (s, 3H), 3.51-3.46 (m, 2H), 3.48 (t, 2H), 3.40-3.32 (m, 2H, partially obscured by the water signal), 3.24 (s, 3H), 2.84-2.67 (m, 2H), 2.43 (s, 3H).

LC/MS (Method 17, ESIpos): R_t=1.40 min, m/z=492.15 [M+H]+.

Example 386

Methyl [1-{[1,3-bis(2-methoxyethyl)-5-methyl-2,4-dioxo-1,2,3,4-tetrahydrothieno[2,3-d]pyrimidin-6-yl]methyl}imidazolidin-2-ylidene]carbamate

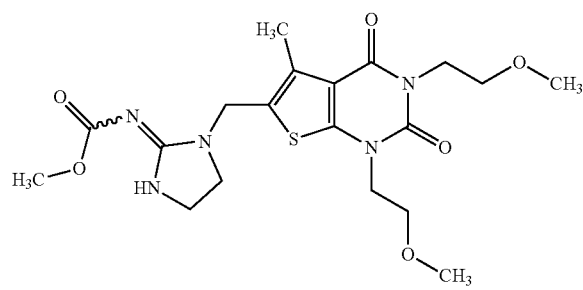

Analogously to the method described in Ex. 379, 323 mg (0.872 mmol) of the compound from Ex. 262A and 204 mg (1.31 mmol) of methyl (dichloromethylene)carbamate were used to obtain 54 mg (13% of theory) of the title compound. The reaction time in this case was about 16 h.

$^1$H-NMR (400 MHz, DMSO-d$_6$, δ/ppm): 8.02 (s, 1H), 4.56 (s, 2H), 4.05 (t, 2H), 4.00 (t, 2H), 3.62 (t, 2H), 3.53 (s, 3H), 3.50 (t, 2H), 3.48-3.42 (m, 2H), 3.37-3.32 (m, 2H, partially obscured by the water signal), 3.24 (s, 3H), 3.23 (s, 3H), 2.41 (s, 3H).

LC/MS (Method 1, ESIpos): R_t=0.59 min, m/z=454 [M+H]+.

Example 387

Methyl [1-{[3-(2-methoxyethyl)-5-methyl-1-(ox-etan-2-ylmethyl)-2,4-dioxo-1,2,3,4-tetrahydrothieno[2,3-d]pyrimidin-6-yl]methyl}imidazolidin-2-ylidene]carbamate (Non-racemic Enantiomer Mixture)

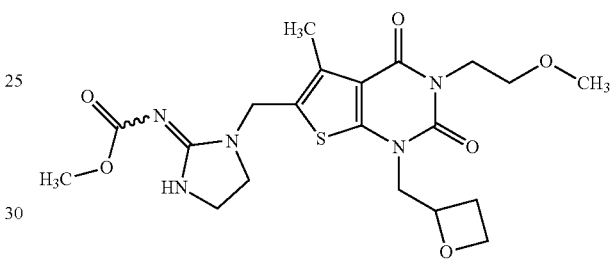

Analogously to the method described in Ex. 385, 350 mg (0.824 mmol, 90% purity) of the compound from Ex. 405A and 257 mg (1.65 mmol) of methyl (dichloromethylene)carbamate were used to obtain 143 mg (37% of theory) of the title compound. The reaction time in this case was about 16 h.

$^1$H-NMR (400 MHz, DMSO-d$_6$, δ/ppm): 8.03 (s, 1H), 5.04-4.94 (m, 1H), 4.56 (s, 2H), 4.52-4.35 (m, 2H), 4.12 (d, 2H), 4.06 (t, 2H), 3.53 (s, 3H), 3.50 (t, 2H), 3.48-3.41 (m, 2H), 3.37-3.32 (m, 2H, partially obscured by the water signal), 3.24 (s, 3H), 2.75-2.62 (m, 1H), 2.52-2.44 (m, 1H, partially obscured by the DMSO signal), 2.41 (s, 3H).

LC/MS (Method 1, ESIpos): R_t=0.62 min, m/z=466 [M+H]+.

Example 388

Methyl [1-{[3-(2-methoxyethyl)-5-methyl-1-(ox-etan-2-ylmethyl)-2,4-dioxo-1,2,3,4-tetrahydrothieno[2,3-d]pyrimidin-6-yl]methyl}imidazolidin-2-ylidene]carbamate (Enantiomer 1)

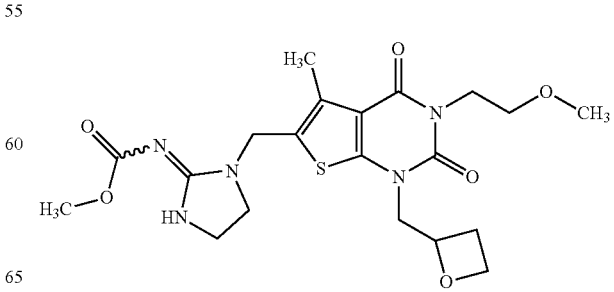

128 mg (0.275 mmol) of the enantiomer mixture from Ex. 387 were dissolved in a mixture of 5 ml of methanol, 4 ml of tert-butyl methyl ether and 3 ml of dichloromethane and, in 15 portions, separated into the enantiomers by preparative HPLC on a chiral phase [column: Daicel Chiralpak IA, 5 µm, 250 mm×30 mm; eluent: tert-butyl methyl ether/methanol 1:1; flow rate: 30 ml/min; temperature: 30° C.; detection: 220 nm]. After concentration of the product fractions and drying under high vacuum, 13 mg (10% of theory) of Enantiomer 1 were obtained (>99% ee, chiral analytical HPLC).

$^1$H-NMR (400 MHz, DMSO-$d_6$, δ/ppm): 8.02 (s, 1H), 5.04-4.93 (m, 1H), 4.56 (s, 2H), 4.51-4.35 (m, 2H), 4.12 (d, 2H), 4.06 (t, 2H), 3.53 (s, 3H), 3.50 (t, 2H), 3.48-3.41 (m, 2H), 3.37-3.32 (m, 2H, partially obscured by the water signal), 3.24 (s, 3H), 2.74-2.62 (m, 1H), 2.53-2.44 (m, 1H, partially obscured by the DMSO signal), 2.41 (s, 3H).

Chiral analytical HPLC [column: Daicel Chiralcel IA, 5 µm, 250 mm×4.6 mm; eluent: tert-butyl methyl ether/methanol 1:1; flow rate: 1 ml/min; temperature: 30° C.; detection: 220 nm]: $R_t$=6.57 min.

Example 389

Methyl [1-{[3-(2-methoxyethyl)-5-methyl-1-(oxetan-2-ylmethyl)-2,4-dioxo-1,2,3,4-tetrahydrothieno[2,3-d]pyrimidin-6-yl]methyl}imidazolidin-2-ylidene]carbamate (Enantiomer 2)

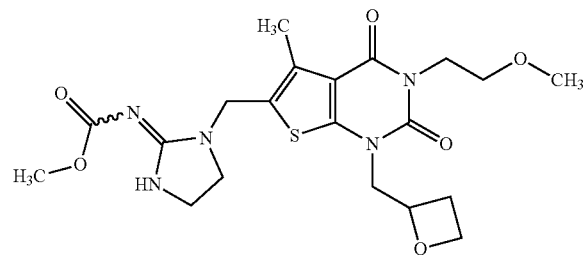

128 mg (0.275 mmol) of the enantiomer mixture from Ex. 387 were dissolved in a mixture of 5 ml of methanol, 4 ml of tert-butyl methyl ether and 3 ml of dichloromethane and, in 15 portions, separated into the enantiomers by preparative HPLC on a chiral phase [column: Daicel Chiralpak IA, 5 µm, 250 mm×30 mm; eluent: tert-butyl methyl ether/methanol 1:1; flow rate: 30 ml/min; temperature: 30° C.; detection: 220 nm]. After concentration of the product fractions and drying under high vacuum, 94 mg (73% of theory) of Enantiomer 2 were obtained (>99% ee, chiral analytical HPLC).

$^1$H-NMR (400 MHz, DMSO-$d_6$, δ/ppm): 8.02 (s, 1H), 5.04-4.93 (m, 1H), 4.56 (s, 2H), 4.51-4.34 (m, 2H), 4.12 (d, 2H), 4.06 (t, 2H), 3.53 (s, 3H), 3.50 (t, 2H), 3.48-3.43 (m, 2H), 3.37-3.28 (m, 2H, partially obscured by the water signal), 3.23 (s, 3H), 2.75-2.63 (m, 1H), 2.52-2.44 (m, 1H, partially obscured by the DMSO signal), 2.41 (s, 3H).

Chiral analytical HPLC [column: Daicel Chiralcel IA, 5 µm, 250 mm×4.6 mm; eluent: tert-butyl methyl ether/methanol 1:1; flow rate: 1 ml/min; temperature: 30° C.; detection: 220 nm]: $R_t$=8.95 min.

Example 390

Methyl [1-{[3-(2-methoxyethyl)-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]carbamate (racemate)

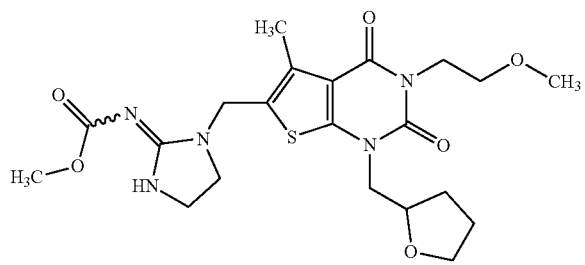

Analogously to the method described in Ex. 371, 875 mg (1.99 mmol, 90% purity) of the compound from Ex. 321A and 310 mg (1.99 mmol) of methyl (dichloromethylene)carbamate were used to obtain 415 mg (43% of theory) of the title compound. The reaction time in this case was 2.5 days.

$^1$H-NMR (400 MHz, DMSO-$d_6$, δ/ppm): 8.02 (s, 1H), 4.55 (s, 2H), 4.27-4.16 (m, 1H), 4.06 (t, 2H), 4.02 (dd, 1H), 3.78-3.55 (m, 3H), 3.53 (s, 3H), 3.50 (t, 2H), 3.48-3.42 (m, 2H), 3.37-3.29 (m, 2H, partially obscured by the water signal), 3.24 (s, 3H), 2.41 (s, 3H), 2.03-1.75 (m, 3H), 1.72-1.60 (m, 1H).

LC/MS (Method 17, ESIpos): $R_t$=1.21 min, m/z=480.19 [M+H]$^+$.

Example 391

Methyl [1-f{[3-(2-methoxyethyl)-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]carbamate (Enantiomer 1)

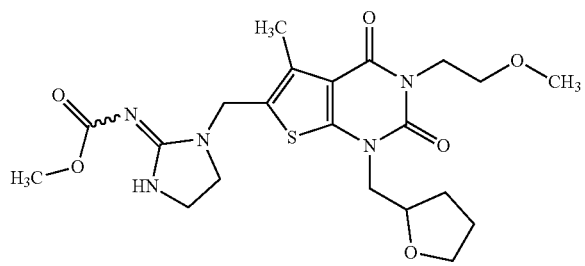

395 mg (0.824 mmol) of the racemic compound from Ex. 390 were dissolved in a mixture of 10 ml of methanol and 4 ml of dichloromethane and, in 140 portions, separated into the enantiomers by preparative SFC on a chiral phase [column: Daicel Chiralcel OD-H, 5 µm, 250 mm×20 mm; eluent: carbon dioxide/methanol 75:25; flow rate: 80 ml/min; temperature: 30° C.; detection: 210 nm]. After concentrating the product fractions, the residue was stirred with pentane with a little added dichloromethane, and the solids were then filtered off with suction and dried under high vacuum. 150 g (75% of theory) of Enantiomer 1 were obtained (99% ee, chiral analytical HPLC).

¹H-NMR (400 MHz, DMSO-d₆, δ/ppm): 8.02 (s, 1H), 4.55 (s, 2H), 4.27-4.17 (m, 1H), 4.06 (t, 2H), 4.03 (dd, 1H), 3.76-3.56 (m, 3H), 3.53 (s, 3H), 3.50 (t, 2H), 3.48-3.43 (m, 2H), 3.37-3.28 (m, 2H, partially obscured by the water signal), 3.24 (s, 3H), 2.41 (s, 3H), 2.03-1.76 (m, 3H), 1.72-1.60 (m, 1H).

Chiral analytical SFC [column: Daicel Chiralcel OD-H, 5 μm, 250 mm×4.6 mm; eluent: carbon dioxide/methanol 75:25; flow rate: 3 ml/min; temperature: 40° C.; detection: 210 nm]: R$_t$=3.77 min.

Example 392

Methyl [1-f{[3-(2-methoxyethyl)-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]carbamate (Enantiomer 2)

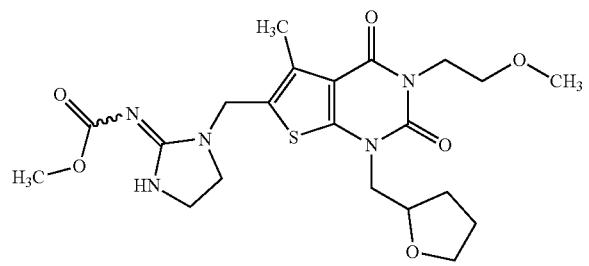

395 mg (0.824 mmol) of the racemic compound from Ex. 390 were dissolved in a mixture of 10 ml of methanol and 4 ml of dichloromethane and, in 140 portions, separated into the enantiomers by preparative SFC on a chiral phase [column: Daicel Chiralcel OD-H, 5 μm, 250 mm×20 mm; eluent: carbon dioxide/methanol 75:25; flow rate: 80 ml/min; temperature: 30° C.; detection: 210 nm]. After concentrating the product fractions, the residue was stirred with pentane with a little added dichloromethane, and the solids were then filtered off with suction and dried under high vacuum. 148 g (74% of theory) of Enantiomer 2 were obtained (98% ee, chiral analytical HPLC).

¹H-NMR (400 MHz, DMSO-d₆, δ/ppm): 8.02 (s, 1H), 4.55 (s, 2H), 4.25-4.18 (m, 1H), 4.06 (t, 2H), 4.03 (dd, 1H), 3.76-3.56 (m, 3H), 3.53 (s, 3H), 3.50 (t, 2H), 3.48-3.43 (m, 2H), 3.37-3.28 (m, 2H, partially obscured by the water signal), 3.24 (s, 3H), 2.41 (s, 3H), 2.02-1.75 (m, 3H), 1.72-1.60 (m, 1H).

Chiral analytical SFC [column: Daicel Chiralcel OD-H, 5 μm, 250 mm×4.6 mm; eluent: carbon dioxide/methanol 75:25; flow rate: 3 ml/min; temperature: 40° C.; detection: 210 nm]: R$_t$=4.33 min.

Example 393

6-[(2,3-Dioxopiperazin-1-yl)methyl]-3-ethyl-1-(fluoromethyl)-5-methylthieno[2,3-d]pyrimidine-2,4(1H,3H)-dione

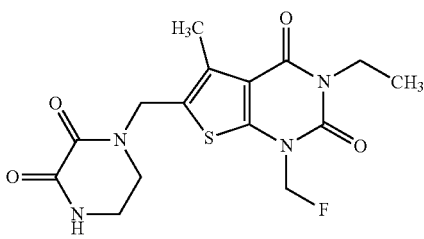 [SMILES: CCn1c(=O)c2c(C)c(CN3CCNC(=O)C3=O)sc2n(CF)c1=O]

110 mg (0.276 mmol) of the compound from Example 397A were dissolved in 5 ml of ethanol, and 408 mg (2.76 mmol) of diethyl oxalate were added. The mixture was stirred at 80° C. for 17 h. Thereafter, the reaction solution was concentrated on a rotary evaporator. The residue was dissolved in 30 ml of dichloromethane and this solution was washed with water and saturated sodium hydrogencarbonate solution. After drying over anhydrous sodium sulphate, the organic phase was filtered and concentrated. The remaining residue was dissolved in 3 ml of DMSO and this solution was purified by means of preparative HPLC (Method 14). Combination of the product fractions and freeze-drying gave 36 mg (33% of theory) of the title compound.

¹H-NMR (400 MHz, DMSO-d₆, δ/ppm): 8.65 (br. s, 1H), 6.01 (d, 2H), 4.71 (s, 2H), 3.90 (q, 2H), 3.51 (dd, 2H), 2.44 (s, 3H), 1.13 (t, 3H).

LC/MS (Method 3, ESIneg): R$_t$=0.79 min, m/z=413 [M−H+HCOOH]⁻.

Example 394

6-[(2,3-Dioxopiperazin-1-yl)methyl]-3-ethyl-5-methyl-1-(3,3,3-trifluoropropyl)thieno[2,3-d]pyrimidine-2,4(1H,3H)-dione

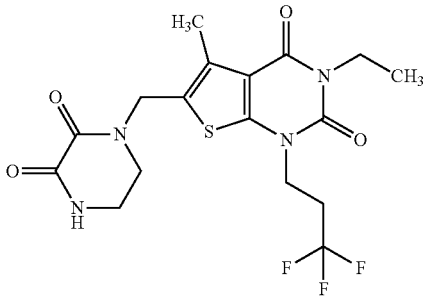 [SMILES: CCn1c(=O)c2c(C)c(CN3CCNC(=O)C3=O)sc2n(CCC(F)(F)F)c1=O]

423 mg (1.12 mmol) of the compound from Example 210A were dissolved in 45 ml of ethanol, and 285 μl (2.07 mmol) of diethyl oxalate were added. The mixture was stirred at 80° C. for about 16 h. Thereafter, the reaction solution was concentrated on a rotary evaporator. The residue was first prepurified by MPLC (Isolera, 25 g of silica gel, dichloromethane/methanol 98:2→90:10). The product thus obtained was then repurified by means of preparative HPLC (Method 8). After combination of the product fractions, concentration and drying under high vacuum, 230 mg (47% of theory) of the title compound were obtained.

$^1$H-NMR (400 MHz, DMSO-$d_6$, δ/ppm): 8.62 (br. s, 1H), 4.71 (s, 2H), 4.10 (t, 2H), 3.90 (q, 2H), 3.55-3.43 (m, 2H), 3.34-3.28 (m, 2H, partially obscured by the water signal), 2.87-2.68 (m, 2H), 2.45 (s, 3H), 1.12 (t, 3H).

LC/MS (Method 1, ESIpos): $R_t$=0.73 min, m/z=433 [M+H]$^+$.

Example 395

1-[2-(Cyclopentyloxy)ethyl]-6-[(2,3-dioxopiperazin-1-yl)methyl]-3-ethyl-5-methylthieno[2,3-d]pyrimidine-2,4(1H,3H)-dione

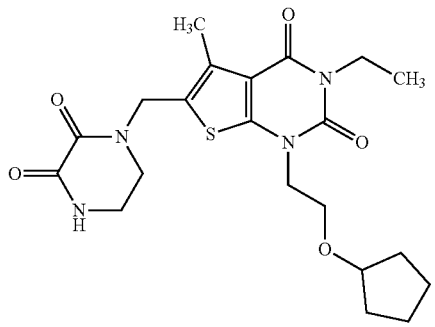 [SMILES: CCn1c(=O)c2c(C)c(CN3CCNC(=O)C3=O)sc2n(CCOC2CCCC2)c1=O]

127 mg (0.264 mmol) of the compound from Example 398A were dissolved in 5 ml of ethanol, and 389 mg (2.64 mmol) of diethyl oxalate were added. The mixture was stirred at 80° C. for 19 h. Thereafter, the reaction solution was concentrated on a rotary evaporator. The residue was dissolved in 30 ml of dichloromethane and this solution was washed with water and saturated sodium hydrogencarbonate solution. After drying over anhydrous sodium sulphate, the organic phase was filtered and concentrated. The remaining residue was dissolved in 3 ml of DMSO and this solution was purified by means of preparative HPLC (Method 14). Combination of the product fractions and freeze-drying gave 57 mg (47% of theory) of the title compound.

$^1$H-NMR (400 MHz, DMSO-$d_6$, δ/ppm): 8.63 (br. s, 1H), 4.68 (s, 2H), 3.97 (t, 2H), 3.94-3.82 (m, 3H), 3.61 (t, 2H), 3.49-3.42 (m, 2H), 3.32-3.26 (m, 2H), 2.43 (s, 3H), 1.59-1.47 (m, 2H), 1.47-1.35 (m, 6H), 1.11 (t, 3H).

LC/MS (Method 3, ESIneg): $R_t$=0.99 min, m/z=493 [M−H+HCOOH]$^-$.

Example 396

6-[(2,3-Dioxopiperazin-1-yl)methyl]-3-ethyl-1-(3-methoxypropyl)-5-methylthieno[2,3-d]pyrimidine-2,4(1H,3H)-dione

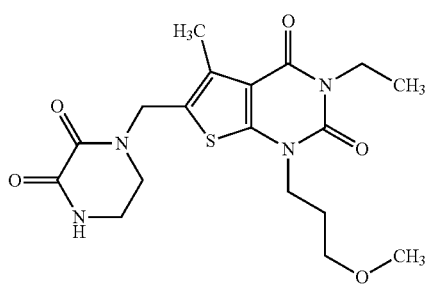 [SMILES: CCn1c(=O)c2c(C)c(CN3CCNC(=O)C3=O)sc2n(CCCOC)c1=O]

90 mg (0.211 mmol) of the compound from Example 401A were dissolved in 4 ml of ethanol, and 311 mg (2.01 mmol) of diethyl oxalate were added. The mixture was stirred at 80° C. for 16 h. Thereafter, the reaction solution was concentrated on a rotary evaporator. The residue was dissolved in 30 ml of dichloromethane and this solution was washed with water and saturated sodium hydrogencarbonate solution. After drying over anhydrous sodium sulphate, the organic phase was filtered and concentrated. The remaining residue was dissolved in 3 ml of DMSO and this solution was purified by means of preparative HPLC (Method 14). Combination of the product fractions and freeze-drying gave 46 mg (54% of theory) of the title compound.

$^1$H-NMR (400 MHz, DMSO-$d_6$, δ/ppm): 8.64 (br. s, 1H), 4.69 (s, 2H), 3.95-3.84 (m, 4H), 3.52-3.44 (m, 2H), 3.19 (s, 3H), 2.43 (s, 3H), 1.89 (quin, 2H), 1.11 (t, 3H) [further signals partly masked by the water signal].

LC/MS (Method 3, ESIpos): $R_t$=0.99 min, m/z=409 [M+H]$^+$.

Example 397

6-[(2,3-Dioxopiperazin-1-yl)methyl]-3-isopropyl-5-methyl-1-(oxetan-2-ylmethyl)thieno[2,3-d]pyrimidine-2,4(1H,3H)-dione (racemate)

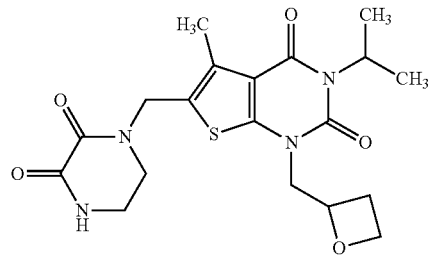 [SMILES: Cc1c(CN2CCNC(=O)C2=O)sc2c1c(=O)n(C(C)C)c(=O)n2CC1CCO1]

250 mg (0.573 mmol, 84% purity) of the compound from Example 311A were dissolved in 14 ml of ethanol, and 146 µl (1.06 mmol) of diethyl oxalate were added. The mixture was stirred at 80° C. for about 16 h. Thereafter, the reaction solution was concentrated on a rotary evaporator. The crude product obtained was purified by preparative HPLC (Method 8). After combination of the product fractions, concentration and drying under high vacuum, 134 mg (52% of theory, 94% purity) of the title compound were obtained.

$^1$H-NMR (400 MHz, DMSO-$d_6$, δ/ppm): 8.61 (br. s, 1H), 5.13 (sept, 1H), 5.00 (quin, 1H), 4.68 (s, 2H), 4.53-4.36 (m, 2H), 4.10 (d, 2H), 3.51-3.42 (m, 2H), 3.32-3.28 (m, 2H, partially obscured by the water signal), 2.76-2.62 (m, 1H), 2.51-2.43 (m, 1H, partially obscured by the DMSO signal), 2.41 (s, 3H), 1.40 (d, 6H).

LC/MS (Method 17, ESIpos): $R_t$=1.17 min, m/z=421.15 [M+H]$^+$.

Example 398

6-[(2,3-Dioxopiperazin-1-yl)methyl]-3-isopropyl-5-methyl-1-(oxetan-2-ylmethyl)thieno[2,3-d]pyrimidine-2,4(1H,3H)-dione (Enantiomer 1)

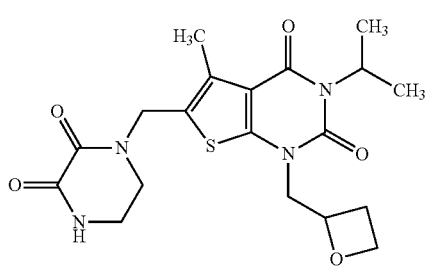

120 mg (0.285 mmol) of the racemic compound from Ex. 397 were dissolved in 5 ml of ethanol and, in 10 portions, separated into the enantiomers by preparative HPLC on a chiral phase [column: Daicel Chiralcel OD-H, 5 µm, 250 mm×20 mm; eluent: isohexane/ethanol 1:1; flow rate: 15 ml/min; temperature: 25° C.; detection: 210 nm]. After concentration of the product fractions, stirring of the residue with pentane with a little added dichloromethane, and filtration with suction and drying of the solids under high vacuum, 39 mg (65% of theory) of Enantiomer 1 were obtained (>99% ee, chiral analytical HPLC).

$^1$H-NMR (400 MHz, DMSO-d$_6$, δ/ppm): 8.61 (br. s, 1H), 5.13 (sept, 1H), 5.00 (quin, 1H), 4.68 (s, 2H), 4.53-4.36 (m, 2H), 4.10 (d, 2H), 3.52-3.41 (m, 2H), 3.32-3.28 (m, 2H, partially obscured by the water signal), 2.75-2.62 (m, 1H), 2.52-2.44 (m, 1H, partially obscured by the DMSO signal), 2.41 (s, 3H), 1.40 (d, 6H).

Chiral analytical HPLC [column: Daicel Chiraltek OD-3, 3 µm, 250 mm×4.6 mm; eluent: isohexane/ethanol 1:1; flow rate: 1 ml/min; temperature: 25° C.; detection: 220 nm]: R$_t$=3.30 min.

Example 399

6-[(2,3-Dioxopiperazin-1-yl)methyl]-3-isopropyl-5-methyl-1-(oxetan-2-ylmethyl)thieno[2,3-d]pyrimidine-2,4(1H,3H)-dione (Enantiomer 2)

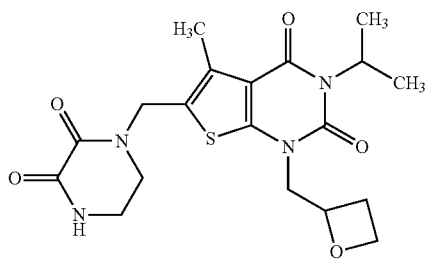 [SMILES: Cc1c(CN2CCNC(=O)C2=O)sc2c1c(=O)n(C(C)C)c(=O)n2CC1CCO1]

120 mg (0.285 mmol) of the racemic compound from Ex. 397 were dissolved in 5 ml of ethanol and, in 10 portions, separated into the enantiomers by preparative HPLC on a chiral phase [column: Daicel Chiralcel OD-H, 5 µm, 250 mm×20 mm; eluent: isohexane/ethanol 1:1; flow rate: 15 ml/min; temperature: 25° C.; detection: 210 nm]. After concentration of the product fractions, stirring of the residue with pentane with a little added dichloromethane, and filtration with suction and drying of the solids under high vacuum, 33 mg (55% of theory) of Enantiomer 2 were obtained (>99% ee, chiral analytical HPLC).

$^1$H-NMR (400 MHz, DMSO-d$_6$, δ/ppm): 8.61 (br. s, 1H), 5.13 (sept, 1H), 5.00 (quin, 1H), 4.68 (s, 2H), 4.53-4.37 (m, 2H), 4.10 (d, 2H), 3.50-3.42 (m, 2H), 3.33-3.28 (m, 2H, partially obscured by the water signal), 2.76-2.62 (m, 1H), 2.53-2.44 (m, 1H, partially obscured by the DMSO signal), 2.41 (s, 3H), 1.40 (d, 6H).

Chiral analytical HPLC [column: Daicel Chiraltek OD-3, 3 µm, 250 mm×4.6 mm; eluent: isohexane/ethanol 1:1; flow rate: 1 ml/min; temperature: 25° C.; detection: 220 nm]: R$_t$=5.45 min.

Example 400

6-[(2,3-Dioxopiperazin-1-yl)methyl]-3-(2-methoxyethyl)-5-methyl-1-(oxetan-2-ylmethyl)thieno[2,3-d]pyrimidine-2,4(1H,3H)-dione (Non-racemic Enantiomer Mixture)

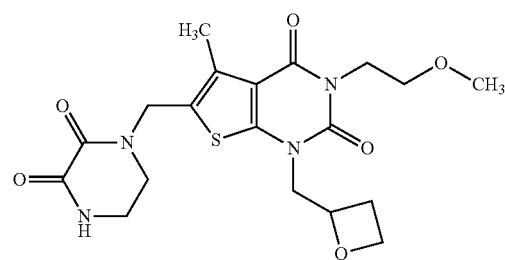 [SMILES: COCCn1c(=O)c2c(C)c(CN3CCNC(=O)C3=O)sc2n(CC2CCO2)c1=O]

Analogously to the method described in Ex. 397, 400 mg (0.878 mmol, 84% purity) of the compound from Ex. 405A and 224 µl (1.63 mmol) of diethyl oxalate were used to obtain 30 mg (7% of theory) of the title compound.

$^1$H-NMR (500 MHz, DMSO-d$_6$, δ/ppm): 8.62 (br. s, 1H), 5.00 (dt, 1H), 4.69 (s, 2H), 4.48 (td, 1H), 4.41 (dt, 1H), 4.17-4.10 (m, 2H), 4.06 (t, 2H), 3.50 (t, 2H), 3.49-3.46 (m, 2H), 3.32-3.28 (m, 2H, partially obscured by the water signal), 3.23 (s, 3H), 2.75-2.60 (m, 1H), 2.52-2.45 (m, 1H, partially obscured by the DMSO signal), 2.42 (s, 3H).

LC/MS (Method 17, ESIpos): R$_t$=0.91 min, m/z=437.15 [M+H]$^+$.

Example 401

6-[(2,3-Dioxopiperazin-1-yl)methyl]-3-(2-methoxyethyl)-5-methyl-1-(oxetan-2-ylmethyl)thieno[2,3-d]pyrimidine-2,4(1H,3H)-dione (Enantiomer 1)

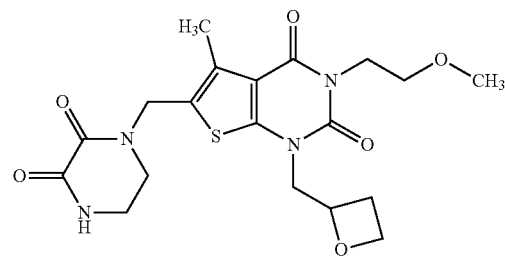 [SMILES: COCCn1c(=O)c2c(C)c(CN3CCNC(=O)C3=O)sc2n(CC2CCO2)c1=O]

30 mg (0.069 mmol) of the enantiomer mixture from Ex. 400 were dissolved in a mixture of 2 ml of methanol and 2 ml of dichloromethane and, in 14 portions, separated into the enantiomers by preparative HPLC on a chiral phase [column: Daicel Chiralpak IC, 5 μm, 250 mm×20 mm; eluent: tert-butyl methyl ether/methanol 1:1; flow rate: 15 ml/min; temperature: 30° C.; detection: 220 nm]. After concentration of the product fractions and drying under high vacuum, 18 mg (60% of theory) of Enantiomer 1 were obtained (>99% ee, chiral analytical HPLC).

$^1$H-NMR (400 MHz, DMSO-d$_6$, δ/ppm): 8.62 (br. s, 1H), 5.00 (dt, 1H), 4.69 (s, 2H), 4.53-4.37 (m, 2H), 4.14 (d, 2H), 4.06 (t, 2H), 3.50 (t, 2H), 3.49-3.46 (m, 2H), 3.33-3.28 (m, 2H, partially obscured by the water signal), 3.23 (s, 3H), 2.74-2.63 (m, 1H), 2.52-2.45 (m, 1H, partially obscured by the DMSO signal), 2.42 (s, 3H).

Chiral analytical HPLC [column: Daicel Chiralpak IC, 5 μm, 250 mm×4.6 mm; eluent: tert-butyl methyl ether/methanol 1:1; flow rate: 1 ml/min; temperature: 30° C.; detection: 220 nm]: R$_t$=11.36 min.

Example 402

6-[(2,3-Dioxopiperazin-1-yl)methyl]-3-(2-methoxyethyl)-5-methyl-1-(oxetan-2-ylmethyl)thieno[2,3-d]pyrimidine-2,4(1H,3H)-dione (Enantiomer 2)

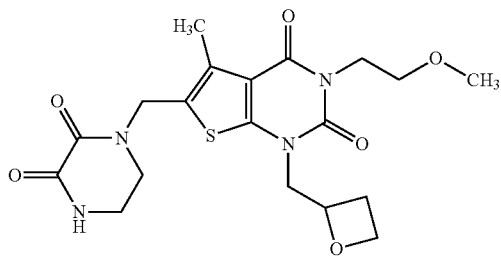 [SMILES: COCCn1c(=O)c2c(C)c(CN3CCNC(=O)C3=O)sc2n(CC2CCO2)c1=O]

30 mg (0.069 mmol) of the enantiomer mixture from Ex. 400 were dissolved in a mixture of 2 ml of methanol and 2 ml of dichloromethane and, in 14 portions, separated into the enantiomers by preparative HPLC on a chiral phase [column: Daicel Chiralpak IC, 5 μm, 250 mm×20 mm; eluent: tert-butyl methyl ether/methanol 1:1; flow rate: 15 ml/min; temperature: 30° C.; detection: 220 nm]. After concentration of the product fractions and drying under high vacuum, 2 mg (6% of theory) of Enantiomer 2 were obtained (99% ee, chiral analytical HPLC).

$^1$H-NMR (500 MHz, DMSO-d$_6$, δ/ppm): 8.62 (br. s, 1H), 5.00 (quin, 1H), 4.69 (s, 2H), 4.52-4.45 (m, 1H), 4.41 (dt, 1H), 4.19-4.10 (m, 2H), 4.06 (t, 2H), 3.50 (t, 2H), 3.49-3.46 (m, 2H), 3.23 (s, 3H), 2.75-2.63 (m, 1H), 2.52-2.45 (m, 1H, partially obscured by the DMSO signal), 2.42 (s, 3H) [further signal masked by the water signal].

Chiral analytical HPLC [column: Daicel Chiralpak IC, 5 μm, 250 mm×4.6 mm; eluent: tert-butyl methyl ether/methanol 1:1; flow rate: 1 ml/min; temperature: 30° C.; detection: 220 nm]: R$_t$=12.52 min.

Example 403

6-[(2,3-Dioxopiperazin-1-yl)methyl]-3-(2-ethoxyethyl)-5-methyl-1-(3,3,3-trifluoropropyl)thieno[2,3-d]pyrimidine-2,4(1H,3H)-dione

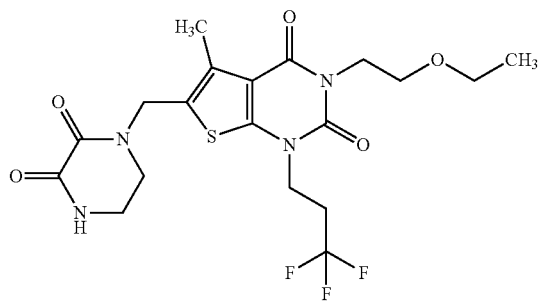 [SMILES: CCOCCn1c(=O)c2c(C)c(CN3CCNC(=O)C3=O)sc2n(CCC(F)(F)F)c1=O]

120 mg (0.253 mmol) of the compound from Example 406A were dissolved in 5 ml of ethanol, and 373 mg (2.53 mmol) of diethyl oxalate were added. The mixture was stirred at 80° C. for 16 h. Thereafter, the reaction solution was concentrated on a rotary evaporator. The residue was dissolved in 30 ml of dichloromethane and this solution was washed with water and saturated sodium hydrogencarbonate solution. After drying over anhydrous sodium sulphate, the organic phase was filtered and concentrated. The remaining residue was dissolved in 3 ml of DMSO and this solution was purified by means of preparative HPLC (Method 14). Combination of the product fractions and freeze-drying gave 54 mg (43% of theory) of the title compound.

$^1$H-NMR (500 MHz, DMSO-d$_6$, δ/ppm): 8.64 (br. s, 1H), 4.71 (s, 2H), 4.10 (t, 2H), 4.04 (t, 2H), 3.50 (q, 4H), 3.44 (q, 2H), 2.82-2.70 (m, 2H), 2.44 (s, 3H), 1.06 (t, 3H) [one further signal completely masked by the water signal].

LC/MS (Method 3, ESIpos): R$_t$=0.94 min, m/z=477 [M+H]$^+$.

Example 404

6-[(2,3-Dioxopiperazin-1-yl)methyl]-3-(2-ethoxyethyl)-1-(2-methoxyethyl)-5-methylthieno[2,3-d]pyrimidine-2,4(1H,3H)-dione

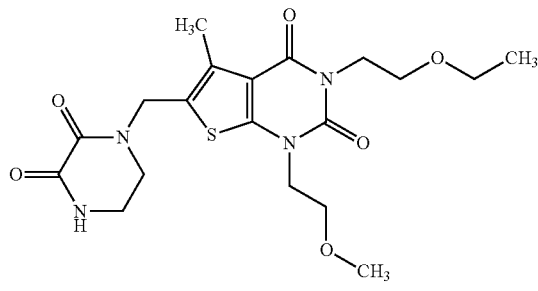 [SMILES: CCOCCn1c(=O)c2c(C)c(CN3CCNC(=O)C3=O)sc2n(CCOC)c1=O]

160 mg (0.291 mmol) of the compound from Example 407A were dissolved in 5 ml of ethanol, and 430 mg (2.91 mmol) of diethyl oxalate were added. The mixture was stirred at 80° C. for 114 h. Thereafter, the reaction solution was concentrated on a rotary evaporator. The residue was dissolved in 30 ml of dichloromethane and this solution was washed with water and saturated sodium hydrogencarbonate solution. After drying over anhydrous sodium sulphate, the organic phase was filtered and concentrated. The remaining residue was dissolved in 3 ml of DMSO and this solution was purified by means of preparative HPLC (Method 14). Combination of the product fractions and freeze-drying gave 87 mg (62% of theory) of the title compound.

$^1$H-NMR (500 MHz, DMSO-$d_6$, δ/ppm): 8.64 (br. s, 1H), 4.69 (s, 2H), 4.07-3.98 (m, 4H), 3.62 (t, 2H), 3.53-3.41 (m, 6H), 3.33-3.28 (m, 2H), 3.24-3.21 (m, 3H), 2.42 (s, 3H), 1.06 (t, 3H).

LC/MS (Method 3, ESIpos): $R_t$=0.8 min, m/z=439 [M+H]$^+$.

Example 405

3-(2-Ethoxyethyl)-1-(3-fluoropropyl)-5-methyl-6-[(2-thioxoimidazolidin-1-yl)methyl]thieno[2,3-d]pyrimidine-2,4(1H,3H)-dione

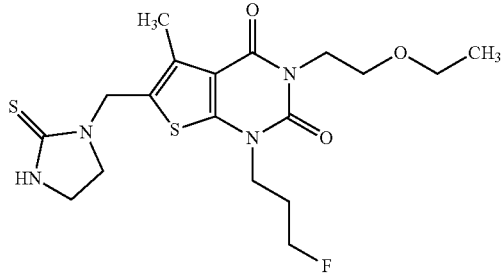 [SMILES: CCOCCn1c(=O)c2c(C)c(CN3CCNC3=S)sc2n(CCCF)c1=O]

200 mg (0.388 mmol) of the compound from Ex. 457A were dissolved in 27 ml of dioxane, and 109 mg (0.582 mmol) of 1,1'-thiocarbonyldiimidazole were added. The mixture was stirred at RT for 15 h. The reaction solution was then concentrated on a rotary evaporator. The residue was dissolved in 6 ml of DMSO and this solution was purified by means of preparative HPLC (Method 14). Combination of the product fractions and freeze-drying gave 126 mg (75% of theory) of the title compound.

$^1$H-NMR (400 MHz, DMSO-$d_6$, δ/ppm): 8.35 (s, 1H), 4.83 (s, 2H), 4.58 (t, 1H), 4.46 (t, 1H), 4.03 (br. t, 2H), 3.97 (br. t, 2H), 3.58-3.37 (m, 8H), 2.43 (s, 3H), 2.14-1.97 (m, 2H), 1.06 (t, 3H).

LC/MS (Method 3, ESIpos): $R_t$=1.02 min, m/z=429 [M+H]$^+$.

Example 406

3-(2,2-Dimethylpropyl)-5-methyl-6-[(2-oxoimidazolidin-1-yl)methyl]-1-(tetrahydrofuran-2-ylmethyl)thieno[2,3-d]pyrimidine-2,4(1H,3H)-dione (racemate)

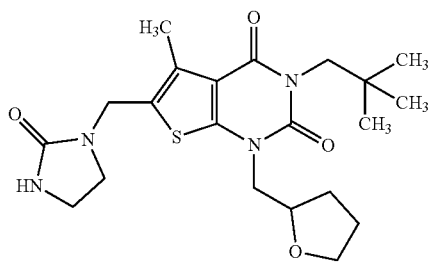 [SMILES: Cc1c(CN2CCNC2=O)sc2c1c(=O)n(CC(C)(C)C)c(=O)n2CC1CCCO1]

To a solution of 560 mg (1.16 mmol, 85% purity) of the compound from Ex. 454A and 244 µl (1.75 mmol) of triethylamine in 12 ml of THF were added 227 mg (1.40 mmol) of CDI, and the mixture was stirred at RT for about 18 h. Subsequently, the mixture was concentrated to dryness. The remaining residue was taken up in ethyl acetate and washed successively with saturated sodium carbonate solution, water and saturated sodium chloride solution. After drying over anhydrous magnesium sulphate, the mixture was filtered and concentrated. The solid residue was stirred in a little acetonitrile at RT. Filtration and drying of the solids under high vacuum gave 260 mg (48% of theory, 95% purity) of the title compound.

$^1$H-NMR (400 MHz, DMSO-$d_6$, δ/ppm): 6.52 (s, 1H), 4.34 (s, 2H), 4.27-4.17 (m, 1H), 4.08-3.95 (m, 1H), 3.82 (br. s, 2H), 3.73 (quin, 2H), 3.65-3.57 (m, 1H), 3.29-3.16 (m, 4H), 2.38 (s, 3H), 2.03-1.75 (m, 3H), 1.72-1.59 (m, 1H), 0.89 (s, 9H).

LC/MS (Method 17, ESIpos): $R_t$=1.78 min, m/z=435.21 [M+H]$^+$.

Example 407

3-(2,2-Dimethylpropyl)-5-methyl-6-[(2-oxoimidazolidin-1-yl)methyl]-1-(tetrahydrofuran-2-ylmethyl)thieno[2,3-d]pyrimidine-2,4(1H,3H)-dione (Enantiomer 1)

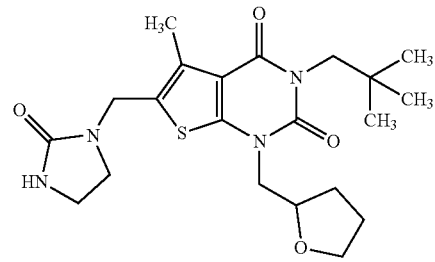 [SMILES: Cc1c(CN2CCNC2=O)sc2c1c(=O)n(CC(C)(C)C)c(=O)n2CC1CCCO1]

250 mg (0.691 mmol, 95% purity) of the racemic compound from Ex. 406 were dissolved in 12 ml of dioxane/methanol mixture and, in 120 portions, separated into the enantiomers by preparative HPLC on a chiral phase [column: Daicel Chiralpak ID, 5 µm, 250 mm×20 mm; eluent: n-heptane/ethanol 1:1; flow rate: 50 ml/min; temperature: 23° C.; detection: 235 nm]. After concentration of the product fractions and drying under high vacuum, 53 mg (44% of theory) of Enantiomer 1 were obtained (>99% ee, chiral analytical HPLC).

$^1$H-NMR (400 MHz, DMSO-$d_6$, δ/ppm): 6.52 (s, 1H), 4.34 (s, 2H), 4.28-4.16 (m, 1H), 4.00 (dd, 1H), 3.82 (br. s, 2H), 3.73 (quin, 2H), 3.66-3.56 (m, 1H), 3.29-3.16 (m, 4H), 2.38 (s, 3H), 2.03-1.74 (m, 3H), 1.72-1.60 (m, 1H), 0.89 (s, 9H).

Chiral analytical HPLC [column: Daicel Chiralpak ID-3, 3 µm, 50 mm×4.6 mm; eluent: n-heptane/ethanol 1:1; flow rate: 1 ml/min; temperature: 40° C.; detection: 220 nm]: $R_t$=3.11 min.

Example 408

3-(2,2-Dimethylpropyl)-5-methyl-6-[(2-oxoimidazolidin-1-yl)methyl]-1-(tetrahydrofuran-2-ylmethyl)thieno[2,3-d]pyrimidine-2,4(1H,3H)-dione (Enantiomer 2)

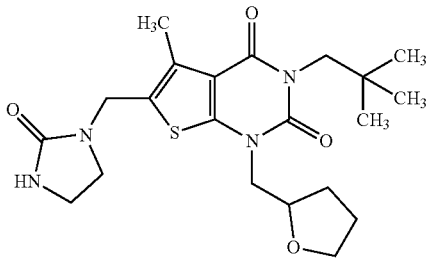 [SMILES: Cc1c(CN2CCNC2=O)sc2c1c(=O)n(CC(C)(C)C)c(=O)n2CC1CCCO1]

250 mg (0.691 mmol, 95% purity) of the racemic compound from Ex. 406 were dissolved in 12 ml of dioxane/methanol mixture and, in 120 portions, separated into the enantiomers by preparative HPLC on a chiral phase [column: Daicel Chiralpak ID, 5 µm, 250 mm×20 mm; eluent: n-heptane/ethanol 1:1; flow rate: 50 ml/min; temperature: 23° C.; detection: 235 nm]. After concentration of the product fractions and drying under high vacuum, 67 mg (56% of theory) of Enantiomer 2 were obtained (84% ee, chiral analytical HPLC).

$^1$H-NMR (400 MHz, DMSO-$d_6$, δ/ppm): 6.52 (s, 1H), 4.34 (s, 2H), 4.28-4.16 (m, 1H), 4.00 (dd, 1H), 3.82 (br. s, 2H), 3.73 (quin, 2H), 3.66-3.56 (m, 1H), 3.29-3.16 (m, 4H), 2.38 (s, 3H), 2.03-1.74 (m, 3H), 1.72-1.60 (m, 1H), 0.89 (s, 9H).

Chiral analytical HPLC [column: Daicel Chiralpak ID-3, 3 µm, 50 mm×4.6 mm; eluent: n-heptane/ethanol 1:1; flow rate: 1 ml/min; temperature: 40° C.; detection: 220 nm]: $R_t$=3.45 min.

Example 409

5-Methyl-6-[(2-oxoimidazolidin-1-yl)methyl]-3-(t1,1,1-trifluoropropan-2-yl)-1-(3,3,3-trifluoropropyl)thieno[2,3-d]pyrimidine-2,4(1H,3H)-dione (racemate)

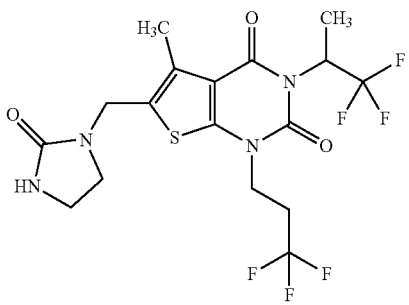 [SMILES: Cc1c(CN2CCNC2=O)sc2c1c(=O)n(C(C)C(F)(F)F)c(=O)n2CCC(F)(F)F]

To a solution of 590 mg (1.11 mmol, 84% purity) of the compound from Ex. 455A and 232 µl (1.67 mmol) of triethylamine in 12 ml of THF were added 216 mg (1.33 mmol) of CDI, and the mixture was stirred at RT for about 18 h. Subsequently, the mixture was concentrated to dryness. The remaining residue was taken up in ethyl acetate and washed successively with saturated sodium carbonate solution, water and saturated sodium chloride solution. After drying over anhydrous magnesium sulphate, the mixture was filtered and concentrated. The solid residue was purified by means of preparative HPLC (Method 8). After concentration of the product fractions and drying under high vacuum, 332 g (63% of theory) of the title compound were obtained.

$^1$H-NMR (400 MHz, DMSO-$d_6$, δ/ppm): 6.55 (s, 1H), 5.84-5.45 (m, 1H), 4.38 (s, 2H), 4.20-4.01 (m, 2H), 3.29-3.16 (m, 4H), 2.87-2.66 (m, 2H), 2.40 (s, 3H), 1.63 (br. d, 3H).

LC/MS (Method 17, ESIneg): $R_t$=1.77 min, m/z=517.10 [M−H+HCO$_2$H]$^-$.

Example 410

1-(2-Methoxyethyl)-5-methyl-6-[(2-oxoimidazolidin-1-yl)methyl]-3-(1,1,1-trifluoropropan-2-yl)thieno[2,3-d]pyrimidine-2,4(1H,3H)-dione (racemate)

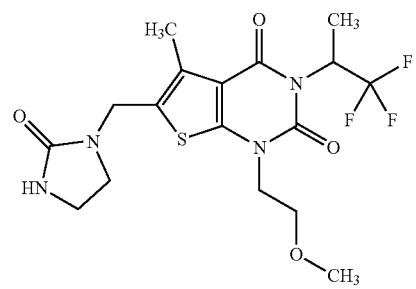 [SMILES: COCCn1c(=O)n(C(C)C(F)(F)F)c(=O)c2c(C)c(CN3CCNC3=O)sc21]

To a solution of 295 mg (0.592 mmol, 82% purity) of the compound from Ex. 456A and 124 µl (0.888 mmol) of triethylamine in 6 ml of THF were added 115 mg (0.711 mmol) of CDI, and the mixture was stirred at RT for about 18 h. Subsequently, the mixture was concentrated to dryness. The remaining residue was taken up in ethyl acetate and washed successively with saturated sodium carbonate solution, water and saturated sodium chloride solution. After drying over anhydrous magnesium sulphate, the mixture was filtered and concentrated. The solid residue was purified by means of preparative HPLC (Method 8). The product fractions were combined and concentrated, and the remaining residue was purified once more by means of preparative HPLC [column: Phenomenex Kinetex C18, 5 µm, 100 mm×30 mm; eluent A: water; eluent B: acetonitrile with 5 ml/l of 2% formic acid in water; gradient: 0-2 min 10% B, 2-2.2 min to 20% B, 2.2-7 min to 60% B, 7-7.5 min to 92% B, 7.5-9 min 92% B; flow rate: 65 ml/min; temperature: 23° C.; UV detection: 200-400 nm]. After reconcentration of the product fractions and drying under high vacuum, 112 mg (43% of theory) of the title compound were obtained.

$^1$H-NMR (400 MHz, DMSO-$d_6$, δ/ppm): 6.54 (s, 1H), 5.84-5.47 (m, 1H), 4.35 (s, 2H), 4.09-3.97 (m, 2H), 3.68-3.57 (m, 2H), 3.29-3.16 (m, 4H), 3.24 (s, 3H), 2.39 (s, 3H), 1.63 (br. d, 3H).

LC/MS (Method 17, ESIpos): $R_t$=1.55 min, m/z=435.13 [M+H]$^+$.

Example 411

3-(2-Ethoxyethyl)-1-(3-fluoropropyl)-5-methyl-6-[(2-oxoimidazolidin-1-yl)methyl]thieno[2,3-d]pyrimidine-2,4(1H,3H)-dione

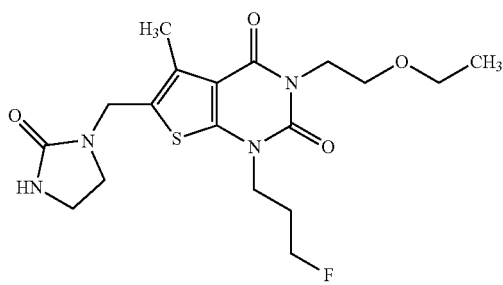 [SMILES: CCOCCn1c(=O)c2c(C)c(CN3CCNC3=O)sc2n(CCCF)c1=O]

290 mg (0.563 mmol) of the compound from Example 457A were dissolved in 25 ml of dioxane, and 141 mg (0.844 mmol) of CDI were added. The mixture was stirred at RT for 15 h. The reaction solution was then concentrated on a rotary evaporator. The residue was dissolved in 6 ml of DMSO and this solution was purified by means of preparative HPLC (Method 14). Combination of the product fractions and freeze-drying gave 199 mg (86% of theory) of the title compound.

$^1$H-NMR (400 MHz, DMSO-$d_6$, δ/ppm): 6.54 (s, 1H), 4.59 (t, 1H), 4.47 (t, 1H), 4.35 (s, 2H), 4.03 (t, 2H), 3.97 (br. t, 2H), 3.50 (t, 2H), 3.44 (q, 2H), 3.29-3.17 (m, 4H), 2.39 (s, 3H), 2.13-1.97 (m, 2H), 1.06 (t, 3H).

LC/MS (Method 3, ESIpos): $R_t$=0.93 min, m/z=413 [M+H]$^+$.

Example 412

3-(2-Methoxypropyl)-5-methyl-6-[(2-oxoimidazolidin-1-yl)methyl]-1-(3,3,3-trifluoropropyl)thieno[2,3-d]pyrimidine-2,4(1H,3H)-dione (racemate)

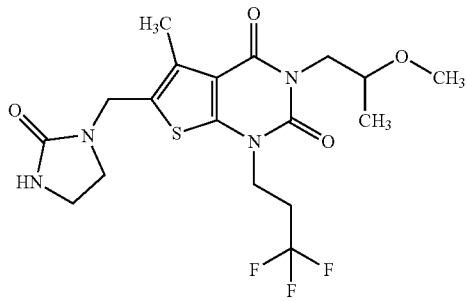 [SMILES: COC(C)Cn1c(=O)c2c(C)c(CN3CCNC3=O)sc2n(CCC(F)(F)F)c1=O]

To a solution of 235 mg (2.62 mmol) of 2-imidazolidinone in 9 ml of THF were added 105 mg (2.62 mmol) of sodium hydride (60% suspension in mineral oil) and the mixture was stirred at RT for 3 h ("Solution 1"). To a solution of 249 mg (0.655 mmol) of the compound from Ex. 452A in 4.5 ml of dichloromethane in another reaction vessel were added, at 0° C., 342 µl (1.97 mmol) of N,N-diisopropylethylamine and 72 µl (0.983 mmol) of thionyl chloride, and the mixture was stirred for 75 min. Subsequently, Solution 1 was added in portions and the mixture was stirred at RT for 18 h. Thereafter, 70 ml of water were added to the reaction mixture. The mixture was extracted with ethyl acetate. The combined organic phases were dried over sodium sulphate, filtered and concentrated. The residue obtained was chromatographed using a silica gel cartridge (Biotage, 10 g of silica gel, eluent: hexane/ethyl acetate). 97 mg (31% of theory) of the title compound were obtained.

$^1$H-NMR (400 MHz, DMSO-$d_6$, δ/ppm): 6.56 (s, 1H), 4.37 (s, 2H), 4.15-4.00 (m, 4H), 3.75 (dd, 1H), 3.68-3.58 (m, 1H), 3.30-3.18 (m, 7H), 2.83-2.69 (m, 2H), 2.40 (s, 3H), 1.05 (d, 3H).

LC/MS (Method 3): $R_t$=1.01 min, m/z=449 [M+H]$^+$.

Example 413

3-(2-Methoxypropyl)-5-methyl-6-[(2-oxoimidazolidin-1-yl)methyl]-1-(3,3,3-trifluoropropyl)thieno[2,3-d]pyrimidine-2,4(1H,3H)-dione (Enantiomer 1)

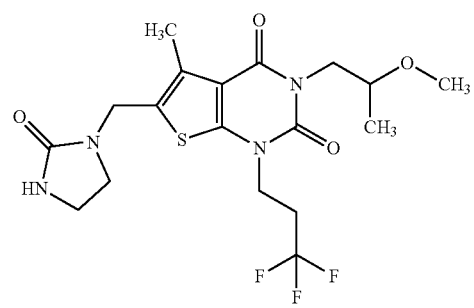 [SMILES: COC(C)Cn1c(=O)c2c(C)c(CN3CCNC3=O)sc2n(CCC(F)(F)F)c1=O]

92 mg of the racemic compound from Ex. 412 were dissolved in 1.5 ml of a methanol/dichloromethane mixture (1:1 v/v) and separated into the enantiomers by means of preparative HPLC on a chiral phase [column: Daicel Chiralpak IC, 5 µm, 250 mm×30 mm; eluent A: acetonitrile, eluent B: ethanol; isocratic 90% A/10% B; flow rate: 50.0 ml/min; UV detection: 254 nm]. The respective product fractions were concentrated on a rotary evaporator, admixed with tert-butanol and freeze-dried. 29 mg of the title compound (Enantiomer 1) and 29 mg of Enantiomer 2 (see Example 414) were obtained.

$^1$H-NMR (400 MHz, DMSO-$d_6$, δ/ppm): 6.56 (s, 1H), 4.36 (s, 2H), 4.15-4.01 (m, 3H), 3.75 (dd, 1H), 3.63 (sext, 1H), 3.30-3.18 (m, 7H), 2.83-2.69 (m, 2H), 2.40 (s, 3H), 1.05 (d, 3H).

Chiral analytical HPLC [column: Daicel Chiralpak IC, 3 µm, 100 mm×4.6 mm; eluent A: acetonitrile+0.1% diethylamine, eluent B: ethanol; isocratic 90% A+10% B; flow rate: 1.4 ml/min; temperature: 25° C.; DAD 254 nm]: $R_t$=3.28 min.

Example 414

3-(2-Methoxypropyl)-5-methyl-6-[(2-oxoimidazolidin-1-yl)methyl]-1-(3,3,3-trifluoropropyl)thieno[2,3-d]pyrimidine-2,4(1H,3H)-dione (Enantiomer 2)

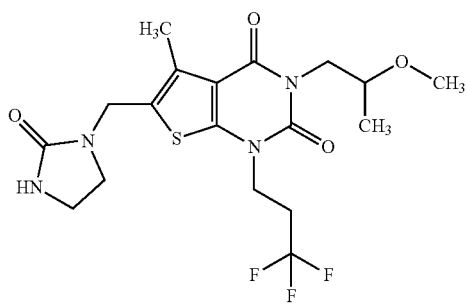 [SMILES: COC(C)Cn1c(=O)c2c(C)c(CN3CCNC3=O)sc2n(CCC(F)(F)F)c1=O]

The title compound (29 mg) was obtained as the second enantiomer in the preparative HPLC separation of the racemate from Ex. 412 described in Ex. 413.

$^1$H-NMR (400 MHz, DMSO-$d_6$, δ/ppm): 6.56 (s, 1H), 4.36 (s, 2H), 4.15-4.00 (m, 3H), 3.75 (dd, 1H), 3.63 (sext, 1H), 3.30-3.18 (m, 7H), 2.83-2.69 (m, 2H), 2.40 (s, 3H), 1.05 (d, 3H).

Chiral analytical HPLC [column: Daicel Chiralpak IC, 3 μm, 100 mm×4.6 mm; eluent A: acetonitrile+0.1% diethylamine, eluent B: ethanol; isocratic 90% A+10% B; flow rate: 1.4 ml/min; temperature: 25° C.; DAD 254 nm]: $R_t$=4.30 min.

Example 415

3-Ethyl-1-(2-methoxyethyl)-5-methyl-6-[(2-oxoimidazolidin-1-yl)(dideutero)methyl]thieno[2,3-d]pyrimidine-2,4(1H,3H)-dione

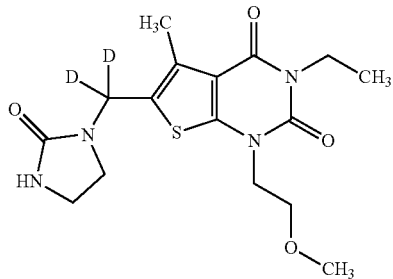 [SMILES: [2H]C([2H])(c1sc2c(c1C)c(=O)n(CC)c(=O)n2CCOC)N1CCNC1=O]

To a solution of 454 mg (5.27 mmol) of imidazolidin-2-one in 13 ml of DMF were added 211 mg (5.27 mmol) of sodium hydride (60% suspension in mineral oil), then the mixture was heated to 60° C. for 15 min and subsequently cooled back down to RT ("Solution 1"). To a solution of 400 mg (1.32 mmol) of the compound from Ex. 453A in 9.5 ml of dichloromethane in another reaction vessel were added, at 0° C., 459 μl (2.64 mmol) of N,N-diisopropylethylamine and 101 μl (1.38 mmol) of thionyl chloride. After 35 min at 0° C., Solution 1 was added in portions and then the cooling bath was removed. The reaction mixture was then stirred at RT for 3 days. All the volatile constituents were then removed on a rotary evaporator. The remaining residue was taken up with ethyl acetate and washed successively with water and saturated aqueous sodium chloride solution. After drying over anhydrous magnesium sulphate, the mixture was filtered and concentrated. The crude product was purified by preparative HPLC (Method 8). The still slightly contaminated product fractions were combined, concentrated and repurified by means of another preparative HPLC [column: Phenomenex Kinetex C18, 5 μm, 150 mm×21.2 mm; eluent A: water; eluent B: methanol; eluent C: 1% formic acid in water; gradient: 0-1 min 65% A 30% B 5% C, 2-6 min to 25% A 70% B 5% C, 6-6.2 min to 65% A 30% B 5% C, 6.2-7.6 min 65% A 30% B 5% C; flow rate: 25 ml/min; temperature: 23° C.; UV detection: 210 nm]. The product fractions were combined and concentrated and the residue was finally stirred with a little diethyl ether/ethyl acetate mixture at RT. In this way, 92 mg (18% of theory) of the title compound were obtained.

$^1$H-NMR (400 MHz, DMSO-$d_6$, δ/ppm): 6.51 (s, 1H), 4.02 (t, 2H), 3.90 (q, 2H), 3.63 (t, 2H), 3.28-3.15 (m, 4H), 3.24 (s, 3H), 2.39 (s, 3H), 1.12 (t, 3H).

LC/MS (Method 17, ESIpos): $R_t$=1.20 min, m/z=369.15 [M+H]$^+$.

Example 416

3-Ethyl-5-methyl-6-[1-(2-oxoimidazolidin-1-yl)ethyl]-1-(3,3,3-trifluoropropyl)thieno[2,3-d]pyrimidine-2,4(1H,3H)-dione (racemate)

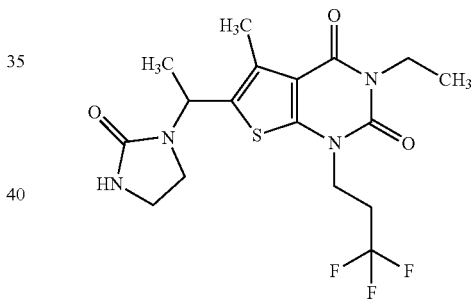

310 mg (0.887 mmol) of the compound from Ex. 461A were dissolved in a mixture of 13 ml of DMF and 6.5 ml of THF, and 80 μl (0.932 mmol) of 2-chloroethyl isocyanate were added at RT. After the reaction mixture had been stirred at RT for 30 min, 149 mg (1.33 mmol) of potassium tert-butoxide were added. After stirring at RT for about 18 h, the reaction mixture was diluted with ethyl acetate and washed successively with saturated sodium hydrogencarbonate solution (three times) and saturated sodium chloride solution. After drying over anhydrous magnesium sulphate, the mixture was filtered and concentrated. The crude product thus obtained was purified by means of preparative HPLC (Method 8). After concentration of the product fractions and drying under high vacuum, 146 mg (34% of theory, 89% purity) of the title compound were obtained.

$^1$H-NMR (400 MHz, DMSO-$d_6$, δ/ppm): 6.39 (s, 1H), 5.31 (q, 1H), 4.12 (td, 2H), 3.90 (q, 2H), 3.43-3.35 (m, 1H), 3.26-3.09 (m, 3H), 2.86-2.69 (m, 2H), 2.39 (s, 3H), 1.46 (d, 3H), 1.11 (t, 3H).

LC/MS (Method 17, ESIpos): $R_t$=1.56 min, m/z=333.09 [M+H—$C_3H_6N_2O$]$^+$.

Example 417

6-[(4-Allyl-5-oxo-4,5-dihydro-1H-1,2,4-triazol-1-yl)methyl]-1-(fluoromethyl)-3-isopropyl-5-methylthieno[2,3-d]pyrimidine-2,4(1H,3H)-dione

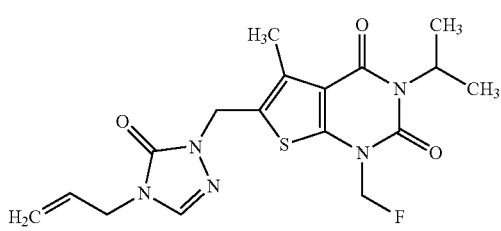 [SMILES: C=CCn1cnn(Cc2sc3c(c2C)c(=O)n(C(C)C)c(=O)n3CF)c1=O]

320 mg (1.05 mmol) of the compound from Ex. 450A and 232 mg (1.26 mmol) of 4-allyl-2,4-dihydro-3H-1,2,4-triazol-3-one were dissolved in 19 ml of dichloromethane, and 455 mg (2.10 mmol) of tri-n-butylphosphine were added. After 20 min, 312 µl (1.58 mmol) of diisopropyl azodicarboxylate (DIAD) were added dropwise. The reaction mixture was then stirred at RT for 17 h. Then 100 ml of dichloromethane were added, and the mixture was washed successively with 50 ml of water and 50 ml of saturated sodium chloride solution. The organic phase was dried over sodium sulphate, filtered and concentrated. The residue obtained was chromatographed using a silica gel cartridge (Biotage, 50 g of silica gel, eluent: hexane/ethyl acetate). 183 mg (42% of theory) of the title compound were obtained.

$^1$H-NMR (400 MHz, DMSO-$d_6$, δ/ppm): 7.97 (s, 1H), 6.04 (s, 1H), 5.95-5.83 (m, 2H), 5.19 (dd, 1H), 5.15-5.04 (m, 2H), 5.02 (s, 2H), 4.20 (dt, 2H), 2.45 (s, 3H), 1.40 (d, 6H).

LC/MS (Method 1, ESIpos): $R_t$=1.09 min, m/z=394 [M+H]$^+$.

Example 418

6-[(4-Allyl-5-oxo-4,5-dihydro-H-1,2,4-triazol-1-yl)methyl]-1-(3-fluoropropyl)-3-isopropyl-5-methylthieno[2,3-d]pyrimidine-2,4(1H,3H)-dione

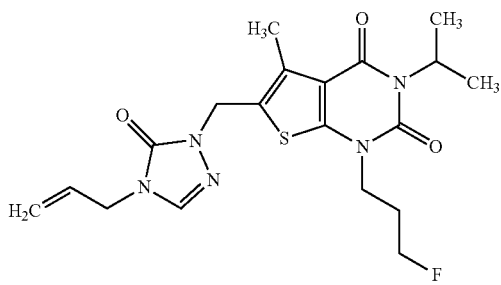 [SMILES: C=CCn1cnn(Cc2sc3c(c2C)c(=O)n(C(C)C)c(=O)n3CCCF)c1=O]

320 mg (0.998 mmol) of the compound from Ex. 451A and 220 mg (1.20 mmol) of 4-allyl-2,4-dihydro-3H-1,2,4-triazol-3-one were dissolved in 18 ml of dichloromethane, and 432 mg (2.0 mmol) of tri-n-butylphosphine were added. After 20 min, 297 µl (1.50 mmol) of diisopropyl azodicarboxylate (DIAD) were added dropwise. The reaction mixture was then stirred at RT for 18 h. Then 100 ml of dichloromethane were added, and the mixture was washed successively with 50 ml of water and 50 ml of saturated sodium chloride solution. The organic phase was dried over sodium sulphate, filtered and concentrated. The residue obtained was chromatographed using a silica gel cartridge (Biotage, 50 g of silica gel, eluent: hexane/ethyl acetate). 198 mg (44% of theory) of the title compound were obtained.

$^1$H-NMR (400 MHz, DMSO-$d_6$, δ/ppm): 7.96 (s, 1H), 5.95-5.84 (m, 1H), 5.19 (dd, 1H), 5.14-5.02 (m, 2H), 4.99 (s, 2H), 4.58 (t, 1H), 4.46 (t, 1H), 4.22-4.17 (m, 2H), 3.93 (br. t, 2H), 2.45 (s, 3H), 2.10-1.95 (m, 2H), 1.39 (d, 6H).

LC/MS (Method 1, ESIpos): $R_t$=1.10 min, m/z=422 [M+H]$^+$.

Example 419

3-Ethyl-5-methyl-6-[(5-oxo-4,5-dihydro-1H-1,2,4-triazol-1-yl)methyl]-1-(tetrahydrofuran-2-ylmethyl)thieno[2,3-d]pyrimidine-2,4(1H,3H)-dione (racemate)

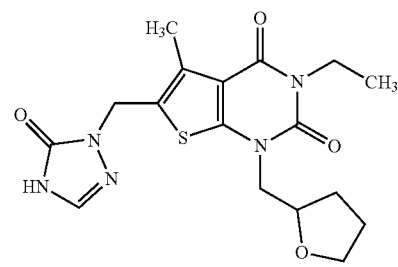 [SMILES: CCn1c(=O)c2c(C)c(Cn3nc[nH]c3=O)sc2n(CC2CCCO2)c1=O]

236 mg (0.490 mmol) of the compound from Ex. 475A were dissolved in a mixture of 12 ml each of methanol and trimethyl orthoformate, and 490 µl (1.96 mmol) of a 4 M solution of hydrogen chloride in dioxane were added at RT. After 2 h of reaction time, a further 245 µl (0.980 mmol) of the 4 M solution of hydrogen chloride and dioxane were added and, after a further 3 h, another 490 µl (1.96 mmol). After a total reaction time of about 20 h, the reaction mixture was admixed with water and extracted with ethyl acetate. The organic extract was concentrated and the remaining residue was purified by means of preparative HPLC (Method 8). After concentration of the product fractions and drying under high vacuum, 201 mg (100% of theory, 96% purity) of the title compound were obtained.

$^1$H-NMR (400 MHz, DMSO-$d_6$, δ/ppm): 11.59 (br. s, 1H), 7.83 (s, 1H), 4.93 (s, 2H), 4.26-4.16 (m, 1H), 4.03 (dd, 1H), 3.90 (q, 2H), 3.78-3.55 (m, 3H), 2.45 (s, 3H), 2.05-1.74 (m, 3H), 1.71-1.60 (m, 1H), 1.11 (t, 3H).

LC/MS (Method 1, ESIpos): $R_t$=0.67 min, m/z=392 [M+H]$^+$.

Example 420

3-Ethyl-5-methyl-6-[(5-oxo-4,5-dihydro-1H-1,2,4-triazol-1-yl)methyl]-1-(tetrahydrofuran-2-ylmethyl)thieno[2,3-d]pyrimidine-2,4(1H,3H)-dione (Enantiomer 1)

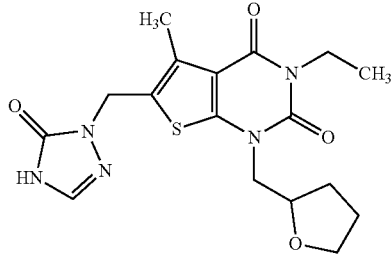

193 mg (0.493 mmol) of the racemic compound from Ex. 419 were dissolved in a mixture of 8 ml of ethanol and 5 ml of acetonitrile and, in 17 portions, separated into the enantiomers by preparative HPLC on a chiral phase [column: Daicel Chiralcel OX-H, 5 μm, 250 mm×20 mm; eluent: n-heptane/ethanol 3:7; flow rate: 15 ml/min; temperature: 25° C.; detection: 210 nm]. After concentration of the product fractions and drying of the solids under high vacuum, 42 mg (43% of theory) of Enantiomer 1 were obtained (99.0% ee, chiral analytical HPLC).

$^1$H-NMR (400 MHz, DMSO-$d_6$, δ/ppm): 11.59 (br. s, 1H), 7.83 (s, 1H), 4.92 (s, 2H), 4.27-4.15 (m, 1H), 4.03 (dd, 1H), 3.90 (q, 2H), 3.78-3.55 (m, 3H), 2.45 (s, 3H), 2.04-1.73 (m, 3H), 1.71-1.59 (m, 1H), 1.11 (t, 3H).

Chiral analytical HPLC [column: Daicel Chiralpak OX-H, 3 μm, 50 mm×4.6 mm; eluent: n-heptane/ethanol 1:1; flow rate: 1 ml/min; temperature: 40° C.; detection: 220 nm]: $R_t$=2.24 min.

Example 421

3-Ethyl-5-methyl-6-[(5-oxo-4,5-dihydro-1H-1,2,4-triazol-1-yl)methyl]-1-(tetrahydrofuran-2-ylmethyl)thieno[2,3-d]pyrimidine-2,4(1H,3H)-dione (Enantiomer 2)

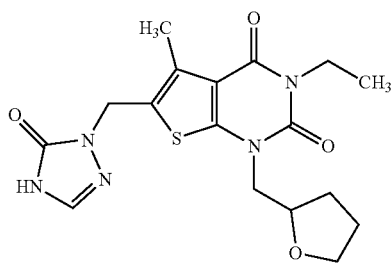

193 mg (0.493 mmol) of the racemic compound from Ex. 419 were dissolved in a mixture of 8 ml of ethanol and 5 ml of acetonitrile and, in 17 portions, separated into the enantiomers by preparative HPLC on a chiral phase [column: Daicel Chiralcel OX-H, 5 μm, 250 mm×20 mm; eluent: n-heptane/ethanol 3:7; flow rate: 15 ml/min; temperature: 25° C.; detection: 210 nm]. After concentration of the product fractions and drying of the solids under high vacuum, 41 mg (42% of theory) of Enantiomer 2 were obtained (98.1% ee, chiral analytical HPLC).

$^1$H-NMR (400 MHz, DMSO-$d_6$, δ/ppm): 11.58 (br. s, 1H), 7.83 (s, 1H), 4.92 (s, 2H), 4.28-4.15 (m, 1H), 4.03 (dd, 1H), 3.90 (q, 2H), 3.78-3.56 (m, 3H), 2.45 (s, 3H), 2.05-1.74 (m, 3H), 1.69-1.61 (m, 1H), 1.11 (t, 3H).

Chiral analytical HPLC [column: Daicel Chiralpak OX-H, 3 μm, 50 mm×4.6 mm; eluent: n-heptane/ethanol 1:1; flow rate: 1 ml/min; temperature: 40° C.; detection: 220 nm]: $R_t$=2.84 min.

Example 422

1-(Fluoromethyl)-3-isopropyl-5-methyl-6-[(5-oxo-4,5-dihydro-1H-1,2,4-triazol-1-yl)methyl]thieno[2,3-d]pyrimidine-2,4(1H,3H)-dione

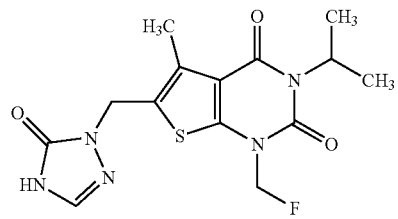 [SMILES: Cc1c(Cn2nc[nH]c2=O)sc2c1c(=O)n(C(C)C)c(=O)n2CF]

180 mg (0.439 mmol) of the compound from Example 417 were dissolved in 5 ml of 1,4-dioxane, and 70 mg (0.264 mmol) of triphenylphosphine were added. To this solution were then added 35 μl (0.922 mmol) of formic acid, 153 μl (1.10 mmol) of triethylamine and 76 mg (0.066 mmol) of tetrakis(triphenylphosphine)palladium(0). The mixture was heated to 125° C. in a microwave oven (Biotage Initiator with dynamic control of irradiation power) for 18 h. The reaction mixture was then added to semisaturated aqueous sodium chloride solution (70 ml). The mixture was extracted with ethyl acetate. The combined organic phases were dried over sodium sulphate, filtered and concentrated. The residue was dissolved in 6 ml of DMSO and this solution was purified by means of preparative HPLC (Method 14). Combination of the product fractions and freeze-drying gave 49 mg (31% of theory) of the title compound.

$^1$H-NMR (400 MHz, DMSO-$d_6$, δ/ppm): 11.65 (br. s, 1H), 7.85 (s, 1H), 5.97 (d, 2H), 5.11 (quin, 1H), 4.96 (s, 2H), 2.45 (s, 3H), 1.40 (d, 6H).

LC/MS (Method 1, ESIpos): $R_t$=0.93 min, m/z=354 [M+H]$^+$.

Example 423

1-(3-Fluoropropyl)-3-isopropyl-5-methyl-6-[(5-oxo-4,5-dihydro-1H-1,2,4-triazol-1-yl)methyl]thieno[2,3-d]pyrimidine-2,4(1H,3H)-dione

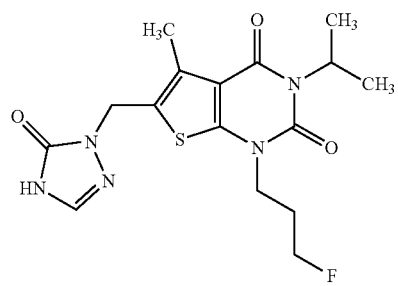 [SMILES: Cc1c(Cn2nc[nH]c2=O)sc2c1c(=O)n(C(C)C)c(=O)n2CCCF]

188 mg (0.419 mmol) of the compound from Example 418 were dissolved in 7.5 ml of 1,4-dioxane, and 66 mg (0.252 mmol) of triphenylphosphine were added. To this solution were then added 33 µl (0.88 mmol) of formic acid, 146 µl (1.05 mmol) of triethylamine and 73 mg (0.063 mmol) of tetrakis(triphenylphosphine)palladium(0). The mixture was heated to 120° C. in a microwave oven (Biotage Initiator with dynamic control of irradiation power) for 120 h. The reaction mixture was then added to semisaturated aqueous sodium chloride solution (70 ml). The mixture was extracted with ethyl acetate. The combined organic phases were dried over sodium sulphate, filtered and concentrated. The residue was dissolved in 3 ml of DMSO and this solution was purified by means of preparative HPLC (Method 14). Combination of the product fractions and freeze-drying gave 85 mg (45% of theory) of the title compound.

$^1$H-NMR (400 MHz, DMSO-$d_6$, δ/ppm): 11.61 (br. s, 1H), 7.84 (s, 1H), 5.12 (sept, 1H), 4.93 (s, 2H), 4.58 (t, 1H), 4.46 (t, 1H), 3.93 (t, 2H), 2.44 (s, 3H), 2.10-1.95 (m, 2H), 1.39 (d, 6H).

LC/MS (Method 1, ESIpos): $R_t$=0.95 min, m/z=382 [M+H]$^+$.

Example 424

3-Isopropyl-5-methyl-6-[(5-oxo-4,5-dihydro-1H-1,2,4-triazol-1-yl)methyl]-1-(tetrahydrofuran-2-ylmethyl)thieno[2,3-d]pyrimidine-2,4(1H,3H)-dione (racemate)

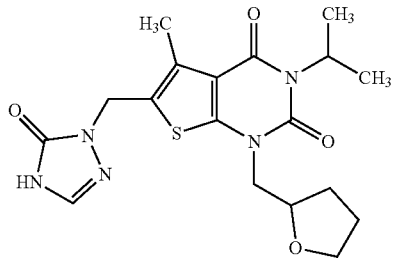

Analogously to the method described in Ex. 419, 366 mg (0.613 mmol, 83% purity) of the compound from Ex. 476A and 16.6 ml (151 mmol) of trimethyl orthoformate were used to prepare 146 mg (58% of theory) of the title compound.

$^1$H-NMR (400 MHz, DMSO-$d_6$, δ/ppm): 11.59 (br. s, 1H), 7.83 (s, 1H), 5.13 (sept, 1H), 4.91 (s, 2H), 4.25-4.14 (m, 1H), 4.02 (dd, 1H), 3.78-3.69 (m, 1H), 3.67-3.56 (m, 2H), 2.44 (s, 3H), 2.03-1.75 (m, 3H), 1.70-1.59 (m, 1H), 1.39 (dd, 6H).

LC/MS (Method 17, ESIpos): $R_t$=1.40 min, m/z=406.15 [M+H]$^+$.

Example 425

3-Isopropyl-5-methyl-6-[(5-oxo-4,5-dihydro-1H-1,2,4-triazol-1-yl)methyl]-1-(tetrahydrofuran-2-ylmethyl)thieno[2,3-d]pyrimidine-2,4(1H,3H)-dione (Enantiomer 1)

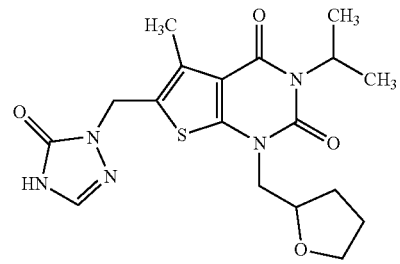 [SMILES: Cc1c(Cn2nc[nH]c2=O)sc2c1c(=O)n(C(C)C)c(=O)n2CC1CCCO1]

139 mg (0.343 mmol) of the racemic compound from Ex. 424 were dissolved in a mixture of 8 ml of ethanol and 4 ml of acetonitrile and, in 24 portions, separated into the enantiomers by preparative HPLC on a chiral phase [column: Daicel Chiralcel OX-H, 5 µm, 250 mm×20 mm; eluent: n-heptane/ethanol 3:7; flow rate: 15 ml/min; temperature: 25° C.; detection: 210 nm]. After concentration of the product fractions and drying of the solids under high vacuum, 68 mg (97% of theory) of Enantiomer 1 were obtained (99.0% ee, chiral analytical HPLC).

$^1$H-NMR (400 MHz, DMSO-$d_6$, δ/ppm): 11.58 (br. s, 1H), 7.83 (s, 1H), 5.13 (sept, 1H), 4.91 (s, 2H), 4.26-4.13 (m, 1H), 4.02 (dd, 1H), 3.79-3.69 (m, 1H), 3.67-3.55 (m, 2H), 2.44 (s, 3H), 2.03-1.74 (m, 3H), 1.71-1.57 (m, 1H), 1.39 (dd, 6H).

Chiral analytical HPLC [column: Daicel Chiraltek OX-H, 3 µm, 50 mm×4.6 mm; eluent: isohexane/ethanol 1:1; flow rate: 1 ml/min; temperature: 40° C.; detection: 220 nm]: $R_t$=3.74 min.

Example 426

3-Isopropyl-5-methyl-6-[(5-oxo-4,5-dihydro-1H-1,2,4-triazol-1-yl)methyl]-1-(tetrahydrofuran-2-ylmethyl)thieno[2,3-d]pyrimidine-2,4(1H,3H)-dione (Enantiomer 2)

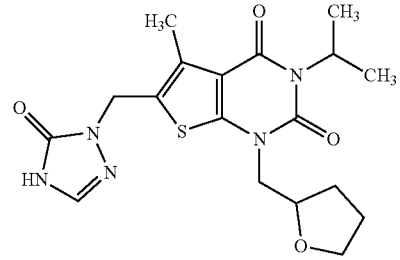 [SMILES: Cc1c(Cn2nc[nH]c2=O)sc2c1c(=O)n(C(C)C)c(=O)n2CC1CCCO1]

139 mg (0.343 mmol) of the racemic compound from Ex. 424 were dissolved in a mixture of 8 ml of ethanol and 4 ml of acetonitrile and, in 24 portions, separated into the enantiomers by preparative HPLC on a chiral phase [column: Daicel Chiralcel OX-H, 5 µm, 250 mm×20 mm; eluent: n-heptane/ethanol 3:7; flow rate: 15 ml/min; temperature: 25° C.; detection: 210 nm]. After concentration of the product fractions and drying of the solids under high vacuum, 67 mg (96% of theory) of Enantiomer 2 were obtained (98.8% ee, chiral analytical HPLC).

¹H-NMR (400 MHz, DMSO-d₆, δ/ppm): 11.58 (br. s, 1H), 7.83 (s, 1H), 5.13 (sept, 1H), 4.91 (s, 2H), 4.25-4.14 (m, 1H), 4.02 (dd, 1H), 3.79-3.69 (m, 1H), 3.67-3.55 (m, 2H), 2.44 (s, 3H), 2.03-1.75 (m, 3H), 1.71-1.58 (m, 1H), 1.39 (dd, 6H).

Chiral analytical HPLC [column: Daicel Chiraltek OX-H, 3 μm, 50 mm×4.6 mm; eluent: isohexane/ethanol 1:1; flow rate: 1 ml/min; temperature: 40° C.; detection: 220 nm]: $R_t$=5.16 min.

Example 427

3-(2,2-Dimethylpropyl)-5-methyl-6-[(5-oxo-4,5-dihydro-1H-1,2,4-triazol-1-yl)methyl]-1-(3,3,3-trifluoropropyl)thieno[2,3-d]pyrimidine-2,4(1H,3H)-dione

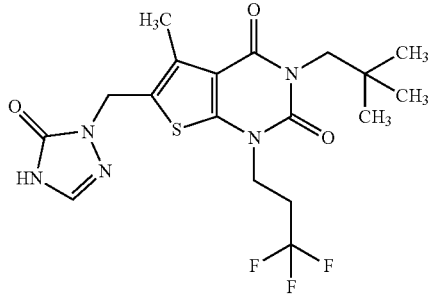 [SMILES: Cc1c(Cn2nc[nH]c2=O)sc2c1c(=O)n(CC(C)(C)C)c(=O)n2CCC(F)(F)F]

Analogously to the method described in Ex. 419, 154 mg (0.262 mmol, 91% purity) of the compound from Ex. 477A and 6.4 ml (62.6 mmol) of trimethyl orthoformate were used to prepare 95 mg (81% of theory) of the title compound.

¹H-NMR (500 MHz, DMSO-d₆, δ/ppm): 11.61 (br. s, 1H), 7.84 (s, 1H), 4.95 (s, 2H), 4.08 (t, 2H), 3.81 (br. s, 2H), 2.83-2.67 (m, 2H), 2.45 (s, 3H), 0.89 (s, 9H).

LC/MS (Method 17, ESIpos): $R_t$=1.81 min, m/z=446.15 [M+H]⁺.

Example 428

3-(2,2-Dimethylpropyl)-1-(2-methoxyethyl)-5-methyl-6-[(5-oxo-4,5-dihydro-1H-1,2,4-triazol-1-yl)methyl]thieno[2,3-d]pyrimidine-2,4(1H,3H)-dione

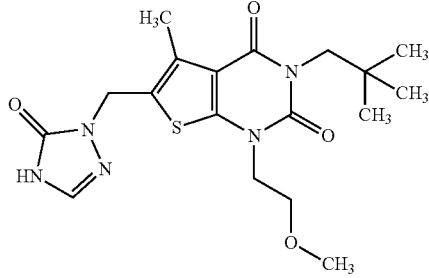

Analogously to the method described in Ex. 419, 120 mg (0.222 mmol, 92% purity) of the compound from Ex. 478A and 5.3 ml (53.1 mmol) of trimethyl orthoformate were used to obtain 35 mg (38% of theory) of the title compound.

¹H-NMR (400 MHz, DMSO-d₆, δ/ppm): 11.60 (br. s, 1H), 7.84 (s, 1H), 4.93 (s, 2H), 4.00 (t, 2H), 3.81 (s, 2H), 3.61 (t, 2H), 3.22 (s, 3H), 2.44 (s, 3H), 0.88 (s, 9H).

LC/MS (Method 17, ESIpos): $R_t$=1.52 min, m/z=408.17 [M+H]⁺.

Example 429

3-(2,2-Dimethylpropyl)-5-methyl-6-[(5-oxo-4,5-dihydro-1H-1,2,4-triazol-1-yl)methyl]-1-(tetrahydrofuran-2-ylmethyl)thieno[2,3-d]pyrimidine-2,4(1H, 3H)-dione (racemate)

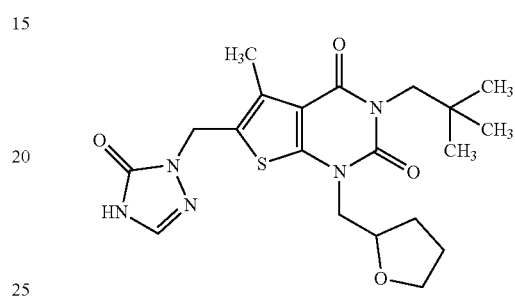

Analogously to the method described in Ex. 419, 530 mg (0.779 mmol, 77% purity) of the compound from Ex. 479A and 20 ml (186 mmol) of trimethyl orthoformate were used to obtain 124 mg (36% of theory) of the title compound.

¹H-NMR (400 MHz, DMSO-d₆, δ/ppm): 11.60 (br. s, 1H), 7.84 (s, 1H), 4.93 (s, 2H), 4.26-4.15 (m, 1H), 4.01 (dd, 1H), 3.81 (br. s, 2H), 3.76-3.65 (m, 2H), 3.64-3.55 (m, 1H), 2.44 (s, 3H), 2.03-1.74 (m, 3H), 1.71-1.59 (m, 1H), 0.88 (s, 9H).

LC/MS (Method 17, ESIpos): $R_t$=1.64 min, m/z=434.19 [M+H]⁺.

Example 430

3-(2,2-Dimethylpropyl)-5-methyl-6-[(5-oxo-4,5-dihydro-1H-1,2,4-triazol-1-yl)methyl]-1-(tetrahydrofuran-2-ylmethyl)thieno[2,3-d]pyrimidine-2,4(1H, 3H)-dione (Enantiomer 1)

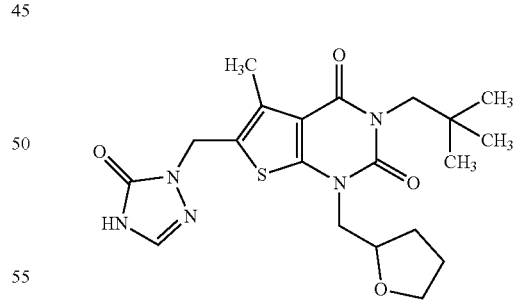

120 mg (0.277 mmol) of the racemic compound from Ex. 429 were dissolved in 7 ml of ethanol and, in 14 portions, separated into the enantiomers by preparative HPLC on a chiral phase [column: Daicel Chiralpak AZ-H, 5 μm, 250 mm×20 mm; eluent: n-heptane/ethanol 1:1; flow rate: 15 ml/min; temperature: 40° C.; detection: 210 nm]. After concentration of the product fractions and drying of the solids under high vacuum, 54 mg (90% of theory) of Enantiomer 1 were obtained (99.0% ee, chiral analytical HPLC).

¹H-NMR (400 MHz, DMSO-d₆, δ/ppm): 11.60 (br. s, 1H), 7.83 (s, 1H), 4.92 (s, 2H), 4.26-4.15 (m, 1H), 4.01 (dd, 1H), 3.81 (br. s, 2H), 3.76-3.65 (m, 2H), 3.64-3.55 (m, 1H), 2.44 (s, 3H), 2.04-1.74 (m, 3H), 1.71-1.59 (m, 1H), 0.88 (s, 9H).

Chiral analytical HPLC [column: Daicel Chiralpak AZ-H, 3 μm, 50 mm×4.6 mm; eluent: isohexane/ethanol 1:1; flow rate: 1 ml/min; temperature: 40° C.; detection: 220 nm]: $R_t$=1.83 min.

Example 431

3-(2,2-Dimethylpropyl)-5-methyl-6-[(5-oxo-4,5-dihydro-1H-1,2,4-triazol-1-yl)methyl]-1-(tetrahydrofuran-2-ylmethyl)thieno[2,3-d]pyrimidine-2,4(1H,3H)-dione (Enantiomer 2)

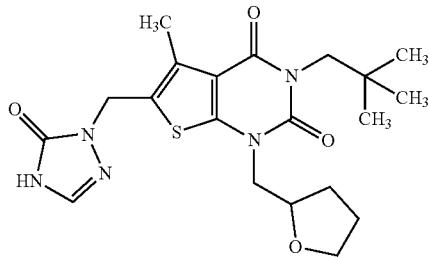 [SMILES: Cc1c(Cn2nc[nH]c2=O)sc2c1c(=O)n(CC(C)(C)C)c(=O)n2CC1CCCO1]

120 mg (0.277 mmol) of the racemic compound from Ex. 429 were dissolved in 7 ml of ethanol and, in 14 portions, separated into the enantiomers by preparative HPLC on a chiral phase [column: Daicel Chiralpak AZ-H, 5 μm, 250 mm×20 mm; eluent: n-heptane/ethanol 1:1; flow rate: 15 ml/min; temperature: 40° C.; detection: 210 nm]. After concentration of the product fractions and drying of the solids under high vacuum, 54 mg (90% of theory) of Enantiomer 2 were obtained (99.0% ee, chiral analytical HPLC).

¹H-NMR (400 MHz, DMSO-d₆, δ/ppm): 11.59 (br. s, 1H), 7.82 (s, 1H), 4.92 (s, 2H), 4.25-4.15 (m, 1H), 4.01 (dd, 1H), 3.81 (br. s, 2H), 3.76-3.65 (m, 2H), 3.64-3.55 (m, 1H), 2.44 (s, 3H), 2.03-1.74 (m, 3H), 1.72-1.60 (m, 1H), 0.88 (s, 9H).

Chiral analytical HPLC [column: Daicel Chiralpak AZ-H, 3 μm, 50 mm×4.6 mm; eluent: isohexane/ethanol 1:1; flow rate: 1 ml/min; temperature: 40° C.; detection: 220 nm]: $R_t$=2.72 min.

Example 432

5-Methyl-6-[(5-oxo-4,5-dihydro-1H-1,2,4-triazol-1-yl)methyl]-3-(2,2,2-trifluoroethyl)-1-(3,3,3-trifluoropropyl)thieno[2,3-d]pyrimidine-2,4(1H,3H)-dione

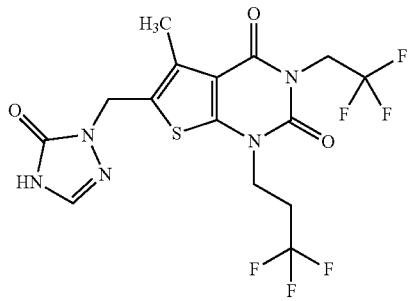 [SMILES: Cc1c(Cn2nc[nH]c2=O)sc2c1c(=O)n(CC(F)(F)F)c(=O)n2CCC(F)(F)F]

Analogously to the method described in Ex. 419, 169 mg (0.306 mmol) of the compound from Ex. 480A and 8 ml (73.1 mmol) of trimethyl orthoformate were used to obtain 88 mg (62% of theory) of the title compound.

¹H-NMR (400 MHz, DMSO-d₆, δ/ppm): 11.62 (br. s, 1H), 7.85 (s, 1H), 4.98 (s, 2H), 4.70 (q, 2H), 4.12 (t, 2H), 2.85-2.68 (m, 2H), 2.46 (s, 3H).

LC/MS (Method 1, ESIpos): $R_t$=0.83 min, m/z=458 [M+H]⁺.

Example 433

1-(2-Methoxyethyl)-5-methyl-6-[(5-oxo-4,5-dihydro-1H-1,2,4-triazol-1-yl)methyl]-3-(2,2,2-trifluoroethyl)thieno[2,3-d]pyrimidine-2,4(1H,3H)-dione

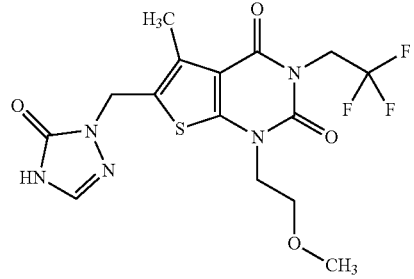 [SMILES: COCCn1c(=O)n(CC(F)(F)F)c(=O)c2c(C)c(Cn3nc[nH]c3=O)sc21]

Analogously to the method described in Ex. 419, 180 mg (0.332 mmol, 94% purity) of the compound from Ex. 481A and 8 ml (73.1 mmol) of trimethyl orthoformate were used to obtain 87 mg (62% of theory) of the title compound.

¹H-NMR (500 MHz, DMSO-d₆, δ/ppm): 11.63 (br. s, 1H), 7.85 (s, 1H), 4.96 (s, 2H), 4.70 (q, 2H), 4.05 (t, 2H), 3.63 (t, 2H), 3.23 (s, 3H), 2.45 (s, 3H).

LC/MS (Method 1, ESIpos): $R_t$=0.76 min, m/z=420 [M+H]⁺.

Example 434

5-Methyl-6-[(5-oxo-4,5-dihydro-H-1,2,4-triazol-1-yl)methyl]-1-(tetrahydrofuran-2-ylmethyl)-3-(2,2,2-trifluoroethyl)thieno[2,3-d]pyrimidine-2,4(1H,3H)-dione (racemate)

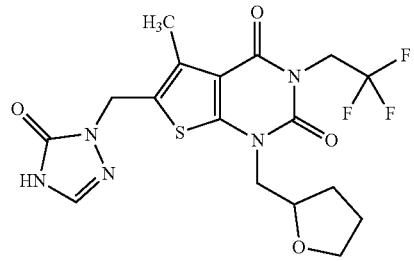 [SMILES: Cc1c(Cn2nc[nH]c2=O)sc2c1c(=O)n(CC(F)(F)F)c(=O)n2CC1CCCO1]

Analogously to the method described in Ex. 419, 400 mg (0.739 mmol) of the compound from Ex. 482A and 20 ml (183 mmol) of trimethyl orthoformate were used to obtain 283 mg (85% of theory) of the title compound.

¹H-NMR (400 MHz, DMSO-d₆, δ/ppm): 11.61 (br. s, 1H), 7.84 (s, 1H), 4.95 (s, 2H), 4.69 (q, 2H), 4.25-4.15 (m, 1H), 4.06 (dd, 1H), 3.78-3.68 (m, 2H), 3.65-3.56 (m, 1H), 2.45 (s, 3H), 2.04-1.75 (m, 3H), 1.72-1.61 (m, 1H).

LC/MS (Method 1, ESIpos): $R_t$=0.76 min, m/z=446 [M+H]$^+$.

Example 435

5-Methyl-6-[(5-oxo-4,5-dihydro-1H-1,2,4-triazol-1-yl)methyl]-1-(tetrahydrofuran-2-ylmethyl)-3-(2,2,2-trifluoroethyl)thieno[2,3-d]pyrimidine-2,4(1H,3H)-dione (Enantiomer 1)

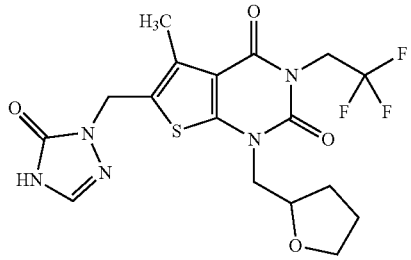 [SMILES: Cc1c(Cn2nc[nH]c2=O)sc2c1c(=O)n(CC(F)(F)F)c(=O)n2CC1CCCO1]

261 mg (0.586 mmol) of the racemic compound from Ex. 434 were dissolved in a mixture of 5 ml of methanol and 10 ml of acetonitrile and, in 15 portions, separated into the enantiomers by preparative HPLC on a chiral phase [column: Daicel Chiralpak AZ-H, 5 μm, 250 mm×20 mm; eluent: n-heptane/ethanol 1:3; flow rate: 15 ml/min; temperature: 25° C.; detection: 220 nm]. After concentration of the product fractions and drying of the solids under high vacuum, 86 mg (65% of theory) of Enantiomer 1 were obtained (99.4% ee, chiral analytical HPLC).

$^1$H-NMR (400 MHz, DMSO-$d_6$, δ/ppm): 11.61 (br. s, 1H), 7.84 (s, 1H), 4.95 (s, 2H), 4.70 (q, 2H), 4.26-4.15 (m, 1H), 4.06 (dd, 1H), 3.78-3.68 (m, 2H), 3.65-3.55 (m, 1H), 2.45 (s, 3H), 2.05-1.75 (m, 3H), 1.71-1.60 (m, 1H).

Chiral analytical HPLC [column: Daicel Chiraltek AZ-3, 3 μm, 50 mm×4.6 mm; eluent: isohexane/ethanol 1:1; flow rate: 1 ml/min; temperature: 40° C.; detection: 220 nm]: $R_t$=3.28 min.

Example 436

5-Methyl-6-[(5-oxo-4,5-dihydro-1H-1,2,4-triazol-1-yl)methyl]-1-(tetrahydrofuran-2-ylmethyl)-3-(2,2,2-trifluoroethyl)thieno[2,3-d]pyrimidine-2,4(1H,3H)-dione (Enantiomer 2)

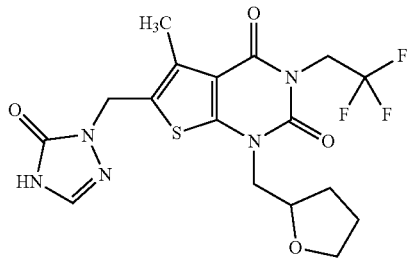 [SMILES: Cc1c(Cn2nc[nH]c2=O)sc2c1c(=O)n(CC(F)(F)F)c(=O)n2CC1CCCO1]

261 mg (0.586 mmol) of the racemic compound from Ex. 434 were dissolved in a mixture of 5 ml of methanol and 10 ml of acetonitrile and, in 15 portions, separated into the enantiomers by preparative HPLC on a chiral phase [column: Daicel Chiralpak AZ-H, 5 μm, 250 mm×20 mm; eluent: n-heptane/ethanol 1:3; flow rate: 15 ml/min; temperature: 25° C.; detection: 220 nm]. After concentration of the product fractions and drying of the solids under high vacuum, 110 mg (84% of theory) of Enantiomer 2 were obtained (99.4% ee, chiral analytical HPLC).

$^1$H-NMR (400 MHz, DMSO-$d_6$, δ/ppm): 11.61 (br. s, 1H), 7.84 (s, 1H), 4.95 (s, 2H), 4.70 (q, 2H), 4.25-4.16 (m, 1H), 4.06 (dd, 1H), 3.77-3.68 (m, 2H), 3.65-3.56 (m, 1H), 2.45 (s, 3H), 2.04-1.75 (m, 3H), 1.72-1.60 (m, 1H).

Chiral analytical HPLC [column: Daicel Chiraltek AZ-3, 3 μm, 50 mm×4.6 mm; eluent: isohexane/ethanol 1:1; flow rate: 1 ml/min; temperature: 40° C.; detection: 220 nm]: $R_t$=5.29 min.

Example 437

5-Methyl-6-[(5-oxo-4,5-dihydro-1H-1,2,4-triazol-1-yl)methyl]-3-(1,1,1-trifluoropropan-2-yl)-1-(3,3,3-trifluoropropyl)thieno[2,3-d]pyrimidine-2,4(1H,3H)-dione (racemate)

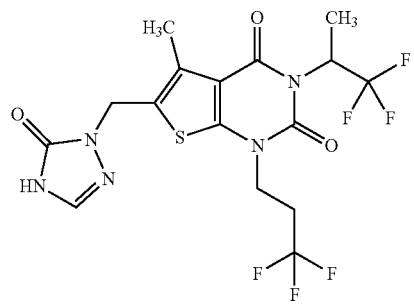 [SMILES: Cc1c(Cn2nc[nH]c2=O)sc2c1c(=O)n(C(C)C(F)(F)F)c(=O)n2CCC(F)(F)F]

Analogously to the method described in Ex. 419, 390 mg (0.695 mmol) of the compound from Ex. 483A and 20 ml (183 mmol) of trimethyl orthoformate were used to obtain 160 mg (48% of theory) of the title compound.

$^1$H-NMR (400 MHz, DMSO-$d_6$, δ/ppm): 11.61 (s, 1H), 7.85 (s, 1H), 5.82-5.45 (m, 1H), 4.97 (s, 2H), 4.18-4.00 (m, 2H), 2.85-2.69 (m, 2H), 2.46 (s, 3H), 1.63 (br. d, 3H).

LC/MS (Method 17, ESIpos): $R_t$=1.69 min, m/z=472.09 [M+H]$^+$.

Example 438

1-(2-Methoxyethyl)-5-methyl-6-[(5-oxo-4,5-dihydro-1H-1,2,4-triazol-1-yl)methyl]-3-(1,1,1-trifluoropropan-2-yl)thieno[2,3-d]pyrimidine-2,4(1H,3H)-dione (racemate)

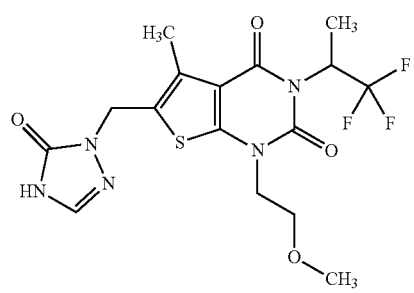 [SMILES: COCCn1c(=O)n(C(C)C(F)(F)F)c(=O)c2c(C)c(Cn3nc[nH]c3=O)sc21]

Analogously to the method described in Ex. 419, 405 mg (0.774 mmol) of the compound from Ex. 484A and 20 ml (183 mmol) of trimethyl orthoformate were used to obtain two fractions of the title compound: 37 mg (11% of theory, 99% purity) and 208 mg (55% of theory, 90% purity)

$^1$H-NMR (400 MHz, DMSO-$d_6$, δ/ppm): 11.60 (br. s, 1H), 7.84 (s, 1H), 5.83-5.47 (m, 1H), 4.94 (s, 2H), 4.09-3.93 (m, 2H), 3.69-3.55 (m, 2H), 3.23 (s, 3H), 2.44 (s, 3H), 1.63 (br. d, 3H).

LC/MS (Method 17, ESIpos): $R_t$=1.44 min, m/z=434.11 [M+H]$^+$.

Example 439

3-(2-Methoxyethyl)-5-methyl-6-[(5-oxo-4,5-dihydro-1H-1,2,4-triazol-1-yl)methyl]-1-(3,3,3-trifluoropropyl)thieno[2,3-d]pyrimidine-2,4(1H,3H)-dione

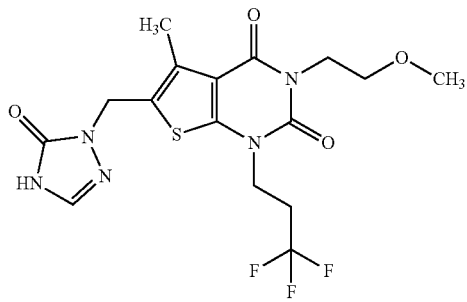

Analogously to the method described in Ex. 419, 185 mg (0.343 mmol, 97% purity) of the compound from Ex. 485A and 10 ml (91.4 mmol) of trimethyl orthoformate were used to obtain 115 mg (77% of theory) of the title compound.

$^1$H-NMR (400 MHz, DMSO-$d_6$, δ/ppm): 11.61 (br. s, 1H), 7.84 (s, 1H), 4.96 (s, 2H), 4.09 (t, 2H), 4.05 (t, 2H), 3.49 (t, 2H), 3.23 (s, 3H), 2.83-2.65 (m, 2H), 2.46 (s, 3H).

LC/MS (Method 1, ESIpos): $R_t$=0.71 min, m/z=434 [M+H]$^+$.

Example 440

3-(2-Methoxypropyl)-5-methyl-6-[(5-oxo-4,5-dihydro-1H-1,2,4-triazol-1-yl)methyl]-1-(3,3,3-trifluoropropyl)thieno[2,3-d]pyrimidine-2,4(1H,3H)-dione (racemate)

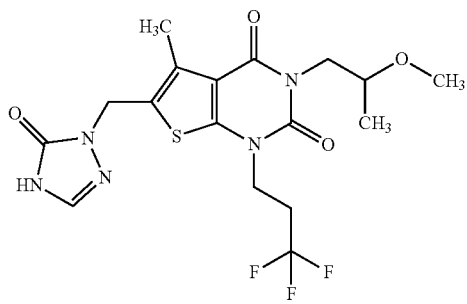 [SMILES: COC(C)Cn1c(=O)c2c(C)c(Cn3nc[nH]c3=O)sc2n(CCC(F)(F)F)c1=O]

340 mg (0.626 mmol) of the compound from Ex. 486A were dissolved in a mixture of 17 ml each of methanol and trimethyl orthoformate, and 626 μl (2.51 mmol) of a 4 M solution of hydrogen chloride in dioxane were added at RT. After about 16 h of reaction time, a further 626 μl (2.51 mmol) of the 4 M solution of hydrogen chloride and dioxane were added and, after a further 2 h, the same amount again. After a total reaction time of about 24 h, the reaction mixture was admixed with water and extracted with ethyl acetate. The organic extract was concentrated and the remaining residue was purified by means of preparative HPLC (Method 8). After concentration of the product fractions and drying under high vacuum, 222 mg (79% of theory) of the title compound were obtained.

$^1$H-NMR (400 MHz, DMSO-$d_6$, δ/ppm): 11.61 (br. s, 1H), 7.84 (s, 1H), 4.96 (s, 2H), 4.17-4.03 (m, 2H), 4.04 (dd, 1H), 3.76 (dd, 1H), 3.62 (sext, 1H), 3.21 (s, 3H), 2.83-2.66 (m, 2H), 2.46 (s, 3H), 1.04 (d, 3H).

LC/MS (Method 1, ESIpos): $R_t$=0.75 min, m/z=448 [M+H]$^+$.

Example 441

3-(2-Methoxypropyl)-5-methyl-6-[(5-oxo-4,5-dihydro-1H-1,2,4-triazol-1-yl)methyl]-1-(3,3,3-trifluoropropyl)thieno[2,3-d]pyrimidine-2,4(1H,3H)-dione (Enantiomer 1)

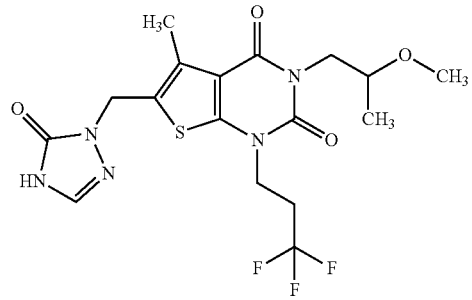 [SMILES: COC(C)Cn1c(=O)c2c(C)c(Cn3nc[nH]c3=O)sc2n(CCC(F)(F)F)c1=O]

202 mg (0.451 mmol) of the racemic compound from Ex. 440 were dissolved in 6 ml of ethanol and, in 24 portions, separated into the enantiomers by preparative HPLC on a chiral phase [column: Daicel Chiralcel OX-H, 5 μm, 250 mm×20 mm; eluent: n-heptane/ethanol 1:1; flow rate: 15 ml/min; temperature: 40° C.; detection: 220 nm]. After concentration of the product fractions and drying of the solids under high vacuum, 78 mg (77% of theory) of Enantiomer 1 were obtained (99.0% ee, chiral analytical HPLC).

$^1$H-NMR (400 MHz, DMSO-$d_6$, δ/ppm): 11.59 (br. s, 1H), 7.84 (s, 1H), 4.96 (s, 2H), 4.13-4.05 (m, 2H), 4.04 (dd, 1H), 3.76 (dd, 1H), 3.62 (sext, 1H), 3.21 (s, 3H), 2.82-2.67 (m, 2H), 2.46 (s, 3H), 1.04 (d, 3H).

Chiral analytical HPLC [column: Daicel Chiralcel OX-H, 5 μm, 250 mm×4.6 mm; eluent: isohexane/ethanol 1:1; flow rate: 1 ml/min; temperature: 40° C.; detection: 220 nm]: $R_t$=6.26 min.

Example 442

3-(2-Methoxypropyl)-5-methyl-6-[(5-oxo-4,5-dihydro-1H-1,2,4-triazol-1-yl)methyl]-1-(3,3,3-trifluoropropyl)thieno[2,3-d]pyrimidine-2,4(1H,3H)-dione (Enantiomer 2)

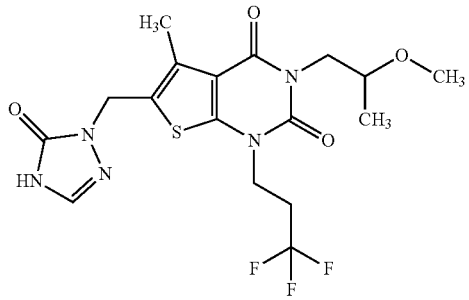 [SMILES: COC(C)Cn1c(=O)c2c(C)c(Cn3nc[nH]c3=O)sc2n(CCC(F)(F)F)c1=O]

202 mg (0.451 mmol) of the racemic compound from Ex. 440 were dissolved in 6 ml of ethanol and, in 24 portions, separated into the enantiomers by preparative HPLC on a chiral phase [column: Daicel Chiralcel OX-H, 5 µm, 250 mm×20 mm; eluent: n-heptane/ethanol 1:1; flow rate: 15 ml/min; temperature: 40° C.; detection: 220 nm]. After concentration of the product fractions and drying of the solids under high vacuum, 92 mg (91% of theory) of Enantiomer 2 were obtained (99.0% ee, chiral analytical HPLC).

$^1$H-NMR (400 MHz, DMSO-$d_6$, δ/ppm): 11.60 (br. s, 1H), 7.84 (s, 1H), 4.96 (s, 2H), 4.13-4.04 (m, 2H), 4.04 (dd, 1H), 3.76 (dd, 1H), 3.62 (sext, 1H), 3.21 (s, 3H), 2.82-2.67 (m, 2H), 2.46 (s, 3H), 1.04 (d, 3H).

Chiral analytical HPLC [column: Daicel Chiralcel OX-H, 5 µm, 250 mm×4.6 mm; eluent: isohexane/ethanol 1:1; flow rate: 1 ml/min; temperature: 40° C.; detection: 220 nm]: $R_t$=7.94 min.

Example 443

[1-{[3-(2,2-Dimethylpropyl)-5-methyl-2,4-dioxo-1-(3,3,3-trifluoropropyl)-1,2,3,4-tetrahydrothieno[2,3-d]pyrimidin-6-yl]methyl}imidazolidin-2-ylidene]cyanamide

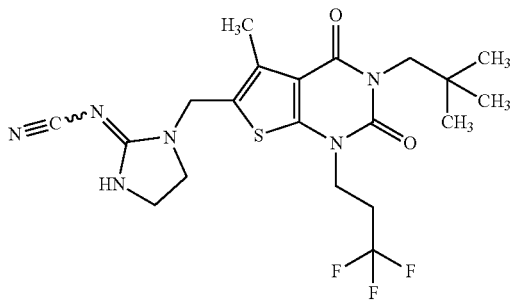 [SMILES: Cc1c(CN2CCNC2=NC#N)sc2c1c(=O)n(CC(C)(C)C)c(=O)n2CCC(F)(F)F]

163 mg (0.12 mmol, 31% purity) of the compound from Ex. 315A were dissolved in 5 ml of DMF, and 28 mg (0.18 mmol) of dimethyl N-cyanodithioiminocarbonate and 33 mg (0.24 mmol) of potassium carbonate were added. The mixture was stirred at 80° C. for 18 h. Thereafter, the reaction mixture was taken up in 30 ml of ethyl acetate. It was washed with 20 ml of saturated sodium hydrogencarbonate solution and with 20 ml of water. The organic phase was dried over sodium sulphate, filtered and concentrated. The residue obtained was dissolved in 3 ml of DMSO and this solution was purified by means of preparative HPLC (Method 14). Combination of the product fractions and freeze-drying gave 15 mg (24% of theory) of the title compound.

$^1$H-NMR (400 MHz, DMSO-$d_6$, δ/ppm): 8.10 (s, 1H), 4.50 (s, 2H), 4.11 (br. t, 2H), 3.81 (br. s, 2H), 3.52-3.38 (m, 4H), 2.83-2.69 (m, 2H), 2.40 (s, 3H), 0.89 (s, 9H).

LC/MS (Method 1, ESIpos): $R_t$=1.29 min, m/z=471 [M+H]$^+$.

Example 444

[1-{[3-(2,2-Dimethylpropyl)-1-(3-fluoropropyl)-5-methyl-2,4-dioxo-1,2,3,4-tetrahydrothieno[2,3-d]pyrimidin-6-yl]methyl}imidazolidin-2-ylidene]cyanamide

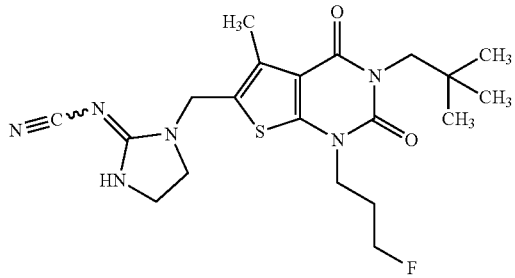 [SMILES: Cc1c(CN2CCNC2=NC#N)sc2c1c(=O)n(CC(C)(C)C)c(=O)n2CCCF]

117 mg (0.225 mmol, 74% purity) of the compound from Ex. 316A were dissolved in 5 ml of DMF, and 52 mg (0.338 mmol) of dimethyl N-cyanodithioiminocarbonate and 62 mg (0.45 mmol) of potassium carbonate were added. The mixture was stirred at 80° C. for 19 h. Thereafter, the reaction mixture was taken up in 30 ml of ethyl acetate. It was washed with 20 ml of saturated sodium hydrogencarbonate solution and with 20 ml of water. The organic phase was dried over sodium sulphate, filtered and concentrated. The residue obtained was dissolved in 3 ml of DMSO and this solution was purified by means of preparative HPLC (Method 14). Combination of the product fractions and freeze-drying gave 68 mg (67% of theory) of the title compound.

$^1$H-NMR (400 MHz, DMSO-$d_6$, δ/ppm): 8.09 (s, 1H), 4.59 (t, 1H), 4.52-4.44 (m, 3H), 3.99 (br. t, 2H), 3.81 (br. s, 2H), 3.51-3.38 (m, 4H), 2.40 (s, 3H), 2.13-1.98 (m, 2H), 0.89 (s, 9H).

LC/MS (Method 1, ESIpos): $R_t$=1.2 min, m/z=435 [M+H]$^+$.

Example 445

[1-{[3-(2,2-Dimethylpropyl)-1-(2-methoxyethyl)-5-methyl-2,4-dioxo-1,2,3,4-tetrahydrothieno[2,3-d]pyrimidin-6-yl]methyl}imidazolidin-2-ylidene]cyanamide

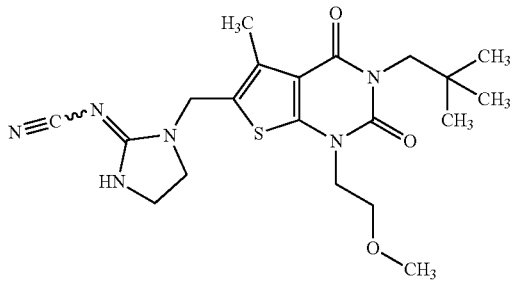 [SMILES: COCCn1c(=O)n(CC(C)(C)C)c(=O)c2c(C)c(CN3CCNC3=NC#N)sc21]

375 mg (0.833 mmol, 85% purity) of the compound from Ex. 317A were dissolved in 10 ml of DMF, and 183 mg (1.25 mmol) of dimethyl N-cyanodithioiminocarbonate and 230 mg (1.67 mmol) of potassium carbonate were added. The mixture was stirred at 80° C. in a microwave oven (Biotage Initiator with dynamic control of irradiation power) for 4 h. Thereafter, the reaction mixture was diluted with ethyl acetate and washed successively with saturated sodium hydrogencarbonate solution, water and saturated sodium chloride solution. After drying over anhydrous magnesium sulphate, the mixture was filtered and concentrated. The crude product was purified by preparative HPLC (Method 8). The product fractions were combined, concentrated and repurified once more by the same method by means of preparative HPLC. Reconcentration of the product fractions and drying under high vacuum gave 82 mg (22% of theory) of the title compound.

$^1$H-NMR (500 MHz, DMSO-$d_6$, δ/ppm): 8.07 (s, 1H), 4.47 (s, 2H), 4.03 (br. t, 2H), 3.81 (br. s, 2H), 3.63 (t, 2H), 3.52-3.38 (m, 4H), 3.23 (s, 3H), 2.39 (s, 3H), 0.89 (s, 9H).

LC/MS (Method 1, ESIpos): $R_t$=0.98 min, m/z=433 [M+H]$^+$.

Example 446

[1-{[3-(2,2-Dimethylpropyl)-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]cyanamide (racemate)

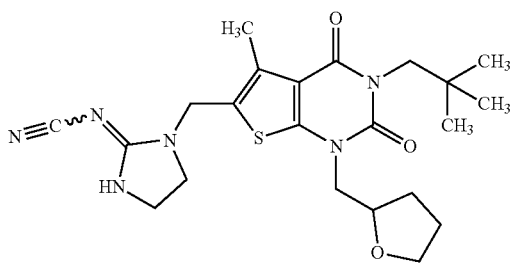 [SMILES: Cc1c(CN2CCNC2=NC#N)sc2c1c(=O)n(CC(C)(C)C)c(=O)n2CC1CCCO1]

560 mg (1.16 mmol, 85% purity) of the compound from Ex. 454A were dissolved in 14 ml of DMF, and 256 mg (1.75 mmol) of dimethyl N-cyanodithioiminocarbonate and 322 mg (2.33 mmol) of potassium carbonate were added. The mixture was stirred at 80° C. in a microwave oven (Biotage Initiator with dynamic control of irradiation power) for 4 h. Thereafter, the reaction mixture was diluted with ethyl acetate and washed successively with saturated sodium hydrogencarbonate solution, water and saturated sodium chloride solution. After drying over anhydrous magnesium sulphate, the mixture was filtered and concentrated. The crude product was purified by preparative HPLC (Method 8). The product fractions were combined, concentrated and dried under high vacuum. 162 mg (30% of theory) of the title compound were obtained.

$^1$H-NMR (500 MHz, DMSO-$d_6$, δ/ppm): 8.07 (s, 1H), 4.47 (s, 2H), 4.27-4.18 (m, 1H), 4.02 (br. dd, 1H), 3.82 (br. s, 2H), 3.78-3.67 (m, 2H), 3.66-3.58 (m, 1H), 3.52-3.36 (m, 4H), 2.39 (s, 3H), 2.03-1.76 (m, 3H), 1.71-1.64 (m, 1H), 0.89 (s, 9H).

LC/MS (Method 17, ESIpos): $R_t$=1.86 min, m/z=459.22 [M+H]$^+$.

Example 447

[1-{[3-(2,2-Dimethylpropyl)-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]cyanamide (Enantiomer 1)

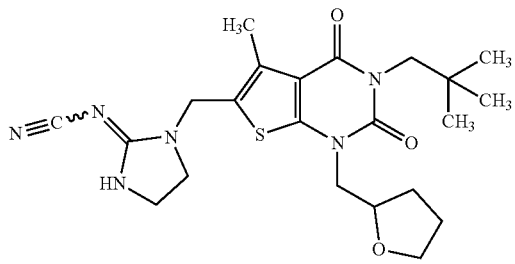 [SMILES: Cc1c(CN2CCNC2=NC#N)sc2c1c(=O)n(CC(C)(C)C)c(=O)n2CC1CCCO1]

155 mg (0.338 mmol) of the racemic compound from Ex. 446 were dissolved in 6 ml of isopropanol and, in 20 portions, separated into the enantiomers by preparative HPLC on a chiral phase [column: Daicel Chiralpak IE, 5 μm, 250 mm×20 mm; eluent: tert-butyl methyl ether/methanol 9:1; flow rate: 15 ml/min; temperature: 30° C.; detection: 220 nm]. After concentration of the product fractions and drying of the solids under high vacuum, 71 mg (91% of theory) of Enantiomer 1 were obtained (99.0% ee, chiral analytical HPLC).

$^1$H-NMR (400 MHz, DMSO-$d_6$, δ/ppm): 8.07 (s, 1H), 4.47 (s, 2H), 4.27-4.16 (m, 1H), 4.02 (dd, 1H), 3.82 (br. s, 2H), 3.78-3.67 (m, 2H), 3.65-3.57 (m, 1H), 3.52-3.37 (m, 4H), 2.39 (s, 3H), 2.04-1.75 (m, 3H), 1.74-1.61 (m, 1H), 0.89 (s, 9H).

Chiral analytical HPLC [column: Daicel Chiraltek IE, 5 μm, 250 mm×4.6 mm; eluent: tert-butyl methyl ether/methanol 9:1; flow rate: 1 ml/min; temperature: 30° C.; detection: 220 nm]: $R_t$=9.14 min.

Example 448

[1-{[3-(2,2-Dimethylpropyl)-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]cyanamide (Enantiomer 2)

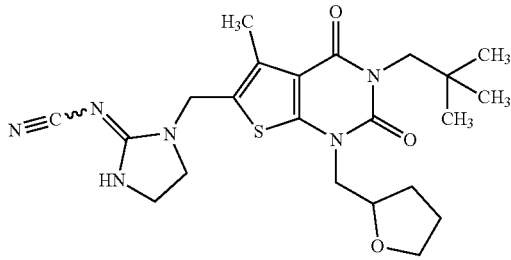 [SMILES: Cc1c(CN2CCNC2=NC#N)sc2c1c(=O)n(CC(C)(C)C)c(=O)n2CC1CCCO1]

155 mg (0.338 mmol) of the racemic compound from Ex. 446 were dissolved in 6 ml of isopropanol and, in 20 portions, separated into the enantiomers by preparative HPLC on a chiral phase [column: Daicel Chiralpak IE, 5 µm, 250 mm×20 mm; eluent: tert-butyl methyl ether/methanol 9:1; flow rate: 15 ml/min; temperature: 30° C.; detection: 220 nm]. After concentration of the product fractions and drying of the solids under high vacuum, 68 mg (87% of theory) of Enantiomer 2 were obtained (99.0% ee, chiral analytical HPLC).

$^1$H-NMR (400 MHz, DMSO-$d_6$, δ/ppm): 8.07 (s, 1H), 4.47 (s, 2H), 4.28-4.17 (m, 1H), 4.02 (dd, 1H), 3.82 (br. s, 2H), 3.79-3.67 (m, 2H), 3.65-3.57 (m, 1H), 3.53-3.36 (m, 4H), 2.39 (s, 3H), 2.04-1.74 (m, 3H), 1.73-1.62 (m, 1H), 0.89 (s, 9H).

Chiral analytical HPLC [column: Daicel Chiraltek IE, 5 µm, 250 mm×4.6 mm; eluent: tert-butyl methyl ether/methanol 9:1; flow rate: 1 ml/min; temperature: 30° C.; detection: 220 nm]: $R_t$=10.67 min.

Example 449

[1-{[5-Methyl-1-(oxetan-2-ylmethyl)-2,4-dioxo-3-(2,2,2-trifluoroethyl)-1,2,3,4-tetrahydrothieno[2,3-d]pyrimidin-6-yl]methyl}imidazolidin-2-ylidene]cyanamide (Enantiomer 1)

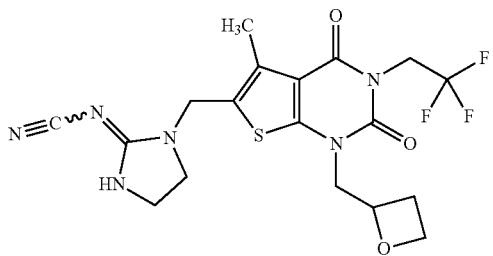 [SMILES: Cc1c(CN2CCNC2=NC#N)sc2c1c(=O)n(CC(F)(F)F)c(=O)n2CC1CCO1]

191 mg (0.418 mmol) of the stereoisomer mixture from Ex. 359 were dissolved in a mixture of 11 ml of ethanol and 5 ml of dichloromethane and, in 40 portions, separated into the enantiomers by preparative HPLC on a chiral phase [column: Daicel Chiralpak IE, 5 µm, 250 mm×20 mm; eluent: isohexane/ethanol 2:3; flow rate: 15 ml/min; temperature: 50° C.; detection: 220 nm]. After the product fractions had been concentrated, the remaining solids were repurified once more by means of preparative HPLC on an achiral phase (Method 8). After concentration of the product fractions and drying of the solids under high vacuum, 122 mg (63% of theory) of Enantiomer 1 were obtained (99.0% ee, chiral analytical HPLC).

$^1$H-NMR (400 MHz, DMSO-$d_6$, δ/ppm): 8.08 (s, 1H), 5.08-4.95 (m, 1H), 4.70 (q, 2H), 4.54-4.36 (m, 2H), 4.49 (s, 2H), 4.26-4.07 (m, 2H), 3.52-3.36 (m, 4H), 2.76-2.62 (m, 1H), 2.55-2.46 (m, 1H, mostly obscured by the DMSO signal), 2.41 (s, 3H).

Chiral analytical HPLC [column: Daicel Chiraltek IE, 5 µm, 250 mm×4.6 mm; eluent: isohexane/ethanol 2:3; flow rate: 1 ml/min; temperature: 50° C.; detection: 220 nm]: $R_t$=7.64 min.

Example 450

[1-{[5-Methyl-1-(oxetan-2-ylmethyl)-2,4-dioxo-3-(2,2,2-trifluoroethyl)-1,2,3,4-tetrahydrothieno[2,3-d]pyrimidin-6-yl]methyl}imidazolidin-2-ylidene]cyanamide (Enantiomer 2)

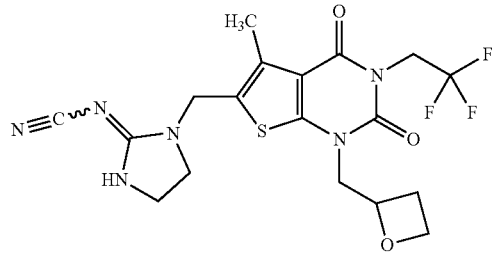 [SMILES: Cc1c(CN2CCNC2=NC#N)sc2c1c(=O)n(CC(F)(F)F)c(=O)n2CC1CCO1]

191 mg (0.418 mmol) of the stereoisomer mixture from Ex. 359 were dissolved in a mixture of 11 ml of ethanol and 5 ml of dichloromethane and, in 40 portions, separated into the enantiomers by preparative HPLC on a chiral phase [column: Daicel Chiralpak IE, 5 µm, 250 mm×20 mm; eluent: isohexane/ethanol 2:3; flow rate: 15 ml/min; temperature: 50° C.; detection: 220 nm]. After the product fractions had been concentrated, the remaining solids were repurified once more by means of preparative HPLC on an achiral phase (Method 8). After concentration of the product fractions and drying of the solids under high vacuum, 13 mg (6% of theory) of Enantiomer 2 were obtained (96.5% ee, chiral analytical HPLC).

$^1$H-NMR (400 MHz, DMSO-$d_6$, δ/ppm): 8.08 (s, 1H), 5.07-4.96 (m, 1H), 4.70 (q, 2H), 4.54-4.37 (m, 2H), 4.49 (s, 2H), 4.27-4.10 (m, 2H), 3.53-3.37 (m, 4H), 2.76-2.63 (m, 1H), 2.55-2.45 (m, 1H, mostly obscured by the DMSO signal), 2.41 (s, 3H).

Chiral analytical HPLC [column: Daicel Chiraltek IE, 5 µm, 250 mm×4.6 mm; eluent: isohexane/ethanol 2:3; flow rate: 1 ml/min; temperature: 50° C.; detection: 220 nm]: $R_t$=8.10 min.

Example 451

[1-{[5-Methyl-2,4-dioxo-3-(1,1,1-trifluoropropan-2-yl)-1-(3,3,3-trifluoropropyl)-1,2,3,4-tetrahydrothieno[2,3-d]pyrimidin-6-yl]methyl}imidazolidin-2-ylidene]cyanamide (racemate)

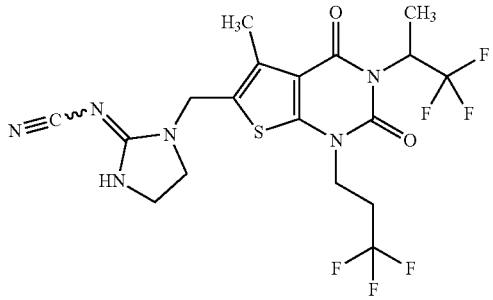 [SMILES: Cc1c(CN2CCNC2=NC#N)sc2c1c(=O)n(C(C)C(F)(F)F)c(=O)n2CCC(F)(F)F]

590 mg (1.11 mmol, 84% purity) of the compound from Ex. 455A were dissolved in 12 ml of DMF, and 243 mg (1.67 mmol) of dimethyl N-cyanodithioiminocarbonate and 307 mg (2.22 mmol) of potassium carbonate were added. The mixture was stirred at 80° C. in a microwave oven (Biotage Initiator with dynamic control of irradiation power) for 4 h. Thereafter, the reaction mixture was diluted with ethyl acetate and washed successively with saturated sodium carbonate solution, water and saturated sodium chloride solution. After drying over anhydrous magnesium sulphate, the mixture was filtered and concentrated. The crude product was purified by preparative HPLC (Method 8). The product fractions were combined and concentrated. 250 mg (45% of theory) of the title compound were obtained.

$^1$H-NMR (400 MHz, DMSO-d$_6$, δ/ppm): 8.10 (s, 1H), 5.84-5.46 (m, 1H), 4.51 (s, 2H), 4.12 (br. t, 2H), 3.55-3.38 (m, 4H), 2.89-2.69 (m, 2H), 2.41 (s, 3H), 1.63 (br. d, 3H).

LC/MS (Method 17, ESIpos): R$_t$=1.86 min, m/z=497.12 [M+H]$^+$.

Example 452

[1-{[1-(2-Methoxyethyl)-5-methyl-2,4-dioxo-3-(1,1,1-trifluoropropan-2-yl)-1,2,3,4-tetrahydrothieno[2,3-d]pyrimidin-6-yl]methyl}imidazolidin-2-ylidene]cyanamide (racemate)

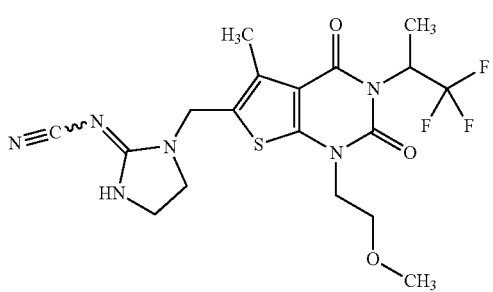 [SMILES: COCCn1c(=O)n(C(C)C(F)(F)F)c(=O)c2c(C)c(CN3CCNC3=NC#N)sc21]

295 mg (0.592 mmol, 82% purity) of the compound from Ex. 456A were dissolved in 10 ml of DMF, and 130 mg (0.888 mmol) of dimethyl N-cyanodithioiminocarbonate and 164 mg (1.18 mmol) of potassium carbonate were added. The mixture was stirred at 80° C. in a microwave oven (Biotage Initiator with dynamic control of irradiation power) for 4 h. Thereafter, the reaction mixture was diluted with ethyl acetate and washed successively with saturated sodium carbonate solution, water and saturated sodium chloride solution. After drying over anhydrous magnesium sulphate, the mixture was filtered and concentrated. The crude product was purified by preparative HPLC (Method 8). The product fractions were combined and concentrated. 67 mg (24% of theory) of the title compound were obtained.

$^1$H-NMR (400 MHz, DMSO-d$_6$, δ/ppm): 8.08 (s, 1H), 5.85-5.46 (m, 1H), 4.48 (s, 2H), 4.14-3.94 (m, 2H), 3.70-3.58 (m, 2H), 3.53-3.37 (m, 4H), 3.24 (s, 3H), 2.40 (s, 3H), 1.63 (br. d, 3H).

LC/MS (Method 17, ESIpos): R$_t$=1.68 min, m/z=459.14 [M+H]$^+$.

Example 453

[1-{[3-(2-Ethoxyethyl)-1-(3-fluoropropyl)-5-methyl-2,4-dioxo-1,2,3,4-tetrahydrothieno[2,3-d]pyrimidin-6-yl]methyl}imidazolidin-2-ylidene]cyanamide

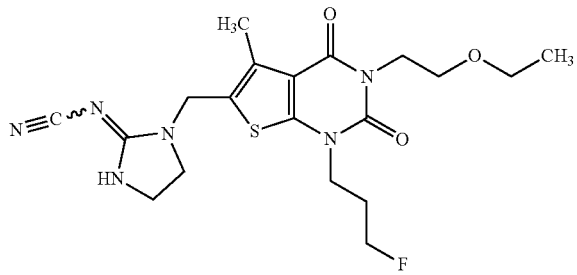 [SMILES: CCOCCn1c(=O)c2c(C)c(CN3CCNC3=NC#N)sc2n(CCCF)c1=O]

200 mg (0.388 mmol, 75% purity) of the compound from Ex. 457A were dissolved in 5 ml of DMF, and 70 mg (0.582 mmol) of dimethyl N-cyanodithioiminocarbonate and 107 mg (0.776 mmol) of potassium carbonate were added. The mixture was stirred at 80° C. for 21 h. Thereafter, the reaction mixture was taken up in 30 ml of ethyl acetate. It was washed with 20 ml of saturated sodium hydrogencarbonate solution and with 20 ml of water. The organic phase was dried over sodium sulphate, filtered and concentrated. The residue obtained was dissolved in 3 ml of DMSO and this solution was purified by means of preparative HPLC (Method 14). Combination of the product fractions and freeze-drying gave 81 mg (48% of theory) of the title compound.

$^1$H-NMR (400 MHz, DMSO-d$_6$, δ/ppm): 8.09 (s, 1H), 4.59 (t, 1H), 4.51-4.44 (m, 3H), 4.03 (t, 2H), 3.99 (br. t, 2H), 3.50 (t, 2H), 3.48-3.37 (m, 5H), 2.41 (s, 2H), 2.14-1.99 (m, 2H), 1.06 (t, 3H).

LC/MS (Method 1, ESIpos): R$_t$=0.98 min, m/z=437 [M+H]$^+$.

Example 454

[1-{[3-(2-Methoxypropyl)-5-methyl-2,4-dioxo-1-(3,3,3-trifluoropropyl)-1,2,3,4-tetrahydrothieno[2,3-d]pyrimidin-6-yl]methyl}imidazolidin-2-ylidene]cyanamide (racemate)

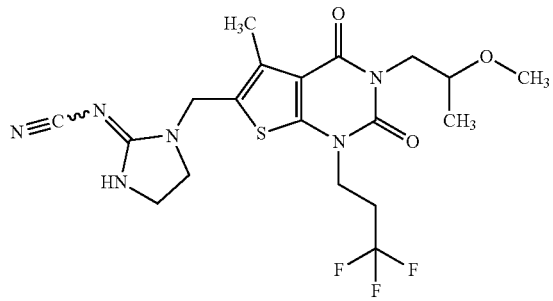 [SMILES: COC(C)Cn1c(=O)c2c(C)c(CN3CCNC3=NC#N)sc2n(CCC(F)(F)F)c1=O]

650 mg (1.23 mmol, 80% purity) of the compound from Ex. 458A were dissolved in 12 ml of DMF, and 270 mg (1.85 mmol) of dimethyl N-cyanodithioiminocarbonate and 340 mg (2.46 mmol) of potassium carbonate were added. The mixture was stirred at 80° C. in a microwave oven (Biotage Initiator with dynamic control of irradiation power) for 4 h. The reaction mixture was then concentrated to dryness and the residue was separated into its components by means of preparative HPLC (Method 8). The product fractions were combined and concentrated. 317 mg (54% of theory) of the title compound were obtained.

$^1$H-NMR (400 MHz, DMSO-$d_6$, δ/ppm): 8.08 (s, 1H), 4.50 (s, 2H), 4.19-4.08 (m, 2H), 4.05 (dd, 1H), 3.76 (dd, 1H), 3.63 (sext, 1H), 3.54-3.37 (m, 4H), 3.21 (s, 3H), 2.84-2.69 (m, 2H), 2.42 (s, 3H), 1.05 (d, 3H).

LC/MS (Method 1, ESIpos): $R_t$=0.85 min, m/z=473 [M+H]$^+$.

Example 455

[1-{[3-(2-Methoxypropyl)-5-methyl-2,4-dioxo-1-(3,3,3-trifluoropropyl)-1,2,3,4-tetrahydrothieno[2,3-d]pyrimidin-6-yl]methyl}imidazolidin-2-ylidene]cyanamide (Enantiomer 1)

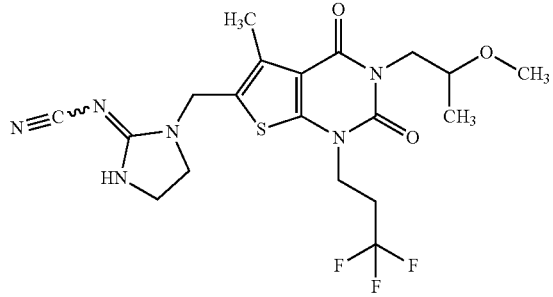 [SMILES: COC(C)Cn1c(=O)c2c(C)c(CN3CCNC3=NC#N)sc2n(CCC(F)(F)F)c1=O]

300 mg (0.635 mmol) of the racemic compound from Ex. 454 were dissolved in 25 ml of methanol and, in 13 portions, separated into the enantiomers by preparative SFC on a chiral phase [column: Daicel Chiralcel OZ-H, 5 μm, 250 mm×20 mm; eluent: carbon dioxide/methanol 7:3; flow rate: 80 ml/min; temperature: 40° C.; detection: 210 nm]. After concentration of the product fractions and drying under high vacuum, 128 mg (85% of theory) of Enantiomer 1 were obtained (>99% ee, chiral analytical HPLC).

$^1$H-NMR (400 MHz, DMSO-$d_6$, δ/ppm): 8.08 (s, 1H), 4.50 (s, 2H), 4.19-4.09 (m, 2H), 4.05 (dd, 1H), 3.76 (dd, 1H), 3.63 (sext, 1H), 3.53-3.38 (m, 4H), 3.21 (s, 3H), 2.85-2.69 (m, 2H), 2.42 (s, 3H), 1.05 (d, 3H).

Chiral analytical SFC [column: Daicel Chiralcel OZ-H, 5 μm, 250 mm×4.6 mm; eluent: carbon dioxide/methanol 3:2; flow rate: 3 ml/min; temperature: 40° C.; detection: 210 nm]: $R_t$=2.80 min.

Example 456

[1-{[3-(2-Methoxypropyl)-5-methyl-2,4-dioxo-1-(3,3,3-trifluoropropyl)-1,2,3,4-tetrahydrothieno[2,3-d]pyrimidin-6-yl]methyl}imidazolidin-2-ylidene]cyanamide (Enantiomer 2)

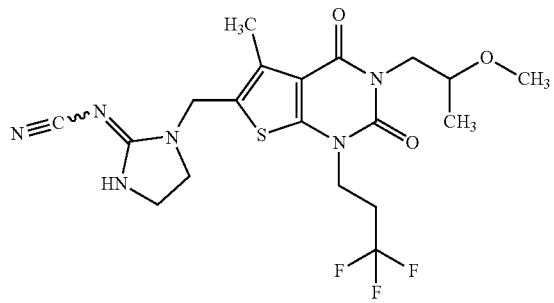 [SMILES: COC(C)Cn1c(=O)c2c(C)c(CN3CCNC3=NC#N)sc2n(CCC(F)(F)F)c1=O]

300 mg (0.635 mmol) of the racemic compound from Ex. 454 were dissolved in 25 ml of methanol and, in 13 portions, separated into the enantiomers by preparative SFC on a chiral phase [column: Daicel Chiralcel OZ-H, 5 μm, 250 mm×20 mm; eluent: carbon dioxide/methanol 7:3; flow rate: 80 ml/min; temperature: 40° C.; detection: 210 nm]. After concentration of the product fractions and drying under high vacuum, 93 mg (62% of theory) of Enantiomer 2 were obtained (>99% ee, chiral analytical HPLC).

$^1$H-NMR (400 MHz, DMSO-$d_6$, δ/ppm): 8.08 (s, 1H), 4.50 (s, 2H), 4.19-4.08 (m, 2H), 4.05 (dd, 1H), 3.76 (dd, 1H), 3.63 (sext, 1H), 3.52-3.37 (m, 4H), 3.21 (s, 3H), 2.85-2.69 (m, 2H), 2.42 (s, 3H), 1.05 (d, 3H).

Chiral analytical SFC [column: Daicel Chiralcel OZ-H, 5 μm, 250 mm×4.6 mm; eluent: carbon dioxide/methanol 3:2; flow rate: 3 ml/min; temperature: 40° C.; detection: 210 nm]: $R_t$=5.11 min.

Example 457

Methyl [1-{[3-isopropyl-5-methyl-1-(oxetan-2-ylmethyl)-2,4-dioxo-1,2,3,4-tetrahydrothieno[2,3-d]pyrimidin-6-yl]methyl}imidazolidin-2-ylidene]carbamate (Enantiomer 1)

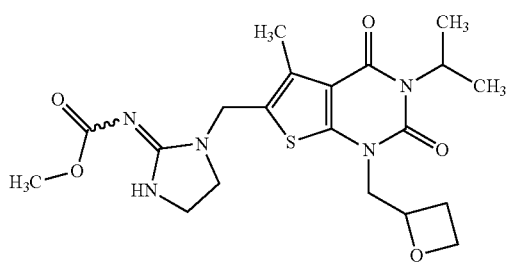 [SMILES: COC(=O)N=C1NCCN1Cc1sc2c(c1C)c(=O)n(C(C)C)c(=O)n2CC1CCO1]

98 mg (0.218 mmol) of the racemic compound from Ex. 379 were dissolved in 6 ml of ethanol and, in 12 portions, separated into the enantiomers by preparative HPLC on a chiral phase [column: Daicel Chiralcel OD-H, 5 µm, 250 mm×20 mm; eluent: isohexane/ethanol 3:7; flow rate: 15 ml/min; temperature: 25° C.; detection: 210 nm]. After concentration of the product fractions and drying under high vacuum, 43 mg (87% of theory) of Enantiomer 1 were obtained (99% ee, chiral analytical HPLC).

$^1$H-NMR (500 MHz, DMSO-$d_6$, δ/ppm): 8.01 (s, 1H), 5.13 (sept, 1H), 5.02-4.93 (m, 1H), 4.55 (s, 2H), 4.47 (td, 1H), 4.41 (dt, 1H), 4.14-4.03 (m, 2H), 3.53 (s, 3H), 3.48-3.41 (m, 2H), 3.35-3.31 (m, 2H, partially obscured by the water signal), 2.74-2.64 (m, 1H), 2.52-2.44 (m, 1H, partially obscured by the DMSO signal), 2.40 (s, 3H), 1.39 (d, 6H).

Chiral analytical HPLC [column: Phenomenex Cellulose, 3 µm, 50 mm×4.6 mm; eluent: isohexane/ethanol 1:1; flow rate: 1 ml/min; temperature: 25° C.; detection: 220 nm]: $R_t$=1.79 min.

Example 458

Methyl [1-{[3-isopropyl-5-methyl-1-(oxetan-2-ylmethyl)-2,4-dioxo-1,2,3,4-tetrahydrothieno[2,3-d]pyrimidin-6-yl]methyl}imidazolidin-2-ylidene]carbamate (Enantiomer 2)

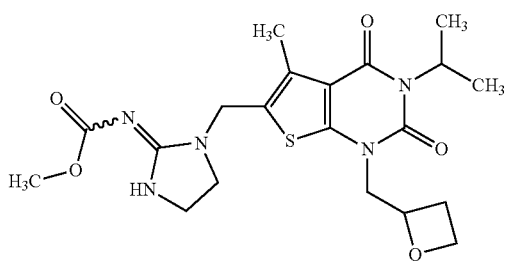 [SMILES: COC(=O)N=C1NCCN1Cc1sc2c(c1C)c(=O)n(C(C)C)c(=O)n2CC1CCO1]

98 mg (0.218 mmol) of the racemic compound from Ex. 379 were dissolved in 6 ml of ethanol and, in 12 portions, separated into the enantiomers by preparative HPLC on a chiral phase [column: Daicel Chiralcel OD-H, 5 µm, 250 mm×20 mm; eluent: isohexane/ethanol 3:7; flow rate: 15 ml/min; temperature: 25° C.; detection: 210 nm]. After concentration of the product fractions and drying under high vacuum, 37 mg (75% of theory) of Enantiomer 2 were obtained (85.9% ee, chiral analytical HPLC). For repurification, this material was chromatographed for a second time under the same HPLC conditions. This gave 25 g (51% of theory) of Enantiomer 2 (99.9% ee, chiral analytical HPLC).

$^1$H-NMR (400 MHz, DMSO-$d_6$, δ/ppm): 8.02 (s, 1H), 5.13 (sept, 1H), 4.98 (dt, 1H), 4.55 (s, 2H), 4.51-4.35 (m, 2H), 4.14-4.04 (m, 2H), 3.53 (s, 3H), 3.49-3.40 (m, 2H), 3.35-3.29 (m, 2H, partially obscured by the water signal), 2.75-2.62 (m, 1H), 2.52-2.44 (m, 1H, partially obscured by the DMSO signal), 2.40 (s, 3H), 1.39 (d, 6H).

Chiral analytical HPLC [column: Phenomenex Cellulose, 3 µm, 50 mm×4.6 mm; eluent: isohexane/ethanol 1:1; flow rate: 1 ml/min; temperature: 25° C.; detection: 220 nm]: $R_t$=4.95 min.

Example 459

Methyl [1-{[3-isopropyl-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]carbamate (Enantiomer 1)

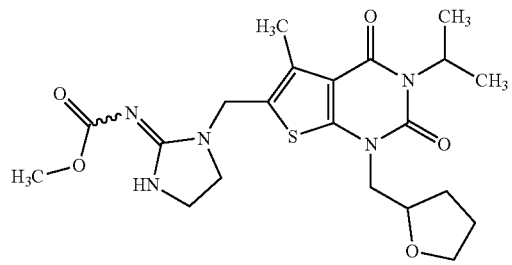 [SMILES: COC(=O)N=C1NCCN1Cc1sc2c(c1C)c(=O)n(C(C)C)c(=O)n2CC1CCCO1]

187 mg (0.403 mmol) of the racemic compound from Ex. 380 were dissolved in 8 ml of ethanol and, in 16 portions, separated into the enantiomers by preparative HPLC on a chiral phase [column: Daicel Chiralcel OX-H, 5 µm, 250 mm×20 mm; eluent: isohexane/ethanol 2:3; flow rate: 15 ml/min; temperature: 50° C.; detection: 220 nm]. After concentration of the product fractions and drying of the solids under high vacuum, 78 mg (83% of theory) of Enantiomer 1 were obtained (99.0% ee, chiral analytical HPLC). Impurities still present were finally removed by means of preparative HPLC on an achiral phase (Method 8). This gave 47 mg (50% of theory) of Enantiomer 1.

$^1$H-NMR (400 MHz, DMSO-$d_6$, δ/ppm): 8.02 (s, 1H), 5.14 (sept, 1H), 4.54 (s, 2H), 4.26-4.15 (m, 1H), 4.02 (dd, 1H), 3.77-3.67 (m, 1H), 3.65-3.55 (m, 2H), 3.53 (s, 3H), 3.49-3.41 (m, 2H), 3.35-3.29 (m, 2H, partially obscured by the water signal), 2.40 (s, 3H), 2.03-1.74 (m, 3H), 1.71-1.58 (m, 1H), 1.40 (dd, 6H).

Chiral analytical HPLC [column: Daicel Chiralcel OX-H, 5 µm, 250 mm×4.6 mm; eluent: isohexane/ethanol 1:1; flow rate: 1 ml/min; temperature: 50° C.; detection: 220 nm]: $R_t$=11.03 min.

Example 460

Methyl [1-{[3-isopropyl-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]carbamate (Enantiomer 2)

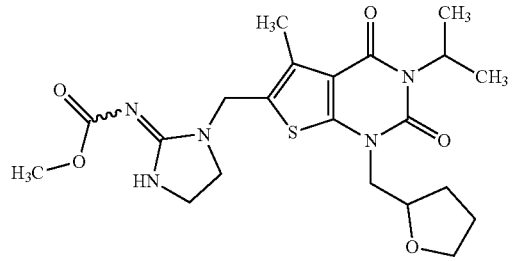 [SMILES: COC(=O)N=C1NCCN1Cc1sc2c(c1C)c(=O)n(C(C)C)c(=O)n2CC1CCCO1]

187 mg (0.403 mmol) of the racemic compound from Ex. 380 were dissolved in 8 ml of ethanol and, in 16 portions, separated into the enantiomers by preparative HPLC on a chiral phase [column: Daicel Chiralcel OX-H, 5 μm, 250 mm×20 mm; eluent: isohexane/ethanol 2:3; flow rate: 15 ml/min; temperature: 50° C.; detection: 220 nm]. After concentration of the product fractions and drying of the solids under high vacuum, 81 mg (86% of theory) of Enantiomer 2 were obtained (99.0% ee, chiral analytical HPLC). Impurities still present were finally removed by means of preparative HPLC on an achiral phase (Method 8). This gave 37 mg (39% of theory) of Enantiomer 2.

$^1$H-NMR (400 MHz, DMSO-$d_6$, δ/ppm): 8.02 (s, 1H), 5.14 (sept, 1H), 4.54 (s, 2H), 4.26-4.15 (m, 1H), 4.02 (dd, 1H), 3.76-3.68 (m, 1H), 3.65-3.55 (m, 2H), 3.53 (s, 3H), 3.49-3.41 (m, 2H), 3.35-3.29 (m, 2H, partially obscured by the water signal), 2.40 (s, 3H), 2.04-1.75 (m, 3H), 1.69-1.61 (m, 1H), 1.40 (dd, 6H).

Chiral analytical HPLC [column: Daicel Chiralcel OX-H, 5 μm, 250 mm×4.6 mm; eluent: isohexane/ethanol 1:1; flow rate: 1 ml/min; temperature: 50° C.; detection: 220 nm]: $R_t$=15.02 min.

Example 461

Methyl [1-{[3-(2,2-dimethylpropyl)-5-methyl-2,4-dioxo-1-(3,3,3-trifluoropropyl)-1,2,3,4-tetrahydrothieno[2,3-d]pyrimidin-6-yl]methyl}imidazolidin-2-ylidene]carbamate

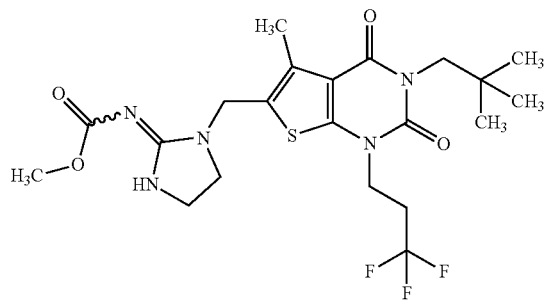 [SMILES: COC(=O)N=C1NCCN1Cc1sc2c(c1C)c(=O)n(CC(C)(C)C)c(=O)n2CCC(F)(F)F]

290 mg (0.552 mmol, 80% purity) of the compound from Ex. 315A and 154 μl (1.10 mmol) of triethylamine were dissolved in 10 ml of dichloromethane, and a solution of 172 mg (1.10 mmol) of methyl (dichloromethylene)carbamate in 5 ml of dichloromethane was added. After the reaction mixture had been stirred at RT for about 18 h, it was concentrated to dryness and the residue was purified by means of preparative HPLC (Method 8). Concentration of the product fractions and drying of the residue under high vacuum gave 157 mg (55% of theory) of the title compound.

$^1$H-NMR (400 MHz, DMSO-$d_6$, δ/ppm): 8.03 (s, 1H), 4.58 (s, 2H), 4.09 (t, 2H), 3.81 (br. s, 2H), 3.53 (s, 3H), 3.50-3.42 (m, 2H), 3.40-3.33 (m, 2H), 2.84-2.66 (m, 2H), 2.42 (s, 3H), 0.89 (s, 9H).

LC/MS (Method 17, ESIpos): $R_t$=1.96 min, m/z=504.19 [M+H]$^+$.

Example 462

Methyl [1-{[3-(2,2-dimethylpropyl)-1-(2-methoxyethyl)-5-methyl-2,4-dioxo-1,2,3,4-tetrahydrothieno[2,3-d]pyrimidin-6-yl]methyl}imidazolidin-2-ylidene]carbamate

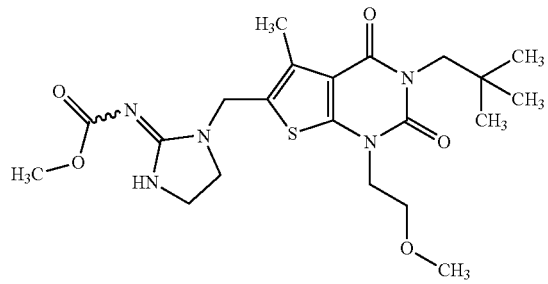 [SMILES: COCCn1c(=O)n(CC(C)(C)C)c(=O)c2c(C)c(CN3CCNC3=NC(=O)OC)sc21]

375 mg (0.833 mmol, 85% purity) of the compound from Ex. 317A and 232 μl (1.67 mmol) of triethylamine were dissolved in 15 ml of dichloromethane, and a solution of 260 mg (1.67 mmol) of methyl (dichloromethylene)carbamate in 5 ml of dichloromethane was added. After the reaction mixture had been stirred at RT for about 18 h, it was diluted with ethyl acetate and washed successively with water and saturated sodium chloride solution. After drying over anhydrous magnesium sulphate, the mixture was filtered and concentrated. The remaining residue was purified by MPLC (Biotage Isolera, cartridge with 100 g of silica gel, cyclohexane/ethyl acetate 50:50→0:100). Concentration of the product fractions and drying of the residue under high vacuum gave 230 mg (59% of theory) of the title compound.

$^1$H-NMR (400 MHz, DMSO-$d_6$, δ/ppm): 8.03 (s, 1H), 4.56 (s, 2H), 4.00 (t, 2H), 3.81 (s, 2H), 3.62 (t, 2H), 3.53 (s, 3H), 3.50-3.42 (m, 2H), 3.40-3.33 (m, 2H), 3.22 (s, 3H), 2.41 (s, 3H), 0.89 (s, 9H).

LC/MS (Method 17, ESIpos): $R_t$=1.65 min, m/z=466.21 [M+H]$^+$.

Example 463

Methyl [1-{[3-(2,2-dimethylpropyl)-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]carbamate (racemate)

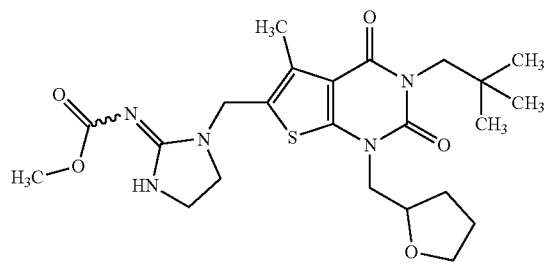 [SMILES: COC(=O)N=C1NCCN1Cc1sc2c(c1C)c(=O)n(CC(C)(C)C)c(=O)n2CC1CCCO1]

560 mg (1.16 mmol, 85% purity) of the compound from Ex. 454A and 325 μl (2.33 mmol) of triethylamine were dissolved in 20 ml of dichloromethane, and a solution of 363 mg (2.33 mmol) of methyl (dichloromethylene)carbamate in 5 ml of dichloromethane was added. After the reaction mixture had been stirred at RT for about 18 h, it was diluted with ethyl acetate and washed successively with saturated sodium carbonate solution and saturated sodium chloride solution. After drying over anhydrous magnesium sulphate, the mixture was filtered and concentrated. The remaining residue was purified by MPLC (Biotage Isolera, cartridge with 50 g of silica gel, cyclohexane/ethyl acetate 2:1). Concentration of the product fractions and drying of the residue under high vacuum gave 320 mg (55% of theory) of the title compound.

$^1$H-NMR (500 MHz, DMSO-$d_6$, δ/ppm): 8.02 (s, 1H), 4.55 (s, 2H), 4.26-4.17 (m, 1H), 4.03-3.97 (m, 1H), 3.81 (br. s, 2H), 3.75-3.64 (m, 2H), 3.63-3.56 (m, 1H), 3.53 (s, 3H), 3.49-3.43 (m, 2H), 3.39-3.33 (m, 2H), 2.41 (s, 3H), 2.02-1.75 (m, 3H), 1.70-1.63 (m, 1H), 0.89 (s, 9H).

LC/MS (Method 17, ESIpos): $R_t$=1.75 min, m/z=492.23 [M+H]$^+$.

Example 464

Methyl [1-{[3-(2,2-dimethylpropyl)-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]carbamate (Enantiomer 1)

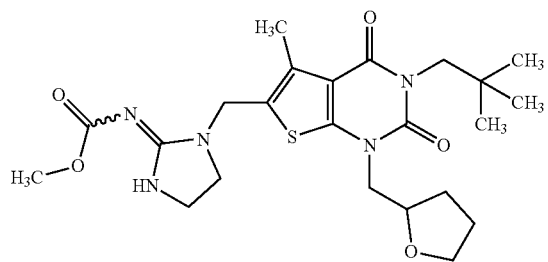 [SMILES: COC(=O)N=C1NCCN1Cc1sc2c(c1C)c(=O)n(CC(C)(C)C)c(=O)n2CC1CCCO1]

308 mg (0.626 mmol) of the racemic compound from Ex. 463 were dissolved in a mixture of 3 ml each of methanol, tert-butyl methyl ether and dichloromethane and, in 36 portions, separated into the enantiomers by preparative HPLC on a chiral phase [column: Daicel Chiralpak IF, 5 μm, 250 mm×20 mm; eluent: tert-butyl methyl ether/methanol 7:3; flow rate: 15 ml/min; temperature: 30° C.; detection: 220 nm]. After concentration of the product fractions, 136 mg (88% of theory) of Enantiomer 1 were obtained (99.0% ee, chiral analytical HPLC).

$^1$H-NMR (500 MHz, DMSO-$d_6$, δ/ppm): 8.03 (br. s, 1H), 4.55 (s, 2H), 4.26-4.16 (m, 1H), 4.01 (br. dd, 1H), 3.82 (br. s, 2H), 3.75-3.64 (m, 2H), 3.63-3.56 (m, 1H), 3.54 (s, 3H), 3.50-3.43 (m, 2H), 3.39-3.33 (m, 2H), 2.41 (s, 3H), 2.02-1.75 (m, 3H), 1.70-1.63 (m, 1H), 0.89 (s, 9H).

Chiral analytical HPLC [column: Daicel Chiraltek IF, 5 μm, 250 mm×4.6 mm; eluent: tert-butyl methyl ether/methanol 7:3; flow rate: 1 ml/min; temperature: 30° C.; detection: 220 nm]: $R_t$=6.25 min.

Example 465

Methyl [1-{[3-(2,2-dimethylpropyl)-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]carbamate (Enantiomer 2)

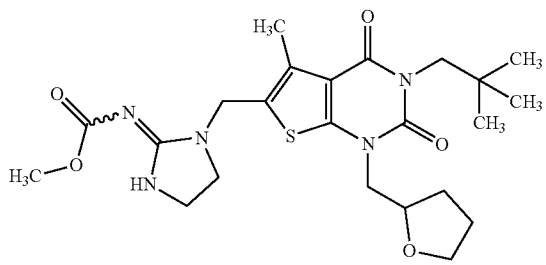 [SMILES: COC(=O)N=C1NCCN1Cc1sc2c(c1C)c(=O)n(CC(C)(C)C)c(=O)n2CC1CCCO1]

308 mg (0.626 mmol) of the racemic compound from Ex. 463 were dissolved in a mixture of 3 ml each of methanol, tert-butyl methyl ether and dichloromethane and, in 36 portions, separated into the enantiomers by preparative HPLC on a chiral phase [column: Daicel Chiralpak IF, 5 μm, 250 mm×20 mm; eluent: tert-butyl methyl ether/methanol 7:3; flow rate: 15 ml/min; temperature: 30° C.; detection: 220 nm]. After concentration of the product fractions, 136 mg (88% of theory) of Enantiomer 2 were obtained (98.8% ee, chiral analytical HPLC).

$^1$H-NMR (500 MHz, DMSO-$d_6$, δ/ppm): 8.04 (br. s, 1H), 4.55 (s, 2H), 4.26-4.17 (m, 1H), 4.01 (br. dd, 1H), 3.82 (br. s, 2H), 3.75-3.64 (m, 2H), 3.63-3.56 (m, 1H), 3.54 (s, 3H), 3.50-3.43 (m, 2H), 3.40-3.33 (m, 2H), 2.41 (s, 3H), 2.02-1.76 (m, 3H), 1.70-1.63 (m, 1H), 0.89 (s, 9H).

Chiral analytical HPLC [column: Daicel Chiraltek IF, 5 μm, 250 mm×4.6 mm; eluent: tert-butyl methyl ether/methanol 7:3; flow rate: 1 ml/min; temperature: 30° C.; detection: 220 nm]: $R_t$=8.15 mm.

Example 466

Methyl [1-{[5-methyl-1-(oxetan-2-ylmethyl)-2,4-dioxo-3-(2,2,2-trifluoroethyl)-1,2,3,4-tetrahydrothieno[2,3-d]pyrimidin-6-yl]methyl}imidazolidin-2-ylidene]carbamate (Enantiomer 1)

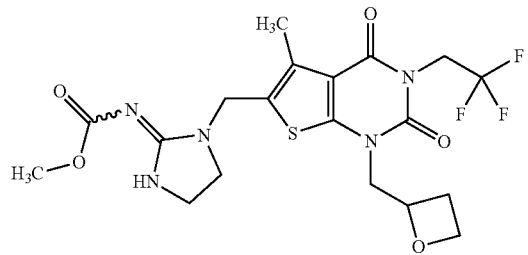 [SMILES: COC(=O)N=C1NCCN1Cc1sc2c(c1C)c(=O)n(CC(F)(F)F)c(=O)n2CC1CCO1]

50 mg (0.102 mmol) of the stereoisomer mixture from Ex. 383 were dissolved in a mixture of 2 ml of ethanol and 3 ml of acetonitrile and, in 7 portions, separated into the enantiomers by preparative HPLC on a chiral phase [column: Daicel Chiralcel OX-H, 5 μm, 250 mm×20 mm; eluent: isohexane/ethanol 1:1; flow rate: 20 ml/min; temperature: 22° C.; detection: 220 nm]. After concentration of the product fractions and drying of the solids under high vacuum, 5 mg (10% of theory) of Enantiomer 1 were obtained (99.5% ee, chiral analytical HPLC).

¹H-NMR (500 MHz, DMSO-d₆, δ/ppm): 8.03 (s, 1H), 5.05-4.95 (m, 1H), 4.70 (q, 2H), 4.57 (s, 2H), 4.51-4.44 (m, 1H), 4.41 (dt, 1H), 4.23-4.09 (m, 2H), 3.54 (s, 3H), 3.49-3.42 (m, 2H), 3.37-3.33 (m, 2H, partially obscured by the water signal), 2.76-2.62 (m, 1H), 2.51-2.44 (m, 1H, mostly obscured by the DMSO signal), 2.42 (s, 3H).

Chiral analytical HPLC [column: Daicel Chiralcel OX-H, 3 μm, 50 mm×4.6 mm; eluent: isohexane/ethanol 1:1; flow rate: 1 ml/min; temperature: 22° C.; detection: 220 nm]: $R_t$=2.99 min.

Example 467

Methyl [1-{[5-methyl-1-(oxetan-2-ylmethyl)-2,4-dioxo-3-(2,2,2-trifluoroethyl)-1,2,3,4-tetrahydrothieno[2,3-d]pyrimidin-6-yl]methyl}imidazolidin-2-ylidene]carbamate (Enantiomer 2)

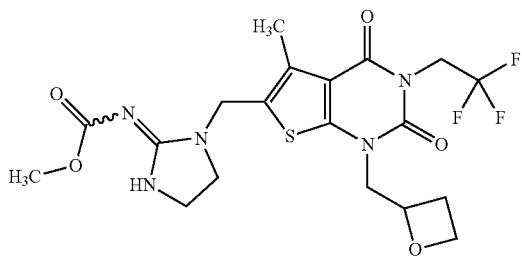 [SMILES: COC(=O)N=C1NCCN1Cc1sc2c(c1C)c(=O)n(CC(F)(F)F)c(=O)n2CC1CCO1]

50 mg (0.102 mmol) of the stereoisomer mixture from Ex. 383 were dissolved in a mixture of 2 ml of ethanol and 3 ml of acetonitrile and, in 7 portions, separated into the enantiomers by preparative HPLC on a chiral phase [column: Daicel Chiralcel OX-H, 5 μm, 250 mm×20 mm; eluent: isohexane/ethanol 1:1; flow rate: 20 ml/min; temperature: 22° C.; detection: 220 nm]. After concentration of the product fractions and drying of the solids under high vacuum, 28 mg (56% of theory) of Enantiomer 2 were obtained (99.5% ee, chiral analytical HPLC). Impurities still present were finally removed by means of preparative HPLC on an achiral phase (Method 8). This gave 20 mg (40% of theory) of Enantiomer 2.

¹H-NMR (400 MHz, DMSO-d₆, δ/ppm): 8.03 (s, 1H), 5.05-4.94 (m, 1H), 4.70 (q, 2H), 4.57 (s, 2H), 4.51-4.44 (m, 1H), 4.40 (dt, 1H), 4.24-4.09 (m, 2H), 3.53 (s, 3H), 3.50-3.42 (m, 2H), 3.37-3.32 (m, 2H, partially obscured by the water signal), 2.76-2.63 (m, 1H), 2.54-2.45 (m, 1H, partially obscured by the DMSO signal), 2.42 (s, 3H).

Chiral analytical HPLC [column: Daicel Chiralcel OX-H, 3 μm, 50 mm×4.6 mm; eluent: isohexane/ethanol 1:1; flow rate: 1 ml/min; temperature: 22° C.; detection: 220 nm]: $R_t$=3.81 min.

Example 468

Methyl [1-{[5-methyl-2,4-dioxo-1-(tetrahydrofuran-2-ylmethyl)-3-(2,2,2-trifluoroethyl)-1,2,3,4-tetrahydrothieno[2,3-d]pyrimidin-6-yl]methyl}imidazolidin-2-ylidene]carbamate (Enantiomer 1)

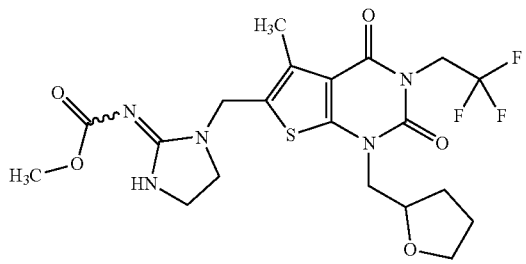 [SMILES: COC(=O)N=C1NCCN1Cc1sc2c(c1C)c(=O)n(CC(F)(F)F)c(=O)n2CC1CCCO1]

175 mg (0.348 mmol) of the racemic compound from Ex. 384 were dissolved in a mixture of 2 ml of ethanol and 2.5 ml of acetonitrile and, in 28 portions, separated into the enantiomers by preparative HPLC on a chiral phase [column: Daicel Chiralpak AS-H, 5 μm, 250 mm×20 mm; eluent: isohexane/ethanol 1:1; flow rate: 20 ml/min; temperature: 22° C.; detection: 220 nm]. After the product fractions had been concentrated, the remaining residue was stirred with pentane with a little added dichloromethane at RT. After the solids had been filtered off with suction and dried under high vacuum, 65 mg (74% of theory) of Enantiomer 1 were obtained (>99% ee, chiral analytical HPLC). Impurities still present were finally removed by means of preparative HPLC on an achiral phase (Method 8). This gave 40 mg (45% of theory) of Enantiomer 1.

¹H-NMR (400 MHz, DMSO-d₆, δ/ppm): 8.06 (br. s, 1H), 4.70 (q, 2H), 4.57 (s, 2H), 4.28-4.17 (m, 1H), 4.06 (dd, 1H), 3.77-3.66 (m, 2H), 3.64-3.56 (m, 1H), 3.54 (s, 3H), 3.50-3.42 (m, 2H), 3.38-3.33 (m, 2H, partially obscured by the water signal), 2.42 (s, 3H), 2.04-1.76 (m, 3H), 1.73-1.61 (m, 1H).

Chiral analytical HPLC [column: Daicel Chiralpak AS-3, 3 μm, 50 mm×4.6 mm; eluent: isohexane/ethanol 1:1; flow rate: 1 ml/min; temperature: 22° C.; detection: 220 nm]: $R_t$=2.05 min.

Example 469

Methyl [1-{[5-methyl-2,4-dioxo-1-(tetrahydrofuran-2-ylmethyl)-3-(2,2,2-trifluoroethyl)-1,2,3,4-tetrahydrothieno[2,3-d]pyrimidin-6-yl]methyl}imidazolidin-2-ylidene]carbamate (Enantiomer 2)

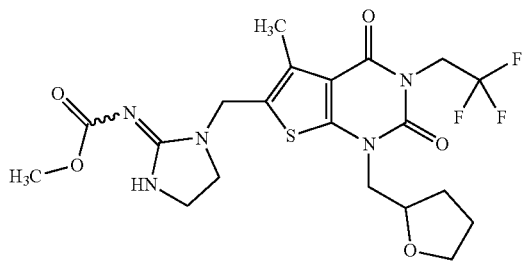 [SMILES: COC(=O)N=C1NCCN1Cc1sc2c(c1C)c(=O)n(CC(F)(F)F)c(=O)n2CC1CCCO1]

175 mg (0.348 mmol) of the racemic compound from Ex. 384 were dissolved in a mixture of 2 ml of ethanol and 2.5 ml of acetonitrile and, in 28 portions, separated into the enantiomers by preparative HPLC on a chiral phase [column: Daicel Chiralpak AS-H, 5 μm, 250 mm×20 mm; eluent: isohexane/ethanol 1:1; flow rate: 20 ml/min; temperature: 22° C.; detection: 220 nm]. After the product fractions had been concentrated, the remaining residue was stirred with pentane with a little added dichloromethane at RT. After the solids had been filtered off with suction and dried under high vacuum, 54 mg (61% of theory) of Enantiomer 2 were obtained (>99% ee, chiral analytical HPLC).

$^1$H-NMR (400 MHz, DMSO-d$_6$, δ/ppm): 8.03 (s, 1H), 4.70 (q, 2H), 4.56 (s, 2H), 4.28-4.17 (m, 1H), 4.05 (dd, 1H), 3.77-3.65 (m, 2H), 3.63-3.56 (m, 1H), 3.53 (s, 3H), 3.49-3.41 (m, 2H), 3.37-3.33 (m, 2H, partially obscured by the water signal), 2.42 (s, 3H), 2.04-1.76 (m, 3H), 1.73-1.61 (m, 1H).

Chiral analytical HPLC [column: Daicel Chiralpak AS-3, 3 μm, 50 mm×4.6 mm; eluent: isohexane/ethanol 1:1; flow rate: 1 ml/min; temperature: 22° C.; detection: 220 nm]: R$_t$=3.15 min.

Example 470

Methyl [1-{[5-methyl-2,4-dioxo-3-(1,1,1-trifluoro-propan-2-yl)-1-(3,3,3-trifluoropropyl)-1,2,3,4-tetrahydrothieno[2,3-d]pyrimidin-6-yl]methyl}imidazolidin-2-ylidene]carbamate (racemate)

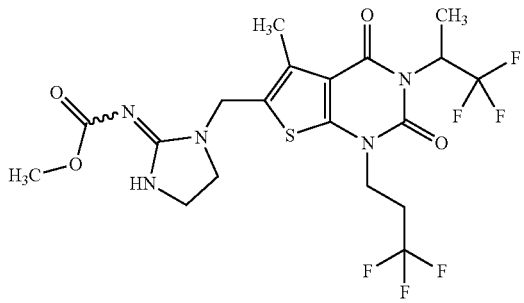 [SMILES: COC(=O)N=C1NCCN1Cc1sc2c(c1C)c(=O)n(C(C)C(F)(F)F)c(=O)n2CCC(F)(F)F]

590 mg (1.11 mmol, 84% purity) of the compound from Ex. 455A and 309 μl (2.22 mmol) of triethylamine were dissolved in 15 ml of dichloromethane, and a solution of 346 mg (2.22 mmol) of methyl (dichloromethylene)carbamate in 5 ml of dichloromethane was added. After the reaction mixture had been stirred at RT for about 18 h, it was concentrated to dryness. The remaining residue was taken up in ethyl acetate and washed successively with water and saturated sodium chloride solution. After drying over anhydrous magnesium sulphate, the mixture was filtered and concentrated. The remaining residue was purified by means of preparative HPLC (Method 8). Concentration of the product fractions and drying of the residue under high vacuum gave 206 mg (35% of theory) of the title compound.

$^1$H-NMR (400 MHz, DMSO-d$_6$, δ/ppm): 8.07 (br. s, 1H), 5.82-5.47 (m, 1H), 4.59 (s, 2H), 4.18-4.02 (m, 2H), 3.54 (s, 3H), 3.51-3.43 (m, 2H), 3.39-3.33 (m, 2H, partially obscured by the water signal), 2.85-2.69 (m, 2H), 2.43 (s, 3H), 1.63 (br. d, 3H).

LC/MS (Method 17, ESIpos): R$_t$=1.82 min, m/z=530.13 [M+H]$^+$.

Example 471

Methyl [1-{[1-(2-methoxyethyl)-5-methyl-2,4-dioxo-3-(1,1,1-trifluoropropan-2-yl)-1,2,3,4-tetrahydrothieno[2,3-d]pyrimidin-6-yl]methyl}imidazolidin-2-ylidene]carbamate (racemate)

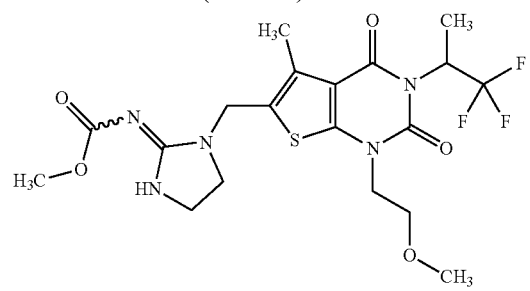

295 mg (0.592 mmol, 82% purity) of the compound from Ex. 456A and 165 μl (1.18 mmol) of triethylamine were dissolved in 10 ml of dichloromethane, and a solution of 185 mg (1.18 mmol) of methyl (dichloromethylene)carbamate in 5 ml of dichloromethane was added. After the reaction mixture had been stirred at RT for about 18 h, it was concentrated to dryness. The remaining residue was taken up in ethyl acetate and washed successively with water and saturated sodium chloride solution. After drying over anhydrous magnesium sulphate, the mixture was filtered and concentrated. The remaining residue was prepurified by means of preparative HPLC (Method 8). The product fractions were combined and concentrated. The residue was dissolved in ethyl acetate and washed successively with 1 M hydrochloric acid and water. After reconcentration, the residue was repurified by another preparative HPLC by the same method. This gave, after concentration of the product fractions and drying of the residue under high vacuum, 46 mg (15% of theory) of the title compound.

$^1$H-NMR (400 MHz, DMSO-d$_6$, δ/ppm): 8.03 (s, 1H), 5.84-5.47 (m, 1H), 4.56 (s, 2H), 4.07-3.95 (m, 2H), 3.67-3.58 (m, 2H), 3.53 (s, 3H), 3.49-3.42 (m, 2H), 3.37-3.32 (m, 2H, partially obscured by the water signal), 3.23 (s, 3H), 2.41 (s, 3H), 1.63 (br. d, 3H).

LC/MS (Method 17, ESIpos): R$_t$=1.54 min, m/z=492.15 [M+H]$^+$.

Example 472

Methyl [1-{[3-(2-methoxypropyl)-5-methyl-2,4-dioxo-1-(3,3,3-trifluoropropyl)-1,2,3,4-tetrahydrothieno[2,3-d]pyrimidin-6-yl]methyl}imidazolidin-2-ylidene]carbamate (racemate)

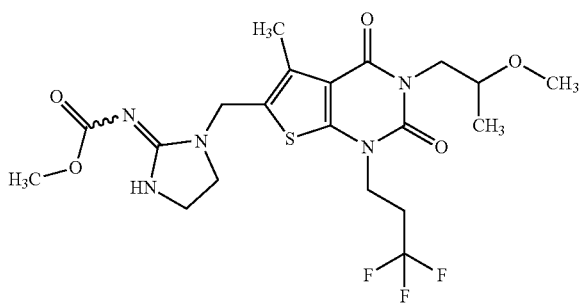

650 mg (1.23 mmol, 80% purity) of the compound from Ex. 458A and 343 µl (2.46 mmol) of triethylamine were dissolved in 15 ml of dichloromethane, and a solution of 384 mg (2.46 mmol) of methyl (dichloromethylene)carbamate in 15 ml of dichloromethane was added. After the reaction mixture had been stirred at RT for 2.5 days, it was concentrated to dryness. The remaining residue was purified by MPLC (Biotage Isolera, cartridge with 100 g of silica gel, cyclohexane/ethyl acetate 90:10→0:100). The product fractions were combined and concentrated. After drying under high vacuum, 260 mg (40% of theory, 97% purity) of the title compound were obtained.

$^1$H-NMR (400 MHz, DMSO-$d_6$, δ/ppm): 8.05 (br. s, 1H), 4.58 (s, 2H), 4.13-4.00 (m, 3H), 3.76 (dd, 1H), 3.69-3.58 (m, 1H), 3.54 (s, 3H), 3.50-3.42 (m, 2H), 3.40-3.34 (m, 2H), 3.21 (s, 3H), 2.83-2.68 (m, 2H), 2.43 (s, 3H), 1.05 (d, 3H).

LC/MS (Method 1, ESIpos): $R_t$=0.77 min, m/z=506 [M+H]$^+$.

Example 473

Methyl [1-{[3-(2-methoxypropyl)-5-methyl-2,4-dioxo-1-(3,3,3-trifluoropropyl)-1,2,3,4-tetrahydrothieno[2,3-d]pyrimidin-6-yl]methyl}imidazolidin-2-ylidene]carbamate (Enantiomer 1)

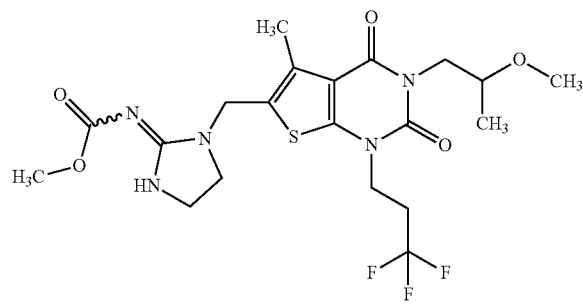

250 mg (494 mmol) of the racemic compound from Ex. 472 were dissolved in 25 ml of methanol and, in 9 portions, separated into the enantiomers by preparative SFC on a chiral phase [column: Daicel Chiralcel OX-H, 5 µm, 250 mm×30 mm; eluent: carbon dioxide/ethanol 7:3; flow rate: 100 ml/min; temperature: 40° C.; detection: 210 nm]. After concentration of the product fractions and drying of the solids under high vacuum, 97 mg (77% of theory) of Enantiomer 1 were obtained (>99% ee, chiral analytical HPLC).

$^1$H-NMR (400 MHz, DMSO-$d_6$, δ/ppm): 8.03 (s, 1H), 4.58 (s, 2H), 4.16-4.00 (m, 3H), 3.76 (dd, 1H), 3.63 (sext, 1H), 3.53 (s, 3H), 3.50-3.42 (m, 2H), 3.41-3.33 (m, 2H), 3.21 (s, 3H), 2.83-2.68 (m, 2H), 2.43 (s, 3H), 1.05 (d, 3H).

Chiral analytical SFC [column: Daicel Chiralcel QX, 3 µm, 50 mm×4.6 mm; eluent: carbon dioxide/ethanol 7:3; flow rate: 3 ml/min; temperature: 40° C.; detection: 210 nm]: $R_t$=2.74 min.

Example 474

Methyl [1-{[3-(2-methoxypropyl)-5-methyl-2,4-dioxo-1-(3,3,3-trifluoropropyl)-1,2,3,4-tetrahydrothieno[2,3-d]pyrimidin-6-yl]methyl}imidazolidin-2-ylidene]carbamate (Enantiomer 2)

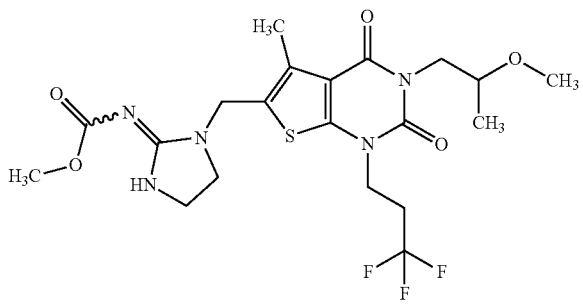

250 mg (494 mmol) of the racemic compound from Ex. 472 were dissolved in 25 ml of methanol and, in 9 portions, separated into the enantiomers by preparative SFC on a chiral phase [column: Daicel Chiralcel OX-H, 5 µm, 250 mm×30 mm; eluent: carbon dioxide/ethanol 7:3; flow rate: 100 ml/min; temperature: 40° C.; detection: 210 nm]. After concentration of the product fractions and drying of the solids under high vacuum, 104 mg (83% of theory) of Enantiomer 2 were obtained (>99% ee, chiral analytical HPLC).

$^1$H-NMR (400 MHz, DMSO-$d_6$, δ/ppm): 8.03 (s, 1H), 4.58 (s, 2H), 4.17-3.99 (m, 3H), 3.76 (dd, 1H), 3.63 (sext, 1H), 3.53 (s, 3H), 3.50-3.42 (m, 2H), 3.40-3.33 (m, 2H), 3.21 (s, 3H), 2.83-2.68 (m, 2H), 2.43 (s, 3H), 1.05 (d, 3H).

Chiral analytical SFC [column: Daicel Chiralcel QX, 3 µm, 50 mm×4.6 mm; eluent: carbon dioxide/ethanol 7:3; flow rate: 3 ml/min; temperature: 40° C.; detection: 210 nm]: $R_t$=5.07 min.

Example 475

6-[(2,3-Dioxopiperazin-1-yl)methyl]-3-ethyl-5-methyl-1-(tetrahydrofuran-2-ylmethyl)thieno[2,3-d]pyrimidine-2,4(1H,3H)-dione (racemate)

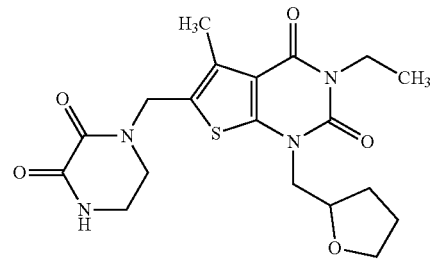 [SMILES: CCn1c(=O)c2c(C)c(CN3CCNC(=O)C3=O)sc2n(CC2CCCO2)c1=O]

1.27 g (2.77 mmol, 80% purity) of the compound from Example 225A were dissolved in 50 ml of ethanol, and 708 µl (5.13 mmol) of diethyl oxalate were added. The mixture was stirred at 80° C. for about 16 h. Thereafter, the reaction solution was concentrated on a rotary evaporator. The crude product obtained was purified by preparative HPLC (Method 8). After combination of the product fractions, concentration and drying under high vacuum, 447 mg (38% of theory) of the title compound were obtained.

$^1$H-NMR (400 MHz, DMSO-d$_6$, δ/ppm): 8.63 (br. s, 1H), 4.69 (s, 2H), 4.28-4.17 (m, 1H), 4.03 (dd, 1H), 3.90 (q, 2H), 3.79-3.66 (m, 2H), 3.65-3.57 (m, 1H), 3.52-3.43 (m, 2H), 3.33-3.30 (m, 2H, almost totally obscured by the water signal), 2.43 (s, 3H), 2.04-1.75 (m, 3H), 1.72-1.59 (m, 1H), 1.11 (t, 3H).

LC/MS (Method 1, ESIpos): R$_t$=0.65 min, m/z=421 [M+H]$^+$.

Example 476

6-[(2,3-Dioxopiperazin-1-yl)methyl]-3-ethyl-5-methyl-1-(tetrahydrofuran-2-ylmethyl)thieno[2,3-d]pyrimidine-2,4(1H,3H)-dione (Enantiomer 1)

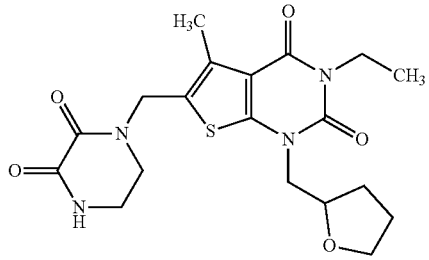 [SMILES: CCn1c(=O)c2c(C)c(CN3CCNC(=O)C3=O)sc2n(CC2CCCO2)c1=O]

440 mg (1.05 mmol) of the racemic compound from Ex. 475 were dissolved in a mixture of 12 ml of ethanol and 15 ml of acetonitrile and, in 36 portions, separated into the enantiomers by preparative HPLC on a chiral phase [column: Daicel Chiralcel OX-H, 5 μm, 250 mm×20 mm; eluent: ethanol; flow rate: 15 ml/min; temperature: 25° C.; detection: 210 nm]. After concentration of the product fractions and drying of the solids under high vacuum, 142 mg (64% of theory) of Enantiomer 1 were obtained (99.0% ee, chiral analytical HPLC).

$^1$H-NMR (400 MHz, DMSO-d$_6$, δ/ppm): 8.61 (br. s, 1H), 4.69 (s, 2H), 4.28-4.17 (m, 1H), 4.03 (dd, 1H), 3.90 (q, 2H), 3.78-3.67 (m, 2H), 3.65-3.57 (m, 1H), 3.51-3.44 (m, 2H), 3.33-3.29 (m, 2H, almost totally obscured by the water signal), 2.43 (s, 3H), 2.05-1.75 (m, 3H), 1.71-1.58 (m, 1H), 1.11 (t, 3H).

Chiral analytical HPLC [column: Daicel Chiralpak OX-H, 3 μm, 50 mm×4.6 mm; eluent: ethanol; flow rate: 1 ml/min; temperature: 40° C.; detection: 220 nm]: R$_t$=2.31 min.

Example 477

6-[(2,3-Dioxopiperazin-1-yl)methyl]-3-ethyl-5-methyl-1-(tetrahydrofuran-2-ylmethyl)thieno[2,3-d]pyrimidine-2,4(1H,3H)-dione (Enantiomer 2)

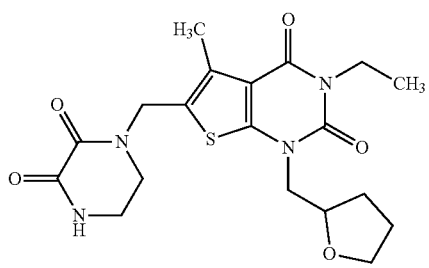 [SMILES: CCn1c(=O)c2c(C)c(CN3CCNC(=O)C3=O)sc2n(CC2CCCO2)c1=O]

440 mg (1.05 mmol) of the racemic compound from Ex. 475 were dissolved in a mixture of 12 ml of ethanol and 15 ml of acetonitrile and, in 36 portions, separated into the enantiomers by preparative HPLC on a chiral phase [column: Daicel Chiralcel OX-H, 5 μm, 250 mm×20 mm; eluent: ethanol; flow rate: 15 ml/min; temperature: 25° C.; detection: 210 nm]. After concentration of the product fractions and drying of the solids under high vacuum, 149 mg (67% of theory) of Enantiomer 2 were obtained (99.0% ee, chiral analytical HPLC).

$^1$H-NMR (400 MHz, DMSO-d$_6$, δ/ppm): 8.61 (br. s, 1H), 4.69 (s, 2H), 4.27-4.17 (m, 1H), 4.03 (dd, 1H), 3.90 (q, 2H), 3.78-3.67 (m, 2H), 3.65-3.56 (m, 1H), 3.51-3.44 (m, 2H), 3.33-3.29 (m, 2H, almost totally obscured by the water signal), 2.43 (s, 3H), 2.04-1.75 (m, 3H), 1.69-1.61 (m, 1H), 1.11 (t, 3H).

Chiral analytical HPLC [column: Daicel Chiralpak OX-H, 3 μm, 50 mm×4.6 mm; eluent: ethanol; flow rate: 1 ml/min; temperature: 40° C.; detection: 220 nm]: R$_t$=3.28 min.

Example 478

6-[(2,3-Dioxopiperazin-1-yl)methyl]-3-isopropyl-5-methyl-1-(3,3,3-trifluoropropyl)thieno[2,3-d]pyrimidine-2,4(1H,3H)-dione

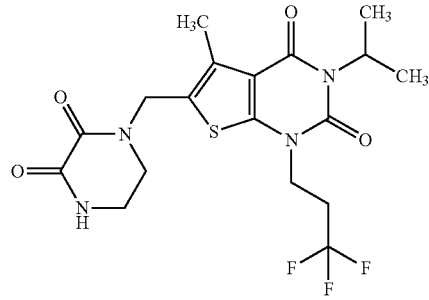 [SMILES: Cc1c(CN2CCNC(=O)C2=O)sc2c1c(=O)n(C(C)C)c(=O)n2CCC(F)(F)F]

Analogously to the method described in Ex. 397, 470 mg (0.934 mmol, 78% purity) of the compound from Ex. 309A and 238 μl (1.73 mmol) of diethyl oxalate were used to obtain 118 mg (27% of theory) of the title compound.

$^1$H-NMR (400 MHz, DMSO-d$_6$, δ/ppm): 8.62 (br. s, 1H), 5.13 (sept, 1H), 4.70 (s, 2H), 4.07 (br. t, 2H), 3.54-3.43 (m, 2H), 3.34-3.29 (m, 2H, almost totally obscured by the water signal), 2.85-2.67 (m, 2H), 2.43 (s, 3H), 1.40 (d, 6H).

LC/MS (Method 17, ESIneg): R$_t$=1.49 min, m/z=491.12 [M−H+HCO$_2$H]$^−$.

Example 479

6-[(2,3-Dioxopiperazin-1-yl)methyl]-3-isopropyl-1-(2-methoxyethyl)-5-methylthieno[2,3-d]pyrimidine-2,4(1H,3H)-dione

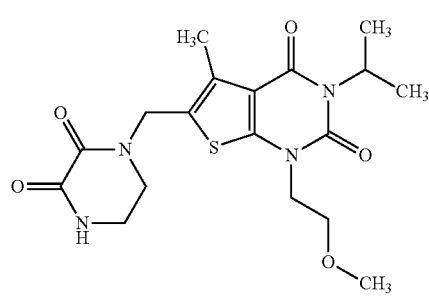 [SMILES: COCCn1c(=O)n(C(C)C)c(=O)c2c(C)c(CN3CCNC(=O)C3=O)sc21]

Analogously to the method described in Ex. 397, 730 mg (1.65 mmol, 80% purity) of the compound from Ex. 310A and 420 μl (3.05 mmol) of diethyl oxalate were used to obtain 200 mg (29% of theory) of the title compound.

¹H-NMR (400 MHz, DMSO-d₆, δ/ppm): 8.61 (br. s, 1H), 5.13 (sept, 1H), 4.68 (s, 2H), 3.99 (t, 2H), 3.61 (t, 2H), 3.51-3.42 (m, 2H), 3.33-3.28 (m, 2H, almost totally obscured by the water signal), 3.24 (s, 3H), 2.41 (s, 3H), 1.40 (d, 6H).

LC/MS (Method 17, ESIneg): $R_t$=1.24 min, m/z=407.14 [M–H]⁻.

Example 480

6-[(2,3-Dioxopiperazin-1-yl)methyl]-3-isopropyl-5-methyl-1-(tetrahydrofuran-2-ylmethyl)thieno[2,3-d]pyrimidine-2,4(1H,3H)-dione (racemate)

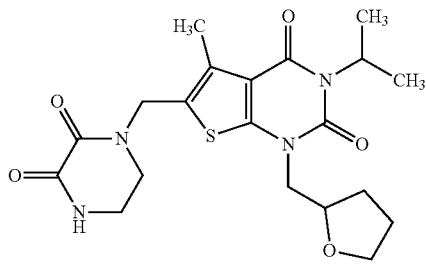 [SMILES: Cc1c(CN2CCNC(=O)C2=O)sc2c1c(=O)n(C(C)C)c(=O)n2CC1CCCO1]

Analogously to the method described in Ex. 397, 560 mg (1.18 mmol, 80% purity) of the compound from Ex. 312A and 300 μl (2.18 mmol) of diethyl oxalate were used to obtain 234 mg (44% of theory) of the title compound. The HPLC purification here was followed by stirring of the product with acetonitrile at RT.

¹H-NMR (400 MHz, DMSO-d₆, δ/ppm): 8.61 (br. s, 1H), 5.14 (sept, 1H), 4.68 (d, 2H), 4.27-4.15 (m, 1H), 4.02 (dd, 1H), 3.78-3.70 (m, 1H), 3.69-3.56 (m, 2H), 3.52-3.41 (m, 2H), 3.33-3.29 (m, 2H, almost totally obscured by the water signal), 2.42 (s, 3H), 2.04-1.74 (m, 3H), 1.71-1.59 (m, 1H), 1.40 (dd, 6H).

LC/MS (Method 1, ESIpos): $R_t$=0.73 min, m/z=435 [M+H]⁺.

Example 481

6-[(2,3-Dioxopiperazin-1-yl)methyl]-3-isopropyl-5-methyl-1-(tetrahydrofuran-2-ylmethyl)thieno[2,3-d]pyrimidine-2,4(1H,3H)-dione (Enantiomer 1)

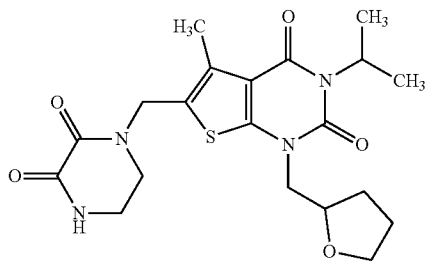 [SMILES: Cc1c(CN2CCNC(=O)C2=O)sc2c1c(=O)n(C(C)C)c(=O)n2CC1CCCO1]

213 mg (0.490 mmol) of the racemic compound from Ex. 480 were dissolved in a mixture of 8 ml of ethanol and 12 ml of acetonitrile and, in 27 portions, separated into the enantiomers by preparative HPLC on a chiral phase [column: Daicel Chiralcel OX-H, 5 μm, 250 mm×20 mm; eluent: ethanol; flow rate: 15 ml/min; temperature: 25° C.; detection: 210 nm]. After concentration of the product fractions and drying of the solids under high vacuum, 89 mg (83% of theory) of Enantiomer 1 were obtained (99.0% ee, chiral analytical HPLC).

¹H-NMR (400 MHz, DMSO-d₆, δ/ppm): 8.61 (br. s, 1H), 5.14 (sept, 1H), 4.68 (d, 2H), 4.26-4.15 (m, 1H), 4.02 (dd, 1H), 3.78-3.70 (m, 1H), 3.69-3.56 (m, 2H), 3.51-3.42 (m, 2H), 3.33-3.29 (m, 2H, almost totally obscured by the water signal), 2.42 (s, 3H), 2.03-1.74 (m, 3H), 1.71-1.58 (m, 1H), 1.40 (dd, 6H).

Chiral analytical HPLC [column: Daicel Chiralpak OX-3, 3 μm, 50 mm×4.6 mm; eluent: ethanol; flow rate: 1 ml/min; temperature: 25° C.; detection: 220 nm]: $R_t$=1.63 min.

Example 482

6-[(2,3-Dioxopiperazin-1-yl)methyl]-3-isopropyl-5-methyl-1-(tetrahydrofuran-2-ylmethyl)thieno[2,3-d]pyrimidine-2,4(1H,3H)-dione (Enantiomer 2)

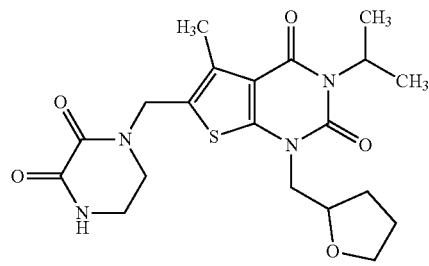 [SMILES: Cc1c(CN2CCNC(=O)C2=O)sc2c1c(=O)n(C(C)C)c(=O)n2CC1CCCO1]

213 mg (0.490 mmol) of the racemic compound from Ex. 480 were dissolved in a mixture of 8 ml of ethanol and 12 ml of acetonitrile and, in 27 portions, separated into the enantiomers by preparative HPLC on a chiral phase [column: Daicel Chiralcel OX-H, 5 μm, 250 mm×20 mm; eluent: ethanol; flow rate: 15 ml/min; temperature: 25° C.; detection: 210 nm]. After concentration of the product fractions and drying of the solids under high vacuum, 88 mg (82% of theory) of Enantiomer 2 were obtained (99.0% ee, chiral analytical HPLC).

¹H-NMR (400 MHz, DMSO-d₆, δ/ppm): 8.61 (br. s, 1H), 5.14 (sept, 1H), 4.68 (d, 2H), 4.28-4.15 (m, 1H), 4.02 (dd, 1H), 3.79-3.70 (m, 1H), 3.69-3.56 (m, 2H), 3.50-3.42 (m, 2H), 3.33-3.29 (m, 2H, almost totally obscured by the water signal), 2.42 (s, 3H), 2.04-1.75 (m, 3H), 1.72-1.58 (m, 1H), 1.40 (dd, 6H).

Chiral analytical HPLC [column: Daicel Chiralpak OX-3, 3 μm, 50 mm×4.6 mm; eluent: ethanol; flow rate: 1 ml/min; temperature: 25° C.; detection: 220 nm]: $R_t$=2.33 min.

Example 483

3-(2,2-Dimethylpropyl)-6-[(2,3-dioxopiperazin-1-yl)methyl]-5-methyl-1-(tetrahydrofuran-2-ylmethyl)thieno[2,3-d]pyrimidine-2,4(1H,3H)-dione (racemate)

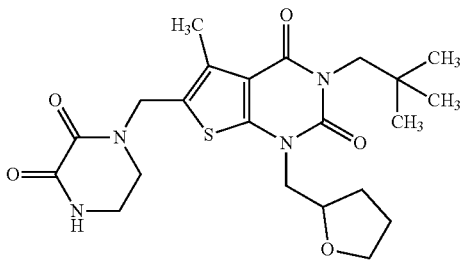 [SMILES: Cc1c(CN2CCNC(=O)C2=O)sc2c1c(=O)n(CC(C)(C)C)c(=O)n2CC1CCCO1]

560 mg (1.17 mmol, 85% purity) of the compound from Example 454A were dissolved in 25 ml of ethanol, and 297 µl (2.16 mmol) of diethyl oxalate were added. The mixture was stirred at 80° C. for about 16 h. Thereafter, the reaction solution was concentrated on a rotary evaporator. The remaining solids were dissolved in ethyl acetate and washed successively with saturated sodium carbonate solution and saturated sodium chloride solution. After drying over anhydrous magnesium sulphate, the mixture was filtered and concentrated again. The crude product obtained was purified by preparative HPLC (Method 8). After combination of the product fractions, concentration and drying under high vacuum, 268 mg (49% of theory) of the title compound were obtained.

$^1$H-NMR (500 MHz, DMSO-d$_6$, δ/ppm): 8.61 (br. s, 1H), 4.69 (s, 2H), 4.27-4.17 (m, 1H), 4.01 (br. dd, 1H), 3.82 (br. s, 2H), 3.77-3.68 (m, 2H), 3.64-3.57 (m, 1H), 3.53-3.45 (m, 2H), 3.34-3.30 (m, 2H, almost totally obscured by the water signal), 2.42 (s, 3H), 2.02-1.76 (m, 3H), 1.69-1.63 (m, 1H), 0.89 (s, 9H).

LC/MS (Method 17, ESIneg): R$_t$=1.56 min, m/z=461.19 [M–H]$^-$.

Example 484

3-(2,2-Dimethylpropyl)-6-[(2,3-dioxopiperazin-1-yl)methyl]-5-methyl-1-(tetrahydrofuran-2-ylmethyl)thieno[2,3-d]pyrimidine-2,4(1H,3H)-dione (Enantiomer 1)

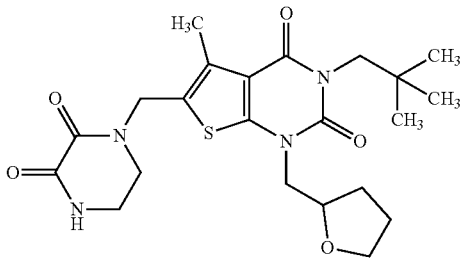 [SMILES: Cc1c(CN2CCNC(=O)C2=O)sc2c1c(=O)n(CC(C)(C)C)c(=O)n2CC1CCCO1]

258 mg (0.558 mmol) of the racemic compound from Ex. 483 were dissolved in 6 ml of acetonitrile and, in 20 portions, separated into the enantiomers by preparative HPLC on a chiral phase [column: Daicel Chiralpak IE, 5 µm, 250 mm×20 mm; eluent: tert-butyl methyl ether/acetonitrile 1:1; flow rate: 15 ml/min; temperature: 30° C.; detection: 220 nm]. After concentration of the product fractions and drying of the solids under high vacuum, 69 mg (53% of theory) of Enantiomer 1 were obtained (98.0% ee, chiral analytical HPLC).

$^1$H-NMR (400 MHz, DMSO-d$_6$, δ/ppm): 8.08 (s, 1H), 5.08-4.95 (m, 1H), 4.70 (q, 2H), 4.54-4.36 (m, 2H), 4.49 (s, 2H), 4.26-4.07 (m, 2H), 3.52-3.36 (m, 4H), 2.76-2.62 (m, 1H), 2.55-2.46 (m, 1H, mostly obscured by the DMSO signal), 2.41 (s, 3H).

Chiral analytical HPLC [column: Daicel Chiralpak IE, 5 µm, 250 mm×4.6 mm; eluent: tert-butyl methyl ether/acetonitrile 1:1; flow rate: 1 ml/min; temperature: 30° C.; detection: 220 nm]: R$_t$=13.13 min.

Example 485

3-(2,2-Dimethylpropyl)-6-[(2,3-dioxopiperazin-1-yl)methyl]-5-methyl-1-(tetrahydrofuran-2-ylmethyl)thieno[2,3-d]pyrimidine-2,4(1H,3H)-dione (Enantiomer 2)

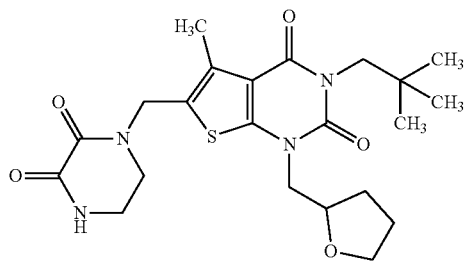 [SMILES: Cc1c(CN2CCNC(=O)C2=O)sc2c1c(=O)n(CC(C)(C)C)c(=O)n2CC1CCCO1]

258 mg (0.558 mmol) of the racemic compound from Ex. 483 were dissolved in 6 ml of acetonitrile and, in 20 portions, separated into the enantiomers by preparative HPLC on a chiral phase [column: Daicel Chiralpak IE, 5 µm, 250 mm×20 mm; eluent: tert-butyl methyl ether/acetonitrile 1:1; flow rate: 15 ml/min; temperature: 30° C.; detection: 220 nm]. After concentration of the product fractions and drying of the solids under high vacuum, 83 mg (64% of theory) of Enantiomer 2 were obtained (91.0% ee, chiral analytical HPLC).

$^1$H-NMR (400 MHz, DMSO-d$_6$, δ/ppm): 8.61 (br. s, 1H), 4.69 (s, 2H), 4.27-4.16 (m, 1H), 4.01 (dd, 1H), 3.82 (br. s, 2H), 3.78-3.68 (m, 2H), 3.66-3.56 (m, 1H), 3.53-3.45 (m, 2H), 3.35-3.30 (m, 2H, almost totally obscured by the water signal), 2.42 (s, 3H), 2.03-1.74 (m, 3H), 1.72-1.59 (m, 1H), 0.89 (s, 9H).

Chiral analytical HPLC [column: Daicel Chiralpak IE, 5 µm, 250 mm×4.6 mm; eluent: tert-butyl methyl ether/acetonitrile 1:1; flow rate: 1 ml/min; temperature: 30° C.; detection: 220 nm]: R$_t$=14.02 min.

Example 486

6-[(2,3-Dioxopiperazin-1-yl)methyl]-1-(2-methoxyethyl)-5-methyl-3-(2,2,2-trifluoroethyl)thieno[2,3-d]pyrimidine-2,4(1H,3H)-dione

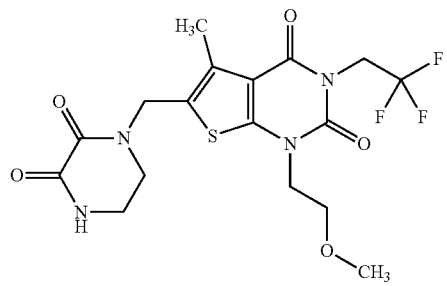 [SMILES: COCCn1c(=O)n(CC(F)(F)F)c(=O)c2c(C)c(CN3CCNC(=O)C3=O)sc21]

Analogously to the method described in Ex. 397, 500 mg (1.01 mmol, 80% purity) of the compound from Ex. 249A and 259 µl (1.88 mmol) of diethyl oxalate were used to obtain 151 mg (33% of theory) of the title compound.

$^1$H-NMR (400 MHz, DMSO-d$_6$, δ/ppm): 8.62 (br. s, 1H), 4.70 (q, 2H), 4.70 (s, 2H), 4.06 (t, 2H), 3.64 (t, 2H), 3.54-3.46 (m, 2H), 3.34-3.29 (m, 2H, almost totally obscured by the water signal), 3.23 (s, 3H), 2.43 (s, 3H).

LC/MS (Method 1, ESIneg): R$_t$=0.69 min, m/z=493 [M−H+HCO$_2$H]$^−$.

Example 487

6-[(2,3-Dioxopiperazin-1-yl)methyl]-5-methyl-1-(tetrahydrofuran-2-ylmethyl)-3-(2,2,2-trifluoroethyl)thieno[2,3-d]pyrimidine-2,4(1H,3H)-dione (racemate)

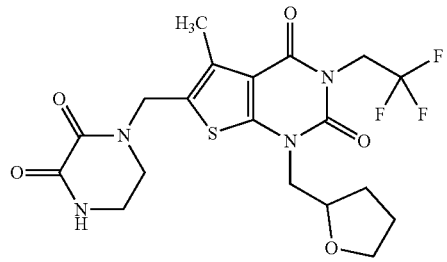 [SMILES: Cc1c(CN2CCNC(=O)C2=O)sc2c1c(=O)n(CC(F)(F)F)c(=O)n2CC1CCCO1]

Analogously to the method described in Ex. 397, 545 mg (1.04 mmol, 80% purity) of the compound from Ex. 252A and 265 µl (1.92 mmol) of diethyl oxalate were used to obtain 275 mg (55% of theory) of the title compound.

$^1$H-NMR (500 MHz, DMSO-d$_6$, δ/ppm): 8.62 (br. s, 1H), 4.70 (q, 2H), 4.70 (s, 2H), 4.27-4.17 (m, 1H), 4.06 (dd, 1H), 3.80-3.70 (m, 2H), 3.65-3.57 (m, 1H), 3.54-3.44 (m, 2H), 3.33-3.29 (m, 2H, almost totally obscured by the water signal), 2.43 (s, 3H), 2.04-1.76 (m, 3H), 1.72-1.60 (m, 1H).

LC/MS (Method 17, ESIneg): R$_t$=1.34 min, m/z=519.12 [M−H+HCO$_2$H]$^−$.

Example 488

6-[(2,3-Dioxopiperazin-1-yl)methyl]-5-methyl-1-(tetrahydrofuran-2-ylmethyl)-3-(2,2,2-trifluoroethyl)thieno[2,3-d]pyrimidine-2,4(1H,3H)-dione (Enantiomer 1)

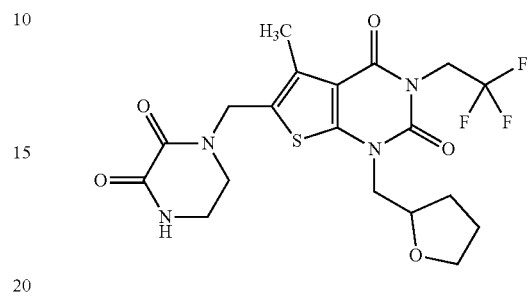

257 mg (0.542 mmol) of the racemic compound from Ex. 487 were dissolved in a mixture of 15 ml each of acetonitrile and methanol and, in 60 portions, separated into the enantiomers by preparative SFC on a chiral phase [column: Daicel Chiralcel OX-H, 5 µm, 250 mm×20 mm; eluent: carbon dioxide/ethanol 72:28; flow rate: 80 ml/min; temperature: 40° C.; detection: 210 nm]. After concentration of the product fractions and drying of the solids under high vacuum, 57 mg (44% of theory) of Enantiomer 1 were obtained (>99% ee, chiral analytical HPLC).

$^1$H-NMR (400 MHz, DMSO-d$_6$, δ/ppm): 8.62 (br. s, 1H), 4.70 (q, 2H), 4.70 (s, 2H), 4.27-4.17 (m, 1H), 4.06 (dd, 1H), 3.81-3.69 (m, 2H), 3.66-3.57 (m, 1H), 3.54-3.45 (m, 2H), 3.34-3.29 (m, 2H, almost totally obscured by the water signal), 2.43 (s, 3H), 2.05-1.75 (m, 3H), 1.72-1.61 (m, 1H).

Chiral analytical SFC [column: Daicel Chiralcel QX, 3 µm, 50 mm×4.6 mm; eluent: carbon dioxide/methanol 7:3; flow rate: 3 ml/min; temperature: 40° C.; detection: 210 nm]: R$_t$=4.73 min.

Example 489

6-[(2,3-Dioxopiperazin-1-yl)methyl]-5-methyl-1-(tetrahydrofuran-2-ylmethyl)-3-(2,2,2-trifluoroethyl)thieno[2,3-d]pyrimidine-2,4(1H,3H)-dione (Enantiomer 2)

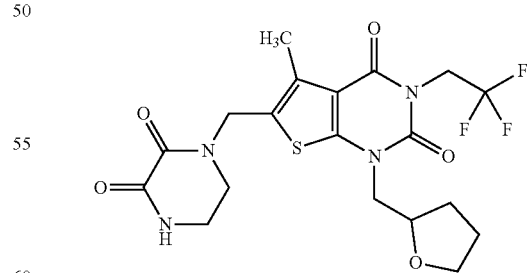

257 mg (0.542 mmol) of the racemic compound from Ex. 487 were dissolved in a mixture of 15 ml each of acetonitrile and methanol and, in 60 portions, separated into the enantiomers by preparative SFC on a chiral phase [column: Daicel Chiralcel OX-H, 5 µm, 250 mm×20 mm; eluent: carbon dioxide/ethanol 72:28; flow rate: 80 ml/min; temperature: 40° C.; detection: 210 nm]. After concentration of the product fractions and drying of the solids under high vacuum, 73 mg (56% of theory) of Enantiomer 2 were obtained (>99% ee, chiral analytical HPLC).

¹H-NMR (400 MHz, DMSO-d₆, δ/ppm): 8.62 (br. s, 1H), 4.70 (q, 2H), 4.70 (s, 2H), 4.27-4.17 (m, 1H), 4.06 (dd, 1H), 3.81-3.68 (m, 2H), 3.66-3.56 (m, 1H), 3.55-3.43 (m, 2H), 3.34-3.29 (m, 2H, almost totally obscured by the water signal), 2.43 (s, 3H), 2.05-1.75 (m, 3H), 1.72-1.61 (m, 1H).

Chiral analytical SFC [column: Daicel Chiralcel QX, 3 μm, 50 mm×4.6 mm; eluent: carbon dioxide/methanol 7:3; flow rate: 3 ml/min; temperature: 40° C.; detection: 210 nm]: $R_t$=7.39 min.

Example 490

6-[(2,3-Dioxopiperazin-1-yl)methyl]-5-methyl-3-(1,1,1-trifluoropropan-2-yl)-1-(3,3,3-trifluoropropyl)thieno[2,3-d]pyrimidine-2,4(1H,3H)-dione (racemate)

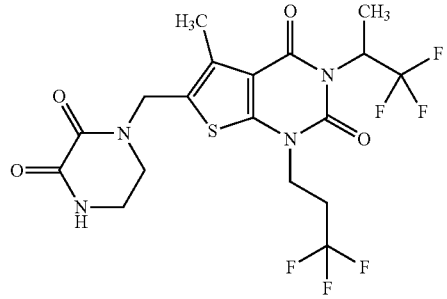 [SMILES: Cc1c(CN2CCNC(=O)C2=O)sc2c1c(=O)n(C(C)C(F)(F)F)c(=O)n2CCC(F)(F)F]

590 mg (1.11 mmol, 84% purity) of the compound from Example 455A were dissolved in 40 ml of ethanol, and 283 μl (2.05 mmol) of diethyl oxalate were added. The mixture was stirred at 80° C. for about 16 h. Thereafter, the reaction solution was concentrated on a rotary evaporator. The crude product obtained was purified by preparative HPLC (Method 8). After combination of the product fractions, concentration and drying under high vacuum, 205 mg (36% of theory) of the title compound were obtained.

¹H-NMR (400 MHz, DMSO-d₆, δ/ppm): 8.63 (br. s, 1H), 5.83-5.47 (m, 1H), 4.72 (s, 2H), 4.22-4.02 (m, 2H), 3.59-3.45 (m, 2H), 2.87-2.69 (m, 2H), 2.44 (s, 3H), 1.63 (br. d, 3H).

LC/MS (Method 17, ESIneg): $R_t$=1.63 min, m/z=545.09 [M−H+HCO₂H]⁻.

Example 491

6-[(2,3-Dioxopiperazin-1-yl)methyl]-1-(2-methoxyethyl)-5-methyl-3-(1,1,1-trifluoropropan-2-yl)thieno[2,3-d]pyrimidine-2,4(1H,3H)-dione (racemate)

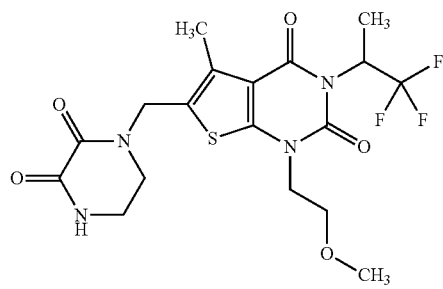 [SMILES: COCCn1c(=O)n(C(C)C(F)(F)F)c(=O)c2c(C)c(CN3CCNC(=O)C3=O)sc21]

Analogously to the method described in Ex. 397, 295 mg (0.592 mmol, 82% purity) of the compound from Ex. 456A and 151 μl (1.10 mmol) of diethyl oxalate were used to obtain 155 mg (56% of theory) of the title compound.

¹H-NMR (400 MHz, DMSO-d₆, δ/ppm): 8.62 (br. s, 1H), 5.84-5.45 (m, 1H), 4.69 (s, 2H), 4.12-3.95 (m, 2H), 3.70-3.56 (m, 2H), 3.55-3.43 (m, 2H), 3.34-3.29 (m, 2H, almost totally obscured by the water signal), 3.23 (s, 3H), 2.42 (s, 3H), 1.63 (br. d, 3H).

LC/MS (Method 17, ESIneg): $R_t$=1.38 min, m/z=507.12 [M−H+HCO₂H]⁻.

Example 492

6-[(2,3-Dioxopiperazin-1-yl)methyl]-3-(2-ethoxyethyl)-1-(3-fluoropropyl)-5-methylthieno[2,3-d]pyrimidine-2,4(1H,3H)-dione

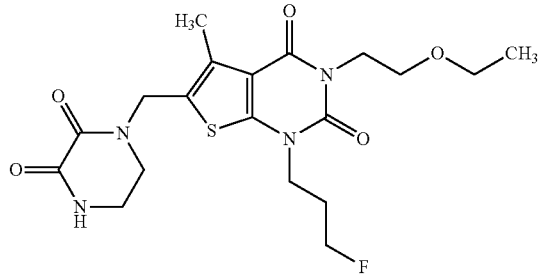 [SMILES: CCOCCn1c(=O)c2c(C)c(CN3CCNC(=O)C3=O)sc2n(CCCF)c1=O]

200 mg (0.388 mmol, 75% purity) of the compound from Example 457A were dissolved in 6.6 ml of ethanol, and 573 mg (3.88 mmol) of diethyl oxalate were added. The mixture was stirred at 80° C. for 16 h. Thereafter, the reaction solution was concentrated on a rotary evaporator. The residue was taken up in 30 ml of dichloromethane and this solution was washed with water and saturated sodium hydrogencarbonate solution. After drying over anhydrous sodium sulphate, the mixture was filtered and concentrated. The remaining residue was dissolved in 3 ml of DMSO and this solution was purified by means of preparative HPLC (Method 14). Combination of the product fractions and freeze-drying gave 118 mg (66% of theory) of the title compound.

¹H-NMR (500 MHz, DMSO-d₆, δ/ppm): 8.64 (br. s, 1H), 4.70 (s, 2H), 4.59 (t, 1H), 4.47 (t, 1H), 4.03 (t, 2H), 3.98 (br. t, 2H), 3.53-3.47 (m, 4H), 3.44 (q, 2H), 3.33-3.29 (m, 2H), 2.43 (s, 3H), 2.13-1.98 (m, 2H), 1.06 (t, 3H).

LC/MS (Method 3, ESIpos): $R_t$=0.84 min, m/z=441 [M+H]⁺.

Example 493

6-[(2,3-Dioxopiperazin-1-yl)methyl]-3-(2-methoxypropyl)-5-methyl-1-(3,3,3-trifluoropropyl)thieno[2,3-d]pyrimidine-2,4(1H,3H)-dione (racemate)

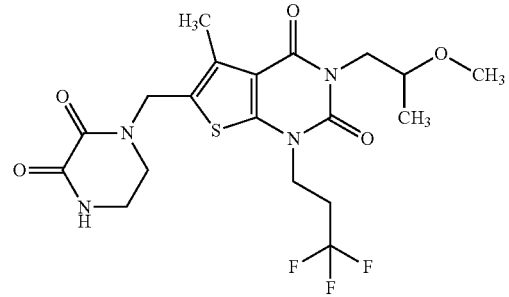 [SMILES: COC(C)Cn1c(=O)c2c(C)c(CN3CCNC(=O)C3=O)sc2n(CCC(F)(F)F)c1=O]

850 mg (1.61 mmol, 80% purity) of the compound from Example 458A were dissolved in 55 ml of ethanol, and 411 µl (2.98 mmol) of diethyl oxalate were added. The mixture was stirred at 80° C. for about 16 h. Thereafter, the reaction solution was concentrated on a rotary evaporator. The crude product obtained was purified by MPLC (Biotage Isolera, cartridge with 100 g of silica gel, dichloromethane/methanol 20:1). After combination of the product fractions, concentration and drying under high vacuum, 475 mg (59% of theory, 96% purity) of the title compound were obtained.

$^{1}$H-NMR (400 MHz, DMSO-d$_{6}$, δ/ppm): 8.62 (br. s, 1H), 4.71 (s, 2H), 4.18-3.97 (m, 3H), 3.76 (dd, 1H), 3.63 (sext, 1H), 3.55-3.46 (m, 2H), 3.38-3.31 (m, 2H), 3.31 (s, 3H), 2.84-2.69 (m, 2H), 2.44 (s, 3H), 1.05 (d, 3H).

LC/MS (Method 1, ESIpos): R$_{t}$=0.79 min, m/z=477 [M+H]$^{+}$.

Example 494

6-[(2,3-Dioxopiperazin-1-yl)methyl]-3-(2-methoxypropyl)-5-methyl-1-(3,3,3-trifluoropropyl)thieno[2,3-d]pyrimidine-2,4(1H,3H)-dione (Enantiomer 1)

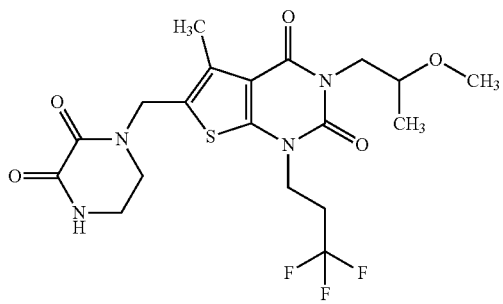 [SMILES: COC(C)Cn1c(=O)c2c(C)c(CN3CCNC(=O)C3=O)sc2n(CCC(F)(F)F)c1=O]

475 mg (0.997 mmol) of the racemic compound from Ex. 493 were dissolved in 10 ml of ethanol and, in 20 portions, separated into the enantiomers by preparative HPLC on a chiral phase [column: Daicel Chiralcel OX-H, 5 µm, 250 mm×20 mm; eluent: n-heptane/ethanol 3:7; flow rate: 15 ml/min; temperature: 25° C.; detection: 210 nm]. After concentration of the product fractions and drying of the solids under high vacuum, 201 mg (84% of theory) of Enantiomer 1 were obtained (99.0% ee, chiral analytical HPLC).

$^{1}$H-NMR (500 MHz, DMSO-d$_{6}$, δ/ppm): 8.62 (br. s, 1H), 4.71 (s, 2H), 4.17-4.08 (m, 2H), 4.05 (dd, 1H), 3.76 (dd, 1H), 3.63 (sext, 1H), 3.54-3.46 (m, 2H), 3.34-3.29 (m, 2H, almost totally obscured by the water signal), 3.21 (s, 3H), 2.83-2.70 (m, 2H), 2.44 (s, 3H), 1.05 (d, 3H).

Chiral analytical HPLC [column: Daicel Chiralpak OX-3, 3 µm, 50 mm×4.6 mm; eluent: ethanol; flow rate: 1 ml/min; temperature: 25° C.; detection: 220 nm]: R$_{t}$=1.24 min.

Example 495

6-[(2,3-Dioxopiperazin-1-yl)methyl]-3-(2-methoxypropyl)-5-methyl-1-(3,3,3-trifluoropropyl)thieno[2,3-d]pyrimidine-2,4(1H,3H)-dione (Enantiomer 2)

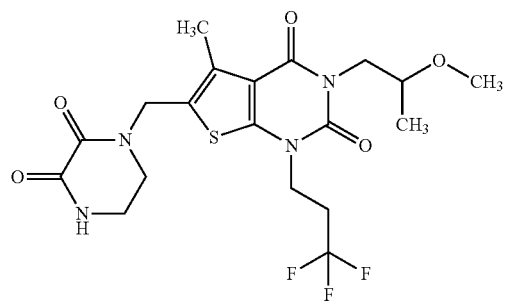 [SMILES: COC(C)Cn1c(=O)c2c(C)c(CN3CCNC(=O)C3=O)sc2n(CCC(F)(F)F)c1=O]

475 mg (0.997 mmol) of the racemic compound from Ex. 493 were dissolved in 10 ml of ethanol and, in 20 portions, separated into the enantiomers by preparative HPLC on a chiral phase [column: Daicel Chiralcel OX-H, 5 µm, 250 mm×20 mm; eluent: n-heptane/ethanol 3:7; flow rate: 15 ml/min; temperature: 25° C.; detection: 210 nm]. After concentration of the product fractions and drying of the solids under high vacuum, 198 mg (83% of theory) of Enantiomer 2 were obtained (99.0% ee, chiral analytical HPLC).

$^{1}$H-NMR (500 MHz, DMSO-d$_{6}$, δ/ppm): 8.62 (br. s, 1H), 4.71 (s, 2H), 4.18-4.08 (m, 2H), 4.05 (dd, 1H), 3.76 (dd, 1H), 3.63 (sext, 1H), 3.56-3.46 (m, 2H), 3.35-3.29 (m, 2H, almost totally obscured by the water signal), 3.21 (s, 3H), 2.83-2.69 (m, 2H), 2.44 (s, 3H), 1.05 (d, 3H).

Chiral analytical HPLC [column: Daicel Chiralpak OX-3, 3 µm, 50 mm×4.6 mm; eluent: ethanol; flow rate: 1 ml/min; temperature: 25° C.; detection: 220 nm]: R$_{t}$=1.51 min.

Example 496

1-(3-Fluoropropyl)-3-isobutyl-6-[(4-isopropyl-2,3-dioxopiperazin-1-yl)methyl]-5-methylthieno[2,3-d]pyrimidine-2,4(1H,3H)-dione

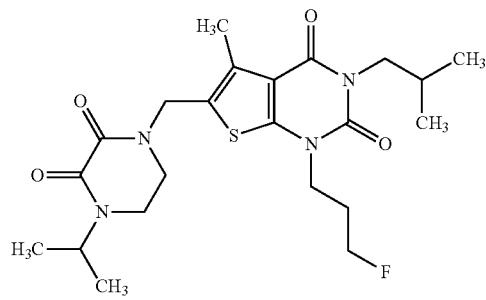 [SMILES: Cc1c(CN2CCN(C(C)C)C(=O)C2=O)sc2c1c(=O)n(CC(C)C)c(=O)n2CCCF]

The title compound (16 mg) was obtained as a by-product of the preparation and purification of the compound described in Example 121.

$^{1}$H-NMR (400 MHz, DMSO-d$_{6}$, δ/ppm): 4.69 (s, 2H), 4.59 (t, 1H), 4.56-4.44 (m, 2H), 3.99 (t, 2H), 3.71 (d, 2H), 3.54-3.47 (m, 2H), 3.44-3.38 (m, 2H), 2.44 (s, 3H), 2.15-1.96 (m, 3H), 1.08 (d, 6H), 0.85 (d, 6H).

LC/MS (Method 3, ESIpos): $R_t$=1.14 min, m/z=467 [M+H]$^+$.

Example 497

6-[(2,5-Dioxopiperazin-1-yl)methyl]-3-ethyl-5-methyl-1-(3,3,3-trifluoropropyl)thieno[2,3-d]pyrimidine-2,4(1H,3H)-dione

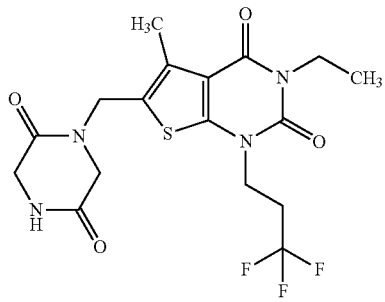 [SMILES: CCn1c(=O)c2c(C)c(CN3CC(=O)NCC3=O)sc2n(CCC(F)(F)F)c1=O]

A solution of 100 mg (0.213 mmol) of the compound from Ex. 489A, 3.5 mg (0.021 mmol) of potassium iodide and 26 mg (0.235 mmol) of potassium tert-butoxide in 4 ml of anhydrous THF was stirred at RT for about 18 h. The mixture was then concentrated to dryness. The remaining residue was separated into its components by means of preparative HPLC (Method 9). The product fractions were concentrated and the residue was dried under high vacuum. 4 mg (4% of theory, 94% purity) of the title compound were obtained.

$^1$H-NMR (400 MHz, DMSO-d$_6$, δ/ppm): 8.15 (br. s, 1H), 4.65 (s, 2H), 4.09 (t, 2H), 3.90 (q, 2H), 3.87 (s, 2H), 3.85 (s, 3H), 2.84-2.69 (m, 2H), 2.45 (s, 3H), 1.11 (t, 3H).

LC/MS (Method 17, ESIpos): $R_t$=1.30 min, m/z=433.11 [M+H]$^+$.

Example 498

1-(2-Methoxyethyl)-5-methyl-6-[(2-oxoimidazolidin-1-yl)methyl]-3-(1,1,1-trifluoropropan-2-yl)thieno[2,3-d]pyrimidine-2,4(1H,3H)-dione (Enantiomer 1)

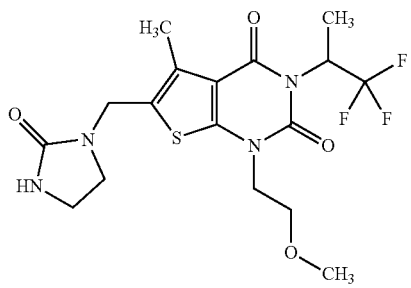 [SMILES: COCCn1c(=O)n(C(C)C(F)(F)F)c(=O)c2c(C)c(CN3CCNC3=O)sc21]

To a solution of 300 mg (0.588 mmol, 80% purity) of the compound from Ex. 514A and 123 μl (0.881 mmol) of triethylamine in 6 ml of THF were added 114 mg (0.705 mmol) of CDI, and the mixture was stirred at RT for about 18 h. Thereafter, the reaction mixture was diluted with ethyl acetate and washed successively with saturated sodium carbonate solution and saturated sodium chloride solution. After drying over anhydrous magnesium sulphate, the mixture was filtered and concentrated. The solid residue was purified by means of preparative HPLC (Method 8). The product fractions were combined, concentrated by evaporation and dried under high vacuum. 152 mg (59% of theory) of the enantiomerically pure title compound were obtained (>99% ee, chiral analytical HPLC).

$^1$H-NMR (400 MHz, DMSO-d$_6$, δ/ppm): 6.54 (s, 1H), 5.81-5.69 and 5.62-5.50 (2 m, tog. 1H), 4.35 (s, 2H), 4.06-3.99 (m, 2H), 3.66-3.60 (m, 2H), 3.28-3.18 (m, 4H), 3.24 (s, 3H), 2.38 and 2.37 (2 s, tog. 3H), 1.67 and 1.63 (2 d, tog. 3H).

LC/MS (Method 17, ESIpos): $R_t$=1.57 min, m/z=435.13 [M+H]$^+$.

Chiral analytical HPLC [column: Daicel Chiralpak AD-3, 3 μm, 50 mm×4.6 mm; eluent: heptane/ethanol 4:1; flow rate: 1 ml/min; temperature: 30° C.; detection: 220 nm]: $R_t$=1.94 min.

Specific optical rotation: $[α]_D^{20}$=−12.7·ml·dm$^{-1}$·g$^{-1}$ (methanol).

Example 499

1-(2-Methoxyethyl)-5-methyl-6-[(2-oxoimidazolidin-1-yl)methyl]-3-(1,1,1-trifluoropropan-2-yl)thieno[2,3-d]pyrimidine-2,4(1H,3H)-dione (Enantiomer 2)

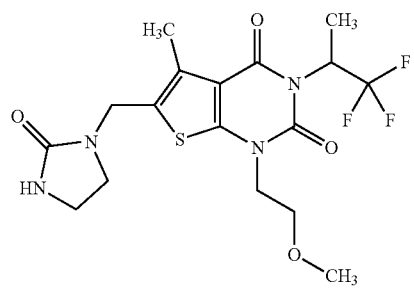 [SMILES: COCCn1c(=O)n(C(C)C(F)(F)F)c(=O)c2c(C)c(CN3CCNC3=O)sc21]

To a solution of 300 mg (0.588 mmol, 80% purity) of the compound from Ex. 515A and 123 μl (0.881 mmol) of triethylamine in 6 ml of THF were added 114 mg (0.705 mmol) of CDI, and the mixture was stirred at RT for about 18 h. Thereafter, the reaction mixture was diluted with ethyl acetate and washed successively with saturated sodium carbonate solution and saturated sodium chloride solution. After drying over anhydrous magnesium sulphate, the mixture was filtered and concentrated. The solid residue was purified by means of preparative HPLC (Method 8). The product fractions were combined, concentrated by evaporation and dried under high vacuum. 125 mg (48% of theory) of the enantiomerically pure title compound were obtained (>99% ee, chiral analytical HPLC).

$^1$H-NMR (400 MHz, DMSO-d$_6$, δ/ppm): 6.54 (s, 1H), 5.80-5.69 and 5.61-5.51 (2 m, tog. 1H), 4.35 (s, 2H), 4.06-3.99 (m, 2H), 3.65-3.60 (m, 2H), 3.28-3.19 (m, 4H), 3.24 (s, 3H), 2.38 and 2.37 (2 s, tog. 3H), 1.68 and 1.63 (2 d, tog. 3H).

LC/MS (Method 17, ESIpos): $R_t$=1.57 min, m/z=435.13 [M+H]$^+$.

Chiral analytical HPLC [column: Daicel Chiralpak AD-3, 3 μm, 50 mm×4.6 mm; eluent: heptane/ethanol 4:1; flow rate: 1 ml/min; temperature: 30° C.; detection: 220 nm]: $R_t$=1.78 min.

Specific optical rotation: $[α]_D^{20}$=+13.5°·ml·dm$^{-1}$·g$^{-1}$ (methanol).

Example 500

1-(2-Methoxyethyl)-5-methyl-6-[(2-oxoimidazolidin-1-yl)(dideutero)methyl]-3-(2,2,2-trifluoroethyl)thieno[2,3-d]pyrimidine-2,4(1H,3H)-dione

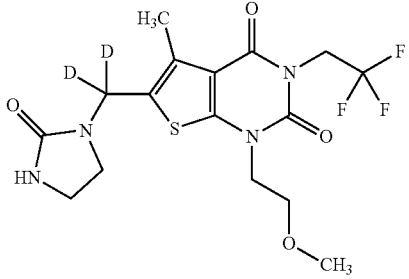 [SMILES: [2H]C([2H])(c1sc2c(c1C)c(=O)n(CC(F)(F)F)c(=O)n2CCOC)N1CCNC1=O]

To a solution of 117 mg (1.36 mmol) of imidazolidin-2-one in 3 ml of DMF were added 54 mg (1.36 mmol) of sodium hydride (60% suspension in mineral oil), then the mixture was heated to 60° C. for 5 min and subsequently cooled back down to RT ("Solution 1"). To a solution of 120 mg (0.339 mmol) of the compound from Ex. 511A in 2.4 ml of dichloromethane in another reaction vessel were added, at 0° C., 118 µl (0.677 mmol) of N,N-diisopropylethylamine and 26 µl (0.356 mmol) of thionyl chloride. After 20 min, Solution 1 was added in portions at 0° C. The reaction mixture was then stirred at RT for 3.5 days. Then it was admixed with water and extracted with ethyl acetate. The organic extract was washed with saturated sodium chloride solution and dried over anhydrous magnesium sulphate. After filtration and concentration, the residue was first prepurified by means of MPLC (Isolera, 25 g silica gel cartridge, cyclohexane/ethyl acetate 1:1→dichloromethane/methanol 10:1). The concentrated product-containing fractions were then purified further in a second chromatography step by means of preparative HPLC (Method 8). Reconcentration and drying of the product-containing fractions were followed by a third chromatography operation for further purification (likewise by preparative HPLC). After concentration of the product fractions and drying under high vacuum once again, 27 mg (18% of theory) of the title compound were thus obtained.

$^1$H-NMR (400 MHz, DMSO-$d_6$, δ/ppm): 6.53 (s, 1H), 4.70 (q, 2H), 4.05 (t, 2H), 3.67-3.59 (m, 2H), 3.29-3.16 (m, 4H), 3.24 (s, 3H), 2.39 (s, 3H).

LC/MS (Method 1, ESIpos): $R_t$=0.75 min, m/z=423 [M+H]$^+$.

Example 501

1-(2-Methoxyethyl)-5-methyl-6-[(2-oxoimidazolidin-1-yl)(dideutero)methyl]-3-[(2R)-1,1,1-trifluoropropan-2-yl]thieno[2,3-d]pyrimidine-2,4(1H,3H)-dione

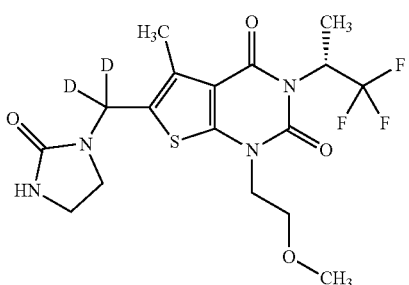

To a solution of 416 mg (4.83 mmol) of imidazolidin-2-one in 12 ml of DMF were added 193 mg (4.83 mmol) of sodium hydride (60% suspension in mineral oil), then the mixture was heated to 60° C. for 5 min and subsequently cooled back down to RT ("Solution 1"). To a solution of 445 mg (1.21 mmol) of the compound from Ex. 512A in 8 ml of dichloromethane in another reaction vessel were added, at 0° C., 421 µl (2.42 mmol) of N,N-diisopropylethylamine and 93 µl (1.27 mmol) of thionyl chloride. After 20 min, Solution 1 was added in portions at 0° C. The reaction mixture was then stirred at RT for about 18 h. Then it was admixed with water and extracted with dichloromethane. The organic extract was washed successively with water and saturated sodium chloride solution and dried over anhydrous magnesium sulphate. After filtration and concentration, the residue was purified by means of preparative HPLC (Method 8). After concentration of the product fractions and drying under high vacuum, 117 mg (22% of theory) of the title compound were obtained (>99% ee, chiral analytical HPLC).

$^1$H-NMR (400 MHz, DMSO-$d_6$, δ/ppm): 6.53 (s, 1H), 5.81-5.69 and 5.61-5.51 (2 m, tog. 1H), 4.09-3.96 (m, 2H), 3.69-3.56 (m, 2H), 3.28-3.18 (m, 4H), 3.24 (s, 3H), 2.38 and 2.37 (2 s, tog. 3H), 1.67 and 1.63 (2 d, tog. 3H).

LC/MS (Method 1, ESIpos): $R_t$=0.84 min, m/z=437 [M+H]$^+$.

Chiral analytical HPLC [column: Daicel Chiralpak ID-3, 3 µm, 50 mm×4.6 mm; eluent: heptane/isopropanol 1:1; flow rate: 1 ml/min; temperature: 30° C.; detection: 220 nm]: $R_t$=1.65 min.

Specific optical rotation: $[α]_D^{20}$=+13.7°·ml·dm$^{-1}$·g$^{-1}$ (methanol).

Example 502

1-(2-Methoxyethyl)-5-methyl-6-[(2-oxoimidazolidin-1-yl)(dideutero)methyl]-3-[(2S)-1,1,1-trifluoropropan-2-yl]thieno[2,3-d]pyrimidine-2,4(1H,3H)-dione

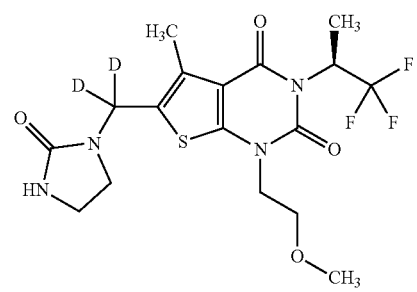 [SMILES: [2H]C([2H])(c1sc2c(c1C)c(=O)n([C@@H](C)C(F)(F)F)c(=O)n2CCOC)N1CCNC1=O]

To a solution of 148 mg (1.72 mmol) of imidazolidin-2-one in 4.5 ml of DMF were added 67 mg (1.72 mmol) of sodium hydride (60% suspension in mineral oil), then the mixture was heated to 60° C. for 5 min and subsequently cooled back down to RT ("Solution 1"). To a solution of 158 mg (0.429 mmol) of the compound from Ex. 513A in 2.5 ml of dichloromethane in another reaction vessel were added, at 0° C., 149 µl (0.858 mmol) of N,N-diisopropylethylamine and 33 µl (0.450 mmol) of thionyl chloride. After 20 min, Solution 1 was added in portions at 0° C. The reaction mixture was then stirred at RT for about 18 h. Then it was concentrated to dryness. The remaining residue was separated into its components by means of preparative HPLC (Method 8). After concentration of the product fractions and drying under high vacuum, 52 mg (27% of theory) of the title compound were obtained (>99% ee, chiral analytical HPLC).

$^1$H-NMR (400 MHz, DMSO-$d_6$, δ/ppm): 6.53 (s, 1H), 5.81-5.69 and 5.61-5.51 (2 m, tog. 1H), 4.06-3.99 (m, 2H), 3.66-3.59 (m, 2H), 3.28-3.18 (m, 4H), 3.24 (s, 3H), 2.38 and 2.37 (2 s, tog. 3H), 1.67 and 1.63 (2 d, tog. 3H).

LC/MS (Method 1, ESIpos): $R_t$=0.84 min, m/z=437 [M+H]$^+$.

Chiral analytical HPLC [column: Daicel Chiralpak ID-3, 3 µm, 50 mm×4.6 mm; eluent: heptane/isopropanol 1:1; flow rate: 1 ml/min; temperature: 30° C.; detection: 220 nm]: $R_t$=1.55 min.

Specific optical rotation: $[α]_D^{20}$=−12.4°·ml·dm$^{-1}$·g$^{-1}$ (methanol).

Example 503

3-Ethyl-5-methyl-6-[1-(2-oxoimidazolidin-1-yl)ethyl]-1-(3,3,3-trifluoropropyl)thieno[2,3-d]pyrimidine-2,4(1H,3H)-dione (Enantiomer 1)

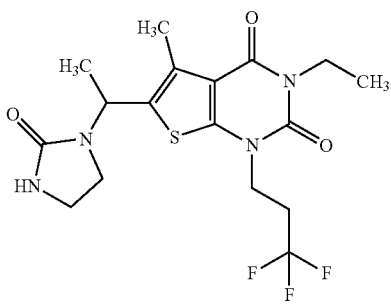 [SMILES: CCn1c(=O)c2c(C)c(C(C)N3CCNC3=O)sc2n(CCC(F)(F)F)c1=O]

140 mg (0.335 mmol) of the racemic compound from Ex. 416 were dissolved in a mixture of 2 ml of ethanol and 2 ml of acetonitrile and, in 26 portions, separated into the enantiomers by preparative HPLC on a chiral phase [column: Daicel Chiralpak IC, 5 µm, 250 mm×20 mm; eluent: ethanol; flow rate: 20 ml/min; temperature: 23° C.; detection: 210 nm]. After concentration of the product fractions and drying under high vacuum, 40 mg (57% of theory) of Enantiomer 1 were obtained (>99% ee, chiral analytical HPLC).

$^1$H-NMR (400 MHz, DMSO-$d_6$, δ/ppm): 6.39 (s, 1H), 5.31 (q, 1H), 4.12 (td, 2H), 3.95-3.85 (m, 2H), 3.46-3.35 (m, 1H), 3.27-3.08 (m, 3H), 2.86-2.70 (m, 2H), 2.39 (s, 3H), 1.46 (d, 3H), 1.11 (t, 3H).

Chiral analytical HPLC [column: Daicel Chiralpak IC-3, 3 µm, 50 mm×4.6 mm; eluent: ethanol; flow rate: 1 ml/min; temperature: 30° C.; detection: 220 nm]: $R_t$=2.24 min.

Example 504

3-Ethyl-5-methyl-6-[1-(2-oxoimidazolidin-1-yl)ethyl]-1-(3,3,3-trifluoropropyl)thieno[2,3-d]pyrimidine-2,4(1H,3H)-dione (Enantiomer 2)

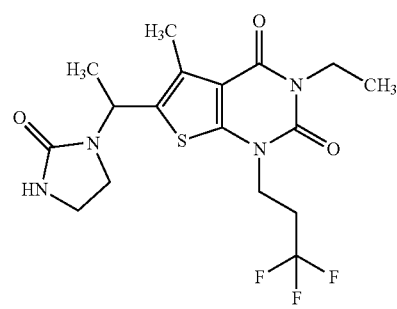 [SMILES: CCn1c(=O)c2c(C)c(C(C)N3CCNC3=O)sc2n(CCC(F)(F)F)c1=O]

140 mg (0.335 mmol) of the racemic compound from Ex. 416 were dissolved in a mixture of 2 ml of ethanol and 2 ml of acetonitrile and, in 26 portions, separated into the enantiomers by preparative HPLC on a chiral phase [column: Daicel Chiralpak IC, 5 µm, 250 mm×20 mm; eluent: ethanol; flow rate: 20 ml/min; temperature: 23° C.; detection: 210 nm]. After concentration of the product fractions and drying under high vacuum, 40 mg (57% of theory) of Enantiomer 2 were obtained (>99% ee, chiral analytical HPLC).

$^1$H-NMR (400 MHz, DMSO-$d_6$, δ/ppm): 6.39 (s, 1H), 5.31 (q, 1H), 4.22-4.02 (m, 2H), 3.90 (q, 2H), 3.45-3.35 (m, 1H), 3.27-3.09 (m, 3H), 2.85-2.70 (m, 2H), 2.39 (s, 3H), 1.46 (d, 3H), 1.11 (t, 3H).

Chiral analytical HPLC [column: Daicel Chiralpak IC-3, 3 µm, 50 mm×4.6 mm; eluent: ethanol; flow rate: 1 ml/min; temperature: 30° C.; detection: 220 nm]: $R_t$=3.52 min.

Example 505

3-(2,2-Dimethylpropyl)-5-methyl-6-[(2-oxo-2,3-dihydro-H-imidazol-1-yl)methyl]-1-(3,3,3-trifluoropropyl)thieno[2,3-d]pyrimidine-2,4(1H,3H)-dione

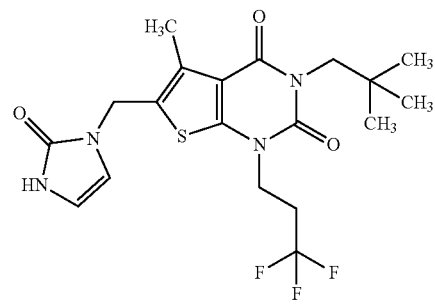 [SMILES: Cc1c(Cn2cc[nH]c2=O)sc2c1c(=O)n(CC(C)(C)C)c(=O)n2CCC(F)(F)F]

To a solution of 79 mg (0.125 mmol, 85% purity) of the compound from Ex. 519A in a mixture of 250 µl of water and 1.4 ml of methanol were added 250 µl (0.125 mmol) of 0.5 M hydrochloric acid. After the reaction mixture had been stirred at RT for 40 h, it was separated into its components directly by means of preparative HPLC (Method 18). Concentration and drying of the product fraction under high vacuum gave 25 mg (46% of theory) of the title compound.

¹H-NMR (400 MHz, DMSO-d₆, δ/ppm): 10.00 (br. s, 1H), 6.46 (dd, 1H), 6.35 (dd, 1H), 4.81 (s, 2H), 4.07 (t, 2H), 3.81 (br. s, 2H), 2.80-2.66 (m, 2H), 2.48 (s, 3H), 0.89 (s, 9H).

LC/MS (Method 17, ESIneg): $R_t$=1.81 min, m/z=443.14 [M−H]⁻.

Example 506

3-(2,2-Dimethylpropyl)-1-(2-methoxyethyl)-5-methyl-6-[(2-oxo-2,3-dihydro-1H-imidazol-1-yl)methyl]thieno[2,3-d]pyrimidine-2,4(1H,3H)-dione

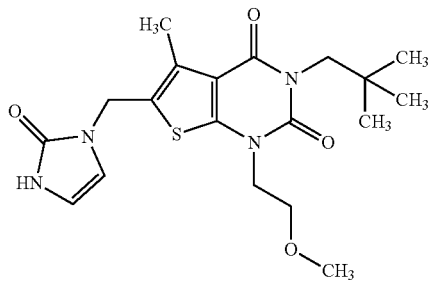 [SMILES: COCCn1c(=O)n(CC(C)(C)C)c(=O)c2c(C)c(Cn3cc[nH]c3=O)sc21]

To a solution of 93 mg (0.138 mmol, 70% purity) of the compound from Ex. 520A in a mixture of 280 μl of water and 1 ml of methanol were added 275 μl (0.137 mmol) of 0.5 M hydrochloric acid. After the reaction mixture had been stirred at RT for 40 h, it was separated into its components directly by means of preparative HPLC (Method 18). Concentration and drying of the product fraction under high vacuum gave 30 mg (54% of theory) of the title compound.

¹H-NMR (400 MHz, DMSO-d₆, δ/ppm): 10.00 (br. s, 1H), 6.45 (dd, 1H), 6.34 (dd, 1H), 4.79 (s, 2H), 4.00 (t, 2H), 3.81 (s, 2H), 3.61 (t, 2H), 3.21 (s, 3H), 2.45 (s, 3H), 0.88 (s, 9H).

LC/MS (Method 17, ESIneg): $R_t$=1.57 min, m/z=405.16 [M−H]⁻.

Example 507

3-(2, 2-Dimethylpropyl)-5-methyl-6-[(2-oxo-2,3-dihydro-1H-imidazol-1-yl)methyl]-1-(tetrahydro-furan-2-ylmethyl)thieno[2,3-d]pyrimidine-2,4(1H, 3H)-dione (racemate)

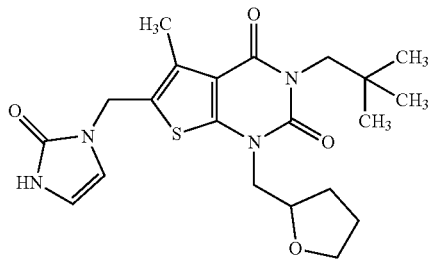 [SMILES: Cc1c(Cn2cc[nH]c2=O)sc2c1c(=O)n(CC(C)(C)C)c(=O)n2CC1CCCO1]

To a solution of 91 mg (0.128 mmol, 70% purity) of the compound from Ex. 521A in a mixture of 260 μl of water and 940 μl of methanol were added 254 μl (0.127 mmol) of 0.5 M hydrochloric acid. After the reaction mixture had been stirred at RT for 40 h, it was separated into its components directly by means of preparative HPLC (Method 18). Concentration and drying of the product fraction under high vacuum gave 47 mg (83% of theory, 98% purity) of the title compound.

¹H-NMR (400 MHz, DMSO-d₆, δ/ppm): 9.99 (br. s, 1H), 6.44 (dd, 1H), 6.34 (dd, 1H), 4.78 (s, 2H), 4.24-4.16 (m, 1H), 4.00 (dd, 1H), 3.81 (br. s, 2H), 3.77-3.67 (m, 2H), 3.62-3.27 (m, 1H), 2.45 (s, 2H), 2.01-1.77 (m, 3H), 1.70-1.61 (m, 1H), 0.89 (s, 9H).

LC/MS (Method 17, ESIneg): $R_t$=1.67 min, m/z=431.18 [M−H]⁻.

Example 508

3-(2, 2-Dimethylpropyl)-5-methyl-6-[(2-oxo-2,3-dihydro-1H-imidazol-1-yl)methyl]-1-(tetrahydro-furan-2-ylmethyl)thieno[2,3-d]pyrimidine-2,4(1H, 3H)-dione (Enantiomer 1)

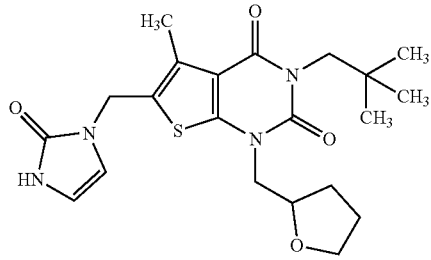

42 mg of the racemic compound from Ex. 507 were dissolved in 1 ml of a methanol/dichloromethane/tert-butyl methyl ether mixture (1:1:2) and separated into the enantiomers by means of preparative HPLC on a chiral phase [column: Daicel Chiralpak IC, 5 μm, 250 mm×20 mm; eluent: tert-butyl methyl ether/methanol 9:1; flow rate: 15 ml/min; temperature: 30° C.; UV detection: 235 nm]. The respective product fractions were concentrated on a rotary evaporator, admixed with tert-butanol and freeze-dried. 8 mg (12% of theory) of the title compound (Enantiomer 1) and 7 mg (11% of theory) of Enantiomer 2 (see Example 509) were obtained.

¹H-NMR (400 MHz, DMSO-d₆, δ/ppm): 9.99 (br. s, 1H), 6.44 (dd, 1H), 6.34 (dd, 1H), 4.78 (s, 2H), 4.24-4.16 (m, 1H), 4.00 (dd, 1H), 3.81 (br. s, 2H), 3.77-3.67 (m, 2H), 3.62-3.27 (m, 1H), 2.45 (s, 2H), 2.01-1.77 (m, 3H), 1.70-1.61 (m, 1H), 0.89 (s, 9H).

Chiral analytical HPLC [column: Daicel Chiralpak IC, 5 μm, 250 mm×4.6 mm; eluent: tert-butanol/methanol/acetic acid 85:15:0.2; flow rate: 1 ml/min; temperature: 25° C.; detection: 235 nm]: $R_t$=6.28 min.

Example 509

3-(2, 2-Dimethylpropyl)-5-methyl-6-[(2-oxo-2,3-dihydro-1H-imidazol-1-yl)methyl]-1-(tetrahydro-furan-2-ylmethyl)thieno[2,3-d]pyrimidine-2,4(1H, 3H)-dione (Enantiomer 2)

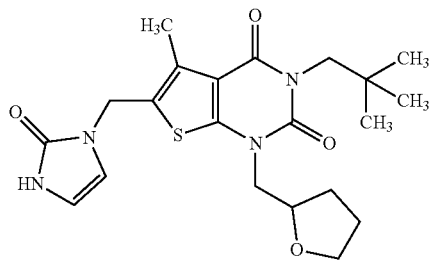

The title compound (7 mg) was obtained as the second enantiomer in the preparative HPLC separation of the racemate from Ex. 507 described in Ex. 508.

¹H-NMR (400 MHz, DMSO-d₆, δ/ppm): 9.99 (br. s, 1H), 6.44 (dd, 1H), 6.34 (dd, 1H), 4.78 (s, 2H), 4.24-4.16 (m, 1H), 4.00 (dd, 1H), 3.81 (br. s, 2H), 3.77-3.67 (m, 2H), 3.62-3.27 (m, 1H), 2.45 (s, 2H), 2.01-1.77 (m, 3H), 1.70-1.61 (m, 1H), 0.89 (s, 9H).

Chiral analytical HPLC [column: Daicel Chiralpak IC, 5 μm, 250 mm×4.6 mm; eluent: tert-butanol/methanol/acetic acid 85:15:0.2; flow rate: 1 ml/min; temperature: 25° C.; detection: 235 nm]: $R_t$=6.77 min.

Example 510

[1-{[1-(2-Methoxyethyl)-5-methyl-2,4-dioxo-3-(1,1,1-trifluoropropan-2-yl)-1,2,3,4-tetrahydrothieno[2,3-d]pyrimidin-6-yl]methyl}imidazolidin-2-ylidene]cyanamide (Enantiomer 1)

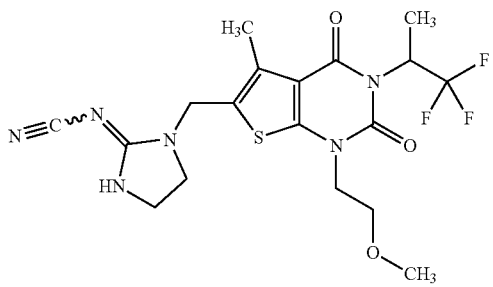 [SMILES: COCCn1c(=O)n(C(C)C(F)(F)F)c(=O)c2c(C)c(CN3CCNC3=NC#N)sc21]

300 mg (0.588 mmol, 80% purity) of the compound from Ex. 514A were dissolved in 10 ml of DMF, and 129 mg (0.881 mmol) of dimethyl N-cyanodithioiminocarbonate and 162 mg (1.17 mmol) of potassium carbonate were added. The mixture was stirred at 80° C. in a microwave oven (Biotage Initiator with dynamic control of irradiation power) for 4 h. Thereafter, the reaction mixture was diluted with ethyl acetate and washed successively with saturated sodium carbonate solution and saturated sodium chloride solution. After drying over anhydrous magnesium sulphate, the mixture was filtered and concentrated. The crude product was purified by preparative HPLC (Method 8). The product fractions were combined, concentrated by evaporation and dried under high vacuum. 92 mg (34% of theory) of the enantiomerically pure title compound were obtained (99% ee, chiral analytical HPLC).

¹H-NMR (400 MHz, DMSO-d₆, δ/ppm): 8.08 (s, 1H), 5.83-5.68 and 5.63-5.45 (2 m, tog. 1H), 4.48 (s, 2H), 4.07-4.00 (m, 2H), 3.66-3.60 (m, 2H), 3.52-3.36 (m, 4H), 3.24 (s, 3H), 2.40 and 2.39 (2 s, tog. 3H), 1.67 and 1.63 (2 d, tog. 3H).

LC/MS (Method 1, ESIpos): $R_t$=0.94 min, m/z=459 [M+H]⁺.

Chiral analytical HPLC [column: Daicel Chiralpak AS-3, 3 μm, 50 mm×4.6 mm; eluent: isohexane/ethanol 1:1; flow rate: 1 ml/min; temperature: 30° C.; detection: 220 nm]: $R_t$=1.81 min.

Specific optical rotation: $[\alpha]_D^{20}$=−12.4°·ml·dm⁻¹·g⁻¹ (methanol).

Example 511

[1-{[1-(2-Methoxyethyl)-5-methyl-2,4-dioxo-3-(1,1,1-trifluoropropan-2-yl)-1,2,3,4-tetrahydrothieno[2,3-d]pyrimidin-6-yl]methyl}imidazolidin-2-ylidene]cyanamide (Enantiomer 2)

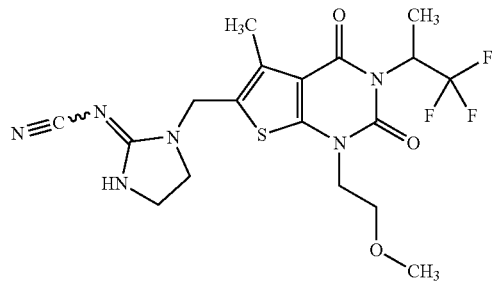 [SMILES: COCCn1c(=O)n(C(C)C(F)(F)F)c(=O)c2c(C)c(CN3CCNC3=NC#N)sc21]

300 mg (0.588 mmol, 80% purity) of the compound from Ex. 515A were dissolved in 10 ml of DMF, and 129 mg (0.881 mmol) of dimethyl N-cyanodithioiminocarbonate and 162 mg (1.17 mmol) of potassium carbonate were added. The mixture was stirred at 80° C. in a microwave oven (Biotage Initiator with dynamic control of irradiation power) for 4 h. Thereafter, the reaction mixture was diluted with ethyl acetate and washed successively with saturated sodium carbonate solution and saturated sodium chloride solution. After drying over anhydrous magnesium sulphate, the mixture was filtered and concentrated. The crude product was purified by preparative HPLC (Method 8). The product fractions were combined, concentrated by evaporation and dried under high vacuum. 119 mg (44% of theory) of the enantiomerically pure title compound were obtained (99% ee, chiral analytical HPLC).

¹H-NMR (400 MHz, DMSO-d₆, δ/ppm): 8.09 (s, 1H), 5.80-5.69 and 5.62-5.50 (2 m, tog. 1H), 4.48 (s, 2H), 4.07-4.00 (m, 2H), 3.67-3.61 (m, 2H), 3.52-3.36 (m, 4H), 3.24 (s, 3H), 2.40 and 2.39 (2 s, tog. 3H), 1.68 and 1.63 (2 d, tog. 3H).

LC/MS (Method 1, ESIpos): $R_t$=0.92 min, m/z=459 [M+H]⁺.

Chiral analytical HPLC [column: Daicel Chiralpak AS-3, 3 μm, 50 mm×4.6 mm; eluent: isohexane/ethanol 1:1; flow rate: 1 ml/min; temperature: 30° C.; detection: 220 nm]: $R_t$=2.18 min.

Specific optical rotation: $[\alpha]_D^{20}$=+13.1°·ml·dm⁻¹·g⁻¹ (methanol).

Example 512

[1-{[3-Isopropyl-1-(2-methoxyethyl)-5-methyl-2,4-dioxo-1,2,3,4-tetrahydrothieno[2,3-d]pyrimidin-6-yl](dideutero)methyl}imidazolidin-2-ylidene]cyanamide

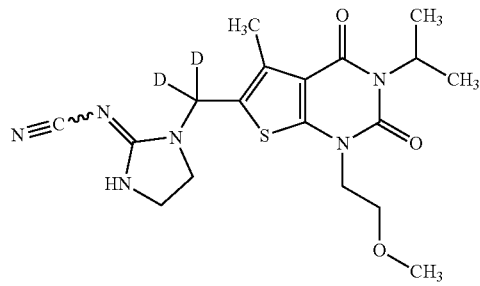 [SMILES: [2H]C([2H])(c1sc2c(c1C)c(=O)n(C(C)C)c(=O)n2CCOC)N1CCNC1=NC#N]

To a solution of 212 mg (1.92 mmol) of imidazolidin-2-ylidenecyanamide [Lit.: J. Zmitek et al., Org. Prep. Proc. Int. 23 (6), 721-728 (1991)] in 13 ml of DMF were added 85 mg (2.14 mmol) of sodium hydride (60% suspension in mineral oil), then the mixture was heated to 60° C. for 5 min and subsequently cooled back down to RT ("Solution 1"). To a solution of 224 mg (0.713 mmol) of the compound from Ex. 510A in 2.2 ml of dichloromethane in another reaction vessel were added, at 0° C., 248 µl (1.42 mmol) of N,N-diisopropylethylamine and 55 µl (0.748 mmol) of thionyl chloride. After 20 min, this solution was added in portions to Solution 1 at 0° C. The reaction mixture was then stirred at RT for 3 days. Then it was admixed with water and extracted with ethyl acetate. The organic extract was washed with saturated aqueous sodium chloride solution and dried over anhydrous magnesium sulphate. After filtration and concentration, the residue was first prepurified by means of MPLC (Isolera, 25 g silica gel cartridge, cyclohexane/ethyl acetate 1:1→dichloromethane/methanol 10:1). The concentrated product-containing fractions were then repurified by means of preparative HPLC (Method 8). Reconcentration and drying under high vacuum gave 58 mg (19% of theory) of the title compound.

$^1$H-NMR (400 MHz, DMSO-$d_6$, δ/ppm): 8.06 (s, 1H), 5.13 (sept, 1H), 4.00 (t, 2H), 3.62 (t, 2H), 3.50-3.36 (m, 4H), 3.24 (s, 3H), 2.39 (s, 3H), 1.40 (d, 6H).

LC/MS (Method 17, ESIpos): $R_t$=1.52 min, m/z=407.18 [M+H]$^+$.

Example 513

[1-{[1-(2-Methoxyethyl)-5-methyl-2,4-dioxo-3-(2,2,2-trifluoroethyl)-1,2,3,4-tetrahydrothieno[2,3-d]pyrimidin-6-yl](dideutero)methyl}imidazolidin-2-ylidene]cyanamide

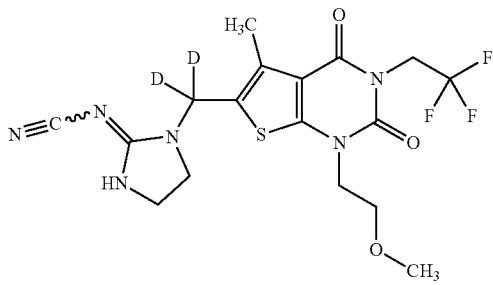 [SMILES: [2H]C([2H])(c1sc2c(c1C)c(=O)n(CC(F)(F)F)c(=O)n2CCOC)N1CCNC1=NC#N]

To a solution of 249 mg (2.27 mmol) of imidazolidin-2-ylidenecyanamide [Lit.: J. Zmitek et al., Org. Prep. Proc. Int. 23 (6), 721-728 (1991)] in 16 ml of DMF were added 101 mg (2.52 mmol) of sodium hydride (60% suspension in mineral oil), then the mixture was heated to 60° C. for 5 min and subsequently cooled back down to RT ("Solution 1"). To a solution of 350 mg (0.840 mmol) of the compound from Ex. 511A in 2.4 ml of dichloromethane in another reaction vessel were added, at 0° C., 292 µl (1.68 mmol) of N,N-diisopropylethylamine and 64 µl (0.882 mmol) of thionyl chloride. After 20 min, this solution was added in portions to Solution 1 at 0° C. The reaction mixture was then stirred at RT for 24 h. Then it was admixed with water and extracted with ethyl acetate. The organic extract was washed with saturated aqueous sodium chloride solution and dried over anhydrous magnesium sulphate. After filtration and concentration, the residue was purified by means of preparative HPLC (Method 8). The product fractions were concentrated and dried under high vacuum. 62 mg (16% of theory, 97% purity) of the title compound were obtained.

$^1$H-NMR (400 MHz, DMSO-$d_6$, δ/ppm): 8.08 (s, 1H), 4.70 (q, 2H), 4.07 (t, 2H), 3.64 (t, 2H), 3.52-3.36 (m, 4H), 3.24 (s, 3H), 2.41 (s, 3H).

LC/MS (Method 17, ESIpos): $R_t$=1.51 min, m/z=447.14 [M+H]$^+$.

Example 514

Methyl [1-{[1-(2-methoxyethyl)-5-methyl-2,4-dioxo-3-(1,1,1-trifluoropropan-2-yl)-1,2,3,4-tetrahydrothieno[2,3-d]pyrimidin-6-yl]methyl}imidazolidin-2-ylidene]carbamate (Enantiomer 1)

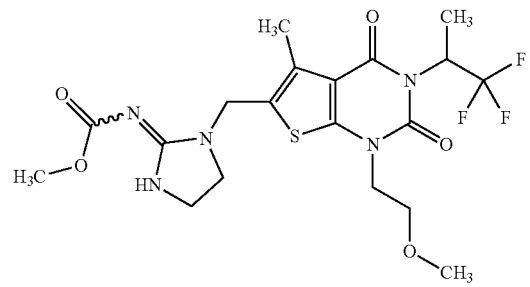 [SMILES: COCCn1c(=O)n(C(C)C(F)(F)F)c(=O)c2c(C)c(CN3CCNC3=NC(=O)OC)sc21]

300 mg (0.588 mmol, 80% purity) of the compound from Ex. 514A and 164 µl (1.18 mmol) of triethylamine were dissolved in 10 ml of dichloromethane, and a solution of 183 mg (1.18 mmol) of methyl (dichloromethylene)carbamate in 5 ml of dichloromethane was added. After the reaction mixture had been stirred at RT for about 18 h, it was concentrated to dryness. The residue was taken up in ethyl acetate and washed successively with water and saturated sodium chloride solution. After drying over anhydrous magnesium sulphate, the mixture was filtered and concentrated. The remaining residue was prepurified by means of preparative HPLC (Method 8). The product fractions were combined, concentrated and repurified by means of MPLC (Isolera, 10 g of SNAP KP-Sil silica gel, cyclohexane/ethyl acetate 10:1→0:1). Reconcentration of the product fractions and drying of the residue under high vacuum gave 67 mg (23% of theory) of the enantiomerically pure title compound (>99% ee, chiral analytical HPLC).

$^1$H-NMR (600 MHz, DMSO-$d_6$, δ/ppm): 8.04 (s, 1H), 5.79-5.71 and 5.60-5.52 (2 m, tog. 1H), 4.56 (s, 2H), 4.04-3.98 (m, 2H), 3.65-3.60 (m, 2H), 3.53 (s, 3H), 3.47-3.44 (m, 2H), 3.37-3.34 (m, 2H, partially obscured by the water signal), 3.23 (s, 3H), 2.41 and 2.40 (2 s, tog. 3H), 1.67 and 1.63 (2 d, tog. 3H).

LC/MS (Method 17, ESIpos): $R_t$=1.48 min, m/z=492.15 [M+H]$^+$.

Chiral analytical HPLC [column: Daicel Chiralcel IC-3, 3 µm, 50 mm×4.6 mm; eluent: isohexane/ethanol 1:1; flow rate: 1 ml/min; temperature: 25° C.; detection: 220 nm]: $R_t$=3.15 min.

Specific optical rotation: $[\alpha]_D^{20}$=−10.9°·ml·dm$^{-1}$·g$^{-1}$ (methanol).

Example 515

Methyl [1-{[1-(2-methoxyethyl)-5-methyl-2,4-dioxo-3-(1,1,1-trifluoropropan-2-yl)-1,2,3,4-tetrahydrothieno[2,3-d]pyrimidin-6-yl]methyl}imidazolidin-2-ylidene]carbamate (Enantiomer 2)

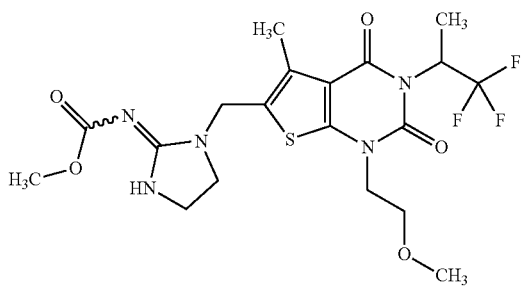

300 mg (0.588 mmol, 80% purity) of the compound from Ex. 515A and 164 µl (1.18 mmol) of triethylamine were dissolved in 10 ml of dichloromethane, and a solution of 183 mg (1.18 mmol) of methyl (dichloromethylene)carbamate in 5 ml of dichloromethane was added. After the reaction mixture had been stirred at RT for about 18 h, it was concentrated to dryness. The residue was taken up in ethyl acetate and washed successively with water and saturated sodium chloride solution. After drying over anhydrous magnesium sulphate, the mixture was filtered and concentrated. The remaining residue was prepurified by means of preparative HPLC (Method 8). The product fractions were combined, concentrated and repurified by means of MPLC (Isolera, 10 g of SNAP KP-Sil silica gel, cyclohexane/ethyl acetate 10:1→0:1). Reconcentration of the product fractions and drying of the residue under high vacuum gave 64 mg (22% of theory) of the enantiomerically pure title compound (>99% ee, chiral analytical HPLC).

$^1$H-NMR (600 MHz, DMSO-$d_6$, δ/ppm): 8.04 (s, 1H), 5.79-5.70 and 5.60-5.52 (2 m, tog. 1H), 4.56 (s, 2H), 4.05-3.98 (m, 2H), 3.65-3.59 (m, 2H), 3.53 (s, 3H), 3.47-3.44 (m, 2H), 3.37-3.34 (m, 2H, partially obscured by the water signal), 3.23 (s, 3H), 2.41 and 2.40 (2 s, tog. 3H), 1.67 and 1.63 (2 d, tog. 3H).

LC/MS (Method 17, ESIpos): $R_t$=1.49 min, m/z=492.15 [M+H]$^+$.

Chiral analytical HPLC [column: Daicel Chiralcel IC-3, 3 µm, 50 mm×4.6 mm; eluent: isohexane/ethanol 1:1; flow rate: 1 ml/min; temperature: 25° C.; detection: 220 nm]: $R_t$=2.93 min.

Specific optical rotation: $[\alpha]_D^{20}$=+9.9°·ml·dm$^{-1}$·g$^{-1}$ (methanol).

Example 516

3-Ethyl-5-methyl-6-[(3-methyl-5-oxo-4,5-dihydro-1H-1,2,4-triazol-1-yl)methyl]-1-(3,3,3-trifluoropropyl)thieno[2,3-d]pyrimidine-2,4(1H,3H)-dione

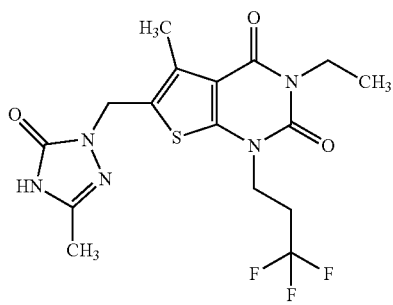 [SMILES: CCn1c(=O)c2c(C)c(Cn3nc(C)[nH]c3=O)sc2n(CCC(F)(F)F)c1=O]

To a solution of 10 mg (0.023 mmol) of the compound from Ex. 523A in 150 µl of ethanol were added 6 µl (0.016 mmol) of a 21% solution of sodium ethoxide in ethanol. After stirring at RT for 1 h, the temperature was increased to 60° C. After 4 h at this temperature, a further 150 µl of ethanol and 6 µl (0.016 mmol) of the 21% solution of sodium ethoxide in ethanol were added. After a further 2 h at 60° C., the reaction mixture was cooled down to RT, diluted with a little DMSO and separated directly into its components by means of preparative HPLC (Method 8). After concentration of the product fraction and drying under high vacuum, 0.5 mg (5% of theory) of the title compound was obtained.

$^1$H-NMR (600 MHz, DMSO-$d_6$, δ/ppm): 11.49 (br. s, 1H), 4.88 (s, 2H), 4.08 (t, 2H), 3.90 (q, 2H), 2.84-2.67 (m, 2H), 2.46 (s, 3H), 2.04 (s, 3H), 1.11 (t, 3H).

LC/MS (Method 17, ESIpos): $R_t$=1.40 min, m/z=418.11 [M+H]$^+$.

B. Assessment of Pharmacological Efficacy

The pharmacological activity of the inventive compounds can be demonstrated by in vitro and in vivo studies, as known to the person skilled in the art. The application examples which follow describe the biological action of the inventive compounds, without restricting the invention to these examples.

B-1. Cellular In Vitro Tests for Determining A2b Receptor Activity and Adenosine Receptor Selectivity The identification of selective antagonists of the human adenosine A2b receptor and the quantification of the efficacy and selectivity of the compounds according to the invention was carried out with the aid of recombinant cell lines for the human adenosine receptors A1, A2a, A2b and A3. These cell lines were originally derived from an ovarepithelial cell of the hamster (Chinese Hamster Ovary, CHO-K1, American Type Culture Collection, Manassas, Va. 20108, USA). In addition to the respective recombinantly expressed adenosine receptor for testing the efficacy at the A1, A2a and A2b receptors, the cell lines contain a reporter gene construct where expression of the firefly (Photinus pyralis) luciferase is under the control of a promoter which can be activated via intracellular signal cascades by stimulation of the receptors with the (not subtype-selective) adenosine receptor agonist NECA (5'-N-ethylcarboxamidoadenosine) [S. J. Hill, J. G. Baker, S. Rhees, Curr. Opin. Pharmacol. 1, 526-532 (2001)].

In the case of the A2a and A2b cell lines, this is a minimal promoter having a plurality of cAMP-responsive elements (CRE). Stimulation of the $G_s$-coupled A2b or A2a receptors by NECA ultimately leads, via formation of cAMP, to CRE-dependent induction of luciferase expression, which is detected 3 hours after the start of the incubation with NECA using a detection solution in a suitable luminometer. For testing the antagonists, initially, in a pre-experiment, the concentration of NECA which, at the test day in question, results in half-maximum stimulation of luciferase expression ($EC_{50}$ concentration) is determined. By joint incubation of this $EC_{50}$ concentration of NECA with the substances to be tested, it is possible to determine their antagonistic activity.

The cell line for testing the $G_i$-coupled A1 receptor contains a different reporter gene construct where expression of the firefly luciferase is under the control of an NFAT (nuclear factor of activated T-cells) promoter. This cell line was, in addition to the A1 receptor and the NFAT reporter gene, also stably transfected with a further gene coding for the promiscuous $G\alpha_{16}$ protein [T. T. Amatruda, D. A. Steele, V. Z. Slepak, M. I. Simon, Proc. Natl. Acad. Sci. USA 88, 5587-5591 (1991)], either independently or as a fusion gene.

The resulting test cells react to stimulation of the usually $G_i$-coupled A1 receptor with an increased intracellular calcium concentration which then leads to a NFAT-dependent luciferase expression. The procedure of the experiment for testing the antagonists at the A1 receptor corresponds to the procedure for testing with the A2a and A2b cell lines.

During generation of the A3 receptor cell line, co-transfection of the A3 receptor and the promiscuous $G\alpha_{16}$ protein were also carried out so that here, too, stimulation of the receptor leads to an increased intracellular calcium concentration. However, in the A3 receptor test, this increase in calcium is measured directly via the calcium-sensitive photoprotein Photina® [S. Bovolenta, M. Foti, S. Lohmer, S. Corazza, *J. Biomol. Screen.* 12, 694-704 (2007)]. After determination of the $EC_{50}$ concentration of NECA, the effects of the substance were measured after 5-10 minutes of pre-incubation with substance by addition of this $EC_{50}$ concentration in measuring position in a suitable luminometer capable of dispensing.

The $IC_{50}$ values from the A2b receptor assay for individual working examples are given in Table 1 below (in some cases as means of a plurality of independent individual determinations and rounded to two significant figures):

TABLE 1

| Example No. | A2b receptor $IC_{50}$ [nmol/L] |
|---|---|
| 1 | 9.7 |
| 2 | 11 |
| 3 | 4.4 |
| 4 | 5.2 |
| 5 | 8.4 |
| 6 | 8.0 |
| 7 | 33 |
| 8 | 120 |
| 9 | 97 |
| 10 | 7.0 |
| 11 | 19 |
| 12 | 12 |
| 13 | 17 |
| 14 | 19 |
| 15 | 3.1 |
| 16 | 2.7 |
| 17 | 16 |
| 18 | 14 |
| 19 | 5.6 |
| 20 | 3.6 |
| 21 | 5.1 |
| 22 | 24 |
| 23 | 16 |
| 24 | 8.8 |
| 25 | 5.7 |
| 26 | 11 |
| 27 | 2.7 |
| 28 | 1.9 |
| 29 | 4.1 |
| 30 | 5.0 |
| 31 | 2.2 |
| 32 | 11 |
| 33 | 12 |
| 34 | 10 |
| 35 | 6.3 |
| 36 | 38 |
| 37 | 220 |
| 38 | 1.9 |
| 39 | 3.6 |
| 40 | 7.0 |
| 41 | 12 |
| 42 | 11 |
| 43 | 7.7 |
| 44 | 5.2 |
| 45 | 12 |
| 46 | 29 |
| 47 | 14 |

TABLE 1-continued

| Example No. | A2b receptor $IC_{50}$ [nmol/L] |
|---|---|
| 48 | 1.4 |
| 49 | 2.5 |
| 50 | 4.6 |
| 51 | 12 |
| 52 | 6.6 |
| 53 | 14 |
| 54 | 4.1 |
| 55 | 1.3 |
| 56 | 8.0 |
| 57 | 0.88 |
| 58 | 2.6 |
| 59 | 5.1 |
| 60 | 13 |
| 61 | 53 |
| 62 | 72 |
| 63 | 39 |
| 64 | 86 |
| 65 | 12 |
| 66 | 4.3 |
| 67 | 29 |
| 68 | 8.9 |
| 69 | 9.8 |
| 70 | 21 |
| 71 | 70 |
| 72 | 8.1 |
| 73 | 79 |
| 74 | 36 |
| 75 | 40 |
| 76 | 9.3 |
| 77 | 5.6 |
| 78 | 1.2 |
| 79 | 9.9 |
| 80 | 1.4 |
| 81 | 14 |
| 82 | 17 |
| 83 | 380 |
| 84 | 3.9 |
| 85 | 18 |
| 86 | 6.4 |
| 87 | 2.3 |
| 88 | 6.7 |
| 89 | 8.7 |
| 90 | 12 |
| 91 | 11 |
| 92 | 9.7 |
| 93 | 11 |
| 94 | 7.7 |
| 95 | 11 |
| 96 | 9.4 |
| 97 | 18 |
| 98 | 130 |
| 99 | 17 |
| 100 | 6.8 |
| 101 | 12 |
| 102 | 4.5 |
| 103 | 3.5 |
| 104 | 120 |
| 105 | 14 |
| 106 | 9.2 |
| 107 | 11 |
| 108 | 3.3 |
| 109 | 4.2 |
| 110 | 79 |
| 111 | 21 |
| 112 | 500 |
| 113 | 8.1 |
| 114 | 39 |
| 115 | 31 |
| 116 | 24 |
| 117 | 5.2 |
| 118 | 3.1 |
| 119 | 2.7 |
| 120 | 12 |
| 121 | 20 |
| 122 | 3.9 |
| 123 | 53 |
| 124 | 60 |

TABLE 1-continued

| Example No. | A2b receptor IC$_{50}$ [nmol/L] |
|---|---|
| 125 | 8.8 |
| 126 | 3.9 |
| 127 | 5.6 |
| 128 | 4.7 |
| 129 | 19 |
| 130 | 30 |
| 131 | 180 |
| 132 | 20 |
| 133 | 26 |
| 134 | 30 |
| 135 | 46 |
| 136 | 360 |
| 137 | 10 |
| 138 | 12 |
| 139 | 2.8 |
| 140 | 4.8 |
| 141 | 120 |
| 142 | 13 |
| 143 | 3.0 |
| 144 | 1.5 |
| 145 | 14 |
| 146 | 11 |
| 147 | 22 |
| 148 | 4.1 |
| 149 | 5.1 |
| 150 | 6.0 |
| 151 | 5.7 |
| 152 | 0.79 |
| 153 | 6.4 |
| 154 | 7.1 |
| 155 | 26 |
| 156 | 5.7 |
| 157 | 5.7 |
| 158 | 5.5 |
| 159 | 14 |
| 160 | 2.9 |
| 161 | 8.5 |
| 162 | 7.9 |
| 163 | 5.2 |
| 164 | 17 |
| 165 | 6.5 |
| 166 | 13 |
| 167 | 1.2 |
| 168 | 15 |
| 169 | 36 |
| 170 | 4.4 |
| 171 | 13 |
| 172 | 7.3 |
| 173 | 73 |
| 174 | 49 |
| 175 | 53 |
| 176 | 1.5 |
| 177 | 15 |
| 178 | 21 |
| 179 | 200 |
| 180 | 30 |
| 181 | 1.5 |
| 182 | 9.0 |
| 183 | 17 |
| 184 | 7.0 |
| 185 | 60 |
| 186 | 13 |
| 187 | 6.3 |
| 188 | 40 |
| 189 | 17 |
| 190 | 38 |
| 191 | 3.3 |
| 192 | 3.2 |
| 193 | 25 |
| 194 | 15 |
| 195 | 41 |
| 196 | 6.5 |
| 197 | 18 |
| 198 | 8.9 |
| 199 | 8.1 |
| 200 | 2.9 |
| 201 | 4.4 |

TABLE 1-continued

| Example No. | A2b receptor IC$_{50}$ [nmol/L] |
|---|---|
| 202 | 7.8 |
| 203 | 57 |
| 204 | 1.1 |
| 205 | 25 |
| 206 | 11 |
| 207 | 43 |
| 208 | 8.9 |
| 209 | 12 |
| 210 | 9.1 |
| 211 | 17 |
| 212 | 17 |
| 213 | 7.6 |
| 214 | 3.1 |
| 215 | 45 |
| 216 | 34 |
| 217 | 79 |
| 218 | 22 |
| 219 | 19 |
| 220 | 15 |
| 221 | 29 |
| 222 | 13 |
| 223 | 14 |
| 224 | 31 |
| 225 | 12 |
| 226 | 36 |
| 227 | 22 |
| 228 | 130 |
| 229 | 4.0 |
| 230 | 12 |
| 231 | 21 |
| 232 | 93 |
| 233 | 23 |
| 234 | 7.8 |
| 235 | 38 |
| 236 | 6.0 |
| 237 | 17 |
| 238 | 99 |
| 239 | 11 |
| 240 | 19 |
| 241 | 1.2 |
| 242 | 1.4 |
| 243 | 14 |
| 244 | 13 |
| 245 | 2.1 |
| 246 | 4.7 |
| 247 | 8.9 |
| 248 | 5.1 |
| 249 | 41 |
| 250 | 18 |
| 251 | 1.3 |
| 252 | 4.1 |
| 253 | 9.9 |
| 254 | 34 |
| 255 | 13 |
| 256 | 11 |
| 257 | 7.1 |
| 258 | 33 |
| 259 | 9.8 |
| 260 | 2.2 |
| 261 | 9.9 |
| 262 | 2.3 |
| 263 | 5.3 |
| 264 | 3.1 |
| 265 | 14 |
| 266 | 75 |
| 267 | 4.6 |
| 268 | 12 |
| 269 | 24 |
| 270 | 38 |
| 271 | 47 |
| 272 | 10 |
| 273 | 19 |
| 274 | 24 |
| 275 | 76 |
| 276 | 9.9 |
| 277 | 68 |
| 278 | 130 |

TABLE 1-continued

| Example No. | A2b receptor IC$_{50}$ [nmol/L] |
|---|---|
| 279 | 20 |
| 280 | 82 |
| 281 | 46 |
| 282 | 30 |
| 283 | 79 |
| 284 | 79 |
| 285 | 91 |
| 286 | 220 |
| 287 | 63 |
| 288 | 140 |
| 289 | 180 |
| 290 | 400 |
| 291 | 190 |
| 292 | 8.3 |
| 293 | 120 |
| 294 | 20 |
| 295 | 220 |
| 296 | 16 |
| 297 | 17 |
| 298 | 2.4 |
| 299 | 5.6 |
| 300 | 14 |
| 301 | 6.5 |
| 302 | 14 |
| 303 | 46 |
| 304 | 73 |
| 305 | 140 |
| 306 | 5.9 |
| 307 | 8.1 |
| 308 | 140 |
| 309 | 36 |
| 310 | 370 |
| 311 | 31 |
| 312 | 22 |
| 313 | 41 |
| 314 | 4.7 |
| 315 | 4.3 |
| 316 | 1.3 |
| 317 | 25 |
| 318 | 1.4 |
| 319 | 2.4 |
| 320 | 0.44 |
| 321 | 1.6 |
| 322 | 1.3 |
| 323 | 34 |
| 324 | 110 |
| 325 | 65 |
| 326 | 10 |
| 327 | 40 |
| 328 | 19 |
| 329 | 900 |
| 330 | 220 |
| 331 | 61 |
| 332 | 110 |
| 333 | 110 |
| 334 | 120 |
| 335 | 270 |
| 336 | 8.7 |
| 337 | 280 |
| 338 | 120 |
| 339 | 5.6 |
| 340 | 18 |
| 341 | 12 |
| 342 | 13 |
| 343 | 25 |
| 344 | 8.5 |
| 345 | 17 |
| 346 | 37 |
| 347 | 56 |
| 348 | 48 |
| 349 | 630 |
| 350 | 210 |
| 352 | 48 |
| 353 | 31 |
| 354 | 120 |
| 355 | 99 |
| 356 | 5.1 |

TABLE 1-continued

| Example No. | A2b receptor IC$_{50}$ [nmol/L] |
|---|---|
| 357 | 32 |
| 358 | 12 |
| 359 | 37 |
| 360 | 10 |
| 361 | 13 |
| 362 | 9.4 |
| 363 | 19 |
| 364 | 170 |
| 365 | 110 |
| 366 | 40 |
| 367 | 33 |
| 368 | 82 |
| 369 | 33 |
| 370 | 2.0 |
| 371 | 9.8 |
| 372 | 27 |
| 373 | 5.9 |
| 374 | 7.0 |
| 375 | 6.3 |
| 376 | 7.9 |
| 377 | 3.4 |
| 378 | 3.1 |
| 379 | 13 |
| 380 | 12 |
| 381 | 4.1 |
| 382 | 6.8 |
| 383 | 15 |
| 384 | 9.8 |
| 385 | 4.7 |
| 386 | 16 |
| 387 | 96 |
| 388 | 33 |
| 389 | 87 |
| 390 | 28 |
| 391 | 34 |
| 392 | 56 |
| 393 | 45 |
| 394 | 3.2 |
| 395 | 94 |
| 396 | 93 |
| 397 | 120 |
| 398 | 240 |
| 399 | 26 |
| 400 | 320 |
| 401 | 660 |
| 402 | 100 |
| 403 | 35 |
| 404 | 120 |
| 405 | 30 |
| 406 | 29 |
| 407 | 32 |
| 408 | 12 |
| 409 | 14 |
| 410 | 12 |
| 411 | 53 |
| 412 | 5.4 |
| 413 | 4.6 |
| 414 | 11 |
| 415 | 9.0 |
| 416 | 79 |
| 419 | 130 |
| 420 | 50 |
| 421 | 71 |
| 422 | 170 |
| 423 | 55 |
| 424 | 88 |
| 425 | 42 |
| 426 | 270 |
| 427 | 37 |
| 428 | 120 |
| 429 | 75 |
| 430 | 280 |
| 431 | 740 |
| 432 | 92 |
| 433 | 58 |
| 434 | 82 |
| 435 | 43 |

TABLE 1-continued

| Example No. | A2b receptor IC$_{50}$ [nmol/L] |
|---|---|
| 436 | 65 |
| 437 | 48 |
| 438 | 150 |
| 439 | 180 |
| 440 | 23 |
| 441 | 8.6 |
| 442 | 60 |
| 443 | 7.4 |
| 444 | 11 |
| 445 | 12 |
| 446 | 19 |
| 447 | 9.7 |
| 448 | 17 |
| 449 | 54 |
| 450 | 14 |
| 451 | 10 |
| 452 | 14 |
| 453 | 72 |
| 454 | 6.1 |
| 455 | 3.6 |
| 456 | 15 |
| 457 | 7.1 |
| 458 | 34 |
| 459 | 4.9 |
| 460 | 22 |
| 461 | 9.2 |
| 462 | 16 |
| 463 | 9.9 |
| 464 | 9.9 |
| 465 | 13 |
| 466 | 6.6 |
| 467 | 30 |
| 468 | 6.1 |
| 469 | 8.8 |
| 470 | 5.1 |
| 471 | 18 |
| 472 | 6.7 |
| 473 | 3.4 |
| 474 | 5.6 |
| 475 | 36 |
| 476 | 140 |
| 477 | 270 |
| 478 | 41 |
| 479 | 140 |
| 480 | 35 |
| 481 | 140 |
| 482 | 410 |
| 483 | 45 |
| 484 | 67 |
| 485 | 52 |
| 486 | 190 |
| 487 | 250 |
| 488 | 68 |
| 489 | 27 |
| 490 | 19 |
| 491 | 52 |
| 492 | 250 |
| 493 | 11 |
| 494 | 20 |
| 495 | 57 |
| 496 | 120 |
| 497 | 730 |
| 498 | 79 |
| 499 | 230 |
| 500 | 10 |
| 501 | 43 |
| 502 | 18 |
| 503 | 39 |
| 504 | 2000 |
| 505 | 5.0 |
| 506 | 12 |
| 507 | 28 |
| 510 | 47 |
| 511 | 110 |
| 512 | 5.1 |
| 513 | 8.4 |
| 514 | 32 |
| 515 | 24 |

B-2. Adenosine Receptor Binding Assays

The binding properties of the test compounds on adenosine receptors were determined in binding studies with radioligands. For this purpose, membrane preparations of the human adenosine receptor subtypes were produced from cell lines having recombinant receptor expression (CHO cells for the A1 receptor, HEK293 cells for the A2a, A2b and A3 receptors). The following radioligands were used in the experiments: [$^3$H]-DPCPX for the A1 receptor, [$^3$H]-CGS 21680 for the A2a receptor, [$^3$H]-CPX for the A2b receptor and [$^{125}$I]-AB-MECA for the A3 receptor. The test substances were each tested in 8 different concentrations and 2 repeat tests per concentration. The displacement of the particular radioligand by the test compound was expressed as percentage inhibition of the specific binding of the controls. The IC$_{50}$ values (concentration which brings about half-maximum inhibition of the specific binding of the controls) and the Hill coefficients (nH) were determined by a non-linear regression analysis, using the competition curves obtained from the mean values of the repeat tests and conducting a curve fit according to the Hill equation:

$$Y = D + [A - D / 1 + (C/C50)^{nH}]$$

(Y=specific binding; A=left-hand asymptote of the curve; D=right-hand asymptote of the curve; C=substance concentration; C50=IC$_{50}$; nH=rise factor).

The inhibition constant (K$_i$) was calculated by the Cheng-Prusoff equation:

$$K_i = IC_{50}/(1+L/K_D)$$

(L=concentration of the radioligand in the assay; K$_D$=receptor affinity of the radioligand for the receptor, determined with a Scatchard plot).

[Literature: A1 receptor: Townsend-Nicholson, A. and Schofield, P. R., *J. Biol. Chem.* 269: 2373-2376 (1994); A2a receptor: Luthin, D. R. et al., *Mol. Pharmacol.* 47: 307-313 (1995); A2b receptor: Stehle, J. H. et al., *Mol. Endocrinol.* 6: 384-393 (1992) and Linden et al., *Mol. Pharmacol.* 56: 705-713 (1999); A3 receptor: Salvatore, C. A. et al., *Proc. Natl. Acad. Sci. U.S.A.* 90: 10365-10369 (1993) and Jacobson, K. A. et al., *Neuropharmacology* 36: 1157-1165 (1997)].

Table 2 below lists the K$_i$ values thus determined from these binding assays for representative working examples:

TABLE 2

| Example No. | A2b receptor K$_i$ [nmol/L] | A1 receptor K$_i$ [nmol/L] | A2a receptor K$_i$ [nmol/L] | A3 receptor K$_i$ [nmol/L] |
|---|---|---|---|---|
| 59 | 2.4 | 330 | 120 | 11000 |
| 66 | 5.2 | 950 | 280 | 6800 |
| 86 | 2.7 | 1100 | 270 | 160000 |
| 109 | 2.8 | 590 | 100 | 14000 |
| 113 | 6.4 | 1500 | 1700 | |
| 116 | 12 | 3300 | 790 | 330 |

B-3. Measurement of NECA-Induced IL-6 Release by LL29 Fibroblasts

Stimulation of fibroblasts with adenosine or the adenosine analog 5'-N-ethylcarboxamidoadenosine (NECA) leads to release of the pro-inflammatory and pro-fibrotic cytokine IL-6 which can be prevented by inhibition of the A2b receptor.

Accordingly, confluent cells of the human fibroblast cell line LL29 were treated with the test substances and stimulated with NECA (10 μM). After an incubation time of 24 hours, the cell supernatant is removed and human IL-6 in the cell supernatant is determined by ELISA (Quantikine® IL6 ELISA, R&D Systems, Minneapolis, USA).

Table 3 below lists the $IC_{50}$ values obtained in this way for inhibition of IL-6 release for some working examples:

TABLE 3

| Example No. | IL-6 release $IC_{50}$ [nmol/L] |
|---|---|
| 3 | 15 |
| 20 | 5 |
| 102 | 5 |

B-4. Animal Model of Monocrotaline-Induced Pulmonary Hypertension

Monocrotaline-induced pulmonary hypertension of the rat is a widely used animal model of pulmonary hypertension. The pyrrolizidine alkaloid monocrotaline is, after subcutaneous injection, metabolized in the liver to the toxic monocrotalinepyrrole, and within a few days endothelium injury in the pulmonary circulation results, followed by remodeling of the small pulmonary arteries (mediahypertrophy, de novo muscularization). A single subcutaneous injection suffices to induce pronounced pulmonary hypertension in rats within 4 weeks [Cowan et al., *Nature Med.* 6, 698-702 (2000)].

Male Sprague-Dawley rats are used for the model. On day 0, the animals receive a subcutaneous injection of 60 mg of monocrotaline/kg. Treatment of the animals with the test substance (by gavage, by addition to the feed or drinking water, using an osmotic minipump, by subcutaneous or intraperitoneal injection or by inhalation) starts 14 days after the monocrotaline injection at the earliest and extends over a period of at least 14 days. At the end of the study, the animals are examined haemodynamically. For the haemodynamic measurement, the rats are initially anaesthetized with pentobarbital (60 mg/kg). The animals are then tracheotomized and artificially ventilated (frequency: 60 breaths/min; ratio inspiration to expiration: 50:50; positive end-expiratory pressure: 1 cm $H_2O$; tidal volume: 10 ml/kg of body weight; $FIO_2$: 0.5). Anaesthesia is maintained by inhalative isofluran anaesthesia. The systemic blood pressure is determined in the left carotid artery using a Millar microtip catheter. A polyethylene catheter is advanced via the right jugular vein into the right ventricle to determine the right-ventricular pressure. Following the haemodynamic measurements, the heart is removed, the ratio of right to left ventricle including septum is determined and the tissue is deep-frozen for expression analyses. The lung is likewise removed, the left half of the lung is fixed in formalin for histopathological examination and the right half of the lung is deep-frozen for expression analyses. Furthermore, plasma samples are obtained to determine biomarkers (for example proBNP) and plasma substance concentrations.

B-5. Animal Model of SU5416/Hypoxia-induced Pulmonary Hypertension

SU5416/hypoxia-induced pulmonary hypertension of the rat is a widely used animal model of pulmonary hypertension. By injection of the VEGF receptor antagonist SU5416 in combination with hypoxia, the effect of the reduced oxygen content may be enhanced, leading to changes in the endothelium in the form of plexiform lesions. A single subcutaneous injection, generally of 20 mg/kg, is, in combination with hypoxia, i.e. increased vascular shear forces by vasoconstriction, sufficient to induce severe pulmonary hypertension [Oka et al., *Circ. Res.* 100, 923-929 (2007)].

Male Sprague-Dawley rats or Dahl-Salz rats are used for the model. On day 0, the animals receive a subcutaneous injection of SU5416 and are kept in a controlled hypoxic atmosphere (10% oxygen). Corresponding control rats receive an injection of vehicle and are kept under normoxic conditions. Chronic hypoxia of at least 14 days with subsequent normoxia of at least 28 days leads to the development of pulmonary hypertension which can be demonstrated both functionally and morphologically. Treatment of the animals with the test substance (by gavage, by addition to the feed or drinking water, using an osmotic minipump, by subcutaneous or intraperitoneal injection or by inhalation) starts 14 days after the SU5416 injection and at the beginning of the animals being kept in a controlled hypoxic atmosphere at the earliest and extends over a period of at least 14-28 days.

At the end of the study, the animals are examined haemodynamically. For the haemodynamic measurement, the rats are initially anaesthetized with pentobarbital (60 mg/kg). The animals are then tracheotomized and artificially ventilated (frequency: 60 breaths/min; ratio inspiration to expiration: 50:50; positive end-expiratory pressure: 1 cm $H_2O$; tidal volume: 10 ml/kg of body weight; $FIO_2$: 0.5). Anaesthesia is maintained by inhalative isofluran anaesthesia. The systemic blood pressure is determined in the left carotid artery using a Millar microtip catheter. A polyethylene catheter is advanced via the right jugular vein into the right ventricle to determine the right-ventricular pressure. Following the haemodynamic measurements, the heart is removed, the ratio of right to left ventricle including septum is determined and the tissue is deep-frozen for expression analyses. The lung is likewise removed, the left half of the lung is fixed in formalin for histopathological examination and the right half of the lung is deep-frozen for expression analyses. Furthermore, plasma samples are obtained to determine biomarkers (for example proBNP) and plasma substance concentrations.

B-6. Animal Model of Bleomycin-induced Pulmonary Fibrosis

Bleomycin-induced pulmonary fibrosis in the mouse or rat is a widely used animal model of pulmonary fibrosis. Bleomycin is a glycopeptide antibiotic employed in oncology for the therapy of testicular tumours and Hodgkin- and Non-Hodgkin tumours. It is eliminated renally, has a half-life of about 3 hours and, as cytostatic, influences various phases of the division cycle [Lazo et al., *Cancer Chemother.* 15, 44-50 (1994)]. Its anti-neoplastic effect is based on an oxidatively damaging action on DNA [Hay et al., *Arch.* 65, 81-94 (1991)]. Lung tissue is at a particular risk when exposed to bleomycin since it contains only a small number of cysteine hydrolases which, in other tissues, lead to inactivation of bleomycin. Following administration of bleomycin, the animals suffer an acute respiratory distress syndrome (ARDS) with subsequent development of pulmonary fibrosis.

Administration of bleomycin may be by single or repeat intratracheal, inhalative, intravenous or intraperitoneal administration. Treatment of the animals with the test substance (by gavage, by addition to the feed or drinking water, using an osmotic minipump, by subcutaneous or intraperitoneal injection or by inhalation) starts at the day of the first bleomycin administration or therapeutically 3-14 days later and extends over a period of 2-6 weeks. At the end of the study, lung function measurements, a bronchio-alveolar lavage to determine the cell content and the pro-inflammatory and pro-fibrotic markers and a histological assessment of pulmonary fibrosis are carried out.

B-7. Animal Model of DQ12 Quartz-induced Pulmonary Fibrosis

DQ12 quartz-induced pulmonary fibrosis in the mouse or rat is a widely used animal model of pulmonary fibrosis [Shimbori et al., *Exp. Lung Res.* 36, 292-301 (2010)]. DQ12 quartz is quartz which is highly active owing to breaking or grinding. In mice and rats, intratracheal or inhalative administration of DQ12 quartz leads to alveolar proteinosis followed by interstitial pulmonary fibrosis. The animals receive a single or repeat intratracheal or inhalative instillation of DQ12 quartz. Treatment of the animals with the test substance (by gavage, by addition to the feed or drinking water, using an osmotic minipump, by subcutaneous or intraperitoneal injection or by inhalation) starts at the day of the first silicate instillation or therapeutically 3-14 days later and extends over a period of 3-20 weeks. At the end of the study, lung function measurements, a bronchio-alveolar lavage to determine the cell content and the pro-inflammatory and pro-fibrotic markers and a histological assessment of pulmonary fibrosis are carried out.

B-8. Animal Model of DQ12 Quartz or FITC-induced Pulmonary Inflammation

In the mouse and the rat, intratracheal administration of DQ12 quartz or fluorescein isothiocyanate (FITC) leads to an inflammation in the lung [Shimbori et al., *Exp. Lung Res.* 36, 292-301 (2010)]. At the day of the instillation of DQ12 quartz or FITC or a day later the animals are treated with the test substance for a duration of 24 h up to 7 days (by gavage, by addition to the feed or drinking water, using an osmotic minipump, by subcutaneous or intraperitoneal injection or by inhalation). At the end of the experiment, a bronchio-alveolar lavage to determine the cell content and the pro-inflammatory and pro-fibrotic markers is carried out.

B-9. Animal Model of Ovalbumin-induced Allergic Respiratory Pathway Inflammation and Hyperreactivity The animal model of ovalbumin-induced respiratory pathway information and hyperreactivity is a widely used animal model for bronchial asthma [Rückert et al., *J. Immunol.* 174, 5507-5515 (2005)]. Mice are sensitized on days 0, 14 and 21 by means of an intraperitoneal injection with the ovalbumin allergen in combination with adjuvant; the negative control receives an intraperitoneal injection of NaCl in combination with adjuvant. On days 28 and 29, the animals receive an intratracheal instillation of ovalbumin.

On day 30, a hyperreactivity test is conducted in the form of an inhalative provocation with a stepwise rise in concentration of a bronchoconstrictor, for example methacholine or adenosine monophosphate. First of all, the animals are anaesthetized by means of injected anaesthetic, then orotracheally intubated or tracheotomized and connected to a lung function system by means of a tube. First of all, lung function is measured by body plethysmography prior to provocation (including parameters such as tidal volume, breathing frequency, dynamic compliance and lung resistance). This is followed by measurement of lung function on inhalative provocation with a stepwise rise in concentration of the bronchoconstrictor. Thereafter, a bronchio-alveolar lavage is conducted to determine the cell content and the pro-inflammatory markers.

B-10. Animal Model of the Elastase-induced Pulmonary Emphysema

The elastase-induced pulmonary emphysema in the mouse, rat or hamster is a widely used animal model of pulmonary emphysema [Sawada et al., *Exp. Lung Res.* 33, 277-288 (2007)]. The animals receive an orotracheal instillation of porcine pancreas elastase. The treatment of the animals starts at the day of the instillation of the porcine pancreas elastase and extends over a period of 3 weeks. At the end of the study, an alveolar morphometry is carried out.

B-11. Animal Model of Permanent Coronary Ligature in Mouse and Rat

Mice or rats are anaesthetized with 5% isoflurane in an anaesthetization cage, intubated, connected to a ventilation pump and ventilated with 2% of isoflurane/$N_2O/O_2$. The body temperature is maintained at 37-38° C. by a heating mat. Temgesic® is administered as painkiller. The chest is opened laterally between the third and fourth ribs, and the heart is exposed. The coronary artery of the left ventricle (LAD) is permanently ligated with an occlusion thread passed underneath shortly below its origin (below the left atrium). The thorax is closed again, and the muscle layers and the epidermis are sutured. From the day of the operation or up to a week later the animals are treated with the test substance over a period of 4-8 weeks (by gavage, by addition of the test substance to the feed or drinking water, using an osmotic minipump, by subcutaneous or intraperitoneal injection or by inhalation). A further control included is a sham group in which only the surgical procedure, but not the LAD occlusion, was performed.

At the end of the experiment, the animals are anaesthetized again [1.5% isoflurane (mouse), 2% isoflurane (rat)/$N_2O$/air], and a pressure catheter is introduced via the carotid artery into the left ventricle. The heart rate, left-ventricular pressure (LVP), left-ventricular end-diastolic pressure (LVEDP), contractility (dp/dt) and relaxation rate (tau) are measured there and analyzed with the aid of the Powerlab system (AD Instruments, ADI-PWLB-4SP) and the Chart5 software (SN 425-0586). A blood sample is then taken to determine the blood levels of the substance and plasma biomarkers, and the animals are sacrificed. The heart (heart chambers, left ventricle plus septum, right ventricle), liver, lung and kidney are removed and weighed.

B-12. Animal Model of Tumour Growth

Syngeneic tumour models in immunocompetent mice and xenogeneic tumour models in immunosuppressed mice are employed for substance assessment. For this purpose, tumour cells are cultivated in vitro and implanted subcutaneously or orthotopically. The animals are treated by oral, subcutaneous, intraperitoneal or intravenous therapy after the establishment of the tumour or starting on the day of tumour inoculation. The efficacy of the test substances is analysed in monotherapy and in combination therapy with other active pharmacological substances. During the experiment, the state of health of the animals is checked daily and the treatments are effected in accordance with animal protection regulations. The tumour area is measured with slide gauges (length L, breadth B=shorter dimension). The tumour volume is calculated by the formula $(L \times B^2)/2$. The inhibition in tumour growth is determined at the end of the study as the T/C ratio of the tumour areas or tumour weights and as the TGI value (tumour growth inhibition, calculated by the formula $[1-(T/C)] \times 100$) (T=tumour size in the treated group; C=tumour size in the untreated control group).

B-13. Animal Model of Formation of Metastases in the Lung

Syngeneic tumour models in immunocompetent mice and xenogeneic tumour models in immunosuppressed mice are employed for substance assessment. For this purpose, tumour cells are cultivated in vitro and injected into the tail vein of the test animals. The animals are treated by oral, subcutaneous, intraperitoneal or intravenous therapy. The efficacy of the test substances is analysed in monotherapy and in combination therapy with other active pharmacological substances. During the experiment, the state of health of the animals is checked daily and the treatments are effected in accordance with animal protection regulations. After the experiment has ended, the lungs of the test animals are examined microscopically with regard to the number of tumour colonies formed.

C. Working Examples for Pharmaceutical Compositions

The compounds of the invention can be converted to pharmaceutical formulations as follows:

Tablet:

Composition:

100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of compound of the invention, lactose and starch is granulated with a 5% solution (w/w) of the PVP in water. The granules are dried and then mixed with the magnesium stearate for 5 minutes. This mixture is compressed in a conventional tabletting press (see above for format of the tablet). The guide value used for the pressing is a pressing force of 15 kN.

Suspension for Oral Administration:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol; the compound of the invention is added to the suspension. The water is added while stirring. The mixture is stirred for about 6 h before swelling of the Rhodigel is complete.

Solution for Oral Administration:

Composition:

500 mg of the compound of the invention, 2.5 g of polysorbate and 97 g of polyethylene glycol 400. 20 g of oral solution correspond to a single dose of 100 mg of the compound of the invention.

Production:

The compound of the invention is suspended in the mixture of polyethylene glycol and polysorbate with stirring. The stirring operation is continued until dissolution of the compound of the invention is complete.

I.V. Solution:

The compound of the invention is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.

The invention claimed is:

1. Compound of the formula (I)

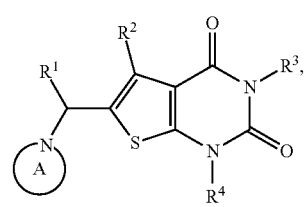

in which the ring A is an azaheterocycle of the formula

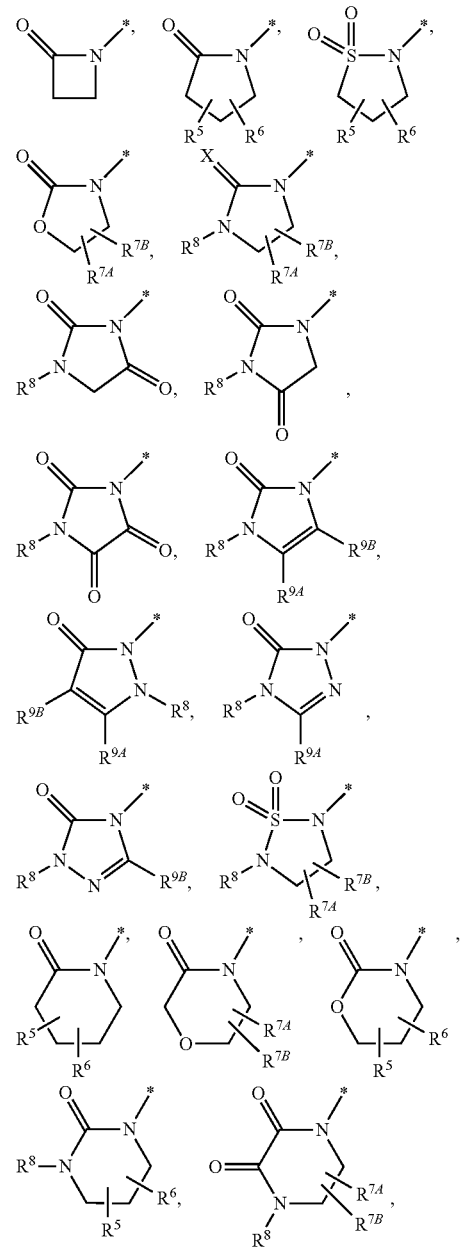

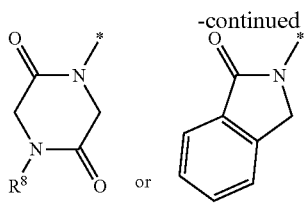

in which * marks the bond to the adjoining CH(R$^1$) group,

R$^5$ is hydrogen, (C$_1$-C$_4$)-alkyl, hydroxyl, (C$_1$-C$_4$)-alkoxy, amino, (C$_1$-C$_5$)-alkanoylamino or (C$_1$-C$_4$)-alkoxycarbonylamino, R$^6$ is hydrogen, methyl or ethyl, R$^{7A}$ and R$^{7B}$ are the same or different and are independently hydrogen or (C$_1$-C$_4$)-alkyl, R$^8$ is hydrogen, (C$_1$-C$_4$)-alkyl, (C$_2$-C$_4$)-alkenyl, (C$_1$-C$_5$)-alkanoyl or (C$_1$-C$_4$)-alkoxycarbonyl,
where (C$_1$-C$_4$)-alkyl may be up to disubstituted by hydroxyl, R$^{9A}$ and R$^{9B}$ are the same or different and are independently hydrogen or (C$_1$-C$_4$)-alkyl and X is O, N(R$^{10}$) or S, in which
R$^{10}$ is hydrogen, cyano or (C$_1$-C$_4$)-alkoxycarbonyl, R$^1$ is hydrogen or methyl, R$^2$ is hydrogen, methyl or ethyl, where methyl and ethyl may be up to trisubstituted by fluorine, R$^3$ is (C$_2$-C$_6$)-alkyl, (C$_2$-C$_6$)-alkenyl or (C$_2$-C$_6$)-alkynyl,
where (C$_2$-C$_6$)-alkyl may be substituted by a radical selected from the group of hydroxyl, methoxy, ethoxy, trifluoromethoxy, cyclopropyl, cyclobutyl, oxetanyl and phenyl, and up to trisubstituted by fluorine, and (C$_2$-C$_6$)-alkenyl may be up to trisubstituted by fluorine, where the cyclopropyl and cyclobutyl groups mentioned may in turn be up to disubstituted, identically or differently, by a radical selected from fluorine and methyl, or R$^3$ is a group of the formula —CH$_2$—R$^{14}$ in which
R$^{14}$ is cyclopropyl, cyclobutyl, oxetanyl or tetrahydrofuranyl, where cyclopropyl, cyclobutyl and oxetanyl may be up to disubstituted, identically or differently, by a radical selected from fluorine and methyl, and R$^4$ is (C$_1$-C$_6$)-alkyl or (C$_2$-C$_6$)-alkenyl,
where (C$_1$-C$_6$)-alkyl may be up to pentasubstituted and (C$_2$-C$_6$)-alkenyl up to trisubstituted by fluorine and where one CH$_2$ group in (C$_1$-C$_6$)-alkyl may be exchanged for —O—, —S— or —S(O)$_2$—, with the proviso that there are at least two carbon atoms between such a heteroatom and the uracil N$^1$ atom, or R$^4$ is a group of the formula —(CH$_2$)$_m$—CN, —(CH$_2$)$_n$—R$^{11}$ or —(CH$_2$)$_p$—R$^{12}$, in which
m is the number 1, 2, 3 or 4,
n is the number 2 or 3,
p is the number 1 or 2,
R$^{11}$ is dimethylamino, diethylamino or azetidino and R$^{12}$ is (C$_3$-C$_6$)-cycloalkyl, oxetanyl, tetrahydrofuranyl, tetrahydropyranyl or 5-membered azaheteroaryl, where (C$_3$-C$_6$)-cycloalkyl may be up to disubstituted, identically or differently, by a radical selected from fluorine and methyl and azaheteroaryl may be up to disubstituted, identically or differently, by a radical selected from methyl and trifluoromethyl, or R$^4$ is a group of the formula —(CH$_2$)$_2$—O—R$^{13}$ in which
R$^{13}$ is (C$_3$-C$_6$)-cycloalkyl, and a salt, a solvate, and a solvate of the salt thereof.

2. Compound of the formula (I) according to claim 1, in which
the ring A is an azaheterocycle of the formula

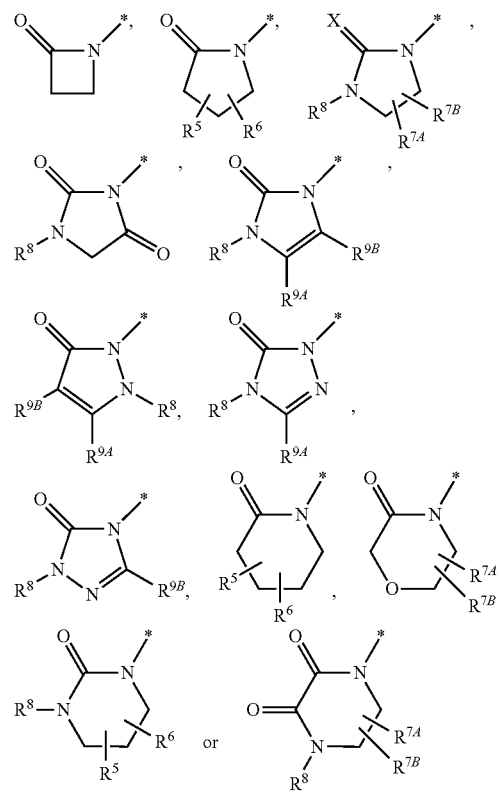

in which * marks the bond to the adjoining CH(R$^1$) group,

R$^5$ is hydrogen, (C$_1$-C$_4$)-alkyl, hydroxyl, (C$_1$-C$_4$)-alkoxy, amino, (C$_1$-C$_5$)-alkanoylamino or (C$_1$-C$_4$)-alkoxycarbonylamino, R$^6$ is hydrogen, methyl or ethyl, R$^{7A}$ and R$^{7B}$ are the same or different and are independently hydrogen or (C$_1$-C$_4$)-alkyl, R$^8$ is hydrogen, (C$_1$-C$_4$)-alkyl, (C$_2$-C$_4$)-alkenyl, (C$_1$-C$_5$)-alkanoyl or (C$_1$-C$_4$)-alkoxycarbonyl,
where (C$_1$-C$_4$)-alkyl may be up to disubstituted by hydroxyl, R$^{9A}$ and R$^{9B}$ are the same or different and are independently hydrogen or (C$_1$-C$_4$)-alkyl and X is O, N(R$^{10}$) or S, in which
R$^{10}$ is hydrogen, cyano or (C$_1$-C$_4$)-alkoxycarbonyl, R$^1$ is hydrogen, R$^2$ is methyl or ethyl which may be up to trisubstituted by fluorine,

671

R³ is (C₂-C₆)-alkyl, (C₂-C₆)-alkenyl or (C₂-C₆)-alkynyl,
where (C₂-C₆)-alkyl may be substituted by a radical selected from the group of hydroxyl, methoxy, ethoxy, trifluoromethoxy, cyclopropyl, cyclobutyl, oxetanyl and phenyl, and up to trisubstituted by fluorine,
and
(C₂-C₆)-alkenyl may be up to trisubstituted by fluorine, where the cyclopropyl and cyclobutyl groups mentioned may in turn be up to disubstituted, identically or differently, by a radical selected from fluorine and methyl, or R³ is a group of the formula —CH₂—R¹⁴ in which
R¹⁴ is cyclopropyl, cyclobutyl, oxetanyl or tetrahydrofuranyl,
where cyclopropyl and cyclobutyl may be up to disubstituted, identically or differently, by a radical selected from fluorine and methyl, and R⁴ is (C₁-C₆)-alkyl or (C₂-C₆)-alkenyl,
where (C₁-C₆)-alkyl and (C₂-C₆)-alkenyl may be up to trisubstituted by fluorine and
where one CH₂ group in (C₁-C₆)-alkyl may be exchanged for —O—, —S— or —S(O)₂—, with the proviso that there are at least two carbon atoms between such a heteroatom and the uracil N¹ atom, or R⁴ is a group of the formula —(CH₂)ₘ—CN, —(CH₂)ₙ—R¹¹ or —(CH₂)ₚ—R¹², in which
m is the number 1, 2, 3 or 4,
n is the number 2 or 3,
P is the number 1 or 2,
R¹¹ is dimethylamino, diethylamino or azetidino
and
R¹² is (C₃-C₆)-cycloalkyl, oxetanyl, tetrahydrofuranyl, tetrahydropyranyl or 5-membered azaheteroaryl,
where (C₃-C₆)-cycloalkyl may be up to disubstituted, identically or differently, by a radical selected from fluorine and methyl and
azaheteroaryl may be up to disubstituted, identically or differently, by a radical selected from methyl and trifluoromethyl, or R⁴ is a group of the formula —(CH₂)₂—O—R¹³ in which
R¹³ is cyclopropyl or cyclobutyl,
and a salt, a solvate, and a solvate of the salt thereof.

3. Compound of the formula (I) according to claim 1, in which the ring A is an azaheterocycle of the formula

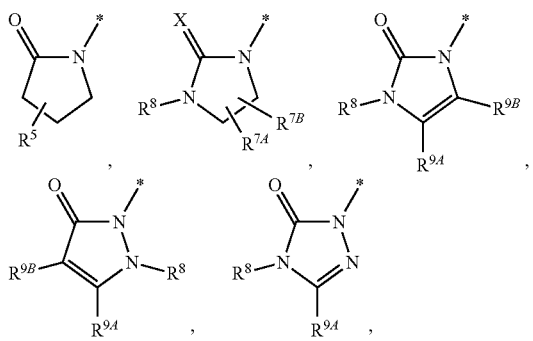

672

-continued

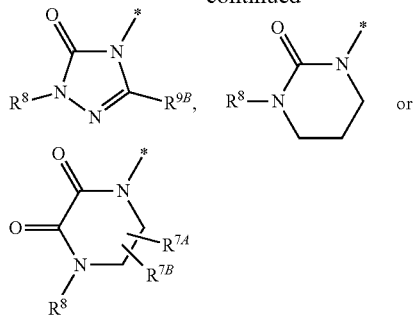

in which * marks the bond to the adjoining CH(R¹) group,
R⁵ is hydroxy, methoxy or ethoxy,
R⁷ᴬ and R⁷ᴮ are each independently hydrogen or methyl,
R⁸ is hydrogen, methyl, ethyl, n-propyl, 2-hydroxyethyl, 3-hydroxypropyl, 2,3-dihydroxypropyl, allyl, formyl or acetyl,
R⁹ᴬ and R⁹ᴮ are each independently hydrogen or methyl
and
X is O, N(R¹⁰) or S, in which
R¹⁰ is cyano or (C₁-C₄)-alkoxycarbonyl,
R¹ is hydrogen,
R² is methyl or ethyl which may be up to trisubstituted by fluorine,
R³ is (C₂-C₅)-alkyl or (C₂-C₄)-alkenyl,
where (C₂-C₅)-alkyl may be substituted by a radical selected from the group of hydroxyl, methoxy, cyclopropyl, cyclobutyl, oxetanyl and phenyl, and up to trisubstituted by fluorine,
and
(C₂-C₄)-alkenyl may be up to trisubstituted by fluorine,
where the cyclopropyl and cyclobutyl groups mentioned may in turn be up to disubstituted by fluorine, or R³ is a group of the formula —CH₂—R¹⁴ in which
R¹⁴ is cyclopropyl, cyclobutyl or oxetanyl,
where cyclopropyl and cyclobutyl may be up to disubstituted, identically or differently, by a radical selected from fluorine and methyl, and R⁴ is (C₁-C₆)-alkyl or (C₂-C₆)-alkenyl,
where (C₁-C₆)-alkyl and (C₂-C₆)-alkenyl may be up to trisubstituted by fluorine and
where one CH₂ group in (C₁-C₆)-alkyl may be exchanged for —O— or —S—, with the proviso that there are at least two carbon atoms between such a heteroatom and the uracil N¹ atom, or R⁴ is the —CH₂—R¹² group in which
R¹² is (C₃-C₆)-cycloalkyl, oxetanyl, tetrahydrofuranyl or tetrahydropyranyl,
where (C₃-C₆)-cycloalkyl may be up to disubstituted, identically or differently, by a radical selected from fluorine and methyl,
and a salt, a solvate, and a solvate of the salt thereof.

4. Compound of the formula (I) according to claim 1, in which
the ring A is an azaheterocycle of the formula

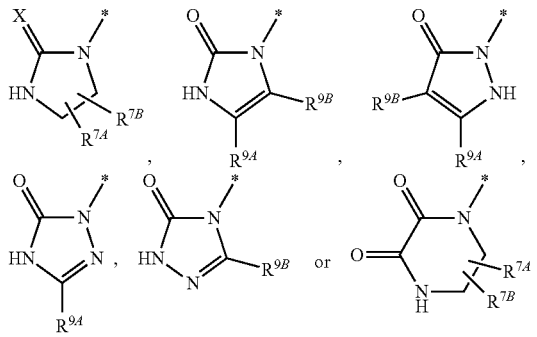

in which * marks the bond to the adjoining CH(R¹) group,
$R^{7A}$ and $R^{7B}$ are each independently hydrogen or methyl,
$R^{9A}$ and $R^{9B}$ are each independently hydrogen or methyl
and
X is O, N($R^{10}$) or S, in which
$R^{10}$ is cyano, methoxycarbonyl, ethoxycarbonyl or tert-butoxycarbonyl,
$R^1$ is hydrogen,
$R^2$ is methyl, difluoromethyl or trifluoromethyl,
$R^3$ is ($C_2$-$C_5$)-alkyl which may be substituted by hydroxyl, methoxy or cyclopropyl or up to trisubstituted by fluorine,
where cyclopropyl may in turn be up to disubstituted by fluorine,
and
$R^4$ is ($C_1$-$C_4$)-alkyl which may be up to trisubstituted by fluorine, is 2-methoxyethyl or 2-ethoxyethyl or is the —$CH_2$—$R^{12}$ group in which
$R^{12}$ is cyclopropyl, cyclobutyl, oxetanyl, tetrahydrofuranyl or tetrahydropyranyl,
where cyclopropyl and cyclobutyl may be up to disubstituted by fluorine,
and a salt, a solvate, and a solvate of the salt thereof.

5. Compound as defined in claim 1, which is 3-Ethyl-1-(2-methoxyethyl)-5-methyl-6-[(2-oxoimidazolidin-1-yl)methyl]thieno[2,3-d]pyrimidine-2,4(1H,3H)-dione of the formula

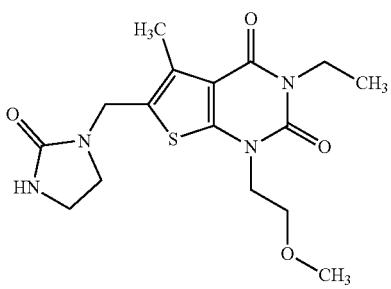 [SMILES: CCn1c(=O)c2c(C)c(CN3CCNC3=O)sc2n(CCOC)c1=O]

or a salt, solvate or solvate of the salt thereof.

6. Compound as defined in claim 1, which is 3-Isopropyl-5-methyl-6-[(2-oxo-2,3-dihydro-1H-imidazol-1-yl)methyl]-1-(tetrahydrofuran-2-ylmethyl)thieno[2,3-d]pyrimidine-2,4(1H,3H)-dione (enantiomer 1) of the formula

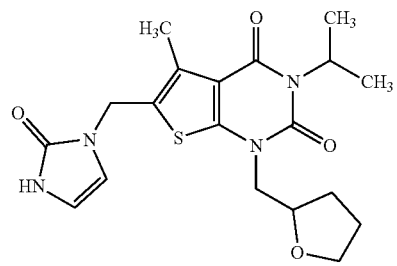 [SMILES: Cc1c(Cn2cc[nH]c2=O)sc2c1c(=O)n(C(C)C)c(=O)n2CC1CCCO1]

or a salt, solvate or solvate of the salt thereof.

7. Compound as defined in claim 1, which is [1-{[3-Ethyl-5-methyl-2,4-dioxo-1-(tetrahydrofuran-2-ylmethyl)-1,2,3,4-tetrahydrothieno[2,3-d]pyrimidin-6-yl]methyl}imidazolidin-2-ylidene]cyanamide (enantiomer 1) of the formula

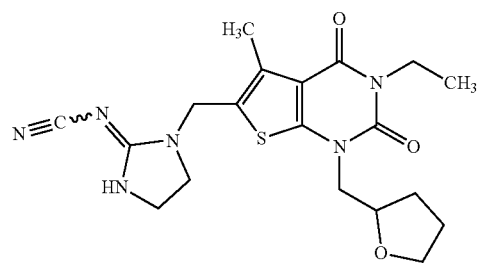 [SMILES: CCn1c(=O)c2c(C)c(CN3CCNC3=NC#N)sc2n(CC2CCCO2)c1=O]

or a salt, solvate or solvate of the salt thereof.

8. Compound as defined in claim 1, which is 3-(4,4-Difluorobut-3-en-1-yl)-1-(2-methoxyethyl)-5-methyl-6-[(2-oxoimidazolidin-1-yl)methyl]thieno[2,3-d]pyrimidine-2,4(1H,3H)-dione of the formula

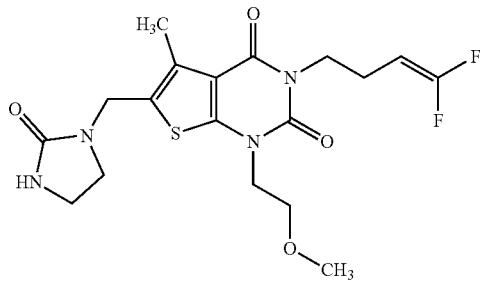 [SMILES: COCCn1c(=O)n(CCC=C(F)F)c(=O)c2c(C)c(CN3CCNC3=O)sc21]

or a salt, solvate or solvate of the salt thereof.

9. Compound as defined in claim 1 for use in a method for treatment of idiopathic pulmonary fibrosis, pulmonary hypertension, Bronchiolitis obliterans syndrome, chronic-obstructive pulmonary disease, asthma, cystic fibrosis, myocardial infarction, heart failure, sickle cell anaemia or cancer.

10. Medicament comprising a compound as defined in claim 1 in combination with one or more inert, nontoxic, pharmaceutically suitable excipients.

11. Medicament comprising a compound as defined in claim 1 in combination with one or more further active ingredients selected from the group consisting of PDE 5 inhibitors, sGC activators, sGC stimulators, prostacyclin analogues, IP receptor agonists, endothelin antagonists, antifibrotic agents, antiinflammatory, immunomodulating, immunosuppressive and/or cytotoxic agents and/or compounds that inhibit the signal transduction cascade.

12. Medicament according to claim 10 for the treatment of idiopathic pulmonary fibrosis, pulmonary hypertension, Bronchiolitis obliterans syndrome, chronic-obstructive pulmonary disease, asthma, cystic fibrosis, myocardial infarction, heart failure, sickle cell anaemia or cancer.

13. Method for treatment of a disease by administration of an effective amount of at least one compound of claim 1.

14. Method for treatment of idiopathic pulmonary fibrosis, pulmonary hypertension, Bronchiolitis obliterans syndrome, chronic-obstructive pulmonary disease, asthma, cystic fibrosis, myocardial infarction, heart failure, sickle cell anaemia or cancer by administration of an effective amount of at least one compound of claim 1.

15. Method for treatment of idiopathic pulmonary fibrosis, pulmonary hypertension, Bronchiolitis obliterans syndrome, chronic-obstructive pulmonary disease, asthma, cystic fibrosis, myocardial infarction, heart failure, sickle cell anaemia or cancer in a human or an animal by administration of an effective amount of at least one medicament as defined in claim 10.

16. Method for providing antagonistic activity at an adenosine A2b receptor by administration of an effective amount of at least one compound of claim 1.

17. Compound of the formula (I-A)

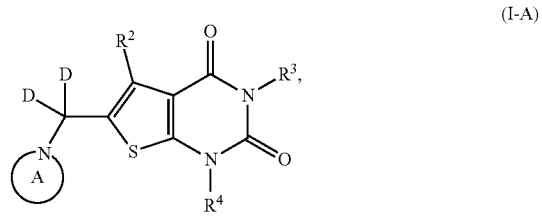

(I-A)

in which the ring A and the $R^2$, $R^3$ and $R^4$ radicals are as defined in claim 1,
and a salt, a solvate and a solvate of the salt thereof.

* * * * *